United States Patent
Funahashi et al.

(10) Patent No.: US 7,973,160 B2
(45) Date of Patent: Jul. 5, 2011

(54) NITROGEN-CONTAINING AROMATIC DERIVATIVES

(75) Inventors: Yasuhiro Funahashi, Nagoya (JP); Toru Haneda, Ushiku (JP); Junichi Kamata, Tsukuba (JP); Tatsuo Watanabe, Inzai (JP); Hiroshi Obaishi, Tsukuba (JP); Junji Matsui, Toride (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 341 days.

(21) Appl. No.: 12/244,227

(22) Filed: Oct. 2, 2008

(65) Prior Publication Data

US 2010/0197911 A1   Aug. 5, 2010

Related U.S. Application Data

(60) Division of application No. 11/293,785, filed on Dec. 2, 2005, now Pat. No. 7,612,092, which is a division of application No. 10/420,466, filed on Apr. 18, 2003, now Pat. No. 7,253,286, which is a continuation-in-part of application No. PCT/JP01/09221, filed on Oct. 19, 2001.

(30) Foreign Application Priority Data

Oct. 20, 2000 (JP) ................................. 2000-320420
Dec. 20, 2000 (JP) ................................. 2000-386195
Feb. 22, 2001 (JP) ................................. 2001-046685

(51) Int. Cl.
  *C07D 487/04* (2006.01)
  *A61K 31/519* (2006.01)
  *A61K 31/47* (2006.01)
  *C07D 215/16* (2006.01)
  *A61P 9/10* (2006.01)
  *A61P 35/04* (2006.01)

(52) U.S. Cl. ...... 544/280; 546/153; 546/155; 514/265.1; 514/312

(58) Field of Classification Search .................. 544/280; 514/265.1
See application file for complete search history.

(56) References Cited

U.S. PATENT DOCUMENTS

| | | |
|---|---|---|
| 4,526,988 A | 7/1985 | Hertel |
| 4,742,003 A | 5/1988 | Derynck et al. |
| 4,764,454 A | 8/1988 | Ichijima et al. |
| 5,180,818 A | 1/1993 | Cech et al. |
| 5,464,826 A | 11/1995 | Grindey et al. |
| 5,487,889 A | 1/1996 | Eckert et al. |
| 5,624,937 A | 4/1997 | Reel et al. |
| 5,656,454 A | 8/1997 | Lee et al. |
| 5,658,374 A | 8/1997 | Glover |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 6,143,764 A | 11/2000 | Kubo et al. |
| 6,156,522 A | 12/2000 | Keay et al. |
| 6,217,866 B1 | 4/2001 | Schlessinger et al. |
| 6,346,398 B1 | 2/2002 | Pavco et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,676,941 B2 | 1/2004 | Thorpe et al. |
| 6,797,823 B1 | 9/2004 | Kubo et al. |
| 6,811,779 B2 | 11/2004 | Rockwell et al. |
| 6,821,987 B2 | 11/2004 | Kubo et al. |
| 7,005,430 B2 | 2/2006 | Ueno et al. |
| 7,135,466 B2 | 11/2006 | Sakai et al. |
| 7,169,789 B2 | 1/2007 | Kubo et al. |
| 7,253,286 B2 | 8/2007 | Funahashi et al. |
| 7,435,590 B2 | 10/2008 | Komurasaki |
| 7,547,703 B2 | 6/2009 | Roth et al. |
| 7,612,092 B2 | 11/2009 | Funahashi et al. |
| 7,612,208 B2 | 11/2009 | Matsushima et al. |
| 7,725,303 B2 | 5/2010 | Tramontana |
| 2002/0040127 A1 | 4/2002 | Jiang et al. |
| 2003/0087907 A1 | 5/2003 | Kubo et al. |
| 2003/0113713 A1 | 6/2003 | Glezer et al. |
| 2003/0215523 A1 | 11/2003 | Ozawa et al. |

(Continued)

FOREIGN PATENT DOCUMENTS

EP   0405425 A2   1/1991

(Continued)

OTHER PUBLICATIONS

Abuzar et al., "Synthesis of some new 7-chloro-4-substituted quinolines as potential antiparasitic agents (1)," Eur J Med Chem 21(1):5-8 (1986).

(Continued)

*Primary Examiner* — Susanna Moore
(74) *Attorney, Agent, or Firm* — Birch, Stewart, Kolasch & Birch, LLP

(57) ABSTRACT

Compounds represented by the following general formula:

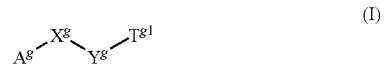

(I)

[wherein $A^g$ is an optionally substituted 5- to 14-membered heterocyclic group, etc.; $X^g$ is —O—, —S—, etc.; $Y^g$ is an optionally substituted $C_{6-14}$ aryl group, an optionally substituted 5- to 14-membered heterocyclic group, etc.; and $T^{g1}$ is a group represented by the following general formula:

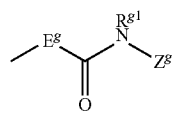

(wherein $E^g$ is a single bond or —N($R^{g2}$)—, $R^{g1}$ and $R^{g2}$ each independently represent a hydrogen atom, an optionally substituted $C_{1-6}$ alkyl group, etc. and $Z^g$ represents a $C_{1-8}$ alkyl group, a $C_{3-8}$ alicyclic hydrocarbon group, a $C_{6-14}$ aryl group, etc.)],
salts thereof or hydrates of the foregoing.

2 Claims, No Drawings

U.S. PATENT DOCUMENTS

| | | |
|---|---|---|
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0132727 A1 | 7/2004 | Sakai et al. |
| 2004/0152759 A1 | 8/2004 | Abrams et al. |
| 2004/0191254 A1 | 9/2004 | Fagin |
| 2004/0242506 A1 | 12/2004 | Barges Causeret et al. |
| 2004/0253205 A1 | 12/2004 | Yamamoto et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0272688 A1 | 12/2005 | Higgins et al. |
| 2005/0277652 A1 | 12/2005 | Matsushima et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2007/0004773 A1 | 1/2007 | Sakaguchi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2008/0207617 A1 | 8/2008 | Miwa et al. |
| 2008/0214604 A1 | 9/2008 | Furitsu et al. |
| 2009/0047278 A1 | 2/2009 | Owa et al. |
| 2009/0047365 A1 | 2/2009 | Owa et al. |
| 2009/0053236 A1 | 2/2009 | Yamamoto |
| 2009/0209580 A1 | 8/2009 | Matsui |
| 2009/0247576 A1 | 10/2009 | Kamata |
| 2010/0105031 A1 | 4/2010 | Matsui et al. |

FOREIGN PATENT DOCUMENTS

| | | |
|---|---|---|
| EP | 0602851 A1 | 6/1994 |
| EP | 0684820 | 12/1995 |
| EP | 0 712 863 A1 | 5/1996 |
| EP | 0795556 A1 | 9/1997 |
| EP | 0837063 A1 | 4/1998 |
| EP | 0 870 842 | 10/1998 |
| EP | 0930305 A1 | 7/1999 |
| EP | 0930310 A1 | 7/1999 |
| EP | 1029853 A1 | 8/2000 |
| EP | 1 153 920 | 11/2001 |
| EP | 0 712 863 B1 | 2/2002 |
| EP | 1415987 A1 | 5/2004 |
| EP | 1 522 540 A1 | 4/2005 |
| EP | 1 535 910 A1 | 6/2005 |
| EP | 1566379 A1 | 8/2005 |
| EP | 1604665 A1 | 12/2005 |
| EP | 1583785 A1 | 7/2006 |
| EP | 1698623 | 9/2006 |
| EP | 1797877 A1 | 6/2007 |
| EP | 1797881 | 6/2007 |
| EP | 1859793 A1 | 11/2007 |
| EP | 1859797 A1 | 11/2007 |
| EP | 1894918 A1 | 3/2008 |
| EP | 1925676 A1 | 5/2008 |
| EP | 1925941 A1 | 5/2008 |
| EP | 1949902 A1 | 7/2008 |
| EP | 1964837 A1 | 9/2008 |
| GB | 2253848 A | 9/1992 |
| JP | 63-28427 A | 2/1988 |
| JP | 64-22874 A | 1/1989 |
| JP | 2-291295 A | 12/1990 |
| JP | 04-341454 | 6/1994 |
| JP | 6-153952 A | 6/1994 |
| JP | H8-048078 | 2/1996 |
| JP | 07-176103 | 1/1997 |
| JP | 9-23885 A | 1/1997 |
| JP | 08-045927 | 9/1997 |
| JP | 9-234074 A | 9/1997 |
| JP | 11-501343 A | 2/1999 |
| JP | 11-158149 | 6/1999 |
| JP | 11-322596 A | 11/1999 |
| JP | 3040486 A | 5/2000 |
| JP | 3088018 A | 9/2000 |
| JP | 11-143429 | 11/2000 |
| JP | 2000-328080 A | 11/2000 |
| JP | 2001-131071 A | 5/2001 |
| JP | 2002-3365 A | 1/2002 |
| JP | 2002-114710 A | 4/2002 |
| JP | 2002-536414 A | 10/2002 |
| JP | 2003-12668 A | 1/2003 |
| JP | 2003-26576 A | 1/2003 |
| JP | 3420549 B2 | 6/2003 |
| JP | 2003-525595 A | 9/2003 |
| JP | 2004-513964 A | 5/2004 |
| JP | 2004-155773 A | 6/2004 |
| JP | 2004-531549 A | 10/2004 |
| JP | 2005-501074 A | 1/2005 |
| JP | 2005/504111 A | 2/2005 |
| JP | 2005/520834 A | 7/2005 |
| JP | 3712393 | 11/2005 |
| JP | 2006-508981 A1 | 3/2006 |
| JP | 2006-515884 | 6/2006 |
| WO | WO 92/20642 A1 | 11/1992 |
| WO | WO 95/15758 A1 | 6/1995 |
| WO | WO 95/19774 A1 | 7/1995 |
| WO | WO 96/09294 A1 | 3/1996 |
| WO | WO 96/17181 A1 | 6/1996 |
| WO | WO 96/26997 A1 | 9/1996 |
| WO | WO 96/30347 A1 | 10/1996 |
| WO | WO 96/33980 A1 | 10/1996 |
| WO | WO 96/39145 A1 | 12/1996 |
| WO | WO 96/40142 A1 | 12/1996 |
| WO | WO 97/03069 A1 | 1/1997 |
| WO | WO 97/13760 A1 | 4/1997 |
| WO | WO 97/13771 A1 | 4/1997 |
| WO | WO 97/17329 | 5/1997 |
| WO | WO 97/21437 A1 | 6/1997 |
| WO | WO 97/38984 A1 | 10/1997 |
| WO | WO 97/48693 A1 | 12/1997 |
| WO | WO-98/00134 | 1/1998 |
| WO | WO 98/02434 A1 | 1/1998 |
| WO | WO 98/02437 A1 | 1/1998 |
| WO | WO 98/02438 A1 | 1/1998 |
| WO | WO 98/13350 A1 | 4/1998 |
| WO | WO 98/14437 A1 | 4/1998 |
| WO | WO 98/23613 A1 | 6/1998 |
| WO | WO 98/32436 A1 | 7/1998 |
| WO | WO 98/35958 A1 | 8/1998 |
| WO | WO 98/37079 | 8/1998 |
| WO | WO 98/50346 A2 | 11/1998 |
| WO | WO 98/52558 A1 | 11/1998 |
| WO | WO 99/00357 | 1/1999 |
| WO | WO-99/32106 | 7/1999 |
| WO | WO 99/32110 A1 | 7/1999 |
| WO | WO 99/32111 A1 | 7/1999 |
| WO | WO-99/32436 | 7/1999 |
| WO | WO 99/35132 A1 | 7/1999 |
| WO | WO 99/35146 A1 | 7/1999 |
| WO | WO 99/43654 A1 | 9/1999 |
| WO | WO 99/62890 A1 | 12/1999 |
| WO | WO 00/31048 A1 | 6/2000 |
| WO | WO-00/42012 | 7/2000 |
| WO | WO 00/43366 | 7/2000 |
| WO | WO 00/43384 A1 | 7/2000 |
| WO | WO 00/44728 A1 | 8/2000 |
| WO | WO 00/47212 A1 | 8/2000 |
| WO | WO 00/50405 A1 | 8/2000 |
| WO | WO 00/71097 A1 | 11/2000 |
| WO | WO 01/02369 A2 | 1/2001 |
| WO | WO 01/23375 A2 | 4/2001 |
| WO | WO 01/27081 A1 | 4/2001 |
| WO | WO 01/32926 A2 | 5/2001 |
| WO | WO 01/36403 A1 | 5/2001 |
| WO | WO 01/40217 A1 | 6/2001 |
| WO | WO 01/45689 | 6/2001 |
| WO | WO 01/47890 | 7/2001 |
| WO | WO 01/47931 | 7/2001 |
| WO | WO 01/60814 A2 | 8/2001 |
| WO | WO 02/16348 A1 | 2/2002 |
| WO | WO 02/32872 A1 | 4/2002 |

| | | |
|---|---|---|
| WO | WO 02/36117 A1 | 5/2002 |
| WO | WO 02/41882 A2 | 5/2002 |
| WO | WO-02/072578 A2 | 9/2002 |
| WO | WO 02/080975 A1 | 10/2002 |
| WO | WO 02/088110 A1 | 11/2002 |
| WO | WO 02/092091 A1 | 11/2002 |
| WO | WO 03/006462 A1 | 1/2003 |
| WO | WO 03/013529 A1 | 2/2003 |
| WO | WO 03/027102 A1 | 4/2003 |
| WO | WO 03/028711 A2 | 4/2003 |
| WO | WO 03/033472 A1 | 4/2003 |
| WO | WO 03/050090 A1 | 6/2003 |
| WO | WO 03/074045 A1 | 9/2003 |
| WO | WO 03/079020 A2 | 9/2003 |
| WO | WO 2004/006862 A2 | 1/2004 |
| WO | WO 2004/020434 A1 | 3/2004 |
| WO | WO 2004/032872 A2 | 4/2004 |
| WO | WO 2004/032937 A1 | 4/2004 |
| WO | WO 2004/035052 A1 | 4/2004 |
| WO | WO 2004/039782 A1 | 5/2004 |
| WO | WO 2004/041308 A1 | 5/2004 |
| WO | WO 2004/043472 A1 | 5/2004 |
| WO | WO-2004/064730 A2 | 8/2004 |
| WO | WO 2004/078477 A2 | 9/2004 |
| WO | WO-2004/080462 A1 | 9/2004 |
| WO | WO-2004/080966 A1 | 9/2004 |
| WO | WO-2004/101526 A1 | 11/2004 |
| WO | WO 2005/027972 A2 | 3/2005 |
| WO | 2005/030140 | 4/2005 |
| WO | WO 2005/044788 A1 | 5/2005 |
| WO | WO 2005/051366 A2 | 6/2005 |
| WO | WO 2005/056764 A2 | 6/2005 |
| WO | WO 2005/063713 A1 | 7/2005 |
| WO | WO 2005/082854 A1 | 9/2005 |
| WO | WO 2005/092896 A1 | 10/2005 |
| WO | WO 2005/117887 A1 | 12/2005 |
| WO | WO 2006/030826 A1 | 3/2006 |
| WO | WO 2006/030941 A1 | 3/2006 |
| WO | WO 2006/030947 A1 | 3/2006 |
| WO | WO 2006/036941 A2 | 4/2006 |
| WO | WO 2006/062984 A2 | 6/2006 |
| WO | WO 2006/090930 A1 | 8/2006 |
| WO | WO 2006/090931 A1 | 8/2006 |
| WO | WO 2006/137474 A1 | 12/2006 |
| WO | WO 2007/014335 A2 | 2/2007 |
| WO | WO 2007/015569 A1 | 2/2007 |
| WO | WO 2007/015578 A1 | 2/2007 |
| WO | WO 2007/040565 A2 | 4/2007 |
| WO | WO 2007/052849 A1 | 5/2007 |
| WO | WO 2007/052850 A1 | 5/2007 |
| WO | WO 2007/061127 A1 | 5/2007 |
| WO | WO 2007/061130 A1 | 5/2007 |
| WO | WO 2007/136103 A1 | 11/2007 |

OTHER PUBLICATIONS

Non-Final Office Action for U.S. Appl. No. 10/797,903, mailed Dec. 11, 2007 (25 pages).

"E7080 (ER-203492-00), a Novel VEGF Receptor Tyrosine Kinase Inhibitor-I. Characterization as an Angiogenesis Inhibitor," Matsui et al., Abstract #51, AACR, Washington, DC, Jul. 11-14, 2003.

"E7080 (ER-203492-00), a Novel VEGF Receptor Tyrosine Kinase Inhibitor-II. Effects on Growth of Human Tumor Xenografts and Life Span of Mice in Colon 38 Orthotopic Transplantation Model," Nakamura et al., Abstract #52, AACR, Washington, DC, Jul. 11-14, 2003.

"E7080 (ER-203942-00), a Novel VEGF Receptor Tyrosine Kinase Inhibitor-III. Significant prolongation of life span in mice transplanted with human ovarian carcinoma based on inhibition of VEGF signaling," Yamamoto, et al., Abstract #50, AACR, Washington, DC, Jul. 11-14, 2003.

"E7080, a novel multitargeted tyrosine kinase inhibitor, has direct anti-tumor activity via inhibition of KIT signaling in small cell lung cancer," Yamamoto et al., Abstract #4636, AACR, Orlando, FL, Mar. 27-31, 2004.

Synthesis, Structure and Biological Activity Relationship of E7080 and its Derivatives as Novel and Potent Antiangiogenic Protein Tyrosine Kinase Inhibitors Including the VEGF Receptors, FGFR1 Receptor and PDGF Receptor, Miyazaki et al., Abstract B-15, AIMECS03, Kyoto, Japan, Oct. 14-17, 2003.

"E7080, a novel multi-receptor Tyrosine Kinase Inhibitor, inhibited in vitro / in vivo VEGF- and SCF-driven angiogenesis SCLC cell line," Matsui et al., Abstract #146, EORTC-NCI-AACR, Geneva, Switzerland, Sep. 28-Oct. 1, 2004.

"VEGFRs inhibitor E7080 inhibits lymph node metastatis of human breast carcinoma, by preventing murine lymphatic endothelial cells from lymphangiogenesis," Matsui et al., Abstract #PD12-8, 18th EORTC-NCI-AACR symposium on "Molecular Targets and Cancer Therapeutics," Prague, Czech Republic, Nov. 7-10, 2006.

"E7080, an oral multi-targeted tyrosine kinase inhibitor, has direct anti-tumor efficacy via inhibition of KIT signaling in gastrointestinal stromal tumor (GIST)," Yamamoto et al., Abstract #4038, 97th annual meeting AACR, Washington, DC, Apr. 1-5, 2006.

"Quantitative analysis of the profile of tumor vessels may be useful as predictive biomarkers for E7080," Matsui et al., Abstract #4631, 98th AACR annual meeting, Los Angeles, CA, Apr. 14-18, 2007.

"E7080, a novel inhibitor that targets multiple kinases, has potent antitumor activities against stem cell factor producing human small cell lung cancer H146, based on angiogenesis inhibition," Matsui et al, International Journal of Cancer (2008) 122: 664-671.

"AZD2171: A Highly Potent, Orally Bioavailable, Vascular Endothelial Growth Factor Receptor-2 Tyrosine Kinase Inhibitor for the Treatment of Cancer," Wedge et al., Cancer Res. (2005) 65: 4389-4400.

"Safety and Pharmacokinetics of the Dual Action Raf Kinase and Vascular Endothelial Growth Factor Receptor Inhibitor, BAY43-9006, in Patients with Advanced Refractory Solid Tumors," Clark et al., Clin. Cancer Res. (2005) 11: 5472-5480.

"In Vivo Antitumor Activity of SU11248, a Novel Tyrosine Kinase Inhibitor Targeting Vascular Endothelial Growth Factor and Platelet-derived Growth Factor Receptors: Determination of a Pharmacokinetic/Pharmacodynamic Relationship," Mendel et al., Clin. Cancer Res. (2003) 9: 327-337.

Nocka et al., "Expression of c-kit gene products in known cellular targets of W mutations in normal and W mutant mice—evidence for an impaired c-kit kinase mutant mice," *Genes & Development* 3:816-826 (1989).

Qin et al., "Abrogation of c-kit/Steel factor-dependent tumorigenesis by kinase defective mutants of the c-kit receptor: c-kit kinase defective mutants as candidate tools for cancer gene therapy," *Cancer Research* 56:4343-4346 (1996).

Gall-Istok, et al., STN Accession No. 99:88018, Abstract of *Acta Chimica Hungarica* 112(2):241-7 (1983).

Cairns, et al., "New antiallergic pyrano[3,2g]quinoline-2,8-dicarboxylic acids with potential for the topical treatment of asthma," *Journal of Medicinal Chemistry* 8(12):1832-42 (1985).

Takano, et al., "Thermal recording materials with improved background stability," Database CA (Online) Chemical Abstracts Service, XP002443195, Feb. 20, 1996.

CancerCare, www.lungcancer/org/reading/types/php, 2009.

Office Action dated Aug. 20, 2009 from U.S. Appl. No. 10/797,903.

NCBI GeneBank Accession No. NM_000222, Feb. 11, 2008.

Boissan et al., "c-Kit and c-Kit mutations in mastocytosis and other hematological diseases," J. Leukoc. Biol., vol. 67, pp. 135-148, Feb. 2000.

Chinese Office Action for Application No. 2005800264687 dated Jun. 26, 2009.

Chinese Office Action for Application No. 2007100070979 dated Mar. 6, 2009.

Ciardiello et al., "ZD1839 (IRESSA), an EGFR-selective tyrosine kinase inhibitor, enhances taxans activity in bcl-2 overexpressing, multidrug-resistant MCF-7 ADR human breast cancer cells," Int. J Cancer, vol. 98, No. 3, pp. 463-469, Mar. 20, 2002.

Croom et al., "Imatinib Mesylate: In the Treatment of Gastrointestinal Stromat Tumours," Drugs, vol. 63, No. 5, pp. 513-522, 2003.

Dermer, "Another Anniversary for the War on Cancer," Biotechnology, vol. 12, pp. 320, Mar. 12, 1994.

European Office Action for Application No. 04025700.8 dated Apr. 10, 2006.

European Search Report for Application No. 04719054.1 dated Apr. 17, 2009.
European Search Report for Application No. 04818213.3 dated Jul. 30, 2007.
European Search Report for Application No. 06832529.9 dated Jul. 29, 2009.
Freshney, "Culture of Animal Cells: A Manual of Basic Technique," Alan R. Liss, New York, pp. 29-32, 1983.
Furitsu et al, "Stable medicinal compositions of quinolinecarboxamide derivative", Database CAPLUS Abstract, Columbus, Ohio, US, 2006.
Gardner et al., "In Vitro Activity of Sorghum-Selective Fluorophenyl Urea Herbicides," Pestic. Biochem. Physiol., vol. 24, pp. 285-297, 1985.
Gura, "Systems for identifying new drugs are often faulty," Science. vol. 278, No. 5340, pp. 1040-1042, Nov. 7, 1997.
Haleblian, "Characterization of Habits and Crystalline Modification of Solids and Their Pharmaceutical Applications," J. Pharma. Sci., vol. 64, No. 8, pp. 1269-1288, Aug. 1975.
Hayek et al., "An in vivo model for study of the angiogenic effects of basic fibroblast growth factor," Biochem. Biophys. Res. Commun., vol. 147, No. 2, pp. 875-880, Sep. 15, 1987.
Heinrich et al., "Inhibition of c-kit receptor tyrosine kinase activity by STI 571, a selective tyrosine kinase inhibitor," Blood, vol. 96, No. 3, pp. 925-932. Aug. 1, 2000.
Heinrich et al., "Inhibition of KIT Tyrosine Kinase Activity: A Novel Molecular Approach to the Treatment of KIT-Positive Malignancies," J. Clin. Oncol., vol. 20, No. 6, pp. 1692-1703, Mar. 15, 2002.
International Preliminary Report on Patentability and Written Opinion of the International Searching Authority for Application No. PCT/JP2004/003087 dated on Feb. 13, 2006.
International Preliminary Report on Patentability and Written Opinion of the International Searching Authority for Application No. PCT/JP2006/312487 dated Dec. 24, 2007.
International Search Report for Application No. PCT/JP01/09221 dated on Jan. 15, 2002.
International Search Report for Application No. PCT/JP2004/003087 dated Jul. 13, 2004.
Jakeman et al., "Developmental expression of binding sites and messenger ribonucleic acid for vascular endothelial growth factor suggests a role for this protein in vasculogenesis and angiogenesis," Endocrinology, vol. 133, No. 2, pp. 848-859, Aug. 1993.
Japanese Office Action for Application No. 2005-515330 dated Apr. 21, 2009.
Korean Office Action for Application No. 10-2007-7013993 dated Jul. 31, 2007.
Longley et al., "Classes of c-KIT activating mutations: proposed mechanisms of action and implications for disease classification and therapy," Leukemia Res., vol. 25, pp. 571-576, 2001.
Myers et al., "The Preparation and SAR of 4-(Anilino), 4-(Phenoxy), and 4-(Thiophenoxy)-Quinazolines: Inhibitors of p56lck and EGF-R Tyrosine Kinase Activity." Bioorg. Med. Chem. Letts., vol. 7, No. 4, pp. 417-420, 1997.
Naruse et al., "Antitumor activity of the selective epidermal growth factor receptor-tyrosine kinase inhibitor (EGFR-TKI) IRESSA (ZD1839) in an EGFR-expressing multidrug-resistant cell line in vitro and in vivo," Int. J. Cancer, vol. 98, No. 2, pp. 310-315, Mar. 10, 2002.
Nugiel et al., "Synthesis and Evaluation of Indenopyrazoles as Cyclin-Dependent Kinase Inhibitors. 2. Probing the Indeno Ring Substituent Pattern," J. Med. Chem., vol. 45, pp. 5224-5232, 2002.
Redefining the Frontiers of Science 94th Annual Meeting, American Association for Cancer Research, vol. 44, 2nd Edition, Washington Convention Center, Washington, D.C., pp. 10-11, Jul. 11-14, 2003.
Taguchi et al., "A novel orally active inhibitor of VEGF receptor tyrosine kinases KRN951: Anti-angiogenic and anti-tumor activity against human solid tumors," Proc. Amer. Assoc. Cancer Res., vol. 45, pp. 595-596, Mar. 2004.
U.S. Office Action dated May 3, 2010 for U.S. Appl. No. 11/662,425, filed Apr. 4, 2008.
U.S. Office Action dated Apr. 1, 2010, for U.S. Appl. No. 10/797,903, filed Mar. 10, 2004.
U.S. Office Action dated Feb. 9, 2009 for U.S. Appl. No. 11/347,749, filed Feb. 3, 2006.
U.S. Office Action dated Mar. 31, 2010 for U.S. Appl. No. 12/400,562, filed Mar. 9, 2009.
U.S. Office Action dated Sep. 23, 2008 for U.S. Appl. No. 10/577,531, filed Apr. 28, 2006.
Wakeling et al., "ZD1839 (Iressa): An Orally Active Inhibitor of Epidermal Growth Factor Signaling with Potential for Cancer Therapy," Cancer Res., vol. 62, pp. 5749-5753, Oct. 15, 2002.
Bellone, et al., "Growth Stimulation of Colorectal Carcinoma Cells via the c-kit Receptor is Inhibited by TGF-β-1", *Journal of Cellular Physiology*, 172: 1-11, 1997.
Berdel, et al., "Recombinant Human Stem Cell Factor Stimulates Growth of a Human Glioblastoma Cell Line Expressing c-kit Protooncogene", *Cancer Research*, 52: 3498-3502, 1992.
Bussolino, et al., "Role of Soluble Mediators in Angiogenesis" *Eur. J. Cancer*, 32A(14): 2401-2412, 1996.
Cohen, et al., "Expression of Stem Cell Factor and c-kit in Human Neuroblastoma", *Blood*, 84(10): 3465-3472, 1994.
Deplanque, et al., "Anti-Angiogenic Agents: Clinical Trial Design and Therapies in Development", *European Journal of Cancer*, 36: 1713-1724, 2000.
Folkman, J., "New Perspective in Clinical Oncology From Angiogenesis Research", *Eur J. Cancer*. 32A(14): 2534-2539, 1996.
Folkman, et al., "Angiogenesis", *The Journal of Biological Chemistry*, 267(16): 10931-10934, 1992.
Folkman, et al., "Clinical Applications of Research on Angiogenesis", *The New England Journal of Medicine*, 333(26): 1757-1763, 1995.
Folkman, J., "What is the Evidence that Tumors are Angiogenesis Dependent?", *Journal of the National Cancer Institute*, 82(1): 4-6, 1990.
Furitsu, et al., "Identification of Mutations in the Coding Sequence of the Proto-Oncogene *c-kit* in a Human Mast Cell Leukemia Cell Line Causing Ligand-Independent Activation of *c-kit* Product" *J. Clin. Invest*. 92: 1736-1744, 1993.
Furuta, et al., "Synthesis and Biological Evaluation of Selective Inhibitors of PDGF Receptor Auto Phosphorylation" *Pharmaceutical Research Laboratories, Kirin Brewery Co., Ltd.*, Takasaki, Gunma, Japan, 2003.
Golkar, et al., "Mastocytosis", *Lancet*, 349: 1379-1385, 1997.
Hamel, et al., The Road Less Travelled: *c-kit* and Stem Cell Factor, *Journal of Neuro-Oncology*, 35: 327-333, 1997.
Hibi, et al., "Coexpression of the Stem Cell Factor and the *c-kit* Genes in Small-Cell Lung Cancer", *Oncogene*, 6: 2291-2296, 1991.
Hines, et al., "Coexpression of the c-kit and Stem Cell Factor Genes in Breast Carcinomas", *Cell Growth & Differentiation*, 6: 769-779, 1995.
Hogaboam, et al., "Novel Role of Transmembrane SCF for Mast Cell Activation and Eotaxin Production in Mast Cell-Fibroblast Interactions", *The Journal of Immunology*, 160: 6166-6171, 1998.
Ikeda, et al., "Changes in Phenotype and Proliferative Potential of Human Acute Myeloblastic Leukemia Cells in Culture with Stem Cell Factor", *Experimental Hematology*, 21: 1686-1694, 1993.
Ikeda, et al., "Expression and Functional Role of the Proto-Oncogene *c-kit* in Acute Myeloblastic Leukemia Cells", *Blood*, 78(11): 2962-2968, 1991.
Blume-Jensen, et al., "Activation of the Human *c-kit* Product by Ligand-Induced Dimerization Mediates Circular Actin Reorganization and Chemotaxis", *The EMBO Journal*, 10(13): 4121-4128, 1991.
Kanakura, et al., "Expression, Function and Activation of the Proto-Oncogene c-kit Product in Human Leukemia Cells", *Leukemia and Lymphoma*, 10: 35-41, 1993.
Kay, et al., "Eosinophils and Eosinophil-Associated Cytokines in Allergic Inflammation", *Int. Arch. Allergy Immunol*. 113: 196-199, 1997.
Kitamura, et al., "Regulation of Development, Survival and Neoplastic Growth of Mast Cells through the *c-kit* Receptor", *Int Arch Allergy Immunol*., 107: 54-56, 1995.
Kolibaba, et al., "Protein Tyrosine Kinases and Cancer", *Biochimica et Biophysica Acta*, 1333: F217-F248, 1997.

Kotva, et al., "Substances with Antineoplastic Activity, LIII. N-(δ-(4-Pyrrolo[2,3-d]Pyrimidinylthio)Valeryl} Amino Acids and Analogous Derivatives of Di-and Triglycine", *Collection Czechoslov. Chem. Commun.* 38: 1438-1444, 1973.

Lasota, et al., "Mutations in Exons 9 and 13 of KIT Gene Are Rare Events in Gastrointestinal Stromal Tumors", *American Journal of Pathology*, 157(4): 1091-1095, 2000.

Lev, et al., "A Specific Combination of Substrates is Involved in Signal Transduction by the Kit-Encoded Receptor", *The EMBO Journal*, 10(3): 647-654, 1991.

Longley, et al., "Altered Metabolism of Mast-Cell Growth Factor (c-kit Ligand) in Cutaneous Mastocytosis", *The New England Journal of Medicine*, 328(18): 1302-1307, 1993.

Longley, et al., "Somatic c-KIT Activating Mutation in Urticaria Pigmentosa and Aggressive Mastocytosis: Establishment of Clonality in a Human Mast Cell Neoplasm", *Nature Genetics*, 12: 312-314, 1996.

Lukacs, et al., "Stem Cell Factor (*c-kit* Ligand) Influences Eosinophil Recruitment and Histamine Levels in Allergic Airway Inflammation", *The Journal of Immunology*, 156: 3945-3951, 1996.

Meltzer, E.O., "The Pharmacological Basis for the Treatment of Perennial Allergic Rhinitis and Non-Allergic Rhinitis with Topical Corticosteroids", *Allergy*, 52: 33-40, 1997.

Metcalfe, D., "Classification and Diagnosis of Mastocytosis: Current Status", *J. Invest. Dermatol*, 96: 2S-4S, 1991.

Metcalfe, et al., "Mast Cells", *Physiological Reviews*, 77(4): 1033-1079, 1997.

Metcalf, et al., "Lineage Commitment in the Progeny of Murine Hematopoietic Preprogenitor Cells: Influence of Thrombopoietin and Interleukin 5", *Proc. Nat'l Acad. Sci. USA*, 95: 6408-6412, 1998.

Naclerio, et al., "Rhinitis and Inhalant Allergens", *JAMA*, 278(22): 1842-1848, 1997.

Nagata, et al., "Elevated Expression of the Proto-Oncogene c-kit in Patients with Mastocytosis", *Leukemia*, 12: 175-181, 1998.

Natali, et al., "Breast Cancer is Associated with Loss of the *c-kit* Oncogene Product", *Int. J. Cancer*, 52: 713-717, 1992.

Okayama, et al., "Activation of Eosinophils with Cytokines Produced by Lung Mast Cells", *Int Arch Allergy Immunol.* 114:(suppl 1): 75-77, 1997.

Okayama, et al., "Human Lung Mast Cells are Enriched in the Capacity to Produce Granulocyte-Macrophage Colony-Stimulating Factor in Response to IgE-Dependent Stimulation", *Eur. J. Immunol.* 28: 708-715, 1998.

Scheijen, et al., "Tyrosine Kinase Oncogenes in Normal Hematopoiesis and Hematological Disease", *Oncogene*, 21: 3314-3333, 2002.

Sekido, et al., "Preferential Expression of *c-kit* Protooncogene Transcripts in Small Cell Lung Cancer", *Cancer Research*, 51: 2416-2418, 1991.

Spacey, et al., "Indolocarbazoles, Potent and Selective Inhibitors of Platelet-Derived Growth Factor Receptor Autophosphorylation" *Biochemical Pharmacology*, 55: 261-271, 1998.

Strohmeyer, et al., "Expression of the *hst-1* and *c-kit* Protoonocogenes in Human Testicular Germ Cell Tumors", *Cancer Research*, 51: 1811-1816, 1991.

Taniguchi, et al., "Effect of c-kit Mutation on Prognosis of Gastrointestinal Stromal Tumors", *Cancer Research*, 59: 4297-4300, 1999.

Thomas, et al., "The Eosinophil and its Role in Asthma", *Gen. Pharmac.* 27(4): 593-597, 1996.

Tian, et al., "Activating *c-kit* Gene Mutations in Human Germ Cell Tumors", *American Journal of Pathology*, 154(6): 1643-1647, 1999.

Tonary, et al., "Lack of Expression of c-KIT in Ovarian Cancers is Associated with Poor Prognosis", *Int. J. Cancer (Pred. Oncol)* 89: 242-250, 2000.

Wang, et al., "A Convenient Set of Bidentate Pyridine Ligands for Combinatorial Synthesis", *Tetrahedron Lett.* 40: 4779-4782, 1999.

Wang, et al., "The Expression of the Proto-Oncogene C-Kit in the Blast Cells of Acute Myeloblastic Leukemia", *Leukemia*, 3(10): 699-702, 1989.

Anderson et al., "Preparation of Water-soluble Compounds through Salt Formation, The Practice of Medicinal Chemistry," Technomics, Sep. 25, 1999, pp. 347-349 and 355-356.

Office Action issued Jun. 1, 2010, in corresponding Japanese Patent Application No. P2005-516605 (with partial translation).

"Asu no Shinyaku" ("The New Drugs of Tomorrow"), Update Summary, Dec. 2006, ISSN 1343-4462, pp. 81-83.

Agarwal et al., "Binding of Discoidin Domain Receptor 2 to Collagen I: An Atomic Force Microscopy Investigation," Biochemistry, vol. 41, pp. 11091-11098, 2002.

Alvares Da Silva et al., "A Novel Germ-Line Point Mutation in RET Exon 8 (Gly533Cys) in a Large Kindred with Familiar Medullary Thyroid Carcinoma", The Journal of Clinical Endocrinology & Metabolism, vol. 88, No. 11, 2003, pp. 5438-5443.

Baker et al., "Blockade of Vascular Endothelial Growth Factor Receptor and Epidermal Growth Factor Receptor Signaling for Therapy of Metastatic Human Pancratic Cancer," Cancer Research, vol. 62, pp. 1996-2003, Apr. 1, 2002.

Benjamin et al., "Selective Ablation of Immature Blood Vessels in Estabished Human Tumors Follows Vascular Endothelial Growth Factor Withdrawal", The Journal of Clinical Investigation, vol. 103, No. 2, Jan. 1999, p. 159-165.

Bergers et al., "Benefits of Targeting Both Pericytes and Endothelial Cells in the Tumor and Vasculature with Kinase Inhibitors", The Journal of Clinical Investigtion, vol. 111, No. 9, May 2003, pp. 1287-1295.

Bruns et al., "Effect of the Vascular Endothelial Growth Factor Receptor-2 Antibody DC101 Plus Gemcitabine on Growth, Metastasis and Angiogenesis of Human Pancreatic Cancer Growing Orthotopically in Nude Mice", Int. J. Cancer, vol. 102, 2002, pp. 101-108.

Cappellen et al., "Frequent Activating Mutations of FGFR3 in Human Bladder and Cervix Carcinomas," Nature Genetics, vol. 23, Sep. 1999, pp. 18-20.

Carlomagno et al., "BAY 43-9006 Inhibition of Oncogenic RET Mutants", Journal of the National Cancer Institute, vol. 98, No. 5, Mar. 1, 2006, pp. 326-334.

Carlomagno et al., "ZD6474, an Orally Available Inhibitor of KDR Tyrosine Kinase Acrivity, Efficiently Blocks Oncogenic RET Kinases, " Cancer Research, vol. 62, pp. 7284-7290, Dec. 15, 2002.

Chen et al., "FGFR3 as a Therapeutic Target of the Small Molecule Inhibitor PKC412 in Hematopoietic Malignancies", Oncogene, vol. 24, 2005, pp. 8259-8267.

Chesi et al., "Activated fibroblast growth factor receptor 3 is an oncogene that contributes to tumor progression in multiple myeloma," Blood, vol. 97, No. 3, pp. 729-736, Feb. 1, 2001.

Chesi et al., "Frequent Translocation t(4;14)(p16.3:q32.3) in Multiple Myeloma is Associated with Increased Expression and Activating Mutations of Fibroblast Growth Factor Receptor 3", Nature Genetics, vol. 16, Jul. 1997, pp. 260-264.

Elisei et al., "Identification of a Novel Point Mutation in the RET Gene (Ala883Thr), Which is Associated with Medullary Thyroid Carcinoma Phenotype Only in Homozygous Condition", The Journal of Clinical Endocrinology & Metabolism, vol. 89, No. 11, 2004, pp. 5823-5827.

Erber et al., "Combined Inhibition of VEGF- and PDGF-Signaling Enforces Tumor Vessel Regression by Interfering with Pericyte-mediated Endothelial Cell Survival Mechanisms", FASEB Journal, vol. 18, No. 2, 2004, pp. 338-340, XP-002548466.

European Office Action for European Application No. 04719054.1, dated Oct. 30, 2009.

Extended European Search Report for European Application No. 06782407.8 dated Jul. 23, 2010.

Gatzemeier et al., "Phase III Comparative Study of High-Dose Cisplatin Versus a Combination of Paclitaxel and Cisplatin in Patients with Advanced Non-Small-Cell Lung Cancer", Journal of Clinical Oncology, vol. 18, No. 19, pp. 3390-3399, Oct. 1, 2000.

Giles, "The Vascular Endothelial Growth Factor (VEGF) Signaling Pathway: A Therapeutic Target in Patients with Hematologic Malignancies", The Oncologist, vol. 6, Suppl. 5, 2001, pp. 32-39.

Haller, "Chemotherapy for Advanced Pancreatic Cancer", Int. J. Radiation Oncology Biol. Phys., vol. 56, No. 4, Supplement, 2003, pp. 16-23.

Hattori et al., "Immunohistochemical Detection of K-sam Protein in Stomach Cancer", Clinical Cancer Research, vol. 2, No. 8, Aug. 1996, pp. 1373-1381.

Haymo et al., "Pericytes in Experimental MDA-MB231 Tumor Angiogenesis", Histochemistry and Cell Biology, vol. 117, No. 6, Jun. 2002, pp. 527-534.

Hurwitz et al., "Bevacizumab Plus Irinotecan, Fluorouracil, and Leucovorin for Metastatic Colorectal Cancer", The New England Journal of Medicine, vol. 350, No. 23, Jun. 3, 2004, pp. 2335-2342.

Inai et al., "Inhibition of Vascular Endothelial Growth Factor (VEGF) Signaling in Cancer Causes Loss of Endothelial Fenestrations, Regression of Tumor Vessels, and Appearance of Basement Membrane Ghosts," American Journal of Pathology, vol. 165, No. 1, pp. 35-52, Jul. 2004.

Inoue et al., "Molecular Target Therapy Targeting Angiogenesis Pathways", The Nishinihon Journal of Urology, vol. 66, 2004, pp. 425-432.

International Search Report for Application No. PCT/JP2006/322514, dated Jan. 23, 2007.

International Search Report for Application No. PCT/JP2006/323881, dated Jan. 23, 2007.

International Search Report for Application No. PCT/JP2007/060560, dated Sep. 11, 2007.

International Search Report for Application No. PCT/JP2007/063525, dated Sep. 4, 2007.

International Search Report for Application No. PCT/JP2007/067088, dated Nov. 20, 2007.

International Search Report for Application No. PCT/JP2008/051024, dated Apr. 1, 2008.

International Search Report for Application No. PCT/JP2008/051697, dated Mar. 4, 2008.

International Search Report for Application No. PCT/JP2008/070321, dated Jan. 20, 2009.

International Search Report for Application No. PCT/JP2009/315698, dated Mar. 24, 2009.

International Search Report for Application No. PCT/JP2006/051244, dated Oct. 17, 2006.

International Search Report for Application PCT/JP2006/315563, dated Sep. 5, 2006.

Itoh et al., "Preferential Alternative Splicing in Cancer Generates a K-sam Messenger RNA with Higher Transforming Acitivity," Cancer Research, vol. 54, pp. 3237-3241, Jun. 15, 1994.

Jhiang, "The RET Proto-Oncogene in Human Cancers", Oncogene, vol. 19, 2000, pp. 5590-5597.

Jiminez et al., "Pheochromocytoma and Medullary Thyroid Carcinoma: A Genotoype-Phenotype Correlation of the RET Protooncogene 891 Germline Mutation" The Journal of Clinical Endocrinology & Metabolism, vol. 89, No. 8, 2004, pp. 4142-4145.

Johnson et al., "Paclitaxel Plus Carboplatin in Advanced Non-Small-Cell Lung Cancer: A Phase II Trial", Journal of Clinical Oncology, vol. 14, No. 7, Jul. 1996, pp. 2054-2060.

Jung et al., "Effects of Combination Anti-Vascular Endothelial Growth Factor Receptor and Anti-Epidermal Therapies on the Growth Model", European Journal of Cancer, vol. 38, 2002, pp. 1133-1140.

Kashuk et al., "Phenotype-Genotype Correlation in Hirschsprung Disease is Illuminated by Comparative Analysis of the RET Protein Sequence", PNAS, vol. 102, No. 25, Jun. 21, 2005. pp. 8949-8954.

Kelly et al., "Randomized Phase III Trial of Paclitaxel Plus Carboplatin Versus Vinorelbine Plus Cisplatin in the Treatment of Patients with Advanced Non-Small-Cell Lung Cancer: A Southwest Oncology Group Trial", Journal of Clinical Oncology, vol. 19, No. 13, Jul. 1, 2001, pp. 3210-3218.

Kim et al., "A Phase II Study of Irinotecan Plus Cisplatin for Patients with Advanced Stage IIIB or IV NSCLC Previously Treated With Nonplatinum-Based Chemotherapy," Cancer, vol. 107, pp. 799-805, 2006.

Kim et al., "An Orally Administered Multitarget Tyrosin Kinase Inhibitor , SU11248, is a Novel Potent Inhibitor of Thyroid Oncogenic RET/Papillary Thyroid Cancer Kinases", The Journal of Clinical Endocrinology & Metabolism, vol. 91, No. 10, 2006, pp. 4070-4076.

Lesueur et al., "Polymorphisms in RET and Its Coreceptors Ligands as Genetic Modifiers of Multiple Endocrine Neoplasia Type 2A," Cancer Research, vol. 66, No. 2, pp. 1177-1180, Jan. 15, 2006.

Lin et al., "The Vascular Endothelial Growth Factor Receptor Tyrosine Kinase Inhibitor PTK787/ZK222584 Inhibits Growth and Migration of Multiple Myeloma Cells in the Bone Marrow Microenvironment," Cancer Research, vol. 62, pp. 5019-5026, Sep. 1, 2002.

Logie et al., "Activating Mutations of the Tyrosine Kinase Receptor FGFR3 Are Associated with Benign Skin Tumors in Mice and Humans", Human Molecular Genetics, vol. 14, No. 9, 2005, pp. 1153-1160.

Matsui et al., "E7080, a novel multi-targeted tyrosine kinase Inhibitor, exhibits anti-angiogenic activity via inhibition of KIT signalling in a small cell lung cancer xenograft model," European Journal of Cancer, vol. 2, No. 8, 2004, p. 47, #146.

McCarty et al., "ZD6474, a Vascular Endothelial Growth Factor Receptor Tyrosine Kinase Inhibitor with Additional Activity Against Epidermal Growth Factor Receptor Tyrosine Kinase, Inhibits Orthotopic Growth and Angiogenesis of Gastric Cancer", Mol. Cancer Ther., vol. 3, No. 9, 2004, pp. 1041-1048.

McCulloch et al., "Astragalus-Based Chinese Herbs and Platinum-Based Chemotherapy for Advanced Non-Small-Cell Lung Cancer: Meta-Analysis of Randomized Trials", Journal of Clinical Oncology, vol. 24, No. 3, Jan. 20, 2006, pp. 419-430.

Miller et al., "Paclitaxel Plus Bevacizumab Versus Paclitaxel Alone for Metastatic Breast Cancer", New England Journal of Medicine, vol. 357, 2007, pp. 2666-2676.

Mologni et al., "Inhibition of RET Tyrosine Kinase of SU5416", Journal of Molecular Endocrinology, vol. 37, No. 2, 2006, pp. 199-212, XP003022512.

Morgan et al., "Dynamic Contrast-Enhanced Magnetic Resonance Imaging As a Biomarker for the Pharmacological Response of PTK787/ZK222584, an Inhibitor of the Vascular Endothelial Growth Factor Receptor Tyrosine Kinases . . .,"Journal of Clinical Oncology, vol. 21, No. 21, Nov. 1, 2003, pp. 3955-3964.

Morikawa et al., "Angiogenesis and Pericytes: Putative Positive Function of Pericytes in Angiogenesis," The Cell, vol. 37, No. 4, 2005, pp. 164-168.

Naski et al., "Graded Activation of Fibroblast Growth Factor Receptor 3 by Mutations Causing Achondroplasia and Thanatophoric Dysplasia", Nature Genetics, vol. 13, pp. 233-237, Jun. 1996.

Ohe et al., "Randomized phase III study of cisplatin plus irinotecan versus carboplatin plus paclitaxel, cisplatin plus gemcitabine, and cisplatin plus vinorelbine for advanced non-small-cell lung cancer . . .," Annals of Oncology, vol. 18, pp. 317-323, 2007.

Olaso et al., "DDR2 Receptor Promotes MMP-2-Mediated Proliferation and Invasion by Hepatic Stellate Cells", The Journal of Clinical Investigation, vol. 108, No. 9, Nov. 2001, pp. 1369-1378.

Ozols et al., "Phase III Trial of Carboplatin and Paclitaxel Compared with Cisplatin and Paclitaxel in Patients with Optimally Resected Stage III Ovarian Cancer: A Gynecologic Oncology Group Study", Journal of Clinical Oncology, vol. 21, No. 17, Sep. 1, 2003, pp. 3194-3200.

Paterson et al., "Preclinical studies of fibroblast growth factor receptor 3 as a therapeutic target in multiple myeloma," British Journal of Haematology, vol. 124, pp. 595-603, 2004.

Plowright et al., "Ectopic expression of fibroblast growth factor receptor 3 promotes myeloma cell proliferation and prevents apoptosis," Blood, vol. 95, No. 3, pp. 992-998, Feb. 1, 2000.

Proceedings of the American Association for Cancer Research, Experimental and Molecular Therapeutics, vol. 47, Apr. 2006, p. 890.

Salmon et al., "Anti-Angiogenic Treatment of Gastrointestinal Malignancies," Cancer Investigation, vol. 23, pp. 712-726, 2005.

Sandler et al., "Phase III Trial Gemcitabine Plus Cisplatin Versus Cisplatin Alone in Patients with Locally Advanced Metastatic Non-Small-Cell Lung Cancer", Journal of Clinical Oncology, vol. 18, No. 1, Jan. 2000, pp. 122-130.

Santoro et al., "Drug Insight: Small-Molecule Inhibitors of Protein Kinases in the Treatment of Thyroid Cancer" Nature Clinical Practice Endocrinology & Metabolism, vol. 2, No. 1, pp. 42-52, Jan. 2006.

Santoro et al., "Minireview: RET: Normal and Abnormal Functions", Endocrinology, vol. 145, No. 12, pp. 5448-5451, 2004.

Shiang et al., "Mutations in the Transmembrane Domain of FGFR3 Cause the Most Common Genetic Form of Dwarfism, Achondroplasia," Cell, vol. 78, pp. 335-342, Jul. 29, 1994.

Shimizu et al., "Orally active anti-proliferation agents: novel diphenylamine derivatives as FGF-R2 autophosphorylation inhibitors," Bioorganic & Medicinal Chemistry Letters, vol. 14, pp. 875-879, 2004.

Supplementary European Search Report for European Application No. 07743994.1 dated May 4, 2010.

Takahashi et al., "A case of inoperable scirrhous gastric cancer that responded remarkably to a combination of TS-1+Paclitaxel . . .," Japanese Journal of Cancer Chemother., vol. 31, No. 7, Jul. 2004, pp. 1093-1095.

Tan et al., "Randomized Study of Vinorelbine-Gemcitabine Versus Vinorelbine-Carboplatin in Patients with Advanced Non-Small Cell Lung Cancer", Lung Cancer, vol. 49, No. 2, 2005, pp. 233-240.

Trudel et al., "CHIR-258, a novel, multitargeted tyrosine kinase inhibitor for the potential treatment of t(4;14) multiple myeloma," Blood, vol. 105, pp. 2941-2948, 2005.

Trudel et al., "Inhibition of fibroblast growth factor receptor 3 induces differentiation and apoptosis in t(4;14) myeloma," Blood, vol. 103, No. 9, pp. 3521-3528, May 1, 2004.

U.S. Office Action for U.S. Appl. No. 11/662,425 dated Sep. 28, 2010.

Ueda et al., "Deletion of the Carboxyl-Terminal Exons of K-sam/FGFR2 by Short Homology-mediated Recombination, Generating Preferential Expression of Specific Messenger RNAs," Cancer Research, vol. 59, pp. 6080-6086, Dec. 15, 1999.

US Office Action for U.S. Appl. No. 10/797,903, dated Aug. 20, 2009.

Van Oers et al., "A Simple and Fast Method for Simultaneous Detection of Nine Fibroblast Growth Factor Receptor 3 Mutations in Bladder Cancer and Voided Urine", Clinical Cancer Research, vol. 11, No. 21, Nov. 1, 2005, pp. 7743-7748.

Vogel et al., "Sensing extracellular matrix: An update on discoidin domain receptor function," Cellular Signalling, vol. 18, pp. 1108-1116, 2006.

Wakui, "Chemotherapy for Scirrhous Gastric Cancer", Jpn. J. Cancer Chemother., vol. 21, No. 14, Oct. 1994, pp. 2398-2406.

Wang et al., "Phase II study of gemcitabine and carboplatin in patients with advanced non-small-cell lung cancer," Cancer Chemother Pharmacol, vol. 60, pp. 601-607, 2007.

Werner et al., "Gastric Adenocarcinoma: Pathomorphology and Molecular Pathology", J. Cancer Res. Clin. Oncol., vol. 127, 2001, pp. 207-216.

Willett et al., "Direct Evidence that the VEGF-Specific Antibody Bevacizumab has Antivascular Effects in Human Rectal Cancer", Nature Medicine, vol. 10, No. 2, Feb. 2004, pp. 145-147.

Wozniak et al., "Randomized Trial Comparing Cisplatin With Cisplatin Plus Vinorelbine in the Treatment of Advanced Non-Small-Cell Lung Cancer: A Southwest Oncology Group Study," Journal of Clinical Oncology, vol. 16, No. 7, Jul. 1998, pp. 2459-2465.

Written Opinion of the International Searching Authority issued Sep. 14, 2010, in PCT International Application No. PCT/JP2010/063804.

Yanagihara et al., "Development and biological analysis of peritoneal metastatis mouse models for human scirrhous stomach cancer," Cancer Science, vol. 96, No. 6, pp. 323-332, Jun. 2005.

Zhu et al., "Fibroblast Growth Factor Receptor 3 Inhibition by Short Hairpin RNAs Leads to Apoptosis in Multiple Myeloma" Molecular Cancer Therapeutics, vol. 4, No. 5, 2005, pp. 787-798.

Zieger et al., "Role of Activating Fibroblast Growth Factor Receptor 3 Mutations in the Development of Bladder Tumors" Clinical Cancer Research, vol. 11, No. 21, Nov. 1, 2005, pp. 7709-7719.

Notice of Allowance issued Dec. 7, 2010, in Japanese Patent Application No. 2005-516605.

Supplementary European Search Report issued Nov. 24, 2010, in European Patent Application No. 06833681.7.

Yamada et al., "New Technique for Staining", Monthly Medical Technology Supplementary Volume, Apr. 1999, only structures were considered.

Office Action issued Feb. 23, 2011, in U.S. Appl. No. 11/997,543.

Zhang et al., "Overexpression of Platelet-Derived Growth Factor Receptor alpha in Endothelial Cells of Hepatocellular Carcinoma Associated with High Metastatic Potential," Clin. Cancer Res., vol. 11, No. 24, pp. 8557-8563, Dec. 15, 2005.

Juurikivi et al., "Inhibition of c-kit tyrosine kinase by imatinib mesylate induces apoptosis in mast cells in rheumatoid synovia . . .," Ann Rheum Dis 2005, vol. 64, pp. 1126-1131.

Office Action issued Jan. 7, 2011, in U.S. Appl. No. 12/092,539.

Vippagunta et al., "Crystalline solids," Advanced Drug Delivery Reviews 2001, vol. 48, pp. 3-26.

European Search Report issued Nov. 11, 2010, in European Patent Application No. 06768437.3.

Hennequin et al., "Novel 4-Anilinoquinazolines with C-7 Basic Side Chains: Design and Structure Activity Relationship of a Series of Potent . . .," J. Med. Chem. 2002, vol. 45, pp. 1300-1312.

Office Action issued Sep. 3, 2010, in U.S. Appl. No. 11/997,719.

Traxler et al., "AEE788: A Dual Family Epiermal Growth Factor Receptor/ErbB2 and Vascular Endothelial Growth Factor Receptor . . .," Cancer Research, vol. 64, pp. 4931-4941, Jul. 15, 2004.

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Synthetic primer for VEGF

<400> SEQUENCE: 1
ccggatccat gaactttctg ctg                                              23

<210> SEQ ID NO 2
<211> LENGTH: 21
<212> TYPE: DNA
<213> ORGANISM: Artificial Sequence
<220> FEATURE:
<223> OTHER INFORMATION: Synthetic primer for VEGF
```

```
<400> SEQUENCE: 2
gtgaattctg tatcgatcgt t                                21
```

NITROGEN-CONTAINING AROMATIC DERIVATIVES

RELATED APPLICATIONS

This is a divisional of Ser. No. 11/293,785 filed on Dec. 2, 2005 U.S. Pat. No. 7,612,092, which is a divisional of Ser. No. 10/420,466 filed on Apr. 18, 2003 U.S. Pat. No. 7,253,286, which is a continuation-in-part application of application serial no. PCT/JP01/09221 filed on Oct. 19, 2001.

BACKGROUND OF THE INVENTION

1. Field of the Invention

The present invention relates to novel compounds which are effective for prevention and treatment of various diseases associated with abnormal angiogenesis, and to medical compositions such as angiogenesis inhibitors and antitumor agents comprising the novel compounds.

2. Related Background of the Invention

Angiogenesis is an essential biological phenomenon for fetal vascular formation and morphological and functional development of organs. New blood vessels are assembled through several processes including endothelial cell migration, proliferation and tube formation, and the participation of mast cells, lymphocytes, interstitial cells and the like has been shown to be important in this process (J. Folkman and Y. Shing, J. Biol. Chem., 267, 10931, 1992). In adult individuals, physiological angiogenesis occurs during the female estrous cycle, but pathological increase in angiogenesis in adult individuals is known to be connected with onset or progression of various diseases. Specific diseases associated with abnormal angiogenesis include cancer, rheumatoid arthritis, atherosclerosis, diabetic retinopathy, angioma, psoriasis, and the like (J. Folkman, N. Engl. J. Med., 333, 1757, 1995). In particular, the literature has indicated angiogenesis dependency for solid tumor growth, and angiogenesis inhibitors are therefore promising as new therapeutic agents for intractable solid tumors (J. Folkman, J. Natl. Cancer Inst., 82, 4, 1990).

The prior art includes compounds based on a urea structure, described in WO99/00357 and WO00/43366. WO99/00357 mentions biphenylurea derivatives which have an inhibiting action on raf kinase and an antitumor effect, but their angiogenesis-inhibiting effect is not disclosed. WO00/43366 describes quinoline derivatives and quinazoline derivatives which exhibit a weak karyomorphism-altering effect on A375 human melanoma cells in vitro and an antiproliferative effect on endothelial cells stimulated by vascular epithelial growth factor (VEGF), and which thus have an antitumor effect, but their effect on angiogenic factors other than VEGF is not disclosed.

SUMMARY OF THE INVENTION

As mentioned above, it is ardently desired to provide angiogenesis-inhibiting compounds which are useful as drugs. However, clinically effective compounds that exhibit excellent angiogenesis-inhibiting effects and high usefulness as medicines have not yet been discovered.

It is an object of the present invention to investigate and discover angiogenesis-inhibiting compounds which (1) exhibit antitumor activity through a powerful angiogenesis-inhibiting effect or a powerful angiogenesis-inhibiting and cancer cells growth-inhibiting effect, (2) are highly useful as drug materials in terms of their properties, biokinetics and safety, and (3) are useful for amelioration, prevention and treatment of various diseases associated with abnormal increase in angiogenesis.

As a result of much diligent research in light of the circumstances described above, the present inventors have succeeded in synthesizing novel compounds represented by the following general formula (I) and their salts or hydrates, and have completed the present invention upon discovering that the compounds of general formula (I) and their salts or hydrates exhibit an excellent angiogenesis-inhibiting effect.

Specifically, the invention relates to:
<1> a compound represented by the following general formula:

(I)

[wherein $A^g$ is an optionally substituted $C_{6-14}$ aryl group or an optionally substituted 5- to 14-membered heterocyclic group; $X^g$ is a single bond, —O—, —S—, a $C_{1-6}$ alkylene group, —SO—, —SO$_2$— or —N(R$^{g3}$)— (wherein R$^{g3}$ is a hydrogen atom, an optionally substituted $C_{1-6}$ alkyl group or an optionally substituted $C_{2-7}$ acyl group); $Y^g$ is an optionally substituted $C_{6-14}$ aryl group, an optionally substituted 5- to 14-membered heterocyclic group, an optionally substituted $C_{1-8}$ alkyl group, an optionally substituted $C_{3-8}$ alicyclic hydrocarbon group, an optionally substituted $C_{6-14}$ aryl-$C_{1-6}$ alkyl group, an optionally substituted 5- to 14-membered heteroaryl-$C_{1-6}$ alkyl group, —(CH$_2$)$_g$SO$_2$— (wherein g is an integer of 1 to 8), —(CH$_2$)$_{fa}$—CH═CH—(CH$_2$)$_{fb}$— (wherein fa and fb each represent 0, 1, 2 or 3), —(CH$_2$)$_{fa}$—CH═CH—(CH$_2$)$_{fb}$—SO$_2$— (wherein fa and fb each represent 0, 1, 2 or 3), —(CH$_2$)$_{fa}$—C≡C—(CH$_2$)$_{fb}$— (wherein fa and fb each represent 0, 1, 2 or 3) or —(CH$_2$)$_{fa}$—C≡C—(CH$_2$)$_{fb}$—SO$_2$— (wherein fa and fb each represent 0, 1, 2 or 3); and $T^{g1}$ is (1) a group represented by the following general formula:

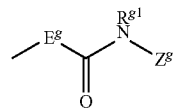

{wherein $E^g$ is a single bond or —N(R$^{g2}$)— (wherein R$^{g2}$ is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{2-7}$ acyl group or an optionally substituted $C_{2-7}$ alkoxycarbonyl group); R$^{g1}$ is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{2-7}$ acyl group or an optionally substituted $C_{2-7}$ alkoxycarbonyl group; and $Z^g$ is a hydrogen atom, an optionally substituted $C_{1-8}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{6-14}$ aryl group, an optionally substituted $C_{6-14}$ aryl-$C_{1-6}$ alkyl group, —OR$^{200}$, —SR$^{200}$, —COR$^{200}$, —SO$_2$R$^{200}$ (wherein R$^{200}$ is a hydrogen atom, an optionally substituted $C_{1-8}$ alkyl group, an optionally substituted $C_{3-8}$ alicyclic hydrocarbon group, an optionally substituted $C_{6-14}$ aryl group, an optionally substituted $C_{6-14}$ aryl-$C_{1-6}$ alkyl group, an optionally substituted 5- to 14-membered heterocyclic group or an optionally substituted 5- to 14-membered heterocyclic-$C_{1-6}$ alkyl group), an optionally substituted 5- to 14-membered heterocyclic group or an optionally substituted 5- to 14-membered heterocyclic-$C_{1-6}$ alkyl group}, or (2) a group represented by the following general formula:

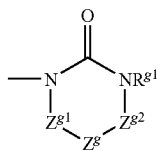

{wherein $R^{g1}$ and $Z^g$ have the same definitions as $R^{g1}$ and $Z^g$ above; and $Z^{g1}$ and $Z^{g2}$ may be the same or different and each is (1) a single bond, (2) an optionally oxo-substituted $C_{1-6}$ alkylene group also optionally having one or more atoms selected from —O—, —S— and a nitrogen atom within or at the end of the chain, or (3) an optionally substituted $C_{2-6}$ alkenyl group}], a salt thereof or a hydrate of the foregoing;

<2> a compound represented by the following general formula:

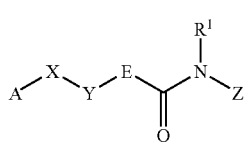

(II)

[wherein A is an optionally substituted 5- to 14-membered aromatic heterocyclic group; X is an oxygen atom, a sulfur atom, —SO— or —SO$_2$; Y is an optionally substituted $C_{6-14}$ aryl group, an optionally substituted 5- to 14-membered aromatic heterocyclic group or an optionally substituted $C_{1-6}$ alkylene group; E is a single bond or —NR$^2$—; $R^1$ and $R^2$ are each independently a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{2-7}$ acyl group or an optionally substituted $C_{2-7}$ alkoxycarbonyl group; and Z is a group represented by the formula —Z$^{11}$—Z$^{12}$ (wherein Z$^{11}$ is a single bond, an oxygen atom, a sulfur atom, —CO—, —SO$_2$— or an optionally substituted $C_{1-6}$ alkylene group and Z$^{12}$ is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{6-14}$ aryl group, an optionally substituted 5- to 14-membered heterocyclic group, an optionally substituted 5- to 14-membered aromatic heterocyclic group or a group represented by the formula:

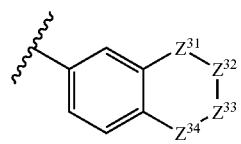

(wherein $Z^{31}$, $Z^{33}$ and $Z^{34}$ are each independently a methylene group, —CO—, —NH— or —O—, and $Z^{32}$ is a single bond, a methylene group, —CO—, —NH— or —O—)), with the proviso that A may be an optionally substituted with 1 to 6 groups, each selected from the group consisting of (1) a cyano group, (2) a halogen atom, (3) a nitro group and (4) the formula —V$^{X1}$—V$^{X2}$—V$^{X22}$—V$^{X3}$ (wherein V$^{X1}$, V$^{X2}$ and V$^{X22}$ are each independently a single bond, an oxygen atom, a sulfur atom, —CO—, —SO—, —SO$_2$—, —NR$^{X1}$—, —CONR$^{X1}$—, —NR$^{X1}$CO—, —SO$_2$NR$^{X1}$—, —NR$^{X1}$SO$_2$—, —O—CO—, —C(O)O—, —NR$^{X1}$C(O)O—, —NR$^{X1}$C(O)NR$^{X2}$—, —O—C(O)NR$^{X1}$—, —O—C(O)O—, an optionally substituted $C_{1-6}$ alkylene group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{6-14}$ aryl group, an optionally substituted 5- to 14-membered heterocyclic group or an optionally substituted 5- to 14-membered aromatic heterocyclic group; and V$^{X3}$, R$^{X1}$ and R$^{X2}$ are each independently a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{6-14}$ aryl group, an optionally substituted 5- to 14-membered heterocyclic group, an optionally substituted 5- to 14-membered aromatic heterocyclic group or an optionally substituted $C_{1-6}$ alkoxy group)], a salt thereof or a hydrate of the foregoing;

<3> a compound according to <2>, a salt of the compound or a hydrate of the foregoing, wherein X is an oxygen atom or a sulfur atom;

<4> a compound according to <2> or <3>, a salt of the compound or a hydrate of the foregoing, wherein Z is an optionally substituted cyclopropyl group, an optionally substituted 2-thiazolyl group or a group represented by the formula:

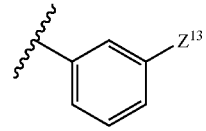

(wherein $Z^{13}$ is a nitrile group, a methylsulfonyl group or a —NHCOCH$_3$ group);

<5> a compound according to any one of <2> to <4>, a salt of the compound or a hydrate of the foregoing, wherein E is a group represented by the formula —NR$^2$— (wherein R$^2$ has the same definition as R$^2$ in <2>), and Y is an optionally substituted phenyl group, an optionally substituted pyridyl group or a group represented by the formula:

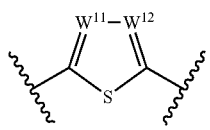

(wherein W$^{11}$ and W$^{12}$ are each independently an optionally substituted carbon atom or a nitrogen atom);

<6> a compound according to any one of <2> to <4>, a salt of the compound or a hydrate of the foregoing, wherein E is a single bond, and Y is a further optionally substituted group represented by the formula:

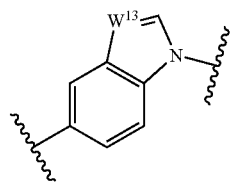

(wherein $W^{13}$ is an optionally substituted carbon atom or a nitrogen atom);

<7> a compound according to any one of <2> to <6>, a salt of the compound or a hydrate of the foregoing, wherein A is a group represented by the formula:

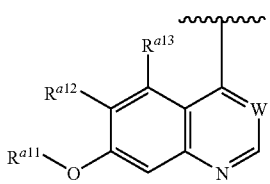

[wherein W is an optionally substituted carbon atom or a nitrogen atom; $R^{a13}$ is a hydrogen atom, a halogen atom, an optionally substituted $C_{1-6}$ alkyl group, an optionally substituted $C_{1-6}$ alkoxy group, an amino group or a nitro group; $R^{a12}$ is a cyano group or a group represented by the formula:

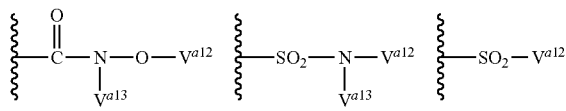

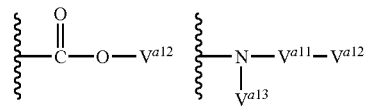

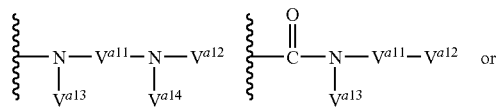

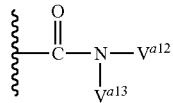

(wherein $V^{a11}$ is —CO— or —SO$_2$—; and $V^{a12}$, $V^{a13}$, and $V^{a14}$ are each independently a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{6-14}$ aryl group, an optionally substituted 5- to 14-membered heterocyclic group or an optionally substituted 5- to 14-membered aromatic heterocyclic group); and $R^{a11}$ is a group represented by the formula —$V^{a21}$—$V^{a22}$—$V^{a23}$ (wherein $V^{a21}$ is an optionally substituted $C_{1-6}$ alkylene group, a single bond or a group represented by the formula:

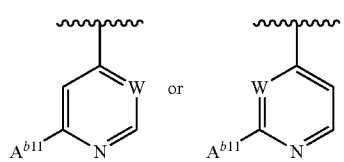

$V^{a22}$ is a single bond, an oxygen atom, a sulfur atom, —CO—, —SO—, —SO$_2$—, —CONR$^{a14}$—, —SO$_2$NR$^{a14}$—, —NR$^{a14}$SO$_2$—, —NR$^{a14}$CO— or —NR$^{a14}$— (wherein $R^{a14}$ is a hydrogen atom, an optionally substituted $C_{1-6}$ alkyl group or an optionally substituted $C_{3-8}$ alicyclic hydrocarbon group); and $V^{a23}$ is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{6-14}$ aryl group, an optionally substituted 5- to 14-membered heterocyclic group or an optionally substituted 5- to 14-membered aromatic heterocyclic group)];

<8> a compound according to any one of <2> to <6>, a salt of the compound or a hydrate of the foregoing, wherein A is a group represented by the formula:

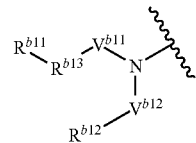

(wherein W is an optionally substituted carbon or a nitrogen atom; and $R^{a11}$, $R^{a12}$ and $R^{a13}$ have the same definitions as $R^{a11}$, $R^{a12}$ and $R^{a13}$ in <7>);

<9> a compound according to any one of <2> to <6>, a salt of the compound or a hydrate of the foregoing, wherein A is a further optionally substituted group represented by the formula:

[wherein W is an optionally substituted carbon atom or a nitrogen atom; and $A^{b11}$ is (1) an optionally substituted 5- to 14-membered heterocyclic group or (2) a group represented by the formula:

(wherein $V^{b11}$ and $V^{b12}$ are each independently a single bond, —SO$_2$—, —NHCO— or a group represented by the formula —(CH$_2$)$_b$—CO— (wherein b is an integer of 0 to 6); $R^{b13}$ is a single bond, an optionally substituted $C_{1-6}$ alkylene group, an optionally substituted $C_{3-8}$ alicyclic hydrocarbon group or an optionally substituted 5- to 14-membered heterocyclic group; and $R^{b11}$ and $R^{b12}$ are each independently a hydrogen atom, a hydroxyl group, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{6-14}$ aryl group, an optionally substituted 5- to 14-membered aromatic heterocyclic group or an optionally substituted 5- to 14-membered heterocyclic group)];

<10> a compound according to any one of <2> to <6>, a salt of the compound or a hydrate of the foregoing, wherein A is a group represented by the formula:

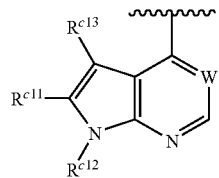

[wherein W is an optionally substituted carbon or a nitrogen atom; $R^{c13}$ is (1) a hydrogen atom, (2) a cyano group, (3) a halogen atom, (4) a formyl group, (5) an optionally substituted $C_{2-6}$ alkyl group, (6) a group represented by the formula:

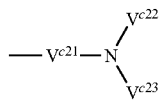

(wherein $V^{c21}$ is —CO— or a methylene group; $V^{c22}$ and $V^{c23}$ are each independently a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted 5- to 14-membered heterocyclic group, an optionally substituted 5- to 14-membered aromatic heterocyclic group or an optionally substituted $C_{6-14}$ aryl group), or (7) a group represented by the formula —$V^{c2}$—O—$V^{c22}$ (wherein $V^{c21}$ and $V^{c22}$ have the same definitions as $V^{c21}$ and $V^{c22}$ above); $R^{c12}$ is a hydrogen atom, an optionally substituted $C_{1-6}$ alkyl group or an optionally substituted $C_{3-8}$ alicyclic hydrocarbon group; and $R^{c11}$ is a group represented by the formula —$V^{c11}$—$V^{c12}$—$V^{c13}$ (wherein $V^{c11}$ is a single bond, an oxygen atom, an optionally substituted benzene ring, an optionally substituted 5- to 14-membered aromatic heterocyclic group or —CO—; $V^{c12}$ is a single bond, an oxygen atom or an optionally substituted $C_{1-6}$ alkylene group; and $V^{c13}$ is (1) an optionally substituted $C_{1-6}$ alkyl group, (2) an optionally substituted $C_{2-6}$ alkenyl group, (3) an optionally substituted $C_{2-6}$ alkynyl group, (4) an optionally substituted $C_{3-8}$ alicyclic hydrocarbon group, (5) a hydroxyl group, (6) a carboxyl group, (7) an optionally substituted $C_{2-7}$ alkoxycarbonyl group, (8) an optionally substituted 5- to 14-membered heterocyclic group, (9) an optionally substituted 5- to 14-membered aromatic heterocyclic group, (10) an optionally substituted $C_{6-14}$ aryl group, (11) a group represented by the formula —$NR^{c21}R^{c22}$ (wherein $R^{c21}$ and $R^{c22}$ are each independently a hydrogen atom or an optionally substituted $C_{1-6}$ alkyl group), or (12) a hydrogen atom)];

<11> a compound represented by the following general formula:

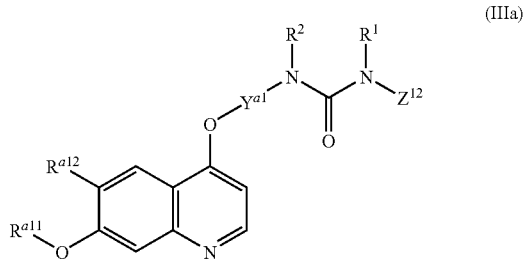

[wherein $R^1$, $R^2$ and $Z^{12}$ have the same definitions as $R^1$, $R^2$ and $Z^{12}$ in <2>, but $Z^{12}$ is not a pyrazolyl group; $Y^{a1}$ is a group represented by the formula:

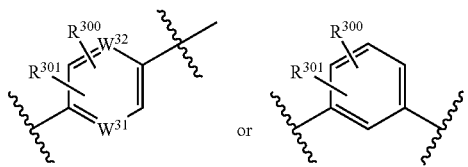

(wherein $W^{31}$ and $W^{32}$ are each independently an optionally substituted carbon atom or a nitrogen atom; $R^{300}$ and $R^{301}$ are each independently a hydrogen atom, a halogen atom, a cyano group, a nitro group, an amino group, an optionally substituted $C_{1-6}$ alkyl group, an optionally substituted $C_{3-8}$ alicyclic hydrocarbon group, an optionally substituted $C_{1-6}$ alkoxy group, an optionally substituted $C_{2-7}$ alkoxycarbonyl group, a formyl group, a group represented by the formula

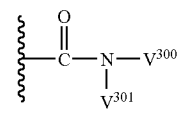

(wherein $V^{300}$ and $V^{301}$ are each independently a hydrogen atom or an optionally substituted $C_{1-6}$ alkyl group), or an optionally substituted $C_{2-7}$ acyl group); and $R^{a11}$ and $R^{a12}$ have the same definitions as $R^{a11}$ and $R^{a12}$ in <7>, with the exception of the following compounds (1) and (2): (1) a compound wherein $R^{a12}$ is a group represented by the formula:

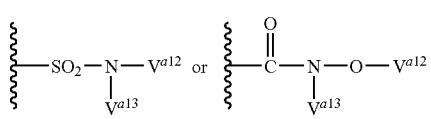

(wherein $V^{a12}$ and $V^{a13}$ have the same definitions as $V^{a12}$ and $V^{a13}$ in <7>), $R^1$ and $R^2$ are hydrogen atoms and $Z^{12}$ is a $C_{6-14}$ aryl group, a 6- to 14-membered heterocyclic group or a 6- to 14-membered aromatic heterocyclic group; (2) a compound wherein $R^{a12}$ is a group selected from the group consisting of the formulas:

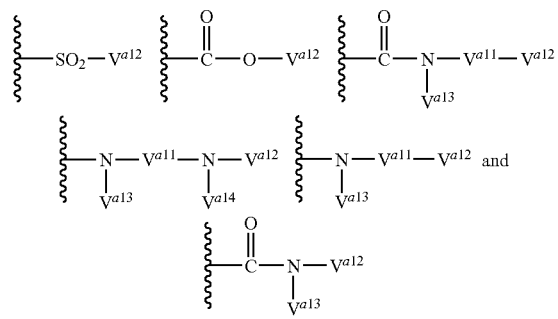

(wherein $V^{a11}$, $V^{a12}$, $V^{a13}$ and $V^{a14}$ have the same definitions as $V^{a11}$, $V^{a12}$, $V^{a13}$ and $V^{a14}$ in <7>), $R^2$ is a hydrogen atom and $Z^{12}$ is (a) a $C_{6-14}$ aryl group, (b) a 5- to 14-membered heterocyclic group, (c) a 5- to 14-membered aromatic heterocyclic group, (d) a $C_{1-6}$ alkyl group substituted with a 5- to 10-membered heterocyclic group or a $C_{5-10}$ alicyclic hydrocarbon group, (e) a $C_{2-6}$ alkenyl group substituted with a 5- to 10-membered heterocyclic group or a $C_{5-10}$ alicyclic hydrocarbon group, (f) a $C_{2-6}$ alkynyl group substituted with a 5- to 10-membered heterocyclic group or a $C_{5-10}$ alicyclic hydrocarbon group, or (g) a $C_{3-8}$ alicyclic hydrocarbon group substituted with a 5- to 10-membered heterocyclic group or a $C_{5-10}$ alicyclic hydrocarbon group], a salt thereof or a hydrate of the foregoing;

<12> a compound according to <11>, a salt of the compound or a hydrate of the foregoing, wherein $R^{a11}$ is a methyl group, a 2-methoxyethyl group or a group represented by the formula:

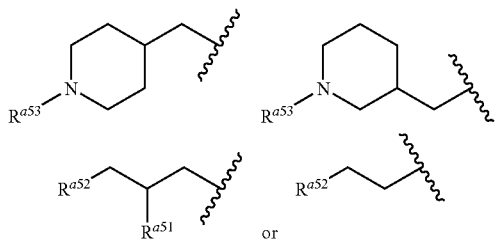

(wherein $R^{a53}$ is a methyl group, a cyclopropylmethyl group or a cyanomethyl group; $R^{a51}$ is a hydrogen atom, a fluorine atom or a hydroxyl group; and $R^{a52}$ is a 1-pyrrolidinyl group, a 1-piperidinyl group, a 4-morpholinyl group, a dimethylamino group or a diethylamino group);

<13> a compound according to <11> or <12>, a salt of the compound or a hydrate of the foregoing, wherein $Z^{12}$ is a methyl group, an ethyl group, a cyclopropyl group, a 2-thiazolyl group or a 4-fluorophenyl group;

<14> a compound according to any one of <11> to <13>, a salt of the compound or a hydrate of the foregoing, wherein $Y^{a1}$ is a group represented by the formula:

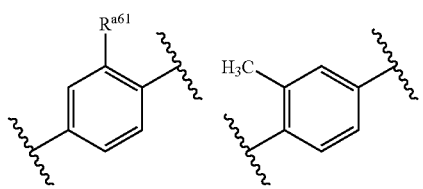

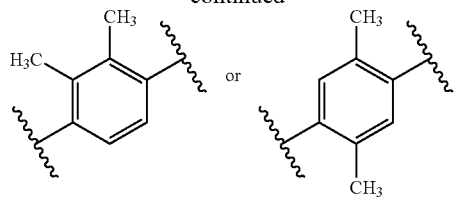

(wherein $R^{a61}$ is a hydrogen atom, a methyl group, a trifluoromethyl group, a chlorine atom or a fluorine atom);

<15> a compound according to any one of <11> to <14>, a salt of the compound or a hydrate of the foregoing, wherein $R^{a12}$ is a cyano group or a group represented by the formula —CONHR$^{a62}$ (wherein R$^{a62}$ is a hydrogen atom, an optionally substituted $C_{1-6}$ alkyl group, an optionally substituted $C_{3-8}$ alicyclic hydrocarbon group, an optionally substituted $C_{1-6}$ alkoxy group or an optionally substituted $C_{3-8}$ cycloalkoxy group);

<16> a compound represented by the following general formula:

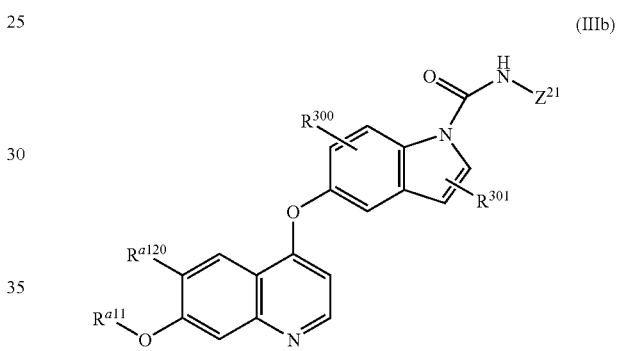

[wherein $Z^{21}$ is a hydrogen atom, an optionally substituted $C_{1-6}$ alkyl group, an optionally substituted $C_{2-6}$ alkenyl group, an optionally substituted $C_{2-6}$ alkynyl group or an optionally substituted $C_{3-8}$ alicyclic hydrocarbon group; $R^{a120}$ is a cyano group or a group represented by the formula:

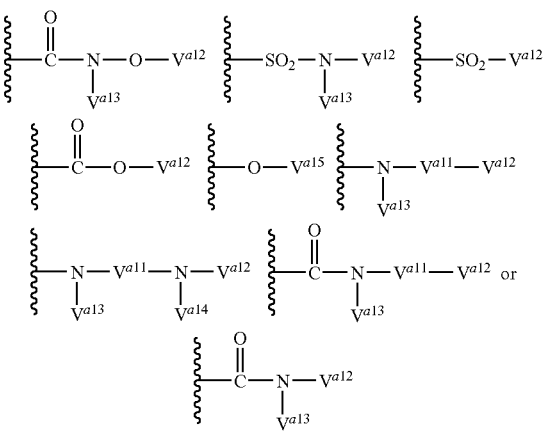

(wherein $V^{a15}$ is an optionally substituted $C_{1-6}$ alkyl group, an optionally substituted $C_{2-6}$ alkenyl group, an optionally substituted $C_{2-6}$ alkynyl group or an optionally substituted $C_{3-8}$ alicyclic hydrocarbon group, and $V^{a11}$, $V^{a12}$, $V^{a13}$ and $V^{a14}$ have the same definitions as $V^{a11}$, $V^{a12}$, $V^{a13}$ and $V^{a14}$ in <7>); $R^{300}$ and $R^{301}$ have the same definitions as $R^{300}$ and $R^{301}$ in <11>; and $R^{a11}$ has the same definition as $R^{a11}$ in <7>, with the exception of a compound wherein $R^{a120}$ is a group selected from the group consisting of the formulas:

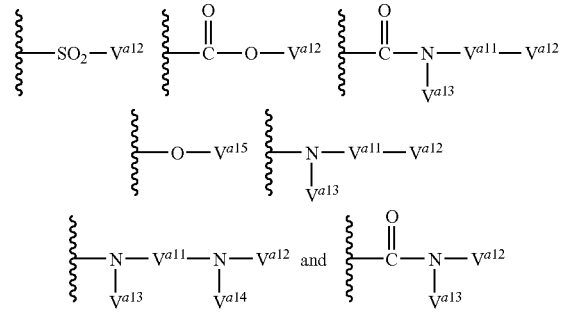

(wherein $V^{a11}$, $V^{a12}$, $V^{a13}$ and $V^{a14}$ have the same definitions as $V^{a11}$, $V^{a12}$, $V^{a13}$ and $V^{a14}$ in <7>, and $V^{a15}$ is as defined above), and $Z^{21}$ is (a) a $C_{3-8}$ alicyclic hydrocarbon group, (b) a $C_{1-6}$ alkyl group substituted with a 5- to 10-membered heterocyclic group or a $C_{5-20}$ alicyclic hydrocarbon group, (c) a $C_{2-6}$ alkenyl group substituted with a 5- to 10-membered heterocyclic group or a $C_{5-10}$ alicyclic hydrocarbon group, or (d) a $C_{2-6}$ alkynyl group substituted with a 5- to 10-membered heterocyclic group or a $C_{5-10}$ alicyclic hydrocarbon group], a salt thereof or a hydrate of the foregoing;

<17> a compound represented by the following general formula:

(IIIc)

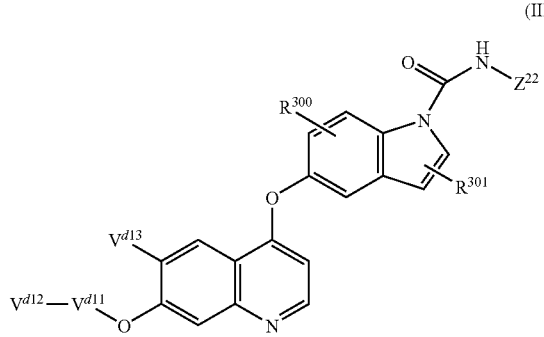

[wherein $Z^{22}$ is an optionally substituted $C_{6-14}$ aryl group, an optionally substituted 5- to 14-membered heterocyclic group or an optionally substituted 5- to 14-membered aromatic heterocyclic group; $R^{300}$ and $R^{301}$ have the same definitions as $R^{300}$ and $R^{301}$ in <11>; $V^{d13}$ is a group selected from the group consisting of the formulas:

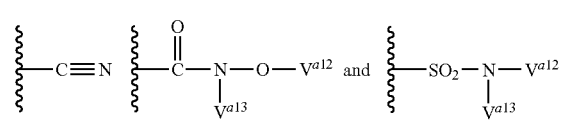

(wherein $V^{a12}$ and $V^{a13}$ have the same definitions as $V^{a12}$ and $V^{a13}$ in <7>); $V^{d11}$ is an optionally substituted $C_{1-6}$ alkylene group or a group represented by the formula:

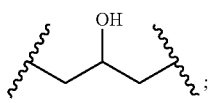

and $V^{d12}$ is (1) a group represented by the formula $-NR^{d11}R^{d12}$ (wherein $R^{d11}$ and $R^{d12}$ are each a hydrogen atom, an optionally substituted $C_{1-6}$ alkyl group, an optionally substituted $C_{3-8}$ alicyclic hydrocarbon group, an optionally substituted $C_{6-14}$ aryl group, an optionally substituted 5- to 14-membered heterocyclic group or an optionally substituted 5- to 14-membered aromatic heterocyclic group), or (2) an optionally substituted 5- to 14-membered heterocyclic group], a salt thereof or a hydrate of the foregoing;

<18> a compound represented by the following general formula:

(IIId)

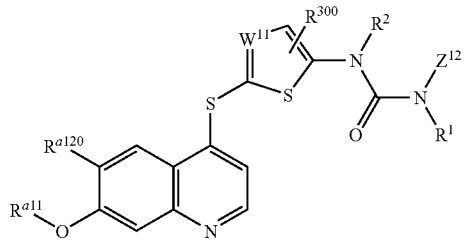

[wherein $R^1$, $R^2$ and $Z^{12}$ have the same definitions as $R^1$, $R^2$ and $Z^{12}$ in <2>; $W^{11}$ is an optionally substituted carbon atom or a nitrogen atom; $R^{300}$ has the same definition as $R^{300}$ in <11>; $R^{a11}$ has the same definition as $R^{11}$ in <7>; and $R^{a120}$ has the same definition as $R^{a120}$ in <16>, with the exception of the following compounds (1) and (2): (1) a compound wherein $R^{a120}$ is a group represented by the formula:

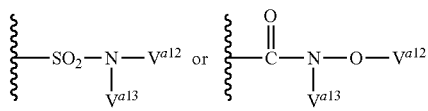

(wherein $V^{a12}$ and $V^{a13}$ have the same definitions as $V^{a12}$ and $V^{a13}$ in <7>) $R^1$ and $R^2$ are hydrogen atoms and $Z^{12}$ is a $C_{6-14}$ aryl group, a 6- to 14-membered heterocyclic group or a 6- to 14-membered aromatic heterocyclic group; (2) a compound wherein $R^{a120}$ is a group selected from the group consisting of the formulas:

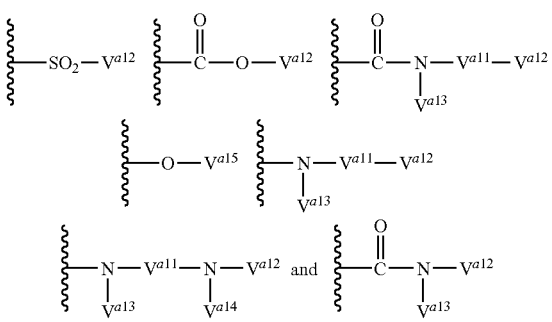

(wherein $V^{a11}$, $V^{a12}$, $V^{a13}$ and $V^{a14}$ have the same definitions as $V^{a11}$, $V^{a12}$, $V^{a13}$ and $V^{a14}$ in <7>, and $V^{a15}$ has the same definition as $V^{a15}$ in <16>), $R^2$ is a hydrogen atom and $Z^{12}$ is (a) a $C_{6-14}$ aryl group, (b) a 5- to 14-membered heterocyclic group, (c) a 5- to 14-membered aromatic heterocyclic group, (d) a $C_{1-6}$ alkyl group substituted with a 5- to 10-membered heterocyclic group or a $C_{5-20}$ alicyclic hydrocarbon group, (e) a $C_{2-6}$ alkenyl group substituted with a 5- to 10-membered heterocyclic group or a $C_{5-10}$ alicyclic hydrocarbon group, (f) a $C_{2-6}$ alkynyl group substituted with a 5- to 10-membered heterocyclic group or a $C_{5-10}$ alicyclic hydrocarbon group, or (g) a $C_{3-8}$ alicyclic hydrocarbon group substituted with a 5- to 10-membered heterocyclic group or a $C_{5-10}$ alicyclic hydrocarbon group], a salt thereof or a hydrate of the foregoing;

<19> a compound represented by the following general formula:

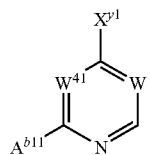

(IIIe)

[wherein $W^{41}$ and $W$ are each independently an optionally substituted carbon atom or a nitrogen atom, but $W_{41}$ and $W$ are not both nitrogen atoms; $X^{y1}$ is an optionally substituted group selected from the group consisting of the following formulas:

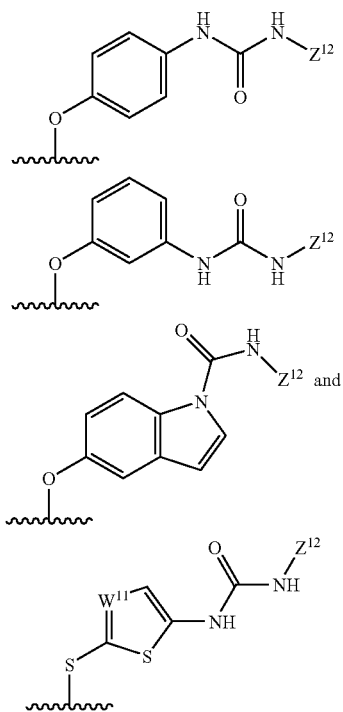

(wherein $Z^{12}$ has the same definition as $Z^{12}$ in <2>, and $W^{11}$ is an optionally substituted carbon atom or a nitrogen atom); and $A^{b11}$ has the same definition as $A^{b11}$ in <9>], a salt thereof or a hydrate of the foregoing;

<20> a compound represented by the following general formula:

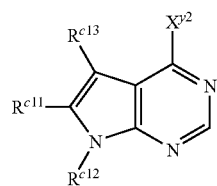

(IIIf)

[wherein $R^{c13}$ has the same definition as $R^{c13}$ in <10>; $X^{y2}$ is an optionally substituted group selected from the group consisting of the following formulas:

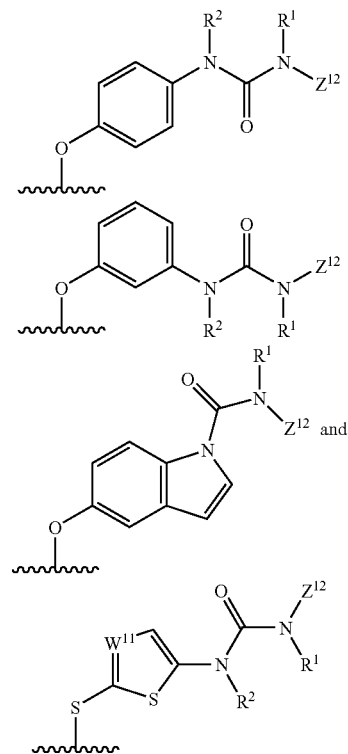

(wherein $Z^{12}$, $R^1$ and $R^2$ have the same definitions as $Z^{12}$, $R^1$ and $R^2$ in <2>, and $W^{11}$ is an optionally substituted carbon atom or a nitrogen atom); and $R^{c11}$ and $R^{c12}$ have the same definitions as $R^{c11}$ and $R^{c12}$ in <10>, with the exception of the following compounds (1) and (2): (1) a compound wherein $R^1$ and $R^2$ are hydrogen atoms and $Z^{12}$ is (a) a $C_{6-14}$ aryl group, (b) a 5- to 14-membered heterocyclic group, (c) a $C_{2-6}$ alkyl group substituted with a 5- to 14-membered aromatic heterocyclic group, a 5- to 10-membered heterocyclic group or a $C_{5-20}$ alicyclic hydrocarbon group, (d) a $C_{2-6}$ alkenyl group substituted with a 5- to 10-membered heterocyclic group or a $C_{5-20}$ alicyclic hydrocarbon group, (e) a $C_{2-6}$ alkynyl group substituted with a 5- to 10-membered heterocyclic group or a $C_{5-20}$ alicyclic hydrocarbon group, or (f) a $C_{3-8}$ alicyclic hydrocarbon group substituted with a 5- to 10-membered heterocyclic group or a $C_{5-10}$ alicyclic hydrocarbon group; (2) a compound wherein $X^{y2}$ is a group represented by the formula:

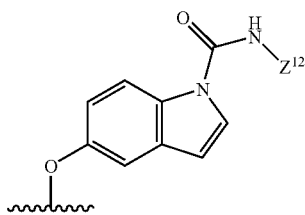

(wherein $Z^{12}$ is (a) a $C_{6-14}$ aryl group, (b) a 5- to 14-membered heterocyclic group, (c) a 5- to 14-membered aromatic heterocyclic group, (d) a $C_{1-6}$ alkyl group substituted with a 5- to 10-membered heterocyclic group or a $C_{5-10}$ alicyclic hydrocarbon group, (e) a $C_{2-6}$ alkenyl group substituted with a 5- to 10-membered heterocyclic group or a $C_{5-10}$ alicyclic hydrocarbon group, (f) a $C_{2-6}$ alkynyl group substituted with a 5- to 10-membered heterocyclic group or a $C_{5-10}$ alicyclic hydrocarbon group, or (g) a $C_{3-8}$ alicyclic hydrocarbon group)], a salt thereof or a hydrate of the foregoing;

<21> a compound according to <10> or <20>, a salt of the compound or a hydrate of the foregoing, wherein $R^{c11}$ is a group represented by the formula:

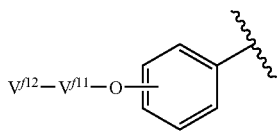

[wherein $V^{f11}$ is a single bond, an optionally substituted $C_{1-6}$ alkylene group or a group represented by the formula:

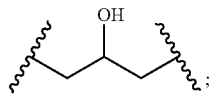

and $V^{f12}$ is (1) a hydrogen atom, (2) a hydroxyl group, (3) an optionally substituted 5- to 14-membered heterocyclic group, (4) an optionally substituted 5- to 14-membered aromatic heterocyclic group, (5) an optionally substituted $C_{6-14}$ aryl group or (6) a group represented by the formula $-NR^{f21}R^{f22}$ (wherein $R^{f21}$ and $R^{f22}$ are each independently a hydrogen atom or an optionally substituted $C_{1-6}$ alkyl group)];

<22> a compound represented by the following general formula:

(IIIg)

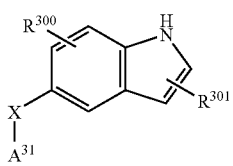

[wherein X has the same definition as X in <2>; $R^{300}$ and $R^{301}$ have the same definitions as $R^{300}$ and $R^{301}$ in <11>; and $A^{31}$ is a group selected from the group consisting of the formulas:

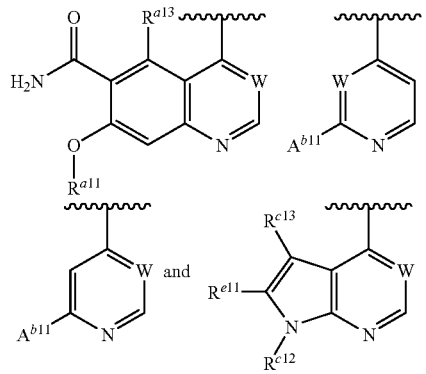

(wherein $R^{c13}$ has the same definition as $R^{c13}$ in <10>; W, $R^{a11}$ and $R^{a13}$ have the same definitions as W, $R^{a11}$ and $R^{a13}$ in <7>; $A^{b11}$ has the same definition as $A^{b11}$ in <9>; $R^{c12}$ has the same definition as $R^{c12}$ in <10>; and $R^{e11}$ is a group represented by the formula:

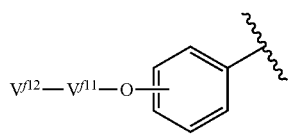

(wherein $V^{f11}$ and $V^{f12}$ have the same definitions as $V^{f11}$ and $V^{f12}$ in <21>, but $V^{f12}$ is not a hydrogen atom))], a salt thereof or a hydrate of the foregoing;

<23> a compound represented by the following general formula:

(IIIh)

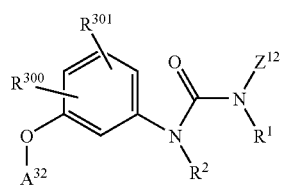

[wherein $Z^{12}$, $R^1$ and $R^2$ have the same definitions as $Z^{12}$, $R^1$ and $R^2$ in <2>; $R^{300}$ and $R^{301}$ have the same definitions as $R^{300}$ and $R^{301}$ in <11>; and $A^{32}$ is a group selected from the group consisting of the formulas:

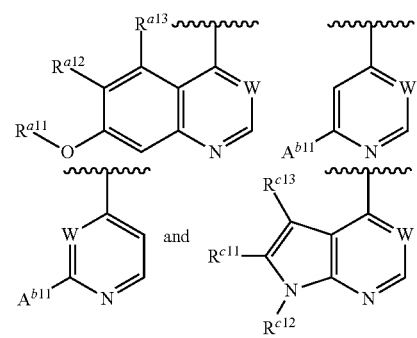

(wherein $R^{c13}$ has the same definition as $R^{c13}$ in <10>; W, $R^{a11}$, $R^{a12}$ and $R^{a13}$ have the same definitions as W, $R^{a11}$, $R^{a12}$ and $R^{a13}$ in <7>; $A^{b11}$ has the same definition as $A^{b11}$ in <9>; and $R^{c11}$ and $R^{c12}$ have the same definitions as $R^{c11}$ and $R^{c12}$ in <10>)], a salt thereof or a hydrate of the foregoing;

<24> a compound according to <1> or <2>, a pharmacologically acceptable salt of the compound or a hydrate of the foregoing, wherein said compound is a compound selected from N-(4-(6-cyano-7-(3-(4-pyridyl)propoxy)-4-quinolyl)oxyphenyl)-N'-(4-methoxyphenyl)urea,
N-(4-(6-cyano-7-(2-(1,2,3-triazol-2-yl)ethoxy)-4-quinolyl)oxyphenyl)-N'-(4-fluorophenyl)urea,
N-(4-(6-cyano-7-(2-(1,2,3-triazol-1-yl)ethoxy)-4-quinolyl)oxyphenyl)-N'-(4-fluorophenyl)urea,
N-(4-(6-cyano-7-(2-(1,2,3-triazol-2-yl)ethoxy)-4-quinolyl)oxyphenyl)-N'-(2,4-difluorophenyl)urea,
N-(4-(6-cyano-7-(2-(1,2,3-triazol-1-yl)ethoxy)-4-quinolyl)oxyphenyl)-N'-(2,4-difluorophenyl)urea,
N-(4-(6-cyano-7-(2-methoxyethoxy)-4-quinolyl)oxyphenyl)-N'-(4-fluorophenyl)urea,
N-(4-(6-cyano-7-(2-methoxyethoxy)-4-quinolyl)oxyphenyl)-N'-(1,3-thiazol-2-yl)urea,
N-(4-(6-cyano-7-(2-methoxyethoxy)-4-quinolyl)oxyphenyl)-N'-(3-cyanophenyl)urea,
N-(4-(6-cyano-7-(2-methoxyethoxy)-4-quinolyl)oxyphenyl)-N'-(2-(methylsulfonyl)phenyl)urea,
N-(4-(6-cyano-7-(2-methoxyethoxy)-4-quinolyl)oxyphenyl)-N'-cyclopropylurea,
N-(4-(6-cyano-7-(2-methoxyethoxy)-4-quinolyl)oxy-2-fluorophenyl)-N'-(1,3-thiazol-2-yl)urea,
N-(4-(6-cyano-7-(2-methoxyethoxy)-4-quinolyl)oxy-2-fluorophenyl)-N'-cyclopropylurea,
N-(4-(6-cyano-7-(2-methoxyethoxy)-4-quinolyl)oxyphenyl)-N'-cyclopropylmethylurea,
N-(4-(6-cyano-7-(3-(morpholin-4-yl)propoxy)quinolin-4-yloxy)-2-fluorophenyl)-N'-(2,4-difluorophenyl)urea,
N-(4-(6-cyano-7-(3-(diethylamino)propoxy)-4-quinolyloxyphenyl)-N'-(4-fluorophenyl)urea,
N-(4-(6-cyano-7-(3-(4-morpholino)propoxy)-4-quinolyl)oxyphenyl)-N'-(4-fluorophenyl)urea,
N-(4-(6-cyano-7-(2-methoxyethoxy)-4-quinolyl)oxy-2-fluorophenyl)-N'-(3-(methylsulfonyl)phenyl)urea,
N-(4-(6-cyano-7-(3-(diethylamino)propoxy)-4-quinolyl)oxy-2-fluorophenyl)-N'-(2,4-difluorophenyl)urea,
N-(4-(6-cyano-7-(3-(1-(4-ethylpiperazino))propoxy)-4-quinolyl)oxyphenyl)-N'-(4-methoxyphenyl)urea,
N-(4-(6-cyano-7-(3-cyanopropoxy)-4-quinolyl)oxy-2-fluorophenyl)-N'-(2,4-difluorophenyl)urea,
N-(4-(6-cyano-7-(2-(methylsulfonyl)ethoxy)-4-quinolyl)oxy-2-fluorophenyl)-N'-(2,4-difluorophenyl)urea,
N-(4-(6-cyano-7-(2-(methylsulfonyl)ethoxy)-4-quinolyl)oxyphenyl)-N'-(4-fluorophenyl)urea,
N-(4-(6-cyano-7-(2-methoxyethoxy)-4-quinolyl)oxyphenyl)-N'-phenylurea,
N-(4-(6-cyano-7-(2-methoxyethoxy)-4-quinolyl)oxy-2-fluorophenyl)-N'-(2,4-difluorophenyl)urea,
N-(4-(6-cyano-7-(3-methoxycarbonylpropoxy)-4-quinolyl)oxyphenyl)-N'-(4-methoxyphenyl)urea,
N-(4-(6-cyano-7-(3-carboxypropoxy)-4-quinolyl)oxyphenyl)-N'-(4-methoxyphenyl)urea,
N-(4-(6-cyano-7-(2-(2-hydroxyethoxy)ethoxy)-4-quinolyl)oxyphenyl)-N'-(4-methoxyphenyl)urea,
N-(4-(6-cyano-7-(3-(diethylamino)propoxy)-4-quinolyloxy)phenyl)-N'-(3-(methylsulfonyl)phenyl)urea,
N-(4-(6-cyano-7-(3-(4-morpholino)propoxy)-4-quinolyl)oxyphenyl)-N'-(3-(methylsulfonyl)phenyl)urea,
N-(4-(6-cyano-7-(3-(diethylamino)propoxy)-4-quinolyloxy)phenyl)-N'-phenylurea,
N-(4-(6-cyano-7-(3-(4-morpholino)propoxy)-4-quinolyl)oxyphenyl)-N'-phenylurea,
N-(4-(6-cyano-7-(3-(4-morpholino)propoxy)-4-quinolyl)oxyphenyl)-N'-(2-oxo-1,2,3,4-tetrahydro-6-quinolyl)urea,
N-(4-(6-cyano-7-(2-methoxyethoxy)-4-quinolyl)oxyphenyl)-N'-(3-acetamidophenyl)urea,
N-(4-(6-cyano-7-benzyloxy-4-quinolyl)oxy-2-fluorophenyl)-N'-(2,4-difluorophenyl)urea,
N-(4-(6-cyano-7-(2-methoxyethoxy)-4-quinolyl)oxy-2-fluorophenyl)-N'-(4-fluorophenyl)urea,
N-(4-(6-cyano-7-(2-methoxyethoxy)-4-quinolyl)oxy-2-fluorophenyl)-N'-phenylurea,
4-(4-((4-fluoroanilino)carbonyl)aminophenoxy)-7-(2-methoxyethoxy)-6-quinolinecarboxamide,
7-(2-methoxyethoxy)-4-(4-((1,3-thiazol-2-ylamino)carbonyl)aminophenoxy)-6-quinolinecarboxamide,
4-(4-((anilinocarbonyl)amino)-3-fluorophenoxy)-7-(2-methoxyethoxy)-6-quinolinecarboxamide,
4-(4-((4-fluoroanilino)carbonyl)aminophenoxy)-7-methoxy-6-quinolinecarboxamide,
4-(4-((cyclopropylamino)carbonyl)aminophenoxy)-7-(2-methoxyethoxy)-6-quinolinecarboxamide,
7-methoxy-4-(4-((1,3-thiazol-2-ylamino)carbonyl)aminophenoxy)-6-quinolinecarboxamide,
4-(4-((2,4-difluoroanilino)carbonyl)amino-3-fluorophenoxy)-7-methoxy-6-quinolinecarboxamide,
4-(4-((cyclopropylamino)carbonyl)aminophenoxy)-7-methoxy-6-quinolinecarboxamide,
4-(5-((anilinocarbonyl)amino)-2-pyridyloxy)-7-methoxy-6-quinolinecarboxamide,
4-(4-(anilinocarbonyl)aminophenoxy)-7-methoxy-6-quinolinecarboxamide,
4-(4-(anilinocarbonyl)aminophenoxy)-7-(2-methoxyethoxy)-6-quinolinecarboxamide,
4-(4-((2,4-difluoroanilino)carbonyl)amino-3-fluorophenoxy)-7-(2-methoxyethoxy)-6-quinolinecarboxamide,
4-(4-((4-fluoroanilino)carbonyl)amino-3-fluorophenoxy)-7-(2-methoxyethoxy)-6-quinolinecarboxamide,
7-(2-methoxyethoxy)-4-(4-((1,3-thiazol-2-ylamino)carbonyl)amino-3-fluorophenoxy)-6-quinolinecarboxamide and
4-(4-((4-fluoroanilino)carbonyl)amino-3-fluorophenoxy)-7-methoxy-6-quinolinecarboxamide;

<25> a compound according to <1> or <2>, a pharmacologically acceptable salt of the compound or a hydrate of the foregoing, wherein said compound is a compound selected from N-(4-(6-cyano-7-(2-methoxyethoxy)-4-quinolyl)oxy-2-fluorophenyl)-N'-(4-fluorophenyl)urea,
N-(2-chloro-4-((6-cyano-7-((1-methyl-4-piperidyl)methoxy)-4-quinolyl)oxy)phenyl)-N'-cyclopropylurea,
N-(4-((6-cyano-7-(((2R)-3-(diethylamino)-2-hydroxypropyl)oxy)-4-quinolyl)oxy)phenyl)-N'-(4-fluorophenyl)urea,
N-(4-((6-cyano-7-(((2R)-2-hydroxy-3-(1-pyrrolidino)propyl)oxy)-4-quinolyl)oxy)phenyl)-N'-(4-fluorophenyl)urea,
N-{4-[6-cyano-7-(2-hydroxy-3-pyrrolidin-1-yl-propoxy)-quinolin-4-yloxy]-2-methylphenyl}-N'-cyclopropyl-urea,
4-(4-(4-fluoroanilino)carbonyl)-4-methylaminophenoxy)-7-methoxy-6-quinolinecarboxamide,
4-(3-chloro-4-(cyclopropylaminocarbonyl)aminophenoxy)-7-methoxy-6-quinolinecarboxamide,
4-(3-chloro-4-(cyclopropylaminocarbonyl)aminophenoxy)-7-(2-methoxyethoxy)-6-quinolinecarboxamide, N6-cyclopropyl-4-(3-chloro-4-(((cyclopropylamino)carbonyl)amino)phenoxy)-7-methoxy-6-quinolinecarboxamide,
N6-(2-methoxyethyl)-4-(3-chloro-4-(((cyclopropylamino)carbonyl)amino)phenoxy)-7-methoxy-6-quinolinecarboxamide,
N6-(2-pyridyl)-4-(3-chloro-4-(((cyclopropylamino)carbonyl)amino)phenoxy)-7-methoxy-6-quinolinecarboxamide,
N6-(2-fluoroethyl)-4-(3-chloro-4-(((cyclopropylamino)carbonyl)amino)phenoxy)-7-methoxy-6-quinolinecarboxamide,
N6-methoxy-4-(3-chloro-4-(((cyclopropylamino)carbonyl)amino)phenoxy)-7-methoxy-6-quinolinecarboxamide,
N6-methyl-4-(3-chloro-4-(((cyclopropylamino)carbonyl)amino)phenoxy)-7-methoxy-6-quinolinecarboxamide,
N6-ethyl-4-(3-chloro-4-(((cyclopropylamino)carbonyl)amino)phenoxy)-7-methoxy-6-quinolinecarboxamide,
6-carbamoyl-4-(1-ethylcarbamoyl-1H-indol-5-yloxy)-7-methoxyquinoline,
6-carbamoyl-7-methoxy-4-(1-propylcarbamoyl-1H-indol-5-yloxy)quinoline,
6-carbamoyl-7-methoxy-4-[1-(1-methyl)ethylcarbamoyl-1H-indol-5-yloxy]quinoline,
N4-(4-{4-[(anilinocarbonyl)amino]-3-chlorophenoxy}-2-pyridyl)-1-methyl-4-piperidinecarboxamide,
N1-phenyl-3-chloro-5-[(2-{[(1-methyl-4-piperidyl)carbonyl]amino}-4-pyridyl)oxy]-1H-1-indolecarboxamide,
N4-[4-(3-chloro-4-{[(4-fluoroanilino)carbonyl]amino}phenoxy)-2-pyridyl]-1-methyl-4-piperidinecarboxamide,
1-(2-chloro-4-{6-[4-(2-diethylaminoethoxy)-phenyl]-7H-pyrrolo[2,3-d]pyrimidin-4-yloxy}phenyl)-3-cyclopropylurea,
1-{2-chloro-4-[6-[4-((2R)-2-hydroxy-3-diethylaminopropoxy)-phenyl]-7H-pyrrolo[2,3-d]pyrimidin-4-yloxy]-phenyl}-3-cyclopropylurea,
1-(2-chloro-4-{6-[4-((2R)-2-hydroxy-3-pyrrolidinopropoxy)-phenyl]-7H-pyrrolo[2,3-d]pyrimidin-4-yloxy}-phenyl)-3-cyclopropylurea and
1-(2-chloro-4-{6-[4-(2-diethylaminopropoxy)-phenyl]-7H-pyrrolo[2,3-d]pyrimidin-4-yloxy}phenyl)-3-cyclopropylurea;

<26> a compound according to <1> or <2>, a pharmacologically acceptable salt of the compound or a hydrate of the foregoing, wherein said compound is a compound selected from
4-(3-chloro-4-(cyclopropylaminocarbonyl)aminophenoxy)-7-methoxy-6-quinolinecarboxamide,
4-(3-chloro-4-(ethylaminocarbonyl)aminophenoxy)-7-methoxy-6-quinolinecarboxamide,
N6-methoxy-4-(3-chloro-4-(((cyclopropylamino)carbonyl)amino)phenoxy)-7-methoxy-6-quinolinecarboxamide,
4-(3-chloro-4-(methylaminocarbonyl)aminophenoxy)-7-methoxy-6-quinolinecarboxamide and
N6-methoxy-4-(3-chloro-4-(((ethylamino)carbonyl)amino)phenoxy)-7-methoxy-6-quinolinecarboxamide;

<27> a medicament (a drug) comprising as an active ingredient, a compound according to any one of <1> to <6>, a pharmacologically acceptable salt thereof or a hydrate of the foregoing;

<28> an angiogenesis inhibiting activity-based medicament (an angiogenesis inhibiting activity-based drug) comprising as an active ingredient, a compound according to any one of <1> to <6>, a pharmacologically acceptable salt thereof or a hydrate of the foregoing;

<29> a pharmaceutical composition comprising a compound represented by the general formula:

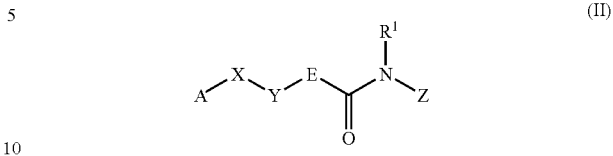

(II)

[wherein A is an optionally substituted 5- to 14-membered aromatic heterocyclic group; X is an oxygen atom, a sulfur atom, —SO— or —SO$_2$; Y is an optionally substituted $C_{6-14}$ aryl group, an optionally substituted 5- to 14-membered aromatic heterocyclic group or an optionally substituted $C_{1-6}$ alkylene group; E is a single bond or —NR$^2$—; R$^1$ and R$^2$ are each independently a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{2-7}$ acyl group or an optionally substituted $C_{2-7}$ alkoxycarbonyl group; and Z is a group represented by the formula —Z$^{11}$—Z$^{12}$ (wherein Z$^{11}$ is a single bond, an oxygen atom, a sulfur atom, —CO—, —SO$_2$— or an optionally substituted $C_{1-6}$ alkylene group and Z$^{12}$ is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{6-14}$ aryl group, an optionally substituted 5- to 14-membered heterocyclic group, an optionally substituted 5- to 14-membered aromatic heterocyclic group or a group represented by the formula:

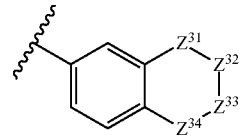

(wherein Z$^{31}$, Z$^{33}$ and Z$^{34}$ are each independently a methylene group, —CO—, —NH— or —O—, and Z$^{32}$ is a single bond, a methylene group, —CO—, —NH— or —O—)), with the proviso that A may be optionally substituted with 1 to 6 groups, each selected from the group consisting of (1) a cyano group, (2) a halogen atom, (3) a nitro group and (4) the formula —V$^{X1}$—V$^{X2}$—V$^{X22}$—V$^{X3}$ (wherein V$^{X1}$, V$^{X2}$ and V$^{X22}$ are each independently a single bond, an oxygen atom, a sulfur atom, —CO—, —SO—, —SO$_2$—, —NR$^{X1}$—, —CONR$^{X1}$—, NR$^{X1}$CO—, —SO$_2$NR$^{X1}$—, —NR$^{X1}$SO$_2$—, —O—CO—, —C(O)O—, —NR$^{X1}$C(O)O—, —NR$^{X1}$C(O)NR$^{X2}$—, —O—C(O)NR$^{X1}$—, —O—C(O)O—, an optionally substituted $C_{1-6}$ alkylene group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{6-14}$ aryl group, an optionally substituted 5- to 14-membered heterocyclic group or an optionally substituted 5- to 14-membered aromatic heterocyclic group; and V$^{X3}$, R$^{X1}$ and R$^{X2}$ are each independently a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, an optionally substituted $C_{6-14}$ aryl group, an optionally substituted 5- to 14-membered heterocyclic group, an optionally substituted 5- to 14-membered aromatic heterocyclic group or an optionally substituted $C_{1-6}$ alkoxy group)], a pharmacologically acceptable salt thereof or a hydrate of the foregoing, together with a pharmacologically acceptable carrier;

<30> a prophylactic or therapeutic agent for a disease for which angiogenesis inhibition is effective, comprising as an active ingredient, a compound according to <1> or <2>, a pharmacologically acceptable salt thereof or a hydrate of the foregoing;

<31> an angiogenesis inhibitor comprising as an active ingredient, a compound according to <1> or <2>, a pharmacologically acceptable salt thereof or a hydrate of the foregoing;

<32> an antitumor agent comprising as an active ingredient, a compound according to <1> or <2>, a pharmacologically acceptable salt thereof or a hydrate of the foregoing;

<33> a therapeutic agent for angioma (an angioma treatment agent) comprising as an active ingredient, a compound according to <1> or <2>, a pharmacologically acceptable salt thereof or a hydrate of the foregoing;

<34> a cancer metastasis inhibitor comprising as an active ingredient, a compound according to <1> or <2>, a pharmacologically acceptable salt thereof or a hydrate of the foregoing;

<35> a therapeutic agent for retinal neovascularization or diabetic retinopathy (a retinal neovascularization treatment agent or diabetic retinopathy treatment agent) comprising as an active ingredient, a compound according to <1> or <2>, a pharmacologically acceptable salt thereof or a hydrate of the foregoing;

<36> a therapeutic agent for an inflammatory disease (an inflammatory disease treatment agent) comprising as an active ingredient, a compound according to <1> or <2>, a pharmacologically acceptable salt thereof or a hydrate of the foregoing;

<37> a therapeutic agent for an inflammatory disease selected from deformant arthritis, rheumatoid arthritis, psoriasis and delayed hypersensitivity reaction (an inflammatory disease treatment agent for deformant arthritis, rheumatoid arthritis, psoriasis or delayed hypersensitivity reaction) comprising as an active ingredient, a compound according to <1> or <2>, a pharmacologically acceptable salt thereof or a hydrate of the foregoing;

<38> a therapeutic agent for atherosclerosis (an atherosclerosis treatment agent) comprising as an active ingredient, a compound according to <1> or <2>, a pharmacologically acceptable salt thereof or a hydrate of the foregoing;

<39> a therapeutic agent for a pancreatic cancer, a gastric cancer, a colon cancer, a breast cancer, a prostate cancer, a lung cancer, a renal cancer, a brain tumor, a blood cancer or an ovarian cancer (a pancreatic cancer treatment agent, a gastric cancer treatment agent, a colon cancer treatment agent, a breast cancer treatment agent, a prostate cancer treatment agent, a pulmonary cancer treatment agent, a renal cancer treatment agent, a brain tumor treatment agent, a blood cancer treatment agent or an ovarian cancer treatment agent) comprising as an active ingredient, a compound according to <1> or <2>, a pharmacologically acceptable salt thereof or a hydrate of the foregoing;

<40> an angiogenesis inhibition-based antitumor agent comprising as an active ingredient, a compound according to <1> or <2>, a pharmacologically acceptable salt thereof or a hydrate of the foregoing;

<41> a prophylactic or therapeutic method for a disease for which angiogenesis inhibition is effective, comprising administering to a patient, a pharmacologically effective dose of a compound according to <1> or <2>, a pharmacologically acceptable salt thereof or a hydrate of the foregoing;

<42> The use of a compound according to <1> or <2>, a pharmacologically acceptable salt thereof or a hydrate of the foregoing for the manufacture of a prophylactic or a therapeutic agent for a disease for which angiogenesis inhibition is effective.

DESCRIPTION OF THE PREFERRED EMBODIMENTS

The present invention will now be explained in greater detail.

Several of the structural formulas given for compounds throughout the present specification will represent a specific isomer for convenience, but the invention is not limited to such specific isomers and encompasses all isomers and isomer mixtures, including geometric isomers, asymmetric carbon-derived optical isomers, stereoisomers and tautomers, implied by the structures of the compounds. Moreover, the compounds of the invention also include those that have been metabolized in the body by oxidation, reduction, hydrolysis, conjugation or the like, and still exhibit the desired activity, while the invention further encompasses all compounds which undergo metabolism such as oxidation, reduction, hydrolysis, etc. in the body to produce the compounds of the invention. Solvates, including those with water, are also encompassed by the invention.

The terms used throughout the present specification will now be defined.

The term "halogen atom" as used throughout the present specification refers to halogen atoms such as fluorine, chlorine, bromine and iodine, with fluorine, chlorine and bromine being preferred.

The term "$C_{1-6}$ alkyl group" as used throughout the present specification refers to a linear or branched alkyl group of 1 to 6 carbons, and as specific examples there may be mentioned methyl, ethyl, n-propyl, i-propyl, n-butyl, i-butyl, sec-butyl, t-butyl, n-pentyl, i-pentyl, sec-pentyl, t-pentyl, neopentyl, 1-methylbutyl, 2-methylbutyl, 1,1-dimethylpropyl, 1,2-dimethylpropyl, n-hexyl, i-hexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably methyl, ethyl, n-propyl, i-propyl, n-butyl, i-butyl, sec-butyl, t-butyl, n-pentyl, i-pentyl, sec-pentyl, t-pentyl, neopentyl, 1-methylbutyl, 2-methylbutyl, 1,1-dimethylpropyl, 1,2-dimethylpropyl, n-hexyl and i-hexyl, more preferably methyl, ethyl, n-propyl, i-propyl, n-butyl, i-butyl, sec-butyl, t-butyl, n-pentyl, i-pentyl, sec-pentyl, t-pentyl, neopentyl, 1-methylbutyl, 2-methylbutyl, 1, 1-dimethylpropyl and 1, 2-dimethylpropyl, even more preferably methyl, ethyl, n-propyl, i-propyl, n-butyl, i-butyl, sec-butyl and t-butyl, and most preferably methyl, ethyl, n-propyl and i-propyl.

The term "$C_{1-6}$ alkylene group" as used throughout the present specification refers to a divalent group derived by removing one hydrogen atom from the aforementioned "$C_{1-6}$ alkyl group", and as specific examples there may be mentioned methylene, ethylene, methylethylene, propylene, ethylethylene, 1,1-dimethylethylene, 1,2-dimethylethylene, trimethylene, 1-methyltrimethylene, 1-ethyltrimethylene, 2-methyltrimethylene, 1,1-dimethyltrimethylene, tetramethylene, pentamethylene and hexamethylene.

The term "$C_{2-6}$ alkenyl group" as used throughout the present specification refers to a linear or branched alkenyl group of 2 to 6 carbons, and it is a substituent with a double bond in a "$C_{1-6}$ alkyl group" of 2 or more carbons. As specific examples there may be mentioned ethenyl, 1-propen-1-yl, 2-propen-1-yl, 3-propen-1-yl, 1-buten-1-yl, 1-buten-2-yl, 1-buten-3-yl, 1-buten-4-yl, 2-buten-1-yl, 2-buten-2-yl, 1-methyl-1-propen-1-yl, 2-methyl-1-propen-1-yl, 1-methyl-2-propen-1-yl, 2-methyl-2-propen-1-yl, 1-methyl-1-buten-1-yl, 2-methyl-1-buten-1-yl, 3-methyl-1-buten-1-yl, 1-methyl-2-buten-1-yl, 2-methyl-2-buten-1-yl, 3-methyl-2-buten-1-yl, 1-methyl-3-buten-1-yl, 2-methyl-3-buten-1-yl, 3-methyl-3-buten-1-yl, 1-ethyl-1-buten-1-yl, 2-ethyl-1-buten-1-yl, 3-ethyl-1-buten-1-yl, 1-ethyl-2-buten-1-yl, 2-ethyl-2-buten-1-yl, 1-yl, 3-ethyl-2-buten-1-yl, 1-ethyl-3-buten-1-yl, 2-ethyl-3-buten-1-yl, 3-ethyl-3-buten-1-yl, 1,1-dimethyl-1-buten-1-yl, 1,2-dimethyl-1-buten-1-yl, 1,3-dimethyl-1-buten-1-yl, 2,2-dimethyl-1-buten-1-yl, 3,3-dimethyl-1-buten-1-yl, 1,1-dimethyl-2-buten-1-yl, 1,2-dimethyl-2-buten-1-yl, 1,3-dimethyl-2-buten-1-yl, 2,2-dimethyl-2-buten-1-yl, 3,3-dimethyl-2-buten-1-yl, 1,1-dimethyl-3-buten-1-yl, 1,2-dimethyl-3-buten-1-yl, 1,3-dimethyl-3-buten-1-yl, 2,2-dimethyl-3-buten-1-yl, 3,3-dimethyl-3-buten-1-yl, 1-penten-1-yl, 2-penten-1-yl, 3-penten-1-yl, 4-penten-1-yl, 1-penten-2-yl, 2-penten-2-yl, 3-penten-2-yl, 4-penten-2-yl, 1-penten-3-yl, 2-penten-3-yl, 1-methyl-1-penten-1-yl, 2-methyl-1-penten-1-yl, 3-methyl-1-penten-1-yl, 4-methyl-1-penten-1-yl, 1-methyl-2-penten-1-yl, 2-methyl-2-penten-1-yl, 3-methyl-2-penten-1-yl, 4-methyl-2-penten-1-yl, 1-methyl-3-penten-1-yl, 2-methyl-3-penten-1-yl, 3-methyl-3-penten-1-yl, 4-methyl-3-penten-1-yl, 1-methyl-4-penten-1-yl, 2-methyl-4-penten-1-yl, 3-methyl-4-penten-1-yl, 4-methyl-4-penten-1-yl, 1-methyl-1-penten-2-yl, 2-methyl-1-penten-2-yl, 3-methyl-1-penten-2-yl, 4-methyl-1-penten-2-yl, 1-methyl-2-penten-2-yl, 2-methyl-2-penten-2-yl, 3-methyl-2-penten-2-yl, 4-methyl-2-penten-2-yl, 1-methyl-3-penten-2-yl, 2-methyl-3-penten-2-yl, 3-methyl-3-penten-2-yl, 4-methyl-3-penten-2-yl, 1-methyl-4-penten-2-yl, 2-methyl-4-penten-2-yl, 3-methyl-4-penten-2-yl, 4-methyl-4-penten-2-yl, 1-methyl-1-penten-3-yl, 2-methyl-1-penten-3-yl, 3-methyl-1-penten-3-yl, 4-methyl-1-penten-3-yl, 1-methyl-2-penten-3-yl, 2-methyl-2-penten-3-yl, 3-methyl-2-penten-3-yl, 4-methyl-2-penten-3-yl, 1-hexen-1-yl, 1-hexen-2-yl, 1-hexen-3-yl, 1-hexen-4-yl, 1-hexen-5-yl, 1-hexen-6-yl, 2-hexen-1-yl, 2-hexen-2-yl, 2-hexen-3-yl, 2-hexen-4-yl, 2-hexen-5-yl, 2-hexen-6-yl, 3-hexen-1-yl, 3-hexen-2-yl, 3-hexen-3-yl, preferably ethenyl, 1-propen-1-yl, 2-propen-1-yl, 3-propen-1-yl, 1-buten-1-yl, 1-buten-2-yl, 1-buten-3-yl, 1-buten-4-yl, 2-buten-1-yl, 2-buten-2-yl, 1-methyl-1-propen-1-yl, 2-methyl-1-propen-1-yl, 1-methyl-2-propen-1-yl, 2-methyl-2-propen-1-yl, 1-methyl-1-buten-1-yl, 2-methyl-1-buten-1-yl, 3-methyl-1-buten-1-yl, 1-methyl-2-buten-1-yl, 2-methyl-2-buten-1-yl, 3-methyl-2-buten-1-yl, 1-methyl-3-buten-1-yl, 2-methyl-3-buten-1-yl, 3-methyl-3-buten-1-yl, 1-ethyl-1-buten-1-yl, 2-ethyl-1-buten-1-yl, 3-ethyl-1-buten-1-yl, 1-ethyl-2-buten-1-yl, 2-ethyl-2-buten-1-yl, 3-ethyl-2-buten-1-yl, 1-ethyl-3-buten-1-yl, 2-ethyl-3-buten-1-yl, 3-ethyl-3-buten-1-yl, 1,1-dimethyl-1-buten-1-yl, 1,2-dimethyl-1-buten-1-yl, 1,3-dimethyl-1-buten-1-yl, 2,2-dimethyl-1-buten-1-yl, 3,3-dimethyl-1-buten-1-yl, 1,1-dimethyl-2-buten-1-yl, 1,2-dimethyl-2-buten-1-yl, 1,3-dimethyl-2-buten-1-yl, 2,2-dimethyl-2-buten-1-yl, 3,3-dimethyl-2-buten-1-yl, 1,1-dimethyl-3-buten-1-yl, 1,2-dimethyl-3-buten-1-yl, 1,3-dimethyl-3-buten-1-yl, 2,2-dimethyl-3-buten-1-yl and 3,3-dimethyl-3-buten-1-yl, more preferably ethenyl, 1-propen-1-yl, 2-propen-1-yl, 3-propen-1-yl, 1-buten-1-yl, 1-buten-2-yl, 1-buten-3-yl, 1-buten-4-yl, 2-buten-1-yl, 2-buten-2-yl, 1-methyl-1-propen-1-yl, 2-methyl-1-propen-1-yl, 1-methyl-2-propen-1-yl, 2-methyl-2-propen-1-yl, 1-methyl-1-buten-1-yl, 2-methyl-1-buten-1-yl, 3-methyl-1-buten-1-yl, 1-methyl-2-buten-1-yl, 2-methyl-2-buten-1-yl, 3-methyl-2-buten-1-yl, 1-methyl-3-buten-1-yl, 2-methyl-3-buten-1-yl and 3-methyl-3-buten-1-yl, and most preferably ethenyl, 1-propen-1-yl, 2-propen-1-yl, 3-propen-1-yl, 1-buten-1-yl, 1-buten-2-yl, 1-buten-3-yl, 1-buten-4-yl, 2-buten-1-yl and 2-buten-2-yl.

The term "$C_{2-6}$ alkynyl group" as used throughout the present specification refers to a linear or branched alkynyl group of 2 to 6 carbons, and it is a substituent with a triple bond in a "$C_{1-6}$ alkyl group" of 2 or more carbons. As specific examples there may be mentioned ethynyl, 1-propyn-1-yl, 2-propyn-1-yl, 3-propyn-1-yl, 1-butyn-1-yl, 1-butyn-2-yl, 1-butyn-3-yl, 1-butyn-4-yl, 2-butyn-1-yl, 2-butyn-2-yl, 1-methyl-1-propyn-1-yl, 2-methyl-1-propyn-1-yl, 1-methyl-2-propyn-1-yl, 2-methyl-2-propyn-1-yl, 1-methyl-1-butyn-1-yl, 2-methyl-1-butyn-1-yl, 3-methyl-1-butyn-1-yl, 1-methyl-2-butyn-1-yl, 2-methyl-2-butyn-1-yl, 3-methyl-2-butyn-1-yl, 1-methyl-3-butyn-1-yl, 2-methyl-3-butyn-1-yl, 3-methyl-3-butyn-1-yl, 1-ethyl-1-butyn-1-yl, 2-ethyl-1-butyn-1-yl, 3-ethyl-1-butyn-1-yl, 1-ethyl-2-butyn-1-yl, 2-ethyl-2-butyn-1-yl, 3-ethyl-2-butyn-1-yl, 1-ethyl-3-butyn-1-yl, 2-ethyl-3-butyn-1-yl, 3-ethyl-3-butyn-1-yl, 1,1-dimethyl-1-butyn-1-yl, 1,2-dimethyl-1-butyn-1-yl, 1,3-dimethyl-1-butyn-1-yl, 2,2-dimethyl-1-butyn-1-yl, 3,3-dimethyl-1-butyn-1-yl, 1,1-dimethyl-2-butyn-1-yl, 1,2-dimethyl-2-butyn-1-yl, 1,3-dimethyl-2-butyn-1-yl, 2,2-dimethyl-2-butyn-1-yl, 3,3-dimethyl-2-butyn-1-yl, 1,1-dimethyl-3-butyn-1-yl, 1,2-dimethyl-3-butyn-1-yl, 1,3-dimethyl-3-butyn-1-yl, 2,2-dimethyl-3-butyn-1-yl, 3,3-dimethyl-3-butyn-1-yl, 1-pentyn-1-yl, 2-pentyn-1-yl, 3-pentyn-1-yl, 4-pentyn-1-yl, 1-pentyn-2-yl, 2-pentyn-2-yl, 3-pentyn-2-yl, 4-pentyn-2-yl, 1-pentyn-3-yl, 2-pentyn-3-yl, 1-methyl-1-pentyn-1-yl, 2-methyl-1-pentyn-1-yl, 3-methyl-1-pentyn-1-yl, 4-methyl-1-pentyn-1-yl, 1-methyl-2-pentyn-1-yl, 2-methyl-2-pentyn-1-yl, 3-methyl-2-pentyn-1-yl, 4-methyl-2-pentyn-1-yl, 1-methyl-3-pentyn-1-yl, 2-methyl-3-pentyn-1-yl, 3-methyl-3-pentyn-1-yl, 4-methyl-3-pentyn-1-yl, 1-methyl-4-pentyn-1-yl, 2-methyl-4-pentyn-1-yl, 3-methyl-4-pentyn-1-yl, 4-methyl-4-pentyn-1-yl, 1-methyl-1-pentyn-2-yl, 2-methyl-1-pentyn-2-yl, 3-methyl-1-pentyn-2-yl, 4-methyl-1-pentyn-2-yl, 1-methyl-2-pentyn-2-yl, 2-methyl-2-pentyn-2-yl, 3-methyl-2-pentyn-2-yl, 4-methyl-2-pentyn-2-yl, 1-methyl-3-pentyn-2-yl, 2-methyl-3-pentyn-2-yl, 3-methyl-3-pentyn-2-yl, 4-methyl-3-pentyn-2-yl, 1-methyl-4-pentyn-2-yl, 2-methyl-4-pentyn-2-yl, 3-methyl-4-pentyn-2-yl, 4-methyl-4-pentyn-2-yl, 1-methyl-1-pentyn-3-yl, 2-methyl-1-pentyn-3-yl, 3-methyl-1-pentyn-3-yl, 4-methyl-1-pentyn-3-yl, 1-methyl-2-pentyn-3-yl, 2-methyl-2-pentyn-3-yl, 3-methyl-2-pentyn-3-yl, 4-methyl-2-pentyn-3-yl, 1-hexyn-1-yl, 1-hexyn-2-yl, 1-hexyn-3-yl, 1-hexyn-4-yl, 1-hexyn-5-yl, 1-hexyn-6-yl, 2-hexyn-1-yl, 2-hexyn-2-yl, 2-hexyn-3-yl, 2-hexyn-4-yl, 2-hexyn-5-yl, 2-hexyn-6-yl, 3-hexyn-1-yl, 3-hexyn-2-yl and 3-hexyn-3-yl, preferably ethynyl, 1-propyn-1-yl, 2-propyn-1-yl, 3-propyn-1-yl, 1-butyn-1-yl, 1-butyn-2-yl, 1-butyn-3-yl, 1-butyn-4-yl, 2-butyn-1-yl, 2-butyn-2-yl, 1-methyl-1-propyn-1-yl, 2-methyl-1-propyn-1-yl, 1-methyl-2-propyn-1-yl, 2-methyl-2-propyn-1-yl, 1-methyl-1-butyn-1-yl, 2-methyl-1-butyn-1-yl, 3-methyl-1-butyn-1-yl, 1-methyl-2-butyn-1-yl, 2-methyl-2-butyn-1-yl, 3-methyl-2-butyn-1-yl, 1-methyl-3-butyn-1-yl, 2-methyl-3-butyn-1-yl, 3-methyl-3-butyn-1-yl, 1-ethyl-1-butyn-1-yl, 2-ethyl-1-butyn-1-yl, 3-ethyl-1-butyn-1-yl, 1-ethyl-2-butyn-1-yl, 2-ethyl-2-butyn-1-yl, 3-ethyl-2-butyn-1-yl, 1-ethyl-3-butyn-1-yl, 2-ethyl-3-butyn-1-yl, 3-ethyl-3-butyn-1-yl, 1,1-dimethyl-1-butyn-1-yl, 1,2- dimethyl-1-butyn-1-yl, 1,3-dimethyl-1-butyn-1-yl, 2,2-dimethyl-1-butyn-1-yl, 3,3-dimethyl-1-butyn-1-yl, 1,1-dimethyl-2-butyn-1-yl, 1,2-dimethyl-2-butyn-1-yl, 1,3-dimethyl-2-butyn-1-yl, 2,2-dimethyl-2-butyn-1-yl, 3,3-dimethyl-2-butyn-1-yl, 1,1-dimethyl-3-butyn-1-yl, 1,2-dimethyl-3-butyn-1-yl, 1,3-dimethyl-3-butyn-1-yl, 2,2-dimethyl-3-butyn-1-yl and 3,3-dimethyl-3-butyn-1-yl, more preferably ethynyl, 1-propyn-1-yl, 2-propyn-1-yl, 3-propyn-1-yl, 1-butyn-1-yl, 1-butyn-2-yl, 1-butyn-3-yl, 1-butyn-4-yl, 2-butyn-1-yl, 2-butyn-2-yl, 1-methyl-1-propyn-1-yl, 2-methyl-1-propyn-1-yl, 1-methyl-2-propyn-1-yl, 2-methyl-2-propyn-1-yl, 1-methyl-1-butyn-1-yl, 2-methyl-1-butyn-1-yl, 3-methyl-1-butyn-1-yl, 1-methyl-2-butyn-1-yl, 2-methyl-2-butyn-1-yl, 3-methyl-2-butyn-1-yl, 1-methyl-3-butyn-1-yl, 2-methyl-3-butyn-1-yl and 3-methyl-3-butyn-1-yl, even more preferably ethynyl, 1-propyn-1-yl, 2-propyn-1-yl, 3-propyn-1-yl, 1-butyn-1-yl, 1-butyn-2-yl, 1-butyn-3-yl, 1-butyn-4-yl, 2-butyn-1-yl and 2-butyn-2-yl, and most preferably ethynyl, 1-propyn-1-yl, 2-propyn-1-yl and 3-propyn-1-yl.

The term "$C_{3-8}$ cycloalkyl group" as used throughout the present specification refers to a cyclic alkyl group of 3 to 8 carbons, and as specific examples there may be mentioned cyclopropyl, cyclobutyl, cyclopentyl and cyclohexyl, with cyclopropyl being preferred.

The term "$C_{3-8}$ cycloalkenyl group" as used throughout the present specification refers to a cyclic alkenyl group of 3 to 8 carbons, and as specific examples there may be mentioned cyclopentenyl and cyclohexenyl.

The term "$C_{3-8}$ cycloalkynyl group" as used throughout the present specification refers to a cyclic alkynyl group of 3 to 8 carbons, and as a specific example there may be mentioned cyclohexynyl.

The term "$C_{3-8}$ cycloalkoxy group" as used throughout the present specification refers to a cyclic alkoxy group of 3 to 8 carbons, and as specific examples there may be mentioned cyclopropoxy, cyclobutoxy, cyclopentyloxy and cyclohexyloxy, with cyclopropoxy being preferred.

The term "$C_{3-8}$ alicyclic hydrocarbon group" as used throughout the present specification refers to a cyclic hydrocarbon of 3 to 8 carbons, and it is a substituent whose definition includes that of the aforementioned "$C_{3-8}$ cycloalkyl group", "$C_{3-8}$ cycloalkenyl group" and "$C_{3-8}$ cycloalkynyl group", with cyclopropyl being preferred.

The term "$C_{1-6}$ alkoxy group" as used throughout the present specification refers to a substituent wherein the aforementioned "$C_{1-6}$ alkyl group" is bonded to an oxygen atom, and as specific examples there may be mentioned methoxy, ethoxy, n-propoxy, i-propoxy, n-butoxy, i-butoxy, sec-butoxy, t-butoxy, n-pentyloxy, i-pentyloxy, sec-pentyloxy, t-pentyloxy, neopentyloxy, 1-methylbutoxy, 2-methylbutoxy, 1,1-dimethylpropoxy, 1,2-dimethylpropoxy, n-hexyloxy, i-hexyloxy, 1-methylpentyloxy, 2-methylpentyloxy, 3-methylpentyloxy, 1,1-dimethylbutoxy, 1,2-dimethylbutoxy, 2,2-dimethylbutoxy, 1,3-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, preferably methoxy, ethoxy, n-propoxy, i-propoxy, n-butoxy, i-butoxy, sec-butoxy, t-butoxy, n-pentyloxy, i-pentyloxy, sec-pentyloxy, t-pentyloxy, neopentyloxy, 1-methylbutoxy, 2-methylbutoxy, 1,1-dimethylpropoxy, 1,2-dimethylpropoxy, n-hexyloxy and i-hexyloxy, more preferably methoxy, ethoxy, n-propoxy, i-propoxy, n-butoxy, i-butoxy, sec-butoxy, t-butoxy, n-pentyloxy, i-pentyloxy, sec-pentyloxy, t-pentyloxy, neopentyloxy, 1-methylbutoxy, 2-methylbutoxy, 1,1-dimethylpropoxy and 1,2-dimethylpropoxy, even more preferably methoxy, ethoxy, n-propoxy, i-propoxy, n-butoxy, i-butoxy, sec-butoxy and t-butoxy, and most preferably methoxy, ethoxy, n-propoxy and i-propoxy.

The term "$C_{2-7}$ acyl group" as used throughout the present specification refers to a substituent wherein a carbonyl group is bonded to the end of the aforementioned "$C_{1-6}$ alkyl group", "$C_{2-6}$ alkenyl group" or "$C_{2-6}$ alkynyl group" or phenyl group, and as specific examples there may be mentioned acetyl, propionyl, butyryl, isobutyryl, valeryl, isovaleryl, pivaloyl, hexanoyl, octanoyl, acryloyl, methacryloyl, crotonyl and benzoyl, preferably acetyl, propionyl, butyryl, isobutyryl, valeryl, isovaleryl, pivaloyl, hexanoyl, octanoyl, acryloyl, methacryloyl, crotonyl and benzoyl, more preferably acetyl, propionyl, butyryl, isobutyryl, valeryl, isovaleryl, pivaloyl, hexanoyl, octanoyl and benzoyl, even more preferably acetyl, propionyl, butyryl, isobutyryl and benzoyl, and most preferably acetyl, propionyl and benzoyl.

The term "$C_{2-7}$ alkoxycarbonyl group" as used throughout the present specification refers to a substituent wherein a carbonyl group is bonded to the aforementioned "$C_{1-6}$ alkoxy group", and as specific examples there may be mentioned ethoxycarbonyl, n-propoxycarbonyl, i-propoxycarbonyl, sec-propoxycarbonyl, n-butoxycarbonyl, i-butoxycarbonyl, 1,2-dimethylpropoxycarbonyl and 2-ethylpropoxycarbonyl.

The term as used throughout the present specification indicates a normal type or primary substituent, "sec-" indicates a secondary substituent, "t-" indicates a tertiary substituent and "i-" indicates an iso type substituent.

The term "$C_{1-6}$ alkylenedioxy group" as used throughout the present specification refers to a substituent having oxygen atoms at each end of a divalent group derived by removing one more hydrogen atom from a "$C_{1-6}$ alkyl group", and as specific examples there may be mentioned methylenedioxy, ethylenedioxy, propylenedioxy, butylenedioxy, pentylenedioxy and hexylenedioxy.

The term "$C_{6-14}$ aryl group" as used throughout the present specification refers to an aromatic ring group of 6 or 14 carbons, and as specific examples there may be mentioned benzene, pentalene, indene, naphthalene, azulene, heptalene, biphenylene, indacene, acenaphthylene, fluorene, phenalene, phenanthrene and anthracene, and preferably benzene, pentalene, indene, naphthalene and azulene.

The term "hetero atom" as used throughout the present specification refers to, specifically, an oxygen atom, sulfur atom, nitrogen atom, phosphorus, arsenic, antimony, silicon, germanium, tin, lead, boron, mercury or the like, and preferably an oxygen atom, sulfur atom or nitrogen atom.

The term "5- to 14-membered aromatic heterocyclic group" as used throughout the present specification refers to an aromatic cyclic group having 5 to 14 atoms forming the cyclic ring and including at least one hetero atom such as nitrogen, sulfur or oxygen among the atoms forming the cyclic ring. As specific examples there may be mentioned nitrogen-containing aromatic heterocycles such as pyrrole, pyridine, pyridone, pyridazine, pyrimidine, pyrazine, pyrazole, imidazole, triazole, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole. As examples of the "5- to 14-membered aromatic heterocyclic group" there may be mentioned preferably, pyridine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzthiazole, phenothiazine, pyrrolopyrimidine, furopyridine and thienopyrimidine, more preferably pyridine, thiophene, benzothiophene, thiazole, benzothiazole, quinoline, quinazoline, cinnoline, pyrrolopyrimidine, pyrimidine, furopyridine and thienopyrimidine.

The term "5- to 14-membered non-aromatic heterocyclic group" as used throughout the present specification refers to a non-aromatic cyclic group having 5 to 14 atoms forming the cyclic ring and including at least one hetero atom such as nitrogen, sulfur or oxygen among the atoms forming the cyclic ring. As specific examples there may be mentioned non-aromatic heterocycles such as pyrrolidinyl, pyrrolinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide and succinimide. As examples of the "5- to 14-membered non-aromatic heterocyclic group" there may be mentioned preferably, pyrrolidinyl, piperidinyl and morpholinyl, and more preferably pyrrolidinyl, piperidinyl, morpholinyl and pyrrole.

The term "5- to 14-membered heterocyclic group" as used throughout the present specification refers to an aromatic or non-aromatic cyclic group having 5 to 14 atoms forming the cyclic ring and including at least one hetero atom such as nitrogen, sulfur or oxygen among the atoms forming the cyclic ring, which is a "5- to 14-membered aromatic heterocyclic group" in the former case and a "5- to 14-membered non-aromatic heterocyclic group" in the latter case. Specific examples of the "5- to 14-membered heterocyclic group" therefore include specific examples of the "5- to 14-membered aromatic heterocyclic group" and specific examples of the "5- to 14-membered non-aromatic heterocyclic group".

As the "5- to 14-membered heterocyclic group" there may be mentioned preferably pyrrolidinyl, piperidinyl, morpholinyl, pyrrole, pyridine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzothiazole, phenothiazine and carbostyryl, more preferably pyrrolidinyl, piperidinyl, morpholinyl, pyrrole, pyridine, thiophene, benzothiophene, thiazole, benzothiazole, quinoline, quinazoline, cinnoline and carbostyryl, and even more preferably thiazole, quinoline, quinazoline, cinnoline and carbostyryl.

The term "6- to 14-membered aromatic heterocyclic group" as used throughout the present specification refers to those substituents defined by "5- to 14-membered aromatic heterocyclic group" which have 6 to 14 atoms forming the cyclic ring. As specific examples there may be mentioned pyridine, pyridone, pyrimidine, indole, quinoline, isoquinoline, quinolizine, phthalazine, naphthyridine, quinazoline, cinnoline, acridine, benzothiophene, benzofuran, thiazole, benzothiazole and phenothiazine.

The term "6- to 14-membered heterocyclic group" as used throughout the present specification refers to those substituents defined by "5- to 14-membered heterocyclic group" which have 6 to 14 atoms forming the cyclic ring. As specific examples there may be mentioned piperidinyl, piperazinyl, N-methylpiperazinyl, morpholinyl, tetrahydropyranyl, 1,4-dioxane and phthalimide.

The term "$C_{6-14}$ aryl-$C_{1-6}$ alkyl group [=aralkyl group]" as used throughout the present specification refers to a "$C_{1-6}$ alkyl group" substituted at substitutable positions with a "$C_{6-14}$ aryl group", and as specific examples there may be mentioned benzyl, phenethyl, 3-phenylpropyl, 4-phenylbutyl, 5-phenylpentyl, 6-phenylhexyl, 1-naphthylmethyl, 2-naphthylmethyl, 1-naphthylethyl, 2-naphthylethyl, 1-naphthylpropyl and 2-naphthylpropyl, preferably benzyl, phenethyl, 3-phenylpropyl, 4-phenylbutyl, 5-phenylpentyl, 6-phenylhexyl, 1-naphthylmethyl, 2-naphthylmethyl, 1-naphthylethyl, 2-naphthylethyl, 1-naphthylpropyl and 2-naphthylpropyl, more preferably benzyl, phenethyl, 3-phenylpropyl, 4-phenylbutyl, 5-phenylpentyl, 6-phenylhexyl, 1-naphthylmethyl, 2-naphthylmethyl, even more preferably benzyl, phenethyl, 3-phenylpropyl, 4-phenylbutyl, and most preferably benzyl and phenethyl.

The term "5- to 14-membered heterocyclic-$C_{1-6}$ alkyl group" as used throughout the present specification refers to a "$C_{1-6}$ alkyl group" substituted at substitutable positions with a "5- to 14-membered heterocyclic group", and as specific examples there may be mentioned 2-pyridylmethyl, 3-pyridylmethyl and 2-quinolinomethyl.

A "leaving group" in the sense used throughout the present specification may be any group commonly known as a leaving group in chemical synthesis, with no special restrictions, and as specific examples there may be mentioned halogen atoms such as chlorine, bromine and iodine; alkylthio groups such as methylthio, ethylthio and propylthio; arylthio groups such as phenylthio, toluylthio and 2-pyridylthio; alkylsulfonyloxy groups such as methanesulfonyloxy, trifluoromethanesulfonyloxy, ethanesulfonyloxy and propanesulfonyloxy; arylsulfonyloxy groups such as benzenesulfonyloxy and p-toluenesulfonyloxy; alkanoyloxy groups such as acetoxy and trifluoroacetoxy; alkoxy groups such as methoxy, ethoxy and propoxy; alkylamino groups such as methylamino, ethylamino, propylamino and butylamino; dialkylamino groups such as dimethylamino, diethylamino, dipropylamino, methylethylamino, ethylpropylamino and methylpropylamino; and substituted phosphoryloxy groups such as diphenoxyphosphoryloxy. Preferred are halogen atoms such as chlorine, bromine and iodine, and trifluoromethanesulfonyloxy.

The term "optionally substituted" as used throughout the present specification is synonymous with "optionally having one or more substituents in any desired combination at substitutable positions", and as specific examples of substituents there may be mentioned (1) halogens, (2) hydroxyl, (3) thiol, (4) nitro, (5) nitrile, (6) oxo, (7) azido, (8) guanidino, (9) hydrazino, (10) isocyano, (11) cyanate, (12) isocyanate, (13) thiocyanate, (14) isothiocyanate, (15) nitroso, (16) carbamido (ureido), (17) formyl, (18) $C_{1-6}$ imidoyl, (19) optionally halogenated or hydroxylated $C_{1-6}$ alkyl groups, $C_{2-6}$ alkenyl groups, $C_{2-6}$ alkynyl groups, $C_{3-6}$ cycloalkyl groups, $C_{3-6}$ cycloalkenyl groups, $C_{3-6}$ cycloalkynyl groups, $C_{1-6}$ alkoxy groups, $C_{2-6}$ alkenyloxy groups, $C_{2-6}$ alkynyloxy groups, $C_{3-8}$ cycloalkoxy groups, $C_{1-6}$ alkylthio groups, $C_{2-6}$ alkenylthio groups, $C_{2-6}$ alkynylthio groups, $C_{3-6}$ cycloalkylthio groups or $C_{1-6}$ alkylenedioxy groups, (20) $C_{6-14}$ aryl groups, (21) 5- to 14-membered heterocyclic groups, (22) carboxyl, (23) trifluoromethyl, (24) $C_{6-14}$ aryl-$C_{1-6}$ alkyl groups, (25) 5- to 14-membered heterocyclic $C_{1-6}$ alkyl groups or (26) the group represented by the formula —$V^{XX1}$—$V^{XX2}$—$V^{XX3}$—

$V^{XX4}$ (wherein $V^{XX1}$, $V^{XX2}$ and $V^{XX3}$ are each independently 1) a single bond, 2) oxygen, 3) sulfur, 4) —CO—, 5) —SO—, 6) —SO$_2$—, 7) —NR$^{XX1}$—, 8) —CONR$^{XX1}$—, 9) —NR$^{XX21}$CO—, 10) —SO$_2$NR$^{XX1}$—, 11) —NR$^{XX1}$SO$_2$—, 12) —O—CO—, 13) —C(O)O—, 14) —NR$^{XX1}$C(O)O—, 15) —NR$^{XX1}$C(O)NR$^{XX2}$—, 16) —O—C(O)NR$^{XX1}$—, 17) —O—C(O)O—, 18) a $C_{1-6}$ alkylene group, 19) a $C_{2-6}$ alkenyl group, 20) a $C_{2-6}$ alkynyl group, 21) a $C_{3-8}$ alicyclic hydrocarbon group, 22) a $C_{6-14}$ aryl group, 23) a 5- to 14-membered heterocyclic group or 24) a 5- to 14-membered aromatic heterocyclic group; and $V^{XX4}$, $R^{XX1}$ and $R^{XX2}$ are each independently 1) hydrogen, 2) a $C_{1-6}$ alkyl group, 3) a $C_{2-6}$ alkenyl group, 4) a $C_{2-6}$ alkynyl group, 5) a $C_{3-8}$ alicyclic hydrocarbon group, 6) a $C_{6-14}$ aryl group, 7) a 5- to 14-membered heterocyclic group, 8) a 5- to 14-membered aromatic heterocyclic group or 9) a $C_{1-6}$ alkoxy group.)

Thus, "optionally substituted" means optionally substituted with a substituent, specific examples of which are hydroxyl; thiol; nitro; morpholino; thiomorpholino; halogens such as fluorine, chlorine, bromine and iodine; nitrile; azide; formyl; alkyl groups such as methyl, ethyl, propyl, isopropyl and butyl; alkenyl groups such as vinyl, allyl and propenyl; alkynyl groups such as ethynyl, butynyl and propargyl, alkoxy groups corresponding to lower alkyl groups, such as methoxy, ethoxy, propoxy and butoxy; halogenoalkyl groups such as fluoromethyl, difluoromethyl, trifluoromethyl and fluoroethyl; hydroxyalkyl groups such as hydroxymethyl, hydroxyethyl and hydroxypropyl; guanidino; formimidoyl; acetoimidoyl; carbamoyl; thiocarbamoyl; carbamoylalkyl groups such as carbamoylmethyl and carbamoylethyl; alkylcarbamoyl groups such as methylcarbamoyl and dimethylcarbamoyl; carbamide; alkanoyl groups such as acetyl; amino; alkylamino groups such as methylamino, ethylamino and isopropylamino; dialkylamino groups such as dimethylamino, methylethylamino and diethylamino; aminoalkyl groups such as aminomethyl, aminoethyl and aminopropyl; carboxy; alkoxycarbonyl groups such as methoxycarbonyl, ethoxycarbonyl and propoxycarbonyl; alkoxycarbonylalkyl groups such as methoxycarbonylmethyl, ethoxycarbonylmethyl, propoxycarbonylmethyl, methoxycarbonylethyl, ethoxycarbonylethyl and propoxycarbonylethyl; alkyloxyalkyl groups such as methyloxymethyl, methyloxyethyl, ethyloxymethyl and ethyloxyethyl; alkylthioalkyl groups such as methylthiomethyl, methylthioethyl, ethylthiomethyl and ethylthioethyl; aminoalkylaminoalkyl groups such as aminomethylaminomethyl andaminoethylaminomethyl; alkylcarbonyloxy groups such as methylcarbonyloxy, ethylcarbonyloxy and isopropylcarbonyloxy; arylalkoxyalkoxyalkyl groups such as oxymethyl and benzyloxyethyloxyethyl; hydroxyalkoxyalkyl groups such as hydroxyethyloxymethyl and hydroxyethyloxyethyl; arylalkoxyalkyl groups such as benzyloxymethyl, benzyloxyethyl and benzyloxypropyl; quaternary ammonio groups such as trimethylammonio, methylethylmethylammonio and triethylammonio; cycloalkyl groups such as cyclopropyl, cyclobutyl, cyclopentyl and cyclohexyl; cycloalkenyl groups such as cyclopropenyl, cyclobutenyl, cyclopentenyl and cyclohexenyl; aryl groups such as phenyl, pyridinyl, thienyl, furyl and pyrrolyl; alkylthio groups such as methylthio, ethylthio, propylthio and butylthio; arylthio groups such as phenylthio, pyridinylthio, thienylthio, furylthio and pyrrolylthio; aryl lower alkyl groups such as benzyl, trityl and dimethoxytrityl; substituted sulfonyl groups such as sulfonyl, mesyl and p-toluenesulfonyl; aroyl groups such as benzoyl; halogenoaryl groups such as fluorophenyl and bromophenyl; and oxyalkoxy groups such as methylenedioxy.

The term "$C_{1-6}$ imidoyl group" as used throughout the present specification refers to, for example, formimidoyl, hexaneimidoyl, succinimidoyl, or the like.

Throughout the present specification, when ring A is a 5- to 14-membered heterocyclic group, it is preferably one selected from among pyridine, pyrimidine, pyridopyrimidine, isoquinoline, phthalazine, quinoline, quinazoline, pyrimidopyrimidine, quinoxaline, pyridopyridine, pyrrolopyridine, pyrrolopyrimidine, indole, pyrazolopyridine, pyrazolopyrimidine, thienopyridine, thienopyrimidine, benzothiazole, thiazolopyridine, thiazolopyrimidine, benzimidazole, imidazopyridine, imidazopyrimidine, thiazole, imidazole, pyrazole, benzofuran, furopyridine, furopyrimidine, benzoxazole, oxazolopyridine, oxazolopyrimidine, pyridopyrimidin-7-one, pyrazine, pyridazine, pyridone, pyrimidone, oxyindole, pyrazoloquinazoline, pyrazoloquinoline, pyrroloquinazoline, pyrroloquinoline, isoindolin-1-one, isoazaindolin-1-one, isoflavone, benzopyran-4-one, benzimidazolin-2-one, 1,3-dioxo-1,3-dihydroisoindole, 2,3-dihydro-pyrrolopyridin-2-one, 2,3-dihydro-pyrroloquinolin-2-one, imidazol-2-one, benzene, naphthalene, oxazole, isoxazole, isothiazole and quinazolin-4-one. There may be mentioned as preferred groups, quinoline, pyridine, pyrrolopyrimidine, pyrimidine, quinazoline, pyridopyridine, pyridopyrimidine, pyrazolopyrimidine, thiazolopyridine, furopyridine and thienopyrimidine, and as more preferred groups, quinoline, pyridine, pyrrolopyrimidine, thienopyrimidine, pyrimidine and furopyridine, although there is no limitation to these.

In cases where Y is a group with a hetero atom, such as a 5- to 14-membered heterocyclic group, the invention naturally encompasses compounds wherein a substituent such as X or $T^{g1}$ is bonded at the hetero atom.

Production methods for the compounds of the invention will now be described. Various methods may be imagined for production of compounds of the invention represented by general formulas (I) and (II) with synthesis carried out by ordinary chemical synthesis means, and the following are representative examples of methods for their production.

[Representative Production Methods]
[Production Method 1]

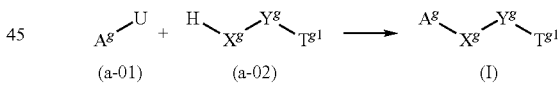

(a-01)    (a-02)    (I)

In formula (a-01), U represents a leaving group. The other symbols have the same definitions as above.

The leaving group may be, for example, a halogen or a trifluoromethanesulfonyl group. There are no particular restrictions on the solvent used for the reaction, though it is preferably one with low reactivity for the starting materials, and as examples there may be mentioned 1-methylpyrrolidone, dimethylformamide, chlorbenzene, and the like. An organic or inorganic base may also be added.

The reaction time may be from 10 minutes to 30 hours, and the reaction temperature from room temperature to reflux temperature.

In the following formulas for the representative production methods Z, $R^{300}$, $R^{301}$, W, $W^{11}$, $R^1$, $R^2$ and Y have the same definitions as above; $X^{sa1}$ is an oxygen or sulfur atom; $R^{sa4}$ has the same definition as $R^2$ above; $R^{sa5}$ is an optionally substituted $C_{1-6}$ alkyl group or optionally substituted $C_{6-14}$ aryl group; compound (a-6) is compound (a-61) or compound (a-62); $R^{sa70}$ is an optionally substituted $C_{1-6}$ alkyl group; $G_1$ is an optionally substituted nitrogen atom or oxygen atom; U is a leaving group; n and s are each integers of 0 to 6; $R^{sa90}$ is a nitro or amino group; $R^{sa82}$ is an amino-protecting group such as t-butoxycarbonyl or benzyl; and $R^{sa1}$, $R^{sa2}$, $R^{sa3}$, $R^{sa50}$, $R^{sa60}$, $R^{sa71}$ and $R^{sa80}$ independently are defined as substituents selected from among the substituents for ring A mentioned above.

[Production Method 2-1]

Representative production method for compound (G2) represented by:

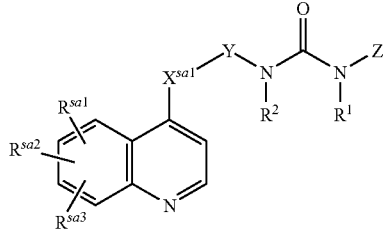

(G2)

(wherein the symbols have the same definitions given above):

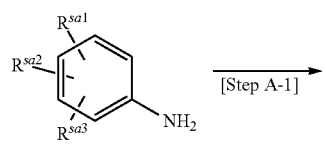

(a-1)

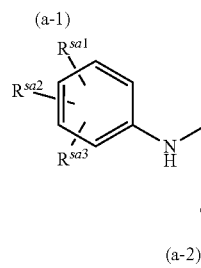

(a-2)

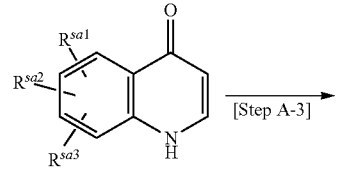

(a-3)

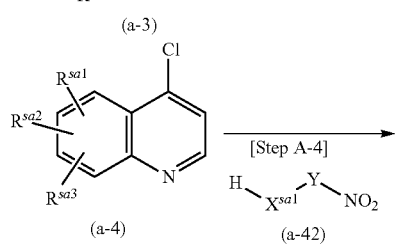

(a-4)

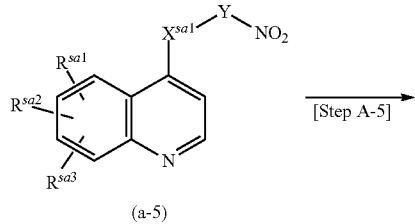

(a-5)

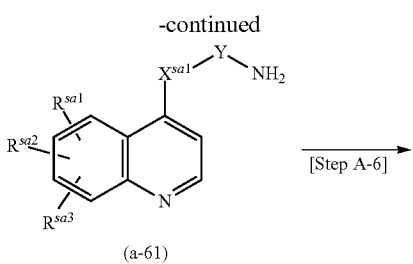

(a-61)

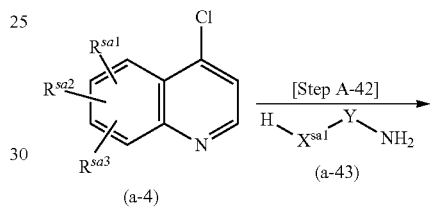

(a-62)

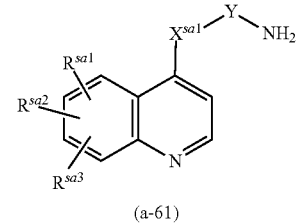

(a-4) (a-43)

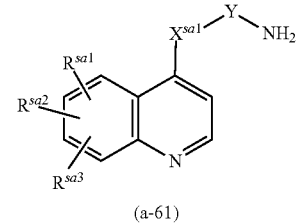

(a-61)

(wherein the symbols have the same definitions given above.)

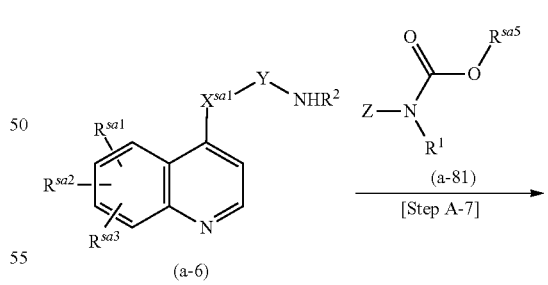

(a-6) (a-81)

[Step A-7]

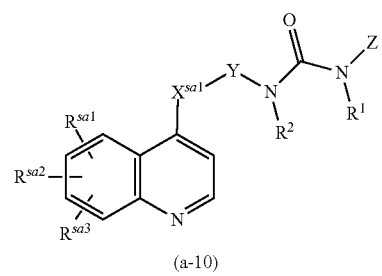

(a-10)

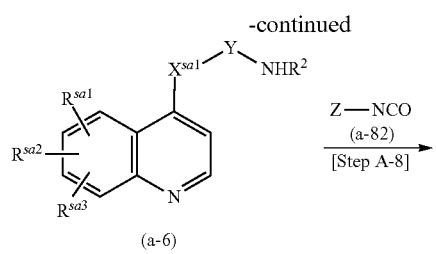

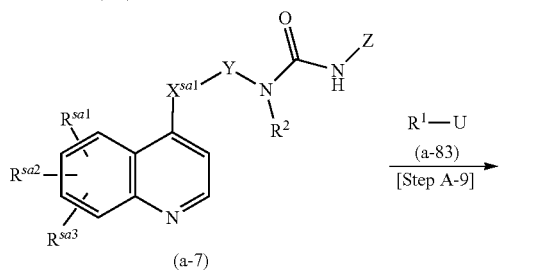

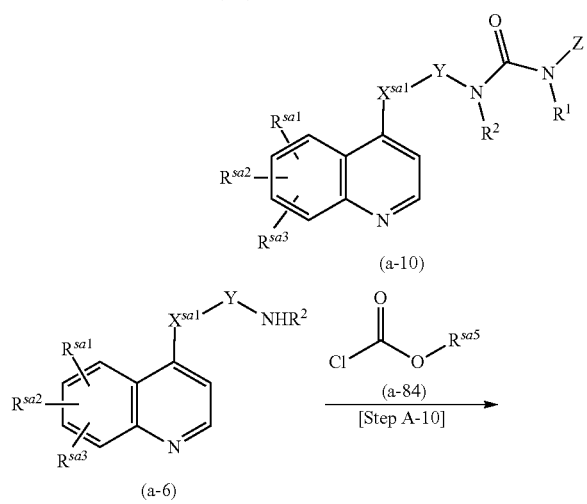

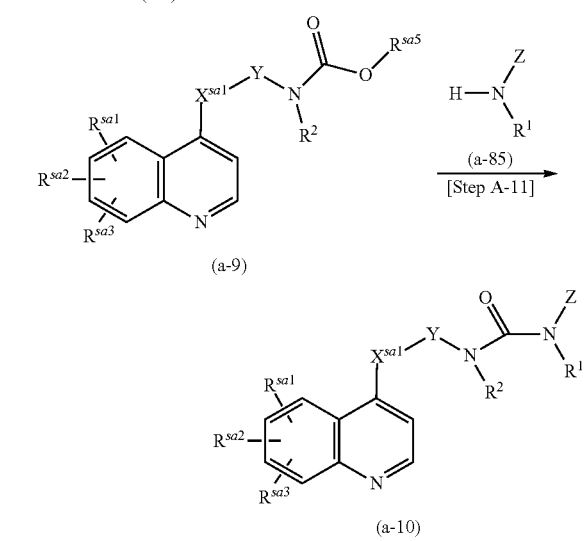

(wherein the symbols have the same definitions given above.)

<Step A-1> <Step A-2>

Steps of cyclization from an aniline derivative (a-1) to a quinolone derivative (a-3). The synthesis may be carried out by the known method reported in Tetrahedron, 53, 1743(1997).

<Step A-1>

Specifically, an aniline derivative having any desired substituents (a-1) may be reacted with an orthoester derivative such as trimethyl orthoformate or triethyl orthoformate and Meldrum acid in an alcohol such as ethanol to obtain compound (a-2). The reaction temperature may be from room temperature to reflux temperature, and the reaction time from 10 minutes to 30 hours.

<Step A-2>

Compound (a-2) is then heated in a mixed solvent of phenyl ether, biphenyl, etc. or Dowtherm A to obtain compound (a-3). The reaction temperature may be from 40° C. to reflux temperature, and the reaction time from 10 minutes to 30 hours.

<Step A-3>

Chlorination step. Compound (a-3) may be reacted with a chlorinating agent such as phosphorus oxychloride or thionyl chloride to obtain compound (a-4). The reaction solvent used may be phosphorus oxychloride, thionyl chloride, benzene, toluene or the like, the reaction temperature from room temperature to reflux temperature, and the reaction time from 10 minutes to 30 hours.

<Step A-4>

Step of reacting compound (a-4) with compound (a-42) to obtain a nitro compound (a-5). The reaction solvent may be 1-methylpyrrolidone, dimethylformamide, chlorbenzene, 2,6-lutidine, or the like. The reaction may be conducted with addition of a base, for example, an organic base such as diisopropylethylamine or 2,6-lutidine, or an inorganic base such as potassium carbonate. The reaction time may be from 10 minutes to 30 hours and the reaction temperature from room temperature to reflux temperature.

<Step A-42>

Step of reacting compound (a-4) with compound (a-43) to obtain an amino compound (a-61). The reaction solvent used may be 1-methylpyrrolidone, dimethylsulfoxide, or the like. A base such as sodium hydride may be used for the reaction. The reaction time may be from 10 minutes to 30 hours and the reaction temperature from room temperature to reflux temperature.

<Step A-5>

Step of reduction reaction of the nitro compound (a-5) to an amino compound (a-61). This may be carried out under conditions commonly employed for reduction of nitro groups to amino groups. Specifically, there may be mentioned reduction with iron-ammonium chloride, iron-hydrochloric acid or iron-acetic acid, or catalytic reduction with palladium hydroxide-hydrogen. The reaction solvent may be methanol, ethanol, tetrahydrofuran, dimethylformamide or the like, and catalytic reduction may be conducted at ordinary pressure or under pressurization. The reaction time may be from 10 minutes to 30 hours and the reaction temperature from room temperature to reflux temperature.

<Step A-6>

Step of alkylation of the amino compound (a-61). The amino compound (a-61) may be reacted with an aldehyde derivative or ketone derivative and the resultant imine reduced with a reducing agent such as sodium cyanoborohydride to obtain compound (a-62).

Alternatively, the amino compound (a-61) may be reacted with an acid chloride derivative or acid anhydride in the presence of a base and then reduced with a reducing agent such as lithium aluminum hydride to obtain compound (a-62).

<Step A-7>

Step of reacting a carbamate derivative (a-81) with the amino derivative (a-61) or compound (a-62) to obtain a urea derivative (a-10). The reaction solvent used may be chloroform, toluene, acetonitrile, dimethylformamide, dimethylsulfoxide or the like. The reaction time may be from 10 minutes to 30 hours and the reaction temperature from below freezing to reflux temperature. The reaction may also be conducted with addition of an organic base such as sodium hydride, triethylamine or pyridine or an inorganic base such as potassium carbonate or sodium carbonate.

<Step A-8>

Step of reacting an isocyanate derivative (a-82) with the amino derivative (a-61) or compound (a-62) to obtain compound (a-7). The reaction solvent used may be chloroform, toluene, acetonitrile, dimethylformamide, dimethylsulfoxide or the like. The reaction time may be from 10 minutes to 30 hours and the reaction temperature from below freezing to reflux temperature. The reaction may also be conducted with addition of an organic base such as sodium hydride, triethylamine or pyridine or an inorganic base such as potassium carbonate or sodium carbonate.

<Step A-9>

Step of reacting compound (a-7) and compound (a-83) in the presence of a base such as pyridine to obtain a urea derivative (a-10). The reaction solvent used may be dimethylsulfoxide, dimethylformamide, tetrahydrofuran or the like, the reaction time from 10 minutes to 30 hours and the reaction temperature from 0° C. to reflux temperature.

<Step A-10>

Step of reacting a carbamating reagent (a-84) such as phenylchloroformate with the amino compound (a-61) or compound (a-62) to obtain a carbamate derivative (a-9). The reaction may be conducted using a base such as pyridine. The reaction solvent used may be dimethylsulfoxide, dimethylformamide, tetrahydrofuran or the like, the reaction time from 10 minutes to 30 hours, and the reaction temperature from 0° C. to reflux temperature.

<Step A-11>

Step of reacting an amine derivative (a-85) with the carbamate derivative (a-9) to obtain a urea derivative (a-10). The reaction may be conducted using a base such as triethylamine. The reaction solvent used may be dimethylsulfoxide, dimethylformamide or the like, the reaction time from 10 minutes to 30 hours, and the reaction temperature from room temperature to reflux temperature.

[Production Method 2-2]

Alternative production method to compound (a-10):

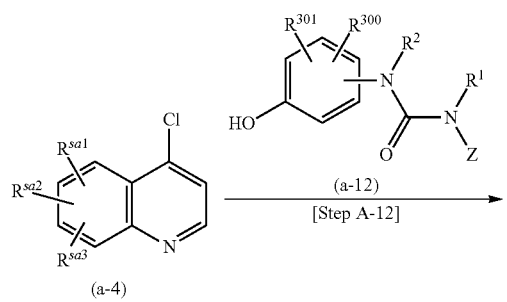

(a-4)

(a-12)

[Step A-12]

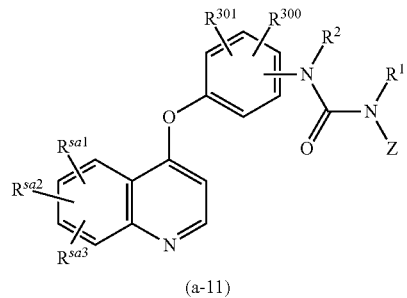

(a-11)

(wherein the symbols have the same definitions given above.)

<Step A-12>

Step of reacting a phenol derivative (a-12) having urea as a part of its structure, with a 4-chloroquinoline derivative (a-4) to obtain the target compound (a-11) by one direct step. The reaction solvent used may be 1-methylpyrrolidone, dimethylformamide, chlorbenzene, or the like. The reaction may be conducted with addition of a suitable base, for example, an organic base such as diisopropylethylamine, or an inorganic base such as potassium carbonate or sodium hydrid. The reaction time may be from 10 minutes to 30 hours and the reaction temperature from room temperature to reflux temperature.

[Production Method 2-3]

Alternative production method to compound (a-5) and compound (a-61):

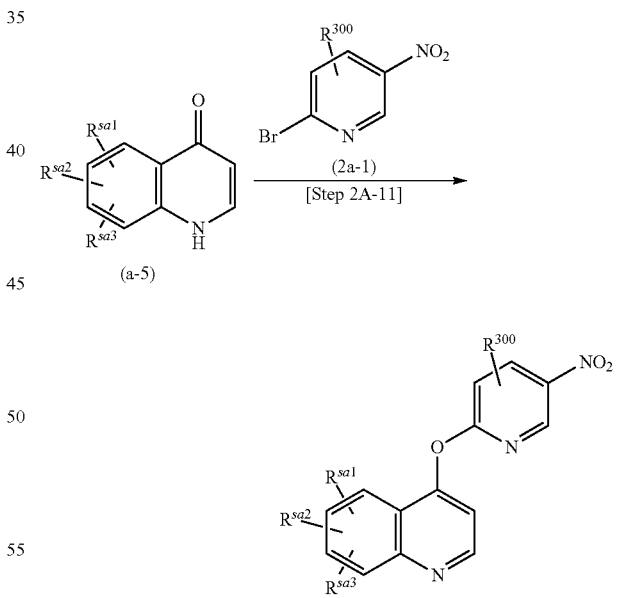

(a-5)

(2a-1)

[Step 2A-11]

(2a-2)

(a-5)

[Step 2A-2]

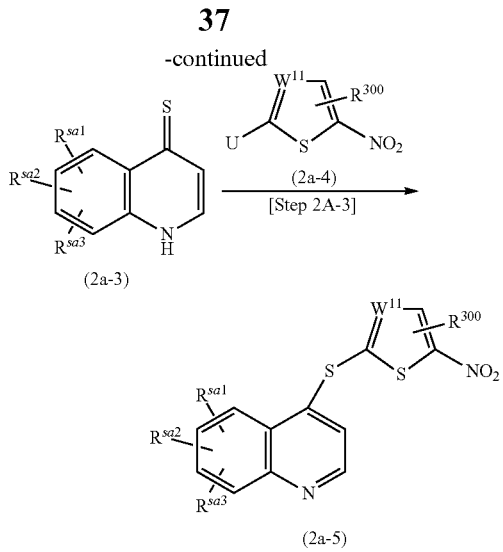

(wherein the symbols have the same definitions given above.)
<Step 2A-1>
Step of reacting a pyridine derivative (2a-1) with compound (a-5) to obtain compound (2a-2). The reaction may be conducted using a base such as potassium carbonate. The reaction solvent used may be dimethylformamide or the like, the reaction time from 10 minutes to 30 hours and the reaction temperature from room temperature to reflux temperature.
<Step 2A-2>
Step of converting a quinolone (a-5) to a thioquinolone (2a-3). A sulfide reagent such as sodium sulfide, phosphorus pentasulfide or the like may be reacted with the quinolone (a-5) to obtain the corresponding thioquinolone. The reaction solvent used may be diglyme, the reaction temperature from room temperature to reflux temperature, and the reaction time from 10 minutes to 30 hours.
<Step 2A-3>
Step of reacting the thioquinolone (2a-3) with compound (2a-4) to obtain compound (2a-5). The reaction solvent used may be dimethylformamide or the like, the reaction temperature from room temperature to reflux temperature, and the reaction time from 10 minutes to 30 hours. An appropriate base such as pyridine may also be used.

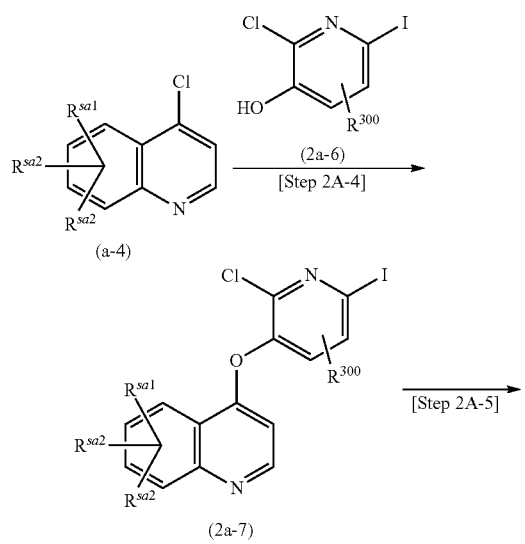

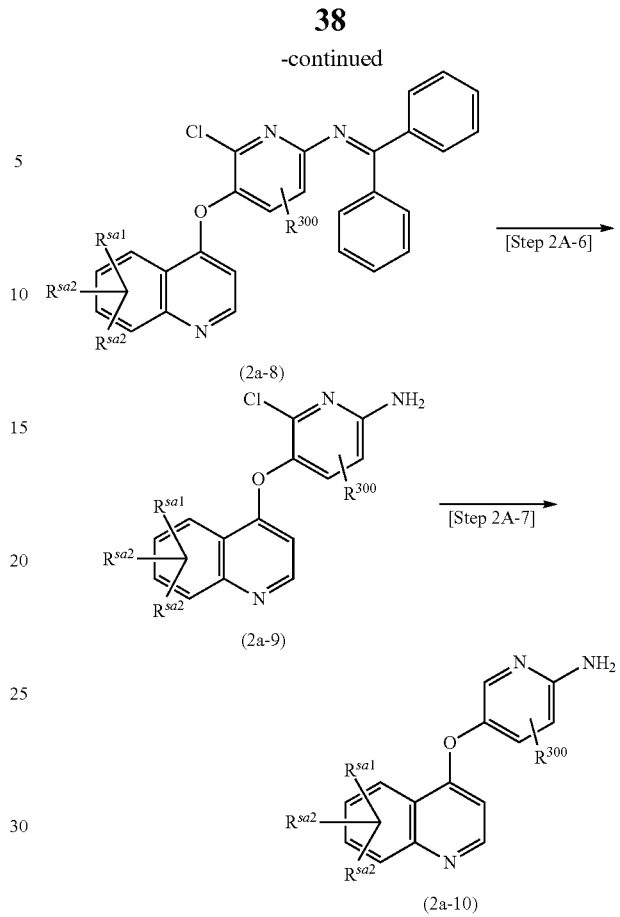

(wherein the symbols have the same definitions given above.)
<Step 2A-4>
Step of reacting a hydroxypyridine derivative (2a-6) with compound (a-4) to obtain compound (2a-7). The solvent used may be 1-methylpyrrolidone, dimethylformamide, chlorbenzene, or the like. The reaction may be conducted with addition of a suitable base, for example, an organic base such as diisopropylethylamine, or an inorganic base such as potassium carbonate. The reaction time may be from 10 minutes to 30 hours, and the reaction temperature from room temperature to reflux temperature.
<Step 2A-5>
Step of palladium coupling reaction between compound (2a-7) and an imine derivative to obtain compound (2a-8). The reaction may be conducted using a solvent such as toluene, a catalyst, for example, a palladium derivative such as tris(dibenzylideneacetone)dipalladium(0) or a phosphine derivative such as 2,2'-bis(diphenylphosphino)-1,1'-binaphthyl), and a base such as t-butoxypotassium. The reaction temperature may be from about 50° C. to reflux temperature, and the reaction time from about 1 hour to 10 hours.
<Step 2A-6>
Step of obtaining an amino derivative (2a-9) from compound (2a-8). The reaction is conducted using ethanol, water or the like, with the action of an acid such as hydrochloric acid. The reaction temperature may be from 0° C. to about 100° C., and the reaction time from 10 minutes to about 10 hours.
<Step 2A-7>
Step of dechlorination of compound (2a-9) to obtain compound (2a-10). This may be accomplished by catalytic reduction or the like using palladium carbon-hydrogen. The reaction solvent may be methanol, ethanol, tetrahydrofuran, or the like, and catalytic reduction may be conducted at ordinary pressure or under pressurization. Triethylamine or the like may also be used as a base. The reaction time may be from 10 minutes to 30 hours and the reaction temperature from room temperature to reflux temperature.

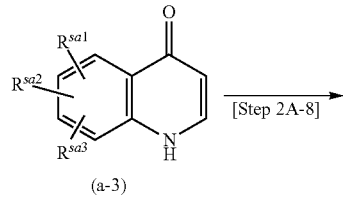
(a-3)

[Step 2A-8]

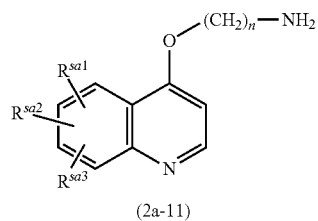
(2a-11)

(wherein the symbols have the same definitions given above.)

<Step 2A-8>

A step of converting a quinolone compound (a-3) into a 4-aminoalkoxyquinoline (2a-11). An N-alkylphthalimide derivative may be reacted with compound (a-3) and deprotection accomplished with hydrazine hydrate or the like to obtain the target compound (2a-11). The solvent used may be dimethylformamide, tetrahydrofuran or the like, the reaction temperature from room temperature to reflux temperature, and the reaction time from 10 minutes to 30 hours. Potassium carbonate or the like may also be used as the base.

[Production Method 2-4]

Alternative production method to compound (a-4):

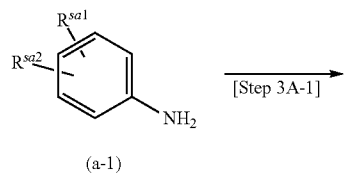
(a-1)

[Step 3A-1]

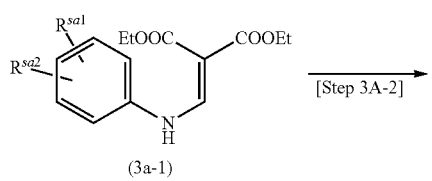
(3a-1)

[Step 3A-2]

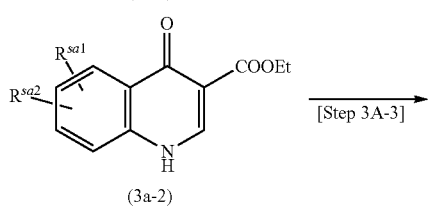
(3a-2)

[Step 3A-3]

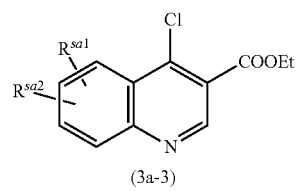
(3a-3)

(wherein the symbols have the same definitions given above.)

<Step 3A-1>

Step of obtaining an enamine (3a-1). Diethyl ethoxymethylenemalonate may be reacted with an aniline derivative (a-1) to obtain compound (3a-1). The reaction proceeds without a solvent. The reaction temperature may be about 100° C., and the reaction time from 30 minutes to several hours.

<Step 3A-2>

Step of cyclization. Compound (3a-1) may be heated from about 200° C. to about 260° C. in a biphenyl ether/biphenyl mixed solvent for cyclization to obtain the target compound (3a-2). The reaction time may be from 30 minutes to 10 hours.

<Step 3A-3>

Step of chlorination. The same procedure as in <Step A-3> may be carried out to obtain the chlorinated compound (3a-3) from compound (3a-2).

[Production Method 3]

Representative production method for compound (G3) represented by:

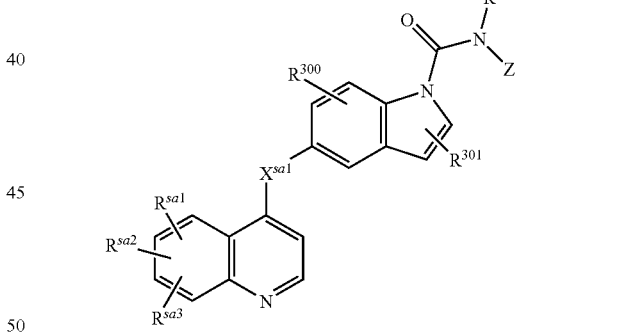
(G3)

(wherein the symbols have the same definitions given above)

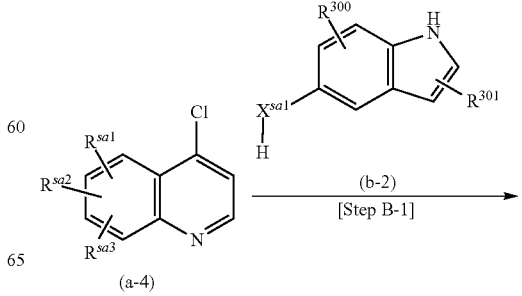
(a-4)

(b-2)
[Step B-1]

-continued

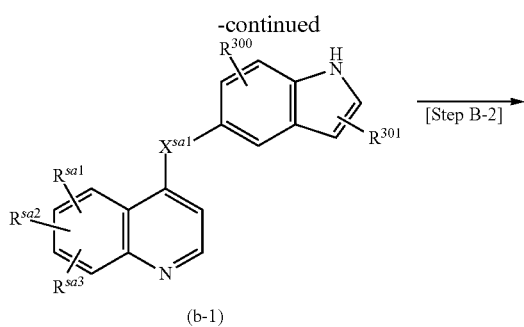

(b-1)

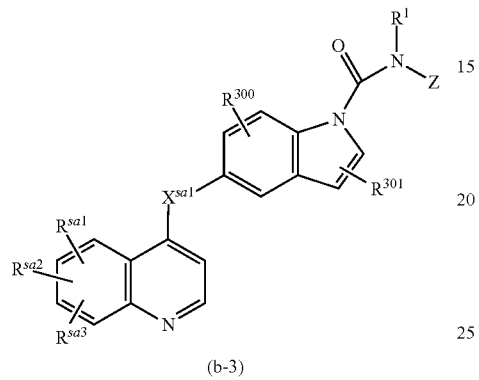

(b-3)

(wherein the symbols have the same definitions given above.)

<Step B-1>

Step of reacting compound (a-4) with an indole derivative (b-2) to obtain compound (b-1). The reaction may be conducted under the same conditions as for <Step A-4> above.

<Step B-2>

Step of obtaining a urea derivative (b-3) from compound (b-1). The reagent used may be the aforementioned isocyanate derivative (a-82) or carbamate derivative (a-81). The reaction may be conducted under the same conditions as for <Step A-7>, <Step A-8> and <Step A-9> above.

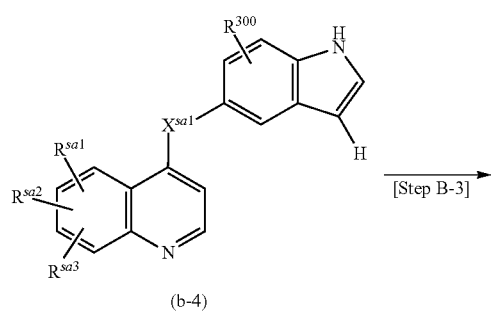

(b-4)

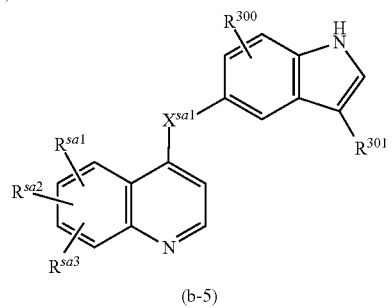

(b-5)

(wherein the symbols have the same definitions given above.)

<Step B-3>

Step of introducing a substituent at the 3-position of the indole. Compound (b-4) may be reacted with a halogenating agent such as N-chlorosuccinimide or N-bromosuccinimide, or with phosphorus oxychloride or a thionyl chloride/dimethylformamide mixed reagent to obtain compound (b-5). The reaction solvent used may be 2-propanol, tetrahydrofuran, acetonitrile, dimethylformamide or the like, the reaction temperature from 0° C. to reflux temperature, and the reaction time from 10 minutes to 30 hours.

[Production Method 4-1]

Representative production method for compound (G4-1) represented by:

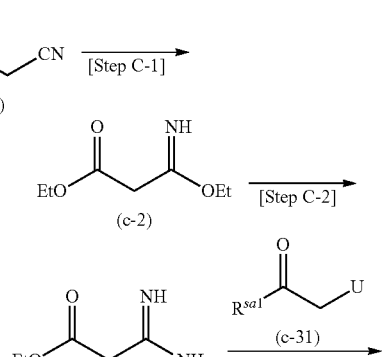

(G4-1)

(wherein the symbols have the same definitions given above)

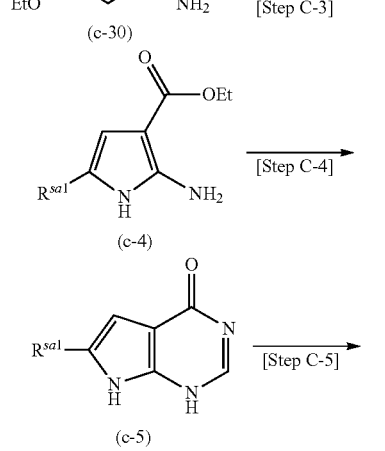

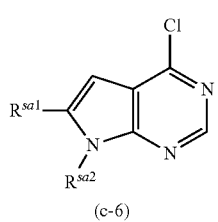

(c-6)

(wherein the symbols have the same definitions given above.)

General formula (G4-1) may be synthesized according to the process described in WO97/02266, PCT/EP96/02728 or Journal of Medicinal Chemistry, 1996, Vol. 39, No. 12, 2285-2292.

<Step C-1>

Step of synthesizing an imidate. Ethyl cyanoacetate may be reacted with hydrochloric acid in a solvent such as dioxane to obtain the target imidate compound (c-2). The reaction temperature is preferably from near 0° C. to room temperature, and the reaction time may be from a few hours to several days.

<Step C-2>

Step of synthesizing an amidine. Compound (c-2) may be reacted with ammonia gas in ethanol to obtain the target amidine compound (c-3). The reaction temperature may be from near 0° C. to room temperature, and the reaction time may be several hours.

<Step C-3>

Step of synthesizing a pyrrole derivative. Compound (c-3) may be reacted with an α-haloketone derivative (c-31) in ethanol to obtain the target pyrrole derivative (c-4). The reaction temperature may be from room temperature to reflux temperature, and the reaction time from a few hours to several days.

<Step C-4>

Ring-closing reaction of pyrrole ring to pyrrolopyrimidine ring. Compound (c-4) may be reacted with formamide and formic acid to obtain the target compound (c-5). The solvent used may be dimethylformamide. The reaction temperature may be from near 100° C. to reflux temperature, and the reaction time from a few hours to several days.

<Step C-5>

Step of chlorination. The same procedure as in <Step A-3> may be carried out to obtain the target chlorinated compound (c-6).

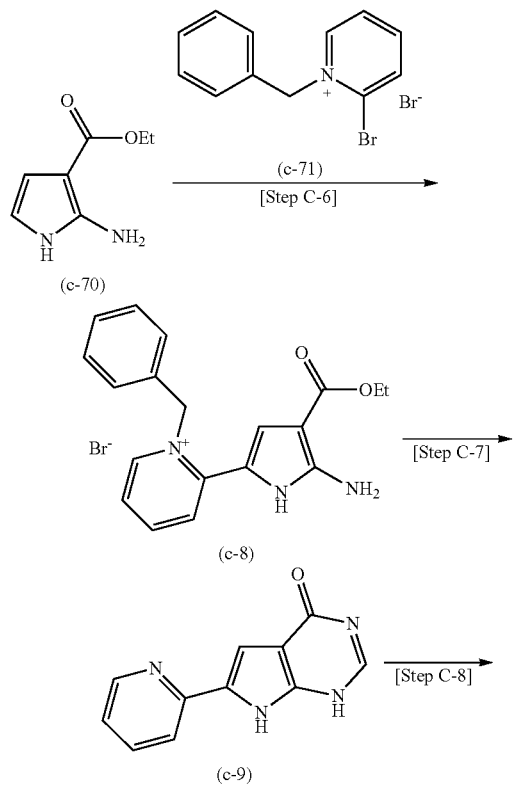

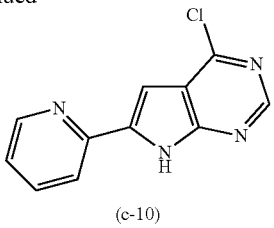

(c-10)

(wherein the symbols have the same definitions given above.)

<Step C-6>

Reaction for introduction of substituent at 5-position of a pyrrole derivative (c-70). Compound (c-70) may be reacted with compound (c-71) in the presence of 2,6-lutidine, in darkness under a nitrogen atmosphere, to obtain the target compound (c-8). The reaction solvent used may be dichloromethane or the like, the reaction temperature from 0° C. to room temperature, and the reaction time from 1 hour to 30 hours.

<Step C-7>

The same procedure as in <Step C-4> may be carried out to obtain compound (c-9).

<Step C-8>

The same procedure as in <Step A-3> may be carried out to obtain compound (c-10).

[Production Method 4-2]

Representative production method for compound (G4-2) represented by:

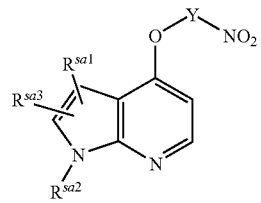

(G4-2)

(wherein the symbols have the same definitions given above.)

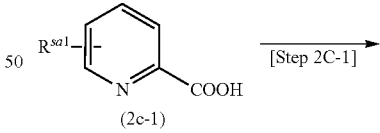

(2c-1)

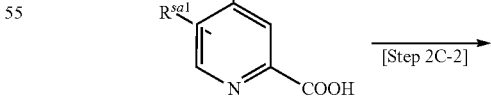

(2c-2)

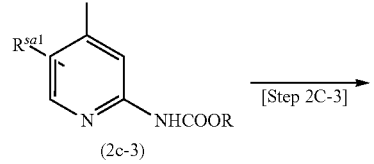

(2c-3)

-continued

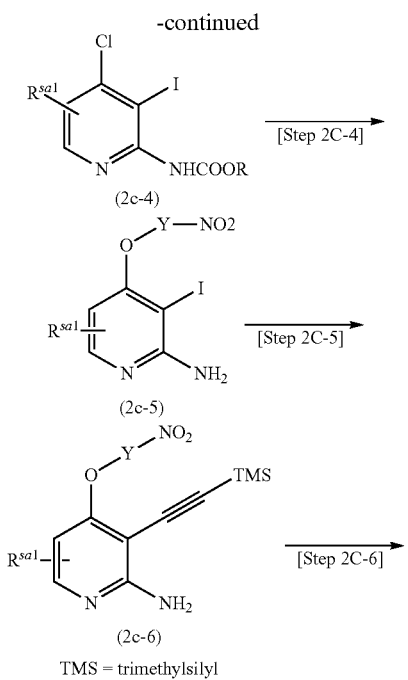

(wherein the symbols have the same definitions given above.)

<Step 2C-1>

Step of chlorination. Compound (2c-1) may be reacted with thionyl chloride to obtain the target compound (2c-2). The reaction solvent used may be thionyl chloride, the reaction temperature may be reflux temperature, and the reaction time from a few hours to several days.

<Step 2C-2>

Rearrangement from carboxylic acid to a carbamate derivative (2c-3). The carboxylic acid derivative (2c-2) may be reacted with tert-butanol, benzyl alcohol, trimethylsilyl alcohol or the like in the presence of diphenylphosphoryl azide and triethylamine to obtain the target carbamate derivative (2c-3). The reaction solvent used may be tert-butanol, benzyl alcohol, dimethylformamide, toluene or the like, the reaction temperature from room temperature to reflux temperature, and the reaction time from 10 minutes to 30 hours.

<Step 2C-3>

Iodination reaction. The target compound (2c-4) may be obtained by using a base to generate an anion at the 3-position of pyridine, reacting iodine therewith to obtain an iodinated compound, and then conducting decarbamating reaction. The reaction solvent for the iodination may be tetrahydrofuran, diethyl ether or the like, the reaction temperature from −78° C. to room temperature, and the reaction time from 10 minutes to 30 hours. The base used may be n-butyllithium or the like, and a base such as N,N,N',N'-tetramethylethenediamine may also be added as appropriate. The reaction solvent used for the decarbamating reaction may be water, an alcohol or the like, as an acid there may be used aqueous hydrobromic acid, aqueous hydrochloric acid or the like, the reaction temperature may be from room temperature to reflux temperature, and the reaction time may be from 1 minute to several hours.

<Step 2C-4>

The same procedure as in <Step A-4> may be carried out to obtain the target compound (2c-5).

<Step 2C-5>

Coupling reaction between the iodo compound (2c-5) and an acetylene derivative. The iodo compound may be reacted with (trimethyl)acetylene in the presence of tetrakis(triphenylphosphine)palladium, copper(I)iodide or the like to obtain the target compound (2c-6). The reaction solvent used may be dimethylformamide or the like, the reaction temperature from room temperature to reflux temperature, and the reaction time from 10 minutes to 30 hours.

<Step 2C-6>

Cyclization reaction. Compound (2c-6) may be heated in the presence of copper (I) iodide to obtain the target cyclized compound (2c-7). The reaction solvent used may be dimethylformamide or the like, the reaction temperature from 80° C. to reflux temperature, and the reaction time from 5 minutes to 10 hours.

[Production Method 4-3]

Alternative production method to compound (2c-7) in Production Method 4-2:

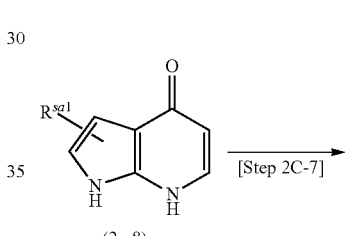

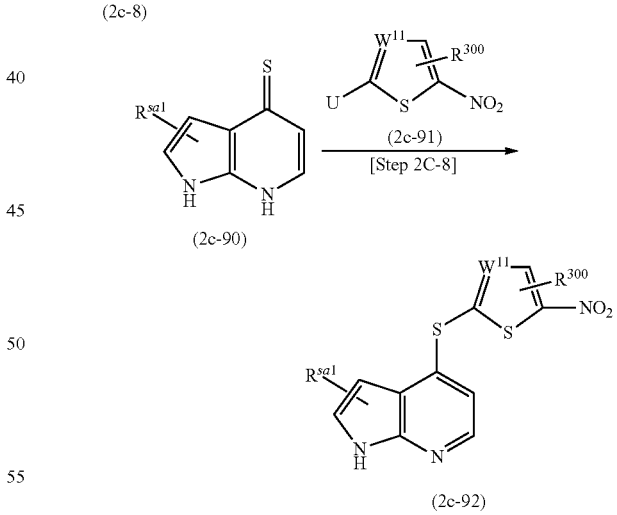

(wherein the symbols have the same definitions given above.)

<Step 2C-7>

Conversion of ketone (2c-8) to thioketone (2c-90). Synthesis may be carried out by the same procedure as in <Step 2A-2>.

<Step 2C-8>

Synthesis may be carried out by the same procedure as in <Step 2A-3>.

[Production Method 5-1]

Representative production method for compound (G5-1) represented by:

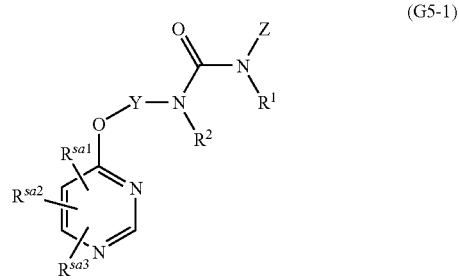

(wherein the symbols have the same definitions given above.)

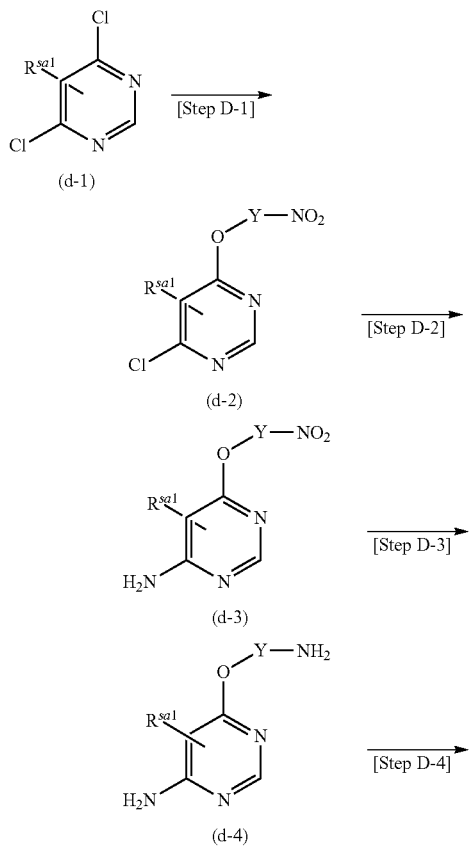

(wherein the symbols have the same definitions given above.)

<Step D-1>
The same procedure as in <Step A-4> may be carried out to obtain the target compound (d-2).

<Step D-2>
Step of amination of chloro group. The 2-chloropyrimidine derivative (d-2) may be reacted with ammonia to obtain the target amino compound (d-3). The reaction solvent used may be ethanol, tetrahydrofuran or the like, the reaction temperature from 0° C. to reflux temperature, and the reaction time from 10 minutes to 30 hours.

<Step D-3>
Reduction of nitro compound (d-3) to amino compound (d-4). The same procedure as in <Step A-5> may be carried out to obtain the target amino compound (d-4).

<Step D-4>
The same procedure as in <Step A-7> may be carried out to obtain the target urea compound (d-5).

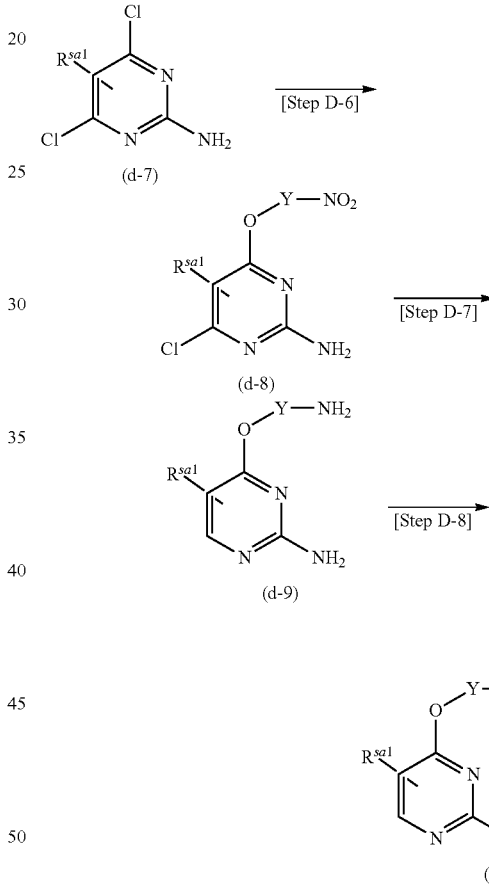

(wherein the symbols have the same definitions given above.)

<Step D-6>
The same procedure as in <Step A-4> may be carried out to obtain the target compound (d-8).

<Step D-7>
Step of dechlorination and nitro group reduction. The target compound (d-9) may be obtained under common catalytic reduction conditions with palladium hydroxide-hydrogen or the like. The reaction solvent used may be methanol, ethanol, tetrahydrofuran, dimethylformamide or the like, and catalytic reduction may be conducted at ordinary pressure or under pressurization. The reaction time may be from 10 minutes to 30 hours and the reaction temperature from room temperature to reflux temperature.

<Step D-8>

The same procedure as in <Step A-7> may be carried out to obtain the target urea compound (d-10).

[Production Method 5-2]

Representative production method for compound (G5-2) represented by:

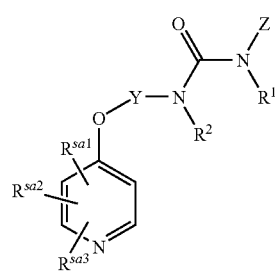
(G5-2)

(wherein the symbols have the same definitions given above.)

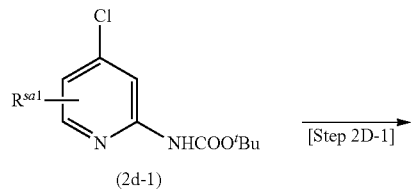
(2d-1)

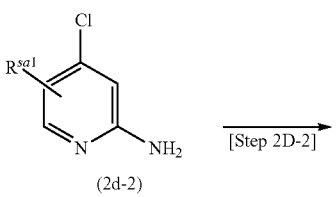
(2d-2)

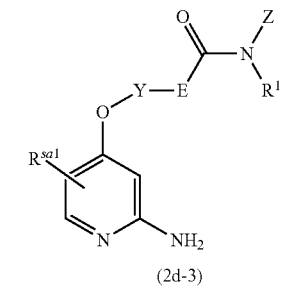
(2d-3)

(wherein the symbols have the same definitions given above.)

<Step 2D-1>

Decarbamating reaction. Compound (2d-1) may be reacted with an acid to obtain the target amine derivative (2d-2). The solvent used may be water, dioxane, tetrahydrofuran, methanol, ethanol or the like, the reaction temperature from room temperature to reflux temperature and the reaction time from 10 minutes to 30 hours. The acid used may be hydrochloric acid, hydrobromic acid, trifluoroacetic acid, or the like.

<Step 2D-2>

Compound (2d-2) may be used in the same procedure from <Step D-6> to <Step D-8> of Production Method 5-1 to obtain a urea derivative (2d-3).

[Production Method 6]

Alternative production method for compounds (G6-1), (G6-2) and (G6-3) represented by:

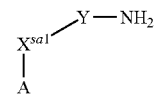
(G6-1)

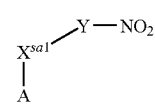
(G6-2)

(G6-3)

(wherein the symbols have the same definitions given above.)

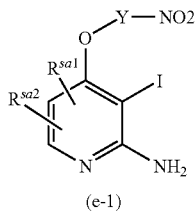
(e-1)

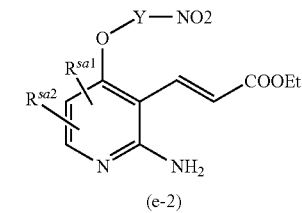
(e-2)

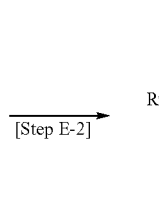
(e-3)

-continued

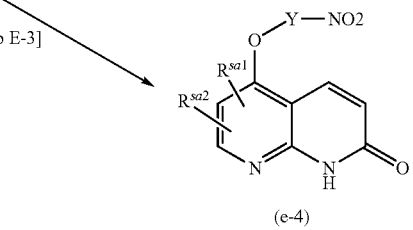

(e-4)

(wherein the symbols have the same definitions given above.)

<Step E-1>

Coupling reaction between iodo compound and ethyl acrylate. Compound (e-1) may be reacted with ethyl acrylate in the presence of a catalyst such as palladium acetate and a tertiary amine such as tributylamine, to obtain the target compound (e-2). The reaction solvent used may be dimethylformamide or the like, the reaction temperature from 100° C. to reflux temperature, and the reaction time from 5 minutes to 30 hours.

<Step E-2>

Reduction of double bond, followed by cyclization and nitro group reduction. Compound (e-2) may be reacted in the presence of palladium carbon-hydrogen for reduction of the double bond, cyclization and nitro group reduction. The reaction solvent used may be methanol, ethanol, tetrahydrofuran, dimethylformaldehyde or the like, and catalytic reduction may be conducted at ordinary pressure or under pressurization. The reaction time may be from 10 minutes to 30 hours and the reaction temperature from room temperature to reflux temperature.

<Step E-3>

Isomerization of double bond by light irradiation followed by cyclization. The reaction solvent used may be methanol or the like, with light irradiation performed in the presence of 2'-acetonaphthone to obtain the target compound (e-4). The reaction time may be from 10 minutes to 30 hours.

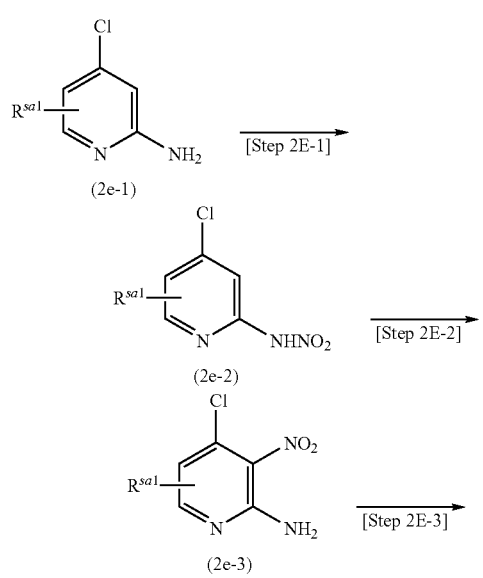

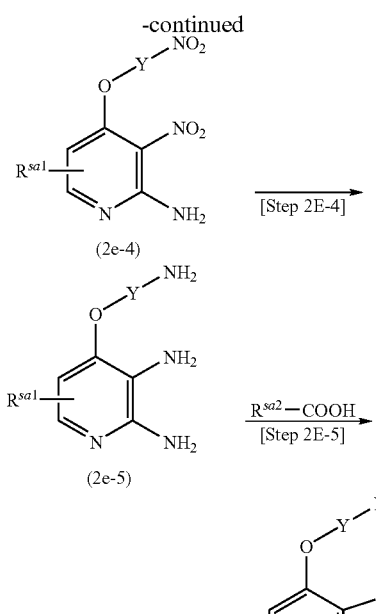

(wherein the symbols have the same definitions given above.)

<Step 2E-1>

Nitration reaction. Compound (2e-1) may be reacted with sulfuric acid and fuming nitric acid to obtain the target compound (2e-2). The reaction solvent used may be sulfuric acid, fuming nitric acid or the like, the reaction temperature from 0° C. to room temperature, and the reaction time from 10 minutes to 30 hours.

<Step 2E-2>

Rearrangement of nitro group. Compound (2e-2) may be reacted with sulfuric acid to obtain the target compound (2e-3). The reaction solvent used may be sulfuric acid or the like, the reaction temperature from 0° C. to reflux temperature, and the reaction time from 10 minutes to 30 hours.

<Step 2E-3>

The target nitro compound (2e-4) may be obtained by nucleophilic substitution of compound <2e-3> using any desired nitro group-containing nucleophilic agent and 1-methylpyrrolidone, dimethylformamide, chlorbenzene or the like as the reaction solvent. The reaction may be conducted with addition of an appropriate base, for example, an organic base such as diisopropylethylamine, or an inorganic base such as potassium carbonate. The reaction time may be from 10 minutes to 30 hours and the reaction temperature from room temperature to reflux temperature.

<Step 2E-4>

Reduction of nitro group to amino group. The same procedure as in <Step A-5> may be carried out to obtain the target compound (2e-5).

<Step 2E-5>

Condensation of a carboxylic acid and the diamine (2e-5). The diamine compound (2e-5) may be reacted with a carboxylic acid to obtain the target compound (2e-6). The reaction solvent used may be pyrophosphoric acid or the like, the reaction temperature from room temperature to reflux temperature, and the reaction time from 10 minutes to 30 hours. Polyphosphoric acid, phosphorus pentoxide or the like may be used as a dehydrating agent.

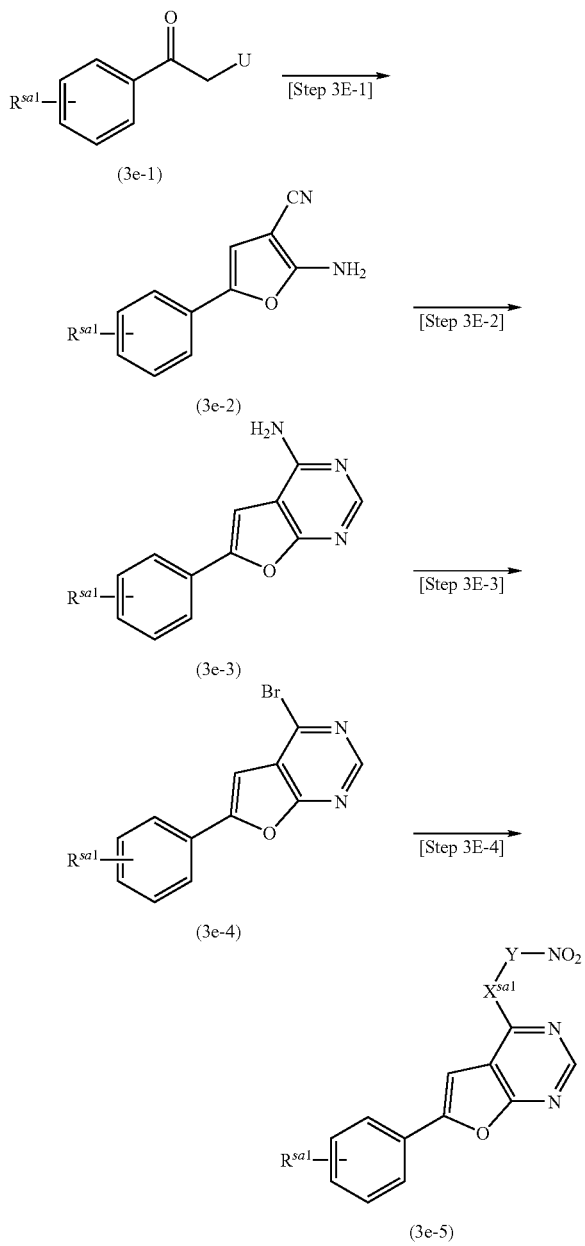

(wherein the symbols have the same definitions given above.)

<Step 3E-1>

This synthesis may be carried out according to the process described in Journal of Heterocyclic Chemistry, 35, 1313 (1998). An α-haloketone derivative (3e-1) may be reacted with malononitrile to synthesize compound (3e-2). The reaction solvent used may be dimethylformamide or the like, the reaction temperature from 0° C. to reflux temperature, and the reaction time from 30 minutes to about 30 hours. Diethylamine may be used as the base.

<Step 3E-2>

Step of forming furopyrimidine ring. Compound (3e-2) may be heated at about 200° C. in formamide with addition of acetic anhydride to obtain the target compound (3e-3). The reaction time may be about a few hours.

<Step 3E-3>

Bromination reaction. Compound (3e-3) may be reacted with dibromomethane and isoamyl nitrite to obtain the target bromo compound (3e-4). The reaction solvent used may be dibromomethane, the reaction temperature from room temperature to reflux temperature, and the reaction time from 30 minutes to 30 hours.

<Step 3E-4>

The same procedure as in <Step A-4> may be carried out to obtain compound (3e-5).

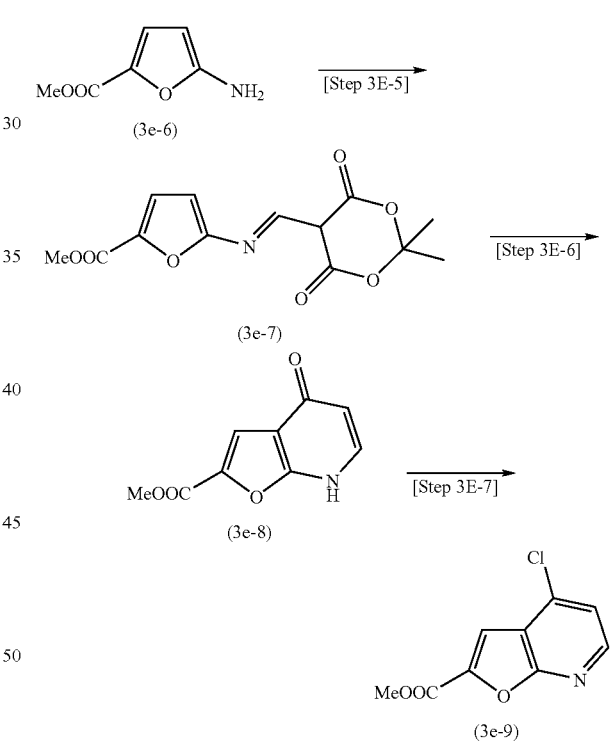

(wherein the symbols have the same definitions given above.)

<Step 3E-5>

The same procedure as in <Step A-1> may be carried out to obtain compound (3e-7).

<Step 3E-6>

The same procedure as in <Step A-2> may be carried out to obtain compound (3e-8).

<Step 3E-7>

The same procedure as in <Step A-3> may be carried out to obtain compound (3e-9).

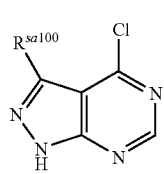

(4e-1)

(wherein the substituent $R^{sa100}$ is optionally substituted phenylamino or optionally substituted benzyl amino). Synthesis of this compound is described in Journal of Medicinal Chemistry, 40, 3601(1997).

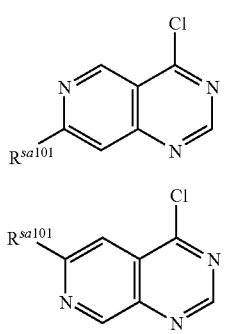

(4e-2)

(4e-3)

(wherein the substituent $R^{sa101}$ is fluorine, optionally substituted amino, optionally substituted $C_{1-6}$ alkoxy or optionally substituted $C_{2-7}$ acylamino). Synthesis of this compound is described in Journal of Medicinal Chemistry, 39, 1823(1996).

[Production Method 7]

Representative production method for compound (II) represented by:

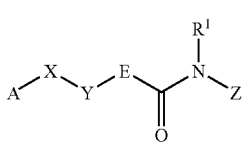

(II)

(wherein the symbols have the same definitions given above.)

(1) Compound (a-01) represented by the formula:

(a-01)

(wherein the symbols have the same definitions given above) may be synthesized utilizing common hitherto known organic reactions. As compound (a-01) there may be used compounds (c-6), (c-10), (2c-4), (d-1), (d-2), (d-7), (3e-4), (2e-4), (3e-9), (4e-1), (4e-2) or (4e-3) described in the aforementioned production methods 4-1, 4-2, 5-1, 5-2 and 6.

Compound (II) may be produced using compound (a-01) under the reaction conditions described in <Step A-4> to <Step A-11> in Production Method 2-1 above, the reaction conditions described in Production Method 2-2 above, the reaction conditions described in Production Method 2-3 above and the reaction conditions described in Production Method 3 above.

(2)

(a-03)

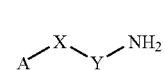

(a-04)

(wherein the symbols have the same definitions given above.)

The urea derivative (II) may be obtained using compound (a-03) or (a-04) with an appropriate combination of the conditions in <Step A-5> to <Step A-11> in Production Method 2-1. Specifically, compound (a-03) or (a-04) may be, for example, (2c-7), (2c-92), (e-4), (3e-5), (e-3) or (e-6).

[Production Method 8-1]

Representative synthesis method for compound represented by:

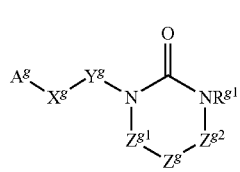

(Ia)

(wherein the symbols have the same definitions given above.)

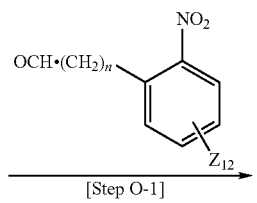

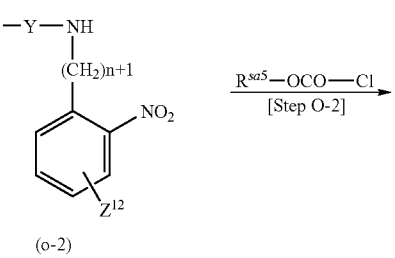

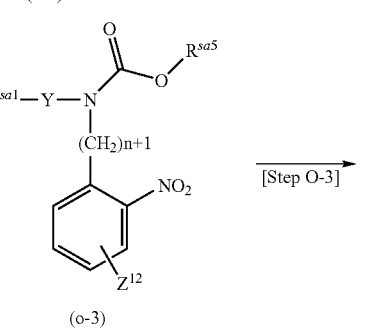

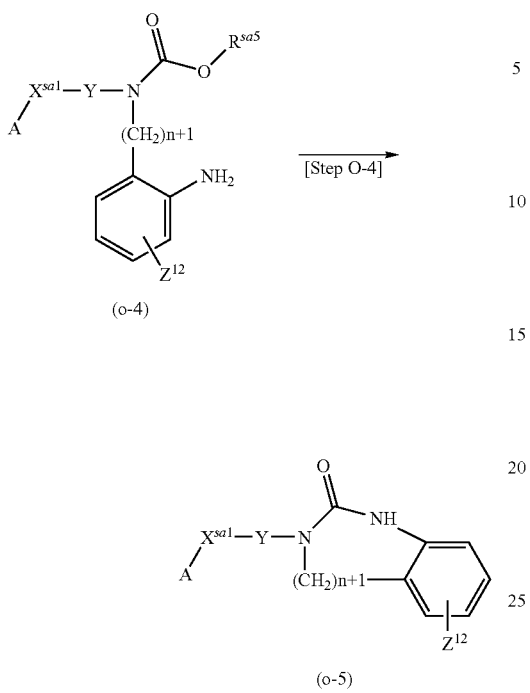

(o-4)

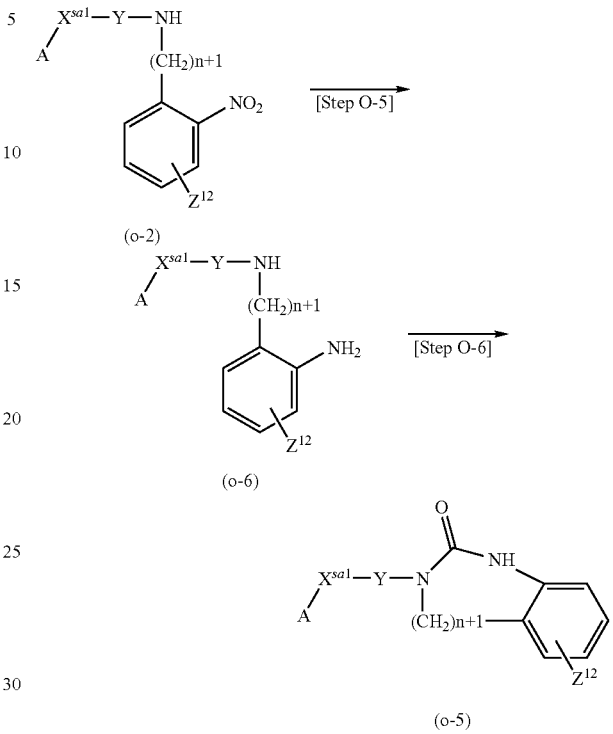

(o-5)

(wherein the symbols have the same definitions given above.)

<Step O-1>

Step of reductive amination. An aldehyde derivative may be reductively reacted with compound (o-1) to obtain the target compound (o-2). The reaction solvent used may be acetic acid, tetrahydrofuran, dichloroethane, dichloromethane, methanol or the like, the reaction temperature from 0° C. to reflux temperature, and the reaction time from 30 minutes to 30 hours. The reducing agent used may be sodium triacetoxyborohydride, sodium borohydride, or the like.

<Step O-2>

Carbamating step. Compound (o-2) may be reacted with a chloroformate derivative to obtain the target compound (o-3). The reaction solvent used may be tetrahydrofuran, dichloromethane or the like, the reaction temperature from 0° C. to reflux temperature, and the reaction time from 30 minutes to 30 hours. Pyridine, triethylamine or the like may be used as the base.

<Step O-3>

Step of reducing nitro group to amino group. The same procedure as in <Step A-5> may be carried out to obtain compound (o-4).

<Step O-4>

Intramolecular cyclization step. The target compound (o-5) may be obtained by reacting the amino group and carbamate group in the molecule. The reaction solvent used may be tetrahydrofuran, dimethylformamide, dimethylsulfoxide, acetonitrile or the like, the reaction temperature from 0° C. to reflux temperature, and the reaction time from 30 minutes to 30 hours. Sodium hydride, pyridine, triethylamine or the like may be used as the base.

[Production Method 8-2]

Alternative production method for compound (o-5).

(wherein the symbols have the same definitions given above.)

<Step O-5>

Step of reducing nitro group to amino group. The same procedure as in <Step A-5> may be carried out to obtain the target diamine compound (o-6).

<Step O-6>

Intramolecular cyclization step. The target compound (o-5) may be obtained by condensing the two amino groups in the molecule using phosgene, triphosgene, 1-ethyl-3-(3-dimethylaminopropyl)carbodiimide hydrochloride, (1H-1,2,3-benzotriazol-1-yloxy) (tri(dimethylamino))phosphonium hexafluorophosphate, 1-ethyl-3-(3-dimethylaminopropyl) carbodiimide hydrochloride, 1,1-carbonyldiimidazole or the like as the condensing agent. The reaction solvent used may be tetrahydrofuran, dimethylformamide, dimethylsulfoxide, acetonitrile or the like, the reaction temperature from 0° C. to reflux temperature, and the reaction time from 30 minutes to 30 hours. Sodium hydride, pyridine, triethylamine or the like may be appropriately used as the base.

[Production Method 9]

Conversion of substituent on ring A of compound (II) represented by

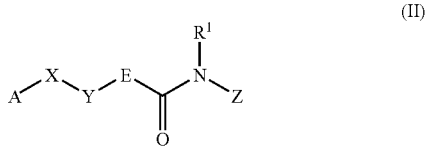

(II)

(wherein the symbols have the same definitions given above.)

This may be accomplished by appropriately employing common organic reactions such as oxidation, reduction, esterification, amidation, protection, deprotection, hydrolysis, dehydration, rearrangement, nucleophilic reaction, nucleophilic substitution or aromatic electrophilic substitution.

Specifically, the substituent conversion on ring A may be carried out by the methods shown below, for example. In addition, (1) the following reactions may be appropriately combined, (2) their products may be used as intermediates as well as final products, and (3) the reactions may be used not only for conversion of substituents dirctly bonded to ring A, but also for conversion of substituents at positions not directly bonded to but within substituents on ring A.

[Production Method 10]

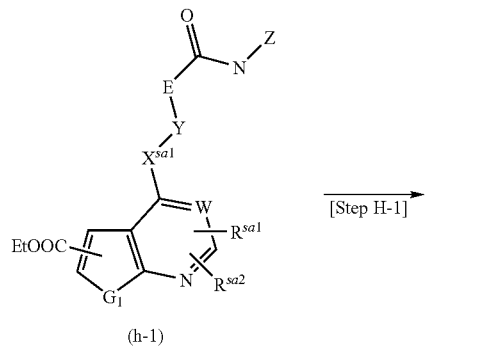

(h-1)

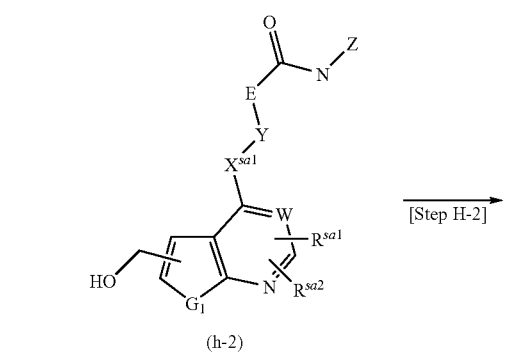

(h-2)

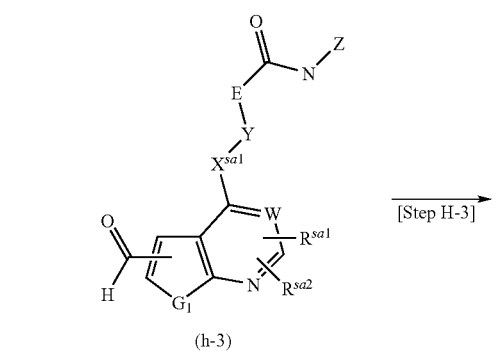

(h-3)

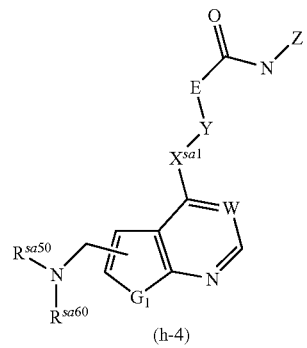

(h-4)

(wherein $G_1$ is an optionally substituted nitrogen atom or oxygen atom, and the remaining symbols have the same definitions given above.)

<Step H-1>

Reduction of ester compound (h-1) to alcohol compound (h-2). The reducing agent used may be lithium borohydride, lithium aluminum hydride or the like, the reaction solvent diethyl ether, tetrahydrofuran or the like, the reaction temperature from 0° C. to reflux temperature and the reaction time from 10 minutes to 30 hours.

<Step H-2>

Oxidation of alcohol compound (h-2) to aldehyde compound (h-3). The oxidizing agent used may be manganese dioxide, pyridium chlorochromate (PCC), pyridium dichromate (PDC) or the like, the reaction solvent chloroform, dichloromethane, toluene or the like, the reaction temperature from 0° C. to reflux temperature and the reaction time from 30 minutes to 30 hours.

<Step H-3>

Reductive amination reaction. Compound (h-4) may be obtained by reaction of an amino derivative with the aldehyde derivative (h-3) to form an imine, followed by reduction with sodium cyanoborohydride or the like. The reaction solvent used may be methanol, tetrahydrofuran or the like, the reaction time from 10 minutes to 30 hours and the reaction temperature from 0° C. to reflux temperature.

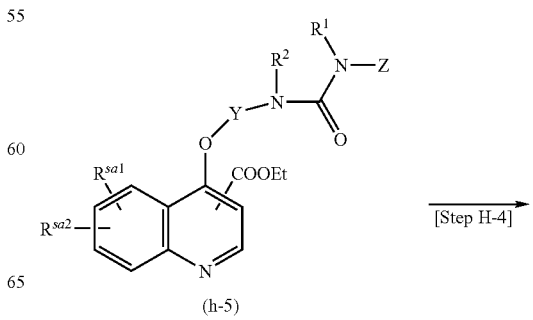

(h-5)

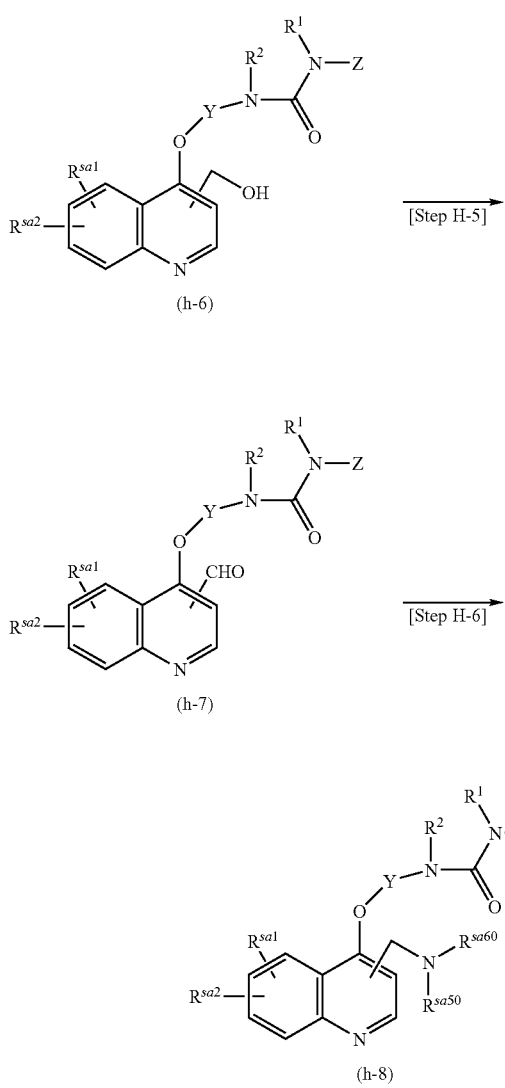

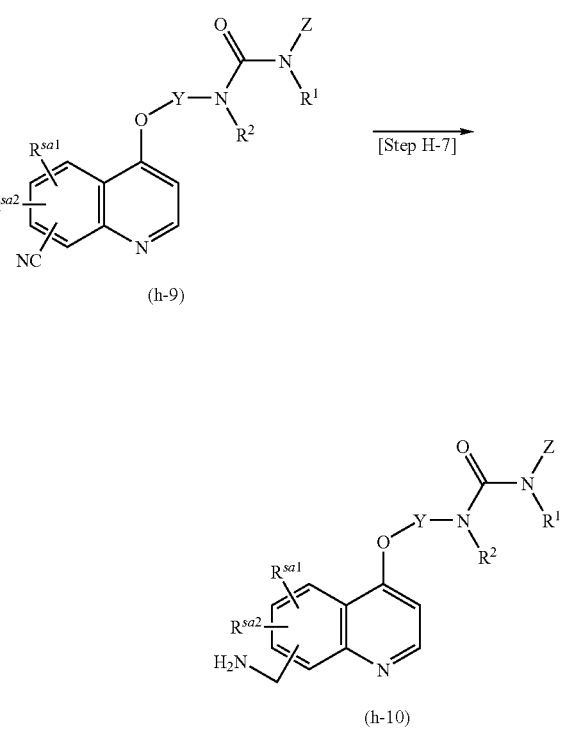

\<Step H-6\>

Reductive amination reaction. The same procedure as in \<Step H-3\> may be carried out to obtain the target compound (h-8) from compound (h-7).

(wherein the symbols have the same definitions given above.)

\<Step H-4\>

Reduction of an ester compound (h-5) to an alcohol compound (h-6). The same procedure as in \<Step H-1\> may be carried out to synthesize the target compound (h-6).

\<Step H-5\>

Oxidation of alcohol compound (h-6) to an aldehyde compound (h-7). The same procedure as in \<Step H-2\> may be carried out to synthesize the target compound (h-7).

\<Step H-7\>

Reduction of cyano group to aminomethyl group. The target compound (h-10) may be obtained from compound (h-9) by common catalytic reduction (palladium-carbon, palladium hydroxide-hydrogen or the like). The reaction solvent used may be tetrahydrofuran, methanol, ethanol or the like. The reaction time may be from 10 minutes to 30 hours, and the reaction temperature from 0° C. to reflux temperature. Trifluoroacetic acid, hydrochloric acid or the like may be added as an acid.

[Production Method 10-2]

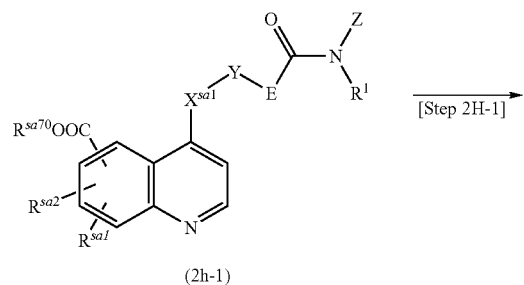

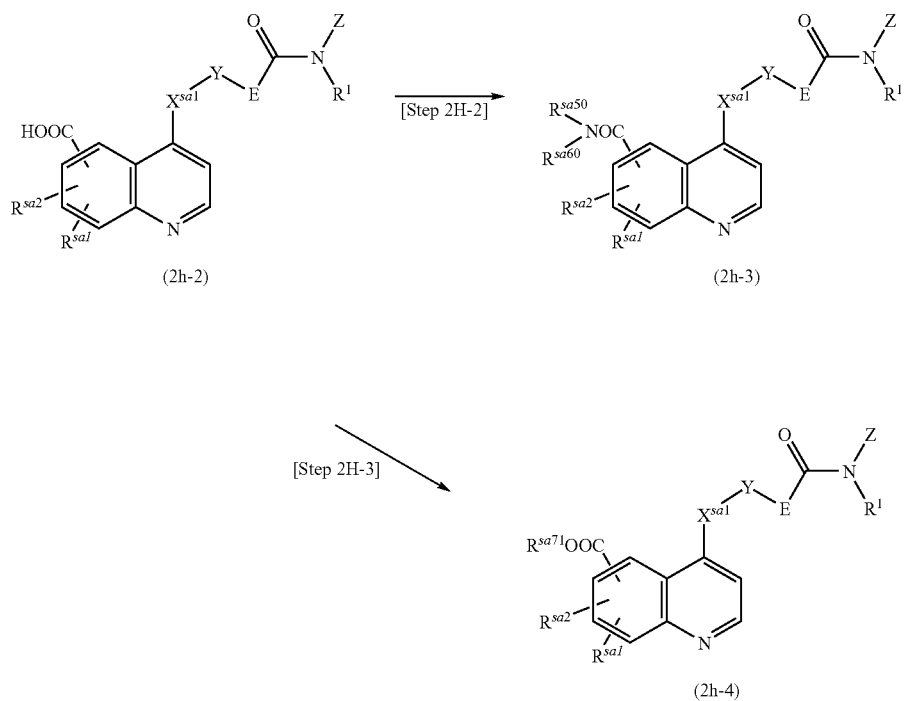

(wherein the symbols have the same definitions given above.)

<Step 2H-1>

Step of hydrolyzing ester in compound (2h-1) to obtain compound (2h-2). A base such as potassium hydroxide, sodium hydroxide, calcium carbonate, sodium carbonate or the like may be used for the reaction. The reaction time may be from 10 minutes to 30 hours, and the reaction temperature from 0° C. to reflux temperature. The solvent used may be water, tetrahydrofuran or the like.

<Step 2H-2>

Synthesis of amide derivative (2h-3) by condensation of carboxylic acid and amine derivative. Compound (2h-3) may be obtained by reacting compound (2h-2) and an amine derivative in the presence of a condensing agent. As condensing agents there may be used 1-ethyl-3-(3-dimethylaminopropyl)carbodiimide hydrochloride, (1H-1,2,3-benzotriazol-1-yloxy)(tri(dimethylamino))phosphonium hexafluorophosphate, or the like. The reaction time may be from 10 minutes to 30 hours, and the reaction temperature from 0° C. to reflux temperature. The solvent used may be dimethylformamide, tetrahydrofuran, or the like.

<Step 2H-3>

Synthesis of ester (2h-4) by condensation of carboxylic acid and an alcohol. Compound (2h-3) may be obtained by reaction of compound (2h-2) and an alcohol derivative in the presence of a condensing agent. As the condensing agent there may be used 1-ethyl-3-(3-dimethylaminopropyl)carbodiimide hydrochloride, or the like. The reaction time may be from 10 minutes to 30 hours, and the reaction temperature from 0° C. to reflux temperature. The solvent used may be dimethylformamide, tetrahydrofuran, or the like.

-continued

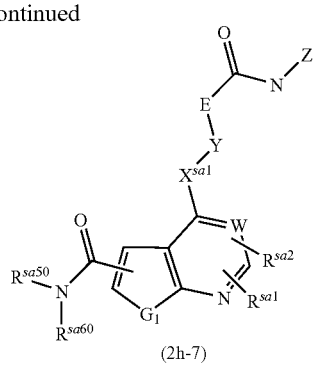

(2h-7)

(wherein the symbols have the same definitions given above.)

<Step 2H-4>

Step of obtaining compound (2h-6) by hydrolysis of ester in compound (2h-5). The same procedure as in <Step 2H-1> may be carried out to synthesize compound (2h-6) from compound (2h-5).

<Step 2H-5>

Synthesis of amide derivative (2h-7) by condensation of carboxylic acid derivative (2h-6) and amino derivative. The same procedure as in <Step 2H-2> may be carried out to synthesize compound (2h-7) from compound (2h-6).

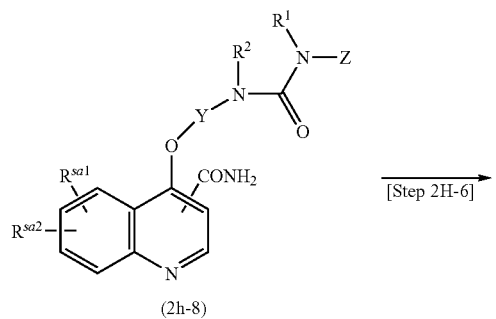

(wherein the symbols have the same definitions given above.)

<Step 2H-6>

Step of obtaining nitrile derivative (2h-9) by dehydration of carbamoyl compound (2h-8). The reaction solvent used may be tetrahydrofuran, diethyl ether or the like, the dehydrating agent used may be thionyl chloride, trifluoroacetic anhydride, dicyclohexyl carbodiimide or the like, and the base used may be pyridine, triethylamine or the like. The reaction temperature may be from 0° C. to reflux temperature, and the reaction time from 30 minutes to 30 hours.

[Production Method 10-3]

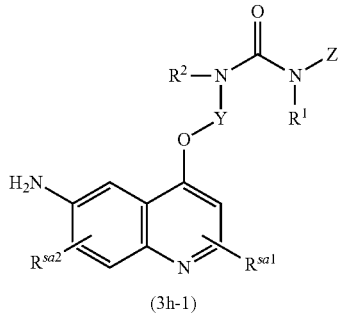

(wherein the symbols have the same definitions given above.)

<Step 3H-1>

Step of acylating amino group. Compound (3h-1) may be reacted with an acid chloride, acid anhydride or the like to obtain the target compound (3h-2). The reaction solvent used may be tetrahydrofuran or the like, the reaction temperature from 0° C. to reflux temperature, and the reaction time from 10 minutes to 30 hours. Triethylamine or the like may be used as the base.

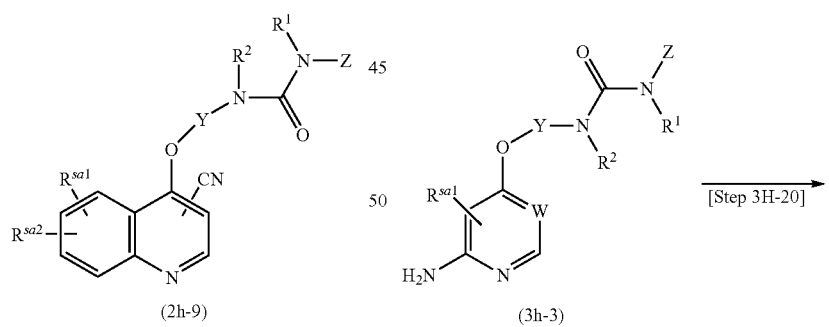

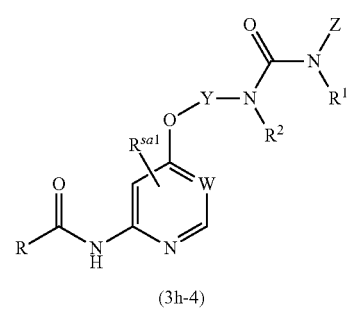

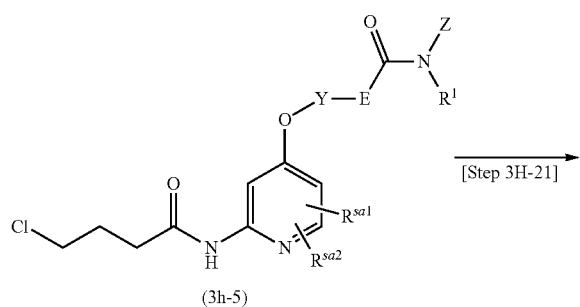

(3h-5)

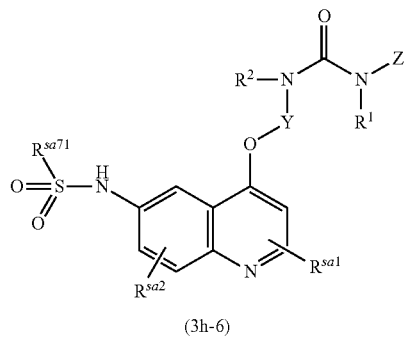

(3h-6)

(wherein the symbols have the same definitions given above.)

<Step 3H-3>

Sulfonamidation step. Compound (3h-5) may be reacted with a sulfonyl chloride derivative to obtain the target compound (3h-6). The reaction solvent used may be tetrahydrofuran, dimethylformamide or the like, the reaction temperature from 0° C. to reflux temperature, and the reaction time from 10 minutes to 30 hours. Triethylamine, pyridine or the like may be used as the base.

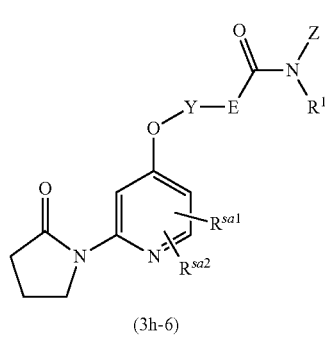

(3h-6)

(wherein the symbols have the same definitions given above.)

<Step 3H-20>

Acylation step. Compound (3h-3) may be reacted with an acid chloride, acid anhydride or the like to obtain the target compound (3h-4). The reaction solvent used may be tetrahydrofuran, pyridine or the like, the reaction temperature from 0° C. to reflux temperature, and the reaction time from 10 minutes to 30 hours. Triethylamine, pyridine or the like may be used as the base.

<Step 3H-21>

Cyclization reaction. The reaction solvent used may be dimethylformamide or the like, the reaction temperature from 100° C. to reflux temperature, and the reaction time from 10 minutes to 30 hours. Potassium carbonate or the like may be used as the base.

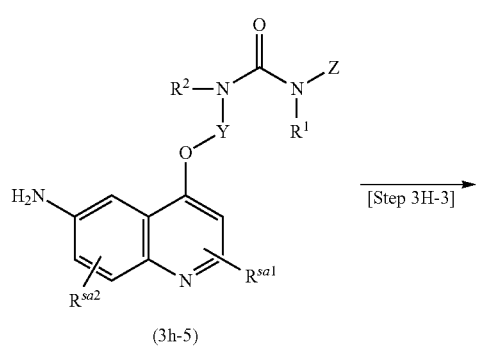

(3h-5)

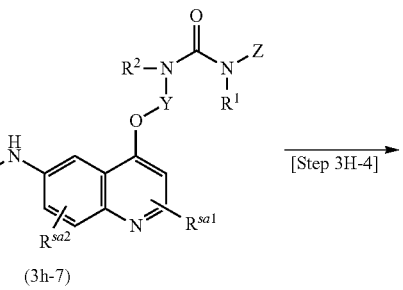

(3h-7)

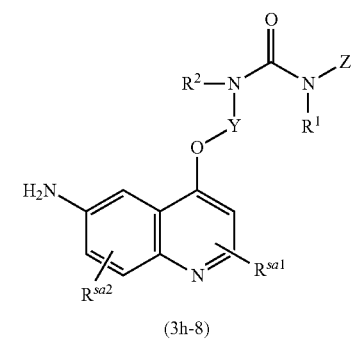

(3h-8)

(wherein the symbols have the same definitions given above.)

<Step 3H-4>

De-benzyloxycarbonylation step. Compound (3h-8) may be obtained from compound (3h-7) by ordinary catalytic reduction (palladium-carbon, palladium hydroxide-carbon and hydrogen, etc.). The solvent used may be tetrahydrofuran, methanol, ethanol or the like. The reaction time may be from 10 minutes to 30 hours and the reaction temperature from 0° C. to reflux temperature. Trifluoroacetic acid, hydrochloric acid or the like may be added as an acid.

[Production Method 11]

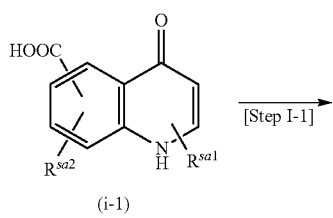

(i-1)

[Step I-1]

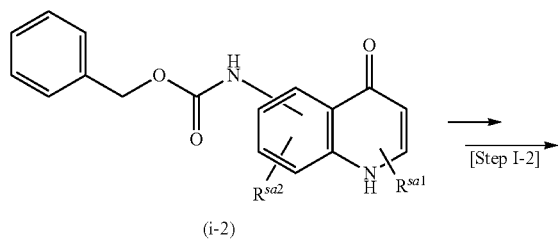

(i-2)

[Step I-2]

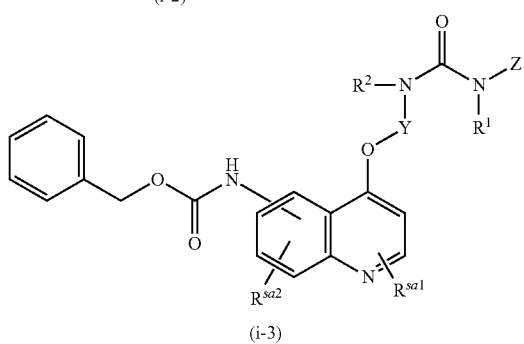

(i-3)

(wherein the symbols have the same definitions given above.)

<Step I-1>

Rearrangement of carboxylic acid to amino derivative (i-2). A carboxylic acid derivative (i-1) may be reacted with benzyl alcohol in the presence of diphenylphosphoryl azide and triethylamine to obtain compound (i-2) from compound (i-1). The reaction solvent used may be benzyl alcohol, dimethylformamide, toluene or the like, the reaction temperature from room temperature to reflux temperature, and the reaction time from 10 minutes to 30 hours.

<Step I-2>

The same procedure as in <Step A-4>, <Step A-5> and <Step A-7> may be carried out to synthesize compound (i-3) from compound (i-2).

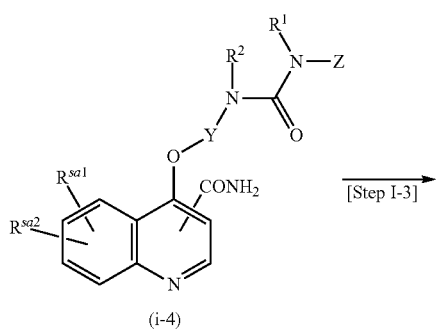

(i-4)

[Step I-3]

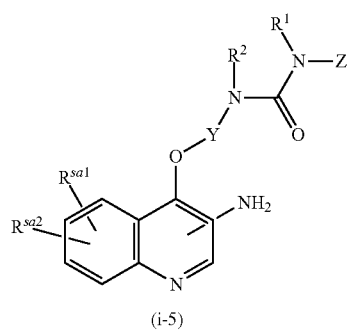

(i-5)

(wherein the symbols have the same definitions given above.)

<Step I-3>

Step of rearrangement of carbamoyl group to amino group.

An amino compound (i-5) may be obtained from compound (i-4) by reaction with a base such as bromine water, sodium hydroxide or the like. The reaction solvent used may be water or the like, the reaction temperature from room temperature to reflux temperature, and the reaction time from 10 minutes to 10 hours.

[Production Method 12-1]

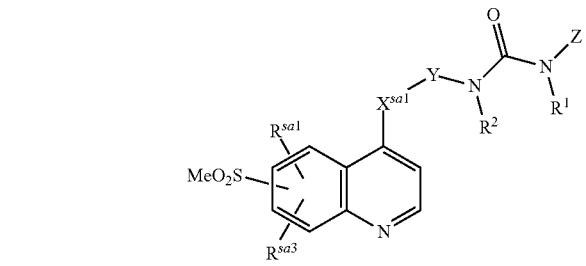

(m-1)

[Step M-1]

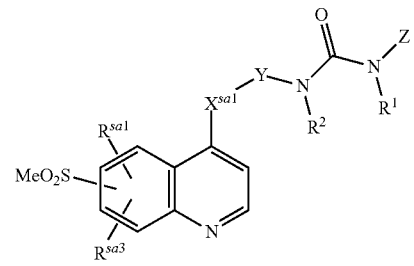

(m-2)

(wherein the symbols have the same definitions given above.)

<Step M-1>

Conversion of methylthio group to methylsulfone group.

Compound (m-1) may be reacted with a peracid to obtain the target compound (m-2). The peracid used may be 3-chloroperbenzoic acid, the reaction solvent methylene chloride, chloroform or the like, the reaction time from 10 minutes to 30 hours and the reaction temperature from 0° C. to room temperature.

[Production Method 12-2]

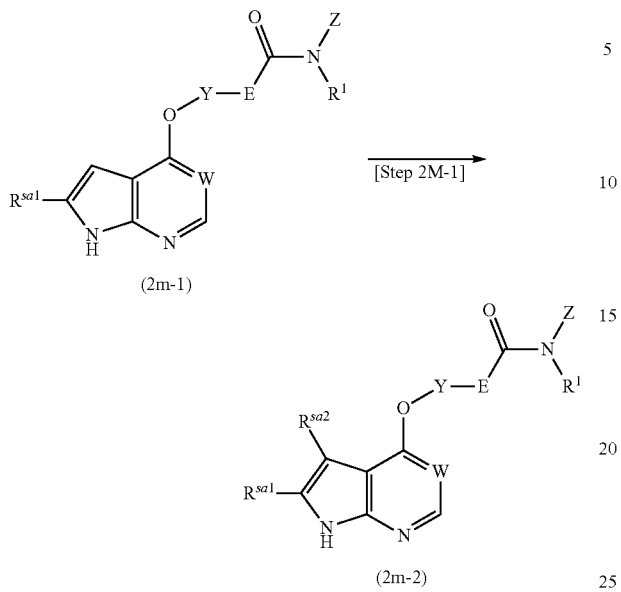

(wherein the symbols have the same definitions given above.)
<Step 2M-1>

Step of introducing substituent into aromatic ring by electrophilic reaction. An electrophilic reagent may be reacted with compound (2m-1) to obtain compound (2m-2) The electrophilic reagent used for the reaction may be, as specific examples, Vilsmeier reagent (which may be prepared from dimethylformamide or N-methylformanilide and phosphorus oxychloride), N-chlorosuccinimide, N-bromosuccinimide, a combination of acyl chloride and a Lewis acid (for example, aluminum chloride, titanium tetrachloride, etc.) or a reagent represented by the formula

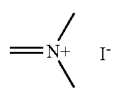

These allow introduction of formyl, chloro, bromo, acyl and dimethylaminomethyl groups, respectively. The reaction solvent used may be dimethylformamide, acetonitrile, dichloromethane, toluene or the like. The reaction temperature maybe from 0° C. to reflux temperature, and the reaction time from 10 minutes to 30 hours.

[Production Method 13]

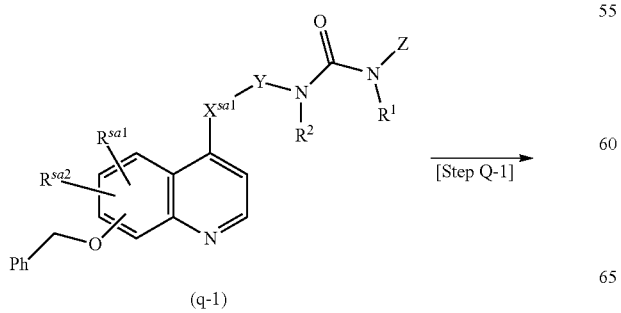

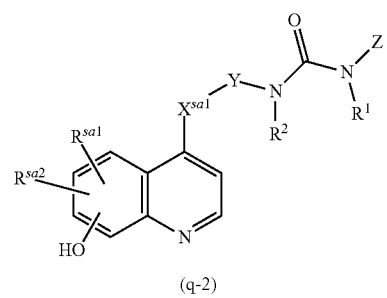

(wherein the symbols have the same definitions given above.)
<Step Q-1>

Step of deprotection of hydroxyl-protecting group of compound (q-1). The reaction may be conducted in the same manner as the conventional method for deprotection of a phenol group protected with a benzyl group. Specifically, the reagent used may be, for example, trifluoroacetic acid-thioanisole, palladium hydroxide-hydrogen, platinum oxide-hydrogen, or the like. The reaction solvent used may be trifluoroacetic acid, dimethylformamide or the like, the reaction time from 10 minutes to 30 hours and the reaction temperature from room temperature to reflux temperature.

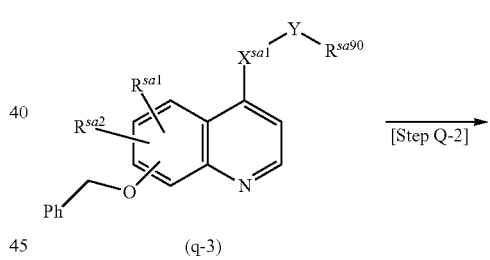

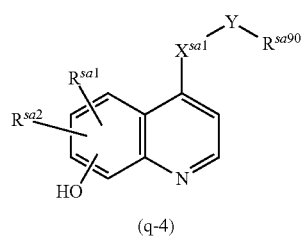

(wherein $R^{sa90}$ is an amino or nitro group, and the other symbols have the same definitions given above.)
<Step Q-2>

Step of deprotection of hydroxyl-protecting group of compound (q-3). The reaction may be conducted under the same conditions as in <Step Q-1> above.

[Production Method 14]

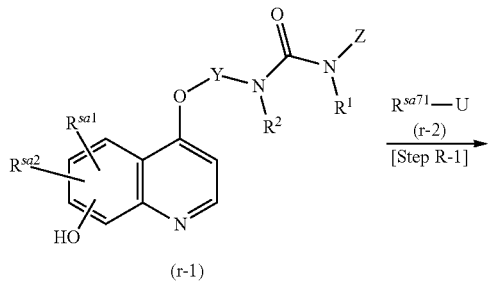

(r-1)

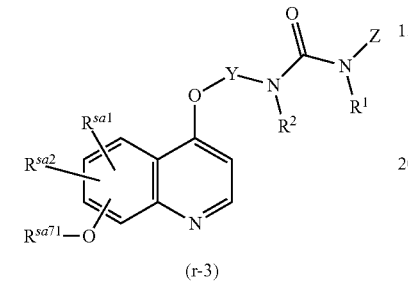

(r-3)

(wherein the symbols have the same definitions given above.)

<Step R-1>

Step of reacting compound (r-1) with an electrophilic reagent such as an alkyl halide derivative (r-2) to obtain compound (r-3). The reaction solvent used may be dimethylformamide, dimethylsulfoxide, tetrahydrofuran or the like, the reaction time from 10 minutes to 30 hours, and the reaction temperature from 0° C. to reflux temperature. The reaction may also employ a base, and specifically, for example, potassium carbonate, cesium carbonate or the like.

As specific examples for the alkyl halide derivative ($R^{sa71}$—U) in the reaction there may be mentioned (1) alkylthio halide derivatives represented by the formula: $R^{sa80}S$—$(CH_2)_s$—Cl (wherein s is an integer of 1-6, and the other symbols have the same definitions given above), (2) alkyl halide derivatives represented by the formula: Br—$(CH_2)_s$—Cl (wherein s is an integer of 1-6), (3) propylene oxide derivatives represented by the formula:

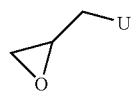

(wherein U is a leaving group), (4) compounds represented by the formula:

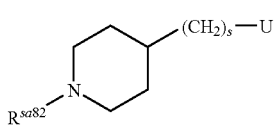

(wherein U is a leaving group, $R^{sa82}$ is an amino-protecting group such as t-butoxycarbonyl or benzyl, and s is an integer of 1-6), and (5) alkyl halide derivatives substituted with $C_{1-6}$ alkoxy groups.

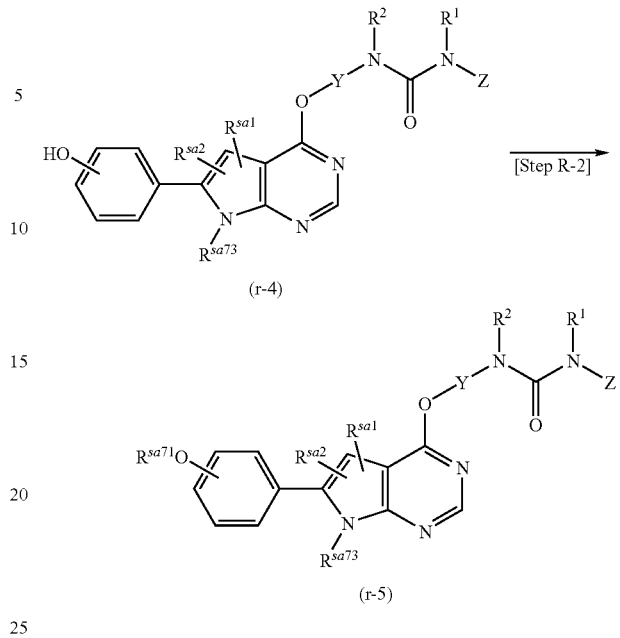

(wherein $R^{sa73}$ is hydrogen or 2-(trimethylsilyl)ethoxymethyl, and the other symbols have the same definitions given above.

<Step R-2>

Step of reaction with a phenol derivative (r-4) to introduce the substituent $R^{sa71}$. The substituent $R^{sa71}$ may be introduced by the same procedure as in <Step R-1>.

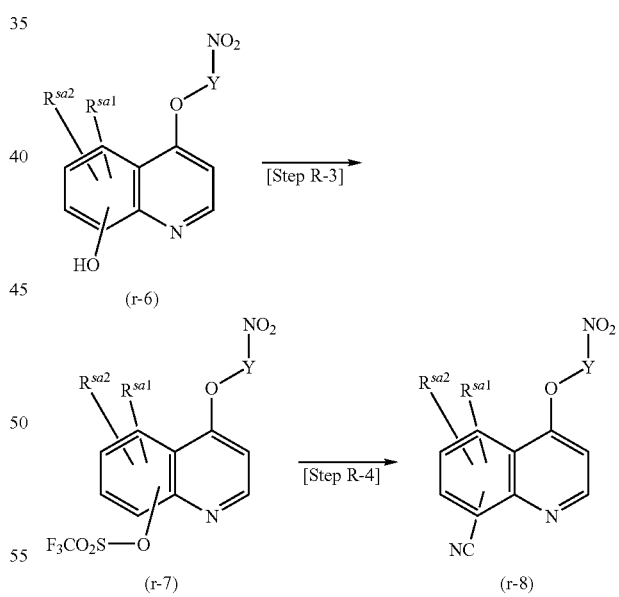

(wherein the symbols have the same definitions given above.)

<Step R-3>

Step of triflating the hydroxyl group. Compound (r-6) may be reacted with a triflating reagent such as paranitrophenyl triflate or the like to obtain the target compound (r-7). The reaction solvent used may be dimethylformamide or the like, the reaction temperature from 0° C. to reflux temperature and the reaction time from 10 minutes to 30 hours. Potassium carbonate or the like may be used as a base.

<Step R-4>

Step of converting the triflate group to a cyano group. Compound (r-7) may be reacted with a cyanating reagent such as zinc cyanide $(Zn(CN)_2)$ or the like to obtain the target compound (r-8). The catalyst used may be tetrakistriphenylphosphine palladium. The reaction solvent used may be dimethylformamide, the reaction temperature from room temperature to reflux temperature, and the reaction time from 10 minutes to 30 hours.

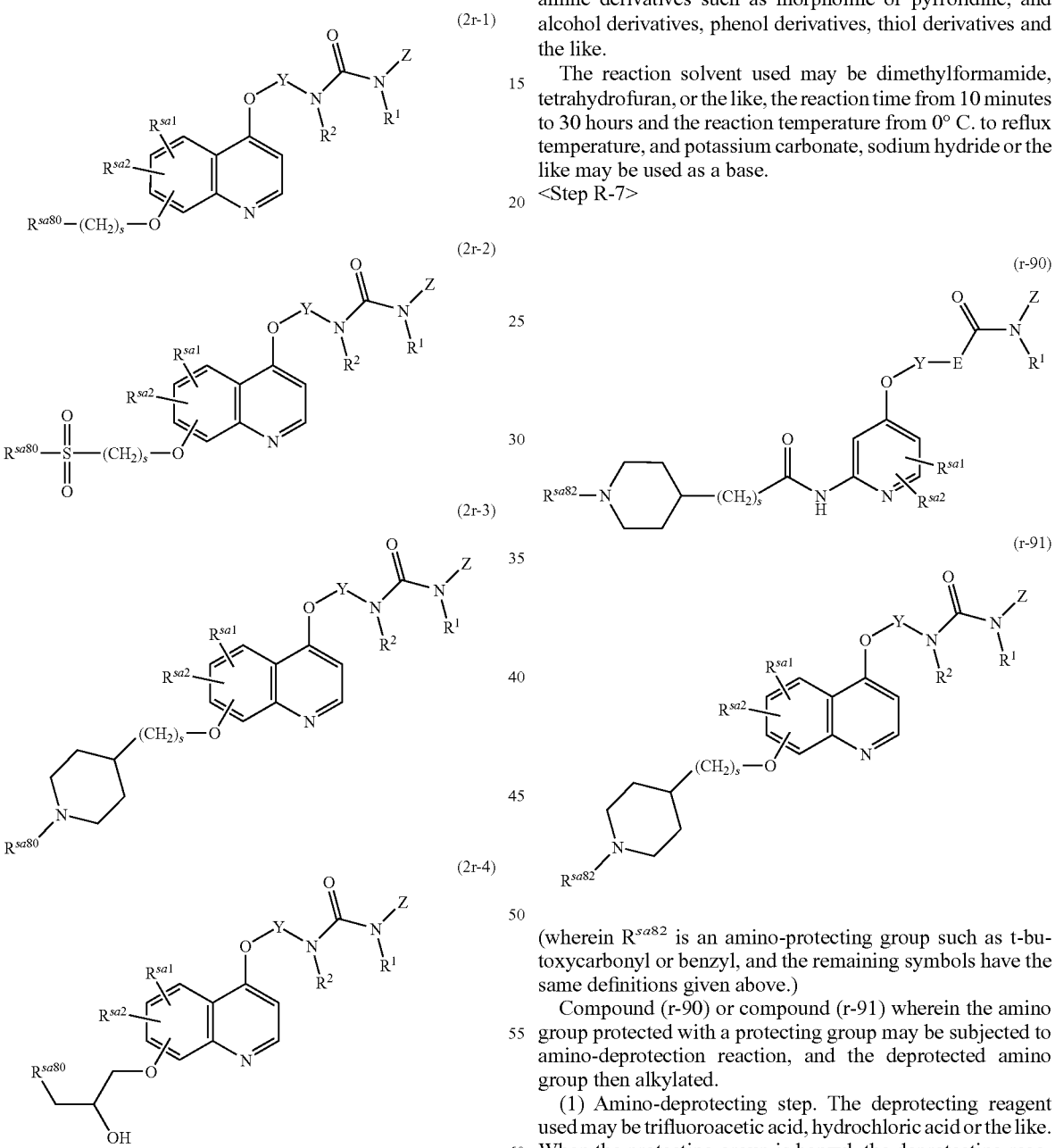

(wherein the symbols have the same definitions given above.)

<Step R-5>

Step of reacting compound (r-3) which has a thioether group in substituent $R^{sa71}$, with an oxidizing agent such as 3-chloroperbenzoic acid to obtain compound (2r-2). The reaction solvent used may be methylene chloride, chloroform or the like, the reaction time from 10 minutes to 30 hours and the reaction temperature from 0° C. to room temperature.

<Step R-6>

Step of reacting a nucleophilic agent with compound (r-3) having a leaving group, for example, a halogen atom such as chlorine, bromine or iodine or a methanesulfonyloxy group, or an epoxide group or the like in substituent $R^{sa71}$, to obtain compound (2r-1) or compound (2r-4). Specific examples of nucleophilic agents which may be used include nitrogen-containing aromatic derivatives such as triazole or imidazole, amine derivatives such as morpholine or pyrrolidine, and alcohol derivatives, phenol derivatives, thiol derivatives and the like.

The reaction solvent used may be dimethylformamide, tetrahydrofuran, or the like, the reaction time from 10 minutes to 30 hours and the reaction temperature from 0° C. to reflux temperature, and potassium carbonate, sodium hydride or the like may be used as a base.

<Step R-7>

(wherein $R^{sa82}$ is an amino-protecting group such as t-butoxycarbonyl or benzyl, and the remaining symbols have the same definitions given above.)

Compound (r-90) or compound (r-91) wherein the amino group protected with a protecting group may be subjected to amino-deprotection reaction, and the deprotected amino group then alkylated.

(1) Amino-deprotecting step. The deprotecting reagent used may be trifluoroacetic acid, hydrochloric acid or the like. When the protecting group is benzyl, the deprotecting reaction may be conducted by common catalytic reduction (palladium hydroxide-hydrogen or the like). The solvent used may be trifluoroacetic acid, methanol, ethanol or the like. The reaction time may be from 10 minutes to 30 hours and the reaction temperature from 0° C. to reflux temperature.

(2) Step of alkylating deprotected amino group. The deprotected amino derivative may be reacted with an aldehyde derivative or ketone derivative to form an imine, which is then reduced with a reducing agent such as sodium cyanoborohydride to obtain compound (2r-3). The reaction solvent used may be methanol, tetrahydrofuran or the like, the reaction time from 10 minutes to 30 hours, and the reaction temperature from 0° C. to reflux temperature.

[Production Method 15]

Alternative synthesis method for compound represented by:

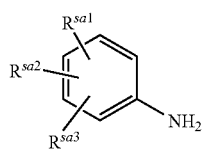

(a-1)

(wherein the symbols have the same definitions given above.)

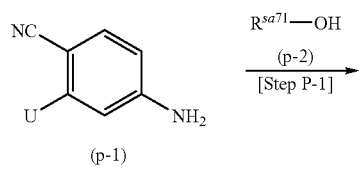

(wherein the symbols have the same definitions given above.)
<Step P-1>

Compound (p-1) may be reacted with an alcohol derivative (p-2) in the presence of a base such as sodium hydride to obtain compound (p-3). The synthesis may be carried out by reaction in a solvent such as 1-methylpyrrolidone or N,N-dimethylformamide. The reaction time may be from 10 minutes to 30 hours, and the reaction temperature from 0° C. to reflux temperature.

[Production Method 16]

Alternative synthesis method for compound represented by:

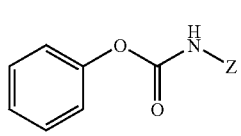

(p-6)

(wherein the symbols have the same definitions given above.)

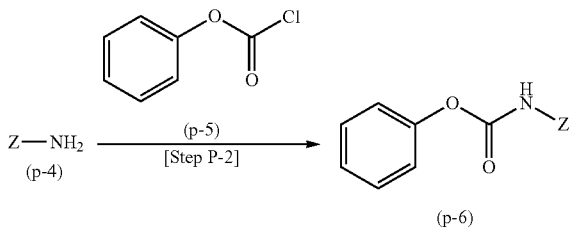

(wherein the symbols have the same definitions given above.)
<Step P-2>

Reaction for obtaining carbamate derivative. It may be obtained by reacting an amino derivative with phenyl chloroformate. The reaction solvent used may be tetrahydrofuran, dimethylformamide or the like, the reaction temperature from 0° C. to reflux temperature, and the reaction time from 30 minutes to 30 hours.

The reaction is carried out while appropriately protecting the reactive functional groups such as amino, hydroxyl and carboxyl.

As amino-protecting groups there may be used any groups conventionally known as protecting groups for amino groups in organic synthesis, with no particular restrictions, and as specific examples there may be mentioned substituted or unsubstituted lower alkanoyl groups such as formyl, acetyl, chloroacetyl, dichloroacetyl, propionyl, phenylacetyl, phenoxyacetyl and thienylacetyl; substituted or unsubstituted lower alkoxycarbonyl groups such as benzyloxycarbonyl, t-butoxycarbonyl and p-nitrobenzyloxycarbonyl; substituted lower alkyl groups such as methyl, t-butyl, 2,2,2-trichloroethyl, trityl, p-methoxybenzyl, p-nitrobenzyl, diphenylmethyl and pivaloyloxymethyl; substituted silyl groups such as trimethylsilyl and t-butyldimethylsilyl; substituted silylalkoxyalkyl groups such as trimethylsilylmethoxymethyl, trimethylsilylethoxymethyl, t-butyldimethylsilylmethoxymethyl and t-butyldimethylsilylethoxymethyl; or substituted or unsubstituted benzylidene groups such as benzylidene, salicylidene, p-nitrobenzylidene, m-chlorbenzylidene, 3,5-di(t-butyl)-4-hydroxybenzylidene and 3,5-di(t-butyl)benzylidene.

These protecting groups may be removed by ordinary methods such as hydrolysis or reduction, depending on the type of protecting group used.

As hydroxyl-protecting groups there may be used any groups conventionally known as protecting groups for hydroxyl groups in organic synthesis, with no particular restrictions, and as specific examples there may be mentioned lower alkylsilyl groups such as trimethylsilyl and t-butyldimethylsilyl; lower alkoxymethyl groups such as methoxymethyl and 2-methoxyethoxymethyl; tetrahydropyranyl; aralkyl groups such as benzyl, p-methoxybenzyl, 2,4-dimethoxybenzyl, o-nitrobenzyl, p-nitrobenzyl and trityl; acyl groups such as formyl and acetyl; lower alkoxycarbonyl groups such as t-butoxycarbonyl, 2-iodoethoxycarbonyl and 2,2,2-trichloroethoxycarbonyl; alkenyloxycarbonyl groups such as 2-propenyloxycarbonyl, 2-chloro-2-propenyloxycarbonyl, 3-methoxycarbonyl-2-propenyloxycarbonyl, 2-methyl-2-propenyloxycarbonyl, 2-butenyloxycarbonyl and cinnamyloxycarbonyl; and aralkyloxycarbonyl groups such as p-methoxybenzyloxycarbonyl, o-nitrobenzyloxycarbonyl and p-nitrobenzyloxycarbonyl.

These protecting groups may be removed by ordinary methods such as hydrolysis or reduction, depending on the type of protecting group used.

As carboxyl-protecting groups there may be used any groups conventionally known as protecting groups for carboxyl groups in organic synthesis, with no particular restrictions, and as specific examples there may be mentioned linear or branched lower alkyl groups of 1-4 carbons such as methyl, ethyl, isopropyl and t-butyl; halogeno lower alkyl groups such as 2-iodoethyl and 2,2,2-trichloroethyl; lower alkoxymethyl groups such as methoxymethyl, ethoxymethyl and isobutoxymethyl; lower aliphatic acyloxymethyl groups such as butyryloxymethyl and pivaloyloxymethyl; 1-lower alkoxycarbonyloxyethyl groups such as 1-methoxycarbonyloxyethyl and 1-ethoxycarbonyloxyethyl, aralkyl groups such as benzyl, p-methoxybenzyl, o-nitrobenzyl and p-nitrobenzyl; benzhydryl, phthalidyl, and the like.

These protecting groups may be removed by ordinary methods such as hydrolysis or reduction, depending on the type of protecting group used.

There are no particular restrictions on esters of the carboxyl groups so long as they are ones commonly used in organic synthesis, and they include physiologically acceptable esters which are hydrolyzed under physiological conditions. As specific examples there may be mentioned alkyl groups of 1 to 6 carbons, aryl groups of 6 to 12 carbons, aralkyl groups of 7 to 20 carbons such as benzyl, heteroarylalkyl groups of 7 to 20 carbons, 4-methoxybenzyl, alkanoyloxyalkyl groups such as acetoxymethyl, propionyloxymethyl or pivaloxymethyl, alkoxycarbonyloxyalkyl groups such as methoxycarbonyloxymethyl ethoxycarbonyloxymethyl or 2-methoxycarbonyloxyethyl, (5-methyl-2-oxo-1,3-dioxo-4-yl)-methyl, and the like.

The solvents to be used for the invention are not particularly restricted so long as they do not impede the reaction and are solvents commonly used in organic synthesis, and as examples there may be mentioned lower alcohols such as methanol, ethanol, propanol and butanol, polyalcohols such as ethyleneglycol and glycerin, ketones such as acetone, methylethyl ketone, diethyl ketone and cyclohexanone, ethers such as diethyl ether, isopropyl ether, tetrahydrofuran, dioxane, 2-methoxyethanol and 1,2-dimethoxyethane, nitriles such as acetonitrile and propionitrile, esters such as methyl acetate, ethyl acetate, isopropyl acetate, butyl acetate and diethyl phthalate, halogenated hydrocarbons such as dichloromethane, chloroform, carbon tetrachloride, 1,2-dichloroethane, trichloroethylene and tetrachloroethylene, aromatic compounds such as benzene, toluene, xylene, monochlorbenzene, nitrobenzene, indene, pyridine, quinoline, collidine and phenol, hydrocarbons such as pentane, cyclohexane, hexane, heptane, octane, isooctane, petroleum benzine and petroleum ether, amines such as ethanolamine, diethylamine, triethylamine, pyrrolidine, piperidine, piperazine, morpholine, aniline, dimethylaniline, benzylamine and toluidine, amides such as formamide, N-methylpyrrolidone, N,N-dimethylimidazolone, N,N-dimethylacetamide and N,N-dimethylformamide, phosphoric/phosphorous amides such as hexamethylphosphoric triamide and hexamethylphosphoroustriamide, and water, as well as other commonly used solvents, either alone or in mixtures of two or more, with no particular restrictions on the solvent ratio.

There are no particular restrictions on bases uses so long as they are commonly known as bases for organic synthesis, and as specific examples there may be mentioned sodium carbonate, sodium bicarbonate, potassium carbonate, sodium hydride, potassium hydride, t-butoxypotassium, pyridine, dimethylaminopyridine, trimethylamine, triethylamine, N,N-diisopropylethylamine, N-methylmorpholine, N-methylpyrrolidine, N-methylpiperidine, N,N-dimethylaniline, 1,8-diazabicyclo[5,4,0]undeca-7-ene (DBU), pyridine, 4-dimethylaminopyridine, picoline, lutidine, quinoline, isoquinoline, sodium hydroxide, potassium hydroxide, lithium hydroxide, butyllithium, and sodium or potassium alcoholates such as sodium methylate, potassium methylate and sodium ethylate.

As specific examples of halogenating agents to be used there may be mentioned halogenating agents conventionally used for synthesis of acid halides, for example, phosgene, diphosgene (phosgene dimer), triphosgene (phosgene trimer), thionyl chloride, thionyl bromide, phosphorus trichloride, phosphorus tribromide, phosphorus oxychloride, phosphorus pentachloride, trichloromethyl chloroformate and oxalyl chloride, as well as Vilsmeier reagents obtained by reacting these halogenating agents with acid amides or phosphoric amides.

There are no particular restrictions on reducing agents so long as they are ones commonly used in organic synthesis, and as examples there may be mentioned contact hydrogenating catalysts such as $NaBH_4$, $LiBH_4$, $Zn(BH_4)_2$, $Me_4NBH(OAc)_3$, $NaBH_3CN$, Selectride, Super Hydride ($LiBHEt_3$), $LiAlH_4$, DIBAL, $LiAlH(t-BuO)_3$, Red-al and binap, as well as platinum, palladium, rhodium, ruthenium, nickel, and the like.

After completion of the reaction, purification may be accomplished by any desired ordinary treatment method, such as column chromatography using silica gel or an adsorption resin, or recrystallization from a suitable solvent.

Throughout the present specification, the term "pharmacologically acceptable salt" is not particularly restrictive on the type of salt, and as examples of such salts there may be mentioned inorganic acid addition salts such as hydrochloric acid salts, sulfuric acid salts, carbonic acid salts, bicarnobate salts, hydrobromic acid salts and hydriodic acid salts; organic carboxylic acid addition salts such as acetic acid salts, maleic acid salts, lactic acid salts, tartaric acid salts and trifluoroacetic acid salts; organic sulfonic acid addition salts such as methanesulfonic acid salts, hydroxymethanesulfonic acid salts, hydroxyethanesulfonic acid salts, benzenesulfonic acid salts, toluenesulfonic acid salts and taurine salts; amine addition salts such as trimethylamine salts, triethylamine salts, pyridine salts, procaine salts, picoline salts, dicyclohexylamine salts, N,N'-dibenzylethylenediamine salts, N-methylglucamine salts, diethanolamine salts, triethanolamine salts, tris(hydroxymethylamino)methane salts and phenethylbenzylamine salts; and amino acid addition salts such as arginine salts, lysine salts, serine salts, glycine salts, aspartic acid salts and glutamic acid salts.

The dosage of a medicine according to the invention will differ depending on the severity of symptoms, patient age, gender and weight, administration form and type of disease, but administration may usually be from 100 µg to 10 g per day for adults, either at once or in divided doses.

There are no particular restrictions on the form of administration of a medicine according to the invention, and it may usually be administered orally or parenterally by conventional methods.

Common excipients, binders, glossy agents, coloring agents, taste correctors and the like, and if necessary stabilizers, emulsifiers, absorption promoters, surfactants and the like, may also be used for formulation, with inclusion of components ordinarily used as starting materials for formulation of pharmaceutical preparations by common methods.

Examples of such components which may be used include animal and vegetable oils (soybean oil, beef tallow, synthetic glycerides, etc.), hydrocarbons (liquid paraffin, squalane, solid paraffin, etc.), ester oils (octyldodecyl myristate, isopropyl myristate, etc.), higher alcohols (cetostearyl alcohol, behenyl alcohol, etc.), silicone resins, silicone oils, surfactants (polyoxyethylene fatty acid esters, sorbitan fatty acid esters, glycerin fatty acid esters, polyoxyethylenesorbitan fatty acid esters, polyoxyethylene hydrogenated castor oil, polyoxyethylenepolyoxypropylene block copolymer, etc.), water-soluble polymers (hydroxyethyl cellulose, polyacrylic acid, carboxyvinyl polymer, polyethyleneglycol, polyvinylpyrrolidone, methyl cellulose, etc.), alcohols (ethanol, isopropanol, etc.), polyhydric alcohols (glycerin, propyleneglycol, dipropyleneglycol, sorbitol, etc.), sugars (glucose, sucrose, etc.), inorganic powders anhydride, aluminium magnesium silicate, aluminium silicate, etc.), purified water and the like. For pH adjustment there may be used inorganic acids (hydrochloric acid, phosphoric acid, etc.), alkali metal salts of inorganic acids (sodium phosphate, etc.), inorganic bases (sodium hydroxide, etc.), organic acids (lower fatty acids, citric acid, lactic acid, etc.), alkali metal salts of organic acids (sodium citrate, sodium lactate, etc.), and organic bases (arginine, ethanolamine, etc.). If necessary, preservatives, antioxidants and the like may also be added.

The compounds of the invention exhibit powerful in vitro inhibition of 1) invasive tube formation by vascular endothelial cells induced by a combination of angiogenic factors, 2) tube formation by vascular endothelial cells specifically induced by single angiogenic factors, and 3) receptor kinases for various angiogenic factors. Among these compound groups having such activity there were also found compounds that inhibit proliferation of cancer cells. Invasion and tube formation by endothelial cells are an important process in angiogenesis, and therefore compounds with inhibiting action against them exhibit angiogenesis-inhibiting effects. In addition, angiogenesis in the body is known to depend not on a single angiogenic factor but rather on the additive and synergistic effect of multiple angiogenic factors ((1) Koolwijk P, van Erck M G M, de Vree W J A, Vermeer M A, Weich H A, Hane maaijer R, van Hinsbergh V W M. Cooperative effect of TNF-alpha, bFGF and VEGF on the formation of tubular structures of human microvascular endothelial cells in a fibrin matrix. Role of urokinase activity. J. Cell Biol. 1996, 132, P1177-1188.; (2) Tallquist M D, Soriano P, Klinghoffer R A. Growth factor signaling pathways in vascular development. Oncogene 1999, 18, P7917-7932.). Thus, the compounds of the invention which inhibit tube formation induced by multiple angiogenic factors produced by cancer cells and the like are expected to exhibit powerful angiogenesis inhibition in vivo, and should be highly useful as angiogenesis inhibitors.

The biochemical activity of the compounds of the invention and their function and effect as medicines (angiogenesis-inhibiting activity, antitumor activity, etc.) may be evaluated by the methods described below.

The following is a list of abbreviations used in the pharmacological test examples described below.

LIST OF ABBEVIATIONS

DNA: Deoxyribonucleic Acid
VEGFR2: Vascular Endothelial Growth Factor Receptor 2
Hepes: N-[2-Hydroxyethyl]piperazine-N'-[2-ethanesulfonic acid]
$MgCl_2$: Magnesium chloride
$MnCl_2$: Manganese chloride
$Na_3VO_4$: Sodium Orthovanadate (V)
ATP: Adenosine 5'-Triphosphate
EDTA: Ethylenediaminetetraacetic acid
HTRF: Homogenous Time-Resolved Fluorescence
FGFR1: Fibroblast Growth Factor Receptor 1
PDGFRβ: Platelet-Derived Growth Factor Receptor β
HGFR: Hepatocyte Growth Factor Receptor
EGFR: Epidermal Growth Factor Receptor
Tris: Tris(hydroxymethyl)aminomethane
NaCl: Sodium chloride
BSA: Bovine Serum Albumin
HRP: Horseradish peroxidase
EGTA: Ethylene glycol bis(2-aminoethyl ether)-N,N,N',N'-tetraacetic acid
SDS: Sodium Dodecyl Sulfate
NP-40: Nonidet P-40
PCR: Polymerase Chain Reaction
RT-PCR: Reverse Transcription-Polymerase Chain Reaction
RNA: Ribonucleic Acid
cDNA: complementary DNA
cRNA: complementary RNA
dNTP: dATP, dCTP, dGTP, dTTP
UTP: Uridine 5'-Triphosphate
CTP: Cytidine 5'-Triphosphate
dATP: 2'-Deoxyadenosine 5'-Triphosphate
dCTP: 2'-Deoxycytidine 5'-Triphosphate
dGTP: 2'-Deoxyguanosine 5'-Triphosphate
dUTP: 2'-Deoxyuridine 5'-Triphosphate
GAPDH: Glyceraldehyde 3-Phosphate Dehydrogenease
FBS: Fetal Bovine Serum
PBS: Phosphate Buffered Saline
MIT: (3-[4,5-Dimethlythiazol-2-yl]-2,5-diphenyltetrazolium bromide; Thiazolyl blue
DMSO: Dimethyl Sulfoxide
PDGF: Platelet-Derived Growth Factor
EGF: Epidermal Growth Factor
FGF2: Fibroblast Growth Factor 2
VEGF: Vascular Endothelial Growth Factor
HGF: Hepatocyte Growth Factor
TNF-α: Tumor Necrosis Factor alpha
FCS: Fetal Calf Serum
EGM-2: Endothelial cell Growth Medium-2

Pharmacological Test Example 1

Inhibition Against Invasive Tube Formation by Vascular Endothelial Cells in Response to Stimulation by Angiogenic Factor Mixture Human Umbilical Vein Endothelial Cells (HUVECs) were isolated according to a reported method (Shinseikagaku Jikken Koza [New Biochemistry Experiment Lectures], "Saibo Baiyo Gijutsu" [Cell Culturing Techniques], p. 197-202), and were cultured in a 5% $CO_2$ incubator (37° C.) using EGM-2 medium (purchased from Clonetics Corp.) until the cells reached confluency. After adding 0.4 ml of bovine fibrinogen (purchased from Sigma Co.) to the inner well of a Transwell culturing plate (purchased from Coster Inc.), it was hardened with 0.7 units/ml of thrombin (purchased from Sigma Co.). The HUVECs were recovered using trypsin-EDTA and then suspended in human endothelial serum free mediumbasal growth medium (hereinafter abbreviated as SFM, purchased from GIBCO BRL), and 0.4 ml of the cell suspension ($1.4 \times 10^5$ cells) was seeded onto the hardened fibrin gel and cultured for approximately 4 hours in a 5% $CO_2$ incubator (37° C.). After 4 hours, there was added to the outer chamber of the Transwell 1.5 ml of an SFM solution containing a mixture of angiogenic factors {10 ng/ml EGF (purchased from GIBCO BRL), 30 ng/ml FGF2 (purchased from GIBCO BRL), 75 ng/ml VEGF (purchased from Wako Pure Chemical Industries Co., Ltd.), 50 ng/ml HGF (purchased from R&D Co.) and 7.5 ng/ml TNF-α (purchased from Genzyme Corp.) [The concentrations of the angiogenic factors differed slightly according to the HUVEC lot.]} and a diluted test substance, and culturing was carried out in a 5% $CO_2$ incubator (37° C.). On the 2nd and 4th days after adding the test substance, the medium was exchanged with 1.5 ml of freshly prepared SFM solution containing the angiogenic factor mixture and test substance. Upon aspirating off the culture supernatant in the inner well on the 6th day after the initial addition of the test substance, 0.4 ml of a 3.3 mg/ml MTT solution dissolved in PBS (purchased from Sigma Corp.) was added and culturing was performed for approximately 1 hour in a 5% $CO_2$ incubator (37° C.). The number of tubes formed in the fibrin gel stained with MTT was scored based on microscope observation. Specifically, the number of tubes formed in the absence of the test substance was designated as +++, while – was assigned if absolutely no tubes formed. The number of tubes formed in the presence of the test substance was scored on the 5-level scale of +++, ++, +, +/–, – to evaluate the strength of inhibition of the test substance.

TABLE 1

[Pharmacological Test Example 1: Inhibition against invasive tube formation by vascular endothelial cells in response to stimulation by angiogenic factor mixture]

| Example No. | 0.01 µM | 0.1 µM | 1.0 µM |
|---|---|---|---|
| 25 | ++ | +/– | +/– |
| 53 | +++ | +/– | – |
| 55 | +++ | +/– | +/– |
| 72 | +++ | – | – |
| 74 | ++ | – | – |
| 75 | +++ | +/– | – |
| 81 | ++ | – | – |
| 100 | ++ | +/– | +/– |
| 153 | +/– | – | – |
| 172 | + | +/– | +/– |
| 189 | +/– | – | – |
| 212 | +/– | – | – |
| 245 | +/– | – | – |
| 298 | +/– | – | – |
| 316 | +/– | – | – |
| 348 | +/– | – | – |
| 368 | – | – | – |
| 374 | +/– | – | – |
| 404 | – | – | – |
| 415 | +/– | – | – |
| 422 | + | – | – |

Pharmacological Test Example 2

Inhibition Against Sandwich tube Formation by Vascular Endothelial Cells in Response to Stimulation by Angiogenic Factor Human Umbilical Vein Endothelial Cells (HUVECs) were isolated by the same method as in Pharmacological Test Example 1, and were cultured in a 5% $CO_2$ incubator (37° C.) using EGM-2 medium (purchased from Clonetics Corp.) until the cells reached confluency.

An ice-cooled mixture of collagen:5×RPMI 1640:reconstitution buffer (all purchased from Nitta Gelatin, Inc.) at 7:2:1 was dispensed at 0.4 ml into each well of a 24-well plate, and then stationed for 40 minutes in a 5% $CO_2$ incubator (37° C.) for gelling. The HUVECs were recovered using trypsin-EDTA and then suspended in human endothelial serum free medium (SFM, purchased from GIBCO BRL) containing added angiogenic factors [20 ng/ml FGF2 (purchased from GIBCO BRL) and 10 ng/ml EGF (purchased from GIBCO BRL), or 25 ng/ml VEGF (purchased from Wako Pure Chemical Industries Co., Ltd.) and 10 ng/ml EGF, or 30 ng/ml HGF (purchased from R&D Co.) and 10 ng/ml EGF], and the cell suspension was added at 0.4 ml to each well (with the cell counts differing slightly according to the HUVEC lot), and cultured overnight in a 5% $CO_2$ incubator (37° C.). On the following day, the medium on the upper layer was aspirated off, and then 0.4 ml of an ice-cooled mixture of collagen:5×RPMI 1640:reconstitution buffer (all purchased from Nitta Gelatin, Inc.) at 7:2:1 was superposed into each well prior to stationing for 4 hours in a 5% $CO_2$ incubator (37° C.) for gelling. After adding 1.5 ml of an SFM solution containing each of the aforementioned angiogenic factors and a diluted test substance onto the upper layer, culturing was performed in a 5% $CO_2$ incubator (37° C.). Upon aspirating off the culture supernatant in each well on the 4th day after addition of the test substance, 0.4 ml of a 3.3 mg/ml MTT solution dissolved in PBS (purchased from Sigma Corp.) was added to each well and culturing was performed for approximately 2 hours in a 5% $CO_2$ incubator (37° C.). The tubes formed in the collagen gel of each well were stained by the MTT, the tube images were loaded into a computer (Macintosh), and the total length of the tubes was determined by image analysis software "MacScope" (purchased from Mitani Corp.). The ratio of the total length of the tubes formed in the well containing the test substance with respect to the total length of the tubes formed in the well containing no test substance was expressed as a percentage, and the concentration of each test substance required for 50% inhibition of tube formation ($IC_{50}$) was determined from the ratio value.

TABLE 2

[Pharmacological Test Example 2: Inhibition against sandwich tube formation by vascular endothelial cells in response to stimulation by VEGF]

| Example No. | $IC_{50}$ (nM) | Example No. | $IC_{50}$ (nM) |
|---|---|---|---|
| 1 | 310 | 12 | 44 |
| 19 | 28 | 23 | 100 |
| 53 | 9.9 | 55 | 35 |
| 59 | 170 | 65 | 5.9 |
| 70 | 58 | 72 | 22 |
| 74 | 5.9 | 75 | 1.4 |
| 81 | 1.8 | 100 | 6.3 |
| 108 | 4.9 | 116 | 8.1 |
| 121 | 42 | 127 | 7.5 |
| 129 | 40 | 137 | 10 |
| 153 | 0.02 | 155 | 1.4 |
| 157 | 0.9 | 159 | 0.6 |
| 186 | 23 | 189 | 0.3 |
| 198 | 1.5 | 202 | 15 |
| 204 | 0.9 | 211 | 0.3 |
| 215 | 22 | 224 | 26 |
| 249 | 1.6 | 253 | 40 |
| 256 | 36 | 265 | 0.6 |
| 266 | 0.6 | 283 | 36 |
| 289 | 4.6 | 296 | 34 |
| 298 | 0.7 | 299 | 1.0 |
| 300 | 7.5 | 304 | 0.3 |
| 308 | 5.2 | 314 | 4.2 |
| 316 | 1.0 | 320 | 2.5 |
| 325 | 1.0 | 326 | 1.0 |
| 327 | 56 | 346 | 25 |
| 368 | 5.4 | 372 | 44 |
| 374 | 3.0 | 381 | 4.7 |
| 382 | 4.6 | 386 | 10 |
| 404 | 2.8 | 405 | 28 |
| 408 | 39 | 415 | 3.8 |
| 419 | 10 | 422 | 4.8 |
| 433 | 5.6 | 436 | 22 |
| 440 | 1.4 | 441 | 3.6 |
| 442 | 7.2 | 444 | 5.5 |

TABLE 2-continued

[Pharmacological Test Example 2: Inhibition against sandwich tube formation by vascular endothelial cells in response to stimulation by VEGF]

| Example No. | IC$_{50}$ (nM) | Example No. | IC$_{50}$ (nM) |
|---|---|---|---|
| 445 | 6.2 | 446 | 4.0 |
| 450 | 4.5 | 454 | 3.7 |
| 455 | 7.8 | 463 | 26 |
| 490 | 26 | 492 | 7.2 |
| 493 | 9.0 | 494 | 9.3 |
| 497 | 4.6 | 503 | 6.4 |
| 504 | 4.6 | 505 | 8.9 |
| 518 | 1.3 | 520 | 1.5 |
| 521 | 0.5 | 578 | 13 |

Pharmacological Test Example 3

Measurement of Inhibition Against Receptor Tyrosine Kinase Activity

This assay is used to determine inhibition of a test substance on tyrosine kinase activity. DNA coding for the cytoplasmic domain of VEGFR2 is obtained by total cDNA synthesis (Edwards M, International Biotechnology Lab 5(3), 19-25, 1987) or by cloning. Expression in an appropriate expression system can produce a polypeptide with tyrosine kinase activity. The cytoplasmic domain of VEGFR2 obtained by expression of recombinant protein in, for example, insect cells has been found to exhibit intrinsic tyrosine kinase activity. For VEGFR2 (Genbank Accession No. L04947), the 1.7 kb DNA fragment described by Terman et al. (Oncogene, 6(9), 1677-1683, 1991), coding for the cytoplasmic domain, beginning with lysine 791 and including the termination codon, was isolated from a human placental cDNA library (purchased from Clontech Laboratories, Inc.) and cloned in a Baculovirus expression vector (pFastBacHis, purchased from GIBCO BRL). The recombinant construct was transfected into insect cells (*Spondoptea frugiperda*9 (Sf9)) to prepare a recombinant Baculovirus. (Instructions for preparation and use of recombinant Baculovirus may be found in standard texts, such as "Bac-To-Bac Baculovirus Expression System" (GIBCO BRL).) The cytoplasmic fragment starting from lysine 398 (FGFR1, Genbank Accession No. X52833), the cytoplasmic fragment starting from lysine 558 (PDGFRβ, Genbank Accession No. M21616) or the cytoplasmic fragment starting from lysine 974 (HGFR, Genbank Accession No. J02958) may be cloned and expressed by the same method for use in assays for other tyrosine kinases. EGFR was purchased from Sigma Co. (Product No. E-2645).

For expression of the VEGFR2 tyrosine kinase, Sf9 cells were infected with the VEGFR2 recombinant virus and collected after 48 hours. The collected cells were rinsed with ice-cooled phosphate buffered saline (PBS) and then resuspended using 20 ml of ice-cooled Lysis Buffer (50 mM Tris-HCl (pH 8.5), 5 mM 2-mercaptoethanol, 100 mM KCl, 1 mM phenylmethylsulfonyl fluoride, 1% (v/v) NP-40) per $1.5 \times 10^8$ cells. The suspension was centrifuged at 12,000 rpm for 30 minutes at 4° C. and the supernatant was obtained.

The supernatant was added to a Ni-NTA agarose column (3 ml, purchased from Qiagen) equilibrated with Buffer A {20 mM Tris-HCl (pH 8.5), 5 mM 2-mercaptoethanol, 500 mM KCl, 20 mM imidazole, 10% (v/v) glycerol}. The column was washed with 30 ml of Buffer A, and then with 6 ml of Buffer B {20 mM Tris-HCl (pH 8.5), 5 mM 2-mercaptoethanol, 1M KCl, 10% (v/v) glycerol}, and finally with 6 ml of Buffer A. After washing, it was eluted with 6 ml of Buffer C {20 mM Tris-HCl (pH 8.5), 5 mM 2-mercaptoethanol, 100 mM KCl, 100 mM imidazole, 10% (v/v) glycerol}. The eluate was placed on a dialysis membrane (purchased from Spectrum Laboratories) and dialyzed with a dialysis buffer {20 mM Tris-HCl (pH 7.5), 10% (v/v) glycerol, 1 mM dithiothreitol, 0.1 mMNa$_3$VO$_4$, 0.1 mM EGTA}. After dialysis, it was supplied for SDS-electrophoresis, and the recombinant protein (His6-VEGFR2, cytoplasmic domain of VEGFR2 fused with 6 histidine residues at the N-terminus) detected at a molecular weight of approximately 100 kDa with Coumassie Brilliant Blue staining was assayed using BSA (bovine serum albumin, purchased from Sigma Co.) as the standard substance, and stored at −80° C. until use. Using the same method for the cytoplasmic domains of FGFR1, PDGFRβ and HGFR yielded respective recombinant proteins fused with 6 histidine residues at the N-termini (His6-FGFR1, His6-PDGFRβ or His6-HGFR).

The tyrosine kinase reaction was conducted as follows. In the case of VEGFR2, for example, 10 µl of a kinase reaction solution {200 mM Hepes (pH 7.4), 80 mM MgCl$_2$, 16 mM MnCl$_2$, 2 mM Na$_3$VO$_4$}, 250 ng of biotin-bound poly(Glu4: Tyr1) (biotin-poly(GT), purchased from CIS Diagnostics Co.) (6 µl of a 15-fold dilution with distilled water), 15 ng of His6-VEGFR2 (10 µl of a 240-fold dilution with 0.4% BSA solution) and the test substance dissolved in dimethylsulfoxide (4 µl of a 100-fold dilution with 0.1% BSA solution) were added into each well of a 96-well round-bottom plate (NUNC Co., Product No. 163320), to a total of 30 µl. Next, 10 µl of 4 µM ATP (diluted with distilled water) was added prior to incubation at 30° C. for 10 minutes, and then 10 µl of 500 mM EDTA (pH 8.0) was added.

The tyrosine phosphorylated biotin-poly(GT) was measured by the Homogenous Time-Resolved Fluorescence (HTRF) method (Analytical Biochemistry, 269, 94-104, 1999). Specifically, the kinase reaction solution was transferred to a 96-well black half-plate (Product No. 3694, Coster, Inc.), 7.5 ng of europium cryptate-labeled anti-phosphotyrosine antibody (Eu(K)-PY20, purchased from CIS Diagnostics Co.) (25 µl of a 250-fold dilution with 20 mM Hepes (pH 7.0), 0.5 M KF, 0.1% BSA solution) and 250 ng of XL665-labeled streptavidin (XL665-SA, purchased from CIS Diagnostics Co.) (25 µl of a 62.5-fold dilution with 20 mM Hepes (pH 7.0), 0.5 M KF and 0.1% BSA solution) were added thereto, the mixture was allowed to stand at room temperature for 30 minutes, and then the fluorescent intensity was measured at 665 nm and 620 nm under irradiation with an excitation wavelength of 337 nm using a Discovery HTRF Microplate Analyzer (Packard Co.). The tyrosine phosphorylation rate for the biotin-poly(GT) was expressed as the delta F % value as described in the HTRF Standard Experiment Methods text by CIS Diagnostics Co. The delta F % value in the presence of the test substance was determined as a ratio (%) with the delta F % value with addition of His6-VEGFR2 in the absence of the test substance defined as 100% and the delta F % value in the absence of both the test substance and His6-VEGFR2 defined as 0%. This ratio (%) was used to calculate the test substance concentration required for 50% inhibition of VEGFR2 kinase activity (IC$_{50}$).

Measurement of inhibition against FGFR1, EGFR and HGFR kinase activity was conducted using 15 ng of His6-FGFR1, 23 ng of EGFR and 30 ng of His6-HGFR, respectively, according to the tyrosine kinase reaction and HTRF method described above.

Measurement of inhibition against PDGFRβ kinase activity was conducted using 50 ng of His6-PDGFRβ according to the tyrosine kinase reaction described above, followed by detection of tyrosine phosphorylated biotin-poly(GT) by the following method.

Specifically, the kinase reaction solution was added to a 96-well streptavidin-coated plate (Product No. 15129, Pierce Chemical) and incubated at room temperature for 30 minutes. After rinsing 3 times with 150 μl of a rinsing solution {20 mM Tris-HCl (pH 7.6), 137 mM NaCl, 0.05% Tween-20, 0.1% BSA}, 70 μl of anti-phosphotyrosine (PY20)-HRP conjugate (Product No. P-11625, Transduction Laboratories) {2000-fold dilution with 20 mM Tris-HCl (pH 7.6), 137 mM NaCl, 0.05% Tween-20, 1% BSA} was added thereto and incubation was performed at room temperature for 1 hour. After incubation, it was rinsed 3 times with 150 μl of the rinsing solution, and 100 μl of TMB Membrane Peroxidase Substrate (Product No. 50-5077-03, Funakoshi Co., Ltd.) was added to initiate the reaction. After stationing at room temperature for 10 minutes, 100 μl of 1 M phosphoric acid was added to suspend the reaction, and the absorbance at 450 nm was measured with a microplate reader (BIO KINETICS READER EL304, Bio-Tek Instruments). The absorbance ratio in the presence of the test substance was determined with respect to 100% as the absorbance with addition of His6-PDGFRβ and no test substance, and 0% as the absorbance without addition of the test substance or His6-PDGFRβ. This absorbance ratio was used to calculate the test substance concentration required for 50% inhibition of PDGFRβ kinase activity ($IC_{50}$).

TABLE 3

[Pharmacological Test Example 3: Inhibition against VEGFR2 kinase]

| Example No. | $IC_{50}$ (nM) | Example No. | $IC_{50}$ (nM) |
|---|---|---|---|
| 1 | 51 | 10 | 4.9 |
| 14 | 2.7 | 15 | 8.7 |
| 21 | 4.3 | 30 | 22 |
| 31 | 17 | 33 | 6.9 |
| 34 | 3.4 | 25 | 5.5 |
| 36 | 14 | 37 | 22 |
| 43 | 18 | 54 | 15 |
| 55 | 29 | 65 | 15 |
| 99 | 8.6 | 100 | 9.6 |
| 111 | 21 | 116 | 4.2 |
| 121 | 8.7 | 143 | 70 |
| 159 | 25 | 173 | 356 |
| 178 | 12 | 182 | 71 |
| 183 | 29 | 184 | 59 |
| 187 | 14 | 208 | 9.2 |
| 252 | 31 | 253 | 23 |
| 259 | 16 | 260 | 11 |
| 262 | 9.5 | 265 | 6.2 |
| 266 | 5.4 | 283 | 26 |
| 314 | 5.3 | 316 | 6.4 |
| 346 | 4.6 | 348 | 4.6 |
| 350 | 43 | 353 | 2.2 |
| 356 | 1.4 | 364 | 8.1 |
| 365 | 5.4 | 368 | 3.0 |
| 374 | 8.4 | 375 | 16 |
| 381 | 2.6 | 382 | 9.0 |
| 387 | 4.1 | 394 | 15 |
| 398 | 3.5 | 404 | 6.5 |
| 410 | 2.2 | 413 | 3.2 |
| 435 | 22 | 437 | 9.9 |
| 441 | 2.8 | 449 | 2.2 |
| 463 | 5.9 | 465 | 13 |
| 556 | 14 | | |

Pharmacological Test Example 4

Inhibition on Cancer Cell and Normal Cell Growth

Cancer cells (for example, KP-4 human pancreatic cancer cells) or normal cells (for example, IEC-18 rat ileal epithelial cells) were subcultured in RPMI 1640 medium containing 10% FBS (purchased from Nissui Pharmaceutical Co., Ltd.) every 3-4 days, and cells in the growth phase were used. After recovering the cells using trypsin-EDTA, the cells were counted and a 0.1 ml cell suspension of each diluted with 10% FBS-containing RPMI 1640 medium (to $2 \times 10^3$ cells/well for KP-4 and $8 \times 10^2$ cells/well for IEC18) was spread onto a 96-well plate for cell culturing. Culturing was performed overnight in a 5% $CO_2$ incubator (37° C.), and then a 0.1 ml solution of the test substance diluted with 10% FBS-containing RPMI 1640 was added and culturing was continued in a 5% $CO_2$ incubator (37° C.). On the 3rd day after addition of the test substance, 0.05 ml of a 3.3 mg/ml MTT solution (purchased from Sigma Co.) was added, and culturing was continued in the 5% $CO_2$ incubator (37° C.) for approximately 2 hours. After aspirating off of the culture supernatant and DMSO dissolution of the formazan produced in each well, the absorbance of each well was measured using an MTP-32 plate reader (Corona Electric) at a measuring wavelength of 540 nm and a reference wavelength of 660 nm. The absorbance ratio in the substance-added well was determined as a percentage with respect to the absorbance of the well without addition of the test substance, and this ratio was used to calculate the test substance concentration required for 50% inhibition of cell growth ($IC_{50}$).

Pharmacological Test Example 5

Effect of L6 (Rat Myoblasts) on PDGF-Dependent Growth

L6 (rat myloblasts) were subcultured in 10% FBS-containing D-MEM medium (purchased from Nissui Pharmaceutical Co., Ltd.) every 3-4 days, and cells in the growth phase were used. The cells were recovered using trypsin-EDTA and rinsed once with 10% FBS-free D-MEM medium, and the cells were counted. After spreading 0.1 ml of a cell suspension diluted with 10% FBS-free D-MEM medium onto a Type I collagen-coated 96-well tissue culturing plate at $5 \times 10^3$ cells/well, culturing was performed overnight in a 5% $CO_2$ incubator (37° C.). On the following day, 0.05 ml of a solution of the test substance diluted with 10% FBS-free D-MEM medium was added, with almost simultaneous addition of 0.05 ml of a 40 nM PDGF solution (10 nM final concentration), and culturing was continued in the 5% $CO_2$ incubator (37° C.). On the 3rd day after addition of the test substance, 0.01 ml of WST-1 solution (purchased from Wako Pure Chemical Industries Co., Ltd.) was added to each well, and culturing was continued in the 5% $CO_2$ incubator (37° C.) for approximately 3 hours until coloration. The absorbance of each well was measured using an MTP-32 plate reader (Corona Electric) at a measuring wavelength of 415 nm and a reference wavelength of 660 nm. The absorbance ratio in the substance-added well was determined as a percentage with respect to the absorbance of the well without addition of the test substance, and this ratio was used to calculate the test substance concentration required for 50% inhibition of cell growth ($IC_{50}$).

Pharmacological Test Example 6

Analysis of mRNA Expression by DNA Microarray/Quantitative PCR

1. Extraction of Total RNA from Sample

The cells were cultured at 37° C. either in 5% $CO_2$ or under low (1%) oxygen conditions. In the case of HUVEC, for example, EGM-2 medium (purchased from Clonetics Corp.) was used for culturing at 37° C. under 5% $CO_2$ conditions. At a prescribed time after reaction with the test substance, the cells were lysed using TRIZOL reagent (purchased from GIBCO BRL) according to the manufacturer's protocol. Specifically, it was accomplished as follows. A 1 ml portion of TRIZOL reagent is added per 10 $cm^2$ culturing area, and pipetting is carried out several times to collect the cells. After centrifuging the sample, the obtained supernatant is allowed to stand at room temperature for 5 minutes, and then chloroform (purchased from Junsei Chemical Co., Ltd.) is added in a proportion of 0.2 ml with respect to 1 ml of TRIZOL reagent used. The solution is vigorously shaken and stirred for 15 seconds and allowed to stand at room temperature for 2-3 minutes, and then centrifuged (12,000×g, 10 min, 4° C.). After centrifugation, the aqueous layer is transferred to a fresh tube, isopropyl alcohol (purchased from Wako Pure Chemical Industries Co., Ltd.) is added in a proportion of 0.5 ml to 1 ml of TRIZOL reagent used, and the mixture is allowed to stand at room temperature for 10 minutes and then centrifuged (12,000×g, 10 min, 4° C.). The obtained precipitate is rinsed with 75% ethanol (purchased from Wako Pure Chemical Industries Co., Ltd.) and then air-dried and supplied as total mRNA for the following procedure.

2. Quantitation of RNA

The RNA may be quantitated by techniques such as Northern blotting analysis, DNA microarray, RT-PCR, quantitative PCR and the like, with DNA microarray and quantitative PCR being preferred. Explanations of these techniques are provided below, but are not intended to be limitative on the invention.

1) Quantitation with a DNA microarray (Schena M. et al., Science, 270 (5235), 467-70, 1995 and Lockhart, D. J. et al., Nature Biotechnology, 14 (13), 1675-1680, 1996) is carried out in the following manner.

[1] cDNA Synthesis and Biotin Labeling

The initially obtained RNA was used as template to synthesize double-stranded cDNA with a SuperScript Choice System (purchased from GIBCO BRL) and T7-d$(T)_{24}$ primer, and then this cDNA was used as template for synthesis of biotinylated cRNA.

Specifically, 5 µg T7-d$(T)_{24}$ primer, 1×first strand buffer, 10 mM DTT, 500 µM dNTP mix and 20 unit/µl SuperScript II Reverse Transcriptase were added to 10 µg of RNA, and reaction was conducted at 42° C. for 1 hour to synthesize single-stranded cDNA. Next, 1×second strand buffer, 200 µM dNTP mix, 67 U/ml DNA ligase, 270 U/ml DNA polymerase I and 13 U/ml RNaseH were added and reaction was conducted at 16° C. for 2 hours to synthesize double-stranded cDNA. Finally, 67 U/ml T4 DNA polymerase I was added for reaction at 16° C. for 5 minutes, after which 10 µl of 0.5M EDTA (purchased from Sigma Co.) was added to suspend the reaction.

The obtained cDNA was purified with phenol/chloroform (purchased from Ambion, Inc.), and an RNA Transcript Labeling Kit (purchased from Enzo Diagnostics, Inc.) was used for labeling with biotinylated UTP and CTP according to the manufacturer's protocol. The reaction product was purified with an RNeasy column (purchased from Qiagen), and then heating was performed for 35 minutes at 94° C. in 200 mM Tris acetate (pH 8.1), 150 mM magnesium acetate and 50 mM potassium acetate, for fragmentation of the cRNA.

[2] DNA Microarray (GeneChip) Hybridization and Measurement

The fragmented cRNA is hybridized with a GeneChip (purchased from Affymetrix Corp.) Hu6800/Human Cancer G110 Array or an equivalent product, in 100 mM MES, 1M sodium salt, 20 mM EDTA, 0.01% Tween20, for example, at 45° C. for 16 hours. After hybridization, the GeneChip is rinsed and dyed according to protocol EukGE-WS2 included with the Affymetrix fluidics station or the optimum protocol for the array used. The dyeing is carried out using streptavidin-phycoerythrin (purchased from Molecular Probe) and biotinylated anti-streptavidin goat antibody (purchased from Vector Laboratories). The dyed GeneChip is scanned using an HP argon-ion laser confocal microscope (purchased from Hewlett Packard Co.), and the fluorescent intensity is measured. The fluorescence was measured with excitation at 488 nm and emission at 570 nm.

All of the quantitative data analysis was carried out using GeneChip software (purchased from Affymetrix Corp.) or Genespring (purchased from Silicon Genetics). For RNA quantitation, the average of the difference (perfect match hybridization signal—mismatch signal) is determined for each probe family, and the gene expression is judged as having significantly "increased" or "decreased" if the value is 5 or greater and the RNA quantities are disparate under 2 conditions, and preferably if they are disparate by a factor of 1.8 or greater.

2) Quantitation by quantitative PCR is conducted in the following manner.

Quantitative PCR is accomplished in the following manner using SYBR Green (purchased from Applied Biosystems) and an ABI Prism 7700 Sequence Detection System (purchased from Perkin-Elmer Applied Biosystems) or an equivalent apparatus.

The procedure is carried out by the two stages of reverse transcription and PCR reaction. In the reverse transcription of the first stage, dNTP, oligo d$(T)_{16}$ primer, RNase Inhibitor and Multiscribe Reverse Transcriptase (purchased from Perkin-Elmer Applied Biosystems) are added to the obtained RNA, the temperature is kept at 25° C. for 10 minutes, and then heating is effected at 48° C. for 30 minutes. The reaction is suspended by heating at 95° C. for 5 minutes.

The obtained cDNA is then supplied to the PCR reaction of the second stage. The PCR reaction is carried out in a reaction system comprising, for example, 4 ng cDNA, 1×SYBR PCR buffer, 3 mM $MgCl_2$, 200 µM each dATP, dCTP and dGTP, 400 µM dUTP, 200 nM primer pair, 0.01 U/µl AmpErase UNG and 0.025 U/µl Ampli Taq Gold DNA Polymerase (purchased from Perkin-Elmer Applied Biosystems). The reaction was conducted under conditions with 50° C. for 2 minutes and 95° C. for 10 minutes followed by 40 cycles of 95° C. for 20 seconds, 55° C. for 20 seconds and 72° C. for 30 seconds. The primers and probes are designed using Primer Expression (purchased from Perkin-Elmer Applied Biosystems) or equivalent software. The different test substances are compared while compensating the quantitative values based on the mRNA level of a housekeeping gene having low transcription level fluctuation, preferably GAPDH, in each specimen.

Pharmacological Test Example 7

Evaluation of In Vivo Angiogenesis-Inducing Activity using Mouse Dorsal Air Sac Model

[1] Construction of VEGF (Vascular Endothelial Growth Factor) Expression Vector

PCR was conducted using a human placenta cDNA library (purchased from Toyobo Co., Ltd.) as the template and the VEGF sequences 5'CCGGATCCATGAACTTTCTGCTG3' (SEQ ID NO: 1) and 5' GTGAATTCTGTATCGATCGTT3' (SEQ ID NO: 2) as primers. After completion of the PCR reaction, the 5' ends were phosphorylated and an approximately 600 bp DNA band was separated by 1.2% agarose gel electrophoresis. After polymerization by self-ligation, the cDNA was cut with EcoRI and BamHI and inserted into the EcoRI and BamHI sites of vector pUC19. This was used to transform E. coli JM83, and plasmids were recovered from the transformed clones. A VEGF cDNA fragment was cut out of the plasmids with HindIII and EcoRI and then inserted into an expression vector containing the neomycin resistance gene.

[2] Preparation of VEGF High-Expressing Strain

After overnight culturing of KP-1 human pancreatic cancer cells ($3\times10^6$ cells) with 10% FCS-containing RPMI 1640 medium, an Effectene Transfection Reagent Kit (purchased from Qiagen) was used for introduction of 3 µg of VEGF expression vector into the KP-1 cells. After culturing in 10% FCS-containing RPMI 1640 medium also containing 600 µg/ml of Geneticin, the high-expressing drug-resistant cells were selected as VEGF high-expressing KP-1 cells (KP-1/VEGF).

[3] Measurement of VEGF Level in Culture Supernatant

The KP-1/VEGF cells were prepared to $5\times10^5$ cells/ml, and 0.5 ml thereof was dispensed into each well of a 24-well plate and cultured at 37° C. for 24 hours. The culture supernatants were collected and the VEGF levels thereof measured using a VEGF measuring kit (purchased from IBL Co., Ltd.) for confirmation of high expression.

[4] Evaluation of In Vivo Angiogenesis-Inducing Activity using Mouse Dorsal Air Sac Model Millipore rings (purchased from Nihon Millipore) were sealed with 0.45 µm Durapore™ filter membranes (purchased from Nihon Millipore) to create chambers. KP-1/VEGF human pancreatic cancer cells ($3\times10^6$) suspended in 0.17 ml of collagen gel were injected into each chamber through the injection port, and the chambers were sealed. Approximately 10 ml of air was then injected in the dorsal skin of 6-week-old C57BL/6N female mice under anesthesia to produce pouches, and the prepared chambers were transplanted therein. About 6 hours after completing transplantation, a test substance suspended in 0.5% methyl cellulose was orally administered (0.1 ml/10 g body weight), and this was continued once a day for the next 4 days.

On the 4th day after transplanting the chambers, 0.2 ml of $^{51}$Cr (Amersham Pharmacia)—labeled mouse erythrocytes ($2.5\times10^6$ cpm/ml) were injected through the caudal veins of each of the mice with the transplanted chambers. After a prescribed period, the skin in contact with the chamber was excised and frozen, the section in direct contact with the chamber was precisely cut off, and the radioactivity was measured with a γ-counter. The blood volume was calculated from the radioactivity and used as an index of the in vivo angiogenesis-inducing activity. The angiogenesis volume was recorded as this measured blood volume minus the blood volume obtained with transplantation of a chamber containing only collagen gel. The experiment was conducted using 10 mice in the control (solvent-administered) group and 5 mice in each compound-administered group.

Pharmacological Test Example 8

Evaluation of Antitumor Activity on KP-1/VEGF Cells in Subcutaneous Xenograft Models VEGF high-expressing pancreatic cancer cells (KP-1/VEGF) suspended in PBS at a concentration of $1\times10^7$ cells/ml were transplanted under the right flank skin of 6-week-old female Balb/c (nu/nu) mice in a volume of 0.1 ml. When the tumor volume reached approximately 100 mm$^3$, the test substance was orally administered over a period of 2 weeks with a schedule of 5 days per week. The test substance was suspended in 0.5% methyl cellulose for an administered volume of 0.1 ml/10 g body weight. The tumor size was measured twice a week using a micrometer caliper. The tumor volume was determined by measuring the long and short diameters of the tumor with a micrometer caliper, and calculating 1/2× (long diameter×short diameter×short diameter). The experiment was conducted using 10 mice in the control (solvent-administered) group and 5 mice in each test substance-administered group.

Pharmacological Test Example 9

Evaluation of Tumor Growth, Cancerous Ascites Accumulation and Survival Period in Orthotopic Transplantation Models of Pancreatic Cancer After abdominal section of 6- to 7-week-old female Balb/c (nu/nu) mice under anesthesia and exposure of the pancreases, VEGF high-expressing pancreatic cancer cells (KP-1/VEGF) suspended in PBS at a concentration of $1\times10^7$ cells/ml were directly transplanted into each pancreas head at a volume of 0.1 ml. Upon the 4th week after transplantation, the test substance was orally administered over a period of 10 weeks with a schedule of 5 days per week. The test substance was suspended in 0.5% methyl cellulose for an administered volume of 0.1 ml/10 g body weight. Body weight was periodically measured twice per week during the test period, and the presence of ascites accumulation was recorded based on appearance. The survival period was based on tabulating the number of mice which died up until completion of the experiment. Tumor weight was measured in individuals suitable for postmortem autopsy. The experiment was conducted using 8 to 10 mice per group.

INDUSTRIAL APPLICABILITY

According to the present invention, it is possible to provide novel compounds that exhibit (1) powerful inhibiting action against invasive tube formation by vascular endothelial cells induced by an angiogenic factor mixture comprising Epidermal Growth Factor (EGF)/VEGF/Fibroblast Growth Factor 2 (FGF2)/Hepatocyte Growth Factor (HGF)/Tumor Necrosis Factor alpha (TNF-α), (2) powerful inhibiting action against tube formation by vascular endothelial cells specifically induced by single angiogenic factors (for example, VEGF, FGF, HGF and other such factors), and 3) powerful inhibiting action against receptor kinases for various angiogenic factors. It is further possible to provide novel compounds which are highly useful as medicines.

Among the group of compounds with the action of (1) to (3) described above there may also be provided a group of compounds with tumor cell growth-inhibiting action.

Incidentally, angiogenesis in the body is known to depend not on a single angiogenic factor but rather on the additive and synergistic effect of multiple angiogenic factors ((1) Koolwijk P, van Erck M G M, de Vree W J A, Vermeer M A, Weich H A, Hane maaijer R, van Hinsbergh V W M. Cooperative effect of TNF-alpha, bFGF and VEGF on the formation of tubular structures of human microvascular endothelial cells in a fibrin matrix. Role of urokinase activity. J. Cell Biol. 1996, 132, P1177-1188.; (2) Tallquist M D, Soriano P, Klinghoffer R A. Growth factor signaling pathways in vascular development. Oncogene 1999, 18, P7917-7932.).

Thus, the compounds of the invention which inhibit tube formation induced by multiple angiogenic factors produced by cancer cells and the like are expected to exhibit powerful angiogenesis inhibition in vivo, and should be highly useful as angiogenesis inhibitors. Moreover, the compounds of the invention may be useful as prophylactic or therapeutic agents for diseases for which angiogenesis inhibition is effective, and specifically as angiogenesis inhibitors, antitumor agents, angioma treatment agents, cancer metastasis inhibitors, retinal neovascularization treatment agents, diabetic retinopathy treatment agents, general inflammatory disease treatment agents, inflammatory disease treatment agents for deformant arthritis, rheumatoid arthritis, psoriasis, delayed hypersensitivity reaction and the like, or atherosclerosis treatment agents, and particularly as antitumor agents, based on their angiogenesis inhibition.

EXAMPLES

The present invention will now be explained in further and more concrete detail through the following examples, with the implied understanding that these examples are in no way limitative on the invention.

PRODUCTION EXAMPLES

Production Example 1

2-(3-Chloropropyl)-1,2,3-triazole (Production Example 1-A)

1-(3-Chloropropyl)-1,2,3-triazole (Production Example 1-B)

A suspension of sodium hydride (1.55 g, 30.8301 mmol, 60% in oil) in hexane was allowed to stand, and after removing the supernatant, dimethylformamide (25 ml) was added thereto to forma suspension and 1H-1,2,3-triazole (1.5 ml, 25.8867 mmol) was added dropwise while cooling on ice. This was stirred at room temperature for 5 minutes to thorough dissolution, and then 1-bromo-3-chloropropane (2.82 ml, 28.4754 mmol) was added and the mixture was stirred at room temperature for 8 hours. After adding water while cooling on ice, the mixture was extracted with diethyl ether and then with ethyl acetate, washed with saturated brine and dried over anhydrous magnesium sulfate, the solvent was distilled off under reduced pressure, and the isomers were separated by NH silica gel column chromatography (hexane-ethyl acetate) and purified to obtain low polarity 2-(3-chloropropyl)-1,2,3-triazole (0.429 g, 2.9466 mmol, 11.38%) and high polarity 1-(3-chloropropyl)-1,2,3-triazole (0.910 g, 6.2504 mmol, 24.15%) as colorless oils.

2-(3-chloropropyl)-1,2,3-triazole (Production Example 1-A)

$^1$H-NMR Spectrum (CDCl$_3$) δ (ppm): 2.42 (2H, tt, J=6.4 Hz, 6.4 Hz), 3.54 (2H, t, J=6.4 Hz), 4.64 (2H, t, J=6.4 Hz), 7.61 (2H, s).

1-(3-chloropropyl)-1,2,3-triazole (Production Example 1-B)

$^1$H-NMR Spectrum (CDCl$_3$) δ (ppm): 2.41 (2H, m), 3.52 (2H, d, J=6.0 Hz), 4.60 (2H, d, J=6.4 Hz), 7.61 (1H, d, J=0.8 Hz), 7.72 (1H, d, J=0.8 Hz).

Production Example 2

1-Chloro-3-(4-pyridyl)propane 3-(4-Pyridyl)-1-propanol (2.68 g, 19.3724 mmol) was dissolved in dichloromethane (100 ml), triphenylphosphine (5.6 g. 21.3096 mmol) was added, and then N-chlorosuccinimide (2.6 g, 19.3724 mmol) was gradually added while cooling on ice prior to stirring overnight. After distilling off the solvent under reduced pressure, the residue was dissolved in ethyl acetate and extracted with 1N hydrochloric acid. Upon neutralization with saturated sodium bicarnobate water, the mixture was extracted with ethyl acetate, washed with saturated brine and dried over anhydrous magnesium sulfate, and the solvent was distilled off under reduced pressure to obtain the title compound (2,375 g, 15.2605 mmol, 78.77%) as a yellowish-brown oil. This was used without further purification for the following reaction.

$^1$H-NMR Spectrum (CDCl$_3$) δ (ppm): 2.11 (2H, m), 2.80 (2H, t, J=7.6 Hz), 3.54 (2H, t, J=6.4 Hz), 7.14 (2H, dd, J=1.6 Hz, 4.4 Hz), 8.52 (2H, dd, J=1.6 Hz, 4.4 Hz).

Production Example 3

4-Amino-3-fluorophenol

3-Fluoro-4-nitrophenol (5.0 g, 31.83 mmol) was dissolved in ethyl acetate (50 ml) and tetrahydrofuran (75 ml), and then palladium carbon (2.0 g) was added and the mixture was stirred for 8.5 hours at room temperature under a hydrogen atmosphere. The catalyst was filtered off, the filtrate was washed with ethanol, the solvent was distilled off under reduced pressure and the obtained crystals were washed with addition of hexane:ethanol=1:1. The crystals were filtered out, washed with diethyl ether and dried by aspiration to obtain the title compound (1.62 g, 12.74 mmol, 40.61%) as light yellow crystals.

$^1$H-NMR Spectrum (DMSO-d$_6$) δ (ppm): 4.35 (1H, brs), 6.32 (1H, dd, J=2.4 Hz, 8.4 Hz), 6.39-6.45 (1H, m), 6.57 (1H, dd, J=8.4 Hz, 10.4 Hz).

Production Example 4

N-(2,4-Difluorophenyl)-N'-(2-fluoro-4-hydroxyphenyl)urea

4-Amino-3-fluoronitrophenol (500 mg, 3.9333 mmol) was dissolved in tetrahydrofuran (15 ml), 2,4-difluoro isocyanate (0.56 ml, 4.7199 mmol) was added dropwise, and the mixture was heated to reflux for 1 hour under a nitrogen atmosphere. After allowing the mixture to cool, the solvent was distilled off under reduced pressure, and the obtained crystals were washed with addition of hexane:ethanol=1:1. The crystals were filtered out, washed with hexane:ethanol=1:1 and dried by aspiration to obtain the title compound (960 mg, 3.4016 mmol, 86.48%) as light violet crystals.

$^1$H-NMR Spectrum (DMSO-d$_6$) δ (ppm): 6.54 (1H, m), 6.60 (1H, ddd, J=2.4 Hz, 2.4 Hz, 8.8 Hz), 7.00 (1H, m), 7.27 (1H, ddd, J=2.8 Hz, 9.0 Hz, 11.6 Hz), 7.69 (1H, m), 8.07 (1H, ddd, J=6.0 Hz, 9.0 Hz, 9.0 Hz), 8.53 (1H, s), 8.72 (1H, s), 9.56 (1H, s).

Production Example 5

7-Benzyloxy-6-cyano-4-(4-nitrophenoxy)quinoline

To the 7-benzyloxy-4-chloro-6-cyanoquinoline (2.60 g, 8.83 mmol) described in WO98/13350 there were added 4-nitrophenol (2.46 g, 17.7 mmol) and lutidine (2.06 ml, 17.7 mmol), and the mixture was heated and stirred at 155-158° C. for 2 hours. After returning the reaction system to room temperature, it was dissolved in tetrahydrofuran, saturated sodium bicarnobate water was added and stirred therewith for 10 minutes, the mixture was concentrated under reduced pressure, the precipitated solid was filtered out and subjected to silica gel column chromatography (Fuji Silysia NH Type, eluent—hexane:ethyl acetate=50:50→ethyl acetate alone), the fraction containing the target substance was concentrated and the obtained solid was washed with diethyl ether. It was then dried under reduced pressure to obtain the title compound (1.84 g, 4.63 mmol, 52.6%).

$^1$H-NMR Spectrum (DMSO-$d_6$) δ (ppm): 5.48 (2H, s), 6.89 (1H, d, J=6.1 Hz), 7.30-7.60 (8H, m), 7.78 (1H, s), 8.36-8.41 (2H, m), 8.80 (1H, s), 8.85 (1H, d, J=6.1 Hz).

Production Example 6

4-(4-Aminophenoxy)-7-(benzyloxy)-6-cyanoquinoline

Iron powder (0.6 g), ammonium chloride (1.4 g), ethanol (100 ml) and water (30 ml) were added to the 7-benzyloxy-6-cyano-4-(4-nitrophenoxy)quinoline obtained in Production Example 5, and the mixture was stirred at 90° C. for 2.5 hours. The reaction system was returned to room temperature and then filtered with celite, the filtrate was subjected to liquid separation, and the organic layer was washed with water and saturated brine in that order, dried over sodium sulfate and then concentrated to dryness under reduced pressure to obtain 1.31 g of a crude product containing the target substance. The crude product was used directly for the following reaction. (Production Example 7).

$^1$H-NMR Spectrum (CDCl$_3$) δ (ppm): 3.75 (2H, br), 5.35 (2H, s), 6.46 (1H, d, J=5.2 Hz), 6.75-6.78 (2H, m), 6.94-6.97 (2H, m), 7.35 (1H, d, J=7.6 Hz), 7.42 (2H, t, J=6.8 Hz), 7.50-7.55 (3H, m), 8.63 (1H, d, J=5.2 Hz), 8.72 (1H, s).

Production Example 7

7-Benzyloxy-6-cyano-4-(3-fluoro-4-nitrophenoxy)quinoline

The 7-benzyloxy-4-chloro-6-cyanoquinoline (8.82 g, 30.0 mmol) described in WO98/13350 was suspended in 1-methylpyrrolidone (30 ml), and then 3-fluoro-4-nitrophenol (5.18 g, 33.0 mmol) and N,N-diisopropylethylamine (3.88 g, 30.0 mmol) were added and the mixture was heated and stirred at 110° C. for 4 hours. After returning the reaction system to room temperature, water was added and a solid precipitated. The obtained solid was filtered out, washed with water, methanol and ethyl acetate and dried at 60° C. to obtain the title compound (4.98 g, 12.0 mmol, 40%) as colorless crystals.

$^1$H-NMR Spectrum (CDCl$_3$) δ (ppm): 5.37 (2H, s), 6.73 (1H, d, J=5.2 Hz), 7.07-7.13 (2H, m), 7.33-7.45 (3H, m), 7.50-7.56 (2H, m), 7.60 (1H, s), 8.21-8.27 (1H, m), 8.55 (1H, s), 8.83 (1H, d, J=5.2 Hz).

Production Example 8

7-Benzyloxy-6-cyano-4-(3-fluoro-4-aminophenoxy)quinoline

The 7-benzyloxy-6-cyano-4-(3-fluoro-4-nitrophenoxy)quinoline (5.30 g, 12.8 mmol) obtained in Production Example 7, iron (3.57 g, 64.0 mmol) and ammonium chloride (6.85 g, 128 mmol) were suspended in an ethanol (120 ml)-water (30 ml) mixed solvent, and the suspension was heated and stirred at 100° C. for 3 hours. After completion of the reaction, the reaction mixture was filtered with celite and washed in an ethyl acetate (500 ml)-N,N-dimethylformamide DMF (50 ml) mixed solvent. The organic layer was washed with water and saturated brine, dried over magnesium sulfate and concentrated. The obtained solid was recrystallized from an ethyl acetate-hexane mixed solvent and then dried to obtain the title compound (2.53 g, 6.56 mmol, 51%) as light brown crystals.

$^1$H-NMR Spectrum (CDCl$_3$) δ (ppm): 3.80 (2H, brs), 5.35 (2H, s), 6.48 (1H, d, J=5.3 Hz), 6.78-6.90 (3H, m), 7.32-7.44 (3H, m), 7.51 (1H, s), 7.52-7.56 (2H, m), 8.66 (1H, d, J=5.3 Hz), 8.69 (1H, s).

Production Example 9

6-Cyano-7-(2-methoxyethoxy)-4-(4-nitrophenoxy)quinoline

A mixture of 4-chloro-6-cyano-7-(2-methoxyethoxy)quinoline (3 g), 4-nitrophenol (3.17 g) and 2,6-lutidine (2.7 ml) was heated and stirred in an oil bath at 155° C. for 1.5 hours. After completion of the reaction, ethyl acetate was added, and the precipitated solid was filtered out. The solid was washed with 1N sodium hydroxide water and then with water and dried to obtain 1.8 g of the title compound.

$^1$H-NMR (DMSO-$d_6$) δ (ppm): 3.36 (3H, s), 3.76-3.79 (2H, m), 4.41-4.44 (2H, m), 6.85 (1H, d, J=5.2 Hz), 7.54 (2H, d, J=9.2 Hz), 7.68 (1H, s), 8.37 (2H, d, J=9.2 HZ), 8.74 (1H, s), 8.83 (1H, d, J=5.2 Hz).

Production Example 10

4-(4-Aminophenoxy)-6-cyano-7-(2-methoxyethoxy)quinoline

6-Cyano-7-(2-methoxyethoxy)-4-(4-nitrophenoxy)quinoline (1.8 g), iron (1.8 g) and ammonium chloride (3.6 g) were suspended in an ethanol (30 ml)-water (7 ml) mixed solvent and the suspension was heated and stirred at 80° C. for 2 hours. After completion of the reaction, the reaction mixture was filtered with celite and washed in ethyl acetate. The organic layer was washed with saturated brine, dried over magnesium sulfate and concentrated. The obtained solid was washed with ether and dried to obtain 1.2 g of the title compound.

$^1$H-NMR (DMSO-$d_6$) δ (ppm): 3.36 (3H, s), 3.75-3.78 (2H, m), 4.38-4.41 (2H, m), 5.19 (2H, brd), 6.45 (1H, d, J=5.2 Hz), 6.65 (2H, d, J=8.8 Hz), 6.93 (2H, d, J=8.8 Hz), 7.59 (1H, s), 8.68 (1H, d, J=5.2 HZ), 8.71 (1H, s).

Production Example 11

6-Cyano-4-(3-fluoro-4-nitrophenoxy)-7-(2-methoxyethoxy)quinoline

4-Chloro-6-cyano-7-(2-methoxyethoxy)quinoline (1.7 g) and 3-fluoro-4-nitrophenol (2.0 g) were suspended in chlorobenzene (20 ml), and the suspension was heated to reflux for 6 hours. After completion of the reaction, the solvent was distilled off, ethyl acetate was added, and a solid precipitated. The solid was filtered out and washed with ether, washed with 1N sodium hydroxide water and with water, and then dried to obtain 1.55 g of the title compound.

$^1$H-NMR (DMSO-d$_6$) δ (ppm): 3.38 (3H, s), 3.78-3.81 (2H, m), 4.44-4.47 (2H, m), 7.02 (1H, d, J=5.2 Hz), 7.33-7.37 (1H, m), 7.69 (1H, dd, J=2.8 Hz, J=12 Hz), 7.72 (1H, s), 8.33 (1H, t, J=8.8 HZ), 8.75 (1H, s), 8.88 (1H, d, J=5.2 Hz).

Production Example 12

4-(4-Amino-3-fluorophenoxy)-6-cyano-7-(2-methoxyethoxy)quinoline

The title compound (1.23 g) was obtained from the nitro compound (1.55 g) obtained in Production Example 11, in the same manner as Production Example 10.

$^1$H-NMR (DMSO-d$_6$) δ (ppm): 3.38 (3H, s), 3.78-3.81 (2H, m), 4.42-4.44 (2H, m), 5.25-5.27 (2H, brd), 6.54 (1H, d, J=5.2 Hz), 6.87-6.89 (2H, m), 7.10-7.14 (1H, m), 7.62 (1H, s), 8.72 (1H, d, J=5.2 HZ), 8.74 (1H, s).

Production Example 13

6-Cyano-7-methoxy-4-(4-nitrophenoxy)quinoline

A mixture of 4-chloro-6-cyano-7-methoxyquinoline (0.35 g) obtained in the same manner as Production Example 7, 4-nitrophenol (0.36 g) and 2,6-lutidine (0.25 ml) was heated and stirred in an oil bath at 170° C. After completion of the reaction, water and ethyl acetate were added to the reaction mixture for extraction. The organic layer was washed with an aqueous saturated sodium bicarnobate solution and saturated brine, dried over magnesium sulfate and concentrated. The obtained residue was passed through an NH silica gel column (Fuji Silysia Chemical), eluted with a solvent (ethyl acetate: hexane=1:2) and concentrated to obtain 0.2 g of the title compound.

$^1$H-NMR (DMSO-d$_6$) δ (ppm): 4.06 (3H, s), 6.87 (1H, d, J=5.6 Hz), 7.54 (2H, d, J=8.8 Hz), 7.65 (1H, s), 8.36 (2H, d, J=8.8 Hz), 8.75 (1H, s), 8.84 (1H, d, J=5.6 Hz).

Production Example 14

4-(4-Aminophenoxy)-6-cyano-7-methoxyquinoline

The title compound (0.17 g) was obtained from 6-cyano-7-methoxy-4-(4-nitrophenoxy)quinoline (0.2 g) in the same manner as Production Example 10.

$^1$H-NMR (DMSO-d$_6$) δ (ppm): 4.06 (3H, s), 5.15-5.20 (2H, m), 6.46 (1H, d, J=5.6 Hz), 6.66 (2H, d, J=8.8 Hz), 6.93 (2H, d, J=8.8 Hz), 7.56 (1H, s), 8.69 (1H, d, J=5.6 Hz), 8.71 (1H, s).

Production Example 15

6-Cyano-4-(3-fluoro-4-nitrophenoxy)-7-methoxyquinoline

The title compound (0.33 g) was obtained from 4-chloro-6-cyano-7-methoxyquinoline (0.5 g) obtained in the same manner as Production Example 7, in the same manner as Production Example 13.

$^1$H-NMR (DMSO-d$_6$) δ (ppm): 4.07 (3H, s), 7.00 (1H, d, J=5.2 Hz), 7.30-7.34 (1H, m), 7.65 (1H, dd, J=2.8 Hz, J=12 Hz), 7.66 (1H, s), 8.30 (1H, t, J=8.8 Hz), 8.72 (1H, s), 8.87 (1H, d, J=5.2 Hz).

Production Example 16

4-(4-Amino-3-fluorophenoxy)-6-cyano-7-methoxyquinoline

The title compound (0.24 g) was obtained from 6-cyano-4-(3-fluoro-4-nitrophenoxy)-7-methoxyquinoline (0.32 g) in the same manner as Production Example 10.

$^1$H-NMR (DMSO-d$_6$) δ (ppm): 4.06 (3H, s), 5.26 (2H, brs), 6.54 (1H, d, J=5.2 Hz), 6.85-6.91 (2H, m), 7.11 (1H, dd, J=2.0 Hz, J=11.2 Hz), 7.59 (1H, s), 8.72 (1H, d, J=5.2 Hz), 8.73 (1H, s).

Production Example 17

Phenyl N-(4-(6-cyano-7-(2-methoxyethoxy)-4-quinolyl)oxyphenyl)carbamate

The 4-(4-aminophenoxy)-6-cyano-7-(2-methoxyethoxy)quinoline (3.354 g, 10.0 mmol) obtained in Production Example 10 was dissolved in dimethylformamide (35 ml) under a nitrogen atmosphere, and then the solution was cooled in an ice water bath, pyridine (2.43 ml, 30.0 mmol) and phenyl chloroformate (1.38 ml, 11.0 mmol) were added in that order, and the mixture was stirred at room temperature for 3 hours. Water (40 ml) was added to the reaction solution and the precipitated crystals were filtered out. The filtrate was extracted with ethyl acetate, and the organic layer was washed with water and saturated brine and dried over anhydrous sodium sulfate. The drying agent was filtered off, and the crystals obtained by concentration under reduced pressure were combined with the previous crystals, suspended in hexane-ethyl acetate (5:1) and stirred overnight, after which the crystals were filtered out and dried under reduced pressure to obtain the title compound (4.334 g, 9.52 mmol, 95.2%) as light brown crystals.

$^1$H-NMR Spectrum (CDCl$_3$) δ (ppm): 3.53 (3H, s), 3.91 (2H, t, J=4.4 Hz), 4.38 (2H, t, J=4.4 Hz), 6.49 (1H, d, J=5.2 Hz), 7.07 (1H, br), 7.17-7.32 (5H, m), 7.40-7.45 (2H, m), 7.44 (1H, s), 7.59 (2H, d, J=8.8 Hz), 8.67 (1H, d, J=5.6 Hz), 8.70 (1H, s).

Production Example 18

Phenyl N-(4-(6-cyano-7-(2-methoxyethoxy)-quinolyl)oxy-2-fluorophenyl)carbamate

The 4-(4-amino-3-fluorophenoxy)-6-cyano-7-(2-methoxyethoxy)quinoline (2500 mg) obtained in Production Example 12 was dissolved in 20 ml of dimethylformamide and 1.7 ml of pyridine, and the solution was cooled to 0° C. under a nitrogen atmosphere. After adding 0.97 ml of phenyl chlorocarbonate to the solution, it was stirred at room temperature for 2 hours. Ethyl acetate and water were added to the reaction solution for distribution, and the organic layer was washed with water and saturated brine in that order, dried over anhydrous sodium sulfate and then concentrated under reduced pressure to obtain 3.7 g of a residue. This was dissolved in tetrahydrofuran, and then n-hexane was added and the precipitated solid was filtered out to obtain 2.2 g of the title compound as light brown crystals (67% yield).

$^1$H-NMR Spectrum (CDCl$_3$) δ (ppm): 3.36 (3H, s), 3.89-3.94 (2H, m), 4.34-4.39 (2H, m), 6.52 (1H, d, J=5.6 Hz), 7.01-7.06 (2H, m), 7.21-7.30 (4H, m), 7.40-7.45 (2H, m), 7.49 (1H, s), 8.26 (1H, brs), 8.66 (1H, s), 8.70 (1H, d, J=5.6 Hz).

Production Example 19

Phenyl N-(4-(6-cyano-7-methoxy-4-quinolyl)oxyphenyl)carbamate

The 4-(4-aminophenoxy)-6-cyano-7-methoxyquinoline (747 mg) obtained in Production Example 14 was dissolved in 7 ml of dimethylformamide and 0.34 ml of pyridine, and the solution was cooled to 0° C. under a nitrogen atmosphere. After adding 0.34 ml of phenyl chlorocarbonate to the solution, it was stirred at room temperature for 2 hours. Ethyl acetate and water were added to the reaction solution, and the precipitated solid was filtered out to obtain 590 mg of the title compound as light brown crystals (56% yield).

$^1$H-NMR Spectrum (DMSO-$d_6$) δ (ppm): 4.04 (3H, s), 6.52 (1H, d, J=5.6 Hz), 7.20-7.30 (5H, m), 7.40-7.46 (2H, m), 7.60 (1H, s), 7.62-7.68 (2H, m), 8.72 (1H, d, J=5.6 Hz), 8.75 (1H, s), 10.4 (1H, brs).

Production Example 20

6-Chloro-4-(4-nitrophenoxy)pyrimidine

After adding 4,6-dichloropyrimidine (750 mg) to a suspension of 4-nitrophenol (700 mg) and sodium hydride (60%) (200 mg) in dimethylformamide (13 ml) at 0° C., the mixture was heated and stirred at 80° C. for 1.5 hours. The reaction solution was poured into saturated brine and extracted with ethyl acetate. The organic layer was dried over magnesium sulfate and then concentrated. The obtained residue was passed through an NH silica gel column (Fuji Silysia Chemical), eluted with a solvent (ethyl acetate-hexane=1-4) and concentrated to obtain 700 mg of the title compound.

$^1$H-NMR (DMSO-$d_6$) δ (ppm): 7.08 (1H, d, J=0.8 Hz), 7.30-7.37 (2H, m), 8.32-8.36 (2H, m), 8.60 (1H, d, J=0.8 Hz).

Production Example 21

4-(4-Amino-3-fluorophenoxy)-7-hydroxyquinoline-6-carbonitrile

After adding 26 ml of trifluoroacetic acid and 2.6 ml of thioanisole to 2.6 g of 7-benzyloxy-6-cyano-4-(3-fluoro-4-nitrophenoxy)quinoline 2.6 g, the mixture was stirred at 70-72° C. for 15 hours and returned to room temperature, and then the reaction system was concentrated, saturated sodium bicarnobate water and methanol were added to the residue, and the precipitated yellow crystals were filtered out. Drying yielded 2.61 g of crystals. To 640 mg of the crystals there were added 950 mg of iron, 1.8 g of ammonium chloride, 10 ml of ethanol, 10 ml of tetrahydrofuran, and 10 ml of water, the mixture was refluxed for 1 hour, the reaction system was filtered with celite, ethyl acetate and water were added to the filtrate for liquid separation and extraction, and the organic layer was concentrated to dryness to obtain 355 mg of the title compound.

$^1$H-NMR Spectrum: (DMSO$d_6$) 5.22 (2H, s), 6.42 (1H, d, J=5.8 Hz), 6.80-6.90 (2H, m), 7.08 (2H, d, J=12.0 Hz), 8.60-8.65 (2H, m), 11.60 (1H, brs)

Production Example 22

Phenyl 3-methylsulfonylphenylcarbamate

1-Amino-3-methylthiobenzene (1.27 ml, 10 mmol) was dissolved in tetrahydrofuran (10 ml), and then triethylamine (1.46 ml, 10.5 mmol) and phenyl chloroformate (1.32 ml, 10.5 mmol) were added dropwise in that order at room temperature under a nitrogen atmosphere and the mixture was stirred overnight. The reaction solution was distributed between ethyl acetate and water, and the organic layer was washed with saturated brine and dried over anhydrous sodium sulfate. After distilling off the solvent and drying under reduced pressure, the residue was dissolved in dichloromethane (50 ml), and 3-chloroperbenzoic acid (4.93 g, 20 mmol) was gradually added while cooling in an ice water bath. An aqueous saturated solution of sodium thiosulfate was added to the reaction solution, and then the insoluble portion was filtered off, and extraction with ethyl acetate was followed by washing with an aqueous saturated solution of sodium carbonate and drying over anhydrous sodium sulfate. The solvent was distilled off, and the residue was purified by silica gel column chromatography (ethyl acetate-hexane=1:1) to obtain the title compound (2.545 g, 8.74 mmol, 87.4%) as white crystals.

$^1$H-NMR Spectrum (CDCl$_3$) δ (ppm): 3.07 (3H, s), 7.18-7.29 (4H, m), 7.40-7.44 (2H, m), 7.55 (1H, t, J=8.0 Hz), 7.68 (1H, d, J=8.0 Hz), 7.80 (1H, d, J=8.0 Hz), 8.05 (1H, s).

Production Example 23

4-[(2,2-Dimethyl-4,6-dioxo[1,3]dioxane-5-ylidenemethyl)-amino]-2-methoxybenzonitrile 4-Amino-2-chlorobenzonitrile (3 g) was dissolved in 1-methyl-2-pyrrolidone (10 ml), and then sodium methoxide (2.12 g) was added and the mixture was heated and stirred for 7 hours at 100° C. The reaction solution was poured into an aqueous saturated solution of ammonium chloride and extracted with ethyl acetate, and the organic layer was dried over magnesium sulfate and concentrated. The obtained residue was subjected to NH silica gel column chromatography and eluted with a solvent (ethyl acetate:n-hexane=1:2) to obtain an aniline compound (1.26 g). The aniline compound (1.26 g) was heated to reflux in ethanol together with ethoxymethylene-Meldrum acid (1.7 g). The solid which precipitated after 2 hours was filtered out, washed with ethanol and then dried to obtain the title compound (1.9 g).

$^1$H-NMR Spectrum (DMSO-$d_6$) δ (ppm): 1.66 (6H, s), 3.94 (3H, s), 7.21-7.26 (1H, m), 7.46-7.50 (1H, m), 7.72 (1H, d, J=8.4 Hz), 8.70 (1H, s).

Production Example 24

7-Methoxy-4-oxo-1,4-dihydroquinoline-6-carbonitrile

4-[(2,2-Dimethyl-4,6-dioxo[1,3]dioxane-5-ylidenemethyl)amino]-2-methoxybenzonitrile (1.9 g) was heated for cyclization in the same manner as Production Example 457-3, to obtain the title compound (1.08 g) as a solid.

$^1$H-NMR Spectrum (DMSO-$d_6$) δ (ppm): 3.96 (3H, s), 6.02 (1H, d, J=7.6 Hz), 7.06 (1H, s), 7.89 (1H, d, J=7.6 Hz), 8.30 (1H, s).

Production Example 25

6-Methoxycarbonyl-7-methoxy-4-(5-indolyloxy)quinoline

After mixing methyl 4-chloro-7-methoxyquinoline-6-carboxylate (described in WO0050405, p. 34, 8.5 g, 33.77 mmol), 5-hydroxyindole (7 g), diisopropylethylamine (8.9 ml) and N-methylpyrrolidone (8.9 ml), the mixture was heated and stirred at 130° C. for 5 hours and then at 150° C. for 8 hours. After standing to cool, the solution was adsorbed onto silica gel and purified with a silica gel column (hexane-ethyl acetate system). Ethanol, diethyl ether and hexane were added to the obtained yellow oil, and crystals precipitated after a period of standing. The crystals were filtered out, washed with diethyl ether and hexane and then dried by aspiration to obtain light yellow crystals (3.506 g, 10.06 mmol, 29.80%).

$^1$H-NMR Spectrum (DMSO-$d_6$) δ (ppm): 3.86 (3H, s), 3.97 (3H, s), 6.38 (1H, d, J=5.2 Hz), 6.46 (1H, s), 6.98 (1H, d, J=8.8 Hz), 7.44-7.52 (4H, m), 8.60-8.65 (2H, m), 11.29 (1H, s).

Production Example 26

7-(2-Methoxyethoxy)-4-oxo-1,4-dihydro-6-quinolinecarboxylic acid

The 7-methoxy-4-oxo-1,4-dihydroquinoline-6-carbonitrile (8.0 g) described in WO9813350 was used to obtain the title compound (6.3 g) by the same procedure as in Production Example 152-1.

$^1$H-NMR Spectrum (DMSO-$d_6$) δ (ppm): 3.33 (3H, s), 3.71-3.73 (2H, m), 4.21-4.22 (2H, m), 6.28 (1H, d, J=7.2 Hz), 7.15 (1H, s), 8.59 (1H, d, J=7.2 Hz), 8.40 (1H, s)

EXAMPLES

Example 1

N-(4-(6-Cyano-7-(3-(4-pyridyl)propoxy)-4-quinolyl)oxyphenyl-N'-(4-methoxyphenyl)urea The sodium 6-cyano-4-(4-((4-methoxyanilino)carbonyl)aminophenoxy)-7-quinolinolate (200 mg) synthesized in Example 87 was dissolved in dimethylformamide (4 ml), and then potassium carbonate (130 mg, 0.9400 mmol), potassium iodide (3 mg) and 1-chloro-3-(4-pyridyl)propane (80 mg, 0.5159 mmol) were added and the mixture was heated and stirred at 80° C. for 5 hours and 30 minutes. After allowing the mixture to stand and adding saturated brine, it was extracted with ethyl acetate, washed with saturated brine and dried over anhydrous magnesium sulfate, the solvent was distilled off under reduced pressure, and the residue was purified by NH silica gel column chromatography (ethyl acetate-methanol system). The obtained crystals were suspended in ethanol, the suspension was diluted with diethyl ether, and the crystals were filtered out, washed with diethyl ether and dried by aspiration to obtain the title compound (60 mg) as light yellow crystals.

$^1$H-NMR Spectrum (DMSO-$d_6$) δ (ppm): 2.17 (2H, d), 2.84 (2H, t, J=7.8 Hz), 3.70 (3H, s), 4.28 (2H, t, J=6.2 Hz), 6.51 (1H, d, J=5.2 Hz), 6.86 (2H, d, J=9.0 Hz), 7.22 (2H, d, J=9.0 Hz), 7.29 (2H, d, J=6.0 Hz), 7.35 (2H, d, J=9.0 Hz), 7.57 (1H, s), 7.58 (2H, d, J=9.0 Hz), 8.46 (2H, d, J=6.0 Hz), 8.49 (1H, s), 8.71 (1H, d, J=5.2 Hz), 8.74 (1H, s), 8.76 (1H, s).

Example 2

N-(4-(6-Cyano-7-(4-picolyloxy)-quinolyl)oxyphenyl)-N'-(4-methoxyphenyl)urea

The sodium 6-cyano-4-(4-((4-methoxyanilino)carbonyl)aminophenoxy)-7-quinolinolate (100 mg) synthesized in Example 87 was dissolved in dimethylformamide (2 ml), and then potassium carbonate (97 mg, 0.7018 mmol), potassium iodide (3 mg) and 4-picolyl chloride (40 mg, 0.2462 mmol) were added and the mixture was heated and stirred at 80° C. for 3 hours. After allowing the mixture to stand and adding water, it was extracted with ethyl acetate, washed with saturated brine and dried over anhydrous magnesium sulfate, the solvent was distilled off under reduced pressure, and the residue was purified by NH silica gel column chromatography (ethyl acetate-methanol system). The obtained crystals were suspended in acetone, the suspension was diluted with diethyl ether, and the crystals were filtered out, washed with diethyl ether and dried by aspiration to obtain the title compound (30 mg) as light yellow crystals.

$^1$H-NMR Spectrum (DMSO-$d_6$) δ (ppm): 3.70 (3H, s), 5.54 (2H, s), 6.53 (1H, d, J=5.2 Hz), 6.86 (2H, d, J=8.8 Hz), 7.22 (2H, d, J=8.8 Hz), 7.36 (2H, d, J=8.8 Hz), 7.52 (2H, d, J=6.4 Hz), 7.59 (2H, d, J=8.8 Hz), 7.66 (1H, s), 8.55 (1H, brs), 8.63 (2H, d, J=6.0 Hz), 8.72 (1H, d, J=5.2 Hz), 8.81 (1H, brs), 8.82 (1H, s).

Example 3

N-(4-(6-Cyano-7-(3-picolyloxy)-4-quinolyl)oxyphenyl)-N'-(4-methoxyphenyl)urea

The sodium 6-cyano-4-(4-((4-methoxyanilino)carbonyl)aminophenoxy)-7-quinolinolate (200 mg) synthesized in Example 87 was used for reaction in the same manner as Example 2 to obtain the title compound (68 mg).

$^1$H-NMR Spectrum (DMSO-$d_6$) δ (ppm): 3.70 (3H, s), 5.50 (2H, s), 6.54 (1H, d, J=5.0 Hz), 6.86 (2H, d, J=8.8 Hz), 7.22 (2H, d, J=8.8 Hz), 7.35 (2H, d, J=8.8 Hz), 7.49 (2H, dd, J=4.8 Hz, 7.6 Hz), 7.58 (2H, d, J=8.8 Hz), 7.74 (1H, s), 7.95 (1H, d, J=7.6 Hz), 8.49 (1H, s), 8.59 (1H, dd, J=1.6, Hz, 4.8 Hz), 7.83-8.80 (3H, m).

Example 4

N-(4-(6-Cyano-7-(2-(1,2,3-triazol-2-yl)ethoxy)-4-quinolyl)oxyphenyl)-N'-(4-fluorophenyl)urea (Example 4-A)

N-(4-(6-Cyano-7-(2-(1,2,3-triazol-1-yl)ethoxy)-4-quinolyl)oxyphenyl)-N'-(4-fluorophenyl)urea (Example 4-B)

The N-(4-(6-cyano-7-(2-chloroethoxy)-quinolyl)oxyphenyl)-N'-(4-fluorophenyl)urea (210 mg, 0.4403 mmol) synthesized in Example 90 was dissolved in N,N-dimethylformamide (2.5 ml), and then potassium carbonate (180 mg, 1.3209 mmol), potassium iodide (15 mg) and 1H-1,2,3-triazole (0.078 ml, 1.3209 mmol) were added and the mixture was heated and stirred at 60° C. for 20 minutes and then at 65° C. for 3 hours. After cooling, tetrahydrofuran and ethyl acetate were added, the mixture was washed with saturated brine and dried over anhydrous magnesium sulfate, the solvent was distilled off under reduced pressure, and the isomers were separated by silica gel column chromatography (ethyl acetate-methanol system). The crystals of the low polarity isomer were suspended in ethanol and then washed with ethanol, filtered and dissolved in dimethylsulfoxide, after which the solution was diluted with ethanol and the precipitated crystals were filtered out, washed with ethanol and then with diethyl ether and dried by aspiration. The crystals of the high polarity isomer were suspended in ethanol, washed with ethanol, filtered out, washed with ethanol and then with diethyl ether and dried by aspiration. These yielded colorless crystals of low polarity N-(4-(6-cyano-7-(2-(1,2,3-triazol-2- yl)ethoxy)-4-quinolyl)oxyphenyl)-N'-(4-fluorophenyl)urea (37 mg, 0.0703 mmol, 16.02%) and high polarity N-(4-(6-cyano-7-(2-(1,2,3-triazol-1-yl)ethoxy)-4-quinolyl)oxyphenyl)-N'-(4-fluorophenyl)urea (62 mg, 0.1182 mmol, 26.85%).

Low Polarity Isomer (Example 4-A)

$^1$H-NMR Spectrum (DMSO-d$_6$) δ (ppm): 4.81 (2H, t, J=4.6 Hz), 4.92 (2H, t, J=4.6 Hz), 6.52 (1H, d, J=5.2 Hz), 7.11 (2H, t, J=8.8 Hz), 7.22 (2H, d, J=8.8 Hz), 7.46 (2H, dd, J=5.0 Hz, 8.8 Hz), 7.59 (2H, d, J=8.8 Hz), 7.65 (1H, s), 7.80 (2H, s), 8.71 (1H, s), 8.72 (1H, d, J=5.2 Hz), 8.77 (1H, s), 8.86 (1H, s).

High Polarity Isomer (Example 4-B)

$^1$H-NMR Spectrum (DMSO-d$_6$) δ (ppm): 4.72 (2H, t, J=4.8 Hz), 4.93 (2H, t, J=4.8 Hz), 6.53 (1H, d, J=5.2 Hz), 7.11 (2H, t, J=8.4 Hz), 7.23 (2H, d, J=8.8 Hz), 7.46 (2H, dd, J=4.4 Hz, 8.4 Hz), 7.59 (2H, d, J=8.8 Hz), 7.64 (1H, s), 7.77 (1H, s), 8.18 (1H, s), 8.73 (1H, d, J=5.2 Hz), 8.73 (1H, s), 8.75 (1H, s), 8.83 (1H, s).

Example 5

N-(4-(6-Cyano-7-(2-(1,2,3-triazol-2-yl)ethoxy)-4-quinolyl)oxyphenyl)-N'-(4-methoxyphenyl)urea (Example 5-A)

N-(4-(6-Cyano-7-(2-(1,2,3-triazol-1-yl)ethoxy)-4-quinolyl)oxyphenyl)-N'-(4-methoxyphenyl)urea (Example 5-B)

The N-(4-(6-cyano-7-(2-chloroethoxy)-4-quinolyl)oxyphenyl)-N'-(4-methoxyphenyl)urea (300 mg, 0.6136 mmol) synthesized in Example 91 was used for reaction in the same manner as Example 4 to obtain low polarity N-(4-(6-cyano-7-(2-(1,2,3-triazol-2-yl)ethoxy)-4-quinolyl)oxyphenyl)-N'-(4-methoxyphenyl)urea (87 mg, 0.1652 mmol, 26.93%) and high polarity N-(4-(6-cyano-7-(2-(1,2,3-triazol-1-yl)ethoxy)-4-quinolyl)oxyphenyl)-N'-(4-methoxyphenyl)urea (83 mg, 0.1576 mmol, 25.69%) as colorless crystals.

Low Polarity Isomer (Example 5-A)

$^1$H-NMR Spectrum (DMSO-d$_6$) δ (ppm): 3.70 (3H, s), 4.81 (2H, t, J=5.0 Hz), 4.92 (2H, t, J=5.0 Hz), 6.52 (1H, d, J=5.4 Hz), 6.86 (2H, d, J=8.8 Hz), 7.21 (2H, d, J=9.2 Hz), 7.35 (2H, d, J=8.8 Hz), 7.57 (2H, d, J=9.2 Hz), 7.65 (1H, s), 7.80 (2H, s), 8.49 (1H, s), 8.71 (1H, s), 8.72 (1H, d, J=5.4 Hz), 8.73 (1H, s).

High Polarity Isomer (Example 5-B)

$^1$H-NMR Spectrum (DMSO-d$_6$) δ (ppm): 3.70 (3H, s), 4.72 (2H, t, J=5.2 Hz), 4.93 (2H, t, J=5.2 Hz), 6.53 (1H, d, J=5.2 Hz), 6.85 (2H, d, J=9.0 Hz), 7.21 (2H, d, J=9.0 Hz), 7.35 (2H, d, J=9.0 Hz), 7.57 (2H, d, J=9.0 Hz), 7.64 (1H, s), 7.77 (1H, s), 8.18 (1H, s), 8.49 (1H, s), 8.72 (1H, d, J=5.2 Hz), 8.73 (1H, s), 8.75 (1H, s).

Example 6

N-(4-(6-Cyano-7-(2-(1,2,3-triazol-2-yl)ethoxy)-4-quinolyl)oxy-3-fluorophenyl)-N'-(2,4-difluorophenyl)urea (Example 6-A)

N-(4-(6-Cyano-7-(2-(1,2,3-triazol-1-yl)ethoxy)-4-quinolyl)oxy-3-fluorophenyl)-N'-(2,4-difluorophenyl)urea (Example 6-B)

Sodium hydride (35 mg, 0.8774 mmol, 60% in oil) was suspended in N,N-dimethylformamide (2.5 ml), and then 1H-1,2,3-triazole (0.051 ml, 0.8774 mmol) was added while cooling on ice and the mixture was stirred at room temperature for 15 minutes to complete dissolution. After then adding N-(4-(6-cyano-7-(2-chloroethoxy)-4-quinolyl)oxyphenyl)-N'-(2,4-difluorophenyl)urea (225 mg, 0.4386 mmol) and potassium iodide (10 mg), the mixture was heated and stirred at 50° C. for 10 hours. Upon cooling, tetrahydrofuran and ethyl acetate were added, the mixture was washed with saturated brine and dried over anhydrous magnesium sulfate, the solvent was distilled off under reduced pressure, and the isomers were separated by silica gel column chromatography (hexane/ethyl acetate/methanol system). The crystals of the low polarity isomer were dissolved in dimethylsulfoxide, the solution was diluted with ethanol, and the precipitated crystals were filtered out, washed with ethanol and then with diethyl ether and dried by aspiration. The crystals of the high polarity isomer were further purified by NH silica gel column chromatography (hexane/ethyl acetate system), and the obtained crystals were suspended in ethanol, washed with ethanol and hexane, and then filtered out, washed with hexane and dried by aspiration. This yielded pink crystals of low polarity N-(4-(6-cyano-7-(2-(1,2,3-triazol-2-yl)ethoxy)-4-quinolyl)oxy-3-fluorophenyl)-N'-(2,4-difluorophenyl)urea (15 mg, 0.0275 mmol, 6.27%) and colorless crystals of high polarity N-(4-(6-cyano-7-(2-(1,2,3-triazol-1-yl)ethoxy)-4-quinolyl)oxy-3-fluorophenyl)-N'-(2,4-difluorophenyl)urea (30 mg, 0.0550 mmol, 12.54%).

Low Polarity Isomer (Example 6-A)

$^1$H-NMR Spectrum (DMSO-d$_6$) δ (ppm): 4.82 (2H, t, J=4.8 Hz), 4.92 (2H, t, J=4.82 Hz), 6.63 (1H, d, J=5.0 Hz), 7.05 (1H, m), 7.14 (1H, d, J=9.6 Hz), 7.32 (1H, m), 7.40 (1H, m), 7.66 (1H, s), 7.80 (2H, s), 8.11 (1H, m), 8.26 (1H, t, J=9.6 Hz), 8.70 (1H, s), 8.75 (1H, d, J=5.0 Hz), 8.99 (1H, s), 9.07 (1H, s).

High Polarity Isomer (Example 6-B)

$^1$H-NMR Spectrum (DMSO-d$_6$) δ (ppm): 4.73 (2H, t, J=5.2 Hz), 4.93 (2H, t, J=5.2 Hz), 6.63 (1H, d, J=5.2 Hz), 7.05 (1H, m), 7.15 (1H, m), 7.32 (1H, ddd, J=2.8 Hz, 8.8 Hz, 11.6 Hz), 7.40 (1H, dd, J=2.8 Hz, 11.6 Hz), 7.66 (1H, s), 7.77 (1H, s), 8.11 (1H, m), 8.18 (1H, s), 8.26 (1H, t, J=8.8 Hz), 8.74 (1H, s), 8.75 (1H, d, J=5.2 Hz), 8.99 (1H, d, J=2.2 Hz), 9.07 (1H, d, J=2.2 Hz).

Example 7

N-(4-(6-Cyano-7-(3-(morpholin-4-yl)propoxy)-4-quinolyl)oxyphenyl)-N'-(4-methoxyphenyl)urea The sodium 6-cyano-4-(4-((4-methoxyanilino)carbonyl)aminophenoxy)-7-quinolinolate (100 mg) synthesized in Example 87 was dissolved in dimethylformamide (2.5 ml), and then potassium carbonate (65 mg, 0.4690 mmol) and 1-chloro-3-(morpholin-4-yl)propane (38 mg, 0.2345 mmol, J. Am. Chem. Soc. 67, 736 (1945)) were added and the mixture was heated and stirred at 80° C. for 2 hours. After allowing the mixture to stand and adding saturated brine, it was extracted with ethyl acetate, the extract was washed with saturated brine and dried over anhydrous magnesium sulfate, the solvent was distilled off under reduced pressure, and the residue was purified by NH silica gel column chromatography (ethyl acetate-methanol system). The obtained crystals were suspended in ethyl acetate, the suspension was diluted with diethyl ether, and the crystals were filtered out, washed with diethyl ether and dried by aspiration to obtain the title compound (120 mg) as light yellow crystals.

$^1$H-NMR Spectrum (DMSO-d$_6$) δ (ppm): 1.99 (2H, m), 2.38 (4H, brs), 2.49 (2H, m), 3.57 (4H, t, J=4.6 Hz), 3.70 (3H, s), 4.33 (2H, t, J=6.2 Hz), 6.51 (1H, d, J=5.6 Hz), 6.86 (2H, d, J=9.2 Hz), 7.22 (2H, d, J=9.2 Hz), 7.35 (2H, d, J=9.2 Hz), 7.58 (2H, d, J=9.2 Hz), 7.59 (1H, s), 8.49 (1H, s), 8.71 (1H, d, J=5.6 Hz), 8.74 (1H, s), 8.75 (1H, s).

Example 8

N-(4-(6-Cyano-7-(3-(1,2,3-triazol-2-yl)propoxy)-4-quinolyl)oxyphenyl)-N'-(4-methoxyphenyl)urea The title compound was obtained from the sodium 6-cyano-4-(4-((4-methoxyanilino)carbonyl)aminophenoxy)-7-quinolinolate synthesized in Example 87 and 2-(3-chloropropyl)1,2,3-triazole, by the same procedure as in Example 7.

$^1$H-NMR Spectrum (DMSO-d$_6$) δ (ppm): 2.41 (2H, m), 3.70 (3H, s), 4.29 (2H, t, J=6.0 Hz), 4.68 (2H, t, J=6.6 Hz), 6.52 (1H, d, J=5.2 Hz), 6.86 (2H, d, J=8.8 Hz), 7.22 (2H, d, J=8.8 Hz), 7.35 (2H, d, J=8.8 Hz), 7.54 (1H, s), 7.58 (2H, d, J=8.8 Hz), 7.78 (2H, s), 8.49 (1H, s), 8.71 (1H, d, J=5.2 Hz), 8.74 (1H, s), 8.77 (1H, s).

Example 9

N-(4-(6-Cyano-7-(3-(1,2,3-triazol-1-yl)propoxy)-4-quinolyl)oxyphenyl)-N'-(4-methoxyphenyl)urea The title compound was obtained from the sodium 6-cyano-4-(4-((4-methoxyanilino)carbonyl)aminophenoxy)-7-quinolinolate synthesized in Example 87 and 1-(3-chloropropyl)-1,2,3-triazole, by the same procedure as in Example 7.

$^1$H-NMR Spectrum (DMSO-d$_6$) δ (ppm): 2.41 (2H, m), 3.70 (3H, s), 4.28 (2H, t, J=6.0 Hz), 4.63 (2H, t, J=6.6 Hz), 6.52 (1H, d, J=5.4 Hz), 6.86 (2H, d, J=8.8 Hz), 7.22 (2H, d, J=8.8 Hz), 7.35 (2H, d, J=8.8 Hz), 7.57 (1H, s), 7.58 (2H, d, J=8.8 Hz), 7.73 (1H, s), 8.19 (1H, s), 8.49 (1H, s), 8.72 (1H, d, J=5.4 Hz), 8.74 (1H, s), 8.77 (1H, s).

Example 10

N-(4-(6-Cyano-7-(2-methoxyethoxy)-4-quinolyl)oxyphenyl)-N'-(4-fluorophenyl)urea 4-(4-Aminophenoxy)-7-(2-methoxyethoxy)-6-cyanoquinoline (109 mg, 0.325 mmol) was dissolved in toluene (5 ml) while heating, and then 4-fluorophenyl isocyanate (0.057 ml, 0.488 mmol) was added and the mixture was heated to reflux for 1 hour. After cooling, the precipitated crystals were filtered out, washed with ethyl acetate and dried under reduced pressure to obtain the title compound (148 mg, 0.311 mmol, 96.4%) as white crystals.

$^1$H-NMR Spectrum (DMSO-d$_6$) δ (ppm): 3.36 (3H, s), 3.76-3.79 (2H, m), 4.41-4.43 (2H, m), 6.52 (1H, d, J=5.2 Hz), 7.11 (2H, t, J=9.0 Hz), 7.23 (2H, d, J=9.0 Hz), 7.46 (2H, q, J=4.8 Hz), 7.57-7.62 (3H, m), 8.71-8.76 (3H, m), 8.82 (1H, s).

Example 11

N-(4-(6-Cyano-7-(2-methoxyethoxy)-4-quinolyl)oxyphenyl)-N'-(2-pyridyl)urea

Phenyl N-(4-(6-cyano-7-(2-methoxyethoxy)-4-quinolyl)oxyphenyl)carbamate (104 mg, 0.228 mmol) was dissolved in dimethylsulfoxide (1 ml), and then 2-aminopyridine (43 mg, 0.457 mmol) was added and the mixture was heated at 85° C. for 3 hours while stirring. After cooling, ethyl acetate and water were added for distribution, and the organic layer was washed with saturated brine and dried over anhydrous sodium sulfate. After filtering off the drying agent and concentrating under reduced pressure, ethyl acetate-hexane was added to the residue and the precipitated crystals were filtered out and dried under reduced pressure to obtain the title compound (86 mg, 0.189 mmol, 82.7%) as white crystals.

$^1$H-NMR Spectrum (DMSO-d$_6$) δ (ppm): 3.36 (3H, s), 3.75-3.78 (2H, m), 4.39-4.42 (2H, m), 6.53 (1H, d, J=5.2 Hz), 6.99 (1H, m), 7.18 (1H, d, J=8.4 Hz), 7.26 (2H, d, J=9.2 Hz), 7.56 (1H, d, J=8.4 Hz), 7.62 (1H, s), 7.68-7.77 (3H, m), 8.26 (1H, d, J=5.2 Hz), 8.72 (1H, d, J=5.2 Hz), 8.77 (1H, s), 9.89 (1H, brs).

Example 12

N-(4-(6-Cyano-7-(2-methoxyethoxy)-4-quinolyl)oxyphenyl)-N'-(1,3-thiazol-2-yl)urea The title compound (37 mg, 0.08 mmol, 34.4%) was obtained as light brown crystals from phenyl N-(4-(6-cyano-7-(2-methoxyethoxy)-4-quinolyl)oxyphenyl)carbamate (106 mg, 0.233 mmol) by the same procedure as in Example 11.

$^1$H-NMR Spectrum (DMSO-d$_6$) δ (ppm): 3.36 (3H, s), 3.75-3.79 (2H, m), 4.40-4.43 (2H, m), 6.53 (1H, d, J=5.6 Hz), 7.10 (1H, d, J=3.2 Hz), 7.72 (1H, d, J=8.8 Hz), 7.37 (1H, m), 7.57-7.67 (3H, m), 8.72 (1H, d, J=5.2 Hz), 8.77 (1H, s), 9.53 (1H, brs).

Example 13

N-(4-(6-Cyano-7-(2-methoxyethoxy)-4-quinolyl)oxyphenyl)-N'-(4-hydroxyphenyl)urea The title compound (52 mg, 0.110 mmol, 43.0%) was obtained as light brown crystals from phenyl N-(4-(6-cyano-7-(2-methoxyethoxy)-4-quinolyl)oxyphenyl)carbamate (117 mg, 0.257 mmol) by the same procedure as in Example 11.

$^1$H-NMR Spectrum (DMSO-d$_6$) δ (ppm): 3.36 (3H, s), 3.77-3.79 (2H, m), 4.41-4.43 (2H, m), 6.51 (1H, d, J=5.2 Hz), 6.67 (2H, d, J=8.0 Hz), 7.15-7.25 (3H, m), 7.57 (2H, d, J=8.0 Hz), 7.62 (1H, s), 8.37 (1H, s), 8.70-8.76 (3H, m), 9.05 (1H, s).

Example 14

N-(4-(6-Cyano-7-(2-methoxyethoxy)-4-quinolyl)oxyphenyl)-N'-(3-methoxyphenyl)urea The title compound (50 mg, 0.103 mmol, 39.2%) was obtained as white crystals from phenyl N-(4-(6-cyano-7-(2-methoxyethoxy)-4-quinolyl)oxyphenyl)carbamate (120 mg, 0.263 mmol) by the same procedure as in Example 11.

$^1$H-NMR Spectrum (DMSO-d$_6$) δ (ppm): 3.36 (3H, s), 3.72 (3H, s), 3.76-3.79 (2H, m), 4.39-4.43 (2H, m), 6.50-6.57 (2H, m), 6.93 (1H, d, J=8.0 Hz), 7.14-7.19 (2H, m), 7.24 (2H, d, J=8.8 Hz), 7.59 (2H, d, J=8.8 Hz), 7.62 (1H, s), 8.69-8.73 (2H, m), 8.76 (1H, s), 8.80 (1H, s).

Example 15

N-(4-(6-Cyano-7-(2-methoxyethoxy)-4-quinolyl)oxyphenyl)-N'-(3-hydroxyphenyl)urea The title compound (25 mg, 0.053 mmol, 23.7%) was obtained as light brown crystals from phenyl N-(4-(6-cyano- 7-(2-methoxyethoxy)-4-quinolyl)oxyphenyl)carbamate (102 mg, 0.234 mmol) by the same procedure as in Example 11.

$^1$H-NMR Spectrum (DMSO-d$_6$) δ (ppm): 3.36 (3H, s), 3.75-3.79 (2H, m), 4.40-4.43 (2H, m), 6.36 (1H, d, J=9.2 Hz), 6.52 (1H, d, J=5.2 Hz), 6.79 (1H, d, J=8.0 Hz), 7.00-7.06 (2H, m), 7.23 (2H, d, J=9.2 Hz), 7.58 (2H, d, J=8.8 Hz), 7.62 (1H, s), 8.59 (1H, s), 8.71 (1H, d, J=4.8 Hz), 8.76 (1H, s), 9.31 (1H, brs).

Example 16

N-(4-(6-Cyano-7-(2-methoxyethoxy)-4-quinolyl)oxyphenyl)-N'-(2-hydroxyphenyl)urea The title compound (78 mg, 0.166 mmol, 69.9%) was obtained as light brown crystals from phenyl N-(4-(6-cyano-7-(2-methoxyethoxy)-4-quinolyl)oxyphenyl)carbamate (108 mg, 0.237 mmol) by the same procedure as in Example 11.

$^1$H-NMR Spectrum (DMSO-d$_6$) δ (ppm): 3.36 (3H, s), 3.76-3.79 (2H, m), 4.40-4.43 (2H, m), 6.52 (1H, d, J=5.6 Hz), 6.69-6.85 (3H, m), 7.22 (2H, d, J=8.8 Hz), 7.57-7.62 (3H, m), 7.99 (1H, d, J=8.0 Hz), 8.34 (1H, br), 8.71 (1H, d, J=5.2 Hz), 8.76 (1H, s), 9.62 (1H, brs).

Example 17

N-(4-(6-Cyano-7-(2-methoxyethoxy)-4-quinolyl)oxyphenyl)-N'-(1H-2-imidazolyl)urea After dissolving 2-aminoimidazole (132 mg, 1.0 mmol) in a dimethylformamide (2 ml) and water (1 ml) mixed solvent, triethylamine (0.42 ml, 3.0 mmol) and phenyl chloroformate (0.14 ml, 1.1 mmol) were added at room temperature, and the mixture was stirred for 10 minutes. After further adding 4-(4-aminophenoxy)-7-(2-methoxyethoxy)-6-cyanoquinoline (168 mg, 0.5 mmol), the mixture was stirred overnight. The reaction solution was diluted with ethyl acetate (30 ml) and then washed with water (10 ml×2) and saturated brine (10 ml), and the organic layer was dried over anhydrous sodium sulfate. The drying agent was filtered off, the filtrate was concentrated under reduced pressure, and the residue was purified by silica gel column chromatography (eluent—ethyl acetate:ethanol=95:5) to obtain the title compound (20 mg, 0.045 mmol, 8.98%) as white crystals.

$^1$H-NMR Spectrum (DMSO-d$_6$) δ (ppm): 3.36 (3H, s), 3.76-3.79 (2H, m), 4.40-4.43 (2H, m), 6.53 (1H, d, J=5.2 Hz), 6.70 (1H, s), 7.24 (2H, d, J=8.8 Hz), 7.57-7.67 (3H, m), 8.72 (1H, d, J=5.6 Hz), 8.76 (1H, s).

Example 18

N-(4-(6-Cyano-7-(2-methoxyethoxy)-4-quinolyl)oxyphenyl)-N'-(2,4-difluorophenyl)urea The title compound (136 mg, 0.277 mmol, 87.7%) was obtained as white crystals from 4-(4-aminophenoxy)-7-(2-methoxyethoxy)-6-cyanoquinoline (106 mg, 0.316 mmol) by the same procedure as in Example 10.

$^1$H-NMR Spectrum (DMSO-d$_6$) δ (ppm): 3.36 (3H, s), 3.76-3.79 (2H, m), 4.40-4.43 (2H, m), 6.52 (1H, d, J=5.2 Hz), 7.04 (1H, m), 7.23-7.34 (3H, m), 7.57-7.62 (3H, m), 8.06 (1H, m), 8.52 (1H, s), 8.71 (1H, d, J=5.6 Hz), 8.76 (1H, s), 9.16 (1H, s).

Example 19

N-(4-(6-Cyano-7-(2-methoxyethoxy)-4-quinolyl)oxyphenyl)-N'-(3-cyanophenyl)urea

The title compound (38 mg, 0.079 mmol, 33.1%) was obtained as light yellow crystals from phenyl N-(4-(6-cyano-7-(2-methoxyethoxy)-4-quinolyl)oxyphenyl)carbamate (109 mg, 0.239 mmol) by the same procedure as in Example 11.

$^1$H-NMR Spectrum (DMSO-d$_6$) δ (ppm): 3.36 (3H, s), 3.76-3.79 (2H, m), 4.40-4.43 (2H, m), 6.52 (1H, d, J=5.2 Hz), 7.26 (2H, d, J=8.8 Hz), 7.41 (1H, d, J=6.4 Hz), 7.49 (1H, t, J=8.0 Hz), 7.55-7.62 (3H, m), 7.68 (1H, dd, J=1.2, 8.8 Hz), 7.97 (1H, s), 8.71 (1H, d, J=6.4 Hz), 8.76 (1H, s), 9.00 (1H, s), 9.05 (1H, s).

Example 20

N-(4-(6-Cyano-7-(2-methoxyethoxy)-4-quinolyl)oxyphenyl)-N'-(2-fluorophenyl)urea

The title compound (75 mg, 0.159 mmol, 48.8%) was obtained as white crystals from 4-(4-aminophenoxy)-7-(2-methoxyethoxy)-6-cyanoquinoline (109 mg, 0.325 mmol) by the same procedure as in Example 10.

$^1$H-NMR Spectrum (DMSO-d$_6$) δ (ppm): 3.36 (3H, s), 3.76-3.79 (2H, m), 4.40-4.43 (2H, m), 6.52 (1H, d, J=5.2 Hz), 7.01 (1H, m), 7.13 (1H, t, J=8.0 Hz), 7.20-7.27 (3H, m), 7.55-7.63 (3H, m), 8.14 (1H, t, J=8.0 Hz), 8.56 (1H, brs), 8.72 (1H, d, J=6.4 Hz), 8.76 (1H, s), 9.22 (1H, s).

Example 21

N-(4-(6-Cyano-7-(2-methoxyethoxy)-4-quinolyl)oxyphenyl)-N'-(3-(methylsulfonyl)phenyl)urea Diisopropylethylamine (0.057 ml, 0.328 mmol) and phenylN-[3-(methylsulfonyl)phenyl]carbamate (96 mg, 0.328 mmol) were reacted with 4-(4-aminophenoxy)-7-(2-methoxyethoxy)-6-cyanoquinoline (100 mg, 0.298 mmol), and the title compound (120 mg, 0.225 mmol, 75.6%) was obtained as white crystals by the same procedure as in Example 34.

$^1$H-NMR Spectrum (DMSO-d$_6$) δ (ppm): 3.19 (3H, s), 3.36 (3H, s), 3.76-3.79 (2H, m), 4.40-4.43 (2H, m), 6.53 (1H, d, J=5.6 Hz), 7.26 (2H, d, J=8.8 Hz), 7.50-7.69 (6H, m), 8.16 (1H, brs), 8.72 (1H, d, J=5.2 Hz), 8.76 (1H, s), 8.95 (1H, s), 9.15 (1H, s).

Example 22

N-(4-(6-Cyano-7-(2-methoxyethoxy)-4-quinolyl)oxyphenyl)-N'-(3-(methylsulfanyl)phenyl)urea The title compound (210 mg, 0.420 mmol, 98.9%) was obtained as white crystals from phenyl N-(4-(6-cyano-7-(2-methoxyethoxy)-4-quinolyl)oxyphenyl)carbamate (193 mg, 0.424 mmol) by the same procedure as in Example 11.

$^1$H-NMR Spectrum (DMSO-d$_6$) δ (ppm): 2.43 (3H, s), 3.36 (3H, s), 3.76-3.79 (2H, m), 4.40-4.43 (2H, m), 6.52 (1H, d, J=5.2 Hz), 6.83 (1H, d, J=7.2 Hz), 7.14-7.24 (4H, m), 7.48 (1H, s), 7.58-7.61 (3H, m), 8.71 (1H, d, J=5.2 Hz), 8.75 (1H, s), 9.62 (1H, s), 9.76 (1H, s).

Example 23

N-(4-(6-Cyano-7-(2-methoxyethoxy)-4-quinolyl) oxyphenyl)-N'-cyclopropylurea

The title compound (145 mg, 0.347 mmol, 80.9%) was obtained as white crystals from phenyl N-(4-(6-cyano-7-(2-methoxyethoxy)-4-quinolyl)oxyphenyl)carbamate (195 mg, 0.428 mmol) by the same procedure as in Example 11.

$^1$H-NMR Spectrum (DMSO-$d_6$) δ (ppm): 0.4 (2H, brs), 0.63 (2H, d, J=6.8 Hz), 2.53 (1H, m), 3.36 (3H, s), 3.76-3.79 (2H, m), 4.40-4.43 (2H, m), 6.42 (1H, s), 6.48 (1H, d, J=5.2 Hz), 6.97 (2H, d, J=9.2 Hz), 7.53 (2H, d, J=9.2 Hz), 7.60 (1H, s), 8.44 (1H, s), 8.70 (1H, d, J=4.8 Hz), 8.74 (1H, s).

Example 24

N-(4-(6-Cyano-7-(2-methoxyethoxy)-4-quinolyl) oxyphenyl)-N'-(4-fluoro-2-hydroxyphenyl)urea

The title compound (132 mg, 0.270 mmol, 78.9%) was obtained as light yellow crystals from phenyl N-(4-(6-cyano-7-(2-methoxyethoxy)-4-quinolyl)oxyphenyl)carbamate (156 mg, 0.343 mmol) by the same procedure as in Example 11.

$^1$H-NMR Spectrum (DMSO-$d_6$) δ (ppm): 3.36 (3H, s), 3.76-3.79 (2H, m), 4.40-4.43 (2H, m), 6.52 (1H, d, J=5.6 Hz), 6.57 (1H, m), 6.62 (1H, m), 7.23 (2H, d, J=8.8 Hz), 7.57 (2H, d, J=8.8 Hz), 7.62 (1H, s), 7.98 (1H, m), 8.12 (1H, s), 8.71 (1H, d, J=5.6 Hz), 9.40 (1H, s), 10.47 (1H, s).

Example 25

N-(4-(6-Cyano-7-(2-methoxyethoxy)-4-quinolyl) oxy-2-fluorophenyl)-N'-(1,3-thiazol-2-yl)urea

Phenyl N-(4 (6-cyano-7-(2-methoxyethoxy)-4-quinolyl) oxy-2-fluorophenyl)carbamate (200 mg) and 2-aminothiazole (85 mg) were dissolved in 1 ml of dimethylformamide, and then 0.12 ml of triethylamine was added thereto and the mixture was heated and stirred at 90° C. for 2 hours. After cooling, water was added and the precipitated solid was filtered out and washed with ethyl acetate to obtain 110 mg of the title compound as light brown crystals (57% yield).

$^1$H-NMR Spectrum (DMSO-$d_6$) δ (ppm): 3.37 (3H, s), 3.75-3.80 (2H, m), 4.40-4.45 (2H, m), 6.63 (1H, d, J=5.6 Hz), 7.14 (1H, d, J=3.2 Hz), 7.16-7.20 (1H, m), 7.39 (1H, d, J=3.2 Hz), 7.42-7.47 (1H, m), 7.64 (1H, s), 8.21-8.27 (1H, m), 8.74-8.76 (2H, m)

Example 26

N-(4-(6-Cyano-7-(2-methoxyethoxy)-4-quinolyl) oxy-2-fluorophenyl)-N'-cyclopropylurea

The title compound (83 mg, 0.190 mmol, 61.3%) was obtained as white crystals from phenyl N-(4-(6-cyano-7-(2-methoxyethoxy)-4-quinolyl)oxy-2-fluorophenyl)carbamate (147 mg, 0.310 mmol) by the same procedure as in Example 25.

$^1$H-NMR Spectrum (DMSO-$d_6$) δ (ppm): 0.40 (2H, br), 0.61-0.66 (2H, m), 2.53 (1H, m), 3.36 (3H, s), 3.76-3.79 (2H, m), 4.40-4.43 (2H, m), 6.58 (1H, d, J=5.6 Hz), 6.79 (1H, d, J=2.0 Hz), 7.08 (1H, dd, J=2.0, 10.4 Hz), 7.32 (1H, dd, J=2.4, 11.6 Hz), 7.62 (1H, s), 8.18-8.22 (2H, m), 8.71-8.74 (2H, m).

Example 27

N-(4-(6-Cyano-7-(2-methoxyethoxy)-4-quinolyl) oxyphenyl)-N'-cyclopropylmethylurea

The title compound (144 mg, 0.333 mmol, 96.6%) was obtained as white crystals from phenyl N-(4-(6-cyano-7-(2-methoxyethoxy)-4-quinolyl)oxyphenyl)carbamate (157 mg, 0.345 mmol) by the same procedure as in Example 11.

$^1$H-NMR Spectrum (DMSO-$d_6$) δ (ppm): 0.16-0.18 (2H, m), 0.39-0.43 (2H, m), 0.94 (1H, m), 2.97 (2H, t, J=6.4 Hz), 3.36 (3H, s), 3.76-3.79 (2H, m), 4.40-4.43 (2H, m), 6.22 (1H, m), 6.49 (1H, d, J=5.6 Hz), 7.17 (2H, d, J=8.8 Hz), 7.52 (2H, d, J=8.8 Hz), 7.61 (1H, s), 8.60 (1H, s), 8.70 (1H, d, J=5.2 Hz), 8.75 (1H, s).

Example 28

N-(4-(6-Cyano-7-(2-methoxyethoxy)-4-quinolyl) oxy-2-fluorophenyl)-N'-cyclopropylmethylurea

The title compound (83 mg, 0.190 mmol, 61.3%) was obtained as white crystals from phenyl N-(4-(6-cyano-7-(2-methoxyethoxy)-4-quinolyl)oxy-2-fluorophenyl)carbamate (147 mg, 0.310 mmol) by the same procedure as in Example 25.

$^1$H-NMR Spectrum (DMSO-$d_6$) δ (ppm): 0.16-0.18 (2H, m), 0.41-0.46 (2H, m), 0.94 (1H, m), 2.99 (2H, t, J=6.0 Hz), 3.36 (3H, s), 3.76-3.79 (2H, m), 4.40-4.43 (2H, m), 6.58 (1H, d, J=5.6 Hz), 6.71 (1H, t, J=5.6 Hz), 7.08 (1H, d, J=9.2 Hz), 7.33 (1H, dd, J=2.8, 11.6 Hz), 7.63 (1H, s), 8.24 (1H, t, J=9.2 Hz), 8.38 (1H, s), 8.55-8.59 (2H, m).

Example 29

N-(4-(6-Cyano-7-(3-(morpholin-4-yl)propoxy)-4-quinolyloxy)-2-fluorophenyl)-N'-(2,4-difluorophenyl)urea

N-(4-(6-Cyano-7-hydroxyquinolin-4-yloxy)-2-fluorophenyl)-N-(2,4-difluorophenyl)urea (100 mg, 0.2220 mmol) was used for reaction in the same manner as Example 7 to obtain the title compound (35 mg, 0.0606 mmol, 27.30%) as light yellow crystals.

$^1$H-NMR Spectrum (DMSO-$d_6$) δ (ppm): 1.99 (2H, m), 2.38 (4H, brs), 2.50 (2H, t, J=7.2 Hz), 3.57 (4H, t, J=4.6 Hz), 4.33 (2H, t, J=6.4 Hz), 6.62 (1H, d, J=5.4 Hz), 7.06 (1H, m), 7.15 (1H, m), 7.32 (1H, ddd, J=2.8 Hz, 8.8 Hz, 11.6 Hz), 7.41 (1H, dd, J=2.8 Hz, 11.6 Hz), 7.61 (1H, s), 8.12 (1H, m), 8.27 (1H, dt, J=2.0 Hz, 9.2 Hz), 8.74 (1H, s), 8.74 (1H, d, J=5.4 Hz), 8.99 (1H, m), 9.07 (1H, m).

Example 30

N-(4-(6-Cyano-7-(3-(diethylamino)propoxy)-4-quinolyloxyphenyl)-N'-(4-fluorophenyl)urea

The title compound (69 mg, 0.131 mmol, 51.9%) was obtained as light brown crystals from sodium 6-cyano-4-(4-((4-fluoroanilino)carbonyl)aminophenoxy)-7-quinolinolate (110 mg, 0.252 mmol) by the same procedure as in Example 7.

$^1$H-NMR Spectrum (DMSO-$d_6$) δ (ppm): 0.95 (6H, t, J=7.2 Hz), 1.89-1.95 (2H, m), 2.44-2.49 (4H, m), 2.58-2.62 (2H, m), 4.31 (2H, t, J=6.0 Hz), 6.51 (1H, d, J=5.2 Hz), 7.11 (2H, t, J=8.4 Hz), 7.23 (2H, d, J=8.8 Hz), 7.44-7.48 (2H, m), 7.56-7.57 (2H, m), 7.60 (1H, s), 8.71 (1H, d, J=5.2 Hz), 8.74-8.76 (2H, m), 8.85 (1H, s).

Example 31

N-(4-(6-Cyano-7-(3-(4-morpholino)propyl)-4-quinolyl)oxyphenyl)-N'-(4-fluorophenyl)urea The title compound (73 mg, 0.135 mmol, 53.5%) was obtained as light brown crystals from sodium 6-cyano-4-(4-((4-fluoroanilino)carbonyl)aminophenoxy)-7-quinolinolate (110 mg, 0.252 mmol) by the same procedure as in Example 7.

$^1$H-NMR Spectrum (DMSO-d$_6$) δ (ppm): 1.99 (2H, t, J=6.4 Hz), 2.30-2.60 (6H, m), 3.55-3.58 (4H, m), 4.31-4.34 (2H, m), 6.51 (1H, d, J=5.2 Hz), 7.11 (2H, t, J=8.8 Hz), 7.23 (2H, d, J=9.2 Hz), 7.44-7.48 (2H, m), 7.57-7.60 (3H, m), 8.70-8.75 (3H, m), 8.82 (1H, s).

Example 32

N-(4-(6-Cyano-7-(2-methoxyethoxy)-4-quinolyl)oxy-2-fluorophenyl)-N'-(2-pyridyl)urea The title compound (210 mg, 84% yield) was obtained as light brown crystals from phenyl N-(4-(6-cyano-7-(2-methoxyethoxy)-4-quinolyl)oxy-2-fluorophenyl)carbamate (250 mg) and 2-aminopyridine (100 mg), in the same manner as Example 25.

$^1$H-NMR Spectrum (DMSO-d$_6$) δ (ppm): 3.36 (3H, s), 3.75-3.80 (2H, m), 4.39-4.45 (2H, m), 6.64 (1H, d, J=5.2 Hz), 7.00-7.05 (1H, m), 7.15-7.19 (1H, m), 7.37-7.47 (2H, m), 7.64 (1H, s), 7.50-7.80 (1H, m), 8.25-8.30 (1H, m), 8.31-8.37 (1H, m), 8.74 (1H, d, J=5.2 Hz), 8.76 (1H, s), 9.87 (1H, s)

Example 33

N-(4-(6-Cyano-7-(2-methoxyethoxy)-4-quinolyl)oxy-2-fluorophenyl)-N'-(3-(methylsulfanyl)phenyl)urea The title compound (100 mg, 61% yield) was obtained as light brown crystals from phenyl N-(4-(6-cyano-7-(2-methoxyethoxy)-4-quinolyl)oxy-2-fluorophenyl)carbamate (160 mg) and 3-(methylthio)aniline (88 mg), in the same manner as Example 25.

$^1$H-NMR Spectrum (DMSO-d$_6$) δ (ppm): 2.43 (3H, s), 3.36 (3H, s), 3.75-3.80 (2H, m), 4.40-4.45 (2H, m), 6.62 (1H, d, J=5.6 Hz), 6.86-6.89 (1H, m), 7.11-7.17 (2H, m), 7.20-7.25 (1H, m), 7.37-7.43 (1H, m), 7.47 (1H, s), 7.63 (1H, s), 8.21-8.28 (1H, m), 8.66 (1H, brs), 8.73-8.76 (2H, m), 9.11-9.13 (1H, m)

Example 34

N-(4-(6-Cyano-7-(2-methoxyethoxy)-4-quinolyl)oxy-2-fluorophenyl)-N'-(3-(methylsulfonyl)phenyl)urea 4-(4-Amino-3-fluorophenoxy)-6-cyano-7-(2-methoxyethoxy)quinoline (106 mg) and phenyl N-(3-(methylsulfonyl)phenyl)carbamate (96 mg) were added to 5 ml of toluene, and then 0.06 ml of diisopropylethylamine was added and the mixture was heated to reflux for 3 hours. After cooling, ethyl acetate was added and the precipitated insoluble portion was filtered out. The filtrate was concentrated, the resulting residue was dissolved in tetrahydrofuran, toluene was added, and the precipitated solid was filtered out to obtain 13 mg of the title compound as light brown crystals (8% yield).

$^1$H-NMR Spectrum (DMSO-d$_6$) δ (ppm): 3.20 (3H, s), 3.35 (3H, s), 3.75-3.80 (2H, m), 4.38-4.43 (2H, m), 6.63 (1H, d, J=5.2 Hz), 7.14-7.17 (1H, m), 7.39-7.45 (1H, m), 7.51-7.61 (2H, m) 7.62-7.70 (2H, m), 8.16-8.27 (2H, m), 8.73-8.76 (3H, m), 9.47-9.49 (1H, m)

Example 35

N-(4-(6-Cyano-7-(2-methoxyethoxy)-4-quinolyl)oxy-2-fluorophenyl)-N'-(2-fluorophenyl)urea 4-(4-Amino-3-fluorophenoxy)-6-cyano-7-(2-methoxyethoxy)quinoline (100 mg) was added to 4.5 ml of toluene, and the mixture was heated to reflux. After then adding 2-fluorophenylisocyanate (0.05 ml), the mixture was further heated to reflux for 1 hour. After cooling, the precipitated solid was filtered out and washed with ethyl acetate/toluene=1/1 to obtain 100 mg of the title compound as light brown crystals (72% yield).

$^1$H-NMR Spectrum (DMSO-d$_6$) δ (ppm): 3.37 (3H, s), 3.75-3.80 (2H, m), 4.40-4.45 (2H, m), 6.62 (1H, d, J=5.6 Hz), 6.97-7.05 (1H, m), 7.11-7.18 (1H, m), 7.21-7.28 (1H, m), 7.38-7.45 (1H, m), 7.64 (1H, s), 8.14-8.20 (1H, m), 8.26-8.33 (1H, m), 8.73-8.76 (2H, m), 9.06 (1H, brs), 9.14 (1H, brs)

Example 36

N-(4-(6-Cyano-7-methoxy-4-quinolyl)oxyphenyl)-N'-(2,4-difluorophenyl)urea 4-(4-Aminophenoxy)-6-cyano-7-methoxyquinoline (180 mg) was added to 5.5 ml of toluene, and the mixture was heated to reflux. After then adding 2,4-difluorophenyl isocyanate (0.12 ml), the mixture was further heated to reflux for 1 hour. After cooling, the precipitated solid was filtered out and washed with ethyl acetate/toluene=1/1 to obtain 195 mg of the title compound as light brown crystals (70% yield).

$^1$H-NMR Spectrum (DMSO-d$_6$) δ (ppm): 4.05 (3H, s), 6.52 (1H, d, J=5.2 Hz), 7.01-7.08 (1H, m), 7.21-7.34 (3H, m), 7.56-7.62 (3H, m), 8.02-8.10 (1H, m), 8.52 (1H, s), 8.72 (1H, d, J=5.2 Hz), 8.76 (1H, s), 9.18 (1H, s).

Example 37

N-(4-(6-Cyano-7-methoxy-4-quinolyl)oxyphenyl)-N'-phenylurea 4-(4-Aminophenoxy)-6-cyano-7-methoxyquinoline (148 mg) was added to 5.5 ml of toluene, and the mixture was heated to reflux. After then adding phenyl isocyanate (0.08 ml), the mixture was further heated to reflux for 1 hour. After cooling, the precipitated solid was filtered out and washed with ethyl acetate/toluene=1/1 to obtain 150 mg of the title compound as light brown crystals. $^1$H-NMR Spectrum (DMSO-d$_6$) δ (ppm): 4.05 (3H, s), 6.50-6.54 (1H, m), 6.96 (t, 1H, 7.2 Hz), 7.23 (2H, d, J=9.2 Hz), 7.27 (2H, d, J=7.2 Hz), 7.44 (2H, d, J=7.2 Hz), 7.56-7.62 (3H, m), 8.68-8.77 (3H, m), 8.83 (1H, brs).

Example 38

N-(4-(6-Cyano-7-methoxy-4-quinolyl)oxyphenyl)-N'-(1-butyl)urea 4-(4-Aminophenoxy)-6-cyano-7-methoxyquinoline (150 mg) was added to 2.5 ml of toluene and 2.5 ml of acetonitrile, and the mixture was heated to reflux. After then adding n-butyl isocyanate (0.12 ml), the mixture was further heated to reflux for 1 hour. After cooling, the precipitated solid was filtered out and washed with ethyl acetate/toluene=1/1 to obtain 110 mg of the title compound as light brown crystals (55% yield).

$^1$H-NMR Spectrum (DMSO-d$_6$) δ (ppm): 0.88 (3H, t, J=7.6 Hz), 1.25-1.45 (4H, m), 3.04-3.11 (2H, m), 4.05 (3H, s), 6.13 (1H, t, J=5.6 Hz), 6.49 (1H, d, J=5.6 Hz), 7.16 (2H, d, J=9.2 Hz), 7.52 (2H, d, J=9.2 Hz), 7.58 (1H, s), 8.55 (1H, s), 8.71 (1H, d, J=5.6 Hz), 8.75 (1H, s)

Example 39

N-(4-(6-Cyano-7-methoxy-4-quinolyl)oxyphenyl)-N'-(4-fluorophenyl)urea 4-(4-Aminophenoxy)-6-cyano-7-methoxyethoxyquinoline (150 mg) was added to 5.0 ml of toluene and 2.5 ml of acetonitrile, and the mixture was heated to reflux. After then adding 4-fluorophenyl isocyanate (0.12 ml), the mixture was further heated to reflux for 1 hour. After cooling, the precipitated solid was filtered out and washed with ethyl acetate/toluene=1/1 to obtain 150 mg of the title compound as light brown crystals (68% yield).

$^1$H-NMR Spectrum (DMSO-d$_6$) δ (ppm): 4.05 (3H, s), 6.52 (1H, d, J=5.6 Hz), 7.08-7.14 (2H, m), 7.23 (2H, d, J=8.8 Hz), 7.43-7.49 (2H, m), 7.56-7.61 (3H, m), 8.71-8.76 (3H, m), 8.85 (1H, s)

Example 40

N-(4-(6-Cyano-7-methoxy-4-quinolyl)oxyphenyl)-N'-(2-pyridyl)urea

Phenyl N-(4-(6-cyano-7-methoxy-4-quinolyl)oxyphenyl) carbamate (150 mg) and 2-aminopyridine (69 mg) were dissolved in 1 ml of dimethylsulfoxide, and the solution was heated and stirred at 80° C. for 1.5 hours. After cooling, water was added, and the precipitated solid was filtered out and washed with ethyl acetate to obtain 82 mg of the title compound as light brown crystals (54% yield).

$^1$H-NMR Spectrum (DMSO-d$_6$) δ (ppm): 4.05 (3H, s), 6.54 (1H, d, J=5.6 Hz), 6.98-7.03 (1H, m), 7.26-7.30 (2H, m), 7.45-7.52 (1H, m), 7.60 (1H, s), 7.63-7.78 (3H, m), 8.25-8.30 (1H, m), 8.73 (1H, d, J=5.6 Hz), 8.78 (1H, s), 9.59 (1H, s), 10.67 (1H, s)

Example 41

N-(4-(6-Cyano-7-methoxyethoxy-4-quinolyl)oxyphenyl)-N'-(3-pyridyl)urea

The title compound (32 mg, 32% yield) was obtained as light brown crystals from phenyl N-(4-(6-cyano-7-methoxy-4-quinolyl)oxyphenyl)carbamate (100 mg) and 3-aminopyridine (46 mg), in the same manner as Example 40.

$^1$H-NMR Spectrum (DMSO-d$_6$) δ (ppm): 4.05 (3H, s), 6.53 (1H, d, J=5.2 Hz), 7.22-7.34 (3H, m), 7.57-7.63 (3H, m), 7.91-7.96 (1H, m), 8.17-8.20 (1H, m), 8.59-8.63 (1H, m), 8.73 (1H, d, J=5.2 Hz), 8.76 (1H, s), 8.91 (1H, brs), 9.00 (1H, brs).

Example 42

N-(4-(6-Cyano-7-methoxyethoxy-4-quinolyl)oxyphenyl)-N'-(4-pyridyl)urea

The title compound (45 mg, 30% yield) was obtained as light brown crystals from phenyl N-(4-(6-cyano-7-methoxy-4-quinolyl)oxyphenyl)carbamate (150 mg) and 4-aminopyridine (69 mg), in the same manner as Example 40.

$^1$H-NMR Spectrum (DMSO-d$_6$) δ (ppm): 4.05 (3H, s), 6.54 (1H, d, J=5.2 Hz), 7.26 (2H, d, J=9.0 Hz), 7.43 (2H, d, J=7.0 Hz), 7.57-7.64 (3H, m), 8.35 (2H, d, J=7.0 Hz), 8.71-8.77 (2H, m), 9.05 (1H, brs), 9.16 (1H, brs).

Example 43

N-(4-(6-Cyano-7-(3-(diethylamino)propoxy)-4-quinolyl)oxyphenyl)-N'-(4-methoxyphenyl)urea The title compound (10 mg) was obtained from sodium 6-cyano-4-(4-((4-methoxyanilino)carbonyl)aminophenoxy)-7-quinolinolate (131 mg) by the same procedure as in Example 7.

$^1$H-NMR(CDCl$_3$) δ (ppm): 2.02-2.15 (2H, m), 2.27 (6H, s), 2.54 (2H, t, J=7.4 Hz), 3.80 (3H, s), 4.28 (2H, t, J=7.4 Hz), 6.42 (1H, d, J=5.3 Hz), 6.80 (1H, brs), 6.90 (2H, d, J=9.3 Hz), 7.03 (1H, brs), 7.08 (2H, d, J=9.3 Hz), 7.28 (2H, d, J=9.3 Hz), 7.46 (1H, s), 7.48 (2H, d, J=9.3 HZ), 8.62 (1H, d, J=5.3 Hz), 8.66 (1H, s)

Example 44

N-[4-(6-Cyano-7-(2-(dimethylamino)ethoxy)-4-quinolyl)oxyphenyl)-N'-(4-methoxyphenyl)urea The title compound (110 mg) was obtained from sodium 6-cyano-4-(4-((4-methoxyanilino)carbonyl)aminophenoxy)-7-quinolinolate (145 mg), by the same procedure as in Example 7.

$^1$H-NMR (DMSO-d$_6$) δ (ppm): 2.28 (6H, s), 2.76 (2H, t, J=5.3 Hz), 3.70 (3H, s), 4.37 (2H, t, J=5.3 Hz), 6.51 (1H, d, J=5.4 Hz), 6.86 (2H, d, J=8.7 Hz), 7.21 (2H, d, J=8.7 Hz), 7.35 (2H, d, J=8.7 Hz), 7.58 (2H, d, J=8.7 Hz), 7.62 (1H, s), 8.50 (1H, s), 8.72 (1H, d, J=5.4 Hz), 8.75 (2H, s)

Example 45

N-(4-(6-Cyano-7-(3-(1-pyrrolidino)propoxy)-4-quinolyl)oxyphenyl-N'-(4-methoxyphenyl)urea N-(4-(6-Cyano-7-(3-chloropropoxy)-4-quinolyl)oxyphenyl)-N'-(4-methoxyphenyl)urea (140 mg) was dissolved in dimethylformamide, pyrrolidine (163 µl) was added, and the mixture was heated and stirred at 80° C. for 6 hours. The reaction solution was poured into saturated brine and extracted with ethyl acetate. The organic layer was dried over magnesium sulfate and concentrated. The residue was passed through NH silica gel (Fuji Silysia Chemical) and eluted with a solvent (ethyl acetate), and then further eluted with another solvent (ethyl acetate:methanol=10:1) and concentrated to obtain 31 mg of the title compound.

$^1$H-NMR (DMSO-d$_6$) δ (ppm): 1.67-1.73 (4H, m), 1.96-2.04 (2H, m), 2.44-2.49 (4H, m), 2.61 (2H, t, J=6.8 Hz), 3.72 (3H, s), 4.34 (2H, t, J=6.4 Hz), 6.53 (1H, d, J=5.2 Hz), 6.88 (2H, d, J=8.8 Hz), 7.23 (2H, d, J=9.2 Hz), 7.37 (2H, d, J=8.8 Hz), 7.60 (1H, s), 7.61 (2H, d, J=9.2 Hz), 8.63 (1H, brs), 8.73 (1H, d, J=5.2 HZ), 8.76 (1H, s), 8.88 (1H, brs).

Example 46

N-(4-(6-Cyano-7-(3-(1-piperidino)propoxy)-4-quinolyl)oxyphenyl)-N'-(4-methoxyphenyl)urea The title compound (67 mg) was obtained from sodium 6-cyano-4-(4-((4-methoxyanilino)carbonyl)aminophenoxy)-7-quinolinolate (156 mg), by the same procedure as in Example 7.

¹H-NMR (DMSO-d₆) δ (ppm): 1.30-1.57 (6H, m), 1.93-2.03 (2H, m), 2.31-2.53 (6H, m), 3.72 (3H, s), 4.33 (2H, t, J=6.5 Hz), 6.52 (1H, d, J=4.9 Hz), 6.87 (2H, d, J=8.9 Hz), 7.23 (2H, d, J=8.9 Hz), 7.38 (2H, d, J=8.9 Hz), 7.57-7.63 (3H, m), 8.53 (1H, brs), 8.72 (1H, d, J=4.9 Hz), 8.76 (1H, s), 8.79 (1H, brs)

Example 47

N-(4-(6-Cyano-7-(2-(1-pyrrolidino)ethoxy)-4-quinolyl)oxyphenyl)-N'-(4-methoxyphenyl)urea The title compound (54 mg) was obtained from sodium 6-cyano-4-(4-((4-methoxyanilino)carbonyl)aminophenoxy)-7-quinolinolate (188 mg), by the same procedure as in Example 7.

¹H-NMR (DMSO-d₆) δ (ppm): 1.68-1.74 (4H, m), 2.58-2.65 (4H, m), 2.93 (2H, t, J=6.4 Hz), 3.72 (3H, s), 4.40 (2H, t, J=6.4 Hz), 6.53 (1H, d, J=5.7 Hz), 6.88 (2H, d, J=9.1 Hz), 7.24 (2H, d, J=9.1 Hz), 7.37 (2H, d, J=9.1 Hz), 7.60 (2H, d, J=9.1 Hz), 7.62 (1H, s), 8.52 (1H, s), 8.73 (1H, d, J=5.7 Hz), 8.77 (2H, s)

Example 48

N-(4-(6-Cyano-7-(3-(diethylamino)propoxy)-4-quinolyl)oxyphenyl)-N'-(4-methoxyphenyl)urea The title compound (45 mg) was obtained from sodium 6-cyano-4-(4-((4-methoxyanilino)carbonyl)aminophenoxy)-7-quinolinolate (134 mg), by the same procedure as in Example 7.

¹H-NMR (DMSO-d₆) δ (ppm): 0.97 (6H, t, J=7.8 Hz), 1.88-1.96 (2H, m), 2.43-2.53 (4H, m), 2.61 (2H, t, J=7.8 Hz), 3.72 (3H, s), 4.33 (2H, t, J=7.8 Hz), 6.53 (1H, d, J=5.2 Hz), 6.88 (2H, d, J=8.8 Hz), 7.24 (2H, d, J=8.8 Hz), 7.38 (2H, d, J=8.8 Hz), 7.53-7.63 (3H, m), 8.55 (1H, s), 8.73 (1H, d, J=5.2 Hz), 8.76 (1H, s), 8.80 (1H, s)

Example 49

N-(4-(6-Cyano-7-(3-(dimethylamino)propoxy)-4-quinolyl)oxy-2-fluorophenyl)-N'-(2,4-difluorophenyl)urea The title compound (35 mg) was obtained from sodium 6-cyano-4-(4-((2,4-difluoroanilino)carbonyl)amino-3-fluorophenoxy)-7-quinolinolate (100 mg), by the same procedure as in Example 7.

¹H-NMR (DMSO-d₆) δ (ppm): 1.94-2.01 (2H, m), 2.43 (2H, t, J=7.2 Hz), 2.50 (6H, s), 4.33 (2H, t, J=7.2 Hz), 6.64 (1H, d, J=5.2 Hz), 7.04-7.46 (4H, m), 7.61 (1H, s), 8.09-8.34 (2H, m), 8.74-8.78 (2H, m), 9.06 (1H, brs), 9.14 (1H, brs).

Example 50

N-(4-(6-Cyano-7-(3-(diethylamino)propoxy)-4-quinolyl)oxy-2-fluorophenyl)-N'-(2,4-difluorophenyl)urea The title compound (43 mg) was obtained from sodium 6-cyano-4-(4-((2,4-difluoroanilino)carbonyl)amino-3-fluorophenoxy)-7-quinolinolate (95 mg), by the same procedure as in Example 7.

¹H-NMR (DMSO-d₆) δ (ppm): 0.97 (6H, t, J=7.8 Hz), 1.88-1.98 (2H, m), 2.45-2.52 (4H, m), 2.61 (2H, t, J=7.8 Hz), 4.33 (2H, t, J=7.8 Hz), 6.63 (1H, d, J=5.9 Hz), 7.03-7.45 (4H, m), 7.60 (1H, s), 8.09-8.17 (1H, m), 8.28 (1H, t, J=11.5 Hz), 8.74-8.78 (2H, m), 9.03 (1H, brs), 9.11 (1H, brs).

Example 51

N-(4-(6-Cyano-7-(4-(dimethylamino)butoxy)-4-quinolyl)oxyphenyl)-N'-(4-methoxyphenyl)urea N-(4-(6-Cyano-7-(4-chlorobutoxy)-4-quinolyl)oxyphenyl)-N'-(4-methoxyphenyl)urea (120 mg) was dissolved in dimethylformamide (3 ml), and then a 50% dimethylamine solution (93 μl) was added and the mixture was heated and stirred at 70° C. for 5 hours. The reaction solution was poured into saturated brine and extracted with ethyl acetate, and the organic layer was dried over magnesium sulfate and concentrated. The residue was passed through NH silica gel (Fuji Silysia Chemical) and eluted with a solvent (ethyl acetate), and then further eluted with another solvent (ethyl acetate:methanol=10:1) and concentrated. The obtained solid was passed through Merck Silica Gel using tetrahydrofuran, and after eluting the insoluble portion with tetrahydrofuran and ethyl acetate, it was further eluted with solvents (tetrahydrofuran:methanol:triethylamine=10:1:1, ethyl acetate:methanol:triethylamine=10:1:1) and concentrated to obtain 10 mg of the title compound as a solid.

¹H-NMR (DMSO-d₆) δ (ppm): 1.71-1.78 (2H, m), 1.82-1.91 (2H, m), 2.42 (6H, s), 2.64-2.72 (2H, m), 3.72 (3H, s), 4.33 (2H, t, J=6.0 Hz), 6.54 (1H, d, J=5.2 Hz), 6.88 (2H, d, J=8.8 Hz), 7.23 (2H, d, J=8.8 Hz), 7.37 (2H, d, J=8.8 Hz), 7.60 (2H, d, J=8.8 Hz), 7.61 (1H, s), 8.64 (1H, brs), 8.73 (1H, d, J=5.2 Hz), 8.78 (1H, s), 8.91 (1H, brs).

Example 52

N-(4-(6-Cyano-7-(4-morpholinobutoxy)-4-quinolyl)oxyphenyl)-N'-4-methoxyphenyl)urea The title compound (11 mg) was obtained from N-(4-(6-cyano-7-(4-chlorobutoxy)-4-quinolyl)oxyphenyl)-N'-(4-methoxyphenyl)urea (110 mg), in the same manner as Example 51.

¹H-NMR (DMSO-d₆) δ (ppm): 1.65-1.77 (2H, m), 1.84-1.93 (2H, m), 2.32-2.48 (6H, m), 3.51-3.66 (4H, m), 3.72 (3H, s), 4.33 (2H, t, J=6.0 Hz), 6.53 (1H, d, J=4.8 Hz), 6.88 (2H, d, J=8.4 Hz), 7.24 (2H, d, J=8.4 Hz), 7.37 (2H, d, J=8.4 Hz), 7.60 (2H, d, J=8.4 Hz), 7.61 (1H, s), 8.57 (1H, brs), 8.73 (1H, d, J=4.8 Hz), 8.78 (1H, s), 8.82 (1H, brs).

Example 53

N-(4-(6-Cyano-7-(3-(1-(4-ethyl)piperazino)propoxy)-4-quinolyl)oxyphenyl)-N'-(4-methoxyphenyl)urea The title compound (16 mg) was obtained from N-(4-(6-cyano-7-(3-chloropropoxy)-4-quinolyl)oxyphenyl)-N'-(4-methoxyphenyl)urea (150 mg), in the same manner as Example 51.

¹H-NMR (DMSO-d₆) δ (ppm): 0.98 (3H, t, J=7.2 Hz), 1.91-2.06 (2H, m), 2.26-2.48 (12H, m), 3.72 (3H, s), 4.33 (2H, t, J=6.0 Hz), 6.53 (1H, d, J=5.2 Hz), 6.88 (2H, d, J=8.8 Hz), 7.23 (2H, d, J=8.8 Hz), 7.37 (2H, d, J=8.8 Hz), 7.59 (1H, s), 7.60 (2H, d, J=8.8 Hz), 8.58 (1H, brs), 8.73 (1H, d, J=5.2 HZ), 8.76 (1H, s), 8.83 (1H, brs).

Example 54

N-(4-(6-Cyano-7-(2-(4-morpholino)ethoxy)-4-quinolyl)oxy-2-fluorophenyl)-N'-(2,4-difluorophenyl)urea The title compound (10 mg) was obtained from sodium 6-cyano-4-(4-((2,4-difluoroanilino)carbonyl)amino-3-fluorophenoxy)-7-quinolinolate (200 mg), by the same procedure as in Example 7.

$^1$H-NMR (DMSO-$d_6$) δ (ppm): 2.56 (4H, t, J=4.4 Hz), 2.83 (2H, t, J=5.6 Hz), 3.59 (4H, t, J=4.4 Hz), 4.43 (2H, t, J=5.6 Hz), 6.64 (1H, d, J=5.2 Hz), 7.04-7.10 (1H, m), 7.14-7.19 (1H, m), 7.30-7.36 (1H, m), 7.42 (1H, dd, J=2.8 Hz, J=12 Hz), 7.66 (1H, s), 8.10-8.16 (1H, m), 8.28 (1H, t, J=9.2 HZ), 8.75 (1H, s), 8.76 (1H, d, J=5.2 Hz), 9.02-9.05 (1H, m), 9.09-9.13 (1H, m).

Example 55

N-(4-(6-Cyano-7-(3-cyanopropoxy)-4-quinolyl)oxy-2-fluorophenyl)-N'-(2,4-difluorophenyl)urea The title compound (15 mg) was obtained from sodium 6-cyano-4-(4-((2,4-difluoroanilino)carbonyl)amino-3-fluorophenoxy)-7-quinolinolate (300 mg), in the same manner as Example 7.

$^1$H-NMR (DMSO-$d_6$) δ (ppm): 2.14-2.21 (2H, m), 2.73 (2H, t, J=7.2 Hz), 4.38 (2H, t, J=6.4 Hz), 6.65 (1H, d, J=5.2 Hz), 7.04-7.11 (1H, m), 7.15-7.19 (1H, m), 7.31-7.37 (1H, m), 7.43 (1H, dd, J=2.8 Hz, J=11.6 Hz), 7.67 (1H, s), 8.10-8.16 (1H, m), 8.29 (1H, t, J=9.2 HZ), 8.77 (1H, d, J=5.2 Hz), 8.79 (1H, s), 9.03-9.06 (1H, m), 9.11-9.14 (1H, m).

Example 56

N-(4-6-Cyano-7-(2-(methylthio)ethoxy-4-quinolyl)oxy-2-fluorophenyl)-N'-(2,4-difluorophenyl)urea The title compound (95 mg) was obtained from sodium 6-cyano-4-(4-((2,4-difluoroanilino)carbonyl)amino-3-fluorophenoxy)-7-quinolinolate (130 mg), in the same manner as Example 7.

$^1$H-NMR (DMSO-$d_6$) δ (ppm): 2.25 (3H, s), 2.99 (2H, t, J=6.0 Hz), 4.49 (2H, t, J=6.0 Hz), 6.64 (1H, d, J=5.2 Hz), 7.04-7.11 (1H, m), 7.15-7.19 (1H, m), 7.30-7.37 (1H, m), 7.43 (1H, dd, J=2.4 Hz, J=11.6 Hz), 7.66 (1H, s), 8.09-8.17 (1H, m), 8.29 (1H, t, J=9.2 Hz), 8.76 (1H, d, J=5.2 Hz), 8.77 (1H, s), 9.01-9.05 (1H, m), 9.09-9.13 (1H, m).

Example 57

N-(4-(6-Cyano-7-(2-(methylsulfonyl)ethoxy)-4-quinolyl)oxy-2-fluorophenyl)-N'-(2,4-difluorophenyl)urea N-(4-(6-Cyano-7-(2-(methylthio)ethoxy)-4-quinolyl)oxy-2-fluorophenyl)-N'-(2,4-difluorophenyl)urea (84 mg) was dissolved in a methanol (1 ml) and methylene chloride (5 ml) mixed solvent, 2 equivalents of meta-perbenzoic acid was added while stirring at 0° C., and the mixture was stirred for 30 minutes. The reaction solution was poured into a saturated aqueous sodium bicarbonate solution and extracted with ethyl acetate, and the organic layer was dried over magnesium sulfate and then concentrated. The residue was passed through NH silica gel (Fuji Silysia Chemical), eluted with a solvent (ethyl acetate:hexane=10:1) and concentrated to obtain 21 mg of the title compound.

$^1$H-NMR (DMSO-$d_6$) δ (ppm): 3.02 (3H, s), 3.79 (2H, t, J=4.8 Hz), 4.67 (2H, t, J=4.8 Hz), 6.67 (1H, d, J=5.2 Hz), 7.04-7.10 (1H, m), 7.15-7.19 (1H, m), 7.31-7.34 (1H, m), 7.43 (1H, dd, J=2.8 Hz, J=12 Hz), 7.73 (1H, s), 8.10-8.16 (1H, m), 8.28 (1H, t, J=9.2 HZ), 8.79 (1H, d, J=5.2 Hz), 8.81 (1H, s), 9.02-9.05 (1H, m), 9.11-9.14 (1H, m).

Example 58

N-(4-(6-Cyano-7-(2-(methylthio)ethoxy)-4-quinolyl)oxyphenyl)-N'-(4-fluorophenyl)urea The title compound (112 mg) was obtained from sodium 6-cyano-4-(4-((2,4-difluoroanilino)carbonyl)amino-3-fluorophenoxy)-7-quinolinolate (300 mg), in the same manner as Example 7.

$^1$H-NMR (DMSO-$d_6$) δ (ppm): 2.25 (3H, s), 2.99 (2H, t, J=6.0 Hz), 4.49 (2H, t, J=6.0 Hz), 6.54 (1H, d, J=5.2 Hz), 7.13 (2H, t, J=8.8 Hz), 7.25 (2H, d, J=8.8 Hz), 7.46-7.51 (2H, m), 7.61 (2H, d, J=8.8 Hz), 7.65 (1H, s), 8.74 (1H, d, J=5.2 Hz), 8.78 (1H, s), 8.82 (1H, brs), 8.91 (1H, brs).

Example 59

N-(4-(6-Cyano-7-(2-(methylsulfonyl)ethoxy)-4-quinolyl)oxyphenyl)-N'-(4-fluorophenyl)urea The title compound (11 mg) was obtained from N-(4-(6-cyano-7-(2-(methylthio)ethoxy)-4-quinolyl)oxyphenyl)-N'-(4-fluorophenyl)urea (100 mg), in the same manner as Example 56.

$^1$H-NMR (DMSO-$d_6$) δ (ppm): 3.20 (3H, s), 3.79 (2H, t, J=5.6 Hz), 4.69 (2H, t, J=5.6 Hz), 6.57 (1H, d, J=5.2 Hz), 7.13 (2H, t, J=8.8 Hz), 7.25 (2H, d, J=8.8 Hz), 7.46-7.52 (2H, m), 7.62 (2H, d, J=8.8 Hz), 7.72 (1H, s), 8.76 (1H, d, J=5.2 Hz), 8.82 (1H, s), 8.90 (1H, brs), 8.99 (1H, brs).

Example 60

N-(4-(6-Chloro-5,7-dimethoxy-4-quinolyl)oxy-2-fluorophenyl)-N'-(2,4-difluorophenyl)urea The title compound (173 mg) was obtained from 4-(4-amino-3-fluorophenoxy)-6-chloro-5,7-dimethoxyquinoline (235 mg) and 2,4-difluorophenyl isocyanate, in the same manner as Example 10.

$^1$H-NMR (DMSO-$d_6$) δ (ppm): 3.93 (3H, s), 4.07 (3H, s), 6.67 (1H, d, J=5.2 Hz), 6.91-6.96 (1H, m), 7.00 (1H, s), 7.03-7.09 (1H, m), 7.20 (1H, dd, J=2.8 Hz, J=8.0 Hz), 7.30-7.37 (1H, m), 8.08-8.20 (2H, m), 8.69 (1H, d, J=5.2 Hz), 9.01 (1H, brd, J=2.0 Hz), 9.04 (1H, brd, J=2.0 Hz).

Example 61

N-(4-(6-Cyano-7-methoxy-4-quinolyl)oxy-2-fluorophenyl)-N'-(2,4-difluorophenyl)urea The title compound (130 mg) was obtained from 4-(4-amino-3-fluorophenoxy)-6-cyano-7-methoxyquinoline (238 mg) and 2,4-difluorophenyl isocyanate, in the same manner as Example 10.

$^1$H-NMR (DMSO-$d_6$) δ (ppm): 4.08 (3H, s), 6.64 (1H, d, J=5.2 Hz), 7.04-7.10 (1H, m), 7.15-7.19 (1H, m), 7.31-7.37

(1H, m), 7.43 (1H, dd, J=2.8 Hz, J=12 Hz), 7.63 (1H, s), 8.13 (1H, dt, J=6.4 Hz, J=9.2 Hz), 8.29 (1H, t, J=9.2 Hz), 8.77 (1H, d, J=5.2 Hz), 8.78 (1H, s), 9.05 (1H, brs), 9.13 (1H, brs).

Example 62

N-(4-(6-Cyano-7-methoxy-4-quinolyl)oxyphenyl)-N'-(4-methoxyphenyl)urea

The title compound (55 mg) was obtained from 4-amino (4-aminophenoxy)-6-cyano-7-methoxyquinoline (170 mg) and 4-methoxyphenyl isocyanate, in the same manner as Example 10.

$^1$H-NMR (DMSO-d$_6$) δ (ppm): 3.72 (3H, s), 4.07 (3H, s), 6.54 (1H, d, J=5.2 Hz), 6.88 (2H, d, J=8.8 Hz), 7.24 (2H, d, J=8.8 Hz), 7.37 (2H, d, J=8.8 Hz), 7.60 (2H, d, J=8.8 Hz), 7.61 (1H, s), 8.62 (1H, brs), 8.74 (1H, d, J=5.2 Hz), 8.78 (1H, s), 8.87 (1H, brs).

Example 63

N-(4-(6-Cyano-7-(2-(4-morpholino)ethoxy)-4-quinolyl)oxyphenyl)-N'-(4-methoxyphenyl)urea The title compound was obtained from sodium 6-cyano-4-(4-((4-methoxyanilino)carbonyl)aminophenoxy)-7-quinolinolate, in the same manner as Example 7.

$^1$H-NMR (DMSO-d$_6$) δ (ppm): 2.50-2.55 (4H, m), 2.87 (2H, t, J=5.6 Hz), 3.57 (4H, t, J=4.4 Hz), 3.60 (3H, s), 4.38 (2H, t, J=5.6 Hz), 6.85 (2H, d, J=8.8 Hz), 7.02 (1H, s), 7.06 (1H, d, J=5.2 Hz), 7.21 (2H, d, J=8.8 Hz), 7.36 (2H, d, J=8.8 Hz), 7.58 (2H, d, J=8.8 Hz), 8.65 (1H, s), 8.68 (1H, brs), 8.73 (1H, d, J=5.2 Hz), 8.92 (1H, brs)

Example 64

N-(4-(6-Cyano-7-(2-methoxyethoxy)-4-quinolyl)oxyphenyl)-N'-cyclohexylurea

The title compound (25 mg) was obtained from 4-(4-aminophenoxy)-6-cyano-7-(2-methoxyethoxy)quinoline (60 mg) and cyclohexyl isocyanate, in the same manner as Example 10.

$^1$H-NMR (DMSO-d$_6$) δ (ppm): 1.12-1.24 (3H, m), 1.26-1.38 (2H, m), 1.51-1.59 (1H, m), 1.63-1.72 (2H, m), 1.78-1.86 (2H, m), 3.38 (3H, s), 3.42-3.52 (1H, m), 3.78-3.80 (2H, m), 4.42-4.44 (2H, m), 6.18 (1H, brd, J=8.0 Hz), 6.50 (1H, d, J=5.2 Hz), 7.18 (2H, d, J=9.2 Hz), 7.53 (2H, d, J=9.2 Hz), 7.63 (1H, s), 8.55 (1H, brs), 8.72 (1H, d, J=5.2 Hz), 8.77 (1H, s).

Example 65

N-(4-(6-Cyano-7-(2-methoxyethoxy)-4-quinolyl)oxyphenyl)-N'-phenylurea 4-(4-Aminophenoxy)-6-cyano-7-(2-methoxyethoxy)quinoline (600 mg) was suspended in toluene (15 ml), and the suspension was heated to reflux for dissolution, after which phenyl isocyanate (292 μl) was added dropwise and the mixture was heated to reflux for 30 minutes. After cooling, the precipitated solid was filtered out, washed with ether and ethyl acetate and dried to obtain 760 mg of the title compound.

$^1$H-NMR (DMSO-d$_6$) δ (ppm): 3.38 (3H, s), 3.78-3.81 (2H, m), 4.42-4.45 (2H, m), 6.54 (1H, d, J=5.2 Hz), 6.98 (1H, t, J=7.2 Hz), 7.24-7.31 (4H, m), 7.47 (2H, d, J=7.2 Hz), 7.62 (2H, d, J=8.8 Hz), 7.64 (1H, s), 8.74 (1H, d, J=5.2 Hz), 8.79 (1H, s), 8.85 (1H, brs), 8.99 (1H, brs).

Example 66

N-(4-(6-Cyano-7-(2-methoxyethoxy)-4-quinolyl)oxy-2-fluorophenyl)-N'-(2,4-difluorophenyl)urea 4-(4-Amino-3-fluorophenoxy)-6-cyano-7-(2-methoxyethoxy)quinoline (352 mg) was suspended in toluene (20 ml) and the suspension was heated to reflux for dissolution, after which 2,4-difluorophenyl isocyanate (236 μl) was added dropwise and the mixture was heated to reflux for 30 minutes. After cooling, the precipitated solid was filtered out, washed with ether and ethyl acetate and dried to obtain 380 mg of the title compound.

$^1$H-NMR (DMSO-d$_6$) δ (ppm): 3.38 (3H, s), 3.78-3.81 (2H, m), 4.42-4.46 (2H, m), 6.64 (1H, d, J=5.2 Hz), 7.04-7.11 (1H, m), 7.15-7.19 (1H, m), 7.31-7.37 (1H, m), 7.43 (1H, dd, J=2.8 Hz, J=8.0 Hz), 7.66 (1H, s), 8.13 (1H, dt, J=6 Hz, J=9.2 Hz), 8.28 (1H, t, J=9.2 Hz), 8.76 (1H, d, J=5.2 Hz), 8.77 (1H, s), 9.05 (1H, brs), 9.13 (1H, brs).

Example 67

N-(4-(6-Cyano-7-(2-methoxyethoxy)-4-quinolyl)oxy-2-fluorophenyl)-N'-(methoxyphenyl)urea The title compound (570 mg) was obtained from 4-(4-amino-3-fluorophenoxy)-6-cyano-7-(2-methoxyethoxy)quinoline (620 mg) and 4-methoxyphenyl isocyanate, in the same manner as Example 10.

$^1$H-NMR (DMSO-d$_6$) δ (ppm): 3.38 (3H, s), 3.73 (3H, s), 3.78-3.81 (2H, m), 4.43-4.45 (2H, m), 6.63 (1H, d, J=5.2 Hz), 6.89 (2H, d, J=8.8 Hz), 7.13-7.17 (1H, m), 7.37 (2H, d, J=8.8 Hz), 7.41 (1H, dd, J=2.8 Hz, J=11.6 Hz), 7.65 (1H, s), 8.28 (1H, t, J=8.8 Hz), 8.60 (1H, brs), 8.76 (1H, d, J=5.2 Hz), 8.77 (1H, s), 8.94 (1H, brs).

Example 68

N-(4-(6-Cyano-7-(methoxyethoxy)-4-quinolyl)oxyphenyl)-N'-(4-methoxyphenyl)urea

The title compound (450 mg) was obtained from 4-(4-aminophenoxy)-6-cyano-7-(2-methoxyethoxy)quinoline (890 mg) and 4-methoxyphenyl isocyanate, in the same manner as Example 10.

$^1$H-NMR (DMSO-d$_6$) δ (ppm): 3.36 (3H, s), 3.70 (3H, s), 3.76-3.79 (2H, m), 4.40-4.42 (2H, m), 6.51 (1H, d, J=5.6 Hz), 6.86 (2H, d, J=8.8 Hz), 7.22 (2H, d, J=8.8 Hz), 7.35 (2H, d, J=8.8 Hz), 7.58 (2H, d, J=8.8 Hz), 7.62 (1H, s), 8.53 (1H, brs), 8.71 (1H, d, J=5.6 Hz), 8.76 (1H, s), 8.80 (1H, brs).

Example 69

N-((4-Pyrimidyl)oxyphenyl)-N'-(4-methoxyphenyl)urea

Palladium hydroxide (20 mg) was added to solution of 6-chloro-4-(4-nitrophenoxy)pyrimidine (300 mg) in an ethyl acetate (10 ml)-methanol (10 ml) mixed solvent, and the mixture was stirred for 13 hours at room temperature under a hydrogen atmosphere at normal pressure. The reaction solution was filtered, the filtrate was concentrated, and the residue was passed through NH silica gel (Fuji Silysia Chemical). Elution was performed with a solvent (ethyl acetate:hexane=1:2) to obtain 70 mg of 4-(4-aminophenoxy)pyrimidine. The title compound (107 mg) was obtained from the obtained 4-(4-aminophenoxy)pyrimidine (70 mg) and 4-methoxyphenyl isocyanate, in the same manner as Example 10.
$^1$H-NMR (DMSO-$d_6$) δ (ppm): 3.72 (3H, s), 6.87 (2H, d, J=8.8 Hz), 7.09 (1H, dd, J=1.6 Hz, J=5.6 Hz), 7.12 (2H, d, J=8.8 Hz), 7.36 (2H, d, J=8.8 Hz), 7.51 (2H, d, J=8.8 Hz), 8.56 (1H, s), 8.66 (1H, d, J=5.6 HZ), 8.74-8.76 (2H, m).

Example 70

N-(4-(6-Cyano-7-(3-methoxycarbonylpropoxy)-4-quinolyl)oxyphenyl)-N'-(4-methoxyphenyl)urea The title compound was obtained from sodium 6-cyano-4-(4-((4-methoxyanilino)carbonyl)aminophenoxy)-7-quinolinolate, in the same manner as Example 7.
$^1$H-NMR (DMSO-$d_6$) δ (ppm): 2.09 (2H, tt, J=6.4 Hz, J=6.4 Hz), 2.56 (2H, t, J=6.4 Hz), 3.62 (3H, s), 3.71 (3H, s), 4.31 (2H, t, J=6.4 Hz), 6.52 (1H, d, J=5.2 Hz), 6.86 (2H, d, J=8.8 Hz), 7.22 (2H, d, J=8.8 Hz), 7.35 (2H, d, J=8.8 Hz), 7.57 (2H, d, J=8.8 Hz), 7.59 (1H, s), 8.50 (1H, s), 8.72 (1H, d, J=5.2 Hz) 8.74 (1H, s), 8.75 (1H, s).

Example 71

N-(4-(6-Cyano-7-(3-carboxypropoxy)-4-quinolyl)oxyphenyl)-N'-(4-methoxyphenyl)urea N-(4-(6-Cyano-7-(3-methoxycarbonylpropoxy)-4-quinolyl)oxyphenyl)-N'-(4-methoxyphenyl)urea (100 mg) was added to a methanol (16 ml) and 2N aqueous sodium hydroxide (3 ml) mixed solvent, and the mixture was heated and stirred at 80° C. for 35 minutes. The reaction solution was filtered, and then 1.2 ml of aqueous 5N hydrochloric acid was added. The precipitated solid was filtered out and washed with methanol and then ether to obtain 50 mg of the target substance as a light yellow solid.
$^1$H-NMR (DMSO-$d_6$) δ (ppm): 2.05 (2H, tt, J=6.4 Hz, J=6.4 Hz), 2.47 (2H, t, J=6.4 Hz), 3.70 (3H, s), 4.31 (2H, t, J=6.4 Hz), 6.52 (1H, d, J=5.2 Hz), 6.86 (2H, d, J=8.8 Hz), 7.22 (2H, d, J=8.8 Hz), 7.35 (2H, d, J=8.8 Hz), 7.57 (2H, d, J=8.8 Hz), 7.59 (1H, s), 8.50 (1H, s), 8.71 (1H, d, J=5.2 Hz) 8.75 (1H, s), 8.76 (1H, s).

Example 72

N-(4-(6-Cyano-7-(2-(2-hydroxyethoxy)ethoxy)-4-quinolyl)oxyphenyl)-N'-(4-methoxyphenyl)urea The title compound was obtained from sodium 6-cyano-4-(4-((4-methoxyanilino)carbonyl)aminophenoxy)-7-quinolinolate, in the same manner as Example 7.
$^1$H-NMR (DMSO-$d_6$) δ (ppm): 3.54-3.57 (4H, m), 3.72 (3H, s), 3.87-3.90 (2H, m), 4.41-4.45 (2H, m), 4.62-4.65 (1H, m), 6.54 (1H, d, J=5.2 Hz), 6.87 (2H, d, J=8.8 Hz), 7.24 (2H, d, J=8.8 Hz), 7.38 (2H, d, J=8.8 Hz), 7.60 (2H, d, J=8.8 Hz), 7.64 (1H, s), 8.62 (1H, brs), 8.74 (1H, d, J=5.2 Hz), 8.78 (1H, s), 8.87 (1H, brs).

Example 73

N-(4-(6-Cyano-7-(3-(diethylamino)propoxy)-4-quinolyloxy)phenyl)-N'-(3-(methylsulfonyl)phenyl)urea The title compound (8.8 mg, 0.015 mmol, 6.0%) was obtained as light brown crystals from N-4-(((6-cyano-7-hydroxy-4-quinolyl)oxy)phenyl-N'-(3-(methylsulfonyl)phenyl)urea (119 mg, 0.25 mmol), by the same procedure as in Example 7.
$^1$H-NMR Spectrum (DMSO-$d_6$) δ (ppm): 0.95 (6H, t, J=7.2 Hz), 1.87-1.95 (2H, m), 2.40-2.70 (6H, m), 3.18 (3H, s), 4.29-4.33 (2H, m), 6.51 (1H, d, J=5.2 Hz), 7.25 (2H, d, J=8.8 Hz), 7.49-7.68 (6H, m), 8.16 (1H, brs), 8.71 (1H, d, J=5.2 Hz), 8.75 (1H, s), 9.02 (1H, brs), 9.21 (1H, brs).

Example 74

N-(4-(6-Cyano-7-(3-(4-morpholino)propoxy)-4-quinolyl)oxyphenyl)-N'-(3-(methylsulfonyl)phenyl)urea The title compound (81 mg, 0.135 mmol, 53.7%) was obtained as light yellow crystals from N-4-((6-cyano-7-hydroxy-4-quinolyl)oxy)phenyl-N'-(3-(methylsulfonyl)phenyl)urea (119 mg, 0.25 mmol), by the same procedure as in Example 7.
$^1$H-NMR Spectrum (DMSO-$d_6$) δ (ppm): 1.95-2.04 (2H, m), 2.34-2.60 (6H, m), 3.18 (3H, s), 3.54-3.60 (4H, m), 4.30-4.36 (2H, m), 6.52 (1H, d, J=5.2 Hz), 7.25 (2H, d, J=8.8 Hz), 7.50-7.68 (6H, m), 8.16 (1H, s), 8.72 (1H, d, J=5.2 Hz), 8.75 (1H, s), 8.95 (1H, s), 9.15 (1H, s).

Example 75

N-(4-(6-Cyano-7-(3-(diethylamino)propoxy)-4-quinolyloxy)phenyl)-N'-phenylurea

The title compound (70 mg, 0.137 mmol, 27.5%) was obtained as light brown crystals from sodium 4-(4-((anilinocarbonyl)amino)phenoxy)-6-cyano-7-quinolinolate (210 mg, 0.50 mmol), by the same procedure as in Example 7.
$^1$H-NMR Spectrum (DMSO-$d_6$) δ (ppm): 0.95 (6H, t, J=7.2 Hz), 1.85-1.95 (2H, m), 2.40-2.55 (4H, m), 2.60 (2H, t, J=6.8 Hz), 4.31 (2H, t, J=6.0 Hz), 6.51 (1H, d, J=5.2 Hz), 6.96 (1H, m), 7.22-7.30 (4H, m), 7.45 (2H, d, J=8.0 Hz), 7.56-7.61 (3H, m), 8.70-8.72 (2H, m), 8.75 (1H, s), 8.84 (1H, s).

Example 76

N-(4-(6-Cyano-7-(3-(4-morpholino)propoxy)-4-quinolyl)oxyphenyl)-N'-phenylurea

The title compound (67 mg, 0.128 mmol, 51.0%) was obtained as light yellow crystals from sodium 4-(4-((anilinocarbonyl)amino)phenoxy)-6-cyano-7-quinolinolate (105 mg, 0.25 mmol), by the same procedure as in Example 7.
$^1$H-NMR Spectrum (DMSO-$d_6$) δ (ppm): 1.92-2.02 (2H, m), 2.35-2.57 (6H, m), 3.55-3.57 (4H, m), 4.30-4.34 (2H, m), 6.51 (1H, d, J=5.6 Hz), 6.96 (1H, t, J=7.2 Hz), 7.22-7.30 (4H, m), 7.45 (2H, d, J=7.6 Hz), 7.58-7.61 (3H, m), 8.69-8.72 (2H, m), 8.75 (1H, s), 8.83 (1H, s).

Example 77

N-(4-(6-Cyano-7-(2-methoxyethoxy)-4-quinolyl)oxyphenyl)-N'-(1H-[d]imidazol-2-yl)urea The title compound (71 mg, 0.14 mmol, 64.7%) was obtained as white crystals from phenyl N-(4-(6-cyano-7-(2-methoxyethoxy)-4-quinolyl)oxyphenyl)carbamate (101 mg, 0.222 mmol), by the same procedure as in Example 11.
$^1$H-NMR (DMSO-$d_6$) δ (ppm): 3.36 (3H, s), 3.75-3.79 (2H, m), 4.40-4.43 (2H, m), 6.54 (1H, d, J=5.2 Hz), 7.04-7.07 (2H, m), 7.26 (2H, d, J=8.8 Hz), 7.34-7.37 (2H, m), 7.62 (1H, s), 7.73 (2H, d, J=8.8 Hz), 8.72 (1H, d, J=5.2 Hz), 8.77 (1H, s).

Example 78

N-(4-(6-Cyano-7-(2-methoxyethoxy)-4-quinolyl)oxyphenyl)-N'-(2-oxo-1,2,3,4-tetrahydro-6-quinolinyl)urea The title compound (70 mg, 0.134 mmol, 60.9%) was obtained as white crystals from phenyl N-(4-(6-cyano-7-(2-methoxyethoxy)-4-quinolyl)oxyphenyl)carbamate (100 mg, 0.220 mmol), by the same procedure as in Example 11.
$^1$H-NMR Spectrum (DMSO-$d_6$) δ (ppm): 2.38-2.43 (2H, m), 2.81-2.85 (2H, m), 3.36 (3H, s), 3.75-3.79 (2H, m), 4.40-4.43 (2H, m), 6.51 (1H, d, J=5.2 Hz), 6.76 (1H, d, J=8.4 Hz), 7.16 (1H, dd, J=2.0, 8.4 Hz), 7.22 (2H, dd, J=8.8 Hz), 7.30 (1H, s), 7.58 (2H, d, J=8.8 Hz), 7.62 (1H, s), 8.52 (1H, s), 8.71 (1H, d, J=5.2 Hz), 8.75 (2H, s), 9.95 (1H, s).

Example 79

N-(4-(6-Cyano-7-(2-methoxyethoxy)-4-quinolyl)oxyphenyl)-N'-(4-acetamidephenyl)urea The title compound (100 mg, 0.197 mmol, 89.6%) was obtained as white crystals from phenyl N-(4-(6-cyano-7-(2-methoxyethoxy)-4-quinolyl)oxyphenyl)carbamate (100 mg, 0.220 mmol), by the same procedure as in Example 11.
$^1$H-NMR Spectrum (DMSO-$d_6$) δ (ppm): 2.00 (3H, s), 3.36 (3H, s), 3.76-3.79 (2H, m), 4.40-4.43 (2H, m), 6.52 (1H, d, J=5.2 Hz), 7.23 (2H, d, J=8.8 Hz), 7.35 (2H, d, J=8.8 Hz), 7.46 (2H, d, J=8.8 Hz), 7.58 (2H, d, J=8.8 Hz), 7.62 (1H, s), 8.59 (1H, s), 8.72 (1H, d, J=5.2 Hz), 8.76 (1H, s), 8.77 (1H, s), 9.80 (1H, s).

Example 80

N-(4-(6-Cyano-7-(2-methoxyethoxy)-4-quinolyl)oxyphenyl)-N'-(3-acetamidephenyl)urea The title compound (95 mg, 0.186 mmol, 84.9%) was obtained as white crystals from phenyl N-(4-(6-cyano-7-(2-methoxyethoxy)-4-quinolyl)oxyphenyl)carbamate (100 mg, 0.220 mmol), by the same procedure as in Example 11.
$^1$H-NMR Spectrum (DMSO-$d_6$) δ (ppm): 2.02 (3H, s), 3.36 (3H, s), 3.76-3.79 (2H, m), 4.40-4.43 (2H, m), 6.52 (1H, d, J=5.6 Hz), 7.15-7.20 (3H, m), 7.23 (2H, d, J=8.8 Hz), 7.59 (2H, d, J=8.8 Hz), 7.62 (1H, s), 7.76 (1H, s), 8.71-8.76 (4H, m), 9.90 (1H, s).

Example 81

N-(4-(6-Cyano-7-benzyloxy-4-quinolyl)oxy-2-fluorophenyl)-N'-(2,4-difluorophenyl)urea N-(2,4-Difluorophenyl)-N'-(2-fluoro-4-hydroxyphenyl)urea (227 mg, 0.8058 mmol) and 4-chloro-6-cyano-7-benzyloxyquinoline (250 mmol, 0.8482 mmol) were used for reaction in the same manner as the second method in Example 86, and after cooling, extraction and washing with water, the solvent was distilled off under reduced pressure and the obtained crystals were suspended in diethyl ether, washed and filtered. They were then dissolved in tetrahydrofuran and filtered with silica gel, and the solvent was distilled off under reduced pressure. These crystals were then suspended in diethyl ether, washed with water and filtered, and then washed with diethyl ether and dried by aspiration to obtain the title compound (70 mg, 0.1295 mmol, 16.07%) as light brown crystals.
$^1$H-NMR Spectrum (DMSO-$d_6$) δ (ppm): 5.45 (2H, s), 6.63 (1H, d, J=5.4 Hz), 7.05 (1H, m), 7.15 (1H, m), 7.29-7.46 (5H, m), 7.54 (2H, d, J=7.6 Hz), 7.71 (1H, s), 8.11 (1H, dt, J=6.0 Hz, 9.2 Hz), 8.27 (1H, d, J=9.2 Hz), 8.74 (1H, d, J=5.4 Hz), 8.77 (1H, s), 8.99 (1H, s), 9.07 (1H, s).

Example 82

N-(4-(7-(Benzyloxy)-6-cyano-4-quinolyl)oxyphenyl-N'-(2-thiazolyl)urea

The title compound (3.19 g, 6.46 mmol, 91%) was obtained as light brown crystals from 4-(4-aminophenoxy)-7-(benzyloxy)-6-cyanoquinoline (2.61 g, 7.10 mmol) and phenyl N-(2-thiazolyl)carbamate (1.88 g, 8.54 mmol), by the same procedure as in Example 34.
$^1$H-NMR Spectrum (DMSO-$d_6$) δ (ppm): 5.47 (2H, s), 6.55 (1H, d, J=5.3 Hz), 7.12 (1H, d, J=3.5 Hz), 7.29 (2H, d, J=8.7 Hz), 7.36-7.58 (6H, m), 7.65 (2H, d, J=8.7 Hz), 7.72 (1H, s), 8.74 (1H, d, J=5.3 Hz), 8.80 (1H, s), 9.18 (1H, s).

Example 83

N-(4-(6-Cyano-7-hydroxy-4-quinolyl)oxyphenyl)-N'-(2-thiazolyl)urea

The N-(4-(7-(benzyloxy)-6-cyano-4-quinolyl)oxyphenyl-N'-(2-thiazole)urea (3.09 g, 7.66 mmol) obtained in Example 82 was dissolved in trifluoroacetic acid (25 ml) and thioanisole (4.50 ml, 38.3 mmol), and the mixture was stirred at 65° C. for 15 hours. The reaction solution was concentrated under reduced pressure, and then a 5% aqueous sodium bicarbonate solution and diethyl ether were added to the resulting residue, the mixture was stirred, and the crystals were filtered out and washed with water and diethyl ether and then dried under reduced pressure. The crude product was suspended in a hexane-ethyl acetate mixed solvent and subjected to sonication, after which the crystals were filtered, washed with diethyl ether and blow-dried at room temperature to obtain the title compound (1.94 g, 4.80 mmol, 63%) as yellow crystals.
$^1$H-NMR Spectrum (DMSO-$d_6$) δ (ppm): 6.44 (1H, d, J=5.2 Hz), 7.12 (1H, d, J=3.7 Hz), 7.28 (2H, d, J=7.8 Hz), 7.39 (1H, d, J=3.7 Hz), 7.42 (1H, s), 7.64 (2H, d, J=7.8 Hz), 8.65 (1H, d, J=5.2 Hz), 8.68 (1H, s), 9.14 (1H, s).

Example 84

N-(4-(6-Cyano-7-(3-(diethylamino)propoxy)-4-quinolyloxy)phenyl-N'-(2-thiazolyl)urea The title compound (26 mg, 0.0503 mmol, 20%) was obtained as colorless crystals from the N-(4-(6-cyano-7-hydroxy-4-quinolyl)oxyphenyl)-N'-(2-thiazolyl)urea (101 mg, 0.250 mmol) obtained in Example 83, by the same procedure as in Example 7.
$^1$H-NMR Spectrum (CDCl$_3$) δ (ppm): 1.05 (6H, t, J=7.2 Hz), 2.03-2.12 (2H, m), 2.58 (4H, q, J=7.2 Hz), 2.71 (2H, t, J=7.0 Hz), 4.28 (2H, t, J=6.2 Hz), 6.47 (1H, d, J=5.3 Hz), 6.92 (1H, d, J=3.7 Hz), 7.17 (2H, d, J=8.8 Hz), 7.43 (1H, d, J=3.7 Hz), 7.47 (1H, s), 7.67 (2H, d, J=8.8 Hz), 8.65 (1H, d, J=5.3 Hz), 8.67 (1H, s).

Example 85

N-(4-(6-Cyano-7-(3-(4-morpholino)propoxy)-4-quinolyl)oxyphenyl)-N'-(2-thiazolyl)urea The title compound (19 mg, 0.0358 mmol, 14%) was obtained as colorless crystals from the N-(4-(6-cyano-7-hydroxy-4-quinolyl)oxyphenyl)-N'-(2-thiazolyl)urea (101 mg, 0.250 mmol) obtained in Example 83, by the same procedure as in Example 7.

$^1$H-NMR Spectrum (CDCl$_3$) δ (ppm): 2.08-2.16 (2H, m), 2.46-2.52 (4H, m), 2.62 (2H, t, J=7.0 Hz), 3.70-3.76 (4H, m), 4.30 (2H, t, J=6.2 Hz), 6.47 (1H, d, J=5.3 Hz), 6.92 (1H, d, J=3.7 Hz), 7.17 (2H, d, J=8.8 Hz), 7.42 (1H, d, J=3.7 Hz), 7.48 (1H, s), 7.67 (2H, d, J=8.8 Hz), 8.66 (1H, d, J=5.3 Hz), 8.69 (1H, s).

Example 86

N-(4-(6-Cyano-7-benzyloxy-4-quinolyl)oxyphenyl)-N'-(4-methoxyphenyl)urea

After adding toluene (60 ml) and acetonitrile (30 ml) to 4-amino(4-aminophenoxy)-7-(benzyloxy)-6-cyanoquinoline (1.0 g) and refluxing the mixture to dissolution, 4-methoxyphenyl isocyanate (0.53 ml) was added while continuing reflux. After stirring for 1 hour with reflux, additional 4-methoxyphenyl isocyanate (0.30 ml) was added. This was further stirred for 40 minutes with reflux and returned to room temperature. The precipitated crystals were filtered out and washed with a mixed solvent of toluene:acetonitrile=1:1 to obtain the title compound (0.60 g) as light brown crystals. The crystals which precipitated from the washing solution were filtered out to obtain more of the title compound (0.20 g) as light brown crystals.

$^1$H-NMR Spectrum (CDCl$_3$) δ (ppm): 3.73 (3H, s), 5.98 (2H, s), 6.56 (1H, d, J=5.2 Hz), 6.89 (2H, d, J=9.3 Hz), 7.24 (2H, d, J=9.3 Hz), 7.33-7.65 (9H, m), 7.72 (1H, s), 8.74 (1H, d, J=5.2 Hz), 8.82 (1H, s), 8.89 (1H, brs), 9.19 (1H, brs).

Example 86-2

N-(4-(6-Cyano-7-benzyloxy-4-quinolyl)oxyphenyl)-N'-(4-methoxyphenyl)urea

After adding 1-methylpyrrolidone (3.4 ml) and diisopropylethylamine (3.6 ml, 20.78 mmol) to N-(4-hydroxyphenyl)-N'-(4-methoxyphenyl)urea (4.25 g, 16.46 mmol), the mixture was heated and stirred at 130° C. to complete dissolution, and then 4-chloro-6-cyano-7-benzyloxyquinoline (5.10 g, 17.32 mmol) was added and the mixture was stirred at 130° C. for 1.5 hours and at 150° C. for 1 hour. Upon addition of diisopropylethylamine (1.2 ml, 6.93 mmol), the mixture was further stirred for 1 hour. After cooling and adding tetrahydrofuran and ethyl acetate, the mixture was washed with saturated sodium bicarnobate water and saturated brine and dried over magnesium sulfate, and the solvent was distilled off under reduced pressure. The obtain crystals were washed with diethyl ether/hexane, acetonitrile/diethyl ether/hexane, methanol and dimethylsulfoxide/water, in that order. The obtained crystals were dissolved in tetrahydrofuran, filtered with silica gel (200 cc silica gel) and flushed with 3000 ml of tetrahydrofuran, and the solvent was distilled off under reduced pressure. The crystals were then washed with diethyl ether, acetonitrile and diethyl ether:ethanol=5:1 and dried by aspiration to obtain the title compound (3.70 g, 7.1627 mmol, 43.52%) as brown crystals.

Example 87

Sodium 6-cyano-4-(4-((4-methoxyanilino)carbonyl)aminophenoxy)-7-quinolinolate

Trifluoroacetic acid (122 ml) and thioanisole (11.7 ml) were added to N-(4-(6-cyano-7-benzyloxy-4-quinolyl)oxyphenyl)-N'-(4-methoxyphenyl)urea (12.2 g), and the mixture was stirred at 50° C. overnight and at 40° C. for 24 hours. Upon confirming disappearance of the starting materials, the reaction system was concentrated under reduced pressure, tetrahydrofuran and saturated sodium bicarnobate water were added, and the precipitated yellow crystals were filtered and dried under reduced pressure to obtain the title compound (6.8 g). Ether was further added to the filtrate and the precipitated yellow crystals were filtered out and dried under reduced pressure to obtain more of the title compound (2.0 g).

$^1$H-NMR Spectrum (CDCl$_3$) δ (ppm): 3.72 (3H, s), 6.56 (1H, d, J=6.1 Hz), 6.88 (2H, d, J=8.7 Hz), 7.23 (2H, d, J=8.7 Hz), 7.37 (2H, d, J=8.7 Hz), 7.44 (1H, s), 7.60 (2H, d, J=8.7 Hz), 8.57 (1H, s), 8.67 (1H, d, J=6.1 Hz), 8.70 (1H, s), 8.82 (1H, s).

Example 88

Sodium 6-cyano-4-(4-((4-fluoroanilino)carbonyl)aminophenoxy)-7-quinolinolate 4-(4-Aminophenoxy)-7-(benzyloxy)-6-cyanoquinoline (7.776 g, 21.2 mmol) was dissolved in a toluene (400 ml) and acetonitrile (200 ml) mixed solvent, and then 4-fluorophenyl isocyanate (3.68 ml, 31.7 mmol) was added and the mixture was heated to reflux at 120° C. for 1 hour. The reaction solution was concentrated under reduced pressure, the residue was suspended in tetrahydrofuran (150 ml), and then hexane (150 ml) was added, sonication was performed, and the precipitated crystals were filtered out and dried under reduced pressure to obtain N-(4-(7-(benzyloxy)-6-cyano-4-quinolyl)oxyphenyl)-N'-(4-fluorophenyl)urea (9.81 g, 19.4 mmol, 91.9%) as light brown crystals. These were dissolved in trifluoroacetic acid (100 ml) and thioanisole (9.13 ml, 77.7 mmol) under a nitrogen atmosphere, and the solution was stirred at 60° C. for 12 hours. The reaction solution was concentrated under reduced pressure, and after adding tetrahydrofuran (50 ml) and then 1N aqueous sodium hydroxide (150 ml) and water (150 ml) to the residue, the mixture was stirred and the precipitated crystals were filtered out and washed with water, diethyl ether and ethyl acetate and dried at 70° C. to obtain the title compound (3.646 g, 8.36 mmol, 43.0%) as yellow crystals. negative ESI-MS 413 (M−Na)$^-$

Example 89

Sodium 6-cyano-4-(4-(2,4-difluoroanilino)carbonyl)amino-3-fluorophenoxy)-7-quinolinolate A mixture of the 7-benzyloxy compound (1.1 g) obtained in Example 81, trifluoroacetic acid (10 ml) and thioanisole (1 ml) was heated and stirred in an oil bath at 63-67° C. for 16 hours. After completion of the reaction, the reaction solution was concentrated, a saturated aqueous sodium bicarbonate solution was added, and the precipitated solid was filtered out.

The obtained solid was washed with water, ether and ethyl acetate and dried to obtain the title compound in a quantitative amount.

$^1$H-NMR (DMSO-$d_6$) δ (ppm): 6.54 (1H, d, J=5.6 Hz), 7.04-7.10 (1H, m), 7.14-7.17 (1H, m), 7.31-7.36 (1H, m), 7.40 (1H, dd, J=2.8 Hz, J=12 Hz), 7.44 (1H, s), 8.10-8.16 (1H, m), 8.27 (1H, t, J=8.8 HZ), 8.67 (1H, s), 8.68 (1H, d, J=5.2 Hz), 8.99-9.03 (1H, m), 9.07-9.11 (1H, m).

Example 90

N-(4-(6-Cyano-7-(2-chloroethoxy)-4-quinolyl)oxyphenyl)-N'-(4-fluorophenyl)urea

N-(4-(6-Cyano-7-hydroxy-4-quinolyl)oxyphenyl)-N'-(4-fluorophenyl)urea (400 mg, 0.9166 mmol) was dissolved in dimethylformamide (5.0 ml), and then 1-bromo-2-chloroethane (0.12 ml, 1.4479 mmol) and potassium carbonate (200 mg, 1.4479 mmol) were added and the mixture was heated and stirred at 55° C. for 4 hours. After cooling, tetrahydrofuran and ethyl acetate were added, the mixture was washed with saturated brine and dried over anhydrous magnesium sulfate, the solvent was distilled off under reduced pressure, and the residue was subjected to NH silica gel column chromatography (ethyl acetate-methanol system). The obtained crystals were suspended in diethyl ether, the suspension was diluted with hexane, and the crystals were filtered out, washed with hexane and dried by aspiration to obtain the title compound (331 mg, 0.6941 mmol, 75.72%) as light yellow crystals.

$^1$H-NMR Spectrum (DMSO-$d_6$) δ (ppm): 4.07 (2H, t, J=5.2 Hz), 4.59 (2H, t, J=5.2 Hz), 6.54 (1H, d, J=5.6 Hz), 7.12 (2H, t, J=9.0 Hz), 7.24 (2H, d, J=9.0 Hz), 7.44-7.48 (2H, m), 7.59 (2H, d, J=9.0 Hz), 7.65 (1H, s), 8.72 (1H, s), 8.73 (1H, d, J=5.6 Hz), 8.78 (1H, s), 8.82 (1H, s).

Example 91

N-(4-(6-Cyano-7-(2-chloroethoxy)-4-quinolyl)oxyphenyl)-N'-(4-methoxyphenyl)urea

The title compound (501 mg, 1.0247 mmol, 87.39%) was obtained as yellow crystals from N-(4-(6-cyano-7-hydroxy-4-quinolyl)oxyphenyl)-N'-(4-methoxyphenyl)urea (500 mg, 1.1725 mmol), in the same manner as Example 90.

$^1$H-NMR Spectrum (DMSO-$d_6$) δ (ppm): 3.70 (3H, s), 4.06 (2H, t, J=5.0 Hz), 4.59 (2H, t, J=5.0 Hz), 6.53 (1H, d, J=5.6 Hz), 6.86 (2H, d, J=9.2 Hz), 7.22 (2H, d, J=9.2 Hz), 7.35 (2H, d, J=9.2 Hz), 7.58 (2H, d, J=9.2 Hz), 7.65 (1H, s), 8.55 (1H, m), 8.73 (1H, d, J=5.6 Hz), 8.78 (1H, m), 8.88 (1H, s).

Example 92

N-(4-(6-Cyano-7-(2-chloroethoxy)-4-quinolyl)oxyphenyl)-N'-(2,4-difluorophenyl)urea The title compound (227 mg, 0.4426 mmol, 66.45%) was obtained as light yellow crystals from N-(4-(6-cyano-7-hydroxy-4-quinolyl)oxyphenyl)-N'-(2,4-difluorophenyl)urea (300 mg, 0.6661 mmol), in the same manner as Example 90.

$^1$H-NMR Spectrum (DMSO-$d_6$) δ (ppm): 4.07 (2H, t, J=5.0 Hz), 4.59 (2H, t, J=5.0 Hz), 6.64 (1H, d, J=5.4 Hz), 7.06 (1H, m), 7.16 (1H, m), 7.32 (1H, ddd, J=2.8 Hz, 8.8 Hz, 11.6 Hz), 7.41 (1H, dd, J=2.8 Hz, 11.6 Hz), 7.67 (1H, s), 7.93 (1H, s), 8.12 (1H, m), 8.27 (1H, dt, J=4.0 Hz, 9.2 Hz), 8.76 (1H, d, J=5.4 Hz), 8.77 (1H, s), 8.97-9.09 (1H, m).

Example 93

N-(4-(6-Cyano-7-(4-chlorobutoxy)-4-quinolyl)oxyphenyl)-N'-(4-methoxyphenyl)urea

N-(4-(6-Cyano-7-hydroxy-4-quinolyl)oxyphenyl)-N'-(4-methoxyphenyl)urea (200 mg), potassium carbonate (65 mg) and 1-bromo-4-chlorobutane (81 μl) were suspended in dimethylformamide (3 ml), and the suspension was heated and stirred for 1 hour and 50 minutes. The reaction solution was poured into saturated brine and extracted with ethyl acetate. After drying the organic layer over magnesium sulfate, it was passed through NH silica (Fuji Silysia Chemical) and washed in ethyl acetate, and the filtrate was concentrated. The obtained solid was washed with ether and dried to obtain 110 mg of the title compound.

$^1$H-NMR (DMSO-$d_6$) δ (ppm): 1.96-2.00 (4H, m), 3.72 (3H, s), 3.77-3.80 (2H, m), 4.33-4.37 (2H, m), 6.53 (1H, d, J=5.2 Hz), 6.88 (2H, d, J=8.8 Hz), 7.23 (2H, d, J=8.8 Hz), 7.38 (2H, d, J=8.8 Hz), 7.60 (2H, d, J=8.8 Hz), 7.62 (1H, s), 8.65 (1H, brs), 8.73 (1H, d, J=5.2 HZ), 8.77 (1H, s), 8.90 (1H, brs).

Example 94

N-(4-(6-Cyano-7-(3-chloropropoxy)-4-quinolyl)oxyphenyl)-N'-(4-methoxyphenyl)urea The title compound (310 mg) was obtained from N-(4-(6-cyano-7-hydroxy-4-quinolyl)oxyphenyl)-N'-(4-methoxyphenyl)urea (500 mg) and 1-chloro-3-iodopropane (188 μl), by the same procedure as in Example 93.

$^1$H-NMR (DMSO-$d_6$) δ (ppm): 2.28-2.35 (2H, m), 3.72 (3H, s), 3.86-3.90 (2H, m), 4.41-4.45 (2H, m), 6.54 (1H, d, J=5.2 Hz), 6.88 (2H, d, J=8.8 Hz), 7.24 (2H, d, J=8.8 Hz), 7.38 (2H, d, J=8.8 Hz), 7.61 (2H, d, J=8.8 Hz), 7.65 (1H, s), 8.66 (1H, brs), 8.74 (1H, d, J=5.2 HZ), 8.79 (1H, s), 8.91 (1H, brs).

Example 95

N-(4-(7-(Benzyloxy)-6-cyano-4-quinolyl)oxyphenyl)-N'-(3-(methylsulfonyl)phenyl)urea After dissolving 4-(4-aminophenoxy)-7-(benzyloxy)-6-cyanoquinoline (919 mg, 2.5 mmol) in dimethylsulfoxide (10 ml), phenyl N-(3-(methylsulfonyl)phenyl)carbamate (801 mg, 2.75 mmol) was added and the mixture was heated at 85° C. for 2 hours. The reaction solution was diluted with ethyl acetate and then washed with 1N aqueous sodium hydroxide (10 ml), water (20 ml×2) and saturated brine (10 ml) and dried over anhydrous sodium sulfate. After filtering off the drying agent, the filtrate was concentrated under reduced pressure and the residue was suspended in ethyl acetate (30 ml), after which hexane (30 ml) was added, sonication was performed and the precipitated crystals were filtered out and dried under reduced pressure to obtain the title compound (1.43 g, 2.5 mmol, quantitative) as light brown crystals.

$^1$H-NMR Spectrum (DMSO-$d_6$) δ (ppm): 3.18 (3H, s), 5.44 (2H, s), 6.53 (1H, d, J=5.2 Hz), 7.24 (2H, d, J=8.8 Hz), 7.37 (1H, d, J=8.0 Hz), 7.44 (2H, t, J=7.2 Hz), 7.45-7.69 (8H, m), 8.16 (1H, s), 8.71 (1H, d, J=5.2 Hz), 8.78 (1H, s), 9.12 (1H, s), 9.31 (1H, s).

Example 96

N-(4-(7-(Benzyloxy)-6-cyano-4-quinolyl)oxyphenyl)-N'-phenylurea

The title compound (1.126 g, 2.3 mmol, 92.5%) was obtained as light brown crystals from 4-(4-aminophenoxy)-7-(benzyloxy)-6-cyanoquinoline (919 mg, 2.5 mmol) and phenyl isocyanate (0.298 ml, 2.75 mmol), by the same procedure as in Example 10.

$^1$H-NMR Spectrum (DMSO-$d_6$) δ (ppm): 5.45 (2H, s), 6.53 (1H, dd, J=1.6, 5.2 Hz), 6.96 (1H, dd, J=6.0, 7.2 Hz), 7.23 (2H, d, J=7.6 Hz), 7.27 (2H, dd, J=7.2, 7.6 Hz), 7.37 (1H, d, J=7.2 Hz), 7.42-7.47 (4H, m), 7.54 (2H, d, J=8.0 Hz), 7.60 (2H, dd, J=1.2, 8.8 Hz), 7.70 (1H, s), 8.71 (1H, dd, J=1.6, 5.2 Hz), 8.78 (1H, d, J=1.2 Hz), 8.88 (1H, brs), 9.02 (1H, brs).

Example 97

N-(4-((6-Cyano-7-hydroxy-4-quinolyl)oxy)phenyl)-N'-(3-(methylsulfonyl)phenyl)urea After dissolving N-(4-(7-(benzyloxy)-6-cyano-4-quinolyl)oxyphenyl)-N'-(3-(methylsulfonyl)phenyl)urea (1.43 g, 2.5 mmol) in trifluoroacetic acid (10 ml) and thioanisole (1.17 ml, 10 mmol) under a nitrogen atmosphere, the solution was stirred at 65° C. for 19 hours. The reaction solution was concentrated under reduced pressure, and after adding 5% aqueous sodium bicarbonate (30 ml) and ethyl acetate (50 ml) to the obtained residue and stirring, the precipitated crystals were filtered out, washed with water and ethyl acetate and dried under reduced pressure. The organic layer of the filtrate was separated, washed with saturated brine and dried over anhydrous sodium sulfate, and then concentrated under reduced pressure to obtain a yellow crystalline residue. This was combined with the previous crystals, suspended in ethyl acetate (40 ml) and subjected to sonication, and then the crystals were filtered out, washed with diethyl ether and dried at 60° C. to obtain the title compound (862 mg, 1.8 mmol, 72.7%) as yellow crystals.

$^1$H-NMR Spectrum (DMSO-$d_6$) δ (ppm): 3.18 (3H, s), 6.43 (1H, d, J=5.2 Hz), 7.22-7.25 (3H, m), 7.43 (1H, s), 7.48-7.68 (5H, m), 8.16 (1H, s), 8.63 (1H, d, J=5.2 Hz), 8.67 (1H, s), 9.36 (1H, s), 9.55 (1H, s).

Example 98

Sodium 4-(4-((anilinocarbonyl)amino)phenoxy)-6-cyano-7-quinolinolate

The title compound (811 mg, 1.94 mmol, 83.8%) was obtained as yellow crystals from N-(4-(7-(benzyloxy)-6-cyano-4-quinolyl)oxyphenyl-N'-phenylurea (1.126 g, 2.31 mmol), by the same procedure as in Example 87.

$^1$H-NMR Spectrum (DMSO-$d_6$) δ (ppm): 6.26 (1H, d, J=5.2 HZ), 6.96 (1H, m), 7.18-7.29 (5H, m), 7.45 (2H, d, J=8.4 Hz), 7.57 (2H, d, J=8.0 Hz), 8.50-8.51 (2H, m), 8.74 (1H, s), 8.86 (1H, s).

Example 99

N-(4-(6-Cyano-7-(2-methoxyethoxy)-4-quinolyl)oxy-2-fluorophenyl)-N'-phenylurea

The title compound was obtained from 4-(4-amino-3-fluorophenoxy)-6-cyano-7-(2-methoxyethoxy)quinoline and phenyl isocyanate, in the same manner as Example 10.

$^1$H-NMR (DMSO-$d_6$) δ (ppm): 3.38 (3H, s), 3.78-3.81 (2H, m), 4.42-4.45 (2H, m), 6.64 (1H, d, J=5.2 Hz), 7.00 (1H, t, J=7.2 Hz), 7.15-7.19 (1H, m), 7.31 (2H, t, J=7.2 Hz), 7.42 (1H, dd, J=2.8 Hz, J=12 Hz), 7.48 (2H, d, J=7.2 Hz), 7.66 (1H, s), 8.28 (1H, t, J=8.8 HZ), 8.72 (1H, brs), 8.76 (1H, d, J=5.2 Hz), 8.78 (1H, s), 9.15 (1H, brs).

Example 100

N-(4-(6-Cyano-7-(2-methoxyethoxy)-4-quinolyl)oxy-2-fluorophenyl)-N'-(4-fluorophenyl)urea The title compound was obtained from 4-(4-amino-3-fluorophenoxy)-6-cyano-7-(2-methoxyethoxy)quinoline and 4-fluoro phenyl isocyanate, in the same manner as Example 10.

$^1$H-NMR (DMSO-$d_6$) δ (ppm): 3.38 (3H, s), 3.78-3.81 (2H, m), 4.42-4.45 (2H, m), 6.64 (1H, d, J=5.2 Hz), 7.12-7.18 (3H, m), 7.42 (1H, dd, J=2.8 Hz, J=12 Hz), 7.46-7.51 (2H, m), 7.65 (1H, s), 8.25 (1H, t, J=9.2 Hz), 8.71 (1H, brs), 8.76 (1H, d, J=5.2 HZ), 8.77 (1H, s), 9.18 (1H, brs).

Example 101

N-(1H-Benzo[d]imidazol-6-yl)-N'-(4-(6-cyano-7-(2-methoxyethoxy)-4-quinolyl)oxyphenyl)urea (Example 101-A)

N-(1H-Benzo[d]imidazol-5-yl)-N'-(4-(6-cyano-7-(2-methoxyethoxy)-4-quinolyl)oxyphenyl)urea (Example 101-B)

A mixture of the title compounds (Example 101-A) and (Example 101-B) (77.5 mg, 0.157 mmol, 71.4%) was obtained as white crystals from phenyl N-(4-(6-cyano-7-(2-methoxyethoxy)-4-quinolyl)oxyphenyl)carbamate (100 mg, 0.220 mmol), by the same procedure as in Example 11.

The mixture of (Example 101-A) and (Example 101-B)
$^1$H-NMR Spectrum (DMSO-$d_6$) δ (ppm): 3.36 (3H, s), 3.76-3.79 (2H, m), 4.40-4.43 (2H, m), 6.53 (1H, d, J=5.6 Hz), 6.99-7.62 (6H, m), 7.82 (2/5H, s), 7.91 (3/5H, s), 8.08 (3/5H, s), 8.13 (2/5H, s), 8.59-8.79 (5H, m), 12.26 (3/5H, s), 12.29 (2/5H, s).

Example 102

N-(4-(6-Cyano-7-(2-methoxyethoxy)-4-quinolyl)oxyphenyl)-N'-(2-oxo-2,3-dihydro-1H-benzo[d]imidazol-5-yl)urea The title compound (104.2 mg, 0.204 mmol, 93.0%) was obtained as white crystals from phenyl N-(4-(6-cyano-7-(2-methoxyethoxy)-4-quinolyl)oxyphenyl)carbamate (100 mg, 0.220 mmol), by the same procedure as in Example 11.

$^1$H-NMR Spectrum (DMSO-$d_6$) δ (ppm): 3.36 (3H, s), 3.76-3.79 (2H, m), 4.40-4.43 (2H, m), 6.52 (1H, d, J=5.2 Hz), 6.81 (2H, s), 7.22 (2H, d, J=8.0 Hz), 7.31 (1H, s), 7.58 (2H, d, J=8.0 Hz), 7.62 (1H, s), 8.53 (1H, s), 8.71-8.76 (3H, m), 10.41 (1H, s), 10.50 (1H, s).

Example 103

N-(4-(6-Cyano-7-(2-methoxyethoxy)-4-quinolyl)oxyphenyl)-N'-(2-oxo-2,3-dihydro-1,3-benzoxazol-5-yl)urea The title compound (101 mg, 0.197 mmol, 89.9%) was obtained as gray crystals from phenyl N-(4-(6-cyano-7-(2- methoxyethoxy)-4-quinolyl)oxyphenyl)carbamate (100 mg, 0.220 mmol), by the same procedure as in Example 11.

¹H-NMR Spectrum (DMSO-d₆) δ (ppm): 3.37 (3H, s), 3.76-3.39 (2H, m), 4.40-4.43 (2H, m), 6.52 (1H, d, J=5.2 Hz), 6.91 (1H, dd, J=2.0, 8.8 Hz), 7.17 (1H, d, J=8.4 Hz), 7.24 (2H, d, J=8.8 Hz), 7.48 (1H, s), 7.59 (2H, d, J=8.8 Hz), 7.62 (1H, s), 8.71-8.77 (3H, m), 8.81 (1H, s), 11.53 (1H, s).

Example 104

N-(4-(6-Cyano-7-(2-methoxyethoxy)-4-quinolyl)oxyphenyl)-N'-(2-oxo-2,3-dihydro-1,3-benzoxazol-6-yl)urea The title compound (111 mg, 0.217 mmol, 98.8%) was obtained as gray crystals from phenyl N-(4-(6-cyano-7-(2-methoxyethoxy)-4-quinolyl)oxyphenyl)carbamate (100 mg, 0.220 mmol), by the same procedure as in Example 11.

¹H-NMR Spectrum (DMSO-d₆) δ (ppm): 3.37 (3H, s), 3.76-3.79 (2H, m), 4.40-4.43 (2H, m), 6.52 (1H, d, J=5.2 Hz), 6.99 (1H, d, J=8.4 Hz), 7.07 (1H, dd, J=2.0, 8.4 Hz), 7.24 (2H, d, J=8.8 Hz), 7.56-7.63 (4H, m), 8.72 (1H, d, J=5.2 Hz), 8.74 (1H, s), 8.76 (1H, s), 8.82 (1H, s), 11.46 (1H, s).

Example 105

N-(4-(6-Cyano-7-(2-methoxyethoxy)-4-quinolyl)oxyphenyl)-N'-(2-oxo-2,3-dihydro-1H-5-indolyl)urea The title compound (69 mg, 0.135 mmol, 61.7%) was obtained as gray crystals from phenyl N-(4-(6-cyano-7-(2-methoxyethoxy)-4-quinolyl)oxyphenyl)carbamate (100 mg, 0.220 mmol), by the same procedure as in Example 11.

¹H-NMR Spectrum (DMSO-d₆) δ (ppm): 3.36 (3H, s), 3.45 (2H, s), 3.76-3.79 (2H, s), 4.40-4.43 (2H, m), 6.51 (1H, d, J=5.2 Hz), 6.72 (1H, d, J=8.4 Hz), 7.17 (1H, dd, J=2.0, 8.4 Hz), 7.22 (2H, d, J=8.8 Hz), 7.37 (1H, s), 7.58 (2H, d, J=8.8 Hz), 7.62 (1H, s), 8.49 (1H, s), 8.71 (1H, d, J=5.2 Hz), 8.74 (1H, s), 8.75 (1H, s), 10.23 (1H, s).

Example 106

N-(4-(6-Cyano-7-(3-hydroxypropoxy)-4-quinolyl)oxyphenyl-N'-(4-fluorophenyl)urea

The title compound (64 mg, 0.135 mmol, 54.2%) was obtained as light yellow crystals from sodium 6-cyano-4-(4-((4-fluoroanilino)carbonyl)aminophenoxy)-7-quinolinolate (109 mg, 0.250 mmol), by the same procedure as in Example 7.

¹H-NMR Spectrum (DMSO-d₆) δ (ppm): 1.97 (2H, t, J=6.0 Hz), 3.63 (2H, m), 4.34 (2H, t, J=6.0 Hz), 4.63 (1H, t, J=5.2 Hz), 6.51 (1H, d, J=5.2 Hz), 7.11 (2H, t, J=8.8 Hz), 7.23 (2H, d, J=8.8 Hz), 7.44-7.47 (2H, m), 7.57-7.60 (3H, m), 8.70-8.75 (3H, m), 8.82 (1H, s).

Example 107

N-(4-(6-Cyano-7-(3-(methylsulfanyl)propoxy)-4-quinolyloxy)phenyl)-N'-(4-fluorophenyl)urea The title compound (37 mg, 0.074 mmol, 29.5%) was obtained as light brown crystals from sodium 6-cyano-4-(4-((4-fluoroanilino)carbonyl)aminophenoxy)-7-quinolinolate (109 mg, 0.250 mmol), by the same procedure as in Example 7.

¹H-NMR Spectrum (DMSO-d₆) δ (ppm): 2.08-2.12 (5H, m), 2.69 (2H, t, J=7.2 Hz), 4.36 (2H, t, J=6.0 Hz), 6.52 (1H, d, J=5.2 Hz), 7.11 (2H, t, J=8.8 Hz), 7.23 (2H, d, J=8.8 Hz), 7.44-7.48 (2H, m), 7.57-7.60 (3H, m), 8.71-8.76 (3H, m), 8.82 (1H, s).

Example 108

N-(4-(6-Cyano-7-(3-(methylsulfonyl)propoxy)-4-quinolyloxy)phenyl)-N'-(4-fluorophenyl)urea The title compound (70 mg, 0.131 mmol, 52.4%) was obtained as light brown crystals from sodium 6-cyano-4-(4-((4-fluoroanilino)carbonyl)aminophenoxy)-7-quinolinolate (109 mg, 0.250 mmol), by the same procedure as in Example 7.

¹H-NMR Spectrum (DMSO-d₆) δ (ppm): 2.27 (2H, m), 3.04 (3H, s), 3.21-3.37 (2H, m), 4.41 (2H, t, J=6.4 Hz), 6.53 (1H, d, J=5.2 Hz), 7.11 (2H, t, J=8.8 Hz), 7.23 (2H, d, J=8.8 Hz), 7.44-7.48 (2H, m), 7.57-7.61 (3H, m), 8.71-8.73 (2H, m), 8.77 (1H, s), 8.82 (1H, s).

Example 109

N-(4-(6-Cyano-7-(3-(2-oxotetrahydro-1H-1-pyrrolyl)propoxy)-4-quinolyloxy)phenyl)-N'-(4-fluorophenyl)urea The title compound (11.2 mg, 0.021 mmol, 8.3%) was obtained as light yellow crystals from sodium 6-cyano-4-(4-((4-fluoroanilino)carbonyl)aminophenoxy)-7-quinolinolate (109 mg, 0.250 mmol), by the same procedure as in Example 7.

¹H-NMR Spectrum (DMSO-d₆) δ (ppm): 1.93 (2H, m), 2.03 (2H, t, J=6.0 Hz), 2.19 (2H, t, J=8.0 Hz), 3.37-3.42 (4H, m), 4.27 (2H, t, J=6.0 Hz), 6.51 (1H, d, J=5.2 Hz), 7.11 (2H, t, J=8.8 Hz), 7.23 (2H, d, J=8.8 Hz), 7.44-7.48 (2H, m), 7.55 (1H, s), 7.58 (2H, d, J=8.8 Hz), 8.70-8.73 (2H, m), 8.75 (1H, s), 8.82 (1H, s).

Example 110

N-(4-(6-Cyano-7-(3-(1,3-dioxo-2,3-dihydro-1H-2-isoindolyl)propoxy)-4-quinolyloxy)phenyl)-N'-(4-fluorophenyl)urea The title compound (416 mg, 0.692 mmol, 69.2%) was obtained as light yellow crystals from sodium 6-cyano-4-(4-((4-fluoroanilino)carbonyl)aminophenoxy)-7-quinolinolate (436 mg, 1.00 mmol), by the same procedure as in Example 7.

¹H-NMR Spectrum (DMSO-d₆) δ (ppm): 2.17 (2H, t, J=5.6 Hz), 3.84 (2H, t, J=6.4 Hz), 4.32 (2H, t, J=6.0 Hz), 6.51 (1H, d, J=5.2 Hz), 7.11 (2H, t, J=8.8 Hz), 7.23 (2H, d, J=9.2 Hz), 7.44-7.48 (2H, m), 7.52 (1H, s), 7.58 (2H, d, J=8.8 Hz), 7.78-7.84 (4H, m), 8.69-8.73 (3H, m), 8.82 (1H, s).

Example 111

N-(3-(6-Cyano-4-(3-fluoro-4-((4-fluoroanilino)carbonyl)aminophenoxy)-7-quinolyl)oxypropyl)methanesulfonamide The title compound (73 mg, 0.129 mmol, 51.3%) was obtained as light brown crystals from sodium 6-cyano-4-(3-fluoro-4-((4-fluoroanilino)carbonyl)aminophenoxy)-7-quinolinolate (114 mg, 0.25 mmol), by the same procedure as in Example 7.

¹H-NMR Spectrum (DMSO-d₆) δ (ppm): 2.02 (2H, t, J=6.4 Hz), 2.91 (3H, s), 3.20 (2H, q, J=6.4 Hz), 4.34 (2H, t, J=6.4 Hz), 6.62 (1H, d, J=5.2 Hz), 7.12-7.38 (4H, m), 7.40 (1H, dd, J=2.8, 11.6 Hz), 7.44-7.48 (2H, m), 7.61 (1H, s), 8.24 (1H, t, J=9.2 Hz), 8.62 (1H, d, J=2.0 Hz), 8.74 (1H, s), 8.75 (1H, s), 9.09 (1H, s).

Example 112

4-(4-((4-Fluoroanilino)carbonyl)aminophenoxy)-7-(2-methoxyethoxy)-6-quinolinecarboxamide The N-(4-(6-cyano-7-(2-methoxyethoxy)-4-quinolyl)oxyphenyl)-N'-(4-fluorophenyl)urea (360 mg, 0.762 mmol) obtained in Example 10 was dissolved in dimethylsulfoxide (4.5 ml), and then 5N aqueous sodium hydroxide (1.5 ml) was added and the mixture was heated at 80° C. while stirring for 60 minutes. The reaction solution was cooled in an ice water bath, 2N hydrochloric acid (3.75 ml) was added for neutralization, and then the mixture was diluted with water (21 ml) and the precipitated crude crystals were filtered out. These were suspended in ethanol (20 ml) and subjected to sonication, and upon filtering out the crystals they were dried under reduced pressure to obtain the title compound (214 mg, 0.436 mmol, 57.3%) as gray crystals.

¹H-NMR Spectrum (DMSO-d₆) δ (ppm): 3.34 (3H, s), 3.78-3.81 (2H, m), 4.38-4.41 (2H, m), 6.46 (1H, d, J=5.6 Hz), 7.11 (2H, d, J=8.8 Hz), 7.23 (2H, d, J=8.4 Hz), 7.46 (2H, m), 7.54 (1H, s), 7.58 (2H, d, J=8.8 Hz), 7.80 (1H, s), 7.82 (1H, s), 8.64 (1H, d, J=5.6 Hz), 8.75 (1H, s), 8.78 (1H, s), 8.83 (1H, s).

Example 113

7-(2-Methoxyethoxy)-4-(4-((1,3-thiazol-2-ylamino)carbonyl)aminophenoxy)-6-quinolinecarboxamide The title compound (181 mg, 0.377 mmol, 42.6%) was obtained as gray crystals from the N-(4-(6-cyano-7-(2-methoxyethoxy)-4-quinolyl)oxyphenyl)-N'-(1,3-thiazol-2-yl)urea (409 mg, 0.886 mmol) obtained in Example 12, by the same procedure as in Example 112.

¹H-NMR Spectrum (DMSO-d₆) δ (ppm): 3.35 (3H, s), 3.78-3.81 (2H, m), 4.39-4.42 (2H, m), 6.47 (1H, d, J=5.2 Hz), 7.11 (1H, brs), 7.26 (2H, d, J=8.8 Hz), 7.37 (1H, d, J=3.2 Hz), 7.55 (1H, s), 7.62 (2H, d, J=8.8 Hz), 7.80 (1H, s), 7.82 (1H, s), 8.65 (1H, d, J=5.2 Hz), 8.78 (1H, s), 9.10 (1H, s).

Example 114

4-4-((Anilinocarbonyl)amino)-3-fluorophenoxy-7-(2-methoxyethoxy)-6-quinolinecarboxamide The title compound (21 mg, 0.043 mmol, 19.1%) was obtained as brown crystals from the N-(4-(6-cyano-7-(2-methoxyethoxy)-4-quinolyl)oxy-2-fluorophenyl)-N'-phenylurea (106 mg, 0.224 mmol) obtained in Example 99, by the same procedure as in Example 112. ¹H-NMR Spectrum (DMSO-d₆) δ (ppm): 3.35 (3H, s), 3.78-3.81 (2H, m), 4.39-4.42 (2H, m), 6.55 (1H, d, J=5.2 Hz), 6.98 (1H, t, J=7.6 Hz), 7.13 (1H, d, J=8.4 Hz), 7.29 (2H, t, J=7.6 Hz), 7.39 (1H, dd, J=2.4, 12.0 Hz), 7.45 (2H, d, J=8.4 Hz), 7.56 (1H, s), 7.82 (2H, brs), 8.25 (1H, m), 8.63 (1H, s), 8.67 (1H, d, J=5.2 Hz), 8.76 (1H, s), 9.06 (1H, s).

Example 115

4-(4-((4-Fluoroanilino)carbonyl)aminophenoxy)-7-methoxy-6-quinolinecarboxamide

The title compound (201 mg, 0.450 mmol, 49.2%) was obtained as gray crystals from the N-(4-(6-cyano-7-methoxy-4-quinolyl)oxyphenyl)-N'-(4-fluorophenyl)urea (391 mg, 0.913 mmol) obtained in Example 39, by the same procedure as in Example 112.

¹H-NMR Spectrum (DMSO-d₆) δ (ppm): 4.02 (3H, s), 6.53 (1H, d, J=5.2 Hz), 7.11 (2H, t, J=8.8 Hz), 7.24 (2H, d, J=8.8 Hz), 7.44-7.48 (2H, m), 7.51 (1H, s), 7.59 (2H, d, J=8.8 Hz), 7.75 (1H, s), 7.87 (1H, s), 8.68-8.70 (2H, m), 8.85 (1H, s), 8.95 (1H, s).

Example 116

4-(4-((Cyclopropylamino)carbonyl)aminophenoxy)-7-(2-methoxyethoxy)-6-quinolinecarboxamide The title compound (71 mg, 0.163 mmol, 45.4%) was obtained as light brown crystals from the N-(6-cyano-7-(2-methoxyethoxy)-4-quinolyl)oxyphenyl)-N'-cyclopropylurea (150 mg, 0.358 mmol) obtained in Example 23, by the same procedure as in Example 112.

¹H-NMR Spectrum (DMSO-d₆) δ (ppm): 0.40-0.44 (2H, m), 0.62-0.66 (2H, m), 2.43-2.48 (1H, m), 3.36 (3H, s), 3.80-3.83 (2H, m), 4.40-4.43 (2H, m), 6.43-6.46 (2H, m), 7.18 (2H, d, J=8.8 Hz), 7.53-7.67 (3H, m), 7.81 (1H, s), 7.83 (1H, s), 8.46 (1H, s), 8.65 (1H, d, J=5.6 Hz), 8.79 (1H, s).

Example 117

N-4-((6-Cyano-7-methoxy-4-quinolyl)oxy)phenyl)-N'-(1,3-thiazol-2-yl)urea

The title compound (390 mg, 0.934 mmol, 93.4%) was obtained as white crystals from 4-(4-aminophenoxy)-6-cyano-7-methoxyquinoline (291 mg, 1.0 mmol) and 2-phenoxycarbamoylamino-1,3-thiazole (264 mg, 1.2 mmol), by the same procedure as in Example 36.

¹H-NMR Spectrum (DMSO-d₆) δ (ppm): 4.05 (3H, s), 6.52 (1H, d, J=5.2 Hz), 7.11 (1H, br), 7.27 (2H, d, J=8.8 Hz), 7.37 (1H, d, J=3.2 Hz), 7.59 (1H, s), 7.62 (2H, d, J=8.8 Hz), 8.72 (1H, d, J=5.2 Hz), 8.77 (1H, s), 9.12 (1H, s).

Example 118

7-Methoxy-4-(4-((1,3-thiazol-2-ylamino)carbonyl)aminophenoxy)-6-quinolinecarboxamide The title compound (195 mg, 0.448 mmol, 52.8%) was obtained as gray crystals from the N-4-((6-cyano-7-methoxy-4-quinolyl)oxy)phenyl-N'-(1,3-thiazol-2-yl)urea (354 mg, 0.848 mmol) obtained in Example 117, by the same procedure as in Example 112.

¹H-NMR Spectrum (DMSO-d₆) δ (ppm): 4.02 (3H, s), 6.47 (1H, d, J=5.2 Hz), 7.10 (1H, br), 7.25 (2H, d, J=8.8 Hz), 7.36 (1H, d, J=3.6 Hz), 7.50 (1H, s), 7.62 (2H, d, J=8.8 Hz), 7.73 (1H, s), 7.85 (1H, s), 8.64 (1H, d, J=5.2 Hz), 8.67 (1H, s), 9.45 (1H, s).

Example 119

4-(4-((2,4-Difluoroanilino)carbonyl)amino-3-fluorophenoxy)-7-methoxy-6-quinolinecarboxamide The title compound (36 mg, 0.448 mmol, 29.4%) was obtained as light pink crystals from the N-(4-(6-cyano-7- methoxy-4-quinolyl)oxy-2-fluorophenyl)-N'-(2,4-difluorophenyl)urea (118 mg, 0.254 mmol) obtained in Example 61, by the same procedure as in Example 112.

$^1$H-NMR Spectrum (DMSO-d$_6$) δ (ppm): 4.02 (3H, s), 6.56 (1H, d, J=5.2 Hz), 7.06 (1H, m), 7.12 (1H, m), 7.33 (1H, m), 7.39 (1H, dd, J=2.8, 11.6 Hz), 7.51 (1H, s), 7.73 (1H, s), 7.84 (1H, s), 8.11 (1H, m), 8.25 (1H, t, J=9.2 Hz), 8.65 (1H, s), 8.66 (1H, d, J=5.2 Hz), 8.99 (1H, s), 9.06 (1H, s).

Example 120

N-4-((6-Cyano-7-methoxy-4-quinolyl)oxy)phenyl-N'-cyclopropylurea

The title compound (293 mg, 0.783 mmol, 59.8%) was obtained as white crystals from 4-(4-aminophenoxy)-6-cyano-7-methoxyquinoline (381 mg, 1.308 mmol), by the same procedure as in Example 36.

$^1$H-NMR Spectrum (DMSO-d$_6$) δ (ppm): 0.40-0.44 (2H, m), 0.62-0.67 (2H, m), 2.53-2.58 (1H, m), 4.07 (3H, m), 6.44 (1H, d, J=2.0 Hz), 6.51 (1H, d, J=5.6 Hz), 7.19 (2H, d, J=8.8 Hz), 7.56 (2H, d, J=8.8 Hz), 7.60 (1H, s), 8.48 (1H, s), 8.73 (1H, d, J=5.6 Hz), 8.77 (1H, s).

Example 121

4-(4-(((Cyclopropylamino)carbonyl)aminophenoxy)-7-methoxy-6-quinolinecarboxamide The title compound (79 mg, 0.201 mmol, 26.9%) was obtained as gray crystals from the N-4-((6-cyano-7-methoxy-4-quinolyl)oxy)phenyl-N'-cyclopropylurea (279 mg, 0.745 mmol) obtained in Example 120, by the same procedure as in Example 112.

$^1$H-NMR Spectrum (DMSO-d$_6$) δ (ppm): 0.40-0.43 (2H, m), 0.62-0.64 (2H, m), 2.42-2.45 (1H, m), 4.02 (3H, s), 6.42-6.44 (2H, m), 7.16 (2H, d, J=8.0 Hz), 7.49 (1H, s), 7.53 (2H, d, J=8.0 Hz), 7.72 (1H, s), 7.84 (1H, s), 8.45 (1H, s), 8.63 (1H, d, J=5.6 Hz), 8.67 (1H, s).

Example 122

N-(4-(5,6-Dimethyl-4-7H-pyrrolo[2,3-d]pyrimidyl)oxyphenyl)-N'-(4-fluorophenyl)urea 4-(4-Aminophenoxy)-5,6-dimethyl-7H-pyrrolo[2,3-d]-pyrimidine was dissolved in toluene (16 mg) (0.8 ml) and acetonitrile (0.5 ml) under reflux, and then 4-fluorophenylisocyanate (7.9 μM) was added. The mixture was stirred for 1 hour and returned to room temperature, and then the reaction system was concentrated, diethyl ether was added to the residue, and the resulting crystals were filtered out. The crystals were washed with diethyl ether to obtain the title compound (5 mg).

MS m/z 392 (M+H)

$^1$H-NMR (DMSO-d$_6$) δ (ppm): 2.29 (3H, s), 2.31 (3H, s), 7.00-7.16 (4H, m), 7.38-7.50 (4H, m), 8.10 (1H, s), 8.50 (2H, s), 11.75 (1H, s)

The intermediates were synthesized in the following manner.

Production Example 122-1

4-(Nitrophenoxy)-5,6-dimethyl-7H-pyrrolo[2,3-d]-pyrimidine

After adding para-nitrophenol (121 mg), potassium carbonate (133 mg) and dimethylformamide (1 ml) to the 4-chloro-5,6-7H-pyrrolo[2,3-d]-pyrimidine (88 mg) described in Journal of Medicinal Chemistry, 1996, Vol. 39, No. 12, 2285-2292, the mixture was stirred at 135-140° C. for 72 hours. This was returned to room temperature, water was added, extraction was performed with a tetrahydrofuran and ethyl acetate mixed solution, and then the organic layer was washed with saturated brine, dried over anhydrous sodium sulfate and concentrated to dryness. The obtained crystals were washed with diethyl ether to obtain the title compound (90 mg).

MS m/z 285 (M+H)

$^1$H-NMR (DMSO-d$_6$) δ (ppm): 2.28 (3H, s), 2.32 (3H, s), 7.50 (2H, d, J=9.5 Hz), 8.20 (1H, s), 8.30 (2H, d, J=9.5 Hz), 11.98 (1H, s)

Production Example 122-2

4-(Aminophenoxy)-5,6-dimethyl-7H-pyrrolo[2,3-d]-pyrimidine

After adding iron powder (0.1 g), ammonium chloride (0.2 g), ethanol (4 ml) and water (1 ml) to the 4-(nitrophenoxy)-5,6-dimethyl-7H-pyrrolo[2,3-d]-pyrimidine (80 mg) synthesized by the intermediate synthesis method described above, the mixture was stirred at 75-82° C. for 1.5 hours. After returning the reaction system to room temperature and adding tetrahydrofuran (3 ml) and ethyl acetate (3 ml), the mixture was filtered with celite, the filtrate was subjected to liquid separation, and the organic layer was washed with water and saturated brine in that order, dried over sodium sulfate, concentrated to dryness under reduced pressure and washed with diethyl ether to obtain the title compound (22 mg).

MS m/z 255 (M+H)

$^1$H-NMR (DMSO-d$_6$) δ (ppm): 2.27 (3H, s), 2.29 (3H, s), 4.90-5.00 (2H, m), 6.52-6.88 (4H, m), 8.06 (1H, s), 11.66 (1H, s)

Example 123

4-(4-(3,4-Dihydroquinazolin-2-one-3-yl)phenyloxy)-6,7-dimethoxyquinoline 6,7-Dimethoxy-4-(4-(2-aminophenyl)methylaminophenyloxy)quinoline (40 mg, 0.0996 mmol) was dissolved in dimethylformamide (0.5 ml), 1,1'-carbonyldiimidazole (19 mg, 0.1196 mmol) was added, and the mixture was stirred at 70° C. for 8 hours. After cooling to room temperature, the reaction solution was diluted with tetrahydrofuran, water was added, and the mixture was extracted with ethyl acetate, washed with saturated brine and dried over anhydrous magnesium sulfate, after which the solvent was distilled off under reduced pressure. The residue was purified with a silica gel column (ethyl acetate-methanol system) and recrystallized with hexane-diethyl ether to obtain the title compound (3 mg, 0.0070 mmol, 7.05%) as colorless crystals.

$^1$H-NMR (CDCl$_3$) δ (ppm): 4.06 (6H, s), 4.89 (2H, s), 6.57 (1H, d, J=5.2 Hz), 6.77 (1H, d, J=7.6 Hz), 6.87 (1H, brs), 7.03 (1H, t, J=7.6 Hz), 7.14 (1H, d, J=7.6 Hz), 7.23 (3H, m, covered by CDCl$_3$), 7.44 (1H, s), 7.48 (2H, d, J=8.8 Hz), 7.55 (1H, s), 8.52 (1H, d, J=5.2 Hz).

The intermediates were synthesized in the following manner.

Production Example 123-1

6,7-Dimethoxy-4-(4-(2-nitrophenylmethylimino)phenyloxy)quinoline 6,7-Dimethoxy-4-(4-aminophenyloxy)quinoline (500 mg, 1.6873 mmol) was dissolved in tetrahydrofuran (64 ml), and after adding 2-nitrobenzaldehyde (320 mg, 2.1091 mmol) and acetic acid (0.58 ml), sodium triacetoxyborohydride (720 mg, 3.3746 mmol) was further added and the mixture was stirred at room temperature for 11 hours and 30 minutes. Water and saturated sodium bicarbonate were added, the mixture was extracted with ethyl acetate, washed with saturated brine and dried over anhydrous magnesium sulfate, and the solvent was distilled off under reduced pressure. The obtained crystals were washed with hexane-diethyl ether, filtered out, washed with hexane and dried by aspiration at room temperature to obtain the title compound (453 mg) as light yellow crystals.

$^1$H-NMR (CDCl$_3$) δ (ppm): 4.06 (6H, s), 6.54 (1H, d, J=5.2 Hz), 7.25 (2H, d, J=8.4 Hz), 7.40 (2H, d, J=8.4 Hz), 7.44 (1H, s), 7.57 (1H, s), 7.65 (1H, dd, J=7.6, 8.0 Hz), 7.77 (1H, dd, J=7.6, 7.6 Hz), 8.10 (1H, d, J=8.0 Hz), 8.33 (1H, d, J=7.6 Hz), 8.51 (1H, d, J=5.2 Hz), 9.01 (1H, s).

Production Example 123-2

6,7-Dimethoxy-4-(4-(2-nitrophenylmethylamino) phenyloxy)quinoline

After adding tetrahydrofuran (2 ml), ethanol (2 ml) and chloroform (1 ml) to 6,7-dimethoxy-4-(4-(2-nitrophenylmethyl-imino)phenyloxy)quinoline (200 mg, 0.4657 mmol) and heating the mixture to complete dissolution, sodium borohydride (35 mg, 0.9314 mmol) was added and the mixture was heated to reflux for 1 hour and 30 minutes. After cooling to room temperature, water was added, the mixture was extracted with ethyl acetate, washed with saturated brine and dried over anhydrous magnesium sulfate, and the solvent was distilled off under reduced pressure. The residue was purified with an NH silica gel column (hexane-ethyl acetate system) to obtain the title compound (151 mg, 0.3500 mmol, 75.15%) as a yellow oil.

$^1$H-NMR (CDCl$_3$) δ (ppm): 4.04 (6H, s), 4.46 (1H, brs), 4.76 (2H, d, J=4.8 Hz), 6.42 (1H, d, J=5.2 Hz), 7.64 (2H, d, J=8.8 Hz), 6.99 (2H, d, J=8.8 Hz), 7.40 (1H, s), 7.47 (1H, dd, J=7.2, 7.2 Hz), 7.57 (1H, s), 7.62 (1H, dd, J=7.2, 7.6 Hz), 7.71 (1H, d, J=7.6 Hz), 8.10 (1H, d, J=7.2 Hz), 8.45 (1H, d, J=5.2 Hz).

Production Example 123-3

6,7-Dimethoxy-4-(4-(2-aminophenylmethylamino) phenyloxy)quinoline 6,7-Dimethoxy-4-(4-(2-nitrophenylmethylamino)phenyloxy)quinoline (150 mg, 0.35 mmol) was dissolved in ethanol (2.8 ml) and water (0.7 ml), and then iron powder (78 mg, 1.4 mmol) and ammonium chloride (150 mg, 2.8 mmol) were added and the mixture was heated to reflux for 1 hour. After cooling to room temperature, the reaction solution was diluted with tetrahydrofuran and water, and the insoluble portion was filtered off. The filtrate was distilled off under reduced pressure, and then the residue was purified with a silica gel column (ethyl acetate system), the obtained amorphous substance was solidified with hexane and ethyl acetate, and the obtained crystals were washed with hexane-ethyl acetate, filtered out, washed with hexane and dried by aspiration at room temperature to obtain the title compound (80 mg, 0.1993 mmol, 56.93%) as milky white crystals.

$^1$H-NMR (CDCl$_3$) δ (ppm): 3.78 (1H, brs), 4.05 (3H, s), 4.06 (3H, s), 4.15 (2H, brs), 4.26 (2H, s), 6.44 (1H, d, J=5.2 Hz), 6.74-6.81 (4H, m), 7.06 (2H, d, J=8.8 Hz), 7.16-7.22 (2H, m), 7.42 (1H, s), 7.60 (1H, s), 8.46 (1H, d, J=5.2 Hz).

Example 124

N-(4-(2-Phenylpyridin-4-yl)oxyphenyl)-N'-(4-fluorophenyl)urea 4-(2-Phenylpyridin-4-yl)oxyaniline (110 mg, 0.42 mM) was added to ethyl acetate (10 ml), and then parafluorophenyl isocyanate (0.56 ml, 4.9 mM) was added while stirring, which was continued for 30 minutes. After adding n-hexane (20 ml) to the reaction solution, the solvent was partially distilled off under reduced pressure and the precipitating solid was filtered out to obtain the target substance (98 mg) as a gray solid.

$^1$H-NMR (DMSO-d$_6$) δ (ppm): 6.81 (1H, dd, J=5.6 Hz, J=2.4 Hz), 7.10-7.20 (4H, m), 7.42-7.52 (6H, m), 7.57 (2H, d, J=8.8 Hz) 8.01 (2H, d, J=8.4 Hz), 8.53 (1H, d, J=5.6 Hz), 8.74 (1H, s), 8.80 (1H, s).

The starting material and intermediate were synthesized in the following manner.

Production Example 124-1

4-(2-Phenylpyridin-4-yl)oxyaniline

4-Chloro-2-phenylpyridine 1.0 g (5.5 mM), paranitrophenol (1.68 g, 12 mM), Hunig's base (diisopropylethylamine, 5 ml) and 1-methylpyrrolidone (10 ml) were stirred at 160° C. for 20 hours. Water was added, extraction was performed with ethyl acetate, and the organic layer was washed 5 times with water. The solvent was distilled off under reduced pressure and the residue was purified by silica gel chromatography (hexane:ethyl acetate=4:1) to obtain 490 mg of 4-(4-nitrophenoxy)-2-phenylpyridine as a light yellow solid.

$^1$H-NMR (DMSO-d$_6$) δ (ppm): 7.08-7.14 (1H, m), 7.40-7.53 (5H, m), 7.74 (1H, s), 8.07-8.13 (2H, m) 8.34 (2H, d, J=8.8 Hz), 8.68 (1H, dd, J=5.6 Hz, J=1.2 Hz).

4-(4-nitrophenoxy)-2-phenylpyridine (490 mg), iron powder (1 g), ammonium chloride (2 g), ethanol (10 ml), dimethylformamide (10 ml) and water (5 ml) were stirred at 100° C. for 10 minutes. The mixture was filtered with celite, water was added to the filtrate, and extraction was performed with ethyl acetate. The organic layer was washed 5 times with water, and then the solvent was distilled off under reduced pressure to obtain 4-(2-phenylpyridin-4-yl)oxyaniline (460 mg) as a brown oil.

$^1$H-NMR (DMSO-d$_6$) δ (ppm): 5.12-5.16 (2H, m), 6.65 (2H, d, J=8.8 Hz), 6.74 (1H, dd, J=5.6 Hz, J=2.4 Hz), 6.89 (2H, d, J=8.8 Hz), 7.38 (1H, d, J=2.4 Hz), 7.40-7.52 (3H, m), 7.98 (2H, d, J=8.0 Hz), 8.48 (1H, d, J=5.6 Hz).

Example 125

N-(4-(3-Phenylpyridin-4-yl)oxyphenyl)-N'-(4-fluorophenyl)urea

Ethyl acetate (10 ml) was added to 4-(3-phenylpyridin-4-yl)oxyaniline (84 mg, 0.32 mM), and then parafluorophenyl isocyanate (0.54 ml, 4.7 mM) was added while stirring, which was continued for 40 minutes. After adding NH type silica gel to the reaction solution, the solvent was distilled off under reduced pressure to adsorb the reaction product onto the silica gel. The silica gel was charged into a dry column packed with NH type silica gel, for column purification (chloroform:methanol=10:1). After adding ethyl acetate and n-hexane to the obtained residue, the solvent was distilled off under reduced pressure to obtain the target compound (82 mg) as a light yellow amorphous substance.

$^1$H-NMR (DMSO-d$_6$) δ (ppm): 6.69 (1H, dd, J=5.6 Hz, J=1.6 Hz), 7.06-7.15 (4H, m), 7.37-7.54 (7H, m), 7.64 (2H, d, J=7.6 Hz), 8.38 (1H, dd, J=5.6 Hz, J=1.6 Hz), 8.51 (1H, d, J=1.6 Hz), 8.70 (1H, s), 8.75 (1H, s).

The starting material and intermediate were synthesized in the following manner.

Production Example 125-1

4-(3-Phenylpyridin-4-yl)oxyaniline

4-Chloro-3-phenylpyridine (200 mg, 1.06 mM), paranitrophenol (440 mg, 3.18 mM), Hunig's base (isoPr$_2$EtN, diisopropylethylamine, 1 ml) and 1-methylpyrrolidone (2 ml) were stirred at 160° C. for 2 hours. Water was added, extraction was performed with ethyl acetate, and the solvent was distilled off under reduced pressure. The residue was purified by silica gel chromatography (hexane:ethyl acetate=4:1, and then 2:1) to obtain 4-(4-nitrophenoxy)-3-phenylpyridine (150 mg) as a light yellow oil.

$^1$H-NMR(CDCl3) δ (ppm): 6.98 (1H, d, J=5.6 Hz), 7.12 (2H, d, J=9.2 Hz), 7.37-7.48 (3H, m), 7.50-7.56 (2H, m) 8.24 (2H, d, J=9.3 Hz), 8.55 (1H, d, J=5.6 Hz), 8.71 (1H, s).

4-(4-Nitrophenoxy)-3-phenylpyridine (150 mg), iron powder (300 mg), ammonium chloride (600 mg), ethanol (5 ml), dimethylformamide (5 ml) and water (2.5 ml) were stirred at 100° C. for 15 minutes. The mixture was filtered with celite, water was added to the filtrate, and extraction was performed with ethyl acetate. The organic layer was washed 5 times with water, and then the solvent was distilled off under reduced pressure to obtain 4-(3-phenylpyridin-4-yl)oxyaniline (84 mg) as a yellow oil.

$^1$H-NMR(CDCl$_3$) δ (ppm): 6.65-6.74 (3H, m), 6.88 (2H, d, J=8.8 Hz), 7.36-7.50 (3H, m), 7.64 (2H, d, J=8.8 Hz), 8.34 (1H, dd, J=5.6 Hz, J=0.8 Hz), 8.54 (1H, s).

Example 126

N-(3-(6,7-Dimethoxyquinolin-4-yl)oxypropyl)-N'-(4-fluorophenyl)urea 6,7-Dimethoxy-4-(3-aminopropoxy)quinoline 150 mg (0.57 mM) and ethyl acetate (20 ml) were stirred at room temperature, and then 4-fluorophenyl isocyanate (0.078 ml, 0.68 mM) was added and the mixture was further stirred for 15 minutes. The precipitated solid was filtered out to obtain the target substance (92 mg) as a white solid.

$^1$H-NMR (DMSO-d$_6$) δ (ppm): 2.03 (2H, tt, J=6.0 Hz, J=6.0 Hz), 3.36 (2H, t, J=6.0 Hz), 3.89 (3H, s), 3.91 (3H, s), 4.27 (2H, t, J=6.0 Hz), 6.29 (1H, t, J=6.0 Hz), 6.88 (1H, d, J=5.2 Hz), 7.00-7.07 (2H, m), 7.31 (1H, s), 7.34-7.41 (3H, m), 8.47 (1H, s), 8.51 (1H, d, J=5.2 Hz).

The starting material and intermediate were synthesized in the following manner.

Production Example 126-1

6,7-Dimethoxy-4-(3-aminopropoxy)quinoline 6,7-Dimethoxy-4-hydroxyquinoline (4.0 g, 19.5 mM), N-(3-bromopropyl)phthalimide (5.8 g, 21.5 mM), potassium carbonate (5.4 g, 39 mM) and DMF dimethylformamide (20 ml) were stirred at 60° C. for 1.5 hours. Water, ethyl acetate and tetrahydrofuran were added to the reaction solution for extraction. The solid which precipitated after standing for a period was filtered out to obtain N-(3-(6,7-dimethoxyquinolin-4-yloxy)propyl)phthalimide (1.1 g).

$^1$H-NMR (DMSO-d$_6$) δ (ppm): 2.22 (2H, tt, J=6.0 Hz, J=6.0 Hz), 3.82 (3H, s), 3.86 (2H, t, J=6.0 Hz), 3.90 (3H, s), 4.29 (2H, t, J=6.0 Hz), 6.82 (1H, d, J=5.2 Hz), 7.27 (1H, s), 7.31 (1H, s), 7.77-7.84 (4H, m), 8.49 (1H, d, J=5.2 Hz).

N-(3-(6,7-Dimethoxyquinolin-4-yloxy)propyl)phthalimide (600 mg, 1.53 mM), hydrazine monohydrate (300 mg, 6.12 mM), ethanol (5 ml), methanol (5 ml) and tetrahydrofuran (5 ml) were stirred for 2 hours under reflux. The solvent was distilled off under reduced pressure, and the residue was purified by silica gel chromatography (Fuji Silysia NH Type Silica Gel, chloroform:methanol=20:1) to obtain the target substance (150 mg) as a brown oil.

$^1$H-NMR (DMSO-d$_6$) δ (ppm): 1.93 (2H, tt, J=6.0 Hz, J=6.0 Hz), 2.77 (2H, t, J=6.0 Hz), 3.88 (3H, s), 3.91 (3H, s), 4.29 (2H, t, J=6.0 Hz), 6.89 (1H, d, J=5.2 Hz), 7.31 (1H, s), 7.34 (1H, s), 8.51 (1H, d, J=5.2 Hz).

Example 127

N-(4-(6-Cyano-7-((1-methylpiperidin-3-yl)methoxy)-4-quinolyl)oxy-2-fluorophenyl)-N'-(4-fluorophenyl)urea After dissolving 6-cyano-4-(4-(4-fluoroanilinocarbonyl)amino-3-fluorophenoxy)quinolin-7-ol sodium salt (222 mg), potassium carbonate (162 mg) and 3-chloromethyl-1-methylpiperidine hydrochloride (86 mg) in dimethylformamide (1.7 ml) and stirring the mixture overnight at 70-80° C., water was added, and extraction was performed with a tetrahydrofuran and ethyl acetate mixed solvent prior to concentration under reduced pressure and purification of the residue with NH Silica (Fuji Silysia Chemical). The obtained solid was washed with ether and dried to obtain the title compound (10 mg).

MS Spectrum: 544 (M+1)

1H-NMR Spectrum: (DMSOd$_6$) 1.30-2.70 (12H, m), 4.17 (2H, d, J=6.7 Hz), 6.61 (1H, d, J=5.0 Hz), 7.06-7.18 (3H, m), 7.36-7.50 (3H, m), 7.60 (1H, s,), 8.20-8.28 (1H, m), 8.63 (1H, s,), 8.74 (1H, d, J=5.0 Hz), 8.75 (1H, s,), 9.10 (1H, s,)

Example 128

N-(3-(5,6-Dimethyl-4-7H-pyrrolo[2,3-d]pyrimidyl)oxyphenyl)-N'-(4-fluorophenyl)urea After dissolving 4-amino(3-aminophenoxy)-5,6-dimethyl-7H-pyrrolo[2,3-d]-pyrimidine (27 mg) in toluene (1 ml) and acetonitrile (0.5 ml) under reflux, 4-fluorophenyl isocyanate (13.3 μM) was added. Upon stirring for 1 hour, the mixture was returned to room temperature and the precipitated crystals were filtered out to obtain the title compound (26 mg).

MS (ESI) m/z 392 (M+1)

$^1$H-NMR (DMSO-d$_6$) δ (ppm): 2.31 (3H, s), 2.46-2.50 (3H, m), 6.78-7.48 (8H, m), 8.14 (1H, s), 8.52 (1H, s), 8.82 (1H, s), 11.79 (1H, s)

The intermediates were synthesized in the following manner.

Production Example 128-1

4-(3-Nitrophenoxy)-5,6-dimethyl-7H-pyrrolo[2,3-d]-pyrimidine

After adding 3-nitrophenol (243 mg), potassium carbonate (268 mg) and dimethylformamide (2 ml) to the 4-chloro-5,6- dimethyl-7H-pyrrolo[2,3-d]-pyrimidine (177 mg) described in Journal of Medicinal Chemistry, 1996, Vol. 39, No. 12, 2285-2292, the mixture was stirred at 120-130° C. for 72 hours. This was returned to room temperature, water was added, extraction was performed with a tetrahydrofuran and ethyl acetate mixed solution, and then the organic layer was washed with saturated brine, dried over anhydrous sodium sulfate and concentrated to dryness. The obtained crystals were washed with diethyl ether to obtain the title compound (130 mg).

MS (ESI) m/z 285 (M+1)

$^1$H-NMR (DMSO-$d_6$) δ (ppm): 2.31 (3H, s), 2.46-2.50 (3H, m), 7.70-8.18 (5H, m), 11.89 (1H, s)

Production Example 128-2

4-(3-Aminophenoxy)-5,6-dimethyl-7H-pyrrolo[2,3-d]-pyrimidine

After adding iron powder (0.12 g), ammonium chloride (0.24 g), ethanol (5 ml) and water (1 ml) to the 4-(3-nitrophenoxy)-5,6-dimethyl-7H-pyrrolo [2,3-d]-pyrimidine (110 mg) synthesized by the intermediate synthesis method described above, the mixture was stirred at 80-90° C. for 3 hours. After returning the reaction system to room temperature and adding tetrahydrofuran (3 ml) and ethyl acetate (3 ml), the mixture was filtered with celite, the filtrate was subjected to liquid separation and extraction with ethyl acetate, and the organic layer was washed with water and saturated brine in that order. It was then dried over sodium sulfate, concentrated to dryness under reduced pressure and washed with diethyl ether to obtain the title compound (37 mg).

$^1$H-NMR (DMSO-$d_6$) δ (ppm): 2.27 (3H, s), 2.29 (3H, s), 5.15-5.24 (2H, m), 6.28 (1H, d, J=8.1 Hz), 6.32 (1H, s), 6.40 (1H, d, J=8.1 Hz), 7.01 (1H, t, J=8.1 Hz), 8.12 (1H, s), 11.72 (1H, s).

Example 129

N-6-((6,7-Dimethoxy-4-quinolyl)oxy)-3-pyridyl-N'-phenylurea 6-((6,7-Dimethoxy-4-quinolyl)oxy)-3-pyridylamine (59.5 mg, 200 mmol) and phenyl isocyanate (26.2 mg, 220 mmol) were stirred in N,N-dimethylformamide (1 ml) at room temperature for 18 hours. After diluting the reaction solution with ethyl acetate, it was washed with water and saturated brine, the organic layer was dried over anhydrous magnesium sulfate, the drying agent was filtered off and the filtrate was distilled off under reduced pressure. The obtained crude product was suspended in ethyl acetate, the suspension was diluted with hexane, and the crystals were filtered out and washed with ethyl acetate and then blow-dried to obtain the title compound (68 mg, 163 mmol, 82%) as colorless crystals.

$^1$H-NMR Spectrum: (DMSO-$d_6$) 3.90 (3H, s), 3.95 (3H, s), 6.55 (1H, d, J=5.2 Hz), 6.96-7.02 (1H, m), 7.26-7.32 (3H, m), 7.40 (1H, s), 7.41 (1H, s), 7.47 (2H, d, J=8.4 Hz), 8.14 (1H, dd, J=2.8, 8.8 Hz), 8.35 (1H, d, J=2.8 Hz), 8.55 (1H, d, J=5.2 Hz), 8.89 (1H, s), 8.99 (1H, s).

The intermediates were synthesized in the following manner.

Production Example 129-1

6,7-Dimethoxy-4-((5-nitro-2-pyridyl)oxy)quinoline 6,7-Dimethoxy-1,4-dihydro-4-quinolinone (4.10 g, 20.0 mmol), 2-bromo-5-nitropyridine (4.46 g, 22.0 mmol) and potassium carbonate (5.53 g, 40.0 mmol) were heated and stirred at 70° C. for 3 hours in N,N-dimethylformamide (20 ml). The reaction solution was diluted with ethyl acetate, the insoluble portion was filtered off, and after washing with water and saturated brine and drying the organic layer over anhydrous magnesium sulfate, the drying agent was filtered off and the filtrate was distilled off under reduced pressure. The obtained crude product was subjected to silica gel column chromatography (eluent: ethyl acetate), and the fraction containing the target substance was concentrated, suspended in ethyl acetate and diluted with hexane, after which the crystals were filtered out, washed with hexane and then blow-dried to obtain the title compound (2.23 g, 6.81 mmol, 34%) as yellow crystals.

$^1$H-NMR Spectrum: (CDCl$_3$) 3.95 (3H, s), 4.06 (3H, s), 7.07 (1H, d, J=5.2 Hz), 7.16 (1H, s), 7.26 (1H, d, J=8.8 Hz), 7.49 (1H, s), 8.60 (1H, dd, J=2.8, 8.8 Hz), 8.74 (1H, d, J=5.2 Hz), 9.08 (1H, d, J=2.8 Hz).

Production Example 129-2

6-((6,7-Dimethoxy-4-quinolyl)oxy)-3-pyridinamine 6,7-Dimethoxy-4-((5-nitro-2-pyridyl)oxy)quinoline (654 mg, 2.00 mmol), iron powder (559 mg, 10.0 mmol) and ammonium chloride (1.07 g, 20.0 mmol) were heated and stirred in ethanol (20 ml)-water (5 ml) at 80° C. for 20 minutes. After completion of the reaction, the reaction mixture was filtered with celite and washed in ethyl acetate. After washing the organic layer with water and saturated brine and drying over anhydrous magnesium sulfate, the drying agent was filtered out and the filtrate was distilled off under reduced pressure. The obtained crude product was suspended in ethyl acetate, the suspension was diluted with hexane, and the crystals were filtered out and washed with ethyl acetate and then blow-dried to obtain the title compound (380 mg, 1.28 mmol, 64%) as light yellow crystals.

$^1$H-NMR Spectrum: (CDCl$_3$) 3.73 (2H, s), 4.02 (3H, s), 4.04 (3H, s), 6.61 (1H, d, J=5.2 Hz), 6.96 (1H, d, J=8.8 Hz), 7.18 (1H, dd, J=2.8, 8.8 Hz), 7.41 (1H, s), 7.53 (1H, s), 7.85 (1H, d, J=2.8 Hz), 8.54 (1H, d, J=5.2 Hz).

Example 130

N-6-((6,7-Dimethoxy-4-quinolyl)oxy)-3-pyridyl-N'-(4-fluorophenyl)urea

The title compound (67 mg, 154 mmol, 77%) was obtained as colorless crystals from 4-fluorophenyl isocyanate (30.1 mg, 220 mmol), by the same procedure as in Example 129.

$^1$H-NMR Spectrum: (DMSO-$d_6$) 3.89 (3H, s), 3.95 (3H, s), 6.79 (1H, d, J=5.0 Hz), 7.11-7.16 (2H, m), 7.29 (1H, d, J=8.6 Hz), 7.39 (1H, s), 7.41 (1H, s), 7.45-7.51 (2H, m), 8.13 (1H, dd, J=2.6, 8.6 Hz), 8.34 (1H, d, J=2.6 Hz), 8.55 (1H, d, J=5.0 Hz), 8.93 (1H, s), 8.99 (1H, s).

Example 131

N-6-((6,7-Dimethoxy-4-quinolyl)oxy)-3-pyridyl-N'-(1,3-thiazol-2-yl)urea

The 6-((6,7-dimethoxy-4-quinolyl)oxy)-3-pyridinamine (89.1 mg, 300 mmol) obtained in Example 129 and phenyl N-(2-thiazolyl)carbamate (79.3 mg, 360 mmol) were stirred in dimethyl sulfoxide (1 ml) at 85° C. for 1 hour. After diluting the reaction solution with ethyl acetate, it was washed with water and saturated brine, the organic layer was dried over anhydrous magnesium sulfate, the drying agent was filtered off and the filtrate was distilled off under reduced pressure. The obtained crude product was suspended in ethyl acetate, the suspension was diluted with hexane, and the crystals were filtered out and washed with ethyl acetate and then blow-dried to obtain the title compound (88 mg, 208 mmol, 69%) as colorless crystals.

$^1$H-NMR Spectrum: (DMSO-d$_6$) 3.89 (3H, s), 3.95 (3H, s), 6.81 (1H, d, J=5.2 Hz), 7.12 (1H, d, J=3.6 Hz), 7.31 (1H, d, J=8.8 Hz), 7.36-7.40 (2H, m), 7.42 (1H, s), 8.18 (1H, dd, J=2.8, 8.8 Hz), 8.37 (1H, d, J=2.8 Hz), 8.56 (1H, d, J=5.2 Hz), 9.30 (1H, s).

Example 132

4-(5-((Anilinocarbonyl)amino)-2-pyridyloxy)-7-methoxy-6-quinolinecarboxamide

The title compound (59 mg, 137 mmol, 78%) was obtained as colorless crystals from 4-((5-amino-2-pyridyl)oxy)-7-methoxy-6-quinolinecarboxamide (55.0 mg, 177 mmol), by the same procedure as in Example 129.

$^1$H-NMR Spectrum: (DMSO-d$_6$) 4.04 (3H, s), 6.86 (1H, d, J=5.2 Hz), 6.96-7.02 (1H, m), 7.26-7.34 (3H, m), 7.47 (2H, d, J=7.6 Hz), 7.54 (1H, s), 7.74 (1H, s), 7.86 (1H, s), 8.15 (1H, dd, J=2.8, 8.8 Hz), 8.36 (1H, d, J=2.8 Hz), 8.55 (1H, s), 8.75 (1H, d, J=5.2 Hz), 8.90 (1H, s), 9.01 (1H, s).

The intermediates were synthesized in the following manner.

Production Example 132-1

7-Methoxy-4-((5-nitro-2-pyridyl)oxy)-6-quinolinecarboxamide

The title compound (93.0 mg, 273 mmol, 5%) was obtained as yellow crystals from 7-methoxy-4-oxo-1,4-hydroxy-6-quinolinecarboxamide (1.09 g, 5.00 mmol) derived by hydrolysis of the 7-methoxy-4-oxo-1,4-dihydro-6-quinolinecarboxamide described in WO98/13350, by the same procedure as in Example 129.

$^1$H-NMR Spectrum: (CDCl$_3$) 4.15 (3H, s), 5.92 (1H, s), 7.21 (1H, d, J=5.2 Hz), 7.35 (1H, d, J=9.2 Hz), 7.63 (1H, s), 7.79 (1H, s), 8.62 (1H, dd, J=2.8, 8.8 Hz), 8.94 (1H, d, J=5.2 Hz), 8.96 (1H, s), 9.02 (1H, d, J=5.2 Hz).

Production Example 132-2

4-((5-Amino-2-pyridyl)oxy)-7-methoxy-6-quinolinecarboxamide

7-Methoxy-4-((5-nitro-2-pyridyl)oxy)-6-quinolinecarboxamide (93.0 mg, 273 mmol), iron powder (76.0 mg, 1.36 mmol) and ammonium chloride (146 mg, 2.73 mmol) were heated and stirred in ethanol (4 ml)-water (1 ml) at 80° C. for 20 minutes. After completion of the reaction, the reaction mixture was filtered with celite and washed in an ethyl acetate-tetrahydrofuran mixed solvent. After washing the organic layer with water and saturated brine and drying over anhydrous magnesium sulfate, the drying agent was filtered out and the filtrate was distilled off under reduced pressure. The obtained crude product was subjected to silica gel column chromatography (eluent-ethyl acetate:methanol=20:1), and the fraction containing the target substance was concentrated, suspended in ethyl acetate and diluted with hexane, after which the crystals were filtered out, washed with hexane and then blow-dried to obtain the title compound (61.0 mg, 197 mmol, 72%) as yellow crystals.

$^1$H-NMR Spectrum: (DMSO-d$_6$) 4.03 (3H, s), 6.60 (1H, d, J=5.4 Hz), 7.04 (1H, d, J=8.4 Hz), 7.18 (1H, dd, J=2.6, 8.4 Hz), 7.50 (1H, s), 7.68 (1H, d, J=2.6 Hz), 7.73 (1H, s), 7.86 (1H, s), 8.61 (1H, s), 8.67 (1H, d, J=5.4 Hz).

Example 133

N-(4-(6-Cyano-7-((3-methylsulfonyl)propoxy)-4-quinolyl)oxy-2-fluorophenyl)-N'-(4-fluorophenyl) urea The title compound (67 mg) was obtained from 6-cyano-4-{4-[4-fluoroanilinocarbonyl]amino-3-fluorophenoxy}quinolin-7-ol sodium salt (100 mg) in the same manner as Example 7.

$^1$H-NMR (DMSO-d$_6$) δ (ppm): 2.24-2.32 (2H, m), 3.05 (3H, s), 3.30-3.35 (2H, m), 4.42 (2H, t, J=6 Hz), 6.63 (1H, d, J=5.6 Hz), 7.11-7.15 (3H, m), 7.40 (1H, dd, J=2.8 Hz, J=8.0 Hz), 7.44-7.48 (2H, m), 7.63 (1H, s), 8.21-8.26 (1H, m), 8.64 (1H, br), 8.75 (1H, d, J=5.6 Hz), 8.77 (1H, s), 9.10 (1H, br).

Example 134

N-(4-(6-Cyano-7-((3-methylthio)propoxy)-4-quinolyl)oxy-2-fluorophenyl)-N'-(4-fluorophenyl) urea The title compound (30 mg) was obtained from 6-cyano-4-{4-[4-fluoroanilinocarbonyl]amino-3-fluorophenoxy}quinolin-7-ol sodium salt (100 mg), in the same manner as Example 7.

$^1$H-NMR (DMSO-d$_6$) δ (ppm): 2.09 (3H, s), 2.06-2.14 (2H, m), 2.67 (2H, t, J=7.2 Hz), 4.37 (2H, t, J=6 Hz), 6.62 (1H, d, J=5.2 Hz), 7.10-7.15 (3H, m), 7.39 (1H, dd, J=2.8 Hz, J=7.6 Hz), 7.44-7.48 (2H, m), 7.60 (1H, s), 8.21-8.26 (1H, m), 8.65 (1H, br), 8.74 (1H, d, J=5.2 Hz), 8.75 (1H, s), 9.12 (1H, brd, J=3.2 Hz).

Example 135

N-(4-(6-Cyano-7-(3-(ethoxycarbonyl)propoxy)-4-quinolyl)oxy-2-fluorophenyl)-N'-(4-fluorophenyl) urea The title compound (850 mg) was obtained from 6-cyano-4-{4-[4-fluoroanilinocarbonyl]amino-3-fluorophenoxy}quinolin-7-ol sodium salt (1.0 g), in the same manner as Example 7.

$^1$H-NMR (DMSO-d$_6$) δ (ppm): 1.17 (3H, t, J=7.2 Hz), 2.05-2.13 (2H, m), 2.53 (2H, t, J=7.2 Hz), 4.07 (2H, q, J=7.2 Hz), 4.31 (2H, t, J=6.4 Hz), 6.61 (1H, d, J=5.2 Hz), 7.10-7.15 (3H, m), 7.40 (1H, dd, J=2.8 Hz, J=7.6 Hz), 7.44-7.48 (2H, m), 7.60 (1H, s), 8.22-8.27 (1H, m), 8.64 (1H, br), 8.74 (1H, d, J=5.2 Hz), 8.74 (1H, s), 9.10 (1H, br).

Example 136

N-(4-(6-Cyano-7-(3-carboxypropoxy)-4-quinolyl)oxy-2-fluorophenyl)-N'-(4-fluorophenyl)urea N-(4-(6-Cyano-7-(3-(ethoxycarbonyl)propoxy)-4-quinolyl)oxy-2-fluorophenyl)-N'-(4-fluorophenyl)urea (800 mg) was dissolved in methanol (45 ml), 2N NaOH water (15 ml) was added, and the mixture was heated and stirred for 40 minutes at 80° C. After completion of the reaction, the reaction solution was poured into ice water and neutralized with 1N HCl, and the precipitated solid was filtered out. The obtained solid was washed with water and dried to obtain 230 mg of the title compound.

$^1$H-NMR (DMSO-d$_6$) δ (ppm): 2.01-2.08 (2H, m), 2.46 (2H, t, J=7.6 Hz), 4.30 (2H, t, J=6.4 Hz), 6.61 (1H, d, J=5.2 Hz), 7.10-7.15 (3H, m), 7.39 (1H, dd, J=2.8 Hz, J=8.0 Hz), 7.44-7.48 (2H, m), 7.59 (1H, s), 8.21-8.26 (1H, m), 8.66 (1H, br), 8.73 (1H, d, J=5.2 Hz), 8.74 (1H, s), 9.13 (1H, br).

Example 137

N-(4-(6-Cyano-7-(3-((cyclopropylamino)carbonyl)propoxy)-4-quinolyl)oxy-2-fluorophenyl)-N'-(4-fluorophenyl)urea N-(4-(6-Cyano-7-(3-carboxypropoxy)-4-quinolyl)oxy-2-fluorophenyl)-N'-(4-fluorophenyl)urea (100 mg) was dissolved in dimethylformamide (3 ml), and then 1-ethyl-3-(3-dimethylaminopropyl)-carbodiimide (44 mg) and 1-hydroxy-1H-benzotriazole (35 mg) were added while stirring on ice and the mixture was stirred at room temperature for 30 minutes. Cyclopropylamine (16 μl) was then added and the mixture was stirred at room temperature for 18 hours. After completion of the reaction, the reaction solution was poured into 1N sodium hydroxide water and extracted with ethyl acetate, and the obtained organic layer was washed with saturated brine and dried over magnesium sulfate. The organic layer was concentrated, and the obtained solid was washed with ether and a small amount of ethyl acetate to obtain 38 mg of the title compound.

$^1$H-NMR (DMSO-d$_6$) δ (ppm): 0.34-0.38 (2H, m), 0.54-0.59 (2H, m), 1.99-2.06 (2H, m), 2.25 (2H, t, J=7.2 Hz), 2.56-2.63 (1H, m), 4.27 (2H, t, J=6.4 Hz), 6.60 (1H, d, J=5.2 Hz), 7.10-7.15 (3H, m), 7.39 (1H, dd, J=2.8 Hz, J=8.0 Hz), 7.44-7.49 (2H, m), 7.59 (1H, s), 7.95 (1H, brd, J=3.6 Hz), 8.21-8.25 (1H, m), 8.67 (1H, br), 8.73 (1H, d, J=5.2 Hz), 8.74 (1H, s), 9.15 (1H, br).

Example 138

N-(4-(6-Cyano-7-(3-((piperidino)carbonyl)propoxy)-4-quinolyl)oxy-2-fluorophenyl)-N'-(4-fluorophenyl)urea The title compound (33 mg) was obtained from N-(4-(6-cyano-7-(3-carboxypropoxy)-4-quinolyl)oxy-2-fluorophenyl)-N'-(4-fluorophenyl)urea (100 mg) by the same procedure as in Example 137.

$^1$H-NMR (DMSO-d$_6$) δ (ppm): 1.38-1.60 (6H, m), 2.01-2.09 (2H, m), 2.53 (2H, t, J=7.2 Hz), 3.39-3.46 (4H, m), 4.31 (2H, t, J=6.0 Hz), 6.61 (1H, d, J=5.2 Hz), 7.10-7.15 (3H, m), 7.40 (1H, dd, J=2.4 Hz, J=8.0 Hz), 7.43-7.49 (2H, m), 7.61 (1H, s), 8.20-8.27 (1H, m), 8.70 (1H, br), 8.73 (1H, d, J=5.2 Hz), 8.74 (1H, s), 9.17 (1H, br).

Example 139

N-(4-(6-Cyano-7-(3-((dimethylamino)sulfonyl)propoxy)-4-quinolyl)oxy-2-fluorophenyl)-N'-(4-fluorophenyl)urea The title compound (35 mg) was obtained from 6-cyano-4-{4-[4-fluoroanilinocarbonyl]amino-3-fluorophenoxy}quinolin-7-ol sodium salt (100 mg), in the same manner as Example 7.

$^1$H-NMR (DMSO-d$_6$) δ (ppm): 2.19-2.27 (2H, m), 2.80 (6H, s), 3.26-3.31 (2H, m), 4.41 (2H, t, J=6.4 Hz), 6.63 (1H, d, J=5.2 Hz), 7.10-7.16 (3H, m), 7.40 (1H, dd, J=2.8 Hz, J=7.6 Hz), 7.44-7.49 (2H, m), 7.61 (1H, s), 8.21-8.27 (1H, m), 8.68 (1H, br), 8.75 (1H, d, J=5.2 Hz), 8.77 (1H, s), 9.15 (1H, br).

Example 140

N-(4-(6-Cyano-7-(3-((cyclopropylamino)sulfonyl)propoxy)-4-quinolyl)oxy-2-fluorophenyl)-N'-(4-fluorophenyl)urea The title compound (31 mg) was obtained from 6-cyano-4-{4-[4-fluoroanilinocarbonyl]amino-3-fluorophenoxy}quinolin-7-ol sodium salt (100 mg), in the same manner as Example 7.

$^1$H-NMR (DMSO-d$_6$) δ (ppm): 0.51-0.63 (4H, m), 2.17-2.25 (2H, m), 3.15-3.22 (1H, m), 3.26-3.33 (2H, m), 4.42 (2H, t, J=6.0 Hz), 6.63 (1H, d, J=5.2 Hz), 7.10-7.16 (3H, m), 7.40 (1H, dd, J=2.8 Hz, J=8.0 Hz), 7.44-7.48 (2H, m), 7.56 (1H, brd, J=2.8 Hz), 7.61 (1H, s), 8.21-8.27 (1H, m), 8.63-8.66 (1H, m), 8.75 (1H, d, J=5.2 Hz), 8.77 (1H, s), 9.11-9.13 (1H, m).

Example 141

N-(4-(7-Benzyloxy-6-cyano-4-quinolyl)oxy-2-fluorophenyl)-N'-(2-thiazolyl)urea

Phenyl N-(4-(6-cyano-7-benzyloxy-4-quinolyl)oxy-2-fluorophenyl)carbamate (6.93 g) and 2-aminothiazole (2.75 g) were dissolved in dimethylformamide (70 ml), and then diisopropylethylamine (4.8 ml) was added and the mixture was heated and stirred at 90° C. for 2 hours. After cooling, water was added and the precipitated solid was filtered out and washed with ethyl acetate to obtain 5.53 g of the title compound as light brown crystals (79% yield).

$^1$H-NMR Spectrum (DMSO-d$_6$) δ (ppm): 5.46 (2H, s), 6.63 (1H, d, J=5.2 Hz), 7.13-7.19 (2H, m), 7.33-7.48 (5H, m), 7.54 (2H, d, J=6.8 Hz), 7.72 (1H, s), 8.21-8.27 (1H, m), 8.73-8.78 (2H, m)

The intermediates were synthesized in the following manner.

Production Example 141-1

Phenyl N-(4-(6-cyano-7-benzyloxy-4-quinolyl)oxy-2-fluorophenyl)carbamate

The 7-benzyloxy-6-cyano-4-(3-fluoro-4-aminophenoxy)quinoline (9.45 g) synthesized in Production Example 8 was dissolved in dimethylformamide (70 ml) and pyridine (5.9 ml), and the mixture was cooled to 0° C. under a nitrogen atmosphere. After adding phenyl chlorocarbonate (3.4 ml), the mixture was stirred for 2 hours. Water was added to the reaction solution, and the precipitated crystals were filtered out and triturated in tetrahydrofuran and toluene to obtain 6.93 g of the title compound as light brown crystals (56% yield).

$^1$H-NMR Spectrum (CDCl$_3$) δ (ppm): 5.36 (2H, s), 6.53 (1H, d, J=5.3 Hz), 6.98-7.05 (2H, m), 7.17-7.47 (9H, m), 7.51-7.58 (3H, m), 8.67-8.71 (2H, m)

Example 142

N-[4-(6-Cyano-7-[3-(morpholin-4-yl)propoxy]-4-quinolyl)oxy-2-fluorophenyl]-N'-(2-thiazolyl)urea N-(4-(6-Cyano-7-hydroxyquinolyl)oxy-2-fluorophenyl)-N'-(2-thiazolyl)urea (150 mg) was dissolved in dimethylformamide (3 ml), and then potassium carbonate (150 mg) and 1-chloro-3-(morpholin-4-yl)propane (70 mg) were added and the mixture was heated and stirred at 60° C. for 2 hours. After cooling, water was added, extraction was performed with ethyl acetate, the organic layer was washed with saturated brine and dried over anhydrous sodium sulfate, and the solvent was distilled off under reduced pressure. The residue was purified by NH silica gel column chromatography (ethyl acetate-methanol system) to obtain the title compound (20 mg).

$^1$H-NMR Spectrum (DMSO-d$_6$) δ (ppm): 1.94-2.04 (2H, m), 2.34-2.52 (6H, m), 3.54-3.61 (4H, m), 4.34 (2H, t, J=6.2 Hz), 6.61 (1H, d, J=5.6 Hz), 7.12-7.20 (2H, m), 7.37-7.47 (2H, m), 7.61 (1H, s), 8.21-8.27 (1H, m), 8.73-8.76 (2H, m)

The intermediates were synthesized in the following manner.

Production Example 142-1

N-(4-(6-Cyano-7-hydroxy-4-quinolyl)oxy-2-fluorophenyl)-N'-(2-thiazolyl)urea

The N-(4-(7-benzyloxy-6-cyanoquinolyl)oxy-2-fluorophenyl)-N'-(2-thiazolyl)urea (5.53 g) synthesized in Example 141 was dissolved in TFA (55 ml), and then thioanisole (5.5 ml) was added and the mixture was heated and stirred at 70° C. for 6 hours. After cooling the reaction solution and concentrating it under reduced pressure, sodium bicarnobate water and methanol were added and the precipitated crystals were filtered. These were washed with diethyl ether to obtain 3.63 g of the title compound (80% yield).

$^1$H-NMR Spectrum (DMSO-d$_6$) δ (ppm): 6.50 (1H, d, J=5.6 Hz), 7.12-7.19 (2H, m), 7.35-7.45 (3H, m), 8.19-8.27 (1H, m), 8.61-8.66 (2H, m)

Example 143

N-(4-(6-Cyano-7-(3-(diethylamino)propoxy)-4-quinolyl)oxy-2-fluorophenyl-N'-(2-thiazolyl)urea The N-(4-(6-cyano-7-hydroxy-4-quinolyl)oxy-2-fluorophenyl)-N'-(2-thiazolyl)urea (150 mg) synthesized in Example 142 was dissolved in dimethylformamide (2.5 ml), and then potassium carbonate (150 mg) and 1-chloro-3-(diethylamino)propane (80 mg) were added and the mixture was heated and stirred at 60° C. for 2 hours. After cooling, water was added, extraction was performed with ethyl acetate, the organic layer was washed with saturated brine and dried over anhydrous sodium sulfate, and the solvent was distilled off under reduced pressure. The residue was purified by NH silica gel column chromatography (ethyl acetate-methanol system) to obtain the title compound (10 mg).

$^1$H-NMR Spectrum (DMSO-d$_6$) δ (ppm): 0.95 (6H, t, J=7.0 Hz), 1.85-1.96 (2H, m), 2.40-2.65 (6H, m), 4.32 (2H, t, J=6.0 Hz), 6.62 (1H, d, J=5.2 Hz), 7.12-7.20 (2H, m), 7.36-7.48 (2H, m), 7.59 (1H, s), 8.20-8.24 (1H, m), 8.73-8.77 (2H, m)

Example 144

N-(4-(6-Cyano-7-(2-methoxyethoxy)-4-quinolyl) oxyphenyl)-N'-(3-methylisoxazol-5-yl)urea The 4-(4-aminophenoxy)-6-cyano-7-(2-methoxyethoxy) quinoline (100 mg) synthesized in Production Example 10 and phenyl N-(3-methylisoxazol-5-yl)carbamate (81 mg) were added to toluene (5 ml), then diisopropylethylamine (0.88 ml) was added and the mixture was heated and stirred at 100° C. for 2 hours. After cooling, the precipitated crystals were filtered and washed with an ethyl acetate:toluene (1:1) mixed solvent to obtain the title compound (102 mg).

$^1$H-NMR Spectrum (DMSO-d$_6$) δ (ppm): 2.16 (3H, s), 3.36 (3H, s), 3.76-3.79 (2H, m), 4.40-4.44 (2H, m), 5.95 (1H, s), 6.52 (1H, d, J=5.2 Hz), 7.26 (2H, d, J=9.2 Hz), 7.58-7.64 (3H, m), 8.71 (1H, d, J=5.2 Hz), 8.76 (1H, s), 9.04 (1H, brs).

The intermediates were synthesized in the following manner.

Production Example 144-1

Phenyl N-(3-Methylisoxazol-5-yl)carbamate

5-Amino-3-methylisoxazole (1 g) purchased from Aldrich Co. was dissolved in tetrahydrofuran (40 ml) and pyridine (1.5 ml), and after cooling to 0° C. under a nitrogen atmosphere, phenyl chlorocarbonate (1.4 ml) was added and the mixture was stirred at room temperature for 1.5 hours. Water was added, extraction was performed twice with ethyl acetate, and then the organic layers were combined, washed with water and saturated brine in that order, dried over anhydrous sodium sulfate and concentrated under reduced pressure. The obtained residue was recrystallized from ethyl acetate and n-hexane to obtain the title compound (450 mg, 20% yield).

$^1$H-NMR Spectrum (CDCl$_3$) δ (ppm): 2.27 (3H, s), 6.03 (1H, s), 7.16-7.30 (3H, m), 7.37-7.44 (2H, m), 7.81 (1H, brs)

Example 145

N-(4-(6-Cyano-7-(2-methoxyethoxy)-4-quinolyl) oxyphenyl)-N'-(5-methylisoxazol-3-yl)urea The 4-(4-aminophenoxy)-6-cyano-7-(2-methoxyethoxy) quinoline (100 mg) synthesized in Production Example 10 and phenyl N-(5-methylisoxazol-3-yl)carbamate (72 mg) were added to toluene (5 ml), and then diisopropylethylamine (0.50 ml) was added and the mixture was heated to reflux for 2 hours. After cooling, the precipitated crystals were filtered and washed with an ethyl acetate/toluene (1/1) mixed solvent to obtain the title compound (120 mg).

$^1$H-NMR Spectrum (DMSO-d$_6$) δ (ppm): 2.36 (3H, s), 3.37 (3H, s) 3.75-3.78 (2H, m), 4.37-4.43 (2H, m), 6.50-6.54 (2H, m), 7.26 (2H, d, J=8.8 Hz), 7.56-7.63 (3H, m), 8.72 (1H, d, J=5.6 Hz), 8.76 (1H, s), 8.99 (1H, brs), 9.51 (1H, brs)

The intermediates were synthesized in the following manner.

Production Example 145-1

Phenyl N-(5-Methylisoxazol-3-yl)carbamate

3-Amino-5-methylisoxazole (1.00 g) purchased from Aldrich Co. was dissolved in tetrahydrofuran (20 ml) and pyridine (1.5 ml), and after cooling to 0° C. under a nitrogen atmosphere, phenyl chlorocarbonate (1.4 ml) was added and the mixture was stirred at room temperature for 2 hours. Water was added, extraction was performed twice with ethyl acetate, and then the organic layers were combined, washed with water and saturated brine in that order, dried over anhydrous sodium sulfate and concentrated under reduced pressure. The obtained residue was triturated with diethyl ether and n-hexane to obtain the title compound (1.54 g) (68% yield).

¹H-NMR Spectrum (CDCl₃) δ (ppm): 2.42 (3H, s), 6.56 (1H, s), 7.15-7.30 (3H, m), 7.36-7.43 (2H, m), 8.18 (1H, brs)

Example 146

N-(4-(6-Cyano-7-(2-methoxyethoxy)-4-quinolyl)oxy-2-fluorophenyl)-N'-(2-oxo-1,2,3,4-tetrahydro-6-quinolinyl)urea The title compound (64 mg) was obtained from phenyl N-(4-(6-cyano-7-(2-methoxyethoxy)-4-quinolyl)oxy-2-fluorophenyl)carbamate (65 mg), in the same manner as Example 25.
¹H-NMR Spectrum (DMSO-d₆) δ (ppm): 2.38-2.45 (2H, m), 2.81-2.90 (2H, m), 3.36 (3H, s), 3.75-3.79 (2H, m), 4.40-4.43 (2H, m), 6.61 (1H, d, J=5.2), 6.77 (1H, d, J=8.4 Hz), 7.10-7.18 (2H, m), 7.30 (1H, brs), 7.36-7.42 (1H, m), 7.63 (1H, s), 8.23-8.29 (1H, m), 8.60 (1H, brs), 8.73-8.76 (2H, m), 8.92-8.94 (1H, m), 9.97 (1H, brs)

Example 147

4-(4-(Anilinocarbonyl)aminophenoxy)-7-methoxy-6-quinolinecarboxamide

The N-(4-(6-cyano-7-methoxy-4-quinolyl)oxyphenyl)-N'-phenylurea (100 mg) synthesized in Example 37 was dissolved in dimethylsulfoxide (3 ml) at 80° C., and then 5N aqueous sodium hydroxide was added and the mixture was heated and stirred for 2 hours. The reaction solution was neutralized with 1N hydrochloric acid, and the precipitated crystals were filtered out and washed with ethanol to obtain the title compound (60 mg).
¹H-NMR Spectrum (DMSO-d₆) δ (ppm): 4.03 (3H, s), 6.56 (1H, d, J=6.0 Hz), 6.96 (1H, t, J=7.6 Hz), 7.22-7.30 (4H, m), 7.45 (2H, d, J=7.6 Hz), 7.52 (1H, s), 7.59-7.62 (2H, m), 7.76 (1H, brs), 7.87 (1H, brs), 8.69-8.73 (2H, m), 8.76 (1H, brs), 8.90 (1H, brs)

Example 148

4-(4-(Anilinocarbonyl)aminophenoxy)-7-(2-methoxyethoxy)-6-quinolinecarboxamide

The title compound (54 mg) was obtained from the N-(4-(6-cyano-7-(methoxyethoxy)-4-quinolyl)oxyphenyl)-N'-phenylurea (95 mg) synthesized in Example 65, in the same manner as Example 147.
¹H-NMR Spectrum (DMSO-d₆) δ (ppm): 3.35 (3H, s), 3.75-3.81 (2H, m), 4.37-4.41 (2H, m), 6.46 (1H, d, J=5.2), 6.96 (1H, t, J=7.6), 7.21-7.30 (4H, m), 7.45 (2H, d, J=8.4 Hz), 7.55 (1H, s), 7.59 (2H, d, J=8.8 Hz), 7.81 (1H, brs), 7.82 (1H, brs), 8.65 (1H, d, J=5.2), 8.77-8.79 (2H, m), 8.91 (1H, brs)

Example 149

4-(4-((2,4-Difluorophenyl)carbonyl)amino-3-fluorophenoxy)-7-(2-methoxyethoxy)-6-quinolinecarboxamide The title compound (35 mg) was obtained from the N-(4-(6-cyano-7-(2-methoxyethoxy)-4-quinolyl)oxy-2-fluorophenyl)-N'-(2,4-difluorophenyl)urea (100 mg) synthesized in Example 66, in the same manner as Example 147.
¹H-NMR Spectrum (DMSO-d₆) δ (ppm): 3.34 (3H, s), 3.78-3.81 (2H, m), 4.39-4.42 (2H, m), 6.56 (1H, d, J=5.2 Hz), 7.03-7.17 (2H, m), 7.28-7.43 (2H, m), 7.56 (1H, s), 7.81 (2H, brs), 8.08-8.16 (1H, m), 8.28-8.29 (1H, m), 8.67 (1H, d, J=5.2), 8.76 (1H, s), 9.00-9.09 (2H, m)

Example 150

4-(4-((4-Fluoroanilino)carbonyl)amino-3-fluorophenoxy)-7-(2-methoxyethoxy)-6-quinolinecarboxamide The title compound (25 mg) was obtained from the N-(4-(6-cyano-7-(2-ethoxyethoxy)-4-quinolyl)oxy-2-fluorophenyl)-N'-(4-fluorophenyl)urea (58 mg) synthesized in Example 100, in the same manner as Example 147.
¹H-NMR Spectrum (DMSO-d₆) δ (ppm): 3.34 (3H, s), 3.78-3.81 (2H, m), 4.39-4.42 (2H, m), 6.56 (1H, d, J=5.2 Hz), 7.10-7.17 (3H, m), 7.36-7.50 (3H, m), 7.56 (1H, s), 7.82 (2H, brs), 8.19-8.26 (1H, m), 8.64-8.69 (2H, m), 8.76 (1H, s), 9.13-9.15 (1H, m)

Example 151

7-(2-Methoxyethoxy)-4-(4-((1,3-thiazol-2-ylamino)carbonyl)amino-3-fluorophenoxy)-6-quinolinecarboxamide The title compound (18 mg) was obtained from the N-(4-(6-cyano-7-(2-methoxyethoxy)-4-quinolyl)oxy-2-fluorophenyl)-N'-(1,3-thiazol-2-yl)urea (100 mg) synthesized in Example 25, in the same manner as Example 147.
¹H-NMR Spectrum (DMSO-d₆) δ (ppm): 3.34 (3H, s), 3.78-3.81 (2H, m), 4.39-4.42 (2H, m), 6.57 (1H, d, J=5.2 Hz), 7.12-7.19 (2H, m), 7.39 (1H, d, J=3.6 Hz), 7.41-7.46 (1H, m), 7.57 (1H, s), 7.82 (1H, brs), 8.21-8.25 (1H, m), 8.68 (1H, d, J=5.2 Hz), 8.76 (1H, s), 9.06 (1H, brs)

Example 152

4-(4-((4-Fluoroanilino)carbonyl)amino-3-fluorophenoxy)-7-methoxy-6-quinolinecarboxamide The title compound (25 mg) was obtained from 6-carbamoyl-4-(4-amino-3-fluorophenoxy)-7-methoxyquinoline (50 mg), in the same manner as Example 10.
¹H-NMR Spectrum (DMSO-d₆) δ (ppm): 4.02 (3H, s), 6.55 (1H, d, J=5.6 Hz), 7.09-7.18 (3H, m), 7.35-7.41 (1H, m), 7.43-7.49 (2H, m), 7.51 (1H, s), 7.74 (1H, brs), 7.85 (1H, brs), 8.18-8.26 (1H, m), 8.61-8.68 (3H, m), 9.09-9.12 (1H, m)
The starting compounds were synthesized in the following manner.

Production Example 152-1

7-Methoxy-4-oxo-1,4-dihydroquinoline-6-carboxylic acid

Glycerol (20 ml) and potassium hydroxide (KOH, 3.0 g) were added to the 7-methoxy-4-oxo-1,4-dihydroquinoline-6-carbonitrile (2 g) of Production Example 24, and after heating and stirring at 160° C. for 3 hours, water (40 ml) was added and the mixture was heated at 80° C. for 30 minutes. After cooling, 2N hydrochloric acid was added to acidity and the precipitated insoluble portion was filtered out, washed with water and then dried under reduced pressure to obtain the title compound (1.6 g).
¹H-NMR Spectrum (DMSO-d₆) δ (ppm): 4.87 (3H, s), 6.14 (1H, d, J=6.0 Hz), 7.04 (1H, s), 7.98 (1H, d, J=6.0), 8.40 (1H, s)

Production Example 152-2

7-Methoxy-4-chloroquinoline-6-carbonyl chloride

Thionyl chloride (10 ml) and a small amount of dimethylformamide (DMF) were added to 7-methoxy-4-oxo-1,4-dihydroquinoline-6-carboxylic acid (2.0 g), and the mixture was heated to reflux for 2 hours. After concentrating under reduced pressure, azeotropic distillation was performed twice with toluene to obtain the title compound (2.7 g).
$^1$H-NMR Spectrum (CDCl$_3$) δ (ppm): 4.20 (3H, s), 7.80-7.90 (1H, m), 8.41 (1H, s), 8.90-9.00 (2H, m)

Production Example 152-3

7-Methoxy-4-chloroquinoline-6-carboxamide

7-Methoxy-4-chloroquinoline-6-carbonyl chloride (2.7 g) was dissolved in tetrahydrofuran (150 ml), and the solution was cooled to 0° C. After adding 30% ammonia water (5 ml), the mixture was stirred at room temperature for 30 minutes. Water was added, extraction was performed 3 times with ethyl acetate, and then the organic layers were combined, washed with water and saturated brine, dried over sodium sulfate and dried under reduced pressure to obtain the title compound (1.35 g).
$^1$H-NMR Spectrum (DMSO-d$_6$) δ (ppm): 4.03 (3H, s), 7.56-7.66 (2H, m), 7.79 (1H, brs), 7.88 (1H, brs), 8.46-8.49 (1H, m), 8.78-8.82 (1H, m)

Production Example 152-4

6-Carbamoyl-4-(3-fluoro-4-nitrophenoxy)-7-methoxyquinoline

The title compound (1.1 g) was obtained from 7-methoxy-4-chloroquinoline-6-carboxamide (1.23 g), in the same manner as Example 7.
$^1$H-NMR Spectrum (DMSO-d$_6$) δ (ppm): 4.03 (3H, s), 6.96 (1H, d, J=5.2 Hz), 7.25-7.30 (1H, m), 7.57 (1H, s), 7.61-7.66 (1H, m), 7.74 (1H, brs), 7.84 (1H, brs), 8.25-8.32 (1H, m), 8.49 (1H, s), 8.80 (1H, d, J=5.2 Hz)

Production Example 152-5

6-Carbamoyl-4-(4-amino-3-fluorophenoxy)-7-methoxyquinoline

The title compound (540 mg) was obtained from 6-carbamoyl-4-(3-fluoro-4-nitrophenoxy)-7-methoxyquinoline (1.08 g), in the same manner as Production Example 10.
$^1$H-NMR Spectrum (DMSO-d$_6$) δ (ppm): 4.01 (3H, s), 5.19-5.23 (2H, m), 6.44 (1H, d, J=5.2), 6.83-6.89 (2H, m), 7.05-7.10 (1H, m), 7.47 (1H, s), 7.71 (1H, brs), 7.83 (1H, brs), 8.60-8.66 (2H, m)

Example 153

1-(2-Chloro-4-{6-[4-(2-diethylaminoethoxy)-phenyl]-7H-pyrrolo[2,3-d]pyrimidin-4-yloxy}phenyl)-3-cyclopropylurea 1-{2-Chloro-4-[6-[4-(2-diethylaminoethoxy)-phenyl]-7-(2-trimethylsilanylethoxymethyl)-7H-pyrrolo[2,3-d]pyrimidin-4-yloxy]-phenyl}-3-cyclopropylurea (40 mg, 0.0601 mmol) was dissolved in 1 ml of tetrahydrofuran, and then 0.5 ml (8.3 equivalents) of tetrabutylammonium fluoride (1M tetrahydrofuran solution) was added dropwise and the mixture was refluxed for 2 hours. After returning to room temperature, 3 ml of water was added, the mixture was allowed to stand for 3 hours, and the precipitating crystals were filtered out, washed with water and ether:hexane=1:1 and dried under reduced pressure to obtain 22 mg of the title compound.
MS Spectrum (ESI): 535 (M+1),
$^1$H-NMR Spectrum: (DMSO-d$_6$) 0.40-0.54 (2H, m), 0.70-0.80 (2H, m), 1.06 (6H, t, J=7.8 Hz) 2.55-2.70 (5H, m), 2.88 (2H, t, J=7.8 Hz), 4.18 (2H, t, J=7.8 Hz), 7.01 (1H, d, J=1.7 Hz), 7.12 (2H, d, J=8.4 Hz), 7.23 (1H, d, J=2.5 Hz), 7.27 (1H, dd, J=8.8 Hz, J'=2.5 Hz), 7.41 (1H, d, J=2.5 Hz), 7.97 (2H, d, J=8.4 Hz), 8.01 (1H, s), 8.24 (1H, d, J=8.8 Hz), 8.36 (1H, s), 12.68 (1H, brs)

The intermediates were synthesized in the following manner.

Production Example 153-1

2-Amino-5-(4-benzyloxyphenyl)-1H-pyrrole-3-carboxylic acid ethyl ester

After adding 700 ml of ethanol to 50.7 g of ethyl 2-amidinoacetate hydrochloride (a publicly known compound described in Liebigs Ann. Chem., 1895(1977)), the mixture was stirred at room temperature, 22.3 g of sodium ethoxide (1 equivalent with respect to ethyl 2-amidinoacetate hydrochloride) was added, and the mixture was stirred for 15 minutes under a nitrogen atmosphere. To this there was added 49.9 g of 1-(4-benzyloxyphenyl)-2-bromoethanone (publicly known compound described in Journal of Heterocyclic Chemistry, vol. 2, 310(1965) and Journal of Medicinal Chemistry, vol. 17, 55(1974)), and the mixture was stirred for 36 hours at room temperature under a nitrogen atmosphere. Water was added, ethyl acetate was used for liquid separation and extraction, and then the organic layer was dried over sodium sulfate and concentrated to dryness to obtain 56.7 g of the title compound.
$^1$H-NMR Spectrum: (DMSO-d$_6$) 1.32 (3H, t, J=7.3 Hz), 4.10 (2H, q, J=7.3 Hz), 5.08 (2H, s,), 5.62 (2H, s), 6.30 (1H, d, J=2.2 Hz), 6.95 (2H, d, J=7.9 Hz), 7.28-7.47 (7H, m), 10.67 (1H, brs)

Production Example 153-2

6-(4-Benzyloxyphenyl)-7H-pyrrolo[2,3-d]pyrimidin-4-ol

After adding 84 ml of formic acid, 338 ml of formamide and 169 ml of dimethylformamide to 56.7 g of the ethyl 2-amino-5-(4-benzyloxyphenyl)-1H-pyrrole-3-carboxylate synthesized in Production Example 153-1, the mixture was stirred at 140° C. for 48 hours and then allowed to stand at room temperature for 24 hours. The precipitated solid was filtered out and dried under reduced pressure to obtain 41 g of the title compound.
$^1$H-NMR Spectrum: (DMSO-d$_6$) 5.12 (2H, s), 6.78 (1H, s), 7.03 (2H, d, J=7.0 Hz), 7.28-7.47 (5H, m), 7.73 (2H, d, J=7.0 Hz), 7.82 (1H, s), 11.80 (1H, brs), 12.20 (1H, brs)

Production Example 153-3

6-(4-Benzyloxyphenyl)-4-chloro-7H-pyrrolo[2,3-d]pyrimidine

After adding 200 ml of phosphorus oxychloride to 20 g of the 6-(4-benzyloxyphenyl)-7H-pyrrolo[2,3-d]pyrimidin-4- ol synthesized in Production Example 153-2, the mixture was stirred at 140° C. for 3 hours and the reaction mixture was cooled to room temperature and the reaction mixture was concentrated. Ice water was added to the residue, and liquid separation and extraction were performed with an ethyl acetate:tetrahydrofuran (5:1) mixed solvent. The organic layer was washed with water and saturated brine, dried over sodium sulfate and concentrated to dryness to obtain 12 g of the title compound.

$^1$H-NMR Spectrum: (DMSO-d$_6$) 5.18 (2H, s), 6.97 (1H, d, J=2.4 Hz), 7.12 (2H, d, J=7.5 Hz), 7.30-7.50 (5H, m), 7.94 (2H, d, J=7.5 Hz), 8.70 (1H, s), 12.90 (1H, brs)

Production Example 153-4

6-(4-Benzyloxyphenyl)-4-chloro-7-(2-trimethylsilanylethoxy-methyl)-7H-pyrrolo[2,3-d]pyrimidine After adding 0.381 g (1.3 equivalents) of sodium hydride (60% dispersion, Aldrich) to a solution of 2.46 g of the 6-(4-benzyloxyphenyl)-4-chloro-7H-pyrrolo[2,3-d]pyrimidine synthesized in Production Example 153-3 in dimethylformamide (30 ml), the mixture was stirred at room temperature for 40 minutes, 1.68 ml (1.3 equivalents) of 2-(chloromethoxy)ethyltrimethylsilane was added, the mixture was stirred at room temperature overnight, and then 20 ml of water and 1 ml of acetic acid were added and liquid separation and extraction were performed with an ethyl acetate:tetrahydrofuran (5:1) mixed solvent. The organic layer was dried over sodium sulfate, concentrated and subjected to NH silica gel column chromatography (ethyl acetate) to obtain 2.83 g of the title compound.

$^1$H-NMR Spectrum: (DMSO-d$_6$) −0.10 (9H, s), 0.84 (2H, t, J=8.0 Hz), 3.62 (2H, t, J=8.0 Hz), 5.20 (2H, s), 5.61 (2H, s), 6.81 (1H, s), 7.19 (2H, d, J=7.7 Hz), 7.33-7.52 (5H, m), 7.88 (2H, d, J=7.7 Hz), 8.70 (1H, s)

Production Example 153-5

4-[6-(4-Benzyloxyphenyl)-7-(2-trimethylsilanylethoxymethyl)-7H-pyrrolo[2,3-d]pyrimidin-4-yloxy]-2-chlorophenylamine After adding 12 ml of dimethylsulfoxide to the 6-(4-benzyloxyphenyl)-4-chloro-7-(2-trimethylsilanylethoxymethyl)-7H-pyrrolo[2,3-d]pyrimidine synthesized in Production Example 153-4, 141 mg (1.5 equivalents) of sodium hydride (60% dispersion, Aldrich) and 507 mg (1.5 equivalents) of 4-amino-3-chlorophenol were added while stirring, and stirring was then continued at room temperature for 10 minutes and then at 135-140° C. for 4 hours. The mixture was returned to room temperature, water was added, and liquid separation and extraction were performed with an ethyl acetate:tetrahydrofuran (5:1) mixed solvent. The organic layer was dried over sodium sulfate, concentrated and subjected to NH silica gel column chromatography (hexane-ethyl acetate) to obtain 1.20 g of the title compound.

$^1$H-NMR Spectrum: (DMSO-d$_6$) −0.90 (9H, s), 0.85 (2H, t, J=8.0 Hz), 3.61 (2H, t, J=8.0 Hz), 5.18 (2H, s), 5.34 (2H, s), 5.59 (2H, s), 6.64 (1H, s,), 6.85 (1H, d, J=8.0 Hz), 6.95-6.99 (1H, m), 7.15-7.20 (3H, m), 7.30-7.55 (5H, m), 7.71 (2H, d, J=8.0 Hz), 8.41 (1H, d, J=1.4 Hz)

Production Example 153-6

1-{4-[6-(4-Benzyloxyphenyl)-7-(2-trimethylsilanylethoxymethyl)-7H-pyrrolo[2,3-d]pyrimidin-4-yloxy]-2-chlorophenyl}-3-cyclopropylurea After dissolving 334 mg of the 4-[6-(4-benzyloxyphenyl)-7-(2-trimethylsilanylethoxymethyl)-7H-pyrrolo[2,3-d]pyrimidin-4-yloxy]-2-chlorophenylamine synthesized in Production Example 153-5 in 4 ml of dimethylformamide, 0.066 ml (1.4 equivalents) of pyridine and 0.102 ml (1.4 equivalents) of phenyl chlorocarbonate were added, and after stirring at room temperature for 2.5 hours, 0.09 ml (2.2 equivalents) of cyclopropylamine was added and the mixture was stirred overnight. Water was added, liquid separation and extraction were performed with ethyl acetate, and the organic layer was washed with saturated brine, dried over sodium sulfate, concentrated and subjected to silica gel column chromatography (hexane-ethyl acetate) to obtain 330 mg of the title compound.

MS Spectrum (ESI): 656 (M+1), 678 (M+23), $^1$H-NMR Spectrum: (DMSO-d$_6$) −0.09 (9H, s), 0.40-0.46 (2H, m), 0.63-0.70 (2H, m), 0.87 (2H, t, J=7.8 Hz), 2.43-2.62 (1H, m), 3.62 (2H, t, J=7.8 Hz), 5.20 (2H, s), 5.60 (2H, s), 6.75 (1H, s), 7.15-7.53 (9H, m), 7.73 (2H, d, J=8.6 Hz), 7.94 (1H, s), 7.93 (1H, s), 8.18 (1H, d, J=9.0 Hz), 8.41 (1H, d, J=1.8 Hz)

Production Example 153-7

1-{2-Chloro-4-[6-(4-hydroxyphenyl)-7-(2-trimethylsilanylethoxymethyl)-7H-pyrrolo[2,3-d]pyrimidin-4-yloxy]-2-phenyl}-3-cyclopropylurea After dissolving 260 mg of the 1-{4-[6-(4-benzyloxyphenyl)-7-(2-trimethylsilanylethoxymethyl)-7H-pyrrolo[2,3-d]pyrimidin-4-yloxy]-2-chlorophenyl}-3-cyclopropylurea synthesized in Production Example 153-6 in 10 ml of ethanol and 5 ml of tetrahydrofuran, 100 mg of platinum oxide was added and the mixture was stirred overnight at room temperature and normal pressure under a hydrogen atmosphere. It was then filtered with celite and concentrated under reduced pressure. The residue was subjected to silica gel column chromatography (hexane-ethyl acetate) to obtain 160 mg of the title compound.

$^1$H-NMR Spectrum: (DMSO-d$_6$) −0.09 (9H, s), 0.40-0.46 (2H, m), 0.63-0.70 (2H, m), 0.86 (2H, t, J=8.1 Hz), 2.53-2.62 (1H, m), 3.62 (2H, t, J=8.1 Hz), 5.58 (2H, s), 6.67 (1H, s,), 6.90 (2H, d, J=8.2 Hz), 7.13-7.22 (2H, m), 7.43-7.47 (1H, m), 7.60 (2H, d, J=8.2 Hz), 7.93 (1H, s), 8.17 (1H, d, J=9.1 Hz), 8.40 (1H, s), 9.38 (1H, brs)

Production Example 153-8

1-{2-Chloro-4-[6-[4-(2-diethylamino-2-hydroxypropoxy)-phenyl]-7-(2-trimethylsilanylethoxymethyl)-7H-pyrrolo[2,3-d]pyrimidin-4-yloxy]-phenyl}-3-cyclopropylurea After dissolving 113 mg of the 1-{2-chloro-4-[6-(4-hydroxyphenyl)-7-(2-trimethylsilanylethoxymethyl)-7H-pyrrolo[2,3-d]pyrimidin-4-yloxy]-2-phenyl}-3-cyclopropylurea synthesized in Production Example 153-7 in 1 ml of dimethylformamide, 120 mg (3.5 equivalents) of 2-chloroethyldiethylamine hydrochloride and 138 mg (5 equivalents) of potassium carbonate were added and the mixture was stirred at 80° C. for 15 hours. The mixture was then returned to room temperature, water was added, and liquid separation and extraction were performed with ethyl acetate. The organic layer was dried over sodium sulfate, concentrated and subjected to NH silica gel column chromatography (hexane-ethyl acetate) to obtain 40 mg of the title compound.

MS Spectrum (ESI): 665 (M+1), $^1$H-NMR Spectrum: (DMSO-d$_6$) −0.09 (9H, s), 0.40-0.47 (2H, m), 0.63-0.70 (2H, m), 0.87 (2H, t, J=8.9 Hz), 0.99 (6H, t, J=8.0 Hz) 2.52-2.62 (5H, m), 2.80 (2H, t, J=8.0 Hz), 3.62

(2H, t, J=8.9 Hz), 4.10 (2H, t, J=8.0 Hz), 5.60 (2H, s), 6.72 (1H, s), 7.08 (2H, d, J=8.1 Hz), 7.17 (1H, d, J=3.2 Hz), 7.21 (1H, dd, J=3.2, 8.4 Hz), 7.46 (1H, d, J=3.2 Hz), 7.71 (2H, d, J=8.1 Hz), 7.94 (1H, s), 8.18 (1H, d, J=8.4 Hz), 8.40 (1H, s,)

Example 154

1-(2-Chloro-4-{6-[4-(2-(1-pyrrolidino)ethoxy)-phenyl]-7H-pyrrolo[2,3-d]pyrimidin-4-yloxy}phenyl)-3-cyclopropylurea The title compound (13 mg) was obtained from 25 mg of 1-{2-chloro-4-[6-[4-(2-pyrrolidinoethoxy)-phenyl]-7-(2-trimethylsilanylethoxymethyl)-7H-pyrrolo[2,3-d]pyrimidin-4-yloxy]-phenyl}-3-cyclopropylurea, in the same manner as Example 153.
MS Spectrum (ESI): 533 (M+1),
$^1$H-NMR Spectrum: (DMSO-$d_6$) 0.40-0.45 (2H, m), 0.60-0.70 (2H, m), 1.65-1.72 (4H, m), 2.47-2.60 (5H, m, covered by DMSO peak), 2.70 (2H, t, J=7.6 Hz), 4.12 (2H, t, J=7.6 Hz), 6.82 (1H, s), 7.02 (2H, d, J=8.5 Hz), 7.13 (1H, d, J=2.6 Hz), 7.17 (1H, dd, J=2.6, 8.5 Hz), 7.41 (1H, d, J=2.6 Hz), 7.87 (2H, d, J=8.5 Hz), 7.91 (1H, s), 8.14 (1H, d, J=8.5 Hz), 8.26 (1H, s), 12.59 (1H, brs)

Production Example 154-1

1-{2-Chloro-4-[6-[4-(2-(1-pyrrolidino)ethoxy)-phenyl]-7-(2-trimethylsilanylethoxymethyl)-7H-pyrrolo[2,3-d]pyrimidin-4-yloxy]phenyl}-3-cyclopropylurea The title compound (27 mg) was obtained from 86 mg of the 1-{2-chloro-4-[6-(4-hydroxyphenyl)-7-(2-trimethylsilanylethoxymethyl)-7H-pyrrolo[2,3-d]pyrimidin-4-yloxy]-2-phenyl}-3-cyclopropylurea synthesized in Production Example 153-7, using 104 mg of 1-(2-chloroethyl)pyrrolidine hydrochloride and 126 mg of potassium carbonate, in the same manner as Production Example 153-8.
MS Spectrum (ESI): 663 (M+1),
$^1$H-NMR Spectrum: (DMSO-$d_6$) −0.09 (9H, s), 0.40-0.44 (2H, m), 0.61-0.69 (2H, m), 0.85 (2H, t, J=8.0 Hz), 1.61-1.76 (4H, m), 2.44-2.61 (5H, m, covered by DMSO peak), 2.86 (2H, t, J=8.0 Hz), 3.61 (2H, t, J=8.0 Hz), 4.13 (2H, t, J=8.0 Hz), 5.79 (2H, s), 6.72 (1H, s), 7.09 (2H, d, J=8.7 Hz), 7.15 (1H, d, J=8.7 Hz), 7.20 (1H, dd, J=2.5, 8.7 Hz), 7.44 (1H, d, J=2.5 Hz), 7.71 (2H, d, J=8.7 Hz), 7.93 (1H, s), 8.16 (1H, d, J=8.7 Hz), 8.39 (1H, s)

Example 155

1-(2-Chloro-4-{6-[4-(2-(1-pyrrolidino)propoxy)phenyl]-7H-pyrrolo[2,3-d]pyrimidin-4-yloxy}phenyl)-3-cyclopropylurea The title compound (11 mg) was obtained from 28 mg of 1-{2-chloro-4-[6-[4-(2-(1-pyrrolidino)propoxy)phenyl]-7-(2-trimethylsilanylethoxymethyl)-7H-pyrrolo[2,3-d]pyrimidin-4-yloxy]phenyl}-3-cyclopropylurea, in the same manner as Example 153.
MS Spectrum (ESI): 547 (M+1), Production Example 155-1

1-{2-Chloro-4-[6-[4-(3-(1-pyrrolidino)propoxy)phenyl]-7-(2-trimethylsilanylethoxymethyl)-7H-pyrrolo[2,3-d]pyrimidin-4-yloxy]phenyl}-3-cyclopropylurea The title compound (28 mg) was obtained from 96 mg of the 1-{2-chloro-4-[6-(4-hydroxyphenyl)-7-(2-trimethylsilanylethoxymethyl)-7H-pyrrolo[2,3-d]pyrimidin-4-yloxy]-2-phenyl}-3-cyclopropylurea synthesized in Production Example 153-7, using 146 mg of 1-(3-chloropropyl)pyrrolidine, 150 mg of potassium carbonate and 15 mg of potassium iodide, in the same manner as Production Example 153-8.
MS Spectrum (ESI): 677 (M+1),
$^1$H-NMR Spectrum: (DMSO-$d_6$) −0.09 (9H, s), 0.39-0.47 (2H, m), 0.63-0.70 (2H, m), 0.87 (2H, t, J=8.0 Hz), 1.63-1.73 (4H, m), 1.88-1.96 (2H, m), 2.40-2.62 (7H, m, covered by DMSO peak), 3.61 (2H, t, J=8.1 Hz), 4.09 (2H, t, J=6.6 Hz), 5.60 (2H, s), 6.72 (1H, s), 7.08 (2H, d, J=8.9 Hz), 7.16 (1H, d, J=2.6 Hz), 7.21 (1H, dd, J=2.4, 8.9 Hz), 7.46 (1H, d, J=2.6 Hz), 7.71 (2H, d, J=8.9 Hz), 7.95 (1H, s), 8.18 (1H, d, J=8.9 Hz), 8.40 (1H, s)

Example 156

1-{2-Chloro-4-[6-[4-((2R)-2-hydroxy-3-diethylaminopropoxy)phenyl]-7H-pyrrolo[2,3-d]pyrimidin-4-yloxy]phenyl}-3-cyclopropylurea The title compound (11 mg) was obtained from 22 mg of 1-{2-chloro-4-[6-[4-((2S)-2-hydroxy-3-diethylaminopropoxy)phenyl]-7-(2-trimethylsilanylethoxymethyl)-7H-pyrrolo[2,3-d]pyrimidin-4-yloxy]phenyl}-3-cyclopropylurea, in the same manner as Example 153.
MS Spectrum (ESI): 565 (M+1),
$^1$H-NMR Spectrum: (DMSO-$d_6$) 0.40-0.47 (2H, m), 0.63-0.70 (2H, m), 0.96 (6H, t, J=6.6 Hz) 2.45-2.63 (7H, m, covered by DMSO peak), 3.80-4.10 (3H, m), 6.93 (1H, s), 7.04 (2H, d, J=8.6 Hz), 7.15 (1H, d, J=2.2 Hz), 7.19 (1H, dd, J=2.2, 8.6 Hz), 7.43 (1H, d, J=2.2 Hz), 7.88 (2H, d, J=8.6 Hz), 7.93 (1H, s), 8.16 (1H, d, J=8.6 Hz), 8.28 (1H, s), 12.60 (1H, brs)

Production Example 156-1

1-{2-Chloro-4-[6-[4-((2S)-2-hydroxy-3-diethylaminopropoxy)phenyl]-7-(2-trimethylsilanylethoxymethyl)-7H-pyrrolo[2,3-d]pyrimidin-4-yloxy]phenyl}-3-cyclopropylurea After dissolving 75 mg of the 1-{2-chloro-4-[6-(4-hydroxyphenyl)-7-(2-trimethylsilanylethoxymethyl)-7H-pyrrolo[2,3-d]pyrimidin-4-yloxy]-2-phenyl}-3-cyclopropylurea synthesized in Production Example 153-7 in 1 ml of dimethylformamide, 91 mg (3 equivalents) of (2S)-(+)-glycidyl p-toluenesulfonate and 92 mg (5 equivalents) of potassium carbonate were added, and the mixture was stirred at 75° C. for 8 hours. After returning it to room temperature, the reaction system was filtered with a Kiriyama funnel, 0.1 ml of diethylamine was added to the filtrate, and the mixture was stirred at 70° C. for 8 hours. Water was then added, and liquid separation and extraction were performed with ethyl acetate and tetrahydrofuran. The organic layer was concentrated and subjected to NH silica gel column chromatography (hexane-ethyl acetate) to obtain 24 mg of the title compound.
MS Spectrum (ESI): 695 (M+1),
$^1$H-NMR Spectrum: (DMSO-$d_6$) −0.09 (9H, s), 0.39-0.47 (2H, m), 0.63-0.70 (2H, m), 0.86 (2H, t, J=8.3 Hz), 0.97 (6H, t, J=7.0 Hz,), 2.38-2.60 (7H, m), 3.61 (2H, t, J=8.3 Hz), 3.83-4.11 (3H, m), 4.82 (1H, brs), 5.59 (2H, s), 6.73 (1H, s), 7.08 (2H, d, J=8.5 Hz), 7.18 (1H, d, J=2.7 Hz), 7.21 (1H, dd, J=2.7, 8.5 Hz), 7.45 (1H, d, J=2.7 Hz), 7.71 (2H, d, J=8.5 Hz), 7.94 (1H, s), 8.18 (1H, d, J=8.5 Hz), 8.40 (1H, s,)

Example 157

1-{2-Chloro-4-[6-[4-((2R)-2-hydroxy-3-diethylaminopropoxy)phenyl]-7-(2-trimethylsilanylethoxymethyl)-7H-pyrrolo[2,3-d]pyrimidin-4-yloxy]phenyl}-3-cyclopropylurea The title compound (11 mg) was obtained from 22 mg of 1-{2-chloro-4-[6-[4-((2R)-2-hydroxy-3-diethylaminopropoxy)phenyl]-7-(2-trimethylsilanylethoxymethyl)-7H-pyrrolo[2,3-d]pyrimidin-4-yloxy]phenyl}-3-cyclopropylurea, in the same manner as Example 153.

MS Spectrum (ESI): 565 (M+1), $^1$H-NMR Spectrum: (DMSO-$d_6$) 0.40-0.47 (2H, m), 0.63-0.70 (2H, m), 0.96 (6H, t, J=6.6 Hz) 2.45-2.63 (7H, m, covered by DMSO peak), 3.80-4.10 (3H, m), 6.93 (1H, s), 7.04 (2H, d, J=8.6 Hz), 7.16 (1H, d, J=2.2 Hz), 7.19 (1H, dd, J=2.2, 8.6 Hz), 7.43 (1H, d, J=2.2 Hz), 7.89 (2H, d, J=8.6 Hz), 7.94 (1H, s), 8.16 (1H, d, J=8.6 Hz), 8.28 (1H, s) 12.60 (1H, brs)

Production Example 157-1

1-{2-Chloro-4-[6-[4-((2R)-2-hydroxy-3-diethylaminopropoxy)phenyl]-7-(2-trimethylsilanylethoxymethyl)-7H-pyrrolo[2,3-d]pyrimidin-4-yloxy]phenyl}-3-cyclopropylurea The title compound (62 mg) was obtained from 127 mg of 1-{2-chloro-4-[6-(4-hydroxyphenyl)-7-(2-trimethylsilanylethoxymethyl)-7H-pyrrolo[2,3-d]pyrimidin-4-yloxy]-2-phenyl}-3-cyclopropylurea, using 154 mg of (2R)-(−)-glycidyl p-toluenesulfonate, 155 mg of potassium carbonate and 0.15 ml of diethylamine, in the same manner as Production Example 153-9.

MS Spectrum (ESI): 695 (M+1), $^1$H-NMR Spectrum: (DMSO-$d_6$) −0.09 (9H, s), 0.39-0.47 (2H, m), 0.63-0.70 (2H, m), 0.86 (2H, t, J=8.3 Hz), 0.97 (6H, t, J=7.0 Hz) 2.38-2.60 (7H, m, covered by DMSO peak), 3.61 (2H, t, J=8.3 Hz), 3.83-4.11 (3H, m), 4.82 (1H, brs), 5.60 (2H, s), 6.73 (1H, s), 7.09 (2H, d, J=8.5 Hz), 7.16 (1H, d, J=2.7 Hz), 7.20 (1H, dd, J=2.7, 8.5 Hz), 7.45 (1H, d, J=2.7 Hz), 7.71 (2H, d, J=8.5 Hz), 7.94 (1H, s), 8.18 (1H, d, J=8.5 Hz), 8.40 (1H, s)

Example 158

1-(2-Chloro-4-{6-[4-((2S)-2-hydroxy-3-pyrrolidinopropoxy)phenyl]-7H-pyrrolo[2,3-d]pyrimidin-4-yloxy]phenyl}-3-cyclopropylurea The title compound (14 mg) was obtained from 30 mg of 1-{2-chloro-4-[6-[4-(2-hydroxy-3-pyrrolidinopropoxy)phenyl]-7-(2-trimethylsilanylethoxymethyl)-7H-pyrrolo[2,3-d]pyrimidin-4-yloxy]phenyl}-3-cyclopropylurea, in the same manner as Example 153.

MS Spectrum (ESI): 563 (M+1), $^1$H-NMR Spectrum: (DMSO-$d_6$) 0.40-0.47 (2H, m), 0.60-0.70 (2H, m), 1.62-1.74 (4H, m), 2.40-2.70 (7H, m, covered by DMSO peak), 3.88-4.10 (3H, m), 4.92 (1H, brs) 6.94 (1H, s), 7.04 (2H, d, J=8.6 Hz), 7.15 (1H, d, J=2.4 Hz), 7.20 (1H, dd, J=2.4, 8.6 Hz), 7.44 (1H, d, J=2.4 Hz), 7.88 (2H, d, J=8.6 Hz), 7.94 (1H, s,), 8.16 (1H, d, J=8.6 Hz), 8.28 (1H, s) 12.60 (1H, brs)

Production Example 158-1

1-{2-Chloro-4-[6-[4-(2S)-2-hydroxy-3-pyrrolidinopropoxy)phenyl]-7-(2-trimethylsilanylethoxymethyl)-7H-pyrrolo[2,3-d]pyrimidin-4-yloxy]phenyl}-3-cyclopropylurea The title compound (30 mg) was obtained from 81 mg of 1-{2-chloro-4-[6-(4-hydroxyphenyl)-7-(2-trimethylsilanylethoxymethyl)-7H-pyrrolo[2,3-d]pyrimidin-4-yloxy]-2-phenyl}-3-cyclopropylurea, using 98 mg of (2S)-(+)-glycidyl p-toluenesulfonate, 99 mg of potassium carbonate and 0.1 ml of pyrrolidine, in the same manner as Production Example 153-9.

MS Spectrum (ESI): 693 (M+1), $^1$H-NMR Spectrum: (DMSO-$d_6$) −0.09 (9H, s), 0.40-0.46 (2H, m), 0.62-0.70 (2H, m), 0.87 (2H, t, J=8.4 Hz), 1.62-1.72 (4H, m), 2.40-2.68 (7H, m, covered by DMSO peak), 3.62 (2H, t, J=8.4 Hz), 3.90-4.10 (3H, m), 4.92 (1H, brs), 5.60 (2H, s,) 6.72 (1H, s,), 7.10 (2H, d, J=8.8 Hz), 7.17 (1H, d, J=2.4 Hz), 7.21 (1H, dd, J=2.4, 8.8 Hz), 7.46 (1H, d, J=2.4 Hz), 7.71 (2H, d, J=8.8 Hz), 7.95 (1H, s), 8.18 (1H, d, J=8.8 Hz), 8.41 (1H, s)

Example 159

1-(2-Chloro-4-{6-[4-((2R)-2-hydroxy-3-pyrrolidinopropoxy)phenyl]-7H-pyrrolo[2,3-d]pyrimidin-4-yloxy]phenyl}-3-cyclopropylurea The title compound (24 mg) was obtained from 70 mg of 1-{2-chloro-4-[6-[4-(2-hydroxy-3-pyrrolidinopropoxy)phenyl]-7-(2-trimethylsilanylethoxymethyl)-7H-pyrrolo[2,3-d]pyrimidin-4-yloxy]phenyl}-3-cyclopropylurea, in the same manner as Example 153.

MS Spectrum (ESI): 563 (M+1), $^1$H-NMR Spectrum: (DMSO-$d_6$) 0.40-0.47 (2H, m), 0.60-0.70 (2H, m), 1.73-1.87 (4H, m), 2.49-2.60 (7H, m, covered by DMSO peak), 3.94-4.19 (3H, m), 4.92 (1H, brs) 6.94 (1H, d, J=1.2 Hz), 7.06 (2H, d, J=8.6 Hz), 7.15-7.22 (2H, m), 7.43 (1H, d, J=2.4 Hz), 7.91 (2H, d, J=8.6 Hz), 7.96 (1H, s), 8.17 (1H, d, J=8.6 Hz), 8.29 (1H, s) 12.61 (1H, brs)

Production Example 159-1

1-{2-Chloro-4-[6-[4-((2R)-2-hydroxy-3-pyrrolidinopropoxy)phenyl]-7-(2-trimethylsilanylethoxymethyl)-7H-pyrrolo[2,3-d]pyrimidin-4-yloxy]phenyl}-3-cyclopropylurea The title compound (72 mg) was obtained from 128 mg of 1-{2-chloro-4-[6-(4-hydroxyphenyl)-7-(2-trimethylsilanylethoxymethyl)-7H-pyrrolo[2,3-d]pyrimidin-4-yloxy]phenyl}-3-cyclopropylurea, using 155 mg of (2R)-(−)-glycidyl p-toluenesulfonate, 156 mg of potassium carbonate and 0.13 ml of pyrrolidine, in the same manner as Production Example 153-9.

MS Spectrum (ESI): 693 (M+1), $^1$H-NMR Spectrum: (DMSO-$d_6$) −0.09 (9H, s), 0.40-0.46 (2H, m), 0.60-0.70 (2H, m), 0.87 (2H, t, J=8.4 Hz), 1.62-1.72 (4H, m), 2.40-2.68 (7H, m, covered by DMSO peak), 3.61 (2H, t, J=8.4 Hz), 3.90-4.10 (3H, m), 4.92 (1H, brs,), 5.60 (2H, s,), 6.72 (1H, s), 7.09 (2H, d, J=8.8 Hz), 7.16 (1H, d, J=2.4 Hz), 7.20 (1H, dd, J=2.4, 8.8 Hz), 7.45 (1H, d, J=2.4 Hz), 7.71 (2H, d, J=8.8 Hz), 7.95 (1H, s), 8.18 (1H, d, J=8.8 Hz), 8.40 (1H, s)

Example 160

1-(2-Chloro-4-{6-[4-(2-diethylaminopropoxy)phenyl]-7H-pyrrolo[2,3-d]pyrimidin-4-yloxy}phenyl)-3-cyclopropylurea The title compound (2 mg) was obtained from 17 mg of 1-{2-chloro-4-[6-[4-(2-diethylaminopropoxy)phenyl]-7-(2-trimethylsilanylethoxymethyl)-7H-pyrrolo[2,3-d]pyrimidin-4-yloxy]phenyl}-3-cyclopropylurea, in the same manner as Example 153.
MS Spectrum (ESI): 549 (M+1),

Production Example 160-1

4-[4-(4-Amino-3-chlorophenoxy)-7-(2-trimethylsilanylethoxymethyl)-7H-pyrrolo[2,3-d]pyrimidin-6-yl]phenol After dissolving 255 mg of the 4-[6-(4-benzyloxyphenyl)-7-(2-trimethylsilanylethoxymethyl)-7H-pyrrolo[2,3-d]pyrimidin-4-yloxy]-2-chlorophenyl amine synthesized in Production Example 153-5 in 10 ml of ethanol and 3 ml of tetrahydrofuran, 100 mg of platinum oxide was added and the mixture was stirred overnight at room temperature under normal pressure in a hydrogen atmosphere. After filtering with celite, the filtrate was concentrated under reduced pressure. The residue was subjected to silica gel column chromatography (hexane-ethyl acetate) to obtain 105 mg of the title compound.
1H-NMR Spectrum: (DMSO-$d_6$) −0.09 (9H, s), 0.83 (2H, t, J=7.8 Hz), 3.52 (2H, t, J=7.8 Hz), 5.33 (2H, s), 5.54 (2H, s), 6.55 (1H, s), 6.83 (1H, d, J=8.8 Hz), 6.88 (2H, d, J=8.8 Hz), 6.94 (1H, dd, J=2.4, 8.8 Hz), 7.17 (1H, d, J=2.4 Hz), 7.58 (2H, d, J=8.8 Hz), 8.35 (1H, s), 9.84 (1H, brs)

Production Example 160-2

2-Chloro-4-[6-[4-(3-diethylaminopropoxy)phenyl]-7-(2-trimethylsilanylethoxymethyl)-7H-pyrrolo[2,3-d]pyrimidin-4-yloxy]phenylamine After dissolving 47 mg of the 4-[4-(4-amino-3-chlorophenoxy)-7-(2-trimethylsilanylethoxymethyl)-7H-pyrrolo[2,3-d]pyrimidin-6-yl]phenol synthesized in Production Example 160-1 in 0.5 ml of dimethylformamide, there were added 56 mg (3.1 equivalents) of (3-chloropropyl)diethylamine hydrochloride and 94 mg (7 equivalents) of potassium carbonate, and the mixture was stirred at 80° C. for 24 hours. It was then returned to room temperature, water was added, and liquid separation and extraction were performed with an ethyl acetate:tetrahydrofuran (5:1) mixed solvent. The organic layer was dried over sodium sulfate, concentrated and subjected to NH silica gel column chromatography (hexane-ethyl acetate) to obtain 49 mg of the title compound.
Ms Spectrum (ESI): 596 (M+1),

Production Example 160-3

1-{2-Chloro-4-[6-[4-(3-diethylaminopropoxy)phenyl]-7-(2-trimethylsilanylethoxymethyl)-7H-pyrrolo[2,3-d]pyrimidin-4-yloxy]phenyl}-3-cyclopropylurea After dissolving the 2-chloro-4-[6-[4-(3-diethylaminopropoxy)phenyl]-7-(2-trimethylsilanylethoxymethyl)-7H-pyrrolo[2,3-d]pyrimidin-4-yloxy]phenylamine synthesized in Production Example 160-2 in 0.6 ml of dimethylsulfoxide, 23 mg of phenyl cyclopropylcarbamate was added and the mixture was stirred at 80° C. for 1.5 hours. After further adding 75 mg of phenyl N-cyclopropylcarbamate and stirring at 100° C. for 5 hours, 70 mg of the same reagent was added prior to stirring overnight. The mixture was then returned to room temperature, water was added, and liquid separation and extraction were performed with an ethyl acetate:tetrahydrofuran (5:1) mixed solvent. The organic layer was dried over sodium sulfate, concentrated and subjected to NH silica gel column chromatography (hexane-ethyl acetate) to obtain 18 mg of the title compound.
MS Spectrum (ESI): 679 (M+1),

Example 161

1-(4-Fluorophenyl)-3-[4-(6-phenyl-7H-pyrrolo[2,3-d]pyrimidin-4-ylsulfanyl)thiazol-5-yl]urea After adding 323 mg of iron powder, 12 ml of ethanol and 2.4 ml of water to 4-(5-nitrothiazol-2-ylsulfanyl)-6-phenyl-7H-pyrrolo[2,3-d]pyrimidine, the mixture was stirred at 80° C. for 10 minutes and then returned to room temperature, after which 7.5 mg of potassium carbonate was added, the mixture was filtered with celite, and ethyl acetate and water were added to the filtrate for liquid separation and extraction. The organic layer was washed with saturated brine, dried over anhydrous sodium sulfate, filtered with plug cotton and concentrated to dryness to obtain 310 mg of a solid. The solid was dissolved in 10 ml of tetrahydrofuran, 10 ml of toluene and 10 ml of acetonitrile under reflux, and then 0.1 ml of 4-fluorophenyl isocyanate was added and the mixture was stirred for 2 hours. It was then returned to room temperature, and the reaction system was concentrated, subjected to silica gel column chromatography and dried to obtain 33 mg of the title compound.
$^1$H-NMR Spectrum: (DMSO-$d_6$) 6.71 (1H, s,), 7.12 (2H, m), 7.36-7.52 (5H, m), 7.62 (1H, s), 7.92 (2H, d, J=8.1 Hz), 8.55 (1H, s), 9.12 (1H, s), 10.24 (1H, s), 12.82 (1H, brs)

The intermediates were synthesized in the following manner.

Production Example 161-1

6-Phenyl-7H-pyrrolo[2,3-d]pyrimidine-4-thiol

After adding 6.19 g of phosphorus pentasulfide, 6.24 g of sodium bicarbonate and 25 ml of diglyme to 2.45 g of the 6-phenyl-7H-pyrrolo[2,3-d]pyrimidin-4-ol described in WO97/02266 and PCT/EP96/02728, and stirring the mixture for 1 hour, an additional 3 g of phosphorus pentasulfide and 3 g of sodium bicarbonate were added and the mixture was stirred for 1 hour. There were further added another 3 g of phosphorus pentasulfide and 3 g of sodium bicarbonate, and the mixture was stirred for 1 hour. It was then returned to room temperature, water was added, the mixture was stirred for 10 minutes, and the precipitated crystals were filtered out, washed with water and dried to obtain 2.5 g of the title compound.
$^1$H-NMR Spectrum: (DMSO-$d_6$) 7.05 (1H, d, J=2.1 Hz), 7.32 (1H, t, J=7.9 Hz), 7.43 (2H, t, J=7.9 Hz), 7.88 (2H, d, J=7.9 Hz), 8.05 (1H, s), 12.68 (1H, brs), 13.36 (1H, brs)

Production Example 161-2

4-(5-Nitrothiazol-2-ylsulfanyl)-6-phenyl-7H-pyrrolo[2,3-d]pyrimidine

After adding 1.06 g of 2-bromo-5-nitrothiazole and 15 ml of dimethlforamide to 6-phenyl-7H-pyrrolo[2,3-d-]pyrimidine-4-thiol, the mixture was stirred at room temperature for 3 hours, and then 0.45 ml of pyridine was added and the mixture was stirred overnight. Water was added, and the precipitated crystals were filtered out, blow-dried and dried under reduced pressure to obtain 1.20 g of the title compound.

$^1$H-NMR Spectrum: (DMSO-d$_6$) 7.26 (1H, J=2.4 Hz), 7.36-7.54 (3H, m), 8.01 (2H, d, J=7.8 Hz), 8.90 (1H, s,), 8.94 (1H, s,), 13.11 (1H, brs), Example 162

1-[5-(6-Phenyl-7H-pyrrolo[2,3-d]pyrimidin-4-ylsulfanyl)-3-thiazol-2-ylurea

After adding 265 mg of phenyl 2-thiazoylcarbamate and ml of dimethylsulfoxide to 354 mg of 5-(6-phenyl-7H-pyrrolo[2,3-d]pyrimidin-4-ylsulfanyl)-2-thiophenylamine, the mixture was stirred at 80° C. for 2 hours. Ethyl acetate and water were added for liquid separation and extraction, the organic layer was concentrated and subjected to silica gel column chromatography and dried, and the obtained solid was washed with ether to obtain 170 mg of the title compound.

$^1$H-NMR Spectrum: (DMSO-d$_6$) 6.55 (1H, brs), 6.94 (1H, d, J=4.2 Hz), 7.05 (1H, d, J=1.9 Hz), 7.26 (1H, d, J=4.2 Hz), 7.28-7.50 (4H, m), 7.82-7.90 (3H, m), 8.49 (1H, s), 10.42 (1H, brs), 12.54 (1H, brs)

The intermediates were synthesized in the following manner.

Production Example 162-1

4-(5-Nitro-2-thiophenylsulfanyl)-6-phenyl-7H-pyrrolo[2,3-d]pyrimidine

After adding 1.05 g of 2-bromo-5-nitrothiophene, 0.95 g of potassium carbonate and 15 ml of dimethylformamide to the 6-phenyl-7H-pyrrolo[2,3-d]pyrimidine-4-thiol synthesized in Production Example 161-1 and stirring the mixture overnight at room temperature, water was added and the precipitated crystals were filtered out, blow-dried and dried under reduced pressure to obtain 1.30 g of the title compound.

$^1$H-NMR Spectrum: (DMSO-d$_6$) 7.08 (1H, s), 7.40 (1H, t, J=8.0 Hz), 7.48 (2H, t, J=8.0 Hz), 7.56 (1H, d, J=4.1 Hz), 7.98 (2H, d, J=8.0 Hz), 8.16 (1H, d, J=4.1 Hz), 8.70 (1H, s), 12.68 (1H, brs)

Production Example 162-2

5-(6-Phenyl-7H-pyrrolo[2,3-d]pyrimidin-4-ylsulfanyl)-thiophen-2-ylamine

After adding 543 mg of iron powder, 1.06 g of ammonium chloride, 10 ml of dimethylformamide, 20 ml of ethanol and 5 ml of water to the 4-(5-nitro-2-thiophenylsulfanyl)-6-phenyl-7H-pyrrolo[2,3-d]pyrimidine synthesized in Production Example 162-1, the mixture was stirred at 90° C. for 2 hours, 30 ml of tetrahydrofuran was added, and then the mixture was returned to room temperature and filtered with celite, and ethyl acetate and water were added to the filtrate for liquid separation and extraction. The organic layer was dried over anhydrous sodium sulfate, filtered with plug cotton and concentrated to dryness to obtain 435 mg of the title compound.

MS Spectrum (ESI): 325 (M+1)

$^1$H-NMR Spectrum: (DMSO-d$_6$) 5.98 (1H, d, J=4.2 Hz), 6.24 (2H, s), 6.27 (1H, d, J=2.0 Hz), 7.00 (1H, d, J=4.2 Hz), 7.30-7.50 (3H, m), 7.80 (2H, d, J=7.6 Hz), 8.46 (1H, s), 12.63 (1H, brs)

Example 163

4-{4-[3-(4-Fluorophenyl)ureido]phenoxy)-7H-pyrrolo[2,3-d]pyrimidine-6-carboxylic acid ethyl ester After dissolving 90 mg of ethyl 4-(4-aminophenoxy)-7H-pyrrolo[2,3-d]pyrimidine-6-carboxylate in 3 ml of toluene and 1 ml of acetonitrile at 110° C., 16.6 µl of 4-fluorophenyl isocyanate was added and the mixture was stirred for 1 hour under reflux. After standing at room temperature, the precipitated crystals were filtered out and dried to obtain 110 mg of the title compound.

$^1$H-NMR Spectrum: (DMSO-d$_6$) 1.31 (3H, t, J=7.9 Hz), 4.32 (2H, q, J=7.9 Hz), 7.07-7.54 (9H, m), 8.42 (1H, s), 8.72 (1H, s), 8.76 (1H, s), 13.03 (1H, brs)

The intermediates were synthesized in the following manner.

Production Example 163-1

4-(4-Nitrophenoxy)-7H-pyrrolo[2,3-d]pyrimidine-6-carboxylic acid ethyl ester

After adding 390 mg of 4-nitrophenol, 703 mg of potassium carbonate and 8.7 ml of dimethylformamide to 577 mg of the 4-chloroethoxycarbonyl-7H-pyrrolo[2,3-d]pyrimidine described in WO9702266(A1) and stirring the mixture at 120° C. for 4 hours, 40 mg of 4-nitrophenol was further added and the mixture was stirred for 1.5 hours. After returning the mixture to room temperature, water was added, liquid separation and extraction were performed with an ethyl acetate-tetrahydrofuran mixed solvent, and the organic layer was washed with saturated brine, dried over anhydrous sodium sulfate, filtered with plug cotton and concentrated to dryness to obtain a solid which was then washed with ether to obtain 520 mg of the title compound.

$^1$H-NMR Spectrum: (DMSO-d$_6$) 1.33 (3H, t, J=7.9 Hz), 4.35 (2H, q, J=7.9 Hz), 7.28 (1H, s), 7.56-7.64 (2H, m), 8.30-8.38 (2H, m), 8.46 (1H, s), 13.21 (1H, brs)

Production Example 163-2

4-(4-Aminophenoxy)-7H-pyrrolo[2,3-d]pyrimidine-6-carboxylic acid ethyl ester

After adding 110 mg of iron powder, 220 mg of ammonium chloride, 10 ml of ethanol and 2 ml of water to 4-(4-nitrophenoxy)-7H-pyrrolo[2,3-d]pyrimidine-6-carboxylic acid ethyl ester, the mixture was stirred at 80-85° C. for 2.5 hours. After returning the mixture to room temperature, 20 ml of tetrahydrofuran was added, the mixture was stirred for 5 minutes and filtered with celite, and 100 ml of ethyl acetate and 50 ml of water were added to the filtrate for liquid separation and extraction. The organic layer was washed with saturated brine, dried over anhydrous sodium sulfate, filtered with plug cotton and concentrated to dryness to obtain 90 mg of the title compound.

$^1$H-NMR Spectrum: (DMSO-d$_6$) 1.31 (3H, t, J=7.9 Hz), 4.31 (2H, q, J=7.9 Hz), 5.10 (2H, s), 6.56-6.62 (2H, m), 6.86-9.92 (3H, m), 8.40 (1H, s), 12.98 (1H, brs)

Example 164

4-{4-[3-(4-Fluorophenyl)ureido]phenoxy)-7H-pyrrolo[2,3-d]pyrimidine-6-carboxylic acid After adding 7 ml of ethanol, 7 ml of water and 31 mg of lithium hydroxide monohydrate to 75 mg of the 4-{4-[3-(4- fluorophenyl)ureido]phenoxy)-7H-pyrrolo[2,3-d]pyrimidine-6-carboxylic acid ethyl ester synthesized in Example 163 and stirring the mixture at 40-45° C. for 24 hours, it was neutralized with 2N HCl and concentrated to dryness to obtain 40 mg of the title compound.

$^1$H-NMR Spectrum: (DMSO-$d_6$) 6.83 (1H, s), 7.06-7.16 (2H, m), 7.19 (2H, m), 7.44-7.48 (2H, m), 7.51 (2H, d, J=8.0 Hz), 8.39 (1H, s), 8.72 (1H, s), 8.76 (1H, s), 12.88 (1H, brs)

Example 165

4-{4-[3-(4-Fluorophenyl)ureido]phenoxyl}-7H-pyrrolo[2,3-d]pyrimidine-6-carboxylic(4-methylpiperazin)amide After adding 1 ml of dimethylformamide, 47 μl of triethylamine, 18.5 μl of diphenylphosphoryl azide and 8.2 μl of 1-methylpiperazine to 12 mg of the 4-{4-[3-(4-fluorophenyl)ureido]phenoxy)-7H-pyrrolo[2,3-d]pyrimidine-6-carboxylic acid synthesized in Example 164, the mixture was stirred overnight at room temperature. Water was added, and the mixture was subjected to liquid separation and extraction with an ethyl acetate-tetrahydrofuran mixed solvent and to NH silica gel column chromatography (ethyl acetate-methanol) to obtain 27 mg of the title compound.

$^1$H-NMR Spectrum: (DMSO-$d_6$) 2.18 (3H, s), 2.28-2.48 (4H, m), 3.58-3.70 (4H, m), 6.56 (1H, s), 7.06-7.56 (8H, m), 8.36 (1H, d, J=1.7 Hz), 8.78 (1H, s), 8.84 (1H, s), 12.67 (1H, brs)

Example 166

4-{4-[3-(4-Fluorophenyl)ureido]phenoxy}-7H-pyrrolo[2,3-d]pyrimidine-6-carboxylic[4-(3-aminopropyl)morpholin]amide After adding 0.8 ml of dimethylformamide, 21 μl of triethylamine, 9.5 μl of diphenylphosphoryl azide (DPPA) and 6.5 μl of 4-(3-aminopropyl)morpholine to 12 mg of the 4-{4-[3-(4-fluorophenyl)ureido]phenoxy}-7H-pyrrolo[2,3-d]pyrimidine-6-carboxylic acid synthesized in Production Example 164, the mixture was stirred at room temperature for 2 days. Saturated aqueous ammonium chloride solution was added, liquid separation and extraction were performed with an ethyl acetate-tetrahydrofuran mixed solvent, and the organic layer was washed with saturated brine, dried over anhydrous sodium sulfate, filtered with plug cotton and concentrated to dryness to obtain 9 mg of the title compound.

MS Spectrum (ESI): 534 (M+1)

$^1$H-NMR Spectrum: (DMSO-$d_6$) 1.62-1.74 (2H, m), 2.20-2.42 (6H, m), 2.88-2.98 (2H, m), 3.46-3.62 (4H, m), 7.06-7.56 (9H, m), 8.34 (1H, s), 8.84-8.90 (2H, m), 12.68 (1H, brs)

Example 167

1-(4-Fluorophenyl)-3-[4-(6-hydroxymethyl-7H-pyrrolo[2,3-d]pyrimidin-4-yloxy)phenyl]urea After adding 9 ml of tetrahydrofuran to 55 mg of the 4-{4-[3-(4-fluorophenyl)ureido]phenoxy)-7H-pyrrolo[2,3-d]pyrimidine-6-carboxylic acid ethyl ester synthesized in Example 163 and stirring the mixture, 25 mg of lithium aluminum hydride was added at room temperature and the mixture was stirred for 2 days. Water was then added, liquid separation and extraction were performed with an ethyl acetate-tetrahydrofuran mixed solvent, and the organic layer was filtered with celite and concentrated to dryness to obtain 35 mg of the title compound.

MS Spectrum (ESI): 394 (M+1), 416 (M+23)

$^1$H-NMR Spectrum: (DMSO-$d_6$) 4.55 (2H, d, J=6.7 Hz), 5.32 (1H, t, J=6.7 Hz), 6.84 (1H, s), 7.06-7.55 (8H, m), 8.22 (1H, s), 8.74 (1H, s), 8.76 (1H, s), 12.11 (1H, brs)

Example 168

1-(4-Fluorophenyl)-3-[4-(6-formyl-7H-pyrrolo[2,3-d]pyrimidin-4-yloxy)phenyl]urea After adding 3 ml of chloroform and 50 mg of manganese dioxide to 18 mg of 1-(4-fluorophenyl)-3-[4-(6-hydroxymethyl-7H-pyrrolo[2,3-d]pyrimidin-4-yloxy)phenyl]urea, the mixture was stirred overnight at room temperature. Tetrahydrofuran and ethyl acetate were added to the reaction system, and the mixture was filtered with celite and concentrated to dryness to obtain 16 mg of the title compound.

$^1$H-NMR Spectrum: (DMSO-$d_6$) 6.82 (1H, s), 7.03-7.60 (8H, m), 8.46 (1H, s), 8.71 (1H, s), 8.75 (1H, s), 9.86 (1H, s), 13.08 (1H, brs)

Example 169

1-(4-Fluorophenyl)-3-[4-(6-morpholin-4-ylmethyl-7H-pyrrolo[2,3-d]pyrimidin-4-yloxy)phenyl]urea After adding 0.5 ml of tetrahydrofuran, 10 μl of morpholine and 26 mg of sodium triacetoxyborohydride to the 1-(4-fluorophenyl)-3-[4-(6-formyl-7H-pyrrolo[2,3-d]pyrimidin-4-yloxy)phenyl]urea synthesized in Example 168, the mixture was stirred overnight at room temperature. The reaction system was subjected to liquid separation and extraction with a tetrahydrofuran-ethyl acetate mixed solvent, and then dried over anhydrous sodium sulfate and concentrated to dryness to obtain 5 mg of the title compound.

MS Spectrum (ESI): 463 (M+1)

Example 170

1-(4-Fluorophenyl)-3-{4-[6-(4-methyl-1-piperazylmethyl)-1-7H-pyrrolo[2,3-d]pyrimidin-4-yloxy]phenyl}urea After adding 0.4 ml of tetrahydrofuran, 11 μl of 1-methylpiperazine and 23 mg of sodium triacetoxyborohydride to the 1-(4-fluorophenyl)-3-[4-(6-formyl-7H-pyrrolo[2,3-d]pyrimidin-4-yloxy)phenyl]urea synthesized in Example 168, the mixture was stirred overnight at room temperature. The reaction system was subjected to liquid separation and extraction with a tetrahydrofuran-ethyl acetate mixed solvent, and then dried over anhydrous sodium sulfate and concentrated to dryness to obtain 5 mg of the title compound.

MS Spectrum (ESI): 476 (M+1)

Example 171

1-(4-Fluorophenyl)-3-[4-(6-phenyl-7H-pyrrolo[2,3-d]pyrimidin-4-yloxy)phenyl]urea After dissolving 40 mg of 4-(6-phenyl-7H-pyrrolo[2,3-d]pyrimidin-4-yloxy)phenylamine in 4.5 ml of toluene and 4.5 ml of acetonitrile at 110° C., 4-fluorophenylisocyanate (16.6 μl) was added and the mixture was stirred for 1 hour. After returning the mixture to room temperature, the precipitated crystals were filtered out and dried to obtain 37 mg of the title compound.

MS Spectrum (ESI): 440 (M+1), 462 (M+23)

$^1$H-NMR Spectrum: (DMSO-d$_6$) 7.02 (1H, s), 7.06-7.52 (11H, m), 7.94 (2H, d, J=8.0 Hz), 8.28 (1H, s), 8.77 (1H, s), 8.79 (1H, s), 12.68 (1H, brs)

The intermediates were synthesized in the following manner.

Production Example 171-1

4-(4-Nitrophenoxy)-6-phenyl-7H-pyrrolo[2,3-d]pyrimidine

After adding 123 mg of 4-nitrophenol, 136 mg of potassium carbonate and 1.5 ml of dimethylformamide to 113 mg of the 4-chloro-6-phenyl-7H-pyrrolo[2,3-d]pyrimidine described in WO97/02266 and PCT/EP96/02728, and stirring the mixture for 15 hours at 130-135° C., and additional 60 mg of 4-nitrophenol and 75 mg of potassium carbonate were added and the mixture was stirred for 6 hours. After returning the mixture to room temperature, water was added, liquid separation and extraction were performed with an ethyl acetate-tetrahydrofuran mixed solvent, and the solid obtained by concentration to dryness was washed with ether to obtain 112 mg of the title compound.

$^1$H-NMR Spectrum: (DMSO-d$_6$) 7.13 (1H, s), 7.37 (1H, t, J=7.7 Hz), 7.47 (2H, t, J=7.7 Hz), 7.56-7.61 (2H, m), 7.74-8.00 (2H, m), 8.30-8.38 (3H, m), 12.82 (1H, brs)

Production Example 171-2

4-(6-Phenyl-7H-pyrrolo[2,3-d]pyrimidin-4-yloxy)phenylamine

After adding 110 mg of iron powder, 220 mg of ammonium chloride, 10 ml of ethanol and 2 ml of water to 110 mg of 4-(4-nitrophenoxy)-6-phenyl-7H-pyrrolo[2,3-d]pyrimidine, the mixture was stirred at 80-85° C. for 2.5 hours. After returning the mixture to room temperature, 20 ml of tetrahydrofuran was added, and the mixture was stirred for 5 minutes and filtered with celite, after which 100 ml of ethyl acetate and 50 ml of water were added to the filtrate for liquid separation and extraction. The organic layer was washed with saturated brine, dried over anhydrous sodium sulfate, filtered with plug cotton and concentrated to dryness to obtain 90 mg of the title compound.

MS spectrum (ESI) m/z 303 (M+1)

$^1$H-NMR Spectrum: (DMSO-d$_6$) 5.04 (2H, brs) 6.57-6.61 (2H, m), 6.84-6.90 (3H, m), 7.34 (1H, t, J=7.7 Hz), 7.45 (2H, t, J=7.7 Hz), 7.87 (2H, t, J=7.7 Hz), 8.26 (1H, s) 12.61 (1H, brs)

Example 172

1-(3-Fluorophenyl)-3-[4-(6-phenyl-7H-pyrrolo[2,3-d]pyrimidin-4-yloxy)phenyl]urea The title compound (24 mg) was obtained by reacting 3-fluorophenyl isocyanate (14 µl) with 36 mg of 4-(6-phenyl-7H-pyrrolo[2,3-d]pyrimidin-4-yloxy)phenylamine, in the same manner as Example 171.

MS Spectrum (ESI): 440 (M+1), 462 (M+23)

$^1$H-NMR Spectrum: (DMSO-d$_6$) 7.02 (1H, s), 7.08-7.54 (11H, m), 7.94 (2H, d, J=8.0 Hz), 8.28 (1H s,), 8.88 (1H s,), 9.00 (1H, s,), 12.68 (1H, brs)

Example 173

1-Cyclopropyl-3-[4-(6-phenyl-7H-pyrrolo[2,3-d]pyrimidin-4-yloxy)phenyl]urea

After adding 30 mg of phenyl cyclopropylcarbamate and 0.5 ml of dimethylsulfoxide to 40 mg of 4-(6-phenyl-7H-pyrrolo[2,3-d]pyrimidin-4-yloxy)phenylamine, the mixture was stirred at 80° C. for 4 hours. The mixture was returned to room temperature, water was added, liquid separation and extraction were performed with ethyl acetate, and the solid obtained by concentration to dryness was washed with ether to obtain 6 mg of the title compound.

$^1$H-NMR Spectrum: (DMSO-d$_6$) 0.30-0.40 (2H, m), 0.55-0.65 (2H, m), 2.43-2.57 (1H, m, covered by DMSO peak), 6.20 (1H, brs), 6.60 (2H, d, J=8.90 Hz), 6.83 (1H, s), 6.87-6.91 (1H, m), 7.10-7.16 (1H, m), 7.30-7.50 (3H, m), 7.90 (2H, d, J=8.1 Hz), 8.26 (1H, d, J=0.4 Hz), 8.92 (1H, brs,), 12.60 (1H, brs)

Example 174

1-[4-(6-Phenyl-7H-pyrrolo[2,3-d]pyrimidin-4-yloxy)phenyl]-3-(thiazol-2-yl)urea

After adding 492 mg of phenyl 2-thiazoylcarbamate to 520 mg of 4-(6-phenyl-7H-pyrrolo[2,3-d]pyrimidin-4-yloxy)phenylamine, the mixture was stirred at 80° C. for 4 hours. The precipitated crystals were filtered out and washed with ethyl acetate and tetrahydrofuran to obtain 275 mg of the title compound.

1H-NMR Spectrum: (DMSO-d$_6$) 7.03 (1H, d, J=2.0 Hz), 7.10 (1H, d, J=3.0 Hz), 7.18-7.50 (7H, m), 7.54 (2H, d, J=8.7 Hz), 7.74 (2H, d, J=8.0 Hz), 8.29 (1H s,), 9.10 (1H, s,), 12.69 (1H, brs)

Example 175

1-(4-Fluorophenyl)-3-[2-fluoro-4-(6-phenyl-7H-pyrrolo[2,3-d]pyrimidin-4-yloxy)phenyl]urea The title compound (26 mg) was obtained from 36 mg of 2-fluoro-4-(6-phenyl-7H-pyrrolo[2,3-d]pyrimidin-4-yloxy)phenylamine, in the same manner as Example 171.

$^1$H-NMR Spectrum: (DMSO-d$_6$) 7.05-7.18 (4H, m), 7.30-7.50 (6H, m), 7.94 (2H, d, J=8.1 Hz), 8.21 (1H, t, J=10.4 Hz), 8.32 (1H, s), 8.55 (1H, d, J=1.9 Hz), 9.09 (1H, s), 12.73 (1H, brs)

The intermediates were synthesized in the following manner.

Production Example 175-1

4-(3-Fluoro-4-nitrophenoxy)-6-phenyl-7H-pyrrolo[2,3-d]pyrimidine

After adding 328 mg of 3-fluoro-4-nitrophenol, 0.22 ml of 2,6-lutidine and 0.9 ml of N-methylpyrrolidine to 360 mg of the 4-chloro-6-phenyl-7H-pyrrolo[2,3-d]pyrimidine described in WO97/02266 and PCT/EP96/02728 and stirring the mixture overnight at 130° C., it was returned to room temperature, water was added, the precipitated solid was filtered out and washed with water and diethyl ether, and the collected solid was dried to obtain 112 mg of the title compound.

¹H-NMR Spectrum: (DMSO-d₆) 7.14 (1H, s), 7.34-7.44 (2H, m), 7.48 (2H, t, J=7.8 Hz), 7.73 (1H, dd, J=2.5 Hz, 11.8 Hz), 7.89 (2H, d, J=7.8 Hz), 8.28 (1H, t, J=8.5 Hz), 8.40 (1H, d, J=1.3 Hz), 12.87 (1H, brs)

Production Example 175-2

4-(6-Phenyl-7H-pyrrolo[2,3-d]pyrimidin-4-yloxy) phenylamine

The title compound (118 mg) was obtained from 125 mg of the 4-(3-fluoro-4-nitrophenoxy)-6-phenyl-7H-pyrrolo[2,3-d]pyrimidine synthesized by the intermediate synthesis method described above, in the same manner as Production Example 171-2.
¹H-NMR Spectrum: (DMSO-d₆) 5.10 (2H, s), 6.78-7.04 (4H, m), 7.37 (1H, t, J=7.9 Hz), 7.47 (2H, t, J=7.9 Hz), 7.92 (2H, d, J=7.9 Hz), 8.38 (1H, s), 12.67 (1H, brs)

Example 176

1-(3-Fluorophenyl)-3-[2-fluoro-4-(6-phenyl-7H-pyrrolo[2,3-d]pyrimidin-4-yloxy)phenyl]urea The title compound (27 mg) was obtained from 33 mg of 2-fluoro-4-(6-phenyl-7H-pyrrolo[2,3-d]pyrimidin-4-yloxy) phenylamine, in the same manner as Example 171.
¹H-NMR Spectrum: (DMSO-d₆) 6.78 (1H, dt, J=3.3, 9.5 Hz), 7.06-7.52 (8H, m), 7.97 (2H, t, J=8.2 Hz), 8.11 (1H, t, J=9.5 Hz), 8.42 (1H, s), 8.62 (1H, s), 8.62 (1H, s), 9.28 (1H, s), 12.73 (1H, brs)

Example 177

1-[2-Fluoro-4-(6-phenyl-7H-pyrrolo[2,3-d]pyrimidin-4-yloxy)phenyl]-3-(thiazol-2-yl)urea The title compound (27 mg) was obtained from 42 mg of 2-fluoro-4-(6-phenyl-7H-pyrrolo[2,3-d]pyrimidin-4-yloxy) phenylamine, in the same manner as Example 171.
¹H-NMR Spectrum: (DMSO-d₆) 7.06-7.16 (3H, m), 7.12-7.44 (3H, m), 7.47 (2H, t, J=8.1 Hz), 7.96 (2H, d, J=8.1 Hz), 8.12 (1H, t, J=9.1 Hz), 8.32 (1H, s), 8.96 (1H, brs), 10.78 (1H, brs), 12.73 (1H, brs)

Example 178

5-[6-(4-Hydroxyphenyl)-7H-pyrrolo[2,3-d]pyrimidin-4-yloxy]indole-1-carboxylic ethylamide After dissolving 30 mg of 5-[6-(4-benzyloxyphenyl)-7-(2-trimethylsilanylethoxymethyl)-7H-pyrrolo[2,3-d]pyrimidin-4-yloxy]indole-1-carboxylic ethylamide in 1 ml of trifluoroacetic acid and 0.1 ml of thioanisole, the mixture was stirred at 50-55° C. The mixture was then returned to room temperature, saturated sodium bicarnobate water was added to alkalinity, and liquid separation and extraction were performed with an ethyl acetate-tetrahydrofuran (5:1) mixed solvent. The organic layer was concentrated, 1 ml of tetrahydrofuran and 1 ml of 2N aqueous sodium hydroxide were added to the residue, and the mixture was stirred at room temperature for 5 minutes. After neutralization with 1N hydrochloric acid, liquid separation and extraction were performed with an ethyl acetate-tetrahydrofuran (5:1) mixed solvent. The organic layer was concentrated and the residue was subjected to silica gel column chromatography (hexane-ethyl acetate) to obtain 5 mg of the title compound.

MS Spectrum (ESI): 468 (M+55); (M+Na+MeOH)
¹H-NMR Spectrum: (DMSO-d₆) 1.18 (3H, t, J=6.7 Hz), 3.20-3.50 (2H, m, covered by H2O peak), 6.67 (1H, d, J=3.5 Hz), 6.78 (1H, s,), 6.83 (2H, d, J=8.4 Hz), 7.12 (1H, dd, J=2.2, 8.4 Hz), 7.44 (1H, d, J=2.2 Hz), 7.74 (2H, d, J=8.4 Hz), 7.89 (1H, d, J=3.3 Hz), 8.16-8.22 (2H, m), 8.25 (1H, d, J=8.4 Hz), 9.80 (1H, brs,), 12.45 (1H, brs), Example 179

6-(4-Benzyloxyphenyl)-4-(1H-5-indolyloxy)-7H-pyrrolo[2,3-d]pyrimidine

After dissolving 1.5 ml of tetrahydrofuran in 22 mg of 5-[6-(4-benzyloxyphenyl)-7-(2-trimethylsilanylethoxymethyl)-7H-pyrrolo[2,3-d]pyrimidin-4-yloxy]-indole-1-carboxylic ethylamide, a 1M solution of tetrabutylammonium fluoride in tetrahydrofuran was added and the mixture was refluxed for 2 hours. After returning it to room temperature, water was added and the precipitated crystals were filtered out and subjected to silica gel column chromatography (hexane-ethyl acetate) to obtain 2 mg of the title compound.
¹H-NMR Spectrum: (DMSO-d₆) 5.17 (2H, s), 6.40-6.43 (1H, m), 6.80 (1H, s,), 6.93 (1H, dd, J=2.5, 8.8 Hz), 7.10 (2H, d, J=8.8 Hz), 7.30-7.50 (8H, m), 7.83 (2H, d, J=8.8 Hz), 8.20 (1H, s), 11.19 (1H, brs), 12.51 (1H, brs),
The intermediates were synthesized in the following manner.

Production Example 179-1

6-(4-Benzyloxyphenyl)-4-(1H-5-indolyloxy)-7-(2-trimethylsilanylethoxymethyl)-7H-pyrrolo[2,3-d] pyrimidine After adding 1.9 ml of dimethylformamide, 180 mg of 5-hydroxyindole and 112 mg of potassium carbonate to 190 mg of 6-(4-benzyloxyphenyl)-4-chloro-7-(2-trimethylsilanylethoxymethyl)-7H-pyrrolo[2,3-d]pyrimidine, the mixture was stirred at 135-140° C. for 4 hours. After returning it to room temperature, water was added, and liquid separation and extraction were performed with an ethyl acetate:tetrahydrofuran (5:1) mixed solvent. The organic layer was concentrated and subjected to NH silica gel column chromatography (hexane-ethyl acetate) to obtain 90 mg of the title compound.
MS Spectrum (ESI): 563 (M+1)
¹H-NMR Spectrum: (DMSO-d₆) −0.09 (9H, s), 0.87 (2H, t, J=8.4 Hz), 3.62 (2H, t, J=8.4 Hz) 5.19 (2H, s), 5.59 (2H, s), 6.42-6.46 (1H, m), 6.65 (1H, s), 6.83 (2H, d, J=8.4 Hz), 6.97 (1H, dd, J=2.6, 8.6 Hz), 7.16 (2H, d, J=8.6 Hz), 7.32-7.50 (8H, m), 7.70 (2H, d, J=8.6 Hz), 8.37 (1H, d, J=1.7 Hz), 11.21 (1H, brs).

Production Example 179-2

5-[6-(4-Benzyloxyphenyl)-7-(2-trimethylsilanylethoxymethyl)-7H-pyrrolo[2,3-d]pyrimidin-4-yloxy]indole-1-carboxylic ethylamide After dissolving 6-(4-benzyloxyphenyl)-4-(1H-5-indolyloxy)-7-(2-trimethylsilanylethoxymethyl)-7H-pyrrolo[2,3-d]pyrimidine (81 mg) in 1 ml of dimethylformamide, 7 mg of sodium hydride (60% dispersion) was added, the mixture was stirred at room temperature for 5 minutes, and then 31 mg of phenyl ethylcarbamate was added and the mixture was stirred for another 2 hours. Water was then added, and ethyl acetate was used for liquid separation and extraction. The organic layer was concentrated and subjected to silica gel column chromatography (hexane-ethyl acetate) to obtain 62 mg of the title compound.

MS Spectrum (ESI): 634 (M+1), 688 (M+55); (M+Na+MeOH)

$^1$H-NMR Spectrum: (DMSO-d$_6$) −0.09 (9H, s,), 0.87 (3H, t, J=8.5 Hz), 1.20 (2H, t, J=6.7 Hz), 3.10-3.70 (4H, m, covered by H2O peak), 5.20 (2H, s), 5.60 (2H, s), 6.67 (1H, s), 6.70 (1H, d, J=3.8 Hz), 7.12-7.20 (3H, m), 7.30-7.52 (6H, m), 7.72 (2H, d, J=9.0 Hz), 7.91 (1H, d, J=3.8 Hz), 8.23 (1H, t, J=5.9 Hz), 8.29 (1H, d, J=9.0 Hz), 8.38 (1H, s)

Example 180

N-[4-(2-Cyclopropyl-3-methylimidazo[4,5-b]pyridin-4-yl)oxyphenyl]-N'-(4-fluorophenyl)urea N-[4-(2-Cyclopropyl-3H-imidazo[4,5-b]pyridin-4-yl)oxyphenyl]-N'-(4-fluorophenyl)urea (25 mg), iodomethane (13 mg), potassium carbonate (26 mg) and dimethylformamide (5 ml) were stirred at 70° C. for 20 minutes. Water was added, extraction was performed with ethyl acetate, and then silica gel was added to the extract and the solvent was distilled off under reduced pressure. The silica gel was charged into a dry column packed with silica gel and purified by column chromatography (ethyl acetate, followed by ethyl acetate:methanol=10:1) to obtain 3 mg of the target substance as a white powder.

$^1$H-NMR(CDCl$_3$) δ (ppm): 1.13-1.19 (2H, m), 1.28-1.35 (2H, m), 2.03-2.11 (1H, m), 3.95 (3H, s), 6.43 (1H, d, J=5.6 Hz), 6.95-7.04 (4H, m), 7.26-7.35 (4H, m), 8.19 (1H, d, J=5.6 Hz).

Example 181

N-[4-(2-Butylaminopyridin-4-yl)oxyphenyl]-N'-(4-fluorophenyl)urea 4-(4-Aminophenoxy)-2-butylaminopyridine (54 mg), p-fluorophenyl isocyanate (34.5 mg) and tetrahydrofuran (5 ml) were stirred at room temperature for 2.5 hours. After adding NH type silica gel to the reaction solution, the solvent was distilled off under reduced pressure, and the reaction product was adsorbed onto the silica gel. The silica gel was charged into a dry column packed with NH type silica gel, and column purification was performed (hexane:ethyl acetate=1:1, followed by ethyl acetate). The solvent was distilled off under reduced pressure and the residue was solidified with ethyl acetate-hexane to obtain 15 mg of the target substance as a light yellow powder.

$^1$H-NMR (DMSO-d$_6$) δ (ppm): 0.87 (3H, t, J=7.2 Hz), 1.30 (2H, tq, J=7.2 Hz, 7.2 Hz), 1.44 (2H, tt, J=7.2 Hz, 7.2 Hz), 3.16 (2H, q, J=7.2 Hz), 5.80 (1H, d, J=2.0 Hz), 6.09 (1H, ddd, J=5.0 Hz, 2.0 Hz, 2.0 Hz), 6.45 (1H, dd, J=5.0 Hz, 5.0 Hz), 7.03-7.18 (4H, m), 7.43-7.55 (4H, m), 7.83 (1H, dd, J=5.0 Hz, 2.0 Hz), 8.70 (1H, s), 8.74 (1H, s).

The intermediate was synthesized in the following manner.

Production Example 181-1

4-(4-Aminophenoxy)-2-butylaminopyridine

After dissolving 80 mg of 4-(4-aminophenoxy)-2-butyrylaminopyridine in 8 ml of tetrahydrofuran, 67 mg of lithium aluminum hydride was added while stirring at room temperature, and the mixture was stirred at 70° C. for 10 minutes. Water was added, extraction was performed with ethyl acetate, and then silica gel was added to the extract and the solvent was distilled off under reduced pressure. The silica gel was charged into a dry column packed with silica gel and purified by column chromatography (ethyl acetate) to obtain 54 mg of the target substance as a brown oil.

$^1$H-NMR(CDCl$_3$) δ (ppm): 0.93 (3H, t, J=7.2 Hz), 1.40 (2H, tq, J=7.2 Hz, 7.2 Hz), 1.56 (2H, tt, J=7.2 Hz, 7.2 Hz), 3.14 (2H, q, J=7.2 Hz), 5.82 (1H, d, J=2.0 Hz), 6.14 (1H, dd, J=6.0 Hz, 2.0 Hz), 6.66-6.74 (2H, m), 6.86-6.94 (2H, m), 7.87 (1H, d, J=6.0 Hz).

Example 182

N-(4-Fluorophenyl)-N'-{4-[(7-oxo-5,6,7,8-tetrahydro[1,8]naphthyridin-4-yl)oxy]phenyl}urea 4-[(7-Oxo-5,6,7,8-tetrahydro[1,8]naphthyridin-4-yl)oxy]aniline (43 mg), p-fluorophenyl isocyanate (28 mg), tetrahydrofuran (5 ml) and dimethylformamide (2 ml) were stirred at room temperature for 30 minutes. Water was added dropwise at room temperature until precipitation of crystals, and these were filtered out to obtain 48 mg of the target substance as white crystals.

$^1$H-NMR (DMSO-d$_6$) δ (ppm): 2.50 (2H, t, J=8.0 Hz), 2.91 (2H, t, J=8.0 Hz), 6.24 (1H, d, J=6.0 Hz), 7.03-7.35 (4H, m), 7.40-7.55 (4H, m), 7.94 (1H, d, J=6.0 Hz), 8.70 (1H, s), 8.74 (1H, s), 10.48 (1H, s).

The intermediates were synthesized in the following manner.

Production Example 182-1

4-Chloro-3-iodo-2-pyridinamine

A solution of 10 g of the publicly known compound tert-butyl N-(4-chloro-2-pyridyl)carbamate, 16.6 ml of N,N,N',N'-tetramethylethylenediamine and 200 ml of tetrahydrofuran was cooled to −75° C., and then 42 ml of n-butyllithium (2.6M solution in hexane) was added dropwise over a period of 30 minutes while stirring. After stirring for 1 hour at −75° C., a solution of 28 g of iodine in 28 ml of tetrahydrofuran was added dropwise over a period of 30 minutes. After completion of the dropwise addition, stirring was continued for another 30 minutes at −75° C., and then the mixture was returned to room temperature, aqueous sodium bisulfate was added and extraction was performed with ethyl acetate. NH type silica gel was added to the extract, the solvent was distilled off under reduced pressure, and the reaction product was adsorbed onto the silica gel. The silica gel was charged into a dry column packed with NH type silica gel, and column purification was performed (hexane:ethyl acetate=3:1). The solvent was distilled off under reduced pressure, 48% HBr water was added to the residue, and the mixture was stirred at 100° C. for 5 minutes. After adding ice water and 5 N sodium hydroxide water to the reaction solution, the precipitated solid was filtered out to obtain 7.4 g of a light yellow solid.

$^1$H-NMR (DMSO-d$_6$) δ (ppm): 6.50 (2H, bs), 6.72 (1H, d, J=5.6 Hz), 7.82 (1H, d, J=5.6 Hz).

Production Example 182-2

3-Iodo-4-(4-nitrophenoxy)-2-pyridinamine

4-Chloro-3-iodo-2-pyridinamine (1.0 g), p-nitrophenol (1.1 g), diisopropylethylamine (1.0 ml) and N-methyl-2-pyrrolidone (2 ml) were stirred at 170° C. for 17 hours. After returning the reaction solution to room temperature, water was added and extraction was performed with ethyl acetate. NH type silica gel was added to the extract, the solvent was distilled off under reduced pressure, and the reaction product was adsorbed onto the silica gel. The silica gel was charged into a dry column packed with NH type silica gel, and column purification was performed (hexane:ethyl acetate=3:1). The solvent was distilled off under reduced pressure, and then ethyl acetate and hexane were added to the residue for solidification to obtain 540 mg of light yellow crystals.

$^1$H-NMR (DMSO-$d_6$) δ (ppm): 6.22 (1H, d, J=5.2 Hz), 6.37 (2H, brs), 7.19 (2H, d, J=9.2 Hz), 7.87 (1H, d, J=5.2 Hz), 8.26 (2H, d, J=9.2 Hz).

Production Example 182-3

Ethyl (E)-3-[2-amino-4-(4-nitrophenoxy)-3-pyridyl]-2-propenoate

3-Iodo-4-(4-nitrophenoxy)-2-pyridinamine (500 mg), ethyl acrylate (0.3 ml), palladium (II) acetate (30 mg), tributylamine (0.66 ml) and dimethylformaldehyde (5 ml) were stirred at 130° C. for 20 minutes. After returning the reaction solution to room temperature, water was added and extraction was performed with ethyl acetate. NH type silica gel was added to the extract, the solvent was distilled off under reduced pressure, and the reaction product was adsorbed onto the silica gel. The silica gel was charged into a dry column packed with NH type silica gel, and column purification was performed (hexane:ethyl acetate=3:1). The solvent was distilled off under reduced pressure to obtain 330 mg of the target substance as a yellow oil.

$^1$H-NMR(CDCl$_3$) δ (ppm): 1.31 (3H, t, J=7.2 Hz), 4.25 (2H, q, J=7.2 Hz), 5.01 (2H, s), 6.18 (1H, d, J=6.0 Hz), 6.57 (1H, d, J=16 Hz), 7.12-7.19 (2H, m), 7.73 (1H, d, J=16 Hz), 7.99 (1H, d, J=6.0 Hz), 8.24-8.32 (2H, m).

Production Example 182-4

4-[(7-Oxo-5,6,7,8-tetrahydro[1,8]naphthyridin-4-yl)oxy]aniline

Ethyl (E)-3-[2-amino-4-(4-nitrophenoxy)-3-pyridyl]-2-propenoate (330 mg), palladium-carbon (10%, aqueous, 100 mg), methanol (5 ml) and tetrahydrofuran (5 ml) were stirred overnight at under a hydrogen atmosphere at 1 atmosphere. The palladium-carbon was filtered off, the filtrate was distilled off under reduced pressure, and then the residue was purified by silica gel column chromatography (ethyl acetate, followed by ethyl acetate:methanol=5:1) to obtain 43 mg of a white solid.

$^1$H-NMR (DMSO-$d_6$) δ (ppm): 2.49 (2H, t, J=8.0 Hz), 2.89 (2H, t, J=8.0 Hz), 5.09 (2H, s), 6.15 (1H, dd J=6.0 Hz, 2.0 Hz), 6.58 (2H, dd, J=8.4 Hz, 2.0 Hz), 6.79 (2H, dd, J=8.4 Hz, 2.0 Hz), 7.89 (1H, dd, J=6.0 Hz, 2.0 Hz), 10.38 (1H, s).

Example 183

N-(4-Fluorophenyl)-N'-{4-[(7-oxo-7,8-dihydro[1,8]naphthyridin-4-yl)oxy]phenyl}urea N-(4-Fluorophenyl)-N'-{4-[(7-oxo-7,8-dihydro[1,8]naphthyridin-4-yl)oxy]aniline (30 mg), p-fluorophenyl isocyanate (0.016 ml) and dimethylformamide (6 ml) were stirred at 70° C. until disappearance of the starting materials. After returning the reaction solution to room temperature, water was added dropwise and the precipitated solid was filtered out to obtain 22 mg of a light brown solid.

$^1$H-NMR (DMSO-$d_6$) δ (ppm): 6.35 (1H, d, J=5.6 Hz), 6.54 (1H, d, J=10 Hz), 7.05-7.20 (4H, m), 7.40-7.60 (4H, m), 8.14 (1H, d, J=10 Hz), 8.29 (1H, d, J=5.6 Hz), 8.70 (1H, s), 8.78 (1H, s), 12.13 (1H, s).

The intermediates were synthesized in the following manner.

Production Example 183-1

4-(4-Nitrophenoxy)-7-oxo-7,8-dihydro[1,8]naphthyridine

Ethyl (E)-3-[2-amino-4-(4-nitrophenoxy)-3-pyridyl]-2-propenoate (350 mg), 2'-acetonaphthone (50 mg) and methanol (80 ml) were irradiated for 4 hours while stirring, and the precipitated solid was filtered out to obtain 156 mg of a light yellow solid.

$^1$H-NMR (DMSO-$d_6$) δ (ppm): 6.57 (1H, d, J=9.6 Hz), 6.70 (1H, d, J=5.6 Hz), 7.46 (2H, d, J=8.0 Hz), 8.05 (1H, d, J=9.6 Hz), 8.33 (2H, d, J=8.0 Hz), 8.42 (1H, d, J=5.6 Hz), 12.31 (1H, s).

Production Example 183-2

4-[(7-Oxo-7,8-dihydro[1,8]naphthyridin-4-yl)oxy]aniline 4-(4-Nitrophenoxy)-7-oxo-7,8-dihydro[1,8]naphthyridine (156 mg), iron powder (300 mg), ammonium chloride (600 mg), dimethylformamide (2 ml), ethanol (1 ml) and water (1 ml) were stirred at 100° C. for 20 minutes. The mixture was filtered with celite, and then water and ethyl acetate were added for extraction. The organic layer was washed 4 times with aqueous ammonium chloride solution and then dried over magnesium sulfate. The drying agent was filtered off and the solvent was distilled off under reduced pressure to obtain 30 mg of the target substance as a light yellow solid.

$^1$H-NMR (DMSO-$d_6$) δ (ppm): 5.19 (2H, brs), 6.29 (1H, d, J=5.6 Hz), 6.51 (1H, d, J=9.6 Hz), 6.30 (2H, d, J=8.0 Hz), 6.87 (2H, d, J=8.0 Hz), 8.12 (1H, d, J=9.6 Hz), 8.25 (1H, d, J=5.6 Hz), 12.10 (1H, s).

Example 184

Ethyl (E)-3-[2-[(cyclopropylcarbonyl)amino]-4-(4-{[(4-fluoroanilino)carbonyl]amino}phenoxy)-3-pyridyl]-2-propenoate Ethyl (E)-3-[2-amino-4-(4-{[(4-fluoroanilino)carbonyl]amino}phenoxy)-3-pyridyl]-2-propenoate (200 mg), cyclopropanecarbonyl chloride (58 mg), triethylamine (0.1 m), tetrahydrofuran (4 ml) and dimethylformamide (1 ml) were stirred at room temperature for 20 minutes. A small amount of water was added dropwise and the precipitated solid was filtered out to obtain 130 mg of a faint yellow solid.

$^1$H-NMR (DMSO-$d_6$) δ (ppm): 0.74 (4H, m), 1.21 (3H, t, J=7.2 Hz), 1.88-1.95 (1H, m), 4.14 (2H, q, J=7.2 Hz), 6.53 (1H, d, J=5.6 Hz), 6.90 (1H, d, J=16 Hz), 7.07-7.19 (4H, m), 7.40-7.48 (3H, m), 7.55 (2H, d, J=8.0 Hz), 8.21 (1H, d, J=5.6 Hz), 8.72 (1H, s), 8.81 (1H, s), 10.61 (1H, s).

The intermediates were obtained in the following manner.

Production Example 184-1

Ethyl (E)-3-[2-amino-4-(4-aminophenoxy)-3-pyridyl]-2-propenoate

Ethyl (E)-3-[2-amino-4-(4-nitrophenoxy)-3-pyridyl]-2-propenoate (350 mg), iron powder (700 mg), ammonium chloride (1.4 g), dimethylformamide (7 ml), ethanol (2 ml) and water (2 ml) were stirred at 100° C. for 20 minutes. The mixture was filtered with celite, and then water and ethyl acetate were added for extraction. The organic layer was washed 5 times with aqueous ammonium chloride solution and then dried over magnesium sulfate. The drying agent was filtered off and the solvent was distilled off under reduced pressure to obtain 230 mg of the target substance as a light yellow solid.

$^1$H-NMR(CDCl$_3$) δ (ppm): 1.33 (3H, t, J=7.2 Hz), 3.68 (2H, brs), 4.26 (2H, q, J=7.2 Hz), 4.87 (2H, bs), 6.02 (1H, d, J=6.0 Hz), 6.68 (1H, d, J=16 Hz), 6.70 (2H, d, J=8.8 Hz), 6.87 (2H, d, J=8.8 Hz), 7.82 (1H, d, J=6.0 Hz), 7.85 (1H, d, J=16 Hz).

Production Example 184-2

Ethyl (E)-3-[2-amino-4-(4-{[(4-fluoroanilino)carbonyl]amino}phenoxy)-3-pyridyl]-2-propenoate Ethyl(E)-3-[2-amino-4-(4-aminophenoxy)-3-pyridyl]-2-propenoate (230 mg), p-fluorophenyl isocyanate (0.11 ml) and tetrahydrofuran (6 ml) were stirred at room temperature for 30 minutes. After adding NH type silica gel to the reaction solution, the solvent was distilled off under reduced pressure, and the reaction product was adsorbed onto the silica gel. The silica gel was charged into a dry column packed with NH type silica gel, and column purification was performed (ethyl acetate). The solvent was distilled off under reduced pressure to obtain 200 mg of a white solid.

$^1$H-NMR (DMSO-d$_6$) δ (ppm): 1.22 (3H, t, J=7.2 Hz), 4.14 (2H, q, J=7.2 Hz), 5.83 (1H, d, J=5.6 Hz), 6.41 (2H, brs), 6.62 (1H, d, J=16 Hz), 7.04-7.14 (4H, m), 7.40-7.53 (4H, m), 7.72 (1H, d, J=16 Hz), 7.79 (1H, d, J=5.6 Hz), 8.69 (1H, s), 8.75 (1H, s).

Example 185

N-(4-Fluorophenyl)-N'-[4-(1H-pyrrolo[2,3-b]pyridin-4-yloxy)phenyl]urea

After dissolving 90 mg of 4-(1H-pyrrolo[2,3-b]pyridin-4-yloxy)aniline in ethyl acetate at room temperature, 0.05 ml of parafluorophenyl isocyanate was added dropwise. The precipitated white crystals were filtered out to obtain 65 mg of the target substance.

$^1$H-NMR (DMSO-d$_6$) δ (ppm): 6.21 (1H, d, J=3.6 Hz), 6.38 (1H, d, J=5.6 Hz), 7.08-7.18 (4H, m), 7.34 (1H, d, J=3.6 Hz), 7.43-7.56 (4H, m), 8.06 (1H, d, J=5.6 Hz), 8.72 (1H, s), 8.76 (1H, s), 11.72 (1H, s).

The intermediates were obtained in the following manner.

Production Example 185-1

4-(4-Nitrophenoxy)-3-[2-(1,1,1-trimethylsilyl)-1-ethynyl]-2-pyridineamine 4-(4-Nitrophenoxy)-3-iodo-pyridineamine (1.5 g), (trimethylsilyl)acetylene (1.5 ml), tetrakis(triphenylphosphine)palladium(0) (480 mg), copper (I) iodide (80 mg), dimethylformamide (3 ml) and triethylamine (3 ml) were stirred at 100° C. for 35 minutes. After returning the mixture to room temperature, water was added and extraction was performed with ethyl acetate. NH type silica gel was added to the extract, the solvent was distilled off under reduced pressure, and the reaction product was adsorbed onto the silica gel. The silica gel was charged into a dry column packed with NH type silica gel, and column purification was performed (hexane:ethyl acetate=4:1). The solvent was distilled off under reduced pressure, and ethyl acetate and hexane were added to the residue for solidification to obtain 560 mg of the target substance as a faint brown powder.

$^1$H-NMR (DMSO-d$_6$) δ (ppm): 0.30 (9H, s), 6.60 (1H, d, J=5.6 Hz), 6.67 (2H, brs), 7.47 (2H, d, J=8.0 Hz), 8.24 (1H, d, J=5.6 Hz), 8.52 (2H, d, J=8.0 Hz).

Production Example 185-2

4-(4-Nitrophenoxy)-1H-pyrrolo[2,3-b]pyridine 4-(4-Nitrophenoxy)-3-[2-(1,1,1-trimethylsilyl)-1-ethynyl]-2-pyridinamine (560 mg), copper (I) iodide (680 mg) and dimethylformamide (5 ml) were stirred for 25 minutes under reflux. After filtering out the insoluble portion, NH type silica gel was added to the reaction solution, the solvent was distilled off under reduced pressure, and the reaction product was adsorbed onto the silica gel. The silica gel was charged into a dry column packed with NH type silica gel, and column purification was performed (hexane:ethyl acetate=2:1, followed by 1:1). The solvent was distilled off under reduced pressure to obtain 84 mg of a light yellow solid.

$^1$H-NMR (DMSO-d$_6$) δ (ppm): 6.14 (1H, d, J=3.6 Hz), 6.78 (1H, d, J=5.2 Hz), 7.28 (2H, d, J=9.2 Hz), 7.43 (1H, d, J=3.6 Hz), 8.21 (1H, d, J=5.2 Hz), 8.27 (2H, d, J=9.2 Hz), 11.92 (1H, brs).

Production Example 185-3

4-(1H-Pyrrolo[2,3-b]pyridin-4-yloxy)aniline 4-(4-Nitrophenoxy)-1H-pyrrolo[2,3-b]pyridine (84 mg), iron powder (160 mg), ammonium chloride (320 mg), dimethylformamide (4 ml), ethanol (2 ml) and water (2 ml) were stirred at 100° C. for 15 minutes. The mixture was filtered with celite, and then water and ethyl acetate were added for extraction. The organic layer was washed 5 times with aqueous ammonium chloride solution and then dried over magnesium sulfate. The drying agent was filtered off and the solvent was distilled off under reduced pressure to obtain 230 mg of the target substance as a brown oil.

$^1$H-NMR(CDCl$_3$) δ (ppm): 6.41 (1H, d, J=3.6 Hz), 6.42 (1H, d, J=5.6 Hz), 6.74 (2H, d, J=8.8 Hz), 7.00 (2H, d, J=8.8 Hz), 7.20 (1H, d, J=3.6 Hz), 8.11 (1H, d, J=5.6 Hz), 10.00 (1H, brs).

Example 186

N1-Cyclopropylcarbonyl-N1-[3-(1-ethynyl)-4-(4-{[(4-fluoroanilino)carbonyl]amino}phenoxy)-2-pyridyl]-1-cyclopropanecarboxamide After adding 57 mg of cyclopropanecarbonyl chloride to a solution of N-(4-{[2-amino-3-(1-ethynyl)-4-pyridyl]oxy}phenyl)-N'-(4-fluorophenyl)urea (100 mg), triethylamine (0.12 ml) and tetrahydrofuran (5 ml) while stirring at room temperature, stirring was continued for 1.5 hours. After adding NH type silica gel to the reaction solution, the solvent was distilled off under reduced pressure, and the reaction product was adsorbed onto the silica gel. The silica gel was charged into a dry column packed with NH type silica gel, and column purification was performed (ethyl acetate). The organic solvent was distilled off under reduced pressure, and methanol and water were added to the residue for solidification to obtain 15 mg of the target substance as a white powder.

$^1$H-NMR (DMSO-$d_6$) δ (ppm): 0.97-1.03 (8H, m), 1.93-2.02 (2H, m), 4.75 (1H, s), 6.74 (1H, d, J=5.6 Hz), 7.08-7.20 (4H, m), 7.42-7.49 (2H, m), 7.56 (2H, d, J=8.8 Hz), 8.35 (1H, d, J=5.6 Hz), 8.72 (1H, s), 8.81 (1H, s).

The intermediates were obtained in the following manner.

Production Example 186-1

3-(1-Ethynyl)-4-(4-nitrophenoxy)-2-pyridineamine 4-(4-Nitrophenoxy)-3-[2-(1,1,1-trimethylsilyl)-1-ethynyl]-2-pyridineamine (560 mg), tetrabutylammonium fluoride (1.0 M solution in tetrahydrofuran, 1 ml) and tetrahydrofuran (2 ml) were stirred at room temperature for 10 minutes. Aqueous ammonium chloride solution and ethyl acetate were added for extraction, and the extract was passed through a glass filter coated with silica gel. The silica gel was thoroughly washed with ethyl acetate and the ethyl acetate was distilled off under reduced pressure to obtain 400 mg of the target substance as a brown powder.

$^1$H-NMR (DMSO-$d_6$) δ (ppm): 4.52 (1H, s), 6.23 (1H, d, J=5.6 Hz), 6.46 (2H, brs), 7.24 (2H, d, J=7.2 Hz), 7.94 (1H, d, J=5.6 Hz), 8.27 (2H, d, J=7.2 Hz).

Production Example 186-2

4-(4-Aminophenoxy)-3-(1-ethynyl)-2-pyridinamine 3-(1-Ethynyl)-4-(4-nitrophenoxy)-2-pyridinamine (400 mg), iron powder (800 mg), ammonium chloride (1.6 g), dimethylformamide (3 ml), ethanol (1 ml) and water (1 ml) were stirred at 100° C. for 30 minutes. The mixture was filtered with celite, and then water and ethyl acetate were added to the filtrate for extraction. The organic layer was washed 5 times with aqueous ammonium chloride solution and then dried over magnesium sulfate. The drying agent was filtered off and the solvent was distilled off under reduced pressure to obtain 260 mg of the target substance as a brown solid.

$^1$H-NMR(CDCl$_3$) δ (ppm): 3.63 (1H, s), 3.64 (2H, brs), 5.12 (2H, brs), 5.95 (1H, d, J=5.6 Hz), 6.69 (2H, dd, J=6.4 Hz, 2.0 Hz), 6.91 (2H, dd, J=6.4 Hz, 2.0 Hz), 7.81 (1H, d, J=5.6 Hz).

Production Example 186-3

N-(4-{[2-Amino-3-(1-ethynyl)-4-pyridyl]oxy}phenyl)-N'-(4-fluorophenyl)urea 4-(4-Aminophenoxy)-3-(1-ethynyl)-2-pyridinamine (260 mg), para-fluorophenyl isocyanate (0.13 ml) and tetrahydrofuran (5 ml) were stirred at room temperature for 20 hours. Water was added to the reaction solution, the tetrahydrofuran was distilled off, and then a small amount of ethyl acetate was added and the precipitated solid was filtered off to obtain 20 mg of a light brown solid.

$^1$H-NMR (DMSO-$d_6$) δ (ppm): 4.53 (1H, s), 5.80 (1H, d, J=5.6 Hz), 6.22 (2H, brs), 7.00-7.15 (4H, m), 7.40-7.53 (4H, m), 7.76 (1H, d, J=5.6 Hz), 8.69 (1H, s), 8.73 (1H, s).

Example 187

N1-Cyclopropyl-5-[(2-{[4-(4-hydroxypiperidino)butanoyl]amino}-4-pyridyl)oxy]-1H-1-indolecarboxamide Phenyl N-cyclopropylcarbamate (120 mg) was added to a solution of 260 mg of 5-[(2-{[4-(4-hydroxypiperidino)butanoyl]amino}-4-pyridyl)oxy]indole, 53 mg of sodium hydride (60% in oil) and 5 ml of dimethylformamide while stirring at room temperature. After stirring for 10 minutes, water was added and extraction was performed with ethyl acetate. NH type silica gel was added to the ethyl acetate layer, the solvent was distilled off under reduced pressure and the reaction product was adsorbed onto the silica gel. The silica gel was charged into a dry column packed with NH type silica gel, and purification was performed by column chromatography (chloroform:methanol=30:1). The solvent was distilled off under reduced pressure, and the residue was dissolved in ethyl acetate and washed twice with 1N aqueous sodium hydroxide. After drying over sodium sulfate, the solvent was distilled off under reduced pressure to obtain 20 mg of the target substance as a white powder.

$^1$H-NMR (DMSO-$d_6$) δ (ppm): 0.57-0.64 (2H, m), 0.68-0.75 (2H, m), 1.24-1.34 (2H, m), 1.55-1.67 (4H, m), 1.83-1.94 (2H, m), 2.17 (2H, t, J=7.2 Hz), 2.28 (2H, t, J=7.2 Hz), 2.55-2.66 (2H, m), 2.73-2.80 (1H, m), 3.30-3.40 (1H, m), 4.47 (1H, d, J=3.6 Hz), 6.62 (1H, dd, J=5.6 Hz, 2.4 Hz), 6.64 (1H, d, J=3.6 Hz), 7.04 (1H, dd, J=8.8 Hz, 2.4 Hz), 7.36 (1H, d, J=2.4 Hz), 7.61 (1H, d, J=2.4 Hz), 7.87 (1H, d, J=3.6 Hz), 8.12 (1H, d, J=5.6 Hz), 8.25-8.30 (2H, m), 10.40 (1H, s).

Example 188

N1-(2-Fluoroethyl)-5-[(2-{[4-(4-hydroxypiperidino)butanoyl]amino}-4-pyridyl)oxy]-1H-1-indolecarboxamide The target substance was obtained using phenyl N-(2-fluoroethyl)carbamate, in the same manner as Example 188.

$^1$H-NMR (DMSO-$d_6$) δ (ppm): 1.24-1.35 (2H, m), 1.57-1.67 (4H, m), 1.88 (2H, t, J=10.4 Hz), 2.17 (2H, t, J=7.2 Hz), 2.28 (2H, t, J=7.2 Hz), 2.56-2.55 (2H, m), 3.30-3.40 (1H, m), 3.55 (1H, q, J=4.8 Hz), 3.61 (1H, q, J=4.8 Hz), 4.48 (1H, d, J=4.0 Hz), 4.52 (1H, t, J=4.8 Hz), 4.64 (1H, t, J=4.8 Hz), 6.62 (1H, dd, J=5.6 Hz, 2.4 Hz), 6.70 (1H, d, J=3.6 Hz), 7.05 (1H, dd, J=8.8 Hz, 2.4 Hz), 7.38 (1H, d, J=2.4 Hz), 7.62 (1H, d, J=2.4 Hz), 7.95 (1H, d, J=3.6 Hz), 8.12 (1H, d, J=5.6 Hz), 8.28 (1H, d, J=8.8 Hz), 8.44-8.49 (1H, m), 10.41 (1H, s).

Example 189

N1-Phenyl-5-[(2-{[4-(4-hydroxypiperidino)butanoyl]amino}-4-pyridyl)oxy]-1H-1-indolecarboxamide The target substance was obtained using phenyl isocyanate, in the same manner as Example 187.

$^1$H-NMR (DMSO-$d_6$) δ (ppm): 1.24-1.35 (2H, m), 1.57-1.67 (4H, m), 1.84-1.96 (2H, m), 2.18 (2H, t, J=6.8 Hz), 2.29 (2H, t, J=6.8 Hz), 2.56-2.66 (2H, m), 3.30-3.40 (1H, m), 4.48 (1H, d, J=4.4 Hz), 6.65 (1H, dd, J=5.6 Hz, 2.4 Hz), 6.77 (1H, d, J=3.6 Hz), 7.09 (1H, dd, J=8.8 Hz, 2.4 Hz), 7.10-7.16 (1H, m), 7.35-7.41 (2H, m), 7.43 (1H, d, J=2.4 Hz), 7.62-7.67 (3H, m), 8.10-8.15 (2H, m), 8.27 (1H, d, J=8.8 Hz), 10.10 (1H, s), 10.42 (1H, s).

Example 190

N1-Cyclopropyl-5-[(2-{[2-(4-hydroxypiperidino)acetyl]amino}-4-pyridyl)oxy]-1H-1-indolecarboxamide The target substance was obtained using 5-[(2-{[2-(4-hydroxypiperidino)acetyl]amino}-4-pyridyl)oxy]indole, in the same manner as Example 188.

¹H-NMR (DMSO-d6) δ (ppm): 0.58-0.63 (2H, m), 0.69-0.75 (2H, m), 1.35-1.45 (2H, m), 1.66-1.74 (2H, m), 2.17-2.25 (2H, m), 2.64-2.72 (2H, m), 2.72-2.80 (1H, m), 3.04 (2H, s), 3.38-3.49 (1H, m), 4.57 (1H, d, J=4.4 Hz), 6.65 (1H, d, J=3.6 Hz), 6.68 (1H, dd, J=5.6 Hz, 2.4 Hz), 7.05 (1H, dd, J=8.8 Hz, 2.4 Hz), 7.38 (1H, d, J=2.8 Hz), 7.59 (1H, d, J=2.8 Hz), 7.87 (1H, d, J=3.6 Hz), 8.15 (1H, d, J=5.6 Hz), 8.27-8.82 (2H, m), 9.85 (1H, s).

The intermediate was obtained in the following manner.

Production Example 190-1

5-[(2-{[2-(4-Hydroxypiperidino)acetyl]amino}-4-pyridyl)oxy]indole

Bromoacetyl chloride (2.14 g) was added to a solution of 2.0 g of N1-cyclopropyl-5-[(2-amino-4-pyridyl)oxy]-1H-1-indolecarboxamide, 2.3 ml of triethylamine and 20 ml of tetrahydrofuran while stirring at room temperature. After stirring for 30 minutes, water was added and extraction was performed with ethyl acetate. The extract was passed through a glass filter coated with silica gel. The silica gel was thoroughly washed with ethyl acetate, and then the ethyl acetate layers were combined and subjected to distillation under reduced pressure to obtain 900 mg of a greenish-brown oil. The 900 mg of oil was stirred at 70° C. for 35 minutes together with 640 mg of 4-hydroxypiperidine, 1.2 g of potassium carbonate and 20 ml of dimethylformamide. Water was added and extraction was performed with ethyl acetate. The extract was washed 3 times with water and once with brine, and then passed through a glass filter coated with silica gel. The silica gel was washed thoroughly with ethyl acetate, and the solvent was distilled off under reduced pressure to obtain 530 mg of the target substance as a light yellow powder.

¹H-NMR (DMSO-d$_6$) δ (ppm): 1.35-1.47 (2H, m), 1.68-1.75 (2H, m), 2.21 (2H, t, J=10.00 Hz), 2.64-2.74 (2H, m), 3.03 (2H, s), 3.40-3.50 (1H, m), 4.57 (1H, d, J=4.0 Hz), 6.42 (1H, s), 6.63 (1H, dd, J=5.6 Hz, 2.4 Hz), 6.86 (1H, dd, J=8.8 Hz, 2.4 Hz), 7.30 (1H, s), 7.42 (1H, d, J=2.4 Hz), 7.45 (1H, d, J=8.8 Hz), 7.59 (1H, d, J=2.4 Hz), 8.12 (1H, d, J=5.6 Hz), 9.81 (1H, s), 11.25 (1H, s).

Example 191

N1-(2-Fluoroethyl)-5-[(2-{[2-(4-hydroxypiperidino)acetyl]amino}-4-pyridyl)oxy]-1H-1-indolecarboxamide The target substance was obtained using 5-[(2-{[2-(4-hydroxypiperidino)acetyl]amino}-4-pyridyl)oxy]indolephenyl and N-(2-fluoroethyl)carbamate, in the same manner as Example 187.

¹H-NMR (DMSO-d$_6$) δ (ppm): 1.35-1.45 (2H, m), 1.66-1.74 (2H, m), 2.21 (2H, t, J=10.0 Hz), 2.65-2.72 (2H, m), 3.04 (2H, s), 3.38-3.50 (1H, m), 3.55 (1H, q, J=4.8 Hz), 3.62 (1H, q, J=4.8 Hz), 4.52 (1H, t, J=4.8 Hz), 4.56 (1H, d, J=4.4 Hz), 4.64 (1H, t, J=4.8 Hz), 6.67 (1H, dd, J=5.6 Hz, 2.4 Hz), 6.70 (1H, d, J=3.6 Hz), 7.06 (1H, dd, J=8.8 Hz, 2.4 Hz), 7.40 (1H, d, J=2.4 Hz), 7.60 (1H, d, J=2.4 Hz), 7.95 (1H, d, J=3.6 Hz), 8.15 (1H, d, J=5.6 Hz), 8.30 (1H, d, J=8.8 Hz), 8.47 (1H, t, J=4.8 Hz), 9.85 (1H, s).

Example 192

N1-Cyclopropyl-5-[(2-{[3-(4-hydroxypiperidino)propionyl]amino}-4-pyridyl)oxy]-1H-1-indolecarboxamide The target substance was obtained using 5-[(2-{[3-(4-hydroxypiperidino)propionyl]amino}-4-pyridyl)oxy]indole, in the same manner as Example 187.

¹H-NMR (DMSO-d$_6$) δ (ppm): 0.58-0.64 (2H, m), 0.70-0.76 (2H, m), 1.29-1.91 (2H, m), 1.62-1.72 (2H, m), 1.95-2.06 (2H, m), 2.38-2.58 (4H, m), 2.63-2.73 (2H, m), 2.70-2.80 (1H, m), 3.35-3.46 (1H, m), 4.51 (1H, s), 6.61-6.66 (2H, m), 7.04 (1H, dd, J=8.8 Hz, 2.4 Hz), 7.36 (1H, d, J=2.4 Hz), 7.59 (1H, d, J=2.4 HZ), 7.87 (1H, d, J=3.6 Hz), 8.13 (1H, d, J=5.6 Hz), 8.25-8.30 (2H, m), 10.77 (1H, s).

The intermediate was obtained in the following manner.

Production Example 192-1

5-[(2-{[3-(4-Hydroxypiperidino)propionyl]amino}-4-pyridyl)oxy]indole

3-Bromopropionyl chloride (1.4 ml) was added to a solution of 2.0 g of N1-cyclopropyl-5-[(2-amino-4-pyridyl)oxy]-1H-1-indolecarboxamide, 2.3 ml of triethylamine and 80 ml of tetrahydrofuran, while stirring on ice. After stirring for 10 minutes, stirring was continued at room temperature for 10 minutes, water was added and extraction was performed with ethyl acetate. The extract was passed through a glass filter coated with silica gel. The silica gel was thoroughly washed with ethyl acetate, and then the ethyl acetate layers were combined and subjected to distillation under reduced pressure to obtain 1.7 g of a faint yellow oil. A 900 mg portion of the oil was stirred at 70° C. for 30 minutes together with 470 mg of 4-hydroxypiperidine, 880 mg of potassium carbonate and 10 ml of dimethylformamide. Water was added and extraction was performed with ethyl acetate. NH type silica gel was added to the ethyl acetate layer, the solvent was distilled off under reduced pressure and the reaction product was adsorbed onto the silica gel. The silica gel was charged into a dry column packed with NH type silica gel, and purification was performed by column chromatography (chloroform:methanol=100:3). The solvent was distilled off under reduced pressure to obtain 170 mg of the target substance as a white powder.

¹H-NMR (DMSO-d$_6$) δ (ppm): 1.29-1.42 (2H, m), 1.62-1.72 (2H, m), 2.00 (2H, t, J=7.2 Hz), 2.37-2.55 (4H, m), 2.62-2.72 (2H, m), 3.35-3.46 (1H, m), 4.52 (1H, d, J=4.0 Hz), 6.42 (1H, s), 6.59 (1H, dd, J=5.6 Hz, 2.4 Hz), 6.85 (1H, dd, J=8.8 Hz, 2.4 Hz), 7.29 (1H, s), 7.41 (1H, d, J=2.4 Hz), 7.44 (1H, d, J=8.8 Hz), 7.59 (1H, d, J=2.4 Hz), 8.10 (1H, d, J=5.6 Hz), 10.74 (1H, s), 11.22 (1H, s).

Example 193

N1-(2-Fluoroethyl)-5-({2-[(4-piperidylcarbonyl)amino]-4-pyridyl}oxy)-1H-1-indolecarboxamide After dissolving 160 mg of N1-(2-fluoroethyl)-5-[(2-{[(1-tert-butyloxycarbonyl-4-piperidyl)carbonyl]amino}-4-pyridyl)oxy]-1H-1-indolecarboxamide in 10 ml of trifluoroacetic acid, the solution was stirred at room temperature for 10 minutes. Ethyl acetate and sodium bicarbonate water were added to alkalinity for liquid separation. The ethyl acetate layer was washed once with brine and dried over magnesium sulfate. The solvent was distilled off under reduced pressure to obtain 86 mg of a colorless powder.

¹H-NMR (DMSO-d$_6$) δ (ppm): 1.60-1.73 (2H, m), 1.83-1.91 (2H, m), 2.65-2.73 (1H, m), 2.77-2.87 (2H, m), 3.22-3.32 (2H, m), 3.55 (1H, q, J=5.2 Hz), 3.62 (1H, q, J=5.2 Hz), 4.52 (1H, t, J=5.2 Hz), 4.64 (1H, t, J=5.2 Hz), 6.67 (1H, dd, J=5.6 Hz, 2.4 Hz), 6.70 (1H, d, J=3.6 Hz), 7.05 (1H, dd, J=8.8 Hz, 2.4 Hz), 7.38 (1H, d, J=2.4 Hz), 7.59 (1H, d, J=2.4 Hz), 7.96 (1H, d, J=3.6 Hz), 8.16 (1H, d, J=5.6 Hz), 8.29 (1H, d, J=8.8 Hz), 8.49 (1H, t, J=5.2 Hz), 10.59 (1H, s).

The intermediates were obtained in the following manner.

Production Example 193-1

N1-(2-Fluoroethyl)-5-[(2-{[(1-tert-butyloxycarbonyl-4-piperidyl)carbonyl]amino}-4-pyridyl)oxy]-1H-1-indolecarboxamide N1-(2-Fluoroethyl)-5-[(2-amino-4-pyridyl)oxy]-1H-1-indolecarboxamide (500 mg), 1-tert-butyloxycarbonylpiperidine-4-carboxylic acid (440 mg), benzotriazol-1-yloxytris(dimethylamino)phosphonium hexafluorophosphate (Bop Reagent) (840 mg), triethylamine (0.44 ml) and dimethylformamide (10 ml) were stirred at room temperature for 17 hours. Water was added, extraction was performed with ethyl acetate, NH type silica gel was added to the extract, the solvent was distilled off under reduced pressure and the reaction product was adsorbed onto the silica gel. The silica gel was charged into a dry column packed with NH type silica gel, and column purification was performed (hexane:ethyl acetate=1:1). The solvent was distilled off under reduced pressure to obtain 160 mg of the target substance as a white powder.

$^1$H-NMR (DMSO-d$_6$) δ (ppm): 1.28-1.40 (2H, m), 1.36 (9H, s), 1.64-1.72 (2H, m), 2.54-2.80 (3H, m), 3.55 (1H, q, J=5.2 Hz), 3.61 (1H, q, J=5.2 Hz), 3.86-3.96 (2H, m), 4.52 (1H, t, J=5.2 Hz), 4.64 (1H, t, J=5.2 Hz), 6.66 (1H, dd, J=5.6 Hz, 2.4 Hz), 6.70 (1H, d, J=3.6 Hz), 7.05 (1H, dd, J=8.8 Hz, 2.4 Hz), 7.38 (1H, d, J=2.4 Hz), 7.59 (1H, d, J=2.4 Hz), 7.95 (1H, d, J=3.6 Hz), 8.14 (1H, d, J=5.6 Hz), 8.28 (1H, d, J=8.8 Hz), 8.48 (1H, t, J=5.2 Hz), 10.49 (1H, s).

Example 194

N1-(2-Fluoroethyl)-5-[(2-{[(1-methyl-4-piperidyl)carbonyl]amino}-4-pyridyl)oxy]-1H-1-indolecarboxamide N1-Cyclopropyl-5-({2-[(4-piperidylcarbonyl)amino]-4-pyridyl}oxy)-1H-1-indolecarboxamide (70 mg), formaldehyde (37% in water, 0.1 ml), acetic acid (20 mg) and tetrahydrofuran (5 ml) were stirred at room temperature for 5 minutes, and then 70 mg of sodium triacetoxyborohydride was added prior to additional stirring for 10 minutes. Sodium bicarbonate water was added and extraction was performed with ethyl acetate. The extract was passed through a glass filter coated with NH type silica gel. The silica gel was thoroughly washed with ethyl acetate, and the ethyl acetate layers were combined and subjected to distillation under reduced pressure to obtain 40 mg of a colorless powder.

$^1$H-NMR (DMSO-d$_6$) δ (ppm): 1.45-1.56 (2H, m), 1.59-1.68 (2H, m), 1.73-1.83 (2H, m), 2.09 (3H, s), 2.30-2.40 (1H, m), 2.69-2.77 (2H, m), 3.56 (1H, q, J=5.2 Hz), 3.62 (1H, q, J=5.2 Hz), 4.52 (1H, t, J=5.2 Hz), 4.64 (1H, t, J=5.2 Hz), 6.65 (1H, dd, J=5.6 Hz, 2.4 Hz), 6.70 (1H, d, J=3.6 Hz), 7.05 (1H, dd, J=8.8 Hz, 2.4 Hz), 7.38 (1H, d, J=2.4 Hz), 7.60 (1H, d, J=2.4 Hz), 7.95 (1H, d, J=3.6 Hz), 8.13 (1H, d, J=5.6 Hz), 8.29 (1H, d, J=8.8 Hz), 8.48 (1H, t, J=5.2 Hz), 10.41 (1H, s).

Example 195

N1-Cyclopropyl-5-({2-[(4-piperidylcarbonyl)amino]-4-pyridyl}oxy)-1H-1-indolecarboxamide The target substance was obtained using N1-cyclopropyl-5-[(2-{[(1-tert-butyloxycarbonyl-4-piperidyl)carbonyl]amino}-4-pyridyl)oxy]-1H-1-indolecarboxamide, in the same manner as Example 193.

$^1$H-NMR (DMSO-d$_6$) δ (ppm): 0.59-0.66 (2H, m), 0.67-0.75 (2H, m), 1.30-1.43 (2H, m), 1.54-1.62 (2H, m), 2.36-2.45 (2H, m), 2.45-2.54 (1H, m), 2.73-2.80 (1H, m), 2.86-2.94 (2H, m), 6.60-6.67 (2H, m), 7.04 (1H, dd, J=8.8 Hz, 2.4 Hz), 7.36 (1H, d, J=2.4 Hz), 7.60 (1H, d, J=2.4 Hz), 7.92 (1H, d, J=2.4 Hz), 8.13 (1H, d, J=5.6 Hz), 8.29 (1H, d, J=8.8 Hz), 8.34 (1H, s), 10.36 (1H, s).

The intermediates were obtained in the following manner.

Production Example 195-1

N1-Cyclopropyl-5-[(2-{[(1-tert-butyloxycarbonyl-4-piperidyl)carbonyl]amino}-4-pyridyl)oxy]-1H-1-indolecarboxamide The target substance was obtained using N1-cyclopropyl-5-[(2-amino-4-pyridyl)oxy]-1H-1-indolecarboxamide, in the same manner as Production Example 193-1.

$^1$H-NMR (DMSO-d$_6$) δ (ppm): 0.59-0.64 (2H, m), 0.70-0.75 (2H, m), 1.28-1.42 (11H, m), 1.64-1.71 (2H, m), 2.55-2.82 (4H, m), 3.87-3.97 (2H, m), 6.64-6.68 (2H, m), 7.03 (1H, dd, J=8.8 Hz, 2.4 Hz), 7.36 (1H, d, J=2.4 Hz), 7.59 (1H, d, J=2.4 Hz), 7.87 (1H, d, J=3.6 Hz), 8.14 (1H, d, J=5.6 Hz), 8.27 (1H, s), 8.29 (1H, d, J=8.8 Hz), 10.48 (1H, s).

Example 196

N1-Cyclopropyl-5-[(2-{[(1-methyl-4-piperidyl)carbonyl]amino}-4-pyridyl)oxy]-1H-1-indolecarboxamide The target substance was obtained using N1-cyclopropyl-5-({2-[(4-piperidylcarbonyl)amino]-4-pyridyl}oxy)-1H-1-indolecarboxamide, in the same manner as Example 194.

$^1$H-NMR (DMSO-d$_6$) δ (ppm): 0.59-0.65 (2H, m), 0.70-0.76 (2H, m), 1.43-1.56 (2H, m), 1.59-1.68 (2H, m), 1.70-1.81 (2H, m), 2.09 (3H, s), 2.30-2.40 (1H, m), 2.69-2.80 (3H, m), 6.62-6.70 (2H, m), 7.04 (1H, dd, J=8.8 Hz, 2.4 Hz), 7.36 (1H, d, J=2.4 Hz), 7.59 (1H, d, J=2.4 Hz), 7.87 (1H, d, J=3.6 Hz), 8.13 (1H, d, J=5.6 Hz), 8.27-8.83 (2H, m), 10.41 (1H, s).

Example 197

N1-Phenyl-5-[(2-{[(1-methyl-4-piperidyl)carbonyl]amino}-4-pyridyl)oxy]-1H-1-indolecarboxamide The target substance was obtained using N1-phenyl-5-({2-[(4-piperidylcarbonyl)amino]-4-pyridyl}oxy)-1H-1-indolecarboxamide, in the same manner Example 194.

$^1$H-NMR (DMSO-d$_6$) δ (ppm): 1.44-1.56 (2H, m), 1.59-1.67 (2H, m), 1.73-1.82 (2H, m), 2.09 (3H, s), 2.30-2.44 (1H, s), 2.69-2.76 (2H, s), 6.66-6.70 (1H, m), 6.77 (1H, d, J=3.6 Hz), 7.07-7.15 (2H, m), 7.35-7.45 (3H, m), 7.60-7.68 (3H, m), 8.10-8.18 (2H, m), 8.27 (1H, d, J=8.8 Hz), 10.10 (1H, s), 10.42 (1H, s).

The intermediates were obtained in the following manner.

Production Example 197-1

N1-Phenyl-5-[(2-amino-4-pyridyl)oxy]-1H-1-indolecarboxamide

After adding 28 mg of sodium hydride (60% in oil) to a solution of 3.0 g of 5-[(2-amino-4-pyridyl)oxy]-1H-indole in dimethylformamide at room temperature and stirring the mixture for 5 minutes, 1.6 g of phenyl isocyanate was added and the mixture was stirred for 20 minutes. Water was added, extraction was performed with ethyl acetate and the organic layer was washed with water, and then silica gel was added and the solvent was distilled off under reduced pressure. The silica gel was charged into a dry column packed with silica gel and purified by column chromatography (ethyl acetate), to obtain 3.4 g of a colorless powder.

$^1$H-NMR (DMSO-$d_6$) δ (ppm): 5.77 (1H, d, J=2.4 Hz), 5.85 (2H, s), 6.14 (1H, dd, J=5.6 Hz, 2.4 Hz), 6.75 (1H, d, J=4.0 Hz), 7.06 (1H, dd, J=8.8 Hz, 2.4 Hz), 7.13 (1H, dd, J=8.0 Hz, 8.0 Hz), 7.36-7.43 (3H, m), 7.64 (2H, d, J=8.0 Hz), 7.77 (1H, d, J=5.6 Hz), 8.10 (1H, d, J=4.0 Hz), 8.25 (1H, d, J=8.8 Hz), 10.08 (1H, s).

Production Example 197-2

Tert-butyl 4-{[(4-{[1-(anilinocarbonyl)-1H-5-indolyl]oxy}-2-pyridyl)amino]carbonyl}-1-piperidine carboxylate The target substance was obtained using N1-phenyl-5-[(2-amino-4-pyridyl)oxy]-1H-1-indolecarboxamide, in the same manner as Production Example 193-1.

$^1$H-NMR (DMSO-$d_6$) δ (ppm): 1.38-1.41 (11H, m), 1.64-1.72 (2H, m), 2.52-2.75 (3H, m), 3.87-3.97 (2H, m), 6.68 (1H, dd, J=5.6 Hz, 2.4 Hz), 6.77 (1H, d, J=3.6 Hz), 7.09 (1H, dd, J=8.8 Hz, 2.4 Hz), 7.13 (1H, dd, J=7.2 Hz, 7.2 Hz), 7.38 (2H, dd, J=7.2 Hz, 7.2 Hz), 7.43 (1H, d, J=2.4 Hz), 7.61 (1H, d, J=2.4 Hz), 7.65 (2H, d, J=7.2 Hz), 8.13 (1H, d, J=3.6 Hz), 8.15 (1H, d, J=5.6 Hz), 8.27 (1H, d, J=8.8 Hz), 10.10 (1H, s), 10.50 (1H, s).

Production Example 197-3

N1-Phenyl-5-({2-[(4-piperidylcarbonyl)amino]-4-pyridyl}oxy)-1H-1-indolecarboxamide The target substance was obtained using tert-butyl 4-{[(4-{[1-(anilinocarbonyl)-1H-5-indolyl]oxy}-2-pyridyl)amino]carbonyl}-1-piperidine carboxylate, in the same manner as Example 193.

$^1$H-NMR (DMSO-$d_6$) δ (ppm): 1.32-1.43 (2H, m), 1.55-1.63 (2H, m), 2.37-2.53 (3H, m), 2.88-2.95 (2H, m), 6.67 (1H, dd, J=5.6 Hz, 2.4 Hz), 6.77 (1H, d, J=3.6 Hz), 7.09 (1H, dd, J=8.8 Hz, 2.4 Hz), 7.13 (1H, dd, J=7.2 Hz, 7.2 Hz), 7.38 (2H, dd, J=7.2 Hz, 7.2 Hz), 7.43 (1H, 2.4 Hz), 7.62-7.67 (3H, m), 8.13 (1H, d, J=3.6 Hz), 8.15 (1H, d, J=5.6 Hz), 8.27 (1H, d, J=8.8 Hz), 10.10 (1H, bs), 10.40 (1H, s).

Example 198

N1-Phenyl-5-{[2-({[(1-cyclopropylmethyl)-4-piperidyl]carbonyl}amino)-4-pyridyl]oxy}-1H-1-indolecarboxamide The target substance was obtained using N1-phenyl-5-({2-[(4-piperidylcarbonyl)amino]-4-pyridyl}oxy)-1H-1-indolecarboxamide and cyclopropanecarboxaldehyde, in the same manner as Example 194.

$^1$H-NMR (DMSO-$d_6$) δ (ppm): 0.00-0.06 (2H, m), 0.39-0.45 (2H, m), 0.72-0.82 (1H, m), 1.46-1.59 (2H, m), 1.60-1.70 (2H, m), 1.80-1.90 (2H, m), 2.10 (2H, d, J=6.0 Hz), 2.33-2.43 (1H, m), 2.90-3.00 (2H, m), 6.67 (1H, dd, J=5.6 Hz, 2.4 Hz), 6.76 (1H, d, J=3.6 Hz), 7.06-7.16 (2H, m), 7.35-7.45 (3H, m), 7.60-7.68 (3H, m), 8.12 (1H, d, J=3.6 Hz), 8.14 (1H, d, J=5.6 Hz), 8.27 (1H, d, J=8.8 Hz), 10.09 (1H, s), 10.40 (1H, s).

Example 199

N4-(4-{4-[(Anilinocarbonyl)amino]-3-chlorophenoxy}-2-pyridyl)-1-methyl-4-piperidinecarboxamide After dissolving 120 mg of t-butyl 4-{[(4-{4-[(anilinocarbonyl)amino]-3-chlorophenoxy}-2-pyridyl)amino]carbonyl}-1-piperidine carboxylate in 5 ml of trifluoroacetic acid, the solution was stirred at room temperature for 5 minutes. Sodium bicarbonate water and 5N aqueous sodium hydroxide were added and extraction was performed with ethyl acetate. The extract was washed with brine and dried over sodium sulfate. The drying agent was filtered off, and the solvent was distilled off under reduced pressure. After adding 5 ml of tetrahydrofuran, 26 mg of acetic acid, 92 mg of sodium triacetoxyborohydride and 0.5 ml of formaldehyde (37% in water) to the residue, the mixture was stirred at room temperature for 10 minutes. Sodium bicarbonate water and 5N aqueous sodium hydroxide were added to the reaction solution, and extraction was performed with ethyl acetate. The extract was washed with brine and then passed through a glass filter coated with NH type silica gel. The silica gel was washed thoroughly with ethyl acetate, the ethyl acetate layers were combined and subjected to distillation under reduced pressure, and the residue was solidified with ethyl acetate and hexane to obtain 80 mg of a colorless powder.

$^1$H-NMR (DMSO-$d_6$) δ (ppm): 1.48-1.62 (2H, m), 1.62-1.72 (2H, m), 1.76-1.86 (2H, m), 2.12 (3H, s), 2.34-2.44 (1H, m), 2.72-2.81 (2H, m), 6.68 (1H, dd, J=5.6 Hz, 2.4 Hz), 6.98 (1H, dd, J=7.2 Hz, 7.2 Hz), 7.15 (1H, dd, J=8.8 Hz, 2.4 Hz), 7.29 (2H, dd, J=7.2 Hz, 7.2 Hz), 7.38 (1H, d, J=2.4 Hz), 7.46 (2H, d, J=7.2 Hz), 7.66 (1H, d, J=2.4 Hz), 8.17 (1H, d, J=5.6 Hz), 8.22 (1H, d, J=8.8 Hz), 8.38 (1H, s), 9.42 (1H, s), 10.49 (1H, s).

Production Example 199-1 t-Butyl 4-({[4-(4-amino-3-chlorophenoxy)-2-pyridyl]amino}carbonyl)-1-piperidinecarboxylate 2-Amino-4-(4-amino-3-chlorophenoxy)pyridine (600 mg), 1-t-butyloxycarbonylpiperidine-4-carboxylic acid (700 mg), benzotriazol-1-yloxytris(dimethylamino)phosphonium hexafluorophosphate (Bop Reagent) (1.4 g), triethylamine (0.71 ml) and dimethylformamide (10 ml) were stirred at 60° C. for 3.5 hours and then at room temperature for 19 hours. Water was added to the reaction solution, extraction was performed with ethyl acetate and the organic layer was washed with water, after which silica gel was added and the solvent was distilled off under reduced pressure. The silica gel was charged into a dry column packed with silica gel, and purification was performed by column chromatography (hexane:ethyl acetate=1:1, followed by ethyl acetate) to obtain 660 mg of a reddish-brown powder.

$^1$H-NMR (DMSO-$d_6$) δ (ppm): 1.30-1.45 (11H, m), 1.65-1.74 (2H, m), 2.56-2.76 (3H, m), 3.88-4.03 (2H, m), 5.37 (2H, s), 6.59 (1H, dd, J=5.6 Hz, 2.4 Hz), 6.82-6.88 (2H, m), 6.07 (1H, d, J=2.4 Hz), 7.57 (1H, d, J=2.4 Hz), 8.12 (1H, d, J=5.6 Hz), 10.48 (1H, s).

Production Example 199-2 t-Butyl 4-{[(4-{3-chloro-4-[(phenoxycarbonyl)amino]phenoxy}-2-pyridyl)amino]carbonyl}-1-piperidinecarboxylate After adding 0.21 ml of phenyl chloroformate to a solution of 660 mg of t-butyl 4-({[4-(4-amino-3-chlorophenoxy)-2- pyridyl]amino}carbonyl)-1-piperidine carboxylate, 0.14 ml of pyridine and 10 ml of tetrahydrofuran while stirring at room temperature, the mixture was further stirred for 13 hours. Water was added to the reaction solution, extraction was performed with ethyl acetate and the organic layer was washed with water, after which silica gel was added and the solvent was distilled off under reduced pressure. The silica gel was charged into a dry column packed with silica gel, and purification was performed by column chromatography (hexane:ethyl acetate=1:1, followed by ethyl acetate) to obtain 500 mg of a colorless oil.

$^1$H-NMR (DMSO-$d_6$) δ (ppm): 1.30-1.45 (11H, m), 1.67-1.77 (2H, m), 2.58-2.80 (3H, m), 3.88-4.00 (2H, m), 6.71 (1H, dd, J=5.6 Hz, 2.4 Hz), 7.17-7.28 (4H, m), 7.37-7.46 (3H, m), 7.67 (1H, d, J=2.4 Hz), 7.79 (1H, d, J=8.8 Hz), 8.20 (1H, d, J=5.6 Hz), 9.78 (1H, bs), 10.58 (1H, s).

Production Example 199-3 t-Butyl 4-{[(4-{4-[(anilinocarbonyl)amino]-3-chlorophenoxy}-2-pyridyl)amino]carbonyl}-1-piperidinecarboxylate t-Butyl 4-{[(4-{3-chloro-4-[(phenoxycarbonyl)amino]phenoxy}-2-pyridyl)amino]carbonyl}-1-piperidine carboxylate (250 mg), aniline (84 mg) and dimethylformamide (3 ml) were stirred at 130° C. for 70 minutes. The mixture was returned to room temperature, water was added and extraction was performed with ethyl acetate. Silica gel was added to the extract, the solvent was distilled off under reduced pressure, and the reaction product was adsorbed onto the silica gel. The silica gel was charged into a dry column packed with silica gel, and column purification was performed (hexane:ethyl acetate=1:1, followed by ethyl acetate). The solvent was distilled off under reduced pressure to obtain 120 mg of a colorless oil.

$^1$H-NMR (DMSO-$d_6$) δ (ppm): 1.28-1.45 (11H, m), 1.67-1.75 (2H, m), 2.57-2.80 (3H, m), 3.87-4.03 (2H, m), 6.69 (1H, dd, J=5.6 Hz, 2.4 Hz), 6.93 (1H, dd, J=7.2 Hz, 7.2 Hz), 7.15 (1H, dd, J=8.8 Hz, 2.4 Hz), 7.28 (2H, dd, J=7.2 Hz, 7.2 Hz), 7.39 (1H, d, J=2.4 Hz), 7.45 (2H, d, J=7.2 Hz), 7.64 (1H, d, J=2.4 Hz), 8.18 (1H, d, J=5.6 Hz), 8.21 (1H, d, J=8.8 Hz), 8.36 (1H, s), 9.33 (1H, s), 10.55 (1H, s).

Example 200

N4-[4-(3-Chloro-4-{[(cyclopropylamino)carbonyl]amino}phenoxy)-2-pyridyl]-1-methyl-4-piperidinecarboxamide The target substance was obtained using t-butyl 4-({[4-(3-chloro-4-{[(cyclopropylamino)carbonyl]amino}phenoxy)-2-pyridyl]amino}carbonyl)-1-piperidine carboxylate, in the same manner as Example 199.

$^1$H-NMR (DMSO-$d_6$) δ (ppm): 0.38-0.48 (2H, brs), 0.60-0.70 (2H, m), 1.50-1.85 (6H, m), 2.11 (3H, s), 2.33-2.45 (1H, m), 2.45-2.58 (1H, m), 2.70-2.80 (2H, m), 6.66 (1H, dd, J=5.6 Hz, 2.4 Hz), 7.09 (1H, dd, J=8.8 Hz, 2.4 Hz), 7.16 (1H, d, J=2.4 Hz), 7.32 (1H, d, J=2.4 Hz), 7.62 (1H, s), 7.93 (1H, s), 8.16 (1H, d, J=5.6 Hz), 8.20 (1H, d, J=8.8 Hz), 10.46 (1H, s).

The intermediates were obtained in the following manner.

Production Example 200-1 t-Butyl 4-({[4-(3-chloro-4-{[(cyclopropylamino)carbonyl]amino}phenoxy)-2-pyridyl]amino}carbonyl)-1-piperidinecarboxylate The target substance was obtained using cyclopropylamine with the starting material synthesized in Production Example 199-2, in the same manner as Production Example 199-3.

$^1$H-NMR (DMSO-$d_6$) δ (ppm): 0.38-0.44 (2H, m), 0.60-0.68 (2H, m), 1.30-1.44 (11H, m), 1.67-1.74 (2H, m), 2.50-2.80 (4H, m), 3.88-4.00 (2H, m), 6.67 (1H, dd, J=5.6 Hz, 2.4 Hz), 7.09 (1H, dd, J=8.8 Hz, 2.4 Hz), 7.16 (1H, d, J=2.4 Hz), 7.32 (1H, d, J=2.4 Hz), 7.61 (1H, s), 7.93 (1H, s), 8.16 (1H, d, J=5.6 Hz), 8.20 (1H, d, J=8.8 Hz), 10.54 (1H, s).

Example 201

N4-[4-(3-Chloro-4-{[(4-fluoroanilino)carbonyl]amino}phenoxy)-2-pyridyl]-4-piperidinecarboxamide After dissolving 320 mg of t-butyl 4-{[4-(3-chloro-4-{[(4-fluoroanilino)carbonyl]amino}phenoxy)-2-pyridyl]amino}carbonyl)-1-piperidinecarboxylate in 10 ml of trifluoroacetic acid, the solution was stirred at room temperature for 5 minutes. Ethyl acetate and sodium bicarbonate water were added to alkalinity for liquid separation. The ethyl acetate layer was washed once with brine and then dried over magnesium sulfate. The solvent was distilled off under reduced pressure to obtain 240 mg of a colorless powder.

$^1$H-NMR (DMSO-$d_6$) δ (ppm): 1.36-1.48 (2H, m), 1.58-1.66 (2H, m), 2.39-2.58 (3H, m), 2.89-2.98 (2H, m), 6.67 (1H, dd, J=5.6 Hz, 2.4 Hz), 7.09-7.18 (3H, m), 7.38 (1H, d, J=2.4 Hz), 7.44-7.50 (2H, m), 7.66 (1H, d, J=2.4 Hz), 8.15 (2H, m), 8.38 (1H, s), 9.48 (1H, s), 10.44 (1H, s).

The intermediates were obtained in the following manner.

Production Example 201-1 t-Butyl 4-{[4-(3-chloro-4-{[(4-fluoroanilino)carbonyl]amino}phenoxy)-2-pyridyl]amino}carbonyl-1-piperidinecarboxylate The target substance was obtained using para-fluoroaniline with the starting material synthesized in Production Example 199-2, in the same manner as Production Example 199-3.

$^1$H-NMR (DMSO-$d_6$) δ (ppm): 1.32-1.46 (11H, m), 1.66-1.75 (2H, m), 2.56-2.78 (3H, m), 3.88-4.00 (2H, m), 6.69 (1H, dd, J=5.6 Hz, 2.4 Hz), 7.10-7.18 (3H, m), 7.38 (1H, d, J=2.4 Hz), 7.43-7.50 (2H, m), 7.64 (1H, d, J=2.4 Hz), 8.17-8.23 (2H, m), 8.37 (1H, s), 9.45 (1H, s), 10.55 (1H, s).

Example 202

N4-[4-(3-Chloro-4-{[(4-fluoroanilino)carbonyl]amino}phenoxy)-2-pyridyl]-1-methyl-4-piperidinecarboxamide The target substance was obtained using N4-[4-(3-chloro-4-{[(4-fluoroanilino)carbonyl]amino}phenoxy)-2-pyridyl]-4-piperidinecarboxamide, in the same manner as Example 199.

$^1$H-NMR (DMSO-$d_6$) δ (ppm): 1.48-1.60 (2H, m), 1.62-1.70 (2H, m), 1.74-1.83 (2H, m), 2.11 (3H, s), 2.33-2.43 (1H, m), 2.70-2.78 (2H, m), 6.68 (1H, dd, J=5.6 Hz, 2.4 Hz), 7.10-7.20 (3H, m), 7.39 (1H, d, J=2.4 Hz), 7.44-7.50 (2H, m), 7.65 (1H, d, J=2.4 Hz), 8.16-8.23 (2H, m), 8.33 (1H, s), 9.41 (1H, s), 10.47 (1H, s).

Example 203

N1-(4-{4-[(Anilinocarbonyl)amino]-3-chlorophenoxy}-2-pyridyl)-2-(1-methyl-4-piperidyl)acetamide The target substance was obtained using tert-butyl 4-{2-[(4-{4-[(anilinocarbonyl)amino]-3-chlorophenoxy}-2-pyridyl)amino]-2-oxoethyl}-1-piperidine carboxylate, in the same manner as Example 199.

$^1$H-NMR (DMSO-d$_6$) δ (ppm): 1.10-1.20 (2H, m), 1.50-1.70 (3H, m), 1.72-1.80 (2H, m), 2.08 (3H, s), 2.24 (2H, d, J=6.8 Hz), 2.63-2.72 (2H, m), 6.66 (1H, d, J=5.6 Hz, 2.4 Hz), 6.97 (1H, dd, J=7.2 Hz, 7.2 Hz), 7.14 (1H, dd, J=8.8 Hz, 2.4 Hz), 7.28 (2H, dd, J=7.2 Hz, 7.2 Hz), 7.39 (1H, d, J=2.4 Hz), 7.47 (2H, d, J=7.2 Hz), 7.68 (1H, d, J=2.4 Hz), 8.16 (1H, d, J=5.6 Hz), 8.20 (1H, d, J=8.8 Hz), 8.40 (1H, s), 9.42 (1H, s), 10.48 (1H, s).

The intermediates were obtained in the following manner.

Production Example 203-1 tert-Butyl 4-(2-{[4-(4-amino-3-chlorophenoxy)-2-pyridyl]amino}-2-oxoethyl)-1-piperidinecarboxylate 2-Amino-4-(4-amino-3-chlorophenoxy)pyridine (1.0 g), Bop reagent (1.9 g), triethylamine (1.2 ml), 2-[1-(tert-butoxycarbonyl)-4-piperidyl]acetic acid (1.0 g) and dimethylformamide (10 ml) were stirred at 60° C. for 2 hours and then at room temperature for 18 hours. Water was added to the reaction solution, and extraction was performed with ethyl acetate. Silica gel was added to the extract solution and the solvent was distilled off under reduced pressure. The silica gel was charged into a dry column packed with silica gel, and purification was performed by column chromatography (hexane:ethyl acetate=1:1) to obtain 570 mg of a light brown oil.

$^1$H-NMR (DMSO-d$_6$) δ (ppm): 0.95-1.07 (2H, m), 1.36 (9H, s), 1.53-1.62 (2H, m), 1.30-1.43 (1H, m), 2.25 (2H, d, J=7.2 Hz), 2.55-2.75 (2H, m), 3.80-3.92 (2H, m), 5.37 (2H, s), 6.58 (1H, dd, J=5.6 Hz, 2.4 Hz), 6.80-6.90 (2H, m), 7.07 (1H, d, J=2.4 Hz), 7.61 (1H, d, J=2.4 Hz), 8.11 (1H, d, J=5.6 Hz), 10.43 (1H, s).

Production Example 203-2 tert-Butyl 4-{2-[(4-{4-[(anilinocarbonyl)amino]-3-chlorophenoxy}-2-pyridyl)amino]-2-oxoethyl}-1-piperidine carboxylate Phenyl chloroformate (210 mg) was added dropwise to a solution of 570 mg of tert-butyl 4-(2-{[4-(4-amino-3-chlorophenoxy)-2-pyridyl]amino}-2-oxoethyl)-1-piperidinecarboxylate, 110 mg of pyridine and 5 ml of dimethylformamide while stirring at room temperature, and the mixture was further stirred for 30 minutes. Water was added and extraction was performed with ethyl acetate. The organic layer was washed twice with water and once with brine, and then silica gel was added and the solvent was distilled off under reduced pressure. This was then charged into a dry column packed with silica gel and purification was performed by column chromatography (hexane:ethyl acetate=1:1, followed by ethyl acetate), to obtain 440 mg of tert-butyl 4-{2-[(4-{3-chloro-4-[(phenoxycarbonyl)amino]phenoxy}-2-pyridyl) amino]-2-oxoethyl}-1-piperidinecarboxylate as a light yellow oil. After adding 71 mg of aniline and 5 ml of dimethylformamide to the oil, it was stirred at 130° C. for 15 minutes. The reaction solution was returned to room temperature, NH type silica gel was added, the solvent was distilled off under reduced pressure and the reaction product was adsorbed onto the silica gel. The silica gel was charged into a dry column packed with NH type silica gel, and column purification was performed (hexane:ethyl acetate=1:1). The solvent was distilled off under reduced pressure to obtain 180 mg of the target substance.

$^1$H-NMR (DMSO-d$_6$) δ (ppm): 0.94-1.06 (2H, m), 1.36 (9H, s), 1.53-1.61 (2H, m), 1.80-1.92 (1H, m), 2.27 (2H, d, J=6.8 Hz), 2.55-2.75 (2H, m), 3.80-3.90 (2H, m), 6.67 (1H, dd, J=5.6 Hz, 2.4 Hz), 6.98 (1H, dd, J=7.2 Hz, 7.2 Hz), 7.15 (1H, dd, J=8.8 Hz, 2.4 Hz), 7.28 (2H, dd, J=7.2 Hz, 7.2 Hz), 7.39 (1H, d, J=2.4 Hz), 7.45 (2H, d, J=7.2 Hz), 7.67 (1H, s), 8.17 (1H, d, J=5.6 Hz), 8.21 (1H, d, J=8.8 Hz), 8.36 (1H, s), 9.38 (1H, s), 10.50 (1H, s).

Example 204

N1-Phenyl-5-[(2-{[2-(1-methyl-4-piperidyl)acetyl]amino}-4-pyridyl)oxy]-1H-1-indolecarboxamide The target substance was obtained using tert-butyl 4-{2-[(4-{[1-(anilinocarbonyl)-1H-5-indolyl]oxy}-2-pyridyl)amino]-2-oxoethyl}-1-piperidinecarboxylate, in the same manner as Example 199.

$^1$H-NMR (DMSO-d$_6$) δ (ppm): 1.08-1.20 (2H, m), 1.48-1.66 (3H, m), 1.71-1.80 (2H, m), 2.07 (3H, s), 2.22 (2H, d, J=7.2 Hz), 2.62-2.69 (2H, m), 6.65 (1H, dd, J=5.6 Hz, 2.4 Hz), 6.77 (1H, d, J=3.6 Hz), 7.07-7.16 (2H, m), 7.38 (2H, dd, J=7.2 Hz, 7.2 Hz), 7.43 (1H, d, J=2.4 Hz), 7.60-7.68 (3H, m), 8.10-8.17 (2H, m), 8.27 (1H, d, J=8.8 Hz), 10.09 (1H, s), 10.43 (1H, s).

The intermediates were obtained in the following manner.

Production Example 204-1 tert-Butyl 4-{2-[(4-{[1-(anilinocarbonyl)-1H-5-indolyl]oxy}-2-pyridyl)amino]-2-oxyethyl}-1-piperidinecarboxylate N1-Phenyl-5-[(2-amino-4-pyridyl)oxy]-1H-1-indolecarboxamide (500 mg), 2-[1-(tert-butoxycarbonyl)-4-piperidyl]acetic acid (350 mg), benzotriazol-1-yltris(dimethylamino)phosphonium hexafluorophosphate (640 mg), triethylamine (0.4 ml) and dimethylformamide (5 ml) were stirred at 60° C. for 1 hour and then at room temperature for 19 hours. Water was added to the reaction solution and extraction was performed with ethyl acetate. The organic layer was washed twice with water and once with brine, and then silica gel was added and the solvent was distilled off under reduced pressure. The silica gel was then charged into a dry column packed with silica gel and purification was performed by column chromatography (hexane:ethyl acetate=1:1, followed by ethyl acetate), to obtain 220 mg of a colorless oil.

$^1$H-NMR (DMSO-d$_6$) δ (ppm): 0.92-1.08 (2H, m), 1.36 (9H, s), 1.50-1.62 (2H, m), 1.77-1.90 (1H, m), 2.24 (2H, d, J=6.8 Hz), 2.55-2.77 (2H, m), 3.78-3.93 (2H, m), 6.66 (1H, dd, J=5.6 Hz, 2.4 Hz), 6.77 (1H, d, J=3.6 Hz), 7.08-7.16 (2H, m), 7.35-7.46 (3H, m), 7.60-7.68 (3H, m), 8.10-8.18 (2H, m), 8.27 (1H, d, J=8.8 Hz), 10.09 (1H, s), 10.44 (1H, s).

Example 205

N1-Phenyl-3-chloro-5-[(2-{[(1-methyl-4-piperidyl)carbonyl]amino}-4-pyridyl)oxy]-1H-1-indolecarboxamide After dissolving 260 mg of tert-butyl 4-{[(4-{[1-(anilinocarbonyl)-3-chloro-1H-5-indolyl]oxy}-2-pyridyl)amino]carbonyl}-1-piperidinecarboxylate in 5 ml of trifluoroacetic acid, the solution was stirred at room temperature for 5 minutes. Sodium bicarbonate water and 5N aqueous sodium hydroxide were added, and the mixture was extracted with ethyl acetate and dried over magnesium sulfate. The drying agent was filtered off and the solvent was distilled off under reduced pressure to obtain 200 mg of N1-phenyl-3-chloro-5-[(2-{[(4-piperidyl)carbonyl]amino}-4-pyridyl)oxy]-1H-1-indolecarboxamide as a faint yellow solid. After adding 0.5 ml of formaldehyde (37% in water), 170 mg of sodium triacetoxyborohydride, 50 mg of acetic acid and 5 ml of tetrahydrofuran to the solid, the mixture was stirred at room temperature for 10 minutes. Sodium bicarbonate water and 5N aqueous sodium hydroxide were added, extraction was performed with ethyl acetate, and the extract was washed once with brine. The obtained ethyl acetate solution was passed through a glass filter coated with NH type silica gel. The silica gel was washed with ethyl acetate, and the solvent was distilled off under reduced pressure to obtain 210 mg of a faint yellow oil. The oil was solidified from a hexane and ethyl acetate mixed solvent to obtain 90 mg of a powder.

$^1$H-NMR (DMSO-$d_6$) δ (ppm): 1.44-1.56 (2H, m), 1.60-1.68 (2H, m), 1.73-1.82 (2H, m), 2.09 (3H, s), 2.30-2.45 (1H, m), 2.70-2.76 (2H, m), 6.69 (1H, dd, J=5.6 Hz, 2.4 Hz), 7.14 (1H, dd, J=7.2 Hz, 7.2 Hz), 7.22 (1H, dd, J=8.8 Hz, 2.4 Hz), 7.34-7.42 (3H, m), 7.60-7.66 (3H, m), 8.17 (1H, d, J=5.6 Hz), 8.33 (1H, d, J=8.8 Hz), 8.38 (1H, s), 10.12 (1H, s), 10.45 (1H, s).

The intermediates were obtained in the following manner.

Production Example 205-1

5-[(2-Amino-4-pyridyl)oxy]-3-chloro-1H-1-indole

5-[(2-Amino-4-pyridyl)oxy]-1H-1-indole (1.0 g), N-chlorosuccinimide (650 mg) and isopropanol (20 ml) were stirred at 80° C. for 25 minutes. Water was added to the reaction solution and extraction was performed with ethyl acetate. The extract was passed through a glass filter coated with NH type silica gel. The silica gel was washed with ethyl acetate, and the solvent was distilled off under reduced pressure to obtain 1.3 g of a reddish-brown oil.

$^1$H-NMR (DMSO-$d_6$) δ (ppm): 5.73 (1H, d, J=2.4 Hz), 5.82 (2H, s), 6.13 (1H, dd, J=5.6 Hz, 2.4 Hz), 6.93 (1H, dd, J=8.8 Hz, 2.4 Hz), 7.15 (1H, d, J=2.4 Hz), 7.48 (1H, d, J=8.8 Hz), 7.58 (1H, d, J=2.4 Hz), 7.75 (1H, d, J=5.6 Hz), 11.48 (1H, s).

Production Example 205-2

N1-Phenyl-5-[(2-amino-4-pyridyl)oxy]-3-chloro-1H-1-indolecarboxamide

Phenyl isocyanate was added dropwise to a solution of 1.3 g of 5-[(2-amino-4-pyridyl)oxy]-3-chloro-1H-1-indole, 180 mg of sodium hydride and 15 ml of dimethylformamide, and the mixture was stirred for 20 minutes. Water was added to the reaction solution and extraction was performed with ethyl acetate. Silica gel was added to the extract and the solvent was distilled off under reduced pressure. The silica gel was charged into a dry column packed with silica gel and purification was performed by column chromatography (hexane:ethyl acetate=1:1, followed by ethyl acetate), to obtain 380 mg of a light red oil.

$^1$H-NMR (DMSO-$d_6$) δ (ppm): 5.79 (1H, d, J=2.4 Hz), 5.89 (2H, s), 6.16 (1H, dd, J=5.6 Hz, 2.4 Hz), 7.12-7.20 (2H, m), 7.28 (1H, d, J=2.4 Hz), 7.35-7.42 (2H, m), 7.64 (2H, d, J=8.0 Hz), 7.79 (1H, d, J=5.6 Hz), 8.31 (1H, d, J=8.8 Hz), 8.35 (1H, s), 10.09 (1H, s).

Production Example 205-3 tert-Butyl 4-{[(4-{[1-(anilinocarbonyl)-3-chloro-1H-5-indolyl]oxy}-2-pyridyl)amino]carbonyl}-1-piperidinecarboxylate The target substance was obtained using N1-phenyl-5-[(2-amino-4-pyridyl)oxy]-3-chloro-1H-1-indolecarboxamide, in the same manner as Production Example 204-1.

$^1$H-NMR (DMSO-$d_6$) δ (ppm): 1.30-1.43 (11H, m), 1.65-1.73 (2H, m), 2.55-2.75 (3H, m), 3.87-4.00 (2H, m), 6.70 (1H, dd, J=5.6 Hz, 2.4 Hz), 7.14 (1H, dd, J=7.2 Hz, 7.2 Hz), 7.22 (1H, dd, J=8.8 Hz, 2.4 Hz), 7.32-7.42 (3H, m), 7.60-7.67 (3H, m), 8.17 (1H, d, J=5.6 Hz), 8.32 (1H, d, J=8.8 Hz), 8.38 (1H, s), 10.12 (1H, s), 10.53 (1H, s).

Example 206

N-(4-Fluorophenyl)-N'-(4-{[2-(2-oxotetrahydro-1H-1-pyrrolyl)-4-pyridyl]oxy}phenyl)urea N-(4-Fluorophenyl)-N'-(4-{[2-(4-chlorobutyrylamino)-4-pyridyl]oxy}phenyl)urea (56 mg), potassium carbonate (46 mg) and dimethylformamide (2 ml) were stirred at 150° C. for 15 minutes. Water and ethyl acetate were added for extraction, and the extract was passed through a glass filter coated with silica gel. The silica gel was washed with ethyl acetate, and the organic layer was distilled off under reduced pressure. Ethyl acetate and hexane were added to the residue, and the precipitated solid was filtered out to obtain 21 mg of a faint brown powder.

$^1$H-NMR (DMSO-$d_6$) (δppm): 1.98 (2H, tt, J=7.6 Hz, 7.6 Hz), 2.50 (2H, t, J=7.6 Hz), 3.95 (2H, t, J=7.6 Hz), 6.70 (1H, d, J=5.6 Hz), 7.05-7.15 (4H, m), 7.45 (2H, dd, J=8.4 Hz, 5.2 Hz), 7.52 (2H, d, J=9.2 Hz), 7.84 (1H, s), 8.22 (1H, d, J=5.6 Hz), 8.77 (1H, s), 8.83 (1H, s).

The intermediates were obtained in the following manner.

Production Example 206-1

4-{[2-(4-Chlorobutyrylamino)-4-pyridyl]oxy}aniline

2-Amino-4-(4-nitrophenoxy)pyridine (300 mg), 4-chlorobutyryl chloride (0.18 ml), triethylamine (0.77 ml), dimethylformamide (1 ml) and tetrahydrofuran (1 ml) were stirred at room temperature for 10 minutes, and then silica gel was added to the reaction solution, the solvent was distilled off under reduced pressure and the reaction product was adsorbed onto the silica gel. The silica gel was charged into a dry column packed with silica gel, for column purification (hexane:ethyl acetate=3:1, followed by 2:1 and 1:1). The solvent was distilled off under reduced pressure, and then 300 mg of iron powder, 600 mg of ammonium chloride, 2 ml of DMF, 1 ml of ethanol and 1 ml of water were added to 150 mg of the resulting residue and the mixture was stirred at 100° C. for 20 minutes. After filtration with celite, water and ethyl acetate were added for extraction. The organic layer was washed 5 times with aqueous ammonium chloride solution and then dried over magnesium sulfate. The drying agent was filtered off and the solvent was distilled off under reduced pressure to obtain 110 mg of the target substance as an oil.

$^1$H-NMR (DMSO-$d_6$) δ (ppm): 1.95 (2H, tt, J=6.8 Hz, 6.8 Hz), 2.48 (2H, t, J=6.8 Hz), 3.62 (2H, t, J=6.8 Hz), 5.10 (2H, brs), 6.55 (1H, dd, J=5.6 Hz, 1.2 Hz), 6.59 (2H, d, J=8.4 Hz), 6.79 (2H, d, J=8.4 Hz), 7.57 (1H, d, J=1.2 Hz), 8.09 (1H, d, J=5.6 Hz).

Production Example 206-2

N-(4-Fluorophenyl)-N'-(4-{[2-(4-chlorobutyry-lamino)-4-pyridyl]oxy}phenyl)urea

4-{[2-(4-Chlorobutyrylamino)-4-pyridyl]oxy}aniline (100 mg), p-fluorophenyl isocyanate (0.037 ml) and tetrahydrofuran (3 ml) were stirred at room temperature for 25 minutes. Water and ethyl acetate were added to the reaction solution for extraction, NH type silica gel was added to the extract, the solvent was distilled off under reduced pressure and the reaction product was adsorbed onto the silica gel. The silica gel was charged into a dry column packed with NH type silica gel, and column purification was performed (hexane:ethyl acetate=1:1, followed by ethyl acetate and ethyl acetate:methanol=10:1). The solvent was distilled off under reduced pressure to obtain 56 mg of the target substance as a white solid.

$^1$H-NMR (DMSO-$d_6$) δ (ppm): 1.95 (2H, tt, J=7.2 Hz, 7.2 Hz), 2.46 (2H, t, J=7.2 Hz), 3.62 (2H, t, J=7.2 Hz), 6.63 (1H, d, J=5.6 Hz), 7.04-7.16 (4H, m), 7.40-7.48 (2H, m), 7.51 (2H, d, J=8.8 Hz), 7.62 (1H, s), 8.15 (1H, d, J=5.6 Hz), 8.71 (1H, s), 8.76 (1H, s), 10.52 (1H, brs).

Example 207

N-[4-(2-Cyclobutanecarbonylaminopyridin-4-yl)oxyphenyl]-N'-(2-thiazolyl)urea 4-(2-Cyclobutanecarbonylaminopyridin-4-yl)oxyaniline (130 mg), phenyl N-(2-thiazolyl)carbamate (110 mg) and dimethylsulfoxide (3 ml) were stirred at 80° C. for 30 minutes. Water and ethyl acetate were added to the reaction solution for extraction, and the ethyl acetate layer was washed 5 times with aqueous ammonium chloride solution and then dried over magnesium sulfate. The drying agent was filtered off, the solvent was distilled off under reduced pressure, ethyl acetate was added to the residue and the precipitated solid was filtered out to obtain 130 mg of the target substance as a light brown solid.

$^1$H-NMR (DMSO-$d_6$) δ (ppm): 1.68 (1H, m), 1.80-1.93 (1H, m), 1.95-2.10 (2H, m), 2.05-2.18 (2H, m), 3.25-3.35 (1H, m), 6.64 (1H, d, J=5.6 Hz), 7.06-7.17 (3H, m), 7.36 (1H, d, J=1.6 Hz), 7.56 (2H, d, J=8.0 Hz), 7.66 (1H, s), 8.14 (1H, d, J=5.6 Hz), 9.15 (1H, brs), 10.29 (1H, s).

The intermediates were obtained in the following manner.

Production Example 207-1

N1-Cyclobutanecarbonyl-N1-[4-(4-nitrophenoxy)-2-pyridyl]-1-cyclobutanecarboxamide 2-Amino-4-(4-nitrophenoxy)pyridine (1.0 g), cyclobutyryl chloride (1.1 g), triethylamine (1.9 ml) and tetrahydrofuran (20 ml) were stirred at room temperature for 40 minutes. After adding water and ethyl acetate for extraction, the extract solution was distilled off under reduced pressure and the residue was purified with a column (hexane:ethyl acetate=1:1) packed with NH type silica gel. The purified product was further purified by silica gel chromatography (hexane:ethyl acetate=4:1, followed by 3:1). The initially eluted substance was the target substance, of which 720 mg was obtained as a colorless oil.

$^1$H-NMR (DMSO-$d_6$) δ (ppm): 1.62-1.96 (8H, m), 2.10-2.23 (4H, m), 3.35-3.45 (2H, m), 7.20 (1H, d, J=5.6 Hz), 7.23 (1H, s), 7.40 (2H, d, J=9.2 Hz), 8.33 (2H, d, J=9.2 Hz), 8.49 (1H, d, J=5.6 Hz).

The second eluted substance was 2-cyclobutanecarbonylamino (4-nitrophenoxy)pyridine, of which 560 mg was obtained as white crystals.

$^1$H-NMR (DMSO-$d_6$) δ (ppm): 1.66-1.80 (1H, m), 1.80-1.94 (1H, m), 1.98-2.20 (4H, m), 3.26-3.36 (1H, m), 6.83 (1H, d, J=5.6 Hz), 7.38 (2H, d, J=9.2 Hz), 7.81 (1H, s), 8.27 (1H, d, J=5.6 Hz), 8.31 (2H, d, J=9.2 Hz).

Production Example 207-2

4-(4-Aminophenoxy)-2-cyclobutanecarbonylaminopyridine

N1-Cyclobutanecarbonyl-N1-[4-(4-nitrophenoxy)-2-pyridyl]-1-cyclobutanecarboxamide (720 mg), iron powder (1.4 g), ammonium chloride (2.4 g), dimethylformamide (52 ml), ethanol (2 ml) and water (2 ml) were stirred at 100° C. for 15 minutes. The mixture was filtered with celite, and then water and ethyl acetate were added for extraction. The organic layer was washed 5 times with aqueous ammonium chloride solution and then dried over magnesium sulfate. The drying agent was filtered off, the solvent was distilled off under reduced pressure, ethyl acetate and hexane were added to the residue and the precipitated solid was filtered out to obtain 130 mg of a solid.

$^1$H-NMR (DMSO-$d_6$) δ (ppm): 1.68-1.80 (1H, m), 1.80-1.93 (1H, m), 1.96-2.19 (4H, m), 3.23-3.34 (1H, m), 5.10 (2H, brs), 6.55 (1H, d, J=5.6 Hz), 6.59 (2H, d, J=8.4 Hz), 6.79 (2H, d, J=8.4 Hz), 7.61 (1H, s), 8.07 (1H, d, J=5.6 Hz), 10.22 (1H, brs).

Example 208

N1-[4-{[(Cyclopropylamino)carbonyl]amino}-3-chlorophenoxy]-2-pyridyl]-1-cyclopropanecarboxamide 2-Amino-4-(4-amino-3-chlorophenoxy)pyridine (2.6 g), cyclopropanecarbonyl chloride (2.3 g), triethylamine (4.6 ml) and tetrahydrofuran (30 ml) were stirred at room temperature for 10 minutes. Water was added, extraction was performed with ethyl acetate, and the mixture was dried over magnesium sulfate. The drying agent was filtered off and the solvent was distilled off under reduced pressure to obtain 3.69 g of a brown oil. A 900 mg portion of the obtained oil was stirred together with 0.37 ml of triethylamine and 10 ml of tetrahydrofuran, while 0.3 ml of phenyl chloroformate was added dropwise at room temperature. After stirring for 15 minutes, 1 ml of cyclopropylamine was added and stirring was continued for 22 hours. Silica gel was added to the reaction solution, the solvent was distilled off under reduced pressure, and the reaction product was adsorbed onto the silica gel. The silica gel was charged into a dry column packed with silica gel, and purification was performed by column chromatography (hexane:ethyl acetate=1:1, followed by ethyl acetate) to obtain 38 mg of the target substance as a brown solid.

$^1$H-NMR (DMSO-$d_6$) δ (ppm): 0.40-0.52 (2H, m), 0.60-0.70 (2H, m), 0.70-0.85 (4H, m), 1.91-2.00 (1H, m), 2.50-2.70 (1H, m), 6.67 (1H, dd, J=5.6 Hz, 2.8 Hz), 7.11 (1H, dd, J=8.4 Hz, 2.8 Hz), 7.17 (1H, d, J=2.8 Hz), 7.33 (1H, d, J=2.8 Hz), 7.61 (1H, d, J=2.8 Hz), 7.94 (1H, s), 8.18 (1H, d, J=5.6 Hz), 8.20 (1H, d, J=8.4 Hz), 10.84 (1H, s).

The intermediates were obtained in the following manner.

Production Example 208-1

2-Amino-4-(4-amino-3-chlorophenoxy)pyridine

The publicly known compound 2-amino-4-chloropyridine (5.0 g), 4-amino-3-chlorophenol (11 g), sodium hydride (60% in oil) (3.1 g) and dimethylsulfoxide (80 ml) were stirred at 160° C. for 9.5 hours. Water was added, extraction was performed with ethyl acetate, and the extract solution was washed 5 times with water. The extract solution was then passed through a glass filter coated with silica gel. The silica gel was washed with ethyl acetate, the ethyl acetate layers were combined, and the solvent was distilled off under reduced pressure to obtain 5.1 g of a dark violet solid.

$^1$H-NMR (DMSO-d$_6$) δ (ppm): 5.32 (2H, s), 5.72 (1H, s), 5.86 (2H, bs), 6.07 (1H, d, J=6.4 Hz), 6.83 (2H, s), 7.01 (1H, s), 7.72 (1H, d, J=6.4 Hz).

Example 209

N1-[5-Bromo-4-(4-{[(cyclopropylamino)carbonyl]amino}-3-chlorophenoxy)-2-pyridyl]-1-cyclopropanecarboxamide A mixture of 67 mg of N1-[5-bromo-4-(4-amino-3-chlorophenoxy)-2-pyridyl]-N1-cyclopropylcarbonyl)-1-cyclopropanecarboxamide, 52 mg of pyridine and 5 ml of dimethylformamide was cooled to 0° C., and 54 mg of phenyl chloroformate was added. After 40 minutes, 80 mg of cyclopropanecarbonyl chloride was added and the mixture was stirred at 60° C. for 20 minutes. The mixture was returned to room temperature, water was added, and extraction was performed with ethyl acetate. Silica gel was added to the extract solution and the solvent was distilled off under reduced pressure. The silica gel was charged into a dry column packed with silica gel, and purification was performed by column chromatography (hexane:ethyl acetate=1:1). Methanol was added to the residue to obtain 11 mg of the target substance as a white solid.

$^1$H-NMR (DMSO-d$_6$) δ (ppm): 0.40 (2H, brs), 0.65 (2H, m), 0.72 (4H, brs), 1.90 (1H, brs), 2.55 (1H, brs), 7.11 (1H, d, J=9.2 Hz), 7.19 (1H, s), 7.38 (1H, s), 7.56 (1H, s), 7.96 (1H, s), 8.22 (1H, d, J=9.2 Hz), 8.42 (1H, s), 10.94 (1H, s).

The intermediates were obtained in the following manner.

Production Example 209-1

2-Amino-3-bromo-4-(4-amino-3-chlorophenoxy)pyridine

2-Amino-4-(4-amino-3-chlorophenoxy)pyridine (1.0 g), N-bromosuccinimide (0.78 g) and isopropanol (10 ml) were stirred for 15 minutes under reflux. The mixture was returned to room temperature, water was added, and extraction was performed with ethyl acetate. Silica gel was added to the extract solution and the solvent was distilled off under reduced pressure. The silica gel was charged into a dry column packed with silica gel, and purification was performed by column chromatography (hexane:ethyl acetate=2:1, followed by 1:1, ethyl acetate) to obtain 400 mg of the target substance as a brown oil.

$^1$H-NMR (DMSO-d$_6$) δ (ppm): 5.39 (2H, brs), 5.68 (1H, s), 6.06 (2H, brs), 6.85 (1H, s), 6.86 (1H, d, J=2.4 Hz), 7.09 (1H, d, J=2.4 Hz), 7.90 (1H, s).

Production Example 209-2

N1-[5-Bromo-4-(4-amino-3-chlorophenoxy)-2-pyridyl]-N1-cyclopropylcarbonyl)-1-cyclopropanecarboxamide Cyclopropanecarbonyl chloride (260 mg) was added to a solution of 400 mg of 2-amino-3-bromo-4-(4-amino-3-chlorophenoxy)pyridine, 0.53 ml of triethylamine and 5 ml of tetrahydrofuran while stirring at room temperature. After 40 minutes, silica gel was added to the reaction solution and the solvent was distilled off under reduced pressure. The silica gel was charged into a dry column packed with silica gel, and purification was performed by column chromatography (hexane:ethyl acetate=2:1, followed by 1:1, ethyl acetate) to obtain 67 mg of the target substance.

$^1$H-NMR (DMSO-d$_6$) δ (ppm): 0.66-1.00 (8H, m), 1.85-1.96 (2H, m), 5.45 (2H, brs), 6.77 (1H, s), 6.84 (1H, d, J=8.8 Hz), 6.92 (1H, dd, J=8.8 Hz, 2.8 Hz), 7.17 (1H, d, J=2.8 Hz), 8.66 (1H, s).

Example 210

N1-[4-(3,5-Dichloro-4-{[(cyclopropylamino)carbonyl]amino}phenoxy)-2-pyridyl]-1-cyclopropanecarboxamide Phenylchloroformate (110 mg) was added to a solution 96 mg of N1-[4-(4-amino-3,5-dichlorophenoxy)-2-pyridyl]-N1-cyclopropylcarbonyl)-1-cyclopropanecarboxamide, 0.076 ml of pyridine and 5 ml of dimethylformamide while stirring. After continuing stirring for 30 minutes, 0.5 ml of cyclopropylamine was added and the mixture was heated at 70° C. for 10 minutes. The mixture was returned to room temperature, water was added, and extraction was performed with ethyl acetate. Silica gel was added to the extract solution and the solvent was distilled off under reduced pressure. The silica gel was charged into a dry column packed with silica gel, and purification was performed by column chromatography (ethyl acetate). Methanol was added to the residue for solidification to obtain 4.8 mg of the target substance as a light brown solid.

$^1$H-NMR (DMSO-d$_6$) δ (ppm): 0.42 (2H, s), 0.57-0.66 (2H, m), 0.70-0.83 (4H, m), 1.92-2.01 (1H, m), 2.43-2.53 (1H, m), 6.62 (1H, s), 6.71 (1H, d, J=5.6 Hz), 7.39 (2H, s), 7.69 (1H, s), 7.89 (1H, s), 8.22 (1H, d, J=5.6 Hz), 10.89 (1H, s).

The intermediates were obtained in the following manner.

Production Example 210-1

2-Amino-4-(4-amino-3,5-dichlorophenoxy)pyridine

2-Amino-4-(4-amino-3-chlorophenoxy)pyridine (700 mg), N-chlorosuccinimide (0.44 g) and isopropanol (10 ml) were stirred at 80° C. for 1 hour. The mixture was returned to room temperature, water was added, and extraction was performed with ethyl acetate. Silica gel was added to the extract solution and the solvent was distilled off under reduced pressure. The silica gel was charged into a dry column packed with silica gel, and purification was performed by column chromatography (ethyl acetate), to obtain 120 mg of a brown oil.

$^1$H-NMR (DMSO-d$_6$) δ (ppm): 5.47 (2H, brs), 5.73 (1H, d, J=2.4 Hz), 5.90 (2H, brs), 6.09 (1H, dd, J=5.6 Hz, 2.4 Hz), 7.13 (2H, s), 7.75 (1H, d, J=5.6 Hz).

Production Example 210-2

N1-[4-(4-Amino-3,5-dichlorophenoxy)-2-pyridyl]-N1-cyclopropylcarbonyl)-1-cyclopropanecarboxamide Cyclopropanecarbonyl chloride (93 mg) was added to a solution of 120 mg of 2-amino-4-(4-amino-3,5-dichlorophenoxy)pyridine, 0.19 ml of triethylamine and 5 ml of tetrahydrofuran while stirring at room temperature. After 20 minutes, silica gel was added to the reaction solution and the solvent was distilled off under reduced pressure. The silica gel was charged into a dry column packed with silica gel, and purification was performed by column chromatography (ethyl acetate) to obtain 120 mg of a brown oil.

$^1$H-NMR (DMSO-$d_6$) δ (ppm): 0.82-0.98 (8H, m), 1.86-1.96 (2H, m), 5.55 (2H, brs), 6.95 (1H, dd, J=5.6 Hz, 2.4 Hz), 7.03 (1H, d, J=2.4 Hz), 7.24 (2H, s), 8.38 (1H, d, J=5.6 Hz).

Example 211

N1-Cyclopropyl-5-({2-[di(cyclopropylcarbonyl)amino]-4-pyridyl}oxy)-1H-1-indolecarboxamide Cyclopropanecarbonyl chloride (51 mg) was added to a solution of 100 mg of N1-cyclopropyl-5-[(2-amino-4-pyridyl)oxy]-1H-1-indolecarboxamide and 49 mg of triethylamine in tetrahydrofuran at 0° C. After 20 minutes of stirring, silica gel was added to the reaction solution, the solvent was distilled off under reduced pressure, and the reaction product was adsorbed onto the silica gel. The silica gel was charged into a dry column packed with silica gel, and purification was performed by column chromatography (hexane:ethyl acetate=1:1, followed by ethyl acetate), after which water was added to the residue to obtain 19 mg of the target substance as a white solid.

$^1$H-NMR (DMSO-$d_6$) δ (ppm): 0.57-0.63 (2H, m), 0.68-0.75 (2H, m), 0.83-0.96 (6H, m), 1.86-1.94 (2H, m), 2.73-2.80 (1H, m), 6.66 (1H, d, J=3.6 Hz), 6.91 (1H, d, J=5.6 Hz), 6.98 (1H, d, J=2.4 Hz), 7.08 (1H, dd, J=9.2 Hz, 2.4 Hz), 7.41 (1H, d, J=2.4 Hz), 7.87 (1H, d, J=3.6 Hz), 8.26-8.32 (2H, m), 8.38 (1H, d, J=5.6 Hz).

The intermediates were obtained in the following manner.

Production Example 211-1

5-[(2-Amino-4-pyridyl)oxy]-1H-indole

2-Amino-4-chloropyridine (2.0 g), 5-hydroxyindole (4.1 g), sodium hydride (60% in oil, 1.25 g) and dimethylsulfoxide (20 ml) were stirred at 160° C. for 9.5 hours. Water was added, extraction was performed with ethyl acetate, and purification was performed by silica gel column chromatography (hexane:ethyl acetate=1:1, ethylacetate). The solvent was distilled off under reduced pressure, a small amount of ethyl acetate was added to the residue and the solid was filtered out to obtain 490 mg of a light brown solid.

$^1$H-NMR (DMSO-$d_6$) δ (ppm): 5.72 (1H, d, J=2.0 Hz), 5.78 (2H, brs), 6.10 (1H, d, J=5.6 Hz), 6.41 (1H, d, J=2.0 Hz), 6.82 (1H, d, J=8.4 Hz), 7.25 (1H, s), 7.36-7.7.44 (2H, m), 7.73 (1H, d, J=5.6 Hz), 11.15 (1H, s).

Production Example 211-2

N1-Cyclopropyl-5-[(2-amino-4-pyridyl)oxy]-1H-1-indolecarboxamide

After adding 28 mg of sodium hydride (60% in oil) to a solution of 150 mg of 5-[(2-amino-4-pyridyl)oxy]-1H-indole in dimethylformamide at room temperature and stirring for 5 minutes, the mixture was cooled to 0° C., 124 mg of phenyl N-cyclopropylcarbamate was added and the mixture was further stirred for 30 minutes. Water was added, extraction was performed with ethyl acetate, the organic layer was washed 3 times with water and once with aqueous ammonium chloride solution, and then silica gel was added and the solvent was distilled off under reduced pressure. The silica gel was charged into a dry column packed with silica gel and purification was performed by column chromatography (hexane:ethyl acetate=1:1, followed by ethyl acetate), to obtain 2.4 g of a colorless powder.

$^1$H-NMR (DMSO-$d_6$) δ (ppm): 0.57-0.64 (2H, m), 0.68-0.76 (2H, m), 2.72-2.79 (1H, m), 5.74 (1H, d, J=2.4 Hz), 5.83 (2H, brs), 6.12 (1H, dd, J=5.6 Hz, 2.4 Hz), 6.64 (1H, d, J=3.6 Hz), 7.01 (1H, dd, J=9.2 Hz, 2.4 Hz), 7.32 (1H, d, J=2.4 Hz), 7.75 (1H, d, J=5.6 Hz), 7.84 (1H, d, J=3.6 Hz), 8.24 (1H, s), 8.25 (1H, d, J=9.2 Hz).

Example 212

N1-Cyclopropyl-5-({2-[(cyclopropylcarbonyl)amino]-4-pyridyl}oxy)-1H-1-indolecarboxamide N1-Cyclopropyl-5-({2-[di(cyclopropylcarbonyl)amino]-4-pyridyl}oxy)-1H-1-indolecarboxamide (190 mg), ammonium chloride (660 mg), dimethylformamide (5 ml), water (5 ml) and ethanol (5 ml) were stirred at 100° C. for 1 hour. Water and ethyl acetate were added for extraction, and the extract was washed 6 times with water. After drying over magnesium sulfate, the drying agent was filtered off and the solvent was distilled off under reduced pressure. Ethyl acetate was added to the residue and the precipitated solid was filtered out to obtain 66 mg of a white powder.

$^1$H-NMR (DMSO-$d_6$) δ (ppm): 0.57-0.64 (2H, m), 0.66-0.78 (6H, m), 1.88-1.98 (1H, m), 2.72-2.80 (1H, m), 6.63-6.69 (2H, m), 7.04 (1H, d, J=8.8 Hz), 7.36 (1H, s), 7.56 (1H, s), 7.87 (1H, d, J=3.6 Hz), 8.14 (1H, d, J=5.6 Hz), 8.26 (1H, d, J=8.8 Hz), 8.28 (1H, s), 10.55 (1H, s).

Example 213

N1-Cyclopropyl-5-{[2-(2,5-dioxotetrahydro-1H-1-pyrrolyl)-4-pyridyl]oxy}-1H-1-indolecarboxamide (Example 213-A) N1-Cyclopropyl-5-{[2-(diacetylamino)-4-pyridyl]oxy}-1H-1-indolecarboxamide (Example 213-B) N1-Cyclopropyl-5-{[2-(acetylamino)-4-pyridyl]oxy}-1H-1-indolecarboxamide (Example 213-C)

N1-Cyclopropyl-5-[(2-amino-4-pyridyl)oxy]-1H-1-indolecarboxamide (830 mg), succinic anhydride (270 mg) and toluene (30 ml) were refluxed together for 30 minutes. After adding 50 ml of acetic anhydride and 82 mg of sodium acetate to the reaction solution, the mixture was stirred at 80° C. for 15 minutes. The solvent was distilled off under reduced pressure, and the residue was purified by silica gel chromatography (ethyl acetate). The second eluted substance was N1-cyclopropyl-5-{[2-(2,5-dioxotetrahydro-1H-1-pyrrolyl)-4-pyridyl]oxy}-1H-1-indolecarboxamide, of which 440 mg was obtained as a colorless powder.

Example 213-A $^1$H-NMR (DMSO-$d_6$) δ (ppm): 0.57-0.63 (2H, m), 0.70-0.75 (2H, m), 2.70-2.80 (1H, m), 2.71 (4H, s), 6.66 (1H, d, J=3.6 Hz), 6.76 (1H, d, J=2.4 Hz), 7.03 (1H, dd, J=5.6 Hz, 2.4 Hz), 7.10 (1H, dd, J=9.2 Hz, 2.4 Hz), 7.43 (1H, d, J=2.4 Hz), 7.87 (1H, d, J=3.6 Hz), 8.29 (1H, s), 8.30 (1H, d, J=9.2 Hz), 8.42 (1H, d, J=5.6 Hz).

The first eluted substance was a mixture of N1-cyclopropyl-5-{[2-(diacetylamino)-4-pyridyl]oxy}-1H-1-indolecarboxamide and N1-cyclopropyl-5-{[2-(acetylamino)-4-pyridyl]oxy}-1H-1-indolecarboxamide. The mixture was purified by silica gel chromatography (chloroform:methanol=50:1). The first eluted substance was N1-cyclopropyl-5-{[2-(diacetylamino)-4-pyridyl]oxy}-1H-1-indolecarboxamide, of which 45 mg was obtained as a white powder.

Example 213-B $^1$H-NMR (DMSO-d$_6$) δ (ppm): 0.57-0.63 (2H, m), 0.70-0.75 (2H, m), 2.13 (6H, s), 2.74-2.80 (1H, m), 6.66 (1H, d, J=3.6 Hz), 6.96 (1H, dd, J=5.6 Hz, 2.4 Hz), 6.99 (1H, d, J=2.4 Hz), 7.09 (1H, dd, J=9.2 Hz, 2.4 Hz), 7.43 (1H, d, J=2.4 Hz), 7.87 (1H, d, J=3.6 Hz), 8.28 (1H, s), 8.30 (1H, d, J=9.2 Hz), 8.38 (1H, d, J=5.6 Hz).

The second eluted substance was N1-cyclopropyl-5-{[2-(acetylamino)-4-pyridyl]oxy}-1H-1-indolecarboxamide, which was solidified from ethyl acetate-hexane to obtain 28 mg.

Example 213-C $^1$H-NMR (DMSO-d$_6$) δ (ppm): 0.57-0.63 (2H, m), 0.70-0.75 (2H, m), 2.00 (3H, s), 2.72-2.80 (1H, m), 6.62 (1H, d, J=5.6 Hz, 2.4 Hz), 6.65 (1H, d, J=3.6 Hz), 7.04 (1H, dd, J=9.2 Hz, 2.4 Hz), 7.36 (1H, d, J=2.4 Hz), 7.60 (1H, s), 7.87 (1H, d, J=3.6 Hz), 8.13 (1H, d, J=9.2H), 8.25-8.30 (2H, m), 10.47 (1H, s).

Example 214

N1-Cyclopropyl-5-{[2-({[2-chloroethylamino]carbonyl}amino)-4-pyridyl]oxy}-1H-1-indolecarboxamide N1-cyclopropyl-5-[(2-amino-4-pyridyl)oxy]-1H-1-indolecarboxamide (400 mg), 2-chloroethylisocyanate (150 mg) and tetrahydrofuran (5 ml) were stirred at 80° C. for 1.5 hours. The mixture was returned to room temperature, silica gel was added, and the solvent was distilled off under reduced pressure. The silica gel was charged into a dry column packed with silica gel, and purification was performed by column chromatography (hexane:ethyl acetate=1:1, followed by ethyl acetate) to obtain 280 mg of a colorless powder.

$^1$H-NMR (DMSO-d$_6$) δ (ppm): 0.57-0.63 (2H, m), 0.70-0.75 (2H, m), 2.73-2.80 (1H, m), 3.42 (2H, q, J=6.0 Hz), 3.61 (2H, t, J=6.0 Hz), 6.52 (1H, dd, J=5.6 Hz, 2.4 Hz), 6.65 (1H, d, J=3.6 Hz), 6.85 (1H, d, J=2.4 Hz), 7.04 (1H, dd, J=8.8 Hz, 2.4 Hz), 7.35 (1H, d, J=2.4 Hz), 7.86 (1H, d, J=3.6 Hz), 8.04 (1H, d, J=5.6 Hz), 8.27 (1H, s), 8.28 (1H, d, J=8.8 Hz), 8.34 (1H, brs), 9.19 (1H, s).

Example 215

N1-(2-Fluoroethyl)-5-({2-[(cyclopropylcarbonyl)amino]-4-pyridyl}oxy)-1H-1-indolecarboxyamide Cyclopropanecarbonyl chloride (330 mg) was added to a solution of 400 mg of N1-(2-fluoroethyl)-5-[(2-amino-4-pyridyl)oxy]-1H-1-indolecarboxamide and 0.53 ml of triethylamine in tetrahydrofuran at room temperature. After stirring for 15 minutes, water and ethyl acetate were added for extraction. The extract was dried over magnesium sulfate and then passed through a glass filter coated with silica gel. The solvent was distilled off under reduced pressure to obtain 490 mg of an oil. After adding 1.5 g of ammonium chloride, 10 ml of dimethylformamide, 10 ml of water and 10 ml of ethanol to the residue, the mixture was stirred at 110° C. for 1.5 hours. After returning it to room temperature, water was added and extraction was performed with ethyl acetate. Silica gel was added to the extract solution, and the solvent was distilled off under reduced pressure for adsorption onto the silica gel. The silica gel was charged into a dry column packed with silica gel and purification was performed by column chromatography (ethyl acetate). Ethyl acetate and hexane were added to the residue for solidification to obtain 180 mg of the target substance as a white solid.

$^1$H-NMR (DMSO-d$_6$) δ (ppm): 0.64-0.80 (4H, m), 1.88-1.97 (1H, m), 3.50-3.65 (2H, m), 4.52 (1H, t, J=4.8 Hz), 4.64 (1H, t, J=4.8 Hz), 6.65 (1H, dd, J=5.6 Hz, 2.4 Hz), 6.69 (1H, d, J=3.6 Hz), 7.05 (1H, dd, J=8.8 Hz, 2.4 Hz), 7.38 (1H, d, J=2.4 Hz), 7.57 (1H, d, J=2.4 Hz), 7.95 (1H, d, J=3.6 Hz), 8.14 (1H, d, J=5.6 Hz), 8.27 (1H, d, J=8.8 Hz), 8.47 (1H, t, J=5.6 Hz), 10.77 (1H, s).

The intermediates were obtained in the following manner.

Production Example 215-1

N1-(2-Fluoroethyl)-5-[(2-amino-4-pyridyl)oxy]-1H-1-indolecarboxamide

Sodium hydride (60% in oil) (360 mg) was added to a solution of 2.0 g of 5-[(2-amino-4-pyridyl)oxy]-1H-indole in 30 ml of dimethylformamide at room temperature. After stirring for 5 minutes, the mixture was placed in an ice bath and 1.8 g of phenyl N-(2-fluoroethyl)carbamate was added while cooling. The mixture was returned to room temperature and stirred for 30 minutes, after which water was added and extraction was performed with ethyl acetate. The extract was passed through a glass filter coated with silica gel. The ethyl acetate layer was washed once with sodium bicarbonate water and dried over magnesium sulfate. The drying agent was filtered off to obtain 1.93 g of a faint brown powder.

$^1$H-NMR (DMSO-d$_6$) δ (ppm): 3.52-3.64 (2H, m), 4.52 (1H, t, J=4.8 Hz), 4.64 (1H, t, J=4.8 Hz), 5.75 (1H, d, J=2.4 Hz), 5.82 (2H, brs), 6.12 (1H, dd, J=5.6 Hz, 2.4 Hz), 6.68 (1H, d, J=3.6 Hz), 7.02 (1H, dd, J=8.8 Hz, 2.4 Hz), 7.33 (1H, d, J=2.4 Hz), 7.76 (1H, d, J=5.6 Hz), 7.92 (1H, d, J=3.6 Hz), 8.26 (1H, d, J=8.8 Hz), 8.44 (1H, t, J=5.2 Hz).

Example 216

N1-Cyclopropyl-5-(4-{[2-(2-oxotetrahydro-1H-1-pyrrolyl)-4-pyridyl]oxy}-1H-1-indolecarboxamide Sodium hydride (60% in oil) (19 mg) was added to a solution of 130 mg of 5-(4-{[2-(2-oxotetrahydro-1H-1-pyrrolyl)-4-pyridyl]oxy}-1H-1-indole in dimethylformamide at room temperature, and then 82 mg of phenyl N-cyclopropylcarbamate was added. After stirring for 10 minutes, water was added and extraction was performed with ethyl acetate. Silica gel was added to the extract solution and the solvent was distilled off for adsorption onto the silica gel. The silica gel was charged into a dry column packed with silica gel and purification was performed by column chromatography (hexane:ethyl acetate=1:1, followed by ethyl acetate). Ethyl acetate and hexane were added to the residue for solidification to obtain 25 mg of the target substance as a white solid.

$^1$H-NMR (DMSO-d$_6$) δ (ppm): 0.58-0.63 (2H, m), 0.68-0.75 (2H, m), 1.97 (2H, tt, J=6.4 Hz, 6.4 Hz), 2.47 (2H, t, J=6.4 Hz), 2.73-2.80 (1H, m), 3.94 (2H, t, J=6.4 Hz), 6.65 (1H, d, J=3.6 Hz), 6.71 (1H, dd, J=5.6 Hz, 2.4 Hz), 7.04 (1H, dd, J=8.8 Hz, 2.4 Hz), 7.36 (1H, d, J=2.4 Hz), 7.81 (1H, d, J=2.4 Hz), 7.86 (1H, d, J=3.6 Hz), 8.22 (1H, d, J=5.6 Hz), 8.27 (1H, brs), 8.28 (1H, d, J=8.8 Hz).

The intermediates were obtained in the following manner.

Production Example 216-1

5-(4-{[2-(2-Oxotetrahydro-1H-1-pyrrolyl)-4-pyridyl]oxy}-1H-1-indole

4-Bromobutyryl chloride (0.8 ml) was added to a solution of 1.0 g of N1-cyclopropyl-5-[(2-amino-4-pyridyl)oxy]-1H-1-indolecarboxamide, 1.1 ml of triethylamine and 20 ml of tetrahydrofuran at room temperature. After stirring for 20 minutes, water was added and extraction was performed with ethyl acetate. The extract was passed through a glass filter coated with silica gel. After adding 950 mg of 4-hydroxypiperidine, 1.7 g of potassium carbonate and 10 ml of dimethylformamide to the obtained oil, the mixture was stirred at 70° C. for 20 minutes. Water was added, extraction was performed with ethyl acetate, silica gel was added to the extract solution, and the solvent was distilled off under reduced pressure for adsorption onto the silica gel. The silica gel was charged into a dry column packed with silica gel and purification was performed by column chromatography (hexane:ethyl acetate=1:1, followed by ethyl acetate). The first eluted substance was the target substance, of which 130 mg was obtained as a white solid.

$^1$H-NMR (DMSO-$d_6$) δ (ppm): 1.97 (2H, tt, J=6.4 Hz, 6.4 Hz), 2.46 (2H, t, J=6.4 Hz), 3.93 (2H, t, J=6.4 Hz), 6.42 (1H, s), 6.66 (1H, d, J=5.6 Hz), 6.85 (1H, d, J=8.8 Hz), 7.29 (1H, s), 7.42 (1H, s), 7.44 (1H, d, J=8.8 Hz), 7.80 (1H, s), 8.18 (1H, d, J=5.6 Hz), 11.05 (1H, s).

The second eluted substance was 5-[(2-{[4-(4-hydroxypiperidino)butanoyl]amino}-4-pyridyl)oxy]indole, of which 520 mg was obtained as a light brown oil.

$^1$H-NMR (DMSO-$d_6$) δ (ppm): 1.25-1.35 (2H, m), 1.55-1.67 (4H, m), 1.85-1.95 (2H, m), 2.17 (2H, t, J=6.8 Hz), 2.28 (2H, t, J=6.8 Hz), 2.57-2.67 (2H, m), 3.15 (1, d, J=3.6 Hz), 3.30-3.42 (1H, m), 4.48 (1H, d, J=3.6 Hz), 6.42 (1H, s), 6.57 (1H, dd, J=5.6 Hz, 2.4 Hz), 6.85 (1H, dd, J=8.8 Hz, 2.4 Hz), 7.29 (1H, d, J=2.4 Hz), 7.40-7.43 (2H, m), 7.60 (1H, d, J=2.4 Hz), 8.09 (1H, d, J=5.6 Hz), 10.37 (1H, s), 11.23 (1H, s).

Example 217

1-(4-[6-Cyano-7-(3-diethylaminopropoxy)-4-quinolyloxy]2-fluorophenyl)-3-(4-fluorophenyl)urea After dissolving 480 mg of 6-cyano-4-{4-[4-fluoroanilinocarbonyl]amino-3-fluorophenoxy}quinolin-7-ol sodium salt in 5 ml of dimethylformamide, 350 mg of potassium carbonate and 204 mg of 3-chloropropyldiethylamine were added and the mixture was heated and stirred at 65° C. for 7 hours. After standing to cool, water was added and extraction was performed with ethyl acetate and tetrahydrofuran, after which the solvent was distilled off under reduced pressure and the residue was purified by NH silica gel column chromatography (ethyl acetate-methanol system) to obtain 135 mg of the title compound.

$^1$H-NMR Spectrum (DMSO-$d_6$) δ (ppm): 0.96 (6H, t, J=7.0 Hz) 1.93 (2H, quint, J=7.0 Hz), 2.45-2.53 (4H, m), 2.61 (2H, t, J=7.0 Hz), 4.32 (2H, t, J=7.0 Hz), 6.62 (1H, d, J=5.3 Hz), 7.10-7.19 (3H, m), 7.41 (1H, dd, J=12.3 Hz, J'=2.8 Hz), 7.46-7.52 (2H, m), 7.60 (1H, s), 8.25 (1H, t, J=9.0 Hz), 8.68 (1H, d, J=2.0 Hz), 8.76-8.78 (2H, m), 9.16 (1H, s)

The intermediates were synthesized in the following manner.

Production Example 217-1

1-(4-[7-Benzyloxy-6-cyano-4-quinolyloxy]-2-fluorophenyl)-3-(4-fluorophenyl)urea After adding 210 mg of toluene and 20 ml of acetonitrile to 6.95 g of the 7-benzyloxy-6-cyano-4-(3-fluoro-4-aminophenoxy)quinoline obtained in Production Example 8, the mixture was heated to reflux. Next, 2.67 ml of 4-fluorophenyl isocyanate was added and the mixture was further heated to reflux for 1 hour. After cooling, the precipitated solid was filtered out and dried under reduced pressure to obtain 7.45 g of the title compound.

$^1$H-NMR Spectrum (DMSO-$d_6$) δ (ppm): 5.49 (2H, s), 6.61 (1H, d, J=5.4 Hz), 7.05-7.57 (11H, m), 7.54 (1H, s), 8.24 (1H, t, 9.5 Hz), 8.63 (1H, s), 8.72 (1H, d, J=5.4 Hz), 8.77 (1H, s), 9.10 (1H, s)

Production Example 217-2

6-Cyano-4-(4-[4-fluoroanilinocarbonyl]amino-3-fluorophenoxy)quinolin-7-ol sodium salt A mixture of 1.7 g of 1-(4-[7-benzyloxy-6-cyanoquinolin-4-yloxy]-2-fluorophenyl)-3-(4-fluorophenyl)urea, 17 ml of trifluoroacetic acid and 1.7 ml of thioanisole was placed in an oil bath and heated and stirred for 20 hours at 70° C. After completion of the reaction, the reaction solution was concentrated, a saturated aqueous sodium bicarbonate solution and methanol were added, the mixture was stirred for 30 minutes, and the precipitated solid was filtered out. The obtained solid was dried under reduced pressure to obtain 1.15 g of the title compound.

$^1$H-NMR Spectrum (DMSO-$d_6$) δ (ppm): 6.62 (1H, d, J=5.3 Hz), 7.18-7.68 (7H, m), 8.24 (1H, t, J=8.5 Hz), 8.70-8.86 (3H, m), 9.20 (1H, s)

Example 218

1-(4-[6-Cyano-7-(3-morpholine-4-propoxyl)-4-quinolyloxy]-2-fluorophenyl)-3-(4-fluorophenyl)urea The title compound (205 mg) was obtained using 450 mg of 6-cyano-4-(4-[4-fluoroanilinocarbonyl]amino-3-fluorophenoxy)quinolin-7-ol sodium salt, 5 ml of dimethylformamide, 328 mg of potassium carbonate and 194 mg of 4-(3-chloropropyl)morpholine, in the same manner as Example 217.

$^1$H-NMR Spectrum (DMSO-$d_6$) δ (ppm): 2.01 (2H, quint, J=6.9 Hz), 2.36-2.44 (4H, m), 2.48-2.54 (2H, covered by DMSO peak), 3.58 (4H, t, J=4.0 Hz), 4.35 (2H, t, J=6.9 Hz), 6.64 (1H, d, J=5.3 Hz), 7.10-7.19 (3H, m), 7.41 (1H, dd, J=2.9, 12.3 Hz), 7.44-7.52 (2H, m), 7.63 (1H, s), 8.25 (1H, t, J=8.9 Hz), 8.64 (1H, d, J=2.0 Hz), 8.74-8.78 (2H, m), 9.20 (1H, s)

Example 219

1-(4-[6-Cyano-7-(3-diethylaminopropoxy)-4-quinolyloxy]-2-fluorophenyl)-3-phenylurea After dissolving 179 mg of 6-cyano-4-(4-[4-anilinocarbonylamino]-3-phenoxy)quinolin-7-ol sodium salt in 2 ml of dimethylformamide, 135 mg of potassium carbonate and 79 mg of 3-chloropropyldiethylamine were added and the mixture was heated and stirred overnight at 65-75° C. After standing to cool, water was added, extraction was performed with ethyl acetate and tetrahydrofuran and the extract was dried over sodium sulfate, after which the solvent was distilled off under reduced pressure and the residue was purified by NH silica gel column chromatography (ethyl acetate-methanol system) to obtain 60 mg of the title compound.

$^1$H-NMR Spectrum (DMSO-d$_6$) δ (ppm): 0.94 (6H, t, J=7.2 Hz) 1.92 (2H, quint, J=7.2 Hz), 2.43-2.55 (4H, covered by DMSO peak), 2.60 (2H, t, J=7.2 Hz), 4.42 (2H, t, J=7.2 Hz), 6.62 (1H, d, J=5.0 Hz), 6.98 (1H, t, J=7.2 Hz), 7.12-7.18 (1H, m), 7.29 (2H, t, J=7.2 Hz), 7.40 (1H, dd, J=11.9 Hz, J'=2.8 Hz), 7.46 (2H, d, J=7.2 Hz), 7.59 (1H, s), 8.26 (1H, t, J=9.0 Hz), 8.67 (1H, s), 8.72-8.78 (2H, m), 9.16 (1H, s)

The intermediates were synthesized in the following manner.

Production Example 219-1

1-(4-[7-Benzyloxy-6-cyano-4-quinolyloxy]-2-fluorophenyl)-3-phenylurea

After adding 1.90 g of the 7-benzyloxy-6-cyano-4-(3-fluoro-4-aminophenoxy)quinoline obtained in Production Example 8 to 60 ml of toluene and 30 ml of acetonitrile, the mixture was heated to reflux. Next, 0.76 ml of phenyl isocyanate was added and the mixture was further heated to reflux for 1 hour. After cooling, the precipitated solid was filtered out and dried under reduced pressure to obtain 1.65 g of the title compound.

$^1$H-NMR Spectrum (DMSO-d$_6$) δ (ppm): 5.45 (2H, s), 6.62 (1H, d, J=5.4 Hz), 6.95-7.57 (12H, m), 7.71 (1H, s), 8.27 (1H, t, 9.2 Hz), 8.66 (1H, s), 8.74 (1H, d, J=5.4 Hz), 8.78 (1H, s), 9.09 (1H, s)

Production Example 219-2

6-Cyano-4-(4-[4-anilinocarbonylamino]-3-fluorophenoxy)quinolin-7-ol sodium salt

A mixture of 1.64 g of 1-(4-[7-benzyloxy-6-cyano-4-quinolyloxy]-2-fluorophenyl)-3-phenylurea, 16 ml of trifluoroacetic acid and 1.6 ml of thioanisole was placed in an oil bath and heated to reflux at 65-72° C. for 14 hours. After completion of the reaction, the reaction solution was concentrated, a saturated aqueous sodium bicarbonate solution and methanol were added, the mixture was stirred for 30 minutes, and the precipitated solid was filtered out. The obtained solid was dried under reduced pressure to obtain 1.35 g of the title compound.

$^1$H-NMR Spectrum (DMSO-d$_6$) δ (ppm): 6.41 (1H, d, J=5.1 Hz), 6.98 (1H, t, J=7.1 Hz), 7.11 (1H, d, J=7.1 Hz), 7.20-7.40 (4H, m), 7.45 (2H, d, J=7.1 Hz), 8.24 (1H, t, J=8.0 Hz), 8.55 (1H, s), 8.57 (1H, d, J=5.1 Hz), 8.66 (1H, s), 9.10 (1H, s), Example 220

1-{4-[6-Cyano-7-(3-morpholino-4-propoxyl)-4-quinolyloxy]-2-fluorophenyl}-3-phenylurea The title compound (301 mg) was obtained using 505 mg of 6-cyano-4-(4-[4-anilinocarbonylamino]-3-phenoxy)-quinolin-7-ol sodium salt, 5 ml of dimethylformamide, 380 mg of potassium carbonate and 195 mg of 4-(3-chloropropyl) morpholine, in the same manner as Example 217.

$^1$H-NMR Spectrum (DMSO-d$_6$) δ (ppm): 1.99 (2H, quint, J=6.8 Hz), 2.33-2.52 (4H, m), 2.48-2.54 (2H, covered by DMSO peak), 3.58 (4H, t, J=4.2 Hz), 4.32 (2H, t, J=6.8 Hz), 6.62 (1H, d, J=5.3 Hz), 6.98 (1H, t, J=7.2 Hz), 7.12-7.48 (6H, m), 7.60 (1H, s), 8.26 (1H, t, J=8.5 Hz), 8.64 (1H, d, J=1.5 Hz), 8.72-8.78 (2H, m), 9.06 (1H, s)

Example 221

N-[4-(6-Cyano-7-[3-(dimethylamino)propoxy]-4-quinolyloxy)phenyl]-N'-(4-fluorophenyl)urea The title compound (20 mg) was obtained from 100 mg of 6-cyano-4-(4-[(4-fluoroanilino)carbonyl]aminophenoxy) quinolin-7-ol sodium salt, by the same procedure as in Example 7.

$^1$H-NMR Spectrum (DMSO-d$_6$) δ (ppm): 1.97 (2H, quint, J=7.1 Hz) 2.18 (6H, s,), 2.42 (2H, t, J=7.1 Hz), 4.32 (2H, t, J=7.1 Hz), 6.54 (1H, d, J=5.6 Hz), 7.05-7.65 (9H, m), 8.63 (1H, d, J=5.6 Hz), 8.76 (1H, s) 8.80 (1H, s). 8.88 (1H, s)

Example 222

N-(5-(6,7-Dimethoxyquinolin-4-yloxy)pyridin-2-yl)-N'-phenylurea 5-(6,7-Dimethoxyquinolin-4-yloxy)pyridin-2-ylamine (29.7 mg, 0.100 mmol) and phenyl isocyanate (13.1 mg, 0.110 mmol) were stirred in dimethylformamide (1 ml) at room temperature for 18 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=20:1), and the fraction containing the target substance was concentrated, suspended in ethyl acetate and diluted with hexane, after which the crystals were filtered out, washed with hexane and then blow-dried to obtain the title compound (30.4 mg, 0.073 mmol, 73%) as colorless crystals.

$^1$H-NMR Spectrum (DMSO-d$_6$) δ (ppm): 3.95 (3H, s), 3.96 (3H, s), 6.53 (1H, d, J=5.4 Hz), 7.00-7.06 (1H, m), 7.28-7.35 (2H, m), 7.41 (1H, s), 7.50-7.56 (3H, m), 7.76-7.82 (2H, m), 8.30-8.33 (1H, m), 8.49 (1H, d, J=5.4 Hz), 9.56 (1H, s), 10.04 (1H, s).

The intermediates were synthesized in the following manner.

Production Example 222-1

2-Chloro-6-iodopyridin-3-ol

After dissolving 2-chloro-3-hydroxypyridine (5.00 g, 38.6 mmol) and sodium iodide (5.79 g, 38.6 mmol) in dimethylformamide (70 ml), Chloramine T (10.9 g, 38.6 mmol) was added while cooling on ice, and then the mixture was stirred at room temperature for 1 hour. Upon adding 2N aqueous hydrochloric acid (19.3 ml, 38.6 mmol) after the reaction, the reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=1:2), and the fraction containing the target substance was concentrated to obtain the title compound (9.00 g, 35.2 mmol, 91%) as colorless crystals.

¹H-NMR Spectrum (CDCl₃) δ (ppm): 5.61 (1H, br s), 7.02 (1H, d, J=8.2 Hz), 7.56 (1H, d, J=8.2 Hz).

Production Example 222-2

4-(2-Chloro-6-iodopyridin-3-yloxy)-6,7-dimethoxyquinoline

4-Chloro-6,7-dimethoxyquinoline (2.23 g, 10.0 mmol), 2-chloro-6-iodopyridin-3-ol (2.55 g, 22.0 mmol) and diisopropylethylamine (1.29 g, 10.0 mmol) were heated and stirred in dimethylformamide (5 ml) at 130° C. for 3 hours. The reaction solution was distributed between an ethyl acetate-tetrahydrofuran mixed solvent and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=3:1), and the fraction containing the target substance was concentrated, suspended in ethyl acetate and diluted with hexane, after which the crystals were filtered out, washed with hexane and then blow-dried to obtain the title compound (2.16 g, 4.88 mmol, 49%) as colorless crystals.

¹H-NMR Spectrum (CDCl₃) δ (ppm): 4.05 (3H, s), 4.06 (3H, s), 6.39 (1H, d, J=5.2 Hz), 7.20 (1H, d, J=8.2 Hz), 7.45 (1H, s), 7.48 (1H, s), 7.75 (1H, d, J=8.2 Hz), 8.55 (1H, d, J=5.2 Hz).

Production Example 222-3

6-Chloro-5-(6,7-dimethoxyquinolin-4-yloxy)pyridin-2-ylamine

Benzophenoneimine (1.67 g, 9.21 mmol) and tert-butoxysodium (885 mg, 9.21 mmol) were heated and stirred in toluene (40 ml) for 1 hour at 80° C. under a nitrogen atmosphere, and then 4-(2-chloro-6-iodopyridin-3-yloxy)-6,7-dimethoxyquinoline (3.72 g, 8.40 mmol), tris(dibenzylideneacetone)dipalladium(0) (86.9 mg, 0.084 mmol) and rac-2,2'-bis(diphenylphosphino)-1,1'-binaphthyl (157 mg, 0.252 mmol) were added and the mixture was heated and stirred at 90° C. for 6 hours. After completion of the reaction, the reaction mixture was filtered with celite, the filtrate was subjected to silica gel column chromatography (eluent—ethyl acetate:hexane=3:1), and the fraction containing the target substance was concentrated to obtain a yellow oil (1.98 g). The yellow oil (1.98 g) was dissolved in ethanol (20 ml), 1N aqueous hydrochloric acid (5 ml) was added and the mixture was stirred at room temperature for 1 hour. After completion of the reaction, the reaction solution was neutralized with 5N aqueous sodium hydroxide (1 ml) and distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate), and the fraction containing the target substance was concentrated to obtain the title compound (506 mg, 1.53 mmol, 18%) as colorless crystals.

¹H-NMR Spectrum (CDCl₃) δ (ppm): 4.06 (3H, s), 4.07 (3H, s), 4.71 (2H, s), 6.34 (1H, d, J=5.2 Hz), 6.53 (1H, d, J=8.8 Hz), 7.37 (1H, d, J=8.8 Hz), 7.43 (1H, s), 7.59 (1H, s), 8.50 (1H, d, J=5.2 Hz).

Production Example 222-4

5-(6,7-Dimethoxyquinolin-4-yloxy)pyridin-2-ylamine

After suspending 6-chloro-5-(6,7-dimethoxyquinolin-4-yloxy)pyridin-2-ylamine (500 mg, 1.51 mmol) in a mixed solvent of methanol (20 ml), tetrahydrofuran (10 ml) and triethylamine (3 ml), palladium carbon (300 mg) was added and the mixture was stirred for 15 hours at room temperature under a hydrogen atmosphere. The catalyst was filtered off by celite filtration, washing was performed with ethanol, and the filtrate was distilled off under reduced pressure. The obtained crude product was subjected to silica gel column chromatography (eluent—ethyl acetate), and the fraction containing the target substance was concentrated, suspended in ethyl acetate and diluted with hexane, after which the crystals were filtered out, washed with hexane and then blow-dried to obtain the title compound (138 mg, 0.465 mmol, 31%) as colorless crystals.

¹H-NMR Spectrum (CDCl₃) δ (ppm): 4.05 (3H, s), 4.07 (3H, s), 4.52 (2H, s), 6.42 (1H, d, J=5.2 Hz), 6.61 (1H, d, J=8.8 Hz), 7.32 (1H, dd, J=2.8, 8.8 Hz), 7.42 (1H, s), 7.57 (1H, s), 8.04 (1H, d, J=2.8 Hz), 8.49 (1H, d, J=5.2 Hz).

Example 223

N-(5-(6,7-Dimethoxyquinolin-4-yloxy)pyridin-2-yl)-N'-(4-fluorophenyl)urea

The title compound (50.9 mg, 117 mmol, 78%) was obtained as colorless crystals from the 5-(6,7-dimethoxyquinolin-4-yloxy)pyridin-2-ylamine (44.5 mg, 0.150 mmol) obtained in Production Example 222-4 and 4-fluorophenyl isocyanate (22.6 mg, 0.165 mmol), in the same manner as Example 222.

¹H-NMR Spectrum (DMSO-d₆) δ (ppm): 3.94 (3H, s), 3.95 (3H, s), 6.53 (1H, d, J=5.2 Hz), 7.13-7.20 (2H, m), 7.41 (1H, s), 7.51-7.57 (3H, m), 7.74-7.82 (2H, m), 8.30-8.33 (1H, m), 8.49 (1H, d, J=5.2 Hz), 9.55 (1H, s), 10.09 (1H, s).

Example 224

N-(5-(6,7-Dimethoxyquinolin-4-yloxy)pyridin-2-yl)-N'-(thiazol-2-yl)urea

The 5-(6,7-dimethoxyquinolin-4-yloxy)pyridin-2-ylamine (44.5 mg, 0.150 mmol) obtained in Production Example 222-4 and thiazol-2-ylcarbamic acid phenyl ester (39.6 mg, 0.180 mmol) were stirred in dimethylsulfoxide (1 ml) at 85° C. for 2 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=30:1), and the fraction containing the target substance was concentrated, suspended in ethyl acetate and diluted with hexane, after which the crystals were filtered out, washed with hexane and then blow-dried to obtain the title compound (46.7 mg, 0.110 mmol, 74%) as colorless crystals.

¹H-NMR Spectrum (DMSO-d₆) δ (ppm): 3.95 (3H, s), 3.96 (3H, s), 6.53 (1H, d, J=5.2 Hz), 7.20 (1H, d, J=3.4 Hz), 7.41 (1H, s), 7.43 (1H, d, J=3.4 Hz), 7.54 (1H, s), 7.80-7.86 (2H, m), 8.36-8.39 (1H, m), 8.49 (1H, d, J=5.2 Hz), 9.92 (1H, br s), 11.55 (1H, br s)

The intermediates were synthesized in the following manner. .

Production Example 224-1

Thiazol-2-ylcarbamic acid phenyl ester

After dissolving 2-aminothiazole (5.01 g, 50.0 mmol) and pyridine (7.91 g, 100 mmol) in dimethylformamide (50 ml), phenyl chloroformate (8.22 g, 52.5 mmol) was added while cooling on ice, and the mixture was stirred at room temperature for 1 hour. The reaction solution was distributed between an ethyl acetate-tetrahydrofuran mixed solvent and water, the organic layer was washed with water and saturated brine and dried over anhydrous magnesium sulfate, the drying agent was filtered off and the filtrate was distilled off under reduced pressure. After adding ethyl acetate and then hexane to the obtained crude product, the precipitated crystals were filtered out and blow-dried to obtain the title compound (10.6 g, 48.1 mmol, 96%) as colorless crystals.

$^1$H-NMR Spectrum (CDCl$_3$) δ (ppm): 6.97 (1H, d, J=3.4 Hz), 7.24-7.32 (3H, m), 7.40-7.46 (2H, m), 7.52 (1H, d, J=3.4 Hz), 13.19 (1H, s).

Example 225

N-(6-Chloro-5-(6,7-dimethoxyquinolin-4-yloxy)pyridin-2-yl)-N'-phenylurea

The 6-chloro-5-(6,7-dimethoxyquinolin-4-yloxy)pyridin-2-ylamine (33.2 mg, 0.100 mmol) obtained in Production Example 222-3 and phenyl isocyanate (13.1 mg, 0.110 mmol) were heated and stirred in dimethylformamide (1 ml) at 60° C. for 2 hours. the reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate), and the fraction containing the target substance was concentrated, suspended in ethyl acetate and diluted with hexane, after which the crystals were filtered out, washed with hexane and then blow-dried to obtain the title compound (17.5 mg, 0.039 mmol, 39%) as colorless crystals.

$^1$H-NMR Spectrum (DMSO-d$_6$) δ (ppm): 3.96 (6H, s), 6.50 (1H, d, J=5.2 Hz), 7.01-7.07 (1H, m), 7.30-7.37 (2H, m), 7.43 (1H, s), 7.46-7.51 (2H, m), 7.54 (1H, s), 7.94-8.00 (2H, m), 8.49 (1H, d, J=5.2 Hz), 9.29 (1H, br s), 9.75 (1H, br s).

Example 226

N-(5-(6,7-Dimethoxyquinolin-4-ylsulfanyl)thiophen-2-yl)-N'-phenylurea 5-(6,7-Dimethoxyquinolin-4-ylsulfanyl)thiophen-2-ylamine (89.0 mg, 0.280 mmol) and phenyl isocyanate (36.6 mg, 0.307 mmol) were stirred in dimethylformamide (1 ml) at room temperature for 1 hour. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=50:1), and the fraction containing the target substance was concentrated, suspended in ethyl acetate and diluted with hexane, after which the crystals were filtered out, washed with hexane and then blow-dried to obtain the title compound (60.0 mg, 0.137 mmol, 48%) as colorless crystals.

$^1$H-NMR Spectrum (DMSO-d$_6$) δ (ppm): 3.95 (3H, s), 3.98 (3H, s), 6.70 (1H, d, J=3.6 Hz), 6.74 (1H, d, J=4.8 Hz), 6.98-7.03 (1H, m), 7.26-7.36 (4H, m), 7.40 (1H, s), 7.43-7.50 (2H, m), 8.48 (1H, d, J=4.8 Hz), 9.02 (1H, br s), 10.27 (1H, br s).

The intermediates were synthesized in the following manner.

Production Example 226-1

6,7-Dimethoxy-1H-quinolin-4-thione

After suspending the 6,7-dimethoxy-1H-quinolin-4-one (10.3 g, 50.0 mmol) described in WO9717329, phosphorus pentasulfide (26.7 g, 60.0 mmol) and sodium bicarbonate (26.7 g, 318 mmol) in diglyme (diethyleneglycol dimethyl ether) (100 ml), the suspension was heated and stirred at 80° C. for 2 hours. The reaction solution was returned to room temperature and poured into ice water (1000 ml), and the precipitated crystals were filtered out, washed with water and blow-dried to obtain the title compound (8.19 g, 37.0 mmol, 74%) as yellow crystals.

$^1$H-NMR Spectrum (DMSO-d$_6$) δ (ppm): 3.87 (3H, s), 3.91 (3H, s), 7.07 (1H, s), 7.19 (1H, d, J=6.8 Hz), 7.74 (1H, d, J=6.8 Hz), 8.11 (1H, s), 12.76 (1H, br s).

Production Example 226-2

6,7-Dimethoxy-4-(5-nitrothiophen-2-ylsulfanyl)quinoline 6,7-Dimethoxy-1H-quinolin-4-thione (2.21 g, 10.0 mmol), 2-bromo-5-nitrothiophene (2.29 g, 11.0 mmol) and potassium carbonate (2.07 g, 15.0 mmol) were stirred in dimethylformamide (30 ml) at room temperature for 1 hour. The reaction solution was distributed between ethyl acetate and water, the organic layer was washed with 1N aqueous sodium hydroxide, water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=3:1), and the fraction containing the target substance was concentrated to obtain the title compound (1.93 g, 5.54 mmol, 55%) as yellow crystals.

$^1$H-NMR Spectrum (CDCl$_3$) δ (ppm): 4.04 (3H, s), 4.06 (3H, s), 7.10 (1H, d, J=4.8 Hz), 7.22 (1H, d, J=4.4 Hz), 7.37 (1H, s), 7.46 (1H, s), 7.89 (1H, d, J=4.4 Hz), 8.60 (1H, d, J=4.8 Hz).

Production Example 226-3

5-(6,7-Dimethoxyquinolin-4-ylsulfanyl)thiophen-2-ylamine

After suspending 6,7-dimethoxy-4-(5-nitrothiophen-2-ylsulfanyl)quinoline (1.39 g, 4.00 mmol), iron (1.12 g, 20.0 mmol) and ammonium chloride (2.18 g, 40.0 mmol) in an ethanol (32 ml)-water (8 ml) mixed solvent, the suspension was heated and stirred at 80° C. for 5 minutes. After completion of the reaction, the reaction mixture was filtered with celite and washed in ethyl acetate. The organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=3:1), and the fraction containing the target substance was concentrated to obtain the title compound (1.93 g, 5.54 mmol, 55%) as yellowish-brown crystals.

$^1$H-NMR Spectrum (CDCl$_3$) δ (ppm): 4.04 (3H, s), 4.06 (3H, s), 4.15 (2H, s), 6.21 (1H, d, J=3.8 Hz), 6.87 (1H, d, J=5.0 Hz), 7.04 (1H, d, J=3.8 Hz), 7.31 (1H, s), 7.40 (1H, s), 8.47 (1H, d, J=5.0 Hz).

Example 227

N-(5-(6,7-Dimethoxyquinolin-4-ylsulfanyl)thiophen-2-yl)-N'-(4-fluorophenyl)urea

The title compound (29.3 mg, 64.3 mmol, 64%) was obtained as colorless crystals from 5-(6,7-dimethoxyquinolin-4-ylsulfanyl)thiophen-2-ylamine (31.8 mg, 0.100 mmol) and 4-fluorophenyl isocyanate (15.1 mg, 0.110 mmol), by the same procedure as in Example 226.

$^1$H-NMR Spectrum (DMSO-d$_6$) δ (ppm): 3.94 (3H, s), 3.97 (3H, s), 6.70 (1H, d, J=4.0 Hz), 6.74 (1H, d, J=5.2 Hz), 7.10-7.18 (2H, m), 7.31 (1H, s), 7.33 (1H, d, J=4.0 Hz), 7.39 (1H, s), 7.45-7.51 (2H, m), 8.48 (1H, d, J=5.2 Hz), 9.05 (1H, br s), 10.29 (1H, br s).

Example 228

N-(5-(6,7-Dimethoxyquinolin-4-ylsulfanyl)thiophen-2-yl)-N'-(3-fluorophenyl)urea

The title compound (62.0 mg, 0.136 mmol, 68%) was obtained as light brown crystals from 5-(6,7-dimethoxyquinolin-4-ylsulfanyl)thiophen-2-ylamine (64.0 mg, 0.200 mmol) and 4-fluorophenyl isocyanate (15.1 mg, 0.110 mmol), by the same procedure as in Example 226.

$^1$H-NMR Spectrum (DMSO-d$_6$) δ (ppm): 3.95 (3H, s), 3.97 (3H, s), 6.72 (1H, d, J=3.6 Hz), 6.75 (1H, d, J=4.6 Hz), 6.80-6.85 (1H, m), 7.17-7.21 (1H, m), 7.29-7.36 (3H, m), 7.40 (1H, s), 7.42-7.48 (1H, m), 8.48 (1H, d, J=4.6 Hz), 9.18 (1H, br s), 10.27 (1H, br s).

Example 229

N-(3-Cyanophenyl)-N'-(5-(6,7-dimethoxyquinolin-4-ylsulfanyl)thiophen-2-yl)urea

The title compound (60.0 mg, 0.130 mmol, 65%) was obtained as light brown crystals from 5-(6,7-dimethoxyquinolin-4-ylsulfanyl)thiophen-2-ylamine (64 mg, 0.200 mmol) and 3-cyanophenyl isocyanate (31.7 mg, 0.220 mmol), by the same procedure as in Example 226.

$^1$H-NMR Spectrum (DMSO-d$_6$) δ (ppm): 3.95 (3H, s), 3.97 (3H, s), 6.73-6.77 (2H, m), 7.31 (1H, s), 7.34 (1H, d, J=4.0 Hz), 7.40 (1H, s), 7.44-7.48 (1H, m), 7.49-7.54 (1H, m), 7.71-7.75 (1H, m), 7.94-7.96 (1H, m), 8.48 (1H, d, J=4.8 Hz), 9.30 (1H, br s), 10.40 (1H, br s).

Example 230

N-(5-(6,7-Dimethoxyquinolin-4-ylsulfanyl)thiophen-2-yl)-N'-(thiazol-2-yl)urea 5-(6,7-Dimethoxyquinolin-4-ylsulfanyl)thiophen-2-ylamine (31.8 mg, 0.100 mmol) and thiazol-2-ylcarbamic acid phenyl ester (33.0 mg, 0.150 mmol) were stirred in dimethylsulfoxide (1 ml) at 85° C. for 2 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=20:1), and the fraction containing the target substance was concentrated, suspended in ethyl acetate and diluted with hexane, after which the crystals were filtered out, washed with hexane and then blow-dried to obtain the title compound (25.6 mg, 0.058 mmol, 58%) as colorless crystals.

$^1$H-NMR Spectrum (DMSO-d$_6$) δ (ppm): 3.95 (3H, s), 3.97 (3H, s), 6.74 (1H, d, J=5.0 Hz), 6.75-6.80 (1H, m), 7.04-7.10 (1H, m), 7.32 (1H, s), 7.34 (1H, d, J=4.0 Hz), 7.36-7.39 (1H, m), 7.40 (1H, s), 8.48 (1H, d, J=5.0 Hz).

Example 231

N-(5-(6,7-Dimethoxyquinolin-4-ylsulfanyl)thiophen-2-yl)-N'-(3-methanesulfonylphenyl)urea The title compound (61.0 mg, 0.118 mmol, 59%) was obtained as light brown crystals from 5-(6,7-dimethoxyquinolin-4-ylsulfanyl)thiophen-2-ylamine (64.0 mg, 0.200 mmol) and (3-methanesulfonylphenyl)carbamic acid phenyl ester (87.4 mg, 0.300 mmol), by the same procedure as in Example 230.

$^1$H-NMR Spectrum (DMSO-d$_6$) δ (ppm): 3.20 (3H, s), 3.95 (3H, s), 3.97 (3H, s), 6.75 (1H, d, J=4.8 Hz), 6.76 (1H, d, J=4.0 Hz), 7.32 (1H, s), 7.35 (1H, d, J=4.0 Hz), 7.40 (1H, s), 7.53-7.60 (2H, m), 7.70-7.74 (1H, m), 8.13-8.16 (1H, m), 8.48 (1H, d, J=4.8 Hz), 9.40 (1H, br s), 10.35 (1H, br s).

Example 232

N-(5-(6,7-Dimethoxyquinolin-4-ylsulfanyl)thiophen-2-yl)-N'-(2-hydroxymethylphenyl)urea The title compound (27.0 mg, 0.058 mmol, 58%) was obtained as colorless crystals from (5-(6,7-dimethoxyquinolin-4-ylsulfanyl)thiophen-2-yl)carbamic acid phenyl ester (43.9 mg, 0.100 mmol) and 2-aminobenzyl alcohol (24.6 mg, 0.200 mmol), by the same procedure as in Example 230.

$^1$H-NMR Spectrum (DMSO-d$_6$) δ (ppm): 3.94 (3H, s), 3.96 (3H, s), 4.54 (2H, d, J=5.6 Hz), 5.51 (1H, t, J=5.6 Hz), 6.65 (1H, d, J=4.0 Hz), 6.74 (1H, d, J=4.8 Hz), 7.02-7.07 (1H, m), 7.22-7.27 (1H, m), 7.28-7.34 (3H, m), 7.39 (1H, s), 7.80-7.84 (1H, m), 8.46-8.50 (2H, m), 10.89 (1H, br s).

The intermediates were synthesized in the following manner.

Production Example 232-1

(5-(6,7-Dimethoxyquinolin-4-ylsulfanyl)thiophen-2-yl)carbamic acid phenyl ester

After dissolving 5-(6,7-dimethoxyquinolin-4-ylsulfanyl)thiophen-2-ylamine (696 mg, 2.00 mmol) and pyridine (174 mg, 2.20 mmol) in a tetrahydrofuran (10 ml)-dimethylformamide (5 ml) mixed solvent, phenyl chloroformate (329 mg, 2.10 mmol) was added while cooling on ice, and the mixture was stirred at room temperature for 1 hour. The reaction solution was distributed between ethyl acetate and water, the organic layer was washed with water and saturated brine and dried over anhydrous magnesium sulfate, the drying agent was filtered off and the filtrate was distilled off under reduced pressure. After adding ethyl acetate and then hexane to the obtained crude product, the precipitated crystals were filtered out and blow-dried to obtain the title compound (720 mg, 1.64 mmol, 82%) as yellowish-brown crystals.

$^1$H-NMR Spectrum (CDCl$_3$) δ (ppm): 4.08 (3H, s), 4.09 (3H, s), 6.86-6.92 (2H, m), 7.10-7.16 (2H, m), 7.20-7.26 (2H, m), 7.34 (1H, s), 7.36-7.41 (2H, m), 7.80-7.85 (1H, m), 8.35 (1H, d, J=5.6 Hz), 8.75 (1H, br s).

Example 233

N-(5-(6,7-Dimethoxyquinolin-4-ylsulfanyl)thiophen-2-yl)-N'-(3-hydroxymethylphenyl)urea The title compound (25.0 mg, 0.054 mmol, 54%) was obtained as light brown crystals from the (5-(6,7-dimethoxyquinolin-4-ylsulfanyl)thiophen-2-yl)carbamic acid phenyl ester (43.9 mg, 0.100 mmol) obtained in Production Example 232-1 and 3-aminobenzyl alcohol (24.6 mg, 0.200 mmol), by the same procedure as in Example 230.

$^1$H-NMR Spectrum (DMSO-d$_6$) δ (ppm): 3.95 (3H, s), 3.97 (3H, s), 4.46 (2H, d, J=5.6 Hz), 5.19 (1H, t, J=5.6 Hz), 6.70 (1H, d, J=4.0 Hz), 6.75 (1H, d, J=4.8 Hz), 6.93-6.97 (1H, m), 7.21-7.26 (1H, m), 7.30-7.34 (3H, m), 7.40 (1H, s), 7.43-7.46 (1H, m), 8.48 (1H, d, J=4.8 Hz), 8.97 (1H, s).

Example 234

N-(5-(6,7-Dimethoxyquinolin-4-ylsulfanyl)thiophen-2-yl)-N'-(4-hydroxymethylphenyl)urea The title compound (27.0 mg, 0.058 mmol, 58%) was obtained as light yellow crystals from (5-(6,7-dimethoxyquinolin-4-ylsulfanyl)thiophen-2-yl)carbamic acid phenyl ester (43.9 mg, 0.100 mmol) and 4-aminobenzyl alcohol (224 mg, 1.82 mmol), by the same procedure as in Example 230.

$^1$H-NMR Spectrum (DMSO-d$_6$) δ (ppm): 3.94 (3H, s), 3.97 (3H, s), 4.42 (2H, d, J=5.6 Hz), 5.07 (1H, t, J=5.6 Hz), 6.69 (1H, d, J=4.0 Hz), 6.75 (1H, d, J=5.0 Hz), 7.21-7.26 (2H, m), 7.30-7.34 (2H, m), 7.38-7.43 (3H, m), 8.47 (1H, d, J=5.0 Hz), 8.88 (1H, s), 10.13 (1H, s).

Example 235

N-(2-(6,7-Dimethoxyquinolin-4-ylsulfanyl)thiazol-5-yl)-N'-phenylurea 2-(6,7-Dimethoxyquinolin-4-ylsulfanyl)thiazol-5-ylamine (64.0 mg, 0.200 mmol) and phenyl isocyanate (26.2 mg, 0.220 mmol) were stirred in dimethylformamide (1 ml) at room temperature for 15 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=30:1), and the fraction containing the target substance was concentrated, suspended in ethyl acetate and diluted with hexane, after which the crystals were filtered out, washed with hexane and then blow-dried to obtain the title compound (53.2 mg, 0.121 mmol, 60%) as colorless crystals.

$^1$H-NMR Spectrum (DMSO-d$_6$) δ (ppm): 3.94 (3H, s), 3.95 (3H, s), 6.98-7.05 (2H, m), 7.26-7.34 (2H, m), 7.39 (1H, s), 7.43-7.47 (3H, m), 7.64 (1H, s), 8.55 (1H, d, J=4.8 Hz), 9.10 (1H, s), 10.29 (1H, br s).

The intermediates were synthesized in the following manner.

Production Example 235-1

6,7-Dimethoxy-4-(5-nitrothiazol-2-ylsulfanyl)quinoline

After suspending 6,7-dimethoxy-1H-quinoline-4-thione (2.21 g, 10.0 mmol) in dimethylformamide (30 ml), 2-bromo-5-nitrothiazole (2.30 g, 11.0 mmol) was added at 0° C., and then the mixture was stirred at room temperature for 1 hour. The reaction solution was distributed between ethyl acetate and 1N aqueous sodium hydroxide, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=3:1), and the fraction containing the target substance was concentrated, suspended in ethyl acetate and diluted with hexane, after which the crystals were filtered out, washed with hexane and then blow-dried to obtain the title compound (1.70 g, 4.87 mmol, 49%) as light yellow crystals.

$^1$H-NMR Spectrum (CDCl$_3$) δ (ppm): 4.00 (3H, s), 4.08 (3H, s), 7.50 (1H, s), 7.54 (1H, s), 7.70 (1H, d, J=4.8 Hz), 8.37 (1H, s), 8.83 (1H, d, J=4.8 Hz).

Production Example 235-2

2-(6,7-Dimethoxyquinolin-4-ylsulfanyl)thiazol-5-ylamine

After suspending 6,7-dimethoxy-4-(5-nitrothiazol-2-ylsulfanyl)quinoline (699 mg, 2.00 mmol), iron (559 mg, 10.0 mmol) and ammonium chloride (1.07 g, 20.0 mmol) in an ethanol (20 ml)-water (5 ml) mixed solvent, the suspension was heated and stirred at 80° C. for 20 minutes. After completion of the reaction, the reaction mixture was filtered with celite and washed in an ethyl acetate-tetrahydrofuran mixed solvent. The organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=30:1), and the fraction containing the target substance was concentrated to obtain the title compound (190 mg, 0.595 mmol, 30%) as yellowish-brown crystals.

$^1$H-NMR Spectrum (CDCl$_3$) δ (ppm): 3.99 (2H, br s), 4.04 (3H, s), 4.05 (3H, s), 7.10 (1H, d, J=5.2 Hz), 7.17 (1H, s), 7.41 (1H, s), 7.42 (1H, s), 8.54 (1H, d, J=5.2 Hz).

Example 236

N-(2-(6,7-Dimethoxyquinolin-4-ylsulfanyl)thiazol-5-yl)-N'-(4-fluorophenyl)urea

The title compound (62.3 mg, 0.136 mmol, 68%) was obtained as colorless crystals from 2-(6,7-dimethoxyquinolin-4-ylsulfanyl)thiazol-5-ylamine (64.0 mg, 0.200 mmol) and 4-fluorophenyl isocyanate (30.1 mg, 0.220 mmol), by the same procedure as in Example 235.

$^1$H-NMR Spectrum (DMSO-d$_6$) δ (ppm): 3.94 (3H, s), 3.95 (3H, s), 7.03 (1H, d, J=4.8 Hz), 7.10-7.18 (2H, m), 7.39 (1H, s), 7.42-7.48 (3H, m), 7.64 (1H, s), 8.55 (1H, d, J=4.8 Hz), 9.14 (1H, s), 10.32 (1H, br s).

Example 237

N-(2-(6,7-Dimethoxyquinolin-4-ylsulfanyl)thiazol-5-yl)-N'-(3-fluorophenyl)urea

The title compound (70.0 mg, 0.153 mmol, 51%) was obtained as colorless crystals from 2-(6,7-dimethoxyquinolin-4-ylsulfanyl)thiazol-5-ylamine (95.8 mg, 0.300 mmol) and 3-fluorophenyl isocyanate (45.2 mg, 0.330 mmol), by the same procedure as in Example 235.

$^1$H-NMR Spectrum (DMSO-d$_6$) δ (ppm): 3.94 (3H, s), 3.95 (3H, s), 6.80-6.86 (1H, m), 7.06 (1H, d, J=4.8 Hz), 7.16-7.20 (1H, m), 7.28-7.35 (1H, m), 7.38-7.45 (3H, m), 7.66 (1H, s), 8.55 (1H, d, J=4.8 Hz), 9.33 (1H, s), 10.37 (1H, br s).

Example 238

N-(3-Cyanophenyl)-N'-(2-(6,7-dimethoxyquinolin-4-ylsulfanyl)thiazol-5-yl)urea

The title compound (94.0 mg, 0.203 mmol, 68%) was obtained as light yellow crystals from 2-(6,7-dimethoxyquinolin-4-ylsulfanyl)thiazol-5-ylamine (95.8 mg, 0.300 mmol) and 3-cyanophenyl isocyanate (47.6 mg, 0.330 mmol), by the same procedure as in Example 235.

$^1$H-NMR Spectrum (DMSO-d$_6$) δ (ppm): 3.94 (3H, s), 3.95 (3H, s), 7.07 (1H, d, J=4.8 Hz), 7.40 (1H, s), 7.43 (1H, s), 7.45-7.54 (2H, m), 7.67 (1H, s), 7.70-7.74 (1H, m), 7.91-7.94 (1H, m), 8.56 (1H, d, J=4.8 Hz), 9.44 (1H, s), 10.49 (1H, br s).

Example 239

N-(2,4-Difluorophenyl)-N'-(2-(6,7-dimethoxyquinolin-4-ylsulfanyl)thiazol-5-yl)urea The title compound (123 mg, 0.259 mmol, 86%) was obtained as light orange crystals from 2-(6,7-dimethoxyquinolin-4-ylsulfanyl)thiazol-5-ylamine (95.8 mg, 0.300 mmol) and 2,4-difluorophenyl isocyanate (51.2 mg, 0.330 mmol), by the same procedure as in Example 235.

$^1$H-NMR Spectrum (DMSO-d$_6$) δ (ppm): 3.94 (3H, s), 3.95 (3H, s), 7.04 (1H, d, J=4.8 Hz), 7.05-7.09 (1H, m), 7.30-7.37 (1H, m), 7.39 (1H, s), 7.43 (1H, s), 7.65 (1H, s), 7.84-7.91 (1H, m), 8.54 (1H, d, J=4.8 Hz), 8.84 (1H, s), 10.48 (1H, br s).

Example 240

N-(2-Chlorophenyl)-N'-(2-(6,7-dimethoxyquinolin-4-ylsulfanyl)thiazol-5-yl)urea

The title compound (132 mg, 0.279 mmol, 93%) was obtained as light brown crystals from 2-(6,7-dimethoxyquinolin-4-ylsulfanyl)thiazol-5-ylamine (95.8 mg, 0.300 mmol) and 2-chlorophenyl isocyanate (50.6 mg, 0.330 mmol), by the same procedure as in Example 235.

$^1$H-NMR Spectrum (DMSO-d$_6$) δ (ppm): 3.94 (3H, s), 3.95 (3H, s), 7.05 (1H, d, J=5.0 Hz), 7.07-7.12 (1H, m), 7.28-7.34 (1H, m), 7.39 (1H, s), 7.43 (1H, s), 7.47-7.50 (1H, m), 7.67 (1H, s), 8.01-8.04 (1H, m), 8.55 (1H, d, J=5.0 Hz), 8.62 (1H, s), 10.85 (1H, br s).

Example 241

N-(3-Chlorophenyl)-N'-(2-(6,7-dimethoxyquinolin-4-ylsulfanyl)thiazol-5-yl)urea

The title compound (124 mg, 0.262 mmol, 87%) was obtained as light brown crystals from 2-(6,7-dimethoxyquinolin-4-ylsulfanyl)thiazol-5-ylamine (95.8 mg, 0.300 mmol) and 3-chlorophenyl isocyanate (50.6 mg, 0.330 mmol), by the same procedure as in Example 235.

$^1$H-NMR Spectrum (DMSO-d$_6$) δ (ppm): 3.94 (3H, s), 3.95 (3H, s), 7.04-7.09 (2H, m), 7.30-7.34 (2H, m), 7.40 (1H, s), 7.43 (1H, s), 7.63-7.66 (2H, m), 8.55 (1H, d, J=4.8 Hz), 9.30 (1H, s), 10.40 (1H, br s).

Example 242

N-(4-Chlorophenyl)-N'-(2-(6,7-dimethoxyquinolin-4-ylsulfanyl)thiazol-5-yl)urea

The title compound (120 mg, 0.253 mmol, 85%) was obtained as colorless crystals from 2-(6,7-dimethoxyquinolin-4-ylsulfanyl)thiazol-5-ylamine (95.8 mg, 0.300 mmol) and 4-chlorophenyl isocyanate (50.6 mg, 0.330 mmol), by the same procedure as in Example 235.

$^1$H-NMR Spectrum (DMSO-d$_6$) δ (ppm): 3.94 (3H, s), 3.95 (3H, s), 7.04 (1H, d, J=4.8 Hz), 7.31-7.36 (2H, m), 7.39 (1H, s), 7.43 (1H, s), 7.45-7.50 (2H, m), 7.65 (1H, s), 8.55 (1H, d, J=4.8 Hz), 9.24 (1H, s), 10.34 (1H, br s).

Example 243

N-(2-(6,7-Dimethoxyquinolin-4-ylsulfanyl)thiazol-5-yl)-N'-(thiazol-2-yl)urea

After dissolving 2-(6,7-dimethoxyquinolin-4-ylsulfanyl)thiazol-5-ylamine (216 mg, 0.676 mmol) and pyridine (58.8 mg, 0.743 mmol) in tetrahydrofuran (3 ml), 4-nitrophenyl chloroformate (150 mg, 0.743 mmol) was added while cooling on ice, the mixture was stirred at room temperature for 30 minutes, 2-aminothiazole (101 mg, 1.01 mmol) and triethylamine (1 ml) were added, and the mixture was heated and stirred at 60° C. for 1 hour. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=30:1), and the fraction containing the target substance was concentrated, suspended in ethyl acetate and diluted with hexane, after which the crystals were filtered out, washed with hexane and then blow-dried to obtain the title compound (57 mg, 0.128 mmol, 19%) as colorless crystals.

$^1$H-NMR Spectrum (DMSO-d$_6$) δ (ppm): 3.94 (3H, s), 3.95 (3H, s), 7.03-7.09 (2H, m), 7.34-7.38 (1H, m), 7.40 (1H, s), 7.43 (1H, s), 7.66 (1H, br s), 8.55 (1H, d, J=4.8 Hz).

Example 244

7-Methoxy-4-(5-(3-phenylureido)thiophen-2-ylsulfanyl)quinoline-6-carboxamide 4-(5-Aminothiophen-2-ylsulfanyl)-7-methoxyquinoline-6-carboxamide (49.0 mg, 0.150 mmol) and phenyl isocyanate (19.6 mg, 0.165 mmol) were stirred in dimethylformamide (1 ml) at room temperature for 2 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was suspended in ethyl acetate and diluted with hexane, and then the crystals were filtered out, washed with hexane and blow-dried to obtain the title compound (25.0 mg, 0.056 mmol, 37%) as light yellow crystals.

$^1$H-NMR Spectrum (DMSO-d$_6$) δ (ppm): 4.02 (3H, s), 6.72 (1H, d, J=3.4 Hz), 6.77 (1H, d, J=4.8 Hz), 6.98-7.03 (1H, m), 7.27-7.34 (2H, m), 7.35 (1H, d, J=3.4 Hz), 7.43-7.49 (2H, m), 7.53 (1H, s), 7.80 (1H, br s), 7.89 (1H, br s), 8.52 (1H, s), 8.65 (1H, d, J=4.8 Hz), 8.95 (1H, br s), 10.21 (1H, br s).

The intermediates were synthesized in the following manner.

Production Example 244-1

7-Methoxy-4-(5-nitrothiophen-2-ylsulfanyl)quinoline-6-carboxamide

4-Chloro-7-methoxyquinoline-6-carboxamide (1.18 g, 5.00 mmol) and sodium sulfide (1.20 g, 5.50 mmol) were heated and stirred in dimethylformamide (10 ml) at 60° C. for 3 hours. After cooling the reaction solution to room temperature, 2-bromo-5-nitrothiophene (1.25 g, 6.00 mmol) was added and the mixture was further heated and stirred at 60° C. for 1 hour. The reaction solution was returned to room temperature and then poured into ice water (50 ml), and the precipitated crystals were filtered out, washed with water and methanol and then blow-dried to obtain the title compound (700 mg, 1.94 mmol, 39%) as yellowish-brown crystals.

$^1$H-NMR Spectrum (DMSO-d$_6$) δ (ppm): 4.04 (3H, s), 7.17 (1H, d, J=4.6 Hz), 7.59 (1H, s), 7.66 (1H, d, J=4.0 Hz), 7.82 (1H, br s), 7.90 (1H, br s), 8.23 (1H, d, J=4.0 Hz), 8.53 (1H, s), 8.76 (1H, d, J=4.6 Hz).

Production Example 244-2

(4-(5-Aminothiophen-2-ylsulfanyl)-7-methoxyquinoline-6-carboxamide)

After suspending 7-methoxy-4-(5-nitrothiophen-2-ylsulfanyl)quinoline-6-carboxamide (320 mg, 0.885 mmol), iron (247 mg, 4.43 mmol) and ammonium chloride (481 mg, 8.85 mmol) in an ethanol (8 ml)-water (2 ml)-dimethylformamide (1 ml) mixed solvent, the suspension was heated and stirred at 80° C. for 15 minutes. After completion of the reaction, the reaction mixture was filtered with celite and washed in a tetrahydrofuran-methanol mixed solvent. After adding ethyl acetate to the organic layer, it was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=20:1), and the fraction containing the target substance was concentrated to obtain the title compound (164 mg, 0.495 mmol, 56%) as yellowish-brown crystals.

$^1$H-NMR Spectrum (DMSO-d$_6$) δ (ppm): 4.02 (3H, s), 6.00 (1H, d, J=4.0 Hz), 6.34 (2H, s), 6.83 (1H, d, J=4.8 Hz), 7.08 (1H, d, J=4.0 Hz), 7.51 (1H, s), 7.77 (1H, br s), 7.86 (1H, br s), 8.47 (1H, s), 8.66 (1H, d, J=4.8 Hz).

Example 245

4-(5-(3-(4-Fluorophenyl)ureido)thiophen-2-ylsulfanyl)-7-methoxyquinoline-6-carboxamide The title compound (50.0 mg, 0.107 mmol, 71%) was obtained as colorless crystals from 4-(5-aminothiophen-2-ylsulfanyl)-7-methoxyquinoline-6-carboxamide (49.0 mg, 0.150 mmol) and 4-fluorophenyl isocyanate (22.6 mg, 0.165 mmol), by the same procedure as in Example 244.

$^1$H-NMR Spectrum (DMSO-d$_6$) δ (ppm): 4.03 (3H, s), 6.72 (1H, d, J=4.0 Hz), 6.76 (1H, d, J=4.8 Hz), 7.10-7.18 (2H, m), 7.35 (1H, d, J=4.0 Hz), 7.45-7.51 (2H, m), 7.53 (1H, s), 7.80 (1H, br s), 7.89 (1H, br s), 8.52 (1H, s), 8.65 (1H, d, J=4.8 Hz), 8.99 (1H, br s), 10.24 (1H, br s).

Example 246

7-Methoxy-4-(5-(3-thiazol-2-ylureido)thiophen-2-ylsulfanyl)quinoline-6-carboxamide 4-(5-Aminothiophen-2-ylsulfanyl)-7-methoxyquinoline-6-carboxamide (66.0 mg, 0.200 mmol) and thiazol-2-ylcarbamic acid phenyl ester (66.0 mg, 0.300 mmol) were stirred in dimethylsulfoxide (1 ml) at 85° C. for 2 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=15:1), and the fraction containing the target substance was concentrated, suspended in ethyl acetate and diluted with hexane, after which the crystals were filtered out, washed with hexane and then blow-dried to obtain the title compound (35.0 mg, 0.077 mmol, 38%) as colorless crystals.

$^1$H-NMR Spectrum (DMSO-d$_6$) δ (ppm): 4.03 (3H, s), 6.77 (1H, d, J=4.8 Hz), 6.77-6.83 (1H, m), 7.01-7.12 (1H, m), 7.34-7.39 (2H, m), 7.51 (1H, s), 7.80 (1H, br s), 7.89 (1H, br s), 8.52 (1H, s), 8.65 (1H, d, J=4.8 Hz).

Example 247

N1-[5-({7-[3-(Dimethylamino)propoxy]-6-methoxy-4-quinolyl}sulfanyl)-2-thienyl]-N'-(4-fluorophenyl)urea 5-({7-[3-(Dimethylamino)propoxy]-6-methoxy-4-quinolyl}sulfanyl)-2-thiophenylamine (190 mg), para-fluorophenyl isocyanate (69 mg) and tetrahydrofuran (30 ml) were stirred together at room temperature for 30 minutes. The organic solvent was distilled off under reduced pressure, and the residue was purified by column chromatography (ethyl acetate, followed by ethyl acetate:methanol=10:1) using NH type silica gel. The solvent was distilled off under reduced pressure, and ethyl acetate was added to the residue for solidification to obtain 16 mg of a yellowish-brown solid.

$^1$H-NMR (DMSO-d$_6$) δ (ppm): 0.93 (6H, t, J=7.2 Hz), 1.87 (2H, tt, J=7.2 Hz, 7.2 Hz), 2.40-2.57 (6H, m), 3.94 (3H, s), 4.15 (2H, t, J=7.2 Hz), 6.68 (1H, d, J=4.0 Hz), 6.71 (1H, d, J=4.8 Hz), 7.11 (2H, dd, J=8.8 Hz, 8.8 Hz), 7.28 (1H, s), 7.30 (1H, d, J=4.0 Hz), 7.34 (1H, s), 7.45 (2H, dd, J=8.8 Hz, 4.8 Hz), 8.44 (1H, d, J=4.8 Hz), 8.94 (1H, bs), 10.15 (1H, bs).

The intermediates were obtained in the following manner.

Production Example 247-1

7-(Benzyloxy)-6-methoxy-1,4-dihydro-4-quinolinethione 7-(Benzyloxy)-6-methoxy-1,4-dihydro-4-quinoline (28.1 g), diphosphorus pentasulfide (53.4 g), sodium bicarbonate (53.7 g) and diethyleneglycol dimethyl ether (200 ml) were stirred together at 80° C. for 2 hours. After returning the mixture to room temperature, it was developed in ice water and stirred for 40 minutes, and then the solid was filtered out and blow-dried at 60° C. to obtain 29.1 g of a yellow powder.

$^1$H-NMR (DMSO-$d_6$) δ (ppm): 3.85 (3H, s), 5.22 (2H, s), 7.15 (1H, s), 7.17 (1H, d, J=6.4 Hz), 7.33-7.50 (5H, m), 7.71 (1H, d, J=6.4 Hz), 8.11 (1H, s).

Production Example 247-2

2-{[7-(Benzyloxy)-6-methoxy-4-quinolyl]sulfanyl}-5-nitrothiophene 7-(Benzyloxy)-6-methoxy-1,4-dihydro-4-quinolinethione (14.3 g), 2-bromo-5-nitrothiophene (10 g), potassium carbonate (9.9 g) and dimethylformamide (150 ml) were stirred together at room temperature for 6 hours. Water was added, and the precipitated solid was filtered out and washed with water and then ethyl acetate to obtain 15.7 g of a yellow powder.

$^1$H-NMR (DMSO-$d_6$) δ (ppm): 3.92 (3H, s), 5.29 (2H, s), 7.23 (1H, dd, J=4.8 Hz, 1.6 Hz), 7.32-7.44 (4H, m), 7.49 (2H, d, J=8.0 Hz), 7.55 (1H, s), 7.57 (1H, dd, J=4.4 Hz, 1.6 Hz), 8.16 (1H, dd, J=4.4 Hz, 2.0 Hz), 8.58 (1H, dd, J=4.8 Hz, 1.6 Hz).

Production Example 247-3

6-Methoxy-4-[(5-nitro-2-thienyl)sulfanyl]-7-quinolinol 7-(Benzyloxy)-6-methoxy-4-[(5-nitro-2-thienyl)sulfanyl]quinoline (4.0 g), trifluoroacetic acid (40 ml) and thioanisole (4 ml) were stirred together at 65° C. for 2 hours. The mixture was returned to room temperature, the solvent was distilled off under reduced pressure, 80 ml of methanol was added to the residue, and then sodium bicarbonate water was added until the foaming subsided. The precipitated solid was filtered out to obtain 2.7 g of a yellow powder.

$^1$H-NMR (DMSO-$d_6$) δ (ppm): 3.92 (3H, s), 7.16 (1H, d, J=4.8 Hz), 7.31 (1H, s), 7.33 (1H, s), 7.55 (1H, d, J=4.0 Hz), 8.15 (1H, d, J=4.0 Hz), 8.52 (1H, d, J=4.8 Hz).

Production Example 247-4

N,N-Diethyl-N-[3-({6-methoxy-4-[(5-nitro-2-thienyl)sulfanyl]-7-quinolyl}oxy)propyl]amine 6-Methoxy-4-[(5-nitro-2-thienyl)sulfanyl]-7-quinolinol (500 mg), 3-diethylaminopropanol (290 mg), diethyl azodicarboxylate (390 mg), triphenylphosphine (590 mg), tetrahydrofuran (30 ml), 1-methyl-2-pyrrolidinone (2 ml) and dimethylsulfoxide (10 ml) were stirred together at 0° C. for 5 hours and then at room temperature for 10 hours. Water was added, extraction was performed with ethyl acetate, and the extract was back extracted with 2N aqueous hydrochloric acid. After adding 5N aqueous sodium hydroxide to the hydrochloric acid extract and performing extraction with ethyl acetate, the extract was washed with water and then with brine and dried over magnesium sulfate. NH type silica gel was coated onto a glass filter, the ethyl acetate layer was passed through the filter, and the solvent was distilled off under reduced pressure to obtain 500 mg of a reddish-brown oil.

$^1$H-NMR (DMSO-$d_6$) δ (ppm): 0.92 (6H, t, J=7.2 Hz), 1.87 (2H, tt, J=7.2 Hz, 7.2 Hz), 2.40-2.58 (6H, m), 3.93 (3H, s), 4.20 (2H, t, J=7.2 Hz), 7.21 (1H, d, J=4.8 Hz), 7.37 (1H, s), 7.42 (1H, s), 7.58 (1H, d, J=4.0 Hz), 8.18 (1H, d, J=4.0 Hz), 8.60 (1H, d, J=4.8 Hz).

Production Example 247-5

5-({7-[3-(Diethylamino)propoxy]-6-methoxy-4-quinolyl}sulfanyl)-2-thiopheneamine

N,N-Diethyl-N-[3-({6-methoxy-4-[(5-nitro-2-thienyl)sulfanyl]-7-quinolyl}oxy)propyl]amine (525 mg), iron powder (330 mg), ammonium chloride (660 mg), ethanol (20 ml) and water (5 ml) were stirred together at 80° C. for 80 minutes. After filtration with celite, NH type silica gel was added to the filtrate, the solvent was distilled off under reduced pressure and the reaction product was adsorbed onto the silica gel. The silica gel was charged into a dry column packed with NH type silica gel, and column purification was performed (ethyl acetate, followed by ethyl acetate:methanol=3:1) to obtain 190 mg of a brown oil.

$^1$H-NMR (DMSO-$d_6$) δ (ppm): 0.91 (6H, t, J=7.2 Hz), 1.88 (2H, tt, J=7.2 Hz, 7.2 Hz), 2.47-2.57 (6H, m), 3.92 (3H, s), 4.16 (2H, t, J=7.2 Hz), 5.96 (1H, d, J=4.0 Hz), 6.76 (1H, d, J=4.8 Hz), 6.25-6.30 (2H, m), 7.04 (1H, d, J=4.0 Hz), 7.22 (1H, s), 7.33 (1H, s), 8.45 (1H, d, J=4.8 Hz).

Example 248

N-[2-({7-[3-(Diethylamino)propoxy]-6-methoxy-4-quinolyl}sulfanyl)-1,3-thiazol-5-yl]-N'-(4-fluorophenyl)urea N,N-Diethyl-N-[3-({6-methoxy-4-[(5-nitro-1,3-thiazol-2-yl)sulfanyl]-7-quinolyl}oxy)propyl]amine (770 mg), iron powder (480 mg), ethanol (17 ml) and acetic acid (3.4 ml) were stirred together at 80° C. for 10 minutes. After adding 100 ml of water, 60 ml of ethyl acetate and 10 g of potassium carbonate to the reaction solution, the mixture was filtered through celite. The filtrate was subjected to liquid separation and ethyl acetate layer was passed through a glass filter coated with NH type silica gel. After adding 0.58 ml of p-fluorophenyl isocyanate to the obtained ethyl acetate solution, the mixture was stirred at room temperature for 17 hours. NH type silica gel was added to the reaction solution, the solvent was distilled off under reduced pressure and the reaction product was adsorbed onto the silica gel. The silica gel was charged into a dry column packed with NH type silica gel, and column purification was performed (ethyl acetate:methanol=100:1, followed by 50:1, 10:1) to obtain 30 mg of the target substance as a light yellow solid.

$^1$H-NMR (DMSO-$d_6$) δ (ppm): 0.93 (6H, t, J=7.2 Hz), 1.88 (2H, tt, J=6.4 Hz, 6.4 Hz), 2.46 (4H, q, J=7.2 Hz), 2.55 (2H, t, J=6.4 Hz), 3.92 (3H, s), 4.17 (2H, t, J=6.4 Hz), 7.00 (1H, d, J=5.2 Hz), 7.10 (2H, dd, J=8.8 Hz, 8.8 Hz), 7.36 (1H, s), 7.38 (1H, s), 7.43 (2H, dd, J=8.8 Hz, 4.8 Hz), 7.60 (1H, s), 8.51 (1H, d, J=5.2 Hz), 9.10 (1H. bs).

The intermediates were obtained in the following manner.

Production Example 248-1

2-{[7-(Benzyloxy)-6-methoxy-4-quinolyl]sulfanyl}-5-nitro-1,3-thiazole 7-(Benzyloxy)-6-methoxy-1,4-dihydro-4-quinolinethione (14.8 g), 2-bromo-5-nitro-1,3-thiazole (10.4 g), potassium carbonate (10.3 g) and dimethylformamide (150 ml) were stirred together at room temperature for 50 minutes. After adding 800 ml of water to the reaction solution, the precipitated solid was filtered out and washed with ethyl acetate to obtain 13.4 g of a light ochre powder.

¹H-NMR (DMSO-d₆) δ (ppm): 3.87 (3H, s), 5.32 (2H, s), 7.32-7.53 (6H, m), 7.64 (1H, s), 7.86 (1H, d, J=4.8 Hz), 8.70 (1H, s), 8.80 (1H, d, J=4.8 Hz).

Production Example 248-2

6-Methoxy-4-[(5-nitro-1,3-thiazol-2-yl)sulfanyl]-7-quinolinol

2-{[7-(Benzyloxy)-6-methoxy-4-quinolyl]sulfanyl}-5-nitro-1,3-thiazole (2.0 g), trifluoroacetic acid (20 ml) and thioanisole (2 ml) were stirred together at 65° C. for 90 minutes. The mixture was returned to room temperature, the solvent was distilled off under reduced pressure, 40 ml of methanol was added to the residue, and then sodium bicarbonate water was added until the foaming subsided. The precipitated solid was filtered out to obtain 1.4 g of a yellow powder.

¹H-NMR (DMSO-d₆) δ (ppm): 3.87 (3H, s), 7.40 (1H, s), 7.43 (1H, s), 7.78 (1H, d, J=4.8 Hz), 8.71 (1H, d, J=2.4 Hz), 8.74 (1H, dd, J=4.8 Hz, 2.4 Hz), 10.52 (1H, s).

Production Example 248-3

N,N-Diethyl-N-[3-({6-methoxy-4-[(5-nitro-1,3-thiazol-2-yl)sulfanyl]-7-quinolyl}oxy)propyl]amine The target substance was obtained using 6-methoxy-4-[(5-nitro-1,3-thiazol-2-yl)sulfanyl]-7-quinolinol, in the same manner as Production Example 247-2.

¹H-NMR (DMSO-d6) δ (ppm): 0.95 (6H, t, J=6.8 Hz), 1.91 (2H, tt, J=6.4 Hz, 6.4 Hz), 2.45-2.65 (6H, m), 3.86 (3H, s), 4.20 (2H, t, J=6.4 Hz), 7.42 (1H, s), 7.49 (1H, s), 7.83 (1H, d, J=4.4 Hz), 8.69 (1H, s), 8.79 (1H, d, J=4.4 Hz).

Example 249

N6-(2-Methoxyethyl)-4-(3-chloro-4-{[(cyclopropylamino)carbonyl]amino}phenoxy)-7-(2-methoxyethoxy)-6-quinolinecarboxamide 4-(3-Chloro-4-{[(cyclopropylamino)carbonyl]amino}phenoxy)-7-(2-methoxyethoxy)-6-quinolinecarboxylic acid (200 mg), 2-methoxyethylamine (38 mg), benzotriazol-1-yloxytris(dimethylamino)phosphonium hexafluorophosphate (Bop reagent) (230 mg), triethylamine (0.12 ml) and dimethylformamide (5 ml) were stirred together at room temperature for 14 hours. Water and ethyl acetate were added to the reaction solution for extraction, NH type silica gel was added to the extract, the solvent was distilled off under reduced pressure and the reaction product was adsorbed onto the silica gel. The silica gel was charged into a dry column packed with NH type silica gel, and column purification was performed (ethyl acetate). The solvent was distilled off under reduced pressure to obtain 120 mg of the target substance as a solid.

¹H-NMR (DMSO-d₆) δ (ppm): 0.38-0.45 (2H, m), 0.62-0.68 (2H, m), 2.48-2.60 (1H, m), 3.30 (3H, s), 3.37 (3H, s), 3.45-3.55 (4H, m), 3.79 (2H, t, J=4.4 Hz), 4.40 (2H, t, J=4.4 Hz), 6.52 (1H, d, J=5.2 Hz), 7.18 (1H, d, J=2.8 Hz), 7.23 (1H, dd, J=9.2 Hz, 2.8 Hz), 7.49 (1H, d, J=2.8 Hz), 7.55 (1H, s), 7.97 (1H, s), 8.26 (1H, d, J=9.2 Hz), 8.42-8.47 (1H, m), 8.66 (1H, d, J=5.2 Hz), 8.74 (1H, s).

The intermediates were obtained in the following manner.

Production Example 249-1

Methyl 4-chloro-7-(2-methoxyethoxy)-6-quinolinecarboxylate 7-(2-Methoxyethoxy)-4-oxo-1,4-dihydro-6-quinoline carboxylic acid (7.5 g), thionyl chloride (60 ml) and dimethylformamide (1 ml) were stirred together at 80° C. for 3 hours. The reaction solution was distilled off under reduced pressure, toluene was added to the residue, and distillation under reduced pressure was repeated twice. After adding methanol to the residue, 10 ml of triethylamine was added. The resulting solution was distilled off under reduced pressure and then water and 5N aqueous sodium hydroxide were added to pH 4 and extraction was performed with ethyl acetate. The obtained ethyl acetate layer was passed through a glass filter coated with NH type silica gel, and then the solvent was distilled off under reduced pressure. Ether was added to the residue, and the solid was filtered out to obtain 3.6 g of the target substance as a light brown solid. The filtrate was purified by column chromatography (hexane:ethyl acetate=3:1) using NH type silica gel to obtain 1.3 g of the target substance as a light yellow solid.

¹H-NMR (DMSO-d₆) δ (ppm): 3.33 (3H, s), 3.71-3.75 (2H, m), 3.86 (3H, s), 4.32-4.35 (2H, m), 7.62 (1H, s), 7.66 (1H, d, J=4.8 Hz), 8.42 (1H, s), 8.83 (1H, d, J=4.8 Hz).

Production Example 249-2

Methyl 4-(4-amino-3-chlorophenoxy)-7-(2-methoxyethoxy)-6-quinolinecarboxylate

Methyl 4-chloro-7-(2-methoxyethoxy)-6-quinolinecarboxylate (4.9 g), 4-amino-3-chlorophenol (2.0 g), sodium hydride (550 mg) and dimethylformamide (20 ml) were stirred together at 100° C. for 2 hours. The mixture was returned to room temperature, water was added, and extraction was performed with ethyl acetate. Silica gel was added to the extract solution and the solvent was distilled off under reduced pressure. The silica gel was charged into a dry column packed with silica gel, and purification was performed by column chromatography (hexane:ethyl acetate=1:1, followed by ethyl acetate) to obtain 3.2 g of the target substance as a violet solid.

¹H-NMR (DMSO-d₆) δ (ppm): 3.34 (3H, s), 3.72 (2H, t, J=4.4 Hz). 3.83 (3H, s), 4.29 (2H, t, J=4.4 Hz), 5.44 (2H, s), 6.44 (1H. d, J=5.6 Hz), 6.88 (1H, d, J=8.8 Hz), 7.00 (1H, dd, J=8.8 Hz, 2.4 Hz), 7.23 (1H, d, J=2.4 Hz), 7.49 (1H, s), 8.53 (1H, s), 8.63 (1H, d, J=5.6 Hz).

Production Example 249-3

Methyl 4-{3-chloro-4-[(phenoxycarbonyl)amino]phenoxy}-7-(2-methoxyethoxy)-6-quinolinecarboxylate Methyl 4-(4-amino-3-chlorophenoxy)-7-(2-methoxyethoxy)-6-quinolinecarboxylate (3.2 g), pyridine (0.71 ml) and tetrahydrofuran (50 ml) were stirred while cooling on ice, and then 1.1 ml of phenyl chloroformate was added dropwise. After 40 minutes, 0.8 ml of pyridine and 1.1 ml of phenyl chloroformate were added and the mixture was stirred for an additional 10 minutes. Water was added, extraction was performed with ethyl acetate, and the extract solution was passed through a glass filter coated with silica gel. The silica gel was washed with ethyl acetate, the solvent was distilled off under reduced pressure, hexane and ethyl acetate were added to the residue and the solid was filtered out to obtain 3.2 g of a faint red solid.

$^1$H-NMR(CDCl$_3$) δ (ppm): 3.50 (3H, s), 3.80 (2H, t, J=4.4 Hz), 3.98 (3H, s), 4.37 (2H, t, J=4.4 Hz), 6.49 (1H, d, J=5.6 Hz), 7.17-7.30 (6H, m), 7.40-7.52 (3H, m), 8.30-8.37 (1H, m), 8.66 (1H, d, J=5.6 Hz), 8.80 (1H, s).

Production Example 249-4

Methyl 4-(3-chloro-4-{[(cyclopropylamino)carbonyl]amino}phenoxy)-7-(2-methoxyethoxy)-6-quinolinecarboxylate Methyl 4-{3-chloro-4-[(phenoxycarbonyl)amino]phenoxy}-7-(2-methoxyethoxy)-6-quinolinecarboxylate (3.2 g), cyclopropylamine (1.3 ml) and dimethylformamide (20 ml) were stirred together at 60° C. for 10 minutes. The mixture was returned to room temperature, water was added, and extraction was performed with ethyl acetate. Silica gel was added to the extract solution and the solvent was distilled off under reduced pressure. The silica gel was charged into a dry column packed with silica gel, and purification was performed by column chromatography (ethyl acetate, followed by ethyl acetate:methanol=50:1, 20:1) to obtain 2.26 g of the target substance as a white powder.

$^1$H-NMR (DMSO-d$_6$) δ (ppm): 0.38-0.45 (2H, m), 0.61-0.69 (2H, m), 2.50-2.58 (1H, m), 3.36 (3H, s), 3.73 (2H, t, J=4.4 Hz), 3.84 (3H, s), 4.31 (2H, t, J=4.4 Hz), 6.51 (1H, d, J=5.2 Hz), 7.18 (1H, s), 7.24 (1H, dd, J=8.8 Hz, 2.4 Hz), 7.49 (1H, d, J=2.4 Hz), 7.52 (1H, s), 7.96 (1H, s), 8.26 (1H, d, J=8.8 Hz), 8.55 (1H, s), 8.67 (1H, d, J=5.2 Hz).

Production Example 249-5

4-(3-Chloro-4-{[(cyclopropylamino)carbonyl]amino}phenoxy)-7-(2-methoxyethoxy)-6-quinolinecarboxylic acid Methyl 4-(3-chloro-4-{[(cyclopropylamino)carbonyl]amino}phenoxy)-7-(2-methoxyethoxy)-6-quinolinecarboxylate (2.26 g), 2N aqueous sodium hydroxide (20 ml), methanol (20 ml) and tetrahydrofuran (20 ml) were stirred together at room temperature for 1 hour. After adding 5N aqueous hydrochloric acid and distilling off 10 ml of the organic solvent, the precipitated solid was filtered out. The solid was washed with a methanol and water mixed solvent to obtain 2.0 g of the target substance as a faint red powder.

$^1$H-NMR (DMSO-d$_6$) δ (ppm): 0.38-0.45 (2H, m), 0.60-0.68 (2H, m), 2.50-2.59 (1H, m), 3.34 (3H, s), 3.73 (2H, t, J=4.4 Hz), 4.30 (2H, t, J=4.4 Hz), 6.51 (1H, d, J=5.2 Hz), 7.23 (1H, dd, J=9.2 Hz, 2.8 Hz), 7.25 (1H, s), 7.49 (1H, d, J=2.8 Hz), 7.50 (1H, s), 8.00 (1H, s), 8.25 (1H, d, J=9.2 Hz), 8.50 (1H, s), 8.66 (1H, d, J=5.2 Hz).

Example 250

N6-(2-Fluoroethyl)-4-(3-chloro-4-{[(cyclopropylamino)carbonyl]amino}phenoxy)-7-(2-methoxyethoxy)-6-quinolinecarboxamide The target substance was obtained using 2-fluoroethylamine hydrochloride, in the same manner as Example 249.

$^1$H-NMR (DMSO-d$_6$) δ (ppm): 0.38-0.45 (2H, m), 0.60-0.68 (2H, m), 2.48-2.58 (1H, m), 3.35 (3H, s), 3.61 (1H, td, J=4.8 Hz, 4.8 Hz), 3.68 (1H, td, J=4.8 Hz, 4.8 Hz), 3.78 (2H, t, J=4.8 Hz), 4.41 (2H, t, J=4.8 Hz), 4.50 (1H, t, J=4.8 Hz), 4.62 (1H, t, J=4.8 Hz), 6.53 (1H, d, J=5.2 Hz), 7.20 (1H, s), 7.24 (1H, dd, J=9.2 Hz, 2.4 Hz), 7.49 (1H, d, J=2.4 Hz), 7.56 (1H, s), 7.98 (1H, s), 8.26 (1H, d, J=9.2 Hz), 8.59 (1H, t, J=4.8 Hz), 8.67 (1H, d, J=5.2 Hz), 8.70 (1H, s).

Example 251

N6-Methoxy-4-(3-chloro-4-{[(cyclopropylamino)carbonyl]amino}phenoxy)-7-(2-methoxyethoxy)-6-quinolinecarboxamide The target substance was obtained using O-methylhydroxylamine hydrochloride, in the same manner as Example 249.

$^1$H-NMR (DMSO-d$_6$) δ (ppm): 0.38-0.44 (2H, m), 0.62-0.98 (2H, m), 2.50-2.60 (1H, m), 3.35 (3H, s), 3.73 (3H, s), 3.77 (2H, t, J=4.4 Hz), 4.35 (2H, t, J=4.4 Hz), 6.52 (1H, d, J=5.2 Hz), 7.18 (1H, s), 7.22 (1H, dd, J=9.2 Hz, 2.4 Hz), 7.47 (1H, d, J=2.4 Hz), 7.52 (1H, s), 7.96 (1H, s), 8.26 (1H, d, J=9.2 Hz), 8.41 (1H, s), 8.66 (1H, d, J=5.2 Hz), 11.30 (1H, s).

Example 252

1-{5-[6-Cyano-7-(2-methoxyethoxy)-quinolin-4-ylsulfanyl]-thiophen-2-yl}-3-(thiazol-2-yl)urea The title compound (45 mg) was obtained as a solid from 4-(5-aminothiophen-2-ylsulfanyl)-7-(2-methoxyethoxy)-quinoline-6-carbonitrile (118 mg) and thiazol-2-ylcarbamic acid phenyl ester (77 mg), in the same manner as Example 246.

$^1$H-NMR Spectrum (DMSO-d$_6$) δ (ppm): 3.36 (3H, s), 3.75-3.78 (2H, m), 4.40-4.42 (2H, m), 6.76-6.79 (1H, m), 6.80 (1H, d, J=5.2 Hz), 7.02-7.08 (1H, m), 7.32-7.38 (1H, m), 7.35 (1H, d, J=4.0 Hz), 7.63 (1H, s), 8.62 (1H, s), 8.70 (1H, d, J=5.2 Hz).

Production Example 252-1

7-(2-Methoxyethoxy)-4-thioxo-1,4-dihydroquinoline-6-carbonitrile

The title compound (9 g) was obtained as a solid from 6-cyano-7-methoxyethoxy-1H-quinolin-4-one (10 g), in the same manner as Production Example 226-1.

$^1$H-NMR Spectrum (DMSO-d$_6$) δ (ppm): 3.35 (3H, s), 3.74-3.77 (2H, m), 4.31-4.34 (2H, m), 7.16-7.19 (2H, m), 7.82 (1H, d, J=6.8 Hz), 8.86 (1H, s), 12.84 (1H, br s).

Production Example 252-2

7-(2-Methoxyethoxy)-4(5-nitrothiophen-2-ylsulfanyl)quinoline-6-carbonitrile

The title compound (2.2 g) was obtained as a solid from 7-(2-methoxyethoxy)-4-thioxo-1,4-dihydroquinoline-6-carbonitrile (7.1 g) and 2-bromo-5-nitrothiophene (6.3 g), by the same procedure as in Production Example 226-2.

$^1$H-NMR Spectrum (DMSO-d$_6$) δ (ppm): 3.35 (3H, s), 3.75-3.78 (2H, m), 4.41-4.44 (2H, m), 7.18 (1H, d, J=4.4 Hz), 7.68 (1H, d, J=4.8 Hz), 7.69 (1H, s), 8.23 (1H, d, J=4.4 Hz), 8.70 (1H, s), 8.79 (1H, d, J=4.8 Hz).

Production Example 252-3

4-(5-Aminothiophen-2-ylsulfanyl)-7-(2-methoxyethoxy)quinoline-6-carbonitrile

The title compound (0.93 g) was obtained as a solid from 7-(2-methoxyethoxy)-4-(5-nitrothiophen-2-ylsulfanyl)quinoline-6-carbonitrile (2.2 g), in the same manner as Production Example 226-3.

$^1$H-NMR Spectrum (DMSO-d$_6$) δ (ppm): 3.35 (3H, s), 3.74-3.78 (2H, m), 4.38-4.41 (2H, m), 5.98 (1H, d, J=3.6 Hz), 6.37 (2H, t, brs), 6.86 (1H, d, J=4.8 Hz), 7.07 (1H, d, J=3.6 Hz), 7.61 (1H, s), 8.54 (1H, s), 8.71 (1H, d, J=4.8 Hz).

Example 253

1-{5-[6-Cyano-7-(2-methoxyethoxy)-quinolin-4-ylsulfanyl]thiophen-2-yl}-3-(4-fluorophenyl)urea The title compound (24 mg) was obtained as a solid from 4-(5-amino-thiophen-2-ylsulfanyl)-7-(2-methoxyethoxy)-quinoline-6-carbonitrile (30 mg) and 4-fluorophenyl isocyanate, in the same manner as Example 252.

$^1$H-NMR Spectrum (DMSO-d$_6$) δ (ppm): 3.36 (3H, s), 3.75-3.78 (2H, m), 4.39-4.43 (2H, m), 6.71 (1H, d, J=3.6 Hz), 6.80 (1H, d, J=4.8 Hz), 7.12 (2H, t, J=9.2 Hz), 7.34 (1H, d, J=4.0 Hz), 7.43-7.47 (2H, m), 7.63 (1H, s), 8.62 (1H, s), 8.70 (1H, d, J=4.8 Hz), 8.97 (1H, br s), 10.23 (1H, br s).

Example 254

1-{5-[6-Cyano-7-(2-methoxyethoxy)quinolin-4-ylsulfanyl]thiophen-2-yl}-3-(3-fluorophenyl)urea The title compound (20 mg) was obtained as a solid from 4-(5-amino-thiophen-2-ylsulfanyl)-7-(2-methoxyethoxy)-quinoline-6-carbonitrile (30 mg) and 3-fluorophenyl isocyanate, in the same manner as Example 252.

$^1$H-NMR Spectrum (DMSO-d$_6$) δ (ppm): 3.36 (3H, s), 3.75-3.78 (2H, m), 4.39-4.43 (2H, m), 6.73 (1H, d, J=4.0 Hz), 6.81 (1H, d, J=4.8 Hz), 6.78-6.85 (1H, m), 7.15-7.19 (1H, m), 7.27-7.32 (1H, m), 7.35 (1H, d, J=4.0 Hz), 7.40-7.45 (1H, m), 7.63 (1H, s), 8.62 (1H, s), 8.70 (1H, d, J=4.8 Hz), 9.18 (1H, br s), 10.30 (1H, br s).

Example 255

1-{5-[6-Cyano-7-(2-methoxyethoxy)quinolin-4-ylsulfanyl]thiophen-2-yl}-3-cyclopropylurea The title compound (15 mg) was obtained as a solid from 4-(5-amino-thiophen-2-ylsulfanyl)-7-(2-methoxyethoxy)-quinoline-6-carbonitrile (35 mg) and cyclopropylamine, by the same procedure as in Example 252.

$^1$H-NMR Spectrum (DMSO-d$_6$) δ (ppm): 0.41-0.46 (2H, m), 0.61-0.68 (2H, m), 2.48-2.55 (1H, m), 3.36 (3H, s), 3.75-3.79 (2H, m), 4.39-4.43 (2H, m), 6.63 (1H, d, J=4.0 Hz), 6.77 (1H, d, J=4.8 Hz), 6.79-7.84 (1H, m), 7.28 (1H, d, J=4.0 Hz), 7.62 (1H, s), 8.60 (1H, s), 8.69 (1H, d, J=4.8 Hz), 9.93 (1H, br s).

Example 256

1-{5-[6-Cyano-7-(2-methoxyethoxy)quinolin-4-ylsulfanyl]thiophen-2-yl}-3-(2-fluorophenyl)urea The title compound (15 mg) was obtained as a solid from 4-(5-aminothiophen-2-ylsulfanyl)-7-(2-methoxyethoxy)quinoline-6-carbonitrile (38 mg) and 2-fluorophenyl isocyanate, in the same manner as Example 252.

$^1$H-NMR Spectrum (DMSO-d$_6$) δ (ppm): 3.36 (3H, s), 3.75-3.78 (2H, m), 4.39-4.43 (2H, m), 6.72 (1H, d, J=4.0 Hz), 6.80 (1H, d, J=4.8 Hz), 7.02-7.08 (1H, m), 7.12-7.16 (1H, m), 7.21-7.27 (1H, m), 7.36 (1H, d, J=4.0 Hz), 7.63 (1H, s), 7.99-8.04 (1H, m), 8.62 (1H, s), 8.70 (1H, d, J=4.8 Hz), 8.74-8.78 (1H, m), 10.45 (1H, brs).

Example 257

1-{5-[6-Cyano-7-(2-methoxyethoxy)quinolin-4-ylsulfanyl]thiophen-2-yl}-3-phenylurea The title compound (12 mg) was obtained as a solid from 4-(5-aminothiophen-2-ylsulfanyl)-7-(2-methoxyethoxy)quinoline-6-carbonitrile (38 mg) and phenyl isocyanate, in the same manner as Example 252.

$^1$H-NMR Spectrum (DMSO-d$_6$) δ (ppm): 3.36 (3H, s), 3.75-3.78 (2H, m), 4.39-4.43 (2H, m), 6.71 (1H, d, J=4.0 Hz), 6.81 (1H, d, J=4.8 Hz), 6.97-7.01 (1H, m), 7.28 (2H, t, J=7.6 Hz), 7.34 (1H, d, J=4.0 Hz), 7.44 (2H, d, J=7.6 Hz), 7.63 (1H, s), 8.62 (1H, s), 8.70 (1H, d, J=4.8 Hz), 8.94 (1H, br s), 10.21 (1H, br s).

Example 258

1-{5-[6-Cyano-7-(2-methoxyethoxy)quinolin-4-ylsulfanyl]thiophen-2-yl}-3-(2,4-difluorophenyl)urea The title compound (18 mg) was obtained as a solid from 4-(5-aminothiophen-2-ylsulfanyl)-7-(2-methoxyethoxy)quinoline-6-carbonitrile (30 mg) and 2,4-difluorophenyl isocyanate, by the same procedure as in Example 252.

$^1$H-NMR Spectrum (DMSO-d$_6$) δ (ppm): 3.35 (3H, s), 3.74-3.78 (2H, m), 4.39-4.43 (2H, m), 6.71 (1H, d, J=4.0 Hz), 6.80 (1H, d, J=4.8 Hz), 7.01-7.08 (1H, m), 7.29-7.34 (1H, m), 7.35 (1H, d, J=4.0 Hz), 7.63 (1H, s), 7.89-7.97 (1H, m), 8.62 (1H, s), 8.70 (1H, d, J=4.8 Hz), 8.73 (1H, br s), 10.44 (1H, br s).

Example 259

1-{5-[6-Cyano-7-(2-methoxyethoxy)quinolin-4-ylsulfanyl]thiophen-2-yl}-3-(para-tolyl)urea The title compound (28 mg) was obtained as a solid from 4-(5-aminothiophen-2-ylsulfanyl)-7-(2-methoxyethoxy)quinoline-6-carbonitrile (30 mg) and para-tolyl isocyanate, by the same procedure as in Example 252.

$^1$H-NMR Spectrum (DMSO-d$_6$) δ (ppm): 2.23 (3H, s), 3.36 (3H, s), 3.75-3.78 (2H, m), 4.39-4.43 (2H, m), 6.69 (1H, d, J=4.0 Hz), 6.80 (1H, d, J=4.8 Hz), 7.08 (2H, d, J=8.0 Hz), 7.32 (2H, d, J=8.0 Hz), 7.33 (1H, d, J=4.0 Hz), 7.63 (1H, s), 8.61 (1H, s), 8.70 (1H, d, J=4.8 Hz), 8.81 (1H, br s), 10.15 (1H, br s).

Example 260

1-{5-[6-Cyano-7-(2-methoxyethoxy)quinolin-4-yl-sulfanyl]-thiophen-2-yl}-3-(3-cyanophenyl)-urea The title compound (33 mg) was obtained as a solid from 4-(5-aminothiophen-2-ylsulfanyl)-7-(2-methoxyethoxy) quinoline-6-carbonitrile (30 mg) and 3-cyanophenyl isocyanate, by the same procedure as in Example 252.

$^1$H-NMR Spectrum (DMSO-d$_6$) δ (ppm): 3.36 (3H, s), 3.75-3.78 (2H, m), 4.39-4.43 (2H, m), 6.75 (1H, d, J=4.0 Hz), 6.80 (1H, d, J=4.8 Hz), 7.36 (1H, d, J=4.0 Hz), 7.43-7.52 (2H, m), 7.63 (1H, s), 7.70-7.73 (1H, m), 7.91-7.94 (1H, m), 8.62 (1H, s), 8.70 (1H, d, J=4.8 Hz), 9.30 (1H, br s), 10.44 (1H, br s).

Example 261

1-{5-[6-Cyano-7-(2-methoxyethoxy)quinolin-4-yl-sulfanyl]thiophen-2-yl}-3-(4-cyanophenyl)urea The title compound (28 mg) was obtained as a solid from 4-(5-aminothiophen-2-ylsulfanyl)-7-(2-methoxyethoxy) quinoline-6-carbonitrile (30 mg) and 4-cyanophenyl isocyanate, by the same procedure as in Example 252.

$^1$H-NMR Spectrum (DMSO-d$_6$) δ (ppm): 3.35 (3H, s), 3.74-3.78 (2H, m), 4.39-4.43 (2H, m), 6.76 (1H, d, J=4.0 Hz), 6.80 (1H, d, J=4.8 Hz), 7.36 (1H, d, J=4.0 Hz), 7.61-7.66 (3H, m), 7.71-7.75 (2H, m), 8.62 (1H, s), 8.70 (1H, d, J=4.8 Hz), 9.48 (1H, br s), 10.44 (1H, br s).

Example 262

N-[4-(7-(2-Methoxyethoxy)-6-cyano-4-quinolyl) oxyphenyl-N'-(4-cyclopropyl)urea

The title compound (220 mg) was obtained as a solid from 7-(2-methoxyethoxy)-6-cyano-4-(4-amino-3-chlorophenoxy)quinoline (380 mg), by the same procedure as in Example 249-4.

$^1$H-NMR Spectrum (DMSO-d$_6$) δ (ppm): 0.38-0.44 (2H, m), 0.63-0.69 (2H, m), 2.53-2.60 (1H, m), 3.36 (3H, s), 3.76-3.79 (2H, m), 4.40-4.43 (2H, m), 6.58 (1H, d, J=5.2 Hz), 7.19 (1H, d, J=2.8 Hz), 7.25 (1H, dd, J=2.8, J=8.8 Hz), 7.50 (1H, d, J=2.8 Hz), 7.63 (1H, s), 7.98 (1H, s), 8.28 (1H, d, J=8.8 Hz), 8.73 (1H, d, J=5.2 Hz), 8.74 (1H, s).

Production Example 262-1

7-(2-Methoxyethoxy)-6-cyano-4-(4-amino-3-chlorophenoxy)quinoline

The title compound (380 mg) was obtained as a solid from 4-chloro-7-methoxyethoxy-6-cyanoquinoline (800 mg) obtained by a publicly known method, by the same procedure as in Production Example 395-1.

$^1$H-NMR Spectrum (DMSO-d$_6$) δ (ppm): 3.36 (3H, s), 3.75-3.78 (2H, m), 4.39-4.41 (2H, m), 5.46 (2H, br s), 6.51 (1H, d, J=5.2 Hz), 6.89 (1H, d, J=8.8 Hz), 7.01 (1H, dd, J=2.8, 8.8 Hz), 7.24 (1H, d, J=2.8 Hz), 7.60 (1H, s), 8.70 (1H, d, J=5.2 Hz), 8.71 (1H, s).

Example 263

(4-{4-[3-(4-Fluorophenyl)ureido]phenoxy}-7-methoxyquinolin-6-yl)carbamic acid benzyl ester The title compound (380 mg) was obtained as a solid from [4-(4-aminophenoxy)-7-methoxyquinolin-6-yl]carbamic acid benzyl ester (330 mg) and 4-fluorophenyl isocyanate, in the same manner as Example 10.

$^1$H-NMR Spectrum (DMSO-d$_6$) δ (ppm): 3.97 (3H, s), 5.19 (2H, s), 6.42 (1H, d, J=5.2 Hz), 7.11 (2H, t, J=8.8 Hz), 7.19 (2H, d, J=8.8 Hz), 7.29-7.49 (8H, m), 7.57 (2H, d, J=8.8 Hz), 8.49 (1H, d, J=5.2 Hz), 8.67 (1H, s), 8.80 (1H, br s), 8.87 (1H, br s), 8.98 (1H, s).

The intermediates were synthesized in the following manner.

Production Example 263-1

(7-Methoxy-4-oxo-1,4-dihydroquinolin-6-yl)carbamic acid benzyl ester

After dissolving 7-methoxy-4-oxo-1,4-dihydroquinoline-6-carboxylic acid (2.58 g) in N,N-dimethylformamide (50 ml), there were added benzyl alcohol (3.29 ml), diphenylphosphoryl azide 2.51 ml) and triethylamine (1.63 ml), and the mixture was heated and stirred at 95° C. for 5 hours. The reaction solution was poured into saturated brine and extracted with ethyl acetate, and the organic layer was dried over magnesium sulfate and concentrated. The obtained residue was subjected to NH silica gel column chromatography and eluted with a solvent (ethyl acetate:methanol=5:1) to obtain the title compound (2.03 g) as a solid.

$^1$H-NMR Spectrum (DMSO-d$_6$) δ (ppm): 3.85 (3H, s), 5.14 (2H, s), 5.93 (1H, d, J=7.2 Hz), 7.07 (1H, s), 7.39-7.43 (5H, m), 7.74-7.81 (1H, m), 8.30 (1H, br s), 8.75 (1H, s), 11.97 (1H, br s).

Production Example 263-2

(4-Chloro-7-methoxyquinolin-6-yl)carbamic acid benzyl ester (7-Methoxy-4-oxo-1,4-dihydroquinolin-6-yl)carbamic acid benzyl ester (2 g) was added to a mixture of thionyl chloride (20 ml) and N,N-dimethylformamide (0.5 ml), and the mixture was heated to reflux for 2 hours. After completion of the reaction, the thionyl chloride was distilled off, and a procedure of toluene addition and concentration was repeated 3 times to obtain the title compound (2.4 g) as a solid.

$^1$H-NMR Spectrum (DMSO-d$_6$) δ (ppm): 3.98 (3H, s), 5.22 (2H, s), 7.26-7.49 (6H, m), 7.55 (1H, d, J=5.2 Hz), 8.63 (1H, d, J=5.2 Hz), 8.65 (1H, s), 9.12 (1H, br s).

Production Example 263-3

[4-(4-Aminophenoxy)-7-methoxyquinolin-6-yl]carbamic acid benzyl ester

A 4-phenoxyquinoline compound (465 mg) was obtained from (4-chloro-7-methoxyquinolin-6-yl)carbamic acid benzyl ester (2.4 g) and 4-nitrophenol (2.07 g), in the same manner as Production Example 7. The 4-phenoxyquinoline compound (450 mg) was reduced in the same manner as Production Example 8 to obtain the title compound (330 mg) as a solid.

$^1$H-NMR Spectrum (DMSO-d$_6$) δ (ppm): 3.96 (3H, s), 5.15 (2H, br s), 5.18 (2H, s), 6.34 (1H, d, J=5.2 Hz), 6.65 (2H, d, J=8.4 Hz), 6.90 (2H, d, J=8.4 Hz), 7.29-7.46 (6H, m), 8.45 (1H, d, J=5.2 Hz), 8.65 (1H, s), 8.95 (1H, s).

Example 264

1-[4-(6-Amino-7-methoxyquinolin-4-yloxy)phenyl]-3-(4-fluorophenyl)urea

After dissolving (4-{4-[3-(4-fluorophenyl)ureido]phenoxy}-7-methoxyquinolin-6-yl)carbamic acid benzyl ester (100 mg) in a mixture of tetrahydrofuran (10 ml)-methanol (10 ml), 10% palladium carbon (10 mg) was added and the mixture was stirred for 7 hours at room temperature under hydrogen gas at 1 atmosphere. The reaction solution was filtered through celite and the filtrate was concentrated to obtain the title compound (60 mg) as a solid.

$^1$H-NMR Spectrum (DMSO-$d_6$) δ (ppm): 3.94 (3H, s), 5.44 (2H, s), 6.34 (1H, d, J=5.2 Hz), 7.07-7.15 (4H, m), 7.23 (1H, s), 7.23 (1H, s), 7.43-7.48 (2H, m), 7.53 (2H, d, J=8.8 Hz), 8.25 (1H, d, J=5.2 Hz), 8.83 (1H, br s), 8.87 (1H, br s).

Example 265

N-(4-{4-[3-(4-Fluorophenyl)ureido]phenoxy}-7-methoxyquinolin-6-yl)acetamide

After dissolving 1-[4-(6-amino-7-methoxyquinolin-4-yloxy)phenoxy]-3-(4-fluorophenyl)urea (50 mg) in pyridine (5 ml), acetic anhydride (0.5 ml) was added and the mixture was allowed to stand at room temperature for 12 hours. The reaction solution was poured into saturated brine and extracted with ethyl acetate, and the organic layer was dried over magnesium sulfate and concentrated to obtain the title compound (50 mg) as a solid.

$^1$H-NMR Spectrum (DMSO-$d_6$) δ (ppm): 2.17 (3H, s), 4.01 (3H, s), 6.41 (1H, d, J=5.6 Hz), 7.11 (2H, t, J=8.8 Hz), 7.18 (2H, d, J=8.8 Hz), 7.42-7.49 (3H, m), 7.57 (2H, d, J=8.8 Hz), 8.49 (1H, d, J=5.6 Hz), 8.78 (1H, br s), 8.85 (1H, br s), 8.98 (1H, s), 9.45 (1H, s).

Example 266

N-(4-{4-[3-(4-Fluorophenyl)ureido]phenoxy}-7-methoxyquinolin-6-yl)methanesulfoneamide After dissolving 1-[4-(6-amino-7-methoxyquinolin-4-yloxy)phenoxy]-3-(4-fluorophenyl)urea (50 mg) in tetrahydrofuran (3 ml), triethylamine (0.3 ml) and methanesulfonyl chloride (14 μl) were added and the mixture was stirred at room temperature for 1 hour. The reaction solution was poured into saturated aqueous ammonium chloride solution and extracted with ethyl acetate, and the organic layer was washed with saturated brine and dried over magnesium sulfate. The organic layer was concentrated and the obtained residue was subjected to silica gel column chromatography for elution with a solvent (ethyl acetate:methanol=5:1) to obtain the title compound (13 mg) as a solid.

$^1$H-NMR Spectrum (DMSO-$d_6$) δ (ppm): 3.05 (3H, s), 3.98 (3H, s), 6.43 (1H, d, J=5.2 Hz), 7.11 (2H, t, J=8.8 Hz), 7.19 (2H, d, J=8.8 Hz), 7.43-7.48 (3H, m), 7.57 (2H, d, J=8.8 Hz), 8.12 (1H, s), 8.53 (1H, d, J=5.2 Hz), 8.76 (1H, br s), 8.84 (1H, br s), 9.31 (1H, br).

Example 267

(4-{3-Fluoro-4-[3-(4-fluorophenyl)ureido]phenoxy}-7-methoxyquinolin-6-yl)carbamic acid benzyl ester The title compound (180 mg) was obtained as a solid from [4-(4-amino-3-fluorophenoxy)-7-methoxyquinolin-6-yl] carbamic acid benzyl ester (166 mg) and 4-fluorophenyl isocyanate, in the same manner as Example 10.

$^1$H-NMR Spectrum (DMSO-$d_6$) δ (ppm): 3.97 (3H, s), 5.18 (2H, s), 6.51 (1H, d, J=5.2 Hz), 7.05-7.09 (1H, m), 7.12 (2H, t, J=8.8 Hz), 7.29-7.41 (4H, m), 7.42-7.49 (5H, m), 8.20 (1H, t, J=8.8 Hz), 8.52 (1H, d, J=5.2 Hz), 8.62-8.64 (1H, m), 8.65 (1H, s), 8.99 (1H, s), 9.12 (1H, br s).

The intermediates were synthesized in the following manner.

Production Example 267-1

[4-(3-Fluoro-4-nitrophenoxy)-7-methoxyquinolin-6-yl]carbamic acid benzyl ester (4-Chloro-7-methoxyquinolin-6-yl)carbamic acid benzyl ester (1.58 g) was added to 1-methyl-2-pyrrolidone (5 ml), and then 3-fluoro-4-nitrophenol (0.87 g) and N,N-diisopropylethylamine (1.2 ml) were added and the mixture was heated and stirred at 130° C. for 6 hours. The reaction solution was poured into saturated aqueous sodium bicarbonate and extracted with ethyl acetate, and the organic layer was washed with saturated brine and dried over magnesium sulfate. The organic layer was concentrated and the obtained residue was subjected to NH silica gel column chromatography for elution with a solvent (ethyl acetate) to obtain the title compound (188 mg) as a solid.

$^1$H-NMR Spectrum (DMSO-$d_6$) δ (ppm): 3.98 (3H, s), 5.16 (2H, s), 6.96 (1H, d, J=5.2 Hz), 7.16-7.21 (1H, m), 7.28-7.43 (5H, m), 7.50 (1H, s), 7.53-7.58 (1H, m), 8.26 (1H, t, J=8.8 Hz), 8.51 (1H, s), 8.66 (1H, d, J=5.2 Hz), 9.04 (1H, br s).

Production Example 267-2

[4-(4-Amino-3-fluorophenoxy)-7-methoxyquinolin-6-yl]carbamic acid benzyl ester

The title compound (170 mg) was obtained as a solid by reduction of [4-(3-fluoro-4-nitrophenoxy)-7-methoxyquinolin-6-yl]carbamic acid benzyl ester (188 mg) in an ethanol/water mixed solvent using iron and ammonium chloride, according to the same procedure as in Production Example 10.

$^1$H-NMR Spectrum (DMSO-$d_6$) δ (ppm): 3.96 (3H, s), 5.18 (4H, br s), 6.40 (1H, d, J=5.2 Hz), 6.79-6.86 (2H, m), 7.04 (1H, dd, J=2.4 Hz, J=12 Hz), 7.29-7.46 (6H, m), 8.47 (1H, d, J=5.2 Hz), 8.63 (1H, s), 8.95 (1H, br s).

Example 268

1-[4-(6-Amino-7-methoxyquinolin-4-yloxy)-2-fluorophenyl]-3-(4-fluorophenyl)urea

The title compound (125 mg) was obtained as a solid from (4-{3-fluoro-4-[3-(4-fluorophenyl)ureido]phenoxy}-7-methoxyquinolin-6-yl)carbamic acid benzyl ester (180 mg), in the same manner as Example 264.

$^1$H-NMR Spectrum (DMSO-$d_6$) δ (ppm): 3.94 (3H, s), 5.45 (2H, br s), 6.45 (1H, d, J=5.2 Hz), 6.96-7.01 (1H, m), 7.12 (2H, t, J=8.8 Hz), 7.17-7.26 (3H, m), 7.42-7.48 (2H, m), 8.13 (1H, t, J=9.2 Hz), 8.29 (1H, d, J=5.2 Hz), 8.58 (1H, br s), 9.10 (1H, br s).

Example 269

N-(4-{3-Fluoro-4-[3-(4-fluorophenyl)ureido]phenoxy}-7-methoxyquinolin-6-yl)acetamide The title compound (50 mg) was obtained as a solid from 1-[4-(6-amino-7-methoxyquinolin-4-yloxy)-2-fluorophenyl]-3-(4-fluorophenyl)urea (60 mg), in the same manner as Example 265.
$^1$H-NMR Spectrum (DMSO-$d_6$) δ (ppm): 2.16 (3H, s), 4.01 (3H, s), 6.50 (1H, d, J=5.2 Hz), 7.05-7.09 (1H, m), 7.12 (2H, t, J=8.8 Hz), 7.33 (1H, dd, J=2.8 Hz, J=12 Hz), 7.43-7.49 (3H, m), 8.16-8.23 (1H, m), 8.52 (1H, d, J=5.2 Hz), 8.62 (1H, br s), 8.96 (1H, br s), 9.12 (1H, br s), 9.45 (1H, br s).

Example 270

{4-[3-Fluoro-4-(3-(thiazol-2-yl)ureido)phenoxy]-7-methoxyquinolin-6-yl}carbamic acid benzyl ester

[4-(4-Amino-3-fluorophenoxy)-7-methoxyquinolin-6-yl]carbamic acid benzyl ester (100 mg) and thiazolyl-2-ylcarbamic acid phenyl ester (79 mg) were heated in dimethylsulfoxide (1 ml) at 80° C., in the same manner as Example 224, to obtain the title compound (38 mg) as a solid.
$^1$H-NMR Spectrum (DMSO-$d_6$) δ (ppm): 3.97 (3H, s), 5.19 (2H, s), 6.53 (1H, d, J=5.2 Hz), 7.09-7.13 (1H, m), 7.14 (1H, d, J=3.6 Hz), 7.29-7.41 (5H, m), 7.42-7.46 (3H, m), 8.20 (1H, t, J=9.2 Hz), 8.53 (1H, d, J=5.2 Hz), 8.65 (1H, s), 9.00 (1H, br s), 9.04 (1H, br), 10.83 (1H, brs).

Example 271

1-[4-(6-Amino-7-methoxyquinolin-4-yloxy)-2-fluorophenyl]-3-(thiazol-2-yl)urea

After adding {4-[3-fluoro-4-(3-(thiazol-2-yl)ureido)phenoxy]-7-methoxyquinolin-6-yl}carbamic acid benzyl ester (100 mg) to a mixture of trifluoroacetic acid (3 ml) and thioanisole (0.1 ml), the mixture was heated and stirred at 60° C. for 2 hours.
The solvent was distilled off and the residue was subjected to NH silica gel column chromatography for elution with a solvent (ethyl acetate:methanol=10:1) to obtain the title compound (23 mg) as a solid.
$^1$H-NMR Spectrum (DMSO-$d_6$) δ (ppm): 3.94 (3H, s), 5.47 (2H, br s), 6.48 (1H, d, J=5.2 Hz), 6.99-7.03 (1H, m), 7.13 (1H, d, J=3.6 Hz), 7.17 (1H, s), 7.23-7.31 (2H, m), 7.38 (1H, d, J=3.6 Hz), 8.13 (1H, t, J=8.8 Hz), 8.29 (1H, d, J=5.2 Hz), 8.97 (1H, br), 10.80 (1H, br).

Example 272

N-{4-[3-Fluoro-4-(3-(thiazol-2-yl)ureido)phenoxy]-7-methoxyquinolin-6-yl}acetamide The title compound (4 mg) was obtained as a solid from 1-[4-(6-amino-7-methoxyquinolin-4-yloxy)-2-fluorophenyl]-3-(thiazol-2-yl)urea (15 mg), in the same manner as Example 265.
$^1$H-NMR Spectrum (DMSO-$d_6$) δ (ppm): 2.15 (3H, s), 4.02 (3H, s), 6.53 (1H, d, J=5.2 Hz), 7.07-7.12 (1H, m), 7.12 (1H, d, J=3.6 Hz), 7.34-7.41 (2H, m), 7.45 (1H, s), 8.19 (1H, t, J=9.2 Hz), 8.53 (1H, d, J=5.2 Hz), 8.95-8.98 (1H, m), 9.07 (1H, br), 9.45 (1H, br s).

Example 273

N-{4-[3-Fluoro-4-(3-(thiazol-2-yl)ureido)phenoxy]-7-methoxyquinolin-6-yl}methanesulfoneamide The title compound (5 mg) was obtained as a solid from 1-[4-(6-amino-7-methoxyquinolin-4-yloxy)-2-fluorophenyl]-3-(thiazol-2-yl)urea (50 mg), in the same manner as Example 266.
$^1$H-NMR Spectrum (DMSO-$d_6$) δ (ppm): 3.06 (3H, s), 4.00 (3H, s), 6.55 (1H, d, J=5.2 Hz), 7.09-7.16 (2H, m), 7.25-7.35 (1H, m), 7.39 (1H, d, J=3.2 Hz), 7.49 (1H, s), 8.10 (1H, s), 8.21 (1H, t, J=9.2 Hz), 8.57 (1H, d, J=5.2 Hz), 9.02 (1H, br s), 9.32 (1H, br s), 10.78 (1H, br s).

Example 274

{4-[4-(Cyclopropylureido)-3-fluorophenoxy]-7-methoxyquinolin-6-yl}carbamic acid benzyl ester

[4-(4-Amino-3-fluorophenoxy)-7-methoxyquinolin-6-yl]carbamic acid benzyl ester (100 mg) and cyclopropylcarbamic acid phenyl ester (64 mg) were heated and stirred in dimethylsulfoxide (0.7 ml) at 85° C. for 5 hours and 40 minutes, in the same manner as Example 224, to obtain the title compound (11 mg) as a solid.
$^1$H-NMR Spectrum (DMSO-$d_6$) δ (ppm): 0.37-0.41 (2H, m), 0.60-0.65 (2H, m), 2.50-2.56 (1H, m), 3.95 (3H, s), 5.16 (2H, s), 6.46 (1H, d, J=5.2 Hz), 6.77-6.80 (1H, m), 6.99-7.03 (1H, m), 7.23-7.45 (7H, m), 8.16 (1H, t, J=9.2 Hz), 8.19 (1H, s), 8.49 (1H, d, J=5.2 Hz), 8.63 (1H, s), 8.97 (1H, s).

Example 275

N-{4-[4-(Cyclopropylureido)3-fluorophenoxy]-7-methoxyquinolin-6-yl}acetamide

{4-[4-(cyclopropylureido)-3-fluorophenoxy]-7-methoxyquinolin-6-yl}carbamic acid benzyl ester (11 mg) was heated and stirred in a mixture of trifluoroacetic acid (3 ml) and thioanisole (0.5 ml) at 60° C., in the same manner as Example 264, for debenzylation. The resulting amino compound was acetylated in the same manner as Example 265 to obtain the title compound (2 mg) as a solid.
$^1$H-NMR Spectrum (DMSO-$d_6$) δ (ppm): 0.36-0.40 (2H, m), 0.58-0.63 (2H, m), 2.14 (3H, s), 2.46-2.55 (1H, m), 3.99 (3H, s), 6.44 (1H, d, J=5.2 Hz), 6.77 (1H, d, J=2.8 Hz), 6.97-7.01 (1H, m), 7.23 (1H, dd, J=2.8 Hz, J=11.6 Hz), 7.41 (1H, s), 8.15 (1H, t, J=8.8 Hz), 8.17 (1H, br s), 8.48 (1H, d, J=5.2 Hz), 8.93 (1H, s), 9.42 (1H, s).

Example 276

4-[4-(Cyclopropylureido)-2-methylphenoxy]-7-methoxyquinoline-6-carboxylic acid amide The title compound (61 mg) was obtained as a solid from [4-(6-carbamoyl-7-methoxyquinolin-4-yloxy)-3-methylphenyl]carbamic acid phenyl ester (100 mg) and cyclopropylamine, in the same manner as Example 11.
$^1$H-NMR Spectrum (DMSO-$d_6$) δ (ppm): 0.37-0.41 (2H, m), 0.59-0.65 (2H, m), 2.04 (3H, s), 2.49-2.55 (1H, m), 4.01 (3H, s), 6.26 (1H, d, J=5.2 Hz), 6.41-6.47 (1H, m), 7.05 (1H, d, J=8.8 Hz), 7.35 (1H, dd, J=2.4 Hz, J=8.8 Hz), 7.42 (1H, d, J=2.4 Hz), 7.48 (1H, s), 7.71 (1H, br s), 7.84 (1H, br s), 8.27-8.42 (1H, m), 8.59 (1H, d, J=5.2 Hz), 8.69 (1H, s).

The intermediates were synthesized in the following manner.

Production Example 276-1

4-(4-Amino-2-methylphenoxy)-7-methoxyquinoline-6-carboxylic acid amide

The title compound (430 mg) was obtained as a solid from 4-chloro-7-methoxyquinoline-6-carboxylic acid amide (1 g) and 4-amino-2-methylphenol, in the same manner as Production Example 458-1.

$^1$H-NMR Spectrum (DMSO-d$_6$) δ (ppm): 1.93 (3H, s), 4.01 (3H, s), 5.06-5.09 (2H, m), 6.27 (1H, d, J=5.2 Hz), 6.49 (1H, dd, J=2.8 Hz, J=8.4 Hz), 6.54 (1H, d, J=2.8 Hz), 6.84 (1H, d, J=8.4 Hz), 7.47 (1H, s), 7.71 (1H, br s), 7.83 (1H, br s), 8.59 (1H, d, J=5.2 Hz), 8.69 (1H, s).

Production Example 276-2

[4-(6-Carbamoyl-7-methoxyquinolin-4-yloxy)-3-methylphenyl]carbamic acid phenyl ester The title compound (112 mg) was obtained as a solid from 4-(4-amino-2-methylphenoxy)-7-methoxyquinoline-6-carboxylic acid amide (330 mg) and phenyl chlorocarbonate, in the same manner as Production Example 17.

$^1$H-NMR Spectrum (DMSO-d$_6$) δ (ppm): 2.08 (3H, s), 4.02 (3H, s), 6.30 (1H, d, J=5.2 Hz), 7.19-7.55 (9H, m), 7.73 (1H, br s), 7.85 (1H, br s), 8.62 (1H, d, J=5.2 Hz), 8.71 (1H, s), 10.33 (1H, br s).

Example 277

1-(3-Fluorophenyl)-3-[4-(6-(pyridin-2-yl)-7H-pyrrolo[2,3-d]pyrimidin-4-yloxy)phenyl]urea The title compound (118 mg) was obtained as a solid from 4-(6-(pyridin-2-yl)-7H-pyrrolo[2,3-d]pyrimidin-4-yloxy)phenylamine (90 mg) and 3-fluorophenyl isocyanate, in the same manner as Example 10.

$^1$H-NMR Spectrum (DMSO-d$_6$) δ (ppm): 6.74-6.80 (1H, m), 7.11-7.15 (1H, m), 7.20 (2H, d, J=8.8 Hz), 7.23 (1H, s), 7.29 (1H, t, J=7.6 Hz), 7.34-7.38 (1H, m), 7.46-7.51 (1H, m), 7.52 (2H, d, J=8.8 Hz), 7.87-7.92 (1H, m), 8.08 (1H, d, J=8.0 Hz), 8.31 (1H, s), 8.63-8.66 (1H, m), 8.82 (1H, br s), 8.93 (1H, br s), 12.78 (1H, br s).

The intermediates were synthesized in the following manner.

Production Example 277-1

4-(4-Nitrophenoxy)-6-(pyridin-2-yl)-7-H-pyrrolo[2,3-d]pyrimidine

The title compound (1.0 g) was obtained as a solid from 4-chloro-6-(pyridin-2-yl)-7H-pyrrolo[2,3-d]pyrimidine (0.8 g) and nitrophenol (1.45 g), by the same procedure as in Production Example 7.

$^1$H-NMR Spectrum (DMSO-d$_6$) δ (ppm): 7.33 (1H, s), 7.37 (1H, dd, J=4.8 Hz, J=7.2 Hz), 7.59 (2H, d, J=9.2 Hz), 7.88-7.94 (1H, m), 8.12 (1H, d, J=7.2 Hz), 8.33 (2H, d, J=9.2 Hz), 8.38 (1H, s), 8.66 (1H, d, J=4.8 Hz), 12.92 (1H, br s).

Production Example 277-2

4-(6-(Pyridin-2-yl)-7H-pyrrolo[2,3-d]pyrimidin-4-yloxy)phenylamine

The title compound (0.4 g) was obtained as a solid from 4-(4-nitrophenoxy)-6-(pyridin-2-yl)-7-H-pyrrolo[2,3-d]pyrimidine (1.0 g), in the same manner as Production Example 8.

$^1$H-NMR Spectrum (DMSO-d$_6$) δ (ppm): 5.06 (2H, br s), 6.60 (2H, d, J=8.8 Hz), 6.90 (2H, d, J=8.8 Hz), 7.07 (1H, s), 7.32-7.36 (1H, m), 7.86-7.91 (1H, m), 8.03 (1H, d, J=8.0 Hz), 8.29 (1H, s), 8.64 (1H, d, J=4 Hz), 12.71 (1H, br s).

Example 278

1-(4-Fluorophenyl)-3-[4-(6-(pyridin-2-yl)-7H-pyrrolo[2,3-d]pyrimidin-4-yloxy)phenyl]urea The title compound (120 mg) was obtained as a solid from 4-(6-(pyridin-2-yl)-7H-pyrrolo[2,3-d]pyrimidin-4-yloxy)phenylamine (100 mg) and 4-fluorophenyl isocyanate, in the same manner as Example 10.

$^1$H-NMR Spectrum (DMSO-d$_6$) δ (ppm): 7.11 (2H, t, J=8.8 Hz), 7.19 (2H, d, J=8.8 Hz), 7.22 (1H, s), 7.35 (1H, dd, J=7.2 Hz, J=7.6 Hz), 7.43-7.48 (2H, m), 7.51 (2H, d, J=8.8 Hz), 7.87-7.92 (1H, m), 8.08 (1H, d, J=8.0 Hz), 8.32 (1H, s), 8.64-8.66 (1H, m), 8.73 (1H, br s), 8.75 (1H, br s), 12.78 (1H, br s).

Example 279

1-[4-(6-(Pyridin-2-yl)-7H-pyrrolo[2,3-d]pyrimidin-4-yloxy)-phenyl]-3-(thiazol-2-yl)urea 4-(6-(Pyridin-2-yl)-7H-pyrrolo[2,3-d]pyrimidin-4-yloxy)phenylamine (100 mg) and (thiazol-2-yl)carbamic acid phenyl ester (116 mg) were heated and stirred in dimethylsulfoxide (2.5 ml) at 80° C. for 1 hour, in the same manner as Example 224, to obtain the title compound (110 mg) as a solid.

$^1$H-NMR Spectrum (DMSO-d$_6$) δ (ppm): 7.10 (1H, d, J=3.6 Hz), 7.23 (2H, d, J=8.8 Hz), 7.24 (1H, s), 7.34-7.40 (2H, m), 7.55 (2H, d, J=8.8 Hz), 7.87-7.93 (1H, m), 8.09 (1H, d, J=8.0 Hz), 8.32 (1H, s), 8.63-8.67 (1H, m), 9.06 (1H, br s), 12.79 (1H, br s).

Example 280

1-(4-Fluorophenyl)-3-[2-fluoro-4-(6-(pyridin-2-yl)-7H-pyrrolo[2,3-d]pyrimidin-4-yloxy)-phenyl]-urea The title compound (110 mg) was obtained as a solid from 2-fluoro-4-(6-(pyridin-2-yl)-7H-pyrrolo[2,3-d]pyrimidin-4-yloxy)phenylamine (100 mg) and 4-fluorophenyl isocyanate, by the same procedure as in Example 10.

$^1$H-NMR Spectrum (DMSO-d$_6$) δ (ppm): 7.07-7.16 (3H, m), 7.28 (1H, s), 7.33-7.38 (2H, m), 7.42-7.48 (2H, m), 7.87-7.93 (1H, m), 8.08-8.14 (2H, m), 8.33 (1H, s), 8.53-8.56 (1H, m), 8.64-8.66 (1H, m), 9.08 (1H, br s), 12.83 (1H, br s).

The intermediates were synthesized in the following manner.

Production Example 280-1

4-(3-Fluoro-4-nitrophenoxy)-6-(pyridin-2-yl)-7H-pyrrolo[2,3-d]pyrimidine

The title compound (0.75 g) was obtained as a solid from the 4-chloro-6-(pyridin-2-yl)-7H-pyrrolo[2,3-d]pyrimidine (0.7 g) described in WO9702266 and PCT/EP96/02728 and fluoronitrophenol (0.95 g), in the same manner as Production Example 7.

$^1$H-NMR Spectrum (DMSO-d$_6$) δ (ppm): 7.34-7.45 (3H, m), 7.74 (1H, dd, J=2.4 Hz, J=12.4 Hz), 7.89-7.94 (1H, m), 8.12 (1H, d, J=8.0 Hz), 8.28 (1H, t, J=8.8 Hz), 8.41 (1H, s), 8.65-8.68 (1H, m), 12.96 (1H, br s).

Production Example 280-2

2-Fluoro-4-(6-(pyridin-2-yl)-7H-pyrrolo[2,3-d]pyrimidin-4-yloxy)phenylamine

The title compound (450 mg) was obtained as a solid from 4-(3-fluoro-4-nitrophenoxy)-6-(pyridin-2-yl)-7H-pyrrolo[2,3-d]pyrimidine (750 mg), by the same procedure as in Production Example 8.

$^1$H-NMR Spectrum (DMSO-d$_6$) δ (ppm): 5.10 (2H, br s), 6.79-6.83 (2H, m), 7.01-7.05 (1H, m), 7.16 (1H, s), 7.32-7.38 (1H, m), 7.86-7.92 (1H, m), 8.06 (1H, d, J=7.6 Hz), 8.31 (1H, s), 8.64 (1H, d, J=4.4 Hz), 12.75 (1H, br s).

Example 281

1-(3-Fluorophenyl)-3-[2-fluoro-4-(6-(pyridin-2-yl)-7H-pyrrolo[2,3-d]pyrimidin-4-yloxy)phenyl]urea The title compound (30 mg) was obtained as a solid from 2-fluoro-4-(6-(pyridin-2-yl)-7H-pyrrolo[2,3-d]pyrimidin-4-yloxy)phenylamine (100 mg) and 3-fluorophenyl isocyanate, in the same manner as Example 10.

$^1$H-NMR Spectrum (DMSO-d$_6$) δ (ppm): 6.76-6.83 (1H, m), 7.11 (2H, d, J=8.8 Hz), 7.27-7.39 (4H, m), 7.48-7.53 (1H, m), 7.87-7.94 (1H, m), 8.11 (2H, d, J=8.8 Hz), 8.34 (1H, s), 8.61-8.65 (1H, m), 8.66 (1H, br d, J=4.0 Hz), 9.27 (1H, br s), 12.83 (1H, br s).

Example 282

1-[2-Fluoro-4-(6-(pyridin-2-yl)-7H-pyrrolo[2,3-d]pyrimidin-4-yloxy)phenyl]-3-(thiazol-2-yl)urea The title compound (100 mg) was obtained as a solid from 2-fluoro-4-(6-(pyridin-2-yl)-7H-pyrrolo[2,3-d]pyrimidin-4-yloxy)phenylamine (100 mg) and (thiazol-2-yl)carbamic acid phenyl ester (109 mg), by the same procedure as in Example 224.

$^1$H-NMR Spectrum (DMSO-d$_6$) δ (ppm): 7.07-7.17 (2H, m), 7.29 (1H, s), 7.35-7.44 (3H, m), 7.87-7.95 (1H, m), 8.08-8.15 (2H, m), 8.34 (1H, s), 8.66 (1H, br d, J=4.0 Hz), 8.99 (1H, br), 10.81 (1H, brs), 12.83 (1H, brs).

Example 283

1-Cyclopropyl-3-[2-fluoro-4-(6-(pyridin-2-yl)-7H-pyrrolo[2,3-d]pyrimidin-4-yloxy)phenyl]urea The title compound (15 mg) was obtained as a solid from 2-fluoro-4-(6-(pyridin-2-yl)-7H-pyrrolo[2,3-d]pyrimidin-4-yloxy)phenylamine (75 mg) and cyclopropylcarbamic acid phenyl ester (66 mg), in the same manner as Example 224.

$^1$H-NMR Spectrum (DMSO-d$_6$) δ (ppm): 0.37-0.42 (2H, m), 0.60-0.66 (2H, m), 2.49-2.57 (1H, m), 6.76 (1H, d, J=2.4 Hz), 7.01-7.05 (1H, m), 7.24-7.29 (2H, m), 7.33-7.37 (1H, m), 7.86-7.92 (1H, m), 8.05-8.12 (2H, m), 8.13-8.16 (1H, m), 8.32 (1H, s), 8.62-8.66 (1H, m), 12.79 (1H, br s).

Example 284

7-((2R)-2-Hydroxy-3-(pyrrolidin-1-yl)propoxy)-4-(1H-indol-5-yloxy)quinoline-6-carbonitrile The title compound (0.56 g) was obtained as a solid from 4-(1H-indol-5-yloxy)-(2R)-7-oxiranylmethoxyquinoline-6-carbonitrile (0.73 g), in the same manner as Example 454.

$^1$H-NMR Spectrum (DMSO-d$_6$) δ (ppm): 2.61-2.72 (4H, m), 2.44-2.58 (6H, m), 2.68-2.73 (1H, m), 3.99-4.06 (1H, m), 4.20 (1H, dd, J=6.0 Hz, J=10.4 Hz), 4.29 (1H, dd, J=3.6 Hz, J=10.4 Hz), 5.02 (1H, br s), 6.42 (1H, d, J=5.2 Hz), 6.44-6.48 (1H, m), 6.99 (1H, dd, J=1.6 Hz, J=8.4 Hz), 7.43-7.47 (2H, m), 7.51 (1H, d, J=8.4 Hz), 7.59 (1H, s), 8.65 (1H, d, J=5.2 Hz), 8.77 (1H, s).

The intermediates were synthesized in the following manner.

Production Example 284-1

4-(1H-Indol-5-yloxy)-(2R)-7-oxiranylmethoxyquinoline-6-carbonitrile

The title compound (0.73 g) was obtained as a solid from 4-(1H-indol-5-yloxy)-7-hydroxyquinoline-6-carbonitrile (1 g) using (2R)-oxiran-2-ylmethyl-4-methyl-1-benzene sulfonate, by the same procedure as in Example 7.

$^1$H-NMR Spectrum (DMSO-d$_6$) δ (ppm): 2.82 (1H, dd, J=2.4 Hz, J=4.8 Hz), 2.91 (1H, t, J=4.8 Hz), 3.44-3.49 (1H, m), 4.17 (1H, dd, J=6.4 Hz, J=11.6 Hz), 4.71 (1H, dd, J=2.4 Hz, J=11.6 Hz), 6.44 (1H, d, J=5.2 Hz), 6.46-6.48 (1H, m), 6.99 (1H, dd, J=2.4 Hz, J=8.8 Hz), 7.44-7.46 (2H, m), 7.52 (1H, d, J=8.8 Hz), 7.62 (1H, s), 8.67 (1H, d, J=5.2 Hz), 8.82 (1H, s), 11.31 (1H, br s).

Example 285

5-[6-Cyano-7-((2R)-2-hydroxy-3-(pyrrolidin-1-yl)propoxy)quinolin-4-yloxy]indole-1-carboxylic acid cyclopropylamide 7-((2R)-2-Hydroxy-3-(pyrrolidin-1-yl)propoxy)-4-(1H-indol-5-yloxy)quinoline-6-carbonitrile (0.56 g) was silyletherified using triethylsilyl chloride and imidazole to obtain 0.48 g of the target substance. Following the same procedure as in Example 310, an amide compound was obtained from the triethylsilyl ether compound (0.2 g), and this was deprotected at 50° C. in a mixture of acetic acid, tetrahydrofuran and water to obtain the title compound (35 mg) as a solid.

$^1$H-NMR Spectrum (DMSO-d$_6$) δ (ppm): 0.58-0.63 (2H, m), 0.71-0.76 (2H, m), 1.84-1.94 (2H, m), 1.98-2.06 (2H, m), 2.73-2.79 (1H, m), 3.07-3.16 (2H, m), 3.33-3.38 (2H, m), 3.57-3.64 (2H, m), 4.28-4.36 (3H, m), 6.55 (1H, d, J=5.6 Hz), 6.70 (1H, d, J=3.6 Hz), 7.19 (1H, dd, J=2.4 Hz, J=8.8 Hz), 7.53 (1H, d, J=2.4 Hz), 7.66 (1H, s), 7.88 (1H, d, J=3.6 Hz), 8.32 (1H, d, J=2.8 Hz), 8.35 (1H, d, J=8.8 Hz), 8.74 (1H, d, J=5.6 Hz), 8.87 (1H, s).

Example 286

5-[6-Cyano-7-(3-(pyrrolidin-1-yl)propoxy)quinolin-4-yloxy]indole-1-carboxylic acid cyclopropylamide The title compound (35 mg) was obtained as a solid from 4-(1H-indol-5-yloxy)-7-(3-(pyrrolidin-1-yl)propoxy)quinoline-6-carbonitrile (150 mg), in the same manner as Example 310.

¹H-NMR Spectrum (DMSO-d₆) δ (ppm): 0.59-0.64 (2H, m), 0.71-0.76 (2H, m), 1.64-1.72 (4H, m), 1.95-2.03 (2H, m), 2.38-2.48 (4H, m), 2.59 (2H, d, J=6.8 Hz), 2.74-2.81 (1H, m), 4.33 (2H, d, J=6.4 Hz), 6.47 (1H, d, J=5.2 Hz), 6.68 (1H, d, J=3.6 Hz), 7.19 (1H, dd, J=2.4 Hz, 8.8 Hz), 7.52 (1H, d, J=2.4 Hz), 7.58 (1H, s), 7.90 (1H, d, J=3.6 Hz), 8.23 (1H, d, J=2.8 Hz), 8.35 (1H, d, J=8.8 Hz), 8.68 (1H, d, J=5.2 Hz), 8.79 (1H, s).

Example 287

5-[6-Cyano-7-(2-methoxyethoxy)quinolin-4-yloxy]indole-1-carboxylic acid cyclopropylamide The title compound (210 mg) was obtained as a solid from 4-(1H-indol-5-yloxy)-7-(2-methoxyethoxyquinoline-6-carbonitrile (450 mg), in the same manner as Example 310.

¹H-NMR Spectrum (DMSO-d₆) δ (ppm): 0.59-0.65 (2H, m), 0.71-0.77 (2H, m), 2.74-2.82 (1H, m), 3.76-3.80 (2H, m), 0.59-0.65 (2H, m), 4.39-4.43 (2H, m), 6.47 (1H, d, J=5.2 Hz), 6.68 (1H, d, J=3.6 Hz), 7.19 (1H, dd, J=2.4 Hz, J=8.8 Hz), 7.52 (1H, d, J=2.4 Hz), 7.62 (1H, s), 7.90 (1H, d, J=3.6 Hz), 8.30 (1H, d, J=2.8 Hz), 8.35 (1H, d, J=8.8 Hz), 8.68 (1H, d, J=5.2 Hz), 8.79 (1H, s).

The intermediates were synthesized in the following manner.

Production Example 287-1

4-(1H-Indol-5-yloxy)-7-(2-methoxyethoxy)quinoline-6-carbonitrile

The title compound (0.8 g) was obtained as a solid from 4-chloro-7-methoxyethoxy-6-cyanoquinoline (1.0 g) and 5-hydroxyindole, in the same manner as Example 309.

¹H-NMR Spectrum (DMSO-d₆) δ (ppm): 3.37 (3H, s), 3.76-3.79 (2H, m), 4.39-4.43 (2H, m), 6.43 (1H, d, J=5.6 Hz), 6.45-6.49 (1H, m), 6.99 (1H, dd, J=2.4 Hz, J=8.8 Hz), 7.43-7.47 (2H, m), 7.52 (1H, d, J=8.8 Hz), 7.61 (1H, s), 8.66 (1H, d, J=5.6 Hz), 8.79 (1H, s), 11.31 (1H, br s).

Example 288

4-(1H-Indol-5-yloxy)-7-(3-(pyrrolidin-1-yl)propoxy)quinoline-6-carbonitrile

The title compound (1.27 g) was obtained as a solid from 4-(1H-Indol-5-yloxy)-7-hydroxyquinoline-6-carbonitrile (1.98 g) and 1-(3-chloropropyl)pyrrolidine hydrochloride, in the same manner as Example 7.

¹H-NMR Spectrum (DMSO-d₆) δ (ppm): 1.64-1.72 (4H, m), 1.95-2.03 (2H, m), 2.42-2.48 (4H, m), 2.59 (2H, t, J=7.2 Hz), 4.32 (2H, t, J=6.4 Hz), 6.43 (1H, d, J=5.2 Hz), 6.46-6.48 (1H, m), 6.99 (1H, dd, J=2.4 Hz, J=8.8 Hz), 7.43-7.47 (2H, m), 7.51 (1H, d, J=8.8 Hz), 7.57 (1H, s), 8.66 (1H, d, J=5.2 Hz), 8.78 (1H, s), 11.30 (1H, br s).

Example 289

5-[6-Cyano-7-(3-(pyrrolidin-1-yl)propoxy)quinolin-4-yloxy]indole-1-carboxylic acid (thiazol-2-yl)amide The title compound (155 mg) was obtained as a solid from 4-(1H-indol-5-yloxy)-7-(3-(pyrrolidin-1-yl)propoxy)quinoline-6-carbonitrile (200 mg), in the same manner as Example 312.

¹H-NMR Spectrum (DMSO-d₆) δ (ppm): 1.66-1.76 (4H, m), 1.98-2.07 (2H, m), 2.52-2.61 (4H, m), 2.70 (2H, t, J=7.2 Hz), 4.34 (2H, t, J=6.4 Hz), 6.51 (1H, d, J=5.2 Hz), 6.63 (1H, d, J=3.6 Hz), 6.95 (1H, d, J=4.4 Hz), 7.16 (1H, dd, J=2.4 Hz, J=8.8 Hz), 7.38 (1H, d, J=4.4 Hz), 7.50 (1H, d, J=2.4 Hz), 7.59 (1H, s), 8.09 (1H, d, J=3.6 Hz), 8.68 (1H, d, J=5.2 Hz), 8.72 (1H, d, J=8.8 Hz), 8.81 (1H, s).

Example 290

5-[6-Cyano-7-(2-methoxyethoxy)quinolin-4-yloxy]indole-1-carboxylic acid (thiazol-2-yl)amide The title compound (31 mg) was obtained as a solid from 4-(1H-indol-5-yloxy)-7-(2-methoxyethoxy)quinoline-6-carbonitrile (100 mg), in the same manner as Example 312.

¹H-NMR Spectrum (DMSO-d₆) δ (ppm): 3.37 (3H, s), 3.77-3.80 (2H, m), 4.41 (2H, m), 6.51 (1H, d, J=5.2 Hz), 6.59-6.64 (1H, m), 6.88-6.95 (1H, m), 7.12-7.18 (1H, m), 7.32-7.39 (1H, m), 7.48-7.51 (1H, m), 7.62 (1H, s), 8.06-8.13 (1H, m), 8.69 (1H, d, J=5.2 Hz), 8.69-8.77 (1H, m), 8.81 (1H, s).

Example 291

5-(7-Benzyloxy-6-cyanoquinolin-4-yloxy]indole-1-carboxylic acid (2-fluoroethyl)-amide The title compound (3.6 g) was obtained as a solid from 5-(7-benzyloxy-6-cyanoquinolin-4-yloxy)indole (4.5 g) and (2-fluoroethyl)carbamic acid phenyl ester, in the same manner as Example 310.

¹H-NMR Spectrum (DMSO-d₆) δ (ppm): 3.54-3.61 (1H, m), 3.61-3.66 (1H, m), 4.53 (1H, t, J=4.8 Hz), 4.65 (1H, t, J=4.8 Hz), 5.45 (2H, s), 6.48 (1H, d, J=5.2 Hz), 6.73 (1H, d, J=3.6 Hz), 7.20 (1H, dd, J=2.4 Hz, J=8.8 Hz), 7.34-7.39 (1H, m), 7.42-7.47 (2H, m), 7.53-7.57 (3H, m), 7.70 (1H, s), 7.98 (1H, d, J=3.6 Hz), 8.36 (1H, d, J=8.8 Hz), 8.50 (1H, t, J=5.2 Hz), 8.68 (1H, d. J=5.2 Hz), 8.82 (1H, s).

Example 292

5-(6-Cyano-7-hydroxyquinolin-4-yloxy]indole-1-carboxylic acid (2-fluoroethyl)amide The title compound (2.17 g) was obtained as a solid from 5-(7-benzyloxy-6-cyanoquinolin-4-yloxy]indole-1-carboxylic acid (2-fluoroethyl)amide (3 g) using trifluoroacetic acid, by the same procedure as in Production Example 21.

¹H-NMR Spectrum (DMSO-d₆) δ (ppm): 3.54-3.59 (1H, m), 3.61-3.65 (1H, m), 4.53 (1H, t, J=5.2 Hz), 4.65 (1H, t, J=5.2 Hz), 6.39 (1H, d, J=5.2 Hz), 6.73 (1H, d, J=3.6 Hz), 7.19 (1H, dd, J=2.4 Hz, J=8.8 Hz), 7.41 (1H, s), 7.53 (1H, d, J=2.4 Hz), 7.98 (1H, d, J=3.6 Hz), 8.35 (1H, d, J=8.8 Hz), 8.50 (1H, t, J=5.2 Hz), 8.61 (1H, d. J=5.2 Hz), 8.71 (1H, s).

Example 293

5-[6-Cyano-7-(piperidin-4-yl)methoxy)quinolin-4-yloxy]indole-1-carboxylic acid (2-fluoroethyl)amide In the same manner as Example 301, a tert-butoxycarbonyl compound (150 mg) was obtained from 5-(6-cyano-7-hydroxyquinolin-4-yloxy]indole-1-carboxylic acid (2-fluoroethyl)amide (1 g) and 4-bromoethylpiperidine-1-carboxylic acid tert-butyl ester, and then the tert-butoxycarbonyl group was deprotected with trifluoroacetic acid to obtain the title compound (97 mg) as a solid.

$^1$H-NMR Spectrum (DMSO-d$_6$) δ (ppm): 1.48-1.61 (2H, m), 1.95-2.02 (2H, m), 2.16-2.26 (1H, m), 2.92-3.01 (2H, m), 3.28-3.38 (2H, m), 3.54-3.59 (1H, m), 3.61-3.66 (1H, m), 4.02-4.07 (1H, m), 4.22 (2H, d, J=6.4 Hz), 4.53 (1H, t, J=5.2 Hz), 4.65 (1H, t, J=5.2 Hz), 6.49 (1H, d, J=5.2 Hz), 6.74 (1H, d, J=4.0 Hz), 7.19 (1H, dd, J=2.4 Hz, J=8.8 HZ), 7.54 (1H, d, J=2.4 Hz), 7.64 (1H, s), 7.99 (1H, d, J=4.0 Hz), 8.36 (1H, d, J=8.8 Hz), 8.51 (1H, t, J=5.6 Hz), 8.82 (1H, s).

Example 294

5-[6-Cyano-7-(1-(methylpiperidin-4-yl)methoxy)quinolinyloxy]indole-1-carboxylic acid (2-fluoroethyl)amide The title compound (35 mg) was obtained as a solid from 5-[6-cyano-7-(piperidin-4-ylmethoxy)quinolinyloxy]indole-1-carboxylic acid (2-fluoroethyl)amide (97 mg), in the same manner as Example 302.

$^1$H-NMR Spectrum (DMSO-d$_6$) δ (ppm): 1.52-1.61 (2H, m), 1.89-2.07 (5H, m), 2.31 (3H, s), 2.92-2.98 (2H, m), 3.69-3.74 (1H, m), 3.76-3.81 (1H, m), 4.30 (2H, d, J=6.0 Hz), 4.68 (1H, t, J=5.2 Hz), 4.80 (1H, t, J=5.2 Hz), 6.63 (1H, d, J=5.2 Hz), 6.88 (1H, d, J=4.0 Hz), 7.35 (1H, dd, J=2.4 Hz, J=8.8 Hz), 7.69 (1H, d, J=2.4 Hz), 7.73 (1H, s), 8.13 (1H, d, J=4.0 Hz), 8.51 (1H, d, J=8.8 Hz), 8.65 (1H, t, J=5.2 Hz), 8.83 (1H, d, J=5.2 Hz), 8.94 (1H, s).

Example 295

5-[6-Cyano-7-(2-methoxyethoxy)quinolin-4-yloxy]indole-1-carboxylic acid ethylamide The title compound (77 mg) was obtained as a solid from 7-(methoxyethoxy)-4-(1H-indol-5-yloxy)quinoline-6-carbonitrile (100 mg), in the same manner as Example 310.

$^1$H-NMR Spectrum (DMSO-d$_6$) δ (ppm): 1.18 (3H, t, J=7.2 Hz), 3.28-3.33 (2H, m), 3.37 (1H, s), 3.76-3.80 (2H, m), 4.40-4.44 (2H, m), 6.48 (1H, d, J=5.2 Hz), 6.71 (1H, d, J=3.6 Hz), 7.19 (1H, dd, J=2.4 Hz, J=8.8 Hz), 7.53 (1H, d, J=2.4 Hz), 7.62 (1H, s), 7.93 (1H, d, J=3.6 Hz), 8.24 (1H, d, J=5.2 Hz), 8.35 (1H, d, J=8.8 Hz), 8.69 (1H, d, J=5.2 Hz), 8.80 (1H, s).

Example 296

7-(3-Diethylaminopropoxy)-4-(1H-indol-5-yloxy)quinoline-6-carbonitrile

The title compound (0.46 g) was obtained as a solid from 4-(1H-indol-5-yloxy)-7-hydroxyquinoline-6-carbonitrile (0.8 g) and 3-diethylaminopropyl chloride, in the same manner as Example 7.

$^1$H-NMR Spectrum (DMSO-d$_6$) δ (ppm): 0.95 (6H, t, J=7.2 Hz), 1.88-1.94 (2H, m), 2.43-2.49 (4H, m), 2.59 (2H, t, J=6.8 Hz), 4.30 (2H, t, J=6.0 Hz), 6.42 (1H, d, J=5.2 Hz), 6.45-6.48 (1H, m), 6.98 (1H, dd, J=2.4 Hz, J=8.8 Hz), 7.43-7.47 (2H, m), 7.51 (1H, d, J=8.8 Hz), 7.55 (1H, s), 8.65 (1H, d, J=5.2 Hz), 8.77 (1H, s), 11.30 (1H, br s).

Example 297

5-[6-Cyano-7-(3-diethylaminopropoxy)quinolin-4-yloxy]indole-1-carboxylic acid ethylamide The title compound (35 mg) was obtained as a solid from 7-(3-diethylaminopropoxy)-4-(1H-indol-5-yloxy)quinoline-6-carbonitrile (230 mg), in the same manner as Example 310.

$^1$H-NMR Spectrum (DMSO-d$_6$) δ (ppm): 0.95 (6H, t, J=7.2 Hz), 1.18 (3H, t, J=7.2 Hz), 1.89-1.94 (2H, m), 2.43-2.49 (4H, m), 2.59 (2H, t, J=7.2 Hz), 3.29-3.37 (2H, m), 4.31 (2H, t, J=6.0 Hz), 6.47 (1H, d, J=5.2 Hz), 6.70 (1H, d, J=3.6 Hz), 7.18 (1H, dd, J=2.4 Hz, J=8.8 Hz), 7.52 (1H, d, J=2.4 Hz), 7.57 (1H, s), 7.93 (1H, d, J=3.6 Hz), 8.24 (1H, t, J=5.2 Hz), 8.35 (1H, d, J=8.8 Hz), 8.67 (1H, d, J=5.2 Hz), 8.78 (1H, s).

Example 298

5-[6-Cyano-7-(3-diethylaminopropoxy)quinolin-4-yloxy]indole-1-carboxylic acid cyclopropylamide The title compound (0.21 g) was obtained as a solid from 7-(3-diethylaminopropoxy)-4-(1H-indol-5-yloxy)quinoline-6-carbonitrile (0.5 g), in the same manner as Example 310.

$^1$H-NMR Spectrum (DMSO-d$_6$) δ (ppm): 0.59-0.64 (2H, m), 0.71-0.76 (2H, m), 0.95 (6H, t, J=7.2 Hz), 1.87-1.95 (2H, m), 2.43-2.49 (4H, m), 2.59 (2H, t, J=6.8 Hz), 2.74-2.81 (1H, m), 4.31 (2H, t, J=6.0 Hz), 6.46 (1H, d, J=5.2 Hz), 6.68 (1H, d, J=3.6 Hz), 7.19 (1H, dd, J=2.4 Hz, J=8.8 Hz), 7.52 (1H, d, J=2.4 Hz), 7.56 (1H, s), 7.90 (1H, d, J=3.6 Hz), 8.30 (1H, d, J=3.2 Hz), 8.35 (1H, d, J=8.8 Hz), 8.67 (1H, d, J=5.2 Hz), 8.78 (1H, s).

Example 299

5-[6-Cyano-7-(3-(pyrrolidin-1-yl)propoxy)quinolin-4-yloxy]indole-1-carboxylic acid ethylamide The title compound (31 mg) was obtained as a solid from 7-(3-(pyrrolidin-1-yl)propoxy)-4-(1H-indol-5-yloxy)quinoline-6-carbonitrile (100 mg), in the same manner as Example 310.

$^1$H-NMR Spectrum (DMSO-d$_6$) δ (ppm): 1.18 (3H, t, J=7.2 Hz), 1.85-1.99 (4H, m), 2.40-2.49 (2H, m), 3.01-3.48 (8H, m), 4.39 (2H, t, J=6.0 Hz), 6.50 (1H, d, J=5.2 Hz), 6.71 (1H, d, J=3.6 Hz), 7.18 (1H, dd, J=2.4 Hz, J=8.8 Hz), 7.53 (1H, d, J=2.4 Hz), 7.62 (1H, s), 7.96 (1H, d, J=3.6 Hz), 8.28 (1H, t, J=5.2 Hz), 8.36 (1H, d, J=8.8 Hz), 8.70 (1H, d, J=5.2 Hz), 8.82 (1H, s).

Example 300

5-[6-Cyano-7-(3-diethylaminopropoxy)quinolin-4-yloxy]indole-1-carboxylic acid (thiazol-2-yl)amide The title compound (5 mg) was obtained as a solid from 7-(3-diethylaminopropoxy)-4-(1H-indol-5-yloxy)quinoline-6-carbonitrile (80 mg), in the same manner as Example 312.

$^1$H-NMR Spectrum (DMSO-d$_6$) δ (ppm): 1.00 (6H, t, J=7.2 Hz), 1.93-2.01 (2H, m), 2.59 (4H, q, J=7.2 Hz), 2.72 (2H, t, J=6.8 Hz), 4.33 (2H, t, J=6.0 Hz), 6.51 (1H, d, J=5.2 Hz), 6.64 (1H, d, J=3.6 Hz), 6.98 (1H, d, J=4.0 Hz), 7.16 (1H, dd, J=2.4 Hz, J=8.8 Hz), 7.40 (1H, d, J=4.0 Hz), 7.50 (1H, d, J=2.4 Hz), 7.58 (1H, s), 8.09 (1H, d, J=3.6 Hz), 8.68 (1H, d, J=5.2 Hz), 8.70 (1H, d, J=8.8 Hz), 8.81 (1H, s).

Example 301

6-Cyano-4-(1H-indol-5-yloxy)-7-(piperidin-4-yl)methyloxyquinoline

6-Cyano-4-(1H-indol-5-yloxy)-7-[(1-(t-butoxycarbonyloxy)piperidin-4-yl)methyloxy]quinoline (0.25 g, 0.5015 mmol) was dissolved in ethanol (2 ml) and tetrahydrofuran (2 ml), and then concentrated hydrochloric acid (0.2 ml) was added at room temperature and the mixture was stirred for 17 hours. The solvent was distilled off under reduced pressure, saturated sodium bicarnobate water was added, and then extraction was performed with a tetrahydrofuran and ethyl acetate mixed solvent, the extract was washed with saturated brine and dried over anhydrous magnesium sulfate, and the solvent was distilled off under reduced pressure. The residue was adsorbed onto NH silica gel and purified by column chromatography (ethyl acetate-methanol system) with NH silica gel, and the obtained crystals were suspended in ethanol and diluted with diethyl ether and hexane. The crystals were filtered out, washed with diethyl ether and dried by aspiration to obtain the title compound (15 mg, 0.0376 mmol, 7.51%).

$^1$H-NMR Spectrum (DMSO-$d_6$) δ (ppm): 1.23-1.29 (2H, m), 1.74-1.77 (2H, m), 1.95 (1H, brs), 2.48-2.55 (2H, m), 2.97-3.00 (2H, m), 4.12 (2H, d, J=5.6 Hz), 6.43 (1H, d, J=5.2 Hz), 6.47 (1H, s), 6.88 (1H, dd, J=2.4, 9.2 Hz), 7.45 (1H, d, J=2.4 Hz), 7.46 (1H, s), 7.52 (1H, d, J=9.2 Hz), 7.57 (1H, s), 8.66 (1H, d, J=5.2 Hz), 8.79 (1H, s), 11.31 (1H, s).

The starting materials were synthesized in the following manner.

Production Example 301-1

7-Benzyloxy-6-cyano-4-(1H-indol-5-yloxy)quinoline

After suspending 7-benzyloxy-6-cyano-4-chloroquinoline (23 g, 78.03 mmol) in N-methylpyrrolidone (15.8 ml), there were added 5-hydroxyindole (12.5 g, 83.64 mmol) and diisopropylethylamine (15.8 ml) and the mixture was heated and stirred at 150° C. for 10 hours. After allowing it to cool to room temperature, water and tetrahydrofuran were added and the crystals were thoroughly dissolved. After extraction with tetrahydrofuran, washing with saturated brine, drying over anhydrous magnesium sulfate and distilling off of the solvent, the residue was adsorbed onto silica gel. Purification was performed by silica gel column chromatography (hexane/tetrahydrofuran system), and then concentrated hydrochloric acid (0.2 ml) was added at room temperature and the mixture was stirred for 17 hours. The solvent was distilled off under reduced pressure, saturated sodium bicarnobate water was added, and then extraction was performed with a tetrahydrofuran and ethyl acetate mixed solvent, the extract was washed with saturated brine and dried over anhydrous magnesium sulfate, and the solvent was distilled off under reduced pressure. The obtained crystals were suspended in ethyl acetate and diluted with diethyl ether and hexane. The crystals were filtered out, washed with diethyl ether/hexane and dried by aspiration to obtain the title compound (12.5 g, 31.93 mmol, 40.92%) as light yellow crystals.

$^1$H-NMR Spectrum (DMSO-$d_6$) δ (ppm): 5.45 (2H, s), 6.44 (1H, d, J=5.2 Hz), 6.47 (1H, m), 6.99 (1H, dd, J=2.4, 8.8 Hz), 7.37 (1H, t, J=7.4 Hz), 7.42-7.46 (4H, m), 7.51-7.56 (3H, m), 7.69 (1H, s), 8.66 (1H, d, J=5.2 Hz), 8.82 (1H, s), 11.29 (1H, s).

Production Example 301-2

6-Cyano-4-(1H-indol-5-yloxy)-7-hydroxyquinoline

After dissolving 7-benzyloxy-6-cyano-4-(1H-indol-5-yloxy)quinoline (3 g, 7.6642 mmol) in tetrahydrofuran (250 ml), 10% palladium carbon powder (500 mg, wet) was added and the mixture was stirred for 11 hours at room temperature under a hydrogen atmosphere. After further adding 10% palladium carbon powder (300 mg, wet) and stirring the mixture for 9 hours at room temperature under a hydrogen atmosphere, additional 10% palladium carbon powder (200 mg, wet) was added and the mixture was stirred for 5 hours at room temperature under a hydrogen atmosphere. The solvent was distilled off, washing was performed with ethanol, and then the filtrate was distilled off under reduced pressure. The obtained crystals were suspended in ethanol and diluted with hexane, and the crystals were filtered out, washed with hexane:ethanol=3:1 and dried by aspiration to obtain the title compound (1.82 g, 6.0402 mmol, 79.12%) as light yellow crystals.

$^1$H-NMR Spectrum (DMSO-$d_6$) δ (ppm): 6.34 (1H, d, J=5.4 Hz), 6.46 (1H, m), 6.98 (1H, dd, J=2.4, 8.8 Hz), 7.40-7.46 (3H, m), 7.51 (1H, d, J=8.8 Hz), 8.58 (1H, d, J=5.4 Hz), 8.70 (1H, s), 11.29 (1H, s), 11.58 (1H, s).

Production Example 301-3

6-Cyano-4-(1H-indol-5-yloxy)-7-[(1-(tert-butoxycarbonyloxy)piperidin-4-yl)methyloxy]quinoline After dissolving 6-cyano-4-(1H-indol-5-yloxy)-7-hydroxyquinoline (1.72 g, 5.7084 mmol) in N,N-dimethylformamide (20 ml), there were added potassium carbonate (0.87 g, 6.2792 mmol) and tert-butyl 4-bromomethylpiperidine-1-carboxylate (1.75 g, 6.2792 mmol), and the mixture was heated and stirred at 70° C. for 7 hours. After allowing it to cool to room temperature, water was added, extraction was performed with ethyl acetate and tetrahydrofuran, the extract was washed with saturated brine and dried over anhydrous magnesium sulfate and the solvent was distilled off under reduced pressure, after which the residue was adsorbed onto silica gel. Purification was performed by silica gel column chromatography (hexane/ethyl acetate system), and then ethyl acetate/ethanol/hexane was added to the obtained yellow oil to precipitate crystals. The crystals were filtered out, washed with hexane:ethanol=10:1 and dried by aspiration to obtain the title compound (1.786 g, 3.3852 mmol, 59.30%) as light yellow crystals.

$^1$H-NMR Spectrum (DMSO-$d_6$) δ (ppm): 1.20-1.33 (2H, m), 1.39 (9H, s), 1.78-1.82 (2H, m), 2.06 (1H, m), 2.78 (2H, m), 3.98-4.02 (2H, n), 4.17 (2H, d, J=6.4 Hz), 6.43 (1H, d, J=5.2 Hz), 6.49 (1H, s), 6.98 (1H, dd, J=2.4 Hz, 8.8 Hz), 7.44-7.46 (2H, m), 7.51 (1H, d, J=8.8 Hz), 7.58 (1H, s), 8.66 (1H, d, J=5.2 Hz), 8.79 (1H, s), 11.30 (1H, s).

Example 302

6-Cyano-4-(1H-indol-5-yloxy)-7-[(1-methylpiperidin-4-yl)methyloxy]quinoline

After dissolving 6-cyano-4-(1H-indol-5-yloxy)-7-[(1-methylpiperidin-4-yl)methyloxy]quinoline (30 mg, 0.0753 mmol) in tetrahydrofuran (2.5 ml) and methanol (2.5 ml), there were added acetic acid (0.009 ml) and an aqueous formalin solution (0.047 ml, 0.5648 mmol, 12N). Sodium cyanoborohydride (10 mg) was added at room temperature, and the mixture was stirred at room temperature for 1 hour. Saturated sodium bicarnobate water was added, extraction was performed with ethyl acetate and tetrahydrofuran, the extract was washed with saturated brine and dried over anhydrous magnesium sulfate, and the solvent was distilled off under reduced pressure, after which the residue was adsorbed onto NH silica gel. Purification was then performed by NH silica gel column chromatography (ethyl acetate:methanol=10:1), and the obtained crystals were suspended in diethyl ether. The crystals were filtered out and dried by aspiration to obtain the title compound (7 mg, 0.0170 mmol, 22.54%) as colorless crystals.

$^1$H-NMR Spectrum (DMSO-d$_6$) δ (ppm): 1.35-1.44 (2H, m), 1.76-1.91 (5H, m), 2.15 (3H, s), 2.78-2.82 (2H, m), 4.14 (2H, d, J=6.0 Hz), 6.42 (1H, d, J=5.2 Hz), 6.47 (1H, s), 6.98 (1H, dd, J=2.4, 8.8 Hz), 7.44-7.46 (2H, m), 7.51 (1H, d, J=8.8 Hz), 7.57 (1H, s), 8.66 (1H, d, J=5.2 Hz), 8.78 (1H, s), 11.31 (1H, s).

Example 303

6-Cyano-4-(1-ethylcarbamoylindol-5-yloxy)-7-[(piperidin-4-yl)methyloxy]quinoline After dissolving 6-cyano-4-(1-ethylcarbamoylindol-5-yloxy)-7-[(1-(t-butoxycarbonyloxy)piperidin-4-yl)methyloxy]quinoline (180 mg, 0.0753 mmol) in trifluoroacetic acid (1 ml), the solution was stirred at room temperature for 0.5 hour. Saturated sodium bicarnobate water was added, extraction was performed with ethyl acetate and tetrahydrofuran, the extract was washed with saturated brine and dried over anhydrous magnesium sulfate, and the solvent was distilled off under reduced pressure, after which ethanol was added to the obtained amorphous substance for crystallization. After dilution with hexane, the crystals were filtered out, washed with hexane and dried by aspiration to obtain the title compound (132 mg, 0.2811 mmol, 88.96%) as colorless crystals.

$^1$H-NMR Spectrum (DMSO-d$_6$) δ (ppm): 1.18 (3H, t, J=7.2 Hz), 1.50-1.59 (2H, m), 1.96-2.01 (2H, m), 2.21 (1H, brs), 2.93-2.99 (2H, m), 3.28-3.37 (4H, m), 4.22 (2H, d, J=6.0 Hz), 6.49 (1H, d, J=5.6 Hz), 6.71 (1H, d, J=3.6 Hz), 7.17 (1H, dd, J=2.4, 8.8 Hz), 7.53 (1H, d, J=2.4 Hz), 7.64 (1H, s), 7.95 (1H, d, J=8.8 Hz), 8.26 (1H, t, J=5.4 Hz), 8.36 (1H, d, J=8.8 Hz), 8.42 (1H, brs), 8.69 (1H, d, J=5.6 Hz), 8.81 (1H, s).

The starting material was synthesized in the following manner.

Production Example 303-1

6-Cyano-4-(1-ethylcarbamoylindol-5-yloxy)-7-[(1-(t-butoxycarbonyloxy)piperidin-4-yl)methyloxy]quinoline The title compound (180 mg, 0.3160 mmol, 44.74%) was obtained as colorless crystals by reaction in the same manner as Example 310, using 6-cyano-4-(1H-indol-5-yloxy)-7-[(1-(t-butoxycarbonyloxy)piperidin-4-yl)methyloxy]quinoline (350 mg, 0.7062 mmol) and phenyl N-ethylcarbamate (140 mg).

$^1$H-NMR Spectrum (DMSO-d$_6$) δ (ppm): 1.18 (3H, t, J=7.0 Hz), 1.18-1.35 (2H, m), 1.40 (9H, s), 1.78-1.82 (2H, m), 2.16 (1H, m), 2.79 (2H, m), 3.32 (2H, q, J=7.0 Hz), 3.98-4.02 (2H, m), 4.18 (2H, d, J=6.0 Hz), 6.48 (1H, d, J=5.2 Hz), 6.70 (1H, d, J=3.8 Hz), 7.18 (1H, dd, J=2.4, 9.2 Hz), 7.52 (1H, d, J=2.4 Hz), 7.59 (1H, s), 7.93 (1H, d, J=3.8 Hz), 8.22 (1H, brs), 8.35 (1H, d, J=9.2 Hz), 8.68 (1H, d, J=5.2 Hz), 8.79 (1H, s).

Example 304

6-Cyano-4-(1-ethylcarbamoylindol-5-yloxy)-7-[(1-methylpiperidin-4-yl)methyloxy]quinoline After reaction in the same manner as Example 302 using 6-cyano-4-(1-ethylcarbamoylindol-5-yloxy)-7-[(piperidin-4-yl)methyloxy]quinoline (122 mg, 0.2598 mmol), the product was purified by NH silica gel column chromatography (ethyl acetate-methanol=10:1). The obtained crystals were suspended in ethanol and diluted with hexane, and the crystals were filtered out and dried by aspiration to obtain the title compound (28 mg, 0.0579 mmol, 22.29%) as colorless crystals.

$^1$H-NMR Spectrum (DMSO-d$_6$) δ (ppm): 1.20 (3H, t, J=7.2 Hz), 1.38-1.47 (2H, m), 1.78-1.93 (5H, m), 2.18 (3H, s), 2.80-2.84 (2H, m), 3.33-3.37 (2H, m), 4.17 (2H, d, J=6.0 Hz), 6.49 (1H, d, J=5.2 Hz), 6.72 (1H, d, J=3.6 Hz), 7.20 (1H, dd, J=2.4, 9.2 Hz), 7.54 (1H, d, J=2.4 Hz), 7.60 (1H, s), 7.95 (1H, d, J=3.6 Hz), 8.25 (1H, m), 8.37 (1H, d, J=9.0 Hz), 8.70 (1H, d, J=5.2 Hz), 8.80 (1H, s).

Example 305

6-Cyano-4-(1-cyclopropylcarbamoylindol-5-yloxy)-7-[(piperidin-4-yl)methyloxy]quinoline The title compound (962 mg, quant.) was obtained using 6-cyano-4-(1-cyclopropylcarbamoylindol-5-yloxy)-7-[(1-(t-butoxycarbonyloxy)piperidin-4-yl)methyloxy]quinoline (965 mg, 1.6590 mmol), in the same manner as Example 301.

$^1$H-NMR Spectrum (DMSO-d$_6$) δ (ppm): 0.60-0.64 (2H, m), 0.71-0.74 (2H, m), 1.50-1.60 (2H, m), 1.96-2.00 (2H, m), 2.21 (1H, m), 2.75-2.81 (1H, m), 2.90-2.98 (2H, m), 3.28-3.36 (2H, m), 4.21 (2H, d, J=6.0 Hz), 6.49 (1H, d, J=5.2 Hz), 6.69 (1H, d, J=3.8 Hz), 7.19 (1H, dd, J=2.4 Hz, 8.8 Hz), 7.52 (1H, d, J=2.4 Hz), 7.64 (1H, s), 7.92 (1H, d, J=3.8 Hz), 8.33 (1H, m), 8.36 (1H, d, J=8.8 Hz), 8.51 (1H, brs), 8.69 (1H, d, J=5.2 Hz), 8.81 (1H, s).

The starting material was synthesized in the following manner.

Production Example 305-1

6-Cyano-4-(1-cyclopropylcarbamoylindol-5-yloxy)-7-[(1-(t-butoxycarbonyloxy)piperidin-4-yl)methyloxy]quinoline The title compound (965 mg, 1.6590 mmol, 82.72%) was obtained as light red crystals by reaction in the same manner as Example 310, using 6-cyano-4-(1H-indol-5-yloxy)-7-[(1-(t-butoxycarbonyloxy)piperidin-4-yl)methyloxy]quinoline (1.0 g, 2.0056 mmol) and phenyl N-cyclopropylcarbamate (426 mg).

$^1$H-NMR Spectrum (DMSO-d$_6$) δ (ppm): 0.59-0.64 (2H, m), 0.71-0.76 (2H, m), 1.21-1.33 (2H, m), 1.40 (9H, s), 1.78-1.82 (2H, m), 2.07 (1H, m), 2.40-2.70 (3H, m), 3.95-4.15 (2H, m), 4.18 (2H, d, J=6.0 Hz), 6.48 (1H, d, J=5.2 Hz), 6.80 (1H, d, J=3.6 Hz), 7.19 (1H, dd, J=2.4 Hz, 8.8 Hz), 7.52 (1H, d, J=2.4 Hz), 7.59 (1H, s), 7.90 (1H, d, J=3.6 Hz), 8.29 (1H, brs), 8.35 (1H, d, J=8.8 Hz), 8.68 (1H, d, J=5.2 Hz), 8.79 (1H, s).

Example 306

6-Cyano-4-(1-cyclopropylcarbamoylindol-5-yloxy)-7-[(1-methylpiperidin-4-yl)methyloxy]quinoline The title compound (335 mg, 0.6760 mmol, 37.76%) was obtained as colorless crystals using 6-cyano-4-(1-cyclopropylcarbamoylindol-5-yloxy)-7-[(piperidin-4-yl)methyloxy]quinoline (862 mg, 1.7900 mmol), by the same procedure as in Example 320.

$^1$H-NMR Spectrum (DMSO-$d_6$) δ (ppm): 0.59-0.64 (2H, m), 0.71-0.76 (2H, m), 1.35-1.45 (2H, m), 1.76-1.91 (5H, m), 2.16 (3H, s), 2.74-2.82 (3H, m), 4.15 (2H, d, J=6.0 Hz), 6.47 (1H, d, J=5.2 Hz), 6.68 (1H, d, J=3.8 Hz), 7.19 (1H, dd, J=2.4 Hz, 8.8 Hz), 7.52 (1H, d, J=2.4 Hz), 7.58 (1H, s), 7.90 (1H, d, J=3.8 Hz), 8.30 (1H, d, J=2.4 Hz), 8.35 (1H, d, J=8.8 Hz), 8.68 (1H, d, J=5.2 Hz), 8.78 (1H, s).

Example 307

6-Cyano-7-[(piperidin-4-yl)methyloxy]-4-[1-(2-thiazolylcarbamoyl)indol-5-yloxy]quinoline The title compound (114 mg, 0.2136 mmol) was obtained as colorless crystals using 6-cyano-4-[1-(2-thiazolylcarbamoyl)indol-5-yloxy]-7-[(1-(t-butoxycarbonyloxy)piperidin-4-yl)methyloxy]quinoline (220 mg, 0.3522 mmol), in the same manner as Example 301.

$^1$H-NMR Spectrum (DMSO-$d_6$) δ (ppm): 1.50-1.60 (2H, m), 1.97-2.01 (2H, m), 2.22 (1H, brs), 2.93-2.99 (2H, m), 3.31-3.37 (2H, m), 4.22 (2H, d, J=5.6 Hz), 6.53 (1H, d, J=5.2 Hz), 6.70 (1H, d, J=3.0 Hz), 7.09 (1H, d, J=4.2 Hz), 7.20 (1H, dd, J=2.4 Hz, 8.8 Hz), 7.47 (1H, d, J=4.2 Hz), 7.53 (1H, d, J=2.4 Hz), 7.65 (1H, s), 8.09 (1H, d, J=3.0 Hz), 8.10-8.67 (1H, brs), 8.67 (1H, d, J=8.8 Hz), 8.70 (1H, d, J=5.2 Hz), 8.83 (1H, s).

The starting material was synthesized in the following manner.

Production Example 307-1

6-Cyano-4-[1-(2-thiazolylcarbamoyl)indol-5-yloxy]-7-[(1-(t-butoxycarbonyloxy)piperidin-4-yl)methyloxy]quinoline The title compound (220 mg, 0.3522 mmol, 58.53%) was obtained as light yellow crystals by reaction in the same manner as Example 312, using 6-cyano-4-(1H-indol-5-yloxy)-7-[(1-(t-butoxycarbonyloxy)piperidin-4-yl)methyloxy]quinoline (300 mg, 0.6017 mmol), sodium hydride (51 mg, 1.2636 mmol, 60% in oil) and phenyl N-(2-thiazolyl)carbamate (146 mg, 0.6619 mmol).

$^1$H-NMR Spectrum (DMSO-$d_6$) δ (ppm): 1.21-1.33 (2H, m), 1.39 (9H, s), 1.78-1.82 (2H, m), 2.06 (1H, m), 2.78 (2H, m), 3.98-4.02 (2H, m), 4.17 (2H, d, J=6.4 Hz), 6.51 (1H, d, J=5.2 Hz), 6.69 (1H, d, J=3.4 Hz), 7.08 (1H, d, J=4.6 Hz), 7.20 (1H, dd, J=2.4 Hz, 9.2 Hz), 7.47 (1H, d, J=4.6 Hz), 7.53 (1H, d, J=2.4 Hz), 7.59 (1H, s), 8.08 (1H, d, J=3.4 Hz), 8.67 (1H, d, J=9.2 Hz), 8.69 (1H, d, J=5.2 Hz), 8.80 (1H, s).

Example 308

6-Cyano-7-[(1-methylpiperidin-4-yl)methyloxy]-4-[1-(2-thiazolylcarbamoyl)indol-5-yloxy]quinoline The same reaction was conducted as in Example 302 using 6-cyano-7-[(piperidin-4-yl)methyloxy]-4-[1-(2-thiazolylcarbamoyl)indol-5-yloxy]quinoline (104 mg, 0.1982 mmol), the product was purified by NH silica gel column chromatography (ethyl acetate:methanol=10:1), the obtained crystals were suspended in ethanol and diluted with hexane, and the crystals were filtered out and dried by aspiration to obtain the title compound (38 mg, 0.0705 mmol, 35.60%) as colorless crystals.

$^1$H-NMR Spectrum (DMSO-$d_6$) δ (ppm): 1.45-1.48 (2H, m), 1.83-1.95 (3H, m), 2.08-2.15 (2H, m), 2.29 (3H, s), 2.93-2.96 (2H, m), 4.19 (2H, d, J=5.6 Hz), 6.53 (1H, d, J=5.2 Hz), 6.67 (1H, d, J=3.4 Hz), 7.01 (1H, d, J=4.4 Hz), 7.19 (1H, dd, J=2.4 Hz, 9.2 Hz), 7.42 (1H, d, J=4.4 Hz), 7.53 (1H, d, J=2.4 Hz), 7.62 (1H, s), 7.81 (1H, d, J=3.4 Hz), 8.71 (1H, d, J=5.2 Hz), 8.73 (1H, d, J=9.2 Hz), 8.83 (1H, s).

Example 309

6-Carbamoyl-4-(1H-indol-5-yloxy)-7-methoxyquinoline

After mixing 6-carbamoyl-4-chloro-7-methoxyquinoline (2.0 g, 8.4509 mmol), 5-hydroxyindole (1.68 g), diisopropylethylamine (2.2 ml) and N-methylpyrrolidone (2.2 ml), the mixture was heated and stirred at 150° C. for 5 hours. After cooling, the partly solidified reaction mixture was dissolved in dimethylsulfoxide and then adsorbed onto NH silica gel and purified by NH silica gel column chromatography (ethyl acetate-methanol system). The obtained crystals were suspended in ethanol, the suspension was diluted with diethyl ether and hexane, and the crystals were filtered out, washed with diethyl ether:hexane=1:5 and dried by aspiration to obtain the title compound (1.291 g, 3.8698 mmol, 45.79%) as light yellow crystals.

$^1$H-NMR Spectrum (DMSO-$d_6$) δ (ppm): 4.02 (3H, s), 6.37 (1H, d, J=5.2 Hz), 6.46 (1H, brs), 6.98 (1H, dd, J=2.4 Hz, 8.4 Hz), 7.43-7.45 (2H, m), 7.48 (1H, s), 7.51 (1H, d, J=8.4 Hz), 7.71 (1H, brs), 7.84 (1H, brs), 8.58 (1H, d, J=5.2 Hz), 8.74 (1H, s), 11.29 (1H, s).

Example 310

6-Carbamoyl-4-[1-(2,4-difluorophenylcarbamoyl)1H-indol-5-yloxy]-7-methoxyquinoline After dissolving 6-carbamoyl-4-(1H-indol-5-yloxy)-7-methoxyquinoline (100 mg, 0.3 mmol) in N,N-dimethylformamide (0.5 ml), there was added sodium hydride (12 mg, 0.3 mmol) while cooling on ice and the mixture was stirred at room temperature for 15 minutes. After adding phenyl N-(2,4-difluorophenyl)carbamate (79 mg, 0.3150 mmol), the mixture was stirred at room temperature for 2 hours. Water was added to the reaction solution, extraction was performed with ethyl acetate and tetrahydrofuran, the extract was washed with saturated brine and dried over anhydrous magnesium sulfate, and the filtrate was distilled off under reduced pressure. The obtained crystals were suspended in ethanol and diluted with hexane, and then the crystals were filtered out, washed with hexane and dried by aspiration to obtain the title compound (84 mg, 0.1718 mmol, 57.28%) as colorless crystals.

$^1$H-NMR Spectrum (DMSO-$d_6$) δ (ppm): 4.03 (3H, s), 6.45 (1H, J, J=5.2 Hz), 6.81 (1H, d, J=3.8 Hz), 7.14-7.19 (1H, m), 7.23 (1H, dd, J=2.4 Hz, 8.8 Hz), 7.39-7.49 (1H, m), 7.51 (1H, s), 7.50-7.58 (2H, m), 7.72 (1H, brs), 7.85 (1H, brs), 8.11 (1H, d, J=3.8 Hz), 8.32 (1H, d, J=8.8 Hz), 8.62 (1H, d, J=5.2 Hz), 8.73 (1H, s), 10.03 (1H, s).

The starting material was synthesized in the following manner.

Production Example 310-1

Phenyl N-(2,4-difluorophenyl)carbamate

After dissolving 2,4-difluoroaniline (10 ml, 98.21 mmol) in tetrahydrofuran (200 ml), pyridine (8.7 ml, 108.33 mmol)

was added at room temperature and the mixture was stirred. It was then cooled on ice, phenyl chloroformate (13.6 ml, 108.33 mmol) was added dropwise over 15 minutes, and the mixture was then stirred at room temperature for 24 hours. Water was added to the reaction solution, extraction was performed with ethyl acetate and tetrahydrofuran, the extract was washed with saturated brine and dried over anhydrous magnesium sulfate, and the filtrate was distilled off under reduced pressure. The obtained crystals were suspended in ethanol and diluted with hexane, and then the crystals were filtered out, washed with hexane and dried by aspiration to obtain the title compound (21.00 g, 84.26 mmol, 85.80%) as light violet crystals.

$^1$H-NMR Spectrum (DMSO-$d_6$) δ (ppm): 7.05-7.12 (1H, m), 7.19 (2H, d, J=7.6 Hz), 7.24 (1H, t, J=7.6 Hz), 7.33 (1H, m), 7.41 (2H, t, J=7.6 Hz), 7.59-7.68 (1H, m), 9.91 (1H, brs).

Example 311

6-Carbamoyl-4-[1-(4-difluorophenylcarbamoyl)1H-indol-5-yloxy]-7-methoxyquinoline The title compound (60 mg, 0.1275 mmol, 42.51%) was obtained as colorless crystals by reaction in the same manner as Example 310, using 6-carbamoyl-4-(1H-indol-5-yloxy)-7-methoxyquinoline (100 mg, 0.3 mmol) and phenyl N-(4-fluorophenyl)carbamate (86 mg).

$^1$H-NMR Spectrum (DMSO-$d_6$) δ (ppm): 4.03 (3H, s), 6.45 (1H, d, J=5.2 Hz), 6.79 (1H, d, J=3.6 Hz), 7.21-7.26 (3H, m), 7.51 (1H, s), 7.57 (1H, d, J=2.0 Hz), 7.67 (2H, dd, J=5.2 Hz, 8.8 Hz), 7.73 (1H, brs), 7.85 (1H, brs), 8.13 (1H, d, J=3.6 Hz), 8.33 (1H, d, J=8.8 Hz), 8.62 (1H, d, J=5.2 Hz), 8.73 (1H, s), 10.16 (1H, s).

The starting material was synthesized in the following manner.

Production Example 311-1

Phenyl N-(4-difluorophenyl)carbamate

The title compound (10.031 g, 43.38 mmol, 82.19%) was obtained as light violet crystals using 4-fluoroaniline (5 ml, 52.78 mmol), by the same procedure as in Production Example 310-1.

$^1$H-NMR Spectrum (DMSO-$d_6$) δ (ppm): 7.13-7.27 (5H, m), 7.39-7.44 (2H, m), 7.48-7.52 (2H, m), 10.26 (1H, s).

Example 312

6-Carbamoyl-4-[1-(2-thiazolylcarbamoyl)1H-indol-5-yloxy]-7-methoxyquinoline

After suspending sodium hydride (50 mg, 1.2524 mmol) in N,N-dimethylformamide (0.5 ml), phenyl N-(2,4-difluorophenyl)carbamate (79 mg, 0.3150 mmol) and then 6-carbamoyl-4-(1H-indol-5-yloxy)-7-methoxyquinoline (200 mg, 0.5964 mmol) were added thereto at room temperature, and the mixture was stirred at room temperature for 10 hours. Water and saturated brine were added to the reaction solution, extraction was performed with ethyl acetate and tetrahydrofuran, the extract was washed with saturated brine and dried over anhydrous magnesium sulfate, and the filtrate was distilled off under reduced pressure. The residue was adsorbed onto silica gel and passed through a silica gel column (hexane-tetrahydrofuran system). The obtained crystals were wetted with one drop of dimethylsulfoxide and then suspended in ethanol, and the crystals were filtered out, washed with ethanol and dried by aspiration to obtain the title compound (138 mg, 0.3003 mmol, 50.36%) as light yellow crystals.

$^1$H-NMR Spectrum (DMSO-$d_6$) δ (ppm): 4.03 (3H, s), 6.46 (1H, d, J=5.2 Hz), 6.69 (1H, d, J=3.6 Hz), 7.09 (1H, d, J=4.4 Hz), 7.20 (1H, dd, J=2.4 Hz, 8.8 Hz), 7.47 (1H, d, J=4.4 Hz), 7.51 (1H, s), 7.52 (1H, d, J=2.4 Hz), 7.73 (1H, brs), 7.86 (1H, brs), 8.08 (1H, d, J=3.6 Hz), 8.62 (1H, d, J=5.2 Hz), 8.67 (1H, d, J=8.8 Hz), 8.74 (1H, s), 13.16 (1H, s).

Example 313

6-Carbamoyl-4-(1-cyclopropylcarbamoyl-1H-indol-5-yloxy)-7-methoxyquinoline

The title compound (35 mg, 0.0840 mmol, 28.02%) was obtained as colorless crystals by reaction in the same manner as Example 310, using 6-carbamoyl-4-(1H-indol-5-yloxy)-7-methoxyquinoline (100 g, 0.3 mmol) and phenyl N-(4-fluorophenyl)carbamate (56 mg).

$^1$H-NMR Spectrum (DMSO-$d_6$) δ (ppm): 0.62 (2H, m), 0.73 (2H, m), 2.78 (1H, m), 4.02 (3H, s), 6.42 (1H, d, J=5.2 Hz), 6.68 (1H, d, J=3.2 Hz), 7.18 (1H, d, J=9.0 Hz), 7.50 (2H, m), 7.73 (1H, s), 7.85 (1H, s), 7.89 (1H, d, J=3.2 Hz), 8.30 (1H, s), 8.34 (1H, d, J=9.0 Hz), 8.61 (1H, d, J=5.2 Hz), 8.72 (1H, s).

The starting material was synthesized in the following manner.

Production Example 313-1

Phenyl N-cyclopropylcarbamate

Cyclopropylamine (3 ml, 43.29 mmol) was used for reaction in the same manner as Production Example 310-1, the obtained crystals were suspended in diethyl ether:hexane=1:2, and the crystals were then filtered out, washed with diethyl ether:hexane=1:2 and dried by aspiration to obtain the title compound (5.832 g, 32.91 mmol, 76.03%) as light yellow crystals $^1$H-NMR Spectrum (CDCl13) δ (ppm): 0.60-0.65 (2H, m), 0.76-0.80 (2H, m), 2.69 (1H, brs), 5.23 (1H, brs), 7.13 (2H, d, J=7.6 Hz), 7.19 (1H, t, J=7.6 Hz), 7.35 (2H, t, J=7.6 Hz).

Example 314

6-Carbamoyl-4-[1-(2-fluoroethylcarbamoyl)1H-indol-5-yloxy]-7-methoxyquinoline

Example 315

4-[1-(2-Fluoroethylcarbamoyl)1H-indol-5-yloxy]-6-(2-fluoroethylureidocarbamoyl)-7-methoxyquinoline 6-Carbamoyl-4-(1H-indol-5-yloxy)-7-methoxyquinoline (800 mg, 2.3998 mmol), sodium hydride (104 mg, 2.5918 mmol) and phenyl N-(2-fluoroethyl)carbamate (483 mg, 2.6398 mmol) were used for reaction in the same manner as Example 310, extraction was performed with ethyl acetate and tetrahydrofuran, the extract was washed with saturated brine and dried over anhydrous magnesium sulfate, and the solvent was distilled off under reduced pressure. The residue was adsorbed onto silica gel and subjected to silica gel column chromatography (ethyl acetate-tetrahydrofuran-methanol system), and after removing off the starting materials, the product was adsorbed onto NH silica gel and subjected to NH silica gel column chromatography (ethyl acetate-tetrahydrofuran-methanol system) to obtain low polarity and high polarity compounds as crystals. These were each suspended in ethanol and diluted with hexane. The crystals were filtered out, washed with hexane and dried by aspiration, to obtain the low polarity compound 4-[1-(2-fluoroethylcarbamoyl)-1H-indol-5-yloxy]-6-(2-fluoroethylureidocarbamoyl)-7-methoxyquinoline (49 mg, 0.0958 mmol, 3.99%) as colorless crystals and the high polarity compound 6-carbamoyl-4-[1-(2-fluoroethylcarbamoyl)1H-indol-5-yloxy]-7-methoxyquinoline (632 mg, 1.4961 mmol, 62.34%) as light yellow crystals.

Low polarity compound (Example 315)
$^1$H-NMR Spectrum (DMSO-$d_6$) δ (ppm): 3.59 (4H, m), 4.01 (3H, s), 4.47 (1H, m), 4.53 (1H, m), 4.59 (1H, m), 4.65 (1H, m), 6.46 (1H, d, J=4.4 Hz), 6.73 (1H, d, J=2.0 Hz), 7.19 (1H, d, J=8.8 Hz), 7.53 (2H, s), 7.97 (1H, d, J=2.0 Hz), 8.35 (1H, d, J=8.8 Hz), 8.50 (1H, m), 8.51 (1H, s), 8.63 (1H, m), 8.64 (1H, d, J=4.4 Hz), 10.62 (1H, s).

High polarity compound (Example 314)
$^1$H-NMR Spectrum (DMSO-$d_6$) δ (ppm): 3.56 (1H, dt, J=5.0 Hz, 5.0 Hz), 3.63 (1H, dt, J=5.0 Hz, 5.0 Hz), 4.02 (3H, s), 4.53 (1H, t, J=5.0 Hz), 4.65 (1H, t, J=5.0 Hz), 6.43 (1H, d, J=5.2 Hz), 6.73 (1H, d, J=3.8 Hz), 7.19 (1H, dd, J=2.4 Hz, 8.8 Hz), 7.50 (1H, s), 7.52 (1H, d, J=2.4 Hz), 7.72 (1H, brs), 7.85 (1H, brs), 7.98 (1H, d, J=3.8 Hz), 8.35 (1H, d, J=8.8 Hz), 8.49 (1H, t, J=5.0 Hz), 8.61 (1H, d, J=5.2 Hz), 8.72 (1H, s).

The starting material was synthesized in the following manner.

Production Example 314-1

Phenyl N-(2-fluoroethyl)carbamate

After dissolving 2-fluoroethylamine (0.5 g, 5.0321 mmol) in dimethylformamide (10 ml), pyridine (0.87 ml, 10.5674 mmol) was added at room temperature and the mixture was stirred. It was then cooled on ice, phenyl chloroformate (0.67 ml, 5.2837 mmol) was added dropwise, and after the dropwise addition the mixture was stirred at room temperature for 2.5 hours. Water was added to the reaction solution, extraction was performed with ethyl acetate, the extract was washed with saturated brine and dried over anhydrous magnesium sulfate, and the solvent was distilled off under reduced pressure. The residue was purified by silica gel column chromatography (hexane:ethyl acetate=2:1) to obtain the title compound (0.797 g, 4.3509 mmol, 86.46%) as light yellow crystals.
$^1$H-NMR Spectrum (CDCl3) δ (ppm): 3.55 (1H, q, J=4.8 Hz), 3.62 (1H, q, J=4.8 Hz), 4.51 (1H, t, J=4.8 Hz), 4.62 (1H, t, J=4.8 Hz), 5.39 (1H, brs), 7.13 (2H, d, J=7.6 Hz), 7.21 (1H, t, J=7.6 Hz), 7.37 (2H, t, J=7.6 Hz).

Example 316

6-Carbamoyl-4-(1-ethylcarbamoyl-1H-indol-5-yloxy)-7-methoxyquinoline

Example 317

4-(1-Ethylcarbamoyl-1H-indol-5-yloxy)-6-ethylureidocarbamoyl-7-methoxyquinoline

6-Carbamoyl-4-(1H-indol-5-yloxy)-7-methoxyquinoline (1.2 g, 3.6141 mmol), phenyl N-4-ethylcarbamate (822 mg, 4.9761 mmol) and sodium hydride (195 mg, 4.8799 mmol) were used for reaction in the same manner as Example 310 to obtain the low polarity compound 4-(1-ethylcarbamoyl-1H-indol-5-yloxy)-6-ethylureidocarbamoyl-7-methoxyquinoline (105 mg, 0.2208 mmol, 6.11%) and the high polarity compound 6-carbamoyl-4-(1-ethylcarbamoyl-1H-indol-5-yloxy)-7-methoxyquinoline (506 mg, 1.2511 mmol, 34.62%), both as colorless crystals.

Low polarity compound (Example 317)
$^1$H-NMR Spectrum (DMSO-$d_6$) δ (ppm): 1.11 (3H, t, J=7.2 Hz), 1.77 (3H, t, J=7.2 Hz), 3.23 (2H, q, J=7.2 Hz), 3.29 (2H, q, J=7.2 Hz), 4.01 (3H, s), 6.45 (1H, d, J=5.2 Hz), 6.70 (1H, d, J=3.6 Hz), 7.17 (1H, dd, J=2.4 Hz, 8.8 Hz), 7.51 (1H, d, J=2.4 Hz), 7.52 (1H, s), 7.93 (1H, d, J=3.6 Hz), 8.24 (1H, t, J=5.6 Hz), 8.35 (1H, d, J=8.8 Hz), 8.44 (1H, m), 8.52 (1H, s), 8.64 (1H, d, J=5.2 Hz), 10.46 (1H, s).

High polarity compound (Example 316)
$^1$H-NMR Spectrum (DMSO-$d_6$) δ (ppm): 1.18 (3H, t, J=7.2 Hz), 3.32 (2H, q, J=7.2 Hz), 4.02 (3H, s), 6.42 (1H, d, J=5.2 Hz), 6.70 (1H, d, J=3.6 Hz), 7.17 (1H, dd, J=2.4 Hz, 8.8 Hz), 7.50 (1H, s), 7.51 (1H, d, J=2.4 Hz), 7.71 (1H, brs), 7.84 (1H, brs), 7.93 (1H, d, J=3.6 Hz), 8.23 (1H, t, J=5.6 Hz), 8.34 (1H, d, J=8.8 Hz), 8.61 (1H, d, J=5.2 Hz), 8.72 (1H, s).

The starting material was synthesized in the following manner.

Production Example 316-1

Phenyl N-ethyl carbamate

Ethylamine hydrochloride (20.3 g, 0.25 mol) was used for reaction in the same manner as Production Example 310-1, the obtained crystals were suspended in hexane, and then the crystals were filtered out, washed with hexane and dried by aspiration to obtain the title compound (33.33 g, 0.2018 mol, 80.71%) as colorless crystals.
$^1$H-NMR Spectrum (CDCl3) δ (ppm): 1.21 (3H, t, J=7.2 Hz), 3.31 (2H, m), 5.02 (1H, brs), 7.12 (2H, d, J=7.6 Hz), 7.19 (1H, t, J=7.6 Hz), 7.35 (2H, t, J=7.6 Hz).

Example 318

6-Carbamoyl-7-methoxy-4-(1-propylcarbamoyl-1H-indol-5-yloxy)quinoline

Example 319

7-Methoxy-4-(1-propylcarbamoyl-1H-indol-5-yloxy)-6-propylureidocarbamoylquinoline 6-Carbamoyl-4-(1H-indol-5-yloxy)-7-methoxyquinoline (400 mg, 1.2 mmol), phenyl N-n-propyl carbamate (237 mg, 1.3199 mmol) and sodium hydride (55 mg, 1.3199 mmol) were used according to the same method as in Example 310 to obtain the low polarity compound 7-methoxy-4-(1-propylcarbamoyl-1H-indol-5-yloxy)-6-propylureidocarbamoylquinoline (49 mg, 0.0973 mmol, 8.11%) and the high polarity compound 6-carbamoyl-7-methoxy-4-(1-normal-propylcarbamoyl-1H-indol-5-yloxy)quinoline (218 mg, 0.5210 mmol, 43.41%), both as light yellow crystals.

Low polarity compound (Example 319)
$^1$H-NMR Spectrum (DMSO-$d_6$) δ (ppm): 0.89 (3H, t, J=7.2 Hz), 0.91 (3H, t, J=7.2 Hz), 1.51 (2H, q, J=7.2 Hz), 1.59 (2H, q, J=7.2 Hz), 3.18 (2H, t, J=7.2 Hz), 3.25 (2H, t, J=7.2 Hz), 4.02 (3H, s), 6.45 (1H, d, J=5.2 Hz), 6.70 (1H, d, J=3.6 Hz), 7.27 (1H, d, J=2.4 Hz, 8.8 Hz), 7.51 (1H, d, J=2.4 Hz), 7.52 (1H, s) 7.95 (1H, d, J=3.6 Hz), 8.22 (1H, m), 8.34 (1H, d, J=8.8 Hz), 8.47 (1H, brs), 8.54 (1H, s), 8.64 (1H, d, J=5.2 Hz), 10.45 (1H, s).

¹H-NMR Spectrum (DMSO-d₆) δ (ppm): 0.92 (3H. t, J=7.2 Hz), 1.58 (2H, q, J=7.2 Hz), 3.24 (2H, q, J=7.2 Hz), 4.02 (3H, s), 6.42 (1H, d, J=5.2 Hz), 6.70 (1H, d, J=3.6 Hz), 7.17 (1H, dd, J=2.4 Hz, 8.8 Hz), 7.50 (1H, s), 7.51 (1H, d, J=2.4 Hz), 7.72 (1H, brs), 7.49 (1H, brs), 7.95 (1H, d, J=3.6 Hz), 8.23 (1H, t, J=5.2 Hz), 8.34 (1H, d, J=8.8 Hz), 8.61 (1H, d, J=5.2 Hz), 8.72 (1H, s).

The starting material was synthesized in the following manner.

Production Example 318-1

Phenyl N-(n-propyl)carbamate n-Propylamine (4.1 ml, 50 mmol) was used for reaction in the same manner as Production Example 310-1, and the obtained crystals were suspended in hexane, filtered out, washed with hexane and dried by aspiration to obtain the title compound (4.502 g, 25.12 mmol, 50.24%) as colorless crystals ¹H-NMR Spectrum (DMSO-d₆) δ (ppm): 0.86 (3H, t, J=7.4 Hz), 1.41-1.50 (2H, m), 3.00 (2H, q, J=6.8 Hz), 7.06 (2H, d, J=8.0 Hz), 7.17 (1H, t, J=8.0 Hz), 7.36 (2H, t, J=8.0 Hz), 7.72 (1H, m).

Example 320

6-Carbamoyl-7-methoxy-4-[1-(1-methyl)ethylcarbamoyl-1H-indol-5-yloxy]quinoline

Example 321

7-Methoxy-4-[1-(1-methyl)ethylcarbamoyl-1H-indol-5-yloxy]-6-(1-methyl)ethylureidocarbamoylquinoline 6-Carbamoyl-4-(1H-indol-5-yloxy)-7-methoxyquinoline (400 mg, 1.2 mmol), phenyl N-(1-methyl)ethyl carbamate (237 mg) and sodium hydride (55 mg, 1.3199 mmol) were used by the same procedure as in Example 310 to obtain the low polarity compound 7-methoxy-4-[1-(1-methyl)ethylcarbamoyl-1H-indol-5-yloxy]-6-(1-methyl)ethylureidocarbamoylquinoline (62 mg, 0.1231 mmol, 10.26%) as light yellow crystals and the high polarity compound 6-carbamoyl-7-methoxy-4-[1-(1-methyl)ethylcarbamoyl-1H-indol-5-yloxy]quinoline (309 mg, 0.7384 mmol, 43.41%) as colorless crystals. The title compound (60 mg, 0.1275 mmol, 61.54%) was obtained as colorless crystals.

Low polarity compound (Example 321)
¹H-NMR Spectrum (DMSO-d₆) δ (ppm): 1.17 (6H, d, J=5.8 Hz), 1.22 (6H, d, J=5.8 Hz), 3.88 (1H, m), 4.01 (3H, s), 4.03 (1H, m), 6.45 (1H, d, J=5.4 Hz), 6.69 (1H, d, J=3.4 Hz), 7.16 (1H, dd, J=2.4 Hz, 8.6 Hz), 7.50 (1H, d, J=2.4 Hz), 7.52 (1H, s), 7.98 (1H, s), 7.99 (1H, d, J=3.4 Hz), 8.33 (2H, m), 8.52 (1H, s), 8.64 (1H, d, J=5.4 Hz), 10.46 (1H, s).

High polarity compound (Example 320)
¹H-NMR Spectrum (DMSO-d₆) δ (ppm): 1.23 (6H, d, J=6.4 Hz), 4.00 (1H, m), 4.33 (3H, s), 6.42 (1H, d, J=5.4 Hz), 6.69 (1H, d, J=3.6 Hz), 7.17 (1H, dd, J=2.4 Hz, 8.8 Hz), 7.50 (1H, s), 7.51 (1H, d, J=2.4 Hz), 7.72 (1H, brs), 7.85 (1H, brs), 7.97 (1H, s), 7.99 (1H, d, J=3.5 Hz), 8.33 (1H, d, J=8.8 Hz), 8.61 (1H, d, J=5.4 Hz), 8.72 (1H, s).

The starting material was synthesized in the following manner.

Production Example 320-1

Phenyl N-(iso-propyl)carbamate i-Propylamine (4.3 ml, 50 mmol) was used for reaction in the same manner as Production Example 310-1, and the obtained crystals were suspended in hexane, filtered out, washed with hexane and dried by aspiration to obtain the title compound (5.105 g, 28.48 mmol, 56.97%) as colorless crystals.
¹H-NMR Spectrum (DMSO-d₆) δ (ppm): 1.01 (6H, d, J=6.4 Hz), 3.58-3.67 (1H, m), 7.07 (2H, d, J=7.6 Hz), 7.17 (1H, t, J=7.6 Hz), 7.35 (2H, t, J=7.6 Hz), 7.65 (1H, m).

Example 322

4-(1-Normalbutylcarbamoyl-1H-indol-5-yloxy)-6-carbamoyl-7-methoxyquinoline

The title compound (203 mg, 0.4694 mmol, 46.94%) was obtained as colorless crystals using 6-carbamoyl-4-(1H-indol-5-yloxy)-7-methoxyquinoline (335 mg, 1.0 mmol), phenyl N-n-butyl carbamate (213 mg, 1.1 mmol) and sodium hydride (44 mg, 1.1 mmol), by the same procedure as in Example 310.
¹H-NMR Spectrum (DMSO-d₆) δ (ppm): 0.92 (3H, t, J=7.2 Hz), 1.36 (2H, m), 1.55 (2H, m), 3.29 (2H, m), 4.02 (3H, s), 6.42 (1H, d, J=5.4 Hz), 6.70 (1H, d, J=3.6 Hz), 7.17 (1H, dd, J=2.4 Hz, 8.8 Hz), 7.50-7.52 (2H, m), 7.73 (1H, brs), 7.85 (1H, brs), 7.94 (1H, d. J=3.6 Hz), 8.22 (1H, t, J=5.4 Hz), 8.34 (1H, d, J=8.8 Hz), 8.61 (1H, d, J=5.4 Hz), 8.72 (1H, s).

The starting material was synthesized in the following manner.

Production Example 322-1

Phenyl N-(n-butyl)carbamate n-Butylamine (4.9 ml, 50 mmol) was used for the same reaction as in Production Example 310-1, and purification was performed by silica gel column chromatography (hexane:ethyl acetate=4:1) to obtain the title compound (8.11 g, 41.97 mmol, 71.97%) as a colorless oil.
¹H-NMR Spectrum (CDCl3) δ (ppm): 0.95 (3H, t, J=7.2 Hz), 1.35-1.45 (2H, m), 1.52-1.60 (2H, m), 3.27 (2H, q, J=7.2 Hz), 5.01 (1H, brs), 7.12 (2H, d, J=7.2 Hz), 7.19 (1H, t, J=7.2 Hz), 7.35 (2H, t, J=7.2 Hz).

Example 323

6-Carbamoyl-4-[1-(1,1-dimethylethylcarbamoyl)1H-indol-5-yloxy]-7-methoxyquinoline The title compound (225 mg, 0.5203 mmol, 52.03%) was obtained as colorless crystals using 6-carbamoyl-4-(1H-indol-5-yloxy)-7-methoxyquinoline (335 mg, 1.0 mmol), phenyl N-(1,1-dimethylethyl)carbamate (213 mg, 1.1 mmol) and sodium hydride (44 mg, 1.1 mmol), by the same procedure as in Example 310.
¹H-NMR Spectrum (DMSO-d₆) δ (ppm): 1.42 (9H, s), 4.02 (3H, s), 6.41 (1H, d, J=5.0 Hz), 6.65 (1H, d, J=3.8 Hz), 7.15 (1H, dd, J=2.4 Hz, 9.2 Hz), 7.50 (2H, s), 7.63 (1H, s), 7.72 (1H, brs), 7.85 (1H, brs), 7.95 (1H, d, J=3.8 Hz), 8.26 (1H, d, J=9.2 Hz), 8.61 (1H, d, J=5.0 Hz), 8.73 (1H, s).

The starting material was synthesized in the following manner.

Production Example 323-1

Phenyl N-(t-butyl)carbamate

The title compound (3.910 g, 20.23 mmol, 40.46%) was obtained as pink crystals using t-butylamine (5.3 ml, 50 mmol), by the same procedure as in Production Example 310-1.

$^1$H-NMR Spectrum (DMSO-d$_6$) δ (ppm): 1.26 (9H, s), 7.05 (2H, d, J=8.0 Hz), 7.16 (1H, t, J=8.0 Hz), 7.35 (2H, t, J=8.0 Hz), 7.53 (1H, s).

Example 324

6-Carbamoyl-4-[1-(3-fluoropropylcarbamoyl)1H-indol-5-yloxy]-7-methoxyquinoline The title compound (105 mg, 0.2406 mmol, 28.82%) was obtained as colorless crystals using 6-carbamoyl-4-(1H-indol-5-yloxy)-7-methoxyquinoline (280 mg, 0.8349 mmol), phenyl N-(3-fluoropropyl)carbamate (181 mg, 0.9184 mmol) and sodium hydride (37 mg, 0.9184 mmol), by the same procedure as in Example 310.

$^1$H-NMR Spectrum (DMSO-d$_6$) δ (ppm): 1.89-2.03 (2H, m), 3.39 (2H, m), 4.02 (3H, s), 4.49 (1H, t, J=6.0 Hz), 4.61 (1H, d, J=6.0 Hz), 6.42 (1H, d, J=5.2 Hz), 6.71 (1H, d, J=3.6 Hz), 7.18 (1H, dd, J=2.4 Hz, 8.8 Hz), 7.50 (1H, s), 7.52 (1H, d, J=2.4 Hz), 7.72 (1H, brs), 7.85 (1H, brs), 7.94 (1H, d, J=3.6 Hz), 8.32 (1H, t, J=5.4 Hz), 8.34 (1H, d, J=8.8 Hz), 8.61 (1H, d, J=5.2 Hz), 8.72 (1H, s).

The starting material was synthesized in the following manner.

Production Example 324-1

Phenyl N-(3-fluoropropyl)carbamate

3-Fluoropropylamine hydrochloride (0.92 g (wet), 8.10 mmol) was used for reaction in the same manner as Production Example 310-1, and purification was performed by silica gel column chromatography (hexane/ethyl acetate system) to obtain the title compound (0.470 g, 2.3832 mmol, 29.42%) as pink crystals.

$^1$H-NMR Spectrum (CDCl$_3$) δ (ppm): 1.96 (1H, m), 2.03 (1H, m), 3.44 (2H, q, J=6.4 Hz), 4.54 (1H, t, J=5.6 Hz), 4.65 (1H, t, J=5.6 Hz), 5.22 (1H, brs), 7.12 (2H, d, J=7.6 Hz), 7.20 (1H, t, J=7.6 Hz), 7.36 (2H, t, J=7.6 Hz).

Example 325

6-Carbamoyl-4-[1-(3-chloropropylcarbamoyl)1H-indol-5-yloxy]-7-methoxyquinoline The title compound (136 mg, 0.3003 mmol, 35.97%) was obtained as colorless crystals using 6-carbamoyl-4-(1H-indol-5-yloxy)-7-methoxyquinoline (280 mg, 0.8349 mmol), phenyl N-(3-chloropropyl)carbamate (197 mg, 0.9184 mmol) and sodium hydride (37 mg, 0.9184 mmol), by the same procedure as in Example 310.

$^1$H-NMR Spectrum (DMSO-d$_6$) δ (ppm): 2.03 (2H, q, J=6.4 Hz), 3.42 (2H, q, J=6.4 Hz), 3.74 (2H, t, J=6.4 Hz), 4.02 (3H, s), 6.42 (1H, d, J=5.2 Hz), 6.71 (1H, d, J=3.6 Hz), 7.18 (1H, dd, J=2.4 Hz, 8.8 Hz), 7.50 (1H, s), 7.52 (1H, d, J=2.4 Hz), 7.72 (1H, brs), 7.85 (1H, brs), 7.94 (1H, d, J=3.6 Hz), 8.30 (1H, d, J=5.4 Hz), 8.34 (1H, d, J=8.8 Hz), 8.61 (1H, d, J=5.2 Hz), 8.72 (1H, s).

The starting material was synthesized in the following manner.

Production Example 325-1

Phenyl N-(3-chloropropyl)carbamate

3-Chloropropylaminehydrochloride (6.5 g, 50 mmol) was used for reaction in the same manner as Production Example 310-1, purification was performed by silica gel column chromatography (hexane/ethyl acetate system), the obtained crystals were suspended in diethyl ether and diluted with hexane, and the crystals were filtered out, washed with hexane and dried by aspiration to obtain the title compound (4.316 g, 20.20 mmol, 40.40%) as colorless crystals.

$^1$H-NMR Spectrum (DMSO-d$_6$) δ (ppm): 1.91 (2H, quintet, J=6.0 Hz), 3.18 (2H, q, J=6.0 Hz), 3.68 (2H, t, J=6.0 Hz), 7.08 (2H, d, J=8.0 Hz), 7.18 (1H, t, J=8.0 Hz), 7.35 (2H, t, J=8.0 Hz), 7.81 (1H, t, J=6.0 Hz).

Example 326

6-Carbamoyl-4-[1-(3-ethoxypropylcarbamoyl)1H-indol-5-yloxy]-7-methoxyquinoline The title compound (103 mg, 0.2227 mmol, 26.67%) was obtained as colorless crystals using 6-carbamoyl-4-(1H-indol-5-yloxy)-7-methoxyquinoline (280 mg, 0.8349 mmol), phenyl N-(3-ethoxypropyl)carbamate (197 mg, 0.9184 mmol) and sodium hydride (37 mg, 0.9184 mmol), by the same procedure as in Example 310.

$^1$H-NMR Spectrum (DMSO-d$_6$) δ (ppm): 1.01 (3H, t, J=6.8 Hz), 1.80 (2H, t, J=6.8 Hz), 3.34 (2H, q, J=6.8 Hz), 3.39-3.46 (4H, m), 4.02 (3H, s), 6.24 (1H, d, J=5.2 Hz), 6.70 (1H, d, J=3.6 Hz), 7.18 (1H, dd, J=2.4 Hz, 8.8 Hz), 7.50 (1H, s), 7.51 (1H, d, J=2.4 Hz), 7.72 (1H, brs), 7.85 (1H, brs), 7.93 (1H, d, J=3.6 Hz), 8.22 (1H, t, J=5.2 Hz), 8.34 (1H, d, J=8.8 Hz), 8.61 (1H, d, J=5.2 Hz), 8.72 (1H, s).

The starting material was synthesized in the following manner.

Production Example 326-1

Phenyl N-(3-ethoxypropyl)carbamate

3-Ethoxypropylamine (6.0 ml, 50 mmol) was dissolved in dimethylformamide (100 ml), the reaction was subsequently conducted in the same manner as Production Example 310-1, and purification was performed by NH silica gel column chromatography (hexane/ethyl acetate system) to obtain the title compound (10.76 g, 48.19 mmol, 96.39%) as a light yellow oil.

$^1$H-NMR Spectrum (CDCl$_3$) δ (ppm): 1.22 (3H, t, J=7.0 Hz), 1.85 (2H, quintet, J=6.0 Hz), 3.40 (2H, q, J=6.0 Hz), 3.51 (2H, q, J=7.0 Hz), 3.56 (2H, t, J=6.0 Hz), 5.58 (1H, brs), 7.12 (2H, d, J=7.6 Hz), 7.18 (1H, t, J=7.6 Hz), 7.35 (2H, t, J=7.6 Hz).

Example 327

6-Carbamoyl-4-[1-(3-diethylaminopropylcarbamoyl)1H-indol-5-yloxy]-7-methoxyquinoline The title compound (65 mg, 0.1328 mmol, 18.55%) was obtained as colorless crystals using 6-carbamoyl-4-(1H-indol-5-yloxy)-7-methoxyquinoline (240 mg, 0.7157 mmol), phenyl N-(3-diethylaminopropyl)carbamate (197 mg, 0.7872 mmol) and sodium hydride (31 mg, 0.7872 mmol), by the same procedure as in Example 310.

$^1$H-NMR Spectrum (DMSO-d$_6$) δ (Ppm): 0.94 (6H, t, J=7.2 Hz), 1.69 (2H, m), 2.42-2.48 (6H, m), 3.27-3.30 (2H, m), 4.02 (3H, s), 6.42 (1H, d, J=5.4 Hz), 6.70 (1H, d, J=3.6 Hz), 7.17 (1H, dd, J=2.4 Hz, 8.8 Hz), 7.50 (1H, s), 7.51 (1H, d, J=2.4 Hz), 7.72 (1H, brs), 7.84 (1H, brs), 7.91 (1H, d, J=3.6 Hz), 8.26 (1H, t, J=5.6 Hz), 8.33 (1H, d, J=8.8 Hz), 8.61 (1H, d, J=5.4 Hz), 8.72 (1H, s).

Production Example 327-1

Phenyl N-(3-diethylaminopropyl)carbamate

3-Diethylaminopropylamine (7.9 ml, 50 mmol) was dissolved in dimethylformamide (100 ml), the reaction was subsequently conducted in the same manner as Production Example 310-1, and purification was performed by NH silica gel column chromatography (hexane/ethyl acetate system) to obtain the title compound (7.21 g, 28.80 mmol, 57.60%) as a light yellow oil.

$^1$H-NMR Spectrum (CDCl$_3$) δ (ppm): 1.06 (6H, t, J=7.0 Hz), 1.71 (2H, quintet, J=6.0 Hz), 2.49-2.57 (6H, m), 3.36 (2H, q, J=6. Hz), 6.83 (1H, brs), 7.12 (2H, t, J=7.6 Hz), 7.17 (1H, t, J=7.6 Hz), 7.34 (2H, t, J=7.6 Hz).

Example 328

6-Carbamoyl-7-methoxy-4-[1-(3-methylthiopropyl) 1H-indol-5-yloxy]quinoline

The title compound (177 mg, 0.3810 mmol, 45.64%) was obtained as colorless crystals using 6-carbamoyl-4-(1H-indol-5-yloxy)-7-methoxyquinoline (280 mg, 0.8349 mmol), phenyl N-(3-methylthiopropyl)carbamate (207 mg, 0.9184 mmol) and sodium hydride (37 mg, 0.9184 mmol), by the same procedure as in Example 310.

$^1$H-NMR Spectrum (DMSO-d$_6$) δ (ppm): 1.84 (2H, tt, J=6.8 Hz, 6.8 Hz), 2.48 (3H, s), 2.55 (2H, t, J=6.8 Hz), 3.57 (2H, m), 4.02 (3H, s), 6.42 (1H, d, J=5.0 Hz), 6.70 (1H, d, J=3.4 Hz), 7.18 (1H, d, J=8.8 Hz), 7.50 (1H, s), 7.51 (1H, s), 7.72 (1H, s), 7.85 (1H, s), 7.94 (1H, d, J=3.4 Hz), 8.27 (1H, brs), 8.34 (1H, d, J=8.8 Hz), 8.61 (1H, d, J=5.0 Hz), 8.72 (1H, s).

Production Example 328-1

Phenyl N-(3-methylthiopropyl)carbamate

3-Methylthiopropylamine (5.5 ml, 50 mmol) was used for reaction in the same manner as Production Example 310-1, and purification was performed by silica gel column chromatography (hexane/ethyl acetate system) to obtain the title compound (10.486 g, 46.54 mmol, 93.08%) as a yellow oil.

$^1$H-NMR Spectrum (CDCl$_3$) δ (ppm): 1.89 (2H, quintet, J=6.8 Hz), 2.12 (3H, s), 2.58 (2H, t, J=6.8 Hz), 3.38 (2H, q, J=6.8 Hz), 5.21 (1H, brs), 7.12 (2H, t, J=7.6 Hz), 7.19 (1H, t, J=7.6 Hz), 7.35 (2H, t, J=7.6 Hz).

Example 329

6-Carbamoyl-4-[1-(2-chloroethylcarbamoyl)1H-indol-5-yloxy]-7-methoxyquinoline

The title compound (36 mg, 0.0820 mmol, 9.82%) was obtained as light yellow crystals using 6-carbamoyl-4-(1H-indol-5-yloxy)-7-methoxyquinoline (280 mg, 0.8349 mmol), phenyl N-(2-chloroethyl)carbamate (184 mg, 0.9184 mmol) and sodium hydride (37 mg, 0.9184 mmol), by the same procedure as in Example 310.

$^1$H-NMR Spectrum (DMSO-d$_6$) δ (ppm): 4.02 (3H, s), 4.03 (2H, t, J=9.2 Hz), 4.59 (2H, t, J=9.2 Hz), 6.44 (1H, d, J=5.6 Hz), 6.75 (1H, d, J=3.6 Hz), 7.24 (1H, dd, J=2.4 Hz, 8.8 Hz), 7.51 (1H, s), 7.57 (1H, d, J=2.4 Hz), 7.72 (1H, brs), 7.76 (1H, d, J=3.6 Hz), 7.85 (1H, brs), 8.38 (1H, d, J=8.8 Hz), 8.62 (1H, d, J=5.6 Hz), 8.72 (1H, s).

Production Example 329-1

Phenyl N-(2-chloroethyl)carbamate

2-Chloroethylamine hydrochloride (5.8 g, 50 mmol) was used for reaction in the same manner as Production Example 310-1, purification was performed by silica gel column chromatography (hexane/ethyl acetate system), the obtained crystals were suspended in diethyl ether/hexane, and the crystals were filtered out, washed with hexane and dried by aspiration to obtain the title compound (6.088 g, 30.49 mmol, 60.99%) as colorless crystals.

$^1$H-NMR Spectrum (DMSO-d$_6$) δ (ppm): 3.38 (2H, q, J=6.0 Hz), 3.66 (2H, t, J=6.0 Hz), 7.09 (2H, t, J=7.6 Hz), 7.19 (1H, t, J=7.6 Hz), 7.36 (2H, t, J=7.6 Hz), 8.01 (1H, t, J=6.0 Hz).

Example 330

4-[1-(2,4-Difluorophenylcarbamoyl)-1H-indol-5-yloxy]-6,7-dimethoxyquinoline

After dissolving 4-(1H-indol-5-yloxy)-6,7-dimethoxyquinoline (40 mg, 0.1249 mmol, described in WO9717329) in N,N-dimethylformamide (0.7 ml), sodium hydride (10 mg,) was added and the mixture was stirred at room temperature for 15 minutes. 2,4-Difluorophenyl isocyanate (0.018 ml, 0.1561 mmol) was further added, and the mixture was stirred at room temperature for 2 hours. Water was added to the reaction solution, extraction was performed with ethyl acetate, the extract was washed with saturated brine and dried over anhydrous magnesium sulfate, and the filtrate was distilled off under reduced pressure. The obtained crystals were suspended in diethyl ether:ethanol=10:1 and diluted with hexane, and then the crystals were filtered out, washed with diethyl ether:ethanol=10:1 and dried by aspiration to obtain the title compound (35 mg, 0.0736 mmol, 58.94%) as colorless crystals.

$^1$H-NMR Spectrum (CDCl$_3$) δ (ppm): 4.06 (3H, s), 4.07 (3H, s), 6.44 (1H, J, J=5.2 Hz), 6.75 (1H, d, J=4.0 Hz), 6.94-7.20 (2H, m), 7.23 (1H, dd, J=2.4, 8.8 Hz), 7.42-7.48 (3H, m), 7.63 (1H, s), 8.14-8.22 (1H, m), 8.29 (1H, d, J=8.8 Hz), 8.47 (1H, d, J=5.2 Hz).

Example 331-1

4-[1-(Phenylcarbamoyl)-1H-indol-5-yloxy]-6,7-dimethoxyquinoline 4-(1H-Indol-5-yloxy)-6,7-dimethoxyquinoline (25 mg, 0.0780 mmol) and phenyl isocyanate (0.013 ml, 0.117 mmol) were used for reaction in the same manner as Example 330, the obtained crystals were suspended in diethyl ether:ethanol=10:1, and then the crystals were filtered out, washed with diethyl ether and dried by aspiration to obtain the title compound (11 mg, 0.0250 mmol, 32.09%) as colorless crystals.

¹H-NMR Spectrum (CDCl₃) δ (ppm): 4.03 (3H, s), 4.12 (3H, s), 6.45 (1H, m), 6.73 (1H, m), 7.16-7.27 (2H, m), 7.38-7.43 (3H, m), 7.65-7.69 (3H, m), 7.97 (2H, m), 8.08 (1H, m), 8.43 (1H, brs), 8.38 (1H, d, J=8.8 Hz).

Example 331-2

4-[1-(2-Thiazolylcarbamoyl)-1H-indol-5-yloxy]-6,7-dimethoxyquinoline

After dissolving 4-(1H-indol-5-yloxy)-6,7-dimethoxyquinoline (25 mg, 0.0780 mmol) in N,N-dimethylformamide (0.4 ml), sodium hydride (6 mg) was added and the mixture was stirred at room temperature for 15 minutes. Phenyl N-(2-thiazolyl)carbamate (30 mg, 0.1362 mmol) was further added and the mixture was stirred at 80° C. for 2 hours. Water was added to the reaction solution, extraction was performed with ethyl acetate, the extract was washed with saturated brine and dried over anhydrous magnesium sulfate, and the filtrate was distilled off under reduced pressure. The residue was subjected to silica gel column chromatography (hexane/ethyl acetate/ethanol system), the obtained crystals were suspended in ethanol and diluted with hexane, and then the crystals were filtered out, washed with hexane and dried by aspiration to obtain the title compound (23 mg, 0.0515 mmol, 66.04%) as light yellow crystals.

¹H-NMR Spectrum (CDCl₃) δ (ppm): 3.94 (6H, s), 6.42 (1H, d, J=5.2 Hz), 6.68 (1H, d, J=3.4 Hz), 7.08 (1H, d, J=4.0 Hz), 7.17 (1H, d, J=8.8 Hz), 7.38 (1H, s), 7.46-7.48 (2H, m), 7.56 (1H, s), 8.07 (1H, d, J=3.4 Hz), 8.43 (1H, d, J=5.2 Hz), 8.65 (1H, d, J=8.8 Hz), 13.13 (1H, brs).

Example 332

4-(1-Cyclopropylcarbamoyl-1H-indol-5-yloxy)-6,7-dimethoxyquinoline

The title compound (30 mg, 0.0744 mmol, 47.64%) was obtained as light red crystals by reaction in the same manner as Example 310, using 4-(1H-indol-5-yloxy)-6,7-dimethoxyquinoline (50 mg, 0.1560 mmol), sodium hydride (8 mg, 0.1873 mmol) and phenyl N-cyclopropylcarbamate (30 mg, 0.1716 mmol).

¹H-NMR Spectrum (DMSO-d₆) δ (ppm): 0.71 (2H, m), 0.94 (2H, m), 2.91 (1H, m), 4.06 (3H, s), 4.07 (3H, s), 5.79 (1H, brs), 6.41 (1H, d, J=5.2 Hz), 6.63 (1H, d, J=3.2 Hz), 7.16 (1H, dd, J=2.4 Hz, 8.8 Hz), 7.26 (1H, s), 7.39-7.43 (2H, m), 7.63 (1H, s), 8.26 (1H, d, J=8.8 Hz), 8.45 (1H, d, J=5.2 Hz).

Example 333

4-[1-(2-Fluoroethylcarbamoyl)1H-indol-5-yloxy]-6,7-dimethoxyquinoline 4-(1H-Indol-5-yloxy)-6,7-dimethoxyquinoline (75 mg, 0.3122 mmol), sodium hydride (13 mg, 0.3278 mmol) and phenyl N-(2-fluoroethyl)carbamate (45 mg, 0.3278 mmol) were used for reaction in the same manner as Example 310, followed by extraction with ethyl acetate/tetrahydrofuran, washing with saturated brine and drying over anhydrous magnesium sulfate, and then the solvent was distilled off under reduced pressure. The residue was adsorbed onto silica gel and subjected to silica gel column chromatography (hexane/ethyl acetate system) to obtain the title compound (24 mg, 0.0586 mmol, 18.78%) as colorless crystals.

¹H-NMR Spectrum (DMSO-d₆) δ (ppm): 3.56 (1H, q, J=5.0 Hz), 3.63 (1H, q, J=5.0 Hz), 3.92 (3H, s), 3.96 (3H, s), 4.53 (1H, t, J=5.0 Hz), 4.65 (1H, t, J=5.0 Hz), 6.39 (1H, d, J=5.0 Hz), 6.71 (1H, d, J=3.8 Hz), 7.17 (1H, dd, J=2.0 Hz, 8.8 Hz), 7.40 (1H, s), 7.49 (1H, d, J=2.0 Hz), 7.55 (1H, s), 7.96 (1H, d, J=3.8 Hz), 8.34 (1H, d, J=8.8 Hz), 8.42 (1H, d, J=5.0 Hz), 8.48 (1H, t, J=5.0 Hz).

Example 334

6,7-Dimethoxy-4-(5-(1-(4-fluorophenylcarbonyl)-indolyl)oxy)quinoline

After dissolving 6,7-dimethoxy-4-(5-indolyloxy)quinoline (25 mg, 0.0780 mmol, described in WO9717329, p. 52) in toluene (1.6 ml), 4-fluorophenyl isocyanate (22 ml, 0.1951 mmol, 2.5 eqM) was added and the mixture was heated to reflux for 5 hours and 30 minutes under a nitrogen atmosphere. After cooling, the reaction solution was diluted with ethyl acetate, washed with saturated brine and dried over anhydrous magnesium sulfate, the solvent was distilled off under reduced pressure, and the residue was purified by silica gel column chromatography (hexane/ethyl acetate system). The obtained crystals were suspended in ethanol and diluted with hexane, and then the crystals were filtered out, washed with hexane and dried by aspiration to obtain the title compound (18 mg, 0.0393 mmol, 50.44%) as colorless crystals.

¹H-NMR Spectrum (CDCl₃) δ (ppm): 4.05 (3H, s), 4.07 (3H, s), 6.43 (1H, d, J=5.6 Hz), 6.72 (1H, d, J=3.4 Hz), 7.12 (2H, t, J=8.8 Hz), 7.22 (1H, dd, J=2.0, 8.8 Hz), 7.43 (3H, m), 7.53 (2H, m), 7.62 (1H, d, J=3.6 Hz), 7.63 (1H, s), 8.29 (1H, d, J=8.8 Hz), 8.46 (1H, d, J=5.6 Hz).

Example 335

6,7-Dimethoxy-4-[5-(1-(4-fluorophenylcarbamoyl)-indolinyl)oxy]quinoline 6,7-Dimethoxy(4-(5-indolinyloxy)quinoline (20 mg, 0.0620 mmol) was used for reaction in the same manner as Example 334 to obtain the title compound (18 mg, 0.0392 mmol, 63.19%) as light yellow crystals.

¹H-NMR Spectrum (CDCl₃) δ (ppm): 3.30 (2H, t, J=8.4 Hz), 4.05 (3H, s), 4.06 (3H, s), 4.12 (2H, t, J=8.4 Hz), 6.45 (1H, d, J=5.2 Hz), 6.47 (1H, brs), 7.01-7.07 (4H, m), 7.42 (2H, dd, J=9.2, 13.2 Hz), 7.43 (1H, s), 7.57 (1H, s), 8.04 (1H, d, J=8.8 Hz), 8.48 (1H, d, J=5.2 Hz).

The intermediate was synthesized in the following manner.

Production Example 335-1

6,7-Dimethoxy-4-(5-indolinyloxy)quinoline

After dissolving 6,7-dimethoxy-4-(5-indolyloxy)quinoline (30 mg, 0.0780 mmol, described in WO9717329, p. 52) in trifluoroacetic acid (0.9 ml), triethylsilane (45 ml, 0.2808 mmol, 3.0 eqM) was added while cooling on ice, and the mixture was stirred for 4 hours and 30 minutes at room temperature under a nitrogen atmosphere. After cooling, the reaction solution was diluted with ethyl acetate, neutralized with saturated sodium bicarnobate water, extracted with ethyl acetate, washed with saturated brine and dried over anhydrous magnesium sulfate, and the solvent was distilled off under reduced pressure. The residue was purified by silica gel column chromatography (ethyl acetate/ethanol system) to obtain the title compound (20 mg, 0.0620 mmol, 66.28%) as light yellow crystals.

¹H-NMR Spectrum (CDCl₃) δ (ppm): 3.08 (2H, t, J=8.4 Hz), 3.65 (2H, t, J=8.4 Hz), 4.06 (6H, s), 6.48 (1H, d, J=5.4

Hz), 6.69 (1H, d, J=8.4 Hz), 6.84 (1H, dd, J=1.6, 8.4 Hz), 6.95 (1H, d, J=1.6 Hz), 7.49 (1H, s), 7.60 (1H, s), 8.48 (1H, d, J=5.4 Hz).

Example 336

N-(4-(6-Cyano-7-(2-methoxyethoxy)-4-quinolyl) oxyphenyl)-N'-(3-methylthiopropyl)urea The title compound (35.7 mg, 0.077 mmol, 87.1%) was obtained as white crystals from phenyl N-(4-(6-cyano-7-(2-methoxyethoxy)-4-quinolyl)oxyphenyl)carbamate (40 mg, 0.088 mmol) and 3-(methylthio)propylamine, by the same procedure as in Example 11.
$^1$H-NMR Spectrum (DMSO-$d_6$) δ (ppm): 1.68 (2H, m), 2.04 (3H, s), 3.16 (2H, m), 3.18-3.35 (2H, m), 3.36 (3H, s), 3.76-3.79 (2H, m), 4.40-4.42 (2H, m), 6.23 (1H, t, J=5.6 Hz), 6.48 (1H, d, J=5.2 Hz), 7.16 (2H, d, J=9.2 Hz), 7.52 (2H, d, J=9.2 Hz), 7.61 (1H, s), 8.59 (1H, s), 8.70 (1H, d, J=4.0 Hz), 8.75 (1H, s).

Example 337

N-(4-(6-Cyano-7-(2-methoxyethoxy)-4-quinolyl) oxyphenyl)-N'-(3-methylsulfonylpropyl)urea The title compound (32.4 mg, 0.065 mmol, 59.2%) was obtained as white crystals from phenyl N-(4-(6-cyano-7-(2-methoxyethoxy)-4-quinolyl)oxyphenyl)carbamate (50 mg, 0.11 mmol) and 3-(methanesulfonyl)propylamine, by the same procedure as in Example 11.
$^1$H-NMR Spectrum (DMSO-$d_6$) δ (ppm): 1.85 (2H, m), 2.97 (3H, s), 3.11 (2H, m), 3.21 (2H, m), 3.36 (3H, s), 3.77 (2H, m), 4.41 (2H, m), 6.30 (1H, m), 6.48 (1H, d, J=5.6 Hz), 7.16 (2H, d, J=8.8 Hz), 7.53 (2H, d, J=8.8 Hz), 7.61 (1H, s), 8.67 (1H, s), 8.70 (1H, d, J=5.2 Hz), 8.75 (1H, s).

Example 338

N-(4-(6-Cyano-7-(2-methoxyethoxy)-4-quinolyl) oxyphenyl)-N'-(methylsulfonyl)urea After suspending sodium hydride (11 mg, 0.275 mmol) in tetrahydrofuran (8 ml) under a nitrogen atmosphere, methanesulfonylamide (31.4 mg, 0.330 mmol) was added while cooling in an ice water bath, and the mixture was stirred at room temperature for 10 minutes. Phenyl N-(4-(6-cyano-7-(2-methoxyethoxy)-4-quinolyl)oxyphenyl)carbamate (50 mg, 0.110 mmol) was added and the mixture was stirred at 60° C. for 1 hour. The insoluble portion was filtered off, and after concentration under reduced pressure, tetrahydrofuranhexane (1:2) was added for crystallization to obtain the title compound (37.6 mg, 0.082 mmol, 75.0%) as gray crystals.
$^1$H-NMR Spectrum (DMSO-$d_6$) δ (ppm): 2.75 (3H, s), 3.36 (3H, s), 3.77 (2H, m), 4.41 (2H, m), 6.47 (1H, d, J=5.2 Hz), 7.05 (1H, d, J=8.8 Hz), 7.61 (2H, d, J=8.8 Hz), 7.64 (1H, s), 8.44 (1H, s), 8.69 (2H, d, J=5.2 Hz), 8.75 (1H, s).

Example 339

Methyl 4-(4-(((4-fluoroanilino)carbonyl)amino)phenoxy)-7-methoxy-6-quinoline carboxylate The title compound (600 mg, 1.3 mmol, 86.8%) was obtained as light brown crystals from 4-(4-aminophenoxy)-7-methoxy-6-methoxycarbonylquinoline (486 mg, 1.5 mmol) and 4-fluorophenyl isocyanate, by the same procedure as in Example 10.
$^1$H-NMR Spectrum (DMSO-$d_6$) δ (ppm): 3.85 (3H, s), 3.96 (3H, s), 6.46 (1H, d, J=5.2 Hz), 7.12 (2H, m), 7.23 (2H, d, J=8.8 Hz), 7.46 (2H, m), 7.51 (1H, s), 7.58 (2H, d, J=8.8 Hz), 8.59 (1H, s), 8.67 (1H, d, J=5.2 Hz), 8.73 (1H, s), 8.82 (1H, s).
The starting material was synthesized in the following manner.

Production Example 339-1

7-Methoxy-6-methoxycarbonyl-4-(4-nitrophenoxy) quinoline

The title compound (1.743 g, 4.91 mmol, 27.2%) was obtained as light brown crystals from the 4-chloro-7-methoxy-6-methoxycarbonylquinoline hydrochloride (5.19 g, 18.0 mmol) described in WO0050405, by the same procedure as in Production Example 11.
$^1$H-NMR Spectrum (CDCl$_3$) δ (ppm): 3.97 (3H, s), 4.07 (3H, s), 6.62 (1H, d, J=5.2 Hz), 7.32 (2H, d, J=9.2 Hz), 7.55 (1H, s), 8.36 (2H, d, J=9.2 Hz), 8.69 (1H, s), 8.76 (1H, d, J=5.2 Hz).

Production Example 339-2

4-(4-Aminophenoxy)-7-methoxy-6-methoxycarbonylquinoline

The title compound (1.053 g, 3.25 mmol, 66.5%) was obtained as light brown crystals from 7-methoxy-6-methoxycarbonyl-4-(4-nitrophenoxy)quinoline (1.73 g, 4.88 mmol), in the same manner as Production Example 10.
$^1$H-NMR Spectrum (CDCl$_3$) δ (ppm): 3.97 (3H, s), 4.04 (3H, s), 6.42 (1H, d, J=5.2 Hz), 6.76 (2H, m), 6.98 (2H, m), 7.48 (1H, s), 8.61 (1H, d, J=5.2 Hz), 8.83 (1H, s).

Example 340

Methyl 7-methoxy-4-(4-(((1,3-thiazol-2-ylamino) carbonyl)amino)phenoxy)-6-quinolinecarboxylate The title compound (306 mg, 0.68 mmol, 45.3%) was obtained as light brown crystals from 4-(4-aminophenoxy)-7-methoxy-6-methoxycarbonylquinoline (486 mg, 1.5 mmol) and phenyl N-(1,3-thiazol-2-yl)carbamate, by the same procedure as in Example 131.
$^1$H-NMR Spectrum (DMSO-$d_6$) δ (ppm): 3.85 (3H, s), 3.97 (3H, s), 6.47 (1H, d, J=5.2 Hz), 7.11 (1H, br), 7.27 (2H, d, J=9.2 Hz), 7.37 (1H, br), 7.52 (1H, s), 7.61 (2H, d, J=9.2 Hz), 8.59 (1H, s), 8.67 (1H, d, J=5.2 Hz), 9.11 (1H, br), 10.53 (1H, br).

Example 341

4-(4-(((4-Fluoroanilino)carbonyl)amino)phenoxy)-7-methoxy-6-quinolinecarboxylic acid After adding methanol (9 ml) and 2N aqueous sodium hydroxide (3 ml) to methyl-4-(4-(((4-fluoroanilino)carbonyl) amino)phenoxy)-7-methoxy-6-quinoline carboxylate (300 mg, 0.65 mmol), the mixture was stirred at room temperature for 2 hours and then at 60° C. for 20 minutes. The reaction solution was cooled to room temperature and 1N hydrochloric acid was added for neutralization, after which methanol (6 ml) and water (6 ml) were added, the mixture was stirred overnight, and the precipitated light brown crystals were filtered out and dried under reduced pressure to obtain the title compound (227 mg, 0.51 mmol, 78.0%).

$^1$H-NMR Spectrum (DMSO-$d_6$) δ (ppm): 3.97 (3H, s), 6.49 (1H, d, J=5.2 Hz), 7.11 (2H, m), 7.23 (2H, d, J=8.8 Hz), 7.46 (2H, m), 7.49 (1H, s), 7.58 (2H, d, J=8.8 Hz), 8.57 (1H, s), 8.67 (1H, d, J=5.2 Hz), 8.75 (1H, s), 8.84 (1H, s).

Example 342

7-Methoxy-4-(4-(((1,3-thiazol-2-ylamino)carbonyl)amino)phenoxy)-6-quinolinecarboxylic acid The title compound (243 mg, 0.56 mmol, 95.4%) was obtained as light brown crystals from methyl 7-methoxy-4-(4-(((1,3-thiazol-2-ylamino)carbonyl)amino)phenoxy)-6-quinoline carboxylate (263 mg, 0.58 mmol), by the same procedure as in Example 341.

$^1$H-NMR Spectrum (DMSO-$d_6$) δ (ppm): 4.00 (3H, s), 6.63 (1H, d, J=5.2 Hz), 7.10 (1H, d, J=3.6 Hz), 7.31 (2H, d, J=8.8 Hz), 7.36 (1H, d, J=3.6 Hz), 7.57 (1H, s), 7.65 (2H, d, J=8.8 Hz), 8.62 (1H, s), 8.78 (1H, d, J=5.2 Hz), 9.64 (1H, s).

Example 343

2-Propyl 4-(4-(((4-fluoroanilino)carbonyl)amino)phenoxy)-7-methoxy-6-quinolinecarboxylate After dissolving 4-(4-(((4-fluoroanilino)carbonyl)amino)phenoxy)-7-methoxy-6-quinolinecarboxylic acid (84 mg, 0.19 mmol) in dimethylformamide (1 ml), there were added 1-ethyl-3-(3-dimethylaminopropyl)carbodiimide hydrochloride (54 mg, 0.28 mmol), 1-hydroxy-1H-benzotriazole monohydrate (38 mg, 0.28 mmol), triethylamine (0.079 ml, 0.56 mmol) and 2-propanol (0.15 ml) while stirring on ice, and the mixture was stirred overnight at room temperature. The reaction solution was directly subjected to silica gel column chromatography (eluent—ethyl acetate), the fraction containing the target substance was concentrated, suspended in ethyl acetate and diluted with hexane, and the crystals were filtered out and blow-dried to obtain the title compound (15.0 mg, 0.03 mmol, 16%) as white crystals.

$^1$H-NMR Spectrum (DMSO-$d_6$) δ (ppm): 1.32 (6H, d, J=6.4 Hz), 3.95 (3H, s), 5.15 (1H, m), 6.45 (1H, d, J=5.2 Hz), 7.11 (2H, m), 7.23 (2H, d, J=9.2 Hz), 7.46 (2H, m), 7.50 (1H, s), 7.58 (2H, d, J=9.2 Hz), 8.48 (1H, s), 8.66 (1H, d, J=5.2 Hz), 8.73 (1H, s), 8.82 (1H, s).

Example 344

2-Methoxyethyl 4-(4-(((4-fluoroanilino)carbonyl)amino)phenoxy)-7-methoxy-6-quinolinecarboxylate After dissolving 4-(4-(((4-fluoroanilino)carbonyl)amino)phenoxy)-7-methoxy-6-quinolinecarboxylic acid (84 mg, 0.19 mmol) in dimethylformamide (1 ml), there were added 1-ethyl-3-(3-dimethylaminopropyl)carbodiimide hydrochloride (54 mg, 0.28 mmol), 1-hydroxy-1H-benzotriazole monohydrate (38 mg, 0.28 mmol), triethylamine (0.079 ml, 0.56 mmol) and 2-methoxyethanol (0.15 ml) while stirring on ice, and the mixture was stirred overnight at room temperature. The reaction solution was directly subjected to silica gel column chromatography (eluent—ethyl acetate), the fraction containing the target substance was concentrated, suspended in ethyl acetate and diluted with hexane, and the crystals were filtered out and blow-dried to obtain the title compound (47.1 mg, 0.093 mmol, 49.6%) as white crystals.

$^1$H-NMR Spectrum (DMSO-$d_6$) δ (ppm): 3.29 (3H, s), 3.65 (2H, m), 3.96 (3H, s), 4.40 (2H, m), 6.46 (1H, d, J=5.2 Hz), 7.11 (2H, m), 7.24 (2H, d, J=8.8 Hz), 7.46 (2H, m), 7.51 (1H, s), 7.58 (2H, d, J=8.8 Hz), 8.56 (1H, s), 8.67 (1H, d, J=5.2 Hz), 8.73 (1H, s), 8.81 (1H, s).

Example 345

2-Methoxyethyl 7-methoxy-4-(4-(((1,3-thiazol-2-ylamino)carbonyl)amino)phenoxy)-6-quinolinecarboxylate After dissolving 7-methoxy-4-(4-(((1,3-thiazol-2-ylamino)carbonyl)amino)phenoxy)-6-quinolinecarboxylic acid (87.3 mg, 0.20 mmol) in dimethylformamide (1 ml), there were added 1-ethyl-3-(3-dimethylaminopropyl)carbodiimide hydrochloride (58 mg, 0.30 mmol), 1-hydroxy-1H-benzotriazole monohydrate (41 mg, 0.30 mmol), triethylamine (0.084 ml, 0.60 mmol) and 2-methoxyethylamine (0.052 ml, 0.60 mmol) while stirring on ice, and the mixture was stirred at room temperature for 5 hours. The reaction solution was distributed between ethyl acetate and water, and the organic layer was washed with water and dried over anhydrous magnesium sulfate. After distilling off the solvent, ethyl acetate and then hexane was added to precipitate crystals, which were filtered out and dried under reduced pressure to obtain the title compound (24.4 mg, 0.049 mmol, 24.7%) as white crystals.

$^1$H-NMR Spectrum (DMSO-$d_6$) δ (ppm): 3.29 (3H, s), 3.48 (4H, s), 4.02 (3H, s), 6.47 (1H, d, J=5.2 Hz), 7.11 (1H, br), 7.26 (2H, d, J=8.8 Hz), 7.37 (1H, br), 7.51 (1H, s), 7.61 (2H, d, J=8.8 Hz), 8.44 (1H, s), 8.62 (1H, s), 8.65 (1H, d, J=5.2 Hz), 9.11 (1H, s), 10.54 (1H, s).

Example 346

N6-Methoxy-7-methoxy-4-(4-(((1,3-thiazol-2-ylamino)carbonyl)amino)phenoxy)-6-quinolinecarboxamide The title compound (36.1 mg, 0.078 mmol, 61.5%) was obtained as light yellow crystals from 7-methoxy-4-(4-(((1,3-thiazol-2-ylamino)carbonyl)amino)phenoxy)-6-quinolinecarboxylic acid (55 mg, 0.13 mmol) and methoxylamine hydrochloride, by the same procedure as in Example 345.

$^1$H-NMR Spectrum (DMSO-$d_6$) δ (ppm): 3.73 (3H, s), 3.97 (3H, s), 6.47 (1H, d, J=5.2 Hz), 7.11 (1H, br), 7.25 (2H, d, J=8.8 Hz), 7.37 (1H, br), 7.48 (1H, s), 7.62 (2H, d, J=8.8 Hz), 8.44 (1H, s), 8.65 (1H, d, J=5.2 Hz), 9.11 (1H, s), 11.44 (1H, s).

Example 347

4-(4-(2,4-Difluoroanilino)carbonyl)aminophenoxy)-7-methoxy-6-quinolinecarboxamide The title compound (59.9 mg, 0.13 mmol, 79.8%) was obtained as light yellow crystals from 4-(4-aminophenoxy)-7-methoxy-6-quinolinecarboxamide (50 mg, 0.16 mmol) and 2,4-difluorophenyl isocyanate, by the same procedure as in Example 10.

$^1$H-NMR Spectrum (DMSO-$d_6$) δ (ppm): 4.00 (3H, s), 6.46 (1H, d, J=5.2 Hz), 7.03 (1H, m), 7.23 (2H, d, J=8.8 Hz), 7.33 (1H, m), 7.50 (1H, s), 7.58 (2H, d, J=8.8 Hz), 7.72 (1H, s), 7.84 (1H, s), 8.07 (1H, m), 8.52 (1H, s), 8.64 (1H, d, J=5.2 Hz), 8.67 (1H, s), 9.16 (1H, s).

The starting material was synthesized in the following manner.

Production Example 347-1

4-(4-Aminophenoxy)-7-methoxy-6-quinolinecarboxamide

The title compound (1.56 g, 5.0 mmol, 43.4%) was obtained as light yellow crystals from the 4-(4-aminophenoxy)-6-cyano-7-methoxyquinoline (4.76 g, 11.6 mmol) described in Production Example 14, by the same procedure as in Example 112.

$^1$H-NMR Spectrum (DMSO-d$_6$) δ (ppm): 4.00 (3H, s), 5.15 (2H, m), 6.39 (1H, d, J=5.2 Hz), 6.65 (2H, d, J=8.8 Hz), 6.92 (2H, d, J=8.8 Hz), 7.46 (1H, s), 7.70 (1H, s), 7.83 (1H, s), 8.60 (1H, d, J=5.2 Hz), 8.66 (1H, s).

Example 348

4-(4-(4-Fluoroanilino)carbonyl)-4-methylaminophenoxy)-7-methoxy-6-quinolinecarboxamide The title compound (265 mg, 0.58 mmol, 64.6%) was obtained as white crystals from 7-methoxy-4-(4-methylaminophenoxy)-6-quinolinecarboxamide (288 mg, 0.89 mmol) and 4-fluorophenyl isocyanate, by the same procedure as in Example 10.

$^1$H-NMR Spectrum (DMSO-d$_6$) δ (ppm): 3.29 (3H, s), 4.00 (3H, s), 6.65 (1H, d, J=5.2 Hz), 7.06 (2H, m), 7.32 (2H, d, J=8.8 Hz), 7.41-7.48 (4H, m), 7.51 (1H, s), 7.73 (1H, s), 7.85 (1H, s), 8.23 (1H, s), 8.67 (1H, s), 8.69 (1H, d, J=5.2 Hz).

The starting material was synthesized in the following manner.

Production Example 348-1

7-Methoxy-4-(4-methylaminophenoxy)-6-quinolinecarboxamide

After dissolving 4-methylaminophenol (1.04 g, 8.45 mmol) in dimethylsulfoxide (10 ml), sodium hydride (290 mg, 8.45 mmol) was gradually added at room temperature and the mixture was stirred for 20 minutes. The 7-methoxy-4-chloro-6-quinolinecarboxamide (1.00 g, 4.23 mmol) obtained in Production Example 152-3 was added, and the mixture was heated at 100° C. for 3 hours while stirring. Upon cooling to room temperature, the reaction solution was distributed between ethyl acetate and water, and the organic layer was washed with water and saturated brine and dried over anhydrous sodium sulfate. The solvent was distilled off and subjected to silica gel column chromatography (eluent—ethyl acetate), the fraction containing the target substance was concentrated, suspended in ethyl acetate and diluted with hexane, and the crystals were filtered out and blow-dried to obtain the title compound (815 mg, 2.52 mmol, 59.6%) as white crystals.

$^1$H-NMR Spectrum (CDCl$_3$) δ (ppm): 2.88 (3H, s), 4.09-4.16 (4H, m), 5.88 (1H, br), 6.45 (1H, d, J=5.6 Hz), 6.68 (2H, m), 7.01 (2H, m), 7.51 (1H, s), 7.80 (1H, br), 8.61 (1H, d, J=5.6 Hz), 9.31 (1H, s).

Example 349

7-Methoxy-4-(4-((2-thiazolylamino)carbonyl)-4-methylaminophenoxy)-6-quinolinecarboxamide The title compound (33.0 mg, 0.073 mmol, 47.5%) was obtained as white crystals from 6-carbamoyl-7-methoxy-4-(4-methylaminophenoxy)quinoline (50 mg, 0.16 mmol) and phenyl N-(1,3-thiazol-2-yl)carbamate, by the same procedure as in Example 131.

$^1$H-NMR Spectrum (DMSO-d$_6$) δ (ppm): 3.37 (3H, s), 4.02 (3H, s), 6.64 (1H, br), 7.02 (1H, br), 7.30-7.33 (3H, m), 7.47 (2H, d, J=8.8 Hz), 7.51 (1H, s), 7.72 (1H, s), 7.85 (1H, s), 8.67 (1H, s), 8.69 (1H, d, J=5.2 Hz).

Example 350

4-(4-(Cyclopropylaminocarbonyl)-4-methylaminophenoxy)-7-methoxy-6-quinolinecarboxamide The title compound (30.0 mg, 0.073 mmol, 49.4%) was obtained as white crystals from 4-nitrophenyl N-(4-(6-carbamoyl-7-methoxy-4-quinolyl)oxyphenyl)-N-methylcarbamate (73 mg, 0.15 mmol) and cyclopropylamine, by the same procedure as in Example 11.

$^1$H-NMR Spectrum (DMSO-d$_6$) δ (ppm): 0.41 (2H, m), 0.54 (2H, m), 2.50 (1H, m), 3.16 (3H, s), 4.03 (3H, s), 6.27 (1H, d, J=2.8 Hz), 6.60 (1H, d, J=5.6 Hz), 7.27 (2H, m), 7.36 (2H, m), 7.52 (1H, s), 7.73 (1H, s), 7.85 (1H, s), 8.66 (1H, s), 8.69 (1H, d, J=5.6 Hz).

The starting material was synthesized in the following manner.

Production Example 350-1

4-Nitrophenyl N-(4-(6-carbamoyl-7-methoxy-4-quinolyl)oxyphenyl)-N-methyl carbamate The title compound (373 mg, 0.076 mmol, 76.4%) was obtained as light yellow crystals from 6-carbamoyl-7-methoxy-4-(4-methylaminophenoxy)quinoline (323 mg, 1.00 mmol) and 4-nitrophenyl chloroformate, by the same procedure as in Production Example 17.

$^1$H-NMR Spectrum (CDCl$_3$) δ (ppm): 3.47 (3H, s), 4.15 (3H, s), 5.89 (1H, br), 6.56 (1H, d, J=5.6 Hz), 7.23-7.45 (6H, m), 7.56 (1H, s), 7.82 (1H, s), 8.27 (2H, d, J=8.8 Hz), 8.69 (1H, d, J=5.6 Hz), 9.29 (1H, s).

Example 351

7-Methoxy-4-(4-((3-methylthiopropylamino)carbonyl)-4-methylaminophenoxy)-6-quinolinecarboxamide The title compound (44.8 mg, 0.099 mmol, 65.9%) was obtained as white crystals from 4-nitrophenyl N-(4-(6-carbamoyl-7-methoxy-4-quinolyl)oxyphenyl)-N-methylcarbamate (73 mg, 0.15 mmol) and 3-(methylthio)propylamine, by the same procedure as in Example 11.

$^1$H-NMR Spectrum (DMSO-d$_6$) δ (ppm): 1.64 (2H, m), 2.01 (3H, s), 2.42 (2H, m), 3.09 (2H, m), 3.16 (3H, s), 4.01 (3H, s), 6.17 (1H, t, J=5.6 Hz), 6.59 (1H, d, J=5.2 Hz), 7.28

(2H, d, J=8.8 Hz), 7.37 (2H, d, J=8.8 Hz), 7.50 (1H, s), 7.72 (1H, s), 7.84 (1H, s), 8.65 (1H, s), 8.67 (1H, d, J=5.2 Hz).

Example 352

4-(4-((3-Methylsulfonylpropylamino)carbonyl)-4-methylaminophenoxy)-7-methoxy-6-quinolinecarboxamide The title compound (42.7 mg, 0.088 mmol, 58.7%) was obtained as white crystals from 4-nitrophenyl N-(4-(6-carbamoyl-7-methoxy-4-quinolyl)oxyphenyl)-N-methylcarbamate (73 mg, 0.15 mmol) and 3-(methylsulfonyl)propylamine, by the same procedure as in Example 11.
$^1$H-NMR Spectrum (DMSO-$d_6$) δ (ppm): 1.81 (2H, m), 2.94 (3H, s), 3.06 (2H, m), 3.12 (2H, m), 3.17 (3H, s), 4.01 (3H, s), 6.26 (1H, t, J=5.6 Hz), 6.60 (1H, d, J=5.2 Hz), 7.28 (2H, d, J=8.8 Hz), 7.39 (2H, d, J=8.8 Hz), 7.51 (1H, s), 7.72 (1H, s), 7.84 (1H, s), 8.65 (1H, s), 8.68 (1H, d, J=5.2 Hz).

Example 353

4-(3-Fluoro-4-((3-methylthiopropylamino)carbonyl)aminophenoxy)-7-methoxy-6-quinolinecarboxamide The title compound (71.1 mg, 0.155 mmol, 77.5%) was obtained as light brown crystals from 4-phenyl N-(4-(6-carbamoyl-7-methoxy-4-quinolyl)oxy-2-fluorophenyl)carbamate (89.5 mg, 0.20 mmol) and 3-(methylthio)propylamine, by the same procedure as in Example 11.
$^1$H-NMR Spectrum (DMSO-$d_6$) δ (ppm): 1.69 (2H, m), 2.04 (3H, s), 2.04-2.05 (2H, m), 3.17 (2H, m), 4.01 (3H, s), 6.51 (1H, d, J=5.2 Hz), 6.65 (1H, t, J=6.0 Hz), 7.05 (1H, d, J=9.6 Hz), 7.30 (1H, dd, J=2.8, 11.6 Hz), 7.49 (1H, s), 7.71 (1H, s), 7.83 (1H, s), 8.21 (1H, s), 8.33 (1H, s), 8.64-8.65 (2H, m).
The starting material was synthesized in the following manner.

Production Example 353-1

Phenyl N-(4-(6-carbamoyl-7-methoxy-4-quinolyl)oxy-2-fluorophenyl) carbamate

The title compound (391.5 mg, 0.875 mmol, 38.1%) was obtained as light yellow crystals from 6-carbamoyl-7-methoxy-4-(3-fluoro-4-aminophenoxy)quinoline (752 mg, 2.30 mmol), by the same procedure as in Production Example 17.
$^1$H-NMR Spectrum (CDCl$_3$) δ (ppm): 4.14 (3H, s), 5.92 (1H, s), 6.52 (1H, d, J=5.6 Hz), 7.02 (2H, m), 7.21-7.31 (4H, m), 7.43 (2H, m), 7.55 (1H, s), 7.81 (1H, s), 8.23 (1H, br), 8.68 (1H, d, J=5.6 Hz), 9.27 (1H, s).

Example 354

4-(3-Fluoro-4-((3-methylsulfonylpropylamino)carbonyl)aminophenoxy)-7-methoxy-6-quinolinecarboxamide The title compound (41.3 mg, 0.084 mmol, 42.1%) was obtained as white crystals from 4-phenyl N-(4-(6-carbamoyl-7-methoxy-4-quinolyl)oxy-2-fluorophenyl)carbamate (89.5 mg, 0.20 mmol) and 3-(methylsulfonyl)propylamine, by the same procedure as in Example 11.
$^1$H-NMR Spectrum (DMSO-$d_6$) δ (ppm): 1.85 (2H, m), 2.97 (3H, s), 3.12 (2H, m), 3.21 (2H, m), 4.01 (3H, s), 6.51 (1H, d, J=5.2 Hz), 6.73 (1H, t, J=5.6 Hz), 7.05 (1H, d, J=9.6 Hz), 7.31 (1H, dd, J=2.8, 11.6 Hz), 7.50 (1H, s), 7.72 (1H, s), 7.83 (1H, s), 8.20 (1H, m), 8.40 (1H, s), 8.64-8.66 (2H, m).

Example 355

4-(3-Fluoro-4-((2,2,2-trifluoroethylamino)carbonyl)aminophenoxy)-7-methoxy-6-quinolinecarboxamide The title compound (47.4 mg, 0.105 mmol, 69.9%) was obtained as light yellow crystals from phenyl N-(4-(6-carbamoyl-7-methoxy-4-quinolyl)oxy-2-fluorophenyl)carbamate (67 mg, 0.15 mmol) and 2,2,2-trifluoroethylamine, by the same procedure as in Example 11.
$^1$H-NMR Spectrum (DMSO-$d_6$) δ (ppm): 3.96 (2H, m), 4.02 (3H, s), 6.53 (1H, d, J=5.2 Hz), 7.09 (1H, d, J=8.8 Hz), 7.17 (1H, t, J=6.4 Hz), 7.35 (1H, dd, J=2.8, 11.6 Hz), 7.50 (1H, s), 7.72 (1H, s), 7.84 (1H, s), 8.16 (1H, m), 8.51 (1H, s), 8.64-8.67 (2H, m).

Example 356

4-(4-((3-Ethoxypropylamino)carbonyl)amino-3-fluorophenoxy)-7-methoxy-6-quinolinecarboxamide The title compound (45.2 mg, 0.099 mmol, 66.0%) was obtained as light brown crystals from phenyl N-(4-(6-carbamoyl-7-methoxy-4-quinolyl)oxy-2-fluorophenyl)carbamate (67 mg, 0.15 mmol) and 3-ethoxypropylamine, by the same procedure as in Example 11.
$^1$H-NMR Spectrum (DMSO-$d_6$) δ (ppm): 1.10 (3H, t, J=7.2 Hz), 1.65 (2H, m), 3.14 (2H, q, J=7.2 Hz), 3.35-3.44 (4H, m), 4.01 (3H, s), 6.52 (1H, d, J=5.2 Hz), 6.61 (1H, m), 7.05 (1H, d, J=8.8 Hz), 7.31 (1H, dd, J=2.8, 11.6 Hz), 7.50 (1H, s), 7.72 (1H, s), 7.84 (1H, s), 8.22 (1H, m), 8.35 (1H, s), 8.64-8.67 (2H, m).

Example 357

4-(3-Fluoro-4-((2-fluoroethylamino)carbonyl)aminophenoxy)-7-methoxy-6-quinolinecarboxamide The title compound (23.9 mg, 0.057 mmol, 77.8%) was obtained as light brown crystals from phenyl N-(4-(6-carbamoyl-7-methoxy-4-quinolyl)oxy-2-fluorophenyl)carbamate (33 mg, 0.074 mmol) and 2-fluoroethylamine hydrochloride, by the same procedure as in Example 11.
$^1$H-NMR Spectrum (DMSO-$d_6$) δ (ppm): 3.08 (2H, m), 4.02 (3H, s), 4.40 (1H, t, J=5.2 Hz), 4.52 (1H, t, J=5.2 Hz), 6.55 (1H, d, J=5.2 Hz), 6.88 (1H, m), 7.08 (1H, d, J=9.2 Hz), 7.33 (1H, dd, J=2.8, 11.6 Hz), 7.51 (1H, s), 7.74 (1H, s), 7.85 (1H, s), 8.21 (1H, m), 8.51 (1H, s), 8.65 (1H, s), 8.67 (1H, d, J=5.2 Hz).

Example 358

4-(4-((3-Chloropropylamino)carbonyl)amino-3-fluorophenoxy)-7-methoxy-6-quinolinecarboxamide The title compound (22.0 mg, 0.049 mmol, 66.8%) was obtained as light yellow crystals from phenyl N-(4-(6-carbamoyl-7-methoxy-4-quinolyl)oxy-2-fluorophenyl)carbamate (33 mg, 0.074 mmol) and 3-chloropropylamine, by the same procedure as in Example 11.
$^1$H-NMR Spectrum (DMSO-$d_6$) δ (ppm): 1.89 (2H, m), 3.22 (2H, m), 3.68 (2H, m), 4.01 (3H, s), 6.52 (1H, d, J=5.2 Hz), 6.71 (1H, m), 7.06 (1H, d, J=8.8 Hz), 7.31 (1H, dd, J=2.8, 11.6 Hz), 7.50 (1H, s), 7.72 (1H, s), 7.84 (1H, s), 8.20 (1H, m), 8.37 (1H, s), 8.64-8.66 (2H, m).

Example 359

4-(3-Fluoro-4-((3-fluoropropylamino)carbonyl)aminophenoxy)-7-methoxy-6-quinolinecarboxamide The title compound (7.9 mg, 0.018 mmol, 12.2%) was obtained as light yellow crystals from phenyl N-(4-(6-carbamoyl-7-methoxy-4-quinolyl)oxy-2-fluorophenyl)carbamate (67 mg, 0.15 mmol) and 3-fluoropropylamine hydrochloride, by the same procedure as in Example 11.

$^1$H-NMR Spectrum (DMSO-$d_6$) δ (ppm): 1.82 (2H, m), 3.20 (2H, m), 4.01 (3H, s), 4.44 (1H, t, J=6.0 Hz), 4.55 (1H, t, J=6.0 Hz), 6.52 (1H, d, J=5.2 Hz), 6.69 (1H, m), 7.06 (1H, d, J=8.8 Hz), 7.31 (1H, dd, J=2.8, 11.6 Hz), 7.50 (1H, s), 7.72 (1H, s), 7.84 (1H, s), 8.21 (1H, m), 8.38 (1H, s), 8.64-8.66 (2H, m).

Example 360

7-(2-Methoxyethoxy)-4-(4-((3-methoxypropylamino)carbonyl)aminophenoxy)-6-quinolinecarboxamide The title compound (35.2 mg, 0.075 mmol, 71.1%) was obtained as white crystals from phenyl N-(4-(6-carbamoyl-7-(2-methoxyethoxy)-4-quinolyl)oxyphenyl)carbamate (50 mg, 0.106 mmol) and 3-methoxypropylamine, by the same procedure as in Example 11.

$^1$H-NMR Spectrum (DMSO-$d_6$) δ (ppm): 1.66 (2H, m), 3.13 (2H, m), 3.23 (3H, s), 3.28-3.34 (2H, m), 3.36 (3H, s), 3.79 (2H, m), 4.40 (2H, m), 6.16 (1H, m), 6.43 (1H, d, J=5.6 Hz), 7.15 (2H, d, J=8.8 Hz), 7.51 (2H, d, J=8.8 Hz), 7.54 (1H, s), 7.79 (1H, s), 7.81 (1H, s), 8.60 (1H, s), 8.63 (1H, d, J=5.6 Hz), 8.77 (1H, s).

The starting material was synthesized in the following manner.

Production Example 360-1

4-(4-Aminophenoxy)-7-(2-methoxyethoxy)-6-quinolinecarboxamide

The title compound (1.303 g) was obtained as brown crystals from the 4-(4-aminophenoxy)-6-cyano-7-(2-methoxyethoxy)quinoline (3.448 g, 9.67 mmol) described in Production Example 10, by the same procedure as in Example 112. This was used directly for the following reaction.

Production Example 360-2

4-Phenyl N-(4-(6-carbamoyl-7-(2-methoxyethoxy)-4-quinolyl)oxyphenyl)carbamate

The title compound (1.462 g, 3.09 mmol, 83.7%) was obtained as light yellow crystals from 4-(4-aminophenoxy)-7-(2-methoxyethoxy)-6-quinolinecarboxamide (1.303 g, 3.69 mmol), by the same procedure as in Production Example 17.

$^1$H-NMR Spectrum (CDCl$_3$) δ (ppm): 3.48 (3H, s), 3.89 (2H, m), 4.44 (2H, m), 5.87 (1H, s), 6.50 (1H, d, J=5.6 Hz), 7.16-7.29 (7H, m), 7.42 (2H, m), 7.58 (1H, s), 7.60 (1H, s), 8.10 (1H, s), 8.64 (1H, d, J=5.6 Hz), 9.31 (1H, s).

Example 361

4-(4-((2-Fluoroethylamino)carbonyl)aminophenoxy)-7-(2-methoxyethoxy)-6-quinolinecarboxamide The title compound (33.1 mg, 0.075 mmol, 74.8%) was obtained as light brown crystals from phenyl N-(4-(6-carbamoyl-7-(2-methoxyethoxy)-4-quinolyl)oxyphenyl)carbamate (47.3 mg, 0.10 mmol) and 2-fluoroethylamine hydrochloride, by the same procedure as in Example 11.

$^1$H-NMR Spectrum (DMSO-$d_6$) δ (ppm): 3.26-3.38 (5H, m), 3.79 (2H, m), 4.38-4.41 (3H, m), 4.51 (1H, t, J=5.2 Hz), 6.39 (1H, m), 6.43 (1H, d, J=5.2 Hz), 7.17 (2H, d, J=8.8 Hz), 7.50-7.54 (3H, m), 7.79 (1H, s), 7.81 (1H, s), 8.63 (1H, d, J=5.2 Hz), 8.71 (1H, s), 8.77 (1H, s).

Example 362

4-(4-((3-Fluoropropylamino)carbonyl)aminophenoxy)-7-(2-methoxyethoxy)-6-quinolinecarboxamide The title compound (8.0 mg, 0.018 mmol, 17.5%) was obtained as light yellow crystals from phenyl N-(4-(6-carbamoyl-7-(2-methoxyethoxy)-4-quinolyl)oxyphenyl)carbamate (47.3 mg, 0.10 mmol) and 3-fluoropropylamine hydrochloride, by the same procedure as in Example 11.

$^1$H-NMR Spectrum (DMSO-$d_6$) δ (ppm): 1.76-1.87 (2H, m), 3.17 (2H, m), 3.36 (3H, s), 3.79 (2H, m), 4.38-4.45 (3H, m), 4.55 (1H, m), 6.24 (1H, m), 6.43 (1H, d, J=5.2 Hz), 7.16 (2H, d, J=8.8 Hz), 7.51 (2H, d, J=8.8 Hz), 7.53 (1H, s), 7.79 (1H, s), 7.81 (1H, s), 8.62-8.64 (2H, m), 8.77 (1H, s).

Example 363

4-(3-Fluoro-4-((3-methoxypropylamino)carbonyl) aminophenoxy)-7-(2-methoxyethoxy)-6-quinolinecarboxamide The title compound (37.2 mg, 0.076 mmol, 75.2%) was obtained as white crystals from phenyl N-(4-(6-carbamoyl-7-(2-methoxyethoxy)-4-quinolyl)oxy-2-fluorophenyl)carbamate (50 mg, 0.102 mmol) and 3-methoxypropylamine, by the same procedure as in Example 11.

$^1$H-NMR Spectrum (DMSO-$d_6$) δ (ppm): 1.66 (2H, m), 3.16 (2H, m), 3.23 (3H, s), 3.28-3.34 (2H, m), 3.36 (3H, s), 3.79 (2H, m), 4.40 (2H, m), 6.52 (1H, d, J=5.6 Hz), 6.62 (1H, m), 7.06 (1H, d, J=11.2 Hz), 7.31 (1H, dd, J=2.8, 11.6 Hz), 7.55 (1H, s), 7.80 (1H, s), 7.81 (1H, s), 8.22 (1H, m), 8.36 (1H, s), 8.65 (1H, d, J=5.6 Hz), 8.75 (1H, s).

The starting material was synthesized in the following manner.

Production Example 363-1

4-(4-Amino-3-fluorophenoxy)-7-(2-methoxyethoxy)-6-quinolinecarboxamide

The title compound (991 mg) was obtained as light yellow crystals from the 4-(4-amino-3-fluorophenoxy)-6-cyano-7-(2-methoxyethoxy)quinoline (6.368 g, 18.0 mmol) described in Production Example 12, by the same procedure as in Example 112. This was used directly for the following reaction.

Production Example 363-2

Phenyl N-(4-(6-carbamoyl-7-(2-methoxyethoxy)-4-quinolyl)oxy-2-fluorophenyl)carbamate The title compound (1.074 g, 2.19 mmol, 81.9%) was obtained as light brown crystals from 4-(4-amino-3-fluorophenoxy)-7-(2-methoxyethoxy)-6-quinolinecarboxamide (991 mg, 2.67 mmol), by the same procedure as in Production Example 17.

$^1$H-NMR Spectrum (CDCl$_3$) δ (ppm): 3.48 (3H, s), 3.90 (2H, m), 4.46 (2H, m), 5.88 (1H, s), 6.58 (1H, d, J=5.2 Hz), 7.02-7.06 (2H, m), 7.21-7.30 (4H, m), 7.43 (2H, m), 7.71 (1H, s), 8.08 (1H, s), 8.27 (1H, br), 8.68 (1H, d, J=5.2 Hz), 9.29 (1H, s).

Example 364

4-(4-(3-Fluoro(2-fluoroethylamino)carbonyl)aminophenoxy)-7-(2-methoxyethoxy)-6-quinolinecarboxamide The title compound (35.4 mg, 0.077 mmol, 76.9%) was obtained as white crystals from phenyl N-(4-(6-carbamoyl-7-(2-methoxyethoxy)-4-quinolyl)oxy-2-fluorophenyl)carbamate (49.1 mg, 0.10 mmol) and 2-fluoroethylamine hydrochloride, by the same procedure as in Example 11.

$^1$H-NMR Spectrum (DMSO-d$_6$) δ (ppm): 3.36 (3H, s), 3.45 (2H, m), 3.79 (2H, m), 4.38-4.41 (3H, m), 4.52 (1H, t, J=4.8 Hz), 6.52 (1H, d, J=5.2 Hz), 6.87 (1H, m), 7.07 (1H, d, J=6.8 Hz), 7.33 (1H, dd, J=2.8, 11.6 Hz), 7.55 (1H, s), 7.79 (1H, s), 7.81 (1H, s), 8.20 (1H, m), 8.49 (1H, s), 8.65 (1H, d, J=5.2 Hz), 8.75 (1H, s).

Example 365

4-(4-(3-Fluoro(2-fluoropropylamino)carbonyl)aminophenoxy)-7-(2-methoxyethoxy)-6-quinolinecarboxamide The title compound (6.8 mg, 0.014 mmol, 14.3%) was obtained as light yellow crystals from phenyl N-(4-(6-carbamoyl-7-(2-methoxyethoxy)-4-quinolyl)oxy-2-fluorophenyl)carbamate (49.1 mg, 0.10 mmol) and 3-fluoropropylamine hydrochloride, by the same procedure as in Example 11.

$^1$H-NMR Spectrum (DMSO-d$_6$) δ (ppm): 1.76-1.87 (2H, m), 3.18 (2H, m), 3.34 (3H, s), 3.79 (2H, m), 4.38-4.45 (3H, m), 4.55 (1H, m), 6.52 (1H, d, J=5.2 Hz), 6.69 (1H, m), 7.07 (1H, d, J=8.8 Hz), 7.32 (1H, dd, J=2.8, 11.6 Hz), 7.55 (1H, s), 7.80 (1H, s), 7.81 (1H, s), 8.21 (1H, m), 8.39 (1H, s), 8.65 (1H, d, J=5.2 Hz), 8.75 (1H, s).

Example 366

4-(3-Chloro-4-((4-fluoroanilino)carbonyl)aminophenoxy)-7-methoxy-6-quinolinecarboxamide The title compound (53.6 mg, 0.111 mmol, 76.9%) was obtained as light brown crystals from 4-(4-amino-3-chlorophenoxy)-7-methoxy-6-quinolinecarboxamide (50 mg, 0.145 mmol) and 4-fluorophenyl isocyanate, by the same procedure as in Example 10.

$^1$H-NMR Spectrum (DMSO-d$_6$) δ (ppm): 4.01 (3H, s), 6.55 (1H, d, J=5.2 Hz), 7.14 (2H, m), 7.28 (1H, dd, J=2.4, 9.2 Hz), 7.47 (2H, m), 7.51 (1H, s), 7.55 (1H, d, J=2.4 Hz), 7.73 (1H, s), 7.85 (1H, s), 8.25 (1H, d, J=9.2 Hz), 8.38 (1H, s), 8.65 (1H, s), 8.67 (1H, d, J=5.2 Hz), 9.43 (1H, s).

The starting material was synthesized in the following manner.

Production Example 366-1

4-(4-Amino-3-chlorophenoxy)-7-methoxy-6-quinolinecarboxamide

After dissolving 4-amino-3-chlorophenol (1.213 g, 8.45 mmol) in dimethylsulfoxide (10 ml), sodium hydride (290 mg, 8.45 mmol) was gradually added at room temperature and the mixture was stirred for 30 minutes. The 7-methoxy-4-chloro-6-quinolinecarboxamide (1.00 g, 4.23 mmol) obtained in Production Example 152-3 was added, and the mixture was heated at 100° C. for 2 hours while stirring. Upon cooling to room temperature, the reaction solution was distributed between ethyl acetate and water, and the organic layer was washed with water and saturated brine and dried over anhydrous sodium sulfate. The solvent was distilled off and subjected to silica gel column chromatography (eluent—ethyl acetate:methanol=9:1), the fraction containing the target substance was concentrated, suspended in tetrahydrofuran and diluted with hexane, and the crystals were filtered out and blow-dried to obtain the title compound (1.216 g, 3.54 mmol, 83.7%) as light brown crystals.

$^1$H-NMR Spectrum (CDCl$_3$) δ (ppm): 4.10 (2H, s), 4.13 (3H, s), 5.90 (1H, br), 6.46 (1H, d, J=5.6 Hz), 6.86 (1H, m), 6.93 (1H, dd, J=2.4, 8.4 Hz), 7.13 (1H, d, J=2.4 Hz), 7.53 (1H, s), 7.80 (1H, br), 8.64 (1H, d, J=5.6 Hz), 9.27 (1H, s).

Example 367

4-(3-Chloro-4-((2-thiazolylamino)carbonyl)aminophenoxy)-7-methoxy-6-quinolinecarboxamide The title compound (38.3 mg, 0.082 mmol, 56.2%) was obtained as light brown crystals from 4-(4-amino-3-chlorophenoxy)-7-methoxy-6-quinolinecarboxamide (50 mg, 0.145 mmol) and phenyl N-(1,3-thiazol-2-yl)carbamate, by the same procedure as in Example 131.

$^1$H-NMR Spectrum (DMSO-d$_6$) δ (ppm): 4.02 (3H, s), 6.56 (1H, d, J=5.2 Hz), 7.15 (1H, s), 7.31 (1H, d, J=8.0 Hz), 7.40 (1H, s), 7.51 (1H, s), 7.59 (1H, s), 7.73 (1H, s), 7.85 (1H, s), 8.27 (1H, d, J=8.0 Hz), 8.65 (1H, s), 8.67 (1H, d, J=5.2 Hz), 11.19 (1H, s).

Example 368

4-(3-Chloro-4-(cyclopropylaminocarbonyl)aminophenoxy)-7-methoxy-6-quinolinecarboxamide The title compound (22.4 mg, 0.052 mmol, 34.8%) was obtained as white crystals from phenyl N-(4-(6-carbamoyl-7-methoxy-4-quinolyl)oxy-2-chlorophenyl)carbamate (70 mg, 0.15 mmol) and cyclopropylamine, by the same procedure as in Example 11.

$^1$H-NMR Spectrum (DMSO-d$_6$) δ (ppm): 0.41 (2H, m), 0.66 (2H, m), 2.56 (1H, m), 4.01 (3H, s), 6.51 (1H, d, J=5.6 Hz), 7.18 (1H, d, J=2.8 Hz), 7.23 (1H, dd, J=2.8, 8.8 Hz), 7.48 (1H, d, J=2.8 Hz), 7.50 (1H, s), 7.72 (1H, s), 7.84 (1H, s), 7.97 (1H, s), 8.25 (1H, d, J=8.8 Hz), 8.64 (1H, s), 8.65 (1H, d, J=5.6 Hz).

The starting material was synthesized in the following manner.

Production Example 368-1

Phenyl N-(4-(6-carbamoyl-7-methoxy-4-quinolyl)oxy-2-chlorophenyl)carbamate

The title compound (708 mg, 1.526 mmol, 87.4%) was obtained as light brown crystals from 4-(4-amino-3-chlorophenoxy)-7-methoxy-6-quinolinecarboxamide (600 mg, 1.745 mmol), by the same procedure as in Production Example 17.

$^1$H-NMR Spectrum (CDCl$_3$) δ (ppm): 4.14 (3H, s), 5.89 (1H, br), 6.50 (1H, d, J=5.6 Hz), 7.16 (2H, dd, J=2.4, 8.8 Hz), 7.22-7.30 (4H, m), 7.44 (2H, m), 7.55 (1H, s), 7.81 (1H, br), 8.31 (1H, d, J=8.8 Hz), 8.68 (1H, d, J=5.6 Hz), 9.27 (1H, s).

Example 369

4-(3-Chloro-4-(2-fluoroethylaminocarbonyl)aminophenoxy)-7-methoxy-6-quinolinecarboxamide The title compound (95.8 mg, 0.221 mmol, 51.3%) was obtained as light brown crystals from phenyl N-(4-(6-carbamoyl-7-methoxy-4-quinolyl)oxy-2-chlorophenyl)carbamate (200 mg, 0.431 mmol) and 2-fluoroethylamine hydrochloride, by the same procedure as in Example 11.

$^1$H-NMR Spectrum (DMSO-d$_6$) δ (ppm): 3.98 (1H, m), 3.46 (1H, m), 4.02 (3H, s), 4.42 (1H, t, J=4.8 Hz), 4.53 (1H, dd, J=4.8, 5.6 Hz), 6.52 (1H, d, J=5.2 Hz), 7.23 (1H, d, J=2.4, 8.8 Hz), 7.29 (1H, m), 7.48 (1H, d, J=2.4 Hz), 7.50 (1H, s), 7.72 (1H, s), 7.84 (1H, s), 8.22-8.25 (2H, m), 8.64-8.66 (2H, m).

Example 370

7-Benzyloxy-4-(4-(cyclopropylaminocarbonyl)amino-3-fluorophenoxy)-6-quinolinecarboxamide The title compound (663 mg, 1.363 mmol, 93.9%) was obtained as light yellow crystals from phenyl N-(4-(7-benzyloxy-6-carbamoyl-4-quinolyl)oxy-2-fluorophenyl)carbamate (760 mg, 1.452 mmol) and cyclopropylamine, by the same procedure as in Example 11.

$^1$H-NMR Spectrum (DMSO-d$_6$) δ (ppm): 0.41 (2H, m), 0.65 (2H, m), 2.56 (1H, m), 5.44 (2H, s), 6.54 (1H, d, J=5.6 Hz), 6.82 (1H, d, J=2.8 Hz), 7.08 (1H, m), 7.33 (1H, dd, J=2.8, 12.0 Hz), 7.38 (1H, d, J=7.2 Hz), 7.44 (2H, m), 7.58 (2H, d, J=7.2 Hz), 7.61 (1H, s), 7.75 (1H, s), 7.84 (1H, s), 8.20-8.24 (2H, m), 8.63 (1H, s), 8.66 (1H, d, J=5.6 Hz).

The starting material was synthesized in the following manner.

Production Example 370-1

4-(4-Amino-3-fluorophenoxy)-7-(benzyloxy)-6-quinolinecarboxamide

The title compound (752 mg, 1.86 mmol, 31.6%) was obtained as light brown crystals from the 4-(4-amino-3-fluorophenoxy)-7-benzyloxy-6-cyanoquinoline (2.27 g, 5.89 mmol) described in Production Example 8, by the same procedure as in Example 112.

$^1$H-NMR Spectrum (CDCl$_3$) δ (ppm): 3.77 (2H, s), 5.34 (2H, s), 5.78 (1H, br), 6.47 (1H, d, J=5.2 Hz), 6.79-6.91 (3H, m), 7.41-7.54 (5H, m), 7.62 (1H, s), 7.81 (1H, br), 8.65 (1H, d, J=5.2 Hz), 9.31 (1H, s).

Production Example 370-2

Phenyl N-(4-(7-benzyloxy-6-carbamoyl-4-quinolyl)oxy-2-fluorophenyl)carbamate The title compound (760 mg, 1.452 mmol, 77.9%) was obtained as light yellow crystals from 4-(4-amino-3-fluorophenoxy)-7-(benzyloxy)-6-quinolinecarboxamide (752 mg, 1.864 mmol), by the same procedure as in Production Example 17.

$^1$H-NMR Spectrum (CDCl$_3$) δ (ppm): 5.35 (2H, s), 5.80 (1H, br), 6.52 (1H, d, J=5.2 Hz), 7.03 (2H, m), 7.22-7.30 (4H, m), 7.41-7.49 (5H, m), 7.53 (2H, d, J=6.8 Hz), 7.64 (1H, s), 7.82 (1H, br), 8.24 (1H, br), 8.69 (1H, d, J=5.2 Hz), 9.30 (1H, s).

Example 371

4-(4-(Cyclopropylaminocarbonyl) amino-3-fluorophenoxy)-7-hydroxy-6-quinolinecarboxamide The title compound (498 mg, 1.256 mmol, 95.5%) was obtained as light yellow crystals from 7-benzyloxy-4-(4-(cyclopropylaminocarbonyl) amino-3-fluorophenoxy)-6-quinolinecarboxamide (640 mg, 1.316 mmol), by the same procedure as in Example 83.

$^1$H-NMR Spectrum (DMSO-d$_6$) δ (ppm): 0.41 (2H, m), 0.66 (2H, m), 2.57 (1H, m), 6.42 (1H, d, J=5.2 Hz), 6.83 (1H, s), 7.31 (1H, d, J=9.2 Hz), 7.30 (1H, s), 7.34 (1H, dd, J=2.8, 11.6 Hz), 8.08 (1H, s), 8.21-8.26 (2H, m), 8.61 (1H, d, J=5.2 Hz), 8.91 (1H, br), 8.96 (1H, s).

Example 372

4-(4-(Cyclopropylaminocarbonyl)amino-3-fluorophenoxy)-7-(3-(N,N-diethylamino)propoxy)-6-quinolinecarboxamide The title compound (34.2 mg, 0.067 mmol, 53.2%) was obtained as light yellow crystals from 4-(4-(cyclopropylaminocarbonyl)amino-3-fluorophenoxy)-7-hydroxy-6-quinolinecarboxamide (50 mg, 0.126 mmol) and N-(3-chloropropyl)-N,N-diethylamine hydrochloride, by the same procedure as in Example 7.

$^1$H-NMR Spectrum (DMSO-d$_6$) δ (ppm): 0.41 (2H, m), 0.65 (2H, m), 0.95 (6H, t, J=7.2 Hz), 1.96 (2H, m), 2.44-2.49 (4H, m), 2.57-2.59 (3H, m), 4.30 (2H, m), 6.52 (1H, d, J=5.2 Hz), 6.70 (1H, s), 7.09 (1H, d, J=10.8 Hz), 7.32 (1H, m), 7.50 (1H, s), 7.79 (1H, s), 7.91 (1H, s), 8.19-8.22 (2H, m), 8.66 (1H, d, J=5.2 Hz), 8.69 (1H, s).

Example 373

4-(4-(Cyclopropylaminocarbonyl)amino-3-fluorophenoxy)-7-(2-(N,N-diethylamino)ethoxy)-6-quinolinecarboxamide The title compound (20.6 mg, 0.042 mmol, 33.0%) was obtained as light yellow crystals from 4-(4-(cyclopropylaminocarbonyl)amino-3-fluorophenoxy)-7-hydroxy-6-quinolinecarboxamide (50 mg, 0.126 mmol) and N-(2-bromoethyl)-N,N-diethylamine hydrobromide, by the same procedure as in Example 7.

$^1$H-NMR Spectrum (DMSO-d$_6$) δ (ppm): 0.41 (2H, m), 0.65 (2H, m), 0.97 (6H, t, J=7.2 Hz), 2.50-2.58 (5H, m), 2.85 (2H, m), 4.36 (2H, m), 6.52 (1H, d, J=5.2 Hz), 6.81 (1H, s), 7.09 (1H, d, J=6.8 Hz), 7.34 (1H, d, J=11.6 Hz), 7.57 (1H, s), 7.81 (1H, s), 8.19-8.22 (2H, m), 8.31 (1H, s), 8.67 (1H, d, J=5.2 Hz), 8.80 (1H, s).

Example 374

4-(4-(Cyclopropylaminocarbonyl)amino-3-fluorophenoxy)-7-(3-(4-morpholino)propoxy)-6-quinolinecarboxamide The title compound (35.0 mg, 0.067 mmol, 53.0%) was obtained as yellow crystals from 4-(4-(cyclopropylaminocarbonyl)amino-3-fluorophenoxy)-7-hydroxy-6-quinolinecarboxamide (50 mg, 0.126 mmol) and N-(3-chloropropyl)morpholine, by the same procedure as in Example 7.

$^1$H-NMR Spectrum (DMSO-d$_6$) δ (ppm): 0.41 (2H, m), 0.65 (2H, m), 2.01 (2H, m), 2.39 (4H, br), 2.46-2.50 (2H, m), 2.56 (1H, m), 3.59 (4H, m), 4.31 (2H, m), 6.52 (1H, d, J=5.2 Hz), 6.82 (1H, s), 7.08 (1H, d, J=8.4 Hz), 7.31 (1H, m), 7.52 (1H, s), 7.78 (2H, s), 8.19-8.24 (2H, m), 8.65-8.67 (2H, m).

Example 375

4-(4-(Cyclopropylaminocarbonyl)amino-3-fluorophenoxy)-7-(2-(4-morpholino)ethoxy)-6-quinolinecarboxamide The title compound (35.1 mg, 0.069 mmol, 54.6%) was obtained as yellow crystals from 4-(4-(cyclopropylaminocarbonyl)amino-3-fluorophenoxy)-7-hydroxy-6-quinolinecarboxamide (50 mg, 0.126 mmol) and N-(2-chloroethyl)morpholine hydrochloride, by the same procedure as in Example 7.

$^1$H-NMR Spectrum (DMSO-d$_6$) δ (ppm): 0.41 (2H, m), 0.65 (2H, m), 2.50-2.56 (5H, m), 2.79 (2H, m), 3.60 (4H, br), 4.41 (2H, m), 6.53 (1H, d, J=5.2 Hz), 6.81 (1H, s), 7.08 (1H, d, J=9.6 Hz), 7.33 (1H, d, J=12.8 Hz), 7.58 (1H, s), 7.87 (1H, s), 8.19-8.23 (2H, m), 8.39 (1H, s), 8.67 (1H, d, J=5.2 Hz), 8.82 (1H, s).

Example 376

4-(4-(Cyclopropylaminocarbonyl)amino-3-fluorophenoxy)-7-((2-pyridyl)methoxy)-6-quinolinecarboxamide The title compound (20.2 mg, 0.041 mmol, 32.8%) was obtained as light brown crystals from 4-(4-(cyclopropylaminocarbonyl)amino-3-fluorophenoxy)-7-hydroxy-6-quinolinecarboxamide (50 mg, 0.126 mmol) and 2-chloromethylpyridine hydrochloride, by the same procedure as in Example 7.

$^1$H-NMR Spectrum (DMSO-d$_6$) δ (ppm): 0.41 (2H, m), 0.65 (2H, m), 2.56 (1H, m), 5.53 (2H, s), 6.54 (1H, d, J=5.2 Hz), 6.80 (1H, s), 7.08 (1H, d, J=10.4 Hz), 7.30-7.40 (2H, m), 7.59 (1H, s), 7.62 (1H, d, J=8.0 Hz), 7.79 (1H, s), 7.86 (1H, dd, J=2.0, 7.6 Hz), 8.19-8.23 (3H, m), 8.61-8.68 (3H, m).

Example 377

4-(4-(Cyclopropylaminocarbonyl)amino-3-fluorophenoxy)-7-((3-pyridyl)methoxy)-6-quinolinecarboxamide The title compound (20.2 mg, 0.041 mmol, 32.8%) was obtained as light yellow crystals from 4-(4-(cyclopropylaminocarbonyl)amino-3-fluorophenoxy)-7-hydroxy-6-quinolinecarboxamide (50 mg, 0.126 mmol) and 3-chloromethylpyridine hydrochloride, by the same procedure as in Example 7.

$^1$H-NMR Spectrum (DMSO-d$_6$) δ (ppm): 0.41 (2H, m), 0.65 (2H, m), 2.56 (1H, m), 5.47 (2H, s), 6.55 (1H, d, J=5.2 Hz), 6.81 (1H, s), 7.08 (1H, d, J=10.0 Hz), 7.32 (1H, d, J=12.4 Hz), 7.45 (1H, m), 7.64 (1H, s), 7.73 (1H, s), 7.83 (1H, s), 7.98 (1H, m), 8.23 (2H, br), 8.57 (2H, br), 8.66 (1H, d, J=5.2 Hz), 8.80 (1H, s).

Example 378

4-(4-(Cyclopropylaminocarbonyl)amino-3-fluorophenoxy)-7-((4-pyridyl)methoxy)-6-quinolinecarboxamide The title compound (29.8 mg, 0.061 mmol, 48.5%) was obtained as light yellow crystals from 4-(4-(cyclopropylaminocarbonyl)amino-3-fluorophenoxy)-7-hydroxy-6-quinolinecarboxamide (50 mg, 0.126 mmol) and 4-chloromethylpyridine hydrochloride, by the same procedure as in Example 7.

$^1$H-NMR Spectrum (DMSO-d$_6$) δ (ppm): 0.41 (2H, m), 0.65 (2H, m), 2.56 (1H, m), 5.50 (2H, s), 6.54 (1H, d, J=5.2 Hz), 6.80 (1H, s), 7.07 (1H, d, J=8.0 Hz), 7.32 (1H, d, J=11.6 Hz), 7.53-7.55 (3H, m), 7.76 (1H, s), 7.92 (1H, s), 8.19-8.22 (2H, m), 8.55 (1H, s), 8.60-8.66 (3H, m).

Example 379

7-Benzyloxy-4-(3-chloro-4-(cyclopropylaminocarbonyl)aminophenoxy)-6-quinolinecarboxamide The title compound (2.433 g, 4.84 mmol, 87.9%) was obtained as light yellow crystals from phenyl N-(4-(7-benzyloxy-6-carbamoyl-4-quinolyl)oxy-2-chlorophenyl)carbamate (2.97 g, 5.50 mmol) and cyclopropylamine, by the same procedure as in Example 11.

$^1$H-NMR Spectrum (DMSO-d$_6$) δ (ppm): 0.41 (2H, m), 0.65 (2H, m), 2.56 (1H, m), 5.41 (2H, s), 6.51 (1H, d, J=5.6 Hz), 7.18 (1H, d, J=2.8 Hz), 7.22 (1H, m), 7.35 (1H, d, J=7.2 Hz), 7.42 (2H, m), 7.48 (1H, s), 7.55 (2H, d, J=7.2 Hz), 7.59 (1H, s), 7.73 (1H, s), 7.82 (1H, s), 7.97 (1H, s), 8.25 (1H, d, J=9.2 Hz), 8.60 (1H, s), 8.64 (1H, d, J=5.6 Hz).

The starting material was synthesized in the following manner.

Production Example 379-1

4-(4-Amino-3-chlorophenoxy)-7-benzyloxy-6-cyanoquinoline

After dissolving 4-amino-3-chlorophenol (10.77 g, 75.0 mmol) in dimethylsulfoxide (150 ml), sodium hydride (3.00 g, 75.0 mmol) was gradually added at room temperature and the mixture was stirred for 30 minutes. 7-Benzyloxy-4-chloro-6-cyanoquinoline (14.737 g, 50.0 mmol) obtained by a publicly known method was added, and the mixture was heated at 100° C. for 2 hours while stirring. Upon cooling to room temperature, the reaction solution was distributed between ethyl acetate and water, and the organic layer was washed with water and saturated brine and dried over anhydrous sodium sulfate. The solvent was distilled off and subjected to silica gel column chromatography (eluent—ethyl acetate), the fraction containing the target substance was concentrated, suspended in ethyl acetate and diluted with hexane, and the crystals were filtered out and blow-dried to obtain the title compound (11.777 g, 29.3 mmol, 58.6%) as light brown crystals.

¹H-NMR Spectrum (CDCl₃) δ (ppm): 4.13 (2H, s), 5.35 (2H, s), 6.47 (1H, d, J=5.2 Hz), 6.85 (1H, d, J=8.8 Hz), 6.92 (1H, dd, J=2.4, 9.2 Hz), 7.13 (1H, d, J=2.4 Hz), 7.36 (1H, d, J=7.6 Hz), 7.42 (2H, m), 7.51-7.55 (3H, m), 8.65 (1H, d, J=5.2 Hz), 8.69 (1H, s).

Production Example 379-2

4-(4-Amino-3-chlorophenoxy)-7-(benzyloxy)-6-quinolinecarboxamide

The title compound (5.74 g, 13.7 mmol, 37.8%) was obtained as light brown crystals from 4-(4-amino-3-chlorophenoxy)-7-benzyloxy-6-cyanoquinoline (14.55 g, 36.2 mmol), by the same procedure as in Example 112.
¹H-NMR Spectrum (CDCl₃) δ (ppm): 4.10 (2H, s), 5.34 (2H, s), 5.78 (1H, br), 6.47 (1H, d, J=5.2 Hz), 6.85 (1H, d, J=8.4 Hz), 6.92 (1H, dd, J=2.4, 8.4 Hz), 7.13 (1H, d, J=2.4 Hz), 7.38-7.53 (4H, m), 7.62 (1H, s), 7.82 (1H, br), 8.62 (1H, s), 8.64 (1H, d, J=5.2 Hz), 9.30 (1H, s).

Production Example 379-3

Phenyl N-(4-(7-benzyloxy-6-carbamoyl-4-quinolyl)oxy-2-chlorophenyl)carbamate

The title compound (2.97 g, 5.50 mmol, 55.0%) was obtained as light brown crystals from 4-(4-amino-3-chlorophenoxy)-7-(benzyloxy)-6-quinolinecarboxamide (4.20 g, 10.0 mmol), by the same procedure as in Production Example 17.
¹H-NMR Spectrum (CDCl₃) δ (ppm): 5.35 (2H, s), 5.81 (1H, br), 6.51 (1H, d, J=5.2 Hz), 7.16 (1H, dd, J=2.8, 8.8 Hz), 7.22-7.30 (4H, m), 7.41-7.54 (8H, m), 7.64 (1H, s), 7.81 (1H, br), 8.32 (1H, d, J=9.2 Hz), 8.69 (1H, d, J=5.2 Hz), 9.30 (1H, s).

Example 380

4-(3-Chloro-4-(cyclopropylaminocarbonyl)aminophenoxy)-7-hydroxy-6-quinolinecarboxamide The title compound (697 mg, 1.69 mmol, 83.6%) was obtained as yellow crystals from 7-benzyloxy-4-(3-chloro-4-(cyclopropylaminocarbonyl)aminophenoxy)-6-quinolinecarboxamide (1.016 g, 2.02 mmol) by the same procedure as in Example 83.
¹H-NMR Spectrum (DMSO-d₆) δ (ppm): 0.43 (2H, m), 0.68 (2H, m), 2.58 (1H, m), 6.56 (1H, d, J=5.6 Hz), 7.23 (1H, s), 7.30 (1H, m), 7.36 (1H, s), 7.55 (1H, d, J=2.4 Hz), 8.01 (1H, s), 8.19 (1H, s), 8.33 (1H, d, J=9.2 Hz), 8.72 (1H, d, J=5.6 Hz), 8.82 (1H, s), 9.01 (1H, s).

Example 381

4-(3-Chloro-4-(cyclopropylaminocarbonyl)aminophenoxy)-7-(2-methoxyethoxy)-6-quinolinecarboxamide The title compound (29.9 mg, 0.063 mmol, 52.4%) was obtained as light yellow crystals from 4-(3-chloro-4-(cyclopropylaminocarbonyl)aminophenoxy)-7-hydroxy-6-quinolinecarboxamide (50 mg, 0.121 mmol) and 2-methoxyethylbromide, by the same procedure as in Example 7.
¹H-NMR Spectrum (DMSO-d₆) δ (ppm): 0.41 (2H, m), 0.65 (2H, m), 2.57 (1H, m), 3.36 (3H, s), 3.81 (2H, m), 4.41 (2H, m), 6.53 (1H, d, J=5.2 Hz), 7.20 (1H, d, J=2.8 Hz), 7.25 (1H, dd, J=2.8, 9.2 Hz), 7.41 (1H, d, J=2.8 Hz), 7.57 (1H, s), 7.82 (1H, s), 7.83 (1H, s), 7.99 (1H, s), 8.28 (1H, d, J=9.2 Hz), 8.68 (1H, d, J=5.2 Hz), 8.77 (1H, s).

Example 382

4-(3-Chloro-4-(cyclopropylaminocarbonyl)aminophenoxy)-7-(3-(4-morpholino)propoxy)-6-quinolinecarboxamide The title compound (30.5 mg, 0.056 mmol, 46.6%) was obtained as light yellow crystals from 4-(3-chloro-4-(cyclopropylaminocarbonyl)aminophenoxy)-7-hydroxy-6-quinolinecarboxamide (50 mg, 0.121 mmol) and N-(3-chloropropyl)morpholine, by the same procedure as in Example 7.
¹H-NMR Spectrum (DMSO-d₆) δ (ppm): 0.41 (2H, m), 0.65 (2H, m), 2.02 (2H, m), 2.39 (4H, br), 2.46-2.59 (3H, m), 3.59 (4H, m), 4.31 (2H, m), 6.53 (1H, d, J=5.2 Hz), 7.20 (1H, d, J=2.8 Hz), 7.25 (1H, dd, J=2.8, 9.2 Hz), 7.49 (1H, d, J=2.8 Hz), 7.52 (1H, s), 7.78 (2H, s), 7.98 (1H, s), 8.28 (1H, d, J=9.2 Hz), 8.65 (1H, s), 8.66 (1H, d, J=5.2 Hz).

Example 383

4-(3-Chloro-4-(cyclopropylaminocarbonyl)aminophenoxy)-7-(2-(4-morpholino)ethoxy)-6-quinolinecarboxamide The title compound (29.8 mg, 0.057 mmol, 46.8%) was obtained as light yellow crystals from 4-(3-chloro-4-(cyclopropylaminocarbonyl)aminophenoxy)-7-hydroxy-6-quinolinecarboxamide (50 mg, 0.121 mmol) and N-(2-chloroethyl)morpholine hydrochloride, by the same procedure as in Example 7.
¹H-NMR Spectrum (DMSO-d₆) δ (ppm): 0.41 (2H, m), 0.65 (2H, m), 2.50-2.56 (5H, m), 2.80 (2H, m), 3.60 (4H, br), 4.41 (2H, m), 6.53 (1H, d, J=5.2 Hz), 7.20 (1H, d, J=2.8 Hz), 7.25 (1H, dd, J=2.8, 8.8 Hz), 7.50 (1H, d, J=2.8 Hz), 7.58 (1H, s), 7.87 (1H, s), 7.99 (1H, s), 8.27 (1H, d, J=8.8 Hz), 8.38 (1H, s), 8.67 (1H, d, J=5.2 Hz), 8.82 (1H, s).

Example 384

4-(3-Chloro-4-(cyclopropylaminocarbonyl)aminophenoxy)-7-(3-(1-piperidino)propoxy)-6-quinolinecarboxamide The title compound (27.3 mg, 0.051 mmol, 41.9%) was obtained as light yellow crystals from 4-(3-chloro-4-(cyclopropylaminocarbonyl)aminophenoxy)-7-hydroxy-6-quinolinecarboxamide (50 mg, 0.121 mmol) and 1-(3-chloropropyl)piperidine hydrochloride, by the same procedure as in Example 7.
¹H-NMR Spectrum (DMSO-d₆) δ (ppm): 0.42 (2H, m), 0.65 (2H, m), 1.36 (2H, m), 1.47 (4H, m), 1.99 (2H, m), 2.33 (4H, br), 2.42 (2H, m), 2.56 (1H, m), 4.27 (2H, m), 6.50 (1H, d, J=5.2 Hz), 7.18 (1H, d, J=2.8 Hz), 7.22 (1H, dd, J=2.8, 8.8 Hz), 7.47 (1H, d, J=2.8 Hz), 7.49 (1H, s), 7.76 (2H, br), 7.96 (1H, s), 8.25 (1H, d, J=8.8 Hz), 8.64 (1H, d, J=5.2 Hz), 8.65 (1H, s).

Example 385

4-(3-Chloro-4-(cyclopropylaminocarbonyl)aminophenoxy)-7-(2-(1-pyrrolidino)ethoxy)-6-quinolinecarboxamide The title compound (24.6 mg, 0.048 mmol, 39.8%) was obtained as light yellow crystals from 4-(3-chloro-4-(cyclopropylaminocarbonyl)aminophenoxy)-7-hydroxy-6-quinolinecarboxamide (50 mg, 0.121 mmol) and 1-(2-chloroethyl)pyrrolidine hydrochloride, by the same procedure as in Example 7.

$^1$H-NMR Spectrum (DMSO-d$_6$) δ (ppm): 0.41 (2H, m), 0.65 (2H, m), 1.67 (4H, br), 2.49-2.58 (5H, m), 2.89 (2H, m), 4.38 (2H, m), 6.51 (1H, d, J=5.2 Hz), 7.18 (1H, d, J=2.8 Hz), 7.23 (1H, dd, J=2.8, 9.2 Hz), 7.48 (1H, d, J=2.8 Hz), 7.56 (1H, s), 7.72 (1H, s), 7.96 (1H, s), 8.25 (1H, d, J=9.2 Hz), 8.33 (1H, s), 8.65 (1H, d, J=5.2 Hz), 8.76 (1H, s).

Example 386

4-(3-Chloro-4-(cyclopropylaminocarbonyl)aminophenoxy)-7-(2-hydroxyethoxy)-6-quinolinecarboxamide The title compound (63.7 mg, 0.139 mmol, 27.9%) was obtained as light yellow crystals from 4-(3-chloro-4-(cyclopropylaminocarbonyl)aminophenoxy)-7-hydroxy-6-quinolinecarboxamide (206 mg, 0.499 mmol) and 2-bromoethanol, by the same procedure as in Example 7.

$^1$H-NMR Spectrum (DMSO-d$_6$) δ (ppm): 0.41 (2H, m), 0.65 (2H, m), 2.56 (1H, m), 3.84 (2H, m), 4.30 (2H, m), 5.12 (1H, t, J=5.2 Hz), 6.51 (1H, d, J=5.2 Hz), 7.19 (1H, d, J=2.8 Hz), 7.24 (1H, dd, J=2.8, 8.8 Hz), 7.49 (1H, d, J=2.8 Hz), 7.54 (1H, s), 7.82 (1H, s), 7.94 (1H, s), 7.97 (1H, s), 8.26 (1H, d, J=8.8 Hz), 8.66 (1H, d, J=5.2 Hz), 8.80 (1H, s).

Example 387

4-(3-Chloro-4-(cyclopropylaminocarbonyl)aminophenoxy)-7-(3-hydroxypropoxy)-6-quinolinecarboxamide The title compound (67.0 mg, 0.142 mmol, 28.5%) was obtained as light yellow crystals from 4-(3-chloro-4-(cyclopropylaminocarbonyl)aminophenoxy)-7-hydroxy-6-quinolinecarboxamide (206 mg, 0.499 mmol) and 3-bromopropanol, by the same procedure as in Example 7.

$^1$H-NMR Spectrum (DMSO-d$_6$) δ (ppm): 0.41 (2H, m), 0.65 (2H, m), 1.98 (2H, m), 2.56 (1H, m), 3.62 (2H, m), 4.32 (2H, m), 4.69 (1H, m), 6.50 (1H, d, J=5.2 Hz), 7.18-7.24 (2H, m), 7.48-7.50 (2H, m), 7.73 (1H, s), 7.86 (1H, s), 7.97 (1H, s), 8.26 (1H, d, J=8.4 Hz), 8.64 (1H, d, J=5.2 Hz), 8.67 (1H, s).

Example 388

4-(3-Chloro-4-(cyclopropylaminocarbonyl)aminophenoxy)-7-((4R)-2,2-dimethyl-1,3-dioxolan-4-yl)methoxy)-6-quinolinecarboxamide The title compound (234.4 mg, 0.445 mmol, 44.5%) was obtained as light yellow crystals from 4-(3-chloro-4-(cyclopropylaminocarbonyl)aminophenoxy)-7-hydroxy-6-quinolinecarboxamide (413 mg, 1.00 mmol) and ((4R)-2,2-dimethyl-1,3-dioxolan-4-yl)methyl 4-toluenesulfonate, by the same procedure as in Example 7.

$^1$H-NMR Spectrum (DMSO-d$_6$) δ (ppm): 0.41 (2H, m), 0.65 (2H, m), 1.33 (3H, s), 1.40 (3H, s), 2.56 (1H, m), 3.99 (1H, m), 4.14 (1H, m), 4.27 (1H, m), 4.41 (1H, m), 4.58 (1H, m), 6.51 (1H, d, J=5.2 Hz), 7.20 (1H, d, J=2.8 Hz), 7.25 (1H, dd, J=2.8, 8.8 Hz), 7.49 (1H, d, J=2.8 Hz), 7.57 (1H, s), 7.84 (2H, br), 7.99 (1H, s), 8.28 (1H, d, J=8.8 Hz), 8.67 (1H, d, J=5.2 Hz), 8.80 (1H, s).

Example 389

4-(3-Chloro-4-(cyclopropylaminocarbonyl)aminophenoxy)-7-((4S)-2,2-dimethyl-1,3-dioxolan-4-yl)methoxy)-6-quinolinecarboxamide The title compound (253 mg, 0.480 mmol, 48.0%) was obtained as light yellow crystals from 4-(3-chloro-4-(cyclopropylaminocarbonyl)aminophenoxy)-7-hydroxy-6-quinolinecarboxamide (413 mg, 1.00 mmol) and ((4S)-2,2-dimethyl-1,3-dioxolan-4-yl)methyl 4-toluenesulfonate), by the same procedure as in Example 7.

Example 390

4-(3-Chloro-4-(cyclopropylaminocarbonyl)aminophenoxy)-7-((2R)-2,3-dihydroxypropyl)oxy-6-quinolinecarboxamide After dissolving 4-(3-chloro-4-(cyclopropylaminocarbonyl)aminophenoxy)-7-((4R)-2,2-dimethyl-1,3-dioxolan-4-yl)methoxy)-6-quinolinecarboxamide (219 mg, 0.416 mmol) in trifluoroacetic acid (2 ml)-tetrahydrofuran (2 ml)-water (1 ml) at room temperature, the solution was stirred for 1 hour. The reaction solution was diluted with water (30 ml), and then sodium bicarbonate (3 g) was gradually added thereto for neutralization, after which extraction was performed with ethyl acetate, and the organic layer was washed with saturated brine and dried over anhydrous sodium sulfate. The solvent was distilled off under reduced pressure and suspended in tetrahydrofuran, and the precipitated crystals were filtered out, washed with a small amount of ethyl acetate and blow-dried to obtain the title compound (121.4 mg, 0.249 mmol, 60.0%) as white crystals.

$^1$H-NMR Spectrum (DMSO-d$_6$) δ (ppm): 0.41 (2H, m), 0.65 (2H, m), 2.56 (1H, m), 3.53 (2H, m), 3.94 (1H, m), 4.24 (1H, m), 4.33 (1H, m), 4.83 (1H, t, J=5.6 Hz), 5.26 (1H, d, J=5.6 Hz), 6.53 (1H, d, J=5.2 Hz), 7.20 (1H, d, J=2.8 Hz), 7.26 (1H, dd, J=2.8, 9.2 Hz), 7.51 (1H, d, J=2.8 Hz), 7.54 (1H, s), 7.84 (1H, s), 7.99 (2H, br), 8.28 (1H, d, J=9.2 Hz), 8.67 (1H, d, J=5.2 Hz), 8.81 (1H, s).

Example 391-1

4-(3-Chloro-4-(cyclopropylaminocarbonyl)aminophenoxy)-7-((2S)-2,3-dihydroxypropyl)oxy-6-quinolinecarboxamide After dissolving 4-(3-chloro-4-(cyclopropylaminocarbonyl)aminophenoxy)-7-((4S)-2,2-dimethyl-1,3-dioxolan-4-yl)methoxy)-6-quinolinecarboxamide (236 mg, 0.448 mmol) in trifluoroacetic acid (2 ml)-tetrahydrofuran (2 ml)-water (1 ml) at room temperature, the solution was stirred for 1 hour. The reaction solution was diluted with water (30 ml), and then sodium bicarbonate (3 g) was gradually added thereto for neutralization, after which extraction was performed with ethyl acetate, and the organic layer was washed with saturated brine and dried over anhydrous sodium sulfate. The solvent was distilled off under reduced pressure and suspended in tetrahydrofuran, and the precipitated crystals were filtered out, washed with a small amount of ethyl acetate and blow-dried to obtain the title compound (115.6 mg, 0.237 mmol, 53.0%) as white crystals.

Example 391-2

4-(3-Chloro-4-(cyclopropylaminocarbonyl)aminophenoxy)-7-(1,3-dioxolan-2-yl)methoxy)-6-quinolinecarboxamide The title compound (71.2 mg, 0.143 mmol, 19.0%) was obtained as white crystals from 4-(3-chloro-4-(cyclopropylaminocarbonyl)aminophenoxy)-7-hydroxy-6-quinolinecarboxamide (310 mg, 0.75 mmol) and 2-(bromomethyl)-1,3-dioxolane, by the same procedure as in Example 7.

$^1$H-NMR Spectrum (DMSO-d$_6$) δ (ppm): 0.42 (2H, m), 0.65 (2H, m), 2.56 (1H, m), 3.92-4.02 (4H, m), 4.36 (2H, m), 5.36 (1H, m), 6.53 (1H, d, J=5.2 Hz), 7.20 (1H, d, J=2.8 Hz), 7.26 (1H, dd, J=2.8, 8.8 Hz), 7.51 (1H, d, J=2.8 Hz), 7.58 (1H, s), 7.81 (1H, s), 7.83 (1H, s), 7.99 (1H, s), 8.28 (1H, d, J=8.8 Hz), 8.68 (1H, d, J=5.2 Hz), 8.75 (1H, s).

Example 392

4-(3-Chloro-4-(cyclopropylaminocarbonyl)aminophenoxy)-7-(3-(N,N-diethylamino)propyl)oxy)-6-quinolinecarboxamide The title compound (119.6 mg, 0.227 mmol, 37.5%) was obtained as light yellow crystals from 4-(3-chloro-4-(cyclopropylaminocarbonyl)aminophenoxy)-7-hydroxy-6-quinolinecarboxamide (250 mg, 0.606 mmol) and N-(3-chloropropyl)-N,N-diethylamine hydrochloride, by the same procedure as in Example 7.

$^1$H-NMR Spectrum (DMSO-d$_6$) δ (ppm): 0.42 (2H, m), 0.65 (2H, m), 0.95 (6H, t, J=7.2 Hz), 1.96 (2H, m), 2.45-2.59 (7H, m), 4.30 (2H, m), 6.52 (1H, d, J=5.2 Hz), 7.20 (1H, d, J=2.8 Hz), 7.24 (1H, dd, J=2.8, 9.2 Hz), 7.49 (1H, d, J=2.8 Hz), 7.50 (1H, s), 7.79 (1H, s), 7.86 (1H, s), 7.99 (1H, s), 8.27 (1H, d, J=9.2 Hz), 8.66 (1H, d, J=5.2 Hz), 8.69 (1H, s).

Example 393 tert-Butyl 4-(((6-(aminocarbonyl)-4-(3-chloro-4-((cyclopropylamino)carbonyl)amino)phenoxy)-7-quinolyl)oxy)methyl)-1-piperidinecarboxylate The title compound (460 mg, 0.754 mmol, 44.5%) was obtained as white crystals from 4-(3-chloro-4-(cyclopropylaminocarbonyl)aminophenoxy)-7-hydroxy-6-quinolinecarboxamide (700 mg, 1.696 mmol) and tert-butyl 4-(bromomethyl)-1-piperidinecarboxylate, by the same procedure as in Example 7.

$^1$H-NMR Spectrum (DMSO-d$_6$) δ (ppm): 0.42 (2H, m), 0.65 (2H, m), 1.17-1.25 (3H, m), 1.39 (9H, s), 1.79 (2H, m), 2.10 (1H, m), 2.56 (1H, m), 2.74 (1H, m), 4.01 (2H, m), 4.12 (2H, m), 6.51 (1H, d, J=5.2 Hz), 7.18 (1H, d, J=2.8 Hz), 7.22 (1H, dd, J=2.8, 9.2 Hz), 7.47 (1H, d, J=2.8 Hz), 7.50 (1H, s), 7.70 (1H, br), 7.71 (1H, br), 7.97 (1H, s), 8.25 (1H, d, J=9.2 Hz), 8.55 (1H, s), 8.64 (1H, d, J=5.2 Hz).

Example 394

4-(3-Chloro-4-(cyclopropylaminocarbonyl)aminophenoxy)-7-((1-methyl-4-piperidyl)methoxy)-6-quinolinecarboxamide After dissolving tert-butyl 4-(((6-(aminocarbonyl)-4-(3-chloro-4-((cyclopropylamino)carbonyl)amino)phenoxy)-7-quinolyl)oxy)methyl)-1-piperidinecarboxylate (460 mg, 0.754 mmol) in trifluoroacetic acid (2.3 ml) at room temperature, the solution was stirred for 2 hours. The reaction solution was concentrated under reduced pressure, saturated aqueous sodium bicarbonate was gradually added for neutralization, and the mixture was extracted with ethyl acetate and dried over anhydrous sodium sulfate. The solvent was distilled off under reduced pressure to obtain 4-(3-chloro-4-(cyclopropylaminocarbonyl) aminophenoxy)-7-((4-piperidyl)methoxy)-6-quinolinecarboxamide as a crude product. This was dissolved in tetrahydrofuran (10 ml)-water (10 ml), and then a 37% aqueous formaldehyde solution (1 ml), acetic acid (0.086 ml, 1.51 mmol) and sodium cyanoborohydride (95 mg, 1.51 mmol) were added at room temperature and the mixture was stirred for 20 minutes. The reaction solution was distributed between ethyl acetate and water, and the organic layer was washed with saturated brine and dried over anhydrous sodium sulfate. After distilling off the solvent, the residue was subjected to silica gel column chromatography (eluent—ethyl acetate), the fraction containing the target substance was concentrated and suspended in ethyl acetate, and the suspension was diluted with hexane and the crystals filtered out and blow-dried to obtain the title compound (226.1 mg, 0.431 mmol, two stages, 57.2%) as white crystals.

$^1$H-NMR Spectrum (DMSO-d$_6$) δ (ppm): 0.41 (2H, m), 0.65 (2H, m), 1.37 (2H, m), 1.74-1.89 (5H, m), 2.15 (3H, s), 2.56 (1H, m), 2.79 (2H, m), 4.11 (2H, m), 6.51 (1H, d, J=5.2 Hz), 7.18 (1H, d, J=2.8 Hz), 7.22 (1H, dd, J=2.8, 9.2 Hz), 7.47 (1H, d, J=2.8 Hz), 7.49 (1H, s), 7.70 (1H, s), 7.74 (1H, s), 7.96 (1H, s), 8.25 (1H, d, J=9.2 Hz), 8.59 (1H, s), 8.64 (1H, d, J=5.2 Hz).

Example 395

Methyl 4-(3-chloro-4-(((cyclopropylamino)carbonyl)amino)phenoxy)-7-methoxy-6-quinolinecarboxylate The title compound (2.894 g, 6.55 mmol, 98.5%) was obtained as light brown crystals from phenyl N-(2-chloro-4-(7-methoxy-6-methoxycarbonyl-4-quinolyl)oxyphenyl)carbamate (3.184 g, 6.65 mmol) and cyclopropylamine, by the same procedure as in Example 11.

$^1$H-NMR Spectrum (DMSO-d$_6$) δ (ppm): 0.41 (2H, m), 0.65 (2H, m), 2.56 (1H, m), 3.85 (3H, s), 3.96 (3H, s), 6.52 (1H, d, J=5.2 Hz), 7.19 (1H, d, J=2.8 Hz), 7.24 (1H, dd, J=2.8, 9.2 Hz), 7.50 (1H, d, J=2.8 Hz), 7.52 (1H, s), 7.97 (1H, s), 8.26 (1H, d, J=9.2 Hz), 8.56 (1H, s), 8.68 (1H, d, J=5.2 Hz).

The starting material was synthesized in the following manner.

Production Example 395-1

Methyl 4-(4-amino-3-chlorophenoxy)-7-methoxy-6-quinolinecarboxylate

After dissolving 4-amino-3-chlorophenol (3.17 g, 22.05 mmol) in dimethylsulfoxide (50 ml), sodium hydride (882 mg, 22.05 mmol) was gradually added at room temperature and the mixture was stirred for 30 minutes. The 4-chloro-7-methoxy-6-methoxycarbonylquinoline (3.70 g, 14.7 mmol) described in WO0050405 was added, and the mixture was heated at 100° C. for 3 hours. After standing to cool to room temperature, the reaction solution was distributed between ethyl acetate and water, and the organic layer was washed with water and saturated brine and dried over anhydrous sodium sulfate. The solvent was distilled off, silica gel column chromatography (eluent—ethyl acetate) was performed, the fraction containing the target substance was concentrated, suspended in ethyl acetate and diluted with hexane, and the crystals were filtered out and blow-dried to obtain the title compound (3.092 g, 8.62 mmol, 57.4%) as light brown crystals.

¹H-NMR Spectrum (CDCl₃) δ (ppm): 3.98 (3H, s), 4.06 (3H, s), 4.12 (2H, s), 6.44 (1H, d, J=5.2 Hz), 6.86 (1H, d, J=8.8 Hz), 6.95 (1H, dd, J=2.8, 8.8 Hz), 7.16 (1H, d, J=2.8 Hz), 7.49 (1H, s), 8.64 (1H, d, J=5.2 Hz), 8.80 (1H, s).

Production Example 395-2

Phenyl N-(2-chloro-4-(7-methoxy-6-methoxycarbonyl-4-quinolyl)oxyphenyl)carbamate The title compound (3.184 g, 6.65 mmol, 77.2%) was obtained as light brown crystals from methyl 4-(4-amino-3-chlorophenoxy)-7-methoxy-6-quinolinecarboxylate (3.09 g, 8.61 mmol) in the same manner as Production Example 17.

¹H-NMR Spectrum (CDCl₃) δ (ppm): 3.98 (3H, s), 4.06 (3H, s), 6.48 (1H, d, J=5.2 Hz), 7.17 (1H, dd, J=2.8, 9.2 Hz), 7.21-7.31 (4H, m), 7.41-7.46 (2H, m), 7.50 (2H, br), 8.32 (1H, d, J=8.8 Hz), 8.67 (1H, d, J=5.2 Hz), 8.77 (1H, s).

Example 396

4-(3-Chloro-4-(((cyclopropylamino)carbonyl)amino)phenoxy)-7-methoxy-6-quinolinecarboxylic acid After adding methanol (48 ml) and 2N aqueous sodium hydroxide (16 ml) to methyl 4-(3-chloro-4-(((cyclopropylamino)carbonyl)amino)phenoxy)-7-methoxy-6-quinolinecarboxylate (2.87 g, 6.50 mmol), the mixture was stirred at room temperature for 1.5 hours and at 60° C. for 15 minutes. The reaction solution was allowed to cool to room temperature, and after neutralization by addition of 1N hydrochloric acid, the methanol was distilled off and the precipitated light brown crystals were filtered out, thoroughly washed with water and dried at 70° C. to obtain the title compound (2.628 g, 6.14 mmol, 94.6%).

¹H-NMR Spectrum (DMSO-d₆) δ (ppm): 0.42 (2H, m), 0.65 (2H, m), 2.56 (1H, m), 3.96 (3H, s), 6.51 (1H, d, J=5.2 Hz), 7.17-7.26 (2H, m), 7.49 (2H, s), 7.96 (1H, s), 8.26 (1H, d, J=9.2 Hz), 8.52 (1H, s), 8.66 (1H, d, J=5.2 Hz), 13.08 (1H, br).

Example 397

N6-Cyclopropyl-4-(3-chloro-4-(((cyclopropylamino)carbonyl)amino)phenoxy)-7-methoxy-6-quinolinecarboxamide After dissolving 4-(3-chloro-4-(((cyclopropylamino)carbonyl)amino)phenoxy)-7-methoxy-6-quinolinecarboxylic acid (86 mg, 0.20 mmol) in dimethylformamide (2 ml), there were added 1-ethyl-3-(3-dimethylaminopropyl)carbodiimide hydrochloride (77 mg, 0.40 mmol), 1-hydroxy-1H-benzotriazole monohydrate (61 mg, 0.40 mmol), triethylamine (0.112 ml, 0.80 mmol) and cyclopropylamine (0.055 ml) while stirring on ice, and the mixture was stirred overnight at room temperature. The reaction solution was distributed between ethyl acetate and water, and the organic layer was washed with water and saturated brine and then dried over anhydrous sodium sulfate. After distilling off the solvent, the residue was suspended in ethyl acetate and diluted with hexane, and the crystals were filtered out and blow-dried to obtain the title compound (40.0 mg, 0.086 mmol, 42.6%) as white crystals.

¹H-NMR Spectrum (DMSO-d₆) δ (ppm): 0.41 (2H, m), 0.57 (2H, m), 0.65 (2H, m), 0.69 (2H, m), 2.57 (1H, m), 2.86 (1H, m), 3.97 (3H, s), 6.51 (1H, d, J=5.2 Hz), 7.18 (1H, d, J=2.8 Hz), 7.21 (1H, dd, J=2.8, 9.2 Hz), 7.46 (1H, d, J=2.8 Hz), 7.47 (1H, s), 7.97 (1H, s), 8.26 (1H, d, J=9.2 Hz), 8.33 (1H, m), 8.40 (1H, s), 8.64 (1H, d, J=5.2 Hz).

Example 398

N6-(2-Methoxyethyl)-4-(3-chloro-4-(((cyclopropylamino)carbonyl)amino)phenoxy)-7-methoxy-6-quinolinecarboxamide The title compound (17.8 mg, 0.037 mmol, 18.3%) was obtained as white crystals from 4-(3-chloro-4-(((cyclopropylamino)carbonyl)amino)phenoxy)-7-methoxy-6-quinolinecarboxylic acid (86 mg, 0.20 mmol) and 2-methoxyethylamine, by the same procedure as in Example 397.

¹H-NMR Spectrum (DMSO-d₆) δ (ppm): 0.42 (2H, m), 0.65 (2H, m), 2.57 (1H, m), 3.29 (3H, s), 3.47 (4H, s), 4.01 (3H, s), 6.51 (1H, d, J=5.2 Hz), 7.18 (1H, d, J=2.8 Hz), 7.22 (1H, dd, J=2.8, 9.2 Hz), 7.48 (1H, d, J=2.8 Hz), 7.51 (1H, s), 7.97 (1H, s), 8.26 (1H, d, J=9.2 Hz), 8.43 (1H, s), 8.59 (1H, s), 8.65 (1H, d, J=5.2 Hz).

Example 399

N6-(2-(4-Morpholino)ethyl)-4-(3-chloro-4-(((cyclopropylamino)carbonyl)amino)phenoxy)-7-methoxy-6-quinolinecarboxamide The title compound (62.9 mg, 0.116 mmol, 57.9%) was obtained as light brown crystals from 4-(3-chloro-4-(((cyclopropylamino)carbonyl)amino)phenoxy)-7-methoxy-6-quinolinecarboxylic acid (86 mg, 0.20 mmol) and N-(2-aminoethyl)morpholine, by the same procedure as in Example 397.

¹H-NMR Spectrum (DMSO-d₆) δ (ppm): 0.42 (2H, m), 0.65 (2H, m), 2.43 (4H, br), 2.47-2.51 (2H, m), 2.56 (1H, m), 3.43 (2H, m), 3.60 (4H, m), 4.04 (3H, s), 6.51 (1H, d, J=5.2 Hz), 7.18 (1H, d, J=2.8 Hz), 7.22 (1H, dd, J=2.8, 9.2 Hz), 7.48 (1H, d, J=2.8 Hz), 7.52 (1H, s), 7.97 (1H, s), 8.26 (1H, d, J=9.2 Hz), 8.48 (1H, m), 8.66 (1H, d, J=5.2 Hz), 8.67 (1H, s).

Example 400

N6-(3-(4-Morpholino)propyl)-4-(3-chloro-4-(((cyclopropylamino)carbonyl)amino)phenoxy)-7-methoxy-6-quinolinecarboxamide The title compound (84.7 mg, 0.153 mmol, 76.1%) was obtained as light brown crystals from 4-(3-chloro-4-(((cyclopropylamino)carbonyl)amino)phenoxy)-7-methoxy-6-quinolinecarboxylic acid (86 mg, 0.20 mmol) and N-(3-aminopropyl)morpholine, by the same procedure as in Example 397.

¹H-NMR Spectrum (DMSO-d₆) δ (ppm): 0.42 (2H, m), 0.65 (2H, m), 1.69 (2H, m), 2.33-2.37 (6H, m), 2.56 (1H, m), 3.30-3.37 (2H, m), 3.56 (4H, m), 4.02 (3H, s), 6.51 (1H, d, J=5.6 Hz), 7.20 (1H, d, J=2.8 Hz), 7.23 (1H, dd, J=2.8, 9.2 Hz), 7.48 (1H, d, J=2.8 Hz), 7.52 (1H, s), 7.98 (1H, s), 8.27 (1H, d, J=9.2 Hz), 8.40 (1H, m), 8.52 (1H, s), 8.66 (1H, d, J=5.6 Hz).

Example 401

N6-(2-(Diethylamino)ethyl)-4-(3-chloro-4-(((cyclopropylamino)carbonyl)amino)phenoxy)-7-methoxy-6-quinolinecarboxamide The title compound (67.7 mg, 0.129 mmol, 64.0%) was obtained as light brown crystals from 4-(3-chloro-4-(((cyclopropylamino)carbonyl)amino)phenoxy)-7-methoxy-6-quinolinecarboxylic acid (86 mg, 0.20 mmol) and N-(2-aminoethyl)-N,N-diethylamine, by the same procedure as in Example 397.

$^1$H-NMR Spectrum (DMSO-d$_6$) δ (ppm): 0.42 (2H, m), 0.65 (2H, m), 0.98 (6H, t, J=7.2 Hz), 2.47-2.59 (7H, m), 3.37 (2H, m), 4.03 (3H, s), 6.51 (1H, d, J=5.2 Hz), 7.18 (1H, d, J=2.8 Hz), 7.22 (1H, dd, J=2.8, 8.8 Hz), 7.47 (1H, d, J=2.8 Hz), 7.52 (1H, s), 7.97 (1H, s), 8.25 (1H, d, J=8.8 Hz), 8.48 (1H, m), 8.65 (1H, d, J=5.2 Hz), 8.69 (1H, s).

Example 402

N6-(3-(1-Pyrrolidino)propyl)-4-(3-chloro-4-(((cyclopropylamino)carbonyl)amino)phenoxy)-7-methoxy-6-quinolinecarboxamide The title compound (87.0 mg, 0.162 mmol, 80.4%) was obtained as light brown crystals from 4-(3-chloro-4-(((cyclopropylamino)carbonyl)amino)phenoxy)-7-methoxy-6-quinolinecarboxylic acid (86 mg, 0.20 mmol) and 1-(3-aminopropyl)pyrrolidine, by the same procedure as in Example 397.

$^1$H-NMR Spectrum (DMSO-d$_6$) δ (ppm): 0.41 (2H, m), 0.65 (2H, m), 1.65-1.72 (6H, m), 2.41-2.49 (6H, m), 2.56 (1H, m), 3.28-3.36 (2H, m), 4.01 (3H, s), 6.51 (1H, d, J=5.2 Hz), 7.18 (1H, m), 7.22 (1H, m), 7.47 (1H, d, J=2.8 Hz), 7.50 (1H, s), 7.96 (1H, s), 8.25 (1H, dd, J=1.2, 9.2 Hz), 8.41 (1H, m), 8.51 (1H, s), 8.65 (1H, d, J=5.2 Hz).

Example 403

N6-(2-(2-Pyridyl)ethyl)-4-(3-chloro-4-(((cyclopropylamino)carbonyl)amino)phenoxy)-7-methoxy-6-quinolinecarboxamide The title compound (78.4 mg, 0.147 mmol, 73.7%) was obtained as light brown crystals from 4-(3-chloro-4-(((cyclopropylamino)carbonyl)amino)phenoxy)-7-methoxy-6-quinolinecarboxylic acid (86 mg, 0.20 mmol) and 2-(2-aminoethyl)pyridine, by the same procedure as in Example 397.

$^1$H-NMR Spectrum (DMSO-d$_6$) δ (ppm): 0.41 (2H, m), 0.65 (2H, m), 2.56 (1H, m), 3.02 (2H, m), 3.68 (2H, m), 3.97 (3H, s), 6.51 (1H, d, J=5.2 Hz), 7.18 (1H, d, J=2.8 Hz), 7.21-7.24 (2H, m), 7.32 (1H, d, J=7.6 Hz), 7.47-7.49 (2H, m), 7.72 (1H, m), 7.97 (1H, s), 8.26 (1H, d, J=8.8 Hz), 8.53-8.59 (3H, m), 8.65 (1H, d, J=5.2 Hz).

Example 404

N6-(2-(Methylsulfonyl)ethyl)-4-(3-chloro-4-(((cyclopropylamino)carbonyl)amino)phenoxy)-7-methoxy-6-quinolinecarboxamide The title compound (58.8 mg, 0.110 mmol, 55.2%) was obtained as light brown crystals from 4-(3-chloro-4-(((cyclopropylamino)carbonyl)amino)phenoxy)-7-methoxy-6-quinolinecarboxylic acid (86 mg, 0.20 mmol) and 2-(methylsulfonyl)ethylamine, by the same procedure as in Example 397.

$^1$H-NMR Spectrum (DMSO-d$_6$) δ (ppm): 0.41 (2H, m), 0.65 (2H, m), 2.56 (1H, m), 3.06 (3H, s), 3.41 (2H, m), 3.75 (2H, m), 4.01 (3H, s), 6.51 (1H, d, J=5.2 Hz), 7.18 (1H, d, J=2.8 Hz), 7.22 (1H, dd, J=2.8, 9.2 Hz), 7.48 (1H, d, J=2.8 Hz), 7.52 (1H, s), 7.97 (1H, s), 8.26 (1H, d, J=9.2 Hz), 8.66 (1H, d, J=5.2 Hz), 8.67 (1H, s), 8.75 (1H, m).

Example 405

N6-(1H-2-Imidazolyl)-4-(3-chloro-4-(((cyclopropylamino)carbonyl)amino)phenoxy)-7-methoxy-6-quinolinecarboxamide The title compound (27.0 mg, 0.055 mmol, 27.3%) was obtained as light brown crystals from 4-(3-chloro-4-(((cyclopropylamino)carbonyl)amino)phenoxy)-7-methoxy-6-quinolinecarboxylic acid (86 mg, 0.20 mmol) and 2-aminoimidazole, by the same procedure as in Example 397.

$^1$H-NMR Spectrum (DMSO-d$_6$) δ (ppm): 0.41 (2H, m), 0.65 (2H, m), 2.56 (1H, m), 4.03 (3H, s), 6.55 (1H, d, J=5.2 Hz), 6.72 (1H, m), 6.85 (1H, m), 7.18 (1H, d, J=2.8 Hz), 7.24 (1H, dd, J=2.8, 8.8 Hz), 7.48 (1H, d, J=2.8 Hz), 7.55 (1H, s), 7.97 (1H, s), 8.26 (1H, d, J=8.8 Hz), 8.52 (1H, s), 8.68 (1H, d, J=5.2 Hz), 11.21 (1H, br), 11.80 (1H, m).

Example 406

N6-(1,3-Thiazol-2-yl)-4-(3-chloro-4-(((cyclopropylamino)carbonyl)amino)phenoxy)-7-methoxy-6-quinolinecarboxamide The title compound (83.7 mg, 0.164 mmol, 81.7%) was obtained as light brown crystals from 4-(3-chloro-4-(((cyclopropylamino)carbonyl)amino)phenoxy)-7-methoxy-6-quinolinecarboxylic acid (86 mg, 0.20 mmol) and 2-aminothiazole, by the same procedure as in Example 397.

$^1$H-NMR Spectrum (DMSO-d$_6$) δ (ppm): 0.41 (2H, m), 0.65 (2H, m), 2.56 (1H, m), 4.03 (3H, s), 6.56 (1H, dd, J=1.6, 5.2 Hz), 7.18 (1H, s), 7.23 (1H, m), 7.30 (1H, s), 7.47-7.57 (3H, m), 7.97 (1H, s), 8.26 (1H, dd, J=1.6, 8.8 Hz), 8.53 (1H, s), 8.69 (1H, dd, J=1.6, 5.2 Hz), 12.28 (1H, s).

Example 407

N6-(2-Pyridyl)-4-(3-chloro-4-(((cyclopropylamino)carbonyl)amino)phenoxy)-7-methoxy-6-quinolinecarboxamide The title compound (17.0 mg, 0.034 mmol, 33.6%) was obtained as light brown crystals from 4-(3-chloro-4-(((cyclopropylamino)carbonyl)amino)phenoxy)-7-methoxy-6-quinolinecarboxylic acid (43 mg, 0.10 mmol) and 2-aminopyridine, by the same procedure as in Example 397.

$^1$H-NMR Spectrum (DMSO-d$_6$) δ (ppm): 0.41 (2H, m), 0.65 (2H, m), 2.56 (1H, m), 4.09 (3H, s), 6.55 (1H, d, J=5.2 Hz), 7.15-7.26 (3H, m), 7.50 (1H, s), 7.59 (1H, s), 7.86 (1H, m), 7.98 (1H, s), 8.26 (2H, d, J=9.2 Hz), 8.36 (1H, m), 8.68-8.70 (2H, m), 10.70 (1H, s).

Example 408

N6-(3-Pyridyl)-4-(3-chloro-4-(((cyclopropylamino)carbonyl)amino)phenoxy)-7-methoxy-6-quinolinecarboxamide The title compound (46.4 mg, 0.092 mmol, 92.1%) was obtained as light brown crystals from 4-(3-chloro-4-(((cyclopropylamino)carbonyl)amino)phenoxy)-7-methoxy-6-quinolinecarboxylic acid (43 mg, 0.10 mmol) and 3-aminopyridine, by the same procedure as in Example 397.

$^1$H-NMR Spectrum (DMSO-d$_6$) δ (ppm): 0.41 (2H, m), 0.65 (2H, m), 2.56 (1H, m), 4.09 (3H, s), 6.56 (1H, d, J=5.2 Hz), 7.23-7.41 (3H, m), 7.46 (1H, s), 7.57 (1H, s), 8.03 (1H, s), 8.18-8.31 (3H, m), 8.48 (1H, s), 8.68 (1H, d, J=5.2 Hz), 8.80 (1H, s), 10.58 (1H, s).

Example 409

N6-(4-Pyridyl)-4-(3-chloro-4-(((cyclopropylamino)carbonyl)amino)phenoxy)-7-methoxy-6-quinolinecarboxamide The title compound (31.1 mg, 0.062 mmol, 61.7%) was obtained as light brown crystals from 4-(3-chloro-4-(((cyclopropylamino)carbonyl)amino)phenoxy)-7-methoxy-6-quinolinecarboxylic acid (43 mg, 0.10 mmol) and 4-aminopyridine, by the same procedure as in Example 397.

$^1$H-NMR Spectrum (DMSO-d$_6$) δ (ppm): 0.41 (2H, m), 0.65 (2H, m), 2.56 (1H, m), 4.01 (3H, s), 6.56 (1H, d, J=5.2 Hz), 7.21-7.24 (2H, m), 7.47 (1H, d, J=2.8 Hz), 7.57 (1H, s), 7.71 (2H, d, J=5.6 Hz), 7.99 (1H, s), 8.26 (1H, d, J=9.2 Hz), 8.44-8.48 (3H, m), 8.69 (1H, d, J=5.2 Hz), 10.73 (1H, s).

Example 410

N6-(2-Hydroxyethyl)-4-(3-chloro-4-(((cyclopropylamino)carbonyl)amino)phenoxy)-7-methoxy-6-quinolinecarboxamide The title compound (34.4 mg, 0.073 mmol, 36.3) was obtained as white crystals from 4-(3-chloro-4-(((cyclopropylamino)carbonyl)amino)phenoxy)-7-methoxy-6-quinolinecarboxylic acid (86 mg, 0.20 mmol) and 2-aminoethanol, by the same procedure as in Example 397.

$^1$H-NMR Spectrum (DMSO-d$_6$) δ (ppm): 0.41 (2H, m), 0.65 (2H, m), 2.56 (1H, m), 3.40 (2H, m), 3.55 (2H, m), 4.03 (3H, s), 4.80 (1H, t, J=5.6 Hz), 6.56 (1H, d, J=5.2 Hz), 7.20 (1H, d, J=2.8 Hz), 7.25 (1H, dd, J=2.8, 9.2 Hz), 7.50 (1H, d, J=2.8 Hz), 7.53 (1H, s), 7.99 (1H, s), 8.28 (1H, d, J=9.2 Hz), 8.42 (1H, m), 8.65 (1H, s), 8.67 (1H, d, J=5.2 Hz).

Example 411

N6-(3-Hydroxypropyl)-4-(3-chloro-4-(((cyclopropylamino)carbonyl)amino)phenoxy)-7-methoxy-6-quinolinecarboxamide The title compound (51.2 mg, 0.106 mmol, 52.5%) was obtained as white crystals from 4-(3-chloro-4-(((cyclopropylamino)carbonyl)amino)phenoxy)-7-methoxy-6-quinolinecarboxylic acid (86 mg, 0.20 mmol) and 3-aminopropanol, by the same procedure as in Example 397.

$^1$H-NMR Spectrum (DMSO-d$_6$) δ (ppm): 0.41 (2H, m), 0.65 (2H, m), 1.67 (2H, m), 2.56 (1H, m), 3.36 (2H, m), 3.50 (2H, m), 4.02 (3H, s), 4.56 (1H, t, J=5.2 Hz), 6.51 (1H, d, J=5.2 Hz), 7.18 (1H, d, J=2.8 Hz), 7.22 (1H, dd, J=2.8, 9.2 Hz), 7.47 (1H, d, J=2.8 Hz), 7.50 (1H, s), 7.97 (1H, s), 8.26 (1H, d, J=9.2 Hz), 8.48 (1H, m), 8.57 (1H, s), 8.65 (1H, d, J=5.2 Hz).

Example 412

N6-((2-Hydroxy-1-(hydroxymethyl)ethyl)-4-(3-chloro-4-(((cyclopropylamino)carbonyl)amino)phenoxy)-7-methoxy-6-quinolinecarboxamide After dissolving 4-(3-chloro-4-(((cyclopropylamino)carbonyl)amino)phenoxy)-7-methoxy-6-quinolinecarboxylic acid (86 mg, 0.20 mmol) in dimethylformamide (4 ml) under a nitrogen atmosphere, serinol (37 mg, 0.40 mmol), triethylamine (0.2 ml) and (1H-1,2,3-benzotriazol-1-yloxy)(tri(dimethylamino))phosphonium hexafluorophosphate (177 mg, 0.40 mmol) were added in that order at room temperature, and the mixture was stirred for 8 hours. The reaction solution was distributed between ethyl acetate and water, and the organic layer was washed with water and saturated brine and dried over anhydrous sodium sulfate. The solvent was distilled off, and purification was performed by silica gel column chromatography (eluent—ethyl acetate:methanol=9:1). The fraction containing the target substance was concentrated under reduced pressure and suspended in ethyl acetate, the suspension was diluted with hexane, and the crystals were filtered out and blow-dried to obtain the title compound (75.8 mg, 0.151 mmol, 75.3%) as white crystals.

$^1$H-NMR Spectrum (DMSO-d$_6$) δ (ppm): 0.42 (2H, m), 0.65 (2H, m), 2.56 (1H, m), 3.50 (2H, m), 3.56 (2H, m), 3.96 (1H, m), 4.03 (3H, s), 4.80 (2H, t, J=5.2 Hz), 6.51 (1H, d, J=5.2 Hz), 7.19 (1H, d, J=2.8 Hz), 7.23 (1H, dd, J=2.8, 9.2 Hz), 7.48 (1H, d, J=2.8 Hz), 7.53 (1H, s), 7.97 (1H, s), 8.26 (1H, d, J=9.2 Hz), 8.29 (1H, m), 8.66 (1H, d, J=5.2 Hz), 8.72 (1H, s).

Example 413

N6-(1,3-Dioxolan-2-ylmethyl)-4-(3-chloro-4-(((cyclopropylamino)carbonyl)amino)phenoxy)-7-methoxy-6-quinolinecarboxamide The title compound (190.3 mg, 0.371 mmol, 79.4%) was obtained as white crystals from 4-(3-chloro-4-(((cyclopropylamino)carbonyl)amino)phenoxy)-7-methoxy-6-quinolinecarboxylic acid (200 mg, 0.467 mmol) and 2-aminomethyl-1,3-dioxolane, by the same procedure as in Example 412.

$^1$H-NMR Spectrum (DMSO-d$_6$) δ (ppm): 0.41 (2H, m), 0.65 (2H, m), 2.56 (1H, m), 3.51 (2H, m), 3.85 (2H, m), 3.96 (2H, m), 4.04 (3H, s), 5.04 (1H, m), 6.51 (1H, d, J=5.2 Hz), 7.20 (1H, d, J=2.8 Hz), 7.25 (1H, dd, J=2.8, 9.2 Hz), 7.49 (1H, d, J=2.8 Hz), 7.54 (1H, s), 7.99 (1H, s), 8.27 (1H, d, J=9.2 Hz), 8.48 (1H, m), 8.64 (1H, s), 8.68 (1H, d, J=5.2 Hz).

Example 414

N6-(tert-Butoxy)-4-(3-chloro-4-(((cyclopropylamino)carbonyl)amino)phenoxy)-7-methoxy-6-quinolinecarboxamide The title compound (360 mg, 0.722 mmol, 72.2%) was obtained as white crystals from 4-(3-chloro-4-(((cyclopropylamino)carbonyl)amino)phenoxy)-7-methoxy-6-quinolinecarboxylic acid (428 mg, 1.00 mmol) and tert-butoxylamine hydrochloride, by the same procedure as in Example 412.

$^1$H-NMR Spectrum (DMSO-d$_6$) δ (ppm): 0.42 (2H, m), 0.65 (2H, m), 1.25 (9H, s), 2.56 (1H, m), 3.97 (3H, s), 6.52 (1H, d, J=5.2 Hz), 7.18 (1H, d, J=2.8 Hz), 7.22 (1H, dd, J=2.8, 9.2 Hz), 7.47 (1H, d, J=2.8 Hz), 7.49 (1H, s), 7.97 (1H, s), 8.24 (1H, s), 8.26 (1H, d, J=9.2 Hz), 8.65 (1H, d, J=5.2 Hz), 10.75 (1H, s).

Example 415

N6-(2-Fluoroethyl)-4-(3-chloro-4-(((cyclopropylamino)carbonyl)amino)phenoxy)-7-methoxy-6-quinolinecarboxamide The title compound (130.7 mg, 0.276 mmol, 69.1%) was obtained as white crystals from 4-(3-chloro-4-(((cyclopropylamino)carbonyl)amino)phenoxy)-7-methoxy-6-quinolinecarboxylic acid (171 mg, 0.40 mmol) and 2-fluoroethylamine hydrochloride, by the same procedure as in Example 412.

$^1$H-NMR Spectrum (DMSO-d$_6$) δ (ppm): 0.41 (2H, m), 0.65 (2H, m), 2.56 (1H, m), 3.59 (1H, m), 3.67 (1H, m), 4.03 (3H, s), 4.50 (1H, m), 4.62 (1H, m), 6.52 (1H, d, J=5.2 Hz), 7.19 (1H, d, J=2.8 Hz), 7.24 (1H, dd, J=2.8, 9.2 Hz), 7.49 (1H, d, J=2.8 Hz), 7.53 (1H, s), 7.99 (1H, s), 8.28 (1H, d, J=9.2 Hz), 8.58-8.62 (2H, m), 8.67 (1H, d, J=5.2 Hz).

Example 416

N6-(2-(Methylthio)ethyl)-4-(3-chloro-4-(((cyclopropylamino)carbonyl)amino)phenoxy)-7-methoxy-6-quinolinecarboxamide The title compound (146.2 mg, 0.292 mmol, 73.0%) was obtained as white crystals from 4-(3-chloro-4-(((cyclopropylamino)carbonyl)amino)phenoxy)-7-methoxy-6-quinolinecarboxylic acid (171 mg, 0.40 mmol) and 2-(methylthio)ethylamine, by the same procedure as in Example 412.

$^1$H-NMR Spectrum (DMSO-d$_6$) δ (ppm): 0.42 (2H, m), 0.65 (2H, m), 2.10 (3H, s), 2.56 (1H, m), 2.67 (2H, m), 3.50 (2H, m), 4.02 (3H, s), 6.51 (1H, d, J=5.2 Hz), 7.18 (1H, d, J=2.8 Hz), 7.22 (1H, dd, J=2.8, 9.2 Hz), 7.48 (1H, d, J=2.8 Hz), 7.51 (1H, s), 7.97 (1H, s), 8.26 (1H, d, J=9.2 Hz), 8.56 (1H, m), 8.61 (1H, s), 8.65 (1H, d, J=5.2 Hz).

Example 417

N6-Methoxy-4-(3-chloro-4-(((cyclopropylamino)carbonyl)amino)phenoxy)-7-methoxy-6-quinolinecarboxamide The title compound (109.3 mg, 0.239 mmol, 59.9%) was obtained as white crystals from 4-(3-chloro-4-(((cyclopropylamino)carbonyl)amino)phenoxy)-7-methoxy-6-quinolinecarboxylic acid (171 mg, 0.40 mmol) and methoxyamine hydrochloride, by the same procedure as in Example 412.

$^1$H-NMR Spectrum (DMSO-d$_6$) δ (ppm): 0.42 (2H, m), 0.65 (2H, m), 2.56 (1H, m), 3.74 (3H, s), 3.99 (3H, s), 6.54 (1H, d, J=5.2 Hz), 7.20 (1H, d, J=2.8 Hz), 7.25 (1H, dd, J=2.8, 9.2 Hz), 7.48 (1H, d, J=2.8 Hz), 7.49 (1H, s), 7.99 (1H, s), 8.28 (1H, d, J=9.2 Hz), 8.43 (1H, s), 8.67 (1H, d, J=5.2 Hz), 11.46 (1H, s).

Example 418

N-(4-((7-(Benzyloxy)-6-cyano-4-quinolyl))oxy-2-chlorophenyl)-N'-cyclopropylurea

After dissolving 4-(4-amino-3-chlorophenoxy)-7-benzyloxy-6-cyanoquinoline (8.037 g, 20.0 mmol) in dimethylformamide (40 ml) under a nitrogen atmosphere, pyridine (1.94 ml, 24.0 mmol) and phenylchloroformate (3.01 ml, 24.0 mmol) were added dropwise at room temperature and the mixture was stirred for 1 hour. Cyclopropylamine (3.46 ml, 50 mmol) was added dropwise, and the mixture was further stirred for 3 hours. Water (400 ml) and diethyl ether (400 ml) were added to the reaction solution, and after stirring overnight, the precipitated crystals were filtered out, washed with water and diethyl ether and dried at 70° C. to obtain the title compound (8.570 g, 17.7 mmol, 88.4%) as light brown crystals.

$^1$H-NMR Spectrum (DMSO-d$_6$) δ (ppm): 0.42 (2H, m), 0.65 (2H, m), 2.56 (1H, m), 5.45 (2H, s), 6.58 (1H, d, J=5.2 Hz), 7.19 (1H, d, J=2.8 Hz), 7.25 (1H, dd, J=2.8, 9.2 Hz), 7.36 (1H, m), 7.44 (2H, t, J=7.2 Hz), 7.50 (1H, d, J=2.8 Hz), 7.54 (2H, d, J=7.2 Hz), 7.71 (1H, s), 7.98 (1H, s), 8.27 (1H, d, J=9.2 Hz), 8.73 (1H, d, J=5.2 Hz), 8.77 (1H, s).

Example 419

N-(2-Chloro-4-((6-cyano-7-(3-(diethylamino)propoxy)-4-quinolyl)oxy)phenyl)-N'-cyclopropylurea An N-(4-(6-cyano-7-hydroxy-4-quinolyl)oxy-2-chlorophenyl)-N'-cyclopropylurea crude product (5.67 g) was obtained as light brown crystals from N-(4-((7-(benzyloxy)-6-cyano-4-quinolyl))oxy-2-chlorophenyl)-N'-cyclopropylurea (8.53 g, 17.6 mmol) by the same procedure as in Example 83. The title compound (200 mg, 0.394 mmol, 24.6%) was obtained as light yellow crystals from the crude product (500 mg, 1.60 mmol) and N-(3-chloropropyl)-N,N-diethylamine hydrochloride, by the same procedure as in Example 7.

$^1$H-NMR Spectrum (CDCl$_3$) δ (ppm): 0.79 (2H, m), 0.96 (2H, m), 1.05 (6H, t, J=7.2 Hz), 2.06 (2H, m), 2.52-2.60 (5H, m), 2.67-2.73 (3H, m), 4.29 (2H, t, J=6.0 Hz), 5.00 (1H, s), 6.49 (1H, d, J=5.2 Hz), 7.12 (1H, dd, J=2.8, 8.8 Hz), 7.48 (1H, s), 7.72 (1H, s), 8.44 (1H, d, J=8.8 Hz), 8.66 (1H, s), 8.68 (1H, d, J=5.2 Hz).

Example 420 tert-Butyl 4-(((4-(3-chloro-4-((cyclopropylamino)carbonyl)aminophenoxy)-6-cyano-7-quinolyl)oxy)methyl)-1-piperidine carboxylate The title compound (275.8 mg, 0.466 mmol, 14.6%) was obtained as white crystals from an N-(4-(6-cyano-7-hydroxy-4-quinolyl)oxy-2-chlorophenyl)-N'-cyclopropylurea crude product (1.00 g, 3.20 mmol) and tert-butyl 4-(bromomethyl)-1-piperidinecarboxylate, by the same procedure as in Example 7.

$^1$H-NMR Spectrum (CDCl$_3$) δ (ppm): 0.79 (2H, m), 0.96 (2H, m), 1.33 (3H, m), 1.48 (9H, s), 1.93 (2H, m), 2.16 (1H, m), 2.68 (1H, m), 2.79 (2H, m), 4.06 (2H, d, J=6.8 Hz), 4.20 (2H, m), 4.99 (1H, s), 6.50 (1H, d, J=5.2 Hz), 7.12 (1H, dd, J=2.8, 9.2 Hz), 7.43 (1H, d, J=2.8 Hz), 7.72 (1H, s), 8.44 (1H, d, J=9.2 Hz), 8.66 (1H, s), 8.68 (1H, d, J=5.2 Hz).

Example 421

N-(2-Chloro-4-((6-cyano-7-(4-piperidylmethoxy)-4-quinolyl)oxy)phenyl)-N'-cyclopropylurea After adding trifluoroacetic acid (2.5 ml) to tert-butyl 4-(((4-(3-chloro-4-((cyclopropylamino)carbonyl)aminophenoxy)-6-cyano-7-quinolyl)oxy)methyl)-1-piperidinecarboxylate (501 mg, 0.846 mmol) at room temperature, the mixture was stirred for 1 hour. The reaction solution was diluted with water (35 ml) while cooling in an ice water bath, and then sodium bicarbonate (3.5 g) was gradually added for neutralization and extraction was performed with ethyl acetate. The organic layer was washed with water and saturated brine, and then dried over anhydrous sodium sulfate. The solvent was distilled off, the residue was suspended in ethyl acetate and diluted with hexane, and the precipitated crystals were filtered out and blow-dried to obtain the title compound (414.4 mg, 0.842 mmol, 99.6%) as white crystals.

$^1$H-NMR Spectrum (DMSO-$d_6$) δ (ppm): 0.41 (2H, m), 0.65 (2H, m), 1.49 (2H, m), 1.92-1.97 (3H, m), 2.48 (1H, m), 2.56 (1H, m), 2.86-2.93 (3H, m), 4.19 (2H, d, J=6.0 Hz), 6.58 (1H, dd, J=1.2, 5.2 Hz), 7.20 (1H, s), 7.24 (1H, d, J=9.2 Hz), 7.48 (1H, d, J=1.2 Hz), 7.63 (1H, s), 7.99 (1H, s), 8.27 (1H, d, J=9.2 Hz), 8.72-8.75 (2H, m).

Example 422

N-(2-Chloro-4-((6-cyano-7-((1-methyl-4-piperidyl)methoxy)-4-quinolyl)oxy)phenyl)-N'-cyclopropylurea After dissolving N-(2-chloro-4-((6-cyano-7-(4-piperidyl-methoxy)-4-quinolyl)oxy)phenyl)-N'-cyclopropylurea (540 mg, 0.846 mmol) in tetrahydrofuran (20 ml)-methanol (20 ml), there were added 37% aqueous formaldehyde (1 ml), acetic acid (0.10 ml, 1.69 mmol) and sodium cyanoborohydride (106 mg, 1.69 mmol) at room temperature, and the mixture was stirred for 1 hour. The reaction solution was distributed between ethyl acetate and saturated aqueous sodium bicarbonate, and the organic layer was washed with saturated brine and dried over anhydrous sodium sulfate. The solvent was distilled off, the residue was suspended in ethyl acetate and diluted with hexane, and the crystals were filtered out and blow-dried to obtain the title compound (282 mg, 0.557 mmol, 65.9%) as white crystals.

$^1$H-NMR Spectrum (DMSO-$d_6$) δ (ppm): 0.41 (2H, m), 0.66 (2H, m), 1.39 (2H, m), 1.75-1.90 (5H, m), 2.15 (3H, s), 2.56 (1H, m), 2.79 (2H, d, J=7.2 Hz), 4.14 (2H, d, J=5.6 Hz), 6.57 (1H, d, J=5.2 Hz), 7.19 (1H, d, J=2.8 Hz), 7.24 (1H, dd, J=2.8, 9.2 Hz), 7.49 (1H, d, J=2.8 Hz), 7.58 (1H, s), 7.98 (1H, s), 8.27 (1H, d, J=9.2 Hz), 8.71-8.75 (2H, m).

Example 423

N-(4-((7-(3-Bromopropoxy)-6-cyano-4-quinolyl)oxy)-2-chlorophenyl)-N'-cyclopropylurea The title compound (129 mg, 0.250 mmol, 15.6%) was obtained as light brown crystals from an N-(4-(6-cyano-7-hydroxy-4-quinolyl)oxy-2-chlorophenyl)-N'-cyclopropylurea crude product (500 mg, 1.60 mmol) and 1,3-dibromopropane, by the same procedure as in Example 7.

$^1$H-NMR Spectrum (DMSO-$d_6$) δ (ppm): 0.43 (2H, m), 0.65 (2H, m), 2.37 (2H, m), 2.56 (1H, m), 3.65 (2H, m), 4.41 (2H, m), 6.60 (1H, d, J=5.2 Hz), 7.20 (1H, d, J=2.8 Hz), 7.26 (1H, dd, J=2.8, 8.8 Hz), 7.51 (1H, d, J=2.8 Hz), 7.65 (1H, s), 7.99 (1H, s), 8.28 (1H, d, J=8.8 Hz), 8.73-8.78 (2H, m).

Example 424

N-(2-Chloro-4-(6-cyano-7-(3-(1-pyrrolidino)propoxy)-4-quinolyl)oxy)phenyl)-N'-cyclopropylurea After dissolving N-(4-((7-(3-bromopropoxy)-6-cyano-4-quinolyl)oxy)-2-chlorophenyl)-N'-cyclopropylurea (116 mg, 0.225 mmol) in dimethylformamide (1.2 ml), pyrrolidine (0.20 ml) was added and the mixture was stirred at room temperature for 4 hours. The reaction solution was distributed between ethyl acetate and water, and the organic layer was washed with saturated brine and dried over anhydrous sodium sulfate. The solvent was distilled off, the residue was subjected to silica gel column chromatography (eluent-ethyl acetate), the fraction containing the target substance was concentrated, suspended in ethyl acetate and diluted with hexane, and the crystals were filtered out and blow-dried to obtain the title compound (57.3 mg, 0.113 mmol, 50.3%) as white crystals.

$^1$H-NMR Spectrum (DMSO-$d_6$) δ (ppm): 0.42 (2H, m), 0.65 (2H, m), 1.68 (4H, br), 1.99 (2H, m), 2.45-2.61 (7H, m), 4.33 (2H, m), 6.56 (1H, d, J=5.2 Hz), 7.19 (1H, d, J=2.8 Hz), 7.24 (1H, dd, J=2.8, 9.2 Hz), 7.49 (1H, d, J=2.8 Hz), 7.59 (1H, s), 7.98 (1H, s), 8.27 (1H, d, J=9.2 Hz), 8.72 (1H, d, J=5.2 Hz), 8.73 (1H, s).

Example 425

N-(2-Chloro-4-((6-cyano-7-((1-methyl-3-piperidyl)methoxy)-4-quinolyl)oxy)phenyl)-N'-cyclopropylurea After dissolving 4-(4-amino-3-chlorophenoxy)-6-cyano-7-((1-methyl-3-piperidyl)methoxy)quinoline (246 mg, 0.582 mmol) in dimethylformamide (6 ml) under a nitrogen atmosphere, pyridine (0.19 ml, 2.33 mmol) and phenylchloroformate (0.15 ml, 1.16 mmol) were added dropwise at room temperature, and the mixture was stirred for 1 hour. Cyclopropylamine (0.20 ml, 2.91 mmol) was added dropwise, and the mixture was further stirred for 3 hours. The reaction solution was distributed between ethyl acetate and saturated aqueous sodium bicarbonate, and the organic layer was washed with water and saturated brine and dried over anhydrous sodium sulfate. The solvent was distilled off, the residue was suspended in methanol and diluted with water, and the crystals were filtered out and dried at 70° C. to obtain the title compound (198.7 mg, 0.393 mmol, 67.5%) as light yellow crystals.

$^1$H-NMR Spectrum (DMSO-$d_6$) δ (ppm): 0.41 (2H, m), 0.65 (2H, m), 1.18 (1H, m), 1.54 (1H, m), 1.68 (1H, m), 1.79 (1H, m), 1.90 (2H, m), 2.11 (1H, m), 2.17 (3H, s), 2.56 (1H, m), 2.65 (1H, m), 2.85 (1H, m), 4.18 (2H, d, J=6.4 Hz), 6.59 (1H, d, J=5.2 Hz), 7.20 (1H, d, J=2.8 Hz), 7.26 (1H, dd, J=2.8, 9.2 Hz), 7.51 (1H, s), 7.60 (1H, s), 8.00 (1H, s), 8.29 (1H, d, J=9.2 Hz), 8.74-8.76 (2H, m).

The starting material was synthesized in the following manner.

Production Example 425-1

4-(4-Amino-3-chlorophenoxy)-6-cyano-7-((1-methyl-3-piperidyl)methoxy)quinoline

A 4-(4-amino-3-chlorophenoxy)-6-cyano-7-hydroxyquinoline crude product (3.306 g) was obtained as light brown crystals from 4-(4-amino-3-chlorophenoxy)-7-benzyloxy-6-cyanoquinoline (3.728 g, 9.28 mmol), by the same procedure as in Example 83. The title compound (246 mg, 0.581 mmol, 36.4%) was obtained as light brown crystals from the crude product (500 mg, 1.60 mmol) and 3-chloromethyl-1-methylpiperidine hydrochloride, by the same procedure as in Example 7.

$^1$H-NMR Spectrum (CDCl$_3$) δ (ppm): 1.25 (1H, m), 1.62-2.01 (5H, m), 2.27 (1H, m), 2.33 (3H, s), 2.33 (1H, m), 2.76 (1H, m), 4.05-4.15 (4H, m), 6.46 (1H, d, J=5.2 Hz), 6.86 (1H, d, J=8.8 Hz), 6.93 (1H, dd, J=2.8, 8.8 Hz), 7.14 (1H, d, J=2.8 Hz), 7.43 (1H, s), 8.65-8.67 (2H, m).

Example 426 tert-Butyl 4-(2-((4-(3-chloro-4-((cyclopropylamino) carbonyl)aminophenoxy)-6-cyano-7-quinolyl)oxy) ethyl)-1-piperidinecarboxylate After dissolving tert-butyl 4-(((4-(4-amino-3-chlorophenoxy)-6-cyano-7-quinolyl)oxy)ethyl)-1-piperidine carboxylate (486.5 mg, 0.930 mmol) in dimethylformamide (5 ml) under a nitrogen atmosphere, pyridine (0.170 ml, 2.09 mmol) and phenyl chloroformate (0.175 ml, 1.34 mmol) were added dropwise at room temperature, and the mixture was stirred for 1 hour. Cyclopropylamine (0.322 ml, 4.65 mmol) was added dropwise, and the mixture was further stirred overnight. The reaction solution was distributed between ethyl acetate and saturated aqueous sodium bicarbonate, and the organic layer was washed with water and saturated brine and dried over anhydrous sodium sulfate. The solvent was distilled off, the residue was subjected to silica gel column chromatography (eluent-ethyl acetate), the fraction containing the target substance was concentrated, suspended in ethyl acetate and diluted with hexane, and the crystals were filtered out and blow-dried to obtain the title compound (343 mg, 0.566 mmol, 60.8%) as light yellow crystals.

$^1$H-NMR Spectrum (CDCl$_3$) δ (ppm): 0.80 (2H, m), 0.95 (2H, m), 1.21-1.28 (3H, m), 1.47 (9H, s), 1.77 (2H, m), 1.89 (2H, m), 2.67 (1H, m), 2.75 (2H, m), 4.12 (2H, m), 4.28 (2H, m), 4.97 (1H, s), 6.50 (1H, d, J=5.2 Hz), 7.12 (1H, dd, J=2.8, 8.8 Hz), 7.25 (1H, d, J=2.8 Hz), 7.45 (1H, s), 7.72 (1H, s), 8.44 (1H, d, J=8.8 Hz), 8.66 (1H, s), 8.68 (1H, d, J=5.2 Hz).

The starting material was synthesized in the following manner.

Production Example 426-1 tert-Butyl 4-(2-(((4-amino-3-chlorophenoxy)-6-cyano-7-quinolyl)oxy)ethyl)-1-piperidinecarboxylate The title compound (492.6 mg, 0.942 mmol, 39.6%) was obtained as light brown crystals from an 4-(4-amino-3-chlorophenoxy)-6-cyano-7-hydroxyquinoline crude product (742 mg, 2.38 mmol) and tert-butyl 4-(bromoethyl)-1-piperidine carboxylate, by the same procedure as in Example 7.

$^1$H-NMR Spectrum (CDCl$_3$) δ (ppm): 1.11-1.31 (4H, m), 1.46 (9H, s), 1.77 (2H, m), 1.90 (2H, m), 2.52-2.56 (3H, m), 4.11 (2H, m), 4.27 (2H, m), 6.48 (1H, d, J=5.2 Hz), 6.86 (1H, d, J=9.2 Hz), 6.93 (1H, dd, J=2.8, 9.2 Hz), 7.14 (1H, d, J=2.8 Hz), 7.44 (1H, s), 8.66-8.68 (2H, m).

Example 427

N-(2-Chloro-4-((6-cyano-7-(2-(4-piperidyl)ethoxy)-4-quinolyl)oxy)phenyl)-N'-cyclopropylurea After adding trifluoroacetic acid (3.0 ml) to tert-butyl 4-(((4-(3-chloro-4-((cyclopropylamino)carbonyl)aminophenoxy)-6-cyano-7-quinolyl)oxy)ethyl)-1-piperidinecarboxylate (343 mg, 0.566 mmol) at room temperature, the mixture was stirred for 1 hour. The reaction solution was diluted with water (40 ml) while cooling in an ice water bath, and then sodium bicarbonate (4.0 g) was gradually added for neutralization and extraction was performed with ethyl acetate. The organic layer was washed with water and saturated brine, and then dried over anhydrous sodium sulfate. The solvent was distilled off, the residue was suspended in ethyl acetate and diluted with hexane, and the precipitated crystals were filtered out and blow-dried to obtain the title compound (286 mg, 0.566 mmol, quantitative) as light yellow crystals.

$^1$H-NMR Spectrum (CDCl$_3$) δ (ppm): 0.78 (2H, m), 0.95 (2H, m), 1.63 (2H, m), 1.96-2.05 (5H, m), 2.66 (1H, m), 2.90 (2H, m), 3.41 (2H, m), 4.27-4.30 (3H, m), 5.10 (1H, s), 6.50 (1H, d, J=5.2 Hz), 7.12 (1H, dd, J=2.8, 8.8 Hz), 7.27 (1H, d, J=2.8 Hz), 7.46 (1H, s), 7.73 (1H, s), 8.44 (1H, d, J=8.8 Hz), 8.66 (1H, s), 8.68 (1H, d, J=5.2 Hz).

Example 428

N-(2-Chloro-4-((6-cyano-7-(2-(1-methyl-4-piperidyl)ethoxy)-4-quinolyl)oxy)phenyl)-N'-cyclopropylurea After dissolving N-(2-chloro-4-((6-cyano-7-(2-(4-piperidylethoxy))-4-quinolyl)oxy)phenyl)-N'-cyclopropylurea (286 mg, 0.566 mmol) in tetrahydrofuran (5 ml)-methanol (5 ml), there were added 37% aqueous formaldehyde (0.5 ml), acetic acid (0.065 ml, 1.13 mmol) and sodium cyanoborohydride (71 mg, 1.13 mmol) at room temperature, and the mixture was stirred for 1 hour. The reaction solution was distributed between ethyl acetate and saturated aqueous sodium bicarbonate, and the organic layer was washed with saturated brine and dried over anhydrous sodium sulfate. The solvent was distilled off, the residue was suspended in ethyl acetate and diluted with hexane, and the crystals were filtered out and blow-dried to obtain the title compound (218.2 mg, 0.420 mmol, 74.1%) as light yellow crystals.

$^1$H-NMR Spectrum (DMSO-d$_6$) δ (ppm): 0.41 (2H, m), 0.65 (2H, m), 1.23 (2H, m), 1.50 (1H, m), 1.71-1.88 (6H, m), 2.15 (3H, s), 2.56 (1H, m), 2.75 (2H, m), 4.33 (2H, t, J=6.4 Hz), 6.58 (1H, d, J=5.2 Hz), 7.20 (1H, d, J=2.8 Hz), 7.26 (1H, dd, J=2.8, 9.2 Hz), 7.50 (1H, d, J=2.8 Hz), 7.62 (1H, s), 8.00 (1H, s), 8.28 (1H, d, J=9.2 Hz), 8.73-8.75 (2H, m).

Example 429

N-(2-Chloro-4-((6-cyano-7-(((2R)-3-(diethylamino)-2-hydroxypropyl)oxy)-4-quinolyl)oxy)phenyl)-N'-cyclopropylurea After dissolving (4-(4-amino-3-chlorophenoxy)-6-cyano-7-(((2R)-3-(diethylamino)-2-hydroxypropyl)oxy)quinoline) (96.9 mg, 0.22 mmol) in dimethylformamide (1 ml) under a nitrogen atmosphere, pyridine (0.027 ml, 0.33 mmol) and phenyl chloroformate (0.035 ml, 0.28 mmol) were added dropwise at room temperature, and the mixture was stirred for 1 hour. Cyclopropylamine (0.10 ml) was added dropwise, and the mixture was further stirred overnight. The reaction solution was distributed between ethyl acetate and saturated aqueous sodium bicarbonate, and the organic layer was washed with water and saturated brine and dried over anhydrous sodium sulfate. The solvent was distilled off, the residue was subjected to silica gel column chromatography (eluent-ethyl acetate), the fraction containing the target substance was concentrated, suspended in ethyl acetate and diluted with hexane, and the crystals were filtered out and blow-dried to obtain the title compound (61.6 mg, 0.118 mmol, 53.5%) as light yellow crystals.

$^1$H-NMR Spectrum (DMSO-d$_6$) δ (ppm): 0.42 (2H, m), 0.65 (2H, m), 0.96 (6H, t, J=7.2 Hz), 2.42-2.67 (7H, m), 3.95 (1H, m), 4.21 (1H, m), 4.30 (1H, m), 4.91 (1H, m), 6.57 (1H, d, J=5.2 Hz), 7.19 (1H, d, J=2.8 Hz), 7.25 (1H, dd, J=2.8, 9.2 Hz), 7.50 (1H, d, J=2.8 Hz), 7.61 (1H, s), 7.98 (1H, s), 8.27 (1H, d, J=9.2 Hz), 8.70 (1H, s), 8.72 (1H, d, J=5.2 Hz).

The starting materials were synthesized in the following manner.

Production Example 429-1

4-(4-Amino-3-chlorophenoxy)-6-cyano-7-((2R)-oxiran-2-yl)methoxyquinoline

The title compound (198 mg, 0.538 mmol, 16.8%) was obtained as light brown crystals from an 4-(4-amino-3-chlorophenoxy)-6-cyano-7-hydroxyquinoline crude product (1.00 g, 3.21 mmol) and (2R)-oxiran-2-ylmethyl 4-methyl-1-benzenesulfonate, by the same procedure as in Example 7.

$^1$H-NMR Spectrum (CDCl$_3$) δ (ppm): 2.93 (1H, m), 2.98 (1H, m), 3.50 (1H, m), 4.12 (2H, m), 4.24 (1H, dd, J=5.2, 11.2 Hz), 4.49 (1H, dd, J=2.8, 11.2 Hz), 6.49 (1H, d, J=5.2 Hz), 6.86 (1H, d, J=8.8 Hz), 6.93 (1H, dd, J=2.8, 8.8 Hz), 7.14 (1H, d, J=2.8 Hz), 7.48 (1H, s), 8.66-8.68 (2H, m).

Production Example 429-2

4-(4-Amino-3-chlorophenoxy)-6-cyano-7-(((2R)-3-(diethylamino)-2-hydroxypropyl)oxy)quinoline After dissolving 4-(4-amino-3-chlorophenoxy)-6-cyano-7-((2R)-oxiran-2-yl)methoxyquinoline (96 mg, 0.261 mmol) in tetrahydrofuran (2.6 ml) under a nitrogen atmosphere, diethylamine (0.5 ml) was added and the mixture was stirred at 50° C. for 5 days. The reaction solution was concentrated under reduced pressure, the residue was subjected to silica gel column chromatography (eluent-ethyl acetate), the fraction containing the target substance was concentrated, suspended in ethyl acetate and diluted with hexane, and the crystals were filtered out and blow-dried to obtain the title compound (96.9 mg, 0.220 mmol, 84.2%) as light yellow crystals.

$^1$H-NMR Spectrum (CDCl$_3$) δ (ppm): 1.09 (6H, t, J=7.2 Hz), 2.57-2.74 (8H, m), 4.12 (2H, m), 4.25 (2H, d, J=4.8 Hz), 6.48 (1H, d, J=5.2 Hz), 6.85 (1H, d, J=8.8 Hz), 6.93 (1H, dd, J=2.8, 8.8 Hz), 7.14 (1H, d, J=2.8 Hz), 7.49 (1H, s), 8.66-8.68 (2H, m).

Example 430

N-(2-Chloro-4-((6-cyano-7-(((2S)-3-(diethylamino)-2-hydroxypropyl)oxy)-4-quinolyl)oxy)phenyl)-N'-cyclopropylurea After dissolving 4-(4-amino-3-chlorophenoxy)-6-cyano-7-(((2S)-3-(diethylamino)-2-hydroxypropyl)oxy)quinoline (78.6 mg, 0.18 mmol) in dimethylformamide (1 ml) under a nitrogen atmosphere, pyridine (0.022 ml, 0.27 mmol) and phenyl chloroformate (0.028 ml, 0.22 mmol) were added dropwise at room temperature, and the mixture was stirred for 1 hour. Cyclopropylamine (0.10 ml) was added dropwise, and the mixture was further stirred overnight. The reaction solution was distributed between ethyl acetate and saturated aqueous sodium bicarbonate, and the organic layer was washed with water and saturated brine and dried over anhydrous sodium sulfate. The solvent was distilled off, the residue was subjected to silica gel column chromatography (eluent-ethyl acetate), the fraction containing the target substance was concentrated, suspended in ethyl acetate and diluted with hexane, and the crystals were filtered out and blow-dried to obtain the title compound (37.8 mg, 0.072 mmol, 40.5%) as light yellow crystals.

The starting materials were synthesized in the following manner.

Production Example 430-1

4-(4-Amino-3-chlorophenoxy)-6-cyano-7-((2S)-oxiran-2-yl)methoxyquinoline

The title compound (147 mg, 0.400 mmol, 12.5%) was obtained as light brown crystals from a 4-(4-amino-3-chlorophenoxy)-6-cyano-7-hydroxyquinoline crude product (1.00 g, 3.21 mmol) and (2S)-oxiran-2-ylmethyl 4-methyl-1-benzenesulfonate, by the same procedure as in Example 7.

Production Example 430-2

4-(4-Amino-3-chlorophenoxy)-6-cyano-7-(((2S)-3-(diethylamino)-2-hydroxypropyl)oxy)quinoline After dissolving 4-(4-amino-3-chlorophenoxy)-6-cyano-7-((2S)-oxiran-2-yl)methoxyquinoline (72 mg, 0.196 mmol) in tetrahydrofuran (2.0 ml) under a nitrogen atmosphere, diethylamine (0.4 ml) was added and the mixture was stirred at 50° C. for 5 days. The reaction solution was concentrated under reduced pressure, the residue was subjected to silica gel column chromatography (eluent-ethyl acetate), the fraction containing the target substance was concentrated, suspended in ethyl acetate and diluted with hexane, and the crystals were filtered out and blow-dried to obtain the title compound (78.6 mg, 0.178 mmol, 91.1%) as light yellow crystals.

Example 431

N-(2-Chloro-4-((6-cyano-7-(((2R)-2-hydroxy-3-(1-pyrrolidino)propyl)oxy)-4-quinolyl)oxy)phenyl)-N'-cyclopropylurea After dissolving 4-(4-amino-3-chlorophenoxy)-6-cyano-7-(((2R)-2-hydroxy-3-(1-pyrrolidino)propyl)oxy)quinoline (95.1 mg, 0.217 mmol) in dimethylformamide (1 ml) under a nitrogen atmosphere, pyridine (0.026 ml, 0.33 mmol) and phenyl chloroformate (0.034 ml, 0.27 mmol) were added dropwise at room temperature, and the mixture was stirred for 1 hour. Cyclopropylamine (0.10 ml) was added dropwise, and the mixture was further stirred overnight. The reaction solution was distributed between ethyl acetate and saturated aqueous sodium bicarbonate, and the organic layer was washed with water and saturated brine and dried over anhydrous sodium sulfate.

The solvent was distilled off, the residue was subjected to silica gel column chromatography (eluent-ethyl acetate), the fraction containing the target substance was concentrated, suspended in ethyl acetate and diluted with hexane, and the crystals were filtered out and blow-dried to obtain the title compound (40.3 mg, 0.077 mmol, 35.6%) as light yellow crystals.

$^1$H-NMR Spectrum (DMSO-d$_6$) δ (ppm): 0.44 (2H, m), 0.68 (2H, m), 1.69 (4H, br), 2.50-2.75 (7H, m), 4.02 (1H, m), 4.22 (1H, dd, J=5.6, 10.4 Hz), 4.31 (1H, dd, J=3.6, 10.4 Hz), 5.04 (1H, m), 6.59 (1H, d, J=5.2 Hz), 7.21 (1H, d, J=2.8 Hz), 7.27 (1H, dd, J=2.8, 9.2 Hz), 7.52 (1H, d, J=2.8 Hz), 7.63 (1H, s), 7.99 (1H, s), 8.29 (1H, d, J=9.2 Hz), 8.72-8.74 (2H, m).

Production Example 431-1

4-(4-Amino-3-chlorophenoxy)-6-cyano-7-(((2R)-2-hydroxy-3-(1-pyrrolidino)propyl)oxy)quinoline After dissolving 4-(4-amino-3-chlorophenoxy)-6-cyano-7-((2R)-oxiran-2-yl)methoxyquinoline (96 mg, 0.261 mmol)

in tetrahydrofuran (2.0 ml) under a nitrogen atmosphere, pyrrolidine (0.2 ml) was added and the mixture was stirred at room temperature for 5 days. The reaction solution was concentrated under reduced pressure, the residue was subjected to silica gel column chromatography (eluent-ethyl acetate), the fraction containing the target substance was concentrated, suspended in ethyl acetate and diluted with hexane, and the crystals were filtered out and blow-dried to obtain the title compound (95.5 mg, 0.218 mmol, 83.4%) as light yellow crystals.

$^1$H-NMR Spectrum (CDCl$_3$) δ (ppm): 1.26 (2H, m), 1.82 (4H, br), 2.58-2.76 (5H, m), 2.94 (1H, m), 4.11 (2H, m), 4.20-4.45 (2H, m), 6.48 (1H, d, J=5.2 Hz), 6.85 (1H, d, J=8.8 Hz), 6.93 (1H, dd, J=2.8, 8.8 Hz), 7.14 (1H, d, J=2.8 Hz), 7.49 (1H, s), 8.66-8.68 (2H, m).

Example 432

N-(2-Chloro-4-((6-cyano-7-(((2S)-2-hydroxy-3-(1-pyrrolidino)propyl)oxy)-4-quinolyl)oxy)phenyl)-N'-cyclopropylurea After dissolving 4-(4-amino-3-chlorophenoxy)-6-cyano-7-(((2R)-2-hydroxy-3-(1-pyrrolidino)propyl)oxy)quinoline (82.0 mg, 0.187 mmol) in dimethylformamide (1 ml) under a nitrogen atmosphere, pyridine (0.023 ml, 0.28 mmol) and phenyl chloroformate (0.029 ml, 0.23 mmol) were added dropwise at room temperature and the mixture was stirred for 1 hour. Cyclopropylamine (0.10 ml) was added dropwise, and the mixture was further stirred overnight. The reaction solution was distributed between ethyl acetate and saturated aqueous sodium bicarbonate, and the organic layer was washed with water and saturated brine and dried over anhydrous sodium sulfate. The solvent was distilled off, the residue was subjected to silica gel column chromatography (eluent-ethyl acetate), the fraction containing the target substance was concentrated, suspended in ethyl acetate and diluted with hexane, and the crystals were filtered out and blow-dried to obtain the title compound (25.0 mg, 0.048 mmol, 25.6%) as light yellow crystals.

Production Example 432-1

4-(4-Amino-3-chlorophenoxy)-6-cyano-7-(((2S)-2-hydroxy-3-(1-pyrrolidino)propyl)oxy)quinoline After dissolving 4-(4-amino-3-chlorophenoxy)-6-cyano-7-((2S)-oxiran-2-yl)methoxyquinoline (72 mg, 0.196 mmol) in tetrahydrofuran (1.5 ml) under a nitrogen atmosphere, pyrrolidine (0.15 ml) was added and the mixture was stirred at room temperature for 5 days. The reaction solution was concentrated under reduced pressure, the residue was subjected to silica gel column chromatography (eluent-ethyl acetate), the fraction containing the target substance was concentrated, suspended in ethyl acetate and diluted with hexane, and the crystals were filtered out and blow-dried to obtain the title compound (82.0 mg, 0.187 mmol, 95.4%) as light yellow crystals.

Example 433

Methyl 4-(4-(((4-fluoroanilino)carbonyl)(methyl)amino)phenoxy)-7-methoxy-6-quinoline carboxylate The title compound (1.078 g, 2.27 mmol, 92.6%) was obtained as white crystals from methyl 7-methoxy-4-(4-(methylamino)phenoxy)quinolinecarboxylate (828 mg, 2.45 mmol) and 4-fluorophenyl isocyanate, by the same procedure as in Example 10.

$^1$H-NMR Spectrum (DMSO-d$_6$) δ (ppm): 3.39 (3H, s), 3.98 (3H, s), 4.06 (3H, s), 6.20 (1H, s), 6.57 (1H, d, J=5.2 Hz), 6.97 (2H, m), 7.24-7.34 (4H, m), 7.46 (2H, m), 7.52 (1H, s), 8.71 (1H, d, J=5.2 Hz), 8.78 (1H, s).

The starting material was synthesized in the following manner.

Production Example 433-1

Methyl 7-methoxy-4-(4-(methylamino)phenoxy)-6-quinolinecarboxylate

After dissolving 4-methylaminophenol (1.11 g, 9.00 mmol) in dimethylsulfoxide (15 ml), sodium hydride (360 mg, 9.00 mmol) was gradually added at room temperature and the mixture was stirred for 20 minutes. 4-Chloro-7-methoxy-6-methoxycarbonylquinoline (1.51 g, 6.00 mmol) obtained by a publicly known method was added, and the mixture was heated at 100° C. for 2 hours while stirring. Upon cooling to room temperature, the reaction solution was distributed between ethyl acetate and water, and the organic layer was washed with water and saturated brine and dried over anhydrous sodium sulfate. The solvent was distilled off and subjected to silica gel column chromatography (eluent-ethyl acetate), the fraction containing the target substance was concentrated, suspended in ethyl acetate and diluted with hexane, and the crystals were filtered out and blow-dried to obtain the title compound (830 mg, 2.45 mmol, 40.9%) as light yellow crystals.

$^1$H-NMR Spectrum (CDCl$_3$) δ (ppm): 2.88 (3H, s), 3.83 (1H, br), 3.97 (3H, s), 4.04 (3H, s), 6.42 (1H, d, J=5.2 Hz), 6.68 (2H, d, J=8.8 Hz), 7.01 (2H, d, J=8.8 Hz), 7.45 (1H, s), 8.60 (1H, d, J=5.2 Hz), 8.84 (1H, s).

Example 434

4-(4-(((4-Fluoroanilino)carbonyl)(methyl)amino)phenoxy)-7-methoxy-6-quinolinecarboxylic acid After adding methanol (20 ml) and 2N aqueous sodium hydroxide (5 ml) to methyl 4-(4-(((4-fluoroanilino)carbonyl)(methyl)amino)phenoxy)-7-methoxy-6-quinolinecarboxylate (1.042 g, 2.19 mmol), the mixture was stirred at room temperature for 3 hours. 2N Hydrochloric acid was added to the reaction solution for neutralization, and then the methanol was distilled off under reduced pressure and the precipitated white crystals were filtered out and dried at 70° C. to obtain the title compound (1.01 g, 2.19 mmol, quantitative).

$^1$H-NMR Spectrum (DMSO-d$_6$) δ (ppm): 3.29 (3H, s), 3.96 (3H, s), 6.64 (1H, d, J=5.2 Hz), 7.06 (2H, t, J=8.8 Hz), 7.33 (2H, d, J=8.8 Hz), 7.42-7.50 (5H, m), 8.23 (1H, s), 8.54 (1H, s), 8.70 (1H, d, J=5.2 Hz), 13.09 (1H, br).

Example 435

N6-Cyclopropyl-4-(4-(((4-fluoroanilino)carbonyl)(methyl)amino)phenoxy)-7-methoxy-6-quinolinecarboxamide After dissolving 4-(4-(((4-fluoroanilino)carbonyl)(methyl)amino)phenoxy)-7-methoxy-6-quinolinecarboxylic acid (115 mg, 0.25 mmol) in dimethylformamide (2 ml) under a nitrogen atmosphere, triethylamine (0.2 ml), (1H-1,2,3-benzotriazol-1-yloxy)(tri(dimethylamino))phosphonium hexafluorophosphate (221 mg, 0.50 mmol) and cyclopropylamine (0.10 ml) were added in that order at room temperature, and the mixture was stirred overnight. The reaction solution was distributed between ethyl acetate and water, and the organic layer was washed with water and saturated brine and dried over anhydrous sodium sulfate. The solvent was distilled off, and purification was performed by silica gel column chromatography (eluent-ethyl acetate). The fraction containing the target substance was concentrated under reduced pressure and suspended in ethyl acetate, the suspension was diluted with hexane, and the crystals were filtered out and blow-dried to obtain the title compound (78.7 mg, 0.157 mmol, 63.1%) as white crystals. $^1$H-NMR Spectrum (DMSO-$d_6$) δ (ppm): 0.57 (2H, m), 0.70 (2H, m), 2.86 (1H, m), 3.29 (3H, s), 3.98 (3H, s), 6.64 (1H, d, J=5.2 Hz), 7.06 (2H, t, J=8.8 Hz), 7.31 (2H, d, J=8.8 Hz), 7.42-7.49 (5H, m), 8.23 (1H, s), 8.34 (1H, d, J=4.0 Hz), 8.43 (1H, s), 8.68 (1H, d, J=5.2 Hz).

Example 436

N6-(2-Methoxyethyl)-4-(4-(((4-fluoroanilino)carbonyl)(methyl)amino)phenoxy)-7-methoxy-6-quinolinecarboxamide The title compound (97.0 mg, 0.187 mmol, 75.1%) was obtained as white crystals from 4-(4-(((4-fluoroanilino)carbonyl)(methyl)amino)phenoxy)-7-methoxy-6-quinolinecarboxylic acid (115 mg, 0.25 mmol) and 2-methoxyethylamine, by the same procedure as in Example 435.
$^1$H-NMR Spectrum (DMSO-$d_6$) δ (ppm): 3.29 (3H, s), 3.30 (3H, s), 3.48 (4H, br), 4.02 (3H, s), 6.65 (1H, d, J=5.2 Hz), 7.06 (2H, t, J=8.8 Hz), 7.32 (2H, d, J=8.8 Hz), 7.43-7.48 (4H, m), 7.52 (1H, s), 8.23 (1H, s), 8.45 (1H, br), 8.62 (1H, s), 8.69 (1H, d, J=5.2 Hz).

Example 437

N6-Methoxy-4-(4-(((4-fluoroanilino)carbonyl)(methyl)amino)phenoxy)-7-methoxy-6-quinolinecarboxamide The title compound (79.2 mg, 0.161 mmol, 64.8%) was obtained as white crystals from 4-(4-(((4-fluoroanilino)carbonyl)(methyl)amino)phenoxy)-7-methoxy-6-quinolinecarboxylic acid (115 mg, 0.25 mmol) and methoxylamine hydrochloride, by the same procedure as in Example 435.
$^1$H-NMR Spectrum (DMSO-$d_6$) δ (ppm): 3.29 (3H, s), 3.73 (3H, s), 3.98 (3H, s), 6.65 (1H, d, J=5.2 Hz), 7.06 (2H, t, J=8.8 Hz), 7.32 (2H, d, J=8.8 Hz), 7.42-7.50 (5H, m), 8.23 (1H, s), 8.44 (1H, s), 8.69 (1H, d, J=5.2 Hz), 11.45 (1H, s).

Example 438

N6-(2-Ethoxyethyl)-4-(3-chloro-4-(((cyclopropylamino)carbonyl)amino)phenoxy)-7-methoxy-6-quinolinecarboxamide After dissolving 4-(3-chloro-4-(((cyclopropylamino)carbonyl)amino)phenoxy)-7-methoxy-6-quinolinecarboxylic acid (86 mg, 0.20 mmol) in dimethylformamide (2 ml) under a nitrogen atmosphere, 2-ethoxyethylamine (0.042 ml, 0.40 mmol), triethylamine (0.2 ml) and ((1H-1,2,3-benzotriazol-1-yloxy)(tri(dimethylamino))phosphonium hexafluorophosphate) (133 mg, 0.20 mmol) were added in that order at room temperature, and the mixture was stirred overnight. The reaction solution was distributed between ethyl acetate and water, and the organic layer was washed with water and saturated brine and dried over anhydrous sodium sulfate. The solvent was distilled off and suspended in ethyl acetate, the suspension was diluted with hexane, and the crystals were filtered out and blow-dried to obtain the title compound (87.7 mg, 0.176 mmol, 87.9%) as white crystals.
$^1$H-NMR Spectrum (DMSO-$d_6$) δ (ppm): 0.42 (2H, m), 0.64 (2H, m), 1.13 (3H, t, J=6.8 Hz), 2.56 (1H, m), 3.44-3.53 (6H, m), 4.02 (3H, s), 6.52 (1H, d, J=5.2 Hz), 7.18 (1H, d, J=2.8 Hz), 7.22 (1H, dd, J=2.8, 9.2 Hz), 7.48 (1H, d, J=2.8 Hz), 7.52 (1H, s), 7.97 (1H, s), 8.25 (1H, s), 8.26 (1H, dd, J=2.8, 9.2 Hz), 8.46 (1H, m), 8.62 (1H, s), 8.66 (1H, d, J=5.2 Hz).

Example 439

N6-(2-(2-Propoxy)ethyl)-4-(3-chloro-4-(((cyclopropylamino)carbonyl)amino)phenoxy)-7-methoxy-6-quinolinecarboxamide The title compound (90.0 mg, 0.175 mmol, 87.7%) was obtained as white crystals from 4-(3-chloro-4-(((cyclopropylamino)carbonyl)amino)phenoxy)-7-methoxy-6-quinolinecarboxylic acid (86 mg, 0.20 mmol) and 2-(2-propoxy)ethylamine, by the same procedure as in Example 438.
$^1$H-NMR Spectrum (DMSO-$d_6$) δ (ppm): 0.42 (2H, m), 0.65 (2H, m), 1.11 (6H, d, J=6.4 Hz), 2.56 (1H, m), 3.43-3.53 (4H, m), 3.60 (1H, m), 4.02 (3H, s), 6.52 (1H, d, J=5.2 Hz), 7.18 (1H, d, J=2.8 Hz), 7.22 (1H, dd, J=2.8, 8.8 Hz), 7.47 (1H, d, J=2.8 Hz), 7.52 (1H, s), 7.97 (1H, s), 8.26 (1H, d, J=8.8 Hz), 8.43 (1H, m), 8.46 (1H, s), 8.66 (1H, d, J=5.2 Hz).

Example 440

N6-(2-Cyanoethyl)-4-(3-chloro-4-(((cyclopropylamino)carbonyl)amino)phenoxy)-7-methoxy-6-quinolinecarboxamide The title compound (73.8 mg, 0.154 mmol, 76.5%) was obtained as white crystals from 4-(3-chloro-4-(((cyclopropylamino)carbonyl)amino)phenoxy)-7-methoxy-6-quinolinecarboxylic acid (86 mg, 0.20 mmol) and 3-aminopropionitrile, by the same procedure as in Example 438.
$^1$H-NMR Spectrum (DMSO-$d_6$) δ (ppm): 0.42 (2H, m), 0.65 (2H, m), 2.56 (1H, m), 2.81 (2H, m), 3.56 (2H, m), 4.02 (3H, s), 6.53 (1H, d, J=5.2 Hz), 7.20 (1H, d, J=2.8 Hz), 7.24 (1H, dd, J=2.8, 8.8 Hz), 7.49 (1H, d, J=2.8 Hz), 7.53 (1H, s), 7.99 (1H, s), 8.27 (1H, d, J=8.8 Hz), 8.61 (1H, s), 8.67 (1H, d, J=5.2 Hz), 8.74 (1H, m).

Example 441

N6-Cyanomethyl-4-(3-chloro-4-(((cyclopropylamino)carbonyl)amino)phenoxy)-7-methoxy-6-quinolinecarboxamide The title compound (82.7 mg, 0.178 mmol, 88.8%) was obtained as white crystals from 4-(3-chloro-4-(((cyclopropylamino)carbonyl)amino)phenoxy)-7-methoxy-6-quinolinecarboxylic acid (86 mg, 0.20 mmol) and 2-aminoacetonitrile hydrochloride, by the same procedure as in Example 438.
$^1$H-NMR Spectrum (DMSO-$d_6$) δ (ppm): 0.42 (2H, m), 0.65 (2H, m), 2.56 (1H, m), 4.05 (3H, s), 4.35 (2H, d, J=5.6 Hz), 6.54 (1H, d, J=5.2 Hz), 7.20 (1H, d, J=2.8 Hz), 7.25 (1H, dd, J=2.8, 9.2 Hz), 7.50 (1H, d, J=2.8 Hz), 7.56 (1H, s), 7.99 (1H, s), 8.28 (1H, d, J=9.2 Hz), 8.69 (1H, d, J=5.2 Hz), 8.71 (1H, s), 9.05 (1H, m).

Example 442

N6-Methyl-4-(3-chloro-4-(((cyclopropylamino)carbonyl)amino)phenoxy)-7-methoxy-6-quinolinecarboxamide The title compound (31.6 mg, 0.072 mmol, 71.7%) was obtained as white crystals from 4-(3-chloro-4-(((cyclopropylamino)carbonyl)amino)phenoxy)-7-methoxy-6-quinolinecarboxylic acid (43 mg, 0.10 mmol) and 40% methylamine (methanol solution), by the same procedure as in Example 438.

$^1$H-NMR Spectrum (DMSO-$d_6$) δ (ppm): 0.42 (2H, m), 0.65 (2H, m), 2.56 (1H, m), 2.82 (3H, d, J=4.8 Hz), 4.00 (3H, s), 6.51 (1H, d, J=5.2 Hz), 7.18 (1H, d, J=2.8 Hz), 7.22 (1H, dd, J=2.8, 9.2 Hz), 7.47 (1H, d, J=2.8 Hz), 7.50 (1H, s), 7.96 (1H, s), 8.26 (1H, d, J=9.2 Hz), 8.34 (1H, m), 8.57 (1H, s), 8.65 (1H, d, J=5.2 Hz).

Example 443

N6-Ethyl-4-(3-chloro-4-(((cyclopropylamino)carbonyl)amino)phenoxy)-7-methoxy-6-quinolinecarboxamide The title compound (29.6 mg, 0.065 mmol, 65.1%) was obtained as white crystals from 4-(3-chloro-4-(((cyclopropylamino)carbonyl)amino)phenoxy)-7-methoxy-6-quinolinecarboxylic acid (43 mg, 0.10 mmol) and 2.0 Methylamine (tetrahydrofuran solution), by the same procedure as in Example 438.

$^1$H-NMR Spectrum (DMSO-$d_6$) δ (ppm): 0.42 (2H, m), 0.65 (2H, m), 1.13 (3H, t, J=7.2 Hz), 2.56 (1H, m), 3.25-3.35 (2H, m), 4.00 (3H, s), 6.51 (1H, d, J=5.2 Hz), 7.18 (1H, d, J=2.8 Hz), 7.21 (1H, dd, J=2.8, 9.2 Hz), 7.46 (1H, d, J=2.8 Hz), 7.49 (1H, s), 7.96 (1H, s), 8.25 (1H, d, J=9.2 Hz), 8.37 (1H, m), 8.52 (1H, s), 8.64 (1H, d, J=5.2 Hz).

Example 444

N6-Propyl-4-(3-chloro-4-(((cyclopropylamino)carbonyl)amino)phenoxy)-7-methoxy-6-quinolinecarboxamide The title compound (21.6 mg, 0.046 mmol, 46.1%) was obtained as white crystals from 4-(3-chloro-4-(((cyclopropylamino)carbonyl)amino)phenoxy)-7-methoxy-6-quinolinecarboxylic acid (43 mg, 0.10 mmol) and propylamine, by the same procedure as in Example 438.

$^1$H-NMR Spectrum (DMSO-$d_6$) δ (ppm): 0.42 (2H, m), 0.65 (2H, m), 0.90 (3H, t, J=7.2 Hz), 1.54 (2H, m), 2.56 (1H, m), 3.22-3.28 (2H, m), 4.00 (3H, s), 6.51 (1H, d, J=5.2 Hz), 7.18 (1H, d, J=2.8 Hz), 7.21 (1H, dd, J=2.8, 9.2 Hz), 7.46 (1H, d, J=2.8 Hz), 7.49 (1H, s), 7.97 (1H, s), 8.27 (1H, d, J=9.2 Hz), 8.35 (1H, m), 8.49 (1H, s), 8.64 (1H, d, J=5.2 Hz).

Example 445

N6-Propargyl-4-(3-chloro-4-(((cyclopropylamino)carbonyl)amino)phenoxy)-7-methoxy-6-quinolinecarboxamide The title compound (25.4 mg, 0.055 mmol, 54.6%) was obtained as a white powder from 4-(3-chloro-4-(((cyclopropylamino)carbonyl)amino)phenoxy)-7-methoxy-6-quinolinecarboxylic acid (43 mg, 0.10 mmol) and propargylamine, by the same procedure as in Example 438.

$^1$H-NMR Spectrum (DMSO-$d_6$) δ (ppm): 0.42 (2H, m), 0.65 (2H, m), 2.56 (1H, m), 3.13 (1H, m), 4.00 (3H, s), 4.10 (2H, m), 6.53 (1H, d, J=5.2 Hz), 7.19 (1H, d, J=2.8 Hz), 7.24 (1H, dd, J=2.8, 9.2 Hz), 7.49 (1H, d, J=2.8 Hz), 7.53 (1H, s), 7.99 (1H, s), 8.27 (1H, d, J=9.2 Hz), 8.59 (1H, s), 8.67 (1H, d, J=5.2 Hz), 8.79 (1H, m).

Example 446

N6-Cyclopropylmethyl-4-(3-chloro-4-(((cyclopropylamino)carbonyl)amino)phenoxy)-7-methoxy-6-quinolinecarboxamide The title compound (25.6 mg, 0.053 mmol, 53.2%) was obtained as white crystals from 4-(3-chloro-4-(((cyclopropylamino)carbonyl)amino)phenoxy)-7-methoxy-6-quinolinecarboxylic acid (43 mg, 0.10 mmol) and (aminomethyl)cyclopropane hydrochloride, by the same procedure as in Example 438.

$^1$H-NMR Spectrum (DMSO-$d_6$) δ (ppm): 0.26 (2H, m), 0.41-0.47 (4H, m), 0.65 (2H, m), 1.06 (1H, m), 2.56 (1H, m), 3.22 (2H, m), 4.03 (3H, s), 6.53 (1H, d, J=5.2 Hz), 7.19 (1H, d, J=2.8 Hz), 7.24 (1H, dd, J=2.8, 9.2 Hz), 7.48 (1H, d, J=2.8 Hz), 7.52 (1H, s), 7.98 (1H, s), 8.27 (1H, d, J=9.2 Hz), 8.45 (1H, m), 8.56 (1H, s), 8.67 (1H, d, J=5.2 Hz).

Example 447

N6-(Cis-2-fluorocyclopropyl)-4-(3-chloro-4-(((cyclopropylamino)carbonyl)amino)phenoxy)-7-methoxy-6-quinolinecarboxamide The title compound (38.4 mg, 0.079 mmol, 79.2%) was obtained as white crystals from 4-(3-chloro-4-(((cyclopropylamino)carbonyl)amino)phenoxy)-7-methoxy-6-quinolinecarboxylic acid (43 mg, 0.10 mmol) and cis-2-fluorocyclopropylamine tosylate, by the same procedure as in Example 438.

$^1$H-NMR Spectrum (DMSO-$d_6$) δ (ppm): 0.42 (2H, m), 0.65 (2H, m), 1.03-1.17 (2H, m), 2.56 (1H, m), 2.91 (1H, m), 4.00 (3H, s), 4.79 (1H, m), 6.51 (1H, d, J=5.2 Hz), 7.20 (1H, d, J=2.8 Hz), 7.24 (1H, dd, J=2.8, 8.8 Hz), 7.47 (1H, d, J=2.8 Hz), 7.51 (1H, s), 7.98 (1H, s), 8.26 (1H, d, J=8.8 Hz), 8.45 (1H, m), 8.50 (1H, s), 8.65 (1H, d, J=5.2 Hz).

Example 448

N6-(3-Methoxypropyl)-4-(3-chloro-4-(((cyclopropylamino)carbonyl)amino)phenoxy)-7-methoxy-6-quinolinecarboxamide The title compound (30.3 mg, 0.061 mmol, 60.7%) was obtained as white crystals from 4-(3-chloro-4-(((cyclopropylamino)carbonyl)amino)phenoxy)-7-methoxy-6-quinolinecarboxylic acid (43 mg, 0.10 mmol) and 3-methoxypropylamine, by the same procedure as in Example 438.

$^1$H-NMR Spectrum (DMSO-$d_6$) δ (ppm): 0.42 (2H, m), 0.65 (2H, m), 1.77 (2H, m), 2.56 (1H, m), 3.24 (3H, s), 3.34-3.42 (4H, m), 4.00 (3H, s), 6.51 (1H, d, J=5.2 Hz), 7.20 (1H, d, J=2.8 Hz), 7.24 (1H, dd, J=2.8, 9.2 Hz), 7.47 (1H, d, J=2.8 Hz), 7.50 (1H, s), 7.96 (1H, s), 8.27 (1H, dd, J=2.8, 9.2 Hz), 8.41 (1H, m), 8.54 (1H, s), 8.65 (1H, d, J=5.2 Hz).

Example 449

N6-(2-Amino-2-oxoethyl)-4-(3-chloro-4-(((cyclopropylamino)carbonyl)amino)phenoxy)-7-methoxy-6-quinolinecarboxamide The title compound (37.4 mg, 0.077 mmol, 77.3%) was obtained as white crystals from 4-(3-chloro-4-(((cyclopropylamino)carbonyl)amino)phenoxy)-7-methoxy-6-quinolinecarboxylic acid (43 mg, 0.10 mmol) and glycinamide hydrochloride, by the same procedure as in Example 438.

$^1$H-NMR Spectrum (DMSO-d$_6$) δ (ppm): 0.42 (2H, m), 0.65 (2H, m), 2.56 (1H, m), 3.94 (2H, d, J=5.6 Hz), 4.07 (3H, s), 6.53 (1H, d, J=5.2 Hz), 7.14 (1H, s), 7.20 (1H, d, J=2.8 Hz), 7.24 (1H, dd, J=2.8, 9.2 Hz), 7.44 (1H, s), 7.50 (1H, d, J=2.8 Hz), 7.56 (1H, s), 7.99 (1H, s), 8.27 (1H, d, J=9.2 Hz), 8.67-8.71 (2H, m), 8.77 (1H, s).

Example 450

N6-((2R)Tetrahydro-2-furanylmethyl)-4-(3-chloro-4-(((cyclopropylamino)carbonyl)amino)phenoxy)-7-methoxy-6-quinolinecarboxamide The title compound (31.8 mg, 0.062 mmol, 62.2%) was obtained as a white powder from 4-(3-chloro-4-(((cyclopropylamino)carbonyl)amino)phenoxy)-7-methoxy-6-quinolinecarboxylic acid (43 mg, 0.10 mmol) and R-tetrahydrofurfurylamine, by the same procedure as in Example 438.

$^1$H-NMR Spectrum (DMSO-d$_6$) δ (ppm): 0.42 (2H, m), 0.65 (2H, m), 1.62 (1H, m), 1.78-1.93 (3H, m), 2.57 (1H, m), 3.38 (2H, m), 3.64 (1H, dd, J=3.6, 14.0 Hz), 3.79 (1H, dd, J=4.0, 14.0 Hz), 3.99 (1H, m), 4.02 (3H, s), 6.51 (1H, d, J=5.2 Hz), 7.18 (1H, s), 7.23 (1H, dd, J=2.8, 8.8 Hz), 7.47 (1H, d, J=2.8 Hz), 7.52 (1H, s), 7.97 (1H, s), 8.26 (1H, d, J=8.8 Hz), 8.41 (1H, m), 8.59 (1H, s), 8.65 (1H, d, J=5.2 Hz).

Example 451

N6-((2S)Tetrahydro-2-furanylmethyl)-4-(3-chloro-4-(((cyclopropylamino)carbonyl)amino)phenoxy)-7-methoxy-6-quinolinecarboxamide The title compound (36.4 mg, 0.071 mmol, 71.2%) was obtained as a white powder from 4-(3-chloro-4-(((cyclopropylamino)carbonyl)amino)phenoxy)-7-methoxy-6-quinolinecarboxylic acid (43 mg, 0.10 mmol) and S-tetrahydrofurfurylamine, by the same procedure as in Example 438.

Example 452

N-(4-(6-Cyano-7-hydroxy-4-quinolyl)oxyphenyl)-N'-(4-fluorophenyl)urea

After dissolving N-(4-(7-(benzyloxy)-6-cyano-4-quinolyl)oxyphenyl)-N'-(4-fluorophenyl)urea (6.20 g, 12.3 mmol) in trifluoroacetic acid (60 ml) and thioanisole (3.6 ml, 30.7 mmol) under a nitrogen atmosphere, the solution was stirred at 60° C. overnight. The reaction solution was concentrated under reduced pressure, and after adding water (100 ml) to the obtained residue, sodium bicarbonate was added to neutralization, diethyl ether (200 ml) was added, the mixture was stirred, and the precipitated crystals were filtered out, washed with water and diethyl ether and dried at 70° C. to obtain the title compound (4.816 g, 11.6 mmol, 94.8%) as yellow crystals.

$^1$H-NMR Spectrum (DMSO-d$_6$) δ (ppm): 6.42 (1H, d, J=5.2 Hz), 7.11 (2H, m), 7.22 (2H, m), 7.41 (1H, s), 7.46 (2H, m), 7.58 (2H, m), 8.64 (1H, d, J=5.2 Hz), 8.67 (1H, s), 8.73 (1H, s), 8.82 (1H, s).

Example 453

N-(4-(6-Cyano-7-((2R)-oxiran-2-yl)methoxy-4-quinolyl)oxyphenyl)-N'-(4-fluorophenyl)urea The title compound (713 mg, 1.52 mmol, 50.5%) was obtained as light yellow crystals from N-(4-(6-cyano-7-hydroxy-4-quinolyl)oxyphenyl)-N'-(4-fluorophenyl)urea (1.24 g, 3.0 mmol) and (2R)-oxiran-2-ylmethyl 4-methyl-1-benzenesulfonate, by the same procedure as in Example 7.

$^1$H-NMR Spectrum (DMSO-d$_6$) δ (ppm): 2.81 (1H, m), 2.92 (1H, m), 3.46 (1H, m), 4.17 (1H, dd, J=6.8, 11.6 Hz), 4.71 (1H, dd, J=2.4, 11.6 Hz), 6.53 (1H, d, J=5.2 Hz), 7.12 (2H, m), 7.24 (2H, m), 7.46 (2H, m), 7.58 (2H, m), 7.63 (1H, s), 8.71-8.73 (2H, m), 8.78 (1H, s), 8.83 (1H, s).

Example 454

N-(4-((6-Cyano-7-(((2R)-2-hydroxy-3-(1-pyrrolidino)propyl)oxy)-4-quinolyl)oxy)phenyl)-N'-(4-fluorophenyl)urea After dissolving N-(4-(6-cyano-7-((2R)-oxiran-2-yl)methoxy-4-quinolyl)oxyphenyl)-N'-(4-fluorophenyl)urea (200 mg, 0.425 mmol) in tetrahydrofuran (5.0 ml) under a nitrogen atmosphere, pyrrolidine (0.5 ml) was added and the mixture was stirred overnight at room temperature. The reaction solution was concentrated under reduced pressure, the residue was subjected to silica gel column chromatography (eluent-ethyl acetate:methanol=9:1), the fraction containing the target substance was concentrated, methanol (5 ml) was added for crystallization, and the crystals were filtered out and blow-dried to obtain the title compound (157.7 mg, 0.291 mmol, 68.5%) as light yellow crystals.

$^1$H-NMR Spectrum (DMSO-d$_6$) δ (ppm): 1.67 (4H, br), 2.47-2.52 (5H, m), 2.69 (1H, m), 4.01 (1H, m), 4.20 (1H, dd, J=5.6, 10.8 Hz), 4.30 (1H, dd, J=3.6, 10.8 Hz), 5.02 (1H, d, J=4.4 Hz), 6.51 (1H, d, J=5.2 Hz), 7.11 (2H, m), 7.23 (2H, m), 7.46 (2H, m), 7.57-7.61 (3H, m), 8.70-8.75 (3H, m), 8.83 (1H, s).

Example 455

N-(4-((6-Cyano-7-(((2R)-3-(diethylamino)-2-hydroxypropyl)oxy)-4-quinolyl)oxy)phenyl)-N'-(4-fluorophenyl)urea After dissolving N-(4-(6-cyano-7-((2R)-oxiran-2-yl)methoxy-4-quinolyl)oxyphenyl)-N'-(4-fluorophenyl)urea (200 mg, 0.425 mmol) in tetrahydrofuran (5.0 ml) under a nitrogen atmosphere, diethylamine (1.0 ml) was added and the mixture was stirred overnight at 60° C. The reaction solution was concentrated under reduced pressure, the residue was subjected to silica gel column chromatography (eluent-ethyl acetate:methanol=9:1), the fraction containing the target substance was concentrated, methanol (5 ml) was added for crystallization, and the crystals were filtered out and blow-dried to obtain the title compound (126.4 mg, 0.233 mmol, 54.7%) as light yellow crystals.

$^1$H-NMR Spectrum (DMSO-d$_6$) δ (ppm): 0.96 (6H, t, J=7.2 Hz), 2.42-2.57 (5H, m), 2.64 (1H, m), 3.95 (1H, m), 4.21 (1H, dd, J=5.6, 10.4 Hz), 4.30 (1H, dd, J=3.6, 10.4 Hz), 4.91 (1H, d, J=4.4 Hz), 6.51 (1H, d, J=5.2 Hz), 7.11 (2H, m), 7.23 (2H, m), 7.46 (2H, m), 7.56-7.60 (3H, m), 8.70-8.75 (3H, m), 8.82 (1H, s).

Example 456

N-(4-((6-Cyano-7-(((2R)-2-hydroxy-3-(1-piperidino) propyl) oxy)-4-quinolyl)oxy)phenyl)-N'-(4-fluorophenyl)urea After dissolving N-(4-(6-cyano-7-((2R)-oxiran-2-yl)methoxy-4-quinolyl)oxyphenyl)-N'-(4-fluorophenyl)urea (200 mg, 0.425 mmol) in tetrahydrofuran (5.0 ml) under a nitrogen atmosphere, piperidine (0.5 ml) was added and the mixture was stirred overnight at 60° C. The reaction solution was concentrated under reduced pressure, the residue was subjected to silica gel column chromatography (eluent-ethyl acetate:methanol=9:1), the fraction containing the target substance was concentrated, methanol (5 ml) was added for crystallization, and the crystals were filtered out and blow-dried to obtain the title compound (169.8 mg, 0.306 mmol, 71.9%) as light yellow crystals.
$^1$H-NMR Spectrum (DMSO-$d_6$) δ (ppm): 1.36 (2H, m), 1.47 (4H, m), 2.34-2.51 (6H, m), 4.02 (1H, m), 4.20 (1H, dd, J=5.6, 10.4 Hz), 4.30 (1H, dd, J=3.2, 10.4 Hz), 4.93 (1H, d, J=4.4 Hz), 6.51 (1H, d, J=5.2 Hz), 7.11 (2H, m), 7.23 (2H, m), 7.46 (2H, m), 7.57-7.62 (3H, m), 8.70-8.75 (3H, m), 8.83 (1H, s).

Example 457

Methyl 7-(benzyloxy)-4-(3-chloro-(4-((cyclopropylamino)carbonyl)amino)phenoxy)-6-quinoline carboxylate After dissolving methyl 4-(4-amino-3-chlorophenoxy)-7-(benzyloxy)-6-quinolinecarboxylate (3.938 g, 9.06 mmol) in dimethylformamide (40 ml) under a nitrogen atmosphere, pyridine (1.10 ml, 13.6 mmol) and phenylchloroformate (1.70 ml, 13.6 mmol) were added dropwise at room temperature and the mixture was stirred for 1 hour. Cyclopropylamine (1.88 ml, 27.2 mmol) was added dropwise, and the mixture was further stirred overnight. The reaction solution was distributed between ethyl acetate (400 ml) and water (200 ml), and then the organic layer was washed with water and concentrated under reduced pressure, ethyl acetate (40 ml) was added and the precipitated crystals were filtered out and blow-dried to obtain the title compound (2.225 g, 4.30 mmol, 47.4%) as light brown crystals.
$^1$H-NMR Spectrum (DMSO-$d_6$) δ (ppm): 0.42 (2H, m), 0.65 (2H, m), 2.56 (1H, m), 3.87 (3H, s), 5.39 (2H, s), 6.51 (1H, d, J=5.2 Hz), 7.18 (1H, d, J=2.8 Hz), 7.24 (1H, dd, J=2.8, 9.2 Hz), 7.32 (1H, m), 7.41 (2H, m), 7.49 (1H, d, J=2.8 Hz), 7.54 (2H, m), 7.61 (1H, s), 7.97 (1H, s), 8.26 (1H, d, J=9.2 Hz), 8.60 (1H, s), 8.67 (1H, d, J=5.2 Hz).

The starting materials were synthesized in the following manner.

Production Example 457-1

Methyl 4-(((2,2-dimethyl-4,6-dioxo-1,3-dioxan-5-ylidene)methyl)amino)-2-hydroxybenzoate After adding Meldrum acid (7.2 g, 50 mmol), triethyl orthoformate (50 ml) and 2-propanol (50 ml) to the publicly known compound methyl 4-amino-2-hydroxybenzoate (7.59 g, 45.4 mmol), the mixture was stirred at 100° C. for 1 hour. Upon cooling to room temperature, the precipitated crystals were filtered out, washed with diethyl ether and blow-dried to obtain the title compound (13.98 g, 43.5 mmol, 95.8%) as white crystals.
$^1$H-NMR Spectrum (CDCl$_3$) δ (ppm): 1.76 (6H, s), 3.97 (3H, s), 6.75 (1H, dd, J=2.4, 8.8 Hz), 6.83 (1H, d, J=2.4 Hz), 7.90 (1H, d, J=8.8 Hz), 8.65 (1H, m), 11.0 (1H, s), 11.20 (1H, m).

Production Example 457-2

Methyl 2-(benzyloxy)-4-(((2,2-dimethyl-4,6-dioxo-1,3-dioxan-5-ylidene)methyl)amino)benzoate After suspending methyl 4-(((2,2-dimethyl-4,6-dioxo-1,3-dioxan-5-ylidene)methyl)amino)-2-hydroxybenzoate (13.975 g, 43.5 mmol) in dimethylformamide (140 ml) at room temperature under a nitrogen atmosphere, sodium hydride (1.87 g, 46.8 mmol) was gradually added. After 1.5 hours, benzyl bromide 5.7 ml, 47.9 mmol) was added dropwise and the mixture was stirred for 2 days. The reaction solution was diluted with water (700 ml) and stirred overnight, and the precipitated crystals were filtered, washed with diethyl ether and dried at 70° C. to obtain the title compound (15.477 g, 37.6 mmol, 86.5%) as white crystals.
$^1$H-NMR Spectrum (CDCl$_3$) δ (ppm): 1.76 (6H, s), 3.91 (3H, s), 5.23 (2H, s), 6.83 (1H, s), 6.88 (1H, m), 7.26-7.54 (5H, m), 7.95 (1H, m), 8.62 (1H, m), 11.24 (1H, m).

Production Example 457-3

Methyl 7-(benzyloxy)-4-oxo-1,4-dihydro-6-quinoline carboxylate

After adding Dowtherm A (160 ml) to methyl 2-(benzyloxy)-4-(((2,2-dimethyl-4,6-dioxo-1,3-dioxan-5-ylidene) methyl)amino)benzoate (15.477 g, 37.6 mmol), the mixture was stirred at 200° C. for 1 hour. Upon cooling to room temperature, the precipitated crystals were filtered, washed with diethyl ether and blow-dried to obtain the title compound (7.19 g, 23.2 mmol, 61.80).
$^1$H-NMR Spectrum (DMSO-$d_6$) δ (ppm): 3.81 (3H, s), 5.26 (2H, s), 5.97 (1H, d, J=7.6 Hz), 7.09 (1H, s), 7.30-7.53 (5H, m), 7.84 (1H, m), 8.46 (1H, s), 11.69 (1H, m).

Production Example 457-4

Methyl 7-(benzyloxy)-4-chloro-6-quinoline carboxylate

After adding thionyl chloride (70 ml) and a catalytic amount of dimethylformamide to methyl 7-(benzyloxy)-4-oxo-1,4-dihydro-6-quinolinecarboxylate (7.19 g, 23.2 mmol), the mixture was heated to reflux for 3 hours while stirring. The reaction solution was concentrated under reduced pressure, a 2N sodium hydroxide solution was gradually added for neutralization, extraction was performed with ethyl acetate, and the organic layer was washed with water and saturated brine and dried over anhydrous sodium sulfate. The solvent was distilled off, diethyl ether was added for crystallization, and the crystals were filtered out and blow-dried to obtain the title compound (4.067 g, 12.4 mmol) as light brown crystals.
$^1$H-NMR Spectrum (CDCl$_3$) δ (ppm): 4.00 (3H, s), 5.33 (2H, s), 7.31-7.58 (7H, m), 8.66 (1H, s), 8.75 (1H, d, J=5.2 Hz).

Production Example 457-5

Methyl 4-(4-amino-3-chlorophenoxy)-7-(benzyloxy)-6-quinolinecarboxylate

After dissolving 4-amino-3-chlorophenol (2.22 g, 15.45 mmol) in dimethylsulfoxide (40 ml), sodium hydride (618 mg, 15.45 mmol) was gradually added at room temperature and the mixture was stirred for 30 minutes. Methyl 7-(benzyloxy)-4-chloro-6-quinolinecarboxylate (4.05 g, 12.36 mmol) was added, and the mixture was heated at 100° C. for 2 hours while stirring. Upon cooling to room temperature, the reaction solution was distributed between ethyl acetate and water, and the organic layer was washed with water and saturated brine and dried over anhydrous sodium sulfate. The solvent was distilled off and subjected to silica gel column chromatography (eluent-ethyl acetate), the fraction containing the target substance was concentrated, suspended in ethyl acetate and diluted with hexane, and the crystals were filtered out and blow-dried to obtain the title compound (3.938 g, 9.06 mmol, 73.3%) as light brown crystals.

$^1$H-NMR Spectrum (CDCl$_3$) δ (ppm): 3.98 (3H, s), 4.11 (2H, m), 5.34 (2H, s), 6.43 (1H, d, J=5.2 Hz), 6.85 (1H, d, J=8.8 Hz), 6.93 (1H, dd, J=2.8, 8.8 Hz), 7.14 (1H, d, J=2.8 Hz), 7.30-7.57 (6H, m), 8.62 (1H, d, J=5.2 Hz), 8.82 (1H, s).

Example 458

N6-(2-Fluoroethyl)-4-(4-((cyclopropylamino)carbonyl)amino-3-methylphenoxy)-7-methoxy-6-quinolinecarboxamide After dissolving methyl 4-(4-amino-3-methylphenoxy)-7-methoxy-6-quinolinecarboxylate (30 mg, 0.0736 mmol) in N,N-dimethylformamide (1.4 ml), there were added triethylamine (0.071 ml) and benzotriazol-1-yltris(dimethylamino)phosphonium hexafluorophosphate (63 mg) and the mixture was stirred at room temperature for 5 hours. Water was added to the reaction solution, extraction was performed with ethyl acetate/tetrahydrofuran, the extract was washed with saturated brine and dried over anhydrous magnesium sulfate, and the filtrate was distilled off under reduced pressure. The obtained crystals were suspended in ethanol, and after diluting the suspension with diethyl ether, the crystals were filtered out, washed with diethyl ether and dried by aspiration to obtain the title compound (22 mg, 0.0486 mmol, 66.03%) as light yellow crystals.

$^1$H-NMR Spectrum (DMSO-d$_6$) δ (ppm): 0.41-0.45 (2H, m), 0.63-0.69 (2H, m), 2.22 (3H, s), 2.52-2.60 (1H, m), 3.61 (1H, q, J=5.2 Hz), 3.67 (1H, q, J=5.2 Hz), 4.03 (3H, s), 4.52 (1H, t, J=5.2 Hz), 4.64 (1H, t, J=5.2 Hz), 6.47 (1H, d, J=5.0 Hz), 6.78 (1H, m), 7.05 (1H, dd, J=2.8 Hz, 8.8 Hz), 7.11 (1H, d, J=2.8 Hz), 7.52 (1H, s), 7.63 (1H, s), 7.94 (1H, d, J=8.8 Hz), 8.59-8.62 (2H, m), 8.66 (1H, d, J=5.0 Hz).

The starting materials were synthesized in the following manner.

Production Example 458-1

Methyl 4-(4-amino-3-methylphenoxy)-7-methoxy-6-quinolinecarboxylate

The title compound (158 mg, 0.4669 mmol, 7.90%) was obtained as brown crystals by the same procedure as in Production Example 395-1 using the methyl 4-chloro-7-methoxy-6-quinolinecarboxylate (1.5 g, 5.9127 mmol) described in WO/0050405 and 4-amino-3-cresol (1.46 g, 11.8254 mmol).

$^1$H-NMR Spectrum (DMSO-d$_6$) δ (ppm): 2.06 (3H, s), 3.84 (3H, s), 3.95 (3H, s), 4.93 (2H, s), 6.40 (1H, d, J=5.0 Hz), 6.69 (1H, d, J=8.4 Hz), 6.82 (1H, d, J=8.4 Hz), 6.86 (1H, s), 7.47 (1H, s), 8.56 (1H, s), 8.62 (1H, d, J=5.0 Hz).

Production Example 458-2

Methyl 4-(4-((cyclopropylamino)carbonyl)amino-3-methylphenoxy)-7-methoxy-6-quinolinecarboxylate 4-(4-Amino-3-methylphenoxy)-7-methoxy-6-methoxycarbonylquinoline (158 mg, 0.4669 mmol) was used for phenyl carbamating reaction by the same procedure as in Production Example 17, and the product was used directly without purification for reaction with cyclopropylamine by the same procedure as in Example 11 to obtain the title compound (173 mg, 0.4105 mmol, 87.92%) as light brown crystals.

$^1$H-NMR Spectrum (DMSO-d$_6$) δ (ppm): 0.40-0.43 (2H, m), 0.61-0.66 (2H, m), 2.20 (3H, s), 2.52-2.57 (1H, m), 3.85 (3H, s), 3.96 (3H, s), 6.45 (1H, d, J=5.4 Hz), 6.75 (1H, s), 7.04 (1H, dd, J=2.4 Hz, 8.8 Hz), 7.10 (1H, d, J=2.4 Hz), 7.51 (1H, s), 7.60 (1H, s), 7.92 (1H, d, J=8.8 Hz), 8.57 (1H, s), 8.66 (1H, d, J=5.4 Hz).

Production Example 458-3

4-(4-((Cyclopropylamino)carbonyl)amino-3-methylphenoxy)-7-methoxy-6-quinolinecarboxylic acid After dissolving N-cyclopropyl-N'-[2-methyl-4-(6-methoxycarbonyl-7-methoxy-4-quinolyl)oxyphenyl]urea (173 mg, 0.3972 mmol) in methanol (3 ml), 2N aqueous sodium hydroxide (1 ml) was added and the mixture was heated and stirred at 60° C. for 45 minutes. The solvent was distilled off under reduced pressure, the precipitated crystals were redissolved in methanol, and then 1N hydrochloric acid was added to pH 4 and saturated brine was further added. After extraction with ethyl acetate/tetrahydrofuran, the extract was washed with saturated brine and dried over anhydrous magnesium sulfate, the solvent was distilled off under reduced pressure, and the obtained crystals were suspended in acetone/diethyl ether and then filtered out and dried by aspiration to obtain the title compound (95 mg, 0.2332 mmol, 56.80%) as brown crystals.

$^1$H-NMR Spectrum (DMSO-d$_6$) δ (ppm): 0.42 (2H, m), 0.66 (2H, m), 2.25 (3H, s), 2.57 (1H, m), 3.51 (1H, brs), 4.05 (3H, s), 6.84 (1H, d, J=6.8 Hz), 7.12 (1H, brs), 7.16 (1H, dd, J=2.4 Hz, 8.8 Hz), 7.21 (1H, brs), 7.74 (1H, s), 7.92 (1H, s), 8.06 (1H, d, J=8.8 Hz), 8.70 (1H, s), 8.95 (1H, d, J=6.8 Hz).

Example 459

N6-(2-Methoxyethyl)-4-(4-((cyclopropylamino)carbonyl)amino-3-methylphenoxy)-7-methoxy-6-quinolinecarboxamide 4-(4-((Cyclopropylamino)carbonyl)amino-3-methylphenoxy)-7-methoxy-6-quinolinecarboxylic acid (30 mg, 0.0736 mmol) and 2-methoxyethylamine (0.0123 ml) were used for reaction in the same manner as Example 458, and after purification by NH silica gel column chromatography (ethyl acetate:methanol=10:1), the obtained crystals were suspended in acetone: diethyl ether=1:5, filtered out, washed with diethyl ether and dried by aspiration to obtain the title compound (17 mg, 0.0366 mmol, 49.73%) as light yellow crystals.

$^1$H-NMR Spectrum (DMSO-d$_6$) δ (ppm): 0.41-0.45 (2H, m), 0.63-0.69 (2H, m), 2.22 (3H, s), 2.54-2.60 (1H, s), 3.30 (3H, s), 3.50 (4H, m), 4.04 (3H, s), 6.47 (1H, d, J=5.0 Hz), 6.78 (1H, m), 7.05 (1H, dd, J=2.4 Hz, 8.4 Hz), 7.12 (1H, d, J=2.4 Hz), 7.52 (1H, s), 7.63 (1H, s), 7.94 (1H, d, J=8.4 Hz), 8.45 (1H, brs), 8.63 (1H, s), 8.66 (1H, d, J=5.0 Hz).

Example 460

N6-Methoxy-4-(4-((cyclopropylamino)carbonyl) amino-3-methylphenoxy)-7-methoxy-6-quinolin- ecarboxamide 4-(4-((Cyclopropylamino)carbonyl)amino-3-methylphenoxy)-7-methoxy-6-quinolinecarboxylic acid (30 mg, 0.0736 mmol) and methoxylamine hydrochloride (0.0123 ml) were used for reaction in the same manner as Example 458, and after purification by NH silica gel column chromatography (ethyl acetate:methanol=10:1), the obtained crystals were suspended in ethanol, diluted with hexane, filtered out, washed with hexane and dried by aspiration to obtain the title compound (7 mg, 0.0160 mmol, 21.74%) as light yellow crystals.

$^1$H-NMR Spectrum (DMSO-d$_6$) δ (ppm): 0.40-0.45 (2H, m), 0.63-0.68 (2H, m), 2.21 (3H, s), 2.51 (3H, s), 2.53-2.59 (1H, m), 3.94 (3H, s), 6.46 (1H, d, J=5.0 Hz), 6.79 (1H, s), 7.04 (1H, d, J=8.4 Hz), 7.09 (1H, s), 7.43 (1H, s), 7.63 (1H, s), 7.92 (1H, d, J=8.4 Hz), 8.04 (1H, s), 8.62 (1H, d, J=5.0 Hz), 9.86 (1H, s).

Example 461

N-[4-(2-Cyclopropyl-3H-imidazo[4,5-b]pyridin-4-yl)oxyphenyl]-N'-(4-fluorophenyl)urea A mixture of 2-cyclopropyl-7-(4-aminophenyloxy)-3H-imidazo[4,5-b]pyridine (130 mg), p-fluorophenyl isocyanate (0.06 ml), tetrahydrofuran (5 ml) and dimethylformamide (0.5 ml) was stirred at room temperature for 35 minutes. NH type silica gel was added to the reaction solution, the solvent was distilled off under reduced pressure and the reaction product was adsorbed onto the silica gel. The silica gel was charged into a dry column packed with NH type silica gel, and column purification was performed (ethyl acetate, followed by ethyl acetate:methanol=10:1). The obtained residue was solidified from ethyl acetate-methanol-hexane to obtain 38 mg of the target substance as a gray solid.

H-NMR (DMSO-d$_6$) δ (ppm): 1.02-1.12 (4H, m), 2.04-2.14 (1H, m), 6.34 (0.75H, d, J=5.6 Hz), 6.35 (0.25H, d, J=5.6 Hz), 7.05-7.18 (4H, m), 7.40-7.55 (4H, m), 7.98 (0.75H, d, J=5.6 Hz), 8.07 (0.25H, d, J=5.6 Hz) 8.69 (0.75H, s), 8.70 (0.25H, s), 8.73 (0.75H, s), 8.76 (0.25H, s).

The starting material was obtained in the following manner.

Production Example 461-1

2-Cyclopropyl-7-(4-aminophenyloxy)-3H-imidazo [4,5-b]pyridine

4-Chloro-2-nitroaminopyridine (9.3 g) was added in small portions at a time to 60 ml of ice-cooled concentrated sulfuric acid. When the addition was complete, the ice bath was immediately removed and the mixture was stirred at room temperature for 2.5 hours. The reaction solution was developed in ice and concentrated ammonia water was added to pH 5. The precipitated solid was filtered out and blow-dried at 60° C. to obtain 11.2 g of a yellow solid. The 11.2 g of the solid was added to a mixture of 10.8 g of p-nitrophenol, 17 ml of Hunig's base and 34 ml of 1-methyl-2-pyrrolidinone, and the mixture was heated and stirred at 120° C. for 3 hours. After returning the mixture to room temperature, 50 ml of water was added and the precipitated solid was filtered out. It was then blow-dried at 60° C. to obtain 4.77 g of a solid. The 4.77 g of solid was dissolved in 100 ml of tetrahydrofuran, 2.0 g of palladium carbon (Pd—C (10%, wet)) was added and the mixture was refluxed under normal pressure for 24 hours. After filtering off the Pd—C, the solvent was distilled off under reduced pressure to obtain 5.2 g of a reddish-brown oil. The 5.2 g of oil was added to a mixture of 4.6 g of cyclopropanecarboxylic acid and 50 ml of phosphoric acid, and the mixture was heated and stirred at 160° C. for 5 hours. The reaction solution was developed in ice, neutralized with 5N aqueous sodium hydroxide and extracted with ethyl acetate. The extract was dried over magnesium sulfate, and the solvent was distilled off under reduced pressure. The obtained residue was purified by NH type silica gel (chloroform:methanol=10:1). The residue obtained by distilling off the solvent under reduced pressure was dissolved in a small amount of ethyl acetate, the solution was allowed to stand, and the precipitated solid was filtered out to obtain 130 mg of the target substance as a blackish-violet solid.

$^1$H-NMR (DMSO-d$_6$) δ (ppm): 1.00-1.12 (4H, m), 2.05-2.14 (1H, m), 5.08 (2H, bs), 6.23 (1H, d, J=5.6 Hz), 6.61 (2H, d, J=8.8 Hz), 6.83 (1.5H, d, J=8.8 Hz), 6.90 (0.5H, d, J=8.8 Hz), 7.92 (0.75H, d, J=5.6 Hz), 8.01 (0.25H, d, J=5.6 Hz), 12.75 (0.75H, s), 12.85 (0.25H, s).

Example 462

N-[4-(2-Cyclobutanecarbonylaminopyridin-4-yl) oxyphenyl]-N'-(4-fluorophenyl)urea After adding 70 mg of cyclobutanecarbonyl chloride to a solution of 100 mg of N-[4-(2-aminopyridin-4-yl)oxyphenyl]-N'-(4-fluorophenyl)urea, 0.12 ml of triethylamine and 10 ml of tetrahydrofuran stirred at room temperature, the mixture was further stirred for 15 minutes. NH type silica gel was added to the reaction solution, the solvent was distilled off under reduced pressure and the reaction product was adsorbed onto the silica gel. The silica gel was charged into a dry column packed with NH type silica gel, and column purification was performed (chloroform:methanol=40:1). The obtained residue was solidified from ethyl acetate-methanol-hexane to obtain 64 mg of the target substance as a white solid.

$^1$H-NMR (DMSO-d$_6$) δ (ppm): 1.68-1.78 (1H, m), 1.80-1.92 (1H, m), 1.95-2.18 (4H, m), 3.24-3.34 (1H, m), 6.63 (1H, dd, J=5.6 Hz, J=2.4 Hz), 7.05-7.15 (4H, m), 7.42-7.49 (2H, m), 7.52 (2H, d, J=8.8 Hz), 7.66 (1H, d, J=2.4 Hz), 8.13 (1H, d, J=5.6 Hz), 8.71 (1H, s), 8.77 (1H, s), 10.29 (1H, s).

The starting materials were obtained in the following manner.

Production Example 462-1

2-Amino-4-(4-nitrophenoxy)pyridine

A mixture of 15.88 g of 2-amino-4-chloropyridine 34.5 g of p-nitrophenol, 52 ml of Hunig's base and 100 ml of 1-methyl-2-pyrrolidinone was stirred at 160° C. for 15 hours.

Water was added, extraction was performed with ethyl acetate, and the solvent was distilled off under reduced pressure. The residue was purified by column chromatography (hexane:ethyl acetate=1:1) using NH type silica gel to obtain 3.24 g of the target substance as a light yellow solid.

$^1$H-NMR (DMSO-d$_6$) δ (ppm): 6.04 (1H, d, J=2.4 Hz), 6.12 (2H, brs), 6.26 (1H, dd, J=6.0 Hz, J=2.4 Hz), 7.32 (2H, d, J=8.8 Hz), 7.92 (1H, d, J=6.0 Hz), 8.31 (2H, d, J=8.8 Hz).

Production Example 462-2

2-Amino-4-(4-aminophenoxy)pyridine

After adding 1 g of 2-amino-4-(4-nitrophenoxy)pyridine to a mixture of 2.0 g of iron powder, 4.0 g of ammonium chloride, 30 ml of ethanol, 30 ml of dimethylformamide and 15 ml of water, the mixture was vigorously stirred at 100° C. for 10 minutes. The reaction solution was filtered with celite and the solvent was distilled off under reduced pressure to obtain 0.53 g of the target substance as a solid.

$^1$H-NMR (DMSO-d6) d (ppm): 5.04 (2H, bs), 5.72 (1H, d, J=1.6 Hz), 5.81 (2H, brs), 6.05 (1H, dd, J=5.6 Hz, J=1.6 Hz), 6.57 (2H, d, J=8.8 Hz), 6.75 (2H, d, J=8.8 Hz), 7.70 (1H, d, J=5.6 Hz).

Production Example 462-3

N-[4-(2-Aminopyridin-4-yl)oxyphenyl]-N'-(4-fluorophenyl)urea

After dissolving 0.53 g of 2-amino-4-(4-aminophenoxy)pyridine in a mixture of 20 ml of tetrahydrofuran and 10 ml of dimethylformamide, 0.36 ml of p-fluorophenyl isocyanate was added and the mixture was stirred for 1 hour. NH type silica gel was added to the reaction solution, the solvent was distilled off under reduced pressure and the reaction product was adsorbed onto the silica gel. The silica gel was charged into a dry column packed with NH type silica gel, and column purification was performed (chloroform:methanol=20:1, followed by 10:1). The solvent was distilled off under reduced pressure to obtain 610 mg of the target substance as a white powder.

$^1$H-NMR (DMSO-d$_6$) δ (ppm): 5.78 (1H, s), 5.87 (1H, s), 5.89 (1H, s), 6.09-6.13 (1H, m), 7.00-7.15 (4H, m), 7.42-7.52 (4H, m), 7.77 (1H, dd, J=6.0 Hz, J=1.6 Hz), 8.69 (1H, s), 8.73 (1H, s).

The following samples were synthesized by the same procedure as in Example 462.

Example 463

N-[4-(2-Butanoylaminopyridin-4-yl)oxyphenyl]-N'-(4-fluorophenyl)urea $^1$H-NMR (DMSO-d$_6$) δ (ppm): 0.85 (3H, t, J=7.2 Hz), 1.52 (2H, tq, J=7.2 Hz, J=7.2 Hz), 2.30 (2H, t, J=7.2 Hz), 6.63 (1H, dd, J=5.6 Hz, J=2.0 Hz), 7.06-7.16 (4H, m), 7.42-7.50 (2H, m), 7.52 (2H, d, J=8.8 Hz), 7.65 (1H, d, J=2.0 Hz), 8.14 (1H, d, J=5.6 Hz), 8.72 (1H, s), 8.77 (1H, s), 10.45 (1H, s).

Example 464

N-{4-[2-(4-Ethoxycarbonylbutanoyl)aminopyridin-4-yl]oxyphenyl}-N'-(4-fluorophenyl)urea $^1$H-NMR (DMSO-d$_6$) δ (ppm): 1.14 (3H, t, J=7.2 Hz), 1.74 (2H, tt, J=7.2 Hz, J=7.2 Hz), 2.26 (2H, t, J=7.2 Hz), 2.35 (2H, t, J=7.2 Hz), 4.01 (2H, q, J=7.2 Hz), 6.62 (1H, dd, J=6.0 Hz, J=2.4 Hz), 7.05-7.15 (4H, m), 7.41-7.49 (2H, m), 7.51 (2H, d, J=8.8 Hz), 7.62 (1H, d, J=2.4 Hz), 8.14 (1H, d, J=6.0 Hz), 8.70 (1H, s), 8.76 (1H, s).

Example 465

N-[4-(2-Nicotinoylaminopyridin-4-yl)oxyphenyl]-N'-(4-fluorophenyl)urea $^1$H-NMR (DMSO-d$_6$) δ (ppm): 6.75 (1H, dd, J=5.6 Hz, J=2.4 Hz), 7.06-7.18 (4H, m), 7.42-7.58 (5H, m), 7.75 (1H, 2.4 Hz), 8.22 (2H, m), 8.72 (2H, brs), 8.78 (1H, s), 9.06 (1H, s).

Example 466

N-{4-[2-(4-Carboxybutanoyl)aminopyridin-4-yl]oxyphenyl}-N'-(4-fluorophenyl)urea

N-{4-[2-(4-Ethoxycarbonylbutyryl)aminopyridin-4-yl]oxyphenyl}-N'-(4-fluorophenyl)urea (22 mg), 2N aqueous sodium hydroxide (1 ml), methanol (2 ml) and dimethylformamide (1 ml) were stirred together at 80° C. for 20 minutes. After returning the mixture to room temperature, 0.4 ml of 5N aqueous hydrochloric acid was added and the precipitated solid was filtered out to obtain 16 mg of the target substance as a white solid.

$^1$H-NMR (DMSO-d$_6$) δ (ppm): 1.72 (2H, tt, J=7.2 Hz, J=7.2 Hz), 2.20 (2H, t, J=7.2 Hz), 2.36 (2H, t, J=7.2 Hz), 6.62 (1H, dd, J=6.0 Hz, J=2.0 Hz), 7.05-7.15 (4H, m), 7.41-7.49 (2H, m), 7.52 (2H, d, J=8.8 Hz), 7.63 (1H, d, J=2.0 Hz), 8.14 (1H, d, J=6.0 Hz), 8.71 (1H, s), 8.76 (1H, s), 10.46 (1H, s), 12.03 (1H, s).

Example 467

N-(4-{2-[(Cyclopropylmethyl)aminocarbonyl]pyridin-4-yl}oxyphenyl)-N'-(4-fluorophenyl)urea After adding 100 mg of 4-(4-Aminophenoxy)-2-[(cyclopropylmethyl)aminocarbonyl]pyridine to 5 ml of tetrahydrofuran, 0.075 ml of p-fluorophenyl isocyanate was added at room temperature and the mixture was stirred for 1 hour. NH type silica gel was added to the reaction solution, the solvent was distilled off under reduced pressure and the reaction product was adsorbed onto the silica gel. The silica gel was charged into a dry column packed with NH type silica gel, and column purification was performed (hexane:ethyl acetate=1:1, followed by ethyl acetate and ethyl acetate:methanol=10:1). The solvent was distilled off under reduced pressure, ethyl acetate and hexane were added to the residue, and the precipitated solid was filtered out to obtain 25 mg of the target substance as a light yellow powder.

$^1$H-NMR (DMSO-d$_6$) δ (ppm): 0.21 (2H, bs), 0.38 (2H, bs), 1.02 (1H, bs), 3.12 (2H, dd, J=6.0 Hz, 6.0 Hz), 7.07-7.21 (5H, m), 7.37 (1H, s), 7.43-7.51 (2H, m), 7.56 (2H, d, J=8.0 Hz), 8.49 (1H, d, J=5.2 Hz), 8.74 (1H, s), 8.81 (1H, s), 8.83 (1H, t, J=6.0 Hz).

The starting materials were obtained in the following manner.

Production Example 467-1

4-Chloro-2-[(cyclopropylmethyl)aminocarbonyl]pyridine

4-Chloro-2-carboxypyridine (2.0 g), (aminomethyl)cyclopropane hydrochloride (1.7 g), 1-ethyl-3-(3-diethylaminopropyl)carbodiimide hydrochloride (WSC) (2.9 g), 1-hydroxybenzotriazole (HOBt) (2.3 g), triethylamine (2.1 ml) and tetrahydrofuran (30 ml) were stirred together at room temperature for 2 hours. Water was added, extraction was performed with ethyl acetate, and then silica gel was added to the extract and the solvent was distilled off under reduced pressure. The silica gel was charged into a dry column packed with silica gel and purified by column chromatography (hexane:ethyl acetate=4:1, followed by 2:1) to obtain 1.5 mg of the target substance as a yellow oil.

$^1$H-NMR (DMSO-$d_6$) δ (ppm): 0.19-0.30 (2H, m), 0.36-0.43 (2H, m), 0.99-1.09 (1H, m), 3.15 (2H, dd, J=6.4 Hz, J=6.4 Hz), 7.75 (1H, d, J=5.6 Hz), 8.01 (1H, s), 8.62 (1H, d, J=5.6 Hz), 8.90 (1H, t, J=6.4 Hz).

Production Example 467-2

2-[(Cyclopropylmethyl)aminocarbonyl]-4-(4-nitrophenoxy)pyridine

4-Chloro-2-[(cyclopropylmethyl)aminocarbonyl]pyridine (1.5 g), p-nitrophenol (2.0 g), Hunig's base (3.1 ml) and 1-methyl-2-pyrrolidinone (6.2 ml) were stirred together at 160° C. for 3 hours. Water was added, extraction was performed with ethyl acetate, and the solvent was distilled off under reduced pressure. The residue was purified by column chromatography (hexane:ethyl acetate=4:1, followed by 2:1) using NH type silica gel to obtain 0.35 g of the target substance as a colorless oil.

$^1$H-NMR (DMSO-$d_6$) δ (ppm): 0.19-0.24 (2H, m), 0.36-0.41 (2H, m), 1.02 (1H, bs), 3.13 (2H, dd, J=6.4 Hz, J=6.4 Hz), 7.34 (1H, dd, J=5.6 Hz, J=1.6 Hz), 7.44 (2H, d, J=8.8 Hz), 7.55 (1H, d, J=1.6 Hz), 8.33 (2H, d, J=8.8 Hz), 8.61 (1H, d, J=5.6 Hz), 8.90 (1H, t, J=6.4 Hz).

Production Example 467-3

4-(4-Aminophenoxy)-2-[(cyclopropylmethyl)aminocarbonyl]pyridine

After adding 0.35 g of 2-[(cyclopropylmethyl)aminocarbonyl]-4-(4-nitrophenoxy)pyridine to a mixture of 0.7 g of iron powder, 1.4 g of ammonium chloride, 10 ml of ethanol, 10 ml of dimethylformamide and 5 ml of water, the mixture was vigorously stirred at 100° C. for 20 minutes. The reaction solution was filtered with celite and the solvent was distilled off under reduced pressure to obtain 0.37 g of the target substance as a light brown oil.

$^1$H-NMR (DMSO-$d_6$) δ (ppm): 0.20-0.30 (2H, m), 0.38-0.44 (2H, m), 0.99-1.10 (1H, m), 3.13 (2H, dd, J=6.4 Hz, J=6.4 Hz), 5.14-5.19 (2H, m), 6.65 (2H, d, J=8.8 Hz), 6.87 (2H, d, J=8.8 Hz), 7.10 (1H, dd, J=5.6 Hz, J=2.8 Hz), 7.35 (1H, d, J=2.8 Hz), 8.47 (1H, d, J=5.6 Hz), 8.81 (1H, t, J=6.4 Hz).

Example 468

N-{4-[2-(Butyroylamino)pyridin-4-yl]oxyphenyl}-N'-cyclopropylurea

Phenyl N-{4-[2-(butyroylamino)pyridin-4-yl]oxyphenyl}carbamate (0.116 g), cyclopropylamine (0.034 g), triethylamine (0.041 ml) and tetrahydrofuran (10 ml) were heated together in a sealed tube at 100° C. for 1 hour. NH type silica gel was added to the reaction solution, the solvent was distilled off under reduced pressure and the reaction product was adsorbed onto the silica gel. The silica gel was charged into a dry column packed with NH type silica gel, and column purification was performed (ethyl acetate). The solvent was distilled off under reduced pressure, ethyl acetate and hexane were added to the residue, and the precipitated solid was filtered out to obtain 20 mg of the target substance as a white solid.

$^1$H-NMR (DMSO-$d_6$) δ (ppm): 0.38-0.45 (2H, m), 0.61-0.67 (2H, m), 0.86 (3H, t, J=7.2 Hz), 1.54 (2H, tq, J=7.2 Hz, J=7.2 Hz), 2.31 (2H, t, J=7.2 Hz), 2.48-2.58 (1H, m), 6.42 (1H, s), 6.62 (1H, dd, J=5.6 Hz, J=2.0 Hz), 7.05 (2H, d, J=8.8 Hz), 7.49 (2H, d, J=8.8 Hz), 7.64 (1H, d, J=2.0 Hz), 8.15 (1H, d, J=5.6 Hz), 8.41 (1H, s), 10.82 (1H, s).

The starting materials were obtained in the following manner.

Production Example 468-1

2-Butyroylamino-4-(4-nitrophenoxy)pyridine

Butyroyl chloride (0.93 ml) was added dropwise to a stirred solution of 2-amino-4-(4-nitrophenoxy)pyridine (1.0 g), triethylamine (1.8 ml) and tetrahydrofuran (20 ml) at room temperature. After stirring for 1 hour, water was added, extraction was performed with ethyl acetate, the extract was dried over magnesium sulfate and the solvent was distilled off under reduced pressure. The residue was purified by silica gel chromatography (hexane:ethyl acetate=2:1) to obtain 0.6 g of the target substance as a colorless oil.

$^1$H-NMR(CDCl$_3$) δ (ppm): 0.99 (3H, t, J=7.2 Hz), 1.73 (2H, tq, J=7.2 Hz, J=7.2 Hz), 2.36 (2H, t, J=7.2 Hz), 6.72 (1H, dd, J=5.6 Hz, 2.4 Hz), 7.21 (2H, d, J=8.8 Hz), 7.95 (1H, d, J=2.4 Hz), 8.22 (1H, d, J=5.6 Hz), 8.25 (1H, brs), 8.30 (2H, d, J=8.8 Hz).

Production Example 468-2

4-(4-Aminophenoxy)-2-(butyrylamino)pyridine

A mixture of 0.6 g of 2-butyrylamino-4-(4-nitrophenoxy)pyridine, 1.2 g of iron powder, 2.8 g of ammonium chloride, 10 ml of ethanol, 10 ml of dimethylformamide and 5 ml of water was vigorously stirred at 100° C. for 10 minutes. The reaction was filtered with celite, the solvent was distilled off under reduced pressure, and then water was added to the filtrate and extraction was performed with ethyl acetate. The extract was dried over magnesium sulfate and the solvent distilled off under reduced pressure to obtain 0.6 g of the target substance as a light yellow solid.

$^1$H-NMR (DMSO-$d_6$) δ (ppm): 0.86 (3H, t, J=7.2 Hz), 1.54 (2H, tq, J=7.2 Hz, J=7.2 Hz), 2.30 (2H, t, J=7.2 Hz), 5.06-5.15 (2H, m), 6.56 (1H, dd, J=5.6 Hz, J=2.4 Hz), 6.61 (2H, d, J=8.8 Hz), 6.81 (2H, d, J=8.8 Hz), 7.61 (1H, d, J=2.4 Hz), 8.10 (1H, d, J=5.6 Hz), 10.38 (1H, s).

Production Example 468-3

Phenyl N-{4-[2-(butyroylamino)pyridin-4-yl]oxyphenyl}carbamate

Phenyl chloroformate (0.14 ml) was added dropwise to an ice-cooled stirred solution of 4-(4-aminophenoxy)-2-(butyrylamino)pyridine (0.3 g), triethylamine (0.14 ml) and tetrahydrofuran (10 ml). The cooling bath was removed and the mixture was stirred at room temperature overnight. Silica gel was added to the reaction solution, the solvent was distilled off under reduced pressure and the reaction product was adsorbed onto the silica gel. The silica gel was charged into a dry column packed with silica gel, and column purification was performed (hexane:ethyl acetate=2:1, followed by 1:1). The solvent was distilled off under reduced pressure to obtain the target substance as a colorless solid.

$^1$H-NMR (DMSO-d$_6$) δ (ppm): 0.86 (3H, t, J=7.2 Hz), 1.54 (2H, tq, J=7.2 Hz, J=7.2 Hz), 2.31 (2H, t, J=7.2 Hz), 6.64-6.80 (1H, m), 7.16 (2H, d, J=8.8 Hz), 7.22-7.31 (3H, m), 7.41-7.48 (2H, m), 7.60 (2H, d, J=8.8 Hz), 7.66 (1H, d, J=2.0 Hz), 8.17 (1H, dd, J=5.6 Hz, J=2.0 Hz) 10.72 (1H, s), 10.90 (1H, s).

Example 469

1-[4-(5-Dimethylaminomethyl-6-phenyl-7H-pyrrolo[2,3-d]pyrimidin-4-yloxy)phenyl]-(3-fluorophenyl)urea N,N-Dimethylmethyleneammonium iodide (Eschenmoser's salt) (29.5 mg) and dimethylformamide (1.5 ml) were added to 1-(3-fluorophenyl)-3-[4-(6-phenyl-7H-pyrrolo[2,3-d]pyrimidin-4-yloxy)phenyl]urea (50 mg), and the mixture was stirred overnight at 100° C., after which water was added and liquid separation and extraction were performed with ethyl acetate. The organic layer was concentrated, dried under reduced pressure and subjected to NH silica gel column chromatography (ethyl acetate/methanol) to obtain 20 mg of the title compound.

MS Spectrum (ESI): 497 (M+1)

$^1$H-NMR Spectrum: (DMSOd$_6$) 2.26 (6H, s), 3.64 (2H, s), 6.73-6.80 (1H, m), 6.85 (1H, s), 7.08-7.58 (10H, m), 8.00 (1H, d, J=7.7 Hz), 8.26 (1H, d, J=0.9 Hz), 8.82 (1H, s), 8.92 (1H, s), 12.54 (1H, brs)

Example 470

1-{4-[6-(4-Benzyloxyphenyl)-7H-pyrrolo[2,3-d]pyrimidin-4-yloxy]-2-chlorophenyl}-3-cyclopropylurea After dissolving 38 mg of 1-{4-[6-(4-benzyloxyphenyl)-7-(2-trimethylsilanylethoxy methyl)-7H-pyrrolo[2,3-d]pyrimidin-4-yloxy]-2-chlorophenyl}-3-cyclopropylurea in 0.8 ml of tetrahydrofuran, 0.2 ml of tetrabutylammonium fluoride (1 M tetrahydrofuran solution) was added dropwise and the mixture was refluxed for 2 hours. It was then returned to room temperature, water was added, and liquid separation and extraction were performed with ethyl acetate and tetrahydrofuran. The organic layer was washed with water and saturated brine, concentrated and dried under reduced pressure to obtain 26 mg of the title compound.

$^1$H-NMR Spectrum: (DMSOd$_6$) 0.39-0.44 (2H, m), 0.60-0.70 (2H, m), 2.50-2.60 (1H, m), 5.18 (2H, s), 6.93 (1H, s), 7.09-7.50 (10H, m), 7.89 (2H, d, J=8.1 Hz), 7.92 (1H, s), 8.13 (1H, d, J=8.1 Hz), 8.28 (1H, d, J=1.0 Hz), 12.60 (1H, brs)

Example 471

1-{2-Chloro-4-[6-(4-hydroxyphenyl)-7H-pyrrolo[2,3-d]pyrimidin-4-yloxy]-phenyl}-3-cyclopropylurea After adding 2 ml of trifluoroacetic acid and 0.1 ml of thioanisole to 24 mg of 1-{4-[6-(4-benzyloxyphenyl)-7H-pyrrolo[2,3-d]pyrimidin-4-yloxy]-2-chlorophenyl}-3-cyclopropylurea, the mixture was stirred at 45° C. for 30 minutes. The reaction mixture was concentrated under reduced pressure, saturated sodium bicarnobate water was added to alkalinity, and then liquid separation and extraction were performed with ethyl acetate and tetrahydrofuran. The organic layer was washed with saturated brine, dried over anhydrous sodium sulfate, concentrated and dried under reduced pressure to obtain 15 mg of the title compound.

$^1$H-NMR Spectrum: (DMSOd$_6$) 0.39-0.44 (2H, m), 0.60-0.67 (2H, m), 2.52-2.60 (1H, m), 6.80-6.88 (3H, m), 7.12 (1H, d, J=2.0 Hz), 7.27 (1H, dd, J=9.0 Hz, J'=2.0 Hz), 7.40 (1H, d, J=2.0 Hz), 7.76 (2H, d, J=9.0 Hz), 7.91 (1H, s), 8.13 (1H, d, J=9.0 Hz), 8.25 (1H, d, J=1.0 Hz), 9.77 (1H, brs), 12.50 (1H, brs)

Example 472

1-{4-[6-(4-Benzyloxyphenyl)-7H-pyrrolo[2,3-d]pyrimidin-4-yloxy]phenyl}-3-(3-fluorophenyl)urea After adding 600 mg of iron powder, 1.1 g of ammonium chloride, 10 ml of ethanol, 20 ml of tetrahydrofuran and ml of water to 550 mg of 6-(4-benzyloxyphenyl)-4-(4-nitrophenoxy)-7H-pyrrolo[2,3-d]pyrimidine, the mixture was stirred at 80-85° C. for 1.5 hours. Upon returning the mixture to room temperature, it was filtered with celite, and ethyl acetate and water were added to the filtrate for liquid separation and extraction. The organic layer was dried over anhydrous sodium sulfate, filtered with plug cotton and concentrated to dryness to obtain 493 mg of an amino compound-containing crude product. After dissolving 490 mg of the crude product in 10 ml of toluene and 10 ml of acetonitrile at 90° C., 0.3 ml of 3-fluorophenyl isocyanate was added and the mixture was stirred for 1 hour. After cooling to room temperature, the precipitated crystals were filtered out and dried to obtain 450 mg of the title compound.

$^1$H-NMR Spectrum: (DMSOd$_6$) 5.17 (2H, s), 6.77 (1H, dt, J=2.9, 7.8 Hz), 6.88 (1H, d, J=1.2 Hz), 7.08-7.53 (14H, m), 7.88 (2H, d, J=9.1 Hz), 8.25 (1H, s), 8.75 (1H, s), 8.98 (1H, s), 12.56 (1H, brs)

Example 473

1-(3-Fluorophenyl)-3-{4-[6-(4-hydroxyphenyl)-7H-pyrrolo[2,3-d]pyrimidin-4-yloxy]phenyl}urea After dissolving 377 mg of 1-{4-[6-(4-benzyloxyphenyl)-7H-pyrrolo[2,3-d]pyrimidin-4-yloxy]phenyl}-3-(3-fluorophenyl)urea in 4 ml of trifluoroacetic acid and 0.4 ml of thioanisole, the solution was stirred at 45° C. for 40 minutes. It was then returned to room temperature, potassium carbonate was added to alkalinity, and liquid separation and extraction were performed with an ethyl acetate-tetrahydrofuran (5:1) mixed solvent. The organic layer was concentrated to dryness to obtain 310 mg of the title compound.

$^1$H-NMR Spectrum: (DMSOd$_6$) 6.70-6.80 (2H, m), 6.82 (2H, d, J=8.3 Hz), 7.10-7.52 (7H, m), 7.75 (2H, d, J=8.3 Hz), 8.23 (1H, s), 8.85 (1H, s), 8.98 (1H, s), 8.98 (1H, s), 12.48 (1H, brs)

Example 474

1-(4-{6-[4-(2-Diethylaminoethoxy)-phenyl]-7H-pyrrolo[2, 3-d]pyrimidin-4-yloxy}phenyl)-3-(3-fluorophenyl) urea After dissolving 114 mg of 1-(3-fluorophenyl)-3-{4-[6-(4-hydroxyphenyl)-7H-pyrrolo [2,3-d]pyrimidin-4-yloxy]phenyl}urea in 2 ml of dimethylformamide, there were added 44 mg (ca. 1 equivalent) of 2-chloroethyldiethylamine hydrochloride and 63 mg (2.5 equivalents) of potassium bicarbonate, and the mixture was stirred at 50-60° C. for 16 hours.

There were then added 17 mg of 2-chloroethyldiethylamine hydrochloride, 20 mg of potassium bicarbonate and 1 ml of dimethylformamide, and the mixture was stirred overnight at the same temperature. It was then returned to room temperature, water was added, and liquid separation and extraction were performed with ethyl acetate-tetrahydrofuran. The organic layer was washed with water and saturated brine, concentrated and subjected to NH silica gel column chromatography (hexane-ethyl acetate) to obtain 33 mg of a crude solid containing the title compound. This was washed with ethyl acetate to obtain 5 mg of the title compound.

MS Spectrum (ESI): 555 (M+1),
$^1$H-NMR Spectrum: (DMSOd$_6$) 0.96 (6H, t, J=7.4 Hz) 2.53 (4H, q, J=7.4 Hz), 2.78 (2H, t, J=6.2 Hz), 4.06 (2H, t, J=6.2 Hz), 6.74-6.88 (2H, m), 7.02 (2H, d, J=9.0 Hz), 7.09-7.54 (7H, m), 7.86 (2H, d, J=9.0 Hz), 8.25 (1H, s), 8.83 (1H, brs), 8.96 (1H, brs), 12.50 (1H, brs)

The intermediate was synthesized in the following manner.

Production Example 474-1

6-(4-Benzyloxyphenyl)-4-(4-nitrophenoxy)-7H-pyrrolo[2,3-d]pyrimidine

After adding 2.97 of potassium carbonate and 30 ml of dimethylformamide to 3.09 g of 4-nitrophenol and stirring the mixture at 130° C. for 10 minutes, 2.49 g of 6-(4-benzyloxyphenyl)-4-chloro-7H-pyrrolo[2,3-d]pyrimidine was added and the mixture was further stirred at 130° C. for 5 hours and at 135° C. overnight. After returning the mixture to room temperature, water was added, the precipitated solid was filtered out and subjected to NH silica gel column chromatography (ethyl acetate) and silica gel column chromatography (ethyl acetate), and then ether and ethyl acetate were added prior to sonication. The solid was filtered out to obtain 1.2 g of the title compound.

$^1$H-NMR Spectrum: (DMSOd$_6$) 5.18 (2H, s), 6.99 (1H, d, J=1.7 Hz), 7.08-7.13 (2H, m), 7.28-7.48 (5H, m), 7.53-7.60 (2H, m), 7.88-7.93 (2H, m), 8.30-8.35 (3H, m), 12.71 (1H, brs)

Example 475

1-(3-Fluorophenyl)-3-{4-[6-(4-pyrrolidin-1-ylphenyl)-7H-pyrrolo[2,3-d]pyrimidin-4-yloxy]phenyl}urea After adding 646 mg of 4-nitrophenol, 817 mg of potassium carbonate and 6.3 ml of dimethylformamide to 630 mg of 4-chloro-6-(4-pyrrolidin-1-ylphenyl)-7H-pyrrolo[2,3-d]pyrimidine, the mixture was stirred overnight at 130° C. Water was added, liquid separation and extraction were performed with ethyl acetate, and the organic layer was washed with water and saturated brine and concentrated to dryness to obtain 510 mg of a solid. After adding to the solid 500 mg of iron powder, 1 g of ammonium chloride, 20 ml of ethanol, 10 ml of tetrahydrofuran 10 ml and 3 ml of water, the mixture was stirred at 80° C. for 2 hours. Upon returning the mixture to room temperature, it was filtered with celite, and ethyl acetate, tetrahydrofuran and water were added to the filtrate for liquid separation and extraction, after which the organic layer was dried over anhydrous sodium sulfate, filtered with plug cotton and concentrated to dryness to obtain 380 mg of a crude product. After adding thereto 5 ml of toluene, 5 ml of acetonitrile and 5 ml of tetrahydrofuran for dissolution at 100° C., the solution was stirred for 1 hour. It was then allowed to cool to room temperature and the precipitated crystals were filtered out, washed with ether and dried under reduced pressure to obtain 40 mg of the title compound.

MS Spectrum (ESI; nega): 509 (M+1)
$^1$H-NMR Spectrum: (DMSOd$_6$) 1.85-2.02 (4H, m), 3.10-3.32 (4H, m), 6.42 (1H, d, J=8.2 Hz), 6.60 (1H, d, J=8.2 Hz), 6.70-6.80 (2H, m), 7.02-7.53 (9H, m), 8.00 (1H, s), 8.99 (1H, s), 9.17 (1H, s), 11.81 (1H, brs)

The intermediates were synthesized in the following manner.

Production Example 475-1

2-Amino-5-(4-pyrrolidine-1-phenyl)-1H-pyrrole-3-carboxylic acid ethyl ester

After adding 150 ml of ethanol to 13.8 g of 2-amidino-ethyl acetate ester hydrochloride (publicly known compound described in Liebigs Ann. Chem., 1895(1977)), there was further added 5.94 g of sodium ethoxide (0.97 equivalent with respect to the 2-amidino-ethyl acetate ester hydrochloride) at 0° C. and the mixture was stirred for 10 minutes under a nitrogen atmosphere. There was further added 12 g of 2-bromo-1-(4-pyrrolidine-1-phenyl)ethanone (Lancaster), and the mixture was stirred at room temperature for 48 hours. Ethyl acetate was added prior to sonication, the solid was filtered out, and the filtrate was concentrated and subjected to silica gel column chromatography (ethyl acetate) to obtain 4.82 g of the title compound.

$^1$H-NMR Spectrum: (DMSOd$_6$) 1.22 (3H, d, J=7.3 Hz), 1.88-1.98 (4H, m), 3.16-3.24 (4H, m), 4.06-4.14 (2H, m), 5.52 (2H, s), 6.13 (1H, d, J=2.8 Hz), 6.48 (2H, d, J=8.8 Hz), 7.28 (2H, d, J=8.8 Hz), 10.48 (1H, s)

Production Example 475-2

6-(4-Pyrrolidin-1-ylphenyl)-7H-pyrrolo[2,3-d]pyrimidin-4-01

After adding 8 ml of formic acid, 31.8 ml of formamide and 15.9 ml of dimethylformamide to 4.80 g of 2-amino-5-(4-pyrrolidine-1-phenyl)-1H-pyrrole-3-carboxylic acid ethyl ester and stirring the mixture at 140° C. for 48 hours, it was allowed to stand at room temperature for 24 hours. The precipitated solid was filtered out and dried under reduced pressure to obtain 3.0 g of the title compound.

$^1$H-NMR Spectrum: (DMSOd$_6$) 1.86-2.00 (4H, m), 3.08-3.13 (4H, m), 6.54 (2H, d, J=8.8 Hz), 6.62 (1H, s), 7.61 (2H, d, J=8.8 Hz), 7.78 (1H, s), 12.40 (1H, brs)

Production Example 475-3

4-Chloro-6-(4-pyrrolidin-1-ylphenyl)-7H-pyrrolo[2,3-d]pyrimidine

After adding 20 ml of phosphorous oxychloride to 1.9 g of 6-(4-pyrrolidin-1-ylphenyl)-7H-pyrrolo[2,3-d]pyrimidin-4-ol and stirring the mixture at 140° C. for 3 hours, the reaction system was returned to room temperature and concentrated. Ice water was added to the residue, sodium bicarbonate was used for neutralization, and liquid separation and extraction were performed with ethyl acetate. The organic layer was dried over sodium sulfate and concentrated to dryness to obtain 12 g of a crude product containing the title compound.

$^1$H-NMR Spectrum: (DMSOd$_6$) 1.86-2.02 (4H, m), 3.10-3.32 (4H, m), 6.60 (2H, d, J=8.9 Hz), 6.77 (1H, d, J=2.0 Hz), 7.81 (2H, d, J=8.9 Hz), 8.46 (1H, s), 12.70 (1H, brs)

Example 476

N-{4-[6-(Methylamino)carbonyl-7-methoxy-4-quinolyl]oxyphenyl}-N'-(4-fluorophenyl)urea The title compound (85 mg) was obtained as light yellow crystals from 4-(4-amino-phenoxy)-7-methoxy-quinoline-6-carboxylic acidmethylamide (65 mg) and 4-fluorophenyl isocyanate (0.05 ml), by the same procedure as in Example 10.
$^1$H-NMR (DMSO-d$_6$) δ (ppm) 2.81-2.84 (3H, m), 4.00 (3H, s), 6.46 (1H, s), 7.07-7.24 (4H, m), 7.43-7.61 (5H, m), 8.32-8.38 (1H, m), 8.59-8.65 (2H, m), 8.80 (1H, brs), 8.89 (1H, brs)
The starting materials were synthesized by the following 3 steps.

Production Example 476-1

4-Chloro-7-methoxyquinoline-6-carboxylic acid methylamide

After dissolving 7-methoxy-4-chloro-quinoline-6-carbonyl chloride synthesized by the method of Production Example 152-2 from 7-methoxy-4-oxo-1,4-dihydroquinoline-6-carboxylic acid (947 mg) in tetrahydrofuran (70 ml), the solution was cooled to 0° C. A 40% aqueous methylamine solution (0.4 ml) was added, and the mixture was stirred at room temperature for 30 minutes. Water was added, extraction was performed 3 times with ethyl acetate, and the organic layers were combined, washed with water and saturated brine, dried over sodium sulfate and then dried under reduced pressure to obtain the title compound (710 mg).
$^1$H-NMR (DMSO-d$_6$) δ (ppm) 3.07-3.10 (3H, m), 4.12 (3H, s), 7.40-7.43 (1H, m), 7.56 (1H, s), 7.83 (1H, brs), 8.73-8.77 (1H, m), 9.13 (1H, s)

Production Example 476-2

7-Methoxy-4-(4-nitrophenoxy)quinoline-6-carboxylic acid methylamide

The title compound (736 mg) was obtained as light yellow crystals from 4-chloro-7-methoxyquinoline-6-carboxylic acid methylamide (492 mg) and 4-nitrophenol (492 mg), by the same procedure as in Production Example 7.
$^1$H-NMR (DMSO-d$_6$) δ (ppm) 2.76-2.82 (3H, m), 4.02 (3H, s), 6.86 (1H, d, J=5.2 Hz), 7.45-7.51 (2H, m), 7.56 (1H, s), 8.32-8.38 (2H, m), 8.45 (1H, s), 8.76-8.79 (1H, m)

Production Example 476-3

4-(4-Aminophenoxy)-7-methoxyquinoline-6-carboxylic acid methylamide

The title compound (250 mg) was obtained from 7-methoxy-4-(4-nitrophenoxy)-quinoline-6-carboxylic acid methylamide (736 mg), by the same procedure as in Production Example 10.
$^1$H-NMR (DMSO-d$_6$) δ (ppm) 2.81-2.84 (3H, m), 3.99 (3H, s), 5.14-5.19 (2H, m), 6.39 (1H, d, J=5.2 Hz), 6.45 (2H, d, J=8.4 Hz), 6.92 (2H, d, J=8.4 Hz), 7.46 (1H, s), 8.30-8.38 (1H, m), 8.57-8.61 (2H, m)

Example 477

N-{4-[6-(Methylamino)carbonyl-7-methoxy-4-quinolyl]oxyphenyl}-N'-(2-thiazolyl)urea The title compound (32 mg) was obtained as light yellow crystals from 4-(4-amino-phenoxy)-7-methoxyquinoline-6-carboxylic acid methylamide (65 mg) and phenyl N-(2-thiazolyl)carbamate (49 mg), by the method described in Example 11.
$^1$H-NMR (DMSO-d$_6$) δ (ppm) 2.80-2.85 (3H, m), 4.00 (3H, s), 6.47 (1H, d, J=5.2 Hz), 7.05-7.15 (1H, m), 7.25 (2H, d, J=8.8 Hz), 7.35-7.40 (1H, m), 7.50 (1H, s), 7.62 (2H, d, J=8.8 Hz), 8.58-8.66 (2H, m)

Example 478

N-{4-[6-(Dimethylamino)carbonyl-7-methoxy-4-quinolyl]oxyphenyl}-N'-(2-thiazolyl)urea The title compound (60 mg) was obtained as light yellow crystals from 4-(4-aminophenoxy)-7-methoxyquinoline-6-carboxylic acid dimethylamide (100 mg) and phenyl N-(2-thiazolyl) carbamate (60 mg), by the method described in Example 11.
$^1$H-NMR (DMSO-d$_6$) δ (ppm) 2.78 (3H, s), 3.00 (3H, s), 3.97 (3H, s), 6.47 (1H, d, J=5.2 Hz), 7.05-7.15 (1H, m), 7.24 (2H, d, J=8.8 Hz), 7.35-7.39 (1H, m), 7.48 (1H, s), 7.60 (2H, d, J=8.8 Hz), 8.04 (1H, s), 8.62 (1H, d, J=5.2 Hz)
The starting materials were synthesized by the following 3 steps.

Production Example 478-1

4-Chloro-7-methoxy-quinoline-6-carboxylic acid dimethylamide

After dissolving 7-methoxy-4-chloro-quinoline-6-carbonyl chloride synthesized by the method of Production Example 152-2 from 7-methoxy-4-oxo-1,4-dihydroquinoline-6-carboxylic acid (1.0 g) in tetrahydrofuran (60 ml), the solution was cooled to 0° C. Diisopropylethylamine (1.6 ml) and a 2.0 M dimethylamine tetrahydrofuran solution (3 ml) were added and the mixture was stirred overnight at room temperature. Water was added, extraction was performed 3 times with ethyl acetate, and the organic layers were combined, washed with water and saturated brine, dried over sodium sulfate and then dried under reduced pressure to obtain the title compound (933 mg).
$^1$H-NMR (DMSO-d$_6$) δ (ppm) 2.75 (3H, s), 3.01 (3H, s), 3.97 (3H, s), 7.57 (1H, s), 7.63 (1H, d, J=4.8 Hz), 7.93 (1H, s), 8.78 (1H, d, J=4.8 Hz)

Production Example 478-2

7-Methoxy-4-(4-nitrophenoxy)-quinoline-6-carboxylic acid dimethylamide

The title compound (904 mg) was obtained as light yellow crystals from acid dimethylamide (933 mg) and 4-nitrophenol (737 mg), by the same procedure as in Production Example 10.
$^1$H-NMR (DMSO-d$_6$) δ (ppm) 2.75 (3H, s), 2.99 (3H, s), 3.95 (3H, s), 6.87 (1H, d, J=5.2 Hz), 7.46 (2H, d, J=7.2 Hz), 7.55 (1H, s), 7.94 (1H, s), 8.33 (2H, d, J=7.2 Hz), 8.76 (1H, d, J=5.2 Hz)

Production Example 478-3

4-(4-Aminophenoxy)-7-methoxyquinoline-6-carboxylic acid dimethylamide

The title compound (511 mg) was obtained from 7-methoxy-4-(4-nitrophenoxy)quinoline-6-carboxylic acid dimethylamide (904 mg), by the same procedure as in Production Example 10.

¹H-NMR(CDCl₃) δ (ppm) 2.90 (3H, s), 3.18 (3H, s), 3.98 (3H, s), 6.43 (1H, d, J=5.6 Hz), 6.75 (2H, d, J=8.8 Hz), 6.95 (2H, d, J=8.8 Hz), 7.45 (1H, s), 8.27 (1H, s), 8.57 (1H, d, J=5.6 Hz)

Example 479

N-{4-[6-(Cyclopropylamino)carbonyl-7-methoxy-4-quinolyl]oxyphenyl}-N'-(4-fluorophenyl)urea After dissolving the N-[4-(6-carboxy-7-methoxy-4-quinolyl)oxyphenyl]-N'-(4-fluorophenyl)urea (60 mg) synthesized in Example 341 in dimethylformamide (1.5 ml), there were added 1-ethyl-3-(3-diethylaminopropyl)-carbodiimide hydrochloride (39 mg), 1-hydroxy-1H-benzotriazole monohydrate (31 mg), triethylamine (30 μl) and cyclopropylamine (0.05 ml) and the mixture was stirred overnight at room temperature. The reaction solution was distributed between ethyl acetate and water, and the organic layer was washed with water and then dried over anhydrous sodium sulfate. After distilling off the solvent, crystals were precipitated with ethyl acetate, filtered out and dried under reduced pressure to obtain the title compound (29 mg) as white crystals.

¹H-NMR(CDCl₃) δ (ppm) 0.45-0.59 (2H, m), 0.67-0.73 (2H, m), 2.82-2.89 (1H, m), 3.97 (3H, s), 6.45 (1H, d, J=5.2 Hz), 7.08-7.23 (4H, m), 7.43-7.50 (3H, m), 7.55-7.60 (2H, m), 8.32-8.35 (1H, m), 8.42 (1H, s), 8.62 (1H, d, J=5.2 Hz), 8.75 (1H, brs), 8.84 (1H, brs)

Example 480

N-[4-(6-Aminomethyl-7-methoxyguinolin-4-yloxy)-phenyl]-N'-phenylurea trifluoroacetate After dissolving the N-[4-(6-cyano-7-methoxyguinolin-4-yloxy)phenyl]-N'-phenylurea (100 mg) synthesized in Example 37 in an ethanol (5 ml) and tetrahydrofuran (5 ml) mixed solvent, there were added trifluoroacetic acid (0.5 ml) and 50% palladium-carbon (50 mg), and the mixture was stirred overnight under a hydrogen atmosphere. After filtering off the palladium carbon, the filtrate was concentrated. The obtained residue was washed with tetrahydrofuran to obtain the title compound (70 mg).

¹H-NMR (DMSO-d₆) δ (ppm) 4.02 (3H, s), 4.24 (2H, s), 6.64 (1H, d, J=5.6 Hz), 6.94-6.99 (1H, m), 7.21-7.31 (4H, m), 7.44-7.49 (2H, m), 7.53 (1H, s), 7.62-7.66 (2H, m), 8.25 (2H, brs), 8.48 (1H, s), 8.76 (1H, d, J=5.6 Hz), 8.87 (1H, brs), 9.04 (1H, brs)

Example 481

N-[4-(6-Acetylaminomethyl-7-methoxyguinolin-4-yloxy)phenyl]-N'-phenylurea

After dissolving N-[4-(6-aminomethyl-7-methoxy-quinolin-4-yloxy)phenyl]-N'-phenylurea trifluoroacetate (40 mg) in pyridine (1.0 ml) and acetic anhydride (1.0 ml), the solution was stirred overnight at room temperature. The reaction solution was concentrated under reduced pressure and the obtained crude product was crystallized with ethyl acetate to obtain the title compound (13 mg).

¹H-NMR (DMSO-d₆) δ (ppm) 1.90 (3H, s), 3.98 (3H, s), 4.37-4.40 (2H, m), 6.46 (1H, d, J=5.2 Hz), 6.93-6.99 (1H, m), 7.18-7.30 (4H, m), 7.40 (1H, s), 7.45 (2H, d, J=7.6 Hz), 7.59 (2H, d, J=8.8 Hz), 8.06 (1H, s), 8.38-8.44 (1H, m), 8.59 (1H, d, J=5.2 Hz) 8.70 (1H, s), 8.83 (1H, s)

Example 482

N-(2-Fluoro-4-[(6-carbamoyl-7-methoxy-4-quinolyl)oxy]phenyl)-N'-cyclopropylurea

Cyclopropylamine (0.10 ml) was added to dimethylsulfoxide (0.8 ml), and then [4-(6-carbamoyl-7-methoxyquinolin-4-yloxy)-2-fluorophenyl]carbamic acid phenyl ester (80 mg) was dissolved therein and the mixture was stirred for 10 minutes. Water and ethyl acetate were added to the reaction solution and the precipitated crystals were filtered out to obtain the title compound (33 mg).

¹H-NMR (DMSO-d₆) δ (ppm) 0.38-0.41 (2H, m), 0.62-0.66 (2H, m), 2.51-2.59 (1H, m), 4.01 (3H, s), 6.52 (1H, d, J=5.2 Hz), 6.78-6.81 (1H, m), 7.04-7.09 (1H, m), 7.28-7.34 (1H, m), 7.50 (1H, s), 7.72 (1H, brs), 7.84 (1H, brs), 8.16-8.23 (2H, m), 8.63-8.67 (2H, m)

The starting material was synthesized in the following manner.

Production Example 482-1

[4-(6-Carbamoyl-7-methoxyquinolin-4-yloxy)-2-fluorophenyl]carbamic acid phenyl ester The title compound was obtained from the 6-carbamoyl-4-(4-amino-3-fluorophenoxy)-7-methoxyquinoline synthesized in Production Example 152-5, by the method described in Production Example 17.

H-NMR(CDCl₃) δ (ppm) 4.13 (3H, s), 5.90 (1H, brs), 6.53 (1H, d, J=5.6 Hz), 6.99-7.06 (2H, m), 7.20-7.30 (4H, m), 7.40-7.45 (2H, m), 7.59 (1H, s), 7.80 (1H, brs), 8.24 (1H, brs), 8.68 (1H, d, J=5.6 Hz), 9.27 (1H, s)

Example 483

N-(2-Fluoro-4-[(6-carbamoyl-7-methoxy-4-quinolyl)oxy]phenyl)-N'-(2-thiazolyl)urea The title compound (24 mg) was obtained as light yellow crystals from the 6-carbamoyl-4-(4-amino-3-fluorophenoxy)-7-methoxyquinoline (60 mg) and phenyl N-(2-thiazolyl)carbamate (60 mg) synthesized in Example 152-5, by the method described in Example 224.

¹H-NMR (DMSO-d₆) δ (ppm) 4.02 (3H, s), 6.57 (1H, d, J=5.2 Hz), 7.12-7.18 (2H, m), 7.37-7.45 (2H, m), 7.51 (1H, s), 7.73 (1H, brs), 7.85 (1H, brs), 8.18-8.26 (1H, m), 8.64-8.69 (2H, m)

Example 484

N-{4-[6-(Methylamino)carbonyl-7-methoxy-4-quinolyl]oxyphenyl}-N'-cyclopropylurea The title compound (33 mg) was obtained as light yellow crystals from N-[4-(7-methoxy-6-methylcarbamoylquinolin-4-yloxy)phenyl]carbamic acid phenyl ester (80 mg) and cyclopropylamine (20 mg), by the method described in Example 11.

¹H-NMR (DMSO-d₆) δ (ppm) 0.39-0.43 (2H, m), 0.62-0.68 (2H, m), 2.50-2.58 (1H, m), 2.84 (3H, d, J=4.8 Hz), 4.02 (3H, s), 6.43-6.46 (2H, m), 7.14-7.20 (2H, m), 7.50 (1H, s), 7.53-7.57 (2H, m), 8.35-8.38 (1H, m), 8.47 (1H, brs), 8.61 (1H, s), 8.64 (1H, d, J=5.2 Hz)

The starting material was synthesized in the following manner.

Production Example 484-1

N-[4-(7-Methoxy-6-methylcarbamoylquinolin-4-yloxy)phenyl]carbamic acid phenyl ester The title compound (60 mg) was obtained from 4-(4-aminophenoxy)-7-methoxyquinoline-6-carboxylic acid methylamide (53 mg), by the method described in Production Example 17.

$^1$H-NMR(CDCl$_3$) δ (ppm) 3.08 (3H, d, J=4.8 Hz), 4.12 (3H, s), 6.48 (1H, d, J=5.2 Hz), 7.14-7.29 (6H, m), 7.37-7.45 (2H, m), 7.55-7.63 (3H, m), 7.89 (1H, brs), 8.63 (1H, d, J=5.2 Hz), 9.28 (1H, s)

Example 485

N-(2-Fluoro-4-[(6-carbamoyl-7-methoxy-4-quinolyl)oxy]phenyl)-N'-cyclobutylurea

The title compound (28 mg) was obtained from [4-(6-carbamoyl-7-methoxyquinolin-4-yloxy)-2-fluorophenyl]carbamic acid phenyl ester (73 mg) and cyclobutylamine (28 mg), by the method described in Example 11.

$^1$H-NMR (DMSO-d$_6$) δ (ppm) 2.52-2.67 (2H, m), 2.72-2.87 (2H, m), 2.14-2.26 (2H, m), 4.01 (3H, s), 4.04-4.18 (1H, m), 6.51 (1H, d, J=5.2 Hz), 6.88 (1H, d, J=8.0 Hz), 7.02-7.08 (1H, m), 7.27-7.34 (1H, m), 7.50 (1H, s), 7.72 (1H, brs), 7.84 (1H, brs), 8.15-8.26 (2H, m), 8.63-8.67 (2H, m)

Example 486

N-(2-Fluoro-4-[(6-carbamoyl-7-methoxy-4-quinolyl)oxy]phenyl)-N'-cyclopentylurea

The title compound (68 mg) was obtained from [4-(6-carbamoyl-7-methoxyquinolin-4-yloxy)-2-fluorophenyl]carbamic acid phenyl ester (80 mg) and cyclopentylamine (38 mg), by the method described in Example 11.

$^1$H-NMR (DMSO-d$_6$) δ (ppm) 1.30-1.40 (2H, m), 1.49-1.59 (4H, m), 1.78-1.88 (2H, m), 3.88-3.98 (1H, m), 4.01 (3H, s), 6.51 (1H, d, J=5.2 Hz), 6.67 (1H, d, J=7.2 Hz), 7.02-7.07 (1H, m), 7.27-7.33 (1H, m), 7.50 (1H, s), 7.72 (1H, brs), 7.84 (1H, brs), 8.20-8.28 (2H, m), 8.63-8.67 (2H, m)

Example 487

N-(2-Fluoro-4-[(6-carbamoyl-7-methoxy-4-quinolyl)oxy]phenyl)-N'-(2-propyl)urea

The title compound (39 mg) was obtained from [4-(6-carbamoyl-7-methoxyquinolin-4-yloxy)-2-fluorophenyl]carbamic acid phenyl ester (60 mg) and isopropylamine (25 mg), by the method described in Example 11.

$^1$H-NMR (DMSO-d$_6$) δ (ppm) 1.09 (6H, d, J=6.4 Hz), 3.70-3.80 (1H, m), 4.01 (3H, s), 6.50-6.55 (2H, m), 7.03-7.07 (1H, m), 7.27-7.34 (1H, m), 7.50 (1H, s), 7.72 (1H, brs), 7.84 (1H, brs), 8.20-8.27 (2H, m), 8.63-8.66 (2H, m)

Example 488

N-[4-(6-Carbamoyl-7-methoxy-4-quinolyl)oxy-2-methyl-phenyl]-N'-cyclopropylurea

Cyclopropylamine (0.10 ml) was added to dimethylsulfoxide (0.8 ml), and then [4-(6-carbamoyl-7-methoxy-4-quinolyl)oxy)-2-methylphenyl]carbamic acid phenyl ester (136 mg) was dissolved therein and the mixture was stirred for 10 minutes. Water and ethyl acetate were added to the reaction solution and the precipitated crystals were filtered out to obtain the title compound (90 mg).

$^1$H-NMR (DMSO-d$_6$) δ (ppm) 0.38-0.44 (2H, m), 0.62-0.69 (2H, m), 2.22 (3H, s), 2.53-2.60 (1H, m), 4.03 (3H, s), 6.46 (1H, d, J=5.2 Hz), 6.75-6.79 (1H, m), 7.01-7.12 (2H, m), 7.50 (1H, s), 7.62 (1H, s), 7.73 (1H, brs), 7.85 (1H, brs), 7.90-7.96 (1H, m), 8.62-8.69 (2H, m)

The starting materials were synthesized by the following 3 steps.

Production Example 488-1

6-Carbamoyl-4-(3-methyl-4-nitrophenoxy)-7-methoxyquinoline

The title compound (1.2 g) was obtained from 7-methoxy-4-chloroquinoline-6-carboxyamide (1.0 g) and 4-nitro-3-methylphenol (810 mg), in the same manner as Production Example 7.

$^1$H-NMR (DMSO-d$_6$) δ (ppm) 2.54 (3H, s), 4.00 (3H, s), 6.80 (1H, d, J=5.2 Hz), 7.28-7.32 (1H, m), 7.41-7.43 (1H, m), 7.54 (1H, s), 7.72 (1H, brs), 7.83 (1H, brs), 8.13-8.16 (1H, m), 8.55 (1H, s), 8.72-8.76 (1H, m)

Production Example 488-2

4-(6-Carbamoyl-7-methoxy-4-quinolyl)oxy-2-methyl-phenylamine

The title compound (0.22 g) was obtained from 6-carbamoyl-4-(3-methyl-4-nitrophenoxy)-7-methoxyquinoline (1.2 g), in the same manner as Production Example 8.

$^1$H-NMR (DMSO-d$_6$) δ (ppm) 2.07 (3H, s), 4.00 (3H, s), 4.88-4.94 (2H, m), 6.39 (1H, d, J=5.2 Hz), 6.70-6.71 (1H, m), 6.77-6.88 (2H, m), 7.46 (1H, s), 7.70 (1H, brs), 7.83 (1H, brs), 8.59 (1H, d, J=5.2 Hz), 8.66 (1H, s)

Production Example 488-3

[4-(6-Carbamoyl-7-methoxy-4-quinolyl)oxy-2-methylphenyl]carbamic acid phenyl ester The title compound was obtained from 4-(6-carbamoyl-7-methoxy-4-quinolyl)oxy-2-methylphenylamine, by the method described in Production Example 141-1.

$^1$H-NMR(CDCl$_3$) δ (ppm) 2.38 (3H, s), 4.12 (3H, s), 5.88 (1H, brs), 6.49 (1H, d, J=5.6 Hz), 6.76 (1H, brs), 7.04-7.09 (2H, m), 7.20-7.29 (3H, m), 7.38-7.45 (2H, m), 7.54 (1H, s), 7.80 (1H, brs), 7.94 (1H, brs), 8.64 (1H, d, J=5.6 Hz), 9.29 (1H, s)

Example 489

N-[4-(6-Carbamoyl-7-methoxy-4-quinolyl)oxy)-2-trifluoro methyl-phenyl]-N'-cyclopropylurea Cyclopropylamine (0.10 ml) was added to dimethylsulfoxide (0.8 ml), and then [4-(6-carbamoyl-7-methoxy-4-quinolyl)oxy)-2-trifluoromethylphenyl]carbamic acid phenyl ester (140 mg) was dissolved therein and the mixture was stirred for 10 minutes. Water and ethyl acetate were added to the reaction solution and the precipitated crystals were filtered out to obtain the title compound (103 mg).

¹H-NMR (DMSO-d₆) δ (ppm) 0.38-0.44 (2H, m), 0.62-0.68 (2H, m), 2.51-2.59 (1H, m), 4.02 (3H, s), 6.52 (1H, d, J=5.2 Hz), 7.18-7.24 (1H, m), 7.50-7.62 (3H, m), 7.70-7.77 (2H, m), 7.84 (1H, brs), 8.07-8.14 (1H, m), 8.64-8.69 (2H, m)

The starting material was synthesized by the following 3 steps.

Production Example 489-1

6-Carbamoyl-4-(3-trifluoromethyl-4-nitrophenoxy)-7-methoxyquinoline

The title compound (1.2 g) was obtained from 7-methoxy-4-chloroquinoline-6-carboxyamide (900 mg) and 4-nitro-3-(trifluoromethyl)phenol, in the same manner as Production Example 7.

¹H-NMR (DMSO-d₆) δ (ppm) 4.03 (3H, s), 6.91 (1H, d, J=5.2 Hz), 7.57 (1H, s), 7.72-7.87 (3H, m), 8.01-8.05 (1H, m), 8.27-8.32 (1H, m), 8.58 (1H, s), 8.75-8.79 (1H, m)

Production Example 489-2

4-(6-Carbamoyl-7-methoxy-4-quinolyl)oxy-2-trifluoromethylphenylamine

After dissolving 6-carbamoyl-4-(3-trifluoromethyl-4-nitrophenoxy)-7-methoxyquinoline (0.60 g) in tetrahydrofuran (10 ml) and methanol (10 ml), the solution was subjected to catalytic reduction with palladium-carbon (600 mg) for 10 hours under a hydrogen atmosphere to obtain the title compound (0.60 g).

¹H-NMR (DMSO-d₆) δ (ppm) 4.00 (3H, s), 5.71 (2H, brs), 6.42 (1H, d, J=5.2 Hz), 6.93-6.98 (1H, m), 7.23-7.30 (2H, m), 7.46-7.52 (1H, m), 7.71 (1H, brs), 7.83 (1H, brs), 8.60-8.69 (2H, m)

Production Example 489-3

[4-(6-Carbamoyl-7-methoxy-4-quinolyl)oxy-2-trifluoromethylphenyl]carbamic acid phenyl ester The title compound was obtained from 4-(6-carbamoyl-7-methoxy-4-quinolyl)oxy-2-trifluoromethyl-phenylamine, by the method described in Production Example 141-1.

H-NMR(CDCl₃) δ (ppm) 4.12 (3H, s), 5.90 (1H, brs), 6.48 (1H, d, J=5.6 Hz), 7.20-7.30 (4H, m), 7.38-7.51 (3H, m), 7.56 (1H, s), 7.80 (1H, brs), 8.27-8.31 (1H, m), 8.70 (1H, d, J=5.2 Hz), 9.26 (1H, s)

Example 490

N-[4-(6-Carbamoyl-7-methoxy-4-quinolyl)oxy-2,3-dimethylphenyl]-N'-cyclopropylurea Cyclopropylamine (0.10 ml) was added to dimethylsulfoxide (3.0 ml), and then [4-(6-carbamoyl-7-methoxy-4-quinolyl)oxy)-2,3-dimethylphenyl]carbamic acid phenyl ester (120 mg) was dissolved therein and the mixture was stirred for 10 minutes. Water and ethyl acetate were added to the reaction solution and the precipitated crystals were filtered out to obtain the title compound (60 mg).

¹H-NMR (DMSO-d₆) δ (ppm) 0.37-0.44 (2H, m), 0.60-0.65 (2H, m), 2.01 (3H, s), 2.14 (3H, s), 4.01 (3H, s), 6.23 (1H, d, J=5.2 Hz), 6.64-6.69 (1H, m), 6.98 (1H, d, J=8.8 Hz), 7.50 (1H, s), 7.60-7.69 (2H, m), 7.73 (1H, brs), 7.85 (1H, brs), 8.60 (1H, d, 5.2 Hz), 8.71 (1H, s)

The starting material was synthesized by the following 2 steps.

Production Example 490-1

4-(6-Carbamoyl-7-methoxy-4-quinolyl)oxy-2,3-dimethylphenylamine

The title compound (840 mg) was obtained from 7-methoxy-4-chloroquinoline-6-carboxyamide (890 mg) and 4-nitro-2,3-dimethylphenol (940 mg), in the same manner as Production Example 7. Next, 6-carbamoyl-4-(2,3-dimethyl-4-nitrophenoxy)-7-methoxyquinoline (840 mg) was dissolved in tetrahydrofuran (25 ml) and methanol (25 ml), and the solution was subjected to catalytic reduction with palladium-carbon (840 mg) for 10 hours under a hydrogen atmosphere to obtain the title compound (639 mg).

¹H-NMR (DMSO-d₆) δ (ppm) 1.92 (3H, s), 2.02 (3H, s) 4.00 (3H, s), 4.82-4.88 (2H, m), 6.22 (1H, d, J=5.2 Hz), 6.60 (1H, d, J=8.4 Hz), 6.75 (1H, d, J=8.4 Hz), 7.471H, s), 7.71 (1H, brs), 7.84 (1H, brs), 8.57 (1H, d, J=5.2 Hz), 8.70 (1H, s)

Production Example 490-2

[4-(6-Carbamoyl-7-methoxy-4-quinolyl)oxy-2,3-dimethylphenyl]carbamic acid phenyl ester The title compound was obtained from 4-(6-carbamoyl-7-methoxy-4-quinolyl)oxy-2,3-dimethylphenylamine, by the method described in Production Example 141-1.

¹H-NMR(CDCl₃-d₆) δ (ppm) 2.13 (3H, s), 2.33 (3H, s), 4.13 (3H, s), 5.88 (1H, brs), 6.29 (1H, d, J=5.6 Hz), 6.98-7.01 (1H, m), 7.20-7.25 (4H, m), 7.38-7.42 (2H, m), 7.54 (1H, s), 7.70 (1H, brs), 7.80 (1H, brs), 8.60 (1H, d, J=5.6 Hz), 9.36 (1H, s)

Example 491

N-[4-(6-Carbamoyl-7-methoxy-4-quinolyl)oxy)-2,5-dimethylphenyl]-N'-cyclopropylurea Cyclopropylamine (0.06 ml) was added to dimethylsulfoxide (2.0 ml), and then [4-(6-carbamoyl-7-methoxy-4-quinolyl)oxy)-2,5-dimethylphenyl]carbamic acid phenyl ester (100 mg) was dissolved therein and the mixture was stirred for 10 minutes. Water and ethyl acetate were added to the reaction solution and the precipitated crystals were filtered out to obtain the title compound (60 mg).

¹H-NMR (DMSO-d₆) δ (ppm) 0.40-0.44 (2H, m), 0.63-0.67 (2H, m), 2.04 (3H, s), 2.17 (3H, s), 2.53-2.60 (1H, m), 4.03 (3H, s), 6.29 (1H, d, J=5.2 Hz), 6.75-6.78 (1H, m), 7.02 (1H, s), 7.51 (1H, s), 7.58 (1H, s), 7.74 (1H, brs), 7.83-7.88 (2H, m), 8.62 (1H, d, 5.2 Hz), 8.72 (1H, s)

The starting material was synthesized by the following 2 steps.

Production Example 491-1

4-(6-Carbamoyl-7-methoxy-4-quinolyl)oxy-2,5-dimethylphenylamine

4-Amino-2,5-dimethylphenol (1.0 g) was dissolved in dimethylsulfoxide (5 ml), and then 60% sodium hydride (1.0 g) was added and the mixture was stirred for a while. After adding 7-methoxy-4-chloroquinoline-6-carboxyamide (900 mg), the mixture was heated at 100° C. for 6 hours. Water was added to the reaction solution, extraction was performed with ethyl acetate, and then the organic layer was washed with water and saturated brine in that order and dried over anhydrous sodium sulfate, and the solvent was distilled off under reduced pressure. The obtained crude product was washed with ethyl acetate to obtain the title compound (135 mg).

$^1$H-NMR (DMSO-d$_6$) δ (ppm) 1.91 (3H, s), 2.03 (3H, s), 4.01 (3H, s), 6.26 (1H, d, J=5.2 Hz), 6.57 (1H, s), 6.77 (1H, s), 7.46 (1H, s), 7.70 (1H, brs), 7.83 (1H, brs), 8.57 (1H, d, J=5.2 Hz), 8.69 (1H, s)

Production Example 491-2

[4-(6-Carbamoyl-7-methoxy-4-quinolyl)oxy-2,5-dimethylphenyl]carbamic acid phenyl ester The title compound was obtained from 4-(6-carbamoyl-7-methoxy-4-quinolyl)oxy-2,5-dimethylphenylamine, by the method described in Production Example 141-1.

$^1$H-NMR(CDCl$_3$) δ (ppm) 2.13 (3H, s), 2.33 (3H, s), 4.13 (3H, s), 5.88 (1H, brs), 6.30 (1H, d, J=5.6 Hz), 6.75 (1H, brs), 6.94 (1H, s), 7.18-7.32 (3H, m), 7.38-7.45 (2H, m), 7.54 (1H, s), 7.82 (2H, brs), 8.62 (1H, d, J=5.6 Hz), 9.32 (1H, s)

Example 492

N-{4-[6-Cyano-7-(2-hydroxy-3-(pyrrolidin-1-yl)propoxy)quinolin-4-yloxy]-2-fluorophenyl}-N'-(4-fluorophenyl)urea After adding tetrahydrofuran (1 ml) and pyrrolidine (0.1 ml) to N-[4-(6-cyano-7-oxiranylmethoxyquinolin-4-yloxy)-2-fluorophenyl]-N'-(4-fluorophenyl)urea (100 mg), the mixture was heated at 50° C. for 30 minutes. The reaction solution was purified by NH silica gel column chromatography (ethyl acetate-methanol system) to obtain the title compound (45 mg) as light yellow crystals.

$^1$H-NMR (DMSO-d$_6$) δ (ppm): 1.60-1.70 (4H, m), 2.40-2.75 (6H, m), 3.95-4.05 (1H, m), 4.20 (1H, dd, J=10, 6.0 Hz), 4.30 (1H, dd, J=10, 4 Hz), 5.02 (1H, d, J=4.4 Hz), 6.61 (1H, d, J=5.2), 7.10-7.17 (3H, m), 7.35-7.50 (3H, m), 7.62 (1H, s), 8.21-8.27 (1H, m), 8.62-8.64 (1H, m), 8.72-8.75 (2H, m), 9.09 (1H, brs)

The starting material was synthesized by the following 2 steps.

Production Example 492-1

4-(4-Amino-3-fluorophenoxy)-7-oxiranylmethoxyquinoline-6-carbonitrile

After adding dimethylformamide (6 ml), epibromohydrin (1.3 ml) and potassium carbonate (380 mg) to 4-(4-amino-3-fluorophenoxy)-6-cyano-7-hydroxyquinoline (400 mg), the mixture was stirred overnight at room temperature. Water was added to the reaction solution, extraction was performed with ethyl acetate, and then the organic layer was washed with water and saturated brine in that order and dried over anhydrous sodium sulfate, and the solvent was distilled off under reduced pressure to obtain the title compound (400 mg).

$^1$H-NMR (DMSO-d$_6$) δ (ppm): 2.79-2.93 (2H, m), 3.42-3.49 (1H, m), 4.15 (1H, dd, J=12, 7.2 Hz), 4.69 (1H, dd, J=12, 2.4 Hz), 5.25 (2H, brs), 6.53 (1H, d, J=5.2), 6.83-6.89 (2H, m), 7.07-7.15 (1H, m), 7.61 (1H, s), 8.69-8.74 (2H, m)

Production Example 492-2

N-[4-(6-Cyano-7-oxiranylmethoxyquinolin-4-yloxy)-2-fluorophenyl]-N'-(4-fluorophenyl)urea After adding dimethylformamide (2 ml) and 4-fluorophenyl isocyanate (0.15 ml) to 4-(4-amino-3-fluorophenoxy)-7-oxiranylmethoxy-quinoline-6-carbonitrile (400 mg), the mixture was stirred overnight at room temperature. Water was added to the reaction solution and the precipitated crystals were filtered off to obtain the title compound (480 mg) as light yellow crystals.

$^1$H-NMR (DMSO-d$_6$) δ (ppm): 2.79-2.95 (2H, m), 3.40-3.50 (1H, m), 4.10-4.20 (1H, m), 4.65-4.76 (1H, m) 6.62 (1H, d, J=6.0 Hz), 7.05-7.18 (3H, m), 7.36-7.50 (3H, m), 7.62 (1H, s), 8.20-8.28 (1H, m), 8.60-8.68 (1H, m), 8.73-8.80 (2H, m), 9.10 (1H, brs)

Example 493

N-{4-[6-Cyano-7-(3-diethylamino-2-hydroxypropoxy)quinolin-4-yloxy]-2-fluorophenyl}-N'-(4-fluorophenyl)urea After adding tetrahydrofuran (1 ml) and diethylamine (0.1 ml) to N-[4-(6-cyano-7-oxiranylmethoxyquinolin-4-yloxy)-2-fluorophenyl]-N'-(4-fluorophenyl)urea (100 mg), the mixture was heated at 50° C. for 30 minutes. The reaction solution was purified by NH silica gel column chromatography (ethyl acetate-methanol system) to obtain the title compound (32 mg) as light yellow crystals.

$^1$H-NMR (DMSO-d$_6$) δ (ppm): 0.958 (6H, t, J=7 Hz), 2.40-2.68 (6H, m), 3.91-3.99 (1H, m), 4.20 (1H, dd, J=10, 5.2 Hz), 4.31 (1H, dd, J=10, 3.6 Hz), 4.91 (1H, d, J=4.4 Hz), 6.61 (1H, d, J=5.2 Hz), 7.10-7.17 (3H, m), 7.37-7.49 (3H, m), 7.62 (1H, s), 8.21-8.27 (1H, m), 8.63 (1H, brs), 8.72-8.75 (2H, m), 9.10 (1H, brs)

Example 494

N-{4-[6-Cyano-7-(2-hydroxy-(3-morpholin-4-yl)propoxy)quinolin-4-yloxy]-2-fluorophenyl}-N'-(4-fluorophenyl)urea After adding tetrahydrofuran (1 ml) and morpholine (0.1 ml) to N-[4-(6-cyano-7-oxiranylmethoxyquinolin-4-yloxy)-2-fluorophenyl]-N'-(4-fluorophenyl)urea (100 mg), the mixture was heated at 50° C. for 30 minutes. The reaction solution was purified by NH silica gel column chromatography (ethyl acetate-methanol system) to obtain the title compound (32 mg) as light yellow crystals.

$^1$H-NMR (DMSO-d$_6$) δ (ppm): 2.38-2.58 (6H, m), 3.53-3.59 (4H, m), 4.03-4.09 (1H, m), 4.22 (1H, dd, J=10, 6.0 Hz), 4.31 (1H, dd, J=10, 4.0 Hz), 5.03 (1H, d, J=4.8), 6.61 (1H, d, J=5.2 Hz), 7.10-7.17 (3H, m), 7.36-7.49 (3H, m), 7.64 (1H, s), 8.20-8.27 (1H, m), 8.60-8.64 (1H, m), 8.73-8.75 (2H, m), 9.10 (1H, brs)

Example 495

N-{4-[6-Cyano-7-(2-hydroxy-3-(pyrrolidin-1-yl)propoxy)guinolin-4-yloxy]-2-fluorophenyl}-N'-(thiazol-2-yl)urea After adding tetrahydrofuran (1 ml) and pyrrolidine (0.1 ml) to N-[4-(6-cyano-7-oxiranylmethoxy-quinolin-4-yloxy)-

2-fluorophenyl]-N'-(thiazol-2-yl)urea (120 mg), the mixture was heated at 50° C. for 40 minutes. The reaction solution was purified by NH silica gel column chromatography (ethyl acetate-methanol system) to obtain the title compound (70 mg) as light yellow crystals.

$^1$H-NMR (DMSO-d$_6$) δ (ppm): 1.60-1.70 (4H, m), 2.40-2.75 (6H, m), 3.95-4.05 (1H, m), 4.20 (1H, dd, J=10, 6.0 Hz), 4.31 (1H, dd, J=10, 4 Hz), 5.02 (1H, brs), 6.62 (1H, d, J=5.2 Hz), 6.85 (1H, s), 7.10-7.20 (2H, m), 7.37-7.47 (2H, m), 7.62 (1H, s), 8.20-8.26 (1H, m), 8.71-8.76 (2H, m), 9.05 (1H, brs)

The starting material was synthesized in the following manner.

Production Example 495-1

N-[4-(6-Cyano-7-oxiranylmethoxyquinolin-4-yloxy)-2-fluorophenyl]-N'-(thiazol-2-yl)urea After adding dimethylsulfoxide (1 ml) and phenyl N-(2-thiazolyl)carbamate (94 mg) to 4-(4-amino-3-fluorophenoxy)-7-oxiranylmethoxyquinoline-6-carbonitrile (100 mg), the mixture was heated at 80° C. for 90 minutes. Water was added and the precipitated crystals were filtered out to obtain the title compound (16 mg) as light yellow crystals.

$^1$H-NMR (DMSO-d$_6$) δ (ppm): 2.78-2.94 (2H, m), 3.41-3.49 (1H, m), 4.17 (1H, dd, J=12, 6.4 Hz), 4.71 (1H, dd, J=12, 2.0), 6.64 (1H, d, J=5.2 Hz), 7.08-7.20 (3H, m), 7.36-7.48 (2H, m), 7.65 (1H, s), 8.20-8.27 (1H, m), 8.73-8.79 (2H, m), 9.07 (1H, brs)

Example 496

N-{4-[6-Cyano-7-(2-hydroxy-3-(piperidin-1-yl)propoxy)quinolin-4-yloxy]-2-fluorophenyl}-N'-(4-fluorophenyl)urea After adding tetrahydrofuran (1.5 ml) and piperidine (0.08 ml) to N-[4-(6-cyano-7-oxiranylmethoxyquinolin-4-yloxy)-2-fluorophenyl]-N'-(4-fluorophenyl)urea (78 mg), the mixture was heated at 50° C. for 30 minutes. The reaction solution was purified by NH silica gel column chromatography (ethyl acetate-methanol system) to obtain the title compound (32 mg) as light yellow crystals.

$^1$H-NMR (DMSO-d$_6$) δ (ppm): 1.30-1.55 (6H, m), 2.35-2.55 (6H, m), 4.00-4.08 (1H, m), 4.20 (1H, dd, J=10, 6.0 Hz), 4.30 (1H, dd, J=10, 4.0 Hz), 4.94 (1H, d, J=4.8 Hz), 6.61 (1H, d, J=5.6 Hz), 7.10-7.17 (3H, m), 7.36-7.50 (3H, m), 7.63 (1H, m), 8.20-8.23 (1H, m), 8.62-8.64 (1H, m), 8.72-8.75 (2H, m), 9.10 (1H, m)

Example 497

N-(4-{6-Cyano-7-[(2R)-2-hydroxy-3-(piperidin-1-yl)propoxy]quinolin-4-yloxy}-2-fluorophenyl)-N'-(4-fluorophenyl)urea The title compound (115 mg) was obtained as light yellow crystals from N-(4-{6-cyano-7-[(2R)-oxiran-2-yl]methoxyquinolin-4-yloxy}-2-fluorophenyl)-N'-(4-fluorophenyl)urea (345 mg), by the same procedure as in Example 496.

$^1$H-NMR (DMSO-d$_6$) δ (ppm): H-NMR (DMSO-d$_6$) δ (ppm): 1.30-1.55 (6H, m), 2.35-2.55 (6H, m), 4.00-4.08 (1H, m), 4.20 (1H, dd, J=10, 6.0 Hz), 4.30 (1H, dd, J=10, 4.0 Hz), 4.94 (1H, d, J=4.8 Hz), 6.61 (1H, d, J=5.6 Hz), 7.10-7.17 (3H, m), 7.36-7.50 (3H, m), 7.63 (1H, m), 8.20-8.23 (1H, m), 8.72-8.75 (2H, m), 9.10 (1H, m)

The starting material was synthesized by the following 2 steps.

Production Example 497-1

4-(4-Amino-3-fluoro-phenoxy)-7-[(2R)-oxiran-2-yl]methoxyquinoline-6-carbonitrile After adding dimethylformamide (8 ml), (2R)-(−)-glycidyl p-toluenesulfonate (1000 mg) and potassium carbonate (940 mg) to 4-(4-amino-3-fluorophenoxy)-6-cyano-7-hydroxyquinoline (1000 mg), the mixture was heated at 50° C. for 4 hours. Water was added to the reaction solution, extraction was performed with ethyl acetate, and then the organic layer was washed with water and saturated brine in that order and dried over anhydrous sodium sulfate, and the solvent was distilled off under reduced pressure. The obtained crude product was purified by silica gel column chromatography (ethyl acetate) to obtain the title compound (659 mg) as light yellow crystals.

$^1$H-NMR (DMSO-d$_6$) δ (ppm): 2.79-2.93 (2H, m), 3.42-3.49 (1H, m), 4.15 (1H, dd, J=12, 7.2 Hz), 4.69 (1H, dd, J=12, 2.4 Hz), 5.25 (2H, brs), 6.53 (1H, d, J=5.2 Hz), 6.83-6.89 (2H, m), 7.07-7.15 (1H, m), 7.61 (1H, s), 8.69-8.74 (2H, m)

Production Example 497-2

N-(4-{6-Cyano-7-[(2R)-oxiran-2-yl]methoxyquinolin-4-yloxy}-2-fluorophenyl)-N'-(4-fluorophenyl)urea The title compound (200 mg) was obtained from 4-(4-amino-3-fluorophenoxy)-7-[(2R)-oxiran-2-yl]methoxyquinoline-6-carbonitrile (150 mg), by the method described in Production Example 492-1.

$^1$H-NMR (DMSO-d$_6$) δ (ppm): 2.79-2.95 (2H, m), 3.40-3.50 (1H, m), 4.10-4.20 (1H, m), 4.65-4.76 (1H, m) 6.62 (1H, d, J=6.0 Hz), 7.05-7.18 (3H, m), 7.36-7.50 (3H, m), 7.62 (1H, s), 8.20-8.28 (1H, m), 8.60-8.68 (1H, m), 8.73-8.80 (2H, m), 9.10 (1H, brs)

Example 498

N-(4-{6-Cyano-7-[3-diethylamino-(2R)-2-hydroxypropoxy]-quinolin-4-yloxy}-2-fluorophenyl)-N'-(4-fluorophenyl)urea The title compound (120 mg) was obtained as light yellow crystals from
N-(4-{6-cyano-7-[(2R)-oxiran-2-yl]methoxyquinolin-4-yloxy}-2-fluorophenyl)-N'-(4-fluorophenyl)urea (200 mg), by the same procedure as in Example 493.

$^1$H-NMR (DMSO-d$_6$) δ (ppm): 0.96 (6H, t, J=7 Hz), 2.40-2.68 (6H, m), 3.91-3.99 (1H, m), 4.20 (1H, dd, J=10, 5.2 Hz), 4.31 (1H, dd, J=10, 3.6 Hz), 4.91 (1H, d, J=4.4 Hz), 6.61 (1H, d, J=5.2 Hz), 7.10-7.17 (3H, m), 7.37-7.49 (3H, m), 7.62 (1H, s), 8.21-8.27 (1H, m), 8.63 (1H, brs), 8.72-8.75 (2H, m), 9.10 (1H, brs)

Example 499

N-(4-{6-Cyano-7-[3-dimethylamino-(2R)-2-hydroxy-propoxy]-quinolin-4-yloxy}-2-fluorophenyl)-N'-(4-fluorophenyl)urea After adding tetrahydrofuran (0.5 ml) and a dimethylamine-2N tetrahydrofuran solution (Aldrich, 0.2 ml) to N-(4-{6-cyano-7-[(2R)-oxiran-2-yl]methoxyquinolin-4-yloxy}-2-fluorophenyl)-N'-(4-fluorophenyl)urea (40 mg), the mixture was stirred overnight at room temperature. The reaction solution was purified by NH silica gel column chromatography (ethyl acetate-methanol system) to obtain the title compound (45 mg) as light yellow crystals.

$^1$H-NMR (DMSO-d$_6$) δ (ppm): 2.20 (6H, m), 2.30-2.58 (2H, m), 3.95-4.95 (1H, m), 4.19 (1H, dd, J=10, 5.6 Hz), 4.29 (1H, dd, J=10, 4.0 Hz), 4.99 (1H, d, J=4.4 Hz), 6.61 (1H, d, J=5.6 Hz), 7.10-7.17 (3H, m), 7.37-7.50 (3H, m), 7.62 (1H, s), 8.20-8.30 (1H, m), 8.64 (1H, brs), 8.70-8.76 (2H, m), 9.11 (1H, brs)

Example 500

N-(4-{6-Cyano-7-[3-diethylamino-(2R)-2-hydroxypropoxy]-quinolin-4-yloxy}-2-fluorophenyl)-N'-(thiazol-2-yl)urea After adding tetrahydrofuran (4 ml) and diethylamine (0.2 ml) to N-(4-{6-cyano-7-[(2R)-oxiran-2-yl]methoxyquinolin-4-yloxy}-2-fluorophenyl)-N'-(thiazol-2-yl)urea (200 mg), the mixture was stirred at 50° C. for 2 hours. The reaction solution was purified by NH silica gel column chromatography (ethyl acetate-methanol system) to obtain the title compound (60 mg) as light yellow crystals.

$^1$H-NMR (DMSO-d$_6$) δ (ppm): 0.96 (6H, t, J=7.0 Hz), 2.40-2.70 (6H, m), 3.90-3.98 (1H, m), 4.21 (1H, dd, J=10, 5.2 Hz), 4.31 (1H, dd, J=10, 3.2 Hz), 4.90-4.95 (1H, m), 6.62 (1H, d, J=5.2 Hz), 7.11-7.20 (2H, m), 7.36-7.47 (2H, m), 7.62 (1H, s), 8.20-8.27 (1H, m), 8.72-8.76 (2H, m)

The starting material was synthesized in the following manner.

Production Example 500-1

N-(4-{6-Cyano-7-[(2R)-oxiran-2-yl]methoxyquinolin-4-yloxy}-2-fluorophenyl)-N'-(thiazol-2-yl)urea The title compound (370 mg) was obtained as light yellow crystals from 4-(4-amino-3-fluorophenoxy)-7-[(2R)-oxiran-2-yl]methoxyquinoline-6-carbonitrile (300 mg), by the method described in Example 495.

H-NMR (DMSO-d$_6$) δ (ppm): 2.78-2.94 (2H, m), 3.41-3.49 (1H, s), 4.17 (1H, dd, J=12, 6.4 Hz), 4.71 (1H, dd, J=12, 2.0 Hz), 6.64 (1H, d, J=5.2 Hz), 7.08-7.20 (2H, m), 7.36-7.48 (2H, m), 7.65 (1H, s), 8.20-8.27 (1H, m), 8.73-8.79 (2H, m), 9.07 (1H, brs)

Example 501

N-(2-Fluoro-4-{[6-cyano-7-(4-piperidylmethoxy)-4-quinolyl]oxy}phenyl)-N'-(4-fluorophenyl)urea After dissolving 4-(6-cyano-4-{3-fluoro-4-[3-(4-fluorophenyl)ureido]phenoxy}quinolin-7-yloxymethyl)piperidine-1-carboxylic acid tert-butyl ester (395 mg) in trifluoroacetic acid (2 ml), the solution was stirred for 10 minutes at room temperature. Water (20 ml) was added, the mixture was neutralized with sodium bicarbonate, and the precipitated crystals were filtered out to obtain the title compound (260 mg).

$^1$H-NMR (DMSO-d$_6$) δ (ppm): 1.15-1.30 (2H, m), 1.69-1.76 (2H, m), 1.85-2.00 (1H, m), 2.44-2.70 (2H, m), 2.90-2.99 (2H, m), 4.09-4.25 (3H, m), 6.61 (1H, d, J=5.2 Hz), 7.05-7.14 (3H, m), 7.34-7.40 (1H, m), 7.48-7.55 (2H, m), 7.59 (1H, s), 8.10-8.17 (1H, m), 8.70-8.76 (2H, m)

The starting material was synthesized by the following 3 steps.

Production Example 501-1

4-[4-(4-Amino-3-fluorophenoxy)-6-cyanoquinolin-7-yloxymethyl]-piperidine-1-carboxylic acid tert-butyl ester After adding dimethylformamide (4 ml), tert-butyl 4-(bromomethyl)-1-piperidine carboxylate (708 mg) and potassium carbonate (467 mg) to 4-(4-amino-3-fluorophenoxy)-6-cyano-7-hydroxyquinoline (500 mg), the mixture was heated at 50° C. for 4 hours. Water was added to the reaction solution, extraction was performed with ethyl acetate and the organic layer was washed with water and saturated brine in that order and then dried over anhydrous sodium sulfate, and the solvent was distilled off under reduced pressure. The obtained crude product was purified by silica gel column chromatography (n-hexane:ethyl acetate) to obtain the title compound (398 mg).

$^1$H-NMR (DMSO-d$_6$) δ (ppm): 1.16-1.31 (2H, m), 1.39 (9H, s), 1.72-1.82 (2H, m), 2.00-2.08 (1H, m), 2.65-2.83 (2H, m), 3.93-4.03 (2H, m), 4.11-4.18 (2H, m), 5.20-5.26 (2H, m), 6.50 (1H, d, J=5.2 Hz), 6.82-6.85 (2H, m), 7.02-7.10 (1H, m), 7.56 (1H, s), 8.65-8.72 (2H, m)

Production Example 501-2

4-(6-Cyano-4-{3-fluoro-4-[3-(4-fluorophenyl)ureido]phenoxy}quinolin-7-yloxymethyl)piperidine-1-carboxylic acid tert-butyl ester The title compound (500 mg) was obtained as light yellow crystals from 4-[4-(4-amino-3-fluorophenoxy)-6-cyanoquinolin-7-yloxymethyl]piperidine-1-carboxylic acid tert-butyl ester (619 mg) and 4-fluorophenyl isocyanate (0.22 ml), by the same procedure as in Example 492.

$^1$H-NMR (DMSO-d$_6$) δ (ppm): 1.20-1.35 (2H, m), 1.39 (9H, s), 1.73-1.85 (2H, m), 2.00-2.10 (1H, m), 2.63-2.86 (2H, m), 3.92-4.06 (2H, m), 4.13-4.20 (2H, m), 6.61 (1H, d, J=5.6 Hz), 7.10-7.16 (3H, m) 7.36-7.50 (3H, m), 7.60 (1H, s), 8.20-8.28 (1H, m), 8.68-8.76 (2H, m), 9.27 (1H, brs)

Example 502

N-{4-[6-Cyano-7-(1-methylpiperidin-4-yl)methoxyquinolin-4-yloxy]-2-fluorophenyl}-N'-(4-fluorophenyl)urea After dissolving N-(2-fluoro-4-{[6-cyano-7-(4-piperidinomethoxy)-4-quinolyl]oxy}phenyl)-N'-(4-fluorophenyl)urea (180 mg) in tetrahydrofuran (10 ml)-methanol (10 ml), there were added 37% aqueous formaldehyde (0.5 ml), acetic acid (0.04 ml) and sodium cyanoborohydride (43 mg) at room temperature, and the mixture was stirred for 1 hour. The reaction solution was distributed between ethyl acetate and saturated aqueous sodium bicarbonate, and the organic layer was washed with saturated brine and dried over anhydrous sodium sulfate. The solvent was distilled off, and after suspension in ethyl acetate and dilution with hexane, the crystals were filtered out and blow-dried to obtain the title compound (130 mg) as white crystals.

$^1$H-NMR (DMSO-d$_6$) δ (ppm): 1.13-1.47 (2H, m), 1.73-1.92 (5H, m), 2.15 (3H, s), 2.77-2.85 (2H, m), 4.13-4.16 (2H, m), 6.61 (1H, d, J=5.6 Hz), 7.10-7.16 (3H, m), 7.36-7.49 (3H, m), 7.59 (1H, s), 8.20-8.26 (1H, m), 8.62-8.68 (1H, m), 8.72-8.76 (2H, m), 9.08-9.15 (1H, m)

Example 503

N-{4-[6-Cyano-7-(piperidin-4-ylmethoxy)quinolin-4-yloxy]-2-fluorophenyl}-N'-(2-thiazolyl)urea The title compound (240 mg) was obtained from 4-{6-cyano-4-[3-fluoro-4-(3-(thiazol-2-yl)ureido)phenoxy]quinolin-7-yloxymethyl}piperidine-1-carboxylic acid tert-butyl ester (370 mg), by the same procedure as in Example 501.

$^1$H-NMR (DMSO-d$_6$) δ (ppm): 1.45-1.56 (2H, m), 1.92-2.00 (2H, m), 2.13-2.23 (1H, m), 2.45-2.50 (2H, m), 2.85-2.98 (2H, m), 4.18-4.23 (2H, m), 6.64 (1H, d, J=5.2 Hz), 7.14-7.19 (2H, m), 7.37-7.47 (2H, m), 7.65 (1H, s), 8.21-8.28 (1H, m), 8.74-8.79 (2H, m), 9.06 (1H, brs)

The starting material was synthesized in the following manner.

Production Example 503-1

4-{6-Cyano-4-[3-fluoro-4-(3-(thiazol-2-yl)ureido)phenoxy]quinolin-7-yloxymethyl}piperidine-1-carboxylic acid tert-butyl ester This was synthesized from 4-[4-(4-amino-3-fluorophenoxy)-6-cyanoquinolin-7-yloxymethyl]piperidine-1-carboxylic acid tert-butyl ester, by the method described for the intermediate synthesis in Example 495.

$^1$H-NMR (DMSO-d$_6$) δ (ppm): 1.18-1.32 (2H, m), 1.39 (9H, s), 1.73-1.83 (2H, m), 2.00-2.10 (1H, m), 2.63-2.86 (2H, m), 3.95-4.05 (2H, m), 4.13-4.20 (2H, m), 6.62 (1H, d, J=5.2 Hz), 7.10-7.20 (2H, m), 7.36-7.47 (2H, m), 7.61 (1H, s), 8.20-8.27 (1H, m), 8.72-8.77 (2H, m)

Example 504

N-{4-[6-Cyano-7-(1-methylpiperidin-4-ylmethoxy)quinolin-4-yloxy]-2-fluorophenyl}-N'-(2-thiazolyl)urea The title compound was obtained from N-{4-[6-cyano-7-(piperidin-4-ylmethoxy)quinolin-4-yloxy]-2-fluorophenyl}-N'-(2-thiazolyl)urea, by the method described in Example 502.

$^1$H-NMR (DMSO-d$_6$) δ (ppm): 1.30-1.46 (2H, m), 1.70-1.93 (5H, m), 2.15 (3H, s), 2.77-2.85 (2H, m), 4.13-4.17 (2H, m), 6.62 (1H, d, J=5.2 Hz), 7.12-7.19 (2H, m), 7.37-7.47 (2H, m), 7.60 (1H, s), 8.20-8.30 (1H, m), 8.73-8.76 (2H, m)

Example 505

N-{4-[6-Cyano-7-(1-methylpiperidin-3-ylmethoxy)quinolin-4-yloxy]-2-fluorophenyl}-N'-(2-thiazolyl)urea The title compound was obtained from 4-(4-amino-3-fluorophenoxy)-7-(1-methylpiperidin-3-ylmethoxy)quinoline-6-carbonitrile by the method described for the intermediate synthesis in Example 495.

$^1$H-NMR (DMSO-d$_6$) δ (ppm): 1.10-1.20 (1H, m), 1.43-1.96 (5H, m), 2.05-2.15 (1H, m), 2.16 (3H, s), 2.61-2.67 (1H, m), 2.80-2.87 (1H, m), 4.15-4.19 (2H, m), 6.62 (1H, d, J=5.6 Hz), 7.12-7.20 (2H, m), 7.37-7.47 (2H, m), 7.60 (1H, s), 8.20-8.26 (1H, m), 8.72-8.77 (2H, m)

The starting material was synthesized in the following manner.

Production Example 505-1

4-(4-Amino-3-fluorophenoxy)-7-(1-methylpiperidin-3-ylmethoxy)quinoline-6-carbonitrile After adding dimethylformamide (4 ml), 3-chloromethyl-1-methylpiperidine hydrochloride (621 mg) and potassium carbonate (840 mg) to 4-(4-amino-3-fluorophenoxy)-6-cyano-7-hydroxyquinoline (400 mg), the mixture was stirred at 20° C. for 3 hours. Water was added to the reaction solution, extraction was performed with ethyl acetate, the organic layer was washed with water and saturated brine in that order and dried over anhydrous sodium sulfate, and the solvent was distilled off under reduced pressure. The obtained crude product was purified by NH silica gel column chromatography (ethyl acetate) to obtain the title compound (60 mg).

H-NMR (DMSO-d$_6$) 1.10-1.20 (1H, m), 1.45-1.95 (5H, m), 2.03-2.14 (1H, m), 2.14 (3H, s), 2.56-2.68 (1H, m), 2.78-2.88 (1H, m), 4.12-4.18 (2H, m), 5.23-5.28 (2H, m), 6.51 (1H, d, J=5.2 Hz), 6.83-6.89 (2H, m), 7.03-7.10 (1H, m), 7.56 (1H, s), 8.65-8.72 (2H, m)

Example 506

N-(4-[(7-Cyano-6-methoxy-4-quinolyl)oxy]phenyl)-N'-(4-fluoro-phenyl)urea

After adding toluene (5 ml), acetonitrile (1.5 ml) and 4-fluorophenyl isocyanate (0.105 ml) to 4-(4-aminophenoxy)-6-methoxyquinoline-7-carbonitrile (180 mg), the mixture was heated to reflux for 30 minutes.

The mixture was cooled, and the precipitated crystals were filtered out and washed with toluene to obtain the title compound (230 mg) as light yellow crystals.

$^1$H-NMR (DMSO-d$_6$) δ (ppm) 4.05 (3H, m), 6.66 (1H, d, J=5.2 Hz), 7.08-7.14 (2H, m), 7.24 (2H, d, J=8.8 Hz), 7.43-7.48 (2H, m), 7.59 (2H, d, J=8.8 Hz), 7.76 (1H, s), 8.54 (1H, s), 8.64 (1H, d, J=5.2 Hz), 8.74 (1H, brs), 8.84 (1H, brs)

The starting material was synthesized by the following 4 steps.

Production Example 506-1

6-Methoxy-4-(4-nitrophenoxy)quinolin-7-ol

After adding trifluoroacetic acid (30 ml) and thioanisole (3 ml) to 7-benzyloxy-6-methoxy-4-(4-nitrophenoxy)quinoline (4.0 g), the mixture was heated and stirred at 70° C. for 2 hours.

After cooling the reaction solution, it was concentrated under reduced pressure, sodium bicarbonate water and methanol were added and the precipitated crystals were filtered out. They were then washed with diethyl ether to obtain 4.0 g of the title compound.

$^1$H-NMR (DMSO-d$_6$) δ (ppm) 3.94 (3H, s), 6.93 (1H, d, J=5.6 Hz), 7.42 (1H, s), 7.55-7.60 (3H, m), 8.40 (2H, d, J=10 Hz), 8.71 (1H, d, J=6 Hz)

Production Example 506-2

Trifluoromethanesulfonic acid 6-methoxy-4-(4-nitrophenoxy)quinolin-7-yl ester

After dissolving 6-methoxy-4-(4-nitrophenoxy)quinolin-7-ol (1.0 g) in dimethylformamide (10 ml), there were added trifluoromethanesulfonic acid 4-nitrophenyl ester (640 mg) and potassium carbonate (1.3 g), and the mixture was stirred at room temperature for 5 hours. Water was added, extraction was performed with ethyl acetate, the organic layer was washed with water and saturated brine in that order and dried over anhydrous sodium sulfate, and the solvent was distilled off under reduced pressure. Ethyl acetate was used for recrystallization to obtain the title compound (1.0 g).

$^1$H-NMR (DMSO-$d_6$) δ (ppm) 4.04 (3H, s), 7.01 (1H, d, J=4.8 Hz), 7.52-7.57 (2H, m), 7.80 (1H, s), 8.18 (1H, s), 8.34-8.39 (2H, m), 8.72-8.76 (1H, m)

Production Example 506-3

6-Methoxy-4-(4-nitrophenoxy)quinoline-7-carbonitrile

After dissolving trifluoromethanesulfonic acid 6-methoxy-4-(4-nitrophenoxy)quinolin-7-yl ester (500 mg) in dimethylformamide (5 ml), there were added zinc cyanide (260 mg) and tetrakistriphenylphosphine palladium (0) (130 mg) and the mixture was heated and stirred at 110° C. for 2 hours under a nitrogen atmosphere. Water was added, extraction was performed with ethyl acetate, the organic layer was washed with water and saturated brine in that order and dried over anhydrous sodium sulfate, and the solvent was distilled off under reduced pressure. Ethyl acetate was used for recrystallization to obtain the title compound (300 mg).

$^1$H-NMR (DMSO-$d_6$) δ (ppm) 4.03 (3H, s), 7.05 (1H, d, J=5.2 Hz), 7.51-7.56 (2H, m), 7.68 (1H, s), 8.34-8.39 (2H, m), 8.62 (1H, s), 8.76 (1H, d, J=5.2 Hz)

Production Example 506-4

4-(4-Aminophenoxy)-6-methoxyquinoline-7-carbonitrile

6-Methoxy-4-(4-nitrophenoxy)quinoline-7-carbonitrile (290 mg) was subjected to iron reduction by the same method as in Production Example 10 to obtain the title compound (180 mg).

$^1$H-NMR (DMSO-$d_6$) δ (ppm) 4.05 (3H, s), 5.19 (2H, s), 6.59 (1H, d, J=5.2 Hz), 6.66 (2H, d, J=8.8 Hz), 6.94 (2H, d, J=8.8 Hz), 7.73 (1H, s), 8.51 (1H, s), 8.61 (1H, d, J=5.2 Hz)

Example 507

N-(4-[(7-Carbamoyl-6-methoxy-4-quinolyl)oxy]phenyl)-N'-(4-fluorophenyl)urea

After dissolving N-(4-[(7-cyano-6-methoxy-4-quinolyl)oxy]phenyl)-N'-(4-fluorophenyl)urea (43 mg) in 1.5 ml of dimethylsulfoxide at 80° C., a 5N aqueous NaOH solution was added thereto and the mixture was heated and stirred for 2 hours. The reaction solution was neutralized with 1N HCl and the precipitated crystals were filtered out and washed with ethanol to obtain 17 mg of the title compound.

$^1$H-NMR (DMSO-$d_6$) δ (ppm) 4.00 (3H, s), 6.58 (1H, d, J=5.2 Hz), 7.06-7.14 (2H, m), 7.17-7.24 (2H, m), 7.45-7.53 (2H, m), 7.55-7.67 (3H, m), 7.70 (1H, brs), 7.86 (1H, brs), 8.22 (1H, s), 8.56 (1H, d, J=5.2 Hz)

Example 508

N-(4-[(7-Aminomethyl-6-methoxy-4-quinolyl)oxy]phenyl)-N'-(4-fluorophenyl)urea trifluoroacetate The title compound (52 mg) was obtained from N-(4-[(7-cyano-6-methoxy-4-quinolyl)oxy]phenyl)-N'-(4-fluorophenyl)urea (50 mg), by the same procedure as in Example 480.

$^1$H-NMR (DMSO-$d_6$) δ (ppm) 4.01 (3H, s), 4.21-4.26 (2H, m), 6.66 (1H, d, J=5.2 Hz), 7.08-7.15 (2H, m), 7.23 (2H, d, J=8.8 Hz), 7.43-7.50 (2H, m), 7.61 (2H, d, J=8.8 Hz), 7.67 (1H, s), 8.08 (1H, s), 8.63 (1H, d, J=5.2 Hz), 8.85 (1H, brs), 8.95 (1H, brs)

Example 509

N-(4-[(7-Acetylaminomethyl-6-methoxy-4-quinolyl)oxy]phenyl)-N'-(4-fluorophenyl)urea The title compound (5 mg) was obtained from N-(4-[(7-aminomethyl-6-methoxy-4-quinolyl)oxy]phenyl)-N'-(4-fluorophenyl)urea trifluoroacetate (30 mg), by the method described in Example 481.

$^1$H-NMR (DMSO-$d_6$) δ (ppm) 1.94 (3H, s), 3.96 (3H, s), 4.37-4.40 (2H, m), 6.51 (1H, d, J=5.2 Hz), 7.08-7.14 (2H, m), 7.20 (2H, d, J=8.8 Hz), 7.43-7.50 (2H, m), 7.50-7.60 (3H, m), 7.74 (1H, s), 8.39-8.45 (1H, m), 8.50 (1H, d, J=5.2 Hz), 8.80 (1H, brs), 8.88 (1H, brs)

Example 510

4-{4-[3-(4-Fluorophenyl)ureido]phenoxy}furo[2,3-b]pyridine-2-carboxylic acid methyl ester After adding toluene (1 ml), acetonitrile (0.5 ml) and 4-fluorophenyl isocyanate (0.02 ml) to 4-(4-aminophenoxy)furo[2,3-b]pyridine-2-carboxylic acid methyl ester (28 mg), the mixture was heated to reflux for 30 minutes. After cooling, the precipitated crystals were filtered off and washed with toluene to obtain the title compound (24 mg) as light yellow crystals.

$^1$H-NMR (DMSO-$d_6$) δ (ppm) 3.87 (3H, s), 6.75 (1H, d, J=5.6 Hz), 7.08-7.14 (2H, m), 7.21-7.25 (2H, m), 7.40 (1H, s), 7.43-7.48 (2H, m), 7.55-7.60 (2H, m), 8.35 (1H, d, J=5.6 Hz), 8.79 (1H, brs), 8.89 (1H, brs)

The starting material was synthesized by the following 5 steps.

Production Example 510-1

5-[(2,2-Dimethyl-4,6-dioxo-[1,3]dioxan-5-ylidenemethyl)amino]furan-2-carboxylic acid methyl ester Methyl 5-amino-2-furoate (4 g) by Lancaster was added to a mixed solution of triethyl orthoformate (20 ml) and isopropyl alcohol (20 ml), and then Meldrum acid (4.5 g) was added and the mixture was heated and stirred at 100° C. for 1 hour. After cooling, the precipitated crystals were filtered out and washed with isopropyl alcohol to obtain the title compound (7.8 g).

$^1$H-NMR(CDCl$_3$) δ (ppm) 1.75 (6H, s), 3.89 (3H, s), 6.04-6.09 (1H, m), 7.08-7.12 (1H, m), 8.56-8.64 (1H, m), 11.4-11.6 (1H, m)

Production Example 510-2

4-Oxo-4,7-dihydrofuro[2,3-b]pyridine-2-carboxylic acid methyl ester

After adding 5-[(2,2-dimethyl-4,6-dioxo-[1.3]dioxan-5-ylidenemethyl)amino]furan-2-carboxylic acid methyl ester (4.0 g) to Dowtherm A (30 ml), the mixture was heated and stirred at 200° C. for 1 hour. After cooling, the precipitated crystals were filtered out and washed with diethyl ether to obtain the title compound (2.0 g).

¹H-NMR (DMSO-d₆) δ (ppm) 3.86 (3H, s), 6.77 (1H, d, J=5.6 Hz), 7.71 (1H, s), 8.18 (1H, d, J=5.6 Hz), 11.85 (1H, brs)

Production Example 510-22

4-Chloro-furo[2,3-b]pyridine-2-carboxylic acid methyl ester

After adding thionyl chloride (8.0 ml) and dimethylformamide (0.08 ml) to 4-oxo-4,7-dihydro-furo[2,3-b]pyridine-2-carboxylic acid methyl ester (2.0 g), the mixture was heated to reflux for 1 hour. After cooling, the mixture was concentrated under reduced pressure and the precipitated crystals were filtered out and washed with tetrahydrofuran and ethyl acetate to obtain the title compound (2.1 g).
¹H-NMR (DMSO-d₆) δ (ppm) 3.92 (3H, s), 7.66 (1H, d, J=5.2 Hz), 7.86 (1H, s), 8.49 (1H, d, J=5.2 Hz)

Production Example 510-3

4-(4-Nitrophenoxy)furo[2,3-b]pyridine-2-carboxylic acid methyl ester

After adding N-methylpyrrolidone (4.0 ml), diisopropylethylamine (1.3 ml) and para-nitrophenol (822 mg) to 4-chlorofuro[2,3-b]pyridine-2-carboxylic acid methyl ester (1.0 g), the mixture was heated and stirred at 140° C. for 5 hours. After cooling, water was added, extraction was performed with ethyl acetate, the organic layer was washed with water and saturated brine in that order and dried over anhydrous sodium sulfate, and the solvent was distilled off under reduced pressure. Tetrahydrofuran was used for recrystallization to obtain the title compound (70 mg).
¹H-NMR (DMSO-d₆) δ (ppm) 3.87 (3H, s), 7.04 (1H, d, J=5.6 Hz), 7.48-7.53 (2H, m), 7.59 (1H, s), 8.32-8.37 (2H, m), 8.47 (1H, d, J=5.6 Hz)

Production Example 510-4

Synthesis of 4-(4-Aminophenoxy)furo[2,3-b]pyridine-2-carboxylic acid methyl ester 4-(4-Nitrophenoxy)-furo[2,3-b]pyridine-2-carboxyl is acid methyl ester (70 mg) was subjected to iron reduction by the same method as in Production Example 10 to obtain the title compound (55 mg).
¹H-NMR (DMSO-d₆) δ (ppm) 3.86 (3H, s), 5.23 (2H, brs), 6.64 (2H, d, J=8.4 Hz), 6.72 (1H, d, J=6.0 Hz), 6.93 (2H, d, J=8.4 Hz), 7.23 (1H, s), 8.31 (1H, d, J=6.0 Hz)

Example 511

N-(4-Fluorophenoxy)-N'-[4-(2-hydroxymethylfuro[2,3-b]pyridin-4-yloxy)phenyl]urea After dissolving 4-{4-[3-(4-fluorophenyl)ureido]phenoxy}-furo[2,3-b]pyridine-2-carboxylic acid methyl ester (13 mg) in tetrahydrofuran (3 ml), lithiumborohydride (10 mg) was added and the mixture was stirred overnight at room temperature. After adding a small amount of acetone, water was added, extraction was performed with ethyl acetate, the organic layer was washed with water and saturated brine in that order and dried over anhydrous sodium sulfate, and the solvent was distilled off under reduced pressure to obtain the title compound (10 mg).

¹H-NMR (DMSO-d₆) δ (ppm) 4.52 (2H, d, J=6.0 Hz), 5.52 (1H, t, J=6.0 Hz), 6.38 (1H, s), 6.69 (1H, d, J=5.6 Hz), 7.07-7.19 (4H, m), 7.43-7.49 (2H, m), 7.51-7.57 (2H, m), 8.11 (1H, d, J=5.4 Hz), 8.11 (1H, brs), 8.81 (1H, brs)

Example 512

N-(4-Fluorophenyl)-N'-[4-(6-phenylfuro[2,3-d]pyrimidin-4-yloxy)phenyl]urea

After adding toluene (1 ml), acetonitrile (0.5 ml) and 4-fluorophenyl isocyanate (0.03 ml) to 4-(6-phenyl-furo[2,3-d]pyrimidin-4-yloxy)phenylamine (40 mg), the mixture was heated to reflux for 30 minutes. After cooling, the precipitated crystals were filtered out and washed with toluene to obtain the title compound (42 mg) as light yellow crystals.
¹H-NMR (DMSO-d₆) δ (ppm) 7.08-7.15 (2H, m), 7.23 (2H, d, J=8.4 Hz), 7.43-7.57 (7H, m), 7.65 (1H, s), 7.97 (2H, d, J=8.4 Hz), 8.50 (1H, s), 8.74-8.81 (2H, m)

The starting material was synthesized by the following 4 steps.

Production Example 512-1

6-Phenylfuro[2,3-d]pyrimidin-4-ylamine

After adding formamide (10 ml) and 2 drops of acetic anhydride to 2-amino-5-phenyl-3-furonitrile (1.8 g) synthesized according to the method described in J. Heterocyclic Chem., 35, 1313 (1998), the mixture was heated and stirred at 200° C. for 2 hours. After cooling, the precipitated crystals were filtered out and washed with diethyl ether to obtain the title compound (1.3 g).
¹H-NMR (DMSO-d₆) δ (ppm) 7.30 (1H, s), 7.35-7.41 (1H, m), 7.46-7.53 (2H, m), 7.74-7.79 (2H, m), 8.16 (1H, m)

Production Example 512-2

4-(4-Nitrophenoxy-6-phenyl-furo[2,3-d]pyrimidine

After adding dibromomethane (1.2 ml) and isoamyl nitrite (1.2 ml) to 6-phenylfuro[2.-d]pyrimidin-4-ylamine (211 mg), the mixture was heated and stirred at 80° C. for 30 minutes. The reaction solution was concentrated under reduced pressure, water was added, extraction was performed with ethyl acetate, the organic layer was washed with water and saturated brine in that order and dried over anhydrous sodium sulfate, and the solvent was distilled off under reduced pressure. After adding dimethylformamide (10 ml), para-nitrobenzene (222 mg) and potassium carbonate (414 mg), the mixture was heated and stirred at 80° C. for 1 hour. Water was added to the reaction solution, extraction was performed with ethyl acetate, and then the organic layer was washed with water and saturated brine in that order and dried over anhydrous sodium sulfate, and the solvent was distilled off under reduced pressure. Ethyl acetate was used for recrystallization to obtain the title compound (150 mg).
¹H-NMR (DMSO-d₆) δ (ppm) 7.43-7.67 (5H, m), 7.76 (1H, s), 7.98-8.03 (2H, m), 8.34-8.39 (2H, m), 8.56 (1H, s)

Production Example 512-3

4-(6-Phenylfuro[2,3-d]pyrimidin-4-yloxy)phenylamine 4-(4-Nitrophenoxy-6-phenylfuro[2,3-d]pyrimidine (150 mg) was subjected to iron reduction by the same method as in Production Example 6 to obtain the title compound (50 mg).

¹H-NMR (DMSO-d₆) 5.10 (2H, brs), 6.59-6.63 (2H, m), 6.91-6.96 (2H, m), 7.42-7.56 (4H, m), 7.91-7.95 (2H, m), 8.47 (1H, s)

Example 513

6-Carboxy-7-methoxy-4-(indol-5-yloxy)quinoline

After dissolving 6-methoxycarbonyl-7-methoxy-4-(indol-5-yloxy)quinoline (400 mg) in tetrahydrofuran (5 ml), a 1.5N aqueous lithium hydroxide solution (2.5 ml) was added and the mixture was stirred at room temperature for 3 hours. The reaction solution was adjusted to pH 4 with 1N aqueous hydrochloric acid, and the precipitated crystals were filtered out and washed with ethyl acetate to obtain the title compound (280 mg).

¹H-NMR (DMSO-d₆) δ (ppm) 3.94 (3H, s), 6.37 (1H, d, J=5.2 Hz), 6.43-6.47 (1H, m), 6.95-7.01 (1H, m), 7.40-7.55 (4H, m), 8.55-8.61 (2H, m), 11.3 (1H, brs)

The intermediate was synthesized in the following manner.

Production Example 513-1

6-Methoxycarbonyl-7-methoxy-4-(indol-5-yloxy)quinoline

After mixing methyl 4-chloro-7-methoxyquinoline-6-carboxylate (WO0050405, P.34, 8.5 g, 33.77 mmol), 5-hydroxyindole (7 g), diisopropylethylamine (8.9 ml) and N-methylpyrrolidone (8.9 ml), the mixture was heated and stirred at 130° C. for 5 hours and then at 150° C. for 8 hours. After cooling, the solution was adsorbed onto silica gel and purified with a silica gel column (hexane-ethyl acetate system). Ethanol, diethyl ether and hexane were added to the obtained yellow oil, and crystals precipitated upon standing. These were filtered out, washed with diethyl ether and hexane and dried by aspiration to obtain light yellow crystals (3.506 g, 10.06 mmol, 29.80%).

¹H-NMR Spectrum (DMSO-d6) δ (ppm): 3.86 (3H, s), 3.97 (3H, s), 6.38 (1H, d, J=5.2 Hz), 6.46 (1H, s), 6.98 (1H, d, J=8.8 Hz), 7.44-7.52 (4H, m), 8.60-8.65 (2H, m), 11.29 (1H, s)

Example 514

6-(2-Methoxyethylcarbamoyl)-7-methoxy-4-(indol-5-yloxy)quinoline

After dissolving 6-carboxy-7-methoxy-4-(indol-5-yloxy)quinoline (100 mg) in dimethylformamide (4.0 ml), there were added methoxyethylamine (0.04 ml), triethylamine (0.08 ml) and benzotriazol-1-yloxytris(dimethylamino)phosphonium hexafluorophosphate (198 mg), and the mixture was stirred at room temperature for 5 hours. Water was added to the reaction solution, extraction was performed with ethyl acetate, and then the organic layer was washed with water and saturated brine in that order and dried over anhydrous sodium sulfate, and the solvent was distilled off under reduced pressure. Ethyl acetate was used for recrystallization to obtain the title compound (86 mg).

¹H-NMR (DMSO-d₆) δ (ppm) 3.29 (3H, s), 3.46-3.49 (4H, m), 4.02 (3H, s), 6.37 (1H, d, J=5.2 Hz), 6.45-6.47 (1H, m), 6.95-7.00 (1H, m), 7.41-7.54 (4H, m), 8.42-8.45 (1H, m), 8.59 (1H, d, J=5.2 Hz), 8.68 (1H, s), 11.3 (1H, brs).

Example 515

6-(2-Methoxyethylcarbonyl)-7-methoxy-4-(1-ethylcarbamoyl-indol-5-yloxy)quinoline After adding 60% sodium hydride (10 mg) to dimethylformamide (1 ml), the mixture was stirred at room temperature, 6-(2-methoxyethylcarbamoyl)-7-methoxy-4-(indol-5-yloxy)quinoline (10 mg) was added, and the mixture was stirred for another 15 minutes. Ethylcarbamic acid phenyl ester (43 mg) was then added and the mixture was stirred for 1 hour. Water was added to the reaction solution, extraction was performed with ethyl acetate, and then the organic layer was washed with water and saturated brine in that order and dried over anhydrous sodium sulfate, and the solvent was distilled off under reduced pressure. Ethyl acetate was used for recrystallization to obtain the title compound (27 mg).

¹H-NMR (DMSO-d₆) δ (ppm) 1.18 (3H, t, J=7.2 Hz), 3.27-3.29 (5H, m), 3.47-3.49 (4H, m), 4.02 (3H, s), 6.42 (1H, d, J=5.2 Hz), 6.70 (1H, d, J=3.6 Hz), 7.15-7.20 (1H, m), 7.50-7.52 (2H, m), 7.93 (1H, d, J=3.6 Hz), 8.20-8.50 (3H, m), 8.61 (1H, d, J=5.2 Hz), 8.67 (1H, s)

Example 516

6-(2-Methoxyethylcarbonyl)-7-methoxy-4-[1-(2-fluoroethylcarbamoyl)indol)-5-yloxy]quinoline The title compound was obtained from 6-(2-methoxyethylcarbamoyl)-7-methoxy-4-(indol-5-yloxy)quinoline using 2-fluoroethylcarbamic acid phenyl ester, by the same procedure as in Example 515.

¹H-NMR (DMSO-d₆) δ (ppm) 3.24 (3H, s), 3.45-3.67 (6H, m), 4.02 (3H, s), 4.50-4.68 (2H, m), 6.43 (1H, d, J=5.2 Hz), 6.72 (1H, d, J=3.6 Hz), 7.16-7.21 (1H, m), 7.50-7.54 (2H, m), 7.98 (1H, d, J=3.6 Hz), 8.35 (1H, d, J=9.2 Hz), 8.42-8.53 (2H, m), 8.61 (1H, d, J=5.2 Hz), 8.76 (1H, s)

Example 517

6-(2-Fluoroethylcarbamoyl)-7-methoxy-4-(indol-5-yloxy)quinoline

The title compound was obtained from 6-carboxy-7-methoxy-4-(indol-5-yloxy)quinoline using 2-fluoroethylamine hydrochloride, by the same procedure as in Example 514.

¹H-NMR (DMSO-d₆) δ (ppm) 3.53-3.71 (2H, m), 4.02 (3H, s), 4.48-4.63 (2H, m), 6.37 (1H, d, J=5.2 Hz), 6.45-6.47 (1H, m), 6.95-7.00 (1H, m), 7.42-7.46 (2H, m), 7.48-7.53 (2H, m), 8.57-8.63 (2H, m), 8.66 (1H, s), 11.6 (1H, brs)

Example 518

6-(2-Fluoroethylcarbonyl)-7-methoxy-4-((1-ethylcarbamoyl)indol-5-yloxy)quinoline The title compound was obtained from 6-(2-fluoroethylcarbamoyl)-7-methoxy-4-(indol-5-yloxy)quinoline, by the same procedure as in Example 515.

¹H-NMR (DMSO-d₆) δ (ppm) 1.18 (3H, t, J=7.2 Hz), 3.27-3.32 (2H, m), 3.56-3.68 (2H, m), 4.02 (3H, s), 4.47-4.65 (2H, m), 6.42 (1H, d, J=5.2 Hz), 6.70 (1H, d, J=4.0 Hz), 7.15-7.20 (1H, m) 7.50-7.52 (2H, m), 7.93 (1H, d, J=4.0 Hz), 8.22-8.27 (1H, m), 8.34 (1H, d, J=8.9 Hz), 8.57-8.66 (3H, m).

Example 519

6-Methoxycarbamoyl-7-methoxy-4-(indol-5-yloxy) quinoline

The title compound was obtained from 6-carboxy-7-methoxy-4-(indol-5-yloxy)quinoline using methylhydroxylamine hydrochloride, by the same procedure as in Example 514.
$^1$H-NMR (DMSO-$d_6$) δ (ppm) 3.73 (3H, s), 3.98 (3H, s), 6.38 (1H, d, J=5.2 Hz), 6.44-6.48 (1H, m), 6.95-7.00 (1H, m), 7.40-7.54 (4H, m), 8.49 (1H, s), 8.59 (1H, d, J=5.2 Hz), 11.29 (1H, brs), 11.45 (1H, brs)

Example 520

6-Methoxycarbamoyl-7-methoxy-4-((1-ethylcarbamoyl)indol-5-yloxy)quinoline

The title compound was obtained from 6-methoxycarbamoyl-7-methoxy-4-(indol-5-yloxy)quinoline, by the same procedure as in Example 515.
$^1$H-NMR (DMSO-$d_6$) δ (ppm) 1.16 (3H, t, J=7.2 Hz), 3.27-3.30 (2H, m), 3.73 (3H, s), 3.98 (3H, s), 6.43 (1H, d, J=5.2 Hz), 6.70 (1H, d, J=3.2 Hz), 7.15-7.20 (1H, m), 7.45-7.53 (2H, m), 7.93 (1H, d, J=3.6 Hz), 8.21-8.26 (1H, m), 8.35 (1H, d, J=8.8 Hz), 8.48 (1H, s), 8.61 (1H, d, J=5.2 Hz), 11.45 (1H, brs)

Example 521

6-Methoxycarbamoyl-7-methoxy-4-((1-cyclopropylcarbamoyl)indol-5-yloxy)quinoline

The title compound was obtained from 6-methoxycarbamoyl-7-methoxy-4-(indol-5-yloxy)quinoline using cyclopropylcarbamic acid phenyl ester, by the same procedure as in Example 515.
$^1$H-NMR (DMSO-$d_6$) δ (ppm) 0.58-0.65 (2H, m), 0.70-0.77 (2H, m), 2.73-2.82 (1H, m), 3.73 (3H, s), 3.98 (3H, s), 6.42 (1H, d, J=5.2 Hz), 6.68 (1H, d, J=3.6 Hz), 7.15-7.20 (1H, m), 7.47-7.52 (2H, m), 7.89 (1H, d, J=3.6 Hz), 8.28-8.36 (2H, m), 8.48 (1H, s), 8.61 (1H, d, J=5.2 Hz), 11.44 (1H, brs)

Example 522

6-(Pyridin-2-ylcarbamoyl)-7-methoxy-4-(indol-5-yloxy)quinoline

The title compound was obtained from 6-carboxy-7-methoxy-4-(indol-5-yloxy)quinoline using 2-aminopyridine, by the same procedure as in Example 514.
$^1$H-NMR (DMSO-$d_6$) δ (ppm) 4.08 (3H, s), 6.39-6.48 (2H, m), 6.97-7.02 (1H, m), 7.15-7.20 (1H, m), 7.43-7.60 (4H, m), 7.83-7.89 (1H, m), 8.25-8.38 (2H, m), 8.60-8.80 (2H, m), 10.70 (1H, brs), 11.30 (1H, brs)

Example 523

6-(Pyridin-2-ylcarbamoyl)-7-methoxy-4-((1-ethylcarbamoyl)indol-5-yloxy)quinoline The title compound was obtained from 6-(pyridin-2-ylcarbamoyl)-7-methoxy-4-(indol-5-yloxy)quinoline, by the same procedure as in Example 515.
$^1$H-NMR (DMSO-$d_6$) δ (ppm) 1.18 (3H, t, J=7.6 Hz), 3.27-3.30 (2H, m), 4.10 (3H, s), 6.46 (1H, d, J=5.2 Hz), 6.71 (1H, d, J=3.6 Hz), 7.15-7.21 (2H, m), 7.53 (1H, d, J=2.8 Hz), 7.60 (1H, s), 7.83-7.89 (1H, m), 7.93 (1H, d, J=3.6 Hz), 8.22-8.38 (4H, m), 8.65 (1H, d, J=5.2 Hz), 8.76 (1H, d, J=5.2 Hz), 10.70 (1H, brs)

Example 524

6-Methoxycarbonyl-7-methoxy-4-[1-(2-fluoroethylcarbamoyl)indol-5-yloxy]quinoline The title compound was obtained from 6-methoxycarbonyl-7-methoxy-4-(indol-5-yloxy)quinoline using 2-fluoroethylcarbamic acid phenyl ester, in the same manner as Example 515.
$^1$H-NMR (DMSO-$d_6$) δ (ppm) 3.50-3.68 (2H, m), 3.84 (3H, s), 3.97 (3H, s), 4.48-4.70 (2H, m), 6.42 (1H, d, J=5.6 Hz), 6.72 (1H, d, J=3.6 Hz), 7.17-7.22 (1H, m), 7.45-7.56 (2H, m), 7.98 (1H, d, J=3.6 Hz), 8.35 (1H, d, J=9.2 Hz), 8.46-8.53 (1H, m), 8.58-8.64 (2H, m)

Example 525

6-Carboxy-7-methoxy-4-[1-(2-fluoroethylcarbamoyl)indol-5-yloxy]quinoline

The title compound was obtained from 6-methoxycarbonyl-7-methoxy-4-[1-(2-fluoroethylcarbamoyl)indol-5-yloxy]quinoline using 2-phenylcarbamic acid phenyl ester, by the same procedure as in Example 513.
$^1$H-NMR (DMSO-$d_6$) δ (ppm) 3.50-3.70 (2H, m), 3.94 (3H, s), 4.48-4.70 (2H, m), 6.42 (1H, d, J=5.2 Hz), 6.72 (1H, d, J=3.6 Hz), 7.18-7.22 (1H, m), 7.42-7.55 (2H, m), 7.98 (1H, d, J=3.6 Hz), 8.35 (1H, d, J=9.2 Hz), 8.46-8.52 (1H, m), 8.54-8.64 (2H, m)

Example 526

6-Methoxycarbamoyl-7-methoxy-4-[1-(2-fluoroethylcarbamoyl)indol-5-yloxy]quinoline The title compound was obtained from 6-carboxy-7-methoxy-4-[1-(2-fluoroethylcarbamoyl)indol-5-yloxy]quinoline using methylhydroxylamine hydrochloride, by the same procedure as in Example 514.
$^1$H-NMR (DMSO-$d_6$) δ (ppm) 3.53-3.66 (2H, m), 3.73 (3H, s), 3.98 (3H, s), 4.50-4.68 (2H, m), 6.43 (1H, d, J=5.2 Hz), 6.73 (1H, d, J=3.6 Hz), 7.15-7.21 (1H, m), 7.47-7.54 (2H, m), 7.98 (1H, d, J=3.6 Hz), 8.35 (1H, d, J=8.4 Hz), 8.46-8.53 (2H, m), 8.61 (1H, d, J=5.2 Hz), 11.5 (1H, brs)

Example 527

6-Isobutoxycarbamoyl-7-methoxy-4-[1-(2-fluoroethylcarbamoyl)indol-5-yloxy]quinoline The title compound was obtained from 6-carboxy-7-methoxy-4-[1-(2-fluoroethylcarbamoyl)indol-5-yloxy]quinoline using o-isobutylhydroxylamine hydrochloride, by the same procedure as in Example 514.
$^1$H-NMR (DMSO-$d_6$) δ (ppm) 0.93 (6H, d), 1.90-2.00 (1H, m), 3.52-3.67 (2H, m), 3.70 (2H, d, J=6.8 Hz), 3.97 (3H, s), 4.50-4.69 (2H, m), 6.43 (1H, d, J=5.6 Hz), 6.73 (1H, d, J=4.0 Hz), 7.15-7.21 (1H, m), 7.47-7.54 (2H, m), 7.98 (1H, d, J=4.0

Hz), 8.35 (1H, d, J=9.2 Hz), 8.41 (1H, s), 8.45-8.55 (1H, m), 8.61 (1H, d, J=5.6 Hz), 11.84 (1H, brs)

Example 528

N-[2-Fluoro-4-([6-cyano-7-([(2R)-2-hydroxy-3-(1-pyrrolidino)propyl]oxy)-4-quinolyl]oxy)phenyl]-N'-(2-thiazolyl)urea The title compound was obtained from N-(4-{6-cyano-7-[(2R)-oxiran-2-yl]methoxyquinolin-4-yloxy}-2-fluorophenyl)-N'-(thiazol-2-yl)urea, by the method described in Example 495.

$^1$H-NMR (DMSO-$d_6$) δ (ppm) 1.60-1.70 (4H, m), 2.40-2.75 (6H, m), 3.95-4.05 (1H, m), 4.20 (1H, dd, J=10, 6.0 Hz), 4.31 (1H, dd, J=10, 4 Hz), 5.02 (1H, brs), 6.62 (1H, d, J=5.2 Hz), 7.10-7.20 (2H, m), 7.37-7.47 (2H, m), 7.62 (1H, s), 8.20-8.26 (1H, m), 8.71-8.76 (2H, m), 9.05 (1H, brs)

Example 529

N-[2-Fluoro-4-([6-cyano-7-([(2R)-2-hydroxy-3-(1-piperidino)propyl]oxy)-4-quinolyl]oxy)phenyl]-N'-(2-thiazolyl)urea The title compound was obtained from N-(4-{6-cyano-7-[(2R)-oxiran-2-yl]methoxyquinolin-4-yloxy}-2-fluorophenyl)-N'-thiazol-2-yl-urea, by the method described in Example 496.

$^1$H-NMR (DMSO-$d_6$) δ (ppm) 1.30-1.55 (6H, m), 2.32-2.55 (6H, m), 3.97-4.16 (1H, m), 4.20 (1H, dd, J=10, 6 Hz), 4.30 (1H, dd, J=10, 4.0 Hz), 4.44 (1H, brs), 6.62 (1H, d, J=5.2 Hz), 7.11-7.21 (2H, m), 7.37-7.47 (2H, m), 7.64 (1H, s), 8.20-8.27 (1H, m), 8.72-8.76 (2H, m)

Example 530

N-[2-Fluoro-4-([6-cyano-7-([(2R)-2-hydroxy-3-(1-pyrrolidino)propyl]oxy)-4-quinolyl]oxy)phenyl]-N'-cyclopropylurea The title compound was obtained from N-(2-fluoro-4-[(6-cyano-7-[(2R)-(oxiran-2-yl)methoxy]-4-quinolyl)oxy]phenyl)-N'-cyclopropylurea, by the method described in Example 492.

$^1$H-NMR (DMSO-$d_6$) δ (ppm) 0.37-0.44 (2H, m), 0.62-0.69 (2H, m), 1.63-1.75 (4H, m), 2.45-2.60 (6H, m), 2.65-2.77 (1H, m), 3.98-4.08 (1H, m), 4.22 (1H, dd, J=10, 5.2 Hz), 4.31 (1H, dd, J=10, 3.6 Hz), 5.04 (1H, brs), 6.59 (1H, d, J=5.6 Hz), 6.82-6.85 (1H, m), 7.08-7.13 (1H, m), 7.32-7.38 (1H, m), 7.63 (1H, s), 8.20-8.28 (2H, m), 8.72-8.76 (2H, m)

The starting material was synthesized by the following 2 steps.

Production Example 530-1

[2-Fluoro-4-([6-cyano-7-([(2R)-(oxiran-2-yl)methoxy]-4-quinolyl]oxy)phenyl]carbamic acid phenyl ester This was synthesized from 4-(4-amino-3-fluoro-phenoxy)-7-[(2R)-oxiran-2-yl]methoxyquinoline-6-carbonitrile, by the method described in Production Example 141-1.

$^1$H-NMR(CDCl$_3$) δ (ppm) 2.90-3.01 (2H, m), 3.44-3.55 (1H, m), 4.21-4.28 (1H, m), 4.47-4.54 (1H, m), 6.53 (1H, d, J=5.2 Hz), 7.00-7.06 (2H, m), 7.19-7.30 (4H, m), 7.40-7.46 (2H, m), 7.48-7.53 (1H, m), 8.27 (1H, brs), 8.65-8.73 (2H, m)

Production Example 530-2

N-(2-Fluoro-4-[(6-cyano-7-[(2R)-(oxiran-2-yl)methoxy]-4-quinolyl)oxy]phenyl)-N'-cyclopropylurea Cyclopropylamine (0.04 ml) was added to dimethylsulfoxide (3 ml), and then [2-fluoro-4-([6-cyano-7-([(2R)-oxiran-2-yl]methoxy)-4-quinolyl]oxy)phenyl]carbamic acid phenyl ester (212 mg) was dissolved therein and the solution was stirred for 10 minutes. Water and ethyl acetate were added to the reaction solution, and the precipitated crystals were filtered out to obtain the title compound (150 mg).

$^1$H-NMR (DMSO-$d_6$) δ (ppm) 0.37-0.44 (2H, m), 0.61-0.69 (2H, m), 2.50-2.60 (1H, m), 2.78-2.79 (2H, m), 3.45-3.50 (1H, m), 4.20 (1H, dd, J=12, 6.0 Hz), 4.73 (1H, dd, J=12, 2.4 Hz), 6.59 (1H, d, J=5.6 Hz), 6.82-6.85 (1H, m), 7.08-7.13 (1H, m), 7.32-7.38 (1H, m), 7.63 (1H, s), 8.20-8.28 (2H, m), 8.72-8.78 (2H, m)

Example 531

N-[2-Fluoro-4-([6-cyano-7-([(2R)-2-hydroxy-3-(1-piperidino)propyl]oxy)-4-quinolyl]oxy)phenyl]-N'-cyclopropylurea The title compound was obtained from N-(2-fluoro-4-[(6-cyano-7-[(2R)-(oxiran-2-yl)methoxy]-4-quinolyl)oxy]phenyl)-N'-cyclopropylurea, by the method described in Example 496.

$^1$H-NMR (DMSO-$d_6$) δ (ppm) 0.38-0.44 (2H, m), 0.62-0.69 (2H, m), 1.33-1.54 (6H, m), 2.30-2.70 (7H, m), 4.00-4.09 (1H, m), 4.21 (1H, dd, J=10.4, 5.6 Hz), 4.32 (1H, dd, J=10.4, 3.2 Hz), 4.95 (1H, d, J=4.4 Hz), 6.59 (1H, d, J=5.6 Hz), 6.83-6.85 (1H, m), 7.08-7.13 (1H, m), 7.32-7.38 (1H, m), 7.64 (1H, s), 8.20-8.28 (2H, m), 8.72-8.78 (2H, m)

Example 532

N-[2-Fluoro-4-([6-cyano-7-([3-(1-piperidino)propyl]oxy)-4-quinolyl]oxy)phenyl]-N'-(2-thiazolyl)urea The title compound was obtained from 2-fluoro-4-([6-cyano-7-([3-(1-piperidino)propyl]oxy)-4-quinolyl]oxy)phenylamine, by the method described in Example 495.

$^1$H-NMR (DMSO-$d_6$) δ (ppm) 1.30-1.53 (6H, m), 1.92-2.00 (2H, m), 2.30-2.50 (6H, m), 4.28-4.35 (2H, m), 6.62 (1H, d, J=5.6 Hz), 7.12-7.20 (2H, m), 7.36-7.47 (2H, m), 7.60 (1H, s), 8.20-8.28 (1H, m), 8.72-8.77 (2H, m).

The starting material was synthesized in the following manner.

Production Example 532-1

2-Fluoro-4-([6-cyano-7-([3-(1-piperidino)propyl]oxy)-4-quinolyl]oxy)phenylamine

After adding dimethylformamide (4 ml), 1-(3-chloropropyl)piperidine)hydrochloride (268 mg) and potassium carbonate (374 mg) to 4-(4-amino-3-fluorophenoxy)-6-cyano-7-hydroxyquinoline (200 mg), the mixture was heated at 60° C. for 8 hours. Water was added to the reaction solution, extraction was performed with ethyl acetate and the organic layer was washed with water and saturated brine in that order and then dried over anhydrous sodium sulfate, and the solvent was distilled off under reduced pressure. The obtained crude product was purified by silica gel column chromatography (ethyl acetate) to obtain the title compound (80 mg) as light yellow crystals.

$^1$H-NMR(CDCl$_3$) δ (ppm) 1.38-1.64 (6H, m), 2.07-2.18 (2H, m), 2.37-2.48 (6H, m), 3.79 (2H, brs), 4.24-4.34 (2H, m), 6.47 (1H, d, J=5.6 Hz), 6.77-6.92 (3H, m), 7.46 (1H, s), 8.63-8.67 (2H, m)

Example 533

N-[2-Fluoro-4-([6-cyano-7-([3-(1-pyrrolidino)propyl]oxy)-4-quinolyl]oxy)phenyl]-N'-(2-thiazolyl) urea The title compound was obtained from 2-fluoro-4-([6-cyano-7-([3-(1-pyrrolidino)propyl]oxy)-4-quinolyl]oxy)phenylamine, by the method described in Example 495.

$^1$H-NMR (DMSO-d$_6$) δ (ppm) 1.65-1.72 (4H, m), 1.94-2.02 (2H, m), 2.40-2.50 (4H, m), 2.56-2.62 (2H, m), 4.30-4.36 (2H, m), 6.63 (1H, d, J=5.6 Hz), 7.13-7.20 (2H, m), 7.37-7.47 (2H, m), 7.60 (1H, s), 8.20-8.27 (1H, m), 8.72-8.76 (2H, m)

The starting material was synthesized in the following manner.

Production Example 533-1

2-Fluoro-4-([6-cyano-7-([3-(1-pyrrolidino)propyl] oxy)-4-quinolyl]oxy)phenylamine After adding dimethylformamide (4 ml), 1-(3-chloropropylpyrrolidine)hydrochloride (376 mg) and potassium carbonate (553 mg) to 4-(4-amino-3-fluorophenoxy)-6-cyano-7-hydroxyquinoline (300 mg), the mixture was heated at 60° C. for 8 hours. Water was added to the reaction solution, extraction was performed with ethyl acetate and the organic layer was washed with water and saturated brine in that order and then dried over anhydrous sodium sulfate, and the solvent was distilled off under reduced pressure. The obtained crude product was purified by silica gel column chromatography (ethyl acetate) to obtain the title compound (200 mg) as light yellow crystals.

$^1$H-NMR (DMSO-d$_6$) δ (ppm) δ (ppm) 1.62-1.72 (4H, m), 1.93-2.03 (2H, m), 2.40-2.49 (4H, m), 2.55-2.61 (2H, m), 4.28-4.35 (2H, m), 5.22-5.25 (2H, m), 6.51 (1H, d, J=4.8 Hz), 6.82-6.90 (2H, m), 7.06-7.12 (1H, m) 7.56 (1H, s), 8.68-8.72 (2H, m)

Example 534

N-(2-Chloro-5-((6-cyano-7-(2-(1-pyrrolidino) ethoxy)-4-quinolyl)oxy)phenyl)-N'-phenylurea The title compound (19.8 mg, 0.038 mmol, 34.5%) was obtained as white crystals from 4-(3-amino-4-chlorophenoxy)-6-cyano-7-(2-(1-pyrrolidino)ethoxy)quinoline (44.5 mg, 0.109 mmol) and phenyl isocyanate, by the same procedure as in Example 11.

$^1$H-NMR Spectrum (DMSO-d$_6$) δ (ppm): 1.69 (4H, m), 2.59 (4H, m), 2.91 (2H, t, J=5.6 Hz), 4.38 (2H, t, J=5.6 Hz), 6.66 (1H, d, J=5.2 Hz), 6.97-7.01 (2H, m), 7.24-7.28 (2H, m), 7.41 (2H, d, J=7.2 Hz), 7.60-7.63 (2H, m), 8.20 (1H, m), 8.51 (1H, s), 8.74-8.76 (2H, m), 9.53 (1H, d, J=4.4 Hz).

The starting materials were synthesized in the following manner.

Production Example 534-1

7-(Benzyloxy)-4-(4-chloro-3-nitrophenoxy)-6-cyanoquinoline

The title compound (4.794 g, 11.10 mmol, 59.9%) was obtained as light brown crystals from 7-(benzyloxy)-4-chloro-6-cyanoquinoline (5.462 g, 18.53 mmol) and 4-chloro-3-nitrophenol, by the same procedure as in Production Example 11.

$^1$H-NMR Spectrum (CDCl$_3$) δ (ppm): 5.74 (2H, s), 6.57 (1H, d, J=5.2 Hz), 7.34-7.55 (6H, m), 7.58 (1H, s), 7.70 (1H, d, J=8.8 Hz), 7.76 (1H, d, J=2.8 Hz), 8.64 (1H, s), 8.76 (1H, d, J=5.2 Hz).

Production Example 534-2

4-(4-Chloro-3-nitrophenoxy)-6-cyano-7-hydroxyquinoline

The title compound (743 mg, 2.17 mmol, 93.9%) was obtained as light yellow crystals from 7-(benzyloxy)-4-(4-chloro-3-nitrophenoxy)-6-cyanoquinoline (1.00 g, 2.32 mmol), by the same procedure as in Example 83.

$^1$H-NMR Spectrum (DMSO-d$_6$) δ (ppm): 6.73 (1H, d, J=5.2 Hz), 7.45 (1H, s), 7.69 (1H, dd, J=2.8, 8.8 Hz), 7.91 (1H, d, J=8.8 Hz), 8.14 (1H, d, J=2.8 Hz), 8.67 (1H, s), 8.71 (1H, d, J=5.2 Hz), 11.71 (1H, br).

Production Example 534-3

4-(3-Amino-4-chlorophenoxy)-6-cyano-7-hydroxyquinoline

The title compound (464 mg, 1.49 mmol, 68.5%) was obtained as light yellow crystals from 4-(4-chloro-3-nitrophenoxy)-6-cyano-7-hydroxyquinoline (743 mg, 2.17 mmol), by the same procedure as in Production Example 6.

$^1$H-NMR Spectrum (DMSO-d$_6$) δ (ppm): 5.62-5.65 (2H, m), 6.43 (1H, dd, J=2.8, 8.8 Hz), 6.54 (1H, d, J=5.2 Hz), 6.63 (1H, d, J=2.8 Hz), 7.30 (1H, d, J=8.8 Hz), 7.41 (1H, s), 8.62 (1H, s), 8.65 (1H, d, J=5.2 Hz).

Production Example 534-4

4-(3-Amino-4-chlorophenoxy)-6-cyano-7-(2-(1-pyrrolidino)ethoxy)quinoline

The title compound (143 mg, 0.350 mmol, 54.5%) was obtained as white crystals from 4-(3-amino-4-chlorophenoxy)-6-cyano-7-hydroxyquinoline (200 mg, 0.642 mmol) and 1-(2-chloroethyl)pyrrolidine hydrochloride, by the same procedure as in Example 7.

$^1$H-NMR Spectrum (CDCl$_3$) δ (ppm): 1.84 (4H, m), 2.74 (4H, m), 3.08 (2H, t, J=5.6 Hz), 4.20-4.24 (2H, m), 4.37 (2H, t, J=5.6 Hz), 6.50 (1H, dd, J=2.8, 8.8 Hz), 6.54 (1H, d, J=5.2 Hz), 6.59 (1H, d, J=2.8 Hz), 7.33 (1H, d, J=8.8 Hz), 7.46 (1H, s), 8.64 (1H, s), 8.68 (1H, d, J=5.2 Hz).

Example 535

N-(2-Chloro-5-((6-cyano-7-(2-(1-pyrrolidino) ethoxy)-4-quinolyl)oxy)phenyl)-N'-(1,3-thiazol-2-yl) urea The title compound (5.7 mg, 0.011 mmol, 9.35%) was obtained as white crystals from 4-(3-amino-4-chlorophenoxy)-6-cyano-7-(2-(1-pyrrolidino)ethoxy)quinoline (46.6 mg, 0.114 mmol) and phenyl N-(1,3-thiazol-2-yl)carbamate, by the same procedure as in Example 131.

¹H-NMR Spectrum (DMSO-d₆) δ (ppm): 1.69 (4H, m), 2.61 (4H, m), 2.93 (2H, m), 4.39 (2H, m), 6.65 (1H, d, J=5.2 Hz), 7.06 (1H, dd, J=2.8, 8.8 Hz), 7.13-7.14 (2H, m), 7.38-7.40 (2H, m), 7.63 (1H, s), 7.66 (1H, d, J=8.8 Hz), 8.19 (1H, d, J=3.2 Hz), 8.75 (1H, d, J=5.2 Hz), 8.77 (1H, s).

Example 536

N-(2-Chloro-5-((6-cyano-7-(2-(1-pyrrolidino)ethoxy)-4-quinolyl)oxy)phenyl)-N'-cyclopropylurea After dissolving 4-(3-amino-4-chlorophenoxy)-6-cyano-7-(2-(1-pyrrolidino)ethoxy)quinoline (47.9 mg, 0.117 mmol) in dimethylformamide (1 ml) in a nitrogen atmosphere, pyridine (0.019 ml, 0.234 mmol) and phenyl chloroformate (0.030 ml, 0.234 mmol) were added dropwise at room temperature and the mixture was stirred for 1 hour. Cyclopropylamine (0.1 ml) was added dropwise, and the mixture was further stirred overnight. The reaction solution was distributed between ethyl acetate and water, washed with saturated brine and dried over anhydrous sodium sulfate. After distilling off the solvent, the crystals precipitated from ethyl acetate were filtered out and blow-dried to obtain the title compound (12.6 mg, 0.026 mmol, 21.9%) as light brown crystals.

¹H-NMR Spectrum (DMSO-d₆) δ (ppm): 0.39 (2H, m), 0.63 (2H, m), 1.70 (4H, m), 2.49-2.53 (1H, m), 2.60 (4H, m), 2.91 (2H, m), 4.40 (2H, m), 6.64 (1H, d, J=5.2 Hz), 6.93 (1H, dd, J=2.8, 8.8 Hz), 7.33 (1H, d, J=2.8 Hz), 7.57 (1H, d, J=8.8 Hz), 7.64 (1H, s), 8.09 (1H, s), 8.19 (1H, d, J=2.8 Hz), 8.75-8.77 (2H, m).

Example 537

N-(2-Chloro-5-((6-cyano-7-((2R)-2-hydroxy-3-(1-pyrrolidino)propoxy)-4-quinolyl)oxy)phenyl)-N'-cyclopropylurea The title compound (20.7 mg, 0.040 mmol, 20.7%) was obtained as a white powder from phenyl N-(2-chloro-5-((6-cyano-7-((2R)-2-hydroxy-3-(1-pyrrolidino)propoxy-4-quinolyl)oxy)phenyl)carbamate) (107 mg, 0.191 mmol) and cyclopropylamine, by the same procedure as in Example 11.

¹H-NMR Spectrum (DMSO-d₆) δ (ppm): 0.40 (2H, m), 0.65 (2H, m), 1.69 (4H, m), 2.49-2.68 (6H, m), 2.72 (1H, m), 4.03 (1H, m), 4.23 (1H, dd, J=5.6, 10.4 Hz), 4.33 (1H, dd, J=4.4, 10.4 Hz), 5.03 (1H, m), 6.64 (1H, d, J=5.2 Hz), 6.94 (1H, dd, J=2.8, 8.4 Hz), 7.33 (1H, m), 7.56-7.93 (2H, m), 8.10 (1H, s), 8.20 (1H, d, J=2.8 Hz), 8.71-8.77 (2H, m).

The starting materials were synthesized in the following manner.

Production Example 537-1

4-(3-Amino-4-chlorophenoxy)-6-cyano-7-((2R)oxiran-2-yl)methoxyquinoline

The title compound (201 mg, 0.547 mmol, 64.6%) was obtained as light yellow crystals from 4-(3-amino-4-chlorophenoxy)-6-cyano-7-hydroxyquinoline (264 mg, 0.847 mmol) and (2R)oxiran-2-ylmethyl 4-methyl-1-benzenesulfonate, by the same procedure as in Example 7.

¹H-NMR Spectrum (CDCl₃) δ (ppm): 2.93 (1H, dd, J=2.4, 4.8 Hz), 2.98 (1H, dd, J=4.0, 4.8 Hz), 3.50 (1H, m), 4.21-4.24 (3H, m), 4.50 (1H, dd, J=3.2, 11.2 Hz), 6.50 (1H, dd, J=2.8, 8.8 Hz), 6.56 (1H, d, J=5.2 Hz), 6.59 (1H, d, J=2.8 Hz), 7.33 (1H, d, J=8.8 Hz), 7.48 (1H, s), 8.67 (1H, s), 8.69 (1H, d, J=5.2 Hz).

Production Example 537-2

4-(3-Amino-4-chlorophenoxy)-6-cyano-7-(((2R)-2-hydroxy-3-(1-pyrrolidino)propyl)oxy)quinoline After dissolving 4-(3-amino-4-chlorophenoxy)-6-cyano-7-((2R)oxiran-2-yl)methoxyquinoline) (201 mg, 0.547 mmol) in tetrahydrofuran (5.0 ml) under a nitrogen atmosphere, pyrrolidine (0.456 ml) was added and the mixture was stirred at room temperature overnight. The reaction solution was concentrated under reduced pressure, the residue was subjected to silica gel column chromatography (eluent—ethyl acetate), the fraction containing the target substance was concentrated, suspended in ethyl acetate and diluted with hexane, and the crystals were filtered out and blow-dried to obtain the title compound (235 mg, 0.535 mmol, 98.0%) as light yellow crystals.

¹H-NMR Spectrum (CDCl₃) δ (ppm): 1.82 (4H, m), 2.59 (2H, m), 2.65 (1H, dd, J=4.0, 12.0 Hz), 2.74 (2H, m), 2.94 (1H, dd, J=5.2, 12.0 Hz), 4.19-4.27 (5H, m), 6.50 (1H, dd, J=2.8, 8.8 Hz), 6.55 (1H, d, J=5.2 Hz), 6.59 (1H, d, J=2.8 Hz), 7.33 (1H, d, J=8.8 Hz), 7.50 (1H, s), 8.65 (1H, s), 8.68 (1H, d, J=5.2 Hz).

Production Example 537-3

Phenyl N-(2-chloro-5-((6-cyano-7-((2R)-2-hydroxy-3-(1-pyrrolidino)propoxy-4-quinolyl)oxy)phenyl)carbamate The title compound (107 mg, 0.191 mmol, 35.7%) was obtained as white crystals from 4-(3-amino-4-chlorophenoxy)-6-cyano-7-(((2R)-2-hydroxy-3-(1-pyrrolidino)propyl)oxy)quinoline (235 mg, 0.535 mmol), by the same procedure as in Production Example 17.

¹H-NMR Spectrum (CDCl₃) δ (ppm): 2.20 (4H, m), 3.39-3.48 (5H, m), 4.11 (1H, m), 4.25 (1H, m), 4.44 (1H, dd, J=4.8, 9.2 Hz), 4.67 (1H, m), 6.50 (1H, m), 6.57-6.60 (2H, m), 6.91 (1H, m), 7.17-7.49 (6H, m), 8.17 (1H, s), 8.66 (1H, d, J=5.2 Hz), 8.71 (1H, d, J=5.6 Hz).

Example 538

N6-Methyl-4-(4-chloro-3-(((4-fluoroanilino)carbonyl)amino)phenoxy)-7-methoxy-6-quinolinecarboxamide The title compound (77.6 mg, 0.157 mmol, 77.9%) was obtained as white crystals from N6-methyl-4-(3-amino-4-chlorophenoxy)-7-methoxy-6-quinolinecarboxamide (72 mg, 0.2 mmol) and 4-fluorophenyl isocyanate, by the same procedure as in Example 11.

¹H-NMR Spectrum (DMSO-d₆) δ (ppm): 2.82 (3H, d, J=4.4 Hz), 4.01 (3H, s), 6.62 (1H, d, J=5.2 Hz), 6.96 (1H, dd, J=2.8, 8.8 Hz), 7.10 (2H, m), 7.40 (2H, m), 7.51 (1H, s), 7.60 (1H, d, J=8.8 Hz), 8.15 (1H, d, J=2.8 Hz), 8.35 (1H, d, J=4.4 Hz), 8.47 (1H, s), 8.54 (1H, s), 8.68 (1H, d, J=5.2 Hz), 9.56 (1H, s).

The starting materials were synthesized in the following manner.

Production Example 538-1

Methyl 4-(4-chloro-3-nitrophenoxy)-7-methoxy-6-quinoline carboxylate

The title compound (2.114 g, 5.44 mmol, 54.4%) was obtained as light yellow crystals from methyl 4-chloro-7-methoxy-6-quinoline carboxylate (2.517 g, 10.0 mmol) and 4-chloro-3-nitrophenol, by the same procedure as in Production Example 11.

$^1$H-NMR Spectrum (CDCl$_3$) δ (ppm): 3.97 (3H, s), 4.06 (3H, s), 6.54 (1H, d, J=5.2 Hz), 7.38 (1H, dd, J=2.8, 8.8 Hz), 7.53 (1H, s), 7.66 (1H, d, J=8.8 Hz), 7.75 (1H, d, J=2.8 Hz), 8.70 (1H, s), 8.73 (1H, d, J=8.8 Hz).

Production Example 538-2

4-(4-Chloro-3-nitrophenoxy)-7-methoxy-6-quinolinecarboxylic acid

After adding methanol (30 ml) and 2N aqueous sodium hydroxide (10 ml) to methyl 4-(4-chloro-3-nitrophenoxy)-7-methoxy-6-quinolinecarboxylate (1.00 g, 2.57 mmol), the mixture was stirred at 60° C. for 1 hour. The reaction solution was allowed to cool to room temperature, 2N hydrochloric acid was added for neutralization, the methanol was distilled off, and the precipitated light brown crystals were filtered out, thoroughly washed with water and dried at 70° C. to obtain the title compound (897 mg, 2.39 mmol, 93.1%).

$^1$H-NMR Spectrum (DMSO-d$_6$) δ (ppm): 3.97 (3H, s), 6.76 (1H, d, J=5.2 Hz), 7.53 (1H, s), 7.70 (1H, dd, J=2.8, 8.8 Hz), 7.91 (1H, d, J=8.8 Hz), 8.16 (1H, d, J=2.8 Hz), 8.49 (1H, s), 8.73 (1H, d, J=5.2 Hz), 13.13 (1H, br).

Production Example 538-3

N6-Methyl-4-(4-chloro-3-nitrophenoxy)-7-methoxy-6-quinolinecarboxamide

After dissolving 4-(4-chloro-3-nitrophenoxy)-7-methoxy-6-quinolinecarboxylic acid (897 mg, 2.39 mmol) in dimethylformamide (10 ml) under a nitrogen atmosphere, a 40% methylamine-methanol solution (2.0 ml), triethylamine (1.0 ml) and (1H-1,2,3-benzotriazol-1-yloxy)(tri(dimethylamino))phosphonium hexafluorophosphate (1.27 g, 2.87 mmol) were added in that order at room temperature and the mixture was stirred for 4 hours. The reaction solution was distributed between ethyl acetate and water, and the organic layer was washed with water and saturated brine and dried over anhydrous sodium sulfate. The solvent was distilled off, the residue was suspended in ethyl acetate and diluted with hexane, and the crystals were filtered out and blow-dried to obtain the title compound (928 mg, quantitative) as white crystals.

$^1$H-NMR Spectrum (DMSO-d$_6$) δ (ppm): 2.82 (3H, d, J=4.4 Hz), 4.01 (3H, s), 6.77 (1H, d, J=5.2 Hz), 7.54 (1H, s), 7.68 (1H, dd, J=2.8, 8.8 Hz), 7.90 (1H, d, J=8.8 Hz), 8.13 (1H, d, J=2.8 Hz), 8.35 (1H, d, J=4.4 Hz), 8.53 (1H, s), 8.72 (1H, d, J=5.2 Hz).

Production Example 538-4

N6-Methyl-4-(3-amino-4-chlorophenoxy)-7-methoxy-6-quinolinecarboxamide

The title compound (614 mg, 1.72 mmol, 71.7%) was obtained as light gray crystals from N6-methyl-4-(4-chloro-3-nitrophenoxy)-7-methoxy-6-quinolinecarboxamide (928 mg, 2.39 mmol), by the same procedure as in Production Example 6.

$^1$H-NMR Spectrum (CDCl$_3$) δ (ppm): 3.08 (3H, d, J=5.2 Hz), 4.12 (3H, s), 4.17-4.21 (2H, m), 6.49-6.54 (2H, m), 6.59 (1H, d, J=2.8 Hz), 7.30 (1H, d, J=8.8 Hz), 7.51 (1H, s), 7.86 (1H, br), 8.64 (1H, d, J=5.2 Hz), 9.23 (1H, s).

Example 539

N6-Methyl-4-(4-chloro-3-(((1,3-thiazol-2-ylamino)carbonyl)amino)phenoxy)-7-methoxy-6-quinolinecarboxamide The title compound (170.4 mg, 0.352 mmol, 88.0%) was obtained as white crystals from N6-methyl-4-(3-amino-4-chlorophenoxy)-7-methoxy-6-quinolinecarboxamide (143 mg, 0.4 mmol) and phenyl N-(1,3-thiazol-2-yl)carbamate, by the same procedure as in Example 131.

$^1$H-NMR Spectrum (DMSO-d$_6$) δ (ppm): 2.82 (3H, d, J=4.8 Hz), 4.01 (3H, s), 6.62 (1H, d, J=5.2 Hz), 7.03 (1H, dd, J=2.8, 8.8 Hz), 7.13 (1H, d, J=3.6 Hz), 7.39 (1H, d, J=3.6 Hz), 7.52 (1H, s), 7.64 (1H, d, J=8.8 Hz), 8.16 (1H, d, J=2.8 Hz), 8.35 (1H, d, J=4.8 Hz), 8.55 (1H, s), 8.68 (1H, d, J=5.2 Hz), 11.30 (1H, br).

Example 540

N6-Methyl-4-(4-chloro-3-(((cyclopropylamino)carbonyl)amino)phenoxy)-7-methoxy-6-quinolinecarboxamide After dissolving N6-methyl-4-(3-amino-4-chlorophenoxy)-7-methoxy-6-quinolinecarboxamide (179 mg, 0.50 mmol) in dimethylformamide (2 ml) under a nitrogen atmosphere, pyridine (0.061 ml, 0.75 mmol) and phenyl chloroformate (0.094 ml, 0.75 mmol) were added dropwise at room temperature and the mixture was stirred for 1 hour. Cyclopropylamine (0.2 ml) was added dropwise and the mixture was further stirred overnight. The reaction solution was distributed between ethyl acetate and water, washed with saturated brine and dried over anhydrous sodium sulfate. After distilling off the solvent, the crystals precipitated from ethyl acetate were filtered out and blow-dried to obtain the title compound (163.9 mg, 0.372 mmol, 74.3%) as white crystals.

$^1$H-NMR Spectrum (DMSO-d$_6$) δ (ppm): 0.39 (2H, m), 0.62 (2H, m), 2.49-2.53 (1H, m), 2.83 (3H, d, J=4.8 Hz), 4.02 (3H, s), 6.60 (1H, d, J=5.2 Hz), 6.90 (1H, dd, J=3.2, 8.8 Hz), 7.32 (1H, d, J=2.8 Hz), 7.52-7.56 (2H, m), 8.07 (1H, s), 8.16 (1H, d, J=3.2 Hz), 8.37 (1H, d, J=4.8 Hz), 8.54 (1H, s), 8.67 (1H, d, J=5.2 Hz).

Example 541

N6-Methyl-4-(4-chloro-3-(((methylamino)carbonyl)amino)phenoxy)-7-methoxy-6-quinolinecarboxamide The title compound (71.9 mg, 0.173 mmol, 57.4%) was obtained as white crystals from N6-methyl-4-(3-amino-4- chlorophenoxy)-7-methoxy-6-quinolinecarboxamide (108 mg, 0.30 mmol), by the same procedure as in Example 540.
¹H-NMR Spectrum (DMSO-d₆) δ (ppm): 2.60 (3H, d, J=4.4 Hz), 2.81 (3H, d, J=4.8 Hz), 4.00 (3H, s), 6.59 (1H, d, J=5.2 Hz), 6.87 (1H, dd, J=2.8, 8.4 Hz), 7.14 (1H, t, J=7.6 Hz), 7.50-7.54 (2H, m), 8.13 (1H, d, J=2.8 Hz), 8.19 (1H, s), 8.35 (1H, d, J=4.4 Hz), 8.53 (1H, s), 8.67 (1H, d, J=5.2 Hz).

Example 542

N6-Methyl-4-(4-chloro-3-(((ethylamino)carbonyl)amino)phenoxy)-7-methoxy-6-quinolinecarboxamide The title compound (90.6 mg, 0.211 mmol, 70.6%) was obtained as white crystals from N6-methyl-4-(3-amino-4-chlorophenoxy)-7-methoxy-6-quinolinecarboxamide (107 mg, 0.30 mmol), by the same procedure as in Example 540.
¹H-NMR Spectrum (DMSO-d₆) δ (ppm): 1.02 (3H, t, J=7.2 Hz), 2.81 (3H, t, J=4.4 Hz), 3.06 (2H, m), 4.00 (3H, s), 6.58 (1H, d, J=5.2 Hz), 6.87 (1H, dd, J=3.2, 8.8 Hz), 7.13 (1H, m), 7.50-7.54 (2H, m), 8.14-8.15 (2H, m), 8.35 (1H, d, J=4.4 Hz), 8.53 (1H, s), 8.67 (1H, d, J=5.2 Hz).

Example 543

N-(2-Chloro-4-(6-cyano-7-(((2R)oxiran-2-ylmethoxy)-4-quinolyl)oxy)phenyl)-N'-cyclopropylurea The title compound (663 mg, 1.47 mmol, 66.5%) was obtained as light yellow crystals from N-(4-(6-cyano-7-hydroxy-4-quinolyl)oxy-2-chlorophenyl)-N'-cyclopropylurea (873 mg, 2.21 mmol) and (2R)oxiran-2-ylmethyl 4-methyl-1-benzenesulfonate, by the same procedure as in Example 7.
¹H-NMR Spectrum (DMSO-d₆) δ (ppm): 0.42 (2H, m), 0.65 (2H, m), 2.56 (1H, m), 2.83 (1H, m), 2.93 (1H, m), 3.48 (1H, m), 4.18 (1H, dd, J=6.4, 12.0 Hz), 4.72 (1H, m), 6.61 (1H, d, J=5.2 Hz), 7.20 (1H, d, J=2.8 Hz), 7.27 (1H, dd, J=2.4, 9.2 Hz), 7.51 (1H, d, J=2.8 Hz), 7.65 (1H, s), 8.00 (1H, s), 8.29 (1H, dd, J=4.0, 9.2 Hz), 8.75 (1H, d, J=5.2 Hz), 8.78 (1H, s).

Example 544

N-(2-Chloro-4-((6-cyano-7-(((2R)-2-hydroxy-3-(1-piperidino)propyl)oxy)-4-quinolyl)oxy)phenyl)-N'-cyclopropylurea After adding tetrahydrofuran (2.5 ml) and piperidine (0.25 ml) to N-(2-chloro-4-(6-cyano-7-(((2R)oxiran-2-ylmethoxy)-4-quinolyl)oxy)phenyl-N'-cyclopropylurea (113 mg, 0.25 mmol), the mixture was stirred overnight at room temperature. The reaction solution was concentrated under reduced pressure, the residue was subjected to silica gel column chromatography (eluent—ethyl acetate), the fraction containing the target substance was concentrated, suspended in ethyl acetate and diluted with hexane, and the crystals were filtered out and blow-dried to obtain the title compound (57.7 mg, 0.108 mmol, 43.1%) as white crystals.
¹H-NMR Spectrum (DMSO-d₆) δ (ppm): 0.42 (2H, m), 0.65 (2H, m), 1.35 (2H, m), 1.48 (4H, m), 2.34-2.51 (6H, m), 2.56 (1H, m), 4.02 (1H, m), 4.19 (1H, dd, J=6.0, 10.4 Hz), 4.29 (1H, dd, J=3.6, 10.4 Hz), 4.93 (1H, d, J=4.0 Hz), 6.57 (1H, d, J=5.2 Hz), 7.19 (1H, d, J=2.8 Hz), 7.25 (1H, dd, J=2.8, 8.8 Hz), 7.50 (1H, d, J=2.8 Hz), 7.62 (1H, s), 7.98 (1H, s), 8.27 (1H, d, J=8.8 Hz), 8.71-8.73 (2H, m).

Example 545

N6-Methyl-4-(4-(((4-fluoroanilino)carbonyl)(methyl)amino)phenoxy)-7-methoxy-6-quinolinecarboxamide The title compound (89.4 mg, 0.188 mmol, 75.6%) was obtained as white crystals from 4-(4-(((4-fluoroanilino)carbonyl)(methyl)amino)phenoxy)-7-methoxy-6-quinolinecarboxylic acid (115 mg, 0.25 mmol) and a 40% methylamine-methanol solution, by the same procedure as in Example 435.
¹H-NMR Spectrum (DMSO-d₆) δ (ppm): 2.83 (3H, d, J=4.8 Hz), 3.28 (3H, s), 4.01 (3H, s), 6.65 (1H, d, J=5.2 Hz), 7.08 (2H, m), 7.32 (2H, m), 7.42-7.48 (4H, m), 7.51 (1H, s), 8.23 (1H, s), 8.35 (1H, d, J=4.8 Hz), 8.60 (1H, s), 8.69 (1H, d, J=5.2 Hz).

Example 546

N6-Ethyl-4-(4-(((4-fluoroanilino)carbonyl)(methyl)amino)phenoxy)-7-methoxy-6-quinolinecarboxamide The title compound (87.0 mg, 0.178 mmol, 71.5%) was obtained as white crystals from 4-(4-(((4-fluoroanilino)carbonyl)(methyl)amino)phenoxy)-7-methoxy-6-quinolinecarboxylic acid (115 mg, 0.25 mmol) and a 2.0 M ethylamine-tetrahydrofuran solution, by the same procedure as in Example 435.
¹H-NMR Spectrum (DMSO-d₆) δ (ppm): 1.13 (3H, t, J=7.2 Hz), 3.28 (3H, s), 3.28-3.36 (2H, m), 4.01 (3H, s), 6.64 (1H, d, J=5.2 Hz), 7.06 (2H, m), 7.31 (2H, m), 7.42-7.48 (4H, m), 7.51 (1H, s), 8.23 (1H, s), 8.39 (1H, t, J=5.2 Hz), 8.55 (1H, s), 8.68 (1H, d, J=5.2 Hz).

Example 547

N6-(2-(1-Pyrrolidino)ethyl)-4-(3-chloro-4-(((cyclopropylamino)carbonyl)amino)phenoxy)-7-methoxy-6-quinolinecarboxamide The title compound (42.9 mg, 0.082 mmol, 81.9%) was obtained as white crystals from 4-(3-chloro-4-(((cyclopropylamino)carbonyl)amino)phenoxy)-7-methoxy-6-quinolinecarboxylic acid (43 mg, 0.10 mmol) and 1-(2-aminoethyl)pyrrolidine, by the same procedure as in Example 438.
¹H-NMR Spectrum (DMSO-d₆) δ (ppm): 0.41 (2H, m), 0.65 (2H, m), 1.70 (4H, m), 2.48-2.61 (7H, m), 3.43 (2H, m), 4.01 (3H, s), 6.52 (1H, d, J=5.2 Hz), 7.18 (1H, s), 7.22 (1H, dd, J=2.4, 8.8 Hz), 7.47 (1H, d, J=2.4 Hz), 7.51 (1H, s), 7.97 (1H, s), 8.26 (1H, d, J=8.8 Hz), 8.50 (1H, m), 8.64 (1H, s), 8.65 (1H, d, J=5.2 Hz).

Example 548

N6-(2-(1-Piperidino)ethyl)-4-(3-chloro-4-(((cyclopropylamino)carbonyl)amino)phenoxy)-7-methoxy-6-quinolinecarboxamide The title compound (44.6 mg, 0.083 mmol, 82.9%) was obtained as white crystals from 4-(3-chloro-4-(((cyclopropylamino)carbonyl)amino)phenoxy)-7-methoxy-6-quinolinecarboxylic acid (43 mg, 0.10 mmol) and 1-(2-aminoethyl)piperidine, by the same procedure as in Example 438.

¹H-NMR Spectrum (DMSO-d₆) δ (ppm): 0.41 (2H, m), 0.65 (2H, m), 1.39 (2H, m), 1.51 (4H, m), 2.39 (4H, m), 2.43-2.49 (2H, m), 2.56 (1H, m), 3.39 (2H, m), 4.05 (3H, s), 6.52 (1H, d, J=5.2 Hz), 7.18 (1H, s), 7.23 (1H, dd, J=2.8, 8.8 Hz), 7.48 (1H, d, J=2.8 Hz), 7.53 (1H, s), 7.96 (1H, s), 8.26 (1H, d, J=8.8 Hz), 8.48 (1H, m), 8.66 (1H, d, J=5.2 Hz), 8.70 (1H, s).

Example 549

N6-(2-Propyl)-4-(3-chloro-4-(((cyclopropylamino)carbonyl)amino)phenoxy)-7-methoxy-6-quinolinecarboxamide The title compound (15.2 mg, 0.032 mmol, 32.4%) was obtained as white crystals from 4-(3-chloro-4-(((cyclopropylamino)carbonyl)amino)phenoxy)-7-methoxy-6-quinolinecarboxylic acid (43 mg, 0.10 mmol) and 2-propylamine, by the same procedure as in Example 438.

¹H-NMR Spectrum (DMSO-d₆) δ (ppm): 0.41 (2H, m), 0.65 (2H, m), 1.17 (6H, d, J=6.8 Hz), 2.56 (1H, m), 3.99 (3H, s), 4.08 (1H, m), 6.51 (1H, d, J=5.2 Hz), 7.19 (1H, s), 7.22 (1H, dd, J=2.8, 8.8 Hz), 7.46 (1H, d, J=2.8 Hz), 7.49 (1H, s), 7.97 (1H, s), 8.15 (1H, d, J=8.0 Hz), 8.26 (1H, d, J=8.8 Hz), 8.43 (1H, s), 8.64 (1H, d, J=5.2 Hz).

Example 550

N6-Cyclopentyl-4-(3-chloro-4-(((cyclopropylamino)carbonyl)amino)phenoxy)-7-methoxy-6-quinolinecarboxamide The title compound (34.3 mg, 0.069 mmol, 69.3%) was obtained as white crystals from 4-(3-chloro-4-(((cyclopropylamino)carbonyl)amino)phenoxy)-7-methoxy-6-quinolinecarboxylic acid (43 mg, 0.10 mmol) and cyclopentylamine, by the same procedure as in Example 438.

¹H-NMR Spectrum (DMSO-d₆) δ (ppm): 0.41 (2H, m), 0.65 (2H, m), 1.53 (4H, m), 1.67 (2H, m), 1.89 (2H, m), 2.56 (1H, m), 4.00 (3H, s), 4.23 (1H, m), 6.51 (1H, d, J=5.2 Hz), 7.18 (1H, s), 7.22 (1H, dd, J=2.8, 8.8 Hz), 7.46 (1H, d, J=2.8 Hz), 7.48 (1H, s), 7.97 (1H, s), 8.23-8.27 (2H, m), 8.41 (1H, s), 8.64 (1H, d, J=5.2 Hz).

Example 551

N-(4-(6-Aminopyrimidin-4-yloxy)phenyl)-N'-phenylurea 6-(4-Aminophenoxy)pyrimidin-4-ylamine (88.9 mg, 0.440 mmol) and phenyl isocyanate (52.4 mg, 0.440 mmol) were stirred together for 3 hours in dimethylformamide (2 ml) at room temperature. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was suspended in ethyl acetate, the suspension was diluted with hexane, and the crystals were filtered out, washed with hexane and then blow-dried to obtain the title compound (98.0 mg, 0.305 mmol, 69%) as colorless crystals.

¹H-NMR Spectrum (DMSO-d₆) δ (ppm): 5.66 (1H, s), 6.81 (2H, brs), 6.94-6.99 (1H, m), 7.03-7.08 (2H, m), 7.25-7.32 (2H, m), 7.43-7.52 (4H, m), 8.07 (1H, s), 8.74 (1H, s), 8.80 (1H, s).

The intermediates were synthesized in the following manner.

Production Example 551-1

4-Chloro-6-(4-nitrophenoxy)pyrimidine 2,4-Dichloropyrimidine (2.98 g, 20.0 mmol), 4-nitrophenol (2.78 g, 20.0 mmol) and potassium carbonate (4.15 g, 30.0 mmol) were stirred together in dimethylformamide (20 ml) at room temperature for 15 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=1:4), and the fraction containing the target substance was concentrated to obtain the title compound (3.89 g, 15.5 mmol, 77%) as colorless crystals.

¹H-NMR Spectrum (CDCl₃) δ (ppm): 7.08 (1H, d, J=0.6 Hz), 7.32-7.37 (2H, m), 8.32-8.37 (2H, m), 8.60 (1H, d, J=0.6 Hz).

Production Example 551-2

6-(4-Nitrophenoxy)pyrimidin-4-ylamine

4-Chloro-6-(4-nitrophenoxy)pyrimidine (1.04 g, 4.00 mmol) was heated and stirred in an ammonia-ethanol solution (14%, 10 ml) at 110° C. for 15 minutes using an autoclave. The reaction solution was distributed between ethyl acetate and water, the organic layer was washed with 1N aqueous sodium hydroxide, water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=1:1), and the fraction containing the target substance was concentrated to obtain the title compound (306 mg, 1.32 mmol, 33%) as colorless crystals.

¹H-NMR Spectrum (CDCl₃) δ (ppm): 5.00 (2H, br s), 6.03 (1H, s), 7.25-7.32 (2H, m), 8.26-8.33 (3H, m).

Production Example 551-3

6-(4-Aminophenoxy)pyrimidin-4-ylamine

After suspending 6-(4-nitrophenoxy)pyrimidin-4-ylamine (306 mg, 1.32 mmol), iron powder (369 mg, 6.60 mmol) and ammonium chloride (706 mg, 13.2 mmol) in an ethanol (20 ml)—water (5 ml) mixed solvent, the suspension was heated and stirred at 80° C. for 20 minutes. After completion of the reaction, the reaction mixture was filtered with celite and washed in ethyl acetate. The organic layer was washed with saturated brine and dried over anhydrous magnesium sulfate, the drying agent was filtered off and the filtrate was concentrated to obtain the title compound (266 mg, 1.32 mmol, 100%) as light yellow crystals.

¹H-NMR Spectrum (DMSO-d₆) δ (ppm): 5.05 (2H, br s), 5.55 (1H, s), 6.57-6.62 (2H, m), 6.73 (2H, br s), 6.77-6.82 (2H, m), 8.04 (1H, s).

Example 552

N-(6-(4-(3-Phenylureido)phenoxy)pyrimidin-4-yl)acetamide

N-(4-(6-Aminopyrimidin-4-yloxy)phenyl)-N'-phenylurea (60.0 mg, 0.187 mmol) was heated and stirred in an acetic anhydride (1 ml)—pyridine (1 ml) mixed solvent at 60° C. for 18 hours. After returning the reaction solution to room temperature, it was poured into water and the precipitated crystals were filtered out, washed with water and methanol and blow-dried to obtain the title compound (35.0 mg, 0.096 mmol, 52%) as colorless crystals.

$^1$H-NMR Spectrum (DMSO-$d_6$) δ (ppm): 2.11 (3H, s), 6.94-7.00 (1H, m), 7.10-7.15 (2H, m), 7.25-7.31 (2H, m), 7.44-7.54 (5H, m), 8.49 (1H, d, J=0.4 Hz), 8.72 (1H, s), 8.80 (1H, s), 10.94 (1H, s).

Example 553

N-(4-(6-Aminopyrimidin-4-yloxy)phenyl)-N'-(4-fluorophenyl)urea

The title compound (100 mg, 0.295 mmol, 65%) was obtained as colorless crystals from 6-(4-aminophenoxy)pyrimidin-4-ylamine (88.9 mg, 0.440 mmol) and 4-fluorophenyl isocyanate (60.3 mg, 0.440 mmol), by the same procedure as in Example 551.

$^1$H-NMR Spectrum (DMSO-$d_6$) δ (ppm): 5.66 (1H, d, J=0.6 Hz), 6.81 (2H, br s), 7.04-7.15 (4H, m), 7.44-7.52 (4H, m), 8.07 (1H, d, J=0.6 Hz), 8.84 (1H, s), 8.85 (1H, s).

Example 554

N-(6-(4-(3-(4-Fluorophenyl)ureido)phenoxy)pyrimidin-4-yl)acetamide

The title compound (56 mg, 0.147 mmol, 79%) was obtained as colorless crystals from N-(4-(6-aminopyrimidin-4-yloxy)phenyl)-N'-(4-fluorophenyl)urea (60.0 mg, 0.176 mmol), by the same procedure as in Example 552.

$^1$H-NMR Spectrum (DMSO-$d_6$) δ (ppm): 2.11 (3H, s), 7.09-7.16 (4H, m), 7.44-7.54 (5H, m), 8.49 (1H, s), 8.80 (1H, s), 8.83 (1H, s), 10.94 (1H, s).

Example 555

N-(4-(6-Aminopyrimidin-4-yloxy)phenyl)-N'-(3-methanesulfonylphenyl)urea 6-(4-Aminophenoxy)pyrimidin-4-ylamine (88.9 mg, 0.440 mmol) and (3-methylsulfonylphenyl)carbamic acid phenyl ester (128 mg, 0.440 mmol) were stirred in dimethylsulfoxide (2 ml) at 85° C. for 18 hours. The reaction solution was distributed between ethyl acetate and water, the organic layer was washed with 1N aqueous sodium hydroxide, water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=30:1), the fraction containing the target substance was concentrated and suspended in ethyl acetate, the suspension was diluted with hexane and the crystals were filtered out, washed with hexane and blow-dried to obtain the title compound (75.0 mg, 0.188 mmol, 43%) as colorless crystals.

$^1$H-NMR Spectrum (DMSO-$d_6$) δ (ppm): 3.20 (3H, s), 5.67 (1H, s), 6.82 (2H, br s), 7.04-7.12 (2H, m), 7.44-7.59 (4H, m), 7.65-7.70 (1H, m), 8.07 (1H, s), 8.16-8.19 (1H, m), 8.92 (1H, br s), 9.19 (1H, br s).

Example 556

N-(6-(4-(3-(3-Methylsulfonylphenyl)ureido)phenoxy)pyrimidin-4-yl)acetamide

The title compound (13 mg, 0.029 mmol, 24%) was obtained as colorless crystals from N-(4-(6-aminopyrimidin-4-yloxy)phenyl)-N'-(3-methylsulfonylphenyl)urea (50.0 mg, 0.125 mmol), by the same procedure as in Example 552.

$^1$H-NMR Spectrum (DMSO-$d_6$) δ (ppm): 2.11 (3H, s), 3.20 (3H, s), 7.11-7.17 (2H, m), 7.50-7.59 (5H, m), 7.66-7.70 (1H, m), 8.16-8.19 (1H, m), 8.50 (1H, s), 9.01 (1H, br s), 9.28 (1H, br s), 10.95 (1H, s).

Example 557

N-(4-(2-Aminopyrimidin-4-yloxy)phenyl)-N'-phenylurea

The title compound (105 mg, 0.327 mmol, 65%) was obtained as colorless crystals from 4-(4-aminophenoxy)pyrimidin-2-ylamine (101 mg, 0.500 mmol) and phenyl isocyanate (59.6 mg, 0.500 mmol), by the same procedure as in Example 551.

$^1$H-NMR Spectrum (DMSO-$d_6$) δ (ppm): 6.07 (1H, d, J=5.8 Hz), 6.61 (2H, br s), 6.94-6.99 (1H, m), 7.05-7.10 (2H, m), 7.25-7.31 (2H, m), 7.43-7.51 (4H, m), 8.08 (1H, d, J=5.8 Hz), 8.74 (1H, br s), 8.79 (1H, br s).

The intermediates were synthesized in the following manner.

Production Example 557-1

4-Chloro-6-(4-nitrophenoxy)pyrimidin-2-ylamine

2-Amino-4,6-dichloropyrimidine (3.28 g, 20.0 mmol), 4-nitrophenol (2.78 g, 20.0 mmol), and potassium carbonate (4.15 g, 30.0 mmol) were heated and stirred in dimethylformamide (20 ml) at 100° C. for 3 hours. After returning the reaction solution to room temperature, it was poured into ice water (100 ml) and the precipitated crystals were filtered out, washed with water and blow-dried to obtain the title compound (4.93 g, 18.5 mmol, 92%) as colorless crystals.

$^1$H-NMR Spectrum (DMSO-$d_6$) δ (ppm): 6.43 (1H, s), 7.25 (2H, br s), 7.46-7.52 (2H, m), 8.28-8.34 (2H, m).

Production Example 557-2

4-(4-Aminophenoxy)pyrimidin-2-ylamine

After suspending 4-chloro-6-(4-nitrophenoxy)pyrimidin-2-ylamine (1.60 g, 1.32 mmol) in a methanol (30 ml)—tetrahydrofuran (30 ml) mixed solvent, palladium hydroxide-carbon (300 mg) was added and the mixture was stirred at room temperature for 18 hours under a hydrogen atmosphere. The catalyst was filtered off by celite filtration, and after washing with ethanol, the filtrate was distilled off under reduced pressure. The obtained crude product was subjected to silica gel column chromatography (eluent—ethyl acetate:hexane=3:1), and the fraction containing the target substance was concentrated to obtain the title compound (910 mg, 4.50 mmol, 75%) as colorless crystals.

$^1$H-NMR Spectrum (DMSO-$d_6$) δ (ppm): 5.01 (2H, br s), 5.93 (1H, d, J=5.4 Hz), 6.50-6.60 (4H, m), 6.76-6.82 (2H, m), 8.03 (1H, d, J=5.4 Hz).

Example 558

N-(4-(2-Aminopyrimidin-4-yloxy)phenyl)-N'-(4-fluorophenyl)urea

The title compound (105 mg, 0.309 mmol, 62%) was obtained as colorless crystals from 4-(4-aminophenoxy)pyrimidin-2-ylamine (101 mg, 0.500 mmol) and 4-fluorophenyl isocyanate (68.6 mg, 0.500 mmol), by the same procedure as in Example 551.

$^1$H-NMR Spectrum (DMSO-d$_6$) δ (ppm): 6.06 (1H, d, J=5.6 Hz), 6.61 (2H, br s), 7.05-7.15 (4H, m), 7.44-7.52 (4H, m), 8.08 (1H, d, J=5.6 Hz), 8.75-8.79 (2H, m).

Example 559

N-(4-(2-Aminopyrimidin-4-yloxy)phenyl)-N'-(3-methylsulfonylphenyl)urea

The title compound (96 mg, 0.240 mmol, 48%) was obtained as colorless crystals from 4-(4-aminophenoxy)pyrimidin-2-ylamine (101 mg, 0.500 mmol) and (3-methylsulfonylphenyl)carbamic acid phenyl ester (146 mg, 0.500 mmol), by the same procedure as in Example 555.

$^1$H-NMR Spectrum (DMSO-d$_6$) δ (ppm): 3.20 (3H, s), 6.07 (1H, d, J=5.8 Hz), 6.61 (2H, br s), 7.06-7.12 (2H, m), 7.46-7.59 (4H, m), 7.65-7.70 (1H, m), 8.09 (1H, d, J=5.8 Hz), 8.16-8.19 (1H, m), 8.89 (1H, br s), 9.18 (1H, br s).

Example 560

4-(3-Fluoro-4-(cyclopropylaminocarbonyl)aminophenoxy)-7-(2-methoxyethoxy)-6-quinolinecarboxamide The title compound (22 mg) was obtained as light yellow crystals from phenyl N-(4-(6-carbamoyl-7-(2-methoxyethoxy)-4-quinolyl)oxy-2-fluorophenyl)carbamate, which was obtained from 4-(4-amino-3-fluorophenoxy)-7-(2-methoxyethoxy)-6-quinolinecarboxamide (100 mg) by the same procedure as in Example 11, and cyclopropylamine.

$^1$H-NMR Spectrum (DMSO-d$_6$) δ (ppm): 0.39 (2H, m), 0.63 (2H, m), 2.49 (1H, m), 3.30 (3H, s), 3.79 (2H, m), 4.39 (2H, m), 6.51 (1H, d, J=5.2 Hz), 6.79 (1H, s), 7.06 (1H, m), 7.31 (1H, m), 7.54 (1H, s), 7.79 (1H, s), 7.83 (1H, s), 8.18-8.22 (2H, m), 8.65 (1H, d, J=5.2 Hz), 8.74 (1H, s).

Example 561

1-[4-(7-Benzyloxy-6-cyanoquinolin-4-yloxy)-2-methylphenyl]-3-cyclopropylurea A carbamate (1.73 g) was obtained as a solid from 4-(4-amino-2-methylphenoxy)-7-benzyloxyquinoline-6-carbonitrile (2 g) and phenyl chlorocarbonate, in the same manner as Production Example 17. The carbamate (1.7 g) was then treated with cyclopropylamine in dimethylsulfoxide at room temperature in the same manner as Example 11, to obtain the title compound (1.4 g) as a solid.

$^1$H-NMR Spectrum (DMSO-d$_6$) δ (ppm): 0.37-0.41 (2H, m), 0.59-0.64 (2H, m), 2.23 (3H. s), 2.50-2.56 (1H, m), 5.42 (2H, s), 6.49 (1H, d, J=5.2 Hz), 6.73-6.75 (1H, m), 7.02 (1H, dd, J=2.8 Hz, J=8.8 Hz), 7.08 (1H, d, J=2.8 Hz), 7.32-7.53 (5H, m), 7.60 (1H, s), 7.66 (1H, s), 7.89 (1H, d, J=8.8 Hz), 8.68 (1H, d, J=5.2 Hz), 8.73 (1H, s).

The intermediate was synthesized in the following manner.

Production Example 561-1

4-(4-Amino-3-methylphenoxy)-7-benzyloxyquinoline-6-carbonitrile

The title compound (3.6 g) was obtained as a solid from 7-benzyloxy-4-chloroquinoline-6-carbonitrile (5 g) and 4-amino-3-methylphenol, in the same manner as Production Example 395-1.

$^1$H-NMR Spectrum (DMSO-d$_6$) δ (ppm): 2.07 (3H, s), 4.94 (2H, s), 5.43 (2H, s), 6.46 (1H, d, J=5, 2 Hz), 6.69 (1H, d, J=8.8 Hz), 6.82 (1H, dd, J=2.8 Hz, J=8.8 Hz), 6.87 (1H, d, J=2.8 Hz), 7.36 (1H, t, J=7.2 Hz), 7.44 (2H, t, J=7.2 Hz), 7.53 (2H, d, J=7.2 Hz), 7.66 (1H, s), 8.67 (1H, d, J=5.2 Hz), 8.73 (1H, s).

Example 562

1-[4-(6-Cyano-7-hydroxyquinolin-4-yloxy)-2-methylphenyl]-3-cyclopropylurea

In the same manner as Production Example 301-2, 1-[4-(7-benzyloxy-6-cyano-quinolin-4-yloxy)-2-methyl-phenyl]-3-cyclopropyl-urea (0.8 g) was debenzylated in tetrahydrofuran using palladium-carbon, to obtain the title compound (0.5 g) as a solid.

$^1$H-NMR Spectrum (DMSO-d$_6$) δ (ppm): 0.36-0.41 (2H, m), 0.59-0.65 (2H, m), 2.17 (3H, s), 2.49-2.56 (1H, m), 6.32 (1H, d, J=5.2 Hz), 6.74 (1H, d, J=2.8 Hz), 7.01 (1H, dd, J=2.4 Hz, J=8.8 Hz), 7.07 (1H, d, J=2.4 Hz), 7.30 (1H, s), 7.59 (1H, s), 7.90 (1H, d, J=8.8 Hz), 8.56 (1H, d, J=5.2 Hz), 8.57 (1H, s).

Example 563

1-[4-(6-Cyano-(2R)-7-oxiranylmethoxyquinolin-4-yloxy)-2-methylphenyl]-3-cyclopropylurea The title compound (312 mg) was obtained as a solid from 1-[4-(6-cyano-7-hydroxyquinolin-4-yloxy)-2-methylphenyl]-3-cyclopropylurea (500 mg), in the same manner as Production Example 284-1.

$^1$H-NMR Spectrum (DMSO-d$_6$) δ (ppm): 0.37-0.42 (2H, m), 0.59-0.65 (2H, m), 2.18 (3H, s), 2.49-2.56 (1H, m), 2.78-2.81 (1H, m), 2.89 (1H, t, J=4.8 Hz), 3.42-3.47 (1H, m), 4.14 (1H, dd, J=6.4 Hz, J=11.6 Hz), 4.68 (1H, dd, J=2.4 Hz, J=11.6 Hz), 6.49 (1H, d, J=5.2 Hz), 6.74 (1H, d, J=2.4 Hz), 7.03 (1H, dd, J=2.4 Hz, J=8.4 Hz), 7.09 (1H, d, J=2.4 Hz), 7.59 (1H, s), 7.61 (1H, s), 7.92 (1H, d, J=8.4 Hz), 8.70 (1H, d, J=5.2 Hz), 8.74 (1H, s).

Example 564

1-{4-[6-Cyano-7-((2R)-2-hydroxy-3-pyrrolidin-1-yl-propoxy)quinolin-4-yloxy]-2-methyl-phenyl}-3-cyclopropyl-urea The title compound (11 mg) was obtained as a solid from 1-[4-(6-cyano-7-(2R)-oxiranylmethoxyquinolin-4-yloxy)-2-methylphenyl]-3-cyclopropyl-urea (55 mg) and pyrrolidine, in the same manner as Example 284.

$^1$H-NMR Spectrum (DMSO-d$_6$) δ (ppm): 0.37-0.41 (2H, m), 0.58-0.65 (2H, m), 2.26 (3H, s), 1.62-1.69 (4H, m), 2.44-2.56 (6H, m), 2.68 (1H, dd, J=6.4 Hz, J=12 Hz), 3.96-4.03 (1H, m), 4.18 (1H, dd, J=5.6 Hz, J=10.4 Hz), 4.28 (1H, dd, J=3.6 Hz, J=10.4 Hz), 5.00 (1H, d, J=5.2 Hz), 6.48 (1H, d, J=5.2 Hz), 6.75 (1H, d, J=2.4 Hz), 7.03 (1H, dd, J=2.4 Hz, J=8.8 Hz), 7.09 (1H, d, J=2.4 Hz), 7.58 (1H, s), 7.60 (1H, s), 7.91 (1H, d, J=8.8 Hz), 8.68 (1H, d, J=5.2 Hz), 8.71 (1H, s).

Example 565

1-{4-[6-Cyano-7-((2R)-2-hydroxy-3-piperidin-1-ylpropoxy)quinolin-4-yloxy]-2-methylphenyl}-3-cyclopropyl-urea The title compound (8 mg) was obtained as a solid from [1-[4-(6-cyano-(2R)-7-oxiranylmethoxyquinolin-4-yloxy)-2-methylphenyl]-3-cyclopropylurea (100 mg) and piperidine, in the same manner as Example 284.
$^1$H-NMR Spectrum (DMSO-d$_6$) δ (ppm): 0.37-0.41 (2H, m), 0.59-0.66 (2H, m), 1.31-1.38 (2H, m), 1.43-1.53 (4H, m), 2.20 (3H, s), 2.33-2.58 (7H, m), 3.99-4.06 (1H, m), 4.19 (1H, dd, J=5.6 Hz, J=10.4 Hz), 4.29 (1H, dd, J=3.2 Hz, J=10.4 Hz), 4.94 (1H, br), 6.49 (1H, d, J=5.2 Hz), 6.75-6.79 (1H, m), 7.02-7.08 (1H, m), 7.09-7.13 (1H, m), 7.60 (1H, s), 7.62 (1H, s), 7.93 (1H, d, J=9.2 Hz), 8.70 (1H, d, J=5.2 Hz), 8.71 (1H, s).

Example 566

1-{4-[6-Cyano-7-(3-diethylamino-(2R)-2-hydroxypropoxy)quinolin-4-yloxy]-2-methyl-phenyl}-3-cyclopropyl-urea The title compound (21 mg) was obtained as a solid from [1-[4-(6-cyano-(2R)-7-oxiranylmethoxyquinolin-4-yloxy)-2-methylphenyl]-3-cyclopropylurea (55 mg) and diethylamine, in the same manner as Example 284.
$^1$H-NMR Spectrum (DMSO-d$_6$) δ (ppm): 0.37-0.41 (2H, m), 0.59-0.65 (2H, m), 0.91-1.00 (6H, m), 2.18 (3H, s), 2.43-2.69 (7H, m), 3.91-4.00 (1H, m), 4.17-4.22 (1H, m), 4.26-4.31 (1H, m), 6.48 (1H, d, J=5.2 Hz), 6.76 (1H, d, J=2.8 Hz), 7.03 (1H, dd, J=2.8 Hz, J=8.8 Hz), 7.09 (1H, d, J=2.4 Hz), 7.58 (1H, s), 7.60 (1H, s), 7.91 (1H, d, J=8.8 Hz), 8.68 (1H, d, J=5.2 Hz), 8.71 (1H, s).

Example 567

1-{4-[6-Cyano-7-(3-pyrrolidin-1-ylpropoxy)quinolin-4-yloxy]-2-methylphenyl}-3-cyclopropylurea The title compound (23 mg) was obtained as a solid from 1-[4-(6-cyano-7-hydroxyquinolin-4-yloxy)-2-methylphenyl]-3-cyclopropylurea (60 mg) and 1-(3-chloropropyl)pyrrolidine, in the same manner as Example 7.
$^1$H-NMR Spectrum (DMSO-d$_6$) δ (ppm): 0.37-0.41 (2H, m), 0.59-0.65 (2H, m), 1.62-1.69 (4H, m), 1.93-2.01 (2H, m), 2.18 (3H, s), 2.39-2.45 (4H, m), 2.49-2.55 (1H, m), 2.57 (2H, t, J=7.2 Hz), 4.30 (2H, t, J=6.4 Hz), 6.48 (1H, d, J=5.2 Hz), 6.75 (1H, d, J=2.8 Hz), 7.03 (1H, dd, J=2.8 Hz, J=8.8 Hz), 7.08 (1H, d, J=2.8 Hz), 7.55 (1H, s), 7.60 (1H, s), 7.91 (1H, d, J=8.8 Hz), 8.68 (1H, d, J=5.2 Hz), 8.71 (1H, s).

Example 568

N-Phenyl-N'-(4-(6-phenylaminopyrimidin-4-yloxy)phenyl)urea

N-(6-(4-Aminophenoxy)pyrimidin-4-yl)phenylamine (55.6 mg, 0.200 mmol) and phenyl isocyanate (26.1 mg, 0.220 mmol) were stirred together in dimethylformamide (1 ml) at room temperature for 12 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was suspended in ethyl acetate, the suspension was diluted with hexane, and the crystals were filtered out, washed with hexane and then blow-dried to obtain the title compound (69.0 mg, 0.174 mmol, 87%) as colorless crystals.
$^1$H-NMR Spectrum (DMSO-d$_6$) δ (ppm): 6.06 (1H, d, J=1.6 Hz), 6.95-7.02 (2H, m), 7.11-7.16 (2H, m), 7.25-7.34 (4H, m), 7.44-7.50 (2H, m), 7.50-7.56 (2H, m), 7.58-7.63 (2H, m), 8.35 (1H, d, J=1.6 Hz), 8.71 (1H, s), 8.79 (1H, s), 9.54 (1H, s).
The intermediates were synthesized in the following manner.

Production Example 568-1

N-(6-(4-Nitrophenoxy)pyrimidin-4-yl)phenylamine

4-Chloro-6-(4-nitrophenoxy)pyrimidine (508 mg, 2.00 mmol) and aniline (559 mg, 6.00 mmol) were heated and stirred in 1-methylpyrrolidone (5 ml) at 90° C. for 3 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=1:3), and the fraction containing the target substance was concentrated to obtain the title compound (508 mg, 1.65 mmol, 82%) as colorless crystals.
$^1$H-NMR Spectrum (CDCl$_3$) δ (ppm): 6.34 (1H, s), 7.03 (1H, br s), 7.21-7.35 (5H, m), 7.40-7.46 (2H, m), 8.26-8.32 (2H, m), 8.35 (1H, s).

Production Example 568-2

N-(6-(4-Aminophenoxy)pyrimidin-4-yl)phenylamine

After suspending N-(6-(4-nitrophenoxy)pyrimidin-4-yl)phenylamine (508 mg, 1.65 mmol), iron powder (461 mg, 8.25 mmol) and ammonium chloride (882 mg, 16.5 mmol) in an ethanol (16 ml)—water (4 ml) mixed solvent, the suspension was heated and stirred at 80° C. for 20 minutes. Upon completion of the reaction, the reaction mixture was filtered with celite and washed in ethyl acetate. The organic layer was washed with saturated brine and dried over anhydrous magnesium sulfate, the drying agent was filtered off and the filtrate was distilled off under reduced pressure. The obtained crude product was suspended in ethyl acetate, the suspension was diluted with hexane, and the crystals were filtered out, washed with hexane and then blow-dried to obtain the title compound (387 mg, 1.39 mmol, 84%) as colorless crystals.
$^1$H-NMR Spectrum (CDCl$_3$) δ (ppm): 3.64 (2H, br s), 6.17 (1H, d, J=0.8 Hz), 6.67-6.73 (2H, m), 6.77 (1H, br s), 6.89-6.95 (2H, m), 7.14-7.20 (1H, m), 7.26-7.32 (2H, m), 7.35-7.41 (2H, m), 8.37 (1H, d, J=0.8 Hz).

Example 569

N-(3-Methylsulfonylphenyl)-N'-(4-(6-phenylaminopyrimidin-4-yloxy)phenyl)urea

N-(6-(4-Aminophenoxy)pyrimidin-4-yl)phenylamine (55.6 mg, 0.200 mmol) and (3-methylsulfonylphenyl)carbamic acid phenyl ester (63.8 mg, 0.220 mmol) were heated and stirred in dimethylsulfoxide (1 ml) at 85° C. for 2 hours. The reaction solution was distributed between ethyl acetate and water, the organic layer was washed with 1N aqueous sodium hydroxide, water and saturated brine and dried over anhydrous magnesium sulfate, the drying agent was filtered off and the filtrate was distilled off under reduced pressure. The obtained crude product was suspended in ethyl acetate, the suspension was diluted with hexane, and the crystals were filtered out, washed with hexane and then blow-dried to obtain the title compound (77.0 mg, 0.162 mmol, 81%) as colorless crystals.

$^1$H-NMR Spectrum (DMSO-$d_6$) δ (ppm): 3.20 (3H, s), 6.07 (1H, s), 6.98-7.03 (1H, m), 7.12-7.17 (2H, m), 7.28-7.34 (2H, m), 7.50-7.63 (6H, m), 7.66-7.72 (1H, m), 8.17-8.20 (1H, m), 8.34 (1H, s), 8.93 (1H, br s), 9.19 (1H, br s), 9.54 (1H, s).

Example 570

N-(4-(6-(4-Methylsulfanylphenylamino)pyrimidin-4-yloxy)phenyl)-N'-phenylurea

N-(6-(4-Aminophenoxy)pyrimidin-4-yl)-4-methylsulfanylphenylamine (194 mg, 0.600 mmol) and phenyl isocyanate (78.6 mg, 0.660 mmol) were stirred in dimethylformamide (2 ml) at room temperature for 18 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was suspended in ethyl acetate, the suspension was diluted with hexane, and the crystals were filtered out, washed with hexane and then blow-dried to obtain the title compound (250 mg, 0.564 mmol, 94%) as colorless crystals.

$^1$H-NMR Spectrum (DMSO-$d_6$) δ (ppm): 2.44 (3H, s), 6.03 (1H, d, J=1.6 Hz), 6.95-7.00 (1H, m), 7.10-7.15 (2H, m), 7.22-7.32 (4H, m), 7.44-7.50 (2H, m), 7.50-7.60 (4H, m), 8.34 (1H, d, J=1.6 Hz), 8.73 (1H, br s), 8.81 (1H, br s), 9.56 (1H, s).

The intermediates were synthesized in the following manner.

Production Example 570-1

N-(6-(4-Nitrophenoxy)pyrimidin-4-yl)-4-methylsulfanylphenylamine

4-Chloro-6-(4-nitrophenoxy)pyrimidine (2.33 g, 9.25 mmol), 4-(methylthio)aniline (1.29 g, 9.25 mmol) and diisopropylethylamine (1.79 g, 13.9 mmol) were heated and stirred in 1-methylpyrrolidone (10 ml) at 80° C. for 18 hours. The reaction solution was distributed between ethyl acetate and water, the organic layer was washed with 1N aqueous sodium hydroxide, water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=1:3), the fraction containing the target substance was concentrated and suspended in ethyl acetate, the suspension was diluted with hexane and the crystals were filtered out, washed with hexane and blow-dried to obtain the title compound (620 mg, 1.75 mmol, 19%) as colorless crystals.

$^1$H-NMR Spectrum (CDCl$_3$) δ (ppm): 2.51 (3H, s), 6.28 (1H, d, J=1.0 Hz), 6.99 (1H, br s), 7.23-7.34 (6H, m), 8.26-8.32 (2H, m), 8.34 (1H, d, J=1.0 Hz).

Production Example 570-2

N-(6-(4-Aminophenoxy)pyrimidin-4-yl)-4-methylsulfanylphenylamine

N-(6-(4-Nitrophenoxy)pyrimidin-4-yl)-4-methylsulfanylphenylamine (620 mg, 1.75 mmol), iron powder (489 mg, 8.75 mmol) and ammonium chloride (936 mg, 17.5 mmol) were suspended in an ethanol (16 ml)—water (4 ml) mixed solvent and the suspension was heated and stirred at 80° C. for 1 hour. Upon completion of the reaction, the reaction mixture was filtered with celite and washed in an ethyl acetate-tetrahydrofuran mixed solvent. The organic layer was washed with water and saturated brine and dried over anhydrous magnesium sulfate, the drying agent was filtered off and the filtrate was distilled off under reduced pressure. The obtained crude product was suspended in ethyl acetate, the suspension was diluted with hexane, and the crystals were filtered out, washed with hexane and then blow-dried to obtain the title compound (392 mg, 1.21 mmol, 69%) as colorless crystals.

$^1$H-NMR Spectrum (CDCl$_3$) δ (ppm): 2.49 (3H, s), 3.65 (2H, br s), 6.10 (1H, d, J=1.0 Hz), 6.66-6.72 (2H, m), 6.76 (1H, br s), 6.88-6.94 (2H, m), 7.21-7.30 (4H, m), 8.35 (1H, d, J=1.0 Hz).

Example 571

N-(3-Methylsulfonylphenyl)-N'-(4-(6-(4-methylsulfanylphenylamino)pyrimidin-4-yloxy)phenyl)urea N-(6-(4-Aminophenoxy)pyrimidin-4-yl)-4-methylsulfanylphenylamine (194 mg, 0.600 mmol) and (3-methylsulfonylphenyl)carbamic acid phenyl ester (192 mg, 0.660 mmol) were heated and stirred in dimethylsulfoxide (2 ml) at 85° C. for 18 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate), the fraction containing the target substance was concentrated and suspended in ethyl acetate, the suspension was diluted with hexane and the crystals were filtered out, washed with hexane and blow-dried to obtain the title compound (297 mg, 0.569 mmol, 95%) as colorless crystals.

$^1$H-NMR Spectrum (DMSO-$d_6$) δ (ppm): 2.44 (3H, s), 3.20 (3H, s), 6.04 (1H, d, J=0.8 Hz), 7.12-7.17 (2H, m), 7.22-7.27 (2H, m), 7.50-7.63 (6H, m), 7.67-7.71 (1H, m), 8.17-8.20 (1H, m), 8.34 (1H, d, J=0.8 Hz), 8.92 (1H, s), 9.17 (1H, s), 9.56 (1H, s).

Example 572

N-(4-(6-(4-Methylsulfonylphenylamino)pyrimidin-4-yloxy)phenyl)-N'-phenylurea

N-(4-(6-(4-Methylsulfanylphenylamino)pyrimidin-4-yloxy)phenyl)-N'-phenylurea (180 mg, 0.406 mmol) and 3-chloroperbenzoic acid (200 mg, 0.812 mmol) were stirred in dichloromethane (6 ml) at room temperature for 12 hours. A saturated aqueous sodium thiosulfate solution was added to suspend the reaction, and then the reaction solution was distributed between ethyl acetate and water, the organic layer was washed with 1N aqueous sodium hydroxide, water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=3:1), the fraction containing the target substance was concentrated and suspended in ethyl acetate, the suspension was diluted with hexane and the crystals were filtered out, washed with hexane and blow-dried to obtain the title compound (137 mg, 0.288 mmol, 71%) as colorless crystals.

$^1$H-NMR Spectrum (DMSO-$d_6$) δ (ppm): 3.16 (3H, s), 6.18 (1H, s), 6.97-7.02 (1H, m), 7.13-7.19 (2H, m), 7.27-7.33 (2H, m), 7.46-7.51 (2H, m), 7.53-7.59 (2H, m), 7.81-7.87 (2H, m), 7.89-7.94 (2H, m), 8.47 (1H, s), 8.72 (1H, s), 8.81 (1H, s), 10.06 (1H, s).

Example 573

N-(3-Methylsulfonylphenyl)-N'-(4-(6-(4-methylsulfonylphenylamino)pyrimidin-4-yloxy)phenyl)urea The title compound (157 mg, 0.284 mmol, 64%) was obtained as colorless crystals from N-(3-methylsulfonylphenyl)-N'-(4-(6-(4-methylsulfanylphenylamino)pyrimidin-4-yloxy)phenyl)urea (230 mg, 0.441 mmol), by the same procedure as in Example 572.

$^1$H-NMR Spectrum (DMSO-$d_6$) δ (ppm): 3.16 (3H, s), 3.20 (3H, s), 6.19 (1H, d, J=1.0 Hz), 7.04-7.10 (2H, m), 7.50-7.60 (4H, m), 7.66-7.70 (1H, m), 7.82-7.88 (2H, m), 7.88-7.94 (2H, m), 8.17-8.20 (1H, m), 8.47 (1H, d, J=1.0 Hz), 8.95 (1H, s), 9.19 (1H, s), 10.06 (1H, s).

Example 574

N-(4-(6-(4-Fluorophenylamino)pyrimidin-4-yloxy)phenyl)-N'-phenylurea

N-(4-(6-Chloropyrimidin-4-yloxy)phenyl)-N'-phenylurea (68.0 mg, 0.200 mmol) and 4-fluoroaniline (111 mg, 1.00 mmol) were heated and stirred in 1-methylpyrrolidone (1 ml) at 130° C. for 3 hours. The reaction solution was distributed between ethyl acetate and water, the organic layer was washed with saturated aqueous sodium bicarbonate, water and saturated brine and dried over anhydrous magnesium sulfate, the drying agent was filtered off and the filtrate was distilled off under reduced pressure. The obtained crude product was suspended in ethyl acetate, the suspension was diluted with hexane, and the crystals were filtered out, washed with hexane and then blow-dried to obtain the title compound (33.0 mg, 0.079 mmol, 40%) as colorless crystals.

$^1$H-NMR Spectrum (DMSO-$d_6$) δ (ppm): 6.00 (1H, d, J=0.8 HZ), 6.95-7.00 (1H, m), 7.10-7.19 (4H, m), 7.26-7.32 (2H, m), 7.44-7.50 (2H, m), 7.50-7.56 (2H, m), 7.57-7.63 (2H, m), 8.33 (1H, d, J=0.8 Hz), 8.68 (1H, s), 8.76 (1H, s), 9.56 (1H, s).

The intermediates were synthesized in the following manner.

Production Example 574-1

4-(6-Chloropyrimidin-4-yloxy)phenylamine

4-Chloro-6-(4-nitrophenoxy)pyrimidine (2.52 g, 10.0 mmol), iron powder (2.79 g, 50.0 mmol) and ammonium chloride (5.35 g, 100 mmol) were suspended in an ethanol (100 ml)—water (25 ml) mixed solvent and the suspension was heated and stirred at 80° C. for 1 hour. Upon completion of the reaction, the reaction mixture was filtered with celite and washed in an ethanol-ethyl acetate mixed solvent. The organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=2:3), and the fraction containing the target substance was concentrated to obtain the title compound (1.74 g, 7.85 mmol, 79%) as colorless crystals.

$^1$H-NMR Spectrum (CDCl$_3$) δ (ppm): 3.71 (2H, br s), 6.70-6.75 (2H, m), 6.84 (1H, s), 6.90-6.95 (2H, m), 8.60 (1H, s).

Production Example 574-2

N-(4-(6-Chloropyrimidin-4-yloxy)phenyl)-N'-phenylurea 4-(6-Chloropyrimidin-4-yloxy)phenylamine (663 mg, 3.00 mmol) and phenyl isocyanate (393 mg, 3.30 mmol) were stirred in dimethylformamide (5 ml) at room temperature for 18 hours. The reaction solution was poured into water and the precipitated crystals were filtered out, washed with water and ethanol and blow-dried to obtain the title compound (988 mg, 2.91 mmol, 97%) as colorless crystals.

$^1$H-NMR Spectrum (DMSO-$d_6$) δ (ppm): 6.94-7.00 (1H, m), 7.14-7.20 (2H, m), 7.25-7.32 (2H, m), 7.33 (1H, d, J=0.8 Hz), 7.43-7.49 (2H, m), 7.50-7.56 (2H, m), 8.65 (1H, d, J=0.8 Hz), 8.70 (1H, s), 8.78 (1H, s).

Example 575

N-(4-(6-(3-Fluorophenylamino)pyrimidin-4-yloxy)phenyl)-N'-phenylurea

N-(4-(6-Chloropyrimidin-4-yloxy)phenyl)-N'-phenylurea (68.0 mg, 0.200 mmol) and 3-fluoroaniline (111 mg, 1.00 mmol) were heated and stirred in 1-methylpyrrolidone (1 ml) at 150° C. for 90 minutes. The reaction solution was distributed between ethyl acetate and water, the organic layer was washed with saturated aqueous sodium bicarbonate, water and saturated brine and dried over anhydrous magnesium sulfate, the drying agent was filtered off and the filtrate was distilled off under reduced pressure. The obtained crude product was suspended in ethyl acetate, the suspension was diluted with hexane, and the crystals were filtered out, washed with hexane and then blow-dried to obtain the title compound (43.0 mg, 0.104 mmol, 52%) as colorless crystals.

$^1$H-NMR Spectrum (DMSO-$d_6$) δ (ppm): 6.09 (1H, s), 6.77-6.83 (1H, m), 6.95-7.00 (1H, m), 7.11-7.17 (2H, m), 7.26-7.36 (4H, m), 7.45-7.50 (2H, m), 7.50-7.55 (2H, m), 7.71-7.77 (1H, m), 8.42 (1H, s), 8.69 (1H, s), 8.77 (1H, s), 9.76 (1H, s).

Example 576

N-(4-(6-(2-Fluorophenylamino)pyrimidin-4-yloxy)phenyl)-N'-phenylurea

N-(4-(6-Chloropyrimidin-4-yloxy)phenyl)-N'-phenylurea (68.0 mg, 0.200 mmol) and 2-fluoroaniline (111 mg, 1.00 mmol) were heated and stirred in 1-methylpyrrolidone (1 ml) at 170° C. for 3 hours. The reaction solution was distributed between ethyl acetate and water, the organic layer was washed with saturated aqueous sodium bicarbonate, water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=3:2), the fraction containing the target substance was concentrated and suspended in ethyl acetate, the suspension was diluted with hexane and the crystals were filtered out, washed with hexane and blow-dried to obtain the title compound (26.0 mg, 0.062 mmol, 31%) as colorless crystals.

$^1$H-NMR Spectrum (DMSO-d$_6$) δ (ppm): 6.17 (1H, d, J=0.8 Hz), 6.95-7.00 (1H, m), 7.10-7.19 (4H, m), 7.22-7.32 (3H, m), 7.45-7.50 (2H, m), 7.50-7.55 (2H, m), 7.86-7.93 (1H, m), 8.29 (1H, d, J=0.8 Hz), 8.69 (1H, s), 8.76 (1H, s), 9.32 (1H, s).

Example 577

N-(4-(6-(3,5-Difluorophenylamino)pyrimidin-4-yloxy)phenyl)-N'-phenylurea

N-(4-(6-Chloropyrimidin-4-yloxy)phenyl)-N'-phenylurea (68.0 mg, 0.200 mmol) and 3,5-difluoroaniline (129 mg, 1.00 mmol) were heated and stirred in 1-methylpyrrolidone (1 ml) at 170° C. for 3 hours. The reaction solution was distributed between ethyl acetate and water, the organic layer was washed with saturated aqueous sodium bicarbonate, water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=1:1), the fraction containing the target substance was concentrated and suspended in ethyl acetate, the suspension was diluted with hexane and the crystals were filtered out, washed with hexane and blow-dried to obtain the title compound (17.5 mg, 0.040 mmol, 20%) as colorless crystals.

$^1$H-NMR Spectrum (DMSO-d$_6$) δ (ppm): 6.09 (1H, s), 6.77-6.85 (1H, m), 6.95-7.00 (1H, m), 7.13-7.19 (2H, m), 7.27-7.33 (2H, m), 7.38-7.50 (4H, m), 7.50-7.58 (2H, m), 8.46 (1H, s), 8.69 (1H, s), 8.78 (1H, s), 9.94 (1H, s).

Example 578

N-Phenyl-N'-(4-(6-(3,4,5-trimethoxyphenylamino)pyrimidin-4-yloxy)phenyl)urea hydrochloride N-(4-(6-Chloropyrimidin-4-yloxy)phenyl)-N'-phenylurea (68.0 mg, 0.200 mmol) and 3,4,5-trimethoxyaniline (183 mg, 1.00 mmol) were heated and stirred in 1-methylpyrrolidone (1 ml) at 150° C. for 2 hours. The reaction solution was distributed between ethyl acetate and water, the organic layer was washed with saturated aqueous sodium bicarbonate, water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=3:1), the fraction containing the target substance was concentrated, converted to a hydrochloride with 1N hydrochloric acid and suspended in methanol, the suspension was diluted with ethyl acetate and the crystals were filtered out, washed with ethyl acetate and blow-dried to obtain the title compound (50.0 mg, 0.095 mmol, 48%) as light green crystals.

$^1$H-NMR Spectrum (DMSO-d$_6$) δ (ppm): 3.61 (3H, s), 3.74 (6H, s), 6.03 (1H, s), 6.90 (2H, s), 6.95-7.00 (1H, m), 7.10-7.16 (2H, m), 7.27-7.33 (2H, m), 7.45-7.50 (2H, m), 7.50-7.55 (2H, m), 8.36 (1H, s), 8.91 (1H, s), 9.02 (1H, s), 9.55 (1H, s).

Example 579

1-(4-(6-(N-Methyl-N-phenylamino)pyrimidin-4-yloxy)phenyl)-3-phenylurea

N-(4-(6-Chloropyrimidin-4-yloxy)phenyl)-N'-phenylurea (68.0 mg, 0.200 mmol) and N-methylaniline (107 mg, 1.00 mmol) were heated and stirred in 1-methylpyrrolidone (1 ml) at 130° C. for 36 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=1:1), the fraction containing the target substance was concentrated and suspended in ethyl acetate, the suspension was diluted with hexane and the crystals were filtered out, washed with hexane and blow-dried to obtain the title compound (38 mg, 0.092 mmol, 46%) as colorless crystals.

$^1$H-NMR Spectrum (DMSO-d$_6$) δ (ppm): 3.42 (3H, s), 5.75 (1H, s), 6.95-7.03 (3H, m), 7.25-7.38 (5H, m), 7.41-7.50 (6H, m), 8.27 (1H, s), 8.64 (1H, s), 8.68 (1H, s).

Example 580

N-(5-Chloro-2-thiazolyl)-N'-(4-(6-cyano-7-(2-methoxyethoxy)-4-quinolyl)oxy-2-fluorophenyl)urea The title compound (66.0 mg, 0.128 mmol, 64%) was obtained as white crystals from 4-(4-amino-3-fluorophenoxy)-6-cyano-7-(2-methoxyethoxy)quinoline (71.0 mg, 0.200 mmol) and phenyl 5-chloro-2-thiazolylcarbamate prepared from 2-amino-5-chlorothiazole and phenyl chloroformate, by the same procedure as in Example 145.

$^1$H-NMR Spectrum (DMSO-d$_6$) δ (ppm): 3.38 (3H, s), 3.80 (2H, m), 4.43 (2H, m), 6.65 (1H, d, J=5.2 Hz), 7.20 (1H, m), 7.44 (1H, s), 7.47 (1H, m), 7.66 (1H, s), 8.20 (1H, m), 8.76 (1H, d, J=5.2 Hz), 8.77 (1H, s), 9.02 (1H, s), 11.01 (1H, s).

Example 581

N-(4-(6-Cyano-7-(2-methoxyethoxy)-4-quinolyl)oxy-2-fluorophenyl)-N'-(4-cyclopropyl-2-thiazolyl)urea The title compound (88.0 mg, 0.169 mmol, 85%) was obtained as white crystals from 4-(4-amino-3-fluorophenoxy)-6-cyano-7-(2-methoxyethoxy)quinoline (71.0 mg, 0.200 mmol) and phenyl 4-cyclopropyl-2-thiazolylcarbamate prepared from 2-amino-4-cyclopropylthiazole and phenyl chloroformate, by the same procedure as in Example 145.

$^1$H-NMR Spectrum (DMSO-d$_6$) δ (ppm): 0.75 (2H, m), 0.84 (2H, m), 1.95 (1H, m), 3.38 (3H, s), 3.80 (2H, m), 4.44 (2H, m), 6.64 (1H, d, J=5.2 Hz), 6.72 (1H, s), 7.19 (1H, m), 7.46 (1H, m), 7.66 (1H, s), 8.25 (1H, m), 8.76 (1H, d, J=5.2 Hz), 8.77 (1H, s), 10.84 (1H, br s).

Example 582

4-(3-Chloro-4-(methylaminocarbonyl)aminophenoxy)-7-methoxy-6-quinolinecarboxamide The title compound (65.0 mg, 0.162 mmol, 50%) was obtained as white crystals from phenyl N-(4-(6-carbamoyl- 7-methoxy-4-quinolyl)oxy-2-chlorophenyl)carbamate (150 mg, 0.324 mmol) and 40% methylamine (methanol solution), by the same procedure as in Example 11.

¹H-NMR Spectrum (DMSO-d₆) δ (ppm): 2.68 (3H, d, J=4.4 Hz), 4.03 (3H, s), 6.53 (1H, d, J=5.0 Hz), 6.88 (1H, q, J=4.4 Hz), 7.23 (1H, dd, J=2.8, 8.2 Hz), 7.48 (1H, d, J=2.8 Hz), 7.52 (1H, s), 7.74 (1H, s), 7.86 (1H, s), 8.12 (1H, s), 8.25 (1H, d, J=8.2 Hz), 8.67 (1H, s), 8.68 (1H, d, J=5.0 Hz).

Example 583

4-(3-Chloro-4-(ethylaminocarbonyl)aminophenoxy)-7-methoxy-6-quinolinecarboxamide The title compound (92.0 mg, 0.221 mmol, 68%) was obtained as white crystals from phenyl N-(4-(6-carbamoyl-7-methoxy-4-quinolyl)oxy-2-chlorophenyl)carbamate (150 mg, 0.324 mmol) and 2 M ethylamine (tetrahydrofuran solution), by the same procedure as in Example 11.

¹H-NMR Spectrum (DMSO-d₆) δ (ppm): 1.08 (3H, t, J=7.2 Hz), 3.14 (2H, m), 4.03 (3H, s), 6.53 (1H, d, J=5.2 Hz), 6.99 (1H, t, J=5.6 Hz), 7.23 (1H, dd, J=2.8, 8.8 Hz), 7.48 (1H, d, J=2.8 Hz), 7.52 (1H, s), 7.73 (1H, s), 7.85 (1H, s), 8.07 (1H, s), 8.27 (1H, d, J=8.8 Hz), 8.66 (1H, s), 8.67 (1H, d, J=5.2 Hz).

Example 584

4-(3-Chloro-4-(1-propylaminocarbonyl)aminophenoxy)-7-methoxy-6-quinolinecarboxamide The title compound (111 mg, 0.258 mmol, 80%) was obtained as white crystals from phenyl N-(4-(6-carbamoyl-7-methoxy-4-quinolyl)oxy-2-chlorophenyl)carbamate (150 mg, 0.324 mmol) and propylamine, by the same procedure as in Example 11.

¹H-NMR Spectrum (DMSO-d₆) δ (ppm): 0.91 (3H, t, J=7.4 Hz), 1.47 (2H, m), 3.08 (2H, m), 4.03 (3H, s), 6.53 (1H, d, J=5.2 Hz), 7.03 (1H, t, J=5.6 Hz), 7.23 (1H, dd, J=2.8, 8.8 Hz), 7.48 (1H, d, J=2.8 Hz), 7.52 (1H, s), 7.74 (1H, s), 7.85 (1H, s), 8.09 (1H, s), 8.28 (1H, d, J=8.8 Hz), 8.66 (1H, s), 8.67 (1H, d, J=5.2 Hz).

Example 585

4-(3-Chloro-4-(cyanomethylaminocarbonyl)aminophenoxy)-7-methoxy-6-quinolinecarboxamide The title compound (107 mg, 0.251 mmol, 77%) was obtained as white crystals from phenyl N-(4-(6-carbamoyl-7-methoxy-4-quinolyl)oxy-2-chlorophenyl)carbamate (150 mg, 0.324 mmol) and 2-aminoacetonitrile hydrochloride, by the same procedure as in Example 11.

¹H-NMR Spectrum (DMSO-d₆) δ (ppm): 4.03 (3H, s), 4.22 (2H, t, J=6.0 Hz), 6.56 (1H, d, J=5.2 Hz), 7.28 (1H, dd, J=2.8, 8.8 Hz), 7.50 (1H, t, J=6.0 Hz), 7.53 (1H, s), 7.54 (1H, d, J=2.8 Hz), 7.74 (1H, s), 7.86 (1H, s), 8.17 (1H, d, J=8.8 Hz), 8.51 (1H, s), 8.66 (1H, s), 8.68 (1H, d, J=5.2 Hz).

Example 586

4-(3-Chloro-4-(2-cyanoethylaminocarbonyl)aminophenoxy)-7-methoxy-6-quinolinecarboxamide The title compound (109 mg, 0.248 mmol, 76%) was obtained as white crystals from phenyl N-(4-(6-carbamoyl-7-methoxy-4-quinolyl)oxy-2-chlorophenyl)carbamate (150 mg, 0.324 mmol) and 3-aminopropionitrile, by the same procedure as in Example 11.

¹H-NMR Spectrum (DMSO-d₆) δ (ppm): 2.72 (2H, t, J=6.4 Hz), 3.41 (2H, m), 4.03 (3H, s), 6.54 (1H, d, J=5.2 Hz), 7.25 (1H, dd, J=2.8, 8.8 Hz), 7.37 (1H, t, J=6.0 Hz), 7.50 (1H, d, J=2.8 Hz), 7.52 (1H, s), 7.74 (1H, s), 7.86 (1H, s), 8.24 (1H, d, J=8.8 Hz), 8.31 (1H, s), 8.66 (1H, s), 8.67 (1H, d, J=5.2 Hz).

Example 589

4-(3-Chloro-4-(cis-2-fluoro-cyclopropylaminocarbonyl)aminophenoxy)-7-methoxy-6-quinolinecarboxamide The title compound (39.0 mg, 0.088 mmol, 27%) was obtained as white crystals from phenyl N-(4-(6-carbamoyl-7-methoxy-4-quinolyl)oxy-2-chlorophenyl)carbamate (150 mg, 0.324 mmol) and cis-2-fluorocyclopropylamine tosylate, by the same procedure as in Example 11.

¹H-NMR Spectrum (DMSO-d₆) δ (ppm): 0.82 (1H, m), 1.11 (1H, m), 2.68 (1H, m), 4.04 (3H, s), 4.78 (1H, m), 6.54 (1H, d, J=5.2 Hz), 7.25 (1H, dd, J=2.8, 8.8 Hz), 7.32 (1H, d, J=3.6 Hz), 7.50 (1H, d, J=2.8 Hz), 7.52 (1H, s), 7.74 (1H, s), 7.86 (1H, s), 8.25 (1H, s), 8.29 (1H, d, J=8.8 Hz), 8.66 (1H, s), 8.67 (1H, d, J=5.2 Hz).

Example 590

4-(3-Chloro-4-(aminocarbonyl)aminophenoxy)-7-methoxy-6-quinolinecarboxamide

The title compound (61.0 mg, 79%) was obtained as light red crystals from phenyl N-(4-(6-carbamoyl-7-methoxy-4-quinolyl)oxy-2-chlorophenyl)carbamate (100 mg, 0.22 mmol) and ammonia water (2 ml), by the same procedure as in Example 11.

¹H-NMR Spectrum (DMSO-d₆) δ (ppm): 4.01 (3H, s), 6.41 (2H, s), 6.51 (1H, d, J=5.2 Hz), 7.21 (1H, d, J=9.2 Hz), 7.47 (1H, d, J=2.8 Hz), 7.50 (1H, s), 7.73 (1H, s), 7.84 (1H, s), 8.15 (1H, s), 8.25 (1H, d, J=8.8 Hz), 8.65 (1H, d, J=5.2 Hz), 8.66 (1H, s).

Example 591

N-(4-(6,7-Dimethoxyquinolin-4-yloxy)phenyl)-N'-thiazol-2-ylurea 4-(6,7-Dimethoxyquinolin-4-yloxy)phenylcarbamic acid phenyl ester (208 mg, 0.500 mmol) and 2-aminothiazole (100 mg, 1.00 mmol) were heated and stirred in dimethylsulfoxide (1 ml) at 85° C. for 1 hour. The reaction solution was distributed between ethyl acetate and water, the organic layer was washed with 1N aqueous sodium hydroxide, water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=20:1), the fraction containing the target substance was concentrated and suspended in ethyl acetate, the suspension was diluted with hexane and the crystals were filtered out, washed with hexane and blow-dried to obtain the title compound (150 mg, 0.355 mmol, 71%) as colorless crystals.

¹H-NMR Spectrum (CDCl₃) δ (ppm): 4.02-4.05 (6H, m), 6.46 (1H, d, J=5.2 Hz), 6.92 (1H, d, J=3.6 Hz), 7.16-7.22 (2H, m), 7.40-7.44 (2H, m), 7.56 (1H, s), 7.61-7.67 (2H, m), 8.48 (1H, d, J=5.2 Hz).

The intermediate was synthesized in the following manner.

Production Example 591-1

4-(6,7-Dimethoxyquinolin-4-yloxy)phenylcarbamic acid phenyl ester

The 4-(6,7-dimethoxyquinolin-4-yloxy)phenylamine (2.96 g, 10.0 mmol) obtained by the method described in WO97/17329 and triethylamine (1.21 g, 12.0 mmol) were dissolved in dimethylformamide (30 ml), and after adding phenyl chloroformate (1.72 g, 11.0 mmol) while cooling on ice, the mixture was stirred at room temperature for 1 hour. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=3:1), the fraction containing the target substance was concentrated and suspended in ethyl acetate, the suspension was diluted with hexane and the crystals were filtered out, washed with hexane and blow-dried to obtain the title compound (2.50 g, 6.00 mmol, 60%) as colorless crystals.

$^1$H-NMR Spectrum (CDCl$_3$) δ (ppm): 4.05 (3H, s), 4.06 (3H, s), 6.46 (1H, d, J=5.2 Hz), 7.12 (1H, br s), 7.16-7.28 (5H, m), 7.38-7.44 (3H, m), 7.53-7.60 (3H, m), 8.49 (1H, d, J=5.2 Hz).

Example 592

N-Cyclopropyl-N'-(4-(6,7-dimethoxyquinolin-4-yloxy)phenyl)urea 4-(6,7-Dimethoxyquinolin-4-yloxy)phenylcarbamic acid phenyl ester (104 mg, 0.250 mmol) and cyclopropylamine (28.5 mg, 0.500 mmol) were stirred in dimethylsulfoxide (1 ml) at room temperature for 2 hours. The reaction solution was distributed between ethyl acetate and water, the organic layer was washed with 1N aqueous sodium hydroxide, water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=15:1), the fraction containing the target substance was concentrated and suspended in ethyl acetate, the suspension was diluted with hexane and the crystals were filtered out, washed with hexane and blow-dried to obtain the title compound (76 mg, 0.200 mmol, 80%) as colorless crystals.

$^1$H-NMR Spectrum (CDCl$_3$) δ (ppm): 0.70-0.75 (2H, m), 0.87-0.92 (2H, m), 2.60-2.66 (1H, m), 4.04-4.07 (6H, m), 4.93 (1H, s), 6.45 (1H, d, J=5.2 Hz), 6.99 (1H, s), 7.12-7.18 (2H, m), 7.42 (1H, s), 7.50-7.56 (2H, m), 7.57 (1H, s), 8.48 (1H, d, J=5.2 Hz).

Example 593

N-(4-(6,7-Dimethoxyquinolin-4-yloxy)-2-fluorophenyl)-N'-thiazol-2-ylurea 4-(6,7-Dimethoxyquinolin-4-yloxy)-2-fluorophenylcarbamic acid phenyl ester (109 mg, 0.250 mmol) and 2-aminothiazole (50.0 mg, 0.500 mmol) were heated and stirred in dimethylsulfoxide (1 ml) at 85° C. for 2 hours. The reaction solution was distributed between ethyl acetate and water, the organic layer was washed with 1N aqueous sodium hydroxide, water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=30:1), the fraction containing the target substance was concentrated and suspended in ethyl acetate, the suspension was diluted with hexane and the crystals were filtered out, washed with hexane and blow-dried to obtain the title compound (95.0 mg, 0.216 mmol, 86%) as colorless crystals.

$^1$H-NMR Spectrum (CDCl$_3$) δ (ppm): 4.05 (3H, s), 4.06 (3H, s), 6.52 (1H, d, J=5.2 Hz), 6.92 (1H, d, J=3.6 Hz), 6.96-7.04 (2H, m), 7.36 (1H, d, J=3.6 Hz), 7.40 (1H, s), 7.53 (1H, s), 8.30-8.36 (1H, m), 8.47 (1H, d, J=5.2 Hz).

The intermediate was synthesized in the following manner.

Production Example 593-1

4-(6,7-Dimethoxyquinolin-4-yloxy)-2-fluorophenylcarbamic acid phenyl ester 4-(6,7-Dimethoxyquinolin-4-yloxy)-2-fluorophenylamine (3.55 g, 9.17 mmol) obtained by the method described in Japanese Unexamined Patent Publication HEI No. 11-158149 and pyridine (3.63 g, 45.8 mmol) were dissolved in dimethylformamide (30 ml), and after adding phenyl chloroformate (1.51 g, 9.64 mmol) while cooling on ice, the mixture was stirred at room temperature for 1 hour. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was subjected to silica gel column chromatography (eluent—ethyl acetate:hexane=2:1), the fraction containing the target substance was concentrated and suspended in ethyl acetate, the suspension was diluted with hexane and the crystals were filtered out, washed with hexane and blow-dried to obtain the title compound (2.30 g, 5.29 mmol, 58%) as colorless crystals.

$^1$H-NMR Spectrum (CDCl$_3$) δ (ppm): 4.05 (3H, s), 4.06 (3H, s), 6.52 (1H, d, J=5.2 Hz), 7.00-7.05 (2H, m), 7.18-7.30 (4H, m), 7.40-7.46 (3H, m), 7.50 (1H, s), 8.21 (1H, br s), 8.53 (1H, d, J=5.2 Hz).

Example 594

N-Cyclopropyl-N'-(4-(6,7-dimethoxyquinolin-4-yloxy)-2-fluorophenyl)urea 4-(6,7-Dimethoxyquinolin-4-yloxy)-2-fluorophenylcarbamic acid phenyl ester (109 mg, 0.250 mmol) and cyclopropylamine (28.5 mg, 0.500 mmol) were stirred in dimethylsulfoxide (1 ml) at room temperature for 2 hours. The reaction solution was distributed between ethyl acetate and water, the organic layer was washed with 1N aqueous sodium hydroxide, water and saturated brine and dried over anhydrous magnesium sulfate, the drying agent was filtered off and the filtrate was distilled off under reduced pressure. The obtained crude product was subjected to silica gel column chromatography (eluent—ethyl acetate:methanol=50:1), the fraction containing the target substance was concentrated and suspended in ethyl acetate, the suspension was diluted with hexane and the crystals were filtered out, washed with hexane and blow-dried to obtain the title compound (73 mg, 0.183 mmol, 73%) as colorless crystals.

¹H-NMR Spectrum (CDCl₃) δ (ppm): 0.71-0.76 (2H, m), 0.90-0.95 (2H, m), 2.60-2.66 (1H, m), 4.05 (3H, s), 4.06 (3H, s), 5.00 (1H, s), 6.50 (1H, d, J=5.2 Hz), 6.95-7.02 (2H, m), 7.23 (1H, s), 7.43 (1H, s), 7.52 (1H, s), 8.25-8.32 (1H, m), 8.51 (1H, d, J=5.2 Hz).

Example 595

4-(3-Chloro-4-(cyclopropylaminocarbonyl)aminophenoxy)-7-(2-ethoxyethoxy)-6-quinolinecarboxamide The title compound (96.0 mg, 0.198 mmol, 39.7%) was obtained as light yellow crystals from 4-(3-chloro-4-(cyclopropylaminocarbonyl)aminophenoxy)-7-hydroxy-6-quinolinecarboxamide (206 mg, 0.499 mmol) and 2-ethoxyethylbromide, by the same procedure as in Example 7.

¹H-NMR Spectrum (DMSO-d₆) δ (ppm): 0.42 (2H, m), 0.65 (2H, m), 1.16 (3H, t, J=7.2 Hz), 2.56 (1H, m), 3.53 (2H, q, J=7.2 Hz), 3.83 (2H, m), 4.40 (2H, m), 6.51 (1H, d, J=5.2 Hz), 7.18 (1H, d, J=2.8 Hz), 7.24 (1H, dd, J=2.8, 9.2 Hz), 7.49 (1H, d, J=2.8 Hz), 7.56 (1H, s), 7.85 (1H, s), 7.87 (1H, s), 7.97 (1H, s), 8.26 (1H, d, J=9.2 Hz), 8.66 (1H, d, J=5.2 Hz), 8.78 (1H, s).

Example 596

4-(3-Chloro-4-(cyclopropylaminocarbonyl)aminophenoxy)-7-cyclopropylmethoxy-6-quinolinecarboxamide The title compound (61.4 mg, 0.132 mmol, 26.4%) was obtained as light yellow crystals from 4-(3-chloro-4-(cyclopropylaminocarbonyl)aminophenoxy)-7-hydroxy-6-quinolinecarboxamide (206 mg, 0.499 mmol) and bromomethylcyclopropane, by the same procedure as in Example 7.

¹H-NMR Spectrum (DMSO-d₆) δ (ppm): 0.41-0.47 (4H, m), 0.60-0.69 (4H, m), 1.39 (1H, m), 2.56 (1H, m), 4.14 (2H, d, J=6.8 Hz), 6.52 (1H, d, J=5.2 Hz), 7.20 (1H, d, J=2.8 Hz), 7.25 (1H, dd, J=2.8, 8.8 Hz), 7.49-7.50 (2H, m), 7.83 (1H, s), 7.85 (1H, s), 7.98 (1H, s), 8.28 (1H, d, J=8.8 Hz), 8.66 (1H, d, J=5.2 Hz), 8.72 (1H, s).

Example 597

4-(3-Fluoro-4-(methylaminocarbonyl)aminophenoxy)-7-methoxy-6-quinolinecarboxamide The title compound (37 mg) was obtained as yellow crystals from phenyl N-(4-(6-carbamoyl-7-methoxy-4-quinolyl)oxy-2-fluorophenyl)carbamate (73 mg) and methylamine (2M tetrahydrofuran solution), by the same procedure as in Example 11.

¹H-NMR Spectrum (DMSO-d₆) δ (ppm): 2.65 (3H, d, J=4.4 Hz), 4.01 (3H, s), 6.45-6.46 (1H, m), 6.51-6.52 (1H, m), 7.04-7.06 (1H, m), 7.28-7.31 (1H, m), 7.50 (1H, s), 7.72 (1H, s), 7.84 (1H, s), 8.17-8.22 (1H, m), 8.40 (1H, s), 8.64-8.65 (2H, m).

Example 598

4-(3-Fluoro-4-(ethylaminocarbonyl)aminophenoxy)-7-methoxy-6-quinolinecarboxamide The title compound (38 mg) was obtained as yellow crystals from phenyl N-(4-(6-carbamoyl-7-methoxy-4-quinolyl)oxy-2-fluorophenyl)carbamate (69 mg) and ethylamine (2M tetrahydrofuran solution), by the same procedure as in Example 11.

¹H-NMR Spectrum (DMSO-d₆) δ (ppm): 1.05 (3H, t, J=7 Hz), 3.11 (2H, q, J=7 Hz), 4.01 (3H, s), 6.50-6.52 (1H, m), 6.57-6.58 (1H, m), 7.04-7.06 (1H, m), 7.28-7.32 (1H, m), 7.50 (1H, s), 7.73 (1H, s), 7.84 (1H, s), 8.19-8.24 (1H, m), 8.33 (1H, s), 8.64-8.65 (2H, m).

Example 599 tert-Butyl 4-((((4-(3-chloro-4-(((cyclopropylamino)carbonyl)amino)phenoxy)-7-methoxy-6-quinolyl)carbonyl)amino)methyl)-1-piperidinecarboxylate 4-(3-Chloro-4-(((cyclopropylamino)carbonyl)amino)phenoxy)-7-methoxy-6-quinolinecarboxylic acid) (171 mg, 0.40 mmol) was dissolved in dimethylformamide (4 ml) under a nitrogen atmosphere, and then tert-butyl 4-aminomethyl-1-piperidinecarboxylate (171 mg, 0.80 mmol), triethylamine (0.2 ml) and 1H-1,2,3-benzotriazol-1-yloxy)(tri(dimethylamino))phosphonium hexafluorophosphate (265 mg, 0.60 mmol) were added in that order at room temperature, and the mixture was stirred overnight. The reaction solution was distributed between ethyl acetate and water, and the organic layer was washed with water and saturated brine and dried over anhydrous sodium sulfate. The solvent was distilled off, the residue was suspended in ethyl acetate and diluted with hexane, and the crystals were filtered out and blow-dried to obtain the title compound (249 mg, quantitative) as white crystals.

¹H-NMR Spectrum (DMSO-d₆) δ (ppm): 0.41 (2H, m), 0.65 (2H, m), 1.05 (2H, m), 1.22 (1H, m), 1.37 (9H, s), 1.66 (2H, m), 2.56 (1H, m), 2.67 (2H, m), 3.20 (2H, m), 3.93 (2H, m), 3.99 (3H, s), 6.51 (1H, d, J=5.2 Hz), 7.17-7.24 (2H, m), 7.46 (1H, d, J=2.8 Hz), 7.49 (1H, s), 7.97 (1H, s), 8.26 (1H, dd, J=2.8, 8.8 Hz), 8.39 (1H, m), 8.46 (1H, s), 8.64 (1H, d, J=5.2 Hz).

Example 600

N6-(1-Methyl-4-piperidylmethyl)-4-(3-chloro-4-(((cyclopropylamino)carbonyl)amino)phenoxy)-7-methoxy-6-quinolinecarboxamide After adding trifluoroacetic acid (1 ml) to tert-butyl 4-((((4-(3-chloro-4-(((cyclopropylamino)carbonyl)amino)phenoxy)-7-methoxy-6-quinolyl)carbonyl)amino)methyl)-1-piperidinecarboxylate (249 mg, 0.40 mmol) at room temperature, the mixture was stirred for 2 hours. The reaction solution was poured into saturated aqueous sodium bicarbonate for neutralization and extracted 3 times with ethyl acetate, and the organic layer was dried over anhydrous sodium sulfate. After distilling off the solvent, the residue was dissolved in tetrahydrofuran (5 ml)—methanol (5 ml), and then 37% aqueous formaldehyde (0.5 ml), acetic acid (0.05 ml) and sodium cyanoborohydride (50 mg, 0.8 mmol) were added in that order at room temperature and the mixture was stirred for 1 hour. The reaction solution was distributed between ethyl acetate and saturated aqueous sodium bicarbonate, and the organic layer was washed with saturated aqueous sodium bicarbonate and saturated brine and dried over anhydrous sodium sulfate. After distilling off the solvent, ethyl acetate was used for crystallization and the crystals were filtered out and blow-dried to obtain the title compound (125.6 mg, 0.233 mmol, 58.4%) as white crystals.

¹H-NMR Spectrum (DMSO-d₆) δ (ppm): 0.42 (2H, m), 0.65 (2H, m), 1.18 (2H, m), 1.49 (1H, m), 1.64 (2H, m), 1.78 (2H, m), 2.11 (3H, s), 2.56 (1H, m), 2.73 (2H, m), 3.18 (2H, m), 3.99 (3H, s), 6.51 (1H, d, J=5.2 Hz), 7.18 (1H, d, J=2.4 Hz), 7.22 (1H, dd, J=2.8, 8.8 Hz), 7.46 (1H, d, J=2.4 Hz), 7.49 (1H, s), 7.97 (1H, s), 8.26 (1H, dd, J=2.8, 8.8 Hz), 8.35 (1H, m), 8.47 (1H, s), 8.64 (1H, d, J=5.2 Hz).

Example 601 tert-Butyl 4-(((4-(3-chloro-4-((cyclopropylamino)carbonyl)amino)phenoxy)-6-(methylaminocarbonyl)-7-quinolyl)oxy)methyl)-1-piperidinecarboxylate The title compound (188.4 mg, 0.302 mmol, 57.1%) was obtained as white crystals from N6-methyl-4-(3-chloro-4-(((cyclopropylamino)carbonyl)amino)phenoxy)-7-hydroxy-6-quinolinecarboxamide (225.5 mg, 0.528 mmol) and tert-butyl 4-(bromomethyl)-1-piperidinecarboxylate, by the same procedure as in Example 7.
¹H-NMR Spectrum (DMSO-d₆) δ (ppm): 0.41 (2H, m), 0.65 (2H, m), 1.13-1.26 (3H, m), 1.39 (9H, s), 1.75 (2H, m), 2.06 (1H, m), 2.56 (1H, m), 2.75 (1H, m), 2.81 (3H, d, J=4.8 Hz), 3.99 (2H, m), 4.10 (2H, m), 6.51 (1H, d, J=5.2 Hz), 7.18 (1H, d, J=2.8 Hz), 7.21 (1H, dd, J=2.8, 9.2 Hz), 7.45 (1H, d, J=2.8 Hz), 7.48 (1H, s), 7.96 (1H, s), 8.18 (1H, d, J=4.8 Hz), 8.25 (1H, d, J=9.2 Hz), 8.43 (1H, s), 8.64 (1H, d, J=5.2 Hz).

Example 602 tert-Butyl 4-(((4-(3-chloro-4-((cyclopropylamino)carbonyl)amino)phenoxy)-6-(ethylaminocarbonyl)-7-quinolyl)oxy)methyl)-1-piperidinecarboxylate The title compound (155.4 mg, 0.244 mmol, 63.0%) was obtained as light yellow crystals from N6-ethyl-4-(3-chloro-4-(((cyclopropylamino)carbonyl)amino)phenoxy)-7-hydroxy-6-quinolinecarboxamide) (170.5 mg, 0.387 mmol) and tert-butyl 4-(bromomethyl)-1-piperidinecarboxylate, by the same procedure as in Example 7.
¹H-NMR Spectrum (DMSO-d₆) δ (ppm): 0.41 (2H, m), 0.65 (2H, m), 1.10-1.16 (4H, m), 1.27 (2H, m), 1.39 (9H, s), 1.76 (2H, m), 2.05 (1H, m), 2.56 (1H, m), 2.75 (1H, m), 3.20-3.40 (2H, m), 4.01 (2H, m), 4.11 (2H, m), 6.51 (1H, d, J=5.2 Hz), 7.17-7.23 (2H, m), 7.45 (1H, d, J=2.8 Hz), 7.48 (1H, s), 7.96 (1H, s), 8.20-8.27 (2H, m), 8.44 (1H, s), 8.64 (1H, d, J=5.2 Hz).

Example 603

N6-Methyl-4-(3-chloro-4-(((cyclopropylamino)carbonyl)amino)phenoxy)-7-((1-methyl-4-piperidyl)methoxy)-6-quinolinecarboxamide After adding trifluoroacetic acid (1 ml) to tert-butyl 4-(((4-(3-chloro-4-((cyclopropylamino)carbonyl)amino)phenoxy)-6-(methylaminocarbonyl)-7-quinolyl)oxy)methyl)-1-piperidinecarboxylate (179.0 mg, 0.287 mmol) at room temperature, the mixture was stirred for 2 hours. The reaction solution was poured into saturated aqueous sodium bicarbonate for neutralization and extracted 5 times with ethyl acetate-tetrahydrofuran (1:1), and the organic layer was dried over anhydrous sodium sulfate. After distilling off the solvent, the residue was dissolved in tetrahydrofuran (5 ml)—methanol (5 ml), and then 37% aqueous formaldehyde (0.3 ml), acetic acid (0.05 ml) and sodium cyanoborohydride (36 mg, 0.57 mmol) were added in that order at room temperature and the mixture was stirred for 1 hour. The reaction solution was distributed between ethyl acetate and saturated aqueous sodium bicarbonate, and the organic layer was washed with saturated aqueous sodium bicarbonate and saturated brine and dried over anhydrous sodium sulfate. After distilling off the solvent, ethyl acetate was used for crystallization and the crystals were filtered out and blow-dried to obtain the title compound (101.0 mg, 0.188 mmol, 65.4%) as white crystals.
¹H-NMR Spectrum (DMSO-d₆) δ (ppm): 0.41 (2H, m), 0.65 (2H, m), 1.34 (2H, m), 1.72-1.89 (5H, m), 2.14 (3H, s), 2.56 (1H, m), 2.78 (2H, m), 2.82 (3H, d, J=4.4 Hz), 4.08 (2H, d, J=6.4 Hz), 6.51 (1H, d, J=5.2 Hz), 7.19-7.23 (2H, m), 7.45 (1H, d, J=2.8 Hz), 7.48 (1H, s), 7.97 (1H, s), 8.20 (1H, d, J=4.4 Hz), 8.25 (1H, d, J=9.2 Hz), 8.45 (1H, s), 8.63 (1H, d, J=5.2 Hz).

Example 604

N6-Ethyl-4-(3-chloro-4-(((cyclopropylamino)carbonyl)amino)phenoxy)-7-((1-methyl-4-piperidyl)methoxy)-6-quinolinecarboxamide The title compound (82.6 mg, 0.150 mmol, 64.8%) was obtained as light yellow crystals from tert-butyl 4-(((4-(3-chloro-4-((cyclopropylamino)carbonyl)amino)phenoxy)-6-(ethylaminocarbonyl)-7-quinolyl)oxy)methyl)-1-piperidinecarboxylate (147.2 mg, 0.231 mmol), by the same procedure as in Example 603.
¹H-NMR Spectrum (DMSO-d₆) δ (ppm): 0.42 (2H, m), 0.65 (2H, m), 1.14 (3H, t, J=7.2 Hz), 1.36 (2H, m), 1.75-1.89 (5H, m), 2.15 (3H, s), 2.56 (1H, m), 2.79 (2H, m), 3.20-3.40 (2H, m), 4.08 (2H, d, J=6.4 Hz), 6.51 (1H, d, J=5.2 Hz), 7.20-7.23 (2H, m), 7.46 (1H, d, J=2.8 Hz), 7.48 (1H, s), 7.98 (1H, s), 8.22-8.27 (2H, m), 8.47 (1H, s), 8.64 (1H, d, J=5.2 Hz).

Example 605

1-[4-(7-Benzyloxy-6-cyanoquinolin-4-yloxy)-2-chloro-phenyl]-3-ethyl-urea

A carbamate (1.51 g) was obtained as a solid from 4-(4-amino-3-chlorophenoxy)-7-benzyloxy-quinoline-6-carbonitrile (1.78 g) and phenyl chlorocarbonate, by the same procedure as in Production Example 17. The carbamate (1.5 g) was then treated with ethylamine in dimethylsulfoxide at room temperature in the same manner as Example 11, to obtain the title compound (1.4 g) as a solid.
¹H-NMR Spectrum (DMSO-d₆) δ (ppm): 1.06 (3H, t, J=7.6 Hz), 3.08-3.16 (2H, m), 5.45 (2H, s), 6.58 (1H, d, J=5.2 Hz), 6.99 (1H, t, J=5.2 Hz), 7.23 (1H, dd, J=2.8 Hz, J=9.2 Hz), 7.36 (1H, t, J=7.2 Hz), 7.44 (2H, t, J=7.2 Hz), 7.48 (1H, d, J=2.8 Hz), 7.54 (2H, d, J=7.2 Hz), 7.70 (1H, s), 8.06 (1H, s), 8.26 (1H, d, J=8.8 Hz), 8.72 (1H, d, J=5.2 Hz), 8.76 (1H, s).

Example 606

1-(2-Chloro-4-(6-cyano-(2R)-7-oxiranylmethoxyquinolin-4-yloxy)-phenyl)-3-ethylurea 1-(4-(7-Benzyloxy-6-cyanoquinolin-4-yloxy)-2-chlorophenyl)-3-ethylurea (1 g) was treated with trifluoroacetic acid and thioanisole for deprotection in the same manner as Production Example 21, and the obtained hydroxy compound (0.48 g) was treated in the same manner as Example 543 to obtain the title compound (0.31 g) as a solid.

¹H-NMR Spectrum (DMSO-d₆) δ (ppm): 1.06 (3H, t, J=7.2 Hz), 2.81 (1H, dd, J=2.8 Hz, J=5.2 Hz), 2.91 (1H, t, J=4.8 Hz), 3.80-3.16 (2H, m), 3.44-3.48 (1H, m), 4.17 (1H, dd, J=6.4 Hz, J=11.6 Hz), 4.71 (1H, dd, J=2 Hz, J=11.6 Hz), 6.59 (1H, d, J=5.2 Hz), 6.99 (1H, t, J=5.2 Hz), 7.24 (1H, dd, J=2.8 Hz, J=9.2 Hz), 7.49 (1H, d, J=2.8 Hz), 7.64 (1H, s), 8.07 (1H, s), 8.27 (1H, d, J=9.2 Hz), 8.73 (1H, d, J=5.2 Hz), 8.76 (1H, s).

Example 607

1-(2-Chloro-4-(6-cyano-7-((2R)-2-hydroxy-3-pyrrolidin-1-ylpropoxy)quinolin-4-yloxy)phenyl)-3-ethylurea The title compound (38 mg) was obtained as a solid from 1-(2-chloro-4-(6-cyano-(2R)-7-oxiranylmethoxyquinolin-4-yloxy)-phenyl)-3-ethylurea (110 mg) and pyrrolidine, in the same manner as Example 544.

¹H-NMR Spectrum (DMSO-d₆) δ (ppm): 1.07 (3H, t, J=7.2 Hz), 1.62-1.72 (4H, m), 2.44-2.56 (5H, m), 2.67-2.73 (1H, m), 3.08-3.16 (2H, m), 3.97-4.04 (1H, m), 4.17-4.23 (1H, m), 4.25-4.32 (1H, m), 5.02 (1H, d, J=4.4 Hz), 6.57 (1H, d, J=5.2 Hz), 6.97-7.03 (1H, m), 7.23 (1H, dd, J=2.4 Hz, J=9.2 Hz), 7.49 (1H, d, J=2.4 Hz), 7.61 (1H, s), 8.07 (1H, s), 8.27 (1H, d, J=9.2 Hz), 8.72 (1H, d, J=5.2 Hz), 8.73 (1H, s).

Example 608

1-(2-Chloro-4-(6-cyano-7-((2R)-3-diethylamino-2-hydroxypropoxy)quinolin-4-yloxy)phenyl)-3-ethylurea The title compound (12 mg) was obtained as a solid from 1-(2-chloro-4-(6-cyano-(2R)-7-oxiranylmethoxyquinolin-4-yloxy)phenyl)-3-ethylurea (100 mg) and diethylamine, in the same manner as Example 544.

¹H-NMR Spectrum (DMSO-d₆) δ (ppm): 0.96 (6H, t, J=7.2 Hz), 1.06 (3H, t, J=7.2 Hz), 2.42-2.57 (5H, m), 2.64 (1H, dd, J=7.6 Hz, J=13.2 Hz), 3.08-3.16 (2H, m), 3.91-4.00 (1H, m), 4.21 (1H, dd, J=5.2 Hz, J=10 Hz), 4.30 (1H, dd, J=3.6 Hz, J=10 Hz), 4.88-4.93 (1H, m), 6.57 (1H, d, J=5.2 Hz), 6.99 (1H, t, J=4.8 Hz), 7.23 (1H, dd, J=2.8 Hz, J=9.2 Hz), 7.49 (1H, d, J=2.8 Hz), 7.61 (1H, s), 8.06 (1H, s), 8.26 (1H, d, J=9.2 Hz), 8.72 (1H, d, J=5.2 Hz), 8.73 (1H, s).

Example 609

1-(2-Chloro-4-(6-cyano-7-((2R)-2-hydroxy-3-piperidin-1-ylpropoxy)quinolin-4-yloxy)phenyl)-3-ethylurea The title compound (46 mg) was obtained as a solid from 1-(2-chloro-4-(6-cyano-(2R)-7-oxiranylmethoxyquinolin-4-yloxy)phenyl)-3-ethylurea (100 mg) and piperidine, in the same manner as Example 544.

¹H-NMR Spectrum (DMSO-d₆) δ (ppm): 1.06 (3H, t, J=7.2 Hz), 1.32-1.39 (2H, m), 1.44-1.53 (4H, m), 2.34-2.51 (6H, m), 3.08-3.16 (2H, m), 3.99-4.07 (1H, m), 4.19 (1H, dd, J=5.6 Hz, J=10.4 Hz), 4.30 (1H, dd, J=3.2 Hz, J=10.4 Hz), 4.93 (1H, d, J=4.4 Hz), 6.57 (1H, d, J=5.2 Hz), 6.99 (1H, t, J=5.2 Hz), 7.23 (1H, dd, J=2.8 Hz, J=9.2 Hz), 7.48 (1H, d, J=2.8 Hz), 7.62 (1H, s), 8.06 (1H, s), 8.27 (1H, d, J=9.2 Hz), 8.72 (1H, d, J=5.2 Hz), 8.72 (1H, s).

Example 610

1-(2-Chloro-4-(6-(4-(piperidin-4-ylmethoxy)phenyl)-7H-pyrrolo[2,3-d]pyrimidin-4-yloxy}phenyl)-3-cyclopropylurea After dissolving 37 mg of 4-(4-(4-(3-chloro-4-(3-cyclopropylureido)phenoxy)-7-(2-trimethylsilanylethoxymethyl)-7H-pyrrolo[2,3-d]pyrimidin-6-yl)phenoxymethyl)piperidine-1-carboxylic acid tert-butyl ester in 1 ml of trifluoroacetic acid, the mixture was stirred at room temperature for 2 hours. The reaction system was concentrated under reduced pressure, saturated sodium bicarbonate water was added to alkalinity and liquid separation and extraction were performed with ethyl acetate. The organic layer was dried over sodium sulfate and concentrated to dryness to obtain the 25 mg of the title compound.
MS Spectrum (ESI): 533 (M+1),

Example 611

1-(2-Chloro-4-{6-(4-(1-methylpiperidin-4-ylmethoxy)phenyl)-7H-pyrrolo[2,3-d]pyrimidin-4-yloxy}phenyl)-3-cyclopropylurea After adding 2 ml of methanol, 2 ml of methylene chloride, 0.05 ml of 37% aqueous formaldehyde and 4.4 μl of acetic acid to 24 mg of 1-(2-chloro-4-{6-[4-(piperidin-4-ylmethoxy)phenyl]-7H-pyrrolo[2,3-d]pyrimidin-4-yloxy}-2-phenyl)-3-cyclopropylurea, 30 mg of sodium triacetoxyborohydride was added while stirring, which was continued at room temperature for 40 minutes. Water was added, extraction was performed with an ethyl acetate-tetrahydrofuran (5:1) mixed solvent, and the extract was concentrated and subjected to NH silica gel column chromatography to obtain 12 mg of the title compound.
MS Spectrum (ESI): 547 (M+1),

Example 612

4-{4-[4-[3-Chloro-4-(3-cyclopropylureido)phenoxy]-7-(2-trimethylsilanylethoxymethyl)-7H-pyrrolo[2,3-d]pyrimidin-6-yl]phenoxymethyl}piperidine-1-carboxylic acid tert-butyl ester After adding 38 mg of 4-bromomethylpiperidine-1-carboxylic acid tert-butyl ester, 59 mg of potassium carbonate and 1 ml of dimethylformamide to 60 mg of 1-{2-chloro-4-[6-(4-hydroxyphenyl)-7-(2-trimethylsilanylethoxymethyl)-7H-pyrrolo[2,3-d]pyrimidin-4-yloxy]-2-phenyl}-3-cyclopropylurea, the mixture was stirred at 70-75° C. for 6 hours. It was then returned to room temperature, water was added, and liquid separation and extraction were performed with ethyl acetate. The organic layer was dried over sodium sulfate and concentrated to dryness to obtain 63 mg of the title compound.
MS Spectrum (ESI): 786 (M+23),

Example 613

4-(2,3-Dimethyl-4-(methylaminocarbonyl)aminophenoxy)-7-methoxy-6-quinolinecarboxamide The title compound (30 mg) was obtained as colorless crystals from phenyl N-(4-(6-carbamoyl-7-methoxy-4- quinolyl)oxy-2,3-dimethylphenyl)carbamate) (56 mg) and methylamine (2M tetrahydrofuran solution), by the same procedure as in Example 11.

$^1$H-NMR Spectrum (DMSO-d$_6$) δ (ppm): 2.01 (3H, s), 2.14 (3H, s), 2.64 (3H, d, J=3.2 Hz), 4.01 (3H, s), 6.24 (1H, d, J=5.2 Hz), 6.28 (1H, d, J=4.4 Hz), 6.97 (1H, d, J=8.8 Hz), 7.49 (1H, s), 7.60 (1H, d, J=8.4 Hz), 7.73-7.85 (3H, m), 8.59 (1H, d, J=4.8 Hz), 8.71 (1H, s).

Example 614

4-(2,3-Dimethyl-4-(ethylaminocarbonyl)aminophenoxy)-7-methoxy-6-quinolinecarboxamide The title compound (33 mg) was obtained as colorless crystals from phenyl N-(4-(6-carbamoyl-7-methoxy-4-quinolyl)oxy-2,3-dimethylphenyl)carbamate (55 mg) and ethylamine (2M tetrahydrofuran solution), by the same procedure as in Example 11.

$^1$H-NMR Spectrum (DMSO-d$_6$) δ (ppm): 1.54 (3H, t, J=7 Hz), 2.01 (3H, s), 2.14 (3H, s), 3.07-3.12 (2H, m), 4.01 (3H, s), 6.24 (1H, d, J=4.8 Hz), 6.41 (1H, m), 6.97 (1H, d, J=8.4 Hz), 7.49 (1H, s), 7.64 (1H, d, J=8.8 Hz), 7.73 (2H, brs), 7.85 (1H, s), 8.59 (1H, d, J=5.2 Hz), 8.71 (1H, s).

Example 615

4-(3-Chloro-4-(((cyclopropylamino)carbonyl)amino)phenoxy)-7-((2R)-2-hydroxy-3-(1-pyrrolidino)propoxy)-6-quinolinecarboxamide After adding (2R)oxiran-2-ylmethyl 4-methyl-1-benzenesulfonate (308 mg, 1.35 mmol), potassium carbonate (149 mg, 1.08 mmol) and dimethylformamide (9 ml) to 4-(3-chloro-4-(((cyclopropylamino)carbonyl)amino)phenoxy)-7-hydroxy-6-quinolinecarboxamide (372.0 mg, 0.90 mmol), the mixture was stirred at 60° C. for 7 hours. The reaction solution was allowed to stand to return to room temperature, and then pyrrolidine (1 ml) was added and the mixture was stirred overnight. The reaction solution was distributed between ethyl acetate and water, and the organic layer was washed with water and saturated brine and then dried over anhydrous sodium sulfate. The solvent was distilled off, the residue was subjected to silica gel column chromatography (eluent—ethyl acetate:methanol=95:5), the fraction containing the target substance was concentrated, and crystals were precipitated from ethyl acetate, filtered out and blow-dried to obtain the title compound (133.3 mg, 0.247 mmol, 27.4%) as white crystals.

$^1$H-NMR Spectrum (DMSO-d$_6$) δ (ppm): 0.42 (2H, m), 0.65 (2H, m), 1.67 (4H, m), 2.45-2.59 (6H, m), 2.69 (1H, m), 4.05 (1H, m), 4.19 (1H, dd, J=6.0, 10.0 Hz), 4.32 (1H, dd, J=3.6, 10.0 Hz), 5.19 (1H, d, J=4.8 Hz), 6.51 (1H, d, J=5.2 Hz), 7.18 (1H, d, J=2.8 Hz), 7.24 (1H, dd, J=2.8, 8.8 Hz), 7.49 (1H, d, J=2.8 Hz), 7.53 (1H, s), 7.82 (1H, s), 7.97 (1H, s), 7.99 (1H, s), 8.26 (1H, d, J=8.8 Hz), 8.66 (1H, d, J=5.2 Hz), 8.80 (1H, s).

Example 616

N-{[4-(6-Carbamoyl-7-methoxy-4-quinolyl)oxy]-2-methylphenyl}-N'-(4-fluorophenyl)-N-methylurea After dissolving 6-carbamoyl-4-chloro-7-methoxyquinoline (100 mg, 0.2982 mmol), N-(4-fluorophenyl)-N'-(4-hydroxy-2-methylphenyl)-N'-methylurea (100 mg, 0.2917 mmol) and diisopropylethylamine (0.1 ml, 0.4375 mmol) in N-methylpyrrolidone (0.1 ml), the mixture was heated and stirred at 150° C. for 3 hours. After cooling to room temperature, water was added to the reaction solution, the mixture was extracted with ethyl acetate, the extract was washed with saturated brine and dried over anhydrous magnesium sulfate, and the solvent was distilled off under reduced pressure. The residue was purified by silica gel column chromatography (hexane-ethyl acetate-ethanol) and then by NH silica gel column chromatography (hexane-ethyl acetate-ethanol), after which diethyl ether was added to the obtained amorphous substance to make a suspension, the suspension was diluted with hexane, and the precipitate was filtered out, washed with diethyl ether:hexane=1:1 and dried by aspiration to obtain the title compound (11 mg, 0.023 mmol, 7.95%) as light yellow crystals.

$^1$H-NMR Spectrum (DMSO-d$_6$) δ (ppm): 2.21 (3H, s), 3.16 (3H, s), 4.02 (3H, s), 6.71 (1H, d, J=5.2 Hz), 7.05 (2H, t, J=8.8 Hz), 7.18 (1H, dd, J=2.8 Hz, 8.4 Hz), 7.28 (1H, d, J=2.8 Hz), 7.39-7.44 (3H, m), 7.51 (1H, s), 7.72 (1H, brs), 7.84 (1H, brs), 7.89 (1H, brs), 8.66 (1H, s), 8.70 (1H, d, J=5.2 Hz).

The starting materials were synthesized in the following manner.

Production Example 616-1

4-Benzyloxy-2-methylaniline

After dissolving 4-amino-3-cresol (10 g, 81.20 mmol) in dimethylsulfoxide (80 ml), sodium hydride (3.25 g, 81.20 mmol, 60% in oil) was added and the mixture was stirred for 15 minutes at room temperature under a nitrogen atmosphere. Benzyl bromide (4.83 ml, 40.60 mmol) was added, and the mixture was stirred overnight at room temperature under a nitrogen atmosphere. Water was added to the reaction solution, extraction was performed with diethyl ether/tetrahydrofuran, the extract was washed with saturated brine and dried over anhydrous magnesium sulfate, and the solvent was distilled off under reduced pressure. The residue was adsorbed onto silica gel, purified by silica gel column chromatography (hexane-ethyl acetate-ethanol) and then by NH silica gel column chromatography (hexane-ethyl acetate) to obtain the title compound (6.55 g, 30.72 mmol, 75.64%) as a violet oil.

$^1$H-NMR Spectrum (CDCl$_3$) δ (ppm): 2.16 (3H, s), 3.36 (2H, brs), 4.99 (2H, s), 6.61 (1H, d, J=8.4 Hz), 6.69 (1H, dd, J=2.8 Hz, 8.4 Hz), 6.75 (1H, d, J=2.8 Hz), 7.30 (1H, t, J=6.8 Hz), 7.37 (2H, t, J=6.8 Hz), 7.42 (2H, d, J=6.8 Hz).

Production Example 616-2

N-Methyl-4-benzyloxy-2-methylaniline

After dissolving 4-benzyloxy-2-methylaniline (6.55 g, 30.72 mmol) in N,N-dimethylformamide (10 ml) and methanol (60 ml), 1H-benzotriazole-1-methanol (4.58 g, 30.72 mmol) was added and the mixture was stirred for 30 minutes at room temperature. N,N-Dimethylformamide (20 ml) was added for complete dissolution of the precipitated crystals, sodium borohydride (2.32 g, 61.44 mmol) was added in small portions at a time at room temperature (internal temperature increase), and the mixture was stirred for 30 minutes. Water was added to the reaction solution, extraction was performed ethyl acetate, the extract was washed with saturated brine and dried over anhydrous magnesium sulfate, and the solvent was distilled off under reduced pressure. The residue was adsorbed onto silica gel and purified by silica gel column chromatography (hexane-ethyl acetate) to obtain the title compound (4.364 g, 19.20 mmol, 62.49%) as a brown oil.

¹H-NMR Spectrum (CDCl₃) δ (ppm): 2.13 (3H, s), 2.86 (3H, s), 4.99 (2H, s), 6.24 (1H, d, J=9.6 Hz), 6.79-6.81 (2H, m), 7.30 (1H, t, J=6.8 Hz), 7.37 (2H, t, J=6.8 Hz), 7.43 (2H, d, J=6.8 Hz).

Production Example 616-3

N-(4-Fluorophenyl)-N'-(4-hydroxy-2-methylphenyl)-N'-methylurea

After dissolving N-methyl-4-benzyloxy-2-methylaniline (2.64 g, 11.61 mmol) in N,N-dimethylformamide (20 ml), sodium hydride (1.16 g, 29.00 mmol, 60% in oil) was added and the mixture was stirred at 85° C. for 45 minutes under a nitrogen atmosphere. Phenyl N-(4-fluorophenyl)carbamate (3.50 g, 12.76 mmol) was added and the mixture was further stirred at 85° C. for 1 hour under a nitrogen atmosphere. After cooling to room temperature, water was added to the reaction solution, extraction was performed with ethyl acetate, the extract was washed with saturated brine and dried over anhydrous magnesium sulfate, and the solvent was distilled off under reduced pressure. The residue was adsorbed onto NH silica gel and subjected to crude purification by NH silica gel column chromatography acetate-ethanol) to obtain N'-(4-benzyloxy-2-methylphenyl)-N-(4-fluorophenyl)-N'-methylurea (2.66 g) as a yellow oil. This was dissolved in methanol (50 ml), and then 10% palladium carbon (0.2 g) was added and the mixture was stirred for 2 hours at room temperature under a hydrogen atmosphere. The catalyst was filtered off, and then filtrate was washed with ethanol, and the solvent was distilled off under reduced pressure. The precipitated crystals were suspended in ethanol, the suspension was diluted with diethyl ether and hexane, and the crystals were filtered out, washed with hexane and dried by aspiration to obtain the title compound (0.83 g, 3.0258 mmol, 41.86%) as brown crystals.

¹H-NMR Spectrum (DMSO-d₆) δ (ppm): 2.07 (3H, s), 3.04 (3H, s), 6.63 (1H, d, J=8.0 Hz), 6.67 (1H, s), 6.97-7.03 (3H, m), 7.34-7.39 (2H, m), 7.54 (1H, brs), 9.46 (1H, s).

Example 617

N-{[4-(7-Benzyloxy-6-cyano-4-quinolyl)oxy]-2-methylphenyl]}-N'-(4-fluorophenyl)-N-methylurea 6-Cyano-4-chloro-7-methoxyquinoline (90 mg, 0.3038 mmol) and N-(4-fluorophenyl)-N'-(4-hydroxy-2-methylphenyl)-N-methylurea (100 mg, 0.3646 mmol) were dissolved in dimethylsulfoxide (3 ml), and then sodium hydride (15 mg, 0.3646 mmol) was added and the mixture was heated and stirred at 85° C. for 1 hour. After cooling to room temperature, water was added to the reaction solution, extraction was performed with ethyl acetate, the extract was washed with saturated brine and dried over anhydrous magnesium sulfate, and the solvent was distilled off under reduced pressure. The residue was purified by NH silica gel column chromatography (ethyl acetate), and the obtained crystals were suspended in diethyl ether and filtered out, washed with diethyl ether and dried by aspiration to obtain the title compound (80 mg, 0.1502 mmol, 49.44%) as pink crystals.

¹H-NMR Spectrum (DMSO-d₆) δ (ppm): 2.21 (3H, s), 3.16 (3H, s), 5.46 (2H, s), 6.76 (1H, d, J=5.4 Hz), 7.05 (2H, t, J=8.8 Hz), 7.20 (1H, dd, J=2.4 Hz, 8.4 Hz), 7.29 (1H, d, J=2.4 Hz), 7.34-7.46 (6H, m), 7.54 (2H, d, J=6.8 Hz), 7.72 (1H, s), 7.91 (1H, brs), 8.75 (1H, s), 8.77 (1H, d, J=5.4 Hz).

Example 618

N-{[4-(6-Carbamoyl-7-methoxy-4-quinolyl)oxy]-2-fluorophenyl]}-N'-(4-fluorophenyl)-N-methylurea 6-Carbamoyl-4-chloro-7-methoxyquinoline (41 mg, 0.1744 mmol) and N-(2-fluoro-4-hydroxyphenyl)-N'-(4-fluorophenyl)-N-methylurea (57 mg, 0.2048 mmol) were dissolved in dimethylsulfoxide (1.0 ml), and then sodium hydride (8.4 mg, 0.2093 mmol) was added and the mixture was heated and stirred at 85° C. for 30 minutes. After cooling the reaction solution to room temperature, water was added and the precipitated crystals were filtered out. The crystals were then suspended in acetone:diethyl ether=1:2 and refiltered out, washed with diethyl ether and dried by aspiration to obtain the title compound (46 mg, 0.0961 mmol, 55.13%) as yellow crystals.

¹H-NMR Spectrum (DMSO-d₆) δ (ppm): 3.44 (3H, s), 4.01 (3H, s), 6.44 (1H, d, J=5.4 Hz), 6.99 (1H, brs), 7.10 (1H, dd, J=2.4 Hz, 8.4 Hz), 7.34 (2H, t, J=8.8 Hz), 7.38 (1H, d, J=8.4 Hz), 7.47 (1H, s), 7.59 (2H, dd, J=5.0 Hz, 8.8 Hz), 7.69 (1H, brs), 7.81 (1H, brs), 8.59 (1H, d, J=5.4 Hz), 8.69 (1H, s).

The starting materials were synthesized in the following manner.

Production Example 618-1

4-Benzyloxy-2-fluoronitrobenzene

3-Fluoro-4-nitrophenol (10 g, 63.65 mmol) was dissolved in N,N-dimethylformamide (120 ml), and then sodium hydride (2.68 g, 67.00 mmol, 60% in oil) was added and the mixture was stirred for 15 minutes at room temperature under a nitrogen atmosphere. After adding benzyl bromide (7.6 ml, 63.65 mmol), the mixture was stirred overnight at room temperature under a nitrogen atmosphere. Water was added to the reaction solution, and the precipitated crystals were filtered out, washed with water and dried by aspiration to obtain the title compound (16.06 g, quant.) as crude light yellow crystals. These were used without further purification for the following reaction.

¹H-NMR Spectrum (DMSO-d₆) δ (ppm): 5.25 (2H, s), 7.04 (1H, dd, J=1.6 Hz, 9.2 Hz), 7.27 (1H, dd, J=2.8 Hz, 14.0 Hz), 7.32-7.42 (3H, m), 7.46 (2H, d, J=6.8 Hz), 8.15 (1H, t, J=9.2 Hz).

Production Example 618-2

4-Benzyloxy-2-fluoroaniline

After dissolving the 4-benzyloxy-2-fluoronitrobenzene crude crystals (16.06 g, 63.65 mmol) in ethanol (1000 ml) and water (200 ml), electrolytic iron powder (14.0 g, 254.60 mmol) and ammonium chloride (27.2 g, 509.20 mmol) were added and the mixture was heated to reflux for 4.5 hours. The reaction solution was cooled to near room temperature, the insoluble portion was filtered off, washing was performed with ethanol and the solvent of the filtrate was distilled off under reduced pressure. The residue was dissolved in ethyl acetate, washed with saturated brine and dried over anhydrous magnesium sulfate, and the solvent was distilled off under reduced pressure. The residue was adsorbed onto silica gel and purified by silica gel column chromatography (hexane-ethyl acetate system) to obtain the title compound (11.25 g, 51.78 mmol, 81.35%) as a brown oil.

¹H-NMR Spectrum (CDCl₃) δ (ppm): 3.44 (2H, brs), 4.98 (2H, s), 6.10 (1H, dd, J=2.8 Hz, 8.8 Hz), 6.68-6.74 (2H, m), 7.30-7.43 (5H, m).

Production Example 618-3

N-{1-(1H-Benzotriazolyl)methyl}-4-benzyloxy-2-fluoroaniline

After dissolving 4-benzyloxy-2-fluoroaniline (11.25 g, 51.78 mmol) in methanol (300 ml), 1H-benzotriazole-1-methanol (8.11 g, 54.37 mmol) was added and the mixture was stirred for 10 hours at room temperature. The precipitated crystals were filtered out, washed with ethanol and dried by aspiration to obtain the title compound (12.01 g, 34.47 mmol, 66.57%) as colorless crystals.
¹H-NMR Spectrum (DMSO-d₆) δ (ppm): 4.92 (2H, s), 6.07 (2H, d, J=6.8 Hz), 6.64 (1H, dd, J=2.8 Hz, 9.2 Hz), 6.78 (1H, dd, J=2.8 Hz, 9.2 Hz), 6.82 (1H, m), 6.99 (1H, t, J=9.2 Hz), 7.24-7.38 (6H, m), 7.53 (1H, t, J=8.4 Hz), 7.99 (1H, d, J=8.4 Hz), 8.10 (1H, d, J=8.4 Hz).

Production Example 618-4

N-Methyl-4-benzyloxy-2-fluoroaniline

After dissolving N-{1-(1H-benzotriazolyl)methyl}-4-benzyloxy-2-fluoroaniline (14.13 g, 40.56 mmol) in N,N-dimethylformamide (200 ml), methanol (150 ml) and ethanol (50 ml), there was added sodium borohydride (3.06 g, 81.12 mmol) and the mixture was stirred for 2.5 hours at room temperature. There was further added sodium borohydride (0.78 g, 20.28 mmol), and the mixture was stirred for 13.5 hours at room temperature. Water was added to the reaction solution, extraction was performed with ethyl acetate-tetrahydrofuran, the extract was washed with saturated brine and dried over anhydrous magnesium sulfate, and the solvent was distilled off under reduced pressure. The residue was adsorbed onto silica gel and purified by silica gel column chromatography (hexane-ethyl acetate system) to obtain the title compound (5.98 g, 26.31 mmol, 64.87%) as light yellow crystals.
¹H-NMR Spectrum (DMSO-d₆) δ (ppm): 2.64 (3H, d, J=4.8 Hz), 4.97 (2H, s), 5.02 (1H, d, J=4.8 Hz), 6.55 (1H, t, J=9.2 Hz), 6.68 (1H, d, J=9.2 Hz), 6.79 (1H, J=13.2 Hz), 7.25-7.50 (5H, m).

Production Example 618-5

N-(4-Benzyloxy-2-fluorophenyl)-N'-(4-fluorophenyl)-N-methylurea

N-Methyl-4-benzyloxy-2-fluoroaniline (250 mg, 1.0805 mmol) was dissolved in N,N-dimethylformamide (5.0 ml), and then sodium hydride (65 mg, 1.6207 mmol, 60% in oil) was added and the mixture was stirred at 95° C. for 45 minutes under a nitrogen atmosphere. After adding 4-fluorophenyl isocyanate (0.14 ml, 1.1836 mmol), the mixture was stirred at 85° C. for 45 minutes under a nitrogen atmosphere. There was further added 4-fluorophenyl isocyanate (0.14 ml, 0.5094 mmol), and the mixture was stirred at 85° C. for 30 minutes under a nitrogen atmosphere. After cooling to room temperature, water was added to the reaction solution, extraction was performed with ethyl acetate, the extract was washed with saturated brine and dried over anhydrous magnesium sulfate, and the solvent was distilled off under reduced pressure. The residue was adsorbed onto NH silica gel and purified by NH silica gel column chromatography (hexane-ethyl acetate system) to obtain the title compound (0.105 g, 0.2881 mmol, 21.67%) as a light yellow oil.
¹H-NMR Spectrum (CDCl₃) δ (ppm): 2.16 (3H, s), 3.44 (3H, s), 5.01 (2H, s), 6.90 (1H, d, J=2.0 Hz), 6.78 (1H, dd, J=2.0 Hz, 8.4 Hz), 6.91 (1H, d, J=8.4 Hz), 7.19 (2H, t, J=8.4 Hz), 7.30-7.46 (5H, m).

Production Example 618-6

N-(2-Fluoro-4-hydroxyphenyl)-N'-(4-fluorophenyl)-N-methylurea

After dissolving N-(4-benzyloxy-2-fluorophenyl)-N'-(4-fluorophenyl)-N-methylurea (105 mg, 0.2881 mmol) in methanol (10 ml), 10% palladium carbon (20 mg) was added and the mixture was stirred for 45 minutes at room temperature under a hydrogen atmosphere. The catalyst was filtered off, and then was washed with ethanol, and the solvent of the filtrate was distilled off under reduced pressure. The precipitated crystals were suspended in diethyl ether, and then filtered out, washed with diethyl ether and dried by aspiration to obtain the title compound (57 mg, 0.2048 mmol, 71.10%) as colorless crystals.
¹H-NMR Spectrum (DMSO-d₆) δ (ppm): 2.07 (3H, s), 6.41 (1H, d, J=1.6 Hz), 6.54 (1H, dd, J=1.6 Hz, 8.4 Hz), 7.00 (1H, d, J=8.4 Hz), 7.38 (2H, t, J=8.8 Hz), 7.53 (2H, dd, J=4.8 Hz, 8.8 Hz).

Example 619

N-Cyclopropyl-N'-{[4-(6-(methoxy)carbamoyl-7-methoxy-4-quinolyl)oxy]-2-fluorophenyl})urea N-{[4-(6-carboxyl-7-methoxy-4-quinolyl)oxy]-2-fluorophenyl}}-N'-cyclopropylurea (40 mg, 0.0972 mmol) and O-methylhydroxylamine hydrochloride (16 mg, 0.1945 mmol) were used for reaction in the same manner as Example 412. After completion of the reaction, water was added to the reaction solution, extraction was performed with ethyl acetate, the extract was washed with saturated brine and dried over anhydrous magnesium sulfate, and the solvent was distilled off under reduced pressure. The obtained crystals were suspended in acetone and diluted with diethyl ether, and the crystals were filtered out, washed with diethyl ether and dried by aspiration to obtain the title compound (20 mg, 0.0454 mmol, 46.71%) as light yellow crystals.
¹H-NMR Spectrum (DMSO-d₆) δ (ppm): 0.41 (2H, m), 0.66 (2H, m), 2.56 (1H, m), 3.75 (3H, s), 3.99 (3H, s), 6.54 (1H, d, J=5.0 Hz), 6.82 (1H, s), 7.08 (1H, d, J=8.4 Hz), 7.32 (1H, d, J=8.4 Hz), 7.50 (1H, s), 8.19-8.24 (2H, m), 8.43 (1H, s), 8.67 (1H, d, J=5.0 Hz), 11.46 (1H, s).

Example 620

N-Cyclopropyl-N'-{[4-(6-(2-ethoxyethyl)carbamoyl-7-methoxy-4-quinolyl)oxy]-2-fluorophenyl]}urea N-{[4-(6-carboxyl-7-methoxy-4-quinolyl)oxy]-2-fluorophenyl]}-N'-cyclopropylurea (40 mg, 0.0972 mmol) and 2-ethoxyethylamine (17 mg, 0.1945 mmol) were used for reaction in the same manner as Example 412. After completion of the reaction, water was added to the reaction solution, and the precipitated crystals were filtered out. These were suspended in acetone and diluted with diethyl ether, and then the crystals were filtered out, washed with diethyl ether and dried by aspiration to obtain the title compound (33 mg, 0.0684 mmol, 70.93%) as light yellow crystals.
$^1$H-NMR Spectrum (DMSO-d$_6$) δ (ppm): 0.39-0.44 (2H, m), 0.63-0.68 (2H, m), 1.14 (3H, t, J=6.6 Hz), 2.57 (1H, m), 3.46-3.55 (6H, m), 4.04 (3H, s), 6.54 (1H, d, J=5.2 Hz), 6.81 (1H, m), 7.08 (1H, m), 7.33 (1H, dd, J=2.4 Hz, 11.6 Hz), 7.53 (1H, s), 8.19-8.24 (2H, m), 8.46 (1H, t, J=5.2 Hz), 8.63 (1H, s), 8.68 (1H, d, J=5.2 Hz).

Example 621

N-Cyclopropyl-N'-{[4-(6-(2-fluorocyclopropyl)carbamoyl-7-methoxy-4-quinolyl)oxy]-2-fluorophenyl]}urea N-{[4-(6-carboxyl-7-methoxy-4-quinolyl)oxy]-2-fluorophenyl]}-N'-cyclopropylurea (40 mg, 0.0972 mmol) and 2-fluorocyclopropylamine tosylate (39 mg, 0.1945 mmol) were used for reaction in the same manner as Example 412. After completion of the reaction, water was added to the reaction solution, extraction was performed with ethyl acetate, the extract was washed with saturated brine and dried over anhydrous magnesium sulfate, and the solvent was distilled off under reduced pressure. The residue was adsorbed onto silica gel and purified by silica gel column chromatography (ethyl acetate-ethanol system), and the obtained crystals were suspended in acetone:diethyl ether=1:3 and filtered out, washed with diethyl ether and dried by aspiration to obtain the title compound (12 mg, 0.0256 mmol, 26.35%) as colorless crystals.
$^1$H-NMR Spectrum (DMSO-d$_6$) δ (ppm): 0.42 (2H, m), 0.65 (2H, m), 1.05-1.18 (2H, m), 2.56 (1H, m), 2.93 (1H, m), 4.01 (3H, m), 4.54-4.93 (1H, m), 6.54 (1H, d, J=5.2 Hz), 6.80 (1H, m), 7.08 (1H, m), 7.32 (1H, dd, J=2.0 Hz, 11.6 Hz), 7.53 (1H, s), 8.22 (2H, m), 8.45 (1H, m), 8.52 (1H, s), 8.67 (1H, d, J=5.2 Hz).

Example 622

N-{[4-(6-(2-Cyanoethyl)carbamoyl-7-methoxy-4-quinolyl)oxy]-2-fluorophenyl]}-N'-cyclopropylurea N-{[4-(6-carboxyl-7-methoxy-4-quinolyl)oxy]-2-fluorophenyl]}-N'-cyclopropylurea (40 mg, 0.0972 mmol) and 2-cyanoethylamine (14 mg, 0.1945 mmol) were used for reaction in the same manner as Example 412. After completion of the reaction, water was added to the reaction solution, extraction was performed with ethyl acetate, the extract was washed with saturated brine and dried over anhydrous magnesium sulfate, and the solvent was distilled off under reduced pressure. The obtained crystals were suspended in acetone and diluted with diethyl ether, and then the crystals were filtered out, washed with diethyl ether and dried by aspiration to obtain the title compound (18 mg, 0.0684 mmol, 39.96%) as light yellow crystals.
$^1$H-NMR Spectrum (DMSO-d$_6$) δ (ppm): 0.41 (2H, m), 0.63-0.66 (2H, m), 2.56 (1H, m), 2.82 (2H, t, J=6.4 Hz), 3.57 (2H, q, J=6.4 Hz), 4.03 (3H, s), 6.54 (1H, d, J=5.2 Hz), 6.81 (1H, m), 7.08 (1H, m), 7.32 (1H, dd, J=2.4 Hz, 11.6 Hz), 7.54 (1H, s), 8.18-8.26 (2H, m), 8.61 (1H, s), 8.68 (1H, d, J=5.2 Hz), 8.73 (1H, m).

Example 623

N-[4-(6-Carbamoyl-7-methoxy-4-quinolyl)oxy-2-methylphenyl]-N'-methylurea

[4-(6-Carbamoyl-7-methoxy-4-quinolyl)oxy-2-methylphenyl]carbamic acid phenyl ester (70 mg) was added to dimethylsulfoxide (0.8 ml), and then a methylamine-containing 2N tetrahydrofuran solution (0.4 ml) was added and the mixture was stirred for 5 minutes. Water and ethyl acetate were added to the reaction solution, and the precipitated crystals were filtered out to obtain the title compound (48 mg).
$^1$H-NMR (DMSO-d$_6$) δ (ppm) 2.20 (3H, s), 2.65 (3H, d, J=4.8 Hz), 4.01 (3H, s), 6.38-6.47 (2H, m), 7.00-7.05 (1H, m), 7.09 (1H, d, J=2.8 Hz), 7.49 (1H, s), 7.71 (1H, brs), 7.74 (1H, s), 7.84 (1H, brs), 7.86-7.92 (1H, m), 8.63 (1H, d, J=5.2 Hz), 8.66 (1H, s)

Example 624

N-[4-(6-Carbamoyl-7-methoxy-4-quinolyl)oxy-2-methyl-phenyl]-N'-ethylurea

[4-(6-carbamoyl-7-methoxy-4-quinolyl)oxy-2-methylphenyl]-carbamic acid phenyl ester (65 mg) was added to dimethylsulfoxide (1.0 ml), and then an ethylamine-containing 2N tetrahydrofuran solution (0.37 ml) was added and the mixture was stirred for 5 minutes. Water and ethyl acetate were added to the reaction solution, and the precipitated crystals were filtered out to obtain the title compound (38 mg).
$^1$H-NMR (DMSO-d$_6$) δ (ppm) 1.06 (3H, t, J=7.2 Hz), 2.20 (3H, s), 3.06-3.16 (2H, m), 4.01 (3H, s), 6.44 (1H, d, J=5.6 Hz), 6.49-6.45 (1H, m), 7.00-7.04 (1H, m), 7.09 (1H, d, J=2.8 Hz), 7.49 (1H, s), 7.68 (1H, s), 7.71 (1H, brs), 7.84 (1H, brs), 7.88-7.95 (1H, m), 8.63 (1H, d, J=5.6 Hz), 8.66 (1H, s)

Example 625

N-[2-Fluoro-4-([6-cyano-7-([3-(1-piperidino)propyl]oxy)-4-quinolyl]oxy)phenyl]-N'-cyclopropylurea Cyclopropylamine (0.05 ml) was added to dimethylsulfoxide (0.5 ml), and then [2-fluoro-4-([6-cyano-7-([3-(1-piperidino)propyl]oxy)-4-quinolyl]oxy)phenyl]carbamic acid phenyl ester (66 mg) was dissolved therein and the solution was stirred for 10 minutes. Water and ethyl acetate were added to the reaction solution, and the precipitated crystals were filtered out to obtain the title compound (33 mg).
$^1$H-NMR (DMSO-d$_6$) δ (ppm) 0.38-0.45 (2H, m), 0.61-0.69 (2H, m), 1.30-1.55 (6H, m), 1.92-2.02 (2H, m), 2.30-2.50 (6H, m), 2.53-2.59 (1H, m), 4.33 (2H, t, J=6.0 Hz), 6.59 (1H, d, J=5.6 Hz), 6.82-6.86 (1H, m), 7.07-7.13 (1H, m), 7.31-7.37 (1H, m), 7.61 (1H, s), 8.20-8.29 (2H, m), 8.72-8.77 (2H, m)

The starting material was synthesized in the following manner.

Production Example 625-1

[2-Fluoro-4-([6-cyano-7-([3-(1-piperidino)propyl]oxy)-4-quinolyl]oxy)phenyl]carbamic acid phenyl ester The title compound (33 mg) was obtained from 2-fluoro-4-([6-cyano-7-([3-(1-piperidino)propyl]oxy)-4-quinolyl]oxy)phenylamine (66 mg), by the method described in Production Example 141-1.
$^1$H-NMR (DMSO-d$_6$) δ (ppm) 1.40-1.75 (6H, m), 1.90-2.15 (4H, m) 2.50-2.67 (2H, m), 3.13-3.27 (2H, m), 4.30-4.38 (2H, m), 6.54 (1H, d, J=5.2 Hz), 6.97-7.06 (2H, m), 7.20-7.30 (6H, m), 8.01 (1H, s), 8.27 (1H, brs), 8.66 (1H, s), 8.72 (1H, d, J=5.2 Hz)

Example 626

N-[4-(7-Benzyloxy-6-cyanoquinolin-4-yloxy)-2-chloro-phenyl]-N'-methylurea

[4-(7-Benzyloxy-6-cyanoquinolin-4-yloxy)-2-chlorophenyl]carbamic acid phenyl ester (1.17 g) was added to dimethylformamide (6 ml), and then a methylamine-containing 2N tetrahydrofuran solution (0.4 ml) was added and the mixture was stirred for 10 minutes. Water (15 ml) was added, and the precipitated crystals were filtered out and washed with diethyl ether to obtain the title compound (968 mg).

$^1$H-NMR (DMSO-$d_6$) δ (ppm) 2.66 (3H, d, J=4.0 Hz), 5.45 (2H, s), 6.59 (1H, d, J=5.2 Hz), 6.86-6.92 (1H, m), 7.24 (1H, dd, J=8.8, 4.8 Hz), 7.32-7.57 (6H, m), 7.71 (1H, s), 8.12 (1H, s), 8.21-8.28 (1H, m), 8.73 (1H, d, J=5.2 Hz), 8.76 (1H, s)

The starting material was synthesized in the following manner.

Production Example 626-1

[4-(7-Benzyloxy-6-cyanoquinolin-4-yloxy)-2-chlorophenyl]-carbamic acid phenyl ester The title compound (1.69 mg) was obtained from 4-(4-amino-3-chlorophenyl)-7-benzyloxy-6-cyanoquinoline (1.68 g), by the method described in Production Example 141-1.

$^1$H-NMR (DMSO-$d_6$) δ (ppm) 5.28 (2H, s), 6.44 (1H, d, J=5.2 Hz), 7.09 (1H, dd, J=2.8, 9.2 Hz), 7.13-7.50 (13H, m), 8.24-8.30 (1H, m), 8.60-8.65 (2H, m)

Example 627

N-[2-Chloro-4-(6-cyano-7-hydroxyquinolin-4-yloxy)-phenyl]-N'-methylurea

After adding N-[4-(7-benzyloxy-6-cyanoquinolin-4-yloxy)-2-chlorophenyl]-N'-methylurea (968 mg) and thioanisole (3.7 ml) to trifluoroacetic acid (10 ml), the mixture was stirred overnight at 50° C. It was then concentrated under reduced pressure, ethyl acetate and aqueous sodium bicarbonate were added and the precipitated crystals were filtered out and washed with ethyl acetate to obtain the title compound (849 mg).

$^1$H-NMR (DMSO-$d_6$) δ (ppm) 2.66 (3H, d, J=4.0 Hz), 5.30 (1H, d, J=5.2 Hz), 6.37 (1H, s), 6.83-6.90 (1H, m), 7.12-7.16 (1H, m), 7.33-7.35 (1H, m), 8.00 (1H, s), 8.08 (1H, brs), 8.14-8.19 (2H, m)

Example 628

N-(4-{6-Cyano-7-[(2R)-oxiran-2-yl]methoxyquinolin-4-yloxy}-2-chlorophenyl)-N'-methylurea N-[2-Chloro-4-(6-cyano-7-hydroxyquinolin-4-yloxy)phenyl]-N'-methylurea (600 mg) was added to dimethylformamide (4 ml), and then (2R)-(–)-glycidyl p-toluenesulfonate (484 mg) and potassium carbonate (450 mg) were added thereto and the mixture was heated at 50° C. for 4 hours. Water was added to the reaction solution, extraction was performed with ethyl acetate, the organic layer was washed with water and saturated brine in that order and dried over anhydrous sodium sulfate, and the solvent was distilled off under reduced pressure. The obtained crude product was recrystallized with ethyl acetate to obtain the title compound (650 mg) as light yellow crystals.

$^1$H-NMR (DMSO-$d_6$) δ (ppm) 2.68 (3H, d, J=4.8 Hz), 2.80-2.96 (2H, m), 3.45-3.51 (1H, m), 4.18 (1H, dd, J=11.6, 6.4 Hz), 4.73 (1H, dd, J=11.6, 2.0 Hz), 6.61 (1H, d, J=5.2 Hz), 6.86-6.93 (1H, m), 7.26 (1H, dd, J=9.2, 2.8 Hz), 7.51 (1H, d, J=2.8 Hz), 7.66 (1H, s), 8.14 (1H, s), 8.27 (1H, d, J=9.2 Hz), 8.75 (1H, d, J=5.2 Hz), 8.78 (1H. s)

Example 629

N-(4-{6-Cyano-7-[(2R)-2-hydroxy-3-pyrrolidin-1-ylpropoxy]quinolin-4-yloxy}-2-chlorophenyl)-N'-methylurea After adding tetrahydrofuran (1.0 ml) and pyrrolidine (0.10 ml) to N-(4-{6-cyano-7-[(2R)-oxiran-2-yl]methoxyquinolin-4-yloxy}-2-chlorophenyl)-N'-methylurea (110 mg), the mixture was heated at 60° C. for 2 hours. The reaction solution was purified by NH silica gel column chromatography (ethyl acetate-methanol system) to obtain the title compound (65 mg) as light yellow crystals.

$^1$H-NMR (DMSO-$d_6$) δ (ppm) 1.55-1.73 (4H, m), 2.45-2.58 (5H, m) 2.68-2.77 (4H, m), 4.00-4.06 (1H, m), 4.22 (1H, dd, J=10.4, 5.6 Hz), 4.32 (1H, dd, J=10.4, 3.2 Hz), 5.00-5.05 (1H, m), 6.59 (1H, d, J=5.2 Hz), 6.86-6.93 (1H, m), 7.26 (1H, dd, J=9.2, 2.8 Hz), 7.51 (1H, d, J=2.8 Hz), 7.63 (1H, s), 8.14 (1H, brs), 8.27 (1H, dd, J=9.2, 2.8 Hz), 8.72-8.76 (2H, m).

Example 630

N-(4-{6-Cyano-7-[(2R)-2-hydroxy-3-piperidin-1-ylpropoxy]quinolin-4-yloxy}-2-chlorophenyl)-N'-methylurea After adding tetrahydrofuran (2.0 ml) and piperidine (0.20 ml) to N-(4-{6-cyano-7-[(2R)-oxiran-2-yl]methoxyquinolin-4-yloxy}-2-chlorophenyl)-N'-methylurea (110 mg), the mixture was heated at 60° C. for 3 hours. The reaction solution was purified by NH silica gel column chromatography (ethyl acetate-methanol system) to obtain the title compound (80 mg) as light yellow crystals.

$^1$H-NMR (DMSO-$d_6$) δ (ppm) 1.30-1.42 (2H, m), 1.45-1.57 (4H, m), 2.35-2.50 (6H, m), 2.68 (3H, d, J=4.4 Hz), 4.00-4.08 (1H, m), 4.22 (1H, dd, J=10.4, 6.0 Hz), 4.32 (1H, dd, J=10.4, 3.2 Hz), 4.93-4.97 (1H, m), 6.59 (1H, d, J=5.6 Hz), 6.86-6.93 (1H, m), 7.26 (1H, dd, J=9.2, 2.8 Hz), 7.51 (1H, d, J=2.8 Hz), 7.64 (1H, s), 8.14 (1H, brs), 8.27 (1H, dd, J=9.2, 2.8 Hz), 8.72-8.76 (2H, m).

Example 631

N-(4-{6-Cyano-7-[3-diethylamino-(2R)-2-hydroxypropoxy]quinolin-4-yloxy}-2-chlorophenyl)-N'-methylurea After adding tetrahydrofuran (3.0 ml) and diethylamine (1.50 ml) to N-(4-{6-cyano-7-[(2R)-oxiran-2-yl]methoxyquinolin-4-yloxy}-2-chlorophenyl)-N'-methylurea (100 mg), the mixture was heated at 60° C. for 5 hours. The reaction solution was purified by NH silica gel column chromatography (ethyl acetate-methanol) to obtain the title compound (75 mg) as light yellow crystals.

$^1$H-NMR (DMSO-$d_6$) δ (ppm) 0.98 (6H, t, J=7.2 Hz), 2.40-2.70 (9H, m), 3.93-4.00 (1H, m), 4.23 (1H, dd, J=10.4, 5.6 Hz), 4.32 (1H, dd, J=10.4, 3.6 Hz), 4.93 (1H, brs), 6.59 (1H, d, J=5.6 Hz), 6.86-6.93 (1H, m), 7.26 (1H, dd, J=9.2, 2.8

Hz), 7.51 (1H, d, J=2.8 Hz), 7.63 (1H, s), 8.14 (1H, brs), 8.27 (1H, dd, J=9.2, 2.8 Hz), 8.72-8.76 (2H, m).

Example 632

Methyl 4-(3-chloro-4-(((methylamino)carbonyl) amino)phenoxy)-7-methoxy-6-quinolinecarboxylate Phenyl N-(2-chloro-4-(7-methoxy-6-methoxycarbonyl-4-quinolyl)oxyphenyl)carbamate (1.92 g, 4.00 mmol) and 40% methylamine (methanol solution) (2 ml) were stirred in dimethylformamide (8 ml) at room temperature for 30 minutes. The reaction solution was distributed between ethyl acetate and water, the organic layer was washed with water and saturated brine and dried over anhydrous magnesium sulfate, and the drying agent was filtered out and the filtrate distilled off under reduced pressure. The obtained crude product was suspended in ethyl acetate, the suspension was diluted with hexane, and the crystals were filtered out, washed with hexane and blow-dried to obtain the title compound (1.41 g, 3.39 mmol, 85%) as white crystals.
$^1$H-NMR Spectrum (DMSO-$d_6$) δ (ppm): 2.68 (3H, d, J=4.4 Hz), 3.87 (3H, s), 3.99 (3H, s), 6.54 (1H, d, J=5.2 Hz), 6.89 (1H, q, J=4.4 Hz), 7.25 (1H, dd, J=2.8, 9.0 Hz), 7.50 (1H, d, J=2.8 Hz), 7.54 (1H, s), 8.13 (1H, s), 8.26 (1H, d, J=9.0 Hz), 8.58 (1H, s), 8.69 (1H, d, J=5.2 Hz).

Example 633

4-(3-Chloro-4-(((methylamino)carbonyl)amino)phenoxy)-7-methoxy-6-quinolinecarboxylic acid After adding methanol (14 ml) and a 2N sodium hydroxide aqueous solution (7 ml) to methyl 4-(3-chloro-4-(((methylamino)carbonyl)amino)phenoxy)-7-methoxy-6-quinolinecarboxylate (1.31 g, 3.15 mmol), the mixture was stirred at 60° C. for 30 minutes. The reaction solution was cooled to room temperature, 2N hydrochloric acid was added for neutralization, the methanol was distilled off, and the precipitated white crystals were filtered out, thoroughly washed with water and dried at 60° C. to obtain the title compound (1.26 g, 3.15 mmol, 100%).
$^1$H-NMR Spectrum (DMSO-$d_6$) δ (ppm): 2.68 (3H, d, J=4.4 Hz), 3.98 (3H, s), 6.54 (1H, d, J=5.0 Hz), 6.89 (1H, q, J=4.4 Hz), 7.25 (1H, dd, J=2.8, 9.0 Hz), 7.48-7.53 (2H, m), 8.13 (1H, s), 8.25 (1H, d, J=9.0 Hz), 8.54 (1H, s), 8.69 (1H, d, J=5.0 Hz), 13.12 (1H, brs).

Example 634

N6-Methyl-4-(3-chloro-4-(((methylamino)carbonyl) amino)phenoxy)-7-methoxy-6-quinolinecarboxamide After dissolving 4-(3-chloro-4-(((methylamino)carbonyl) amino)phenoxy)-7-methoxy-6-quinolinecarboxylic acid (100 mg, 0.250 mmol) in dimethylformamide (3 ml), there were added a 40% methylamine-methanol solution (0.100 ml), triethylamine (0.250 ml) and 1H-1,2,3-benzotriazol-1-yloxy)(tri(dimethylamino))phosphoniumhexafluorophosphate (221 mg, 0.500 mmol) in that order at room temperature, and the mixture was stirred for 15 hours. The reaction solution was distributed between ethyl acetate and water, and the organic layer was washed with water and saturated brine and dried over anhydrous magnesium sulfate. The solvent was distilled off, the residue was suspended in ethyl acetate and diluted with hexane, and the crystals were filtered out and blow-dried to obtain the title compound (85.0 mg, 0.204 mmol, 82%) as white crystals.
$^1$H-NMR Spectrum (DMSO-$d_6$) δ (ppm): 2.68 (3H, d, J=4.2 Hz), 2.84 (3H, d, J=4.2 Hz), 4.02 (3H, s), 6.53 (1H, d, J=5.2 Hz), 6.88 (1H, q, J=4.2 Hz), 7.22 (1H, dd, J=2.8, 9.2 Hz), 7.45 (1H, d, J=2.8 Hz), 7.52 (1H, s), 8.12 (1H, s), 8.24 (1H, d, J=9.2 Hz), 8.36 (1H, q, J=4.2 Hz), 8.59 (1H, s), 8.67 (1H, d, J=5.2 Hz).

Example 635

N6-Ethyl-4-(3-chloro-4-(((methylamino)carbonyl) amino)phenoxy)-7-methoxy-6-quinolinecarboxamide The title compound (93.0 mg, 0.217 mmol, 87%) was obtained as white crystals from 4-(3-chloro-4-(((methylamino)carbonyl)amino)phenoxy)-7-methoxy-6-quinolinecarboxylic acid (100 mg, 0.250 mmol) and 2.0M ethylamine (tetrahydrofuran solution), by the same procedure as in Example 634.
$^1$H-NMR Spectrum (DMSO-$d_6$) δ (ppm): 1.15 (3H, t, J=7.2 Hz), 2.68 (3H, d, J=4.4 Hz), 3.28-3.38 (2H, m), 4.02 (3H, s), 6.53 (1H, d, J=5.2 Hz), 6.87 (1H, q, J=4.4 Hz), 7.21 (1H, dd, J=2.8, 9.2 Hz), 7.47 (1H, d, J=2.8 Hz), 7.51 (1H, s), 8.11 (1H, s), 8.25 (1H, d, J=9.2 Hz), 8.38 (1H, m), 8.54 (1H, s), 8.66 (1H, d, J=5.2 Hz).

Example 636

N6-Cyclopropyl-4-(3-chloro-4-(((methylamino)carbonyl)amino)phenoxy)-7-methoxy-6-quinolinecarboxamide The title compound (66.0 mg, 0.150 mmol, 60%) was obtained as white crystals from 4-(3-chloro-4-(((methylamino)carbonyl)amino)phenoxy)-7-methoxy-6-quinolinecarboxylic acid (100 mg, 0.250 mmol) and cyclopropylamine, by the same procedure as in Example 634.
$^1$H-NMR Spectrum (DMSO-$d_6$) δ (ppm): 0.59 (2H, m), 0.69 (2H, m), 2.68 (3H, d, J=4.8 Hz), 2.87 (1H, m), 3.99 (3H, s), 6.53 (1H, d, J=5.2 Hz), 6.88 (1H, q, J=4.8 Hz), 7.22 (1H, dd, J=2.8, 9.2 Hz), 7.47 (1H, d, J=2.8 Hz), 7.49 (1H, s), 8.12 (1H, s), 8.25 (1H, d, J=9.2 Hz), 8.34 (1H, d, J=4.0 Hz), 8.41 (1H, s), 8.66 (1H, d, J=5.2 Hz).

Example 637

N6-Methoxy-4-(3-chloro-4-(((methylamino)carbonyl)amino)phenoxy)-7-methoxy-6-quinolinecarboxamide The title compound (51.0 mg, 0.118 mmol, 47%) was obtained as white crystals from 4-(3-chloro-4-(((methylamino)carbonyl)amino)phenoxy)-7-methoxy-6-quinolinecarboxylic acid (100 mg, 0.250 mmol) and methoxyamine hydrochloride, by the same procedure as in Example 634.
$^1$H-NMR Spectrum (DMSO-$d_6$) δ (ppm): 2.56 (3H, d, J=4.4 Hz), 3.74 (3H, s), 3.99 (3H, s), 6.54 (1H, d, J=5.2 Hz), 6.88 (1H, q, J=4.4 Hz), 7.24 (1H, dd, J=2.8, 9.2 Hz), 7.48 (1H, d, J=2.8 Hz), 7.50 (1H, s), 8.12 (1H, s), 8.25 (1H, d, J=9.2 Hz), 8.43 (1H, s), 8.67 (1H, d, J=5.2 Hz), 11.46 (1H, s).

Example 638

N6-(2-Methoxyethyl)-4-(3-chloro-4-(((methylamino)carbonyl)amino)phenoxy)-7-methoxy-6-quinolinecarboxamide The title compound (71.0 mg, 0.154 mmol, 62%) was obtained as white crystals from 4-(3-chloro-4-(((methylamino)carbonyl)amino)phenoxy)-7-methoxy-6-quinolinecarboxylic acid (100 mg, 0.250 mmol) and 2-methoxyethylamine, by the same procedure as in Example 634.

$^1$H-NMR Spectrum (DMSO-$d_6$) d (ppm): 2.68 (3H, d, J=4.4 Hz), 3.30 (3H, s), 3.46-3.52 (4H, m), 4.03 (3H, s), 6.54 (1H, d, J=5.2 Hz), 6.88 (1H, q, J=4.4 Hz), 7.23 (1H, dd, J=2.8, 9.2 Hz), 7.48 (1H, d, J=2.8 Hz), 7.53 (1H, s), 8.12 (1H, s), 8.25 (1H, d, J=9.2 Hz), 8.46 (1H, m), 8.61 (1H, s), 8.67 (1H, d, J=5.2 Hz).

Example 639

N6-(2-Fluoroethyl)-4-(3-chloro-4-(((methylamino)carbonyl)amino)phenoxy)-7-methoxy-6-quinolinecarboxamide The title compound (86.0 mg, 0.192 mmol, 77%) was obtained as white crystals from 4-(3-chloro-4-(((methylamino)carbonyl)amino)phenoxy)-7-methoxy-6-quinolinecarboxylic acid (100 mg, 0.250 mmol) and 2-fluoroethylamine hydrochloride, by the same procedure as in Example 634.

$^1$H-NMR Spectrum (DMSO-$d_6$) δ (ppm): 2.68 (3H, d, J=4.4 Hz), 3.59 (1H, m), 3.67 (1H, m), 4.03 (3H, s), 4.50 (1H, m), 4.62 (1H, m), 6.54 (1H, d, J=5.2 Hz), 6.88 (1H, q, J=4.4 Hz), 7.24 (1H, dd, J=2.8, 9.2 Hz), 7.48 (1H, d, J=2.8 Hz), 7.53 (1H, s), 8.12 (1H, s), 8.24 (1H, d, J=9.2 Hz), 8.58-8.62 (2H, m), 8.67 (1H, d, J=5.2 Hz).

Example 640

N6-((2R)Tetrahydro-2-furanylmethyl)-4-(3-chloro-4-(((methylamino)carbonyl)amino)phenoxy)-7-methoxy-6-quinolinecarboxamide The title compound (81.0 mg, 0.167 mmol, 67%) was obtained as a white powder from 4-(3-chloro-4-(((methylamino)carbonyl)amino)phenoxy)-7-methoxy-6-quinolinecarboxylic acid (100 mg, 0.250 mmol) and R-tetrahydrofurfurylamine, by the same procedure as in Example 634.

$^1$H-NMR Spectrum (DMSO-$d_6$) δ (ppm): 1.62 (1H, m), 1.80-2.00 (3H, m), 2.68 (3H, d, J=4.4 Hz), 3.40 (2H, m), 3.66 (1H, dd, J=3.6, 14.0 Hz), 3.81 (1H, dd, J=4.0, 14.0 Hz), 3.99 (1H, m), 4.02 (3H, s), 6.54 (1H, d, J=5.2 Hz), 6.88 (1H, q, J=4.4 Hz), 7.23 (1H, dd, J=2.8, 8.8 Hz), 7.48 (1H, d, J=2.8 Hz), 7.54 (1H, s), 8.12 (1H, s), 8.24 (1H, d, J=8.8 Hz), 8.43 (1H, m), 8.61 (1H, s), 8.67 (1H, d, J=5.2 Hz).

Example 641

N6-((2S)Tetrahydro-2-furanylmethyl)-4-(3-chloro-4-(((methylamino)carbonyl)amino)phenoxy)-7-methoxy-6-quinolinecarboxamide The title compound (85.0 mg, 0.175 mmol, 70%) was obtained as a white powder from 4-(3-chloro-4-(((methylamino)carbonyl)amino)phenoxy)-7-methoxy-6-quinolinecarboxylic acid (100 mg, 0.250 mmol) and S-tetrahydrofurfurylamine), by the same procedure as in Example 634.

Example 642

N6-(2-Ethoxyethyl)-4-(3-chloro-4-(((methylamino)carbonyl)amino)phenoxy)-7-methoxy-6-quinolinecarboxamide The title compound (94.0 mg, 0.199 mmol, 80%) was obtained as a white powder from 4-(3-chloro-4-(((methylamino)carbonyl)amino)phenoxy)-7-methoxy-6-quinolinecarboxylic acid (100 mg, 0.250 mmol) and 2-ethoxyethylamine, by the same procedure as in Example 634.

$^1$H-NMR Spectrum (DMSO-$d_6$) δ (ppm): 1.15 (3H, t, J=6.8 Hz), 2.68 (3H, d, J=4.4 Hz), 3.45-3.56 (6H, m), 4.04 (3H, s), 6.54 (1H, d, J=5.2 Hz), 6.89 (1H, q, J=4.4 Hz), 7.23 (1H, dd, J=2.8, 9.2 Hz), 7.48 (1H, d, J=2.8 Hz), 7.54 (1H, s), 8.13 (1H, s), 8.25 (1H, dd, J=2.8, 9.2 Hz), 8.46 (1H, m), 8.64 (1H, s), 8.67 (1H, d, J=5.2 Hz).

Example 643

N6-Isobutoxy-4-(3-chloro-4-(((methylamino)carbonyl)amino)phenoxy)-7-methoxy-6-quinolinecarboxamide The title compound (72.0 mg, 0.152 mmol, 61%) was obtained as a white powder from 4-(3-chloro-4-(((methylamino)carbonyl)amino)phenoxy)-7-methoxy-6-quinolinecarboxylic acid (100 mg, 0.250 mmol) and isobutoxylamine hydrochloride, by the same procedure as in Example 634.

$^1$H-NMR Spectrum (DMSO-$d_6$) δ (ppm): 0.95 (6H, d, J=6.8 Hz), 1.97 (1H, m), 2.68 (3H, d, J=4.4 Hz), 3.71 (2H, d, J=6.8 Hz), 3.99 (3H, s), 6.54 (1H, d, J=5.2 Hz), 6.89 (1H, q, J=4.4 Hz), 7.23 (1H, dd, J=2.8, 9.2 Hz), 7.48 (1H, d, J=2.8 Hz), 7.50 (1H, s), 8.13 (1H, s), 8.25 (1H, dd, J=2.8, 9.2 Hz), 8.36 (1H, s), 8.67 (1H, d, J=5.2 Hz), 11.35 (1H, br s).

Example 644

4-(3-Chloro-4-(((cyclopropylamino)carbonyl)amino)phenoxy)-7-((2R)-3-diethylamino-2-hydroxypropoxy)-6-quinolinecarboxamide After adding (2R)oxiran-2-ylmethyl 4-methyl-1-benzenesulfonate (308 mg, 1.35 mmol), potassium carbonate (149 mg, 1.08 mmol) and dimethylformamide (9 ml) to 4-(3-chloro-4-(((cyclopropylamino)carbonyl)amino)phenoxy)-7-hydroxy-6-quinolinecarboxamide (372.0 mg, 0.90 mmol), the mixture was stirred at 60° C. for 6 hours. Next, diethylamine (2 ml) was added and the mixture was further stirred overnight at 50° C. The reaction solution was distributed between ethyl acetate and water, and the organic layer was washed with water and saturated brine and then dried over anhydrous sodium sulfate. The solvent was distilled off, the residue was subjected to silica gel column chromatography (eluent—ethyl acetate:methanol=95:5), the fraction containing the target substance was concentrated, and crystals were precipitated from diethyl ether, filtered out and blow-dried to obtain the title compound (177.5 mg, 0.327 mmol, 36.3%) as white crystals.

$^1$H-NMR Spectrum (DMSO-$d_6$) δ (ppm): 0.42 (2H, m), 0.65 (2H, m), 0.94 (6H, t, J=7.2 Hz), 2.44-2.60 (7H, m), 3.98 (1H, m), 4.21 (1H, dd, J=5.6, 10.0 Hz), 4.31 (1H, dd, J=3.2, 10.0 Hz), 5.09 (1H, d, J=4.4 Hz), 6.51 (1H, d, J=5.2 Hz), 7.18 (1H, d, J=2.8 Hz), 7.24 (1H, dd, J=2.8, 8.8 Hz), 7.49 (1H, d, J=2.8 Hz), 7.52 (1H, s), 7.84 (1H, s), 7.97 (1H, s), 8.00 (1H, s), 8.26 (1H, d, J=8.8 Hz), 8.65 (1H, d, J=5.2 Hz), 8.81 (1H, s).

Example 645

N6-Methyl-7-(benzyloxy)-4-(3-chloro-(4-((methylamino)carbonyl)amino)phenoxy)-6-quinolinecarboxamide The title compound (466 mg, 0.950 mmol, 81.6%) was obtained as light brown crystals from phenyl N-(4-(7-(benzyloxy)-6-(methylamino)carbonyl-4-quinolyl)oxy-2-chlorophenyl)carbamate (645 mg, 1.16 mmol) and 2M methylamine-tetrahydrofuran solution, by the same procedure as in Example 11.
$^1$H-NMR Spectrum (DMSO-$d_6$) δ (ppm): 2.66 (3H, d, J=4.4 Hz), 2.81 (3H, d, J=4.4 Hz), 5.42 (2H, s), 6.51 (1H, d, J=5.2 Hz), 6.86 (1H, q, J=4.4 Hz), 7.21 (1H, dd, J=2.8, 9.2 Hz), 7.30-7.45 (4H, m), 7.52-7.55 (3H, m), 8.10 (1H, s), 8.22 (1H, d, J=9.2 Hz), 8.38 (1H, q, J=4.4 Hz), 8.49 (1H, s), 8.62 (1H, d, J=5.2 Hz).
The starting materials were synthesized in the following manner.

Production Example 645-1

Phenyl 4-(((2,2-dimethyl-4,6-dioxo-1,3-dioxan-5-ylidene)methyl)amino)-2-hydroxy benzoate After adding Meldrum acid (29.2 g, 202 mmol), triethyl orthoformate (200 ml) and isopropanol (200 ml) to phenyl 4-aminosalicylate (42.2 g, 184 mmol), the mixture was heated and stirred at 100° C. for 1 hour. After allowing the reaction solution to cool to room temperature, it was further stirred overnight. The precipitated crystals were filtered out, washed with isopropanol and diethyl ether and blow-dried to obtain the title compound (69.5 g, 181 mmol, 99%) as white crystals.
$^1$H-NMR Spectrum (DMSO-$d_6$) δ (ppm): 1.69 (6H, s), 7.21-7.28 (2H, m), 7.29-7.36 (3H, m), 7.44-7.52 (2H, m), 8.04 (1H, d, J=8.4 Hz), 8.64 (1H, s), 10.52 (1H, br s), 11.24 (1H, br s).

Production Example 645-2

Phenyl 7-(benzyloxy)-4-oxo-1,4-dihydro-6-quinolinecarboxylate

Phenyl 4-(((2,2-dimethyl-4,6-dioxo-1,3-dioxan-5-ylidene)methyl)amino)-2-hydroxybenzoate (11.5 g, 0.030 mmol), benzyl bromide (5.64 g, 0.033 mmol) and potassium carbonate (4.56 g, 0.033 mmol) were stirred in dimethylformamide (45 ml) at 80° C. for 3 hours. The reaction solution was distributed between a diethyl ether-tetrahydrofuran mixed solvent and water, the organic layer was washed with water and saturated brine and dried over anhydrous magnesium sulfate, and the drying agent was filtered out and the filtrate distilled off under reduced pressure. The obtained crude product was suspended in ethanol, the suspension was diluted with hexane, and the crystals were filtered out, washed with hexane and blow-dried to obtain white crystals. The crystals were then heated and stirred for 1 hour in Dowtherm A (50 ml) at 200° C. After allowing the reaction solution to cool to room temperature, diethyl ether (25 ml) was added and the mixture was further stirred overnight. The precipitated crystals were filtered out, washed with diethyl ether and blow-dried to obtain the title compound (1.20 g, 3.23 mmol, 11%) as white crystals.
$^1$H-NMR Spectrum (DMSO-$d_6$) δ (ppm): 5.33 (2H, s), 6.03 (1H, d, J=7.4 Hz), 7.19 (1H, s), 7.21-7.27 (2H, m), 7.28-7.36 (2H, m), 7.36-7.43 (2H, m), 7.43-7.50 (2H, m), 7.52-7.58 (2H, m), 7.90 (1H, d, J=7.4 Hz), 8.71 (1H, s), 11.79 (1H, br s).

Production Example 645-3

N6-Methyl-7-(benzyloxy)-4-chloro-6-quinolinecarboxamide

After adding thionyl chloride (12 ml) and a catalytic amount of dimethylformamide to phenyl 7-(benzyloxy)-4-oxo-1,4-dihydro-6-quinolinecarboxylate (1.20 g, 3.23 mmol), the mixture was heated to reflux for 2 hours while stirring. The reaction solution was concentrated under reduced pressure and azeotropically distilled twice with toluene, the residue was suspended in dimethylformamide (20 ml), a 40% methylamine-methanol solution (5 ml) was gradually added while cooling in an ice water bath, and the mixture was stirred for 1 hour. The reaction solution was distributed between ethyl acetate-tetrahydrofuran (1:1) and water, and the organic layer was washed with saturated aqueous ammonium chloride solution, water and saturated brine and then dried over anhydrous sodium sulfate. The solvent was distilled off, diethyl ether and then hexane were added for crystallization, and the crystals were filtered out and blow-dried to obtain the title compound (947 mg, 2.90 mmol, 89.7%) as light yellow crystals.
$^1$H-NMR Spectrum (CDCl$_3$) δ (ppm): 2.97 (3H, d, J=4.8 Hz), 5.35 (2H, s), 7.40-7.52 (6H, m), 7.64 (1H, s), 7.91 (1H, m), 8.75 (1H, q, J=4.8 Hz), 9.16 (1H, s).

Production Example 645-4

N6-Methyl-4-(4-amino-3-chlorophenoxy)-7-(benzyloxy)-6-quinolinecarboxamide

After dissolving 4-amino-3-chlorophenol (624 mg, 4.35 mmol) in dimethylsulfoxide (15 ml), sodium hydride (174 mg, 4.35 mmol) was gradually added at room temperature and the mixture was stirred for 30 minutes. N6-Methyl-7-(benzyloxy)-4-chloro-6-quinolinecarboxamide (947 mg, 2.90 mmol) was added, and the mixture was heated at 100° C. while stirring for 2 hours. After cooling to room temperature, the reaction solution was distributed between ethyl acetate and water, and the organic layer was washed with 1N aqueous sodium hydroxide, water and saturated brine and dried over anhydrous sodium sulfate. The solvent was distilled off, the residue was suspended in ethyl acetate, the suspension was diluted with hexane and the crystals were filtered out and blow-dried to obtain the title compound (1.098 g, 2.53 mmol, 87.3%) as light brown crystals.
$^1$H-NMR Spectrum (CDCl$_3$) δ (ppm): 2.96 (3H, d, J=4.8 Hz), 4.10 (2H, m), 5.35 (2H, s), 6.46 (1H, d, J=5.2 Hz), 6.84 (1H, d, J=8.8 Hz), 6.93 (1H, dd, J=2.8, 8.8 Hz), 7.14 (1H, d, J=2.8 Hz), 7.39-7.54 (5H, m), 7.58 (1H, s), 7.95 (1H, br), 8.62 (1H, d, J=5.2 Hz), 9.28 (1H, s).

Production Example 645-5

Phenyl N-(4-(7-(benzyloxy)-6-(methylamino)carbonyl-4-quinolyl)oxy-2-chlorophenyl)carbamate The title compound (1.291 g, 2.33 mmol, 92.1%) was obtained as light brown crystals from N6-methyl-4-(4- amino-3-chlorophenoxy)-7-(benzyloxy)-6-quinolinecarboxamide (1.098 g, 2.53 mmol), in the same manner as Production Example 17.

$^1$H-NMR Spectrum (CDCl$_3$) δ (ppm): 2.96 (3H, d, J=4.8 Hz), 5.35 (2H, s), 6.50 (1H, d, J=5.2 Hz), 7.15 (1H, dd, J=2.8, 8.8 Hz), 7.19-7.30 (6H, m), 7.40-7.52 (6H, m), 7.61 (1H, s), 7.95 (1H, m), 8.30 (1H, q, J=4.8 Hz), 8.67 (1H, d, J=5.2 Hz), 9.27 (1H, s).

Example 646

N6-Methyl-7-(benzyloxy)-4-(3-chloro-(4-((ethylamino)carbonyl)amino)phenoxy)-6-quinolinecarboxamide The title compound (579 mg, 1.15 mmol, 98.4%) was obtained as light brown crystals from phenyl N-(4-(7-(benzyloxy)-6-(methylamino)carbonyl-4-quinolyl)oxy-2-chlorophenyl)carbamate (645 mg, 1.16 mmol) and a 2 M ethylamine-tetrahydrofuran solution, by the same procedure as in Example 11.

$^1$H-NMR Spectrum (DMSO-d$_6$) δ (ppm): 1.06 (3H, t, J=7.2 Hz), 2.81 (3H, d, J=4.8 Hz), 3.11 (2H, m), 5.42 (2H, s), 6.51 (1H, d, J=5.2 Hz), 6.99 (1H, m), 7.19 (1H, dd, J=2.8, 9.2 Hz), 7.30-7.45 (4H, m), 7.52-7.55 (3H, m), 8.06 (1H, s), 8.24 (1H, d, J=9.2 Hz), 8.38 (1H, q, J=4.8 Hz), 8.49 (1H, s), 8.62 (1H, d, J=5.2 Hz).

Example 647

N6-Methyl-4-(3-chloro-4-(((methylamino)carbonyl)amino)phenoxy)-7-hydroxy-6-quinolinecarboxamide The title compound (365.7 mg, 0.91 mmol, 96.1%) was obtained as yellow crystals from N6-methyl-7-(benzyloxy)-4-(3-chloro-4-(((methylamino)carbonyl)amino)phenoxy)-6-quinolinecarboxamide (466.3 mg, 0.95 mmol), by the same procedure as in Example 83.

$^1$H-NMR Spectrum (DMSO-d$_6$) δ (ppm): 2.66 (3H, brs), 2.85 (3H, brs), 6.37 (1H, m), 6.86 (1H, m), 7.10-7.30 (2H, m), 7.45 (1H, m), 8.09 (1H, brs), 8.22 (1H, m), 8.56 (1H, m), 8.84 (1H, brs).

Example 648

N6-Methyl-4-(3-chloro-4-(((ethylamino)carbonyl)amino)phenoxy)-7-hydroxy-6-quinolinecarboxamide The title compound (431.4 mg, 1.04 mmol, 90.8%) was obtained as light yellow crystals from N6-methyl-7-(benzyloxy)-4-(3-chloro-4-(((ethylamino)carbonyl)amino)phenoxy)-6-quinolinecarboxamide (578.5 mg, 1.15 mmol), by the same procedure as in Example 83.

$^1$H-NMR Spectrum (DMSO-d$_6$) δ (ppm): 1.06 (3H, t, J=7.2 Hz), 2.85 (3H, brs), 3.12 (2H, m), 6.36 (1H, m), 6.98 (1H, m), 7.20-7.24 (2H, m), 7.45 (1H, d, J=2.8 Hz), 8.05 (1H, s), 8.25 (1H, d, J=9.2 Hz), 8.55 (1H, m), 8.84 (1H, s).

Example 649 tert-Butyl 4-(((4-(3-chloro-4-((methylamino)carbonyl)amino)phenoxy)-6-(methylaminocarbonyl)-7-quinolyl)oxy)methyl)-1-piperidinecarboxylate The title compound (98.4 mg, 0.165 mmol, 55.0%) was obtained as light brown crystals from N6-methyl-4-(3-chloro-4-(((methylamino)carbonyl)amino)phenoxy)-7-hydroxy-6-quinolinecarboxamide (120 mg, 0.299 mmol) and tert-butyl 4-(bromomethyl)-1-piperidinecarboxylate), by the same procedure as in Example 7.

$^1$H-NMR Spectrum (DMSO-d$_6$) δ (ppm): 1.17-1.33 (3H, m), 1.39 (9H, s), 1.75 (2H, m), 2.06 (1H, m), 2.66 (3H, d, J=4.4 Hz), 2.77 (1H, m), 2.81 (3H, d, J=4.8 Hz), 3.97 (2H, m), 4.10 (2H, d, J=6.0 Hz), 6.51 (1H, d, J=5.2 Hz), 6.85 (1H, q, J=4.4 Hz), 7.20 (1H, dd, J=2.8, 8.8 Hz), 7.44 (1H, d, J=2.8 Hz), 7.48 (1H, s), 8.10 (1H, s), 8.18 (1H, q, J=4.8 Hz), 8.22 (1H, d, J=8.8 Hz), 8.43 (1H, s), 8.63 (1H, d, J=5.2 Hz).

Example 650 tert-Butyl 4-(((4-(3-chloro-4-((ethylamino)carbonyl)amino)phenoxy)-6-(methylaminocarbonyl)-7-quinolyl)oxy)methyl)-1-piperidinecarboxylate The title compound (119.5 mg, 0.195 mmol, 56.6%) was obtained as light brown crystals from N6-methyl-4-(3-chloro-4-(((ethylamino)carbonyl)amino)phenoxy)-7-hydroxy-6-quinolinecarboxamide (143 mg, 0.345 mmol) and tert-butyl 4-(bromomethyl)-1-piperidinecarboxylate, by the same procedure as in Example 7.

$^1$H-NMR Spectrum (DMSO-d$_6$) δ (ppm): 1.06 (3H, t, J=7.2 Hz), 1.18-1.26 (3H, m), 1.39 (9H, s), 1.76 (2H, m), 2.06 (1H, m), 2.77 (1H, m), 2.81 (3H, d, J=4.8 Hz), 3.12 (2H, m), 3.98 (2H, m), 4.10 (2H, d, J=6.0 Hz), 6.51 (1H, d, J=5.2 Hz), 6.97 (1H, m), 7.19 (1H, dd, J=2.8, 8.8 Hz), 7.44 (1H, d, J=2.8 Hz), 7.48 (1H, s), 8.04 (1H, s), 8.18 (1H, q, J=4.8 Hz), 8.24 (1H, d, J=8.8 Hz), 8.43 (1H, s), 8.63 (1H, d, J=5.2 Hz).

Example 651

N6-Methyl-4-(3-chloro-4-(((methylamino)carbonyl)amino)phenoxy)-7-((1-methyl-4-piperidyl)methoxy)-6-quinolinecarboxamide After adding trifluoroacetic acid (1 ml) to tert-butyl 4-(((4-(3-chloro-4-((methylamino)carbonyl)amino)phenoxy)-6-(methylaminocarbonyl)-7-quinolyl)oxy)methyl)-1-piperidinecarboxylate (98.4 mg, 0.165 mmol) at room temperature, the mixture was stirred for 2 hours. The reaction solution was concentrated under reduced pressure, and then the residue was dissolved in methanol, and triethylamine was added dropwise for neutralization. After distilling off the solvent, the residue was dissolved in tetrahydrofuran (2 ml)—methanol (2 ml), and then 37% aqueous formaldehyde (0.3 ml), acetic acid (0.05 ml) and sodium cyanoborohydride (21 mg, 0.33 mmol) were added in that order at room temperature and the mixture was stirred for 30 minutes. The reaction solution was distributed between ethyl acetate-tetrahydrofuran (1:1) and saturated aqueous sodium bicarbonate, and the organic layer was washed with saturated aqueous sodium bicarbonate and saturated brine and dried over anhydrous sodium sulfate. After distilling off the solvent, the residue was subjected to silica gel column chromatography, and the target fraction was concentrated under reduced pressure and crystallized with ethyl acetate-hexane (1:5), after which the crystals were filtered out and blow-dried to obtain the title compound (64.2 mg, 0.125 mmol, 76.2%) as white crystals.

$^1$H-NMR Spectrum (DMSO-d$_6$) δ (ppm): 1.34 (2H, m), 1.72-1.89 (5H, m), 2.15 (3H, s), 2.66 (3H, d, J=4.4 Hz), 2.77-2.83 (5H, m), 4.08 (2H, d, J=6.4 Hz), 6.51 (1H, d, J=5.2 Hz), 6.85 (1H, q, J=4.8 Hz), 7.20 (1H, dd, J=2.8, 8.8 Hz), 7.44 (1H, d, J=2.8 Hz), 7.48 (1H, s), 8.10 (1H, s), 8.20 (1H, q, J=4.4 Hz), 8.22 (1H, d, J=8.8 Hz), 8.45 (1H, s), 8.63 (1H, d, J=5.2 Hz).

Example 652

N6-Methyl-4-(3-chloro-4-(((ethylamino)carbonyl) amino)phenoxy)-7-((1-methyl-4-piperidyl)methoxy)-6-quinolinecarboxamide After adding trifluoroacetic acid (1 ml) to tert-butyl 4-(((4-(3-chloro-4-((ethylamino)carbonyl)amino)phenoxy)-6-(methylaminocarbonyl)-7-quinolyl)oxy)methyl)-1-piperidinecarboxylate (119.5 mg, 0.195 mmol) at room temperature, the mixture was stirred for 2 hours. The reaction solution was concentrated under reduced pressure, and then the residue was dissolved in methanol and triethylamine was added dropwise for neutralization. After distilling off the solvent, the residue was dissolved in tetrahydrofuran (2 ml)—methanol (2 ml), and then 37% aqueous formaldehyde (0.3 ml), acetic acid (0.05 ml) and sodium cyanoborohydride (25 mg, 0.39 mmol) were added in that order at room temperature and the mixture was stirred for 30 minutes. The reaction solution was distributed between ethyl acetate-tetrahydrofuran (1:1) and saturated aqueous sodium bicarbonate, and the organic layer was washed with saturated aqueous sodium bicarbonate and saturated brine and dried over anhydrous sodium sulfate. After distilling off the solvent, the residue was subjected to silica gel column chromatography, and the target fraction was concentrated under reduced pressure and crystallized with ethyl acetate-hexane (1:5), after which the crystals were filtered out and blow-dried to obtain the title compound (78.3 mg, 0.149 mmol, 76.2%) as white crystals.

$^1$H-NMR Spectrum (DMSO-$d_6$) δ (ppm): 1.06 (3H, t, J=7.2 Hz), 1.34 (2H, m), 1.72-1.89 (5H, m), 2.15 (3H, s), 2.76-2.82 (5H, m), 3.12 (2H, m), 4.08 (2H, d, J=6.4 Hz), 6.51 (1H, d, J=5.2 Hz), 6.97 (1H, m), 7.19 (1H, dd, J=2.8, 8.8 Hz), 7.44 (1H, d, J=2.8 Hz), 7.48 (1H, s), 8.04 (1H, s), 8.19 (1H, q, J=4.4 Hz), 8.24 (1H, d, J=8.8 Hz), 8.45 (1H, s), 8.63 (1H, d, J=5.2 Hz).

Example 653

N6-Methyl-4-(3-chloro-4-(((methylamino)carbonyl) amino)phenoxy)-7-((2R)-3-diethylamino-2-hydroxypropoxy)-6-quinolinecarboxamide After adding (2R)oxiran-2-ylmethyl 4-methyl-1-benzenesulfonate (103 mg, 0.499 mmol), potassium carbonate (50 mg, 0.359 mmol) and dimethylformamide (3 ml) to N6-methyl-4-(3-chloro-4-(((methylamino)carbonyl)amino)phenoxy)-7-hydroxy-6-quinolinecarboxamide (120 mg, 0.299 mmol), the mixture was stirred at 60° C. for 7 hours. Next, diethylamine (1.5 ml) was added and the mixture was further stirred overnight at 60° C. The reaction solution was distributed between ethyl acetate-tetrahydrofuran (1:1) and water, and the organic layer was washed with water and saturated brine and then dried over anhydrous sodium sulfate. The solvent was distilled off, the residue was subjected to silica gel column chromatography (eluent—ethyl acetate:methanol=95:5), the fraction containing the target substance was concentrated, and crystals were precipitated from ethyl acetate-hexane (1:1), filtered out and blow-dried to obtain the title compound (71.8 mg, 0.135 mmol, 45.2%) as white crystals.

$^1$H-NMR Spectrum (DMSO-$d_6$) δ (ppm): 0.95 (6H, t, J=7.2 Hz), 2.40-2.60 (6H, m), 2.66 (3H, d, J=4.8 Hz), 2.85 (3H, d, J=4.8 Hz), 4.00 (1H, m), 4.18 (1H, dd, J=6.0, 10.0 Hz), 4.32 (1H, dd, J=3.2, 10.0 Hz), 5.12 (1H, d, J=4.0 Hz), 6.52 (1H, d, J=5.2 Hz), 6.86 (1H, q, J=4.8 Hz), 7.22 (1H, dd, J=2.8, 9.2 Hz), 7.47 (1H, d, J=2.8 Hz), 7.53 (1H, s), 8.10 (1H, s), 8.23 (1H, d, J=9.2 Hz), 8.50 (1H, q, J=4.8 Hz), 8.65 (1H, d, J=5.2 Hz), 8.71 (1H, s).

Example 654

N6-Methyl-4-(3-chloro-4-(((ethylamino)carbonyl) amino)phenoxy)-7-((2R)-3-diethylamino-2-hydroxypropoxy)-6-quinolinecarboxamide The title compound (92.4 mg, 0.170 mmol, 49.3%) was obtained as white crystals from N6-methyl-4-(3-chloro-4-(((ethylamino)carbonyl)amino)phenoxy)-7-hydroxy-6-quinolinecarboxamide (143 mg, 0.345 mmol), by the same procedure as in Example 653.

$^1$H-NMR Spectrum (DMSO-$d_6$) δ (ppm): 0.95 (6H, t, J=7.2 Hz), 1.06 (3H, t, J=7.2 Hz), 2.40-2.60 (6H, m), 2.85 (3H, d, J=4.8 Hz), 3.12 (2H, m), 4.00 (1H, m), 4.18 (1H, dd, J=6.0, 9.6 Hz), 4.32 (1H, dd, J=3.2, 9.6 Hz), 5.12 (1H, d, J=4.4 Hz), 6.51 (1H, d, J=5.2 Hz), 6.98 (1H, m), 7.22 (1H, dd, J=2.8, 9.2 Hz), 7.47 (1H, d, J=2.8 Hz), 7.53 (1H, s), 8.05 (1H, s), 8.25 (1H, d, J=9.2 Hz), 8.50 (1H, q, J=4.8 Hz), 8.65 (1H, d, J=5.2 Hz), 8.72 (1H, s).

Example 655

N6-Methyl-4-(3-chloro-4-(((methylamino)carbonyl) amino)phenoxy)-7-((2R)-2-hydroxy-3-(1-pyrrolidino)propoxy)-6-quinolinecarboxamide After adding (2R)oxiran-2-ylmethyl 4-methyl-1-benzenesulfonate (103 mg, 0.499 mmol), potassium carbonate (50 mg, 0.359 mmol) and dimethylformamide (3 ml) to N6-methyl-4-(3-chloro-4-(((methylamino)carbonyl)amino)phenoxy)-7-hydroxy-6-quinolinecarboxamide (120 mg, 0.299 mmol), the mixture was stirred at 60° C. for 7 hours. After allowing the reaction solution to cool to room temperature, pyrrolidine (0.5 ml) was added and the mixture was further stirred overnight. The reaction solution was distributed between ethyl acetate-tetrahydrofuran (1:1) and water, and the organic layer was washed with water and saturated brine and then dried over anhydrous sodium sulfate. The solvent was distilled off, the residue was subjected to silica gel column chromatography (eluent-ethyl acetate:methanol=95:5), the fraction containing the target substance was concentrated, and crystals were precipitated from ethyl acetate-hexane (1:1), filtered out and blow-dried to obtain the title compound (79.3 mg, 0.150 mmol, 50.2%) as white crystals.

$^1$H-NMR Spectrum (DMSO-$d_6$) δ (ppm): 1.67 (4H, m), 2.40-2.60 (5H, m), 2.64-2.69 (4H, m), 2.85 (3H, d, J=4.8 Hz), 4.06 (1H, m), 4.17 (1H, m), 4.33 (1H, dd, J=3.6, 10.4 Hz), 5.23 (1H, d, J=4.8 Hz), 6.52 (1H, d, J=5.2 Hz), 6.86 (1H, q, J=4.8 Hz), 7.22 (1H, dd, J=2.8, 9.2 Hz), 7.47 (1H, d, J=2.8 Hz), 7.54 (1H, s), 8.10 (1H, s), 8.23 (1H, d, J=9.2 Hz), 8.50 (1H, q, J=4.8 Hz), 8.65 (1H, d, J=5.2 Hz), 8.71 (1H, s).

Example 656

N6-Methyl-4-(3-chloro-4-(((ethylamino)carbonyl) amino)phenoxy)-7-((2R)-2-hydroxy-3-(1-pyrrolidino)propoxy)-6-quinolinecarboxamide The title compound (94.8 mg, 0.175 mmol, 50.7%) was obtained as white crystals from N6-methyl-4-(3-chloro-4-(((ethylamino)carbonyl)amino)phenoxy)-7-hydroxy-6-quinolinecarboxamide (143 mg, 0.345 mmol), by the same procedure as in Example 655.

¹H-NMR Spectrum (DMSO-d₆) δ (ppm): 1.06 (3H, t, J=7.2 Hz), 1.67 (4H, m), 2.40-2.60 (5H, m), 2.66 (1H, dd, J=6.4, 12.4 Hz), 2.85 (3H, d, J=4.8 Hz), 3.12 (2H, m), 4.06 (1H, m), 4.16 (1H, dd, J=6.0, 10.0 Hz), 4.33 (1H, dd, J=3.2, 10.0 Hz), 5.23 (1H, d, J=5.2 Hz), 6.51 (1H, d, J=5.2 Hz), 6.98 (1H, m), 7.21 (1H, dd, J=2.8, 8.8 Hz), 7.47 (1H, d, J=2.8 Hz), 7.53 (1H, s), 8.05 (1H, s), 8.25 (1H, d, J=8.8 Hz), 8.50 (1H, q, J=4.8 Hz), 8.65 (1H, d, J=5.2 Hz), 8.71 (1H, s).

Example 657

N-Cyclopropyl-N'-(4-(6-(4-(2-diethylaminoethoxy)-phenyl)-7H-pyrrolo[2,3-d]pyrimidin-4-yloxy)-2-fluorophenyl)urea After dissolving 65 mg of N-cyclopropyl-N'-(4-(6-(4-(2-diethylaminoethoxy)-phenyl)-7-(2-trimethylsilanylethoxymethyl)-7H-pyrrolo[2,3-d]pyrimidin-4-yloxy)-2-fluorophenyl)urea in 2 ml of tetrahydrofuran, there was added dropwise 0.5 ml of tetrabutylammonium fluoride (1M tetrahydrofuran solution) and the mixture was refluxed for 3 hours. After returning it to room temperature, water was added, the mixture was stirred, and the precipitated crystals were filtered out, washed with water and ether-hexane (1:1) and dried under reduced pressure to obtain 25 mg of the title compound.
MS Spectrum (ESI): 519 (M+1),
¹H-NMR Spectrum: (DMSOd₆)0.38-0.43 (2H, m), 0.62-0.68 (2H, m), 0.99 (6H, t, J=7.3 Hz) 2.53-2.61 (5H, m), 2.80 (2H, t, J=6.9 Hz), 4.08 (2H, t, J=6.9 Hz), 6.79-6.84 (1H, m), 6.91 (1H, s), 7.01-7.07 (3H, m), 7.26 (1H, dd, J=2.9, 11.2 Hz), 7.88 (2H, d, J=9.0 Hz), 8.05-8.16 (1H, m), 8.18 (1H, brs), 8.28 (1H, s), 12.68 (1H, brs)
The intermediates were synthesized in the following manner.

Production Example 657-1

6-(4-Benzyloxyphenyl)-4-(3-fluoro-4-nitrophenoxy)-7-(trimethylsilanylethoxymethyl)-7H-pyrrolo[2,3-d]pyrimidine After adding 248 mg of 3-fluoro-4-nitrophenol, 0.208 ml of 2,6-lutidine and 1 ml of N-methylpyrrolidine to 490 mg of 6-(4-benzyloxyphenyl)-4-chloro-7-(2-trimethylsilanylethoxymethyl)-7H-pyrrolo[2,3-d]pyrimidine, the mixture was stirred at 130° C. for 24 hours. After returning it to room temperature, water was added, liquid separation and extraction were performed with an ethyl acetate-tetrahydrofuran mixed solvent, and the organic layer was washed with saturated brine, dried over sodium sulfate, concentrated and subjected to NH silica gel column chromatography (ethyl acetate) to obtain 472 mg of the title compound.
1H-NMR Spectrum: (DMSOd6) –0.08 (9H, s), 0.87 (2H, t, J=7.4 Hz), 3.63 (2H, t, J=7.4 Hz), 5.20 (2H, s), 5.61 (2H, s), 6.83 (1H, s), 7.00-7.80 (11H, m), 8.30 (1H, t, J=8.6 Hz), 8.40 (1H, s).

Production Example 657-2

4-(6-(4-Benzyloxyphenyl)-7-(trimethylsilanylethoxymethyl)-7H-pyrrolo[2,3-d]pyrimidin-4-yloxy)-2-fluorophenylamine After adding 400 mg of iron powder, 1 g of ammonium chloride, 20 ml of ethanol, 10 ml of tetrahydrofuran and 10 ml of water to 470 mg of 6-(4-benzyloxyphenyl)-4-(3-fluoro-4-nitrophenoxy)-7-(trimethylsilanylethoxymethyl)-7H-pyrrolo[2,3-d]pyrimidine, the mixture was stirred at 85° C. for 3 hours. After returning it to room temperature, it was filtered with celite, and ethyl acetate and water were added to the filtrate for liquid separation and extraction. The organic layer was washed with saturated brine, dried over anhydrous sodium sulfate, filtered with plug cotton, concentrated and subjected to NH silica gel column chromatography (hexane-ethyl acetate) to obtain 263 mg of the title compound.
MS Spectrum (ESI): 557 (M+1).
¹H-NMR Spectrum: (DMSOd₆)-0.09 (9H, s), 0.85 (2H, t, J=8.9 Hz), 3.61 (2H, t, J=8.9 Hz), 5.09-5.13 (2H, m), 5.19 (2H, s), 5.59 (2H, s), 6.60 (1H, s), 6.79-6.73 (2H, m), 7.03 (1H, d, J=11.5 Hz), 7.16 (2H, d, J=9.6 Hz), 7.32-7.50 (5H, m), 7.70 (2H, d, J=9.6 Hz), 8.40 (1H, s).

Production Example 657-3

N-(4-(6-(4-Benzyloxyphenyl)-7-(2-trimethylsilanylethoxymethyl)-7H-pyrrolo[2,3-d]pyrimidin-4-yloxy)-2-fluorophenyl)-N'-cyclopropylurea After dissolving 261 mg of 4-[6-(4-benzyloxyphenyl)-7-(trimethylsilanylethoxymethyl)-7H-pyrrolo[2,3-d]pyrimidin-4-yloxy]-2-fluorophenylamine in 3 ml of dimethylformamide, 0.053 ml of pyridine and 0.082 ml of phenyl chlorocarbonate were added, the mixture was stirred at room temperature for 2 hours, 0.081 ml of cyclopropylamine was added and the mixture was further stirred overnight. Water was added, liquid separation and extraction were performed with ethyl acetate, and the organic layer was washed with saturated brine, dried over sodium sulfate, concentrated and subjected to silica gel column chromatography (hexane-ethyl acetate) to obtain 265 mg of the title compound.
¹H-NMR Spectrum: (DMSOd₆)-0.09 (9H, s), 0.38-0.43 (2H, m), 0.60-0.70 (2H, m), 0.87 (2H, t, J=7.5 Hz), 2.50-2.60 (1H, m), 3.61 (2H, t, J=7.5 Hz), 5.20 (2H, s), 5.60 (2H, s), 6.61 (1H, s), 6.68-6.72 (1H, m), 7.04 (1H, d, J=8.3 Hz), 7.18 (2H, d, J=9.0 Hz), 7.28 (1H, dd, J=3.4, 11.7 Hz), 7.32-7.53 (5H, m), 7.72 (2H, d, J=9.0 Hz), 8.10 (1H, t, J=8.2 Hz), 8.18 (1H, brs), 8.40 (1H, s).

Production Example 657-4

N-Cyclopropyl-N'-(2-fluoro-4-(6-(4-hydroxyphenyl)-7-(2-trimethylsilanylethoxymethyl)-7H-pyrrolo[2,3-d]pyrimidin-4-yloxy)phenyl)urea After dissolving 263 mg of 1-(4-(6-(4-benzyloxyphenyl)-7-(2-trimethylsilanylethoxymethyl)-7H-pyrrolo[2,3-d]pyrimidin-4-yloxy)-2-fluorophenyl)-3-cyclopropylurea in 7 ml of ethanol and 3 ml of tetrahydrofuran, 30 mg of platinum oxide was added and the mixture was stirred overnight at room temperature and ordinary pressure under a hydrogen atmosphere, after which it was filtered with celite and concentrated under reduced pressure. The residue was subjected to silica gel column chromatography (hexane-ethyl acetate) to obtain 160 mg of the title compound.
¹H-NMR Spectrum: (DMSOd₆)-0.08 (9H, s), 0.39-0.43 (2H, m), 0.61-0.68 (2H, m), 0.86 (2H, t, J=7.5 Hz), 2.50-2.60 (1H, m), 3.61 (2H, t, J=7.5 Hz), 5.58 (2H, s), 6.63 (1H, s), 6.78-6.82 (1H, m), 6.90 (2H, d, J=8.6 Hz), 7.01-7.07 (1H, m,), 7.28 (1H, dd, J=3.3, 11.9 Hz), 7.60 (2H, d, J=8.6 Hz), 8.06-8.13 (1H, m,), 8.19 (1H, brs), 8.40 (1H, s).

Production Example 657-5

N-Cyclopropyl-N'-(4-(6-(4-(2-diethylaminoethoxy)-phenyl)-7-(2-trimethylsilanylethoxymethyl)-7H-pyrrolo[2,3-d]pyrimidin-4-yloxy)-2-fluorophenyl)urea After dissolving 100 mg of N-cyclopropyl-N'-(2-fluoro-4-(6-(4-hydroxyphenyl)-7-(2-trimethylsilanylethoxymethyl)-7H-pyrrolo[2,3-d]pyrimidin-4-yloxy)-2-phenyl)urea in 1 ml of dimethylformamide, 110 mg of 2-chloroethyldiethylamine hydrochloride and 126 mg of potassium carbonate were added and the mixture was stirred at 80° C. for 15 hours. The mixture was then returned to room temperature, water was added, and liquid separation and extraction were performed with an ethyl acetate-tetrahydrofuran mixed solvent. The organic layer was washed with saturated brine, dried over sodium sulfate, concentrated and subjected to NH silica gel column chromatography (hexane-ethyl acetate) to obtain 67 mg of the title compound.
MS Spectrum (ESI): 649 (M+1).

Example 658

N-Cyclopropyl-N'-(2-fluoro-4-(6-(4-((2R)-2-hydroxy-3-pyrrolidin-1-ylpropoxy)-phenyl)-7H-pyrrolo[2,3-d]pyrimidin-4-yloxy)-phenyl)urea The title compound (30 mg) was obtained from 63 mg of N-cyclopropyl-N'-(2-fluoro-4-(6-(4-((2R)-2-hydroxy-3-pyrrolidinopropoxy)phenyl)-7-(2-trimethylsilanylethoxymethyl)-7H-pyrrolo[2,3-d]pyrimidin-4-yloxy)-phenyl)urea, by the same procedure as in Example 657.
MS Spectrum (ESI): 547 (M+1),
$^1$H-NMR Spectrum: (DMSOd$_6$) 0.38-0.43 (2H, m), 0.60-0.69 (2H, m), 1.65-1.72 (4H, m), 2.45-2.70 (7H, m, covered by DMSO peak), 3.90-4.10 (3H, m), 4.96 (1H, brs) 6.91 (1H, s), 6.76-6.80 (1H, m), 7.01-7.07 (3H, m), 7.26 (1H, dd, J=10.9, 2.4 Hz), 7.88 (2H, d, J=9.1 Hz), 8.06-8.14 (1H, m,), 8.15 (1H, brs,), 8.28 (1H, s,) 12.60 (1H, brs)

The intermediate was synthesized in the following manner.

Production Example 658-1

N-Cyclopropyl-N'-(2-fluoro-4-(6-(4-((2R)-2-hydroxy-3-pyrrolidinopropoxy)phenyl)-7-(2-trimethylsilanylethoxymethyl)-7H-pyrrolo[2,3-d]pyrimidin-4-yloxy)phenyl)urea After dissolving N-cyclopropyl-N'-(2-fluoro-4-(6-(4-hydroxyphenyl)-7-(2-trimethylsilanylethoxymethyl)-7H-pyrrolo[2,3-d]pyrimidin-4-yloxy)phenyl)urea (89 mg) in dimethylformamide (2 ml), there were added (2R)-(-)-glycidyl p-toluenesulfonate (111 mg, 3 equivalents) and potassium carbonate (112 mg, 5 equivalents), and the mixture was stirred overnight at 65° C. It was then returned to room temperature and stationed, and the supernatant was decanted (1.8 ml portion of dimethylformamide). After adding 0.1 ml of pyrrolidine thereto, the mixture was stirred at 65° C. for 3 hours. Water was then added and liquid separation and extraction were performed with ethyl acetate-tetrahydrofuran. The organic layer was concentrated and subjected to NH silica gel column chromatography (hexane-ethyl acetate) to obtain 63 mg of the title compound.
MS Spectrum (ESI): 677 (M+1).

Example 659

N-Cyclopropyl-N'-(4-(6-(4-(3-diethylamino-(2R)-2-hydroxypropoxy)phenyl)-7H-pyrrolo[2,3-d]pyrimidin-4-yloxy)-2-fluorophenyl)urea The title compound (1 mg) was obtained from 5 mg of N-cyclopropyl-N'-(4-(6-(4-(3-diethylamino-(2R)-2-hydroxypropoxy)-phenyl])-7-(2-trimethylsilanylethoxymethyl)-7H-pyrrolo[2,3-d]pyrimidin-4-yloxy)-2-fluorophenyl)urea, by the same procedure as in Example 657.
MS Spectrum (ESI): 549 (M+1).

The intermediate was synthesized in the following manner.

Production Example 659-1

N-Cyclopropyl-N'-(4-(6-(4-(3-diethylamino-(2R)-2-hydroxypropoxy)-phenyl))-7-(2-trimethylsilanylethoxymethyl)-7H-pyrrolo[2,3-d]pyrimidin-4-yloxy)-2-fluorophenyl)urea After dissolving N-cyclopropyl-N'-(2-fluoro-4-(6-(4-hydroxyphenyl)-7-(2-trimethylsilanylethoxymethyl)-7H-pyrrolo[2,3-d]pyrimidin-4-yloxy)-2-phenyl)urea (89 mg) in dimethylformamide (2 ml), there were added (2R)-(-)-glycidyl p-toluenesulfonate (111 mg, 3 equivalents) and potassium carbonate (112 mg, 5 equivalents), and the mixture was stirred overnight at 65° C. It was then returned to room temperature and stationed, and the supernatant was decanted (0.2 ml portion of dimethylformamide). After adding 1 ml of tetrahydrofuran and 0.4 ml of diethylamine thereto, the mixture was stirred at 65° C. for 30 minutes. Water was then added and liquid separation and extraction were performed with ethyl acetate-tetrahydrofuran. The organic layer was concentrated and subjected to NH silica gel column chromatography (hexane-ethyl acetate) to obtain 5 mg of the title compound.
MS Spectrum (ESI): 679 (M+1).

Example 660

7-(Benzyloxy)-4-(3-chloro-(4-((cyclopropylamino)carbonyl)amino)phenoxy)-6-quinolinecarboxylic acid After adding methanol (30 ml) and a 2N sodium hydroxide aqueous solution (10 ml) to methyl 7-(benzyloxy)-4-(3-chloro-(4-((cyclopropylamino)carbonyl)amino)phenoxy)-6-quinolinecarboxylate (2.218 g, 4.28 mmol), the mixture was stirred at 60° C. for 1 hour. The reaction solution was allowed to cool to room temperature, and after neutralization by addition of 1N hydrochloric acid, the methanol was distilled off and the precipitated light brown crystals were filtered out, thoroughly washed with water and dried at 70° C. to obtain the title compound (2.121 g, 4.21 mmol, 98.3%).
$^1$H-NMR Spectrum (DMSO-d$_6$) δ (ppm): 0.43 (2H, m), 0.67 (2H, m), 2.57 (1H, m), 5.40 (2H, s), 6.56 (1H, d, J=5.2 Hz), 7.21 (1H, d, J=2.8 Hz), 7.26 (1H, dd, J=2.8, 8.8 Hz), 7.32-7.44 (3H, m), 7.51 (1H, d, J=2.8 Hz), 7.56 (2H, d, J=6.8 Hz), 7.60 (1H, s), 8.00 (1H, s), 8.28 (1H, dd, J=2.8, 8.8 Hz), 8.57 (1H, s), 8.69 (1H, d, J=5.2 Hz).

Example 661

N6-Methyl-7-(benzyloxy)-4-(3-chloro-4-(((cyclopropylamino)carbonyl)amino)phenoxy)-6-quinolinecarboxamide After dissolving 7-(benzyloxy)-4-(3-chloro-(4-((cyclopropylamino)carbonyl)amino)phenoxy)-6-quinolinecarboxylic acid (1.056 g, 2.10 mmol) in dimethylformamide (10 ml) under a nitrogen atmosphere, there were added a 40% methylamine-methanol solution (2 ml), triethylamine (1 ml) and (1H-1,2,3-benzotriazol-1-yloxy)(tri(dimethylamino))phosphoniumhexafluorophosphate (1.11 g, 2.52 mmol) in that order at room temperature, and the mixture was stirred for 6 hours. Water was added to the reaction solution to precipitate crystals, and these were filtered out, washed thoroughly with water and dried at 70° C. to obtain the title compound (988 mg, 1.91 mmol, 91.2%) as white crystals.

$^1$H-NMR Spectrum (DMSO-d$_6$) δ (ppm): 0.42 (2H, m), 0.65 (2H, m), 2.56 (1H, m), 2.82 (3H, d, J=4.4 Hz), 5.42 (2H, s), 6.51 (1H, d, J=5.2 Hz), 7.18 (1H, d, J=2.8 Hz), 7.21 (1H, dd, J=2.8, 8.8 Hz), 7.30-7.55 (7H, m), 7.96 (1H, s), 8.25 (1H, d, J=8.8 Hz), 8.38 (1H, q, J=4.4 Hz), 8.49 (1H, s), 8.62 (1H, d, J=5.2 Hz).

Example 662

N6-Ethyl-7-(benzyloxy)-4-(3-chloro-4-(((cyclopropylamino)carbonyl)amino)phenoxy)-6-quinolinecarboxamide The title compound (1.022 g, 1.92 mmol, 91.8%) was obtained as white crystals from 7-(benzyloxy)-4-(3-chloro-(4-((cyclopropylamino)carbonyl)amino)phenoxy)-6-quinolinecarboxylic acid (1.056 g, 2.10 mmol) and 2M ethylamine-tetrahydrofuran solution, by the same procedure as in Example 661.

$^1$H-NMR Spectrum (DMSO-d$_6$) δ (ppm): 0.42 (2H, m), 0.65 (2H, m), 1.04 (3H, t, J=7.2 Hz), 2.56 (1H, m), 3.25-3.31 (2H, m), 5.39 (2H, s), 6.52 (1H, d, J=5.2 Hz), 7.18 (1H, d, J=2.8 Hz), 7.22 (1H, dd, J=2.8, 8.8 Hz), 7.32-7.44 (3H, m), 7.47 (1H, d, J=2.8 Hz), 7.56 (2H, d, J=7.2 Hz), 7.59 (1H, s), 7.97 (1H, s), 8.26 (1H, d, J=8.8 Hz), 8.34 (1H, t, J=7.2 Hz), 8.49 (1H, s), 8.64 (1H, d, J=5.2 Hz).

Example 663

N6-Methyl-4-(3-chloro-4-(((cyclopropylamino)carbonyl)amino)phenoxy)-7-hydroxy-6-quinolinecarboxamide The title compound (811 mg, 1.90 mmol, quantitative) was obtained as light yellow crystals from N6-methyl-7-(benzyloxy)-4-(3-chloro-4-(((cyclopropylamino)carbonyl)amino)phenoxy)-6-quinolinecarboxamide) (983 mg, 1.90 mmol), by the same procedure as in Example 83.

$^1$H-NMR Spectrum (DMSO-d$_6$) δ (ppm): 0.42 (2H, m), 0.65 (2H, m), 2.56 (1H, m), 2.85 (3H, s), 6.32 (1H, br), 7.18-7.24 (4H, m), 7.45 (1H, s), 7.96 (1H, s), 8.25 (1H, d, J=9.2 Hz), 8.51 (1H, m), 8.81 (1H, s).

Example 664

N6-Ethyl-4-(3-chloro-4-(((cyclopropylamino)carbonyl)amino)phenoxy)-7-hydroxy-6-quinolinecarboxamide The title compound (845 mg, 1.91 mmol, quantitative) was obtained as light yellow crystals from N6-ethyl-7-(benzyloxy)-4-(3-chloro-4-(((cyclopropylamino)carbonyl)amino)phenoxy)-6-quinolinecarboxamide) (1.016 g, 1.91 mmol), by the same procedure as in Example 83.

$^1$H-NMR Spectrum (DMSO-d$_6$) δ (ppm): 0.42 (2H, m), 0.65 (2H, m), 1.16 (3H, t, J=7.2 Hz), 2.56 (1H, m), 3.36 (2H, m), 6.41 (1H, d, J=5.2 Hz), 7.15-7.35 (4H, m), 7.49 (1H, d, J=2.4 Hz), 7.97 (1H, s), 8.27 (1H, dd, J=4.0, 9.2 Hz), 8.60 (1H, d, J=5.2 Hz), 8.88 (1H, s), 12.68 (1H, br).

Example 665

N6-Methyl-4-(3-chloro-4-(((cyclopropylamino)carbonyl)amino)phenoxy)-7-(3-(1-pyrrolidino)propoxy)-6-quinolinecarboxamide The title compound (78.4 mg, 0.146 mmol, 29.1%) was obtained as light yellow crystals from N6-methyl-4-(3-chloro-4-(((cyclopropylamino)carbonyl)amino)phenoxy)-7-hydroxy-6-quinolinecarboxamide (213.4 mg, 0.50 mmol) and 1-(3-chloropropyl)pyrrolidine hydrochloride, by the same procedure as in Example 7.

$^1$H-NMR Spectrum (DMSO-d$_6$) δ (ppm): 0.42 (2H, m), 0.65 (2H, m), 1.68 (4H, m), 1.99 (2H, m), 2.44 (4H, m), 2.54-2.59 (3H, m), 2.83 (3H, d, J=4.8 Hz), 4.28 (2H, m), 6.51 (1H, d, J=5.2 Hz), 7.18 (1H, d, J=2.8 Hz), 7.22 (1H, dd, J=2.8, 8.8 Hz), 7.47 (1H, d, J=2.8 Hz), 7.49 (1H, s), 7.96 (1H, s), 8.24-8.27 (2H, m), 8.53 (1H, s), 8.64 (1H, d, J=5.2 Hz).

Example 666

N6-Ethyl-4-(3-chloro-4-(((cyclopropylamino)carbonyl)amino)phenoxy)-7-(3-(1-pyrrolidino)propoxy)-6-quinolinecarboxamide The title compound (85.0 mg, 0.154 mmol, 30.8%) was obtained as light yellow crystals from N6-ethyl-4-(3-chloro-4-(((cyclopropylamino)carbonyl)amino)phenoxy)-7-hydroxy-6-quinolinecarboxamide (213.4 mg, 0.50 mmol) and 1-(3-chloropropyl)pyrrolidine hydrochloride, by the same procedure as in Example 7.

$^1$H-NMR Spectrum (DMSO-d$_6$) δ (ppm): 0.42 (2H, m), 0.65 (2H, m), 1.16 (3H, t, J=7.2 Hz), 1.68 (4H, m), 2.00 (2H, m), 2.44 (4H, m), 2.53-2.60 (3H, m), 3.32-3.36 (2H, m), 4.27 (2H, m), 6.51 (1H, d, J=5.2 Hz), 7.18 (1H, d, J=2.8 Hz), 7.22 (1H, dd, J=2.8, 9.2 Hz), 7.47 (1H, d, J=2.8 Hz), 7.48 (1H, s), 7.96 (1H, s), 8.24-8.27 (2H, m), 8.51 (1H, s), 8.64 (1H, d, J=5.2 Hz).

Example 667

N6-Methyl-4-(3-chloro-4-(((cyclopropylamino)carbonyl)amino)phenoxy)-7-((2R)oxiran-2-yl)methoxy-6-quinolinecarboxamide The title compound (230.0 mg, 0.476 mmol, 47.6%) was obtained as light yellow crystals from N6-methyl-4-(3-chloro-4-(((cyclopropylamino)carbonyl)amino)phenoxy)-7-hydroxy-6-quinolinecarboxamide (426.9 mg, 1.00 mmol) and (2R)oxiran-2-ylmethyl 4-methyl-1-benzenesulfonate, by the same procedure as in Example 7.

$^1$H-NMR Spectrum (DMSO-d$_6$) δ (ppm): 0.42 (2H, m), 0.65 (2H, m), 2.56 (1H, m), 2.79-2.90 (2H, m), 2.84 (3H, d, J=4.4 Hz), 3.47 (1H, m), 4.16 (1H, dd, J=6.0, 11.6 Hz), 4.63 (1H, dd, J=2.4, 11.6 Hz), 6.52 (1H, d, J=5.2 Hz), 7.18 (1H, d, J=2.8 Hz), 7.22 (1H, dd, J=2.8, 8.8 Hz), 7.47 (1H, d, J=2.8 Hz), 7.54 (1H, s), 7.97 (1H, s), 8.24-8.28 (2H, m), 8.53 (1H, s), 8.65 (1H, d, J=5.2 Hz).

Example 668

N6-Ethyl-4-(3-chloro-4-(((cyclopropylamino)carbonyl)amino)phenoxy)-7-((2R)oxiran-2-yl)methoxy-6-quinolinecarboxamide The title compound (235.4 mg, 0.474 mmol, 47.4%) was obtained as light yellow crystals from N6-ethyl-4-(3-chloro- 4-(((cyclopropylamino)carbonyl)amino)phenoxy)-7-hydroxy-6-quinolinecarboxamide) (440.9 mg, 1.00 mmol) and (2R)oxiran-2-ylmethyl 4-methyl-1-benzenesulfonate, by the same procedure as in Example 7.

$^1$H-NMR Spectrum (DMSO-d$_6$) δ (ppm): 0.42 (2H, m), 0.65 (2H, m), 1.15 (3H, t, J=7.2 Hz), 2.56 (1H, m), 2.82 (1H, m), 2.89 (1H, m), 3.28-3.36 (2H, m), 3.48 (1H, m), 4.17 (1H, dd, J=2.0, 11.2 Hz), 4.62 (1H, dd, J=2.4, 11.2 Hz), 6.52 (1H, d, J=5.2 Hz), 7.18 (1H, d, J=2.8 Hz), 7.22 (1H, dd, J=2.8, 9.2 Hz), 7.47 (1H, d, J=2.8 Hz), 7.53 (1H, s), 7.97 (1H, s), 8.24-8.30 (2H, m), 8.52 (1H, s), 8.65 (1H, d, J=5.2 Hz).

Example 669

N6-Methyl-4-(3-chloro-4-(((cyclopropylamino)carbonyl)amino)phenoxy)-7-((2R)-2-hydroxy-3-(1-pyrrolidino)propoxy-6-quinolinecarboxamide After dissolving N6-methyl-4-(3-chloro-4-(((cyclopropylamino)carbonyl)amino)phenoxy)-7-((2R)oxiran-2-yl)methoxy-6-quinolinecarboxamide (225 mg, 0.466 mmol) in tetrahydrofuran (5.0 ml) under a nitrogen atmosphere, pyrrolidine (1.0 ml) was added and the mixture was stirred overnight at room temperature. The reaction solution was concentrated under reduced pressure, the residue was subjected to silica gel column chromatography (eluent-ethyl acetate:methanol=95:5), the fraction containing the target substance was concentrated, and crystals precipitated from ethyl acetate were filtered out and blow-dried to obtain the title compound (164.5 mg, 0.297 mmol, 63.7%) as light yellow crystals.

$^1$H-NMR Spectrum (DMSO-d$_6$) δ (ppm): 0.42 (2H, m), 0.65 (2H, m), 1.67 (4H, m), 2.48-2.59 (6H, m), 2.66 (1H, dd, J=6.4, 12.0 Hz), 2.85 (3H, d, J=4.8 Hz), 4.05 (1H, m), 4.16 (1H, dd, J=6.0, 10.0 Hz), 4.34 (1H, dd, J=3.2, 10.0 Hz), 5.24 (1H, d, J=4.8 Hz), 6.51 (1H, d, J=5.2 Hz), 7.18-7.25 (2H, m), 7.48 (1H, d, J=2.8 Hz), 7.54 (1H, s), 7.97 (1H, s), 8.26 (1H, d, J=9.2 Hz), 8.50 (1H, q, J=4.8 Hz), 8.65 (1H, d, J=5.2 Hz), 8.71 (1H, s).

Example 670

N6-Ethyl-4-(3-chloro-4-(((cyclopropylamino)carbonyl)amino)phenoxy)-7-((2R)-2-hydroxy-3-(1-pyrrolidino)propoxy)-6-quinolinecarboxamide The title compound (146.0 mg, 0.257 mmol, 55.5%) was obtained as light yellow crystals from N6-ethyl-4-(3-chloro-4-(((cyclopropylamino)carbonyl)amino)phenoxy)-7-((2R)oxiran-2-yl)methoxy-6-quinolinecarboxamide) (230 mg, 0.463 mmol), by the same procedure as in Example 669.

$^1$H-NMR Spectrum (DMSO-d$_6$) δ (ppm): 0.42 (2H, m), 0.65 (2H, m), 1.16 (3H, t, J=7.2 Hz), 1.67 (4H, m), 2.47-2.58 (6H, m), 2.68 (1H, dd, J=6.8, 12.0 Hz), 3.30-3.40 (2H, m), 4.04 (1H, m), 4.19 (1H, dd, J=5.6, 9.6 Hz), 4.33 (1H, dd, J=3.2, 9.6 Hz), 5.18 (1H, d, J=4.8 Hz), 6.51 (1H, d, J=5.2 Hz), 7.18-7.25 (2H, m), 7.48 (1H, d, J=2.8 Hz), 7.52 (1H, s), 7.97 (1H, s), 8.26 (1H, d, J=9.2 Hz), 8.53 (1H, m), 8.65 (1H, d, J=5.2 Hz), 8.71 (1H, s).

Example 670-1

N-(4-((6-Cyano-7-((1-methyl-4-piperidyl)methoxy]-4-quinolyl)oxy)-2-fluorophenyl)-N'-cyclopropylurea After suspending 320 mg of N-(4-((6-cyano-7-(4-piperidylmethoxy)-4-quinolyl)oxy)-2-fluorophenyl)-N'-cyclopropylurea in 20 ml of tetrahydrofuran, there were added 1 ml of formaldehyde (37% aqueous solution), 80 mg of acetic acid and 280 mg of sodium triacetoxyborohydride while stirring at room temperature. After stirring for 20 minutes, a 2N aqueous sodium hydroxide solution and ethyl acetate were added for extraction. The extract was passed through a glass filter coated with NH type silica gel, and the silica gel was thoroughly washed with an ethyl acetate:methanol=20:1 mixed solvent. The organic solvents were combined and distilled off under reduced pressure. Ethyl acetate was added to the residue, and the mixture was filtered to obtain 130 mg of a light yellow solid.

$^1$H-NMR (DMSO-d$_6$) δ (ppm): 0.35-0.45 (2H, m), 0.59-0.69 (2H, m), 1.32-1.46 (2H, m), 1.71-1.89 (5H, m), 2.14 (3H, s), 2.49-2.59 (1H, m), 2.74-2.84 (2H, m), 4.12 (2H, d, J=5.2 Hz), 6.56 (1H, d, J=5.2 Hz), 6.80 (1H, s), 7.07 (1H, d, J=9.2 Hz), 7.31 (1H, d, J=11.2 Hz), 7.55 (1H, s), 8.16-8.27 (2H, m), 8.69 (1H, s), 8.70 (1H, d, J=5.2 Hz).

The intermediates were obtained in the following manner.

Production Example 670-1-1 tert-Butyl 4-(((4-(4-amino-3-fluorophenoxy)-6-cyano-7-quinolyl)oxy)methyl)-1-piperidinecarboxylate 4-(4-Amino-3-fluorophenoxy)-7-hydroxy-6-quinoline carbonitrile (500 mg), tert-butyl 4-(bromomethyl)-1-piperidinecarboxylate (550 mg), potassium carbonate (700 mg) and dimethylformamide (5 ml) were stirred together at 60° c. for 2 hours. Water and ethyl acetate were added for extraction, and the extract was dried over magnesium sulfate. The drying agent was filtered out, and silica gel was added to the filtrate which was then distilled off under reduced pressure for adsorption. The reaction solution-adsorbed silica gel was subjected to column chromatography (hexane:ethyl acetate=1:1, followed by 1:2, 1:3, ethyl acetate) in a dry column packed with silica gel, to obtain 423 mg of a brown oil.

$^1$H-NMR (DMSO-d$_6$) δ (ppm): 1.20-1.32 (2H, m), 1.39 (9H, s), 1.75-1.83 (2H, m), 1.98-2.10 (1H, m), 2.67-2.88 (2H, m), 3.94-4.05 (2H, m), 4.15 (2H, d, J=6.4 Hz), 5.25 (2H, bs), 6.51 (1H, d, J=5.2 Hz), 6.83-6.88 (2H, m), 7.06-7.7.11 (1H, m), 7.55 (1H, s), 8.69 (1H, s), 8.70 (1H, d, J=5.2 Hz).

Production Example 670-1-2 tert-Butyl 4-(((6-cyano-4-(3-fluoro-4-((phenoxycarbonyl)amino)phenoxy)-7-quinolyl)oxy)methyl)-1-piperidinecarboxylate tert-Butyl 4-(((4-(4-amino-3-fluorophenoxy)-6-cyano-7-quinolyl)oxy)methyl)-1-piperidinecarboxylate (523 mg), pyridine (0.17 ml) and tetrahydrofuran (10 ml) were stirred while cooling on ice, and then phenyl chloroformate was added dropwise. Immediately after completion of the dropwise addition, the cooling bath was removed and the mixture was returned to room temperature. After 15 minutes of stirring, water and ethyl acetate were added for extraction. Silica gel was added to the extract and the solvent was distilled off under reduced pressure for adsorption. The reaction solution-adsorbed silica gel was purified by column chromatography (hexane:ethyl acetate=1:1, followed by 1:2, ethyl acetate) in a dry column packed with silica gel, to obtain 490 mg of a yellow powder.

$^1$H-NMR (DMSO-d$_6$) δ (ppm): 1.20-1.32 (2H, m), 1.39 (9H, s), 1.75-1.83 (2H, m), 1.98-2.10 (1H, m), 2.70-2.85 (2H, m), 3.95-4.04 (2H, m), 4.16 (2H, d, J=6.0 Hz), 6.64 (1H, d, J=5.2 Hz), 7.16-7.28 (4H, m), 7.38-7.46 (3H, m), 7.59 (1H, s), 7.80 (1H, dd, J=8.8 Hz, 8.8 Hz), 8.72 (1H, s), 8.75 (1H, d, J=5.2 Hz), 10.02 (1H, brs).

Production Example 670-1-3 tert-Butyl 4-(((6-cyano-4-(4-(((cyclopropylamino) carbonyl)amino)-3-fluorophenoxy)-7-quinolyl)oxy) methyl)-1-piperidinecarboxylate tert-Butyl 4-(((6-cyano-4-(3-fluoro-4-((phenoxycarbonyl) amino)phenoxy)-7-quinolyl)oxy)methyl)-1-piperidinecarboxylate (490 mg), cyclopropylamine (0.72 ml) and tetrahydrofuran (5 ml) were stirred together at 60° C. for 35 minutes. Silica gel was added to the reaction solution and the solvent was distilled off under reduced pressure for adsorption. The reaction solution-adsorbed silica gel was purified by column chromatography (ethyl acetate, followed by ethyl acetate: methanol=20:1) in a dry column packed with silica gel, to obtain 340 mg of a light yellow solid.

$^1$H-NMR (DMSO-$d_6$) δ (ppm): 0.37-0.44 (2H, m), 0.59-0.69 (2H, m), 1.29-1.32 (2H, m), 1.39 (9H, s), 1.77-1.84 (2H, m), 1.99-2.11 (1H, m), 2.39-2.59 (1H, m), 2.59-2.87 (2H, m), 3.96-4.04 (2H, m), 4.16 (2H, d, J=6.4 Hz), 6.57 (1H, d, J=5.2 Hz), 6.80 (1H, d, J=2.8 Hz), 7.05-7.11 (1H, m), 7.31 (1H, dd, J=12.0 Hz, 2.8 Hz), 7.58 (1H, s), 8.19-8.27 (2H, m), 8.71 (1H, s), 8.73 (1H, d, J=5.2 Hz)

Production Example 670-1-4

N-(4-((6-Cyano-7-(4-piperidylmethoxy)-4-quinolyl) oxy)-2-fluorophenyl)-N'-cyclopropylurea After adding 5 ml of trifluoroacetic acid to 340 mg of tert-butyl 4-(((6-cyano-4-(4-(((cyclopropylamino)carbonyl) amino)-3-fluorophenoxy)-7-quinolyl)oxy)methyl)-1-piperidinecarboxylate, the mixture was stirred at room temperature for 7 minutes. Saturated sodium bicarnobate water and ethyl acetate were added to the reaction solution for extraction. The ethyl acetate layer was washed with brine and dried over sodium sulfate. The drying agent was filtered off and the solvent was distilled off under reduced pressure to obtain 320 mg of a light yellow solid.

$^1$H-NMR (DMSO-$d_6$) δ (ppm): 0.37-0.44 (2H, m), 0.59-0.69 (2H, m), 1.47-1.59 (2H, m), 1.92-2.02 (2H, m), 2.14-2.25 (1H, m), 2.47-2.57 (3H, m), 2.87-2.98 (2H, m), 4.19 (2H, d, J=6.4 Hz), 6.59 (1H, d, J=5.2 Hz), 6.88 (1H, d, J=2.8 Hz), 7.05-7.10 (1H, m), 7.31 (1H, dd, J=12.0 Hz, 2.8 Hz), 7.63 (1H, s), 8.11 (1H, dd, J=9.2 Hz, 9.2 Hz), 8.28 (1H, s), 8.73 (1H, d, J=5.2 Hz), 8.74 (1H, s).

Example 671

4-(4-(3-Ethylureido)-3-fluorophenoxy)-7-methoxyquinoline-6-carboxylic acid methyl ester Phenyl N-(2-fluoro-4-(7-methoxy-6-methoxycarbonyl-4-quinolyl)oxyphenyl)carbamate (0.9 g) was treated with ethylamine in dimethylsulfoxide at room temperature in the same manner as Example 11, to obtain the title compound (0.6 g) as a solid.

$^1$H-NMR Spectrum (DMSO-$d_6$) δ (ppm): 1.05 (3H, t, J=7.2 Hz), 3.07-3.15 (2H, m), 3.85 (3H, s), 3.96 (3H, s), 6.52 (1H, d, J=5.2 Hz), 6.58 (1H, t, J=5.2 Hz), 7.04-7.08 (1H, m), 7.31 (1H, dd, J=2.8 Hz, J=12 Hz), 7.51 (1H, s), 8.21 (1H, t, J=9.2 Hz), 8.33 (1H, br s), 8.55 (1H, s), 8.67 (1H, d, J=5.2 Hz).

The intermediates were synthesized in the following manner.

Production Example 671-1

Methyl 4-(4-nitro-3-fluorophenoxy)-7-methoxy-6-quinolinecarboxylate

Methyl 4-(4-nitro-3-fluorophenoxy)-7-methoxy-6-quinolinecarboxylate (2.44 g) was obtained from 4-chloro-7-methoxy-6-methoxycarbonylquinoline (2.51 g), by the same procedure as in Production Example 7.

$^1$H-NMR Spectrum (DMSO-$d_6$) δ (ppm): 3.83 (3H, s), 3.99 (3H, s), 6.93 (1H, d, J=5.1 Hz), 7.30-7.33 (1H, m), 7.58 (1H, m), 7.65-7.69 (1H, m), 8.27-831 (1H, m), 8.44 (1H, s), 8.81 (1H, d, J=5.1 Hz).

Production Example 671-2

Methyl 4-(4-amino-3-fluorophenoxy)-7-methoxy-6-quinolinecarboxylate

Methyl 4-(4-amino-3-fluorophenoxy)-7-methoxy-6-quinolinecarboxylate (1.54 g) was obtained from methyl 4-(4-nitro-3-fluorophenoxy)-7-methoxy-6-quinolinecarboxylate (2.40 g), by the same procedure as in Production Example 8.

$^1$H-NMR Spectrum (DMSO-$d_6$) δ (ppm): 3.84 (3H, s), 3.95 (3H, s), 5.21 (2H, brd), 6.46 (1H, d, J=5.1 Hz), 6.85-6.86 (2H, m), 7.09 (1H, d, J=11.9 Hz), 7.49 (1H, s), 8.55 (1H, s), 8.65 (1H, d, J=5.1 Hz).

Production Example 671-3

Phenyl N-(2-fluoro-4-(7-methoxy-6-methoxycarbonyl-4-quinolyl)oxyphenyl)carbamate Phenyl N-(2-fluoro-4-(7-methoxy-6-methoxycarbonyl-4-quinolyl)oxyphenyl)carbamate (1.87 g) was obtained from methyl 4-(4-amino-3-fluorophenoxy)-7-methoxy-6-quinolinecarboxylate (1.50 g), by the same procedure as in Production Example 17.

$^1$H-NMR Spectrum (CDCl$_3$) δ (ppm): 3.98 (3H, s), 4.05 (3H, s), 6.49 (1H, d, J=5.3 Hz), 7.03-7.05 (2H, m), 7.22-7.28 (4H, m), 7.50 (1H, s), 8.25 (1H, brs), 8.67 (1H, d, J=5.1 Hz), 8.77 (1H, s).

Example 672

4-(4-(3-Cyclopropylureido)-3-fluorophenoxy)-7-methoxyquinoline-6-carboxylic acid methyl ester Phenyl N-(2-fluoro-4-(7-methoxy-6-methoxycarbonyl-4-quinolyl)oxyphenyl)carbamate (0.9 g) was treated with cyclopropylamine in dimethylsulfoxide at room temperature in the same manner as Example 11, to obtain the title compound (0.5 g) as a solid.

$^1$H-NMR Spectrum (DMSO-$d_6$) δ (ppm): 0.37-0.41 (2H, m), 0.60-0.66 (2H, m), 2.51-2.57 (1H, m), 3.47 (3H, s), 3.59 (3H, s), 6.52 (1H, d, J=5.6 Hz), 6.79-6.82 (1H, m), 7.05-7.10 (1H, m), 7.32 (1H, dd, J=2.8 Hz, J=11.6 Hz), 7.51 (1H, s), 8.17-8.24 (2H, m), 8.55 (1H, s), 8.30 (1H, d, J=5.6 Hz).

Example 673

4-(4-(3-Ethylureido)-3-fluorophenoxy)-7-methoxyquinoline-6-carboxylic acid 4-(4-(3-Ethylureido)-3-fluorophenoxy)-7-methoxyquinoline-6-carboxylic acid methyl ester (600 mg) was hydrolyzed in the same manner as Example 633, to obtain the title compound (210 mg) as a solid.
$^1$H-NMR Spectrum (DMSO-$d_6$) δ (ppm): 1.05 (3H, t, J=7.2 Hz), 3.07-3.15 (2H, m), 3.96 (3H, s), 6.54 (1H, d, J=5.2 Hz), 6.77 (1H, t, J=5.6 Hz), 7.03-7.09 (1H, m), 7.31 (1H, dd, J=2.4 Hz, J=11.6 Hz), 7.50 (1H, s), 8.21 (1H, t, J=9.2 Hz), 8.45 (1H, br s), 8.56 (1H, s), 8.67 (1H, d, J=5.2 Hz).

Example 674

4-(4-(3-Cyclopropylureido)-3-fluorophenoxy)-7-methoxyquinoline-6-carboxylic acid 4-(4-(3-Cyclopropylureido)-3-fluorophenoxy)-7-methoxy-quinoline-6-carboxylic acid methyl ester (500 mg) was hydrolyzed in the same manner as Example 633, to obtain the title compound (220 mg) as a solid.
$^1$H-NMR Spectrum (DMSO-$d_6$) δ (ppm): 0.38-0.43 (2H, m), 0.61-0.67 (2H, m), 2.51-2.58 (1H, m), 3.95 (3H, s), 6.52 (1H, d, J=5.2 Hz), 6.83 (1H, d, J=2.8 Hz), 7.05-7.09 (1H, m), 7.31 (1H, dd, J=2.4 Hz, J=11.6 Hz), 7.47 (1H, s), 8.20 (1H, t, J=9.2 Hz), 8.22-8.26 (1H, m), 8.46 (1H, s), 8.65 (1H, d, J=5.2 Hz).

Example 675

4-(4-(3-Ethylureido)-3-fluorophenoxy)-7-methoxyquinoline-6-carboxylic acid methoxyamide 4-(4-(3-Ethylureido)-3-fluorophenoxy)-7-methoxyquinoline-6-carboxylic acid (65 mg) was treated with methoxylamine, triethylamine and benzotriazol-1-yloxytris(dimethylamino)phosphonium hexafluorophosphate in the same manner as Example 634, to obtain the title compound (21 mg) as a solid.
$^1$H-NMR Spectrum (DMSO-$d_6$) δ (ppm): 1.05 (3H, t, J=7.2 Hz), 3.08-3.15 (2H, m), 3.73 (3H, s), 3.97 (3H, s), 6.52 (1H, d, J=5.2 Hz), 6.56-6.61 (1H, m), 7.02-7.07 (1H, m), 7.30 (1H, dd, J=2.4 Hz, J=11.6 Hz), 7.48 (1H, s), 8.22 (1H, t, J=9.2 Hz), 8.33 (1H, br s), 8.41 (1H, s), 8.65 (1H, d, J=5.2 Hz), 11.44 (1H, br s).

Example 676

4-(4-(3-Ethylureido)-3-fluorophenoxy)-7-methoxyquinoline-6-carboxylic acid cis-(2-fluorocyclopropyl)amide 4-(4-(3-Ethylureido)-3-fluorophenoxy)-7-methoxyquinoline-6-carboxylic acid (20 mg) was treated with cis-2-fluoro-cyclopropylamine, triethylamine and benzotriazol-1-yloxytris(dimethylamino)phosphonium hexafluorophosphate in the same manner as Example 634, to obtain the title compound (9 mg) as a solid.
$^1$H-NMR Spectrum (DMSO-$d_6$) δ (ppm): 1.05 (3H, t, J=7.2 Hz), 1.04-1.18 (2H, m), 2.87-2.95 (1H, m), 3.08-3.15 (2H, m), 3.99 (3H, s), 4.69-4.74 (0.5H, m), 4.86-4.90 (0.5H, m), 6.52 (1H, d, J=5.2 Hz), 6.58 (1H, t, J=5.2 Hz), 7.02-7.07 (1H, m), 7.30 (1H, dd, J=2.4 Hz, J=11.6 Hz), 7.51 (1H, s), 8.21 (1H, t, J=9.2 Hz), 8.31-8.35 (1H, m), 8.45 (1H, d, J=4 Hz), 8.50 (1H, s), 8.65 (1H, d, J=5.2 Hz).

Example 677

4-(4-(3-Ethylureido)-3-fluorophenoxy)-7-methoxyquinoline-6-carboxylic acid (2-ethoxyethyl)-amide 4-(4-(3-Ethylureido)-3-fluorophenoxy)-7-methoxyquinoline-6-carboxylic acid (50 mg) was treated with ethoxyethylamine, triethylamine and benzotriazol-1-yloxytris(dimethylamino)phosphonium hexafluorophosphate in the same manner as Example 634, to obtain the title compound (18 mg) as a solid.
$^1$H-NMR Spectrum (DMSO-$d_6$) δ (ppm): 1.05 (3H, t, J=7.2 Hz), 1.13 (3H, t, J=7.2 Hz), 3.07-3.15 (2H, m), 3.46-3.57 (6H, m), 4.02 (3H, s), 6.52 (1H, d, J=5.2 Hz), 6.58 (1H, t, J=5.2 Hz), 7.02-7.07 (1H, m), 7.30 (1H, dd, J=2.4 Hz, J=11.6 Hz), 7.51 (1H, s), 8.21 (1H, t, J=9.2 Hz), 8.31-8.35 (1H, m), 8.44 (1H, t, J=5.2 Hz), 8.61 (1H, s), 8.65 (1H, d, J=5.2 Hz).

Example 678

4-(4-(3-Ethylureido)-3-fluoro-phenoxy)-7-methoxyquinoline-6-carboxylic acid (2-cyanoethyl)amide 4-(4-(3-Ethylureido)-3-fluoro-phenoxy)-7-methoxyquinoline-6-carboxylic acid (40 mg) was treated with cyanoethylamine, triethylamine and benzotriazol-1-yloxytris(dimethylamino)phosphonium hexafluorophosphate in the same manner as Example 634, to obtain the title compound (29 mg) as a solid.
$^1$H-NMR Spectrum (DMSO-$d_6$) δ (ppm): 1.05 (3H, t, J=7.2 Hz), 2.78 (2H, t, J=6.4 Hz), 3.07-3.15 (2H, m), 3.52-3.58 (2H, m), 4.01 (3H, s), 6.52 (1H, d, J=5.2 Hz), 6.56-6.61 (1H, m), 7.02-7.07 (1H, m), 7.30 (1H, dd, J=2.4 Hz, J=11.6 Hz), 7.52 (1H, s), 8.21 (1H, t, J=9.2 Hz), 8.33 (1H, br s), 8.59 (1H, s), 8.65 (1H, d, J=5.2 Hz), 8.72 (1H, t, J=6 Hz).

Example 679

1-(4-(7-Benzyloxy-6-cyanoquinolin-4-yloxy)-2-methylphenyl)-3-ethylurea

A carbamate (2.1 g) was obtained as a solid from 4-(4-amino-3-methylphenoxy)-7-benzyloxyquinoline-6-carbonitrile (2 g) and phenyl chlorocarbonate, in the same manner as Production Example 17. The carbamate (1 g) was then treated with ethylamine in dimethylsulfoxide at room temperature in the same manner as Example 11, to obtain the title compound (0.87 g) as a solid.
$^1$H-NMR Spectrum (DMSO-$d_6$) δ (ppm): 1.57 (3H, t, J=7.2 Hz), 2.20 (3H, s), 3.07-3.15 (2H, m), 5.43 (2H, s), 6.48-6.55 (2H, m), 7.02 (1H, dd, J=2.8 Hz, J=8.8 Hz), 7.08 (1H, d, J=2.8 Hz), 7.34-7.55 (5H, m), 7.68 (2H, s), 7.92 (1H, d, J=8.8 Hz), 8.70 (1H, d, J=5.6 Hz), 8.74 (1H, s).

Example 680

N-(4-(6-Cyano-7-hydroxyquinolin-4-yloxy)-2-methylphenyl)-N'-ethylurea

In the same manner as Production Example 301-2, N-(4-(7-benzyloxy-6-cyanoquinolin-4-yloxy)-2-methylphenyl)-

N'-ethylurea (0.8 g) was debenzylated in tetrahydrofuran using palladium-carbon, to obtain the title compound (0.42 g) as a solid.

$^1$H-NMR Spectrum (DMSO-d$_6$) δ (ppm): 1.06 (3H, t, J=7.2 Hz), 2.20 (3H, s), 3.07-3.15 (2H, m), 6.37 (1H, d, J=5.2 Hz), 6.52 (1H, t, J=5.6 Hz), 7.01 (1H, dd, J=2.8 Hz, J=8.8 Hz), 7.08 (1H, d, J=2.8 Hz), 7.35 (1H, s), 7.68 (1H, s), 7.93 (1H, d, J=8.8 Hz), 8.59 (1H, d, J=5.2 Hz), 8.61 (1H, s).

Example 681

N-(4-(6-Cyano-7-(piperidin-4-ylmethoxy)quinolin-4-yloxy)-2-methylphenyl)-N'-cyclopropylurea The target substance was obtained from N-(4-(6-cyano-7-hydroxyquinolin-4-yloxy)-2-methylphenyl)-N'-cyclopropylurea (410 mg) and 4-bromoethyl-piperidine-1-carboxylic acid tert-butyl ester, in the same manner as Example 7, and was deprotected to obtain the title compound (15 mg) as a solid.

$^1$H-NMR Spectrum (DMSO-d$_6$) δ (ppm): 0.37-0.43 (2H, m), 0.63-0.66 (2H, m), 1.44-1.56 (2H, m), 1.92-1.98 (2H, m), 2.11-2.20 (1H, m), 2.20 (3H, s), 2.51-2.58 (1H, m), 2.85-2.94 (2H, m), 3.15-3.45 (2H, m), 4.19 (2H, d, J=6.4 Hz), 6.51 (1H, d, J=5.2 Hz), 6.79 (1H, d, J=2.8 Hz), 7.04 (1H, dd, J=2.8 Hz, J=8.8 Hz), 7.10 (1H, d, J=2.8 Hz), 7.62 (1H, s), 7.64 (1H, s), 7.93 (1H, d, J=8.8 Hz), 8.71 (1H, d, J=5.2 Hz), 8.75 (1H, s).

Example 682

N-(4-(6-Cyano-7-(1-methyl-piperidin-4-ylmethoxy)quinolin-4-yloxy)-2-methylphenyl)-N'-cyclopropylurea The title compound (3 mg) was obtained as a solid from N-(4-(6-cyano-7-(piperidin-4-ylmethoxy)quinolin-4-yloxy)-2-methylphenyl)-N'-cyclopropylurea (10 mg), in the same manner as Example 670.

$^1$H-NMR Spectrum (DMSO-d$_6$) δ (ppm): 0.38-0.44 (2H, m), 0.61-0.67 (2H, m), 1.38-1.50 (2H, m), 1.78-1.85 (2H, m), 2.04-2.13 (1H, m), 2.20 (3H, s), 2.26 (3H, br s), 2.48-2.58 (1H, m), 2.84-2.99 (2H, m), 3.04-3.54 (2H, m), 4.15 (2H, d, J=6 Hz), 6.50 (1H, d, J=5.2 Hz), 6.82 (1H, d, J=2.8 Hz), 7.04 (1H, dd, J=2.4 Hz, J=8.8 Hz), 7.10 (1H, d, J=2.4 Hz), 7.58 (1H, s), 7.66 (1H, s), 7.93 (1H, d, J=8.8 Hz), 8.71 (1H, d, J=5.2 Hz), 8.73 (1H, s).

Example 683

N-(4-(6-Cyano-7-(piperidin-4-ylmethoxy)quinolin-4-yloxy)-2-methylphenyl)-N'-ethylurea The target substance was obtained from N-(4-(6-cyano-7-hydroxyquinolin-4-yloxy)-2-methylphenyl)-N'-ethylurea (410 mg) and 4-bromoethyl-piperidine-1-carboxylic acid tert-butyl ester, in the same manner as Example 7, and was deprotected to obtain the title compound (15 mg) as a solid.

$^1$H-NMR Spectrum (DMSO-d$_6$) δ (ppm): 1.06 (3H, t, J=7.2 Hz), 1.44-1.57 (2H, m), 1.93-1.99 (2H, m), 2.11-2.20 (1H, m), 2.20 (3H, s), 2.88-2.98 (2H, m), 3.07-3.14 (2H, m), 3.15-3.45 (2H, m), 4.19 (2H, d, J=6 Hz), 6.51 (1H, d, J=5.2 Hz), 6.57 (1H, t, J=5.6 Hz), 7.02 (1H, dd, J=2.4 Hz, J=8.8 Hz), 7.09 (1H, d, J=2.4 Hz), 7.62 (1H, s), 7.73 (1H, s), 7.94 (1H, d, J=8.8 Hz), 8.71 (1H, d, J=5.2 Hz), 8.74 (1H, s).

Example 684

N-(4-(6-Cyano-7-(1-methyl-piperidin-4-ylmethoxy)quinolin-4-yloxy)-2-methylphenyl)-N'-ethylurea The title compound (5 mg) was obtained as a solid from N-(4-(6-cyano-7-(piperidin-4-ylmethoxy)quinolin-4-yloxy)-2-methylphenyl)-N'-ethylurea (15 mg), in the same manner as Example 670.

$^1$H-NMR Spectrum (DMSO-d$_6$) δ (ppm): 1.06 (3H, t, J=7.2 Hz), 1.38-1.51 (2H, m), 1.78-1.86 (2H, m), 2.07-2.18 (1H, m), 2.20 (3H, s), 2.28 (3H, br s), 2.89-2.97 (2H, m), 3.07-3.15 (2H, m), 3.15-3.41 (2H, m), 4.15 (2H, d, J=6 Hz), 6.50 (1H, d, J=5.2 Hz), 6.58 (1H, t, J=5.6 Hz), 7.03 (1H, dd, J=2.8 Hz, J=8.8 Hz), 7.09 (1H, d, J=2.4 Hz), 7.58 (1H, s), 7.73 (1H, s), 7.94 (1H, d, J=8.8 Hz), 8.79 (1H, d, J=5.2 Hz), 8.73 (1H, s).

Example 697

Methyl 4-(3-chloro-4-(((ethylamino)carbonyl)amino)phenoxy)-7-methoxy-6-quinolinecarboxylate Phenyl N-(2-chloro-4-(7-methoxy-6-methoxycarbonyl-4-quinolyl)oxyphenyl)carbamate (1.92 g, 4.00 mmol) and 2 M ethylamine (tetrahydrofuran solution) (4 ml) were stirred in dimethylformamide (8 ml) at room temperature for 30 minutes. The reaction solution was distributed between ethyl acetate and water, the organic layer was washed with water and saturated brine and dried over anhydrous magnesium sulfate, and the drying agent was filtered out and the filtrate distilled off under reduced pressure. The obtained crude product was suspended in ethyl acetate, the suspension was diluted with hexane, and the crystals were filtered out, washed with hexane and blow-dried to obtain the title compound (1.60 g, 3.72 mmol, 93%) as white crystals.

$^1$H-NMR Spectrum (DMSO-d$_6$) δ (ppm): 1.09 (3H, t, J=7.4 Hz), 3.15 (2H, m), 3.87 (3H, s), 3.99 (3H, s), 6.54 (1H, d, J=5.2 Hz), 7.01 (1H, t, J=5.4 Hz), 7.25 (1H, dd, J=2.8, 9.0 Hz), 7.50 (1H, d, J=2.8 Hz), 7.54 (1H, s), 8.08 (1H, s), 8.28 (1H, d, J=9.0 Hz), 8.58 (1H, s), 8.69 (1H, d, J=5.2 Hz).

Example 698

4-(3-Chloro-4-(((ethylamino)carbonyl)amino)phenoxy)-7-methoxy-6-quinolinecarboxylic acid After adding methanol (14 ml) and 2N sodium hydroxide aqueous solution (7 ml) to methyl 4-(3-chloro-4-(((ethylamino)carbonyl)amino)phenoxy)-7-methoxy-6-quinolinecarboxylate (1.50 g, 3.49 mmol), the mixture was stirred at 60° C. for 90 minutes. The reaction solution was allowed to cool to room temperature, and after neutralization by addition of 2N hydrochloric acid, the methanol was distilled off and the precipitated white crystals were filtered out, thoroughly washed with water and dried at 60° C. to obtain the title compound (1.36 g, 3.27 mmol, 94%).

$^1$H-NMR Spectrum (DMSO-d$_6$) δ (ppm): 1.09 (3H, t, J=7.4 Hz), 3.15 (2H, m), 3.98 (3H, s), 6.53 (1H, d, J=5.0 Hz), 7.00 (1H, t, J=5.4 Hz), 7.25 (1H, dd, J=2.8, 9.0 Hz), 7.48-7.53 (2H, m), 8.08 (1H, s), 8.27 (1H, d, J=9.0 Hz), 8.54 (1H, s), 8.68 (1H, d, J=5.0 Hz), 13.12 (1H, brs).

Example 699

N6-Methyl-4-(3-chloro-4-(((ethylamino)carbonyl)amino)phenoxy)-7-methoxy-6-quinolinecarboxamide After dissolving 4-(3-chloro-4-(((ethylamino)carbonyl)amino)phenoxy)-7-methoxy-6-quinolinecarboxylic acid (104 mg, 0.250 mmol) in dimethylformamide (3 ml), there were added a 40% methylamine-methanol solution (0.100 ml), triethylamine (0.250 ml) and 1H-1,2,3-benzotriazol-1-yloxy)(tri(dimethylamino))phosphoniumhexafluorophosphate (221 mg, 0.500 mmol) in that order at room temperature, and the mixture was stirred for 15 hours. The reaction solution was distributed between ethyl acetate and water, and the organic layer was washed with water and saturated brine and dried over anhydrous magnesium sulfate. After distilling off the solvent, the residue was suspended in ethyl acetate, the suspension was diluted with hexane and the crystals were filtered out and blow-dried to obtain the title compound (79.0 mg, 0.184 mmol, 74%) as white crystals.

$^1$H-NMR Spectrum (DMSO-$d_6$) δ (ppm): 1.08 (3H, t, J=7.4 Hz), 2.85 (3H, d, J=4.2 Hz), 3.15 (2H, m), 4.02 (3H, s), 6.53 (1H, d, J=5.2 Hz), 7.00 (1H, t, J=5.2 Hz), 7.22 (1H, dd, J=2.8, 9.2 Hz), 7.47 (1H, d, J=2.8 Hz), 7.52 (1H, s), 8.07 (1H, s), 8.26 (1H, d, J=9.2 Hz), 8.36 (1H, q, J=4.2 Hz), 8.59 (1H, s), 8.67 (1H, d, J=5.2 Hz).

Example 700

N6-Ethyl-4-(3-chloro-4-(((ethylamino)carbonyl)amino)phenoxy)-7-methoxy-6-quinolinecarboxamide The title compound (90.0 mg, 0.203 mmol, 81%) was obtained as white crystals from 4-(3-chloro-4-(((ethylamino)carbonyl)amino)phenoxy)-7-methoxy-6-quinolinecarboxylic acid (104 mg, 0.250 mmol) and 2.0 M ethylamine (tetrahydrofuran solution), by the same procedure as in Example 699.

$^1$H-NMR Spectrum (DMSO-$d_6$) δ (ppm): 1.09 (3H, t, J=7.4 Hz), 1.15 (3H, t, J=7.2 Hz), 3.15 (2H, m), 3.28-3.38 (2H, m), 4.02 (3H, s), 6.53 (1H, d, J=5.2 Hz), 7.00 (1H, t, J=5.4 Hz), 7.22 (1H, dd, J=2.8, 9.2 Hz), 7.47 (1H, d, J=2.8 Hz), 7.51 (1H, s), 8.07 (1H, s), 8.27 (1H, d, J=9.2 Hz), 8.40 (1H, t, J=5.4 Hz), 8.54 (1H, s), 8.66 (1H, d, J=5.2 Hz).

Example 701

N6-Cyclopropyl-4-(3-chloro-4-(((ethylamino)carbonyl)amino)phenoxy)-7-methoxy-6-quinolinecarboxamide The title compound (83.0 mg, 0.182 mmol, 73%) was obtained as white crystals from 4-(3-chloro-4-(((ethylamino)carbonyl)amino)phenoxy)-7-methoxy-6-quinolinecarboxylic acid (104 mg, 0.250 mmol) and cyclopropylamine, by the same procedure as in Example 699.

$^1$H-NMR Spectrum (DMSO-$d_6$) δ (ppm): 0.58 (2H, m), 0.71 (2H, m), 1.08 (3H, t, J=7.4 Hz), 2.87 (1H, m), 3.14 (2H, m), 3.99 (3H, s), 6.53 (1H, d, J=5.2 Hz), 7.00 (1H, t, J=4.8 Hz), 7.21 (1H, dd, J=2.8, 9.2 Hz), 7.47 (1H, d, J=2.8 Hz), 7.49 (1H, s), 8.07 (1H, s), 8.27 (1H, d, J=9.2 Hz), 8.34 (1H, d, J=4.0 Hz), 8.42 (1H, s), 8.66 (1H, d, J=5.2 Hz).

Example 702

N6-Methoxy-4-(3-chloro-4-(((ethylamino)carbonyl)amino)phenoxy)-7-methoxy-6-quinolinecarboxamide The title compound (52.0 mg, 0.117 mmol, 47%) was obtained as white crystals from 4-(3-chloro-4-(((ethylamino)carbonyl)amino)phenoxy)-7-methoxy-6-quinolinecarboxylic acid (104 mg, 0.250 mmol) and methoxylamine hydrochloride, by the same procedure as in Example 699.

$^1$H-NMR Spectrum (DMSO-$d_6$) δ (ppm): 1.09 (3H, t, J=7.4 Hz), 3.15 (2H, m), 3.75 (3H, s), 4.00 (3H, s), 6.54 (1H, d, J=5.2 Hz), 7.00 (1H, t, J=5.4 Hz), 7.23 (1H, dd, J=2.8, 9.2 Hz), 7.48 (1H, d, J=2.8 Hz), 7.50 (1H, s), 8.07 (1H, s), 8.27 (1H, d, J=9.2 Hz), 8.43 (1H, s), 8.67 (1H, d, J=5.2 Hz), 11.45 (1H, s).

Example 703

N6-(2-Methoxyethyl)-4-(3-chloro-4-(((ethylamino)carbonyl)amino)phenoxy)-7-methoxy-6-quinolinecarboxamide The title compound (71.0 mg, 0.150 mmol, 60%) was obtained as white crystals from 4-(3-chloro-4-(((ethylamino)carbonyl)amino)phenoxy)-7-methoxy-6-quinolinecarboxylic acid (104 mg, 0.250 mmol) and 2-methoxyethylamine, by the same procedure as in Example 699.

$^1$H-NMR Spectrum (DMSO-$d_6$) d (ppm): 1.08 (3H, t, J=7.4 Hz), 3.15 (2H, m), 3.30 (3H, s), 3.47-3.52 (4H, m), 4.03 (3H, s), 6.54 (1H, d, J=5.2 Hz), 7.00 (1H, t, J=5.4 Hz), 7.23 (1H, dd, J=2.8, 9.2 Hz), 7.48 (1H, d, J=2.8 Hz), 7.53 (1H, s), 8.07 (1H, s), 8.27 (1H, d, J=9.2 Hz), 8.44 (1H, m), 8.62 (1H, s), 8.67 (1H, d, J=5.2 Hz).

Example 704

N6-(2-Fluoroethyl)-4-(3-chloro-4-(((ethylamino)carbonyl)amino)phenoxy)-7-methoxy-6-quinolinecarboxamide The title compound (80.0 mg, 0.174 mmol, 69%) was obtained as white crystals from 4-(3-chloro-4-(((ethylamino)carbonyl)amino)phenoxy)-7-methoxy-6-quinolinecarboxylic acid (104 mg, 0.250 mmol) and 2-fluoroethylamine hydrochloride, by the same procedure as in Example 699.

$^1$H-NMR Spectrum (DMSO-$d_6$) δ (ppm): 1.08 (3H, t, J=7.4 Hz), 3.15 (2H, m), 3.59 (1H, m), 3.67 (1H, m), 4.03 (3H, s), 4.51 (1H, m), 4.63 (1H, m), 6.54 (1H, d, J=5.2 Hz), 7.00 (1H, t, J=5.4 Hz), 7.23 (1H, dd, J=2.8, 9.2 Hz), 7.48 (1H, d, J=2.8 Hz), 7.53 (1H, s), 8.07 (1H, s), 8.27 (1H, d, J=9.2 Hz), 8.58-8.62 (2H, m), 8.67 (1H, d, J=5.2 Hz).

Example 705

N6-((2R)Tetrahydro-2-furanylmethyl)-4-(3-chloro-4-(((ethylamino)carbonyl)amino)phenoxy)-7-methoxy-6-quinolinecarboxamide The title compound (99.0 mg, 0.198 mmol, 79%) was obtained as a white powder from 4-(3-chloro-4-(((ethylamino)carbonyl)amino)phenoxy)-7-methoxy-6-quinolinecarboxylic acid (104 mg, 0.250 mmol) and R-tetrahydrofurfurylamine, by the same procedure as in Example 699.

$^1$H-NMR Spectrum (DMSO-$d_6$) δ (ppm): 1.08 (3H, t, J=7.4 Hz), 1.62 (1H, m), 1.80-2.00 (3H, m), 3.15 (2H, m), 3.40 (2H, m), 3.66 (1H, dd, J=3.6, 14.0 Hz), 3.81 (1H, dd, J=4.0, 14.0 Hz), 3.99 (1H, m), 4.04 (3H, s), 6.54 (1H, d, J=5.2 Hz), 7.00 (1H, t, J=5.4 Hz), 7.23 (1H, dd, J=2.8, 8.8 Hz), 7.48 (1H, d, J=2.8 Hz), 7.54 (1H, s), 8.07 (1H, s), 8.26 (1H, d, J=8.8 Hz), 8.43 (1H, t, J=5.6 Hz), 8.61 (1H, s), 8.67 (1H, d, J=5.2 Hz).

Example 706

N6-((2S)Tetrahydro-2-furanylmethyl)-4-(3-chloro-4-(((ethylamino)carbonyl)amino)phenoxy)-7-methoxy-6-quinolinecarboxamide The title compound (87.0 mg, 0.174 mmol, 70%) was obtained as a white powder from 4-(3-chloro-4-(((ethylamino)carbonyl)amino)phenoxy)-7-methoxy-6-quinolinecarboxylic acid (104 mg, 0.250 mmol) and S-tetrahydrofurfurylamine, by the same procedure as in Example 699.

Example 707

N6-(2-Ethoxyethyl)-4-(3-chloro-4-(((ethylamino)carbonyl)amino)phenoxy)-7-methoxy-6-quinolinecarboxamide The title compound (112 mg, 0.239 mmol, 95%) was obtained as a white powder from 4-(3-chloro-4-(((ethylamino)carbonyl)amino)phenoxy)-7-methoxy-6-quinolinecarboxylic acid (104 mg, 0.250 mmol) and 2-ethoxyethylamine, by the same procedure as in Example 699.

$^1$H-NMR Spectrum (DMSO-d$_6$) δ (ppm): 1.08 (3H, t, J=7.4 Hz), 1.16 (3H, t, J=6.8 Hz), 3.15 (2H, m), 3.45-3.56 (6H, m), 4.03 (3H, s), 6.54 (1H, d, J=5.2 Hz), 7.01 (1H, m), 7.23 (1H, dd, J=2.8, 9.2 Hz), 7.48 (1H, d, J=2.8 Hz), 7.54 (1H, s), 8.08 (1H, s), 8.27 (1H, dd, J=2.8, 9.2 Hz), 8.46 (1H, m), 8.64 (1H, d, J=2.0 Hz), 8.68 (1H, d, J=5.2 Hz).

Example 708

N6-Isobutoxy-4-(3-chloro-4-(((ethylamino)carbonyl)amino)phenoxy)-7-methoxy-6-quinolinecarboxamide The title compound (64.0 mg, 0.131 mmol, 53%) was obtained as a white powder from 4-(3-chloro-4-(((ethylamino)carbonyl)amino)phenoxy)-7-methoxy-6-quinolinecarboxylic acid (104 mg, 0.250 mmol) and isobutoxylamine hydrochloride, by the same procedure as in Example 699.

$^1$H-NMR Spectrum (DMSO-d$_6$) δ (ppm): 0.95 (6H, d, J=6.8 Hz), 1.08 (3H, t, J=7.4 Hz), 1.97 (1H, m), 3.15 (2H, m), 3.71 (2H, d, J=6.8 Hz), 3.99 (3H, s), 6.54 (1H, d, J=5.2 Hz), 7.00 (1H, m), 7.23 (1H, dd, J=2.8, 9.2 Hz), 7.47 (1H, d, J=2.8 Hz), 7.50 (1H, s), 8.08 (1H, s), 8.27 (1H, dd, J=2.8, 9.2 Hz), 8.36 (1H, s), 8.67 (1H, d, J=5.2 Hz), 11.36 (1H, br s).

Example 709

N6-Ethyl-4-(3-chloro-4-(((methylamino)carbonyl)amino)phenoxy)-7-((2R)-3-diethylamino-2-hydroxypropoxy)-6-quinolinecarboxamide After adding (2R)oxiran-2-ylmethyl 4-methyl-1-benzenesulfonate (66 mg, 0.290 mmol), potassium carbonate (32 mg, 0.231 mmol) and dimethylformamide (2 ml) to N6-ethyl-4-(3-chloro-4-(((methylamino)carbonyl)amino)phenoxy)-7-hydroxy-6-quinolinecarboxamide (80.0 mg, 0.193 mmol), the mixture was stirred at 60° C. for 7 hours. Diethylamine (1 ml) was then added, and the mixture was stirred at 60° C. overnight. The reaction solution was distributed between ethyl acetate-tetrahydrofuran (1:1) and water, and the organic layer was washed with water and saturated brine and then dried over anhydrous sodium sulfate. The solvent was distilled off, the residue was subjected to silica gel column chromatography (eluent-ethyl acetate:methanol=95:5), the fraction containing the target substance was concentrated, and crystals were precipitated from ethyl acetate-hexane (1:1), filtered out and blow-dried to obtain the title compound (51.7 mg, 0.095 mmol, 49.3%) as white crystals.

$^1$H-NMR Spectrum (DMSO-d$_6$) δ (ppm): 0.94 (6H, t, J=7.2 Hz), 1.16 (3H, t, J=7.2 Hz), 2.40-2.60 (6H, m), 2.66 (3H, d, J=4.8 Hz), 3.20-3.40 (2H, m), 3.98 (1H, m), 4.19 (1H, dd, J=5.2, 10.0 Hz), 4.31 (1H, dd, J=3.2, 10.0 Hz), 5.09 (1H, d, J=4.8 Hz), 6.51 (1H, d, J=5.2 Hz), 6.86 (1H, q, J=4.8 Hz), 7.22 (1H, dd, J=2.8, 9.2 Hz), 7.47 (1H, d, J=2.8 Hz), 7.52 (1H, s), 8.10 (1H, s), 8.23 (1H, d, J=9.2 Hz), 8.54 (1H, m), 8.65 (1H, d, J=5.2 Hz), 8.73 (1H, s).

Example 710

N6-Ethyl-4-(3-chloro-4-(((ethylamino)carbonyl)amino)phenoxy)-7-((2R)-3-diethylamino-2-hydroxypropoxy)-6-quinolinecarboxamide The title compound (44.5 mg, 0.080 mmol, 43.8%) was obtained as white crystals from N6-ethyl-4-(3-chloro-4-(((ethylamino)carbonyl)amino)phenoxy)-7-hydroxy-6-quinolinecarboxamide (78.0 mg, 0.182 mmol), by the same procedure as in Example 709.

$^1$H-NMR Spectrum (DMSO-d$_6$) δ (ppm): 0.94 (6H, t, J=7.2 Hz), 1.06 (3H, t, J=7.2 Hz), 1.16 (3H, t, J=7.2 Hz), 2.40-2.60 (6H, m), 3.12 (2H, m), 3.20-3.40 (2H, m), 3.98 (1H, m), 4.22 (1H, dd, J=5.6, 9.6 Hz), 4.31 (1H, dd, J=3.2, 9.6 Hz), 5.08 (1H, d, J=4.4 Hz), 6.51 (1H, d, J=5.2 Hz), 6.98 (1H, m), 7.22 (1H, dd, J=2.8, 9.2 Hz), 7.47 (1H, d, J=2.8 Hz), 7.52 (1H, s), 8.05 (1H, s), 8.25 (1H, d, J=9.2 Hz), 8.54 (1H, m), 8.65 (1H, d, J=5.2 Hz), 8.73 (1H, s).

Example 711

N6-Ethyl-4-(3-chloro-4-(((methylamino)carbonyl)amino)phenoxy)-7-((2R)-2-hydroxy-3-(1-pyrrolidino)propoxy)-6-quinolinecarboxamide After adding (2R)oxiran-2-ylmethyl 4-methyl-1-benzenesulfonate (66 mg, 0.290 mmol), potassium carbonate (32 mg, 0.231 mmol) and dimethylformamide (2 ml) to N6-ethyl-4-(3-chloro-4-(((methylamino)carbonyl)amino)phenoxy)-7-hydroxy-6-quinolinecarboxamide (80.0 mg, 0.193 mmol), the mixture was stirred at 60° C. for 7 hours. After allowing the reaction solution to cool to room temperature, pyrrolidine (0.5 ml) was added and the mixture was further stirred overnight. The reaction solution was distributed between ethyl acetate-tetrahydrofuran (1:1) and water, and the organic layer was washed with water and saturated brine and then dried over anhydrous sodium sulfate. The solvent was distilled off, the residue was subjected to silica gel column chromatography (eluent-ethyl acetate:methanol=95:5), the fraction containing the target substance was concentrated, and crystals were precipitated from ethyl acetate-hexane (1:1), filtered out and blow-dried to obtain the title compound (54.8 mg, 0.101 mmol, 52.4%) as white crystals.

$^1$H-NMR Spectrum (DMSO-d$_6$) δ (ppm): 1.16 (3H, t, J=7.2 Hz), 1.67 (4H, m), 2.40-2.60 (5H, m), 2.65-2.71 (4H, m), 3.20-3.40 (2H, m), 4.05 (1H, m), 4.19 (1H, dd, J=6.0, 10.0

Hz), 4.32 (1H, dd, J=3.6, 10.0 Hz), 5.18 (1H, d, J=4.4 Hz), 6.52 (1H, d, J=4.0 Hz), 6.86 (1H, q, J=4.8 Hz), 7.22 (1H, d, J=9.2 Hz), 7.47 (1H, s), 7.52 (1H, s), 8.10 (1H, s), 8.23 (1H, d, J=9.2 Hz), 8.53 (1H, m), 8.65 (1H, d, J=4.0 Hz), 8.71 (1H, s).

Example 712

N6-Ethyl-4-(3-chloro-4-(((ethylamino)carbonyl) amino)phenoxy)-7-((2R)-2-hydroxy-3-(1-pyrrolidino)propoxy)-6-quinolinecarboxamide The title compound (47.3 mg, 0.085 mmol, 46.8%) was obtained as white crystals from N6-ethyl-4-(3-chloro-4-(((ethylamino)carbonyl)amino)phenoxy)-7-hydroxy-6-quinolinecarboxamide (78.0 mg, 0.182 mmol), by the same procedure as in Example 711.

$^1$H-NMR Spectrum (DMSO-d$_6$) δ (ppm): 1.06 (3H, t, J=7.2 Hz), 1.16 (3H, t, J=7.2 Hz), 1.67 (4H, m), 2.40-2.60 (5H, m), 2.68 (1H, dd, J=6.4, 12.0 Hz), 3.12 (2H, m), 3.35 (2H, m), 4.05 (1H, m), 4.19 (1H, dd, J=6.4, 10.0 Hz), 4.32 (1H, dd, J=3.6, 10.0 Hz), 5.18 (1H, d, J=4.8 Hz), 6.51 (1H, d, J=5.2 Hz), 6.98 (1H, m), 7.21 (1H, dd, J=2.8, 9.2 Hz), 7.47 (1H, d, J=2.8 Hz), 7.52 (1H, s), 8.05 (1H, s), 8.25 (1H, d, J=9.2 Hz), 8.53 (1H, m), 8.65 (1H, d, J=5.2 Hz), 8.71 (1H, s).

Example 713

N-(4-((6-Cyano-7-(((2R)-3-(diethylamino)-2-hydroxypropyl)oxy)-4-quinolyl)oxy)phenyl)-N'-(thiazol-2-yl)urea After dissolving 4-(4-aminophenoxy)-6-cyano-7-(((2R)-3-(diethylamino)-2-hydroxypropyl)oxy)quinoline (105 mg, 0.2583 mmol) in dimethylsulfoxide (1 ml), there was added phenyl(thiazol-2-yl)carbamate (60 mg, 0.2712 mmol), and the mixture was heated and stirred at 85° C. for 40 minutes. After cooling to room temperature, water was added to the reaction solution, extraction was performed with ethyl acetate-tetrahydrofuran, and the extract was washed with saturated brine and dried over anhydrous sodium sulfate. Upon distilling off the solvent, the residue was dissolved in acetone and diluted with diethyl ether, and the precipitate was washed with diethyl ether and blow-dried to obtain the title compound (75 mg, 0.1408 mmol, 54.51%) as a light yellow powder.

$^1$H-NMR Spectrum (DMSO-d$_6$) δ (ppm): 0.96 (6H, t, J=7.0 Hz), 2.41-2.68 (6H, m), 3.96 (1H, m), 4.21 (1H, dd, J=5.2, 10.0 Hz), 4.31 (1H, dd, J=3.2, 10.0 Hz), 4.92 (1H, brs), 6.52 (1H, d, J=5.2 Hz), 7.10 (1H, d, J=3.6 Hz), 7.27 (2H, d, J=9.0 Hz), 7.37 (1H, d, J=3.6 Hz), 7.61 (1H, s), 7.63 (2H, d, J=9.0 Hz), 8.72 (1H, d, J=5.2 Hz), 8.76 (1H, s), 9.15 (1H, brs).

The starting materials were synthesized in the following manner.

Production Example 713-1

4-(4-Aminophenoxy)-6-cyano-7-hydroxyquinoline 6-cyano-7-hydroxy-4-(4-nitrophenoxy)quinoline (1.23 g, 4.00 mmol), obtained by deprotecting the benzyl group of the 7-benzyloxy-6-cyano-4-(4-nitrophenoxy)quinoline obtained in Production Example 5 according to the method of Production Example 21, was used in a reaction for reduction of the nitro group in the same manner as Production Example 21, to obtain the title compound (0.864 g, 3.1160 mmol, 77.90%) as yellowish-brown crystals.

$^1$H-NMR Spectrum (CDCl$_3$) δ (ppm): 5.18 (2H, brs), 6.36 (1H, d, J=5.2 Hz), 6.65 (2H, d, J=8.4 Hz), 6.92 (2H, d, J=8.4 Hz), 7.38 (1H, s), 8.60 (1H, d, J=5.2 Hz), 8.62 (1H, s).

Production Example 713-2

4-(4-Aminophenoxy)-6-cyano-7-((2R)-oxiran-2-yl) methoxyquinoline

After dissolving 4-(4-aminophenoxy)-6-cyano-7-hydroxyquinoline (277 mg, 1.00 mmol) in dimethylformamide (3.0 ml), sodium hydride (40 mg, 1.00 mmol, 60% in oil) was added at room temperature and the mixture was stirred. There was then added (2R)-oxiran-2-ylmethyl 4-methyl-1-benzenesulfonate (228 mg, 1.00 mmol), and the mixture was heated and stirred at 60° C. for 5 hours. After cooling to room temperature, the reaction solution was distributed between ethyl acetate and water. The organic layer was washed with saturated brine and dried over anhydrous sodium sulfate, and the solvent was distilled off to obtain the title compound (322 mg, 0.97 mmol, 97%) as a yellow solid.

$^1$H-NMR Spectrum (DMSO-d6) δ (ppm): 2.82 (1H, dd, J=2.8, 4.8 Hz), 2.93 (1H, dd, J=4.8, 4.8 Hz), 3.48 (1H, m), 4.17 (1H, dd, J=6.6, 12.0 Hz), 4.71 (1H, dd, J=2.0, 12.0 Hz), 5.20 (2H, m), 6.49 (1H, d, J=5.2 Hz), 6.68 (2H, d, J=8.8 Hz), 6.96 (2H, d, J=8.8 Hz), 7.62 (1H, s), 8.71 (1H, d, J=5.2 Hz), 8.76 (1H, s).

Production Example 713-3

4-(4-Aminophenoxy)-6-cyano-7-(((2R)-3-(diethylamino)-2-hydroxypropyl)oxy)quinoline The title compound (105 mg, 0.2583 mmol, 29.02%) was obtained as a light yellow oil using 4-(4-aminophenoxy)-6-cyano-7-((2R)-oxiran-2-yl)methoxyquinoline (297 mg, 0.8900 mmol), by the same procedure as in Production Example 429-2.

$^1$H-NMR Spectrum (CDCl$_3$) δ (ppm): 1.08 (6H, t, J=7.0 Hz), 1.50-2.50 (1H, brs), 2.55-2.76 (6H, m), 3.79 (2H, brs), 4.15 (1H, m), 4.24 (2H, d, J=4.8 Hz), 6.46 (1H, d, J=5.4 Hz), 6.77 (2H, d, J=8.8 Hz), 6.96 (2H, d, J=8.8 Hz), 7.48 (1H, s), 8.64 (1H, d, J=5.4 Hz), 8.69 (1H, s).

Example 714

N-(4-((6-Cyano-7-(((2R)-2-hydroxy-3-(pyrrolidin-1-yl)propyl)oxy)-4-quinolyl)oxy)phenyl)-N'-(thiazol-2-yl)urea 4-(4-Aminophenoxy)-6-cyano-7-((2R)-oxiran-2-yl)methoxyquinoline (322 mg, 0.966 mmol) and thiazol-2-ylcarbamic acid phenyl ester (255 mg, 1.26 mmol) were heated and stirred in dimethylsulfoxide (2 ml) at 85° C. for 4 hours. The reaction solution was distributed between an ethyl acetate-tetrahydrofuran mixed solvent and water, the organic layer was washed with water and saturated brine and then dried over anhydrous magnesium sulfate, and the drying agent was filtered off and the filtrate distilled off under reduced pressure. The obtained product and pyrrolidine (343 mg, 4.83 mmol) were stirred in dimethylformamide (3 ml) at room temperature for 15 hours. The reaction solution was distributed between ethyl acetate and water, the organic layer was washed with water and saturated brine and dried over anhydrous magnesium sulfate, the drying agent was filtered off, and the filtrate was distilled off under reduced pressure. The obtained crude product was subjected to silica gel column chromatography (eluent-ethyl acetate:methanol=15:1), the fraction containing the target substance was concentrated and suspended in ethyl acetate, the suspension was diluted with hexane, and the crystals were filtered out, washed with hexane and blow-dried to obtain the title compound (45 mg, 0.085 mmol, 9%) as light yellow crystals.

$^1$H-NMR Spectrum (DMSO-d$_6$) δ (ppm): 1.67 (4H, m), 2.40-2.60 (5H, m), 2.73 (1H, dd, J=6.4, 12.4 Hz), 4.03 (1H, m), 4.22 (1H, dd, J=6.0, 10.0 Hz), 4.33 (1H, dd, J=3.2, 10.0 Hz), 5.04 (1H, d, J=5.2 Hz), 6.54 (1H, d, J=5.2 Hz), 7.12 (1H, d, J=3.6 Hz), 7.27-7.32 (2H, m), 7.38 (1H, d, J=3.6 Hz), 7.62-7.69 (3H, m), 8.74 (1H, d, J=5.2 Hz), 8.77 (1H, s), 9.25 (1H, br s), 10.73 (1H, br s).

Example 715

4-{6-Cyano-4-[4-(3-thiazol-2-ylureido)phenoxy]quinolin-7-yloxymethyl}piperidine-1-carboxylic acid tert-butyl ester 4-(4-(4-Aminophenoxy)-6-cyanoquinolin-7-yloxymethyl)-piperidine-1-carboxylic acid tert-butyl ester (225 mg) was heated in dimethylsulfoxide together with thiazol-2-ylcarbamic acid phenyl ester at 80° C. in the same manner as Example 713 to obtain the title compound (240 mg) as a solid.

$^1$H-NMR Spectrum (DMSO-d$_6$) δ (ppm): 1.19-1.32 (2H, m), 1.39 (9H, s), 1.75-1.84 (2H, m), 2.01-2.11 (1H, m), 2.66-2.87 (2H, m), 3.94-4.04 (2H, m), 4.17 (2H, d, J=5.6 Hz), 6.52 (1H, d, J=5.2 Hz), 7.11 (1H, d, J=3.2 Hz), 7.27 (2H, d, J=8.8 Hz), 7.37 (1H, d, J=3.2 Hz), 7.58 (1H, s), 7.62 (2H, d, J=8.8 Hz), 8.71 (1H, d, J=5.2 Hz), 8.75 (1H, s), 9.14 (1H, brs).

The intermediate was synthesized in the following manner.

Production Example 715-1

4-(4-(4-Aminophenoxy)-6-cyanoquinolin-7-yloxymethyl)-piperidine-1-carboxylic acid tert-butyl ester After treating 4-(4-aminophenoxy)-7-hydroxyquinoline-6-carbonitrile (0.32 g) with sodium hydride in dimethylformamide in the same manner as Production Example 713-2, it was reacted with 4-bromoethylpiperidine-1-carboxylic acid tert-butyl ester to obtain the title compound (225 mg) as a solid.

$^1$H-NMR Spectrum (DMSO-d$_6$) δ (ppm): 1.18-1.32 (2H, m), 1.39 (9H, s), 1.75-1.82 (2H, m), 1.98-2.10 (1H, m), 2.62-2.92 (2H, m), 3.94-4.03 (2H, m), 4.15 (2H, d, J=6 Hz), 5.16-5.21 (2H, m), 6.45 (1H, d, J=5.2 Hz), 6.65 (2H, d, J=8.8 Hz), 6.93 (2H, d, J=8.8 Hz), 7.55 (1H, s), 8.68 (1H, d, J=5.2 Hz), 8.70 (1H, s).

Example 716

1-(4-(6-Cyano-7-(piperidin-4-ylmethoxy)quinolin-4-yloxy)phenyl)-3-(thiazol-2-yl)urea 4-(6-Cyano-4-(4-(3-thiazol-2-yl-ureido)-phenoxy)-quinolin-7-yloxymethyl)-piperidine-1-carboxylic acid tert-butyl-ester (240 mg) was deprotected with trifluoroacetic acid in the same manner as Production Example 670-4 to obtain the title compound (220 mg) as a solid.

$^1$H-NMR Spectrum (DMSO-d$_6$) δ (ppm): 1.46-1.59 (2H, m), 1.87-1.96 (2H, m), 2.06-2.18 (1H, m), 2.78-2.89 (2H, m), 3.08-3.38 (2H, m), 4.13 (2H, d, J=6 Hz), 6.43 (1H, d, J=5.2 Hz), 7.07 (1H, d, J=3.2 Hz), 7.20 (2H, d, J=9.2 Hz), 7.36 (1H, d, J=3.2 Hz), 7.57 (1H, s), 7.68 (2H, d, J=9.2 Hz), 8.63 (1H, d, J=5.2 Hz), 8.71 (1H, s), 9.82 (1H, br).

Example 717

1-(4-(6-Cyano-7-(1-methylpiperidin-4-ylmethoxy)quinolin-4-yloxy)phenyl)-3-(thiazol-2-yl)urea The title compound (51 mg) was obtained as a solid from 1-(4-(6-cyano-7-(piperidin-4-ylmethoxy)quinolin-4-yloxy)phenyl)-3-(thiazol-2-yl)urea (220 mg), in the same manner as Example 670.

$^1$H-NMR Spectrum (DMSO-d$_6$) δ (ppm): 1.35-1.48 (2H, m), 1.75-1.85 (2H, m), 1.89-1.96 (1H, m), 2.18 (3H, brs), 2.79-2.86 (2H, m), 3.18-3.38 (2H, m), 4.15 (2H, d, J=5.6 Hz), 6.52 (1H, d, J=5.2 Hz), 7.10 (1H, d, J=3.2 Hz), 7.27 (2H, d, J=9.2 Hz), 7.37 (1H, d, J=3.2 Hz), 7.58 (1H, s), 7.63 (2H, d, J=9.2 Hz), 8.72 (1H, d, J=5.2 Hz), 8.76 (1H, s), 9.20 (1H, br).

Example 718

N-(4-(6-Carbamoyl-7-methoxy-4-quinolyl)oxy-2-trifluoromethylphenyl)-N'-ethylurea Ethylamine 2N tetrahydrofuran solution (0.10 ml) was added to dimethylsulfoxide (0.5 ml), and then (4-(6-carbamoyl-7-methoxy-4-quinolyl)oxy-2-trifluoromethylphenyl)carbamic acid phenyl ester (25 mg) was dissolved therein and the mixture was stirred for 10 minutes. Water and ethyl acetate were added to the reaction solution, and the precipitated crystals were filtered out to obtain the title compound (5.0 mg).

$^1$H-NMR (DMSO-d$_6$) δ (ppm) 1.08 (3H, t, J=7.2 Hz), 3.10-3.18 (2H, m), 4.04 (3H, s), 6.54 (1H, d, J=5.2 Hz), 7.00-7.07 (1H, m), 7.51-7.63 (3H, m), 7.74 (1H, brs), 7.82-7.88 (2H, m), 8.06-8.13 (1H, m), 8.66-8.70 (2H, m)

Example 719

N-[4-(6-Carbamoyl-7-methoxy-4-quinolyl)oxy-2-trifluoromethylphenyl]-N'-methylurea After adding [4-(6-carbamoyl-7-methoxy-4-quinolyl)oxy-2-trifluoromethylphenyl]carbamic acid phenyl ester (25 mg) to methylamine 2N tetrahydrofuran solution (1.00 ml), the mixture was stirred for 10 minutes. The precipitated crystals were filtered out and washed with tetrahydrofuran to obtain the title compound (10 mg).

$^1$H-NMR (DMSO-d$_6$) δ (ppm) 2.68 (3H, d, J=4.0 Hz), 4.04 (3H, s), 6.54 (1H, d, J=5.6 Hz), 6.87-6.94 (1H, m), 7.51-7.63 (3H, m), 7.75 (1H, brs), 7.86 (1H, brs), 7.90 (1H, brs), 8.03-8.09 (1H, m), 8.66-8.70 (2H, m)

Example 720

N-(4-(7-Benzyloxy-6-cyano-quinolin-4-yloxy)-2,3-dimethylphenyl)-N'-cyclopropylurea Cyclopropylamine (1 ml) was added to dimethylformamide (10 ml), and then (4-(7-benzyloxy-6-cyano-quinolin-4-yloxy)-2,3-dimethylphenyl)carbamic acid phenyl ester (1.99 g) was added thereto and the mixture was stirred at room temperature for 10 minutes. Water (30 ml) and ethyl acetate (30 ml) were added, and the precipitated crystals were filtered out and washed with ethyl acetate to obtain the title compound (1660 mg).

¹H-NMR (DMSO-d₆) δ (ppm) 0.40-0.45 (2H, m), 0.62-0.67 (2H, m), 2.03 (3H, s), 2.16 (3H, s), 2.52-2.59 (1H, m), 5.47 (2H, s), 6.33 (1H, d, J=5.2 Hz), 6.68-6.74 (1H, m), 7.00 (1H, d, J=8.8 Hz), 7.35-7.49 (3H, m), 7.52-7.73 (5H, m), 8.69 (1H, d, J=5.2 Hz), 8.76 (1H, s)

The starting material was synthesized by the following 2 steps.

Production Example 720-1

4-(4-Amino-2,3-dimethylphenoxy)-7-benzyloxy-6-cyanoquinoline

4-Amino-2,3-xylenol (2.80 g) purchased from Tokyo Chemical Industries was dissolved in dimethylsulfoxide (15 ml), and after gradually adding sodium hydride (816 mg) at room temperature, the mixture was stirred for 20 minutes. 7-Benzyloxy-4-chloro-6-cyanoquinoline (3.0 g) was added, and the mixture was heated at 100° C. for 4 hours while stirring. After cooling to room temperature, the reaction solution was distributed between ethyl acetate and water, and the organic layer was washed with water, 1N aqueous sodium hydroxide and saturated brine and dried over anhydrous sodium sulfate. The solvent was distilled off, and the obtained crude product was washed with ethyl acetate to obtain the title compound (1.72 g) as light brown crystals.

¹H-NMR (DMSO-d₆) δ (ppm) 1.91 (3H, s), 2.01 (3H, s), 4.83-4.90 (2H, m), 5.44 (2H, s), 6.30 (1H, d, J=5.2 Hz), 6.60 (1H, d, J=8.4 Hz), 6.73-6.79 (1H, m), 7.33-7.47 (3H, m), 7.51-7.58 (2H, m), 7.67 (1H, s), 8.65 (1H, d, J=5.2 Hz), 8.80 (1H, s)

Production Example 720-2

[4-(7-Benzyloxy-6-cyanoquinolin-4-yloxy)-2,3-dimethylphenyl]carbamic acid phenyl ester The title compound (1.99 g) was obtained as light brown crystals from 4-(4-amino-2,3-dimethylphenoxy)-7-benzyloxy-6-cyanoquinoline (1.72 g), by the method described in Production Example 141-1.

¹H-NMR(CDCl₃) δ (ppm) 2.02 (3H, s), 2.13 (3H, s), 5.36 (2H, s), 6.32 (1H, d, J=5.2 Hz), 6.78 (1H, brs), 7.00 (1H, d, J=8.8 Hz), 7.20-7.80 (12H, m), 8.62 (1H, d, J=5.2 Hz), 8.78 (1H, s)

Example 721

N-[2,3-Dimethyl-4-(6-cyano-7-hydroxyquinolin-4-yloxy)phenyl]-N'-cyclopropylurea

After adding N-[4-(7-benzyloxy-6-cyanoquinolin-4-yloxy)-2,3-dimethylphenyl]-N'-cyclopropylurea (1600 mg) to tetrahydrofuran (400 ml), palladium-carbon (2000 mg) was further added and the mixture was stirred overnight at room temperature under a hydrogen atmosphere. The palladium-carbon was removed by filtration, washing was performed with dimethylformamide, and the filtrate was concentrated under reduced pressure to obtain the title compound (827 mg).

¹H-NMR (DMSO-d₆) δ (ppm) 0.40-0.46 (2H, m), 0.62-0.67 (2H, m), 2.03 (3H, s), 2.16 (3H, s), 2.54-2.60 (1H, m), 6.20 (1H, d, J=5.2 Hz), 6.68 (1H, d, J=3.2 Hz), 7.00 (1H, d, J=8.8 Hz), 7.39 (1H, brs), 7.65 (1H, d, J=8.8 Hz) 7.69 (1H, s), 8.59 (1H, d, J=5.2 Hz), 8.71 (1H, s)

Example 722

N-(4-(6-Cyano-7-(3-pyrrolidin-1-ylpropoxy)quinolin-4-yloxy)-2,3-dimethylphenyl)-N'-cyclopropylurea After adding the N-[2,3-dimethyl-4-(6-cyano-7-hydroxyquinolin-4-yloxy)phenyl]-N'-cyclopropylurea (100 mg) synthesized in Example 721, 1-(3-chloropropyl)pyrrolidine hydrochloride (95 mg) and potassium carbonate (150 mg) to dimethylformamide (2 ml), the mixture was heated at 60° C. for 7 hours. Water was added to the reaction solution, extraction was performed with ethyl acetate, and then the organic layer was washed with water and saturated brine in that order and dried over anhydrous sodium sulfate, and the solvent was distilled off under reduced pressure. The obtained crude product was washed with ethyl acetate to obtain the title compound (49 mg) as light yellow crystals.

¹H-NMR(CDCl₃) δ (ppm) 0.38-0.44 (2H, m), 0.59-0.66 (2H, m), 1.64-1.71 (4H, m), 1.94-2.00 (2H, m), 2.01 (3H, s), 2.14 (3H, s), 2.40-2.60 (7H, m), 4.33 (2H, t, J=6.4 Hz), 6.30 (1H, d, J=5.6 Hz), 6.82 (1H, brs), 6.99 (1H, d, J=8.8 Hz), 7.58 (1H, s), 7.64 (1H, d, J=8.8 Hz) 7.69 (1H, brs), 8.67 (1H, d, J=5.6 Hz), 8.80 (1H, s).

Example 723

N-(4-(6-Cyano-7-((2R)-2-hydroxy-3-pyrrolidin-1-ylpropoxy)quinolin-4-yloxy)-2,3-dimethylphenyl)-N'-cyclopropylurea After adding tetrahydrofuran (2.0 ml) and pyrrolidine (0.20 ml) to N-(4-(6-cyano-7-((2R)-oxiran-2-yl)methoxyquinolin-4-yloxy)-2,3-dimethylphenyl)-N'-cyclopropylurea (110 mg), the mixture was heated at 60° C. for 2 hours. After allowing the reaction solution to cool, the precipitated crystals were filtered out to obtain the title compound (18 mg) as light brown crystals.

¹H-NMR (DMSO-d₆) δ (ppm) 0.40-0.46 (2H, m), 0.62-0.68 (2H, m), 1.65-1.73 (4H, m), 2.03 (3H, s), 2.16 (3H, s), 2.45-2.70 (7H, m), 4.00-4.08 (1H, m), 4.22 (1H, dd, J=10.4, 5.6 Hz), 4.32 (1H, dd, J=10.4, 3.6 Hz), 5.04 (1H, d, J=4.4 Hz), 6.32 (1H, d, J=5.6 Hz), 6.67-6.72 (1H, m), 7.02 (1H, d, J=8.8 Hz), 7.61-7.72 (3H, m), 8.69 (1H, d, J=5.6 Hz), 8.82 (1H, s).

The starting material was synthesized in the following manner.

Production Example 723-1

N-(4-(6-Cyano-7-((2R)-oxiran-2-yl)methoxyquinolin-4-yloxy)-2,3-dimethylphenyl)-N'-cyclopropylurea Dimethylformamide (4 ml) was added to N-(2,3-dimethyl-4-(6-cyano-7-hydroxy-quinolin-4-yloxy)-phenyl)-N'-cyclopropylurea (476 mg), and then (2R)-(−)-glycidyl p-toluenesulfonate (365 mg) and potassium carbonate (340 mg) were further added and the mixture was heated at 50° C. for 4 hours. Water was added to the reaction solution, extraction was performed with ethyl acetate, the organic layer was washed with water and saturated brine in that order and dried over anhydrous sodium sulfate, and the solvent was distilled off under reduced pressure. The obtained crude product was washed with ethyl acetate to obtain the title compound (270 mg) as light yellow crystals.

¹H-NMR (DMSO-d₆) δ (ppm) 0.40-0.46 (2H, m), 0.62-0.68 (2H, m), 2.03 (3H, s), 2.16 (3H, s), 2.52-2.60 (1H, m), 2.80-2.96 (2H, m), 3.45-3.52 (1H, m), 4.18 (1H, dd, J=11.6, 6.4 Hz), 4.73 (1H, dd, J=11.6, 2.0 Hz), 6.34 (1H, d, J=5.6 Hz), 6.69-6.74 (1H, m), 7.01 (1H, d, J=8.8 Hz), 7.61-7.75 (2H, m), 7.95 (1H, brs), 8.70 (1H, d, J=5.6 Hz), 8.85 (1H, s).

Example 724

N-(4-(6-Cyano-7-((2R)-2-hydroxy-3-piperidin-1-ylpropoxy)quinolin-4-yloxy)-2,3-dimethylphenyl)-N'-cyclopropylurea After adding tetrahydrofuran (2.0 ml) and piperidine (0.20 ml) to N-(4-(6-cyano-7-((2R)-oxiran-2-yl)methoxy-quinolin-4-yloxy)-2,3-dimethylphenyl)-N'-cyclopropylurea (80 mg), the mixture was heated at 60° C. for 4 hours. After allowing the reaction solution to cool, the precipitated crystals were filtered out to obtain the title compound (50 mg) as light brown crystals.
$^1$H-NMR (DMSO-d$_6$) δ (ppm) 0.40-0.46 (2H, m), 0.62-0.68 (2H, m), 1.30-1.55 (6H, m), 2.03 (3H, s), 2.16 (3H, s), 2.30-2.70 (7H, m), 4.00-4.09 (1H, m), 4.22 (1H, dd, J=10.4, 5.6 Hz), 4.32 (1H, dd, J=10.4, 3.6 Hz), 4.95 (1H, d, J=4.0 Hz), 6.32 (1H, d, J=5.6 Hz), 6.71-6.74 (1H, m), 7.02 (1H, d, J=8.8 Hz), 7.62-7.70 (2H, m), 7.73 (1H, brs), 8.69 (1H, d, J=5.6 Hz), 8.82 (1H, s).

Example 725

N-(4-(6-Cyano-7-(3-diethylamino-(2R)-2-hydroxypropoxy)quinolin-4-yloxy)-2,3-dimethylphenyl)-N'-cyclopropylurea After adding tetrahydrofuran (2.0 ml) and diethylamine (0.50 ml) to N-(4-(6-cyano-7-((2R)-oxiran-2-yl)methoxyquinolin-4-yloxy)-2,3-dimethylphenyl)-N'-cyclopropylurea (80 mg), the mixture was heated at 60° C. for 6 hours. The reaction solution was allowed to cool, and the precipitated crystals were filtered out to obtain the title compound (32 mg) as light brown crystals.
$^1$H-NMR (DMSO-d$_6$) δ (ppm) 0.40-0.46 (2H, m), 0.62-0.69 (2H, m), 0.98 (6H, t, J=7.2 Hz), 2.03 (3H, s), 2.16 (3H, s), 2.40-2.70 (7H, m), 3.90-4.02 (1H, m), 4.22 (1H, dd, J=10.4, 5.6 Hz), 4.32 (1H, dd, J=10.4, 3.6 Hz), 4.93 (1H, d, J=4.0 Hz), 6.32 (1H, d, J=5.6 Hz), 6.71-6.74 (1H, m), 7.02 (1H, d, J=8.8 Hz), 7.61-7.70 (2H, m), 7.72 (1H, brs), 8.69 (1H, d, J=5.6 Hz), 8.82 (1H, s).

Example 726

N6-Ethyl-7-benzyloxy-4-(3-chloro-(4-((methylamino)carbonyl)amino)phenoxy)-6-quinolinecarboxamide N6-Ethyl-4-(4-amino-3-chlorophenoxy)-7-benzyloxy-6-quinolinecarboxamide) (870 mg, 1.94 mmol) and pyridine (460 mg, 5.82 mmol) were dissolved in dimethylformamide (10 ml), and after adding phenyl chloroformate (456 mg, 2.91 mmol) while cooling on ice, the mixture was stirred at room temperature for 18 hours. The reaction solution was distributed between ethyl acetate and water, the organic layer was washed with water and saturated brine and dried over anhydrous magnesium sulfate, the drying agent was filtered off, and the filtrate was distilled off under reduced pressure. A portion of the obtained product (460 mg, 0.810 mmol) and a 40% methylamine-methanol solution (0.810 ml) were stirred together in dimethylformamide (5 ml) at room temperature for 30 minutes. The reaction solution was distributed between ethyl acetate and water, the organic layer was washed with water and saturated brine and dried over anhydrous magnesium sulfate, the drying agent was filtered off, and the filtrate was distilled off under reduced pressure. The obtained crude product was suspended in ethyl acetate and diluted with hexane, and then the crystals were filtered out, washed with hexane and blow-dried to obtain the title compound (359 mg, 0.711 mmol, 74%) as white crystals.
$^1$H-NMR Spectrum (DMSO-d$_6$) δ (ppm): 1.07 (3H, t, J=7.4 Hz), 2.68 (3H, d, J=4.0 Hz), 3.30 (2H, m), 5.41 (2H, s), 6.54 (1H, d, J=5.2 Hz), 6.89 (1H, m), 7.23 (1H, dd, J=2.8, 9.2 Hz), 7.34-7.40 (1H, m), 7.40-7.49 (3H, m), 7.55-7.60 (2H, m), 7.61 (1H, s), 8.13 (1H, s), 8.25 (1H, dd, J=3.2, 9.2 Hz), 8.36 (1H, t, J=5.2 Hz), 8.51 (1H, s), 8.66 (1H, d, J=5.2 Hz).

The starting materials were synthesized in the following manner.

Production Example 726-1

N6-Ethyl-7-benzyloxy-4-chloro-6-quinolinecarboxamide

After adding thionyl chloride (10 ml) and a catalytic amount of dimethylformamide to phenyl 7-benzyloxy-4-oxo-1,4-dihydro-6-quinolinecarboxylate (2.32 g, 6.25 mmol), the mixture was heated to reflux for 2 hours while stirring. The reaction solution was concentrated under reduced pressure and azeotropically distilled twice with toluene, the residue was dissolved in a dimethylformamide (10 ml) and triethylamine (5 ml) mixed solvent, 2M ethylamine (tetrahydrofuran solution) (6.25 ml, 12.5 mmol) was gradually added thereto while cooling in an ice water bath, and the mixture was stirred at room temperature for 3 hours. The reaction solution was distributed between ethyl acetate and water, and then the organic layer was washed with ammonia water, water and saturated brine and dried over anhydrous magnesium sulfate. The solvent was distilled off, after which ethyl acetate and then diethyl ether were added for crystallization and the crystals were filtered out and blow-dried to obtain the title compound (723 mg, 2.12 mmol, 34%) as yellow crystals.
$^1$H-NMR Spectrum (DMSO-d$_6$) δ (ppm): 1.08 (3H, t, J=7.2 Hz), 3.30 (2H, m), 5.41 (2H, s), 7.34-7.39 (1H, m), 7.40-7.46 (2H, m), 7.54-7.59 (2H, m), 7.66 (1H, d, J=4.8 Hz), 7.70 (1H, s), 8.36 (1H, s), 8.42 (1H, m), 8.81 (1H, d, J=4.8 Hz).

Production Example 726-2

N6-Ethyl-4-(4-amino-3-chlorophenoxy)-7-benzyloxy-6-quinolinecarboxamide

After dissolving 4-amino-3-chlorophenol (379 mg, 2.64 mmol) in dimethylsulfoxide (10 ml), sodium hydride (106 mg, 2.64 mmol) was gradually added at room temperature and the mixture was stirred for 30 minutes. N6-Ethyl-7-benzyloxy-4-chloro-6-quinolinecarboxamide (720 mg, 2.11 mmol) was added, and the mixture was heated at 100° C. for 2 hours while stirring. Upon cooling to room temperature, the reaction solution was distributed between ethyl acetate and water, and the organic layer was washed with ammonia water, water and saturated brine and dried over anhydrous sodium sulfate. The solvent was distilled off, suspended in ethyl acetate and diluted with hexane, and the crystals were filtered out and blow-dried to obtain the title compound (870 mg, 1.94 mmol, 92%) as brown crystals.
$^1$H-NMR Spectrum (DMSO-d$_6$) δ (ppm): 1.07 (3H, t, J=7.2 Hz), 3.30 (2H, m), 5.40 (2H, s), 5.43-5.49 (2H, m), 6.47

(1H, d, J=5.2 Hz), 6.91 (1H, d, J=8.8 Hz), 7.01 (1H, dd, J=2.8, 8.8 Hz), 7.24 (1H, d, J=2.8 Hz), 7.34-7.39 (1H, m), 7.41-7.46 (2H, m), 7.55-7.60 (3H, m), 8.36 (1H, t, J=5.2 Hz), 8.52 (1H, s), 8.62 (1H, d, J=5.2 Hz).

Example 727

N6-Ethyl-7-benzyloxy-4-(3-chloro-(4-((ethylamino) carbonyl)amino)phenoxy)-6-quinolinecarboxamide After dissolving N6-ethyl-4-(4-amino-3-chlorophenoxy)-7-benzyloxy-6-quinolinecarboxamide (870 mg, 1.94 mmol) and pyridine (460 mg, 5.82 mmol) in dimethylformamide (10 ml), phenyl chloroformate (456 mg, 2.91 mmol) was added while cooling on ice, and the mixture was stirred at room temperature for 18 hours. The reaction solution was distributed between ethyl acetate and water, the organic layer was washed with water and saturated brine and dried over anhydrous magnesium sulfate, the drying agent was filtered off and the filtrate was distilled off under reduced pressure. A portion of the obtained product (460 mg, 0.810 mmol) and a 2 M ethylamine-tetrahydrofuran solution (4.05 ml) were stirred together in dimethylformamide (5 ml) at room temperature for 30 minutes. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was suspended in ethyl acetate and diluted with hexane, and then the crystals were filtered out, washed with hexane and blow-dried to obtain the title compound (347 mg, 0.669 mmol, 83%) as white crystals.

$^1$H-NMR Spectrum (DMSO-$d_6$) δ (ppm): 1.03-1.11 (6H, m), 3.14 (2H, m), 3.30 (2H, m), 5.41 (2H, s), 6.54 (1H, d, J=5.2 Hz), 7.01 (1H, m), 7.23 (1H, dd, J=2.8, 9.2 Hz), 7.34-7.40 (1H, m), 7.41-7.49 (3H, m), 7.55-7.60 (2H, m), 7.61 (1H, s), 8.07 (1H, s), 8.27 (1H, dd, J=3.2, 9.2 Hz), 8.36 (1H, t, J=5.2 Hz), 8.51 (1H, s), 8.66 (1H, d, J=5.2 Hz).

Example 728

N6-Ethyl-4-(3-chloro-4-(((methylamino)carbonyl) amino)phenoxy)-7-hydroxy-6-quinolinecarboxamide The title compound (253 mg, 0.609 mmol, 90%) was obtained as yellow crystals from N6-ethyl-7-benzyloxy-4-(3-chloro-(4-((methylamino)carbonyl)amino)phenoxy)-6-quinolinecarboxamide (344 mg, 0.681 mmol), by the same procedure as in Example 83.

$^1$H-NMR Spectrum (DMSO-$d_6$) δ (ppm): 1.18 (3H, t, J=7.2 Hz), 2.68 (3H, d, J=4.4 Hz), 3.38 (2H, m), 6.42 (1H, d, J=5.2 Hz), 6.88 (1H, q, J=4.4 Hz), 7.25 (1H, dd, J=2.8, 9.2 Hz), 7.31 (1H, s), 7.49 (1H, d, J=2.8 Hz), 8.13 (1H, s), 8.27 (1H, d, J=9.2 Hz), 8.61 (1H, d, J=5.2 Hz), 8.89 (1H, s).

Example 729

N6-Ethyl-4-(3-chloro-4-(((ethylamino)carbonyl) amino)phenoxy)-7-hydroxy-6-quinolinecarboxamide The title compound (247 mg, 0.576 mmol, 90%) was obtained as yellow crystals from N6-ethyl-7-benzyloxy-4-(3-chloro-(4-((ethylamino)carbonyl)amino)phenoxy)-6-quinolinecarboxamide (332 mg, 0.640 mmol), by the same procedure as in Example 83.

$^1$H-NMR Spectrum (DMSO-$d_6$) δ (ppm): 1.08 (3H, t, J=7.2 Hz), 1.18 (3H, t, J=7.2 Hz), 3.14 (2H, m), 3.39 (2H, m), 6.42 (1H, d, J=5.2 Hz), 7.00 (1H, t, J=5.2 Hz), 7.25 (1H, dd, J=2.8, 9.2 Hz), 7.30 (1H, s), 7.49 (1H, d, J=2.8 Hz), 8.08 (1H, s), 8.29 (1H, d, J=9.2 Hz), 8.61 (1H, d, J=5.2 Hz), 8.90 (1H, s).

Example 730

N6-Ethyl-4-(3-chloro-4-(((methylamino)carbonyl) amino)phenoxy)-7-((1-methyl-4-piperidyl)methoxy)-6-quinolinecarboxamide N6-Ethyl-4-(3-chloro-4-(((methylamino)carbonyl) amino)phenoxy)-7-hydroxy-6-quinolinecarboxamide) (80.0 mg, 0.193 mmol), tert-butyl 4-(bromomethyl)-1-piperidinecarboxylate (80.5 mg, 0.289 mmol) and potassium carbonate (33.3 mg, 0.241 mmol) were heated and stirred in dimethylformamide (1 ml) at 60° C. for 15 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained product was stirred in trifluoroacetic acid (1 ml) at room temperature for 1 hour, and then the reaction solution was concentrated under reduced pressure, the residue was dissolved in methanol and triethylamine was added dropwise for neutralization. After distilling off the solvent, the residue was dissolved in a tetrahydrofuran (2 ml)-methanol (2 ml) mixed solvent, and then a 37% formaldehyde aqueous solution (0.360 ml), acetic acid (0.070 ml) and sodium cyanoborohydride (36.3 mg, 0.579 mmol) were added in that order at room temperature and the mixture was stirred for 15 minutes. After adding basic silica gel to the reaction solution and concentrating it, it was subjected to silica gel column chromatography, the target fraction was concentrated under reduced pressure, the obtained crude product was suspended in ethyl acetate, the suspension was diluted with hexane, and the crystals were filtered out, washed with hexane and blow-dried to obtain the title compound (57.5 mg, 0.109 mmol, 57%) as white crystals.

$^1$H-NMR Spectrum (DMSO-$d_6$) δ (ppm): 1.16 (3H, t, J=7.2 Hz), 1.38 (2H, m), 1.72-1.92 (5H, m), 2.17 (3H, s), 2.68 (3H, d, J=4.4 Hz), 2.81 (2H, m), 3.36 (2H, m), 4.11 (2H, d, J=6.0 Hz), 6.53 (1H, d, J=5.2 Hz), 6.87 (1H, m), 7.22 (1H, dd, J=2.8, 8.8 Hz), 7.46 (1H, d, J=2.8 Hz), 7.49 (1H, s), 8.12 (1H, s), 8.20-8.28 (2H, m), 8.50 (1H, s), 8.65 (1H, d, J=5.2 Hz).

Example 731

N6-Ethyl-4-(3-chloro-4-(((ethylamino)carbonyl) amino)phenoxy)-7-((1-methyl-4-piperidyl)methoxy)-6-quinolinecarboxamide N6-Ethyl-4-(3-chloro-4-(((ethylamino)carbonyl)amino) phenoxy)-7-hydroxy-6-quinolinecarboxamide (78.0 mg, 0.182 mmol), tert-butyl 4-(bromomethyl)-1-piperidinecarboxylate (75.9 mg, 0.273 mmol) and potassium carbonate (31.4 mg, 0.228 mmol) were heated and stirred in dimethylformamide (1 ml) at 60° C. for 15 hours. The reaction solution was distributed between ethyl acetate and water, the organic layer was washed with water and saturated brine and dried over anhydrous magnesium sulfate, the drying agent was filtered off and the filtrate was distilled off under reduced pressure. The obtained product was stirred in trifluoroacetic acid (1 ml) at room temperature for 1 hour, and then the reaction solution was concentrated under reduced pressure, the residue was dissolved in methanol and triethylamine was added dropwise for neutralization. After distilling off the solvent, the residue was dissolved in a tetrahydrofuran (2 ml)-methanol (2 ml) mixed solvent, and then a 37% formaldehyde aqueous solution (0.340 ml), acetic acid (0.070 ml) and sodium cyanoborohydride (34.3 mg, 0.546 mmol) were added in that order at room temperature and the mixture was stirred for 15 minutes. After adding basic silica gel to the reaction solution and concentrating it, it was subjected to silica gel column chromatography, the target fraction was concentrated under reduced pressure, the obtained crude product was suspended in ethyl acetate, the suspension was diluted with hexane, and the crystals were filtered out, washed with hexane and blow-dried to obtain the title compound (58.1 mg, 0.108 mmol, 59%) as white crystals.

$^1$H-NMR Spectrum (DMSO-d$_6$) δ (ppm): 1.08 (3H, t, J=7.2 Hz), 1.16 (3H, t, J=7.2 Hz), 1.38 (2H, m), 1.72-1.92 (5H, m), 2.17 (3H, s), 2.81 (2H, m), 3.14 (2H, m), 3.35 (2H, m), 4.10 (2H, d, J=6.0 Hz), 6.53 (1H, d, J=5.2 Hz), 7.00 (1H, m), 7.22 (1H, dd, J=2.8, 8.8 Hz), 7.47 (1H, d, J=2.8 Hz), 7.49 (1H, s), 8.07 (1H, s), 8.22-8.29 (2H, m), 8.50 (1H, s), 8.66 (1H, d, J=5.2 Hz).

Example 732

N6-Methoxy-7-benzyloxy-4-(3-chloro-(4-((ethylamino)carbonyl)amino)phenoxy)-6-quinolinecarboxamide N6-Methoxy-4-(4-amino-3-chlorophenoxy)-7-benzyloxy-6-quinolinecarboxamide (81.0 mg, 0.180 mmol) and pyridine (32.0 mg, 0.404 mmol) were dissolved in dimethylformamide (2 ml), and after adding phenyl chloroformate (42.3 mg, 0.270 mmol) while cooling on ice, the mixture was stirred at room temperature for 30 minutes. A 2 M ethylamine-tetrahydrofuran solution (0.270 ml) was added to the reaction solution, and the mixture was further stirred at room temperature for 30 minutes. The reaction solution was distributed between ethyl acetate and water, the organic layer was washed with water and saturated brine and dried over anhydrous magnesium sulfate, the drying agent was filtered off and the filtrate was distilled off under reduced pressure. The obtained crude product was suspended in diethyl ether and diluted with hexane, and then the crystals were filtered out, washed with hexane and blow-dried to obtain the title compound (68.5 mg, 0.131 mmol, 73%) as white crystals.

$^1$H-NMR Spectrum (DMSO-d$_6$) δ (ppm): 1.08 (3H, t, J=7.2 Hz), 3.15 (2H, m), 3.72 (3H, s), 5.40 (2H, s), 6.54 (1H, d, J=5.2 Hz), 7.01 (1H, m), 7.22 (1H, dd, J=2.8, 9.2 Hz), 7.32-7.37 (1H, m), 7.40-7.46 (2H, m), 7.47 (1H, d, J=2.8 Hz), 7.53-7.60 (3H, m), 8.07 (1H, s), 8.27 (1H, dd, J=3.2, 9.2 Hz), 8.34 (1H, s), 8.65 (1H, d, J=5.2 Hz), 11.53 (1H, br s).

The starting materials were synthesized in the following manner.

Production Example 732-1

N6-Methoxy-7-benzyloxy-4-chloro-6-quinolinecarboxamide

After adding thionyl chloride (10 ml) and a catalytic amount of dimethylformamide to phenyl 7-benzyloxy-4-oxo-1,4-dihydro-6-quinolinecarboxylate (2.32 g, 6.25 mmol), the mixture was heated to reflux for 2 hours while stirring. The reaction solution was concentrated under reduced pressure and azeotropically distilled twice with toluene, the residue was dissolved in a dimethylformamide (20 ml) and triethylamine (20 ml) mixed solvent, methoxylamine hydrochloride (10.4 g, 125 mmol) was added thereto while cooling in an ice water bath, and the mixture was stirred at room temperature for 18 hours. The reaction solution was distributed between ethyl acetate and water, and then the organic layer was washed with water and saturated brine and dried over anhydrous magnesium sulfate. After distilling off the solvent, it was subjected to silica gel column chromatography, the target fraction was concentrated under reduced pressure, the obtained crude product was suspended in ethyl acetate, the suspension was diluted with hexane, and the crystals were filtered out, washed with hexane and blow-dried to obtain the title compound (392 mg, 1.14 mmol, 18%) as white crystals.

$^1$H-NMR Spectrum (DMSO-d$_6$) δ (ppm): 3.72 (3H, s), 5.41 (2H, s), 7.32-7.38 (1H, m), 7.40-7.46 (2H, m), 7.52-7.56 (2H, m), 7.64-7.70 (2H, m), 8.22 (1H, s), 8.82 (1H, d, J=4.8 Hz), 11.60 (1H, br s).

Production Example 732-2

N6-Methoxy-4-(4-amino-3-chlorophenoxy)-7-benzyloxy-6-quinolinecarboxamide

After dissolving 4-amino-3-chlorophenol (408 mg, 2.84 mmol) in dimethylsulfoxide (10 ml), sodium hydride (114 mg, 2.84 mmol) was gradually added at room temperature and the mixture was stirred for 30 minutes. N6-Methoxy-7-benzyloxy-4-chloro-6-quinolinecarboxamide (388 mg, 1.14 mmol) was added, and the mixture was heated at 100° C. for 18 hours while stirring. Upon cooling to room temperature, the reaction solution was distributed between ethyl acetate and water, and the organic layer was washed with water and saturated brine and dried over anhydrous magnesium sulfate. After distilling off the solvent, it was subjected to silica gel column chromatography, the target fraction was concentrated under reduced pressure, the obtained crude product was suspended in ethyl acetate, the suspension was diluted with hexane, and the crystals were filtered out, washed with hexane and blow-dried to obtain the title compound (81.0 mg, 0.180 mmol, 16%) as light red crystals.

$^1$H-NMR Spectrum (CDCl$_3$) δ (ppm): 3.81 (3H, s), 4.22 (2H, br s), 5.43 (2H, s), 6.68 (1H, d, J=6.2 Hz), 6.88 (1H, d, J=8.8 Hz), 6.94 (1H, dd, J=2.8, 8.8 Hz), 7.16 (1H, d, J=2.8 Hz), 7.41-7.58 (5H, m), 8.14 (1H, s), 8.66 (1H, d, J=6.2 Hz), 9.35 (1H, s), 10.19 (1H, s).

Example 733

N6-Methoxy-4-(3-chloro-4-(((ethylamino)carbonyl)amino)phenoxy)-7-hydroxy-6-quinolinecarboxamide The title compound (43.3 mg, 0.101 mmol, 77%) was obtained as yellow crystals from N6-methoxy-7-benzyloxy-4-(3-chloro-(4-((ethylamino)carbonyl)amino)phenoxy)-6-quinolinecarboxamide) (68.3 mg, 0.131 mmol), by the same procedure as in Example 83.

$^1$H-NMR Spectrum (DMSO-d$_6$) δ (ppm): 1.08 (3H, t, J=7.2 Hz), 3.14 (2H, m), 3.76 (3H, s), 6.43 (1H, d, J=5.2 Hz), 7.00 (1H, t, J=5.2 Hz), 7.25 (1H, dd, J=2.8, 9.2 Hz), 7.34 (1H, brs), 7.48 (1H, d, J=2.8 Hz), 8.07 (1H, s), 8.27 (1H, d, J=9.2 Hz), 8.60 (1H, d, J=5.2 Hz), 8.64 (1H, s).

Example 734

N6-Methyl-4-(3-chloro-4-(((cyclopropylamino)carbonyl)amino)phenoxy)-7-(2-methoxyethoxy)-6-quinolinecarboxamide The target substance was obtained using a methylamine-containing methanol solution, in the same manner as Example 249.

¹H-NMR (DMSO-d₆) δ (ppm): 0.38-0.44 (2H, m), 2.62-2.68 (2H, m), 2.50-2.60 (1H, m), 2.85 (3H, d, J=4.8 Hz), 3.37 (3H, s), 3.79 (2H, t, J=4.4 Hz), 4.39 (2H, t, J=4.4 Hz), 6.52 (1H, d, J=5.2 Hz), 7.18 (1H, d, J=2.4 Hz), 7.23 (1H, dd, J=8.8 Hz, 2.4 Hz), 7.48 (1H, d, J=2.4 Hz), 7.55 (1H, s), 7.96 (1H, s), 8.26 (1H, d, J=8.8 Hz), 8.35 (1H, q, J=4.8 Hz), 8.65 (1H, d, J=5.2 Hz), 8.66 (1H, s).

Example 735

N6-Ethyl-4-(3-chloro-4-(((cyclopropylamino)carbonyl)amino)phenoxy)-7-(2-methoxyethoxy)-6-quinolinecarboxamide The target substance was obtained using an ethylamine-containing tetrahydrofuran solution, in the same manner as Example 249.

¹H-NMR (DMSO-d₆) δ (ppm): 0.38-0.44 (2H, m), 2.62-2.68 (2H, m), 1.15 (3H, t, J=7.2 Hz), 2.50-2.60 (1H, m), 3.27-3.40 (2H, m), 3.36 (3H, s), 3.79 (2H, t, J=4.4 Hz), 4.39 (2H, t, J=4.4 Hz), 6.51 (1H, d, J=5.6 Hz), 7.18 (1H, d, J=2.8 Hz), 7.23 (1H, dd, J=8.8 Hz, 2.8 Hz), 7.48 (1H, d, J=2.8 Hz), 7.54 (1H, s), 7.96 (1H, s), 8.26 (1H, d, J=8.8 Hz), 8.34 (1H, t, J=4.8 Hz), 8.65 (1H, d, J=5.6 Hz), 8.68 (1H, s).

Example 736

N-(2-Chloro-4-(6-cyano-7-(3-(1-piperidino)propoxy)-4-quinolyl)oxyphenyl)-N'-cyclopropylurea The title compound (102.2 mg, 0.197 mmol, 12.3%) was obtained as light yellow crystals from N-(4-(6-cyano-7-hydroxy-4-quinolyl)oxy-2-chlorophenyl)-N'-cyclopropylurea (500 mg, 1.60 mmol) and 1-(3-chloropropyl)piperidine hydrochloride, by the same procedure as in Example 7.

¹H-NMR Spectrum (DMSO-d₆) δ (ppm): 0.42 (2H, m), 0.65 (2H, m), 1.37 (2H, m), 1.48 (2H, m), 1.96 (2H, m), 2.34 (4H, m), 2.43-2.49 (4H, m), 2.56 (1H, m), 4.31 (2H, m), 6.57 (1H, d, J=5.2 Hz), 7.19 (1H, d, J=2.8 Hz), 7.25 (1H, dd, J=2.8, 8.8 Hz), 7.49 (1H, d, J=2.8 Hz), 7.59 (1H, s), 7.98 (1H, s), 8.27 (1H, d, J=8.8 Hz), 8.71-8.74 (2H, m).

Example 737

N-(3-Fluorophenyl)-N'-(4-(thieno[2,3-d]pyrimidin-4-yloxy)phenyl)urea

After adding 370 mg of iron powder, 750 mg of ammonium chloride, 30 ml of ethanol and 3 ml of water to 250 mg of 4-(4-nitrophenoxy)thieno[2,3-d]pyrimidine, the mixture was stirred at 80-85° C. for 2.5 hours. After returning the mixture to room temperature, tetrahydrofuran was added, the mixture was filtered with celite, and ethyl acetate and water were added to the filtrate for liquid separation and extraction. The organic layer was washed with saturated brine, dried over anhydrous sodium sulfate, filtered with plug cotton and concentrated to dryness to obtain 182 mg of an amino compound. A 70 mg portion of this compound was refluxed to dissolution in 4 ml of toluene and 4 ml of acetonitrile, and after adding 3-fluorophenylisocyanate (90 μl), the mixture was stirred for 1 hour. Upon returning the mixture to room temperature, the precipitated crystals were filtered out and dried to obtain 73 mg of the title compound.

¹H-NMR Spectrum: (DMSOd₆) 6.72-6.80 (1H, m), 7.12 (1H, d, J=7.7 Hz), 7.22 (1H, d, J=7.7 Hz), 7.28 (1H, dd, J=14.2 Hz, 7.1 Hz), 7.49 (1H, d, J=14.2 Hz), 7.52 (2H, d, J=7.7 Hz) 7.64 (1H, dd, J=6.5 Hz, 1.5 Hz), 7.84 (1H, d, J=6.5 Hz), 8.60 (1H, s,), 9.00 (1H, s,), 9.10 (1H, s)

The intermediate was synthesized in the following manner.

Production Example 737-1

4-(4-Nitrophenoxy)thieno[2,3-d]pyrimidine

After adding 600 mg of 4-nitrophenol, 1.2 g of potassium carbonate and 2 ml of dimethylformamide to 302 mg of the 4-chlorothieno[2,3-d]pyrimidine described in Seans Acad. Sci., Ser, C (1967) 264(2)207, and stirring the mixture for 30 hours at 130° C., the mixture was returned to room temperature, water was added, liquid separation and extraction were performed with an ethyl acetate-tetrahydrofuran mixed solvent, and the solid obtained by concentration to dryness was washed with ether to obtain 250 mg of the title compound.

¹H-NMR Spectrum: (DMSOd₆) 7.63 (2H, d, J=8.7 Hz), 7.68 (1H, d, J=6.1 Hz), 8.00 (1H, d, J=6.1 Hz), 8.35 (2H, d, J=8.7 Hz), 8.65 (1H, s,)

Example 738

N-(4-Fluorophenyl)-N'-(4-(thieno[2,3-d]pyrimidin-4-yloxy)phenyl)urea

The title compound (92 mg) was obtained from 90 mg of the amino compound described in Example 737, using 4-fluorophenyl isocyanate (90 μl), by the same procedure as in Example 737.

¹H-NMR Spectrum: (DMSOd₆) 7.12 (2H, t, J=9.6 Hz), 7.20 (2H, d, J=8.6 Hz), 7.46 (2H, dd, J=9.6 Hz, 5.2 Hz), 7.52 (2H, d, J=8.6 Hz), 7.63 (1H, d, J=6.2 Hz), 7.94 (1H, d, J=6.2 Hz), 8.59 (1H, s), 8.89 (1H, s), 8.94 (1H, s)

Example 739

N-(3-Fluorophenyl)-N'-(4-(thieno[3,2-d]pyrimidin-4-yloxy)phenyl)urea

An amino compound (310 mg) was obtained from 4-(4-nitrophenoxy)thieno[3,2-d]pyrimidine (375 mg) by the method described in Example 737. The title compound (250 mg) was obtained from 135 mg of the amino compound using 3-fluorophenyl isocyanate (90 μl), by the method described in Example 737.

¹H-NMR Spectrum: (DMSOd₆) 6.72-7.56 (8H, m), 7.65 (1H, d, J=6.2 Hz), 8.44 (1H, d, J=6.2 Hz), 8.68 (1H, s,), 8.86 (1H, s,), 8.95 (1H, s)

The intermediate was synthesized in the following manner.

Production Example 739-1

4-(4-Nitrophenoxy)thieno[3,2-d]pyrimidine

The title compound (382 mg) was obtained from 315 mg of the 4-chlorothieno[3,2-d]pyrimidine described in Seans Acad. Sci., Ser, C (1967) 264(1)100, by the method described in Production Example 737-1.

¹H-NMR Spectrum: (DMSOd₆) 7.63-7.69 (2H, m), 7.70 (1H, d, J=6.1 Hz), 8.32-8.38 (2H, m), 8.51 (1H, d, J=6.1 Hz), 8.73 (1H, s,)

Example 740

N-(4-Fluorophenyl)-N'-(4-(thieno[3,2-d]pyrimidin-4-yloxy)phenyl)urea

The title compound (135 mg) was obtained from 150 mg of the amino compound described in Example 739 using 4-fluorophenyl isocyanate (94 μl), by the same procedure as in Example 737.

$^1$H-NMR Spectrum: (DMSOd$_6$) 7.00-7.56 (8H, m), 7.65 (1H, d, J=6.1 Hz), 8.44 (1H, d, J=6.1 Hz), 8.67 (1H, s), 8.73 (1H, s), 8.78 (1H, s)

Example 741

N-(4-(6,7-Dimethoxyquinolin-4-yloxy)phenyl)-N'-(3-methanesulfonylphenyl)urea

The 4-(6,7-dimethoxyquinolin-4-yloxy)phenylamine (296 mg, 1.00 mmol) obtained by the method described in WO97/17329 and (3-methanesulfonylphenyl)carbamic acid phenyl ester (291 mg, 1.00 mmol) were heated and stirred in dimethylsulfoxide (3 ml) at 85° C. for 2 hours. The reaction solution was distributed between ethyl acetate and water, the organic layer was washed with 1N aqueous sodium hydroxide, water and saturated brine and dried over anhydrous magnesium sulfate, the drying agent was filtered off and the filtrate was distilled off under reduced pressure. The obtained crude product was subjected to silica gel column chromatography (eluent-ethyl acetate:methanol=30:1), the fraction containing the target substance was concentrated and suspended in ethyl acetate, the suspension was diluted with hexane and the crystals were filtered out, washed with hexane and blow-dried to obtain the title compound (430 mg, 0.871 mmol, 87%) as colorless crystals.

$^1$H-NMR Spectrum (CDCl$_3$) δ (ppm): 3.16 (3H, s), 4.03 (3H, s), 4.05 (3H, s), 6.46 (1H, d, J=5.2 Hz), 7.12-7.18 (2H, m), 7.41 (1H, s), 7.50-7.62 (6H, m), 7.81 (1H, s), 7.93 (1H, s), 8.11-8.15 (1H, m), 8.48 (1H, d, J=5.2 Hz).

Example 742

N-(2-Chloro-4-((6-cyano-7-(4-piperidylmethoxy)-4-quinolyl)oxy)phenyl)-N'-methylurea

N-(2-chloro-4-(6-cyano-7-hydroxyquinolin-4-yloxy)phenyl)-N'-methylurea (125 mg) was added to dimethylformamide (1.5 ml), and then tert-butyl 4-(bromomethyl)-1-piperidinecarboxylate (141 mg) and potassium carbonate (93 mg) were added thereto and the mixture was heated at 60° C. for 3 hours. Water was added to the reaction solution, extraction was performed with ethyl acetate, the organic layer was washed with water and saturated brine in that order and dried over anhydrous sodium sulfate, and the solvent was distilled off under reduced pressure. The obtained crude product was recrystallized with ethyl acetate to obtain tert-butyl 4-(((4-(3-chloro-4-((methylamino)carbonyl)aminophenoxy)-6-cyano-7-quinolyl)oxy)methyl)-1-piperidinecarboxylate (21 mg) as light yellow crystals. These were dissolved in trifluoroacetic acid (1.0 ml), and the solution was stirred for 10 minutes at room temperature. Water (2 ml) was added, the mixture was neutralized with sodium bicarbonate, and the precipitated crystals were filtered out to obtain the title compound (16 mg).

H-NMR (DMSO-d$_6$) δ (ppm): 1.20-1.35 (4H, m), 1.70-1.80 (2H, m), 1.90-2.01 (1H, m), 2.66 (3H, d, J=4.4 Hz), 2.95-3.05 (2H, m), 4.12 (2H, d, J=6.0 Hz), 6.58 (1H, d, J=5.2 Hz), 6.84-6.92 (1H, m), 7.21-7.26 (1H, m), 7.48 (1H, d, J=2.4 Hz), 7.59 (1H, s), 8.12 (1H, s), 8.22-8.28 (1H, m), 8.71-8.78 (2H, m).

Example 743

N-(2-Chloro-4-((6-cyano-7-((1-methyl-4-piperidyl)methoxy)-4-quinolyl)oxy)phenyl)-N'-methylurea

After dissolving N-(2-chloro-4-((6-cyano-7-(4-piperidylmethoxy)-4-quinolyl)oxy)phenyl)-N'-methylurea (15 mg) in tetrahydrofuran (0.5 ml) and methanol (0.5 ml), there were added 37% aqueous formaldehyde (0.03 ml), acetic acid (0.06 ml) and sodium cyanoborohydride (5.0 mg) at room temperature, and the mixture was stirred for 1 hour. Water was added to the reaction solution, saturated aqueous sodium bicarbonate was added for neutralization, and extraction was performed with ethyl acetate. The organic layer was washed with water and the solvent was distilled off to obtain a crude product. This was recrystallized with ethyl acetate to obtain the title compound (10 mg) as white crystals.

H-NMR (DMSO-d$_6$) δ (ppm): 1.13-1.47 (2H, m), 1.75-1.95 (5H, m), 2.17 (3H, s), 2.68 (3H, s), 2.78-2.87 (2H, m), 4.17 (2H, d, J=6.0 Hz), 6.59 (1H, d, J=5.2 Hz), 6.95 (1H, brs), 7.22-7.28 (1H, m), 7.48 (1H, d, J=2.4 Hz), 7.61 (1H, s), 8.18 (1H, brs), 8.22-8.29 (1H, m), 8.72-8.77 (2H, m).

The structural formulas for the compounds obtained in the preceding Production Examples and Examples are shown below in Tables 4 to 51.

TABLE 4

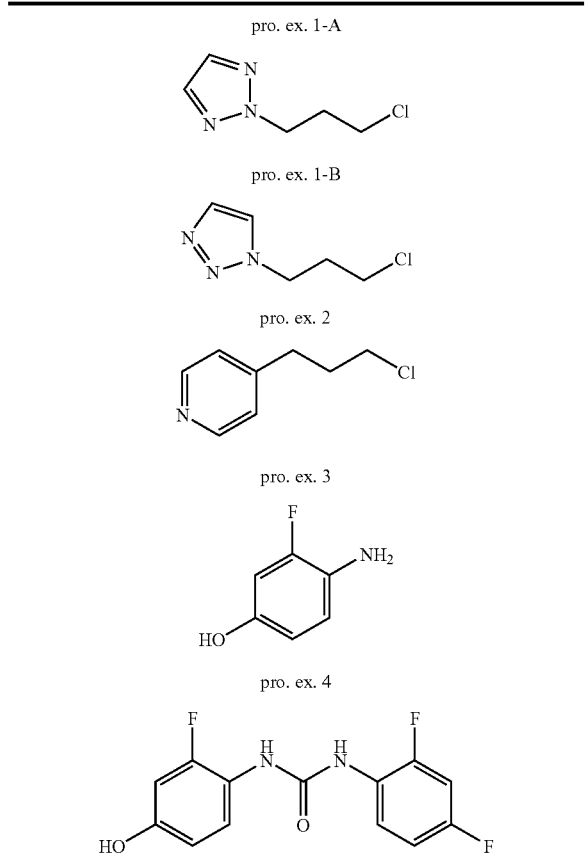

TABLE 4-continued
pro. ex. 5
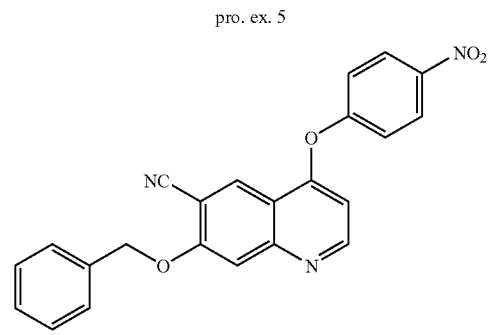
pro. ex. 6

pro. ex. 7
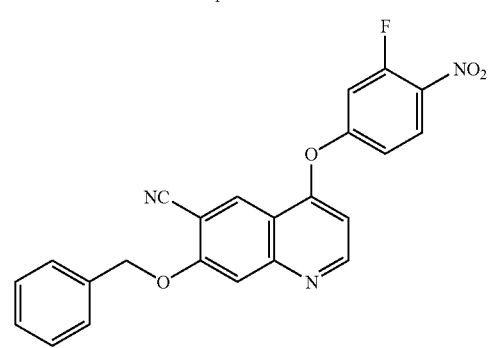
pro. ex. 8
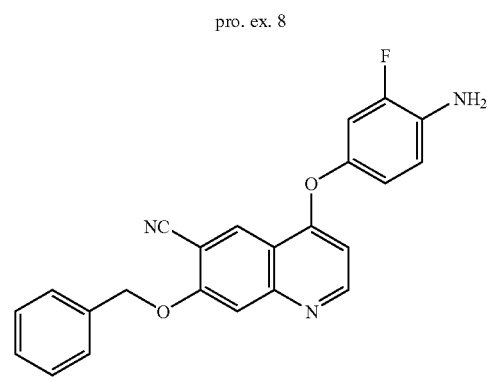
TABLE 4-continued
pro. ex. 9
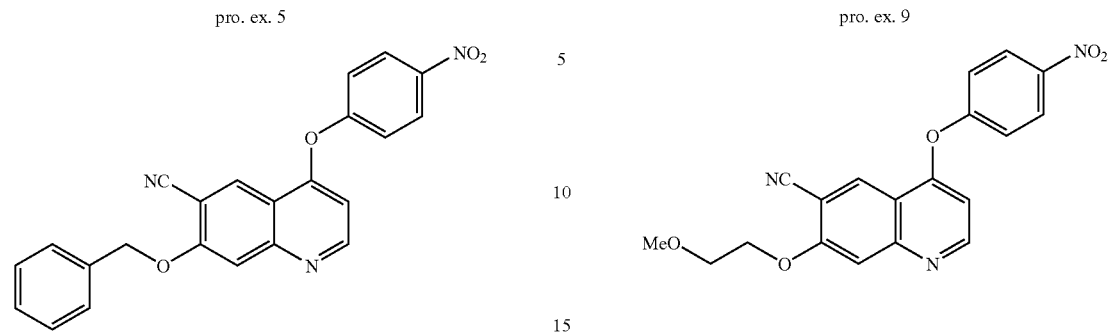
pro. ex. 10
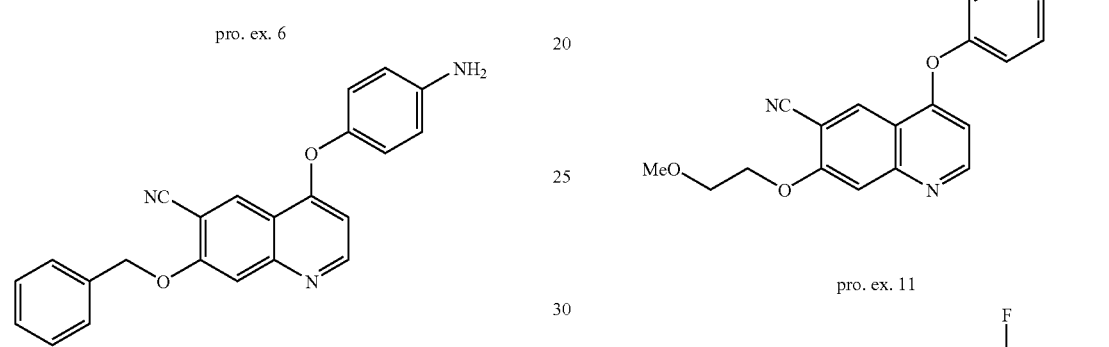
pro. ex. 11
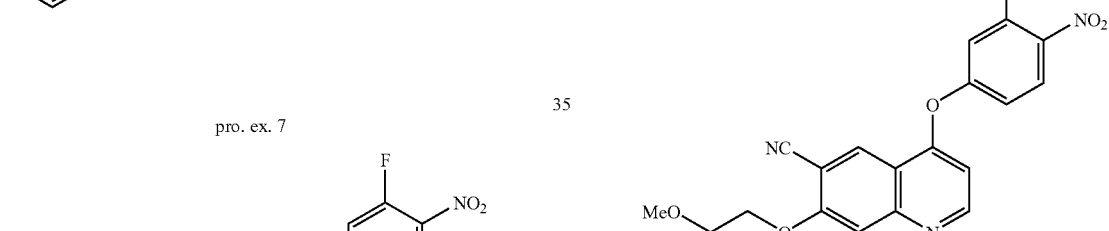
pro. ex. 12
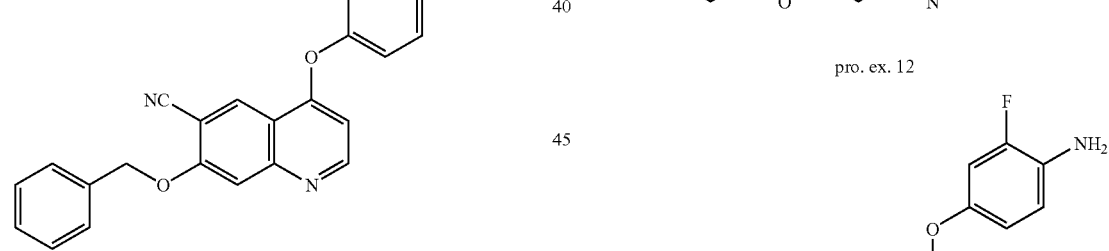
pro. ex. 13
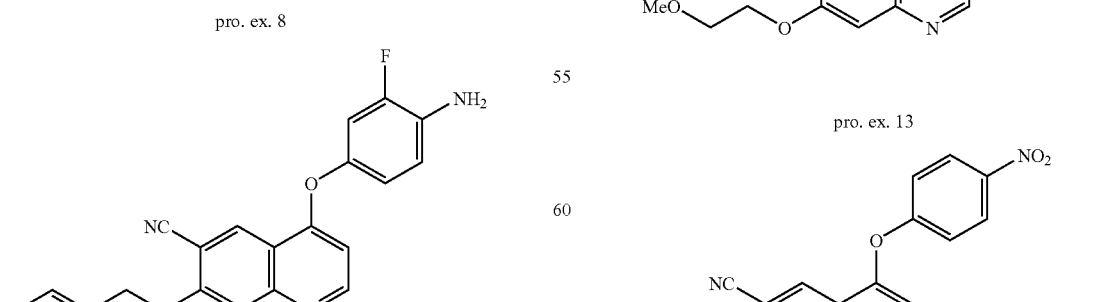

TABLE 4-continued
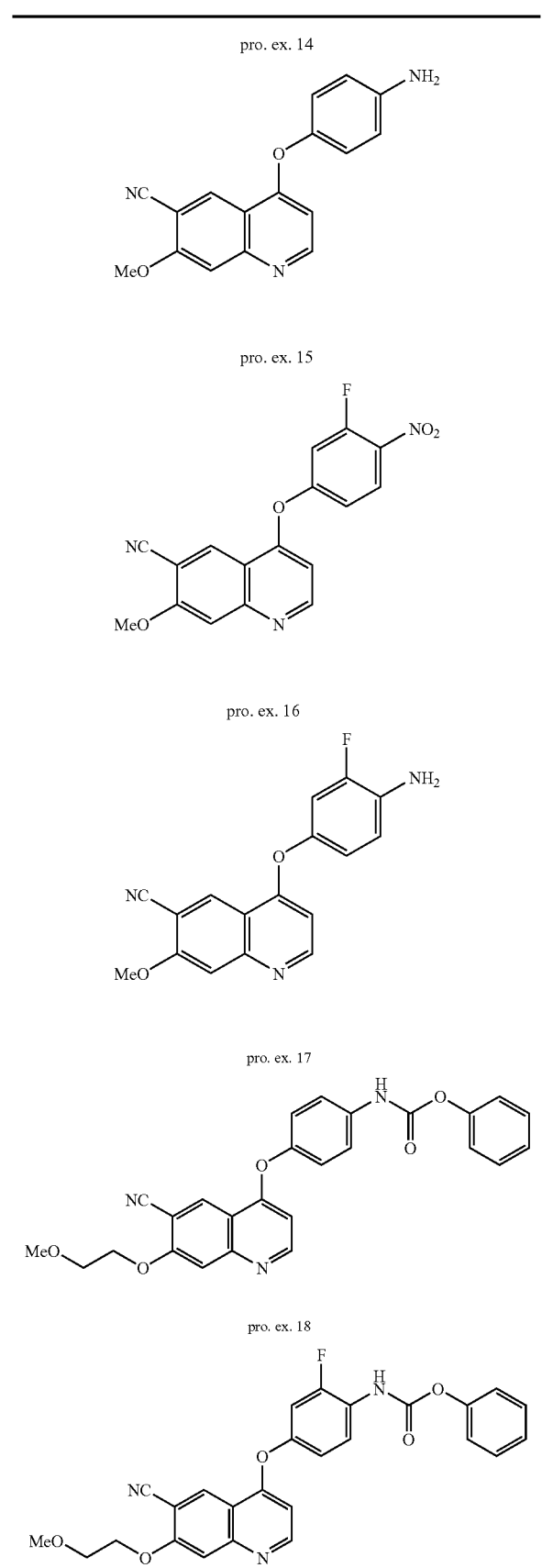
pro. ex. 14
pro. ex. 15
pro. ex. 16
pro. ex. 17
pro. ex. 18
TABLE 4-continued
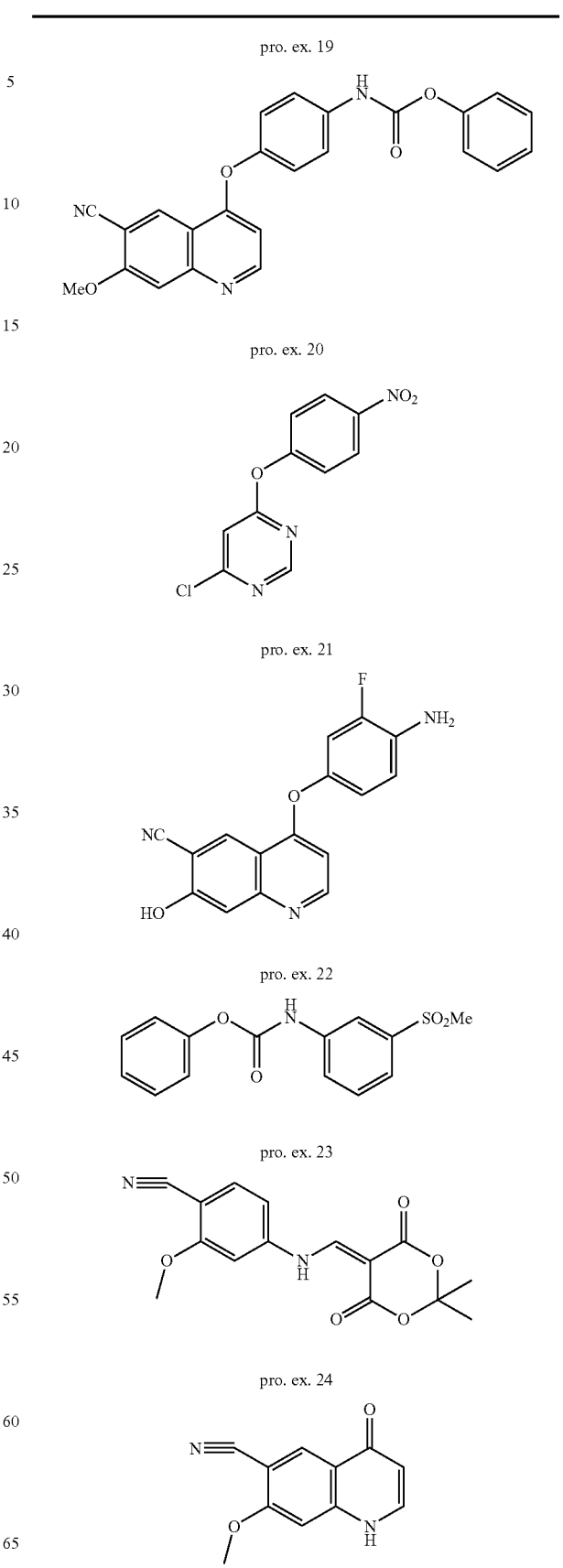
pro. ex. 19
pro. ex. 20
pro. ex. 21
pro. ex. 22
pro. ex. 23
pro. ex. 24

TABLE 4-continued
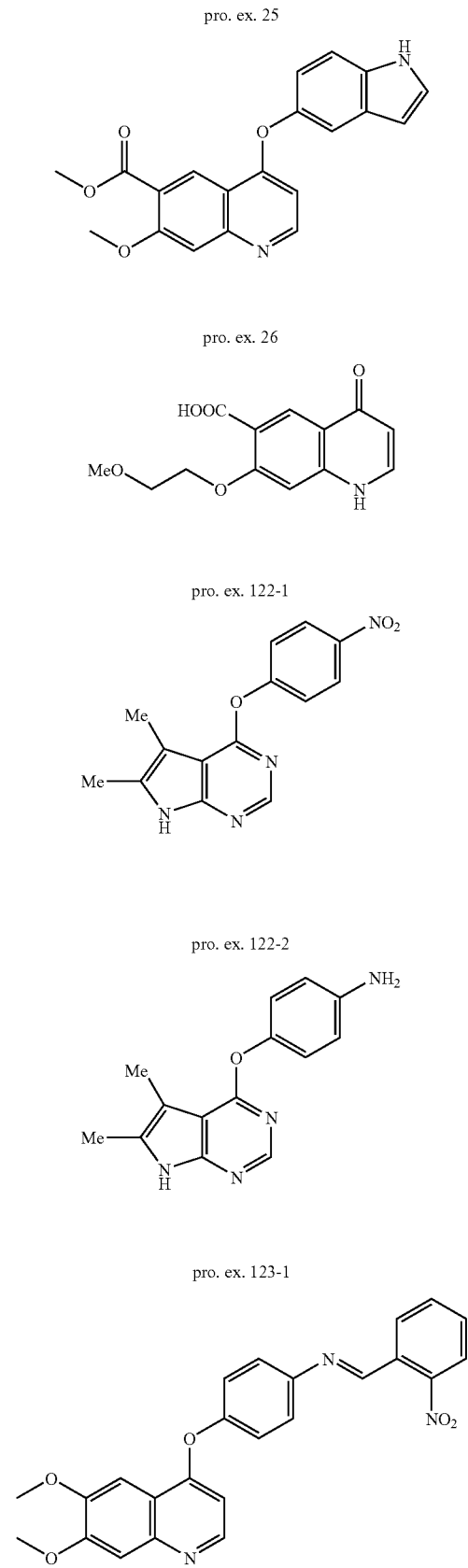
TABLE 4-continued
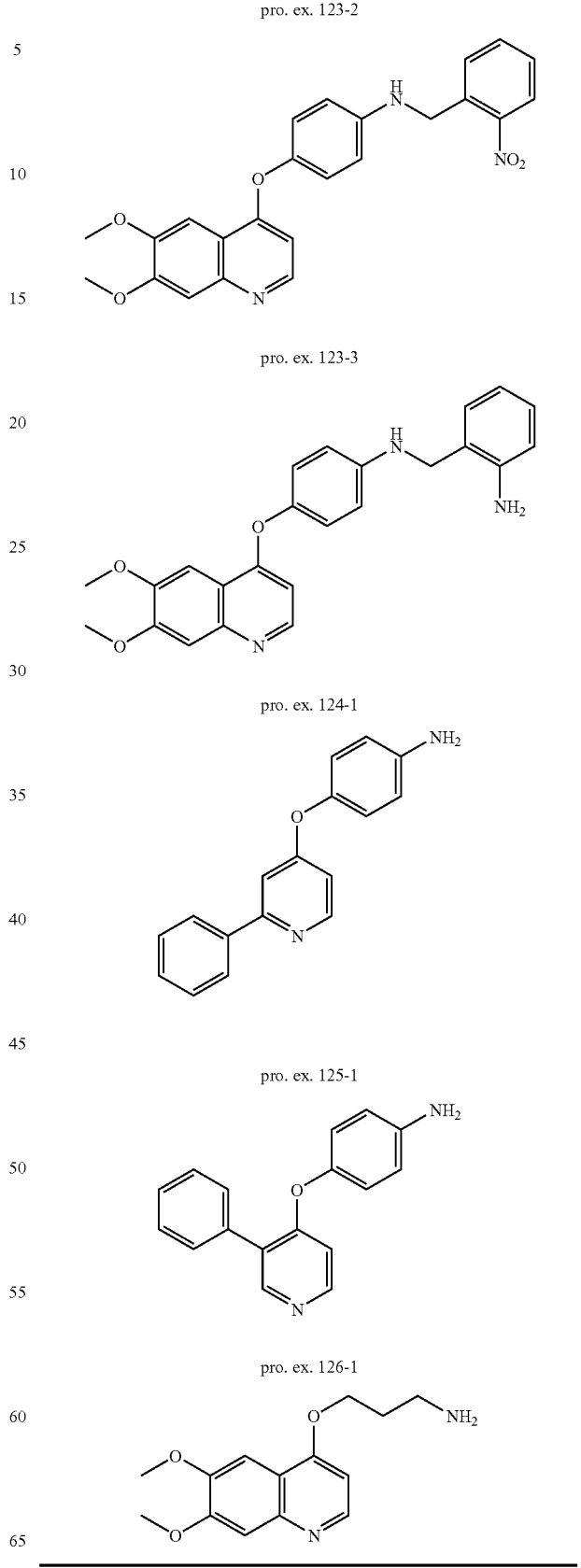

TABLE 5
pro. ex. 128-2
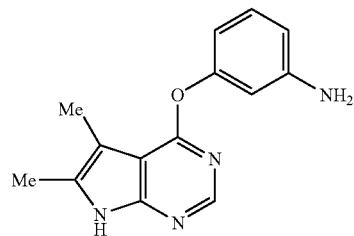
pro. ex. 129-1
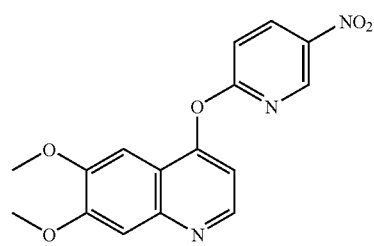
pro. ex. 129-2
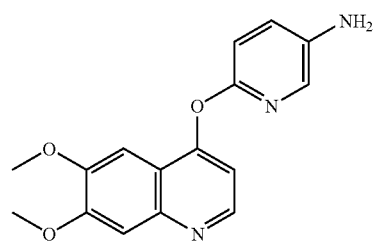
pro. ex. 132-1
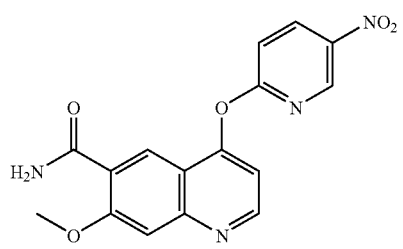
pro. ex. 132-2
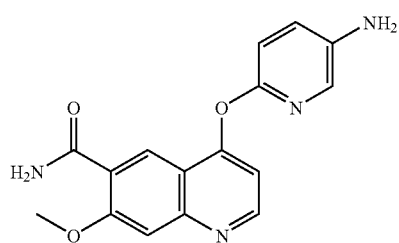

TABLE 5-continued
pro. ex. 141-1
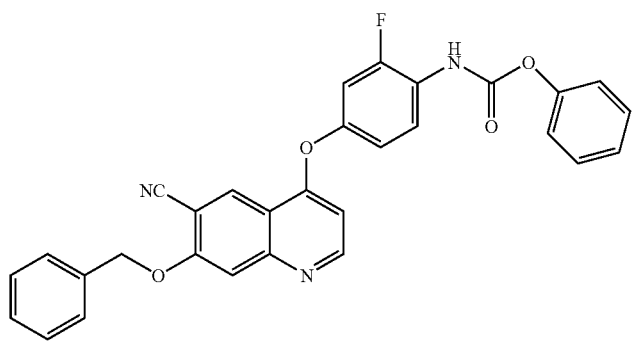
pro. ex. 142-1
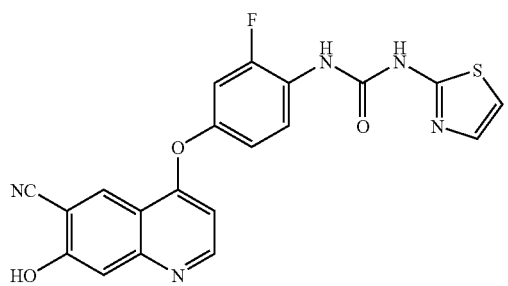
pro. ex. 144-1
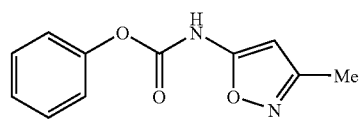
pro. ex. 145-1
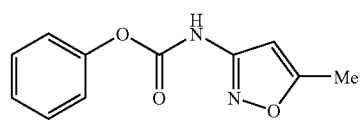
pro. ex. 152-1
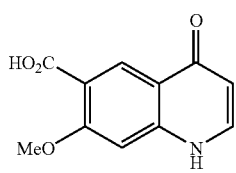
pro. ex. 152-2
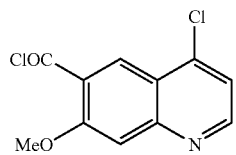
pro. ex. 152-3
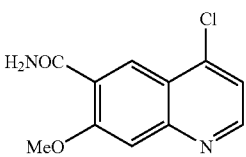

TABLE 5-continued
pro. ex. 152-4
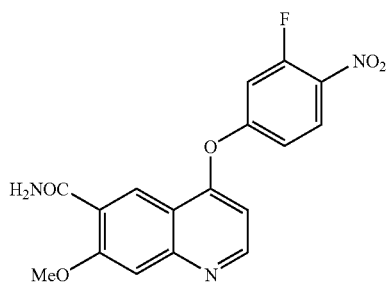
pro. ex. 152-5
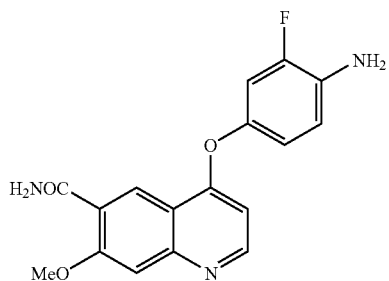
pro. ex. 153-1
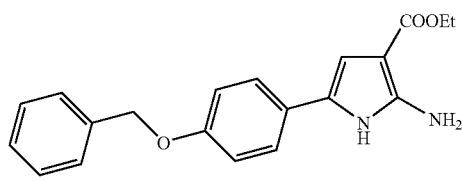
pro. ex. 153-2
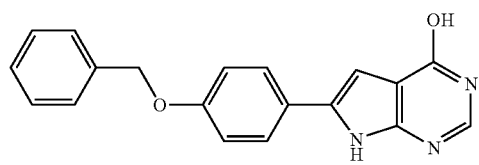
pro. ex. 153-3
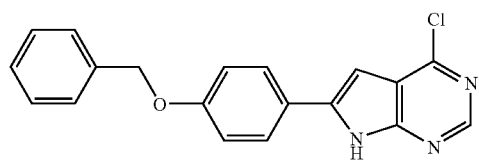

TABLE 5-continued
pro. ex. 153-4
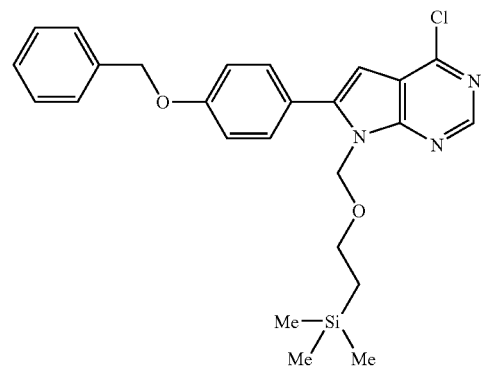
pro. ex. 153-5
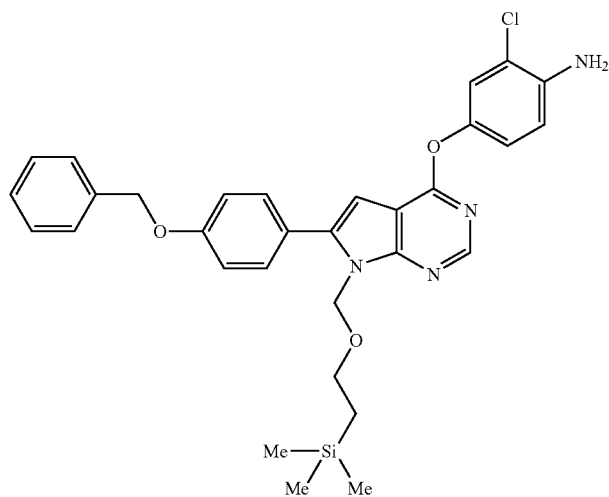
pro. ex. 153-6
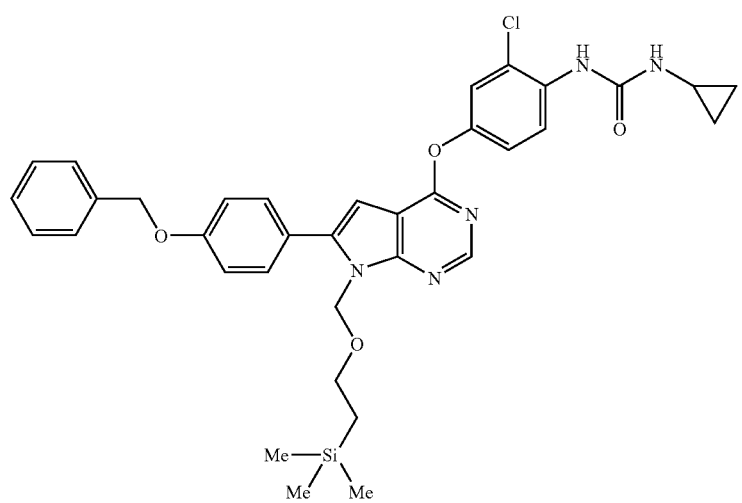

TABLE 5-continued
pro. ex. 153-7
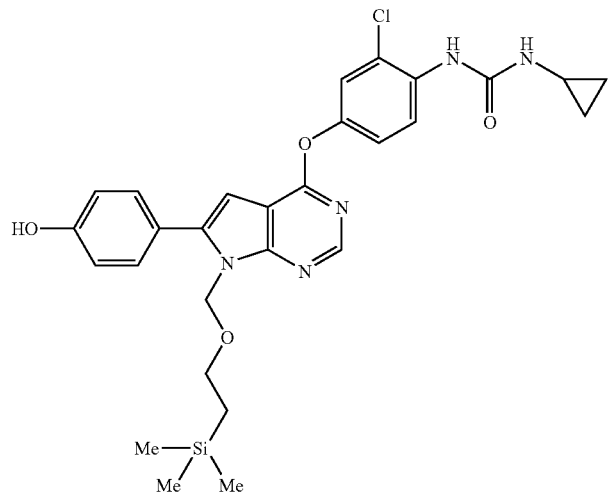
pro. ex. 153-8
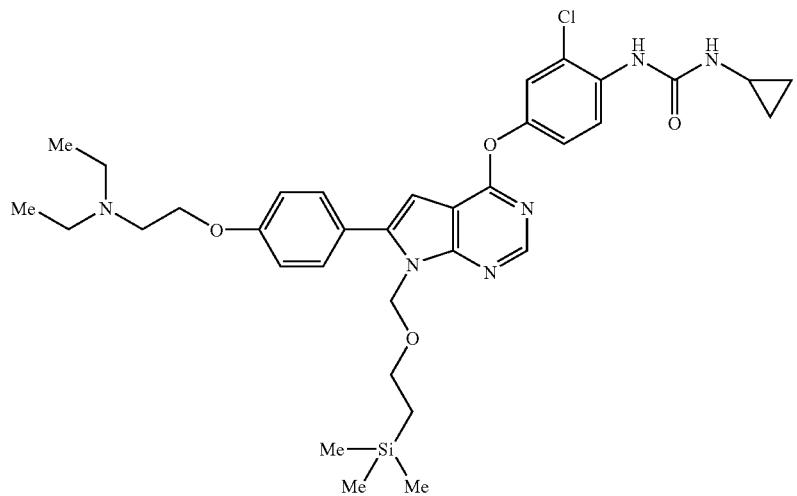
pro. ex. 154-1
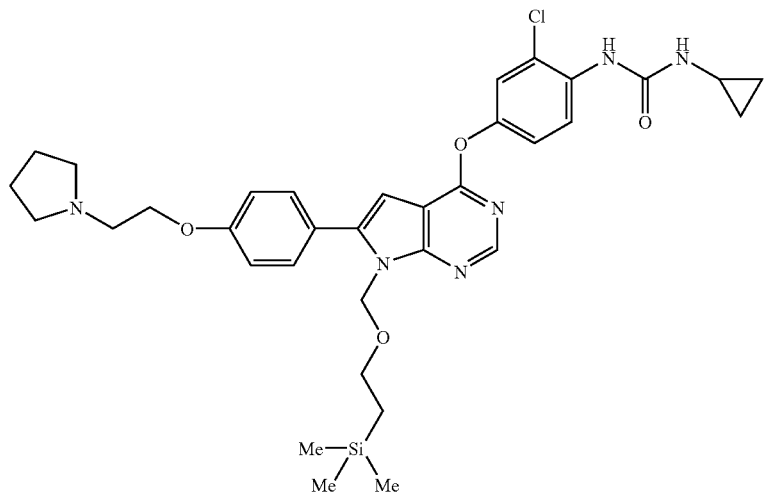

TABLE 5-continued
pro. ex. 155-1
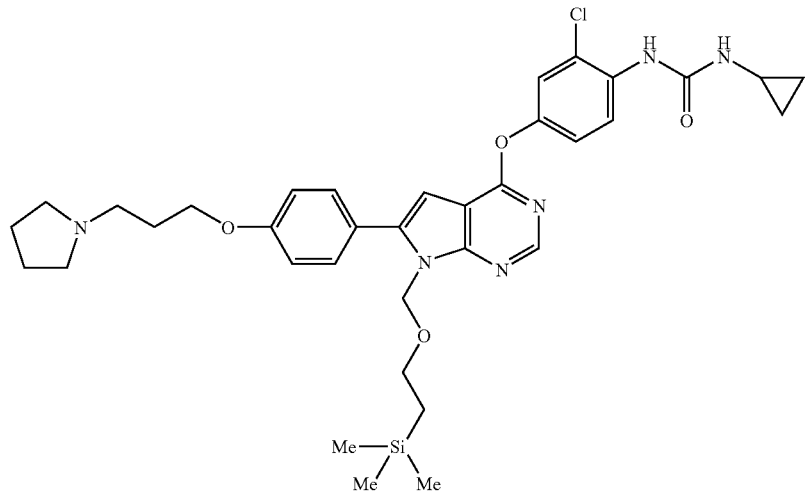
pro. ex. 156-1
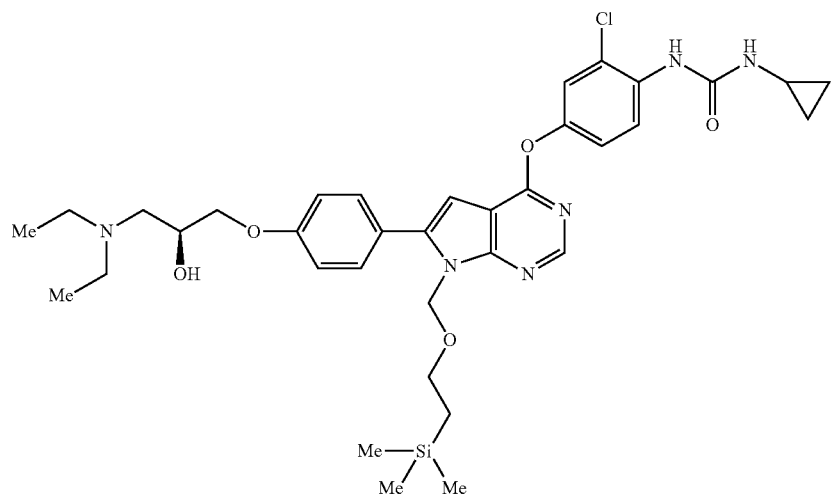

TABLE 6
pro. ex. 157-1
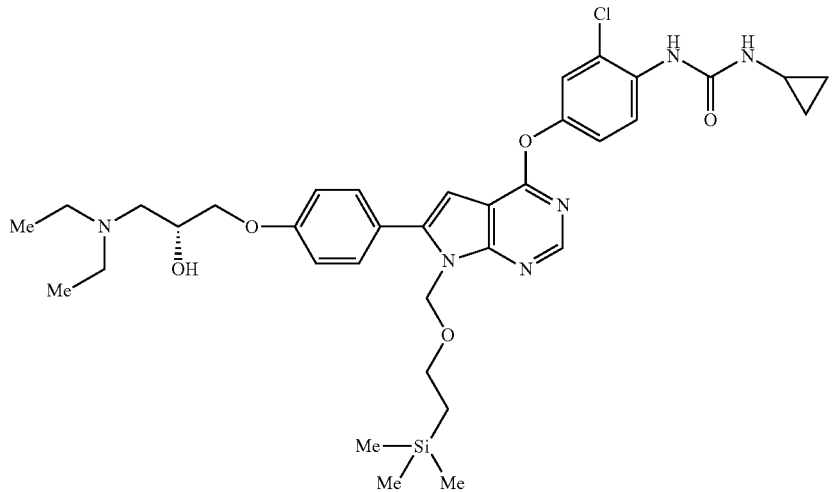
pro. ex. 158-1
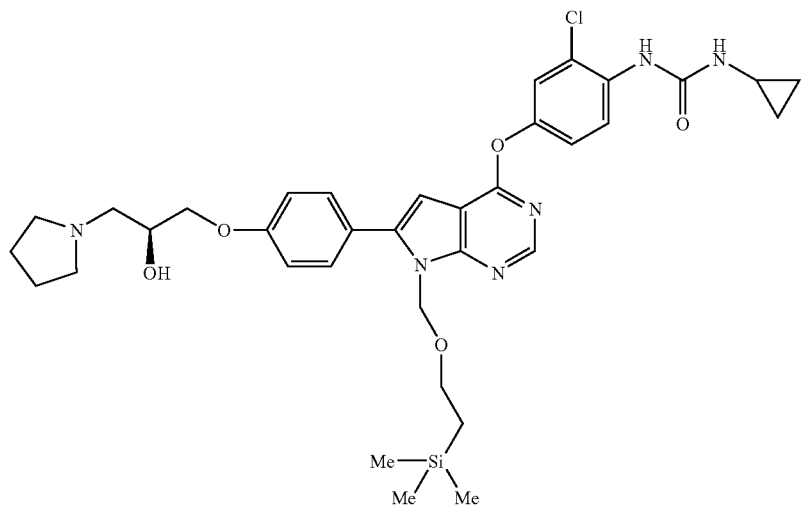
pro. ex. 159-1
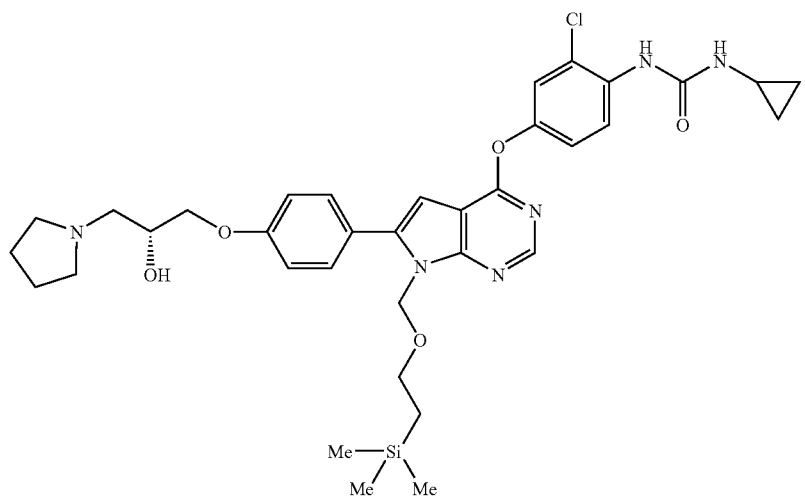

TABLE 6-continued
pro. ex. 160-1
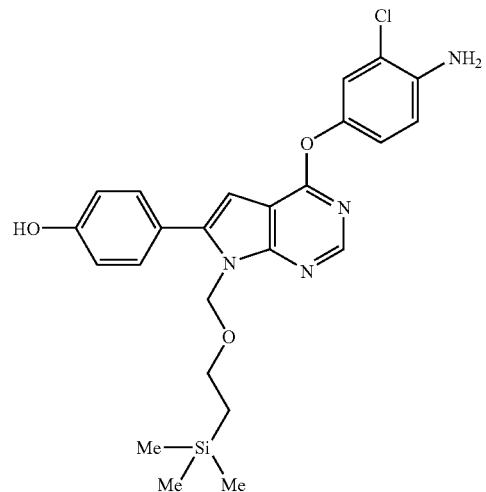
pro. ex. 160-2
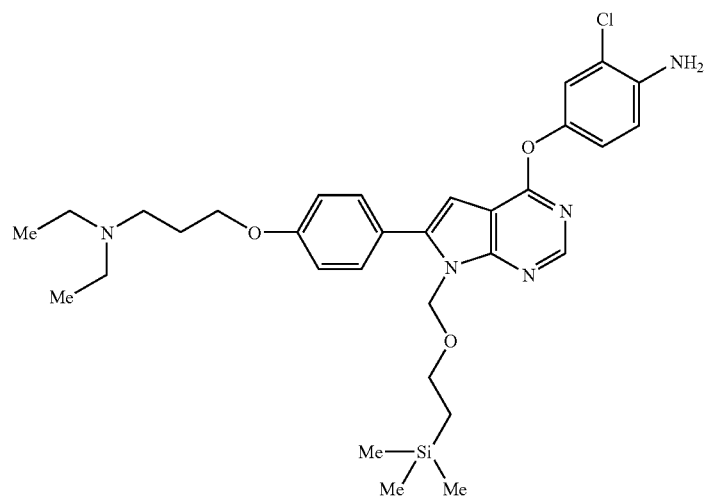
pro. ex. 160-3
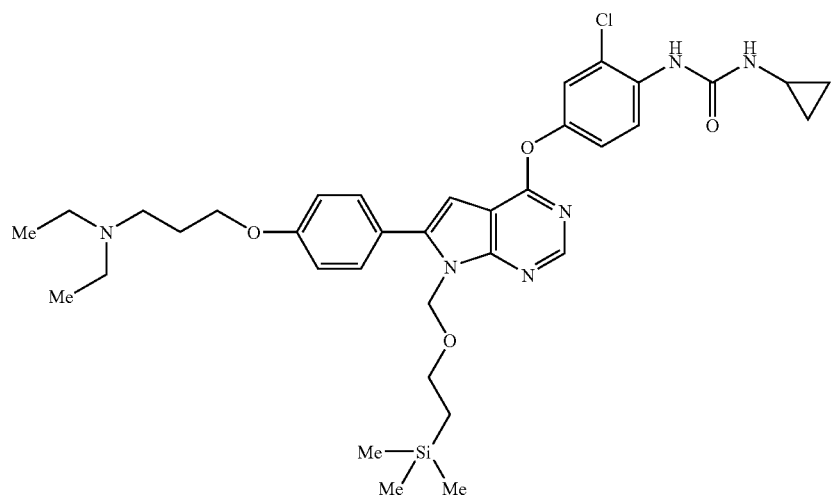

TABLE 6-continued
pro. ex. 161-1
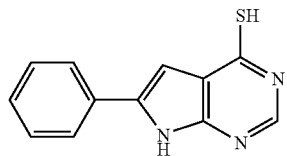
pro. ex. 161-2
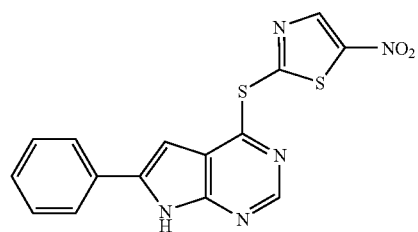
pro. ex. 162-1
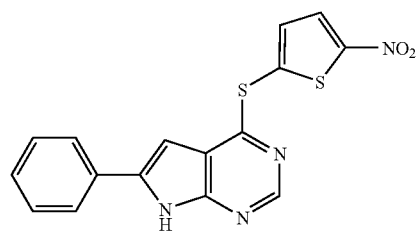
pro. ex. 162-2
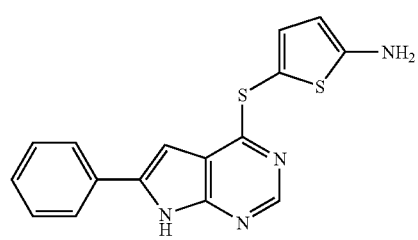
pro. ex. 163-1
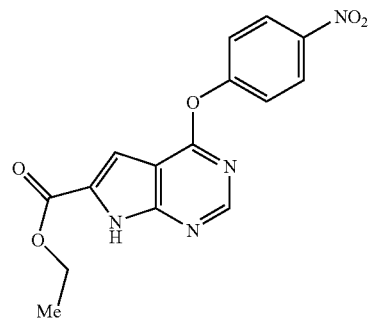

TABLE 6-continued
pro. ex. 163-2
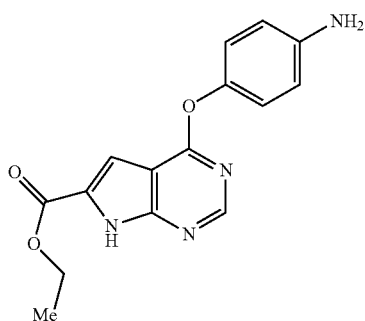
pro. ex. 171-1
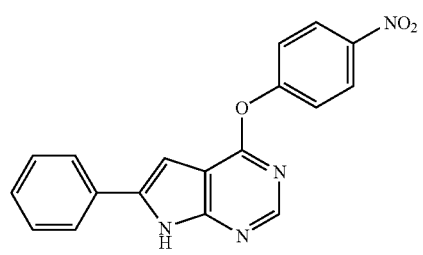
pro. ex. 171-2
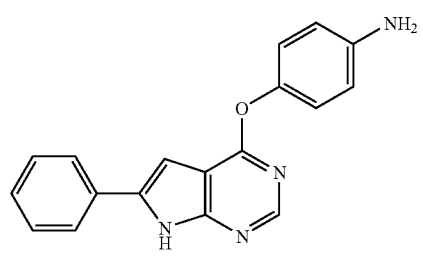
pro. ex. 175-1
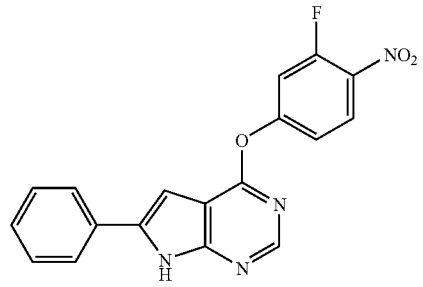
pro. ex. 171-2
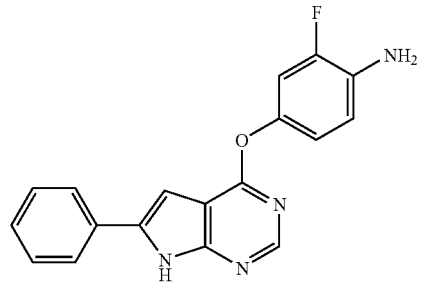

TABLE 6-continued
pro. ex. 179-1
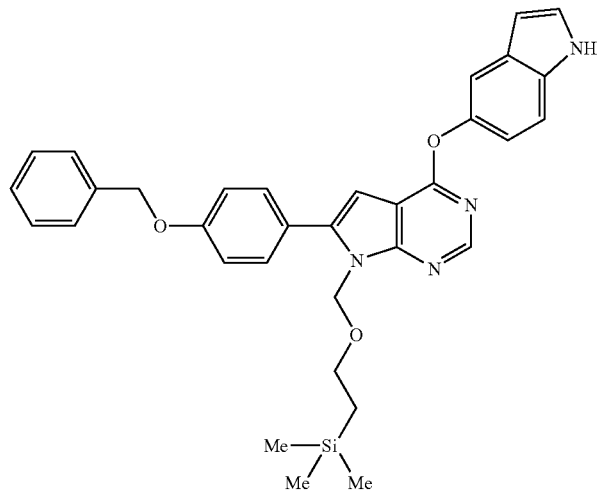
pro. ex. 179-2
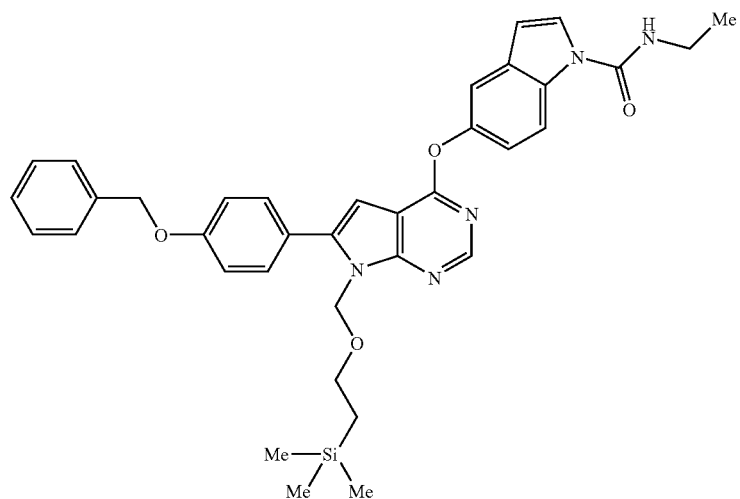
pro. ex. 181-1
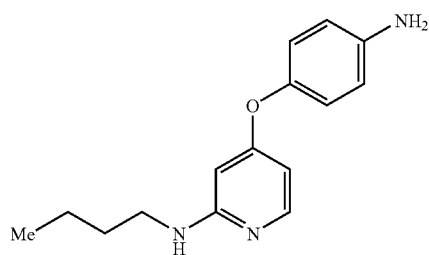
pro. ex. 182-1
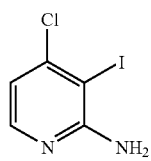

TABLE 6-continued
pro. ex. 182-2
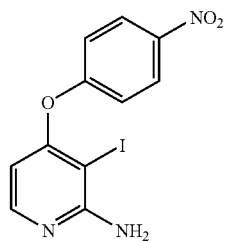
TABLE 7
pro. ex. 182-3
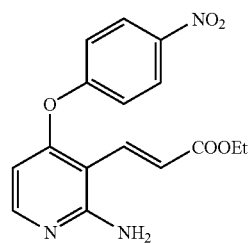
pro. ex. 182-4
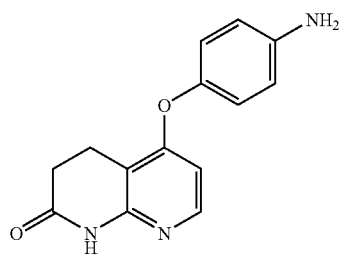
pro. ex. 183-1
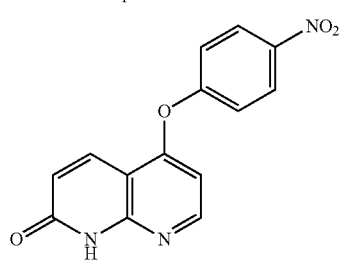
pro. ex. 183-2
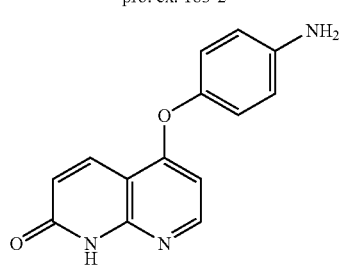

TABLE 7-continued
pro. ex. 184-1
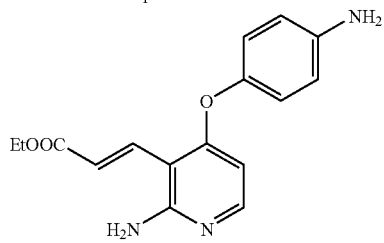
pro. ex. 184-2
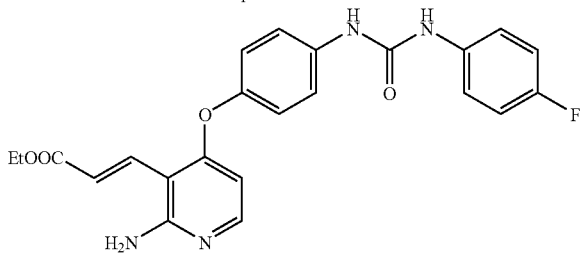
pro. ex. 185-1
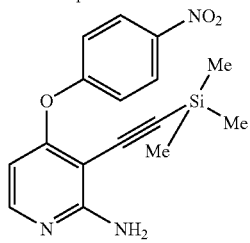
pro. ex. 185-2
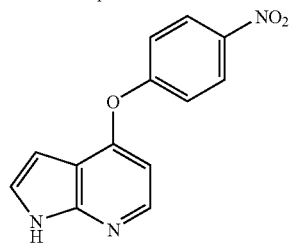
pro. ex. 185-3
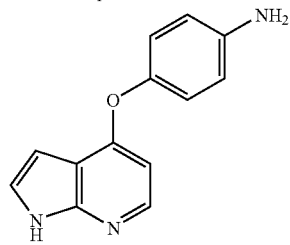
pro. ex. 186-1
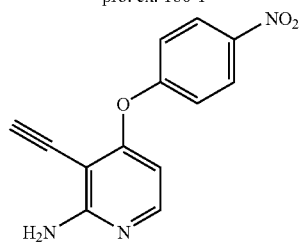

TABLE 7-continued
pro. ex. 186-2
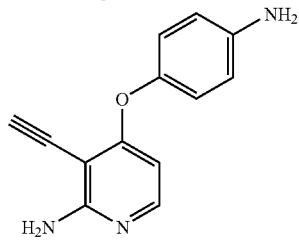
pro. ex. 186-3
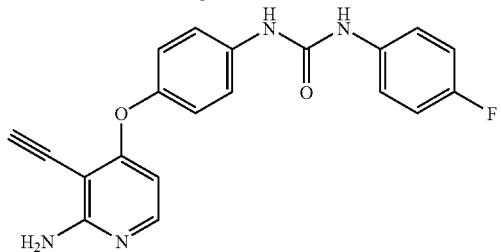
pro. ex. 190-1
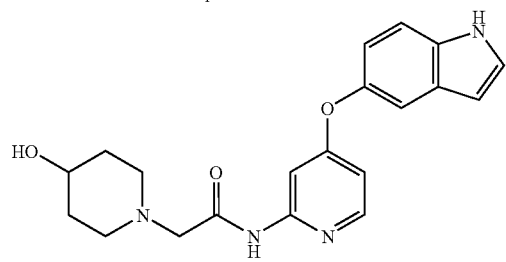
pro. ex. 192-1
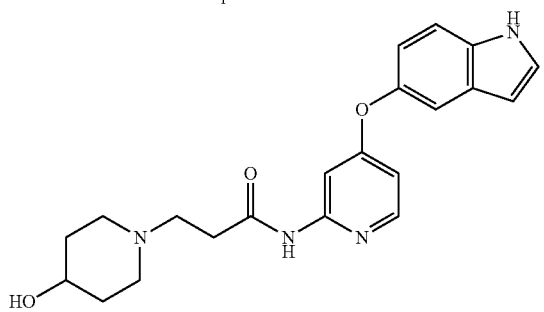
pro. ex. 193-1
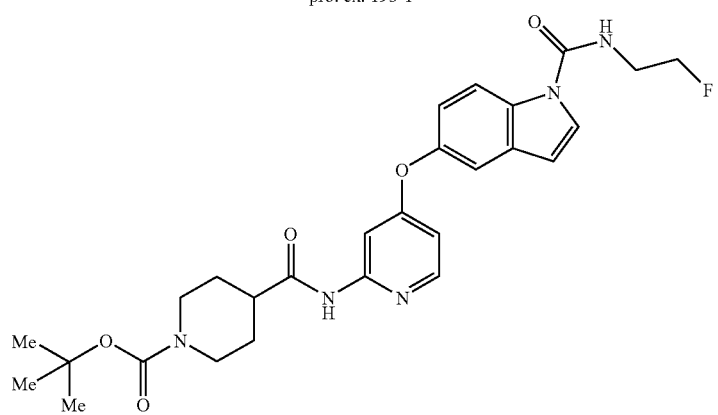

TABLE 7-continued
pro. ex. 195-1
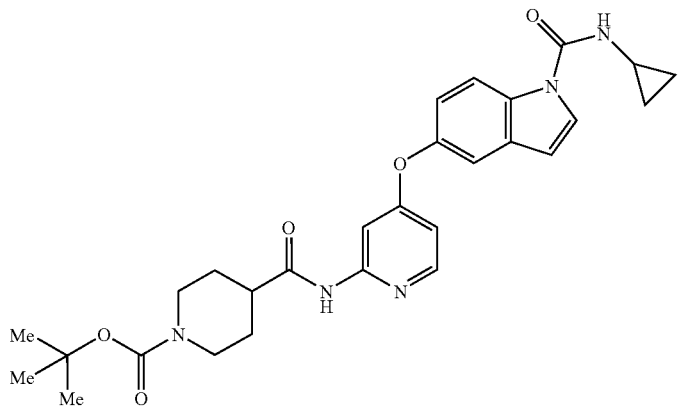
pro. ex. 197-1
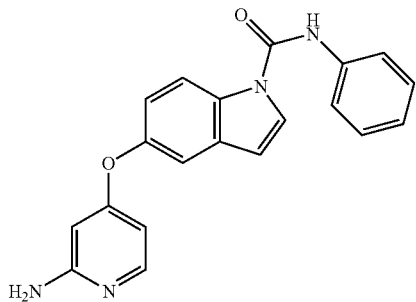
pro. ex. 197-2
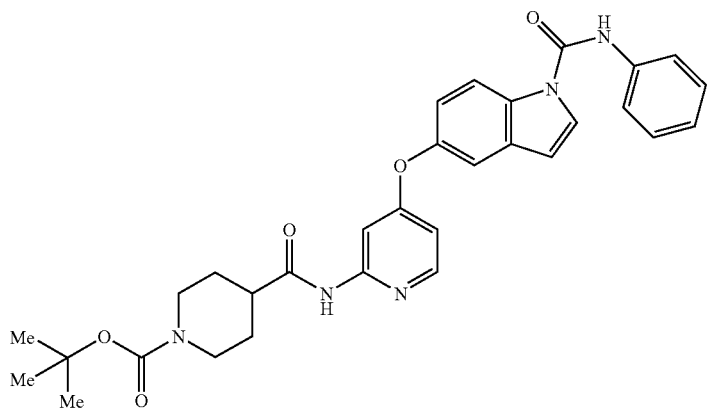
pro. ex. 197-3
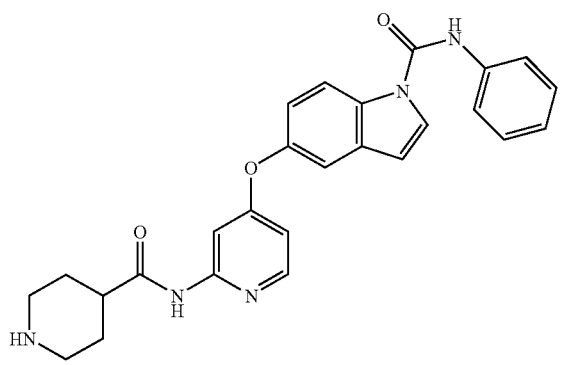

TABLE 7-continued
pro. ex. 199-1
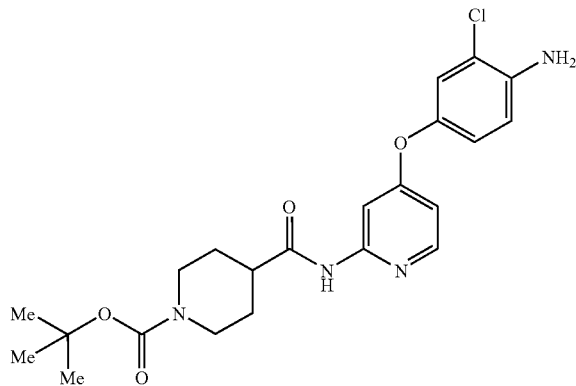
pro. ex. 199-2
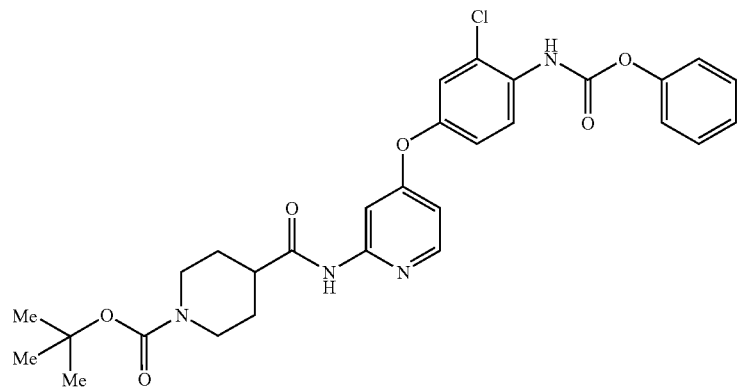
TABLE 8
pro. ex. 199-3
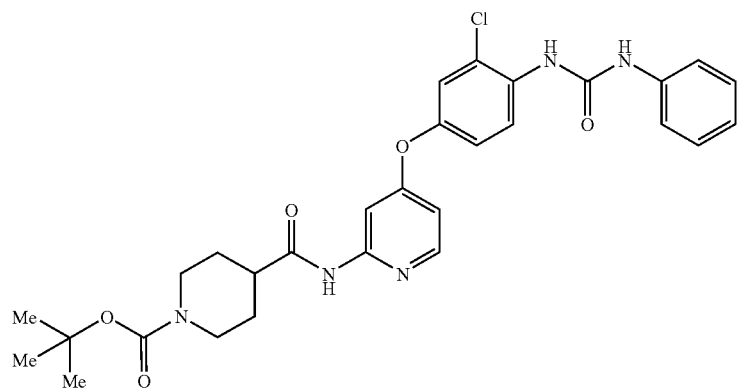

TABLE 8-continued
pro. ex. 200-1
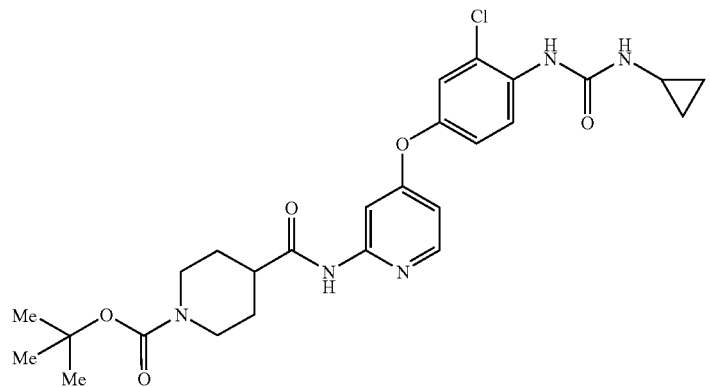
pro. ex. 201-1
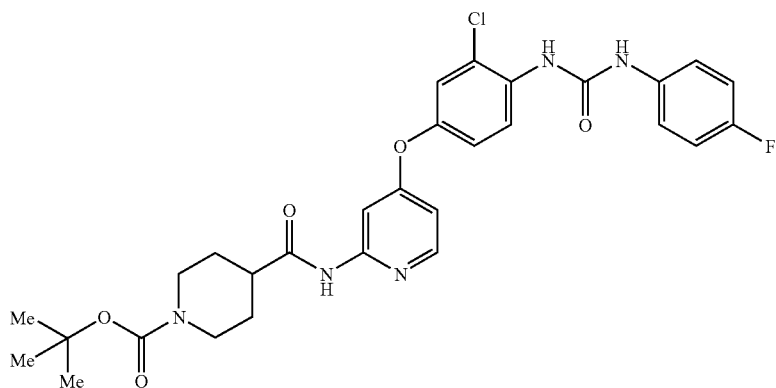
pro. ex. 203-1
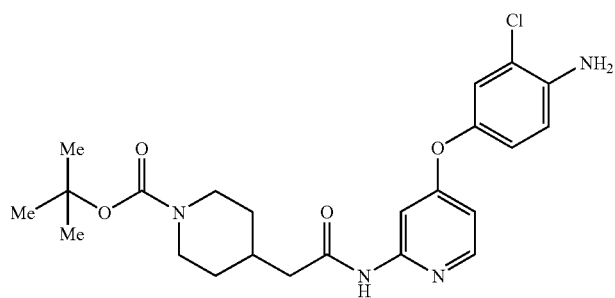
pro. ex. 203-2
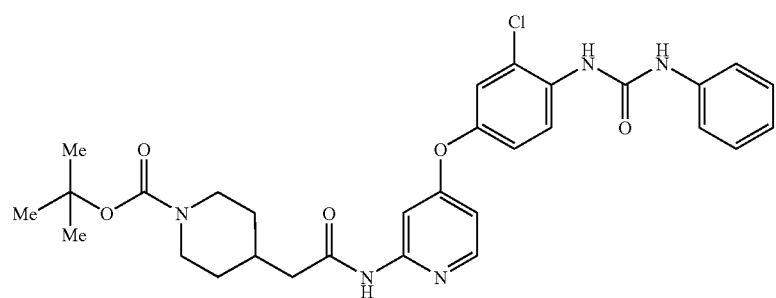

TABLE 8-continued
pro. ex. 204-1
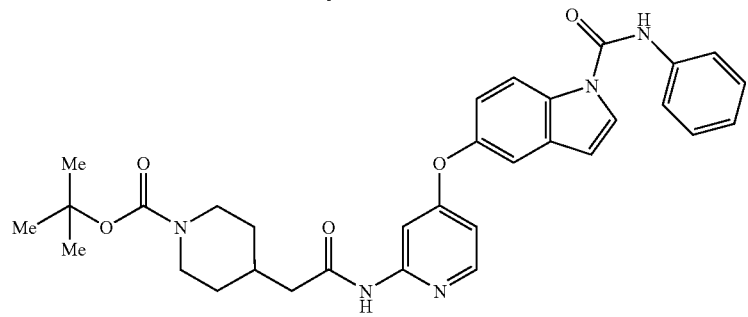
pro. ex. 205-1
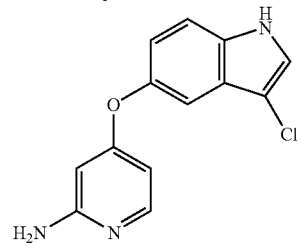
pro. ex. 205-2
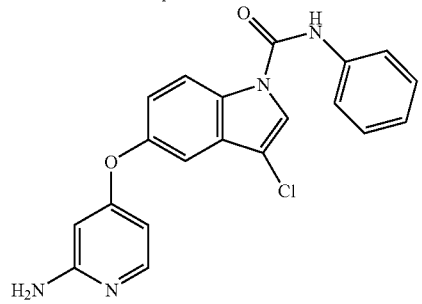
pro. ex. 205-3
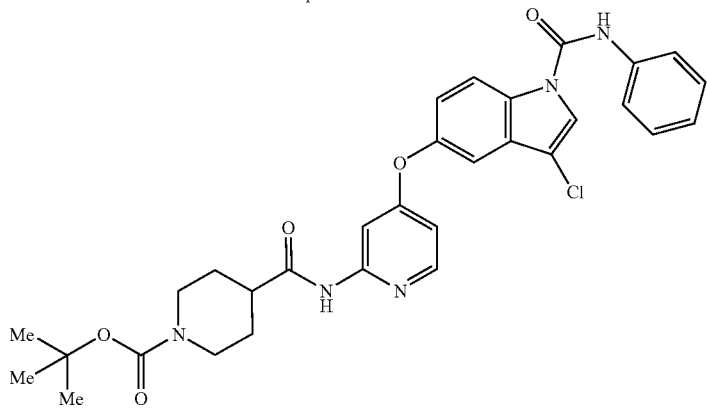
pro. ex. 206-1
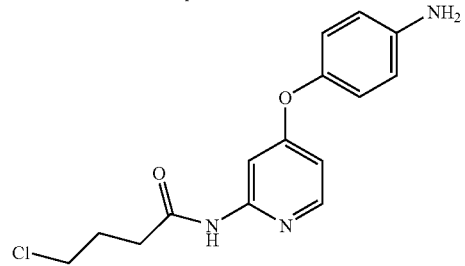

TABLE 8-continued
pro. ex. 206-2
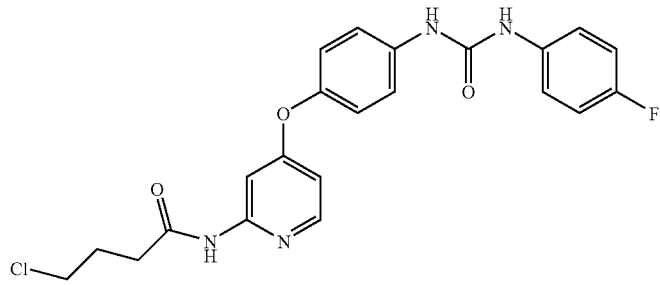
pro. ex. 207-1
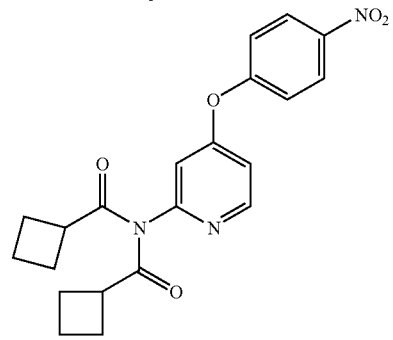
pro. ex. 207-2
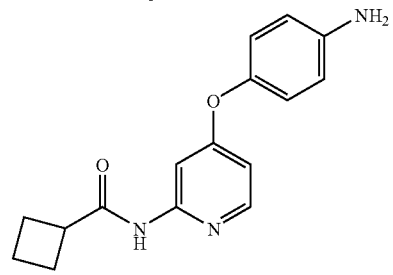
pro. ex. 208-1
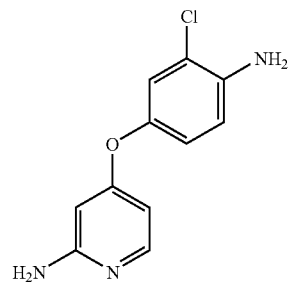
pro. ex. 209-1
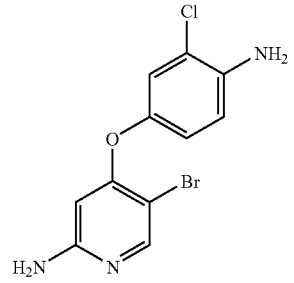

TABLE 8-continued
pro. ex. 209-2
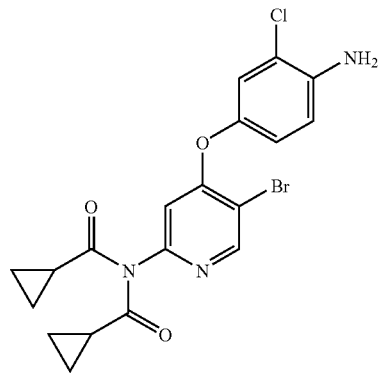
pro. ex. 210-1
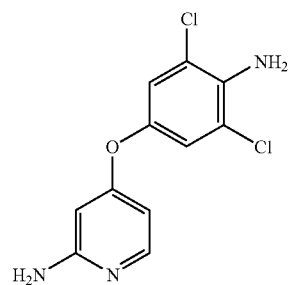
pro. ex. 210-2
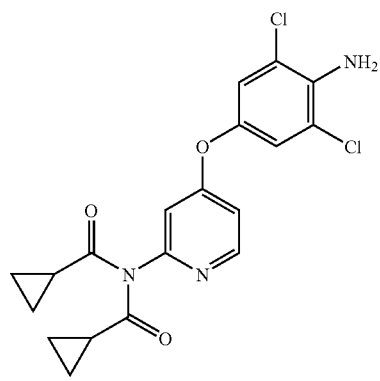
pro. ex. 211-1
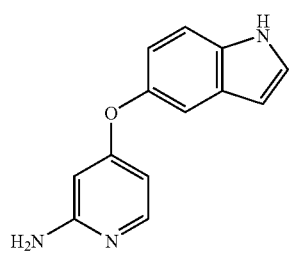

TABLE 8-continued
pro. ex. 211-2
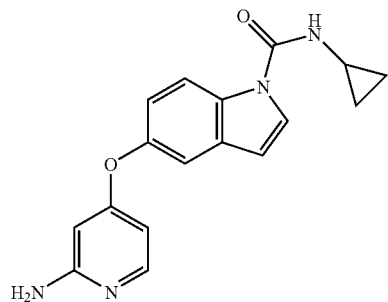
pro. ex. 215-1
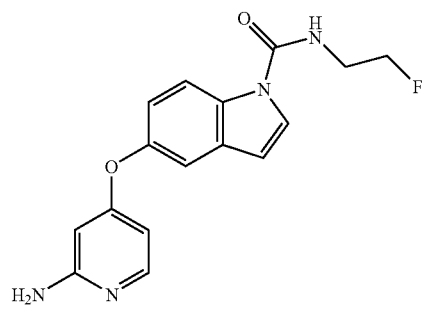
TABLE 9
pro. ex. 216-1
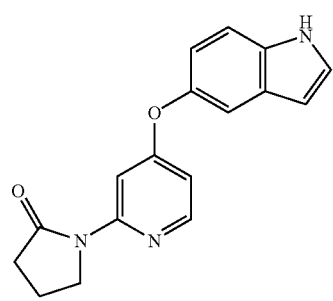
pro. ex. 217-1
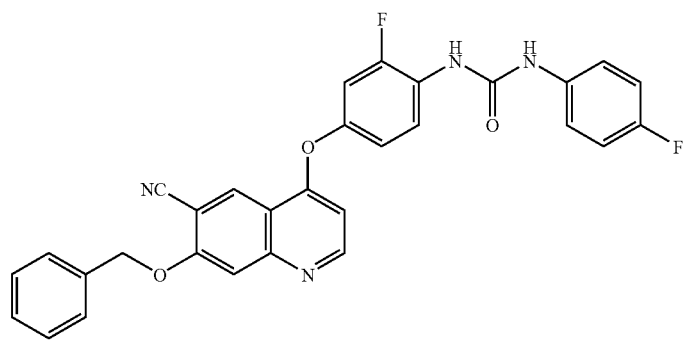

TABLE 9-continued
pro. ex. 217-2
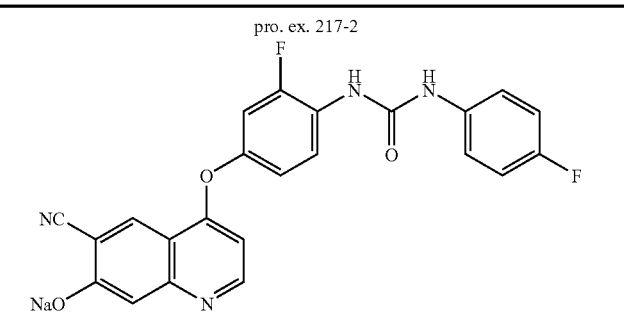
pro. ex. 219-1
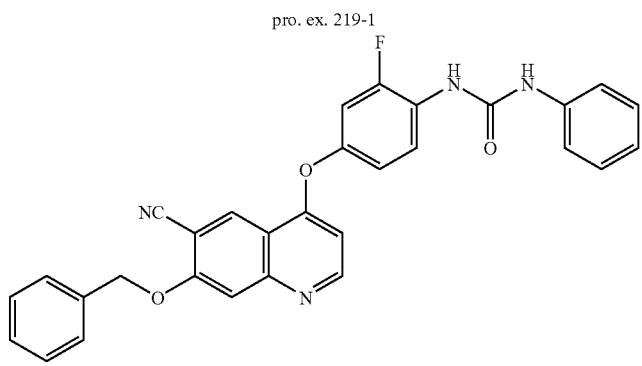
pro. ex. 219-2
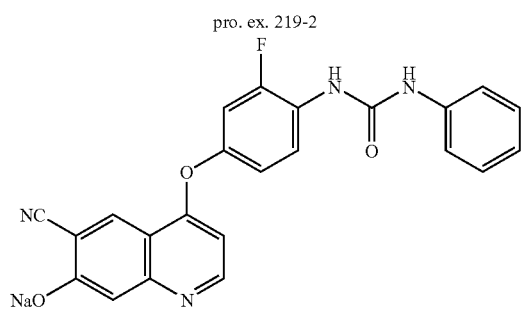
pro. ex. 222-1
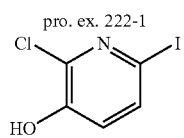
pro. ex. 222-2
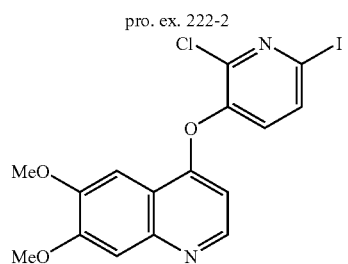
pro. ex. 222-3
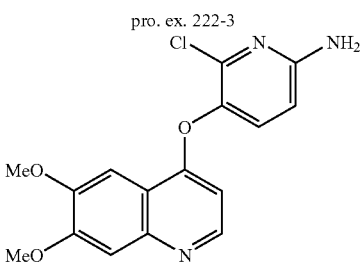

TABLE 9-continued
pro. ex. 222-4
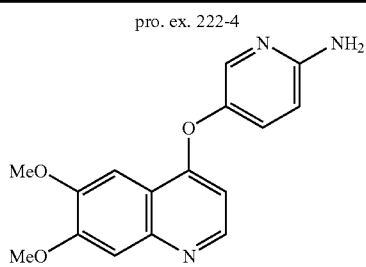
pro. ex. 224-1
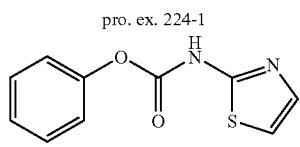
pro. ex. 226-1
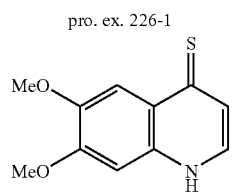
pro. ex. 226-2
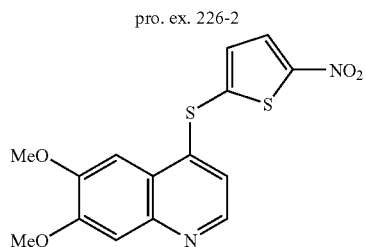
pro. ex. 226-3
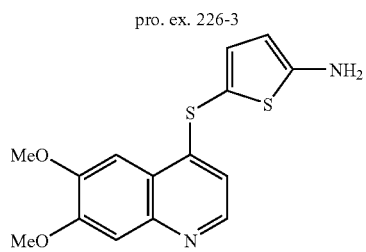
pro. ex. 232-1
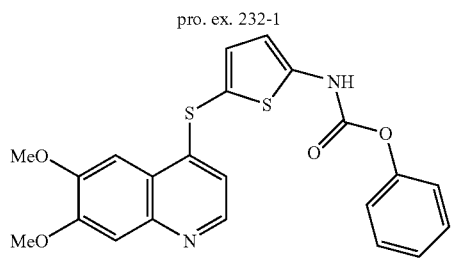
pro. ex. 235-1
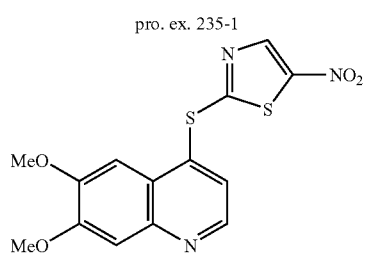

TABLE 9-continued
pro. ex. 235-2
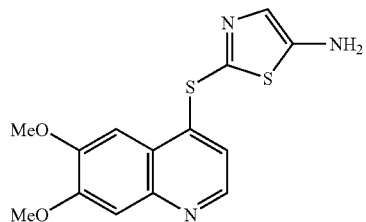
pro. ex. 244-1
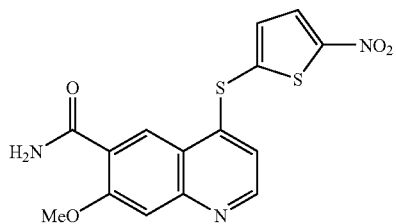
pro. ex. 244-2
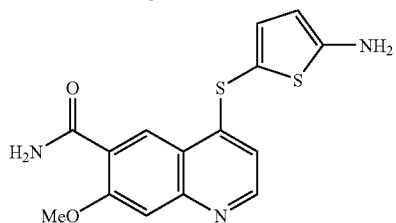
pro. ex. 247-1
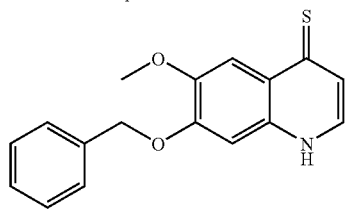
pro. ex. 247-2
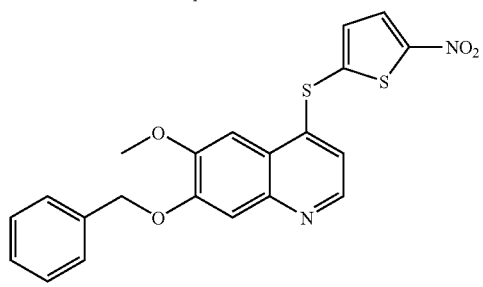
pro. ex. 247-3
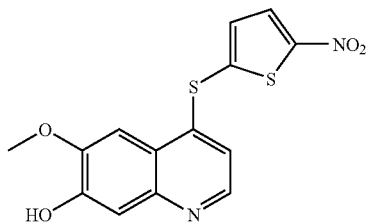

TABLE 10
pro. ex. 247-4
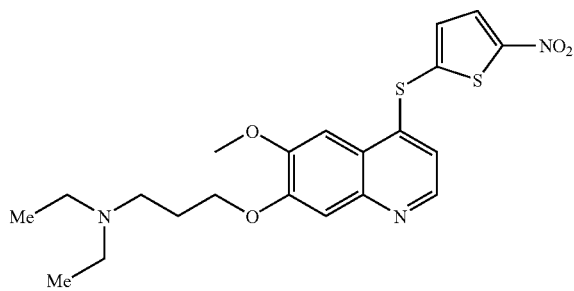
pro. ex. 247-5
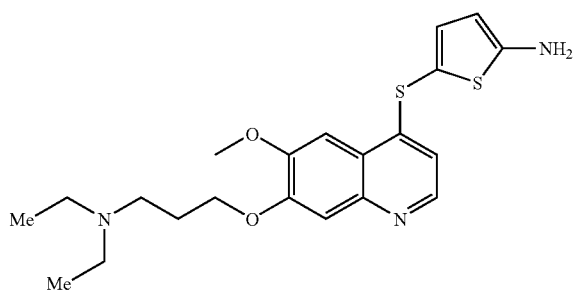
pro. ex. 248-1
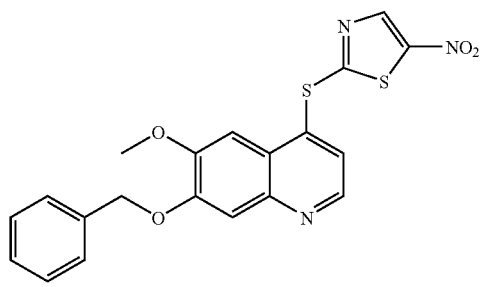
pro. ex. 248-2
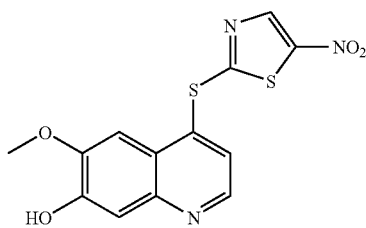
pro. ex. 248-3
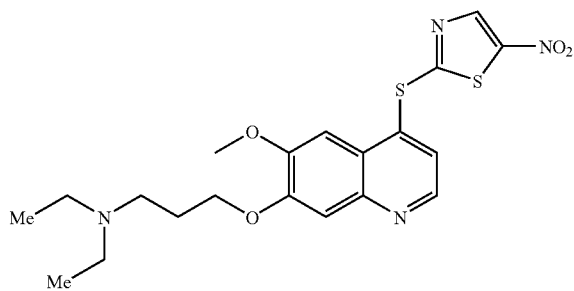

TABLE 10-continued
pro. ex. 249-1
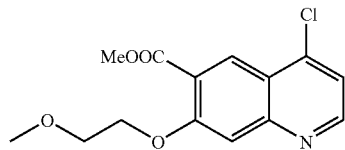
pro. ex. 249-2
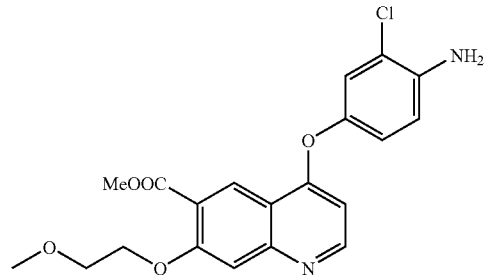
pro. ex. 249-3
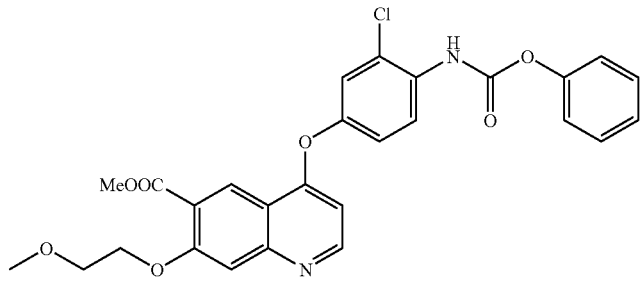
pro. ex. 249-4
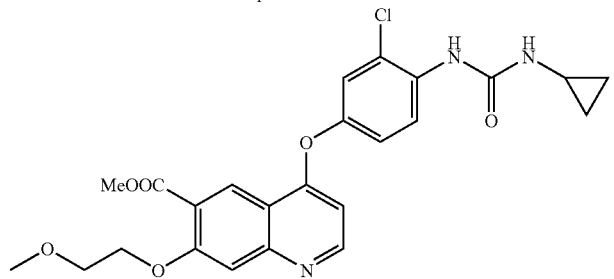
pro. ex. 249-5
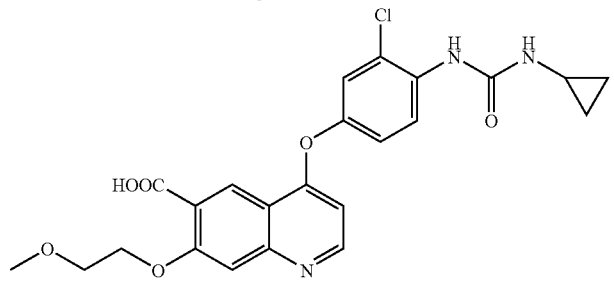
pro. ex. 252-1
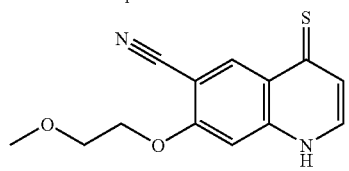

TABLE 10-continued
pro. ex. 252-2
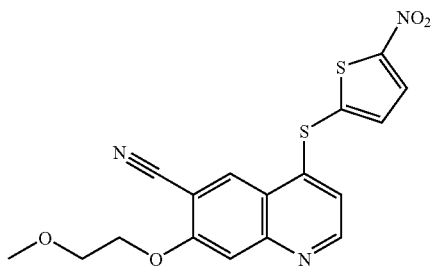
pro. ex. 252-3
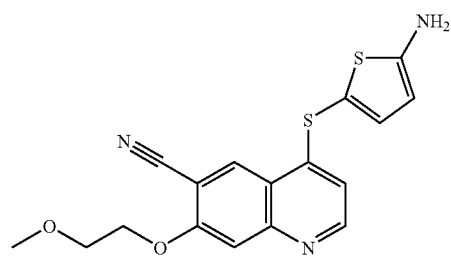
pro. ex. 262-1
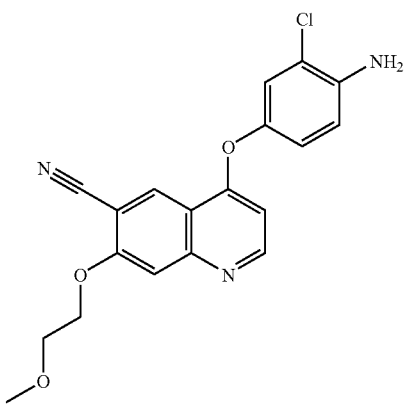
pro. ex. 263-1
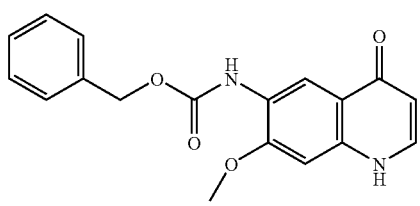
pro. ex. 263-2
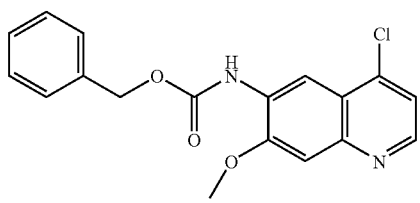

TABLE 10-continued
pro. ex. 263-3
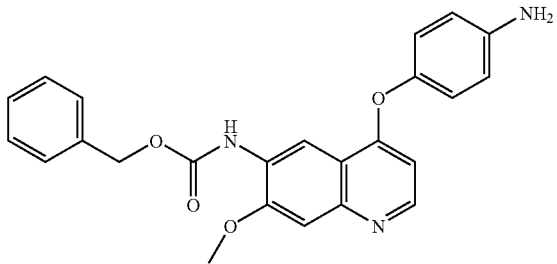
pro. ex. 267-1
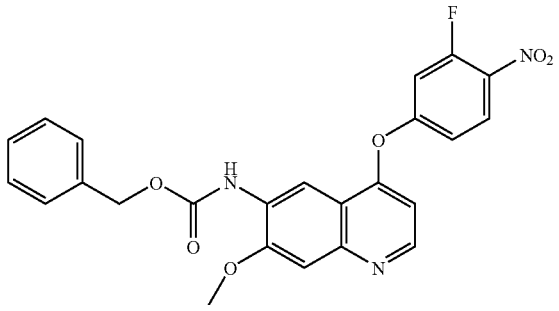
pro. ex. 267-2
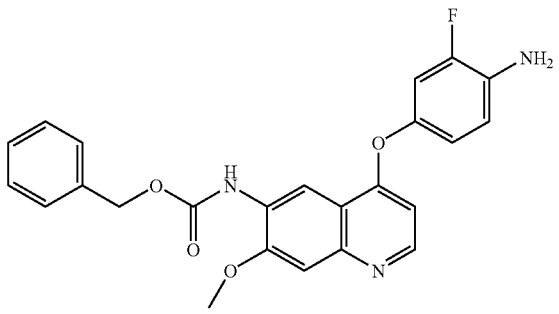
pro. ex. 276-1
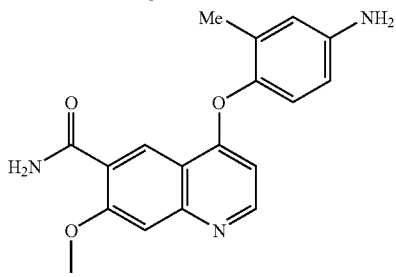
pro. ex. 276-2
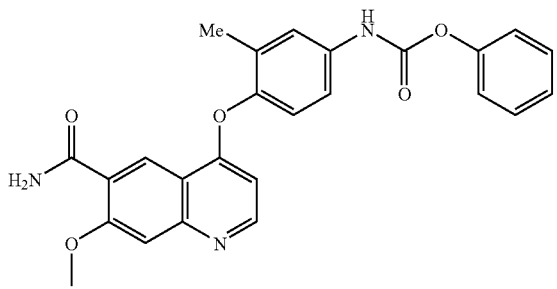

TABLE 11
pro. ex. 277-1
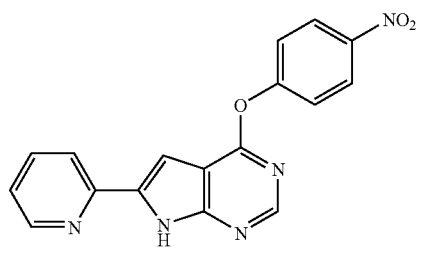
pro. ex. 277-2
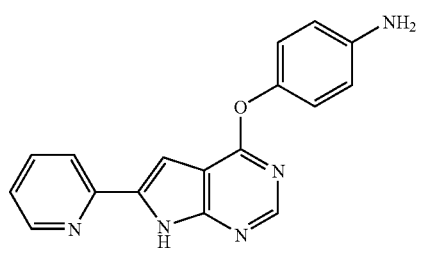
pro. ex. 280-1
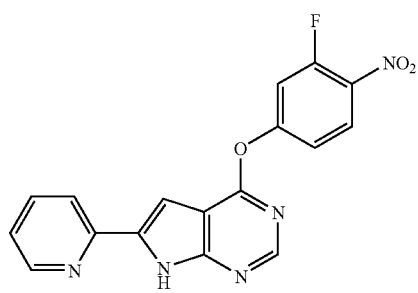
pro. ex. 280-2
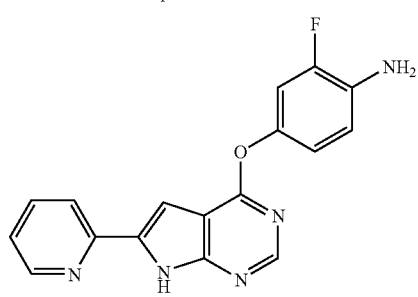
pro. ex. 284-1
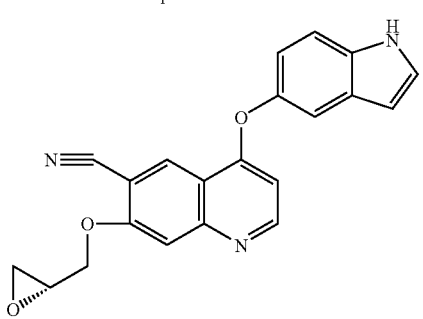

TABLE 11-continued
pro. ex. 287-1
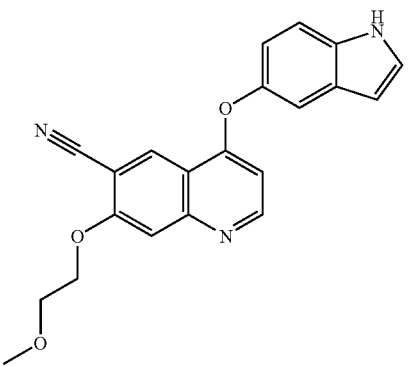
pro. ex. 301-1
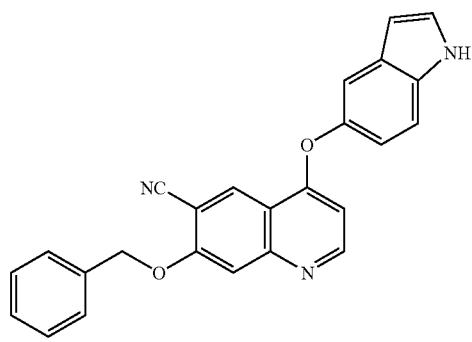
pro. ex. 302-2
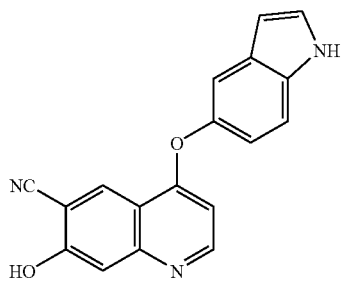
pro. ex. 302-3
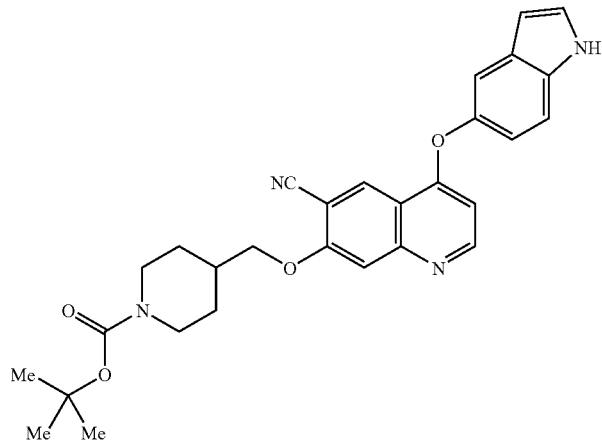

TABLE 11-continued
pro. ex. 303-1
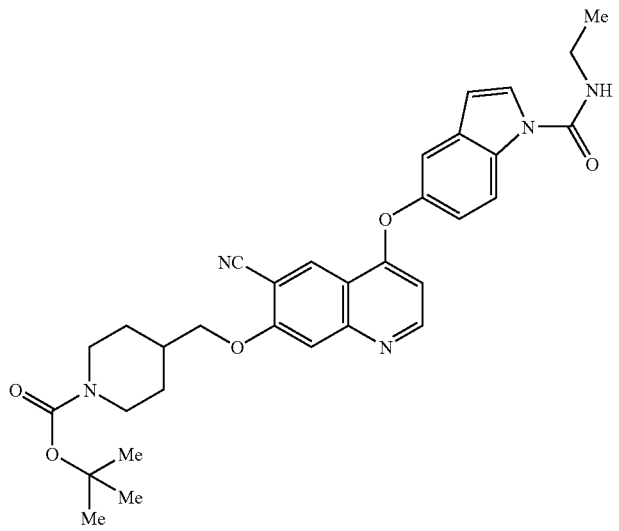
pro. ex. 305-1
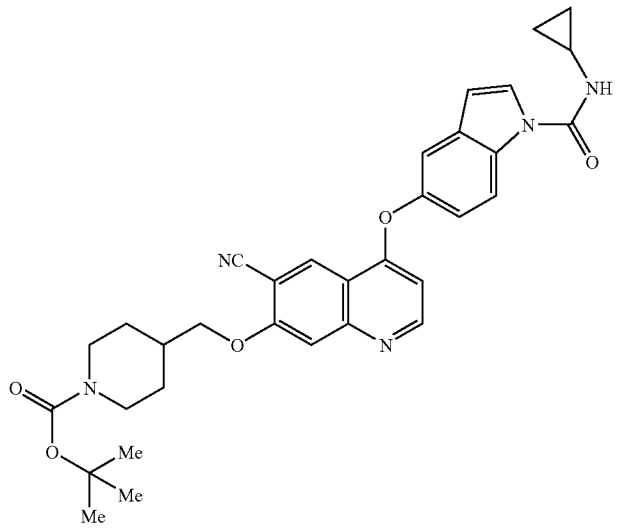
pro. ex. 307-1
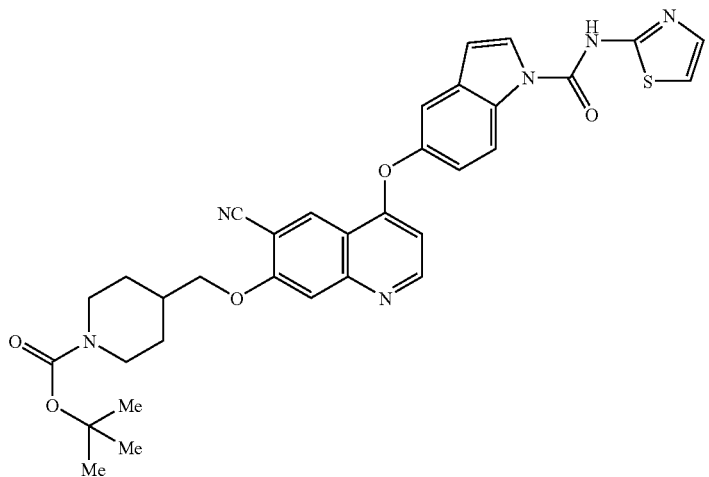

TABLE 11-continued
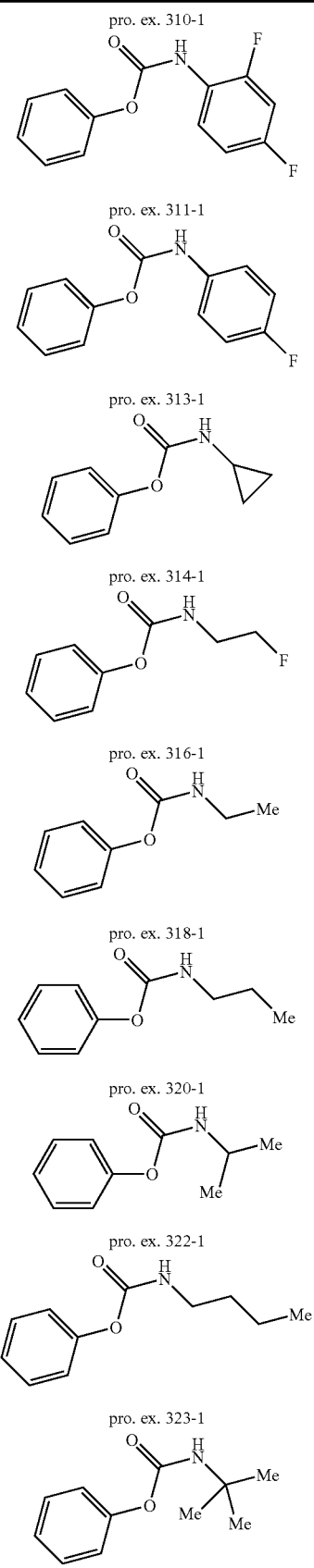

TABLE 12
pro. ex. 324-1
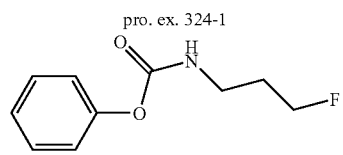
pro. ex. 325-1
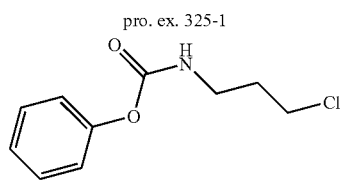
pro. ex. 326-1
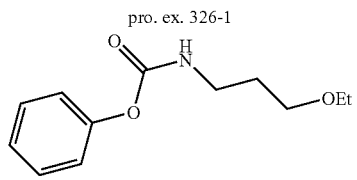
pro. ex. 327-1
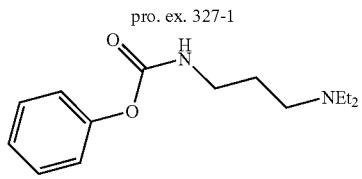
pro. ex. 328-1
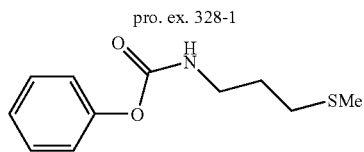
pro. ex. 329-1
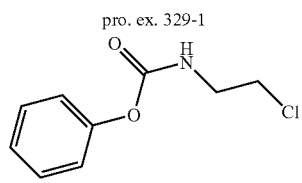
pro. ex. 335-1
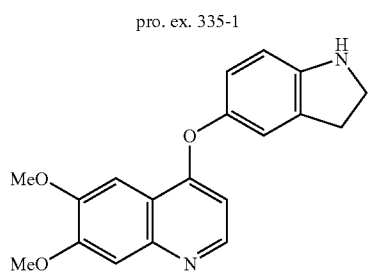
pro. ex. 339-1
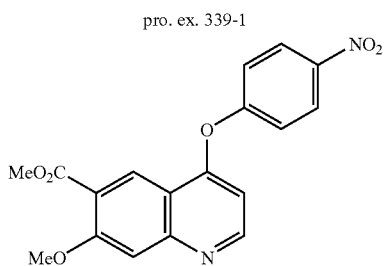

TABLE 12-continued
pro. ex. 339-2
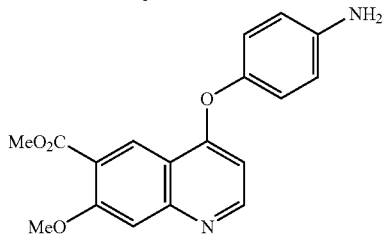
pro. ex. 347-1
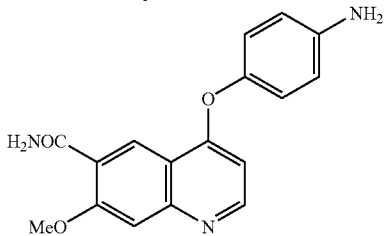
pro. ex. 348-1
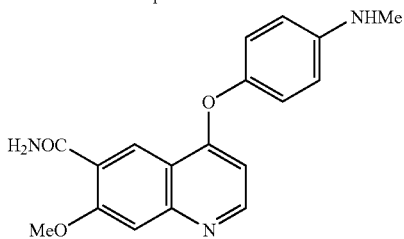
pro. ex. 350-1
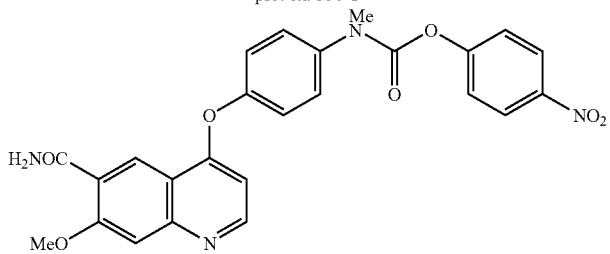
pro. ex. 353-1
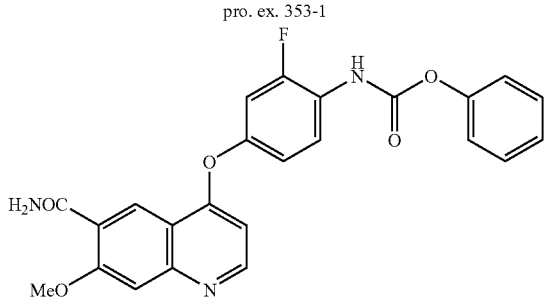
pro. ex. 360-1
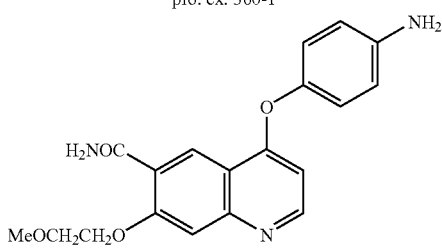

TABLE 12-continued
pro. ex. 360-2
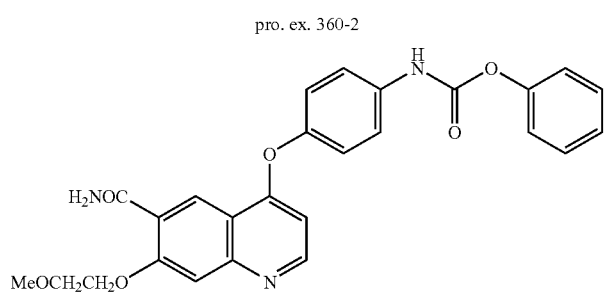
pro. ex. 363-1
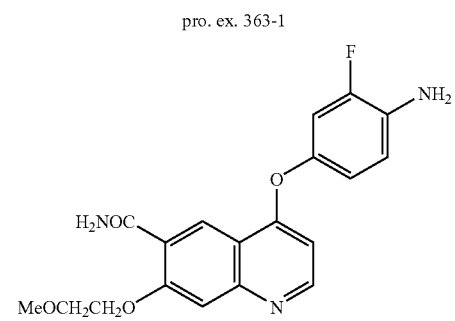
pro. ex. 363-2
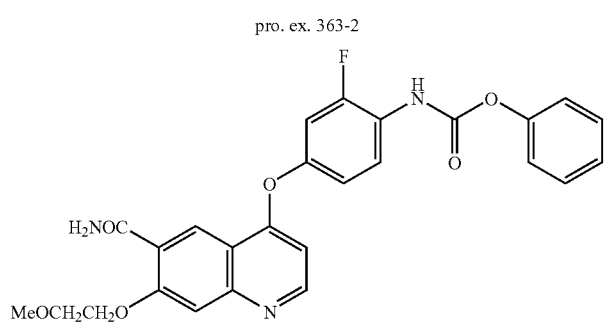
pro. ex. 366-1
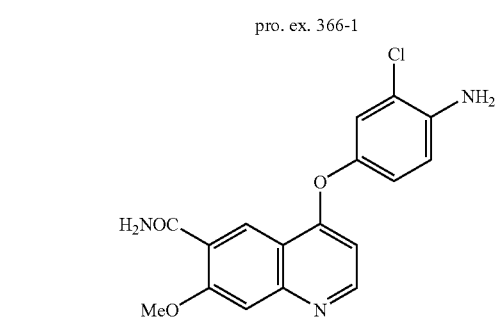
pro. ex. 368-1
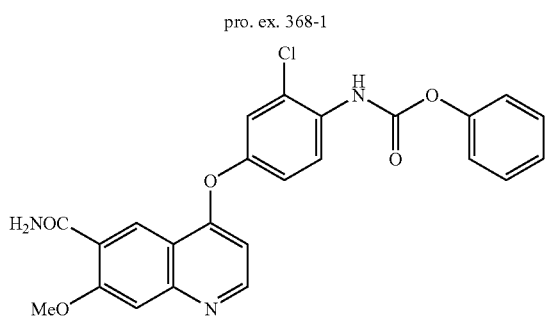

TABLE 12-continued
pro. ex. 370-1
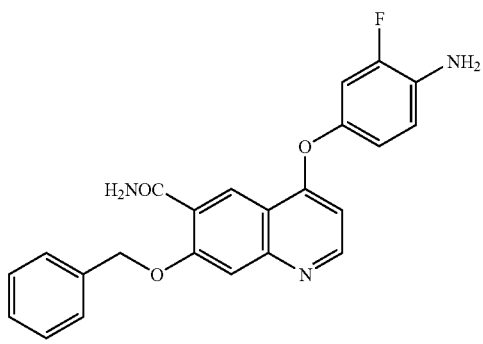
pro. ex. 370-2
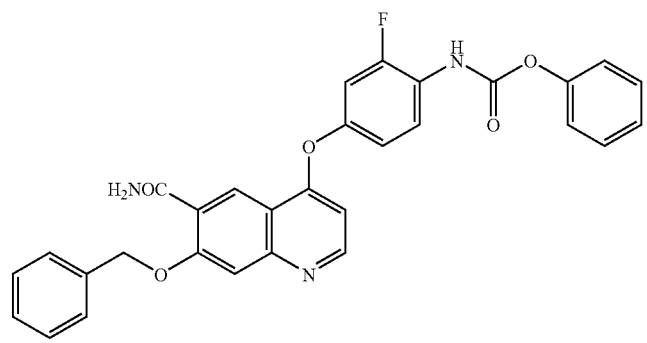
TABLE 13
pro. ex. 379-1
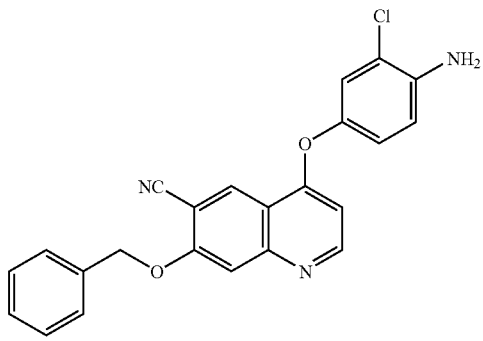
pro. ex. 379-2
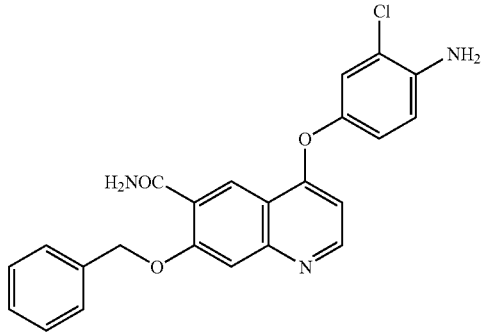

TABLE 13-continued
pro. ex. 379-3
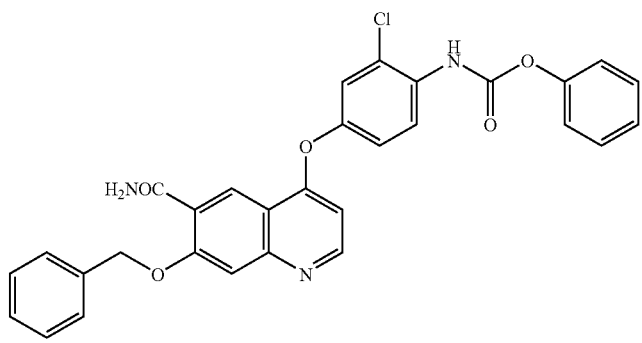
pro. ex. 395-1
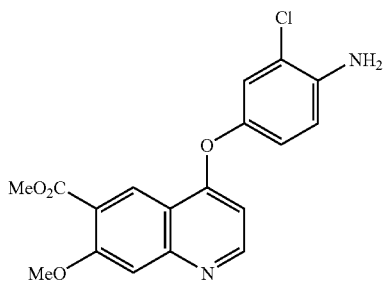
pro. ex. 395-2
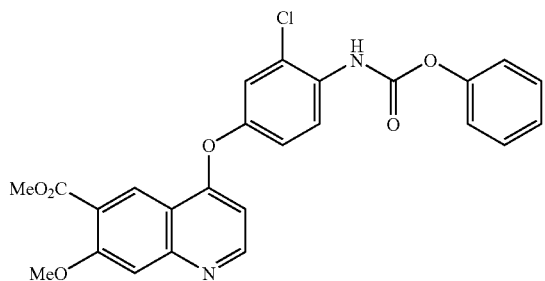
pro. ex. 425-1
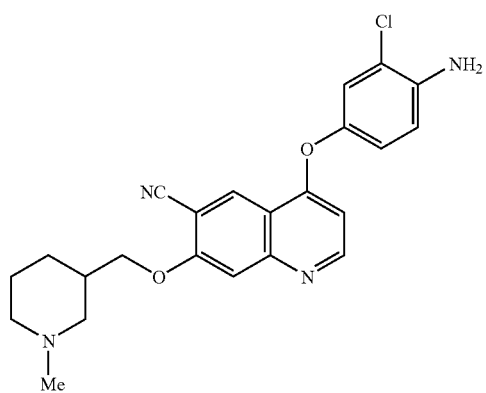

TABLE 13-continued
pro. ex. 426-1
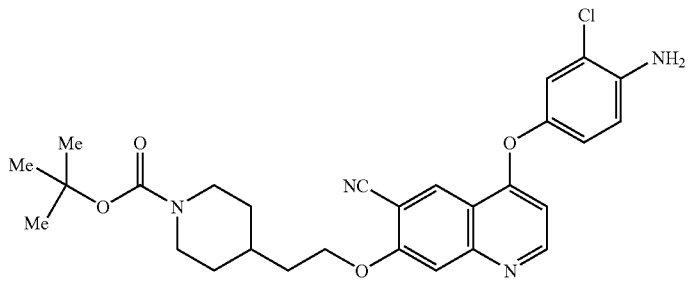
pro. ex. 429-1
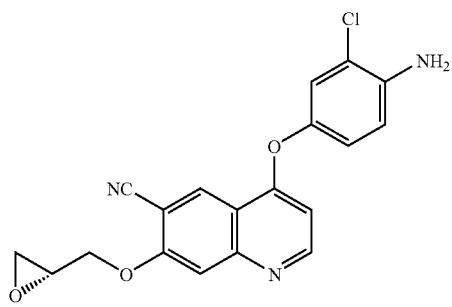
pro. ex. 429-2
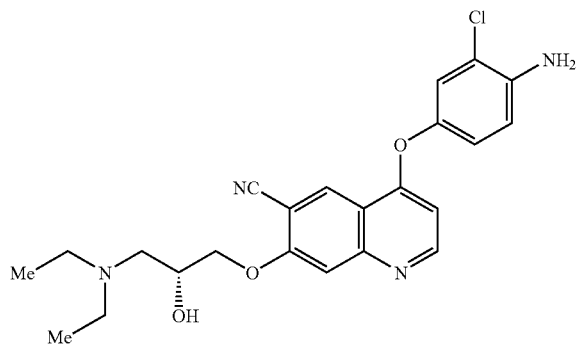
pro. ex. 430-1
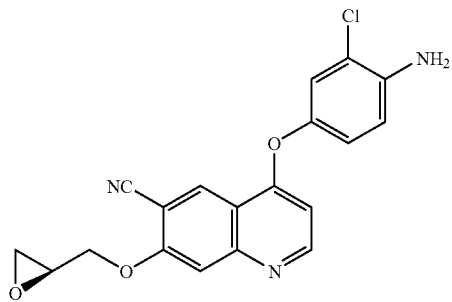

TABLE 13-continued
pro. ex. 430-2
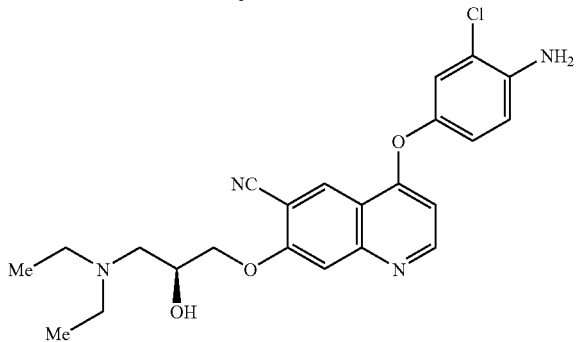
pro. ex. 431-1
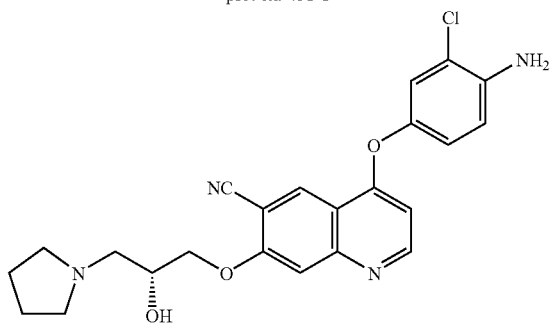
pro. ex. 432-1
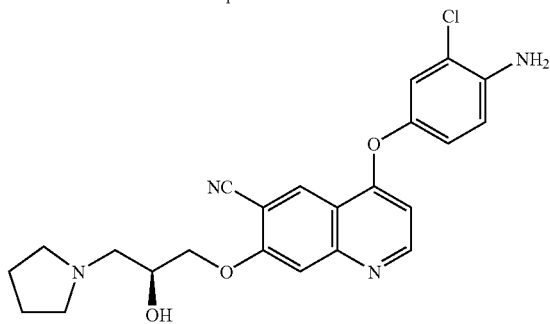
pro. ex. 433-1
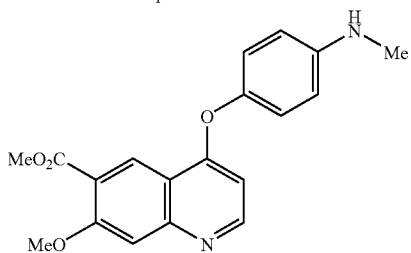
pro. ex. 457-1
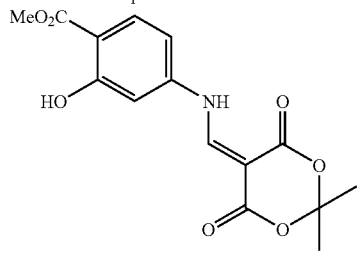

TABLE 13-continued
pro. ex. 457-2
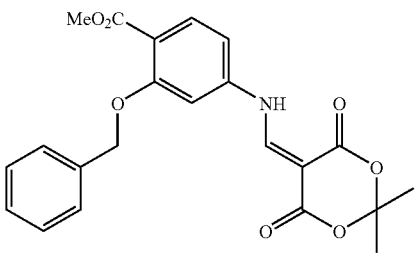
pro. ex. 457-3
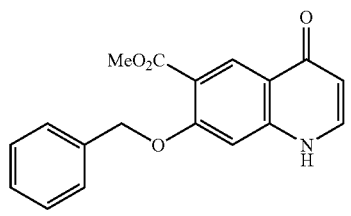
pro. ex. 457-4
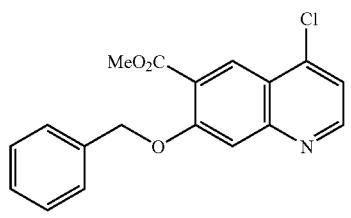
pro. ex. 457-5
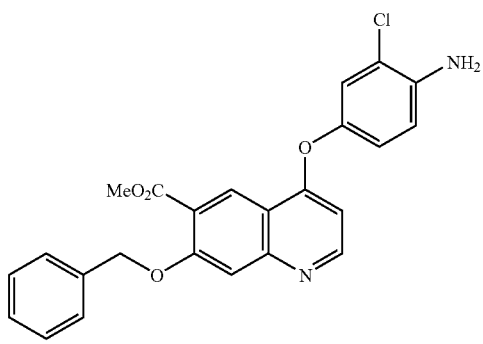
pro. ex. 458-1
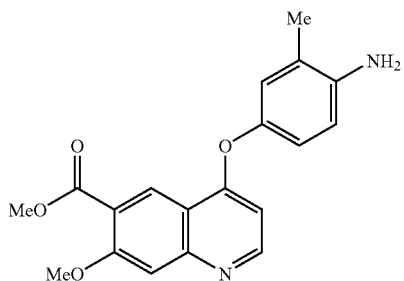

TABLE 13-continued
pro. ex. 458-2
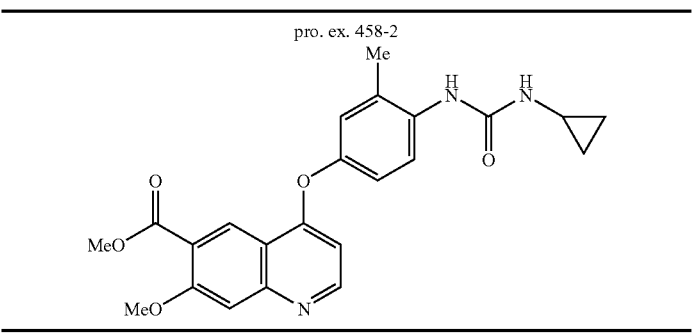
TABLE 14
pro. ex. 458-3
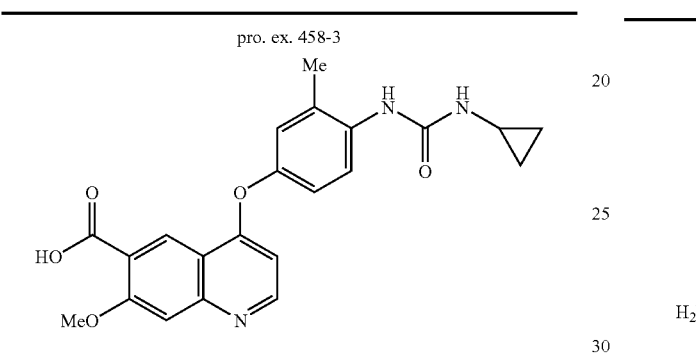
pro. ex. 461-1
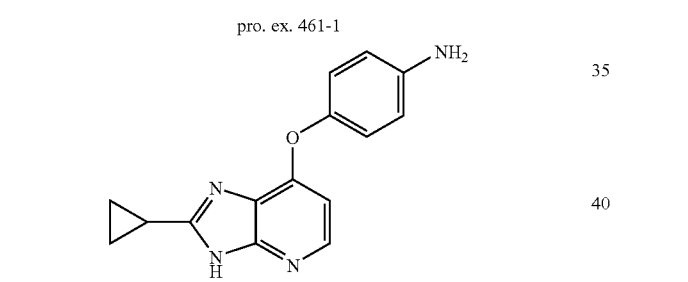
pro. ex. 462-1
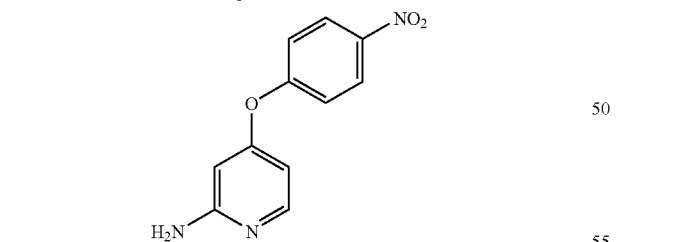
pro. ex. 462-2
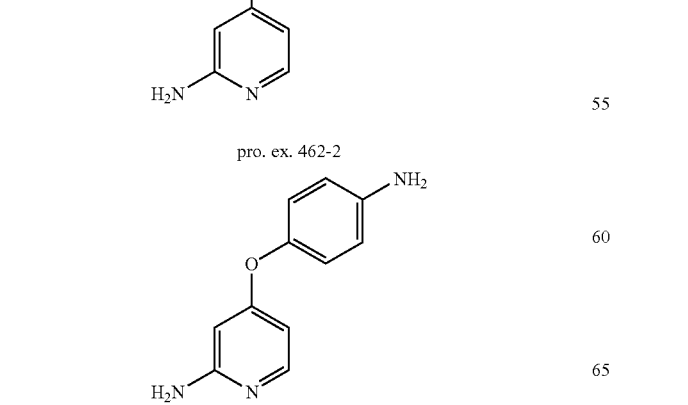
TABLE 14-continued
pro. ex. 462-3
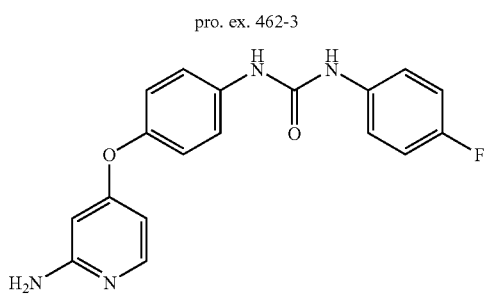
pro. ex. 467-1
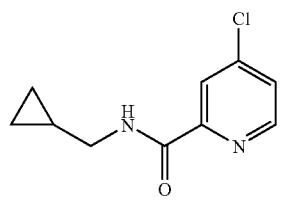
pro. ex. 467-2
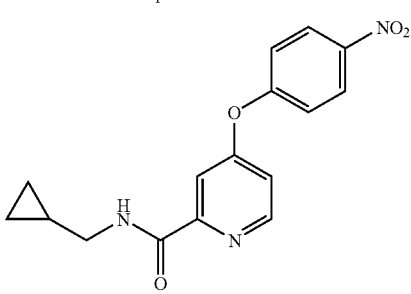
pro. ex. 467-3
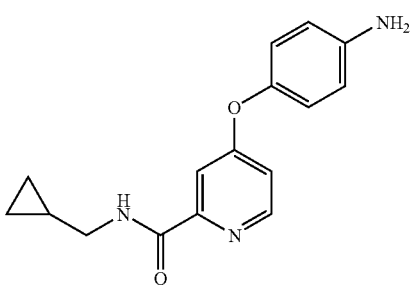

TABLE 14-continued
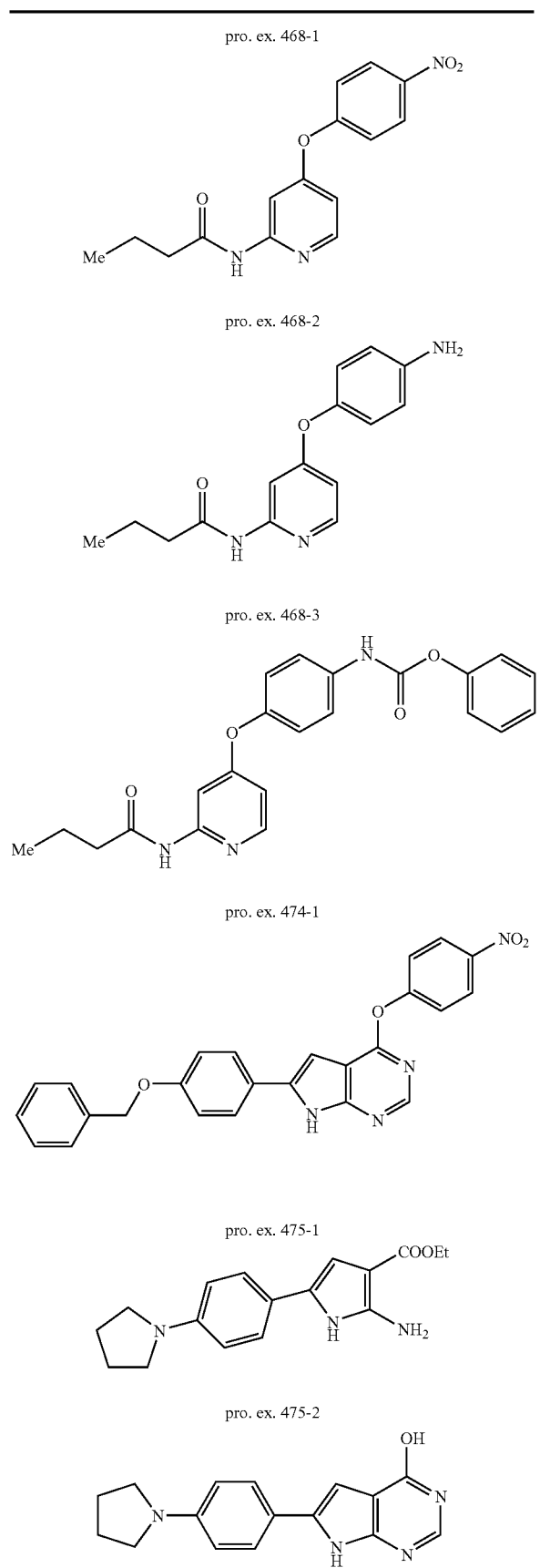
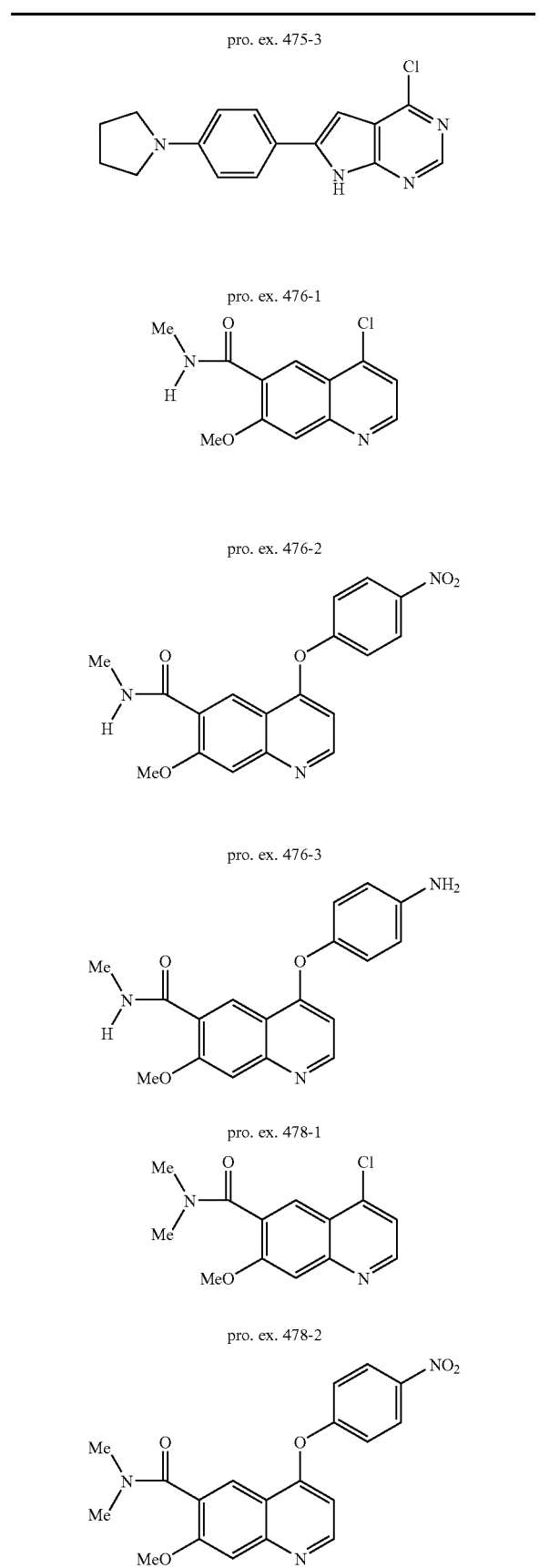

TABLE 14-continued
pro. ex. 478-3
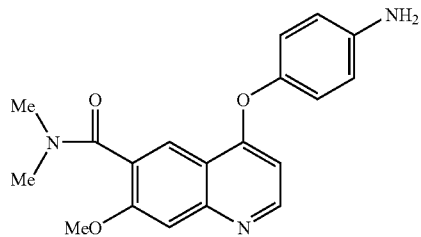
pro. ex. 482-1
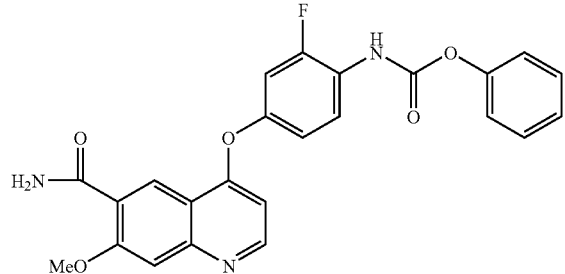
TABLE 14-continued
pro. ex. 484-1
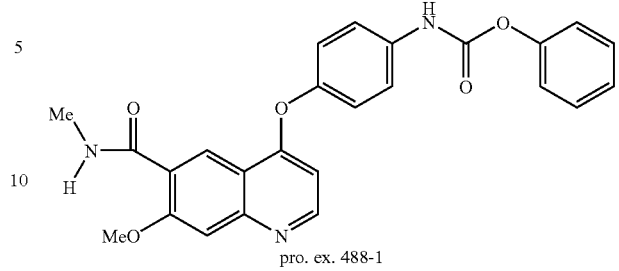
pro. ex. 488-1
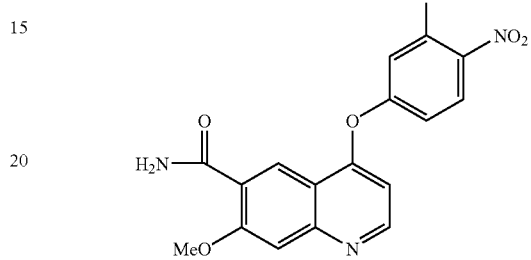
TABLE 15
pro. ex. 488-2
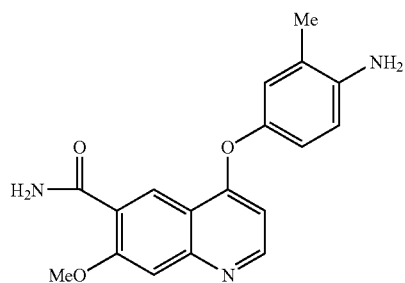
pro. ex. 488-3
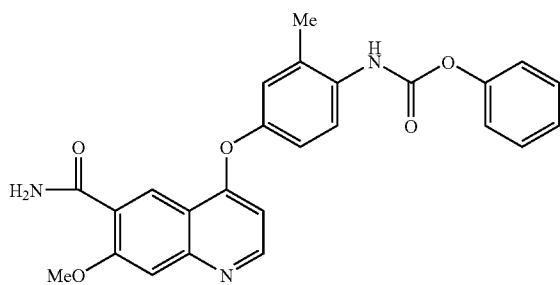
pro. ex. 489-1
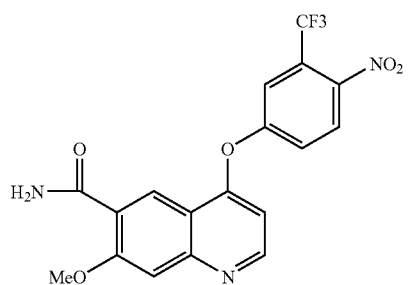

TABLE 15-continued
pro. ex. 489-2
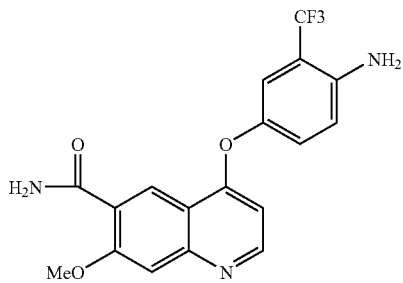
pro. ex. 489-3
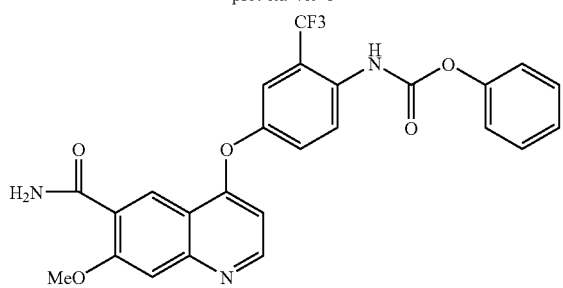
pro. ex. 490-1
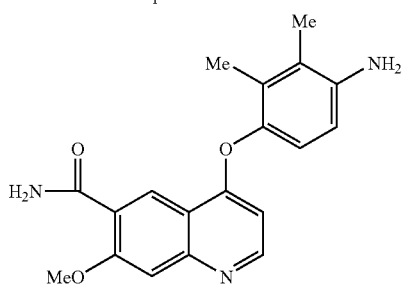
pro. ex. 490-2
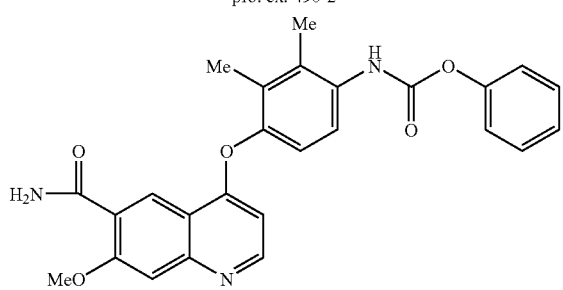
pro. ex. 491-1
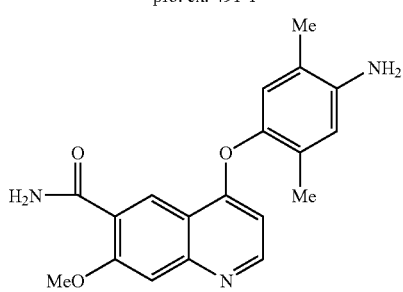

TABLE 15-continued
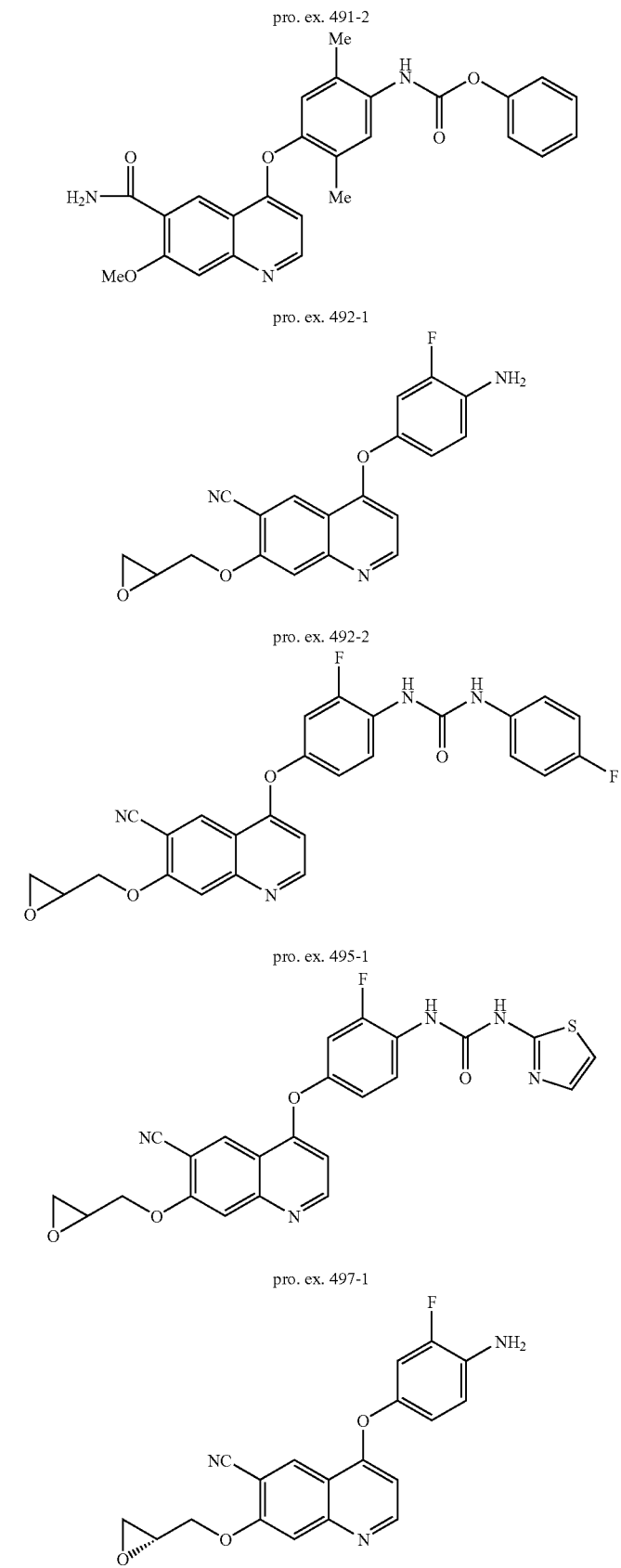

TABLE 15-continued
pro. ex. 497-2
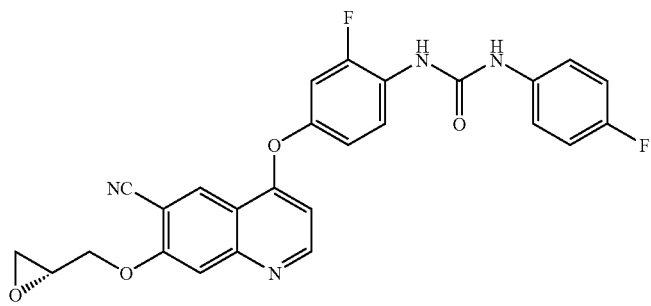
pro. ex. 500-1
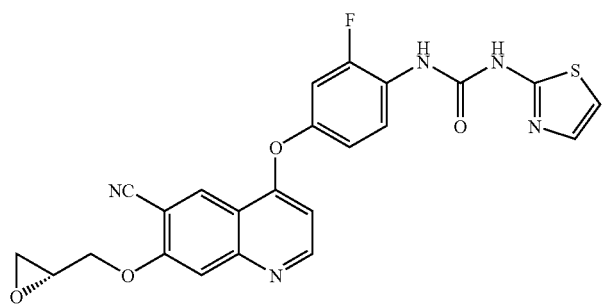
pro. ex. 501-1
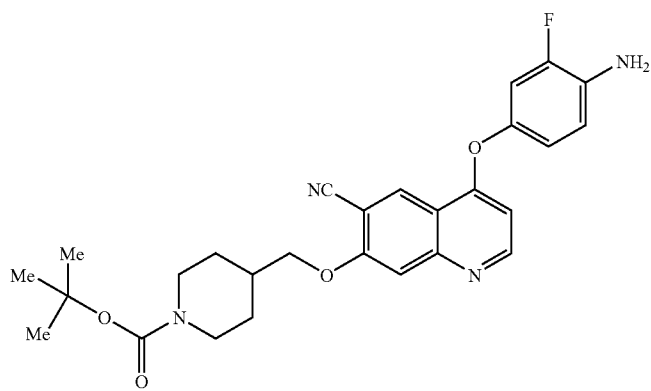
pro. ex. 501-2
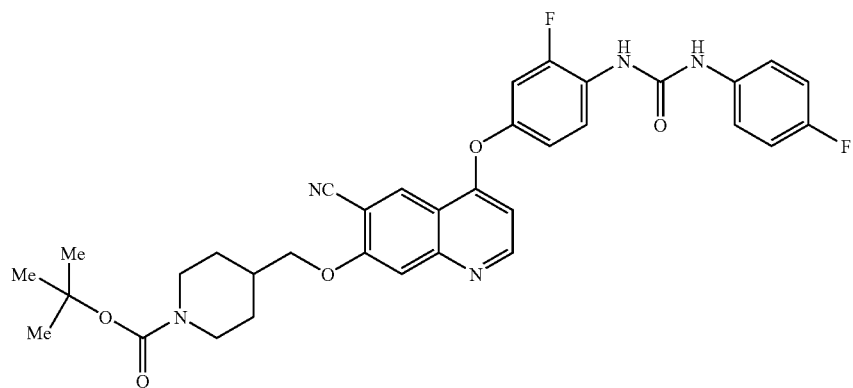

TABLE 15-continued
pro. ex. 503-1
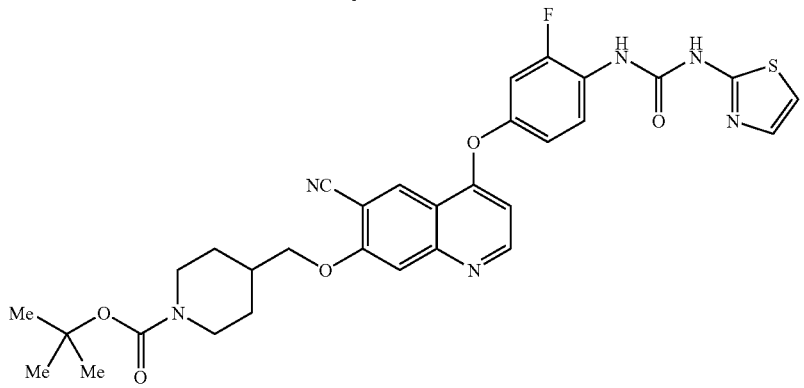
pro. ex. 505-1
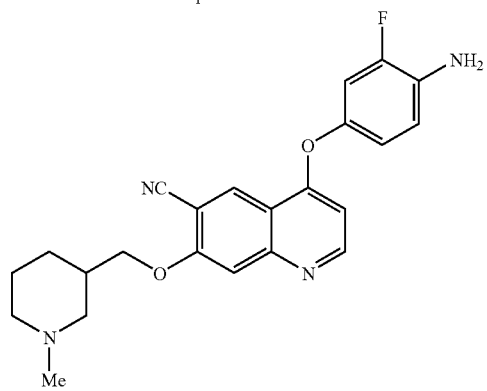
pro. ex. 506-1
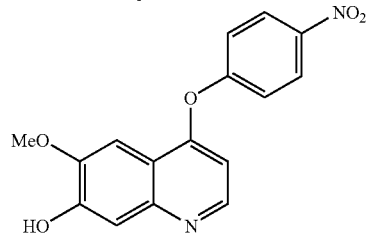
pro. ex. 506-2
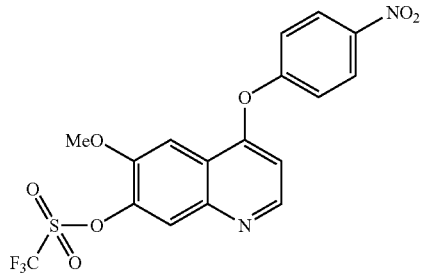
pro. ex. 506-3
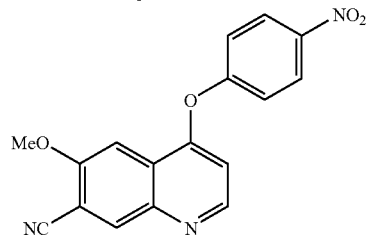

TABLE 15-continued
pro. ex. 506-4
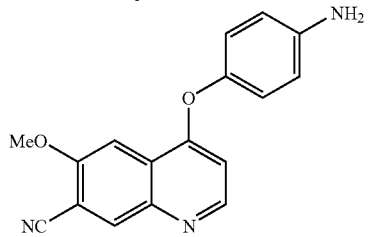
TABLE 16
pro. ex. 510-1
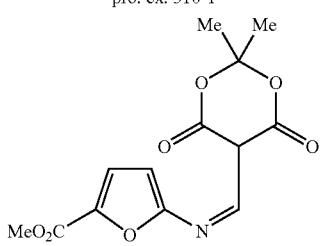
pro. ex. 510-2
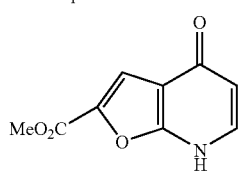
pro. ex. 510-22
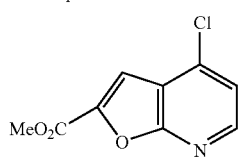
pro. ex. 510-3
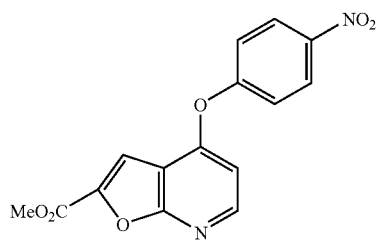
pro. ex. 510-4
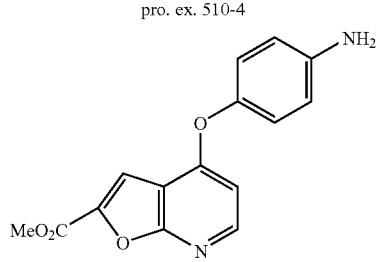
TABLE 16-continued
pro. ex. 512-1
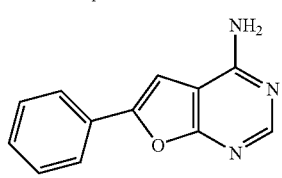
pro. ex. 512-2
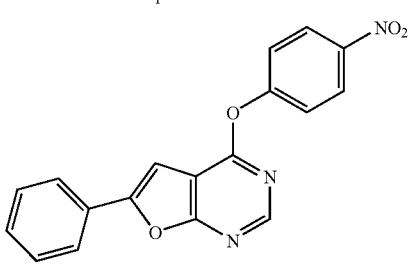
pro. ex. 512-3
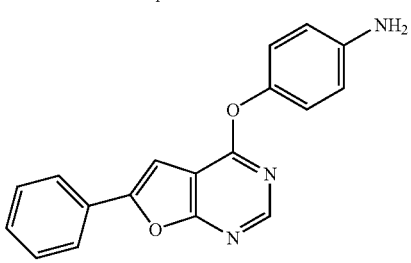
pro. ex. 513-1
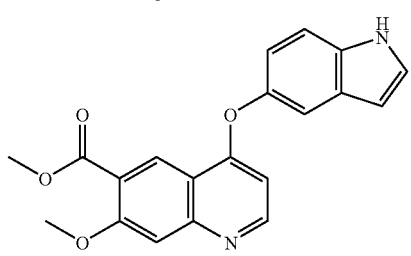

TABLE 16-continued
pro. ex. 530-1
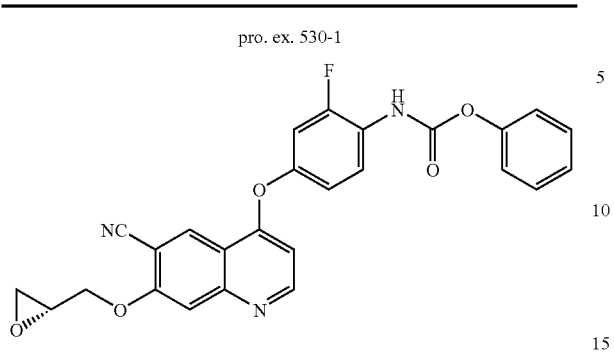
pro. ex. 530-2
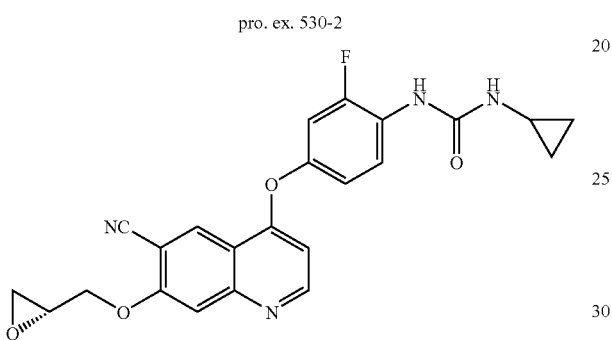
pro. ex. 532-1
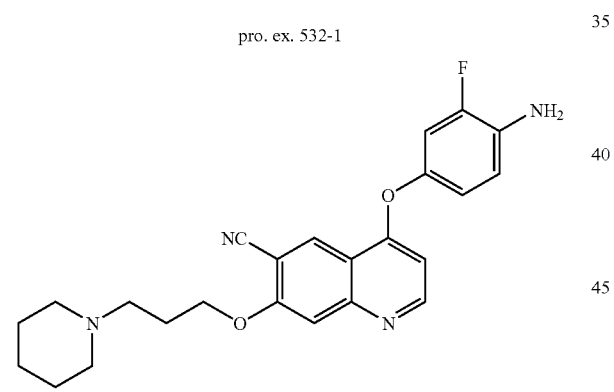
pro. ex. 533-1
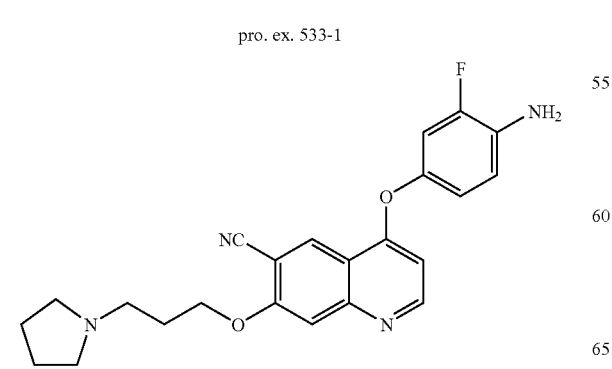
TABLE 16-continued
pro. ex. 534-1
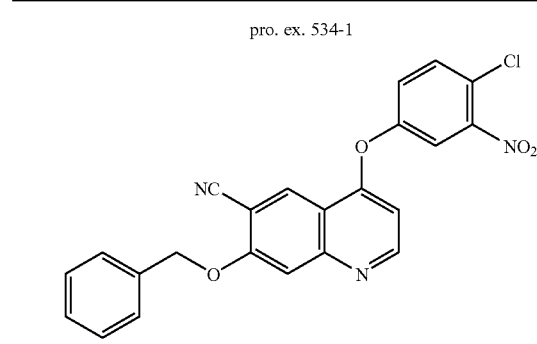
pro. ex. 534-2
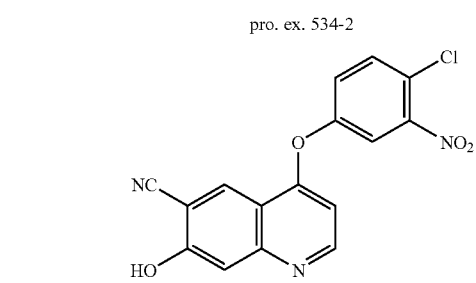
pro. ex. 534-3
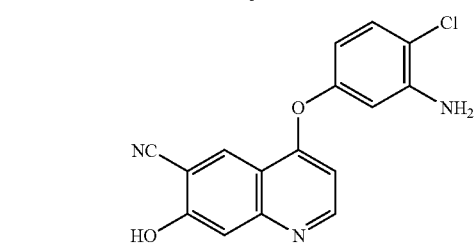
pro. ex. 534-4
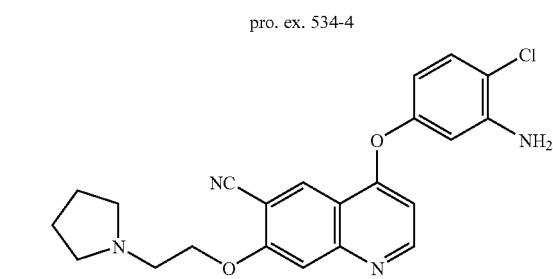
pro. ex. 537-1
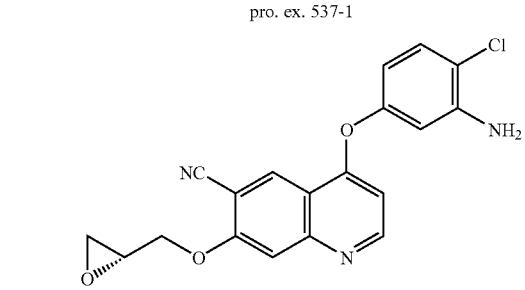

TABLE 16-continued
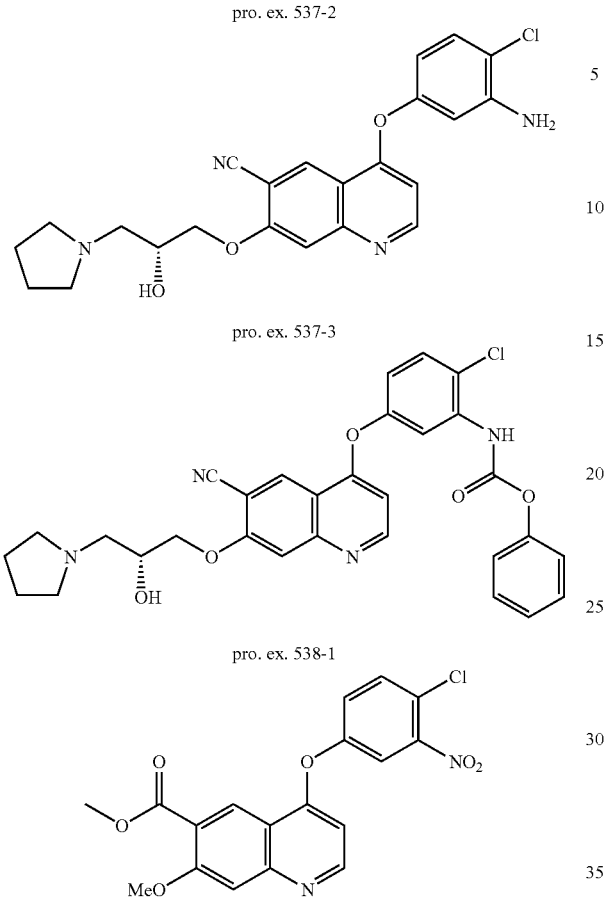
TABLE 16-continued
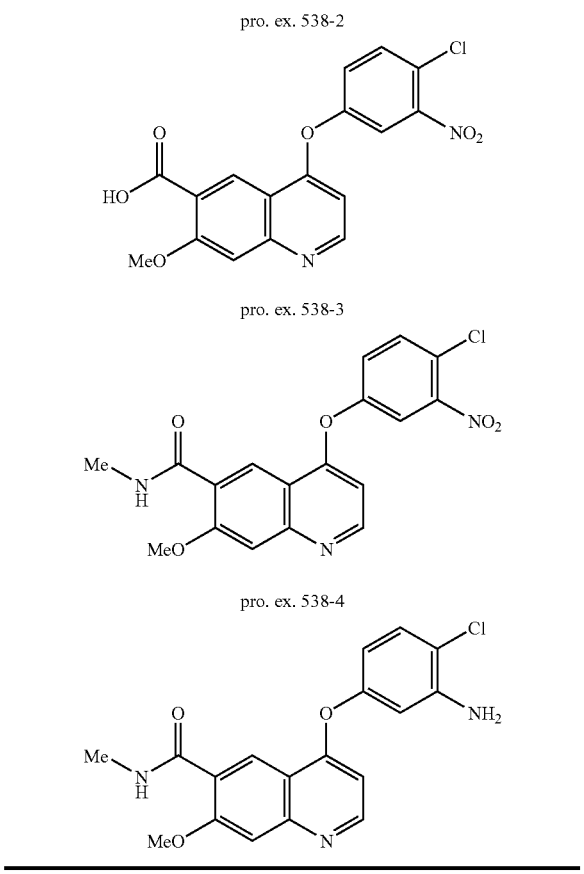
TABLE 17
pro. ex. 551-1
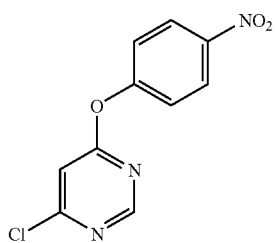
pro. ex. 551-2
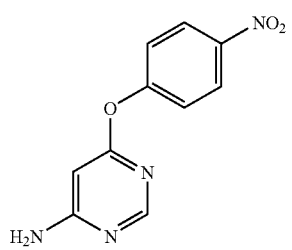

TABLE 17-continued
pro. ex. 551-3
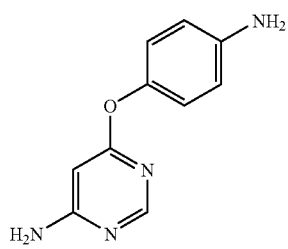
pro. ex. 557-1
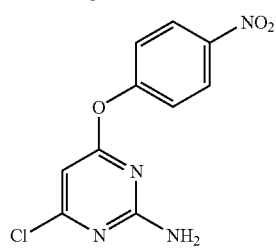
pro. ex. 557-2
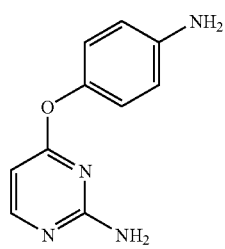
pro. ex. 561-1
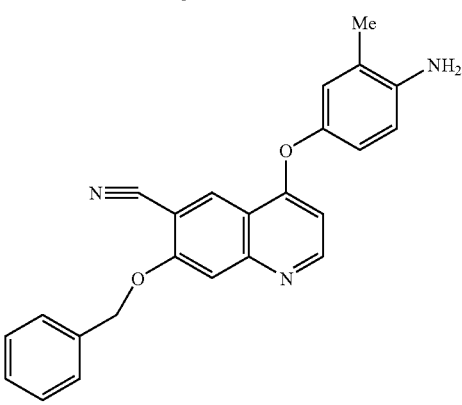
pro. ex. 568-1
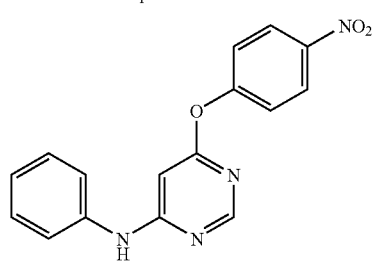

TABLE 17-continued
pro. ex. 568-2
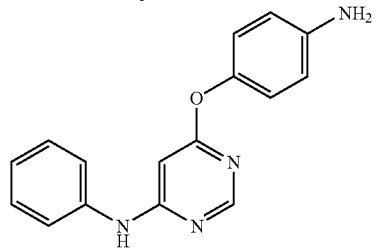
pro. ex. 574-1
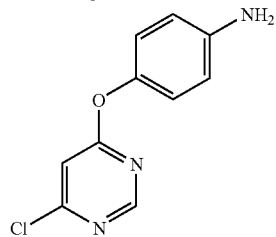
pro. ex. 574-2
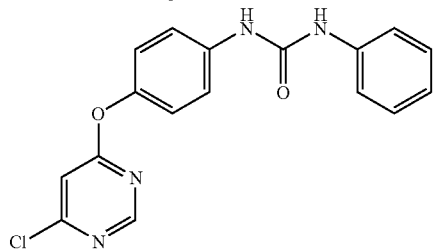
pro. ex. 591-1
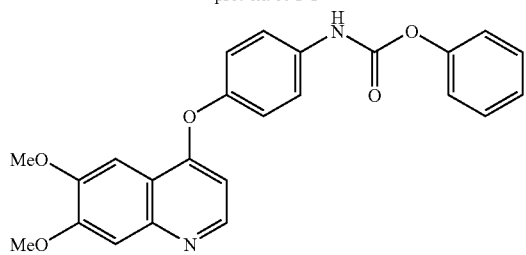
pro. ex. 593-1
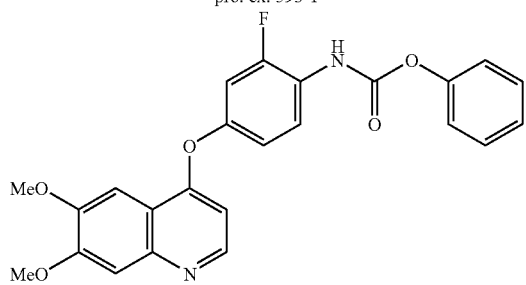
pro. ex. 616-1
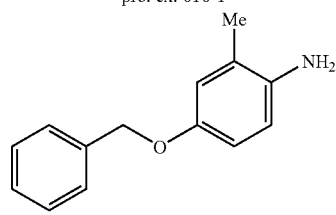

TABLE 17-continued
pro. ex. 616-2
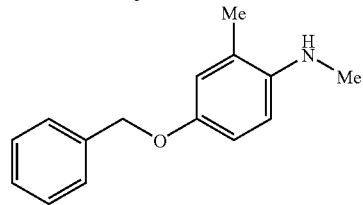
pro. ex. 616-3
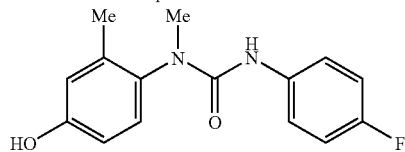
pro. ex. 618-1
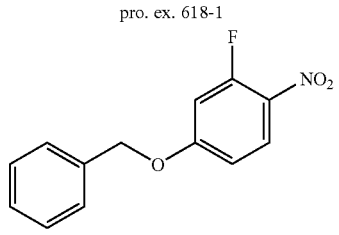
pro. ex. 618-2
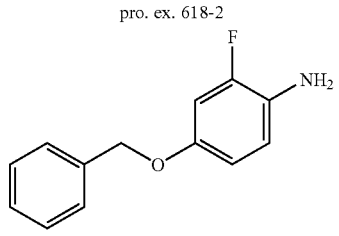
pro. ex. 618-3
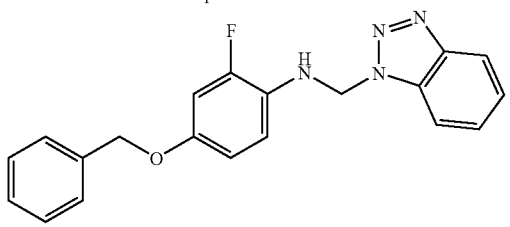
pro. ex. 618-4
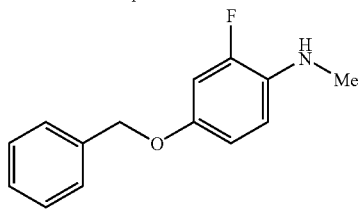
pro. ex. 618-5
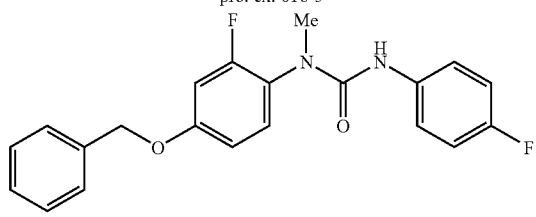

TABLE 17-continued
pro. ex. 618-6
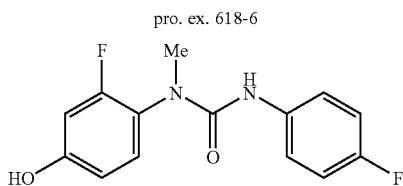
pro. ex. 625-1
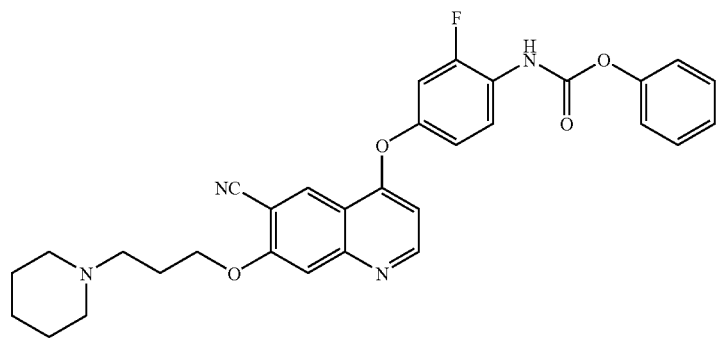
pro. ex. 626-1
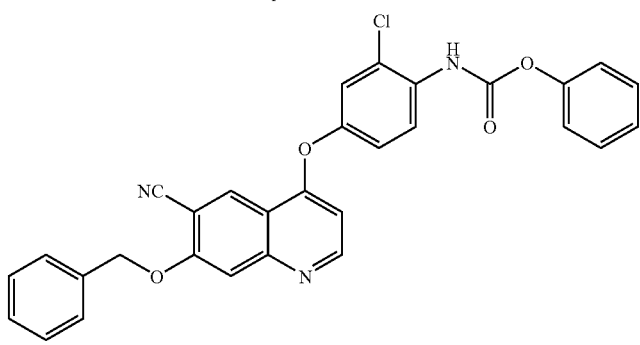
pro. ex. 645-1
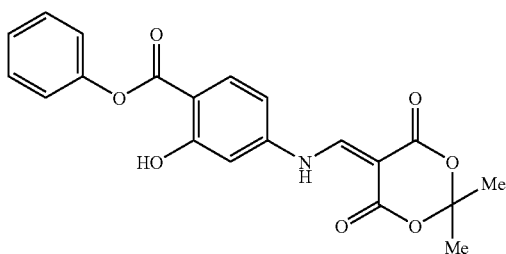
TABLE 18
pro. ex. 645-2
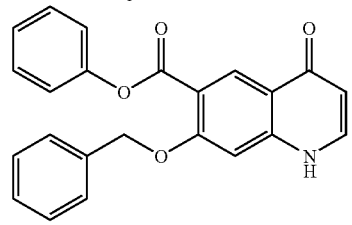

TABLE 18-continued
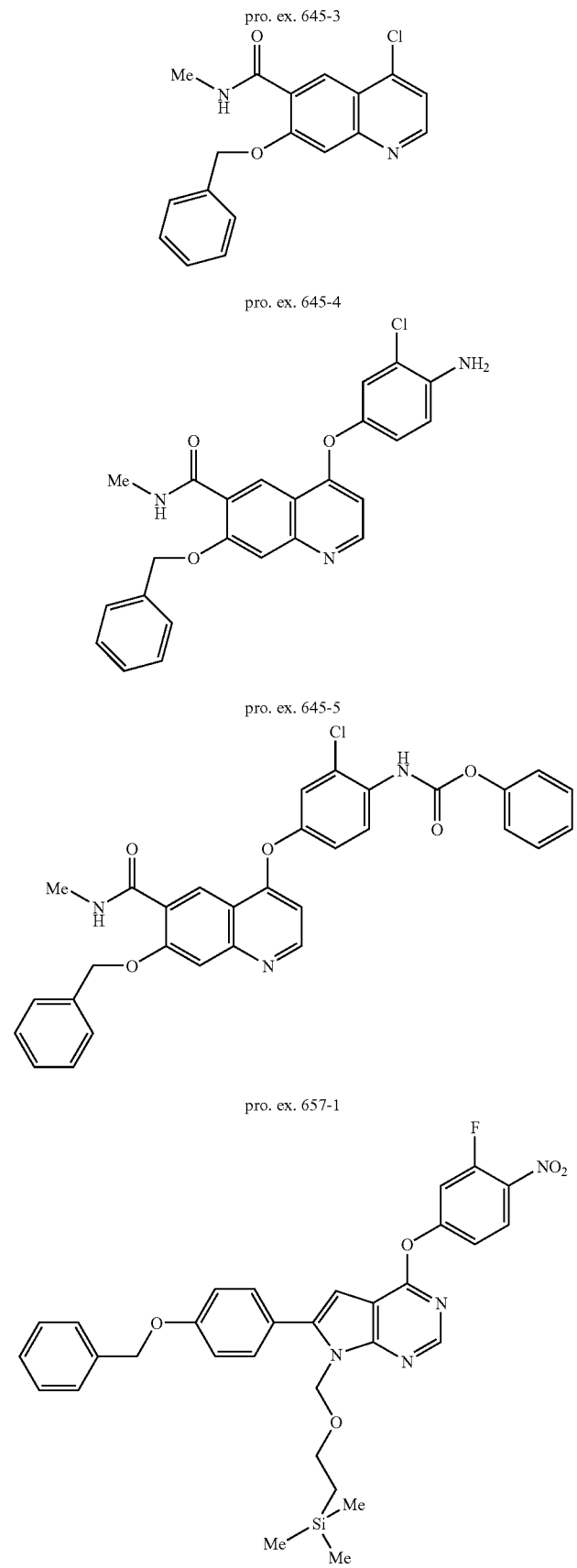

TABLE 18-continued
pro. ex. 657-2
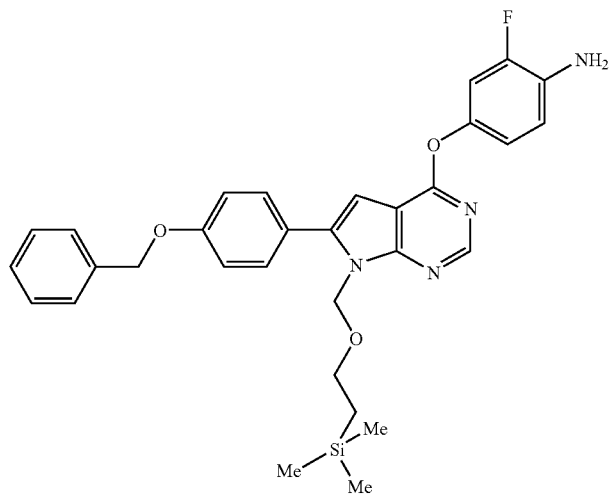
pro. ex. 657-3
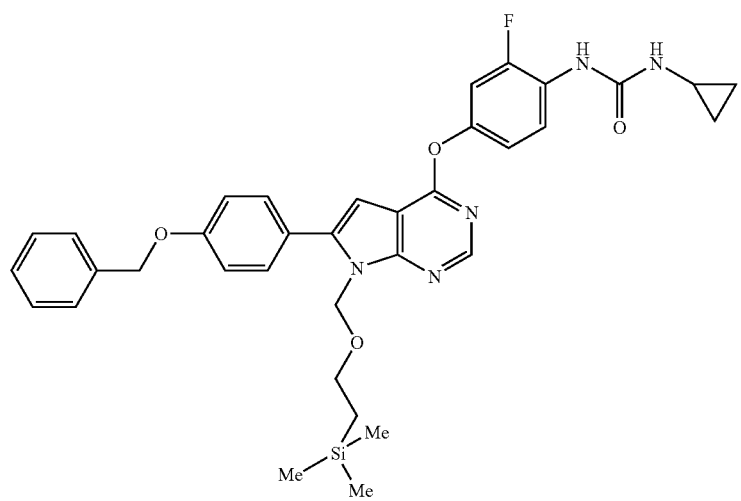
pro. ex. 657-4
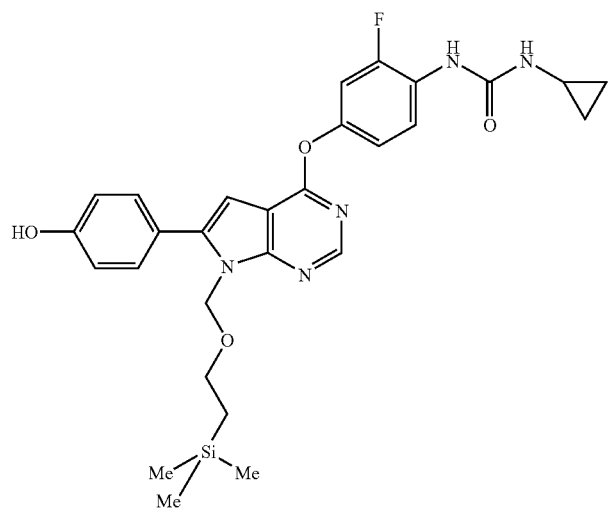

TABLE 18-continued
pro. ex. 657-5
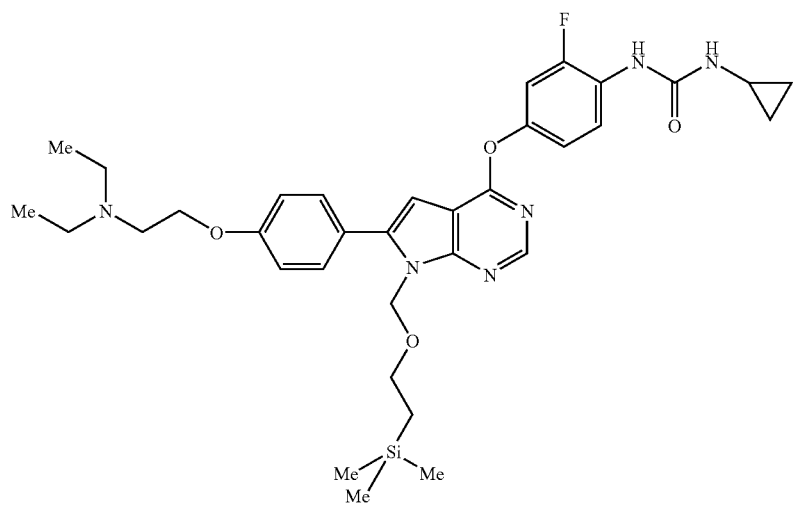
pro. ex. 658-1
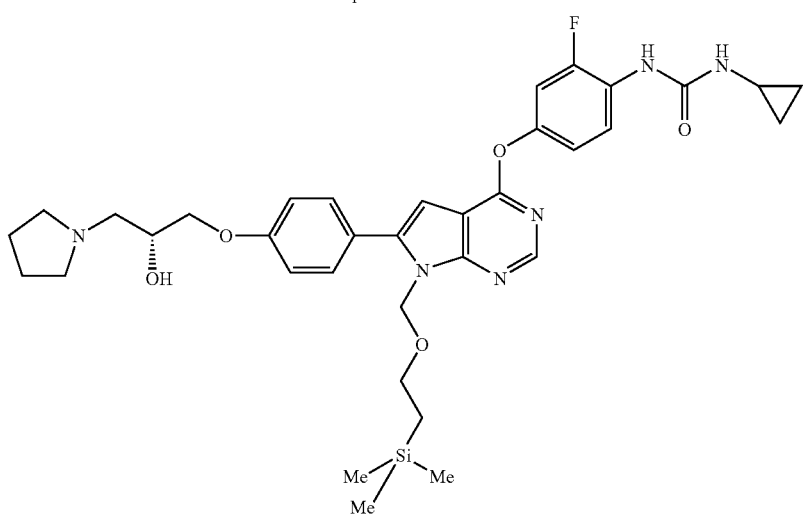
pro. ex. 659-1
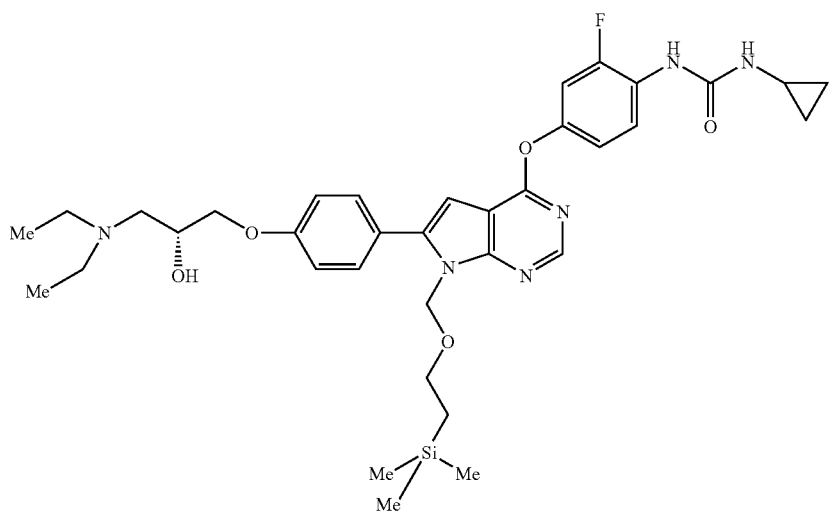

TABLE 18-continued
pro. ex. 670-1-1
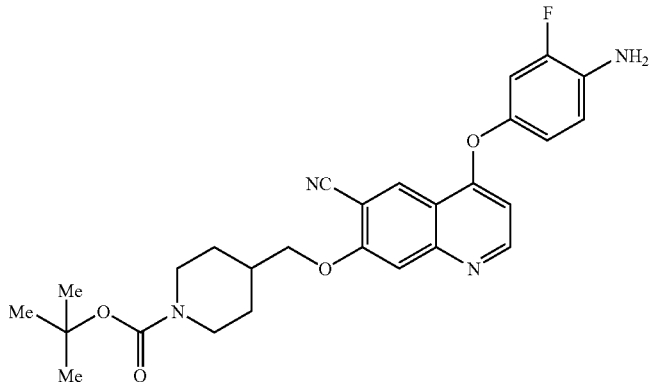
pro. ex. 670-1-2
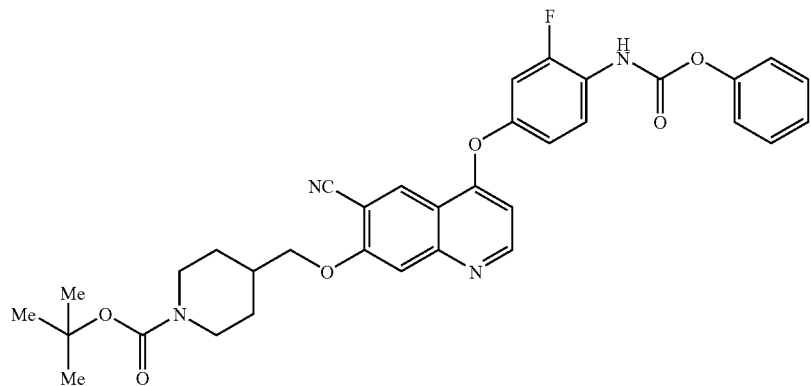
pro. ex. 670-1-3
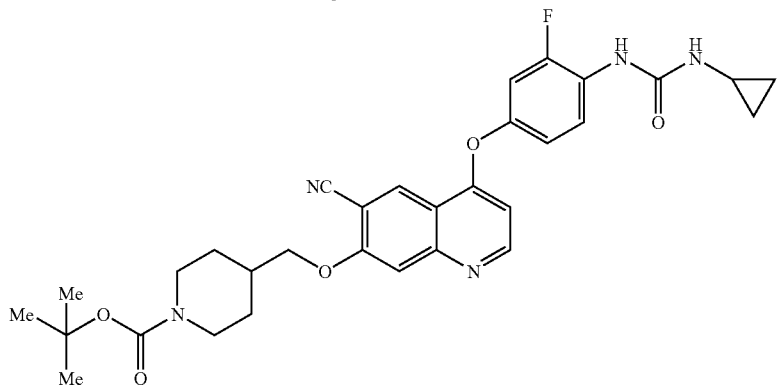
pro. ex. 670-1-4
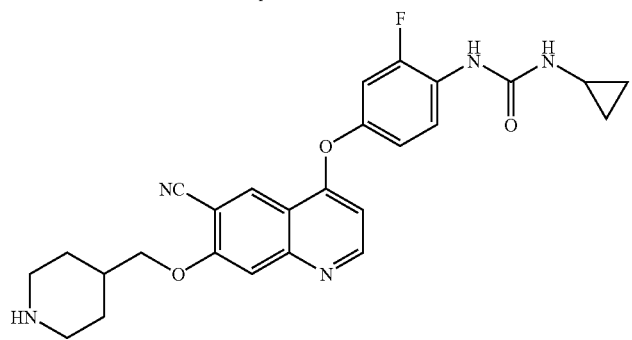

TABLE 18-continued
pro. ex. 671-1
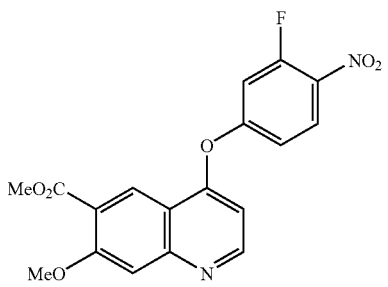
pro. ex. 671-2
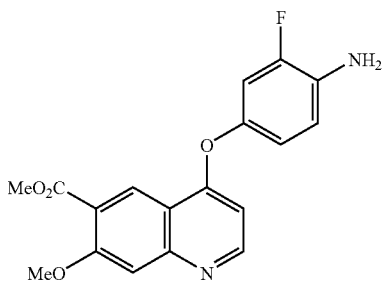
pro. ex. 671-3
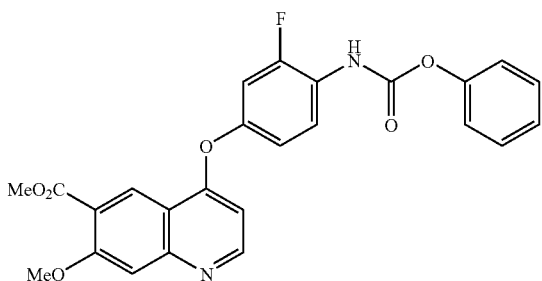
TABLE 19
pro. ex. 713-1
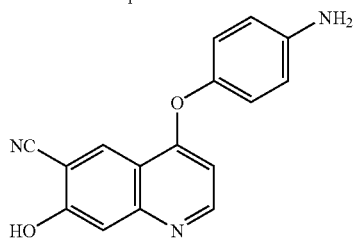
pro. ex. 713-2
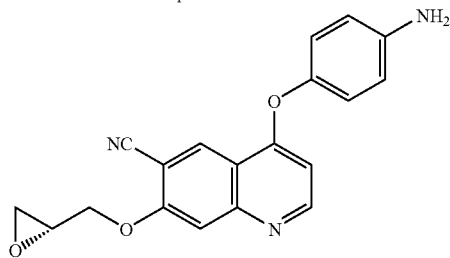

TABLE 19-continued
pro. ex. 713-3
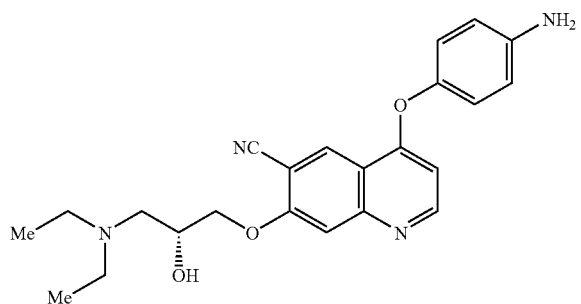
pro. ex. 715-1
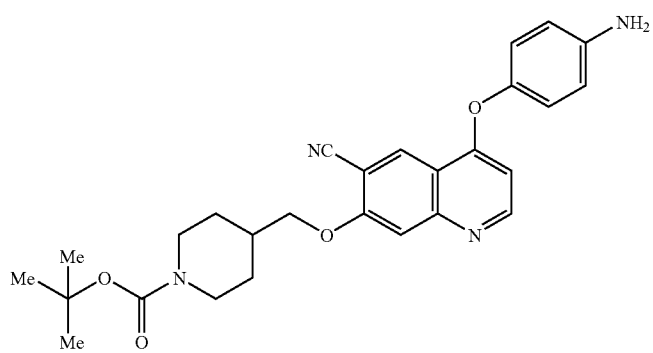
pro. ex. 720-1
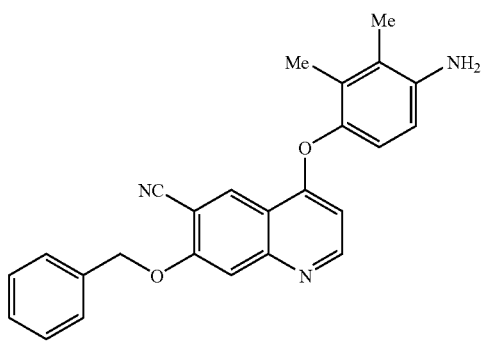
pro. ex. 720-2
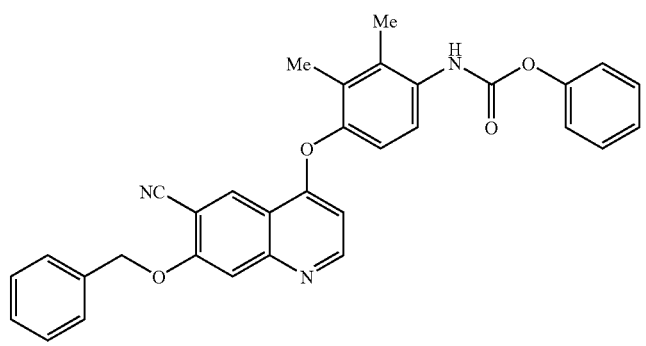

TABLE 19-continued
pro. ex. 723-1
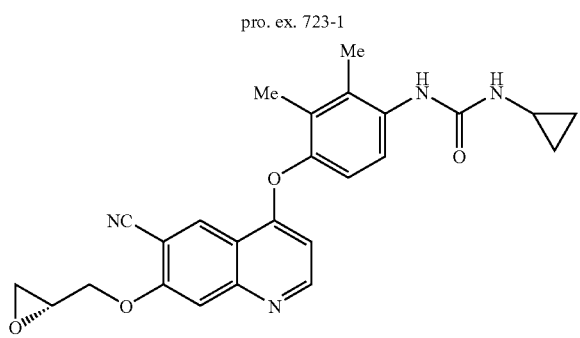
pro. ex. 726-1
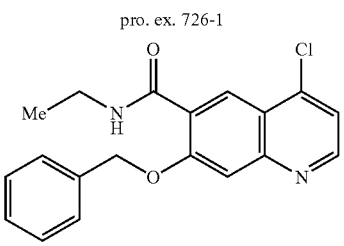
pro. ex. 726-2
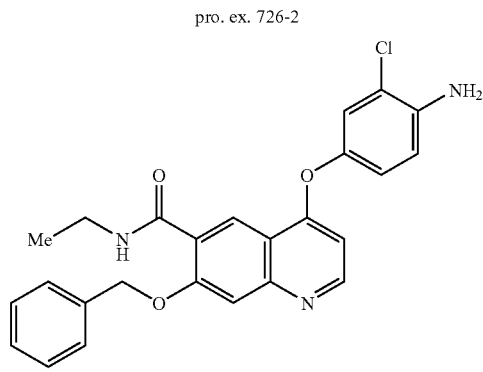
pro. ex. 732-1
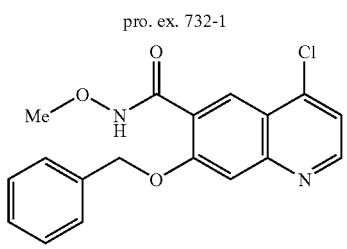
pro. ex. 732-2
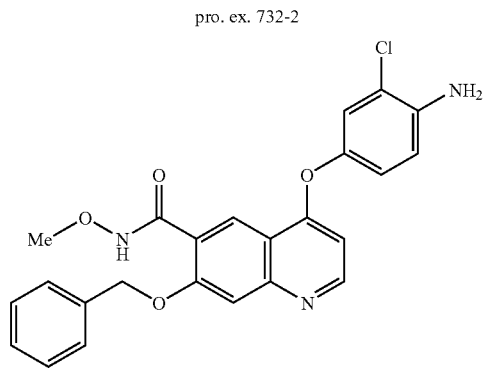

TABLE 19-continued
pro. ex. 737-1
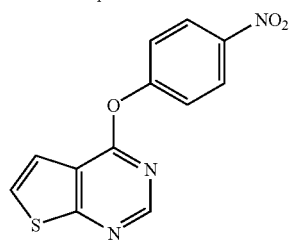
pro. ex. 739-1
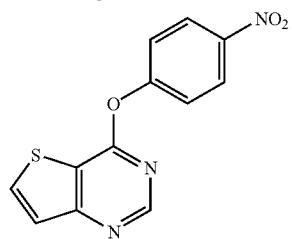
TABLE 20
ex. 1
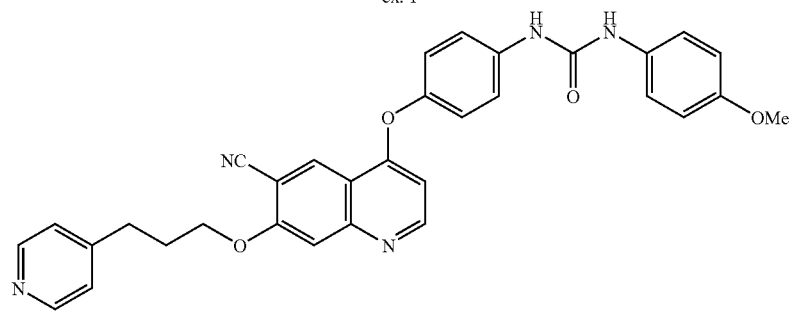
ex. 2
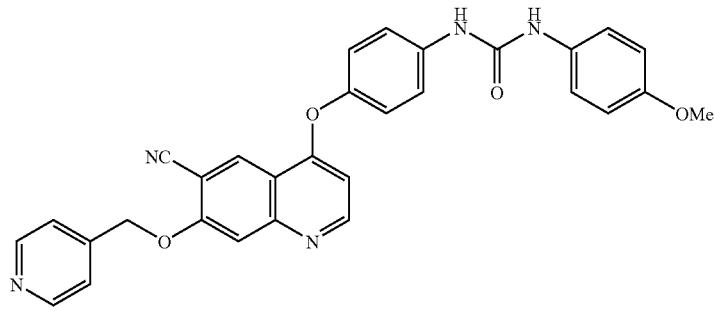
ex. 3
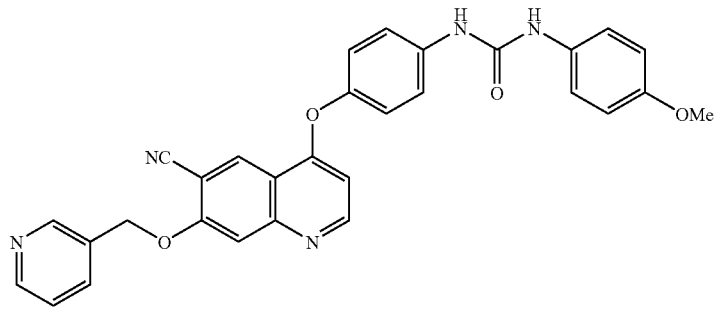

TABLE 20-continued
ex. 4-A
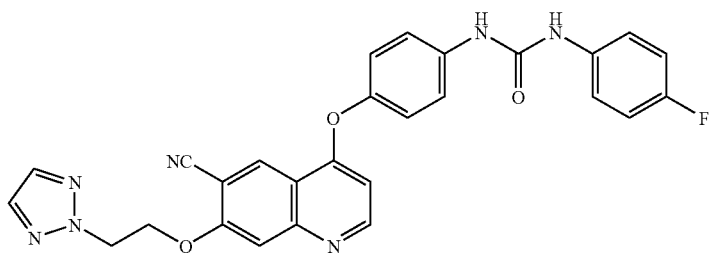
ex. 4-B
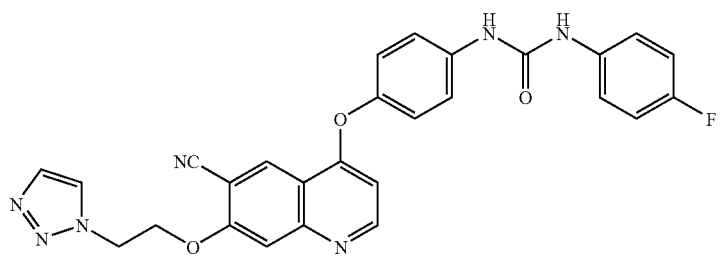
ex. 5-A
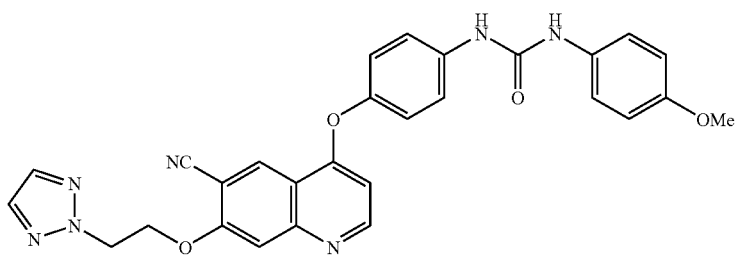
ex. 5-B
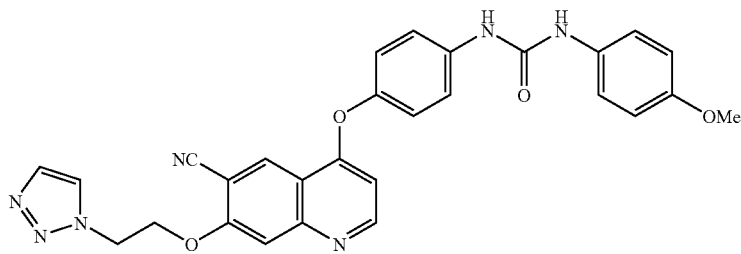
ex. 6-A
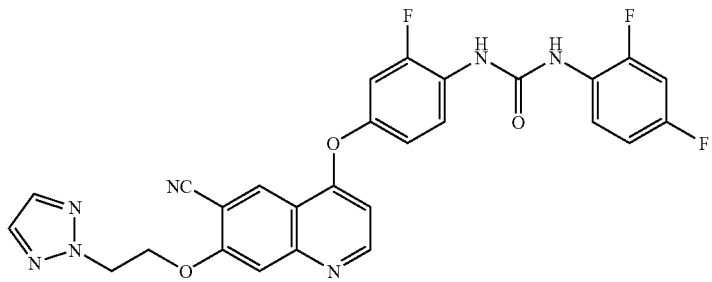

TABLE 20-continued
ex. 6-B
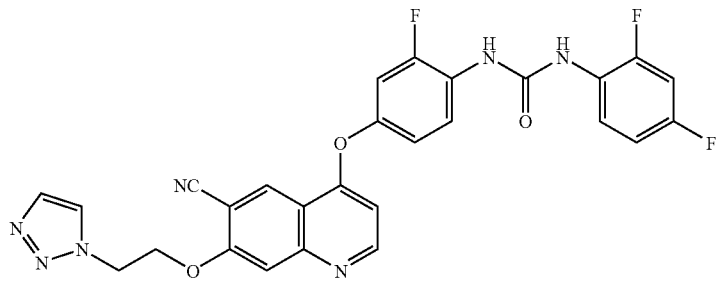
ex. 7
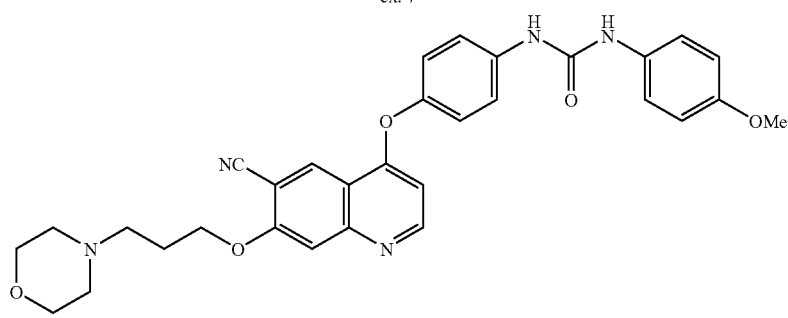
ex. 8
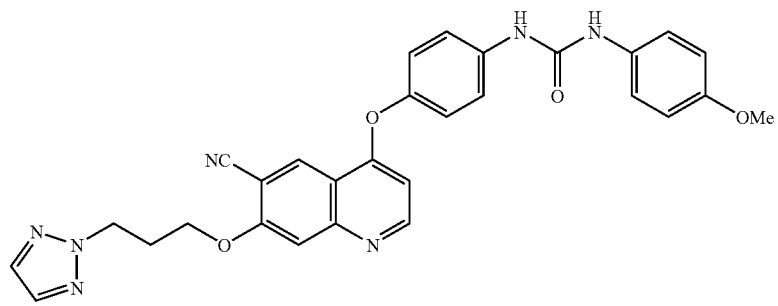
ex. 9
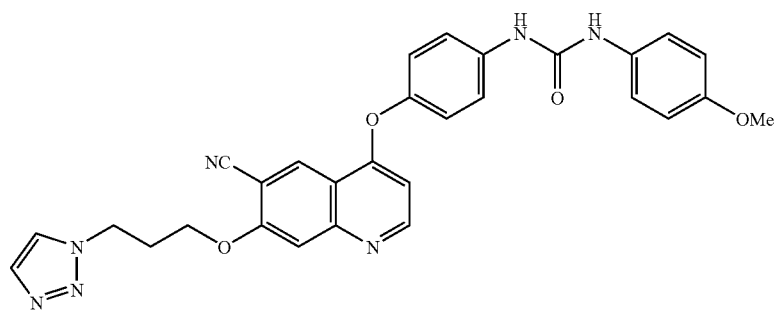
ex. 10
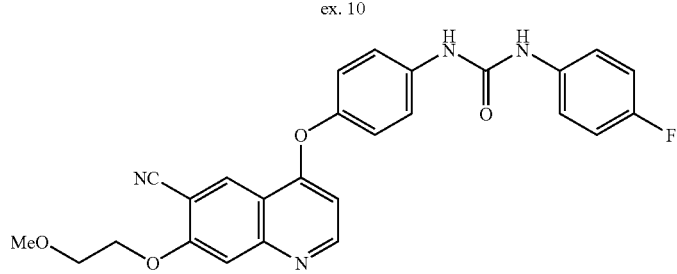

TABLE 20-continued
ex. 11
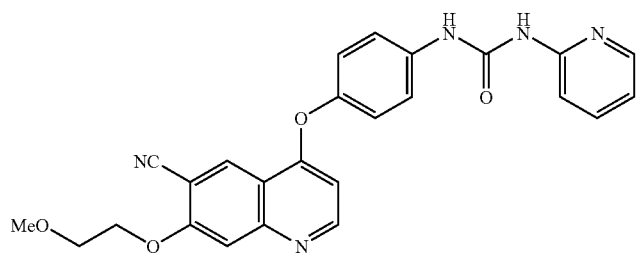
ex. 12
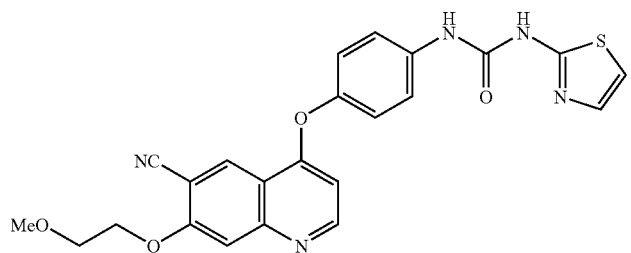
ex. 13
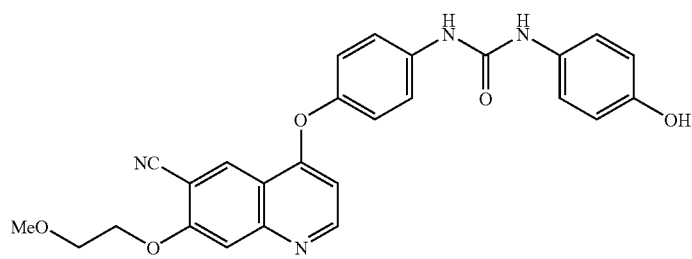
ex. 14
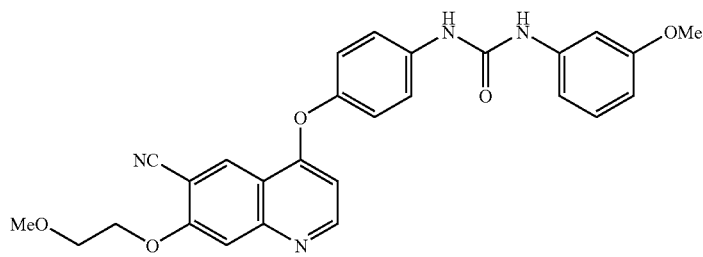
ex. 15
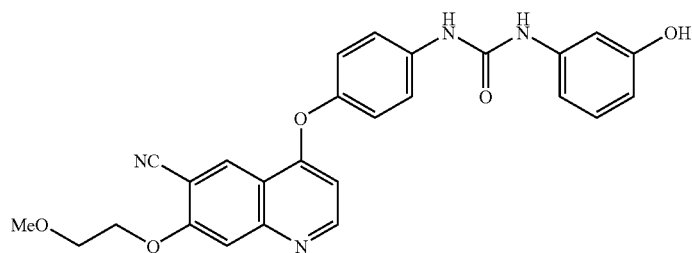

TABLE 20-continued
ex. 16
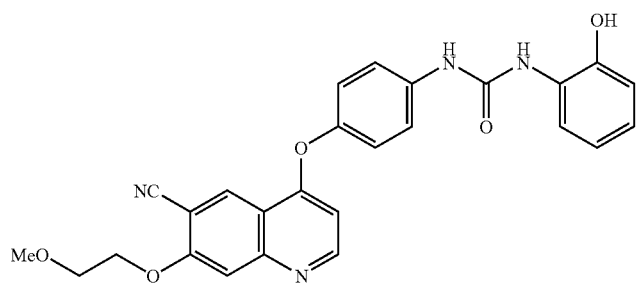
ex. 17
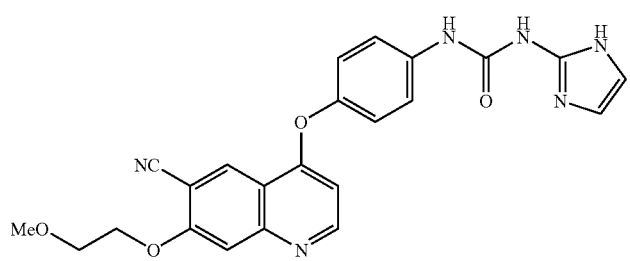
ex. 18
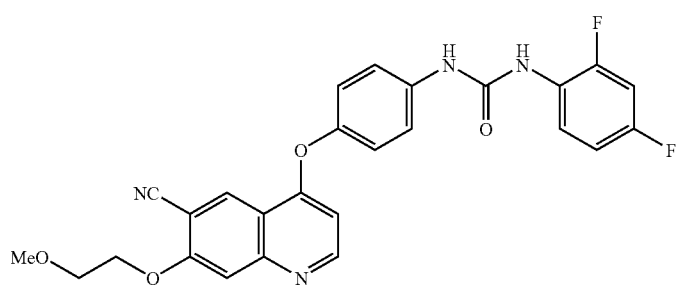
ex. 19
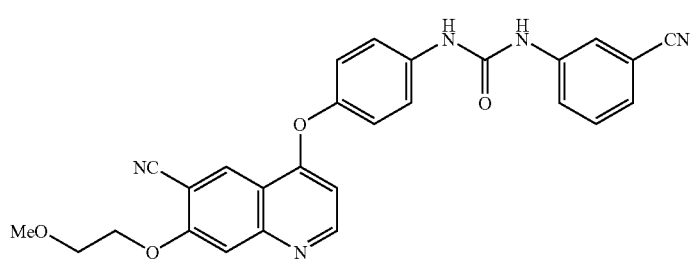
ex. 20
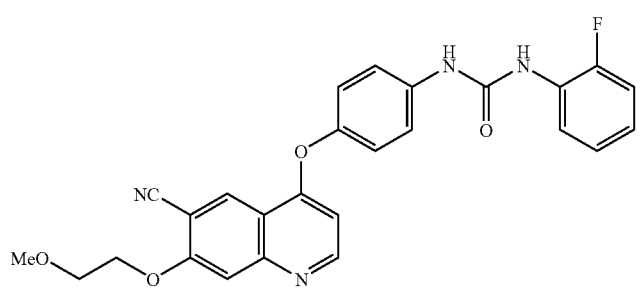

TABLE 20-continued
ex. 21
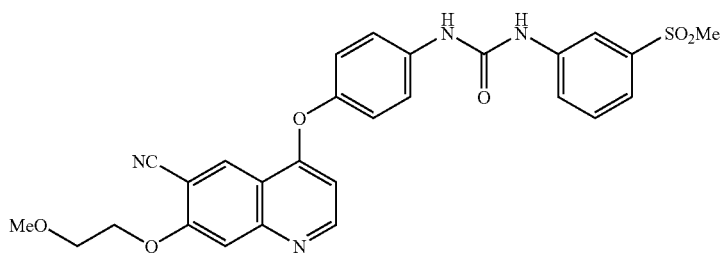
TABLE 21
ex. 22
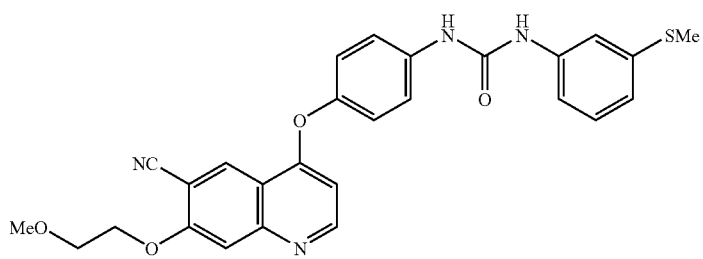
ex. 23
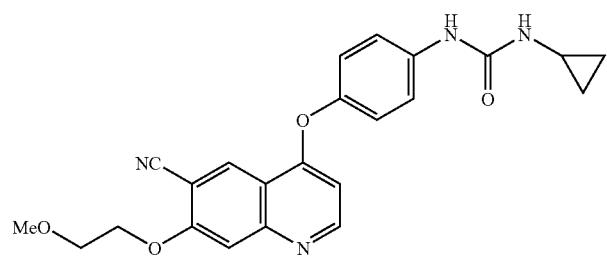
ex. 24
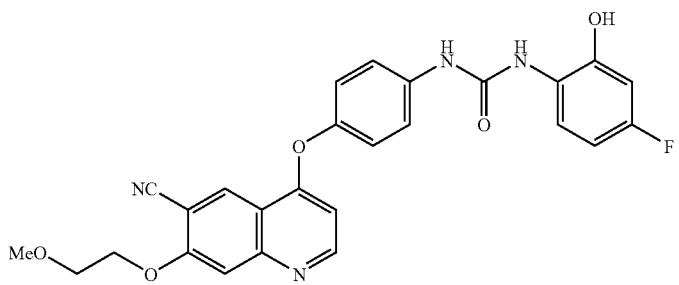
ex. 25
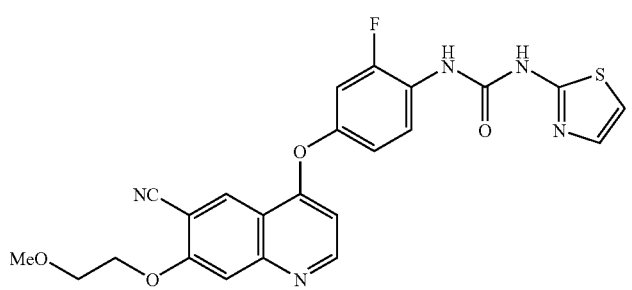

TABLE 21-continued
ex. 26
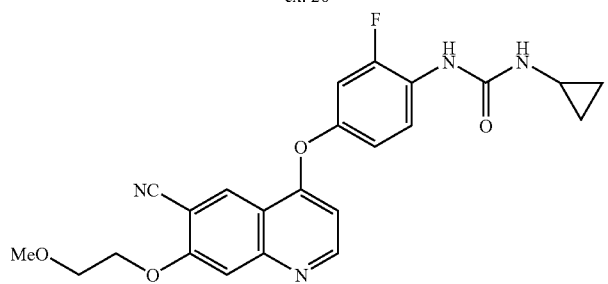
ex. 27
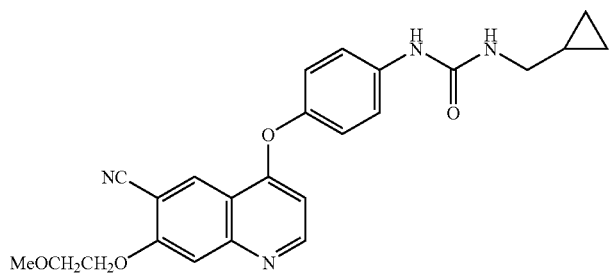
ex. 28
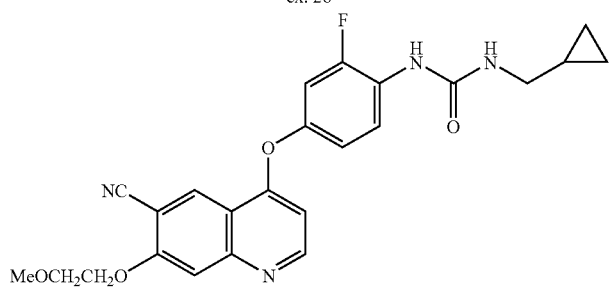
ex. 29
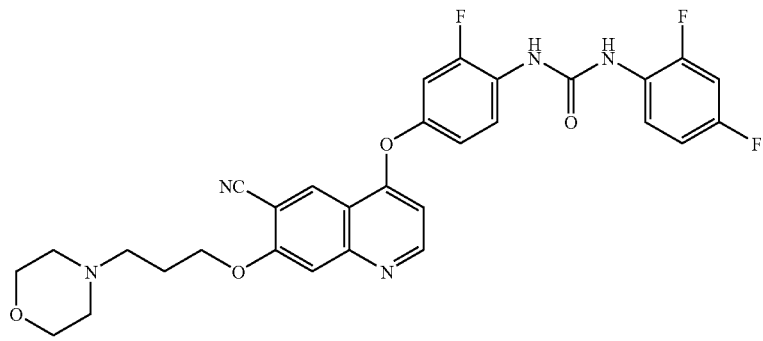
ex. 30
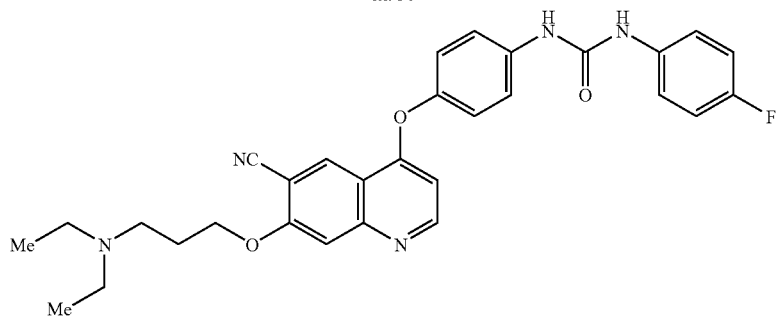

TABLE 21-continued
ex. 31
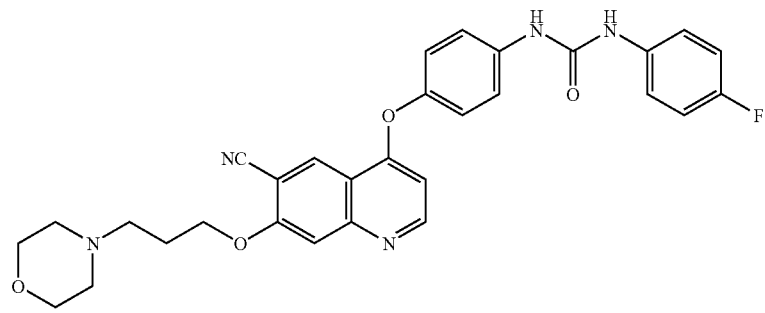
ex. 32
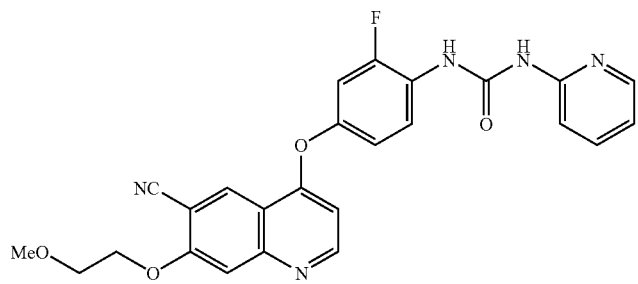
ex. 33
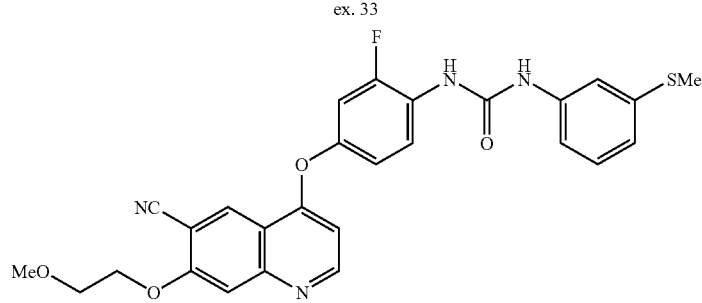
ex. 34
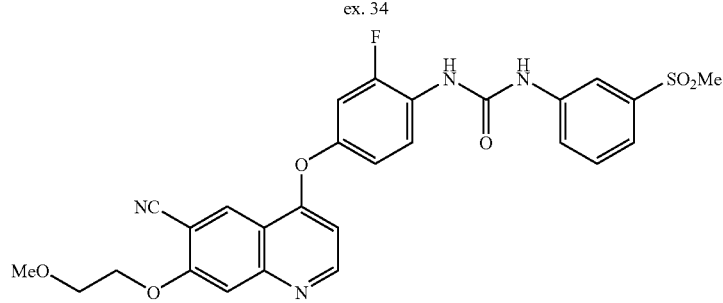
ex. 35
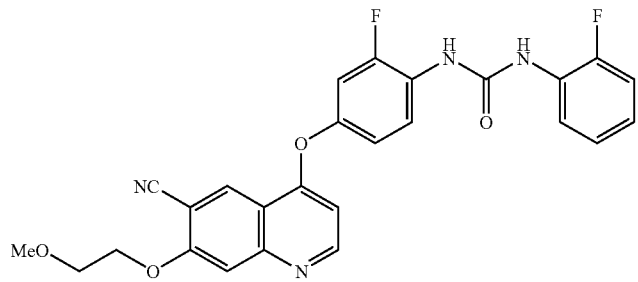

TABLE 21-continued
ex. 36
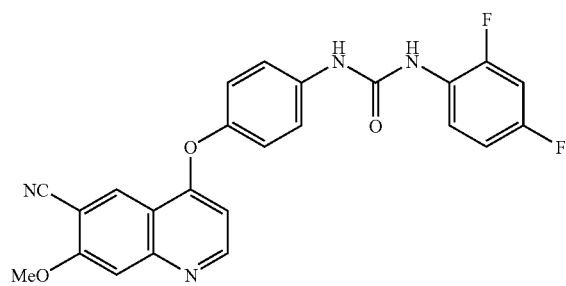
ex. 37
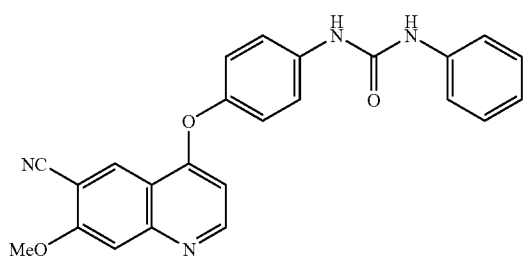
ex. 38
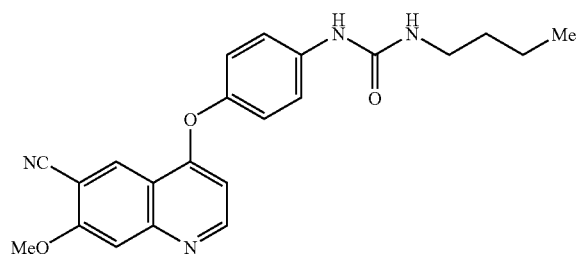
ex. 39
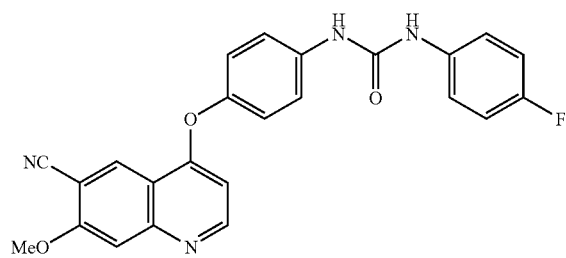
ex. 40
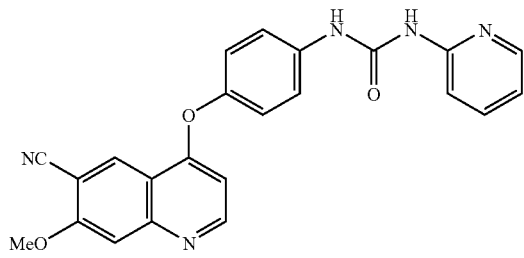

TABLE 21-continued
ex. 41
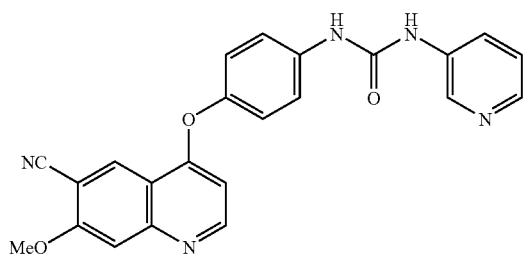
ex. 42
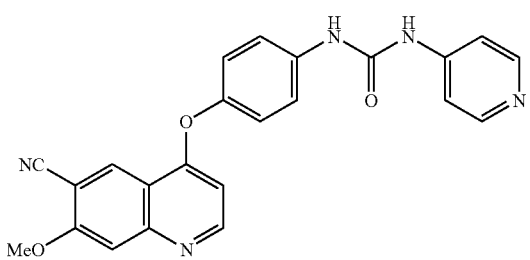
ex. 43
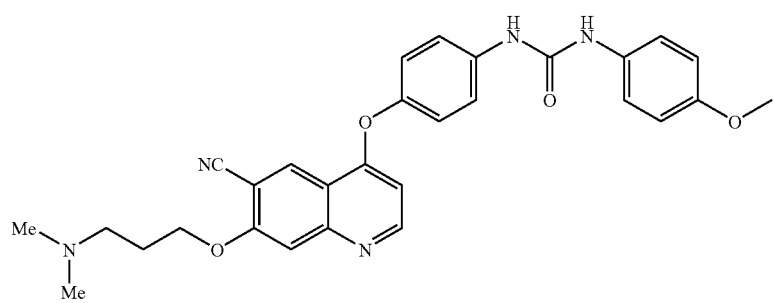
ex. 44
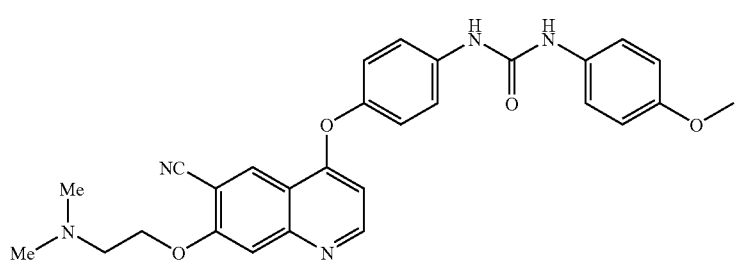
ex. 45
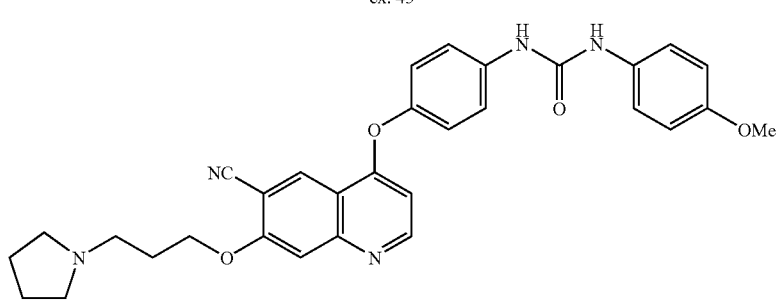

TABLE 22
ex. 46
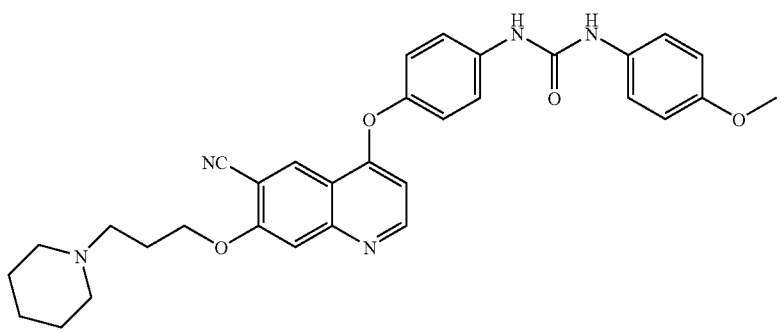
ex. 47
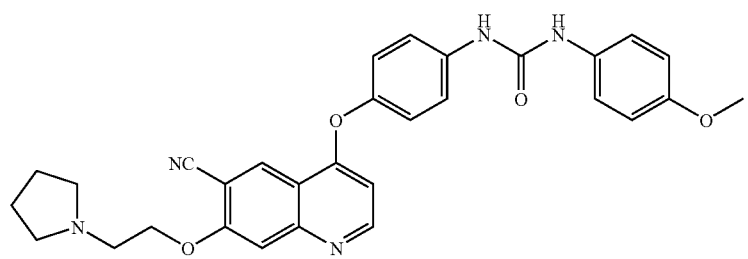
ex. 48
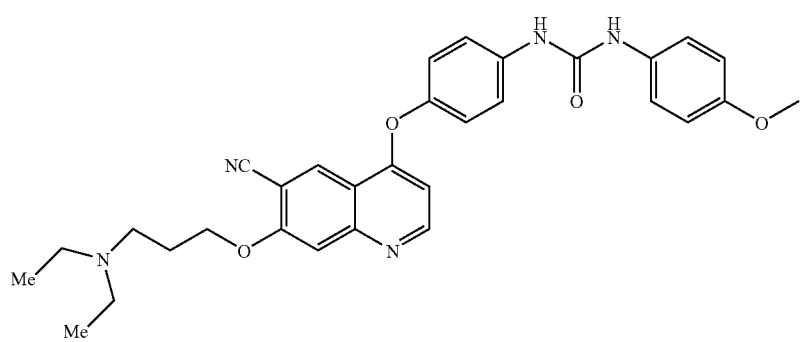
ex. 49
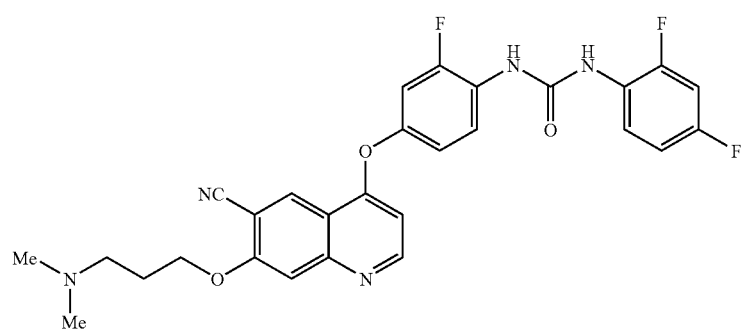

TABLE 22-continued
ex. 50
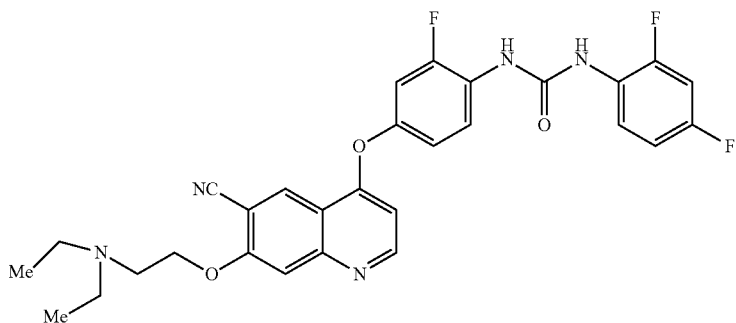
ex. 51
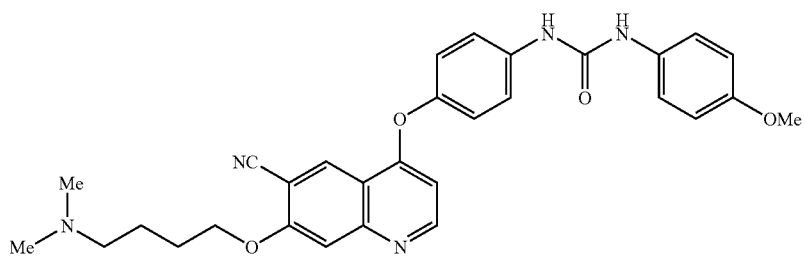
ex. 52
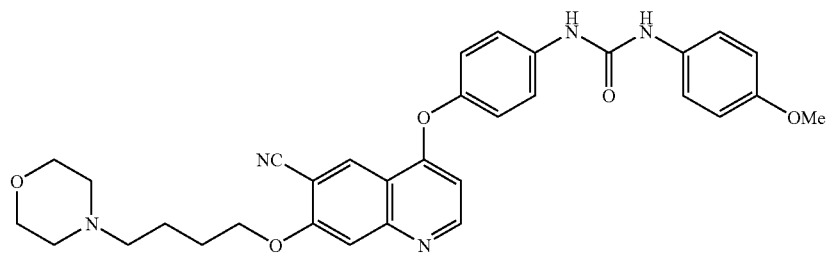
ex. 53
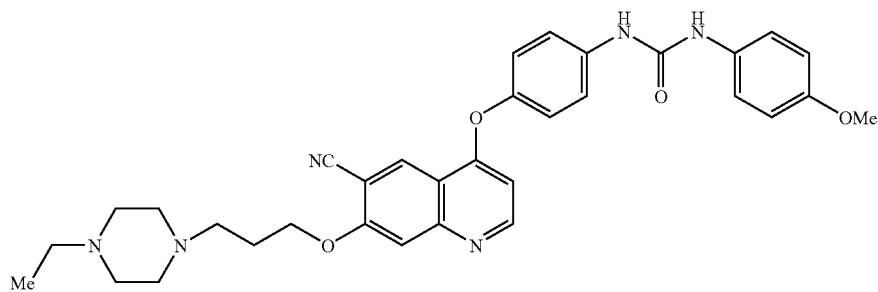
ex. 54
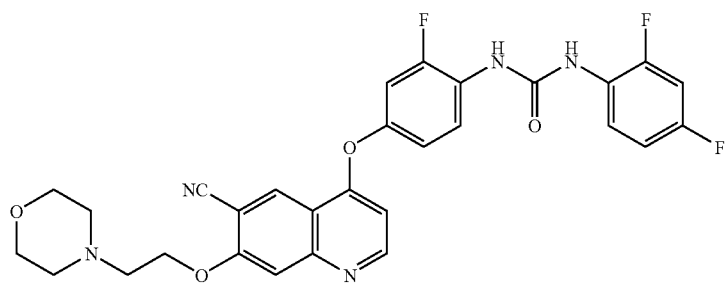

TABLE 22-continued
ex. 55
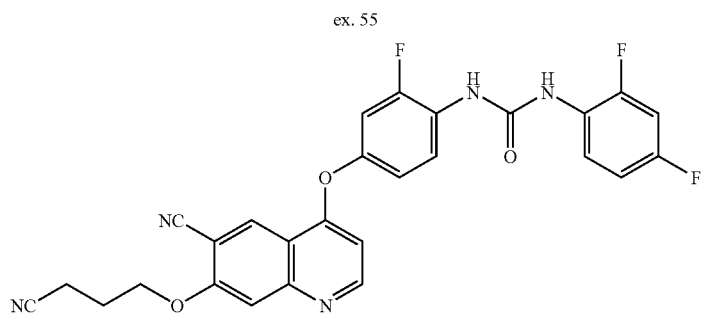
ex. 56
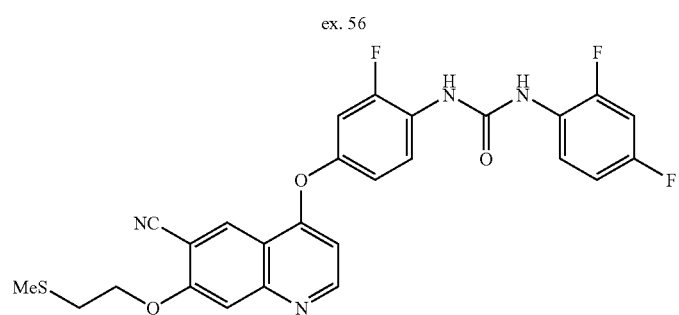
ex. 57
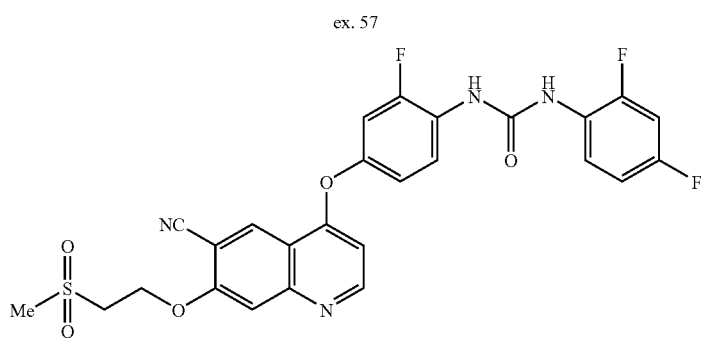
ex. 58
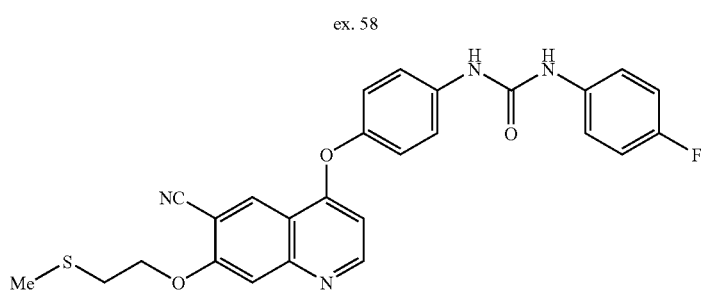
ex. 59
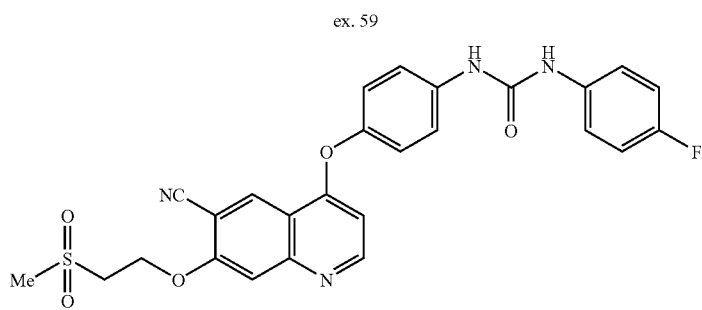

TABLE 22-continued
ex. 60
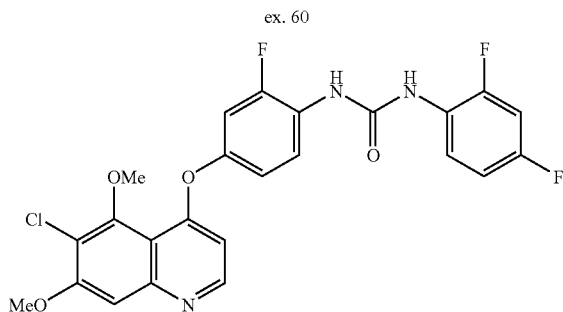
ex. 61
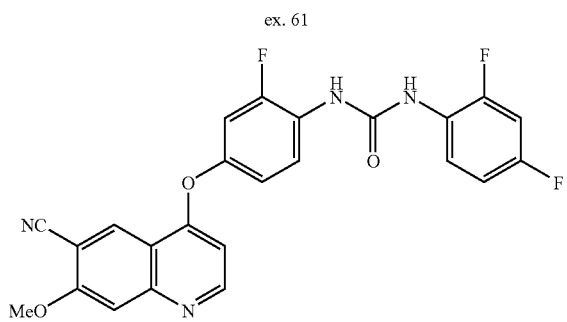
ex. 62
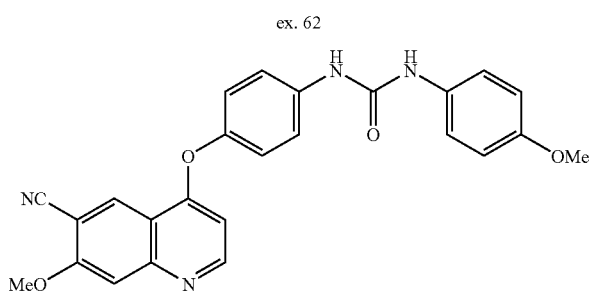
ex. 63
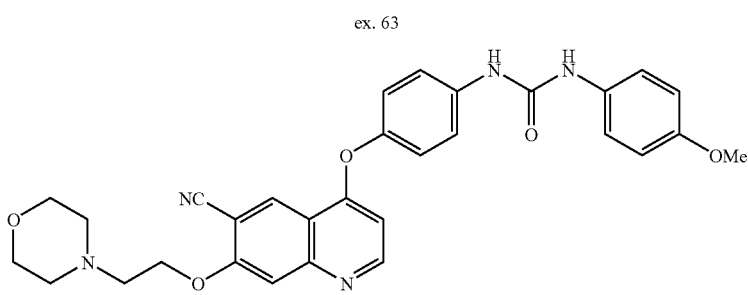
ex. 64
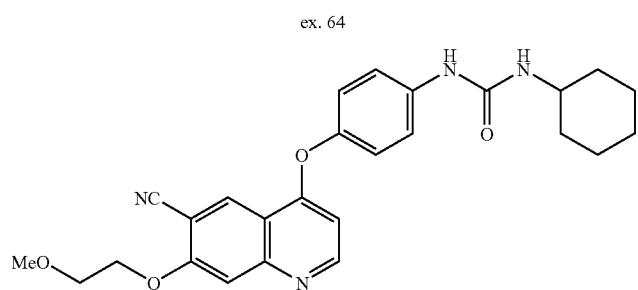

TABLE 22-continued
ex. 65
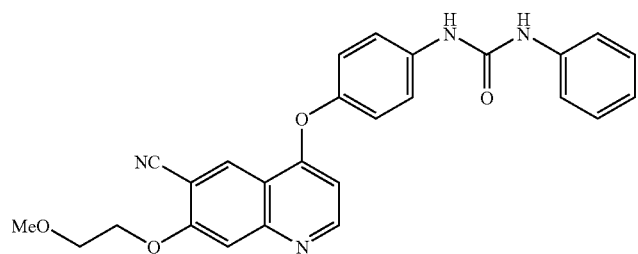
ex. 66
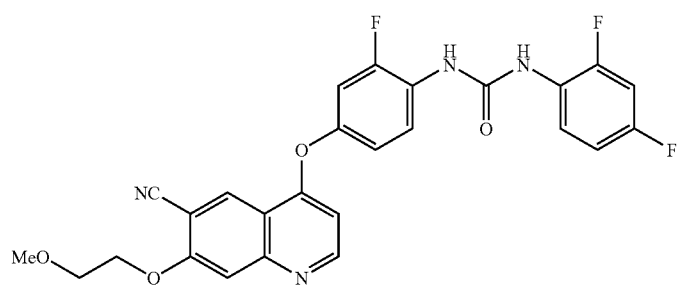
ex. 67
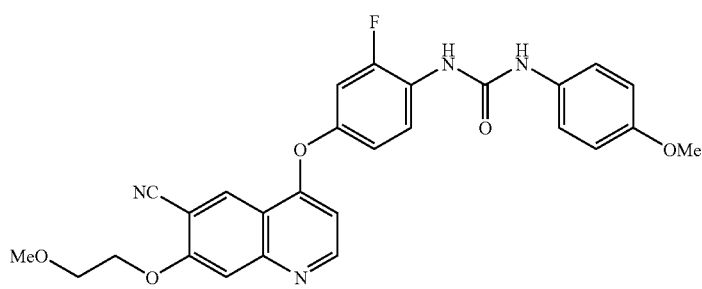
ex. 68
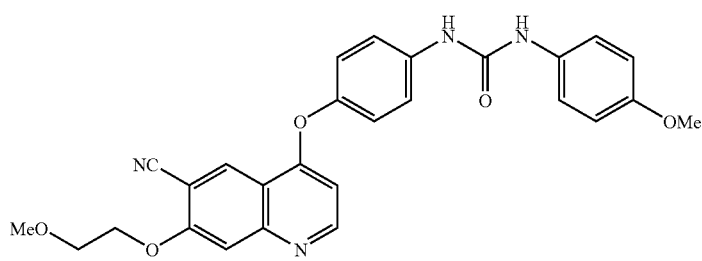
ex. 69
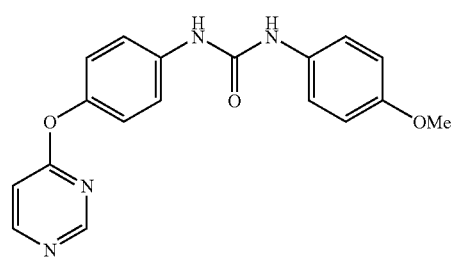

TABLE 23
ex. 70
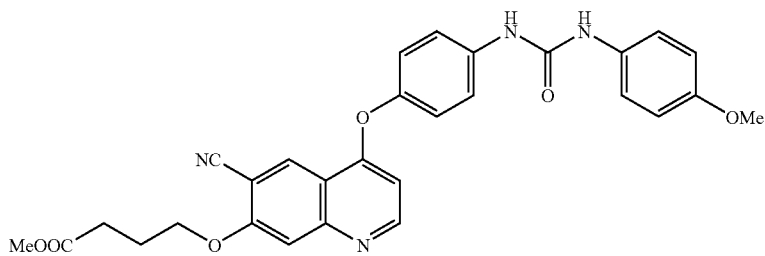
ex. 71
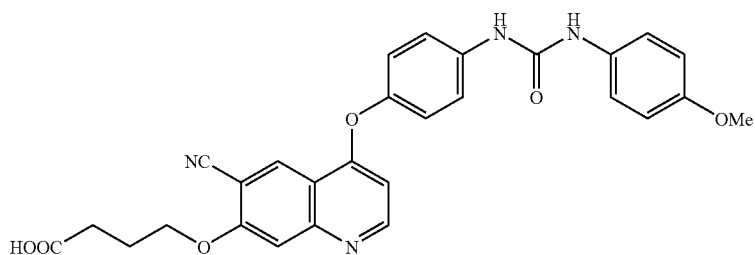
ex. 72
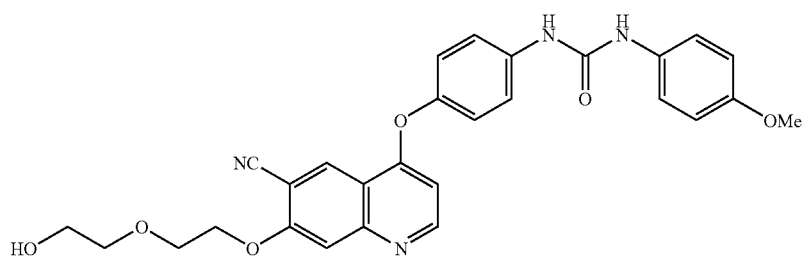
ex. 73
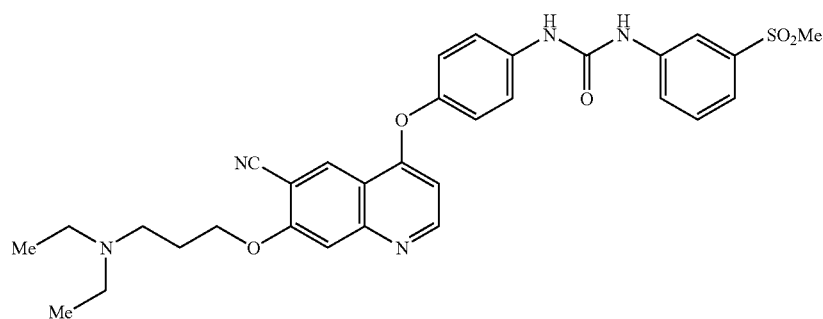
ex. 74
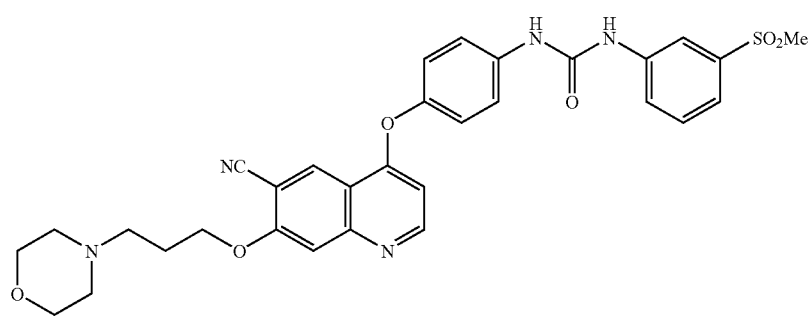

TABLE 23-continued
ex. 75
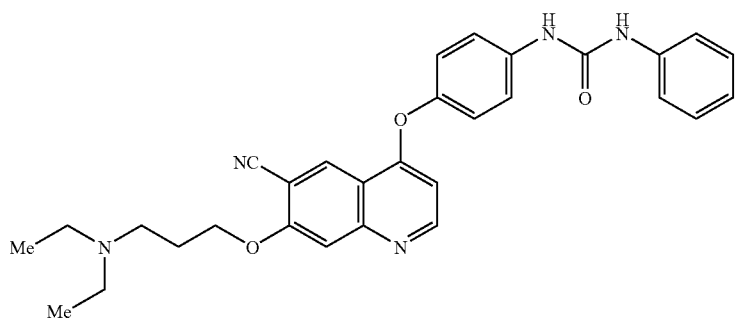
ex. 76
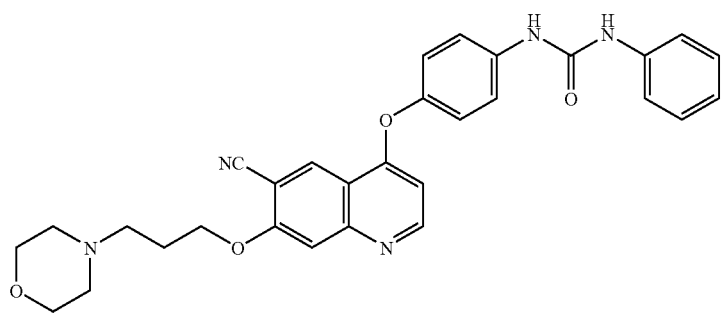
ex. 77
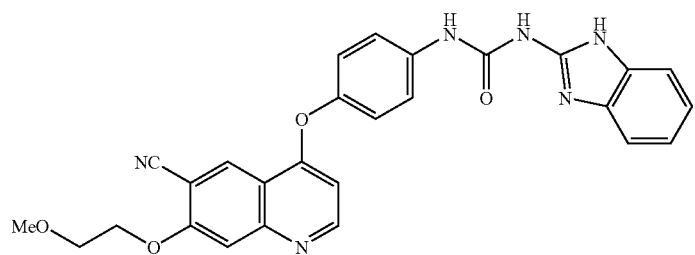
ex. 78
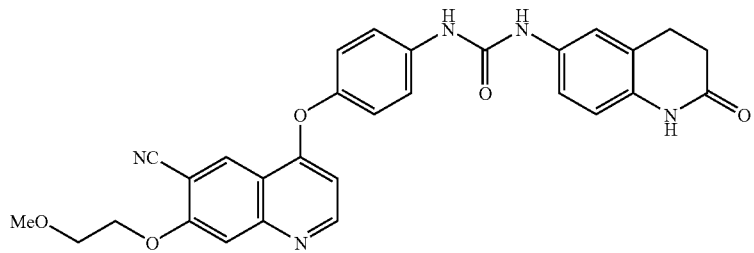
ex. 79
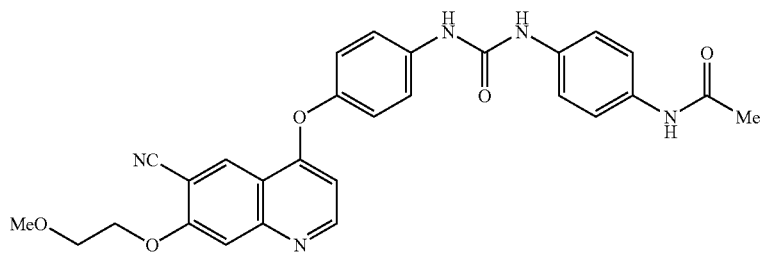

TABLE 23-continued
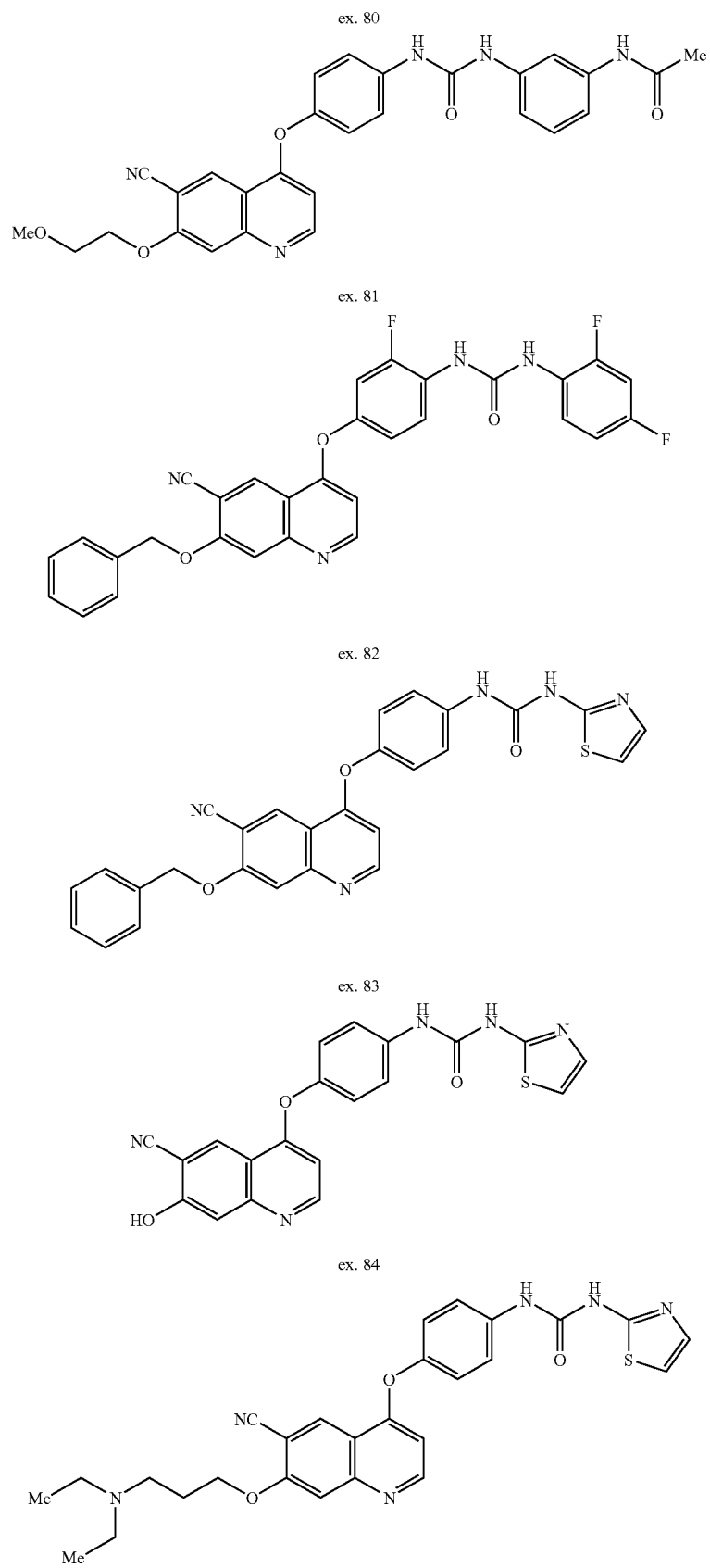

TABLE 23-continued
ex. 85
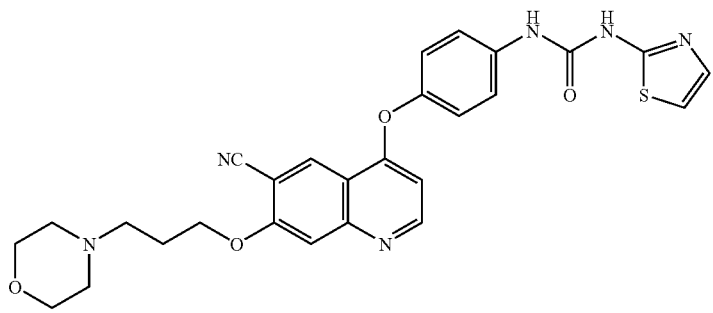
ex. 86
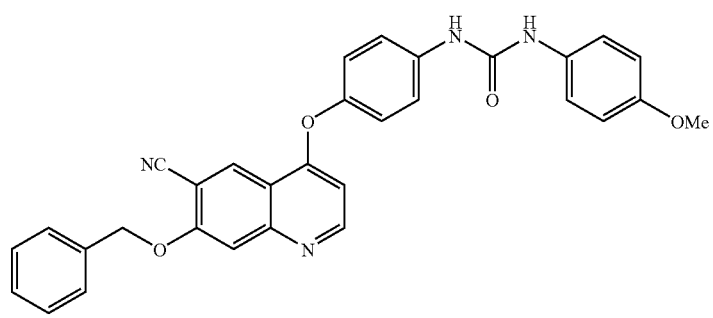
ex. 87
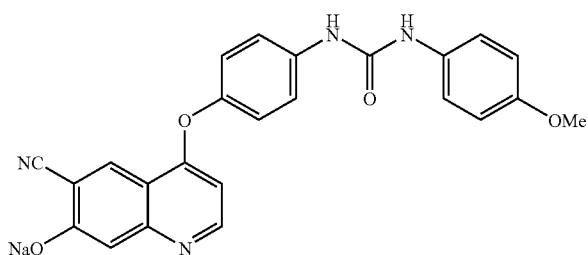
ex. 88
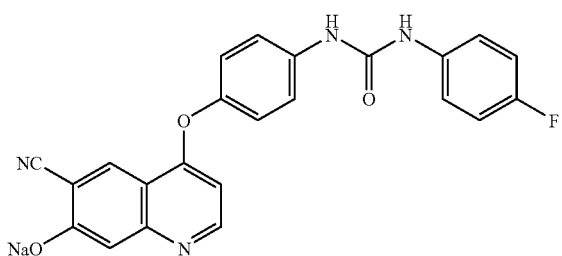
ex. 89
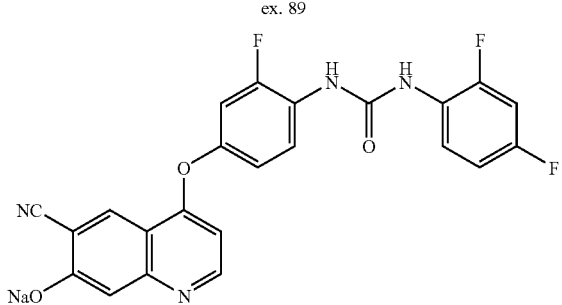

TABLE 23-continued ex. 90 ex. 91 ex. 92 ex. 93

TABLE 24 ex. 94

TABLE 24-continued
ex. 95
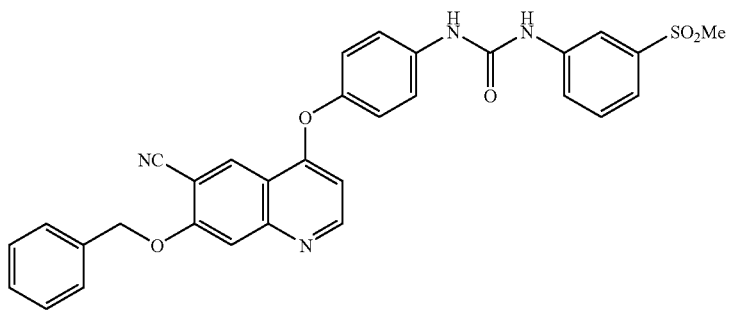
ex. 96
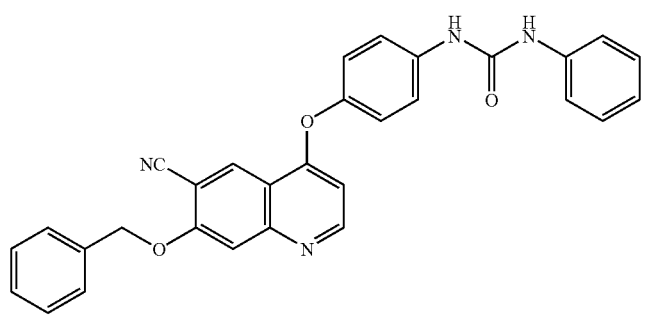
ex. 97
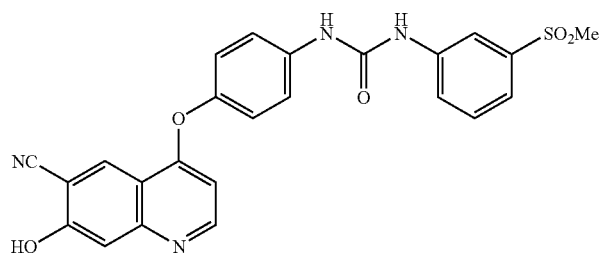
ex. 98
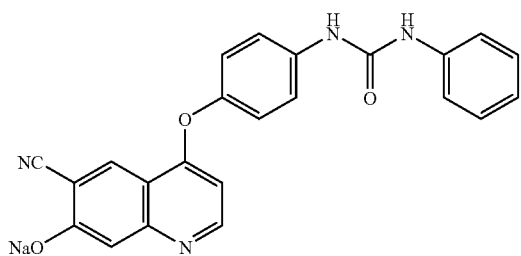
ex. 99
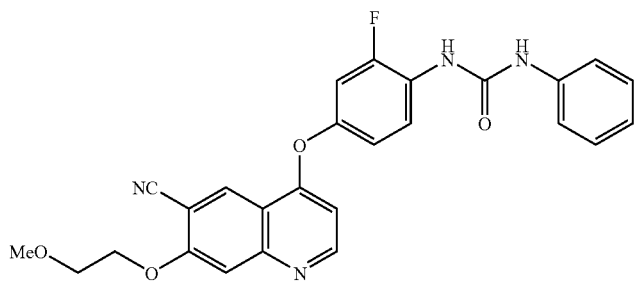

TABLE 24-continued
ex. 100
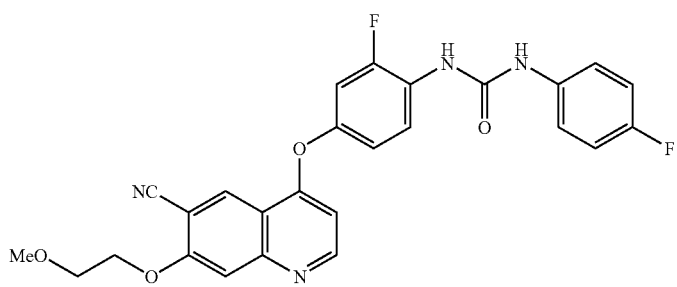
ex. 101-B
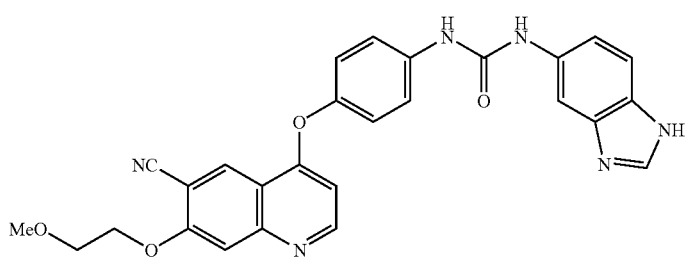
ex. 101-A
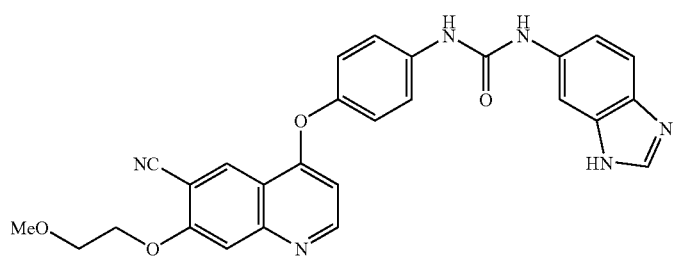
ex. 102
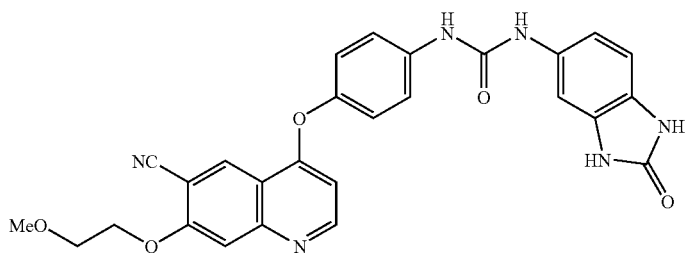
ex. 103
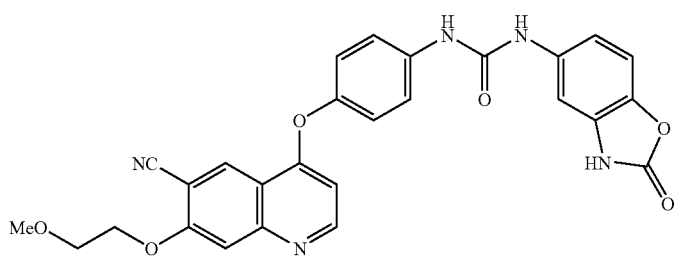

TABLE 24-continued
ex. 104
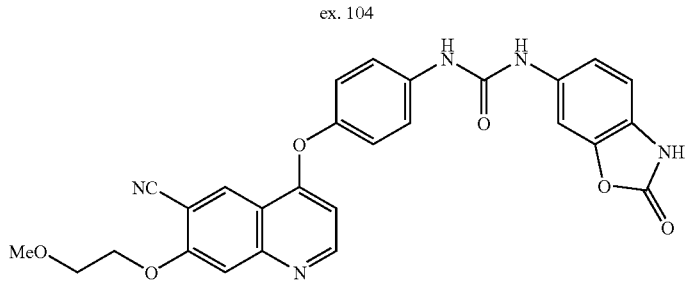
ex. 105
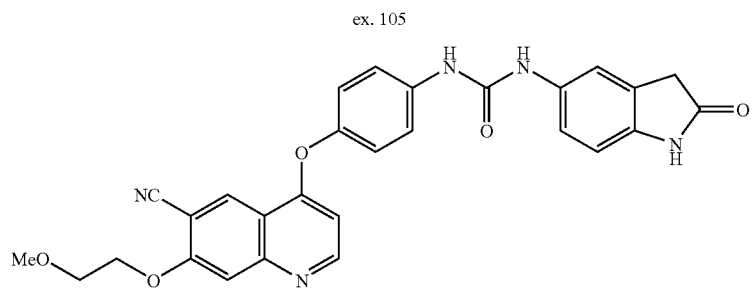
ex. 106
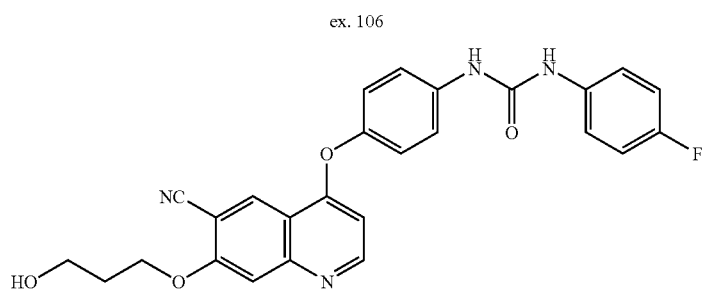
ex. 107
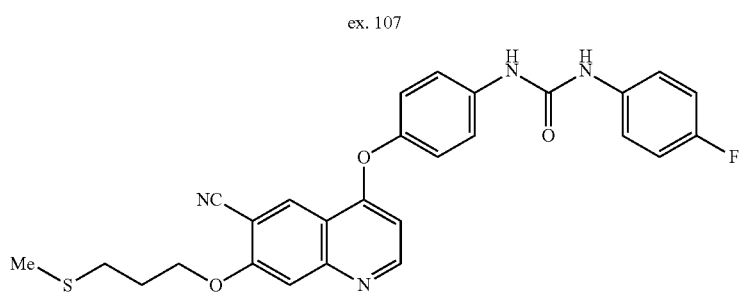
ex. 108
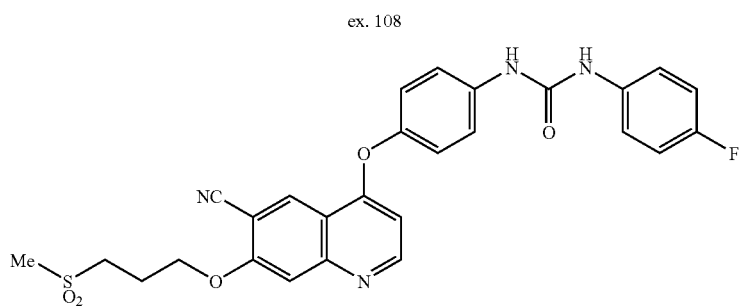

TABLE 24-continued
ex. 109
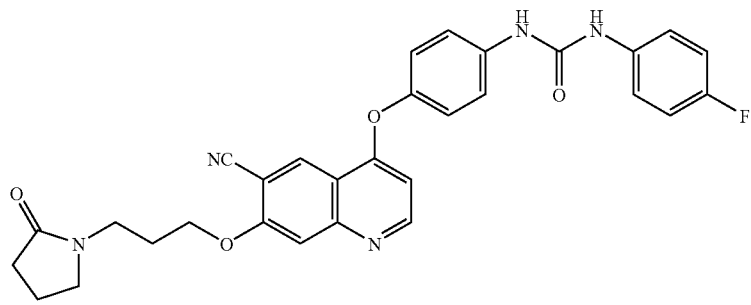
ex. 110
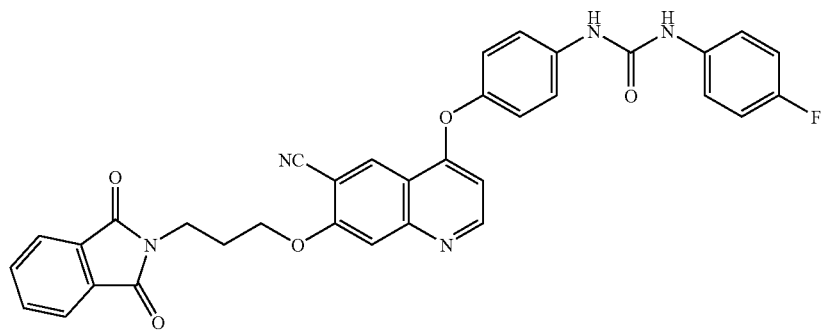
ex. 111
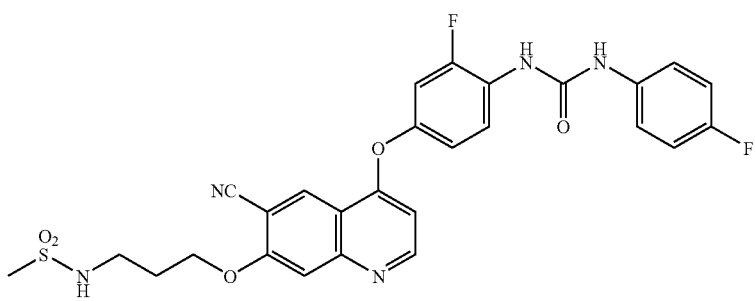
ex. 112
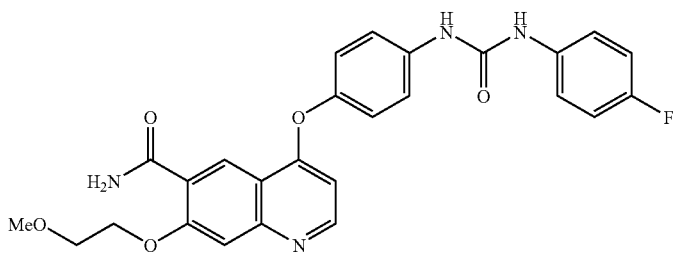
ex. 113
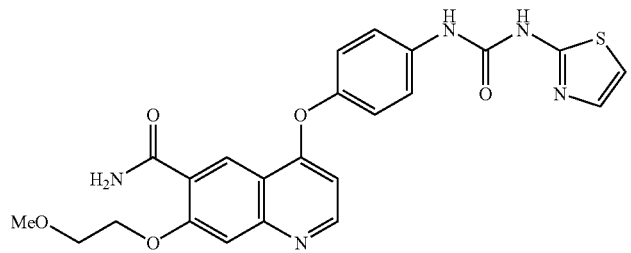

TABLE 24-continued
ex. 114
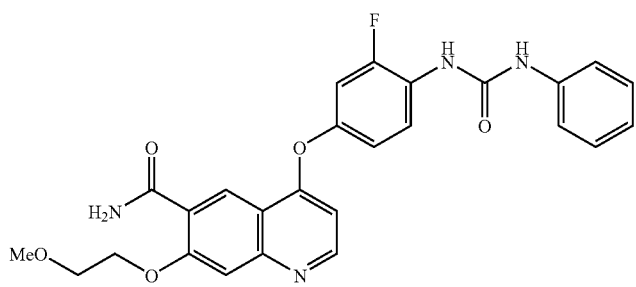
ex. 115
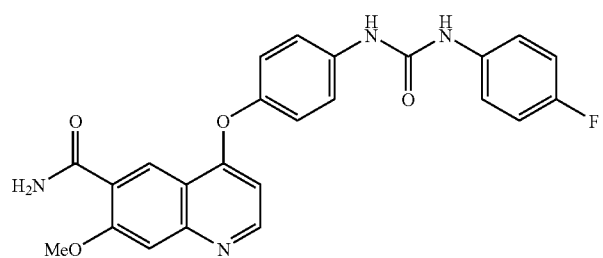
ex. 116
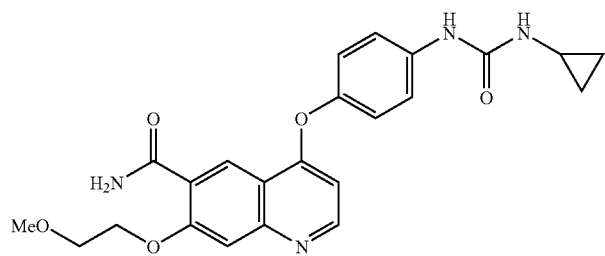
TABLE 25
ex. 117
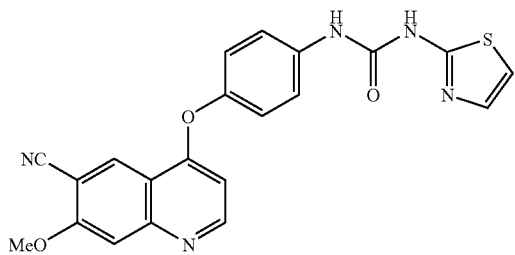
ex. 118
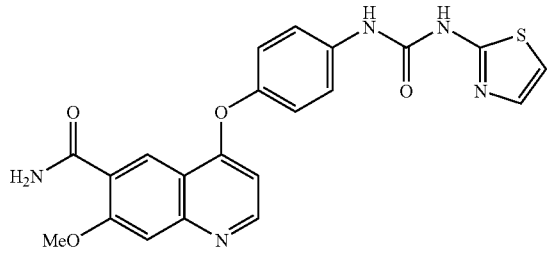

TABLE 25-continued
ex. 119
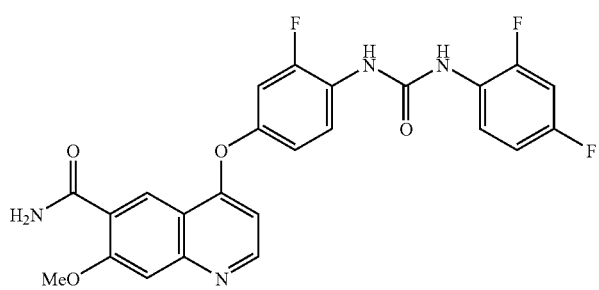
ex. 120
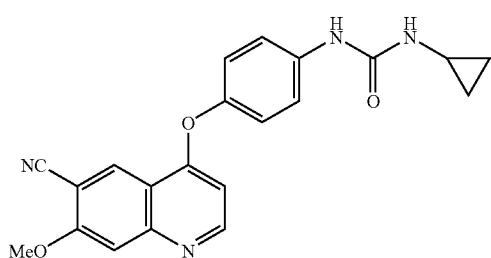
ex. 121
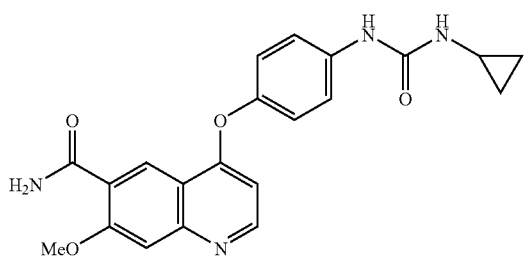
ex. 122
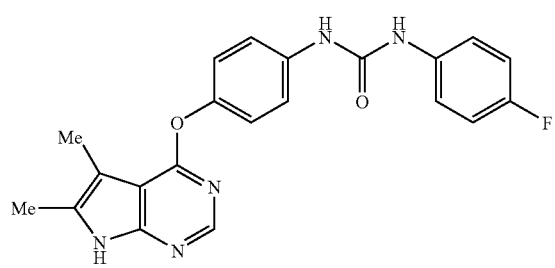
ex. 123
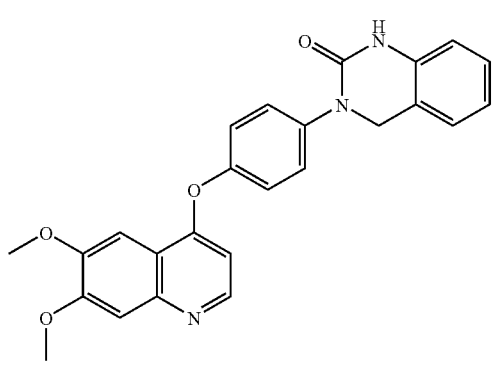

TABLE 25-continued
ex. 124
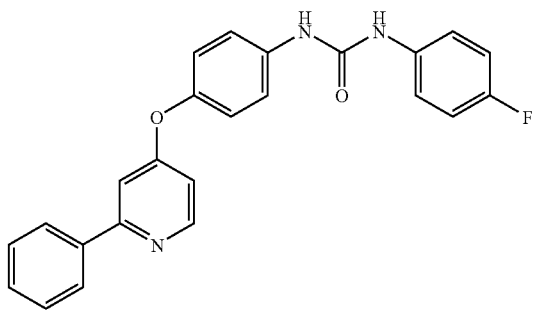
ex. 125
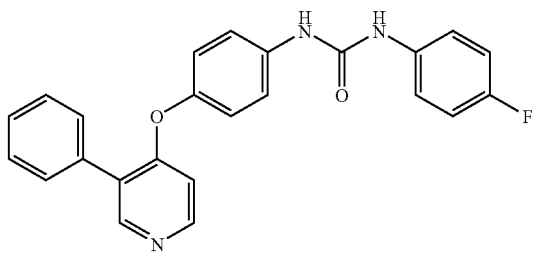
ex. 126
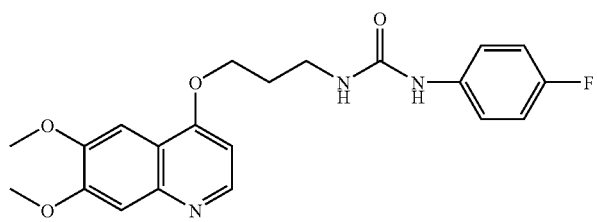
ex. 127
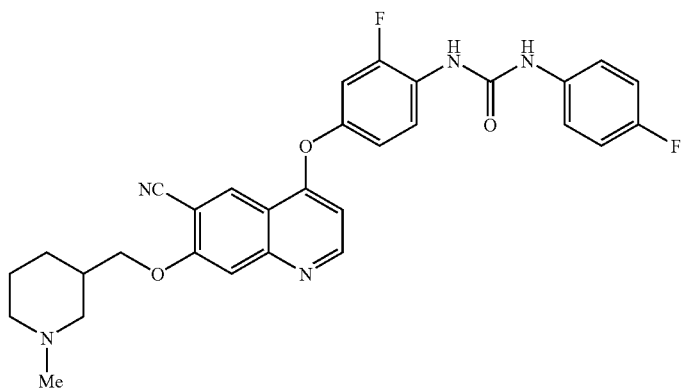
ex. 128
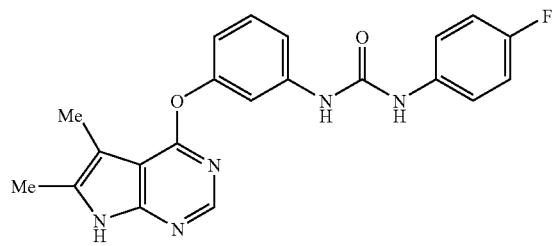

TABLE 25-continued
ex. 129
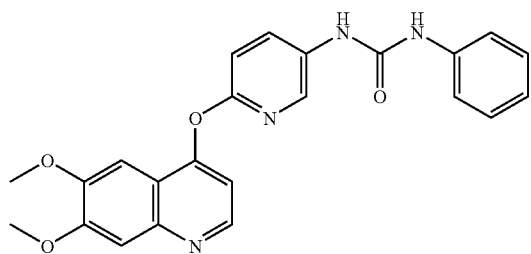
ex. 130
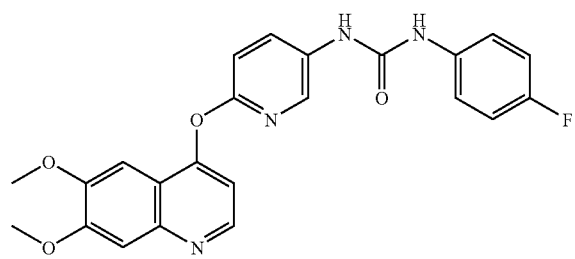
ex. 131
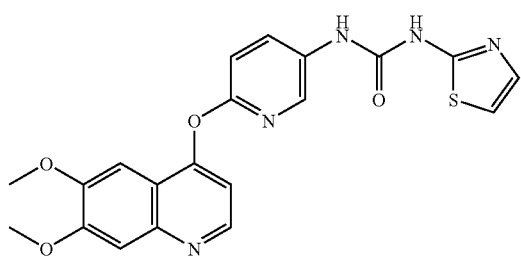
ex. 132
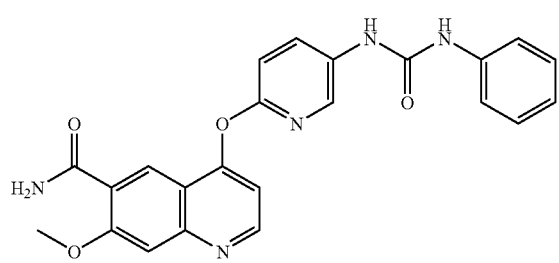
ex. 133
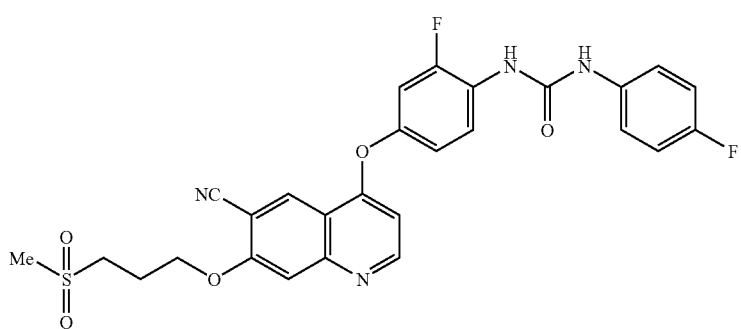

TABLE 25-continued
ex. 134
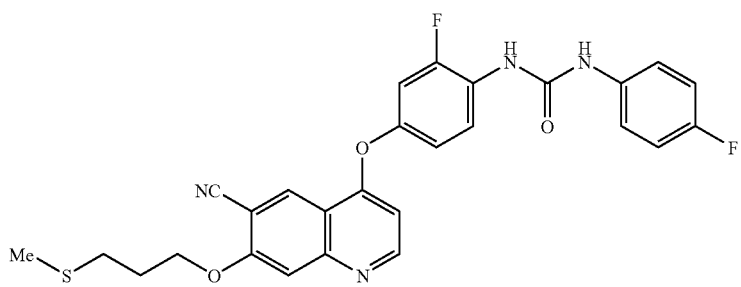
ex. 135
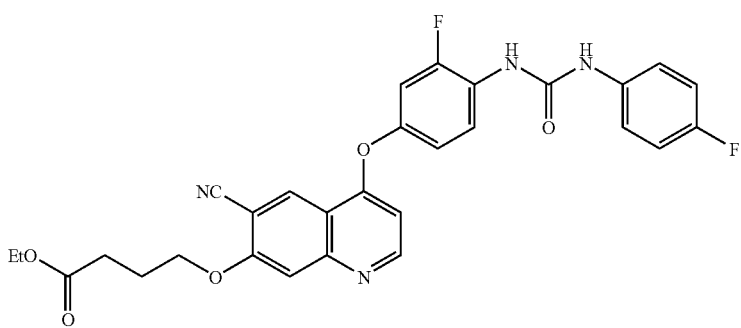
ex. 136
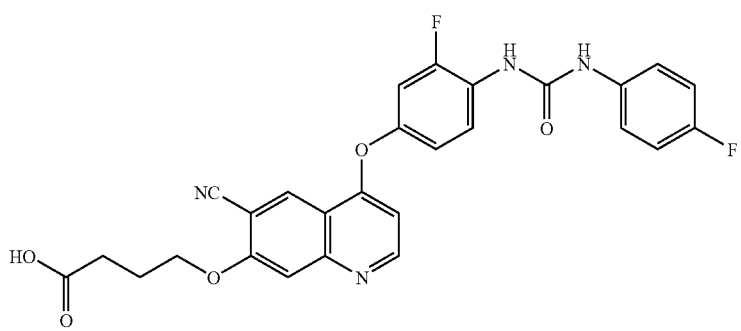
ex. 137
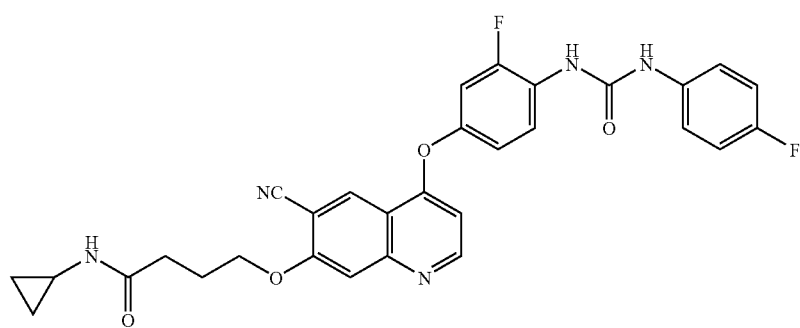

TABLE 25-continued
ex. 138
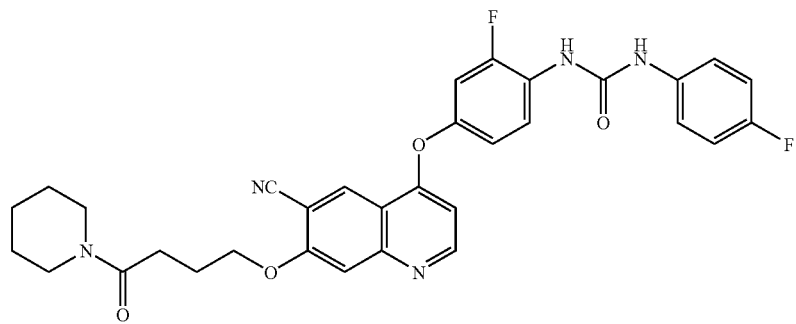
ex. 139
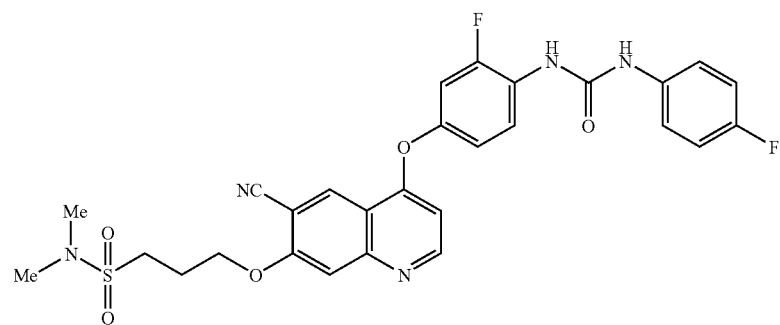
ex. 140
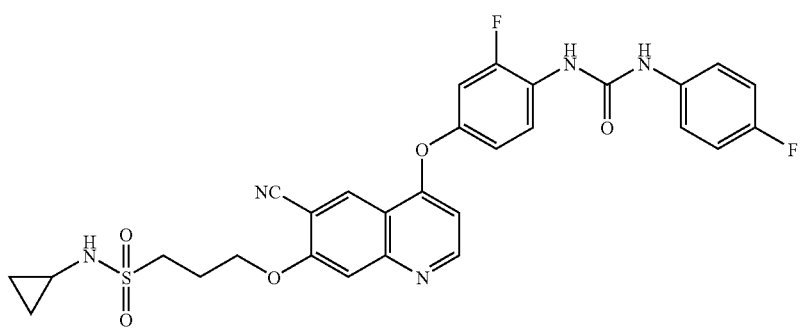
TABLE 26
ex. 141
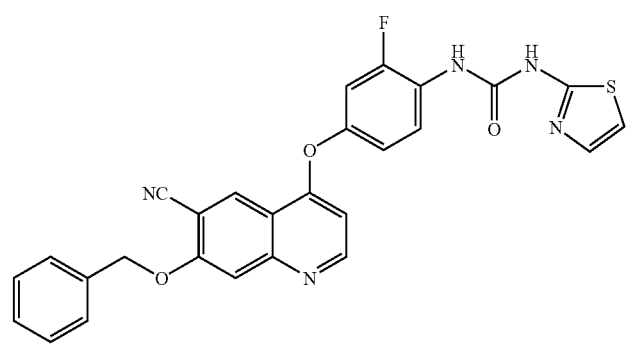

TABLE 26-continued
ex. 142
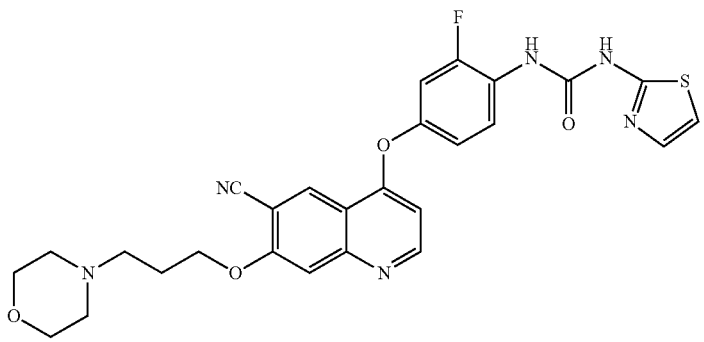
ex. 143
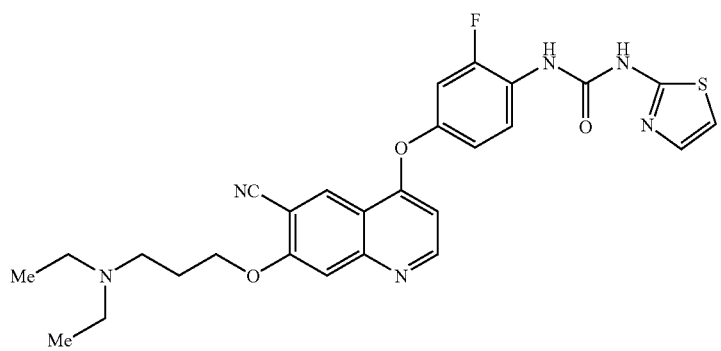
ex. 144
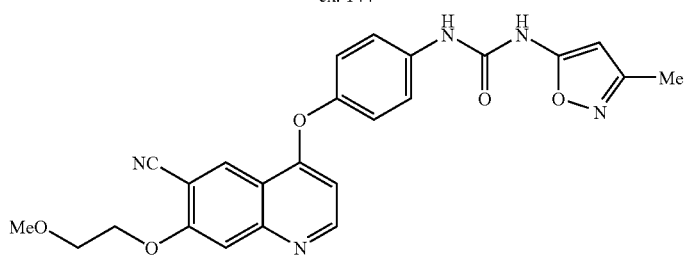
ex. 145
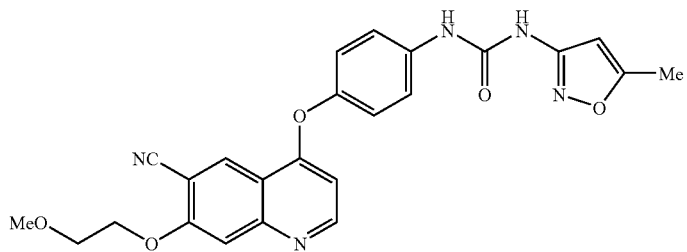
ex. 146
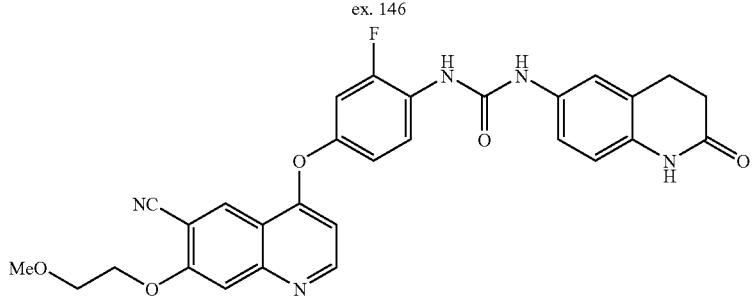

TABLE 26-continued
ex. 147
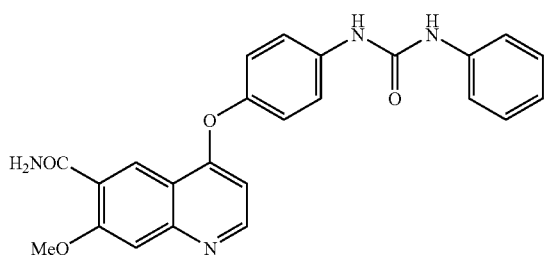
ex. 148
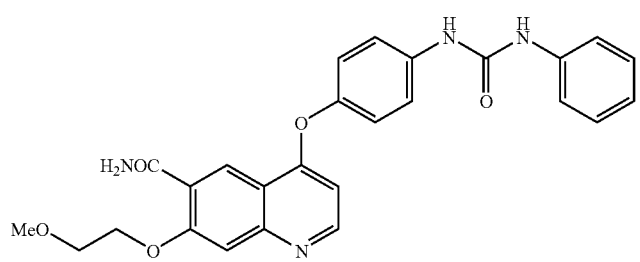
ex. 149
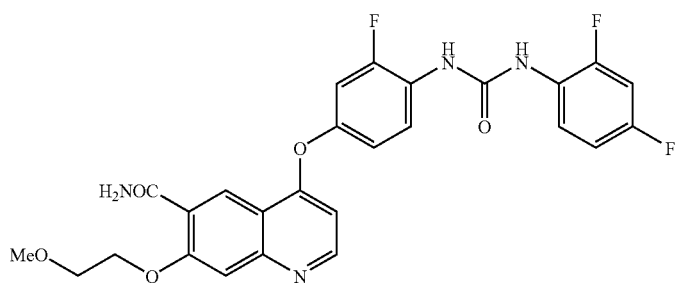
ex. 150
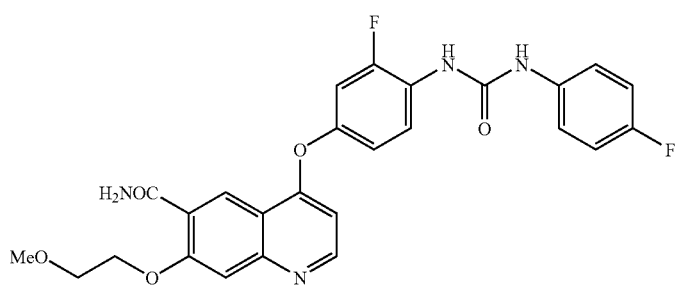
ex. 151
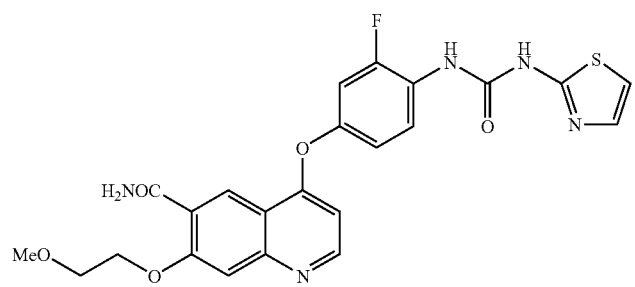

TABLE 26-continued
ex. 152
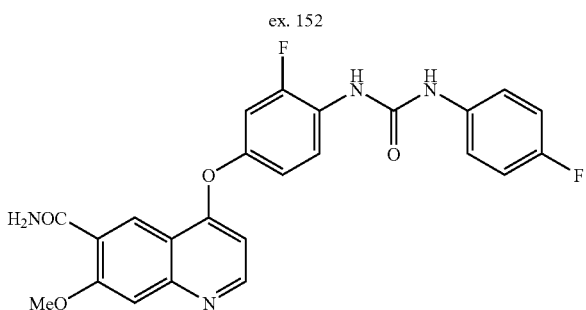
ex. 153
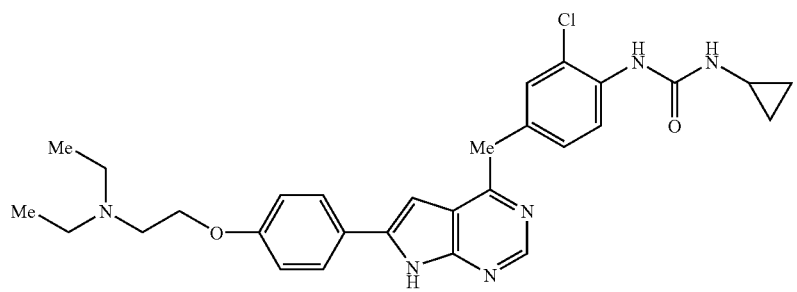
ex. 154
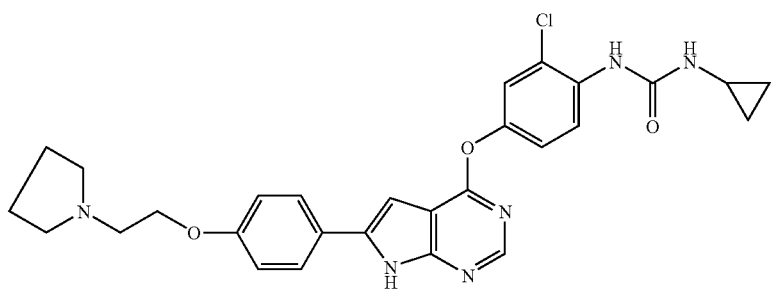
ex. 155
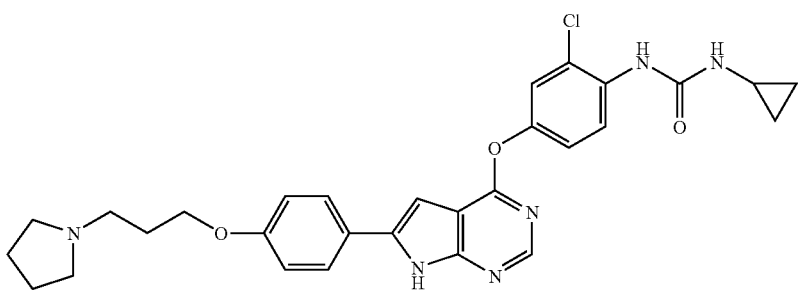
ex. 156
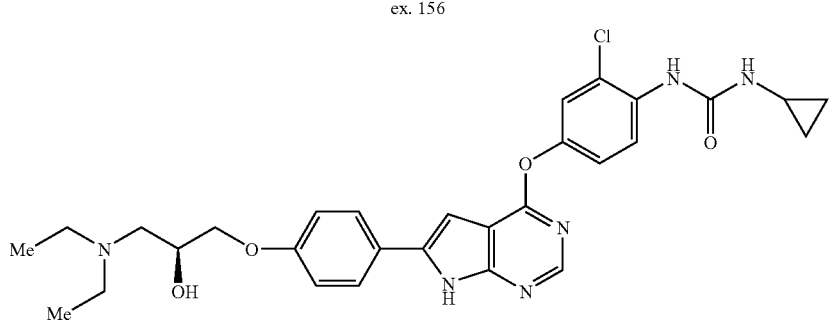

TABLE 26-continued
ex. 157
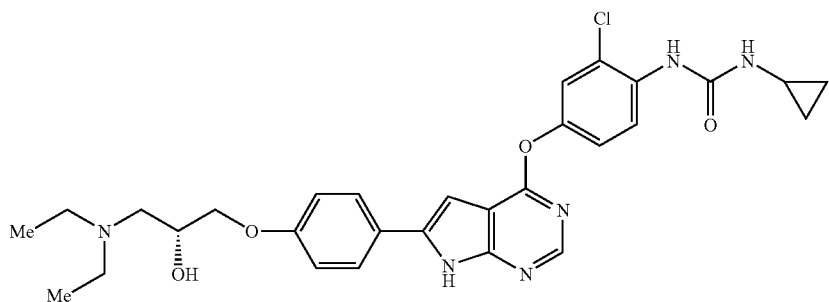
ex. 158
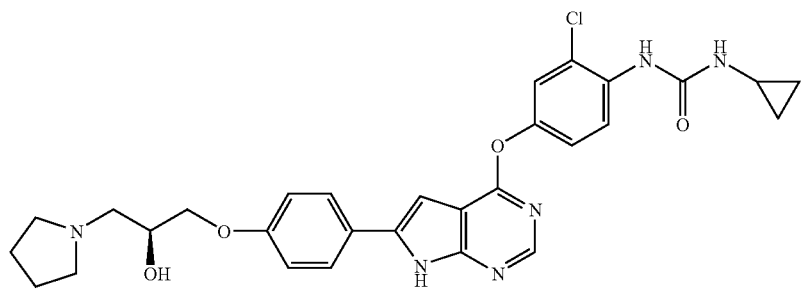
ex. 159
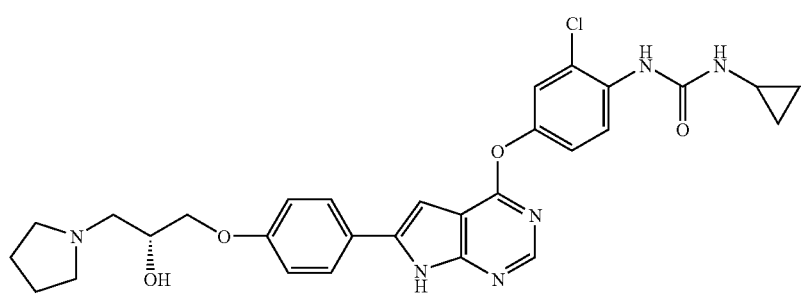
ex. 160
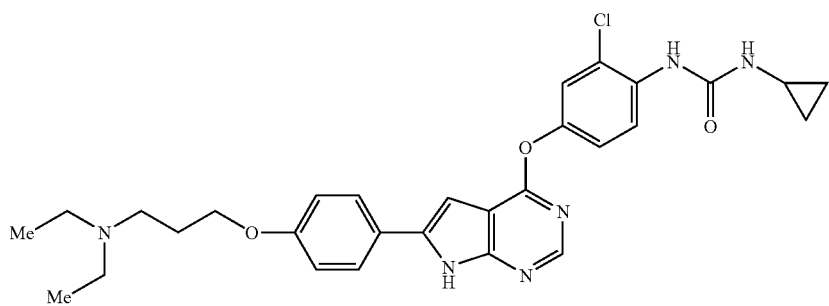

TABLE 26-continued
ex. 161
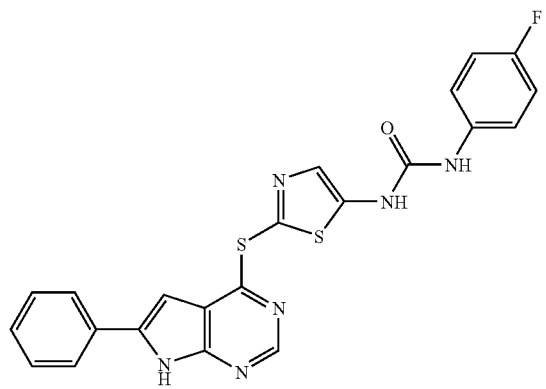
ex. 162
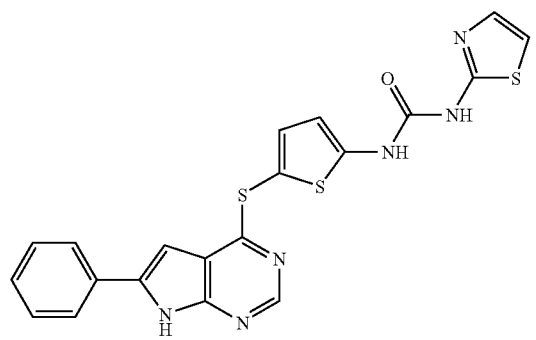
ex. 163
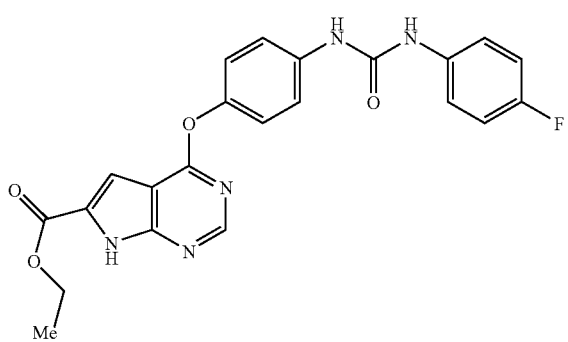
ex. 164
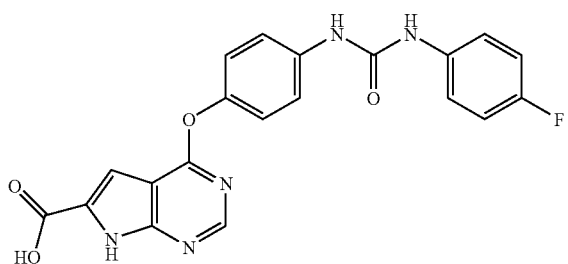

TABLE 27
ex. 165
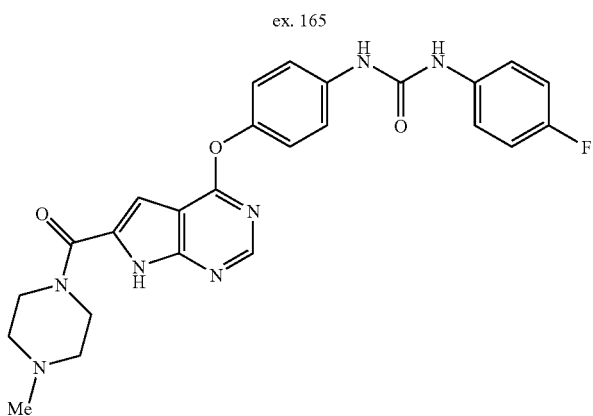
ex. 166
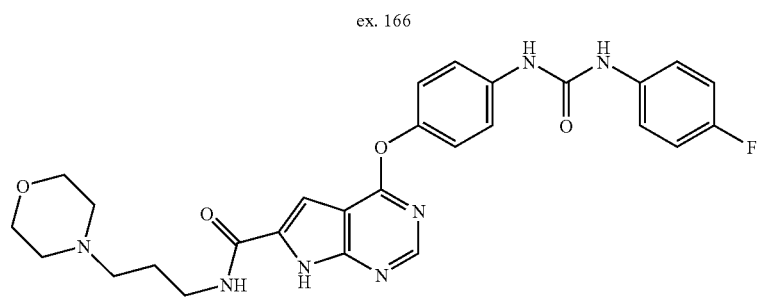
ex. 167
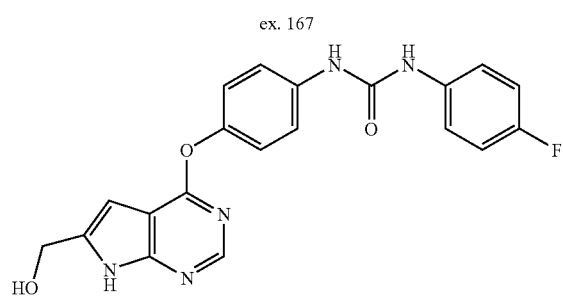
ex. 168
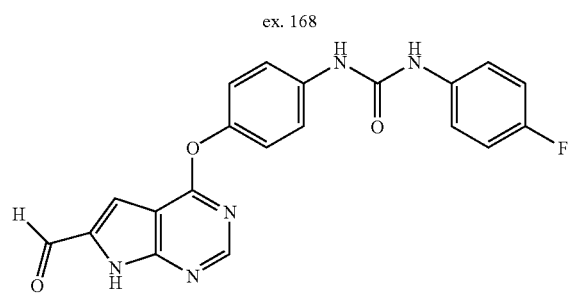
ex. 169
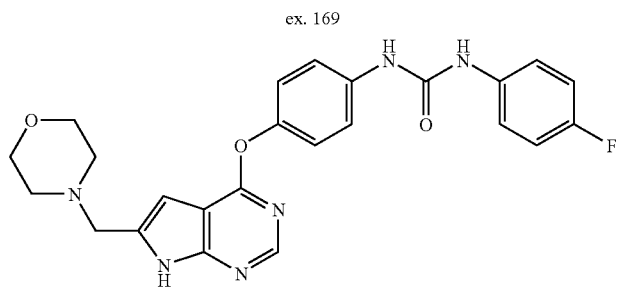

TABLE 27-continued
ex. 170
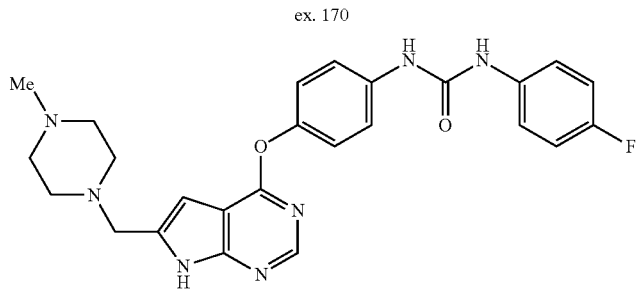
ex. 171
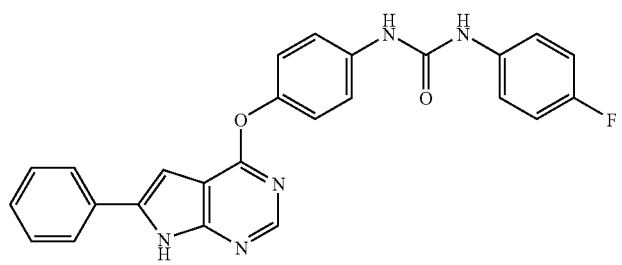
ex. 172
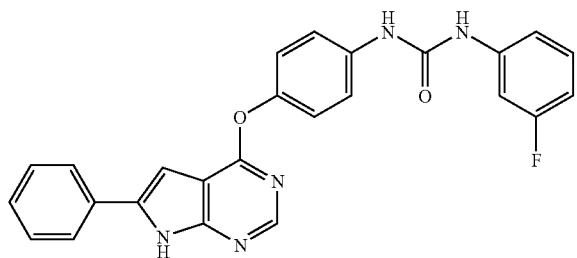
ex. 173
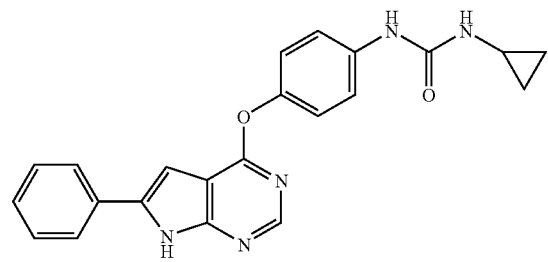
ex. 174
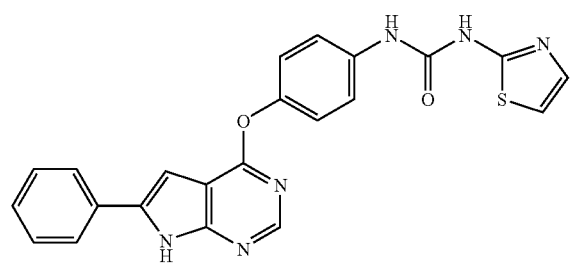

TABLE 27-continued
ex. 175
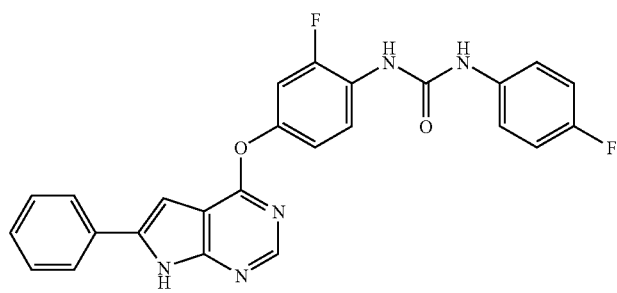
ex. 176
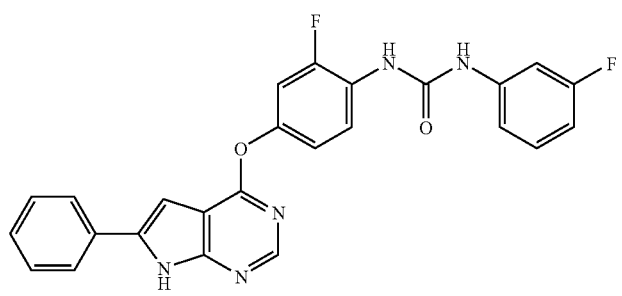
ex. 177
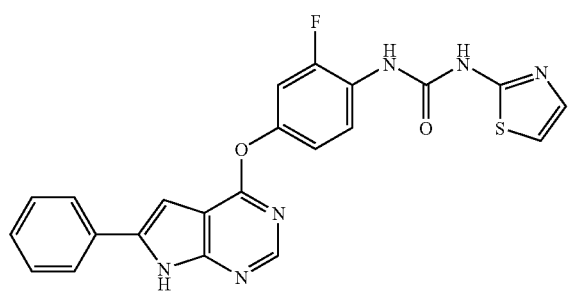
ex. 178
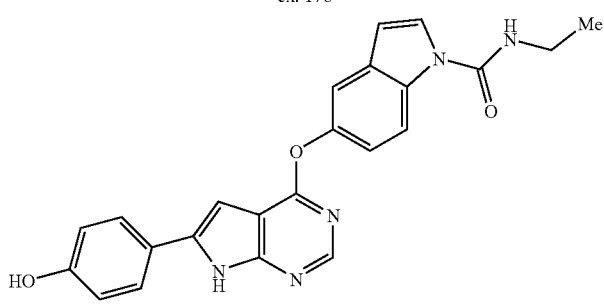
ex. 179
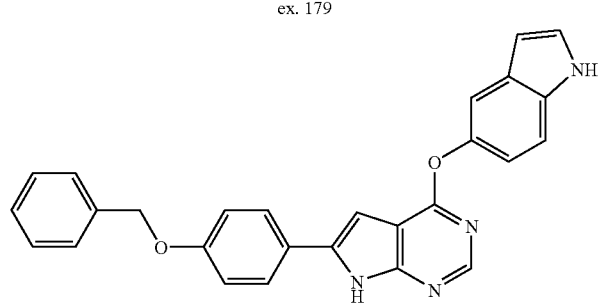

TABLE 27-continued
ex. 180
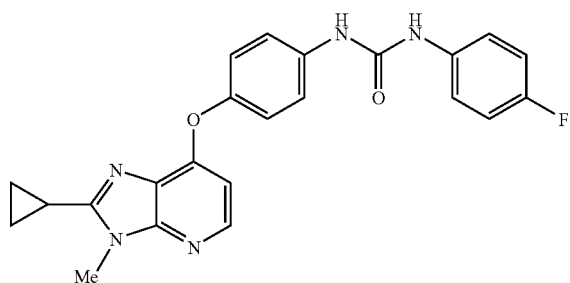
ex. 181
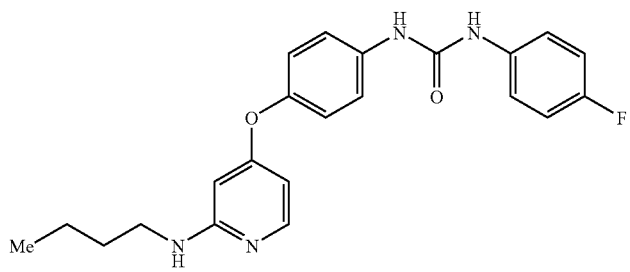
ex. 182
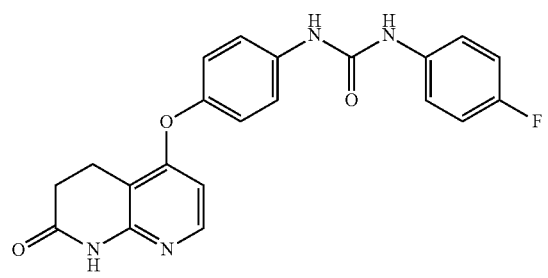
ex. 183
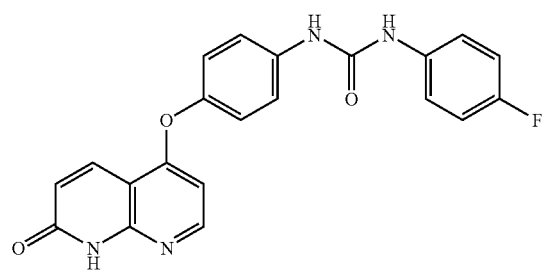
ex. 184
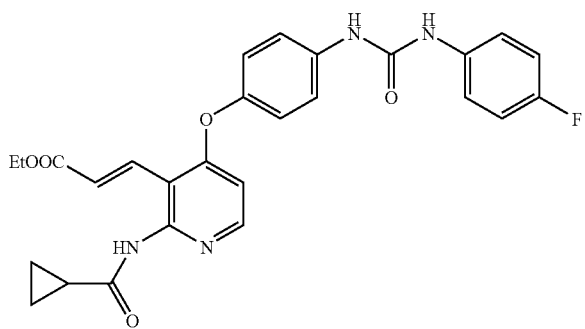

TABLE 27-continued
ex. 185
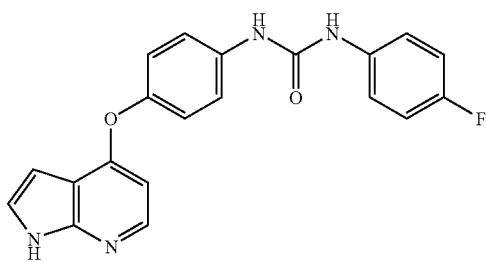
ex. 186
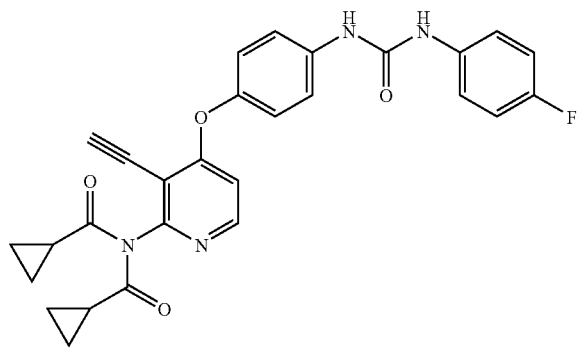
ex. 187
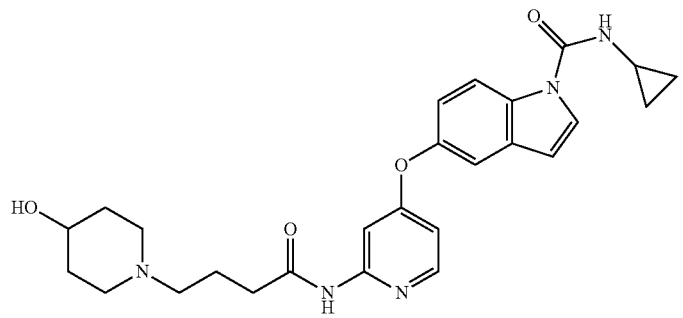
ex. 188
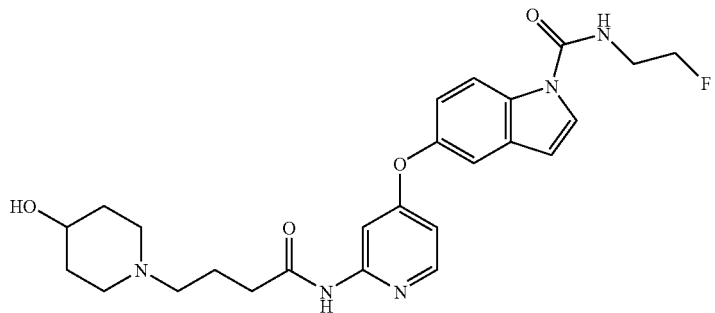

TABLE 28
ex. 189
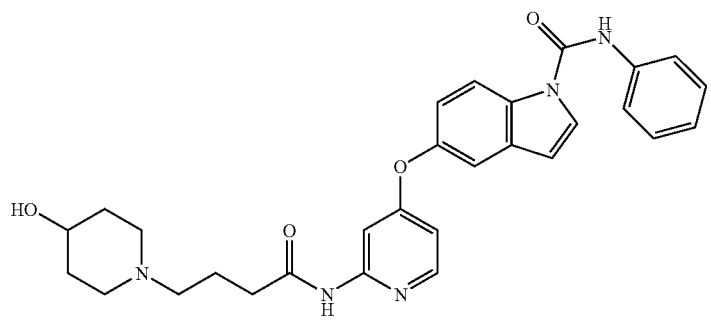
ex. 190
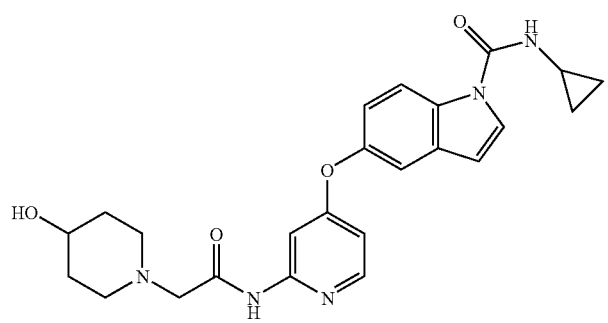
ex. 191
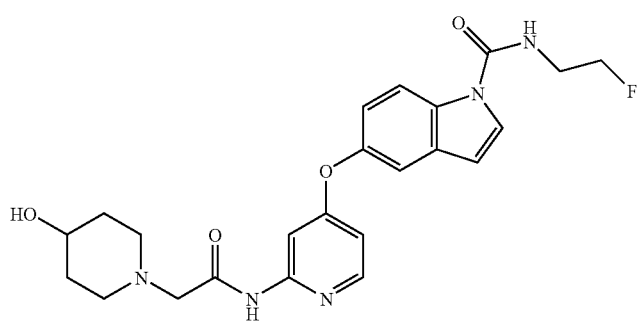
ex. 192
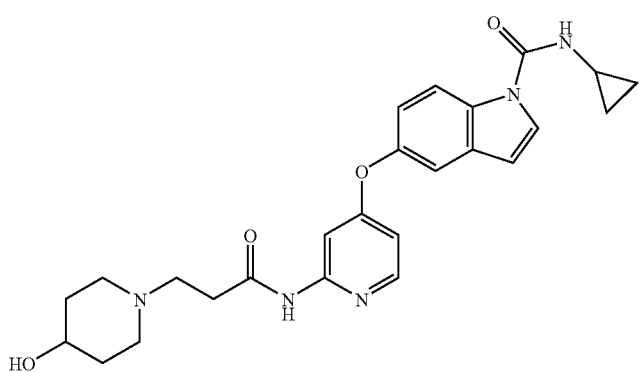

TABLE 28-continued
ex. 193
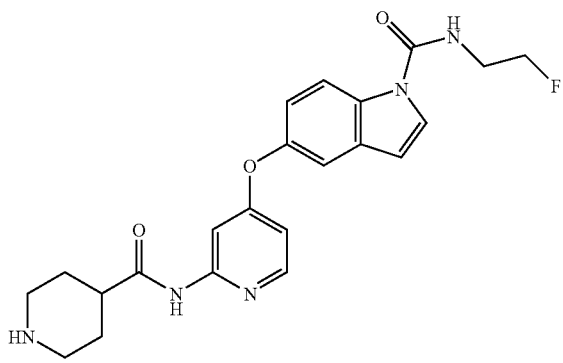
ex. 194
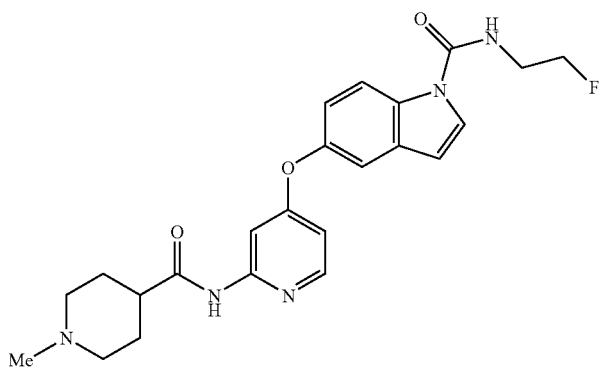
ex. 195
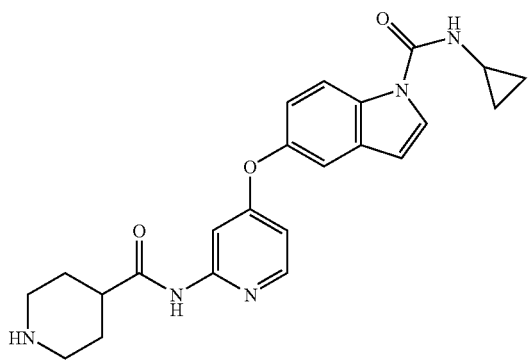
ex. 196
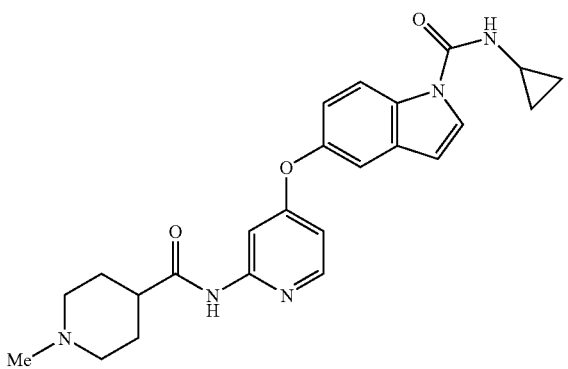

TABLE 28-continued
ex. 197
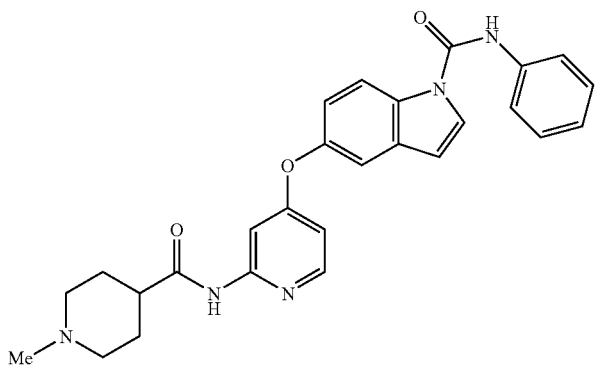
ex. 198
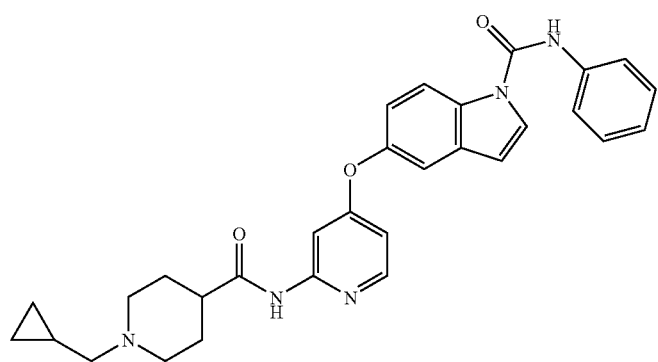
ex. 199
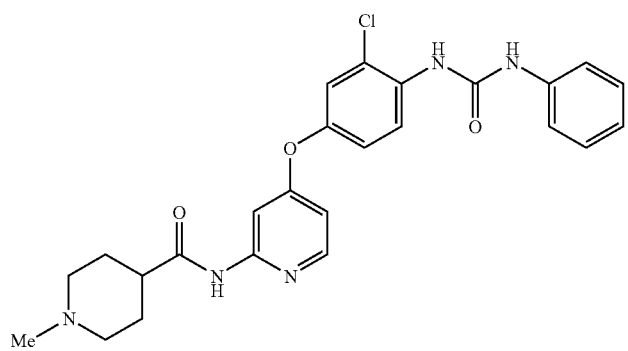
ex. 200
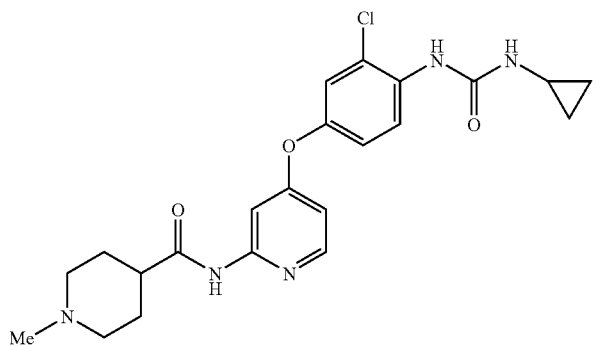

TABLE 28-continued
ex. 201
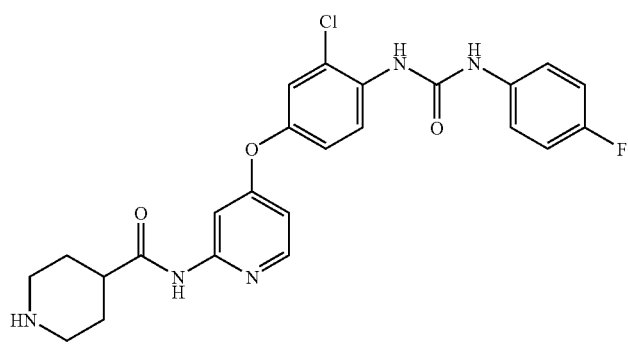
ex. 202
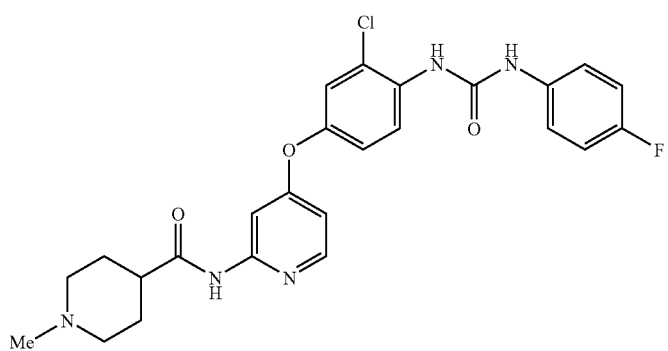
ex. 203
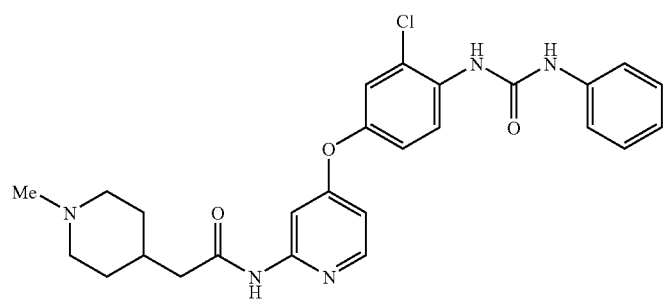
ex. 204
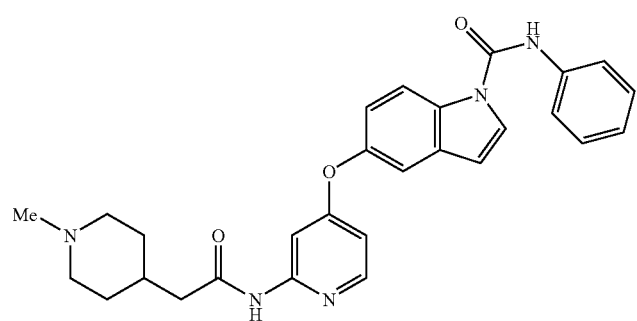

TABLE 28-continued
ex. 205
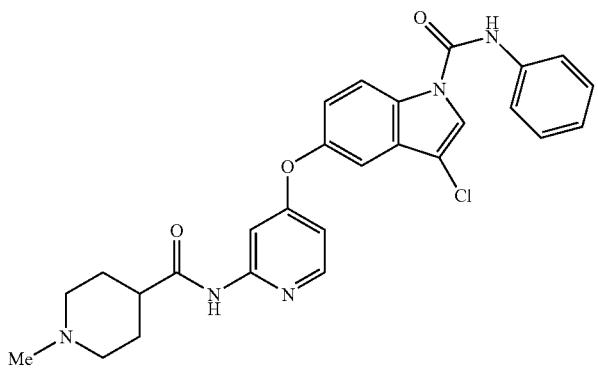
ex. 206
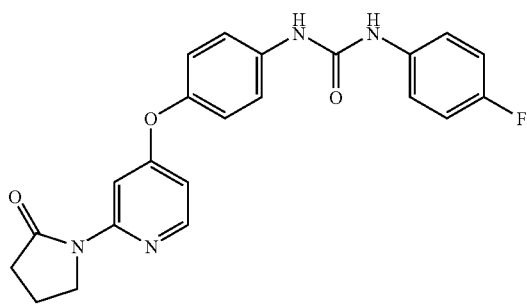
ex. 207
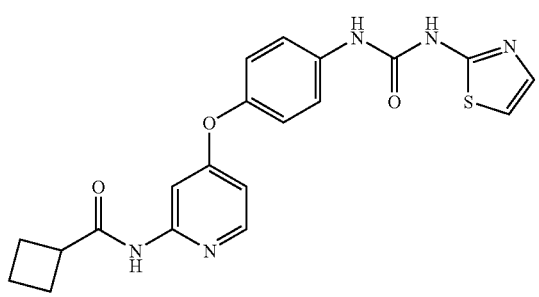
ex. 208
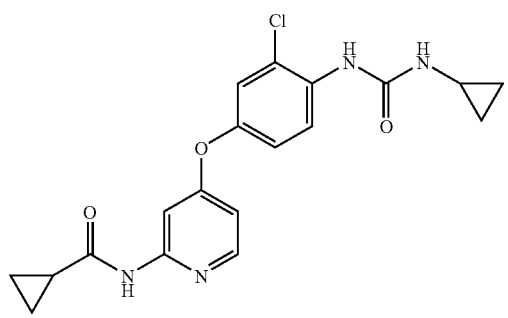

TABLE 28-continued
ex. 209
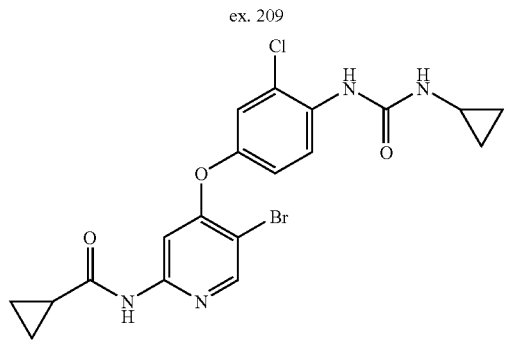
ex. 210
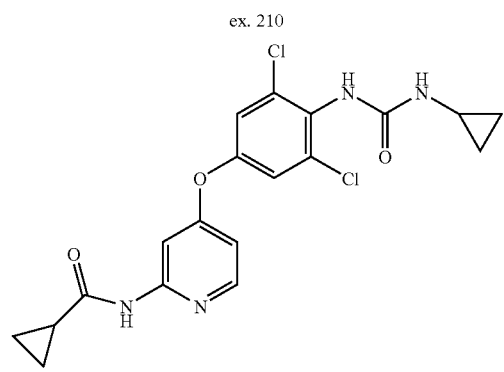
ex. 211
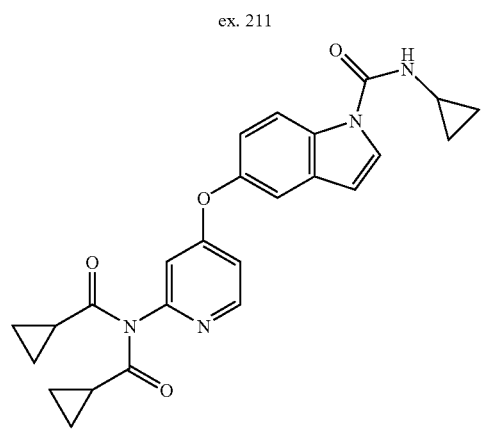
ex. 212
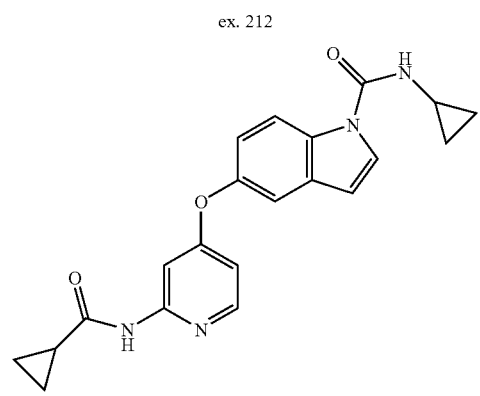

TABLE 29
ex. 213-A
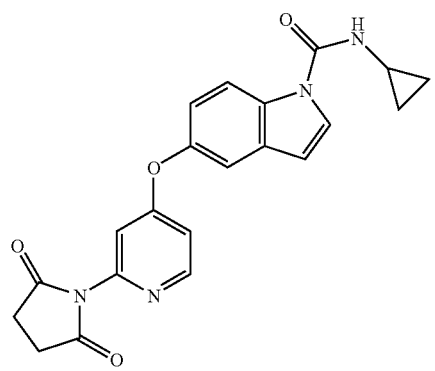
ex. 213-B
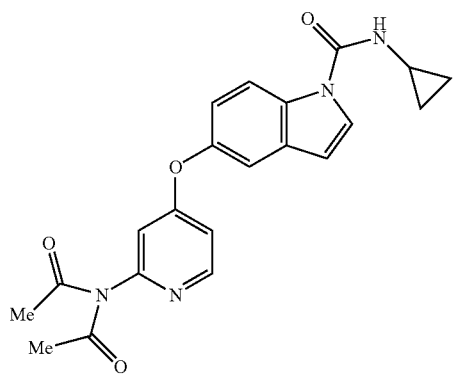
ex. 213-C
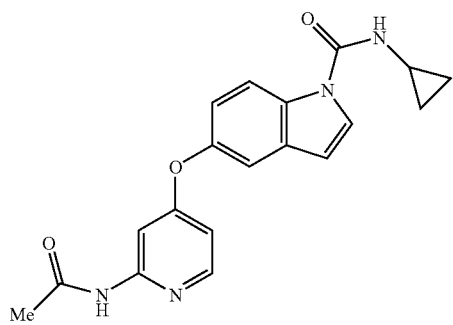
ex. 214
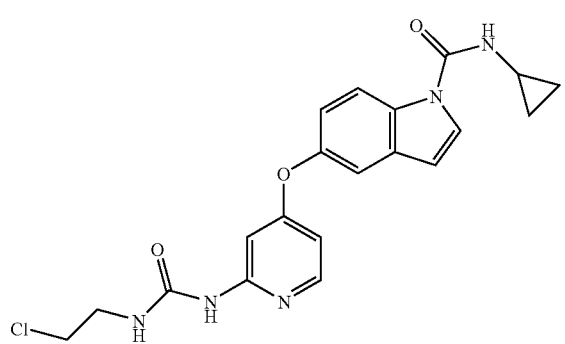

TABLE 29-continued
ex. 215
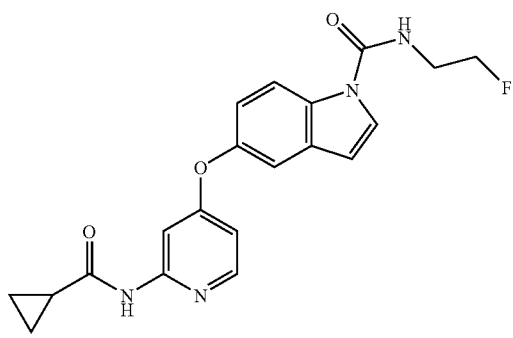
ex. 216
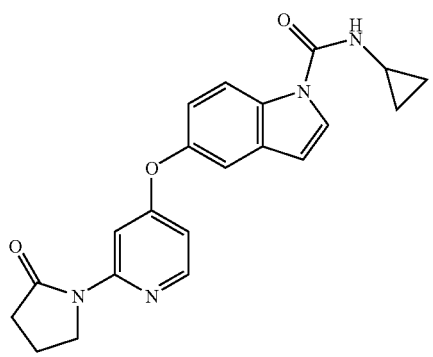
ex. 217
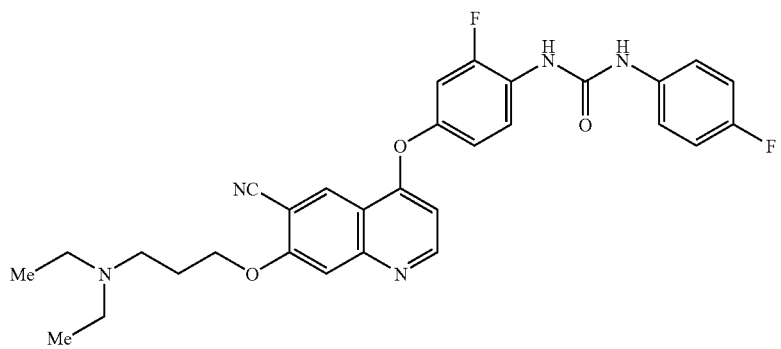
ex. 218
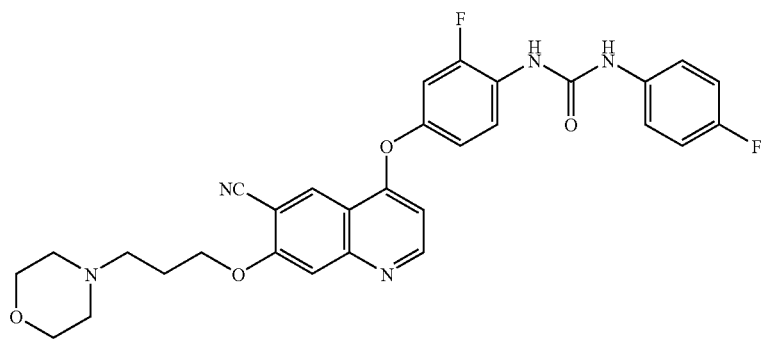

TABLE 29-continued
ex. 219
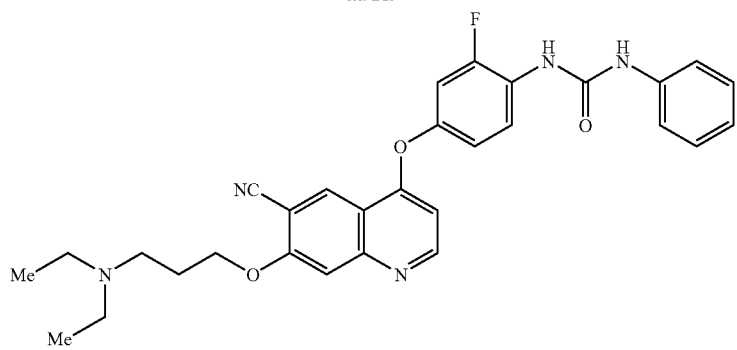
ex. 220
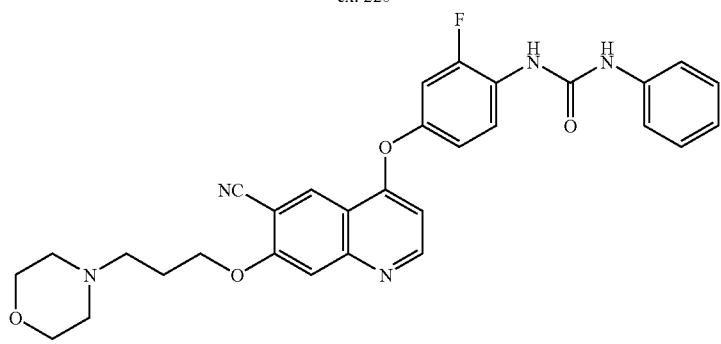
ex. 221
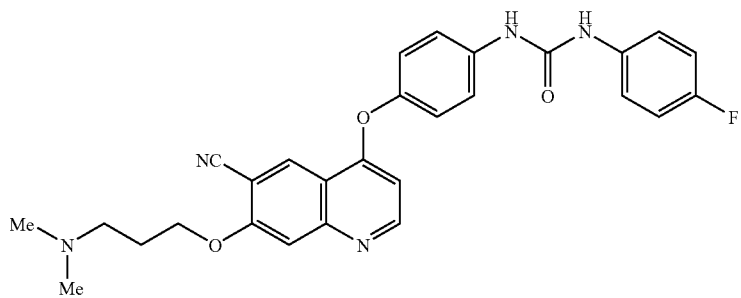
ex. 222
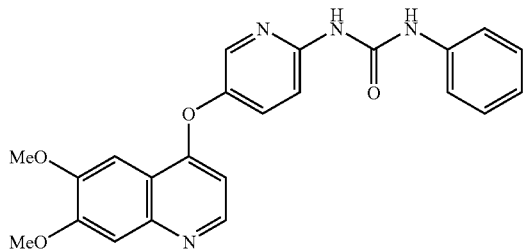
ex. 223
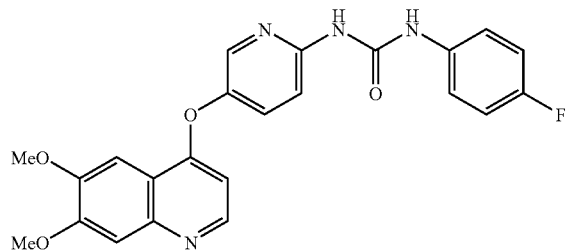

TABLE 29-continued
ex. 224
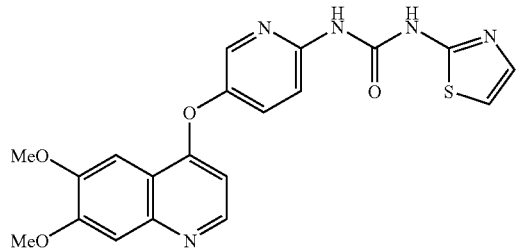
ex. 225
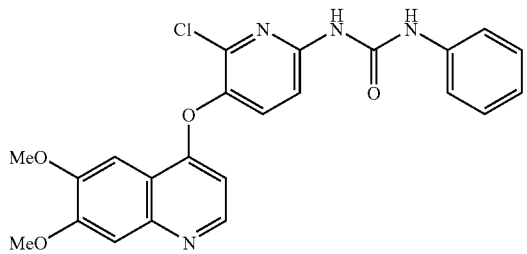
ex. 226
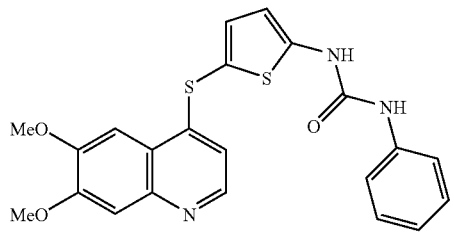
ex. 227
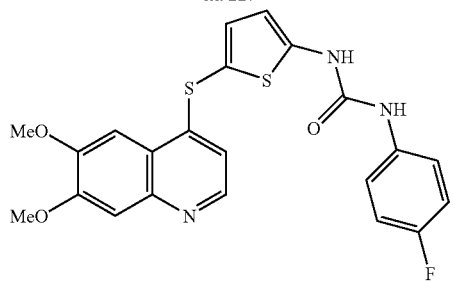
ex. 228
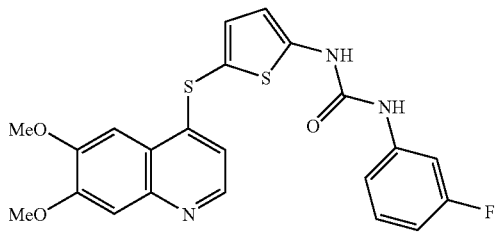
ex. 229
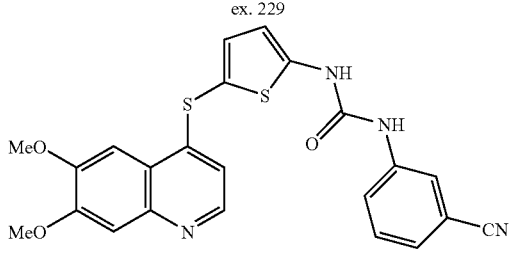

TABLE 29-continued
ex. 230
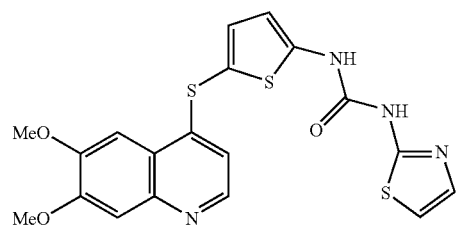
ex. 231
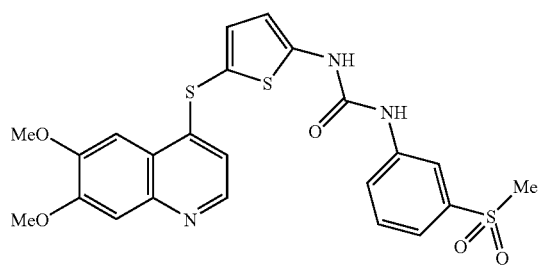
ex. 232
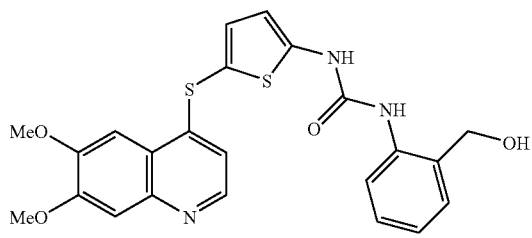
ex. 233
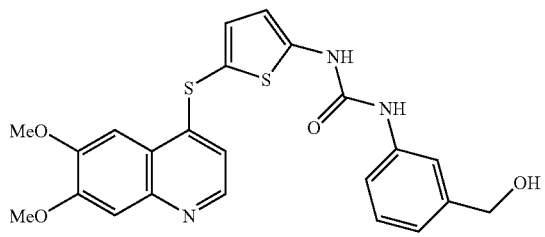
ex. 234
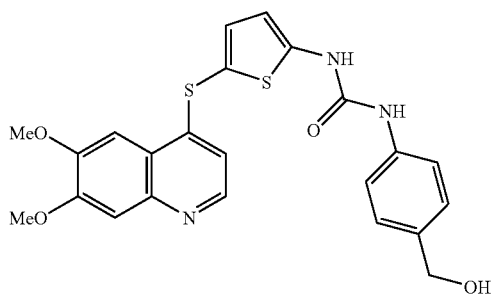

TABLE 30
ex. 235
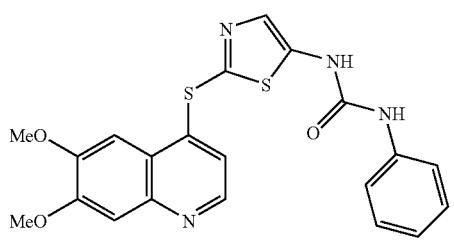
ex. 236
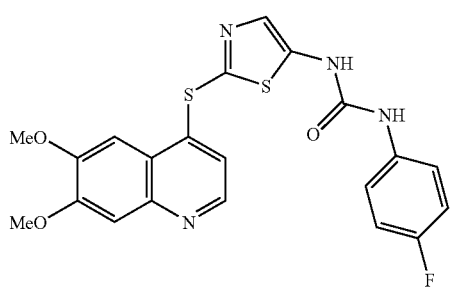
ex. 237
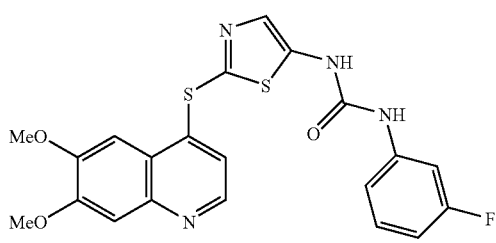
ex. 238
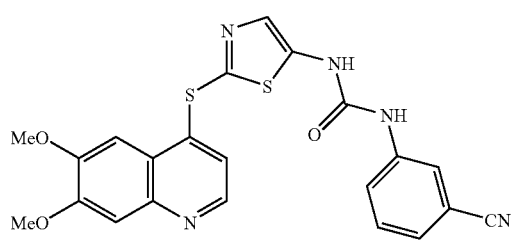
ex. 239
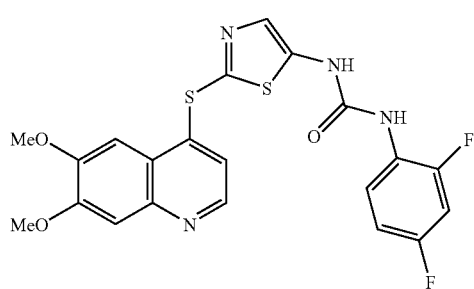

TABLE 30-continued
ex. 240
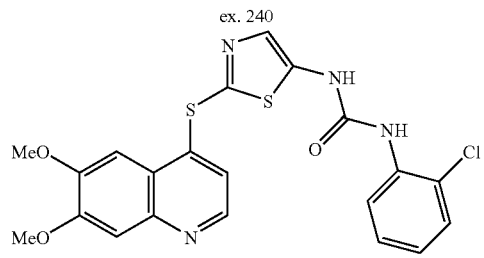
ex. 241
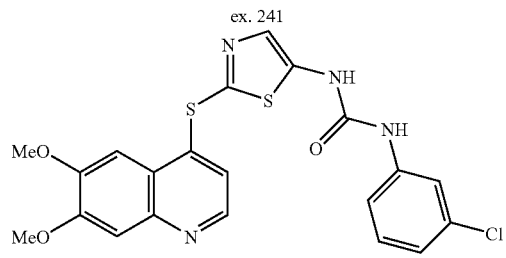
ex. 242
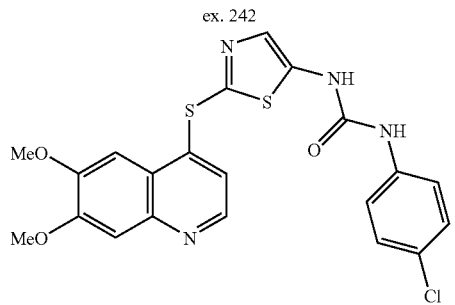
ex. 243
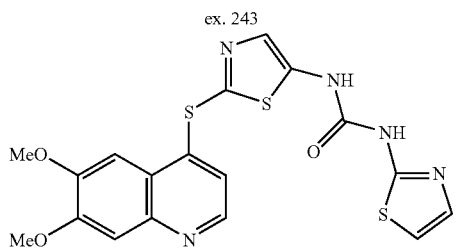
ex. 244
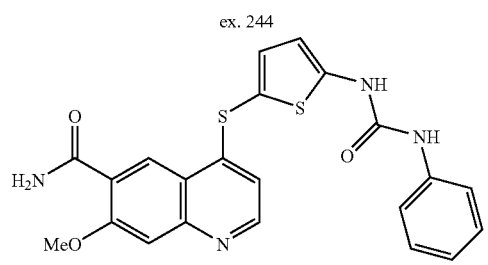
ex. 245
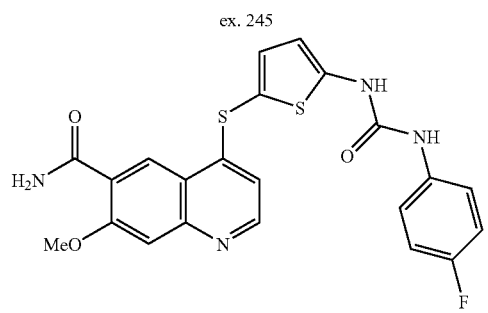

TABLE 30-continued
ex. 246
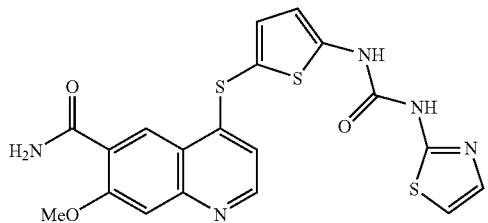
ex. 247
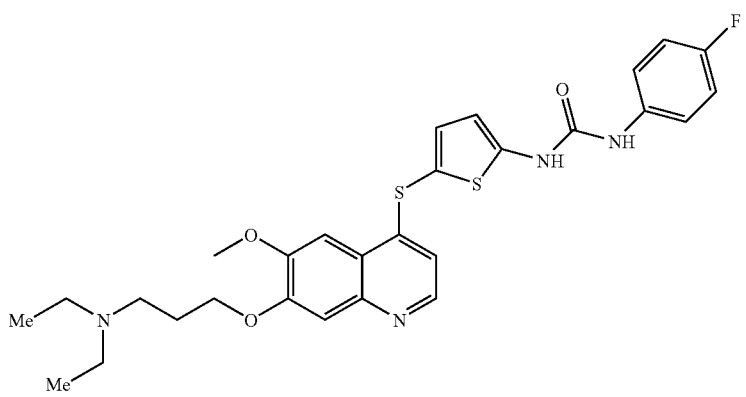
ex. 248
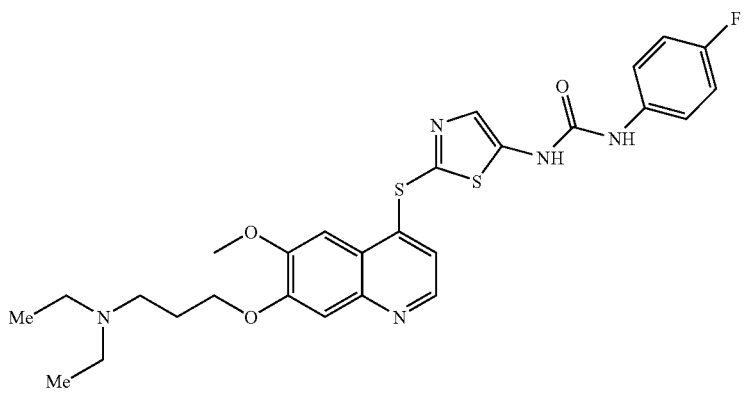
ex. 249
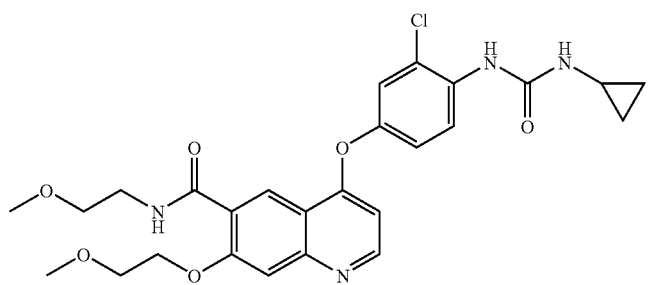

TABLE 30-continued
ex. 250
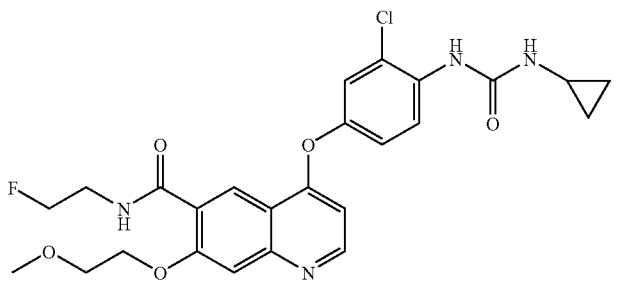
ex. 251
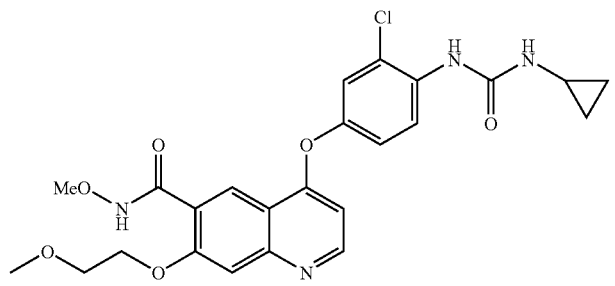
ex. 252
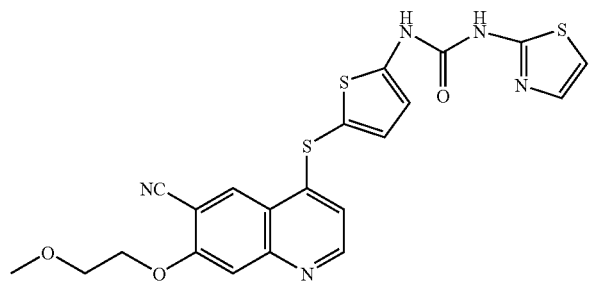
ex. 253
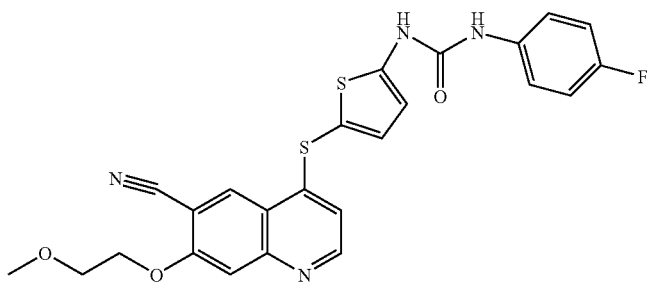
ex. 254
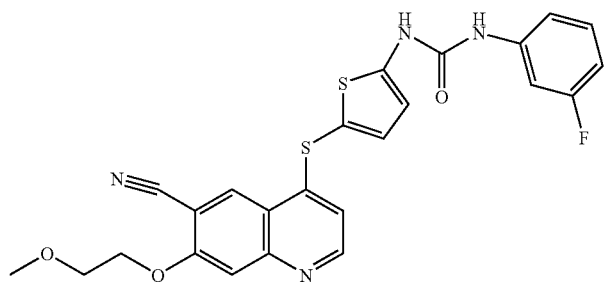

TABLE 30-continued
ex. 255
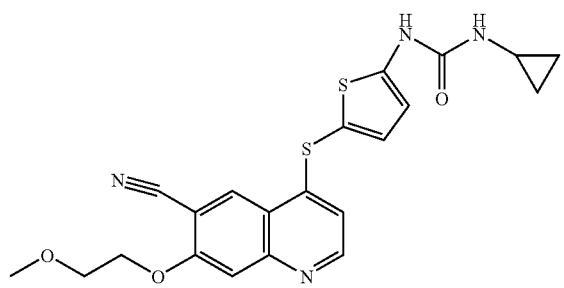
ex. 256
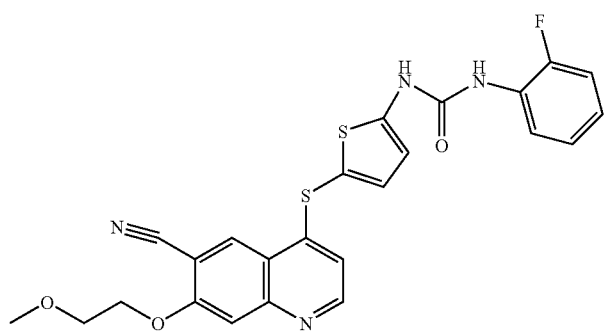
ex. 257
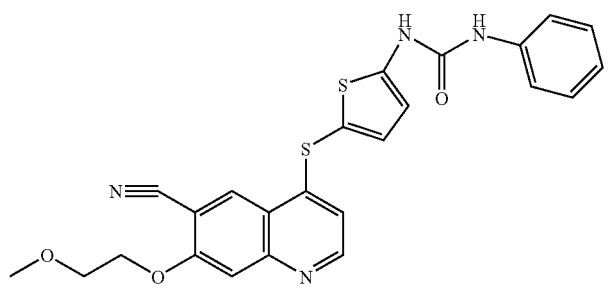
ex. 258
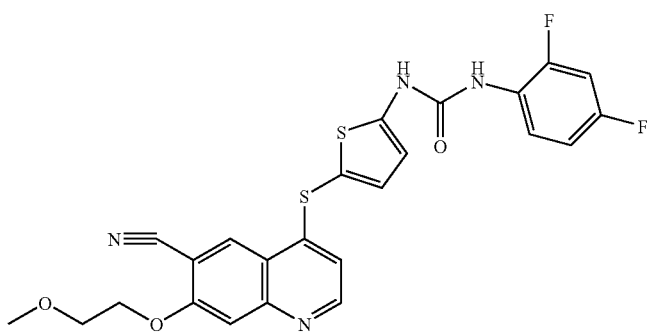

TABLE 31
ex. 259
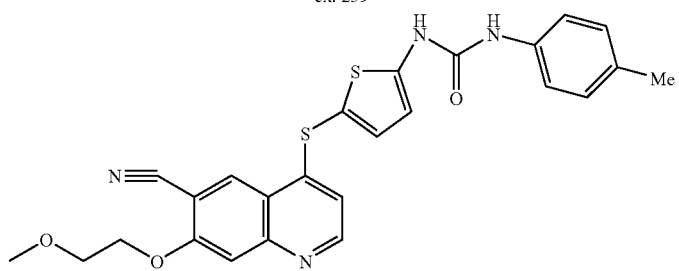
ex. 260
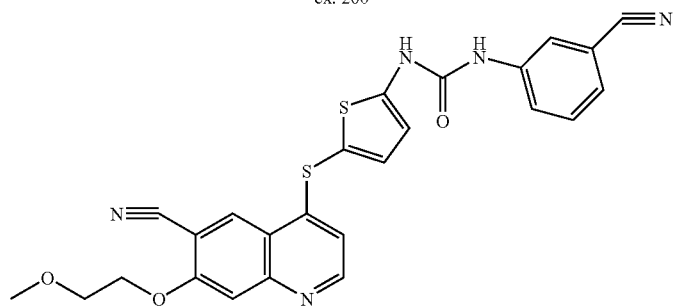
ex. 261
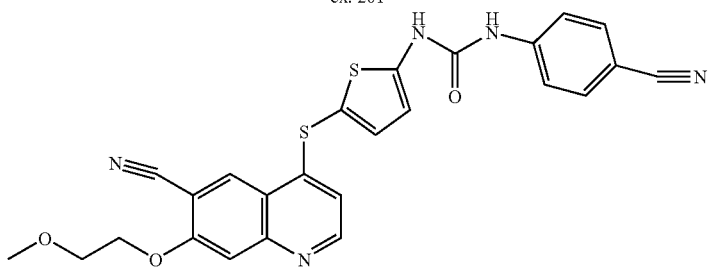
ex. 262
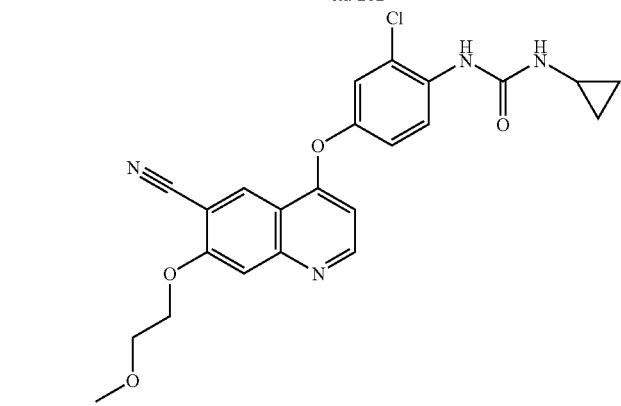
ex. 263
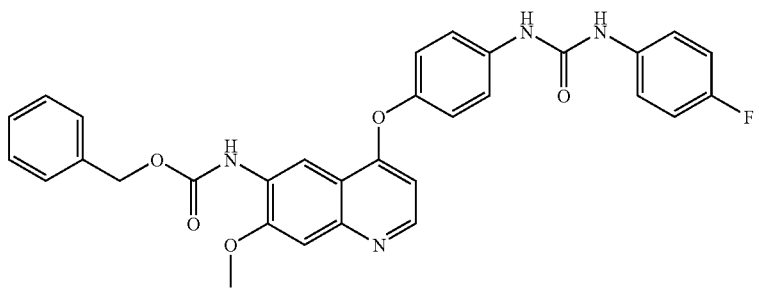

TABLE 31-continued
ex. 264
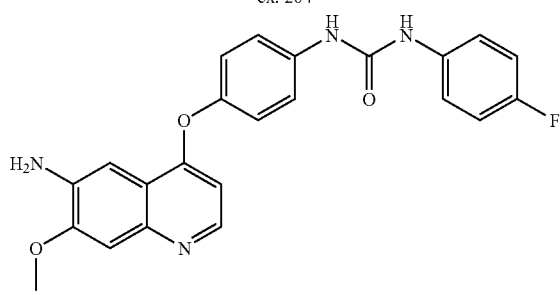
ex. 265
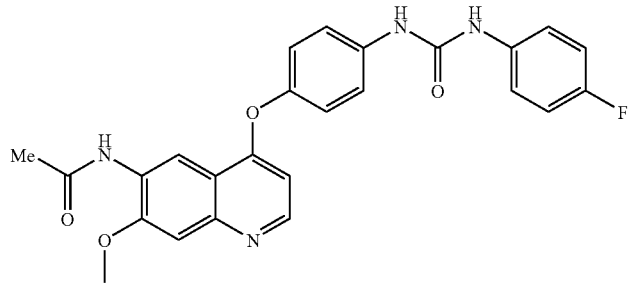
ex. 266
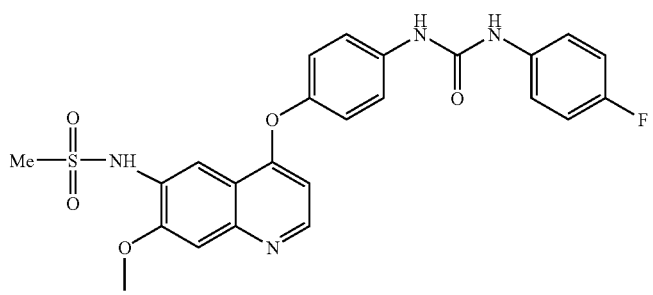
ex. 267
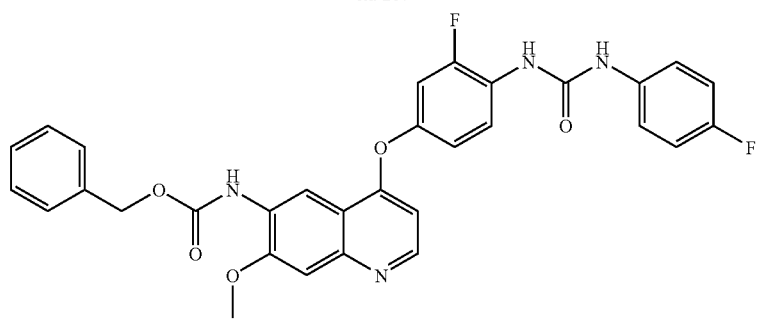
ex. 268
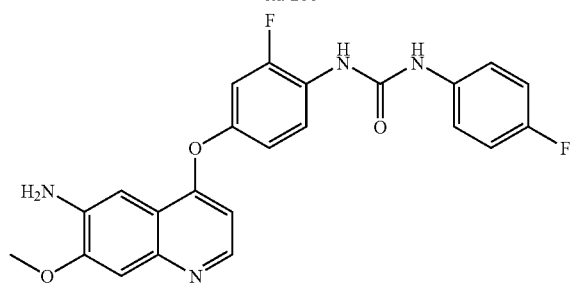

TABLE 31-continued
ex. 269
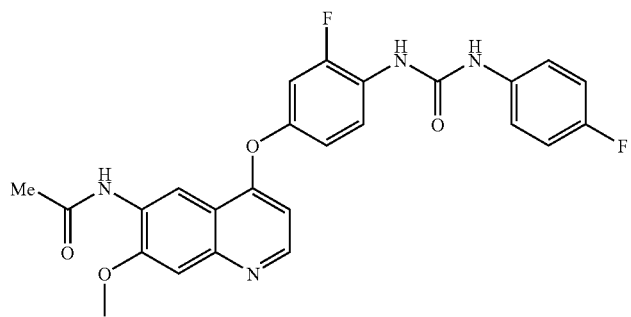
ex. 270
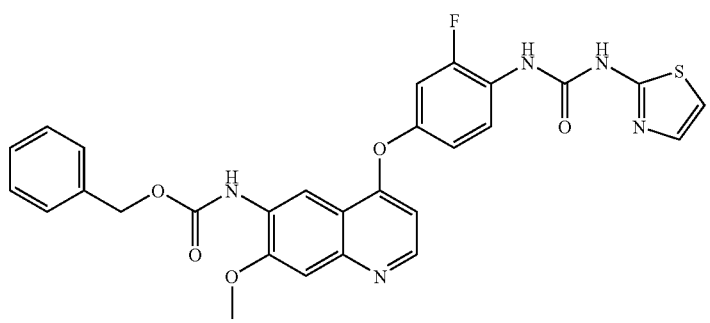
ex. 271
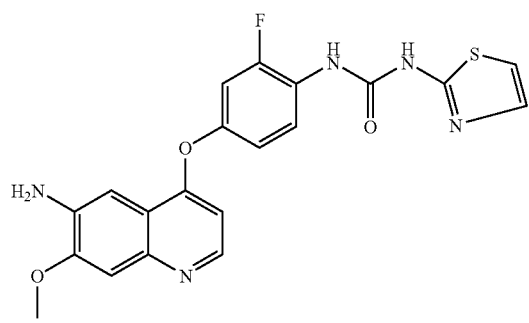
ex. 272
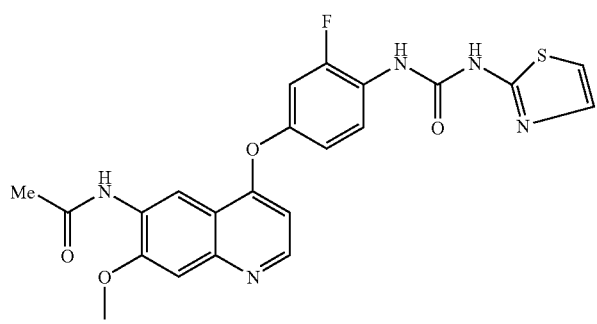

TABLE 31-continued
ex. 273
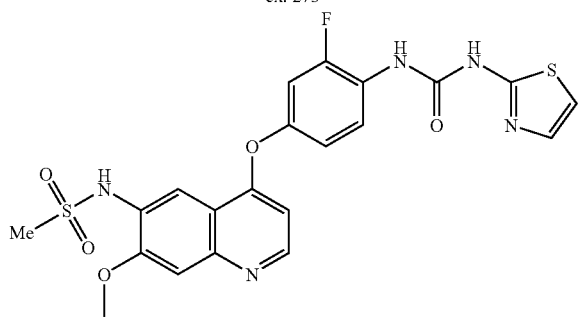
ex. 274
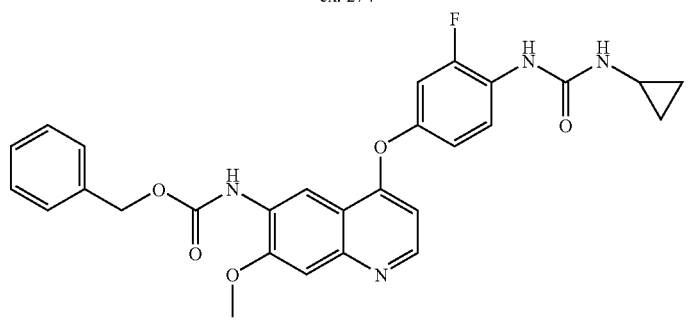
ex. 275
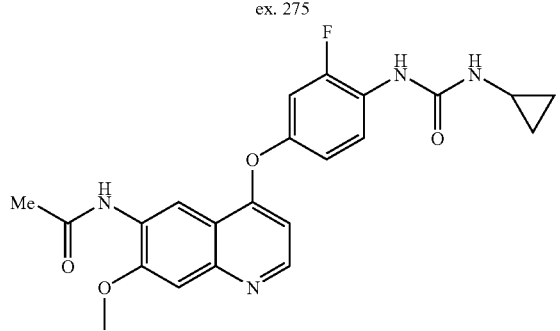
ex. 276
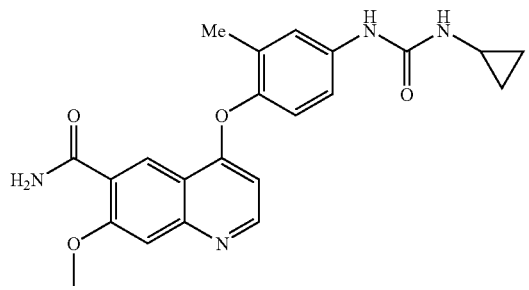
ex. 277
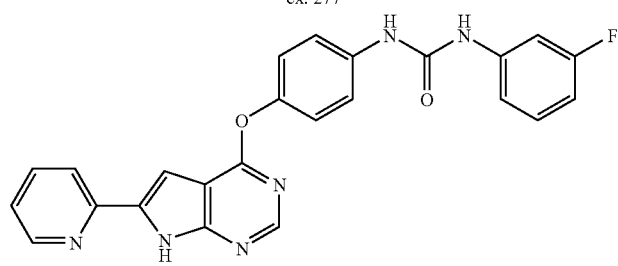

TABLE 31-continued
ex. 278
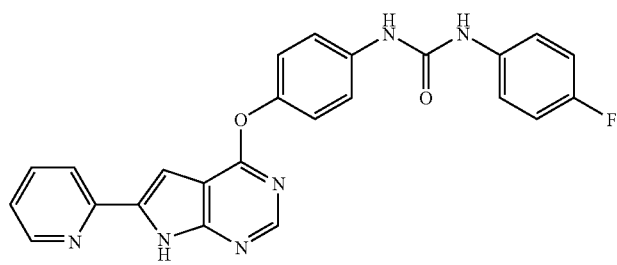
ex. 279
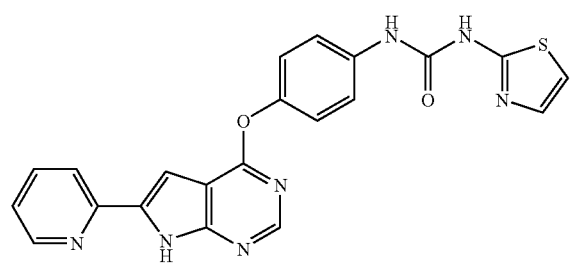
ex. 280
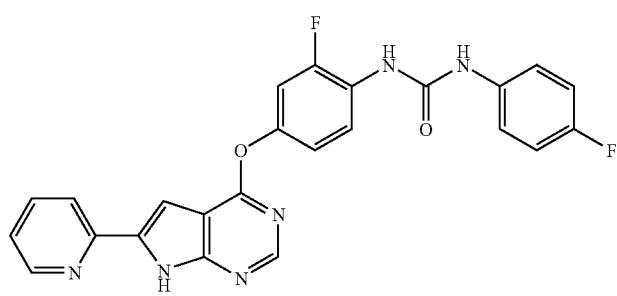
ex. 281
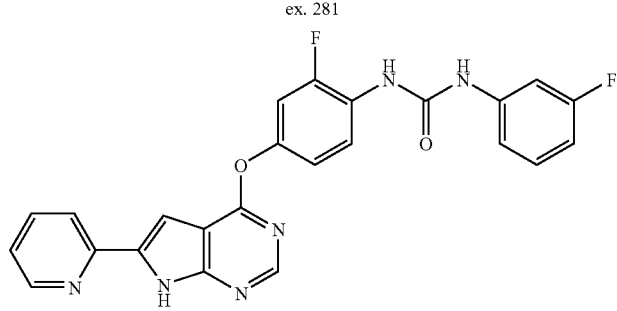
ex. 282
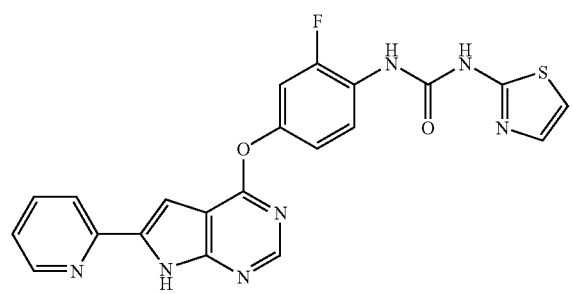

TABLE 32
ex. 283
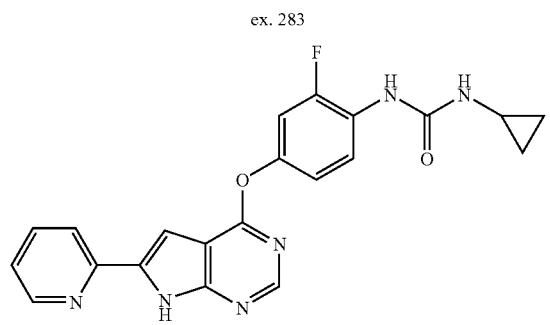
ex. 284
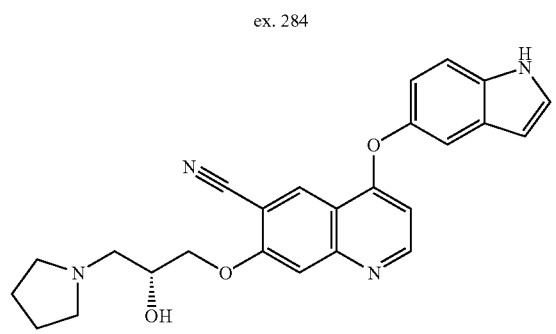
ex. 285
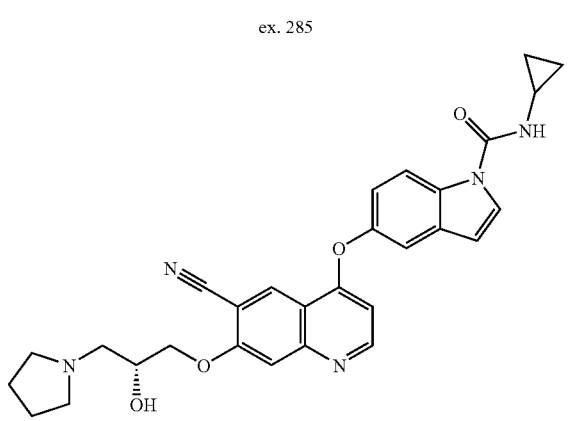
ex. 286
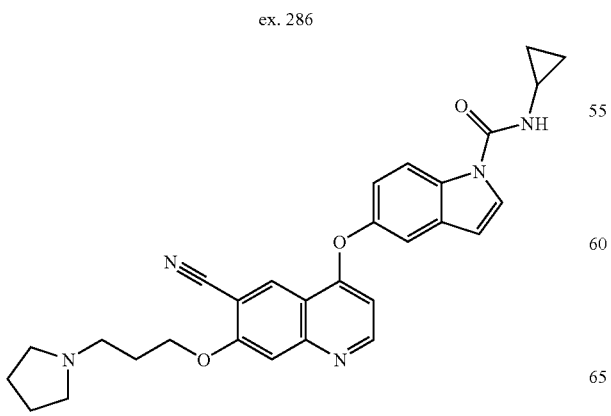
TABLE 32-continued
ex. 287
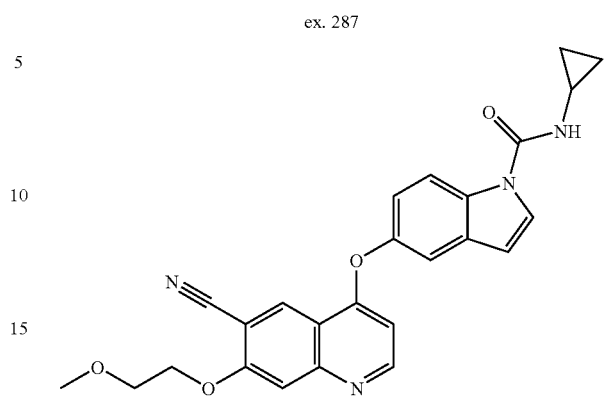
ex. 288
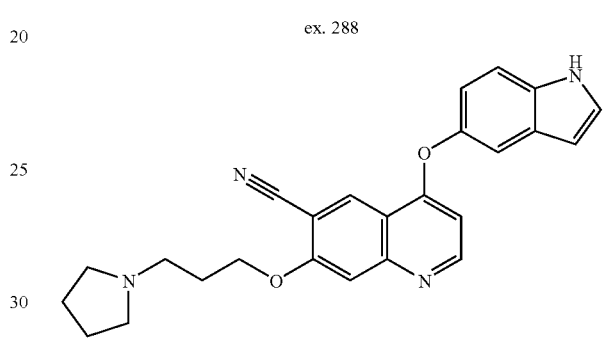
ex. 289
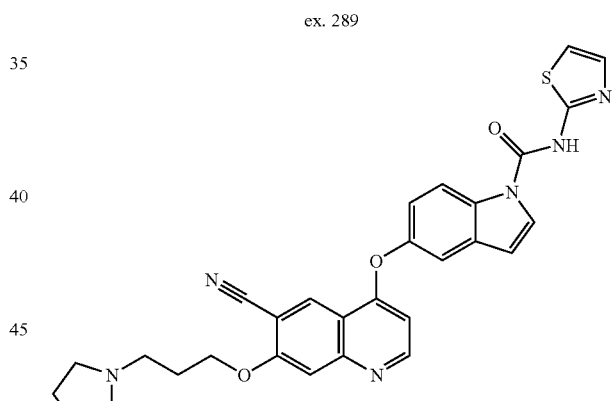
ex. 290
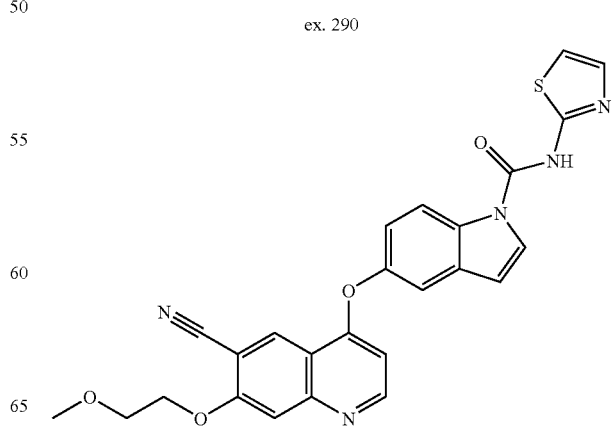

TABLE 32-continued
ex. 291
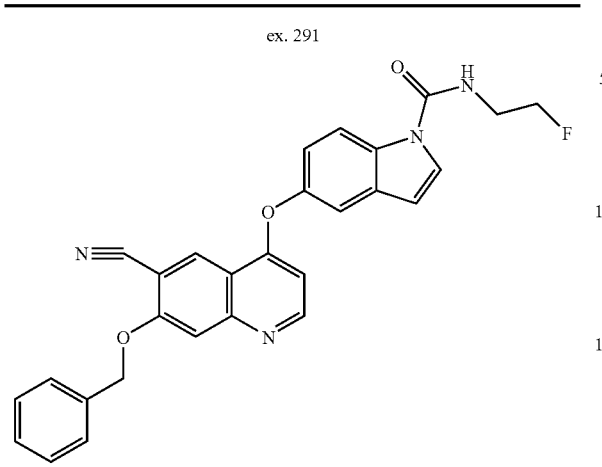
ex. 292
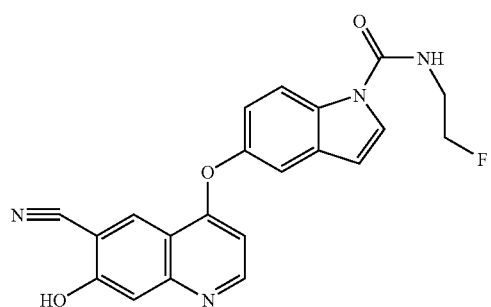
ex. 293
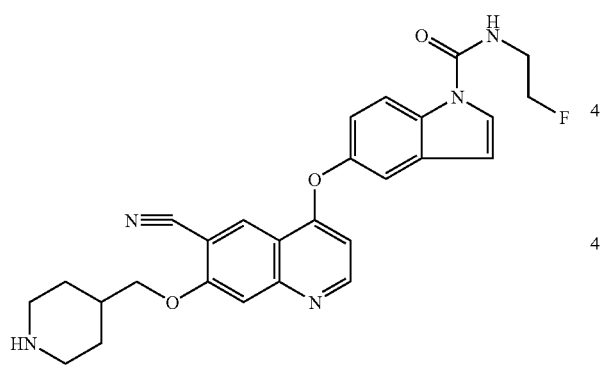
ex. 294
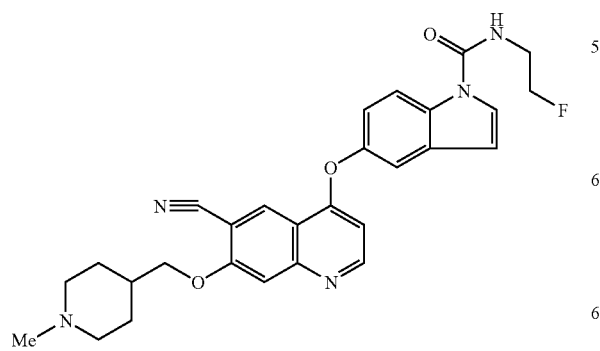
TABLE 32-continued
ex. 295
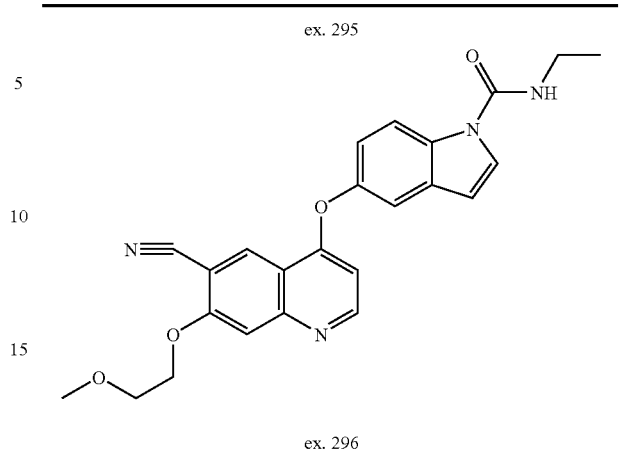
ex. 296
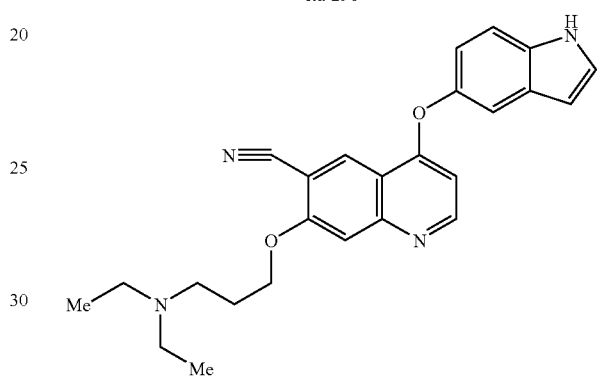
ex. 297
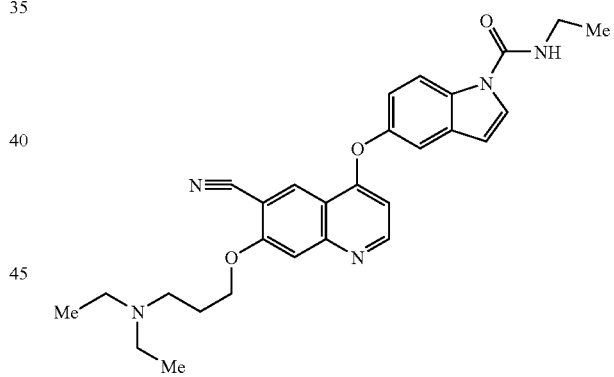
ex. 298
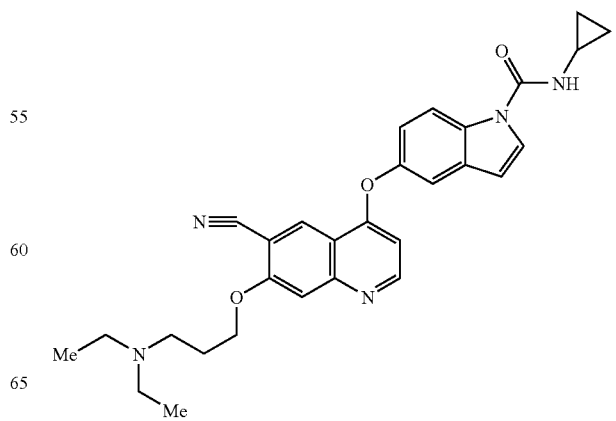

TABLE 32-continued
ex. 299
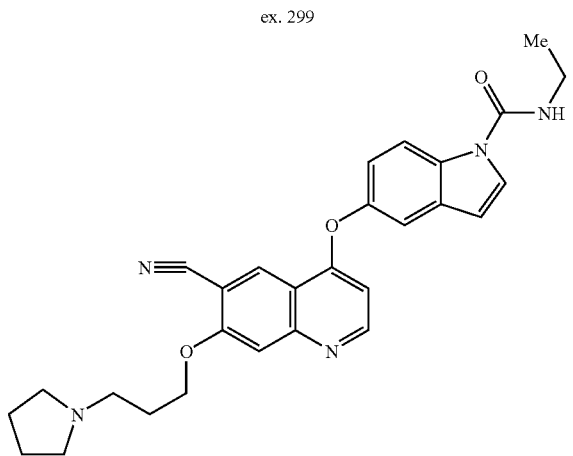
ex. 300
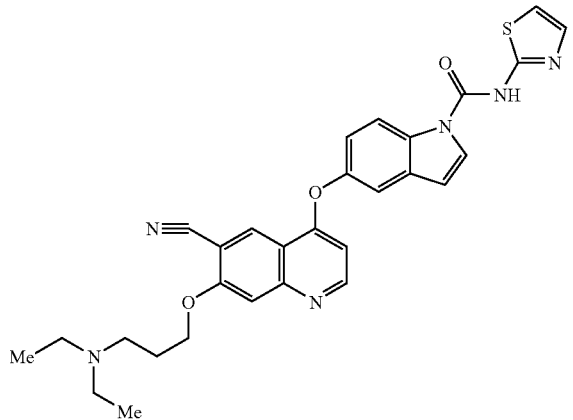
ex. 301
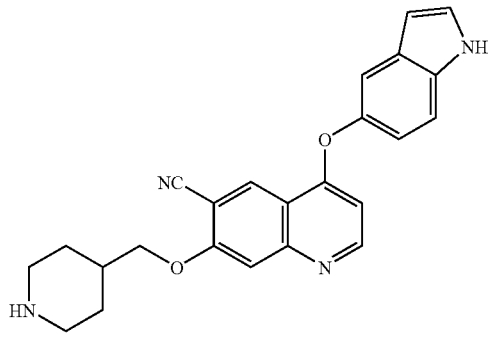
ex. 302
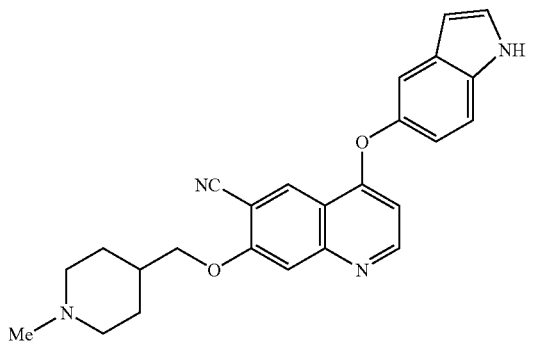
TABLE 32-continued
ex. 303
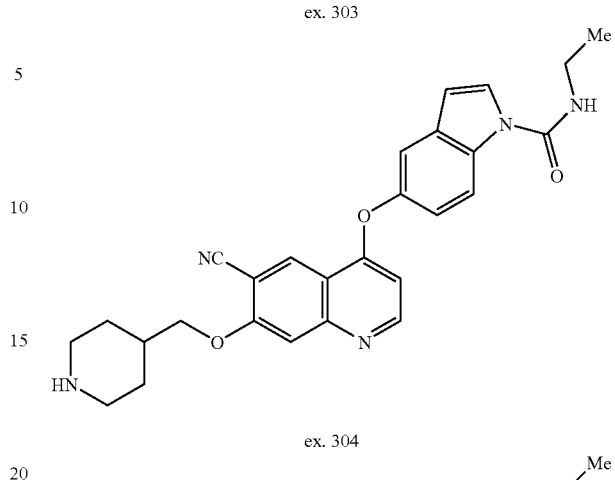
ex. 304
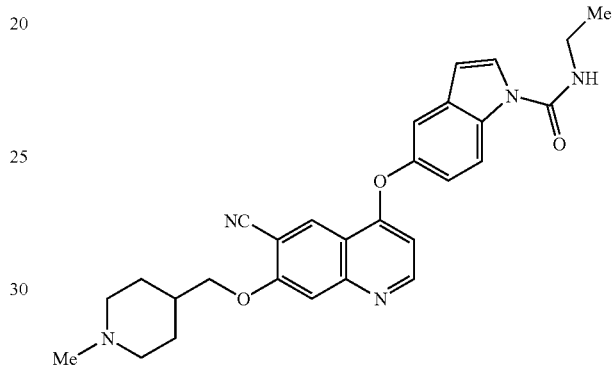
ex. 305
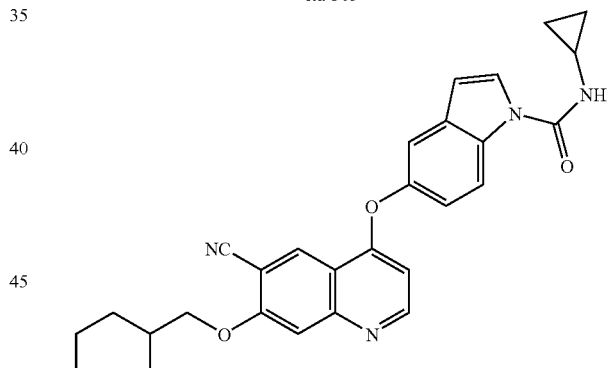
ex. 306
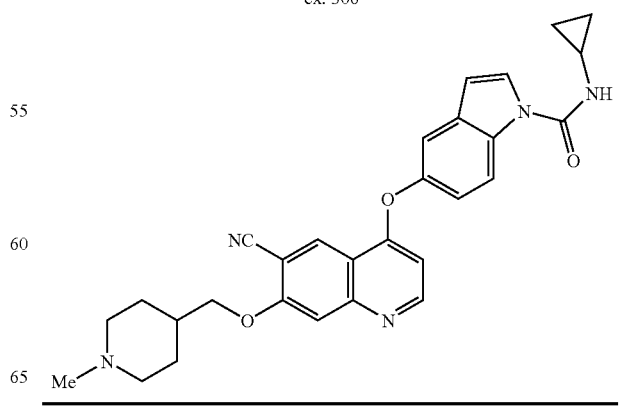

TABLE 33
ex. 307
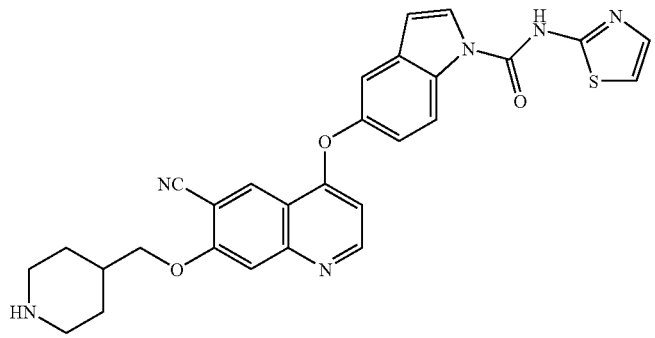
ex. 308
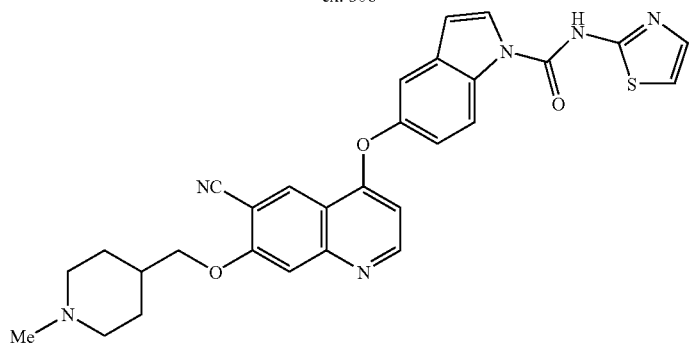
ex. 309
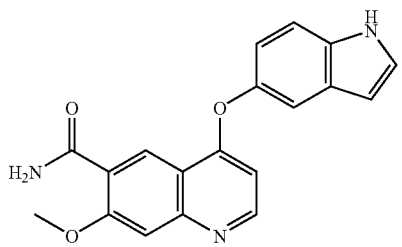
ex. 310
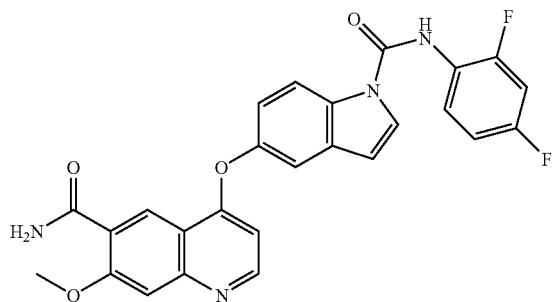
ex. 311
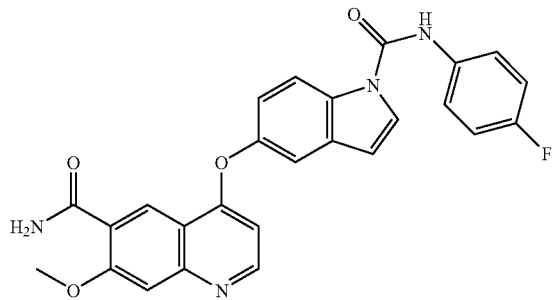

TABLE 33-continued
ex. 312
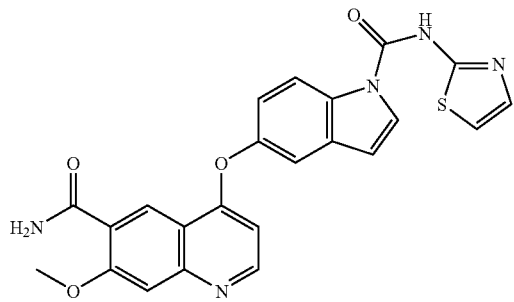
ex. 313
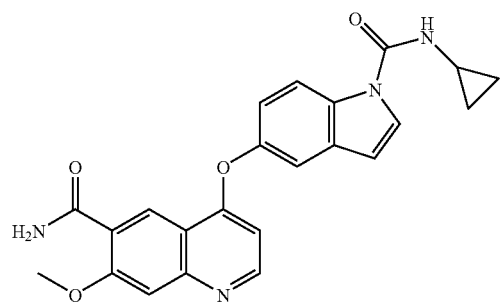
ex. 314
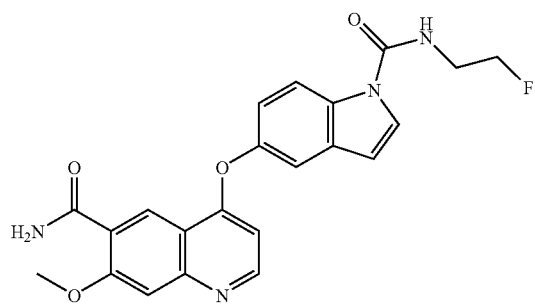
ex. 315
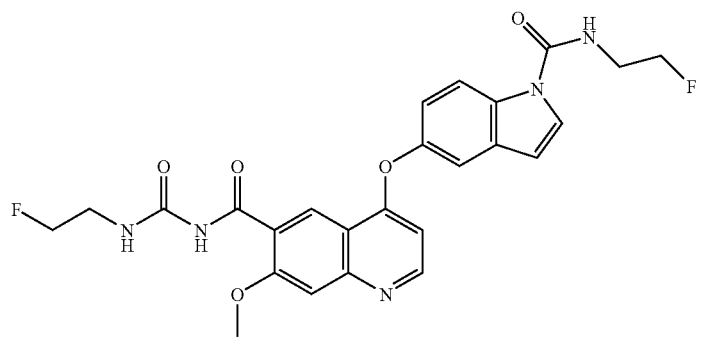

TABLE 33-continued
ex. 316
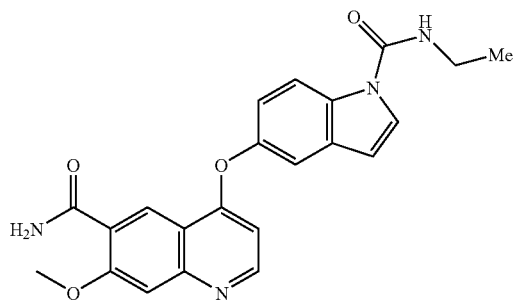
ex. 317
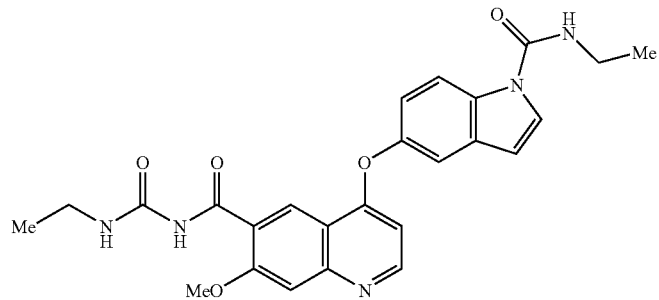
ex. 318
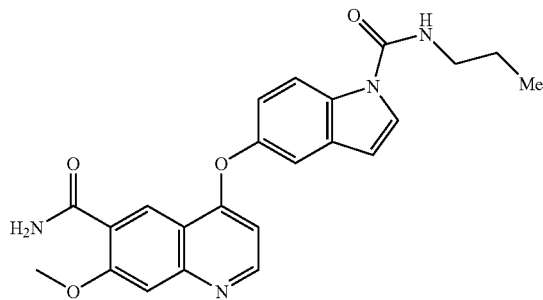
ex. 319
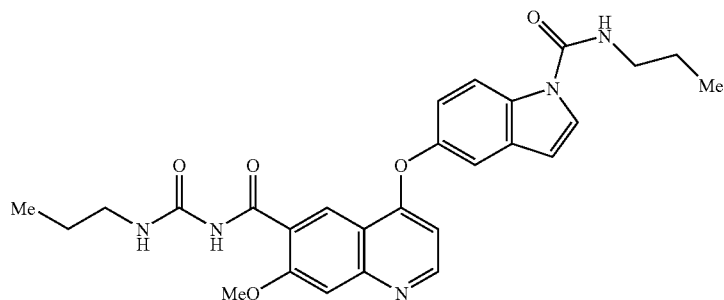
ex. 320
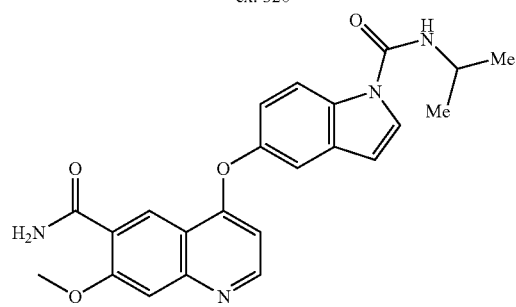

TABLE 33-continued
ex. 321
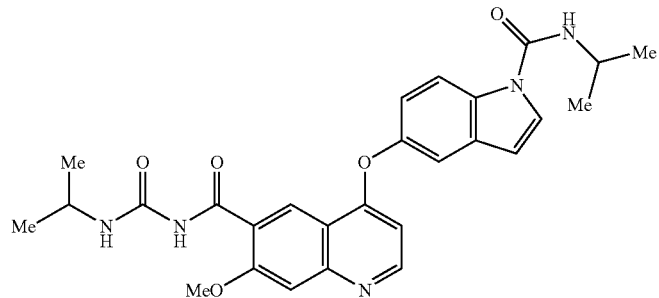
ex. 322
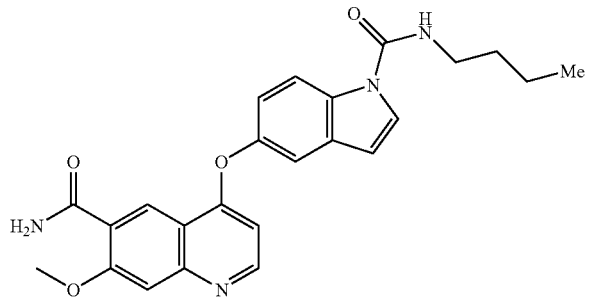
ex. 323
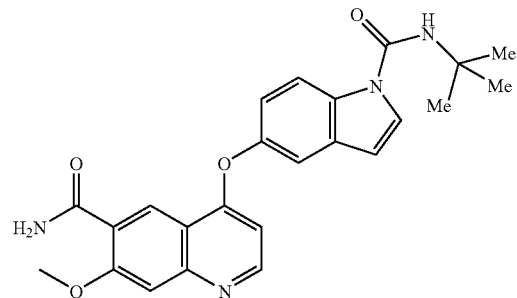
ex. 324
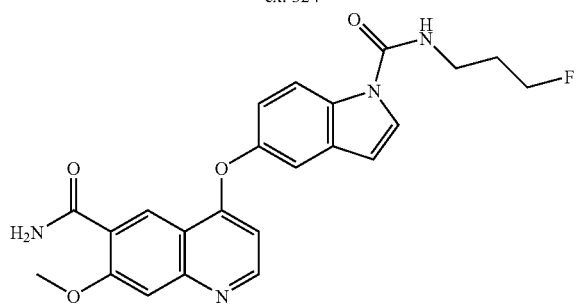
ex. 325
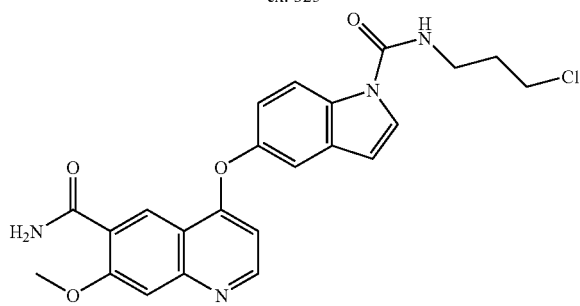

TABLE 33-continued
ex. 326
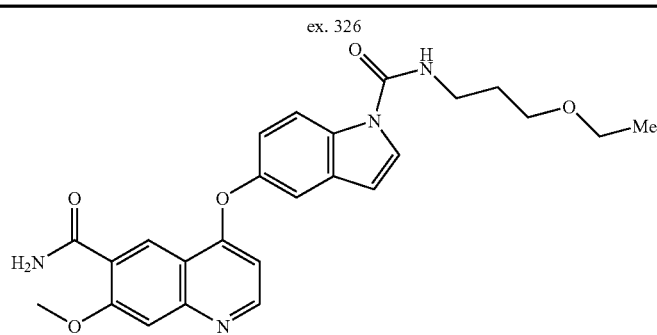
ex. 327
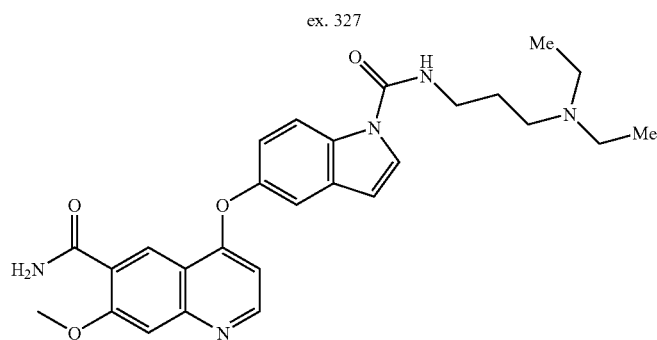
ex. 328
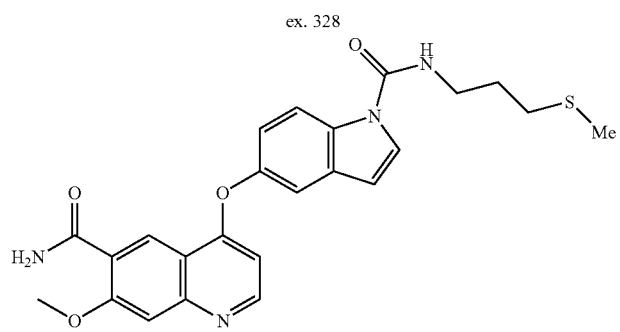
ex. 329
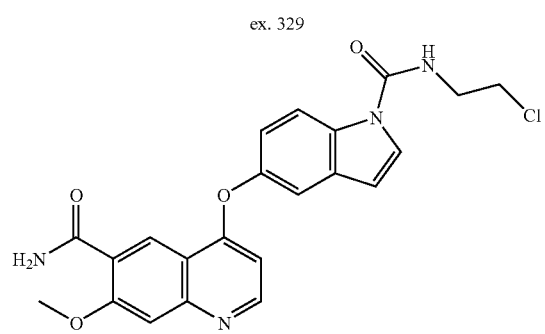
ex. 330
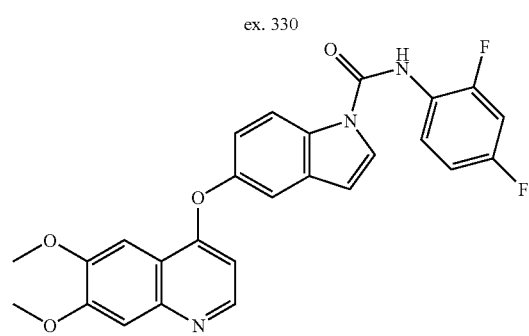

TABLE 34
ex. 331-1
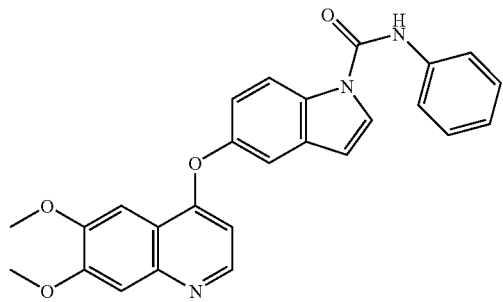
ex. 331-2
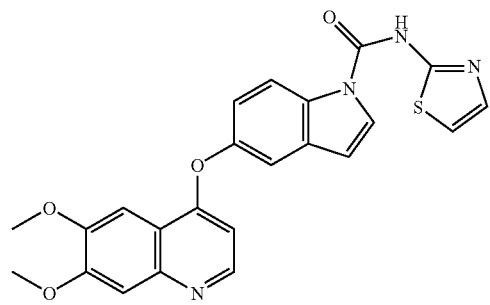
ex. 332
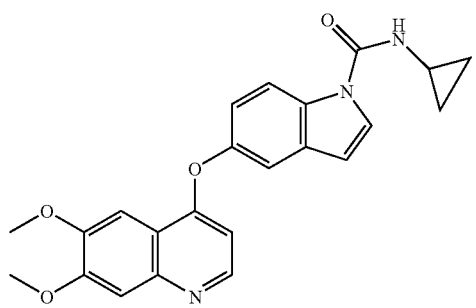
ex. 333
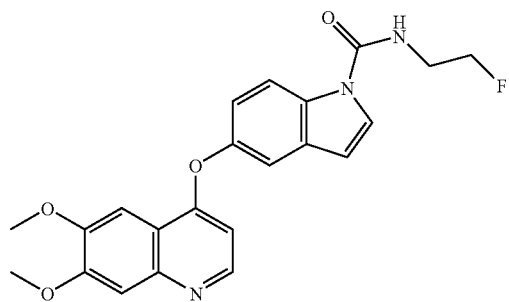

TABLE 34-continued
ex. 334
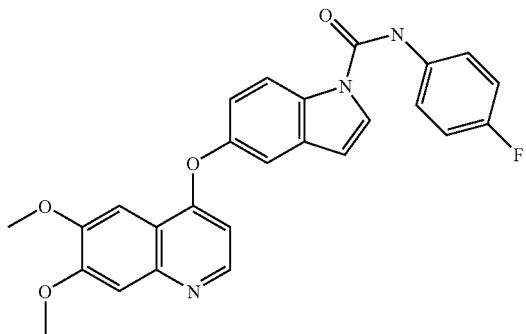
ex. 335
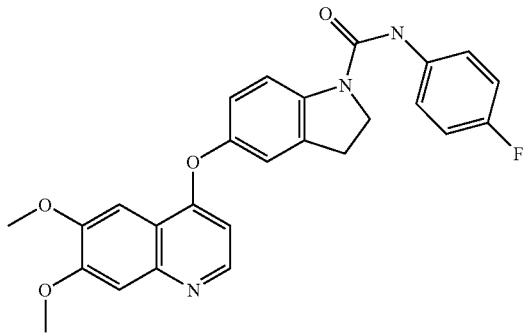
ex. 336
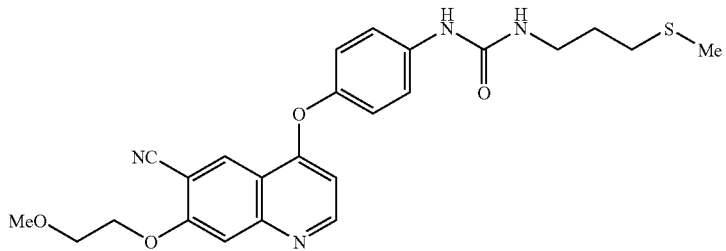
ex. 337
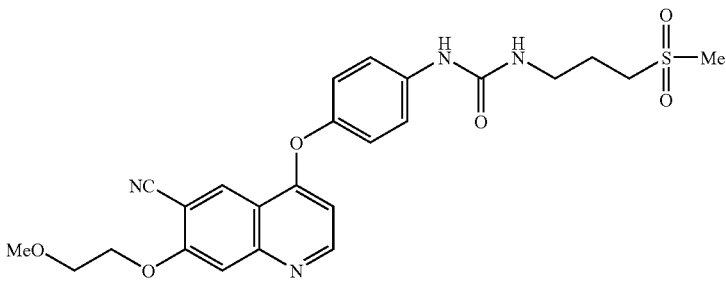
ex. 338
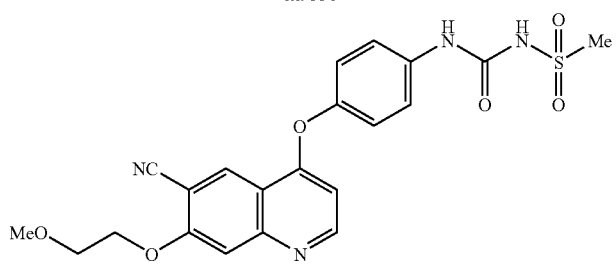

TABLE 34-continued
ex. 339
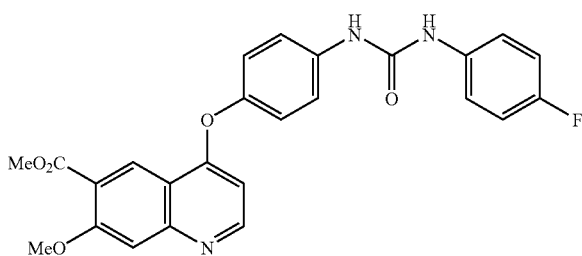
ex. 340
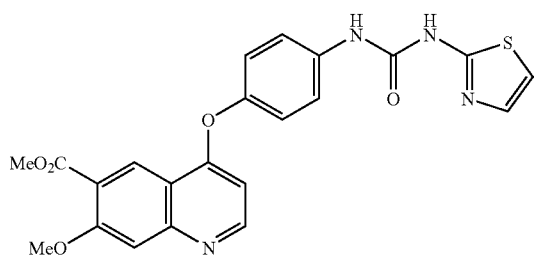
ex. 341
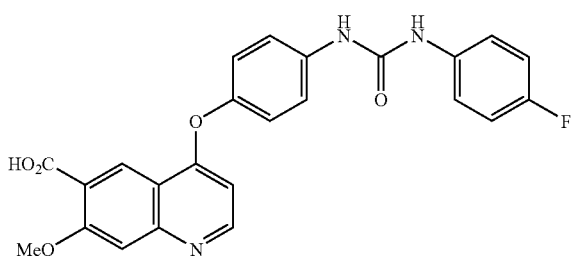
ex. 342
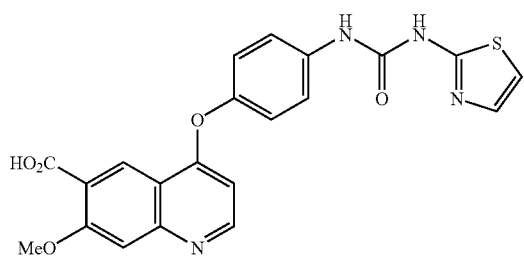
ex. 343
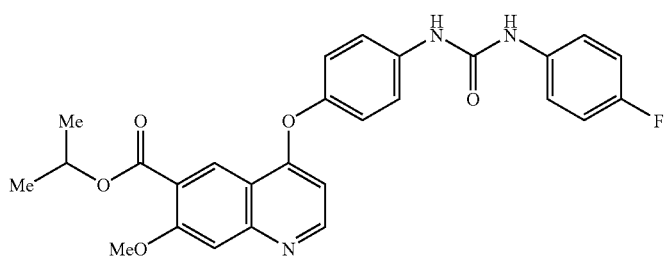

TABLE 34-continued
ex. 344
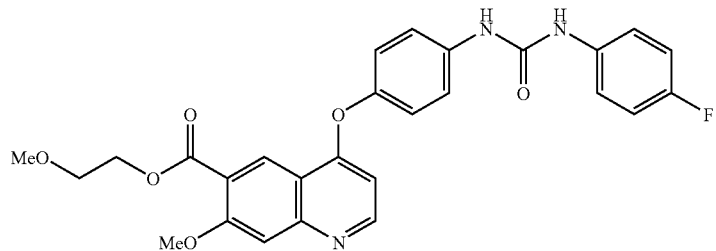
ex. 345
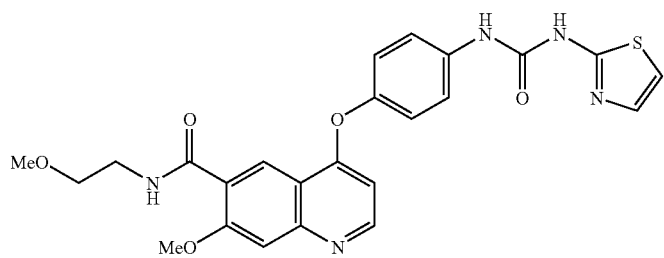
ex. 346
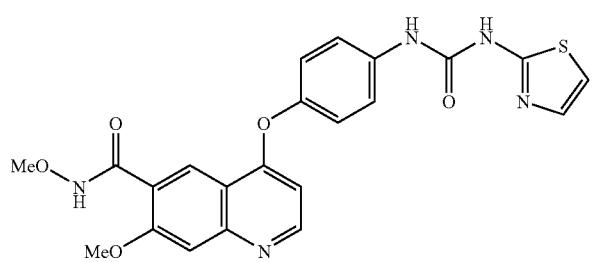
ex. 347
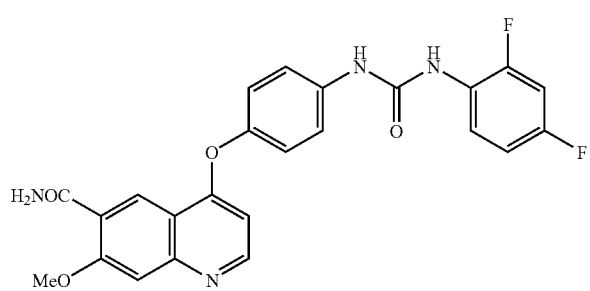
ex. 348
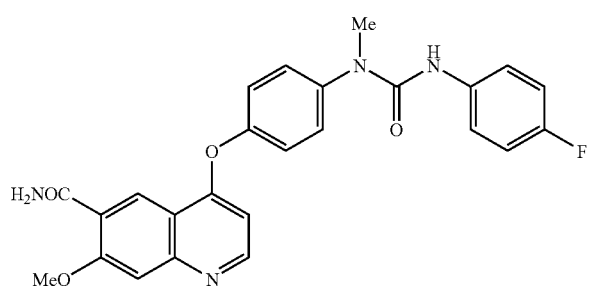

TABLE 34-continued
ex. 349
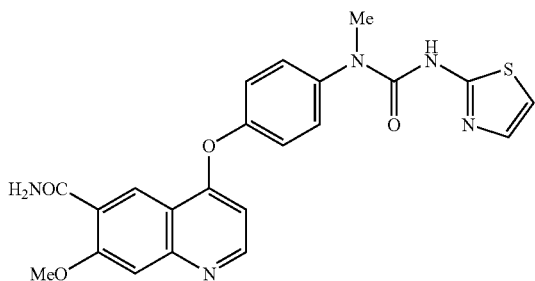
ex. 350
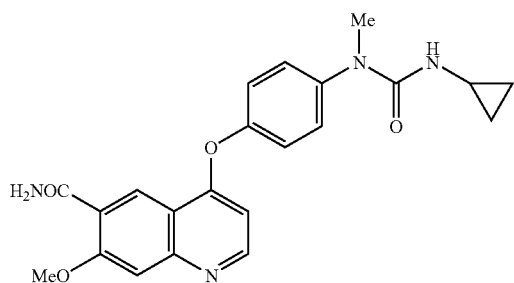
ex. 351
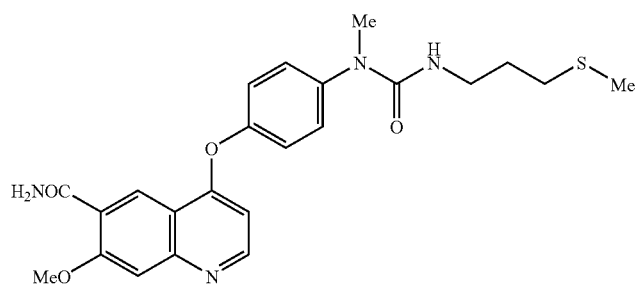
ex. 352
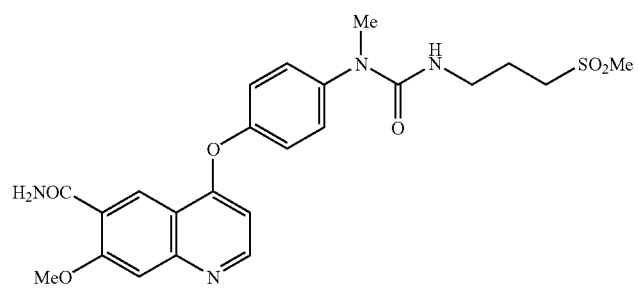
ex. 353
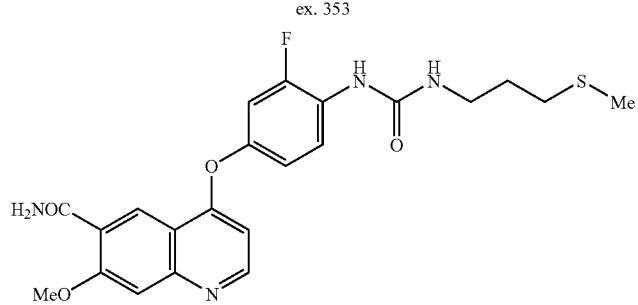

TABLE 34-continued
ex. 354
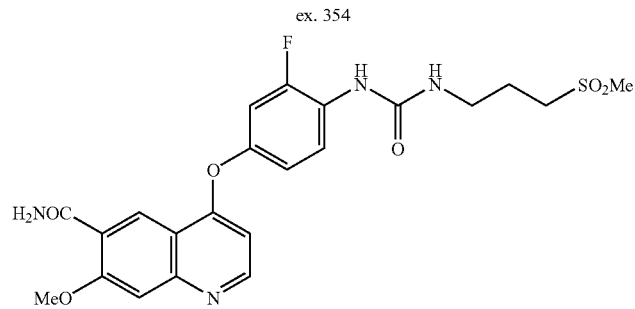
TABLE 35
ex. 355
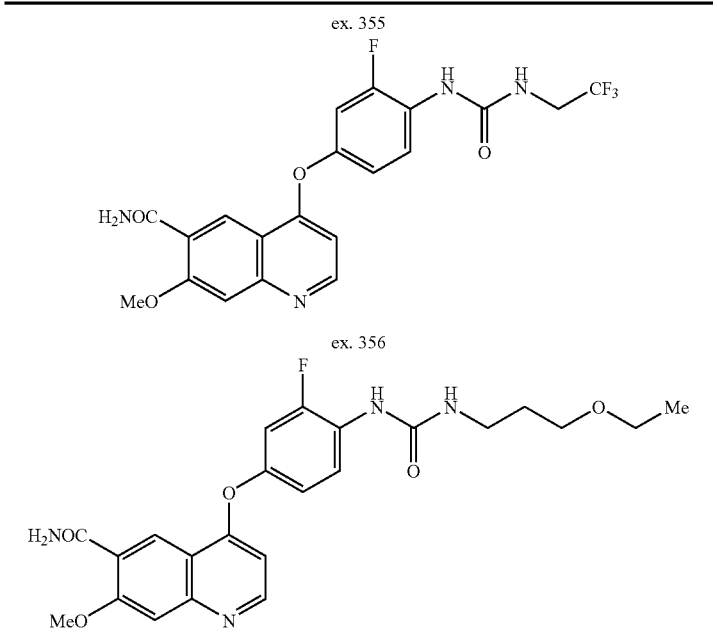
ex. 356
ex. 357
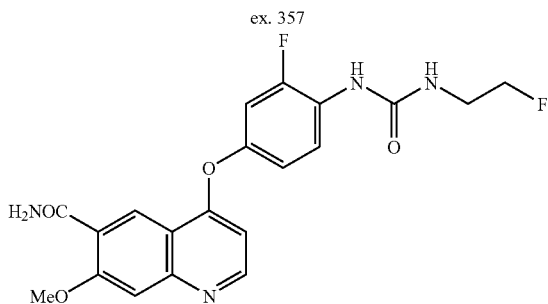
ex. 358
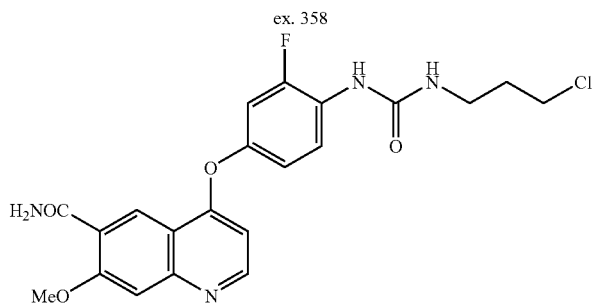

TABLE 35-continued
ex. 359
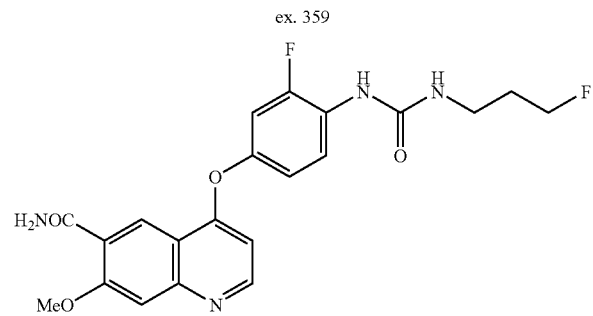
ex. 360
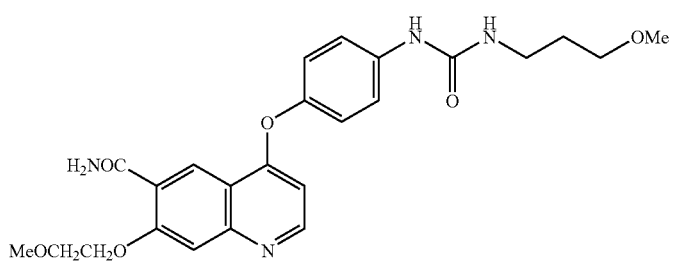
ex. 361
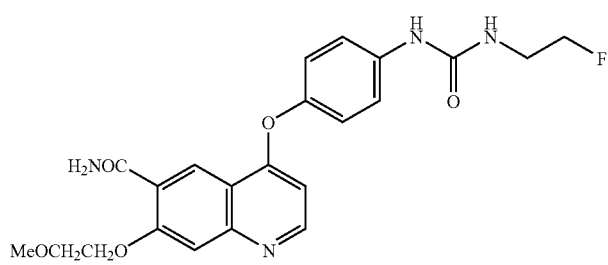
ex. 362
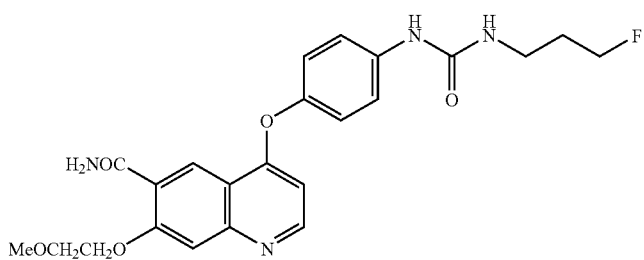
ex. 363
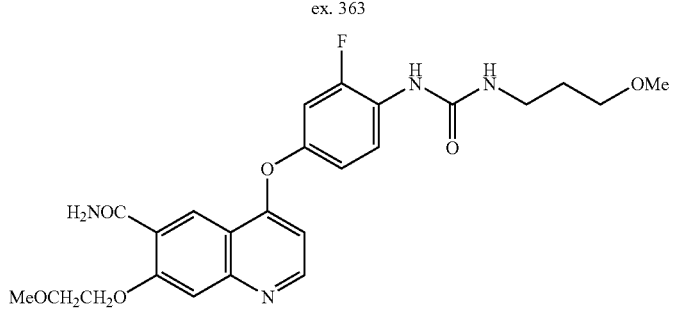

TABLE 35-continued
ex. 364
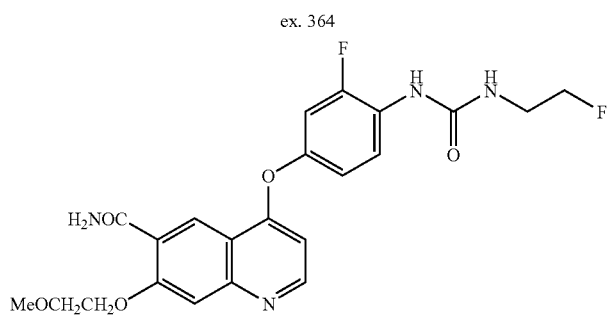
ex. 365
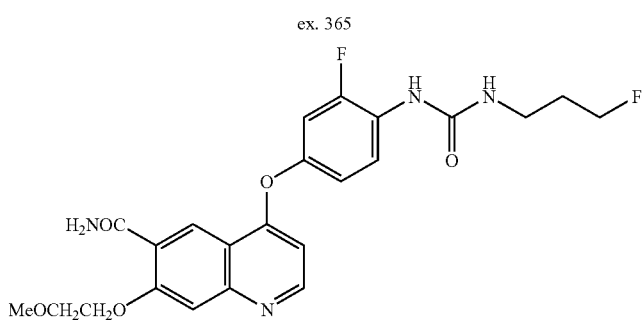
ex. 366
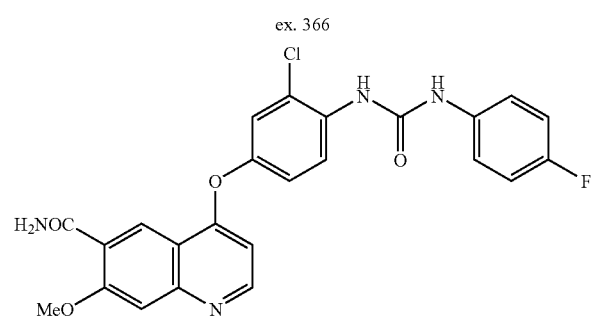
ex. 367
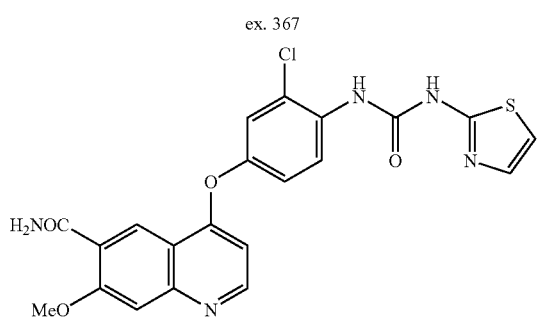
ex. 368
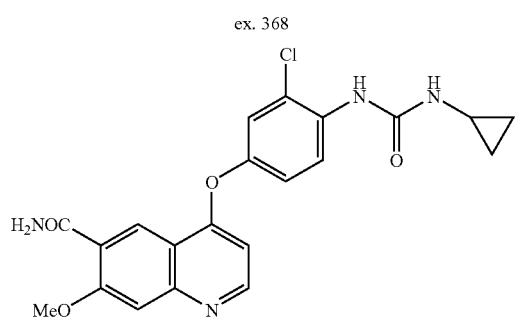

TABLE 35-continued
ex. 369
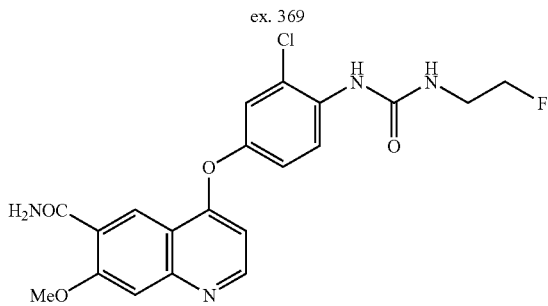
ex. 370
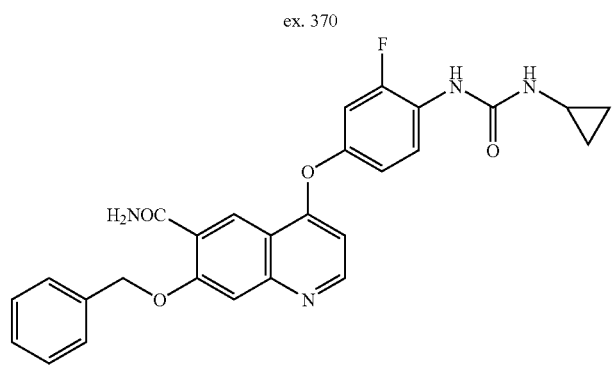
ex. 371
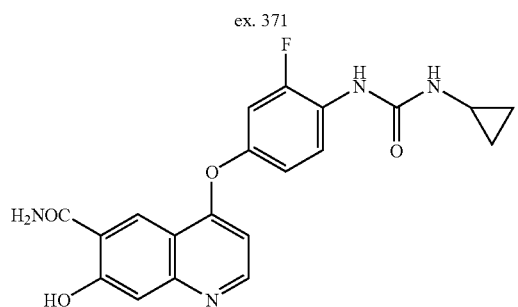
ex. 372
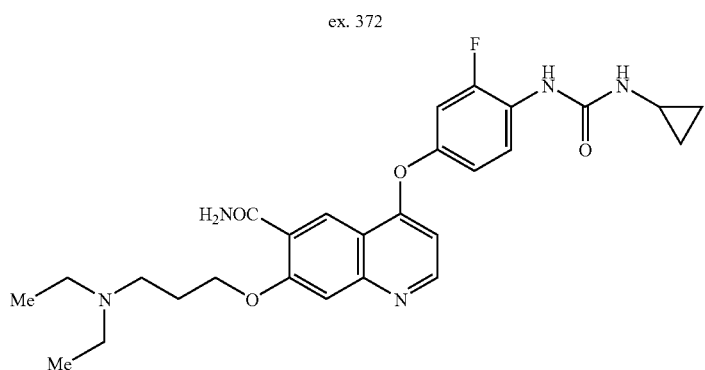
ex. 373
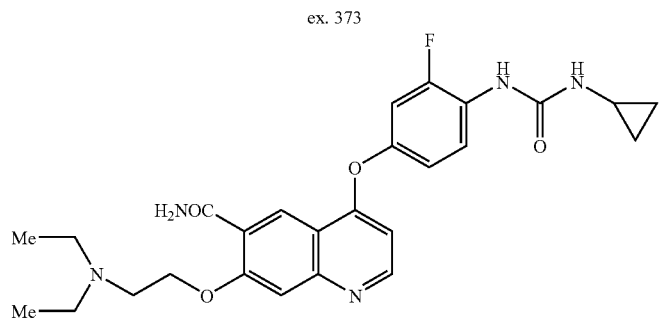

TABLE 35-continued
ex. 374
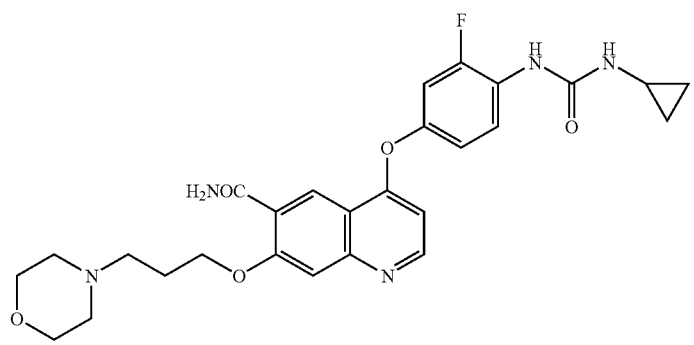
ex. 375
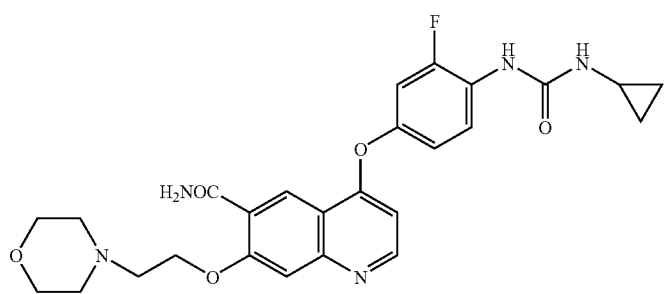
ex. 376
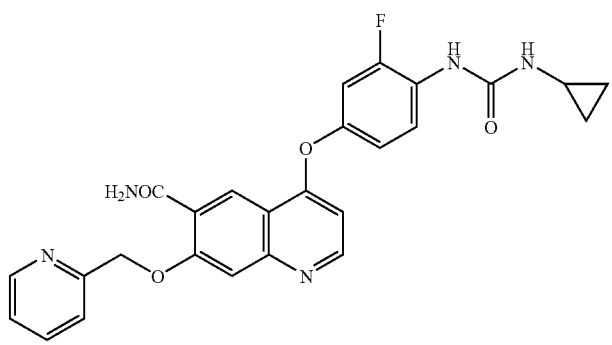
ex. 377
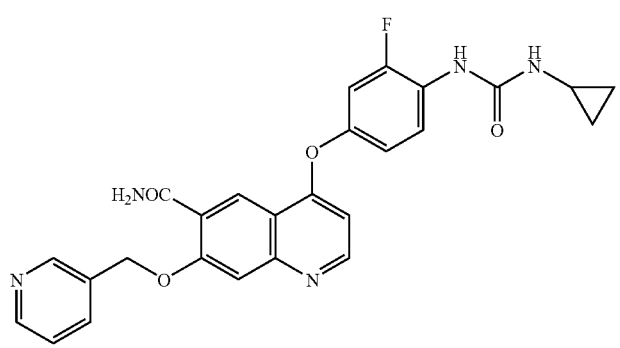

TABLE 35-continued
ex. 378
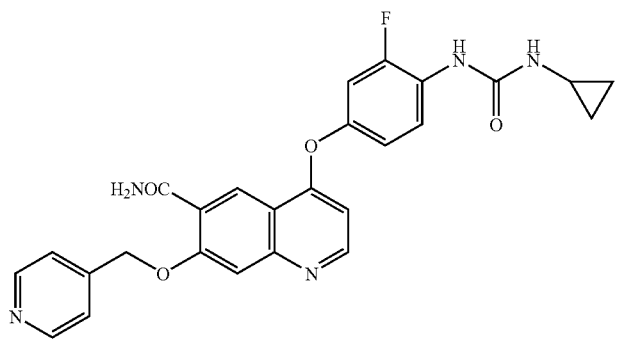
TABLE 36
ex. 379
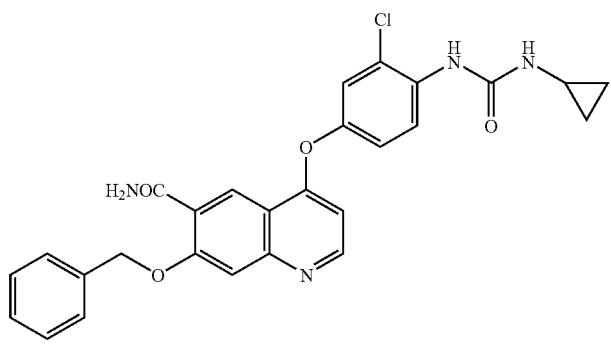
ex. 380
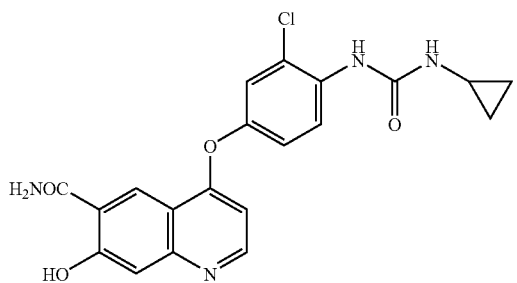
ex. 381
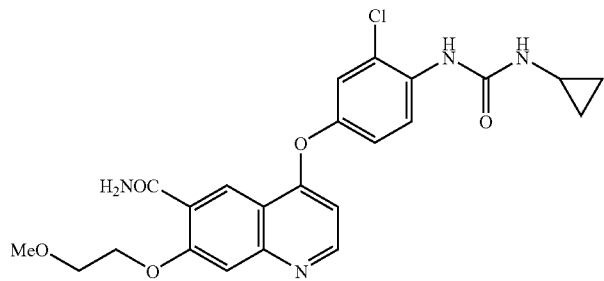

TABLE 36-continued
ex. 382
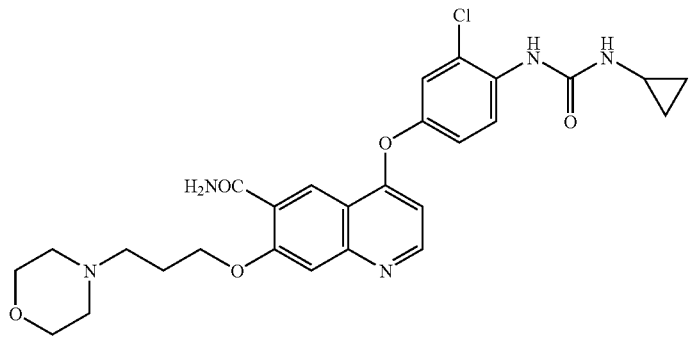
ex. 383
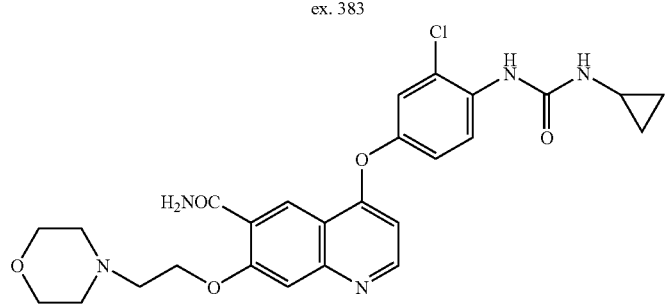
ex. 384
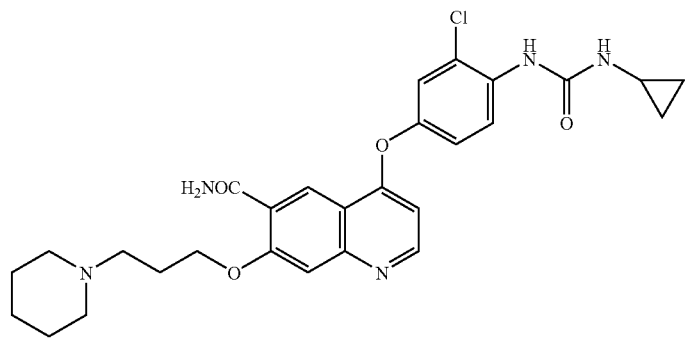
ex. 385
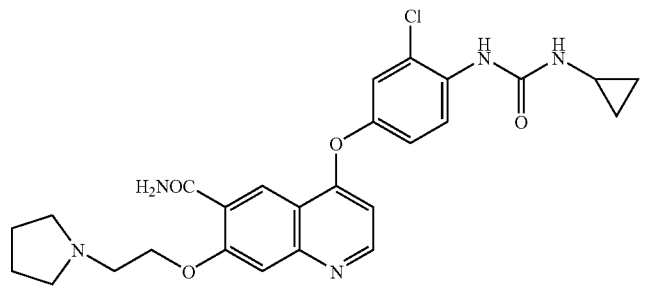
ex. 386
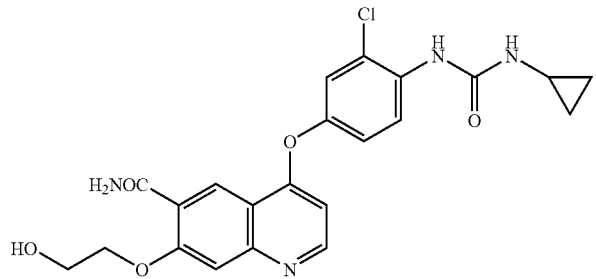

TABLE 36-continued
ex. 387
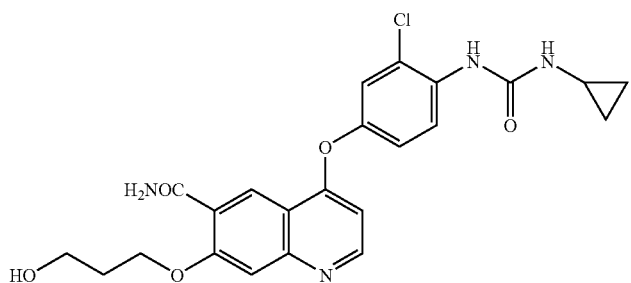
ex. 388
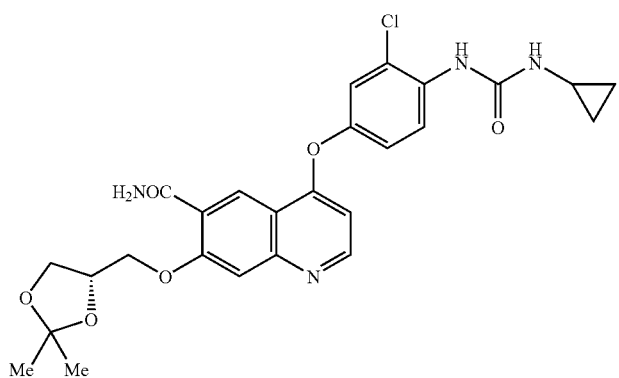
ex. 389
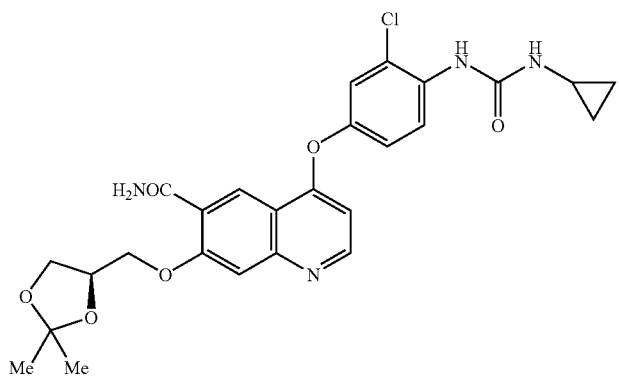
ex. 390
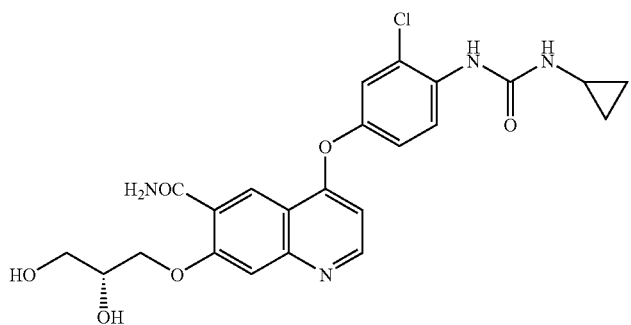

TABLE 36-continued
ex. 391-1
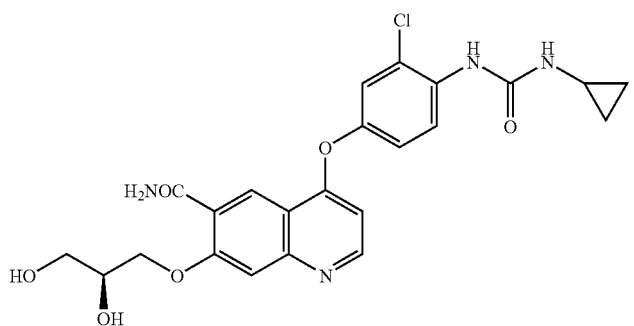
ex. 391-2
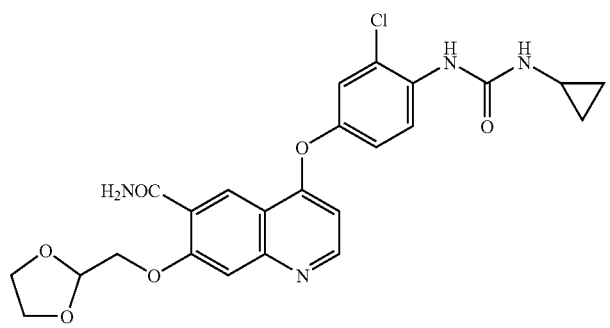
ex. 392
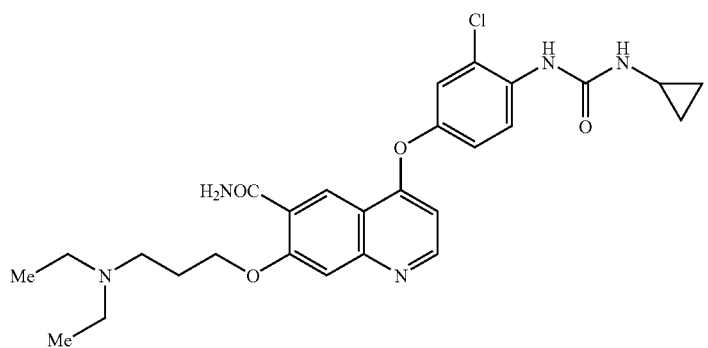
ex. 393
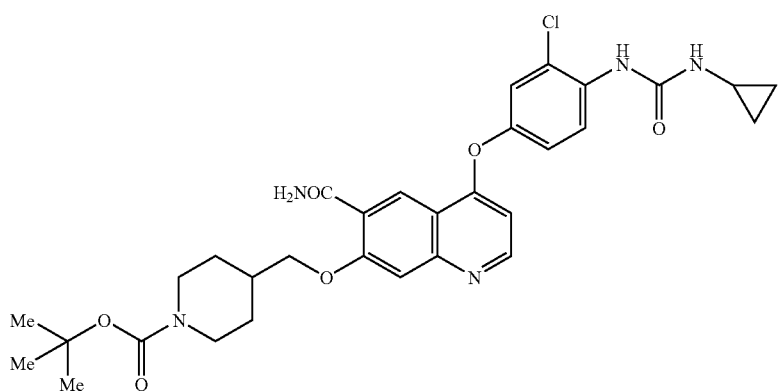

TABLE 36-continued
ex. 394
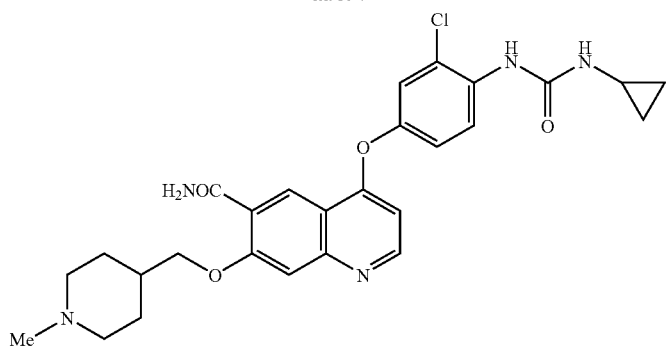
ex. 395
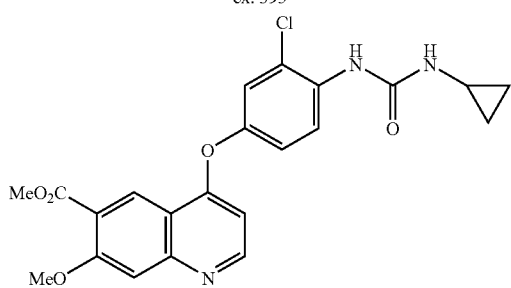
ex. 396
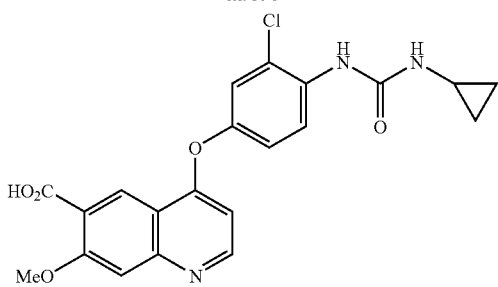
ex. 397
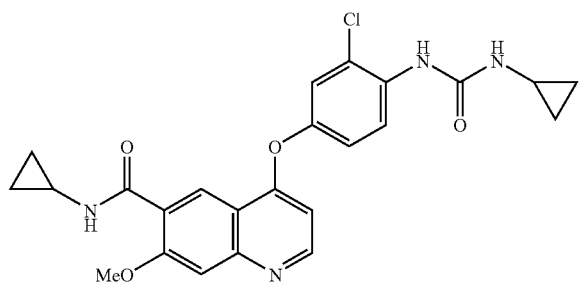
ex. 398
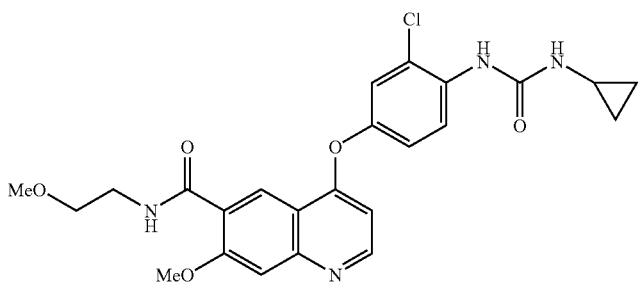

TABLE 36-continued
ex. 399
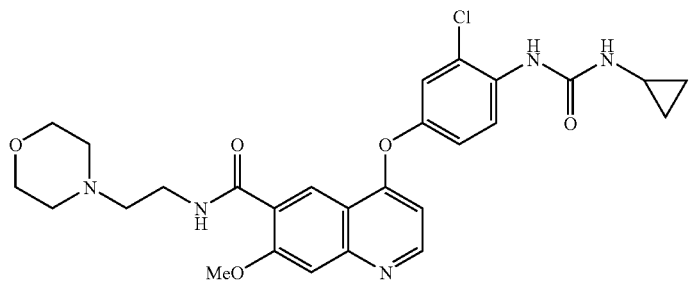
ex. 400
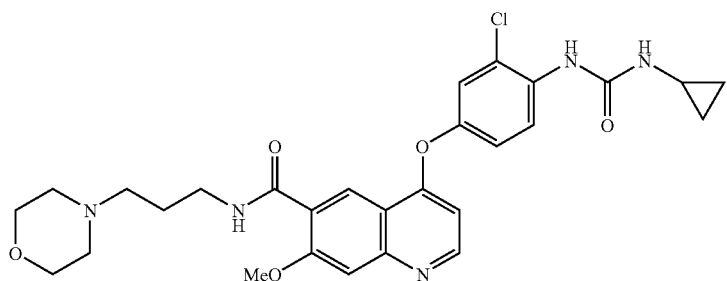
ex. 401
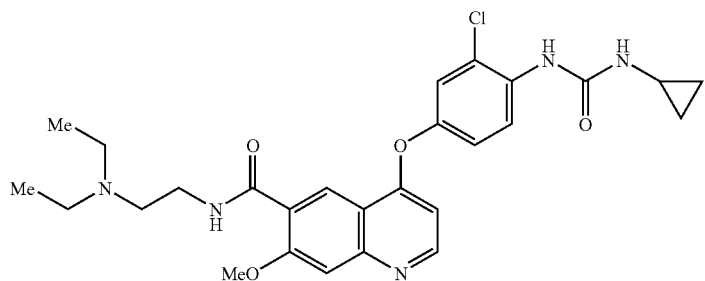
ex. 402
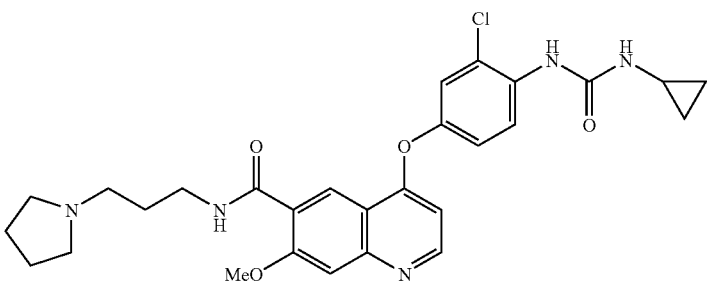
TABLE 37
ex. 403
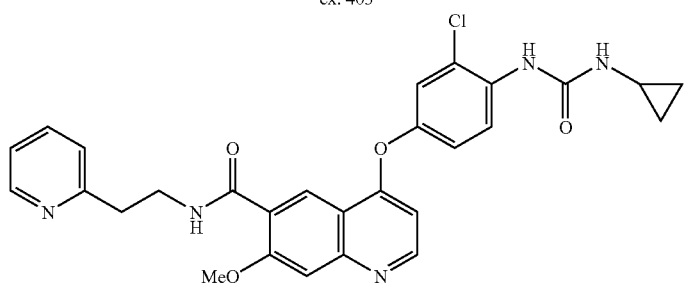

TABLE 37-continued
ex. 404
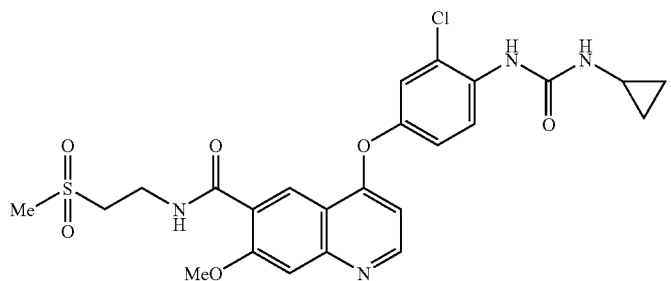
ex. 405
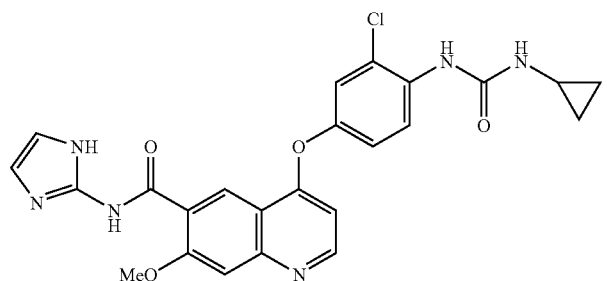
ex. 406
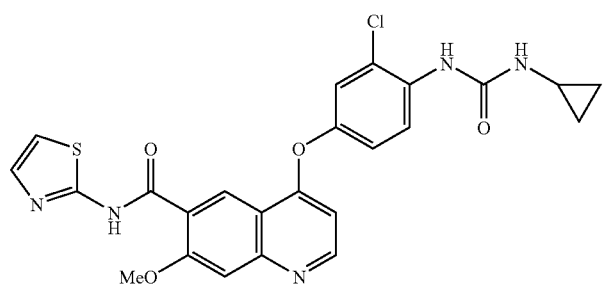
ex. 407
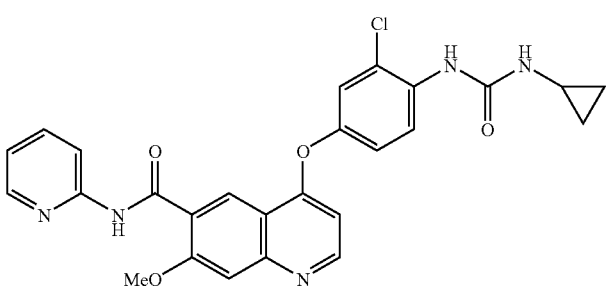
ex. 408
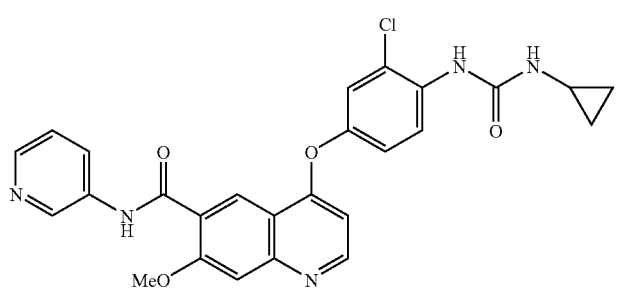

TABLE 37-continued
ex. 409
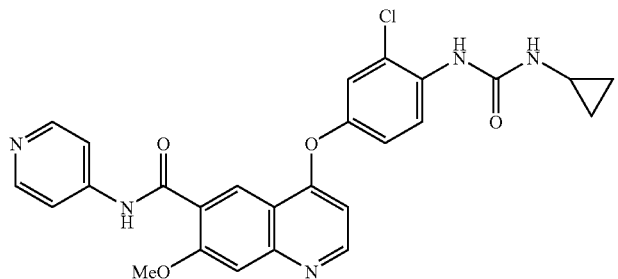
ex. 410
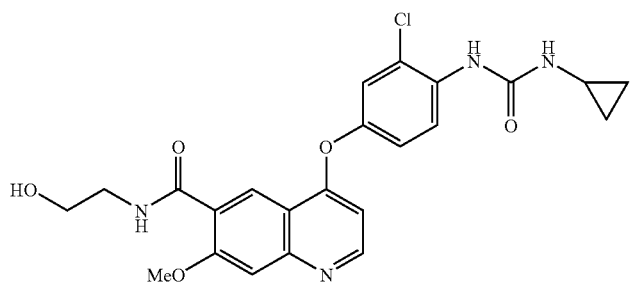
ex. 411
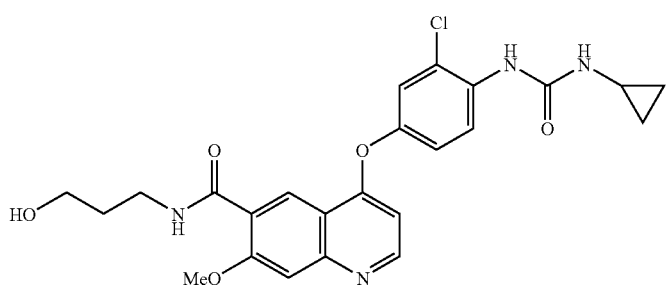
ex. 412
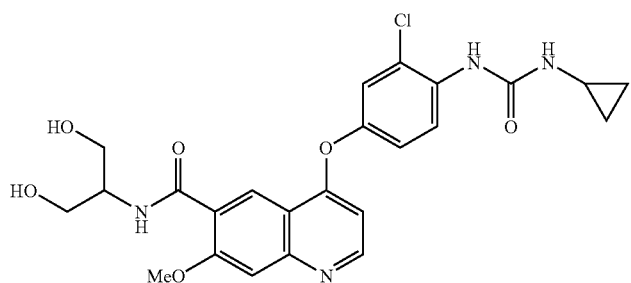
ex. 413
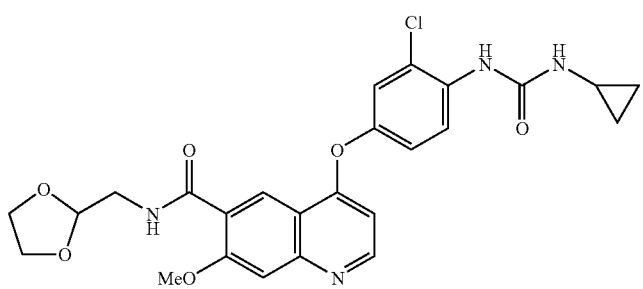

TABLE 37-continued
ex. 414
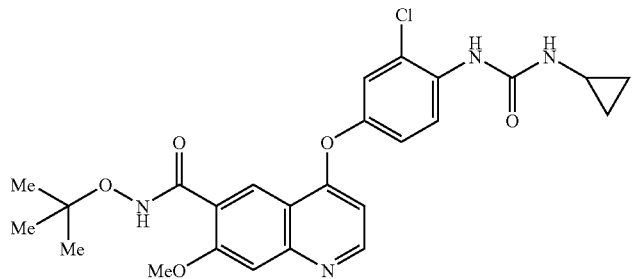
ex. 415
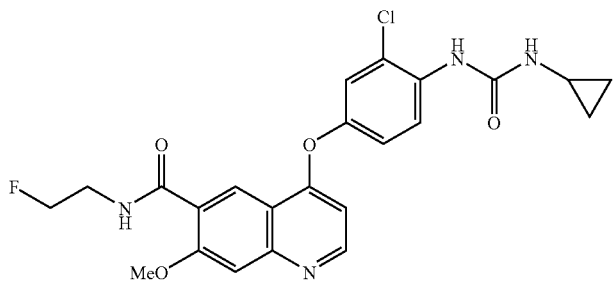
ex. 416
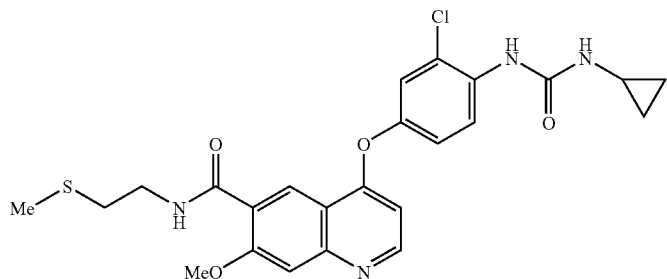
ex. 417
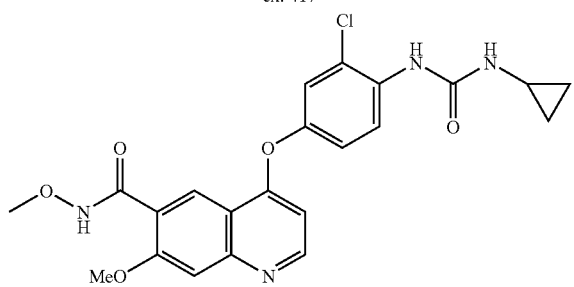
ex. 418
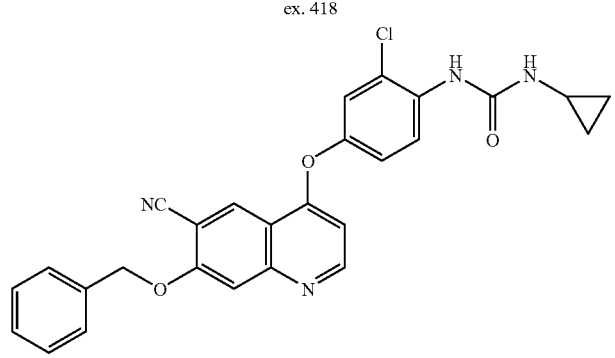

TABLE 37-continued
ex. 419
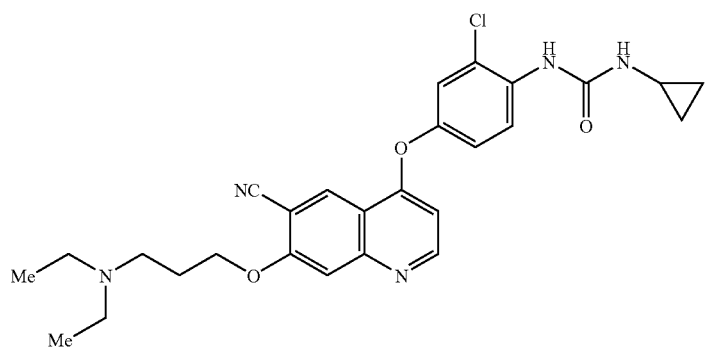
ex. 420
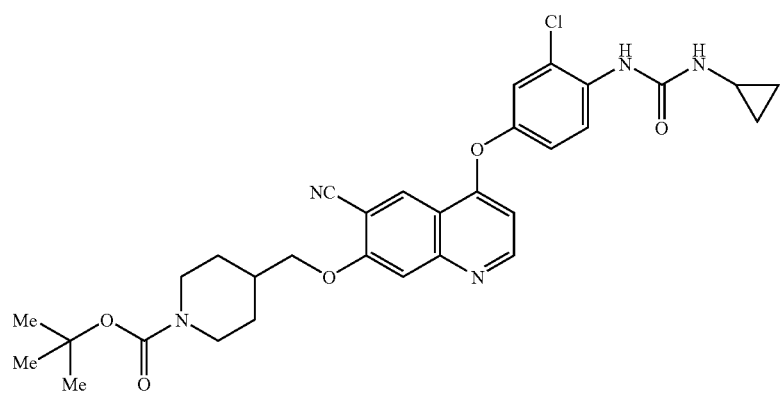
ex. 421
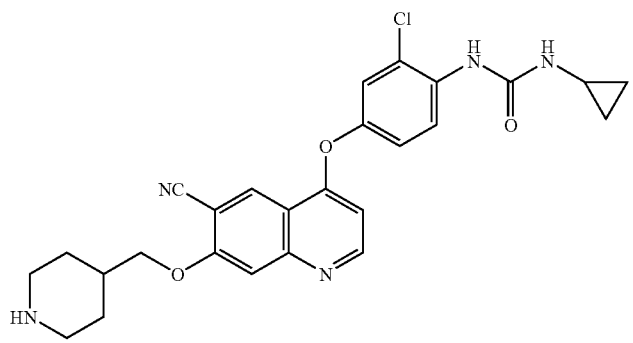
ex. 422
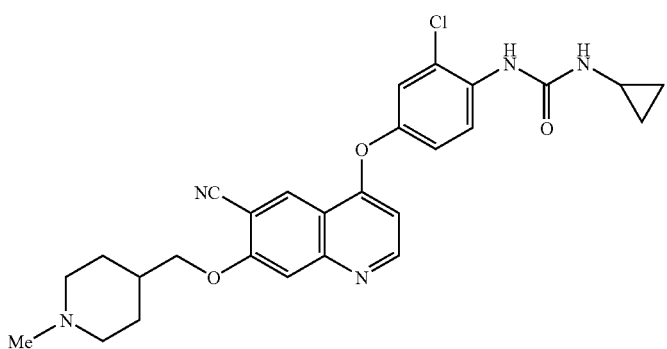

TABLE 37-continued
ex. 423
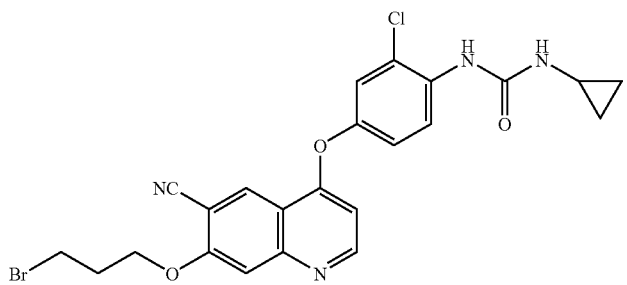
ex. 424
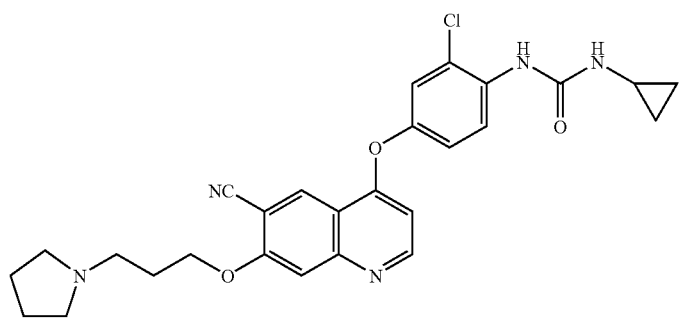
ex. 425
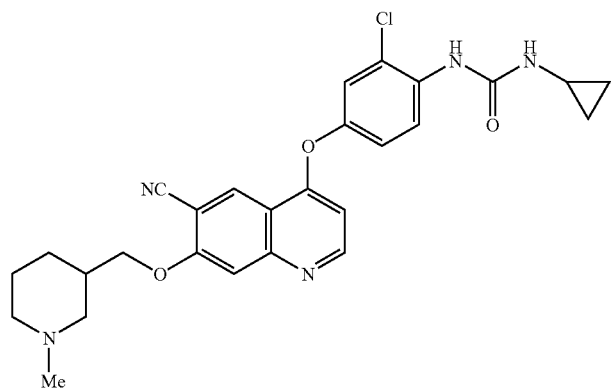
ex. 426
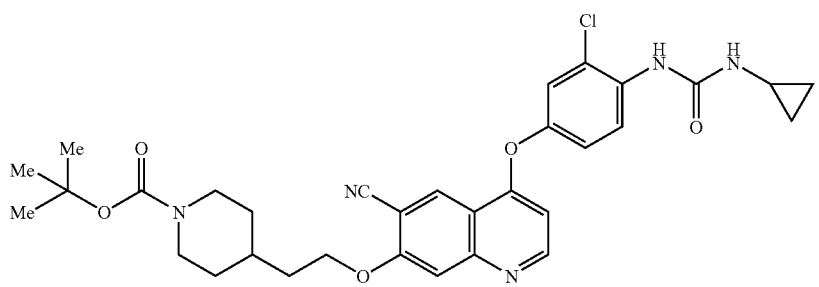

TABLE 38
ex. 427
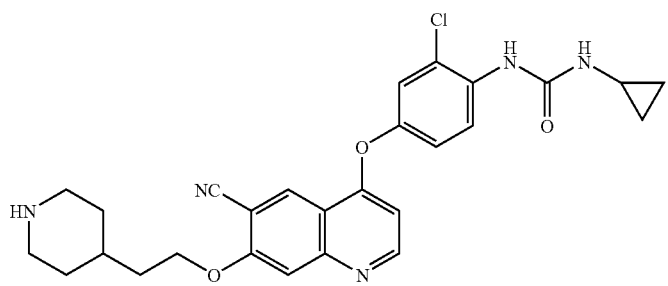
ex. 428
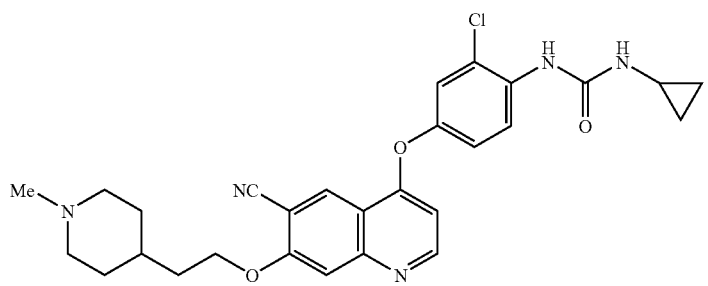
ex. 429
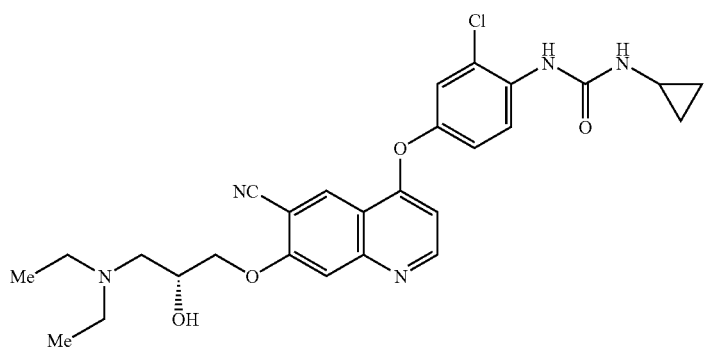
ex. 430
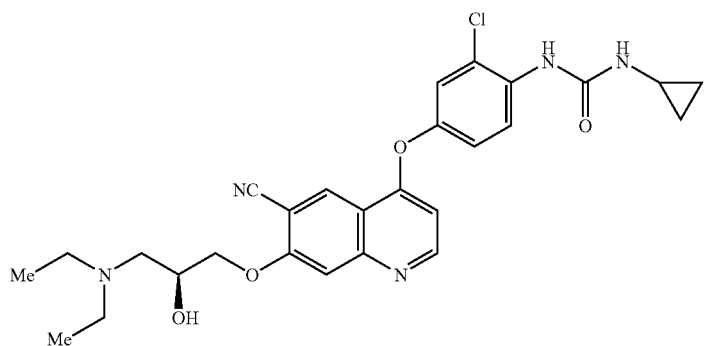

TABLE 38-continued
ex. 431
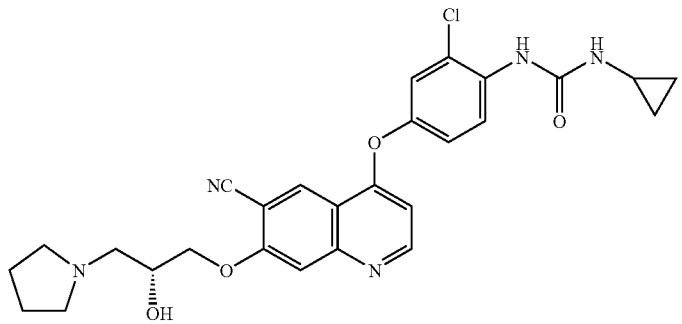
ex. 432
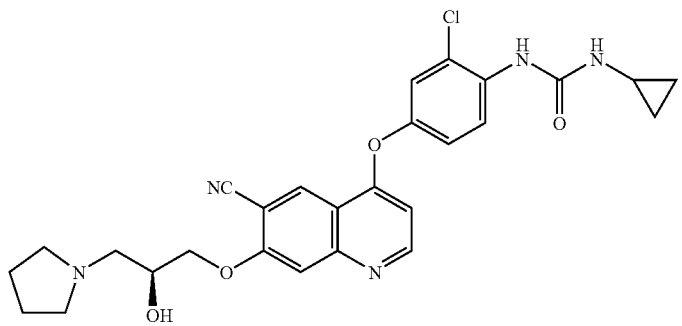
ex. 433
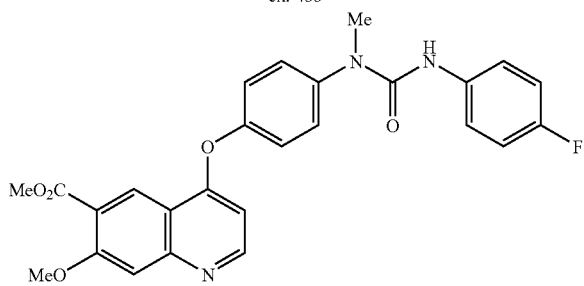
ex. 434
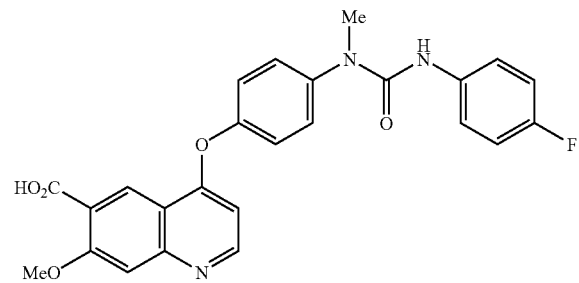
ex. 435
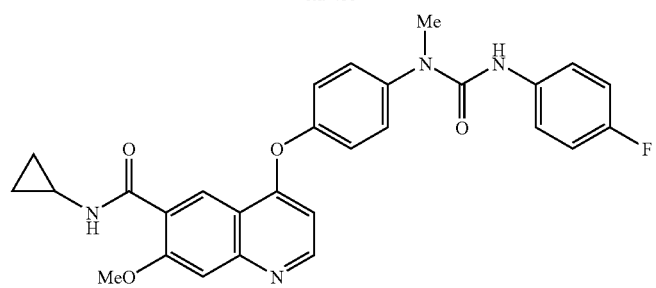

TABLE 38-continued
ex. 436
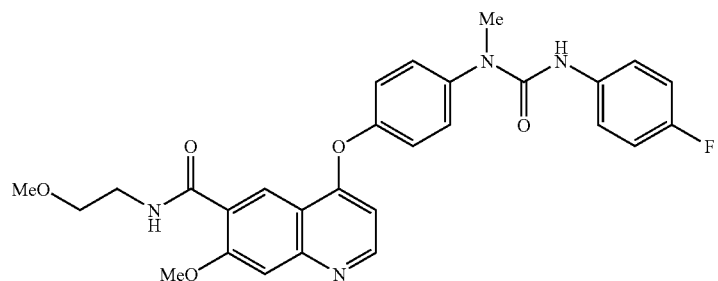
ex. 437
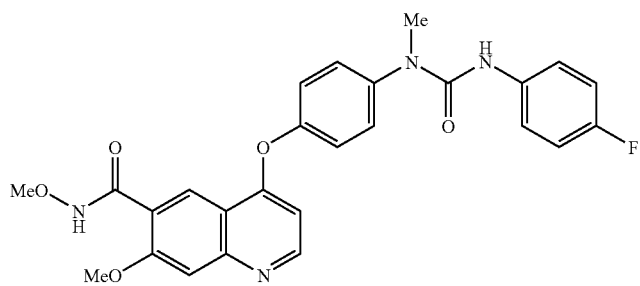
ex. 438
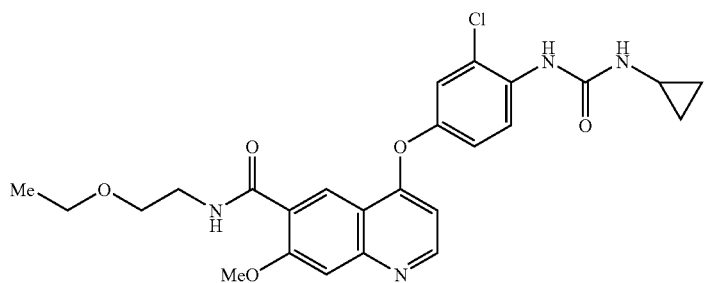
ex. 439
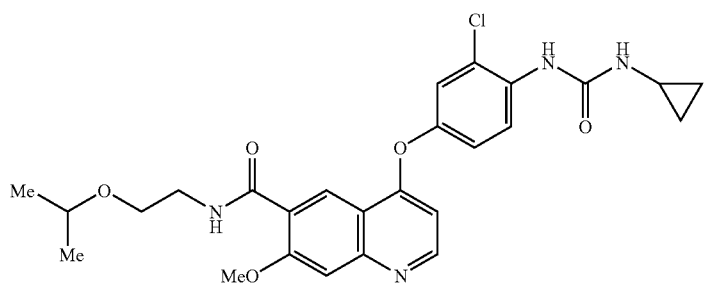
ex. 440
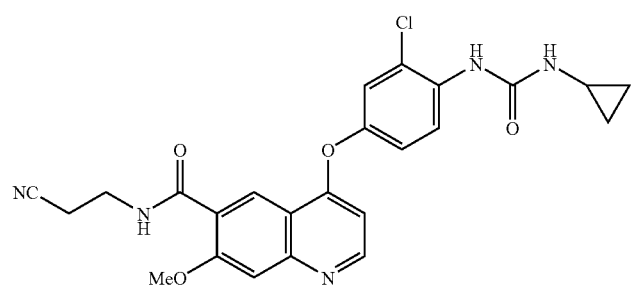

TABLE 38-continued
ex. 441
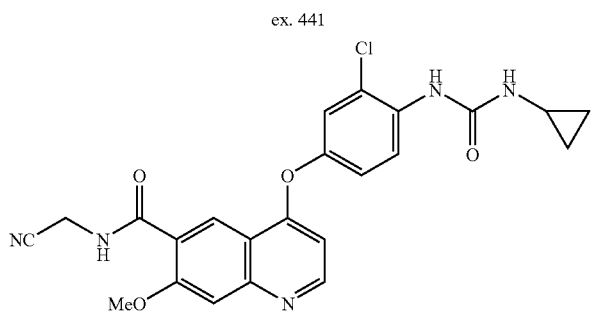
ex. 442
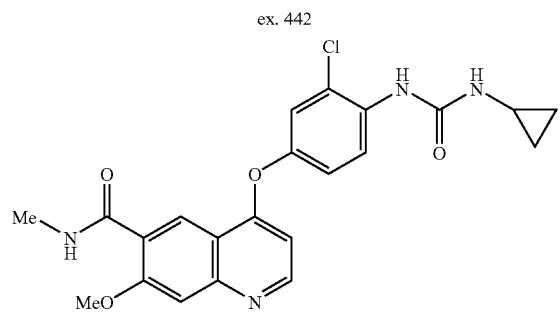
ex. 443
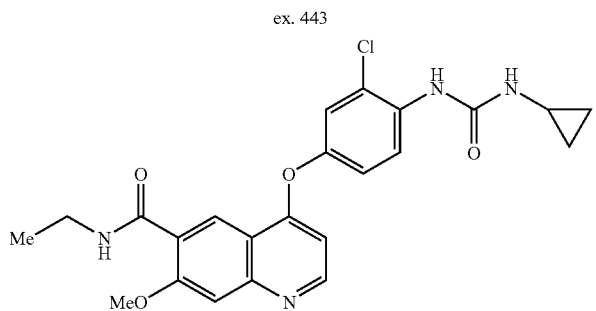
ex. 444
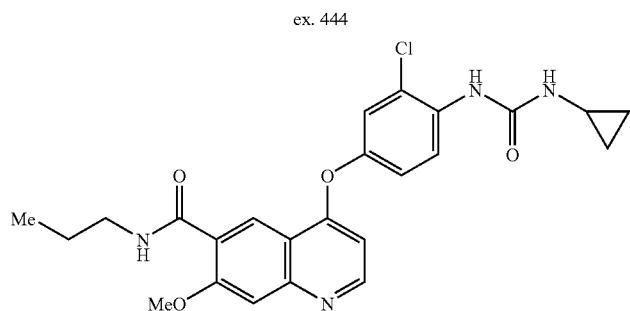
ex. 445
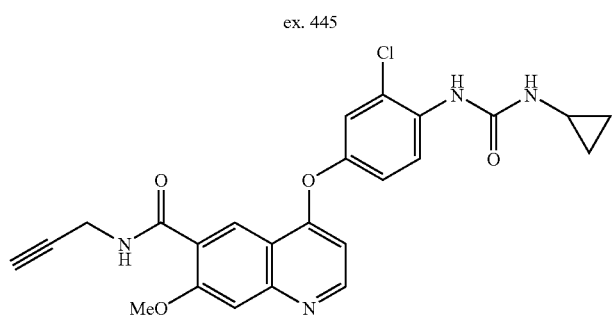

TABLE 38-continued
ex. 446
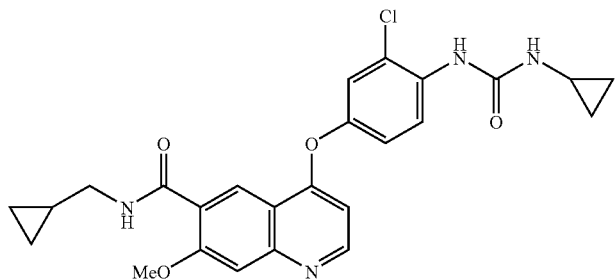
ex. 447
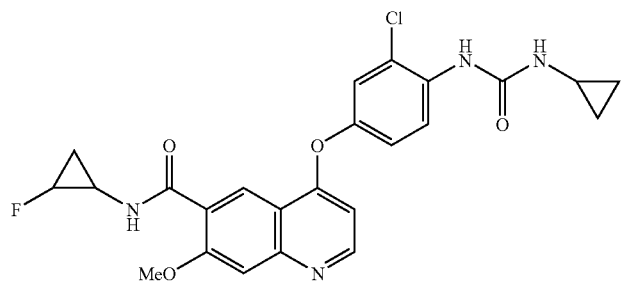
ex. 448
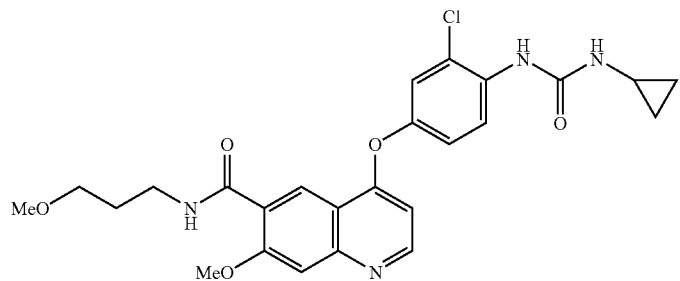
ex. 449
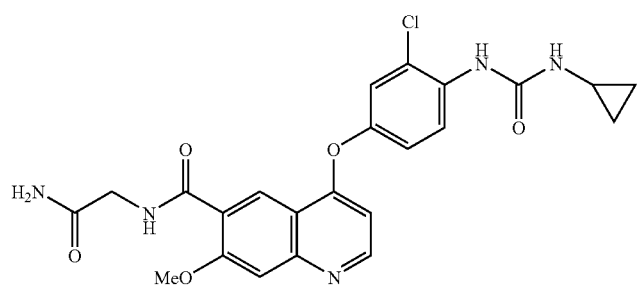
ex. 450
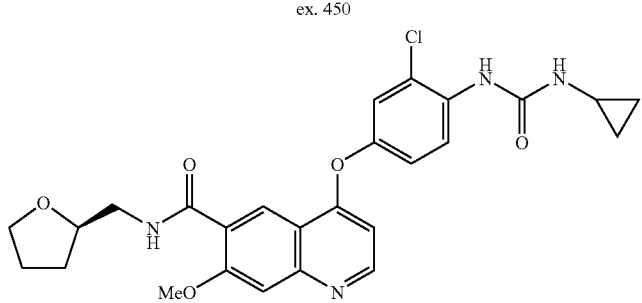

TABLE 39
ex. 451
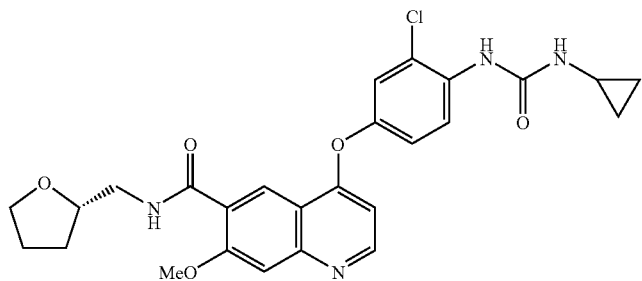
ex. 452
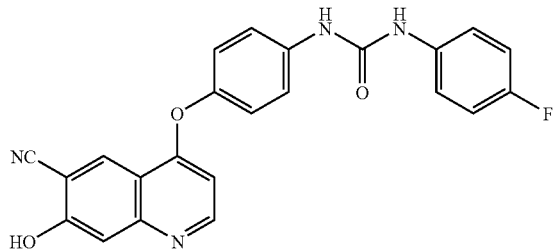
ex. 453
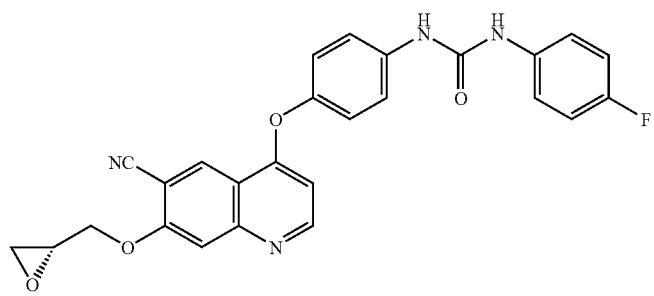
ex. 454
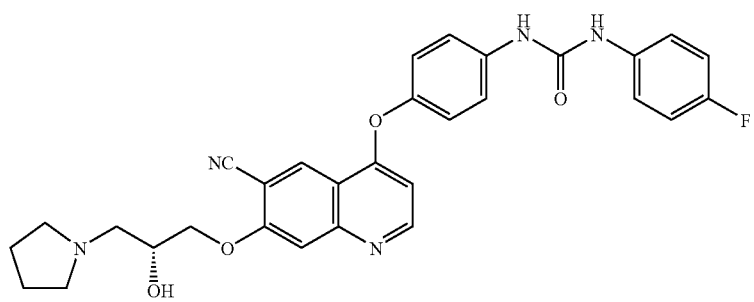
ex. 455
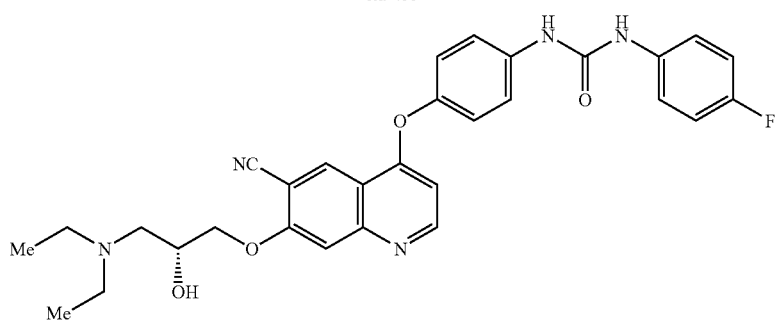

TABLE 39-continued
ex. 456
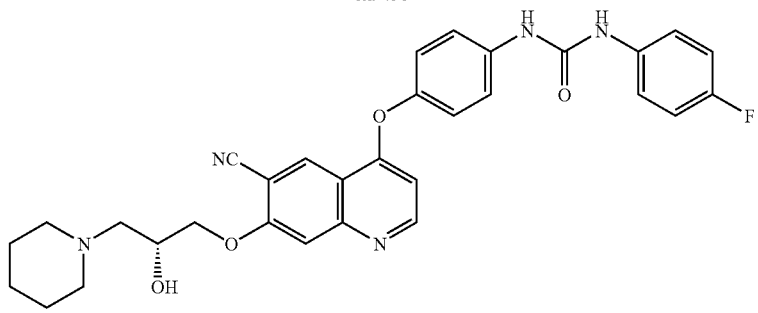
ex. 457
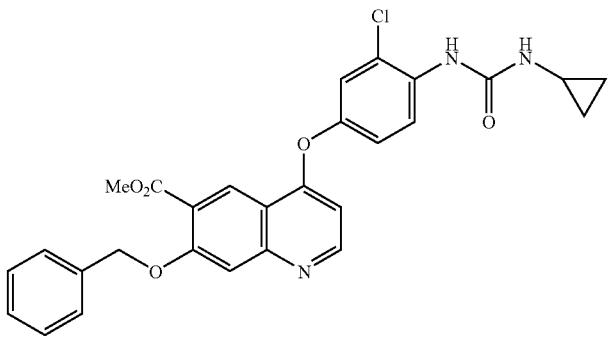
ex. 458
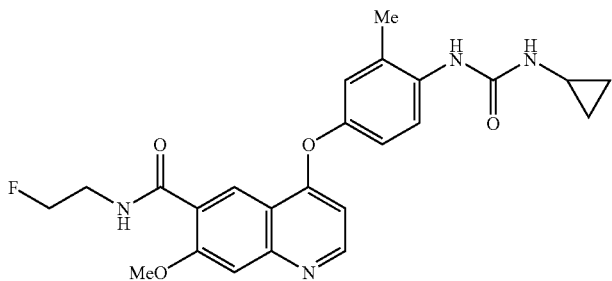
ex. 459
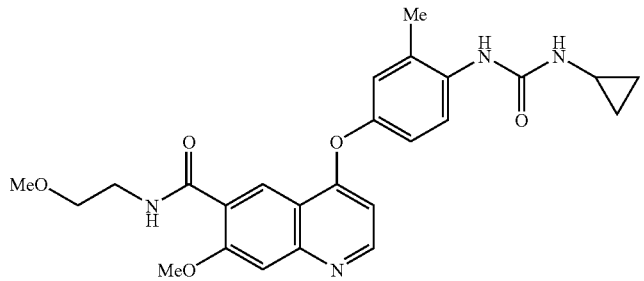
ex. 460
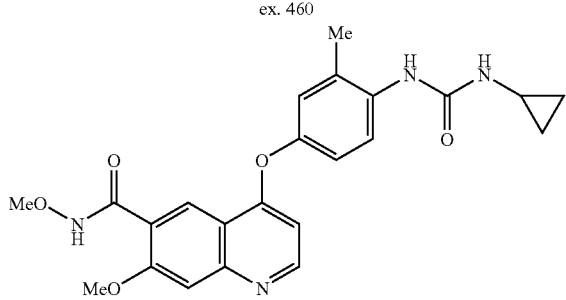

TABLE 39-continued
ex. 461
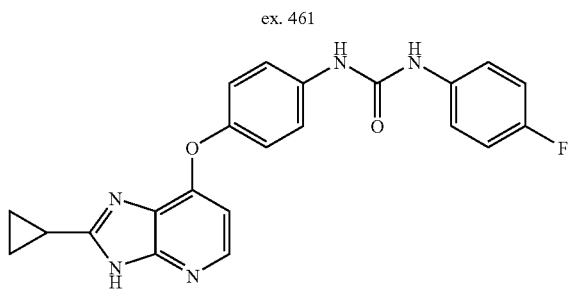
ex. 462
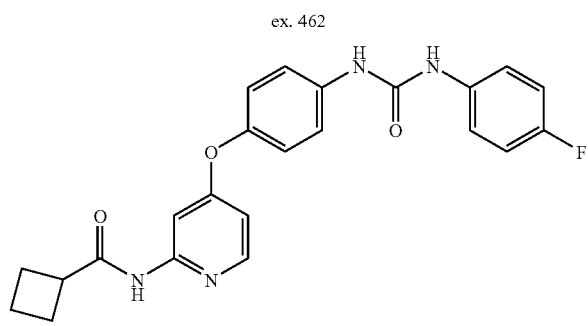
ex. 463
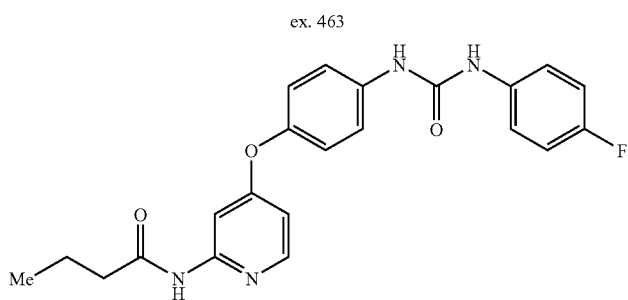
ex. 464
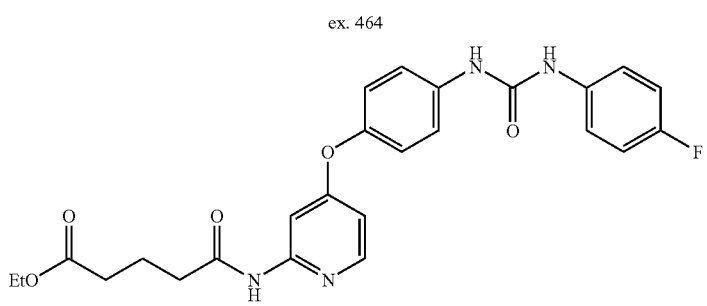
ex. 465
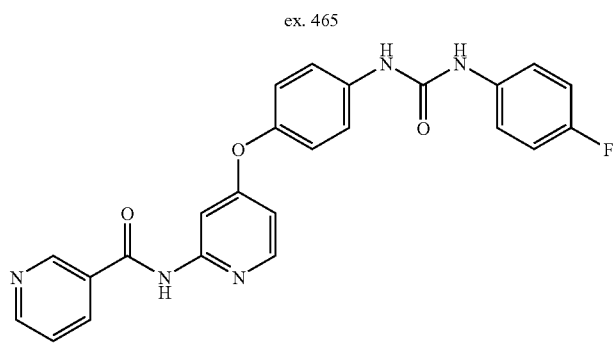

TABLE 39-continued
ex. 466
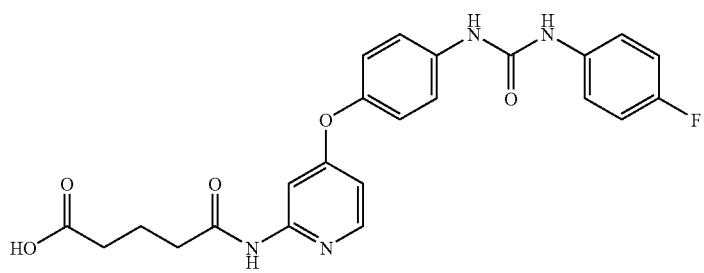
ex. 467
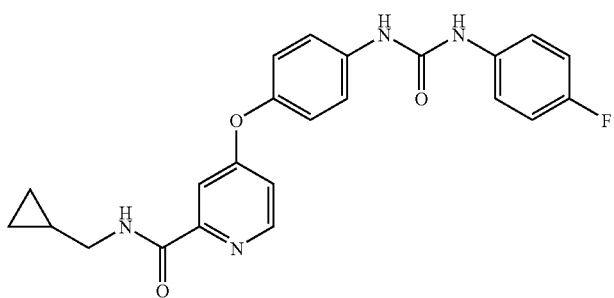
ex. 468
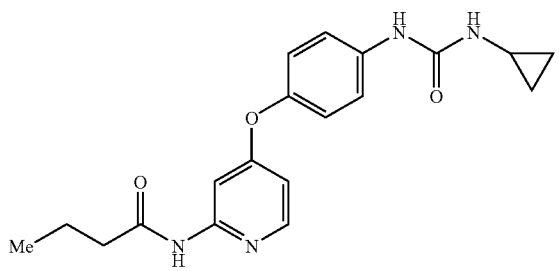
ex. 469
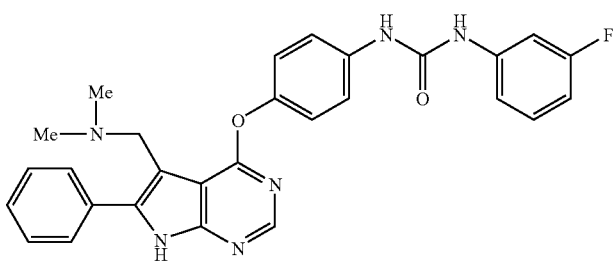
ex. 470
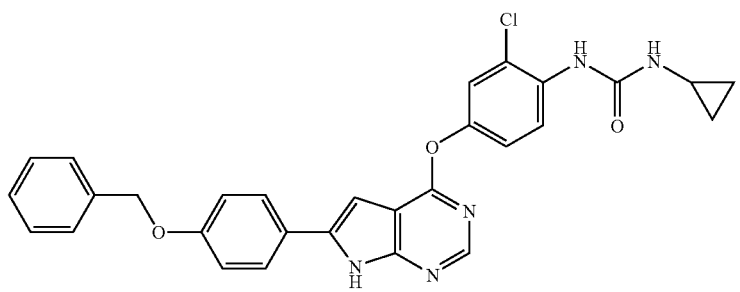

TABLE 39-continued
ex. 471
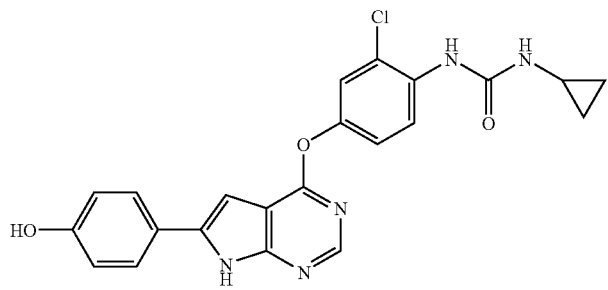
ex. 472
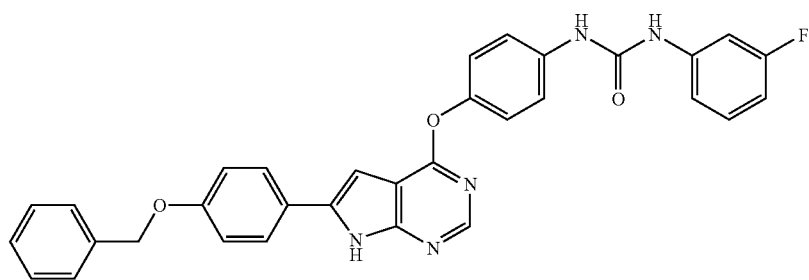
ex. 473
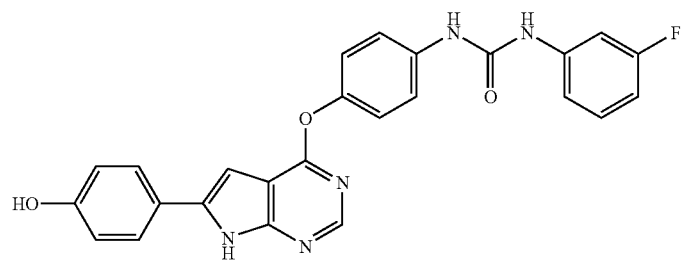
ex. 474
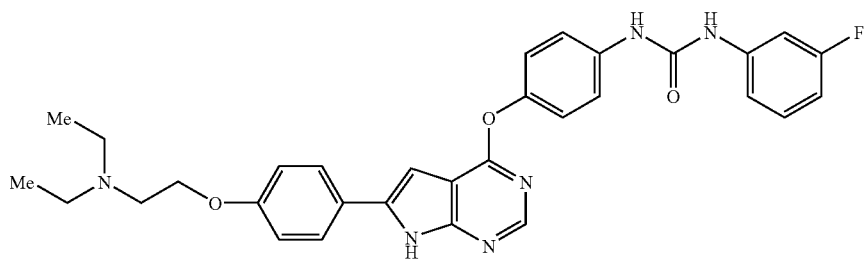
TABLE 40
ex. 475
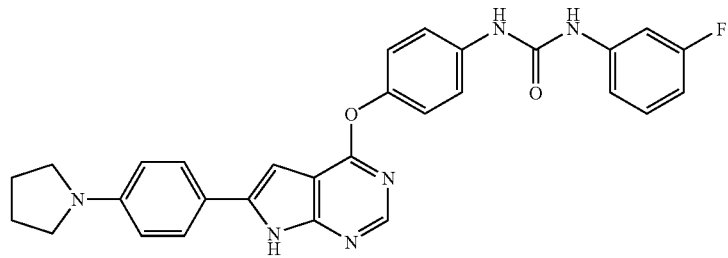

TABLE 40-continued
ex. 476
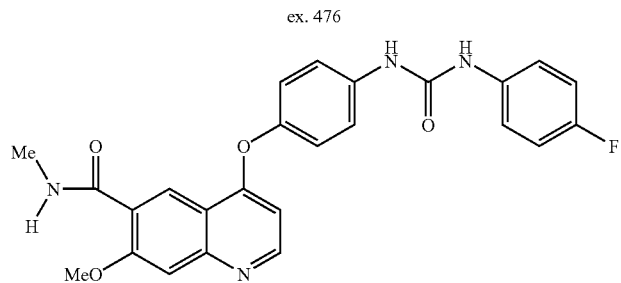
ex. 477
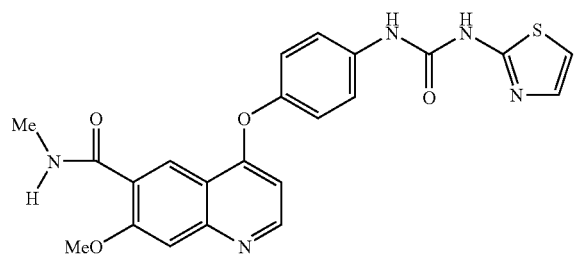
ex. 478
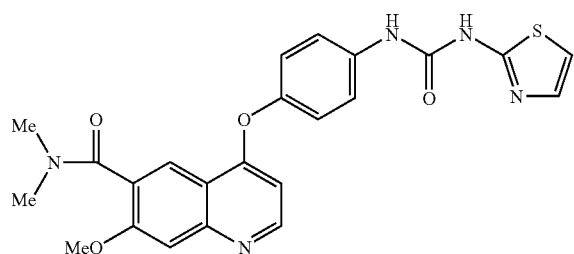
ex. 479
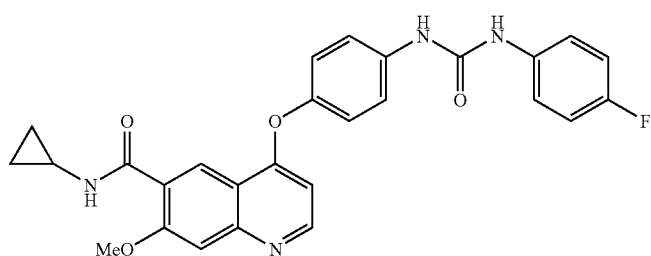
ex. 480
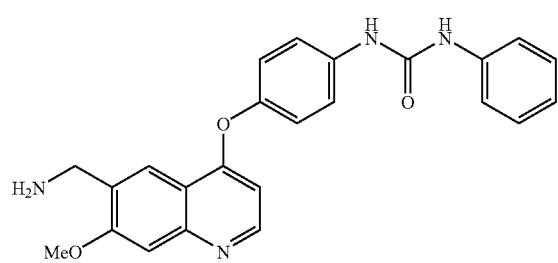

TABLE 40-continued
ex. 481
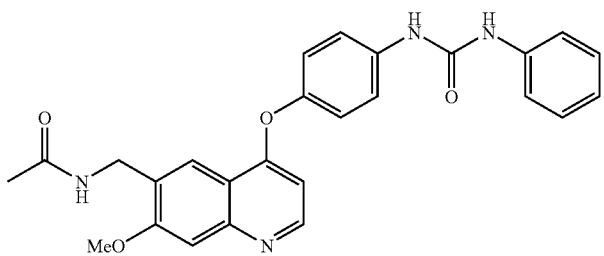
ex. 482
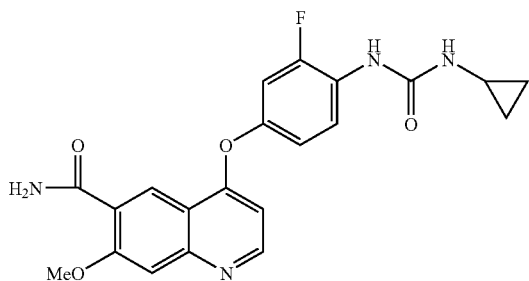
ex. 483
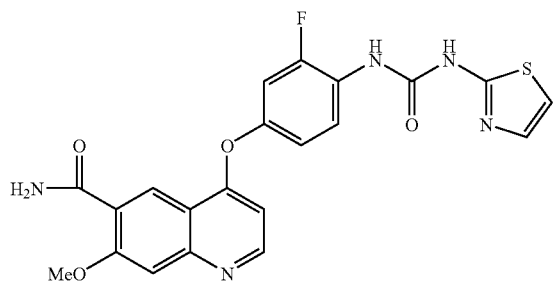
ex. 484
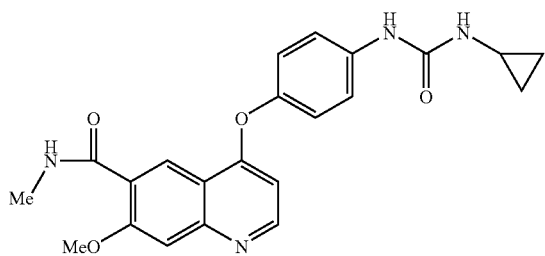
ex. 485
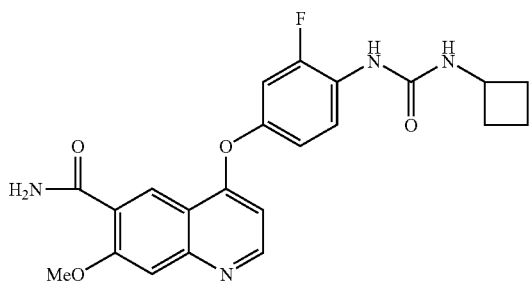

TABLE 40-continued
ex. 486
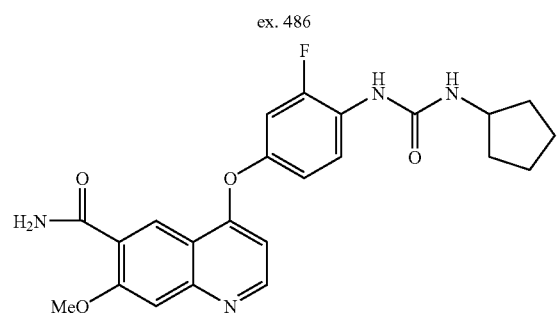
ex. 487
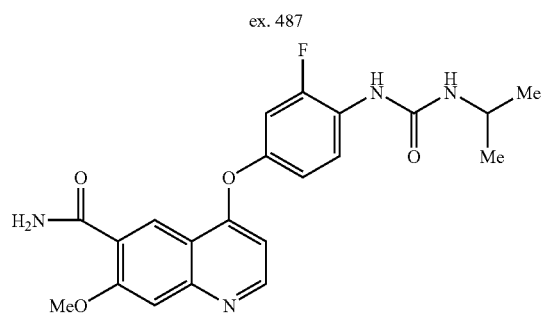
ex. 488
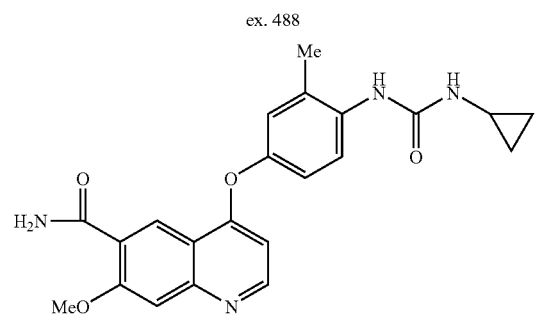
ex. 489
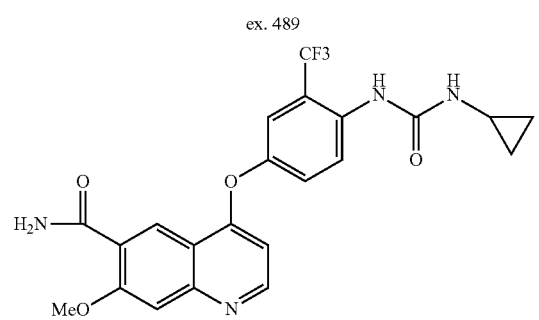
ex. 490
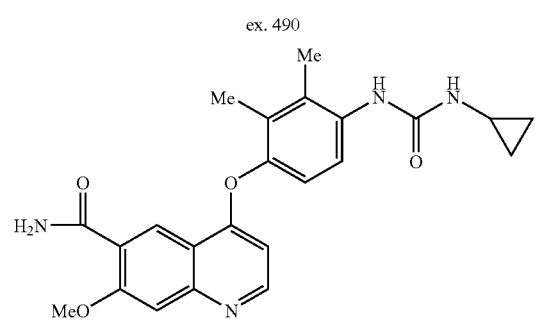

TABLE 40-continued
ex. 491
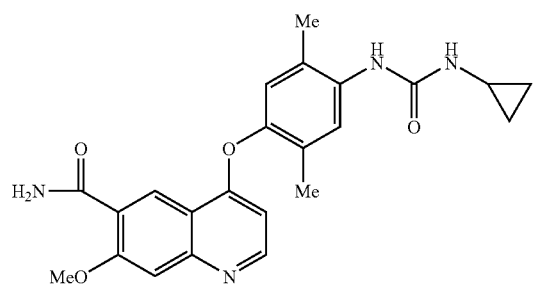
ex. 492
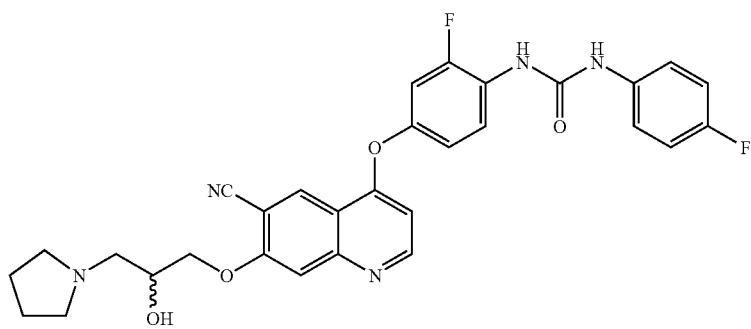
ex. 493
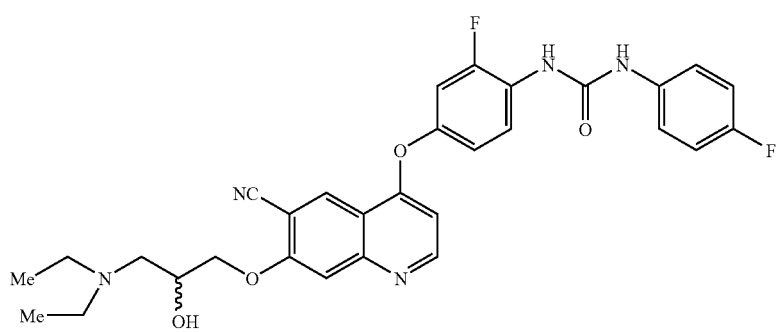
ex. 494
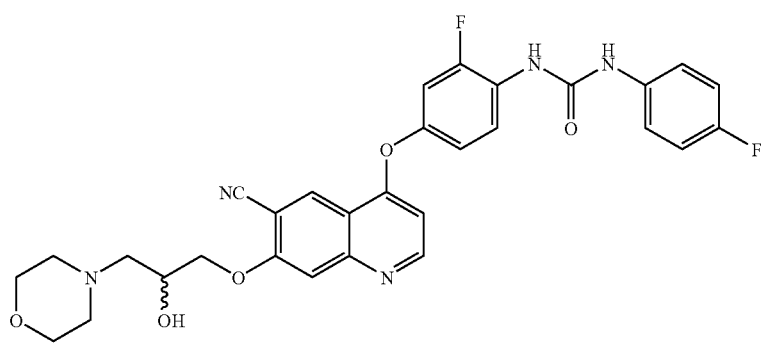

TABLE 40-continued
ex. 495
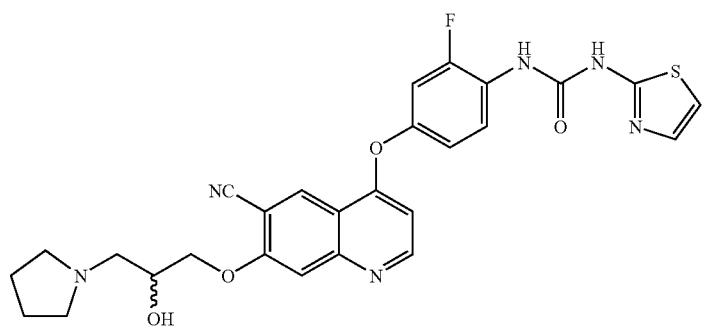
ex. 496
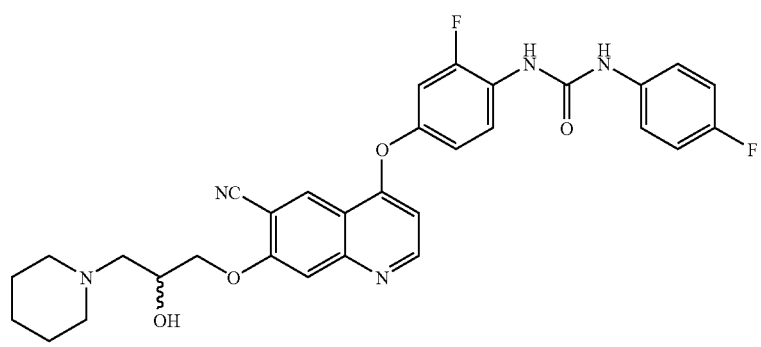
ex. 497
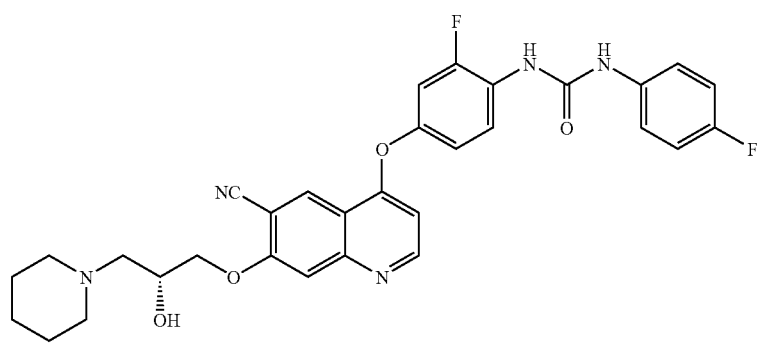
ex. 498
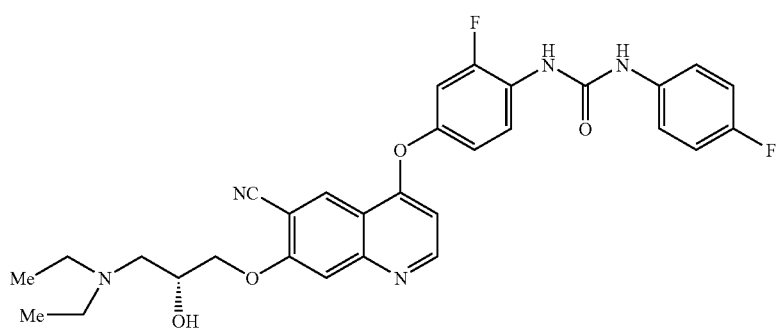

TABLE 41
ex. 499
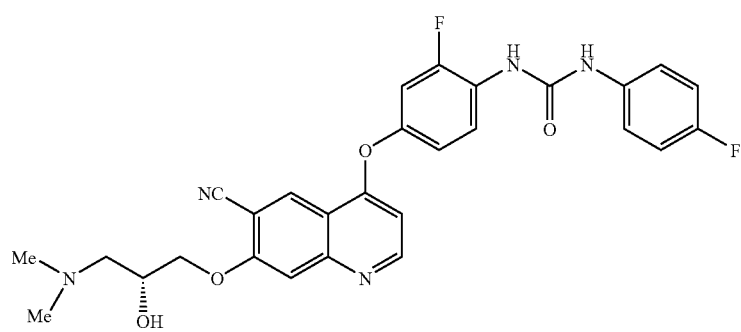
ex. 500
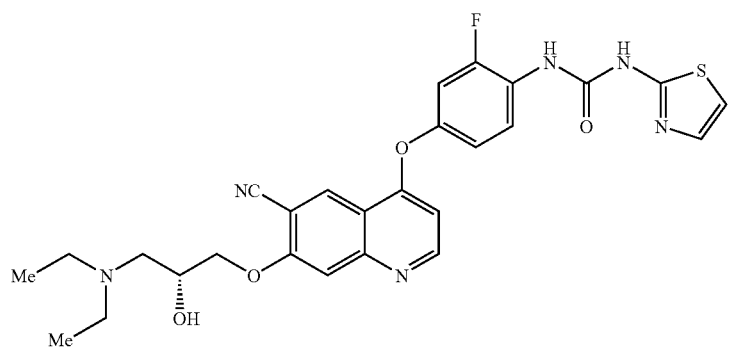
ex. 501
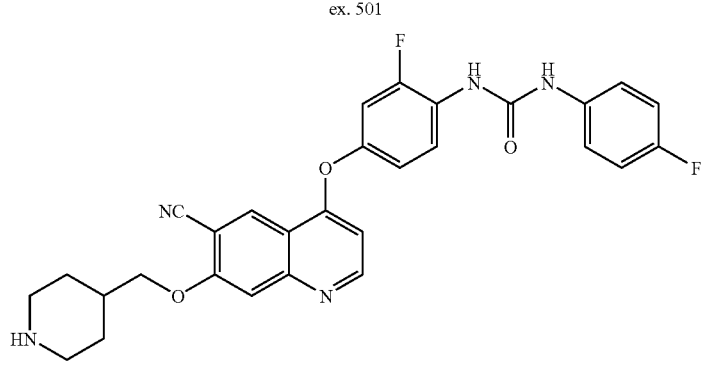
ex. 502
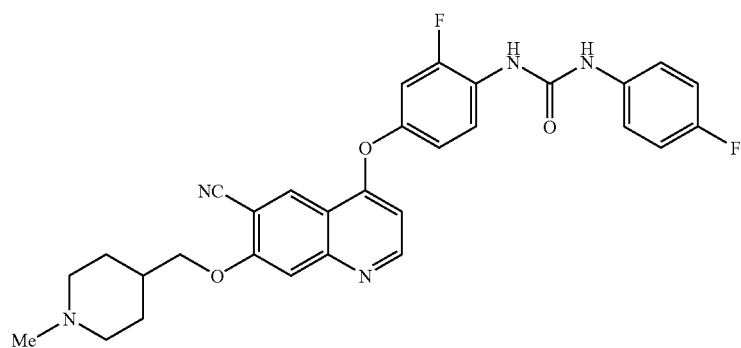

TABLE 41-continued
ex. 503
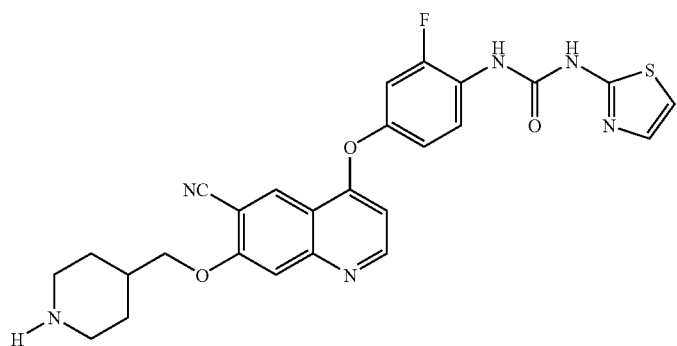
ex. 504
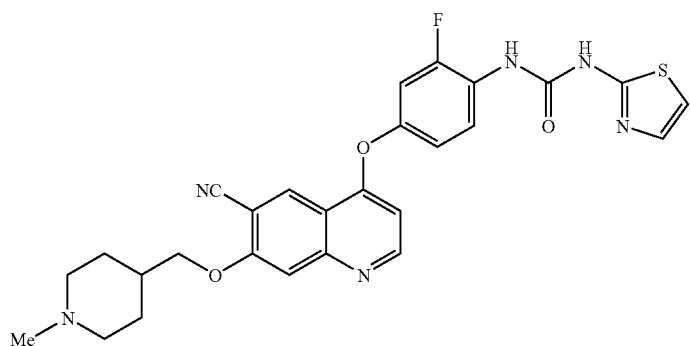
ex. 505
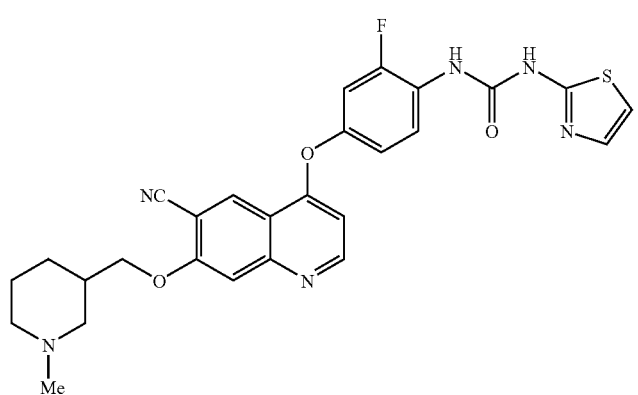
ex. 506
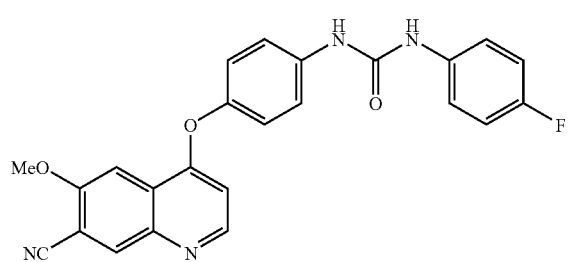

TABLE 41-continued
ex. 507
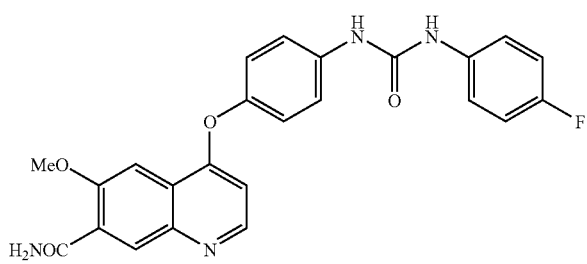
ex. 508
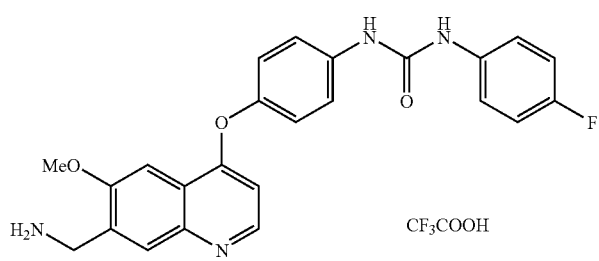
ex. 509
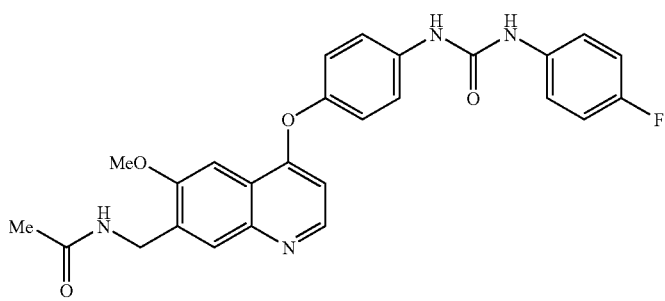
ex. 510
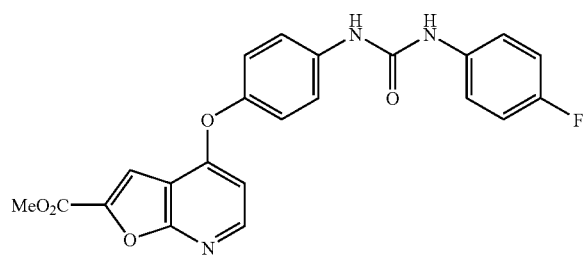
ex. 511
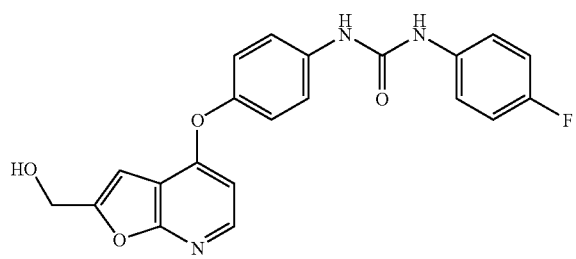

TABLE 41-continued
ex. 512
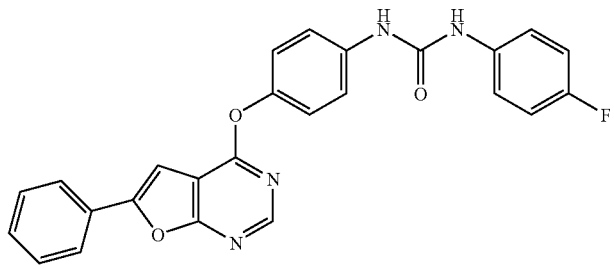
ex. 513
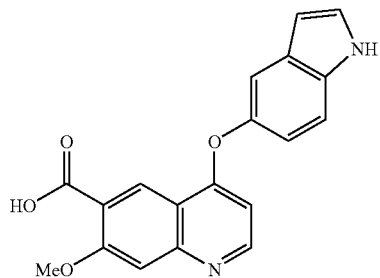
ex. 514
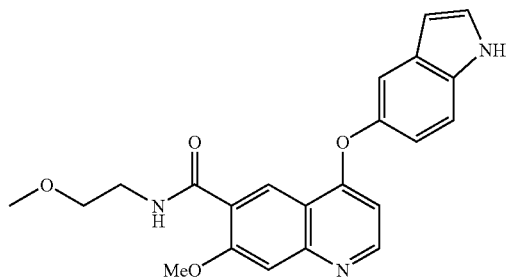
ex. 515
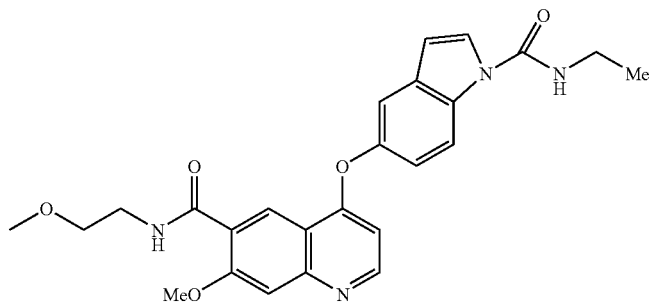
ex. 516
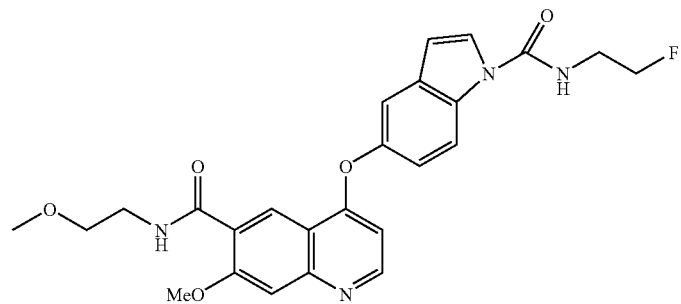

TABLE 41-continued
ex. 517
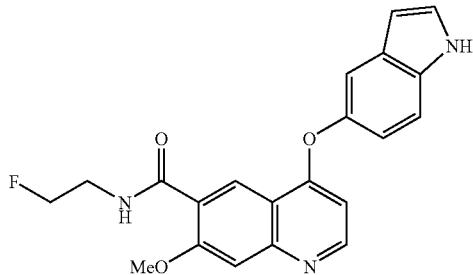
ex. 518
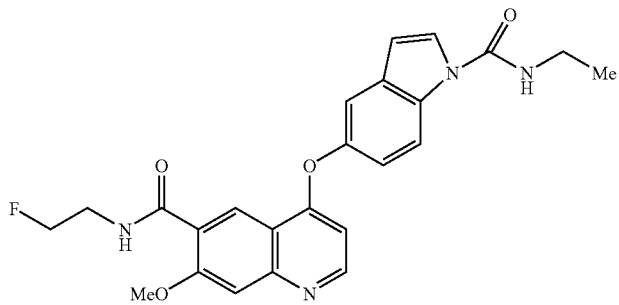
ex. 519
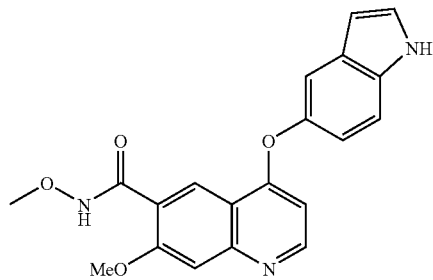
ex. 520
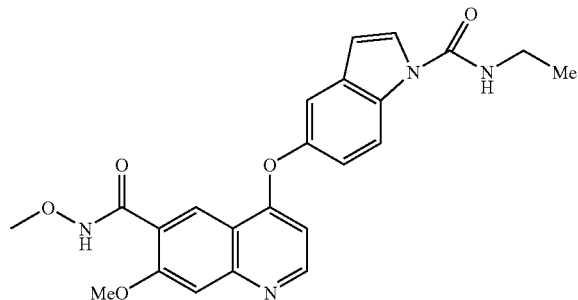
ex. 521
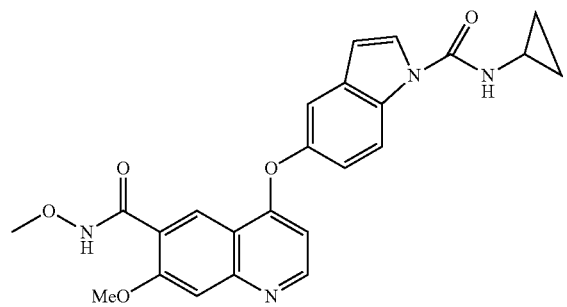

TABLE 41-continued
ex. 522
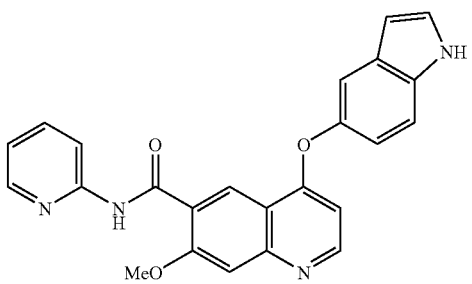
TABLE 42
ex. 523
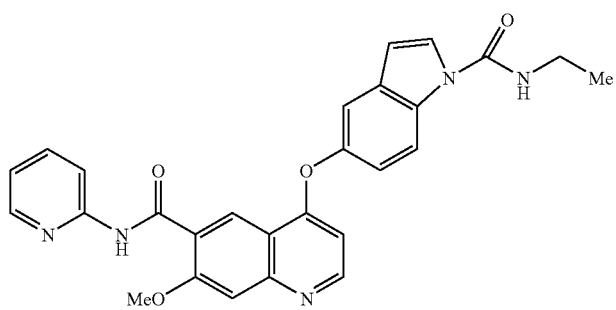
ex. 524
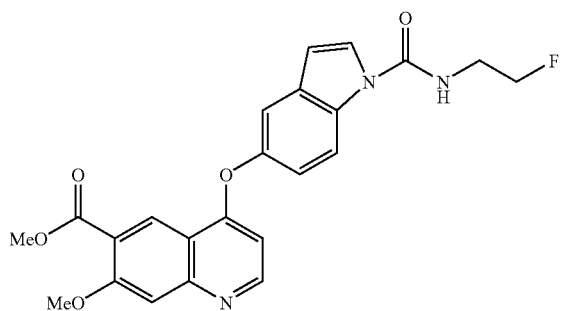
ex. 525
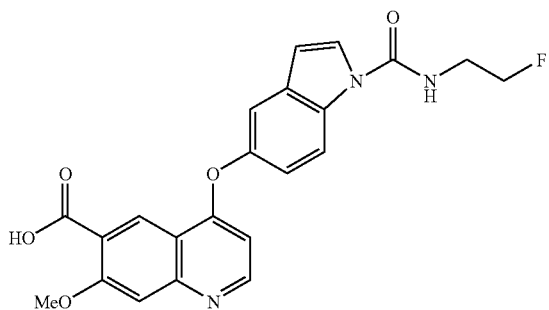

TABLE 42-continued
ex. 526
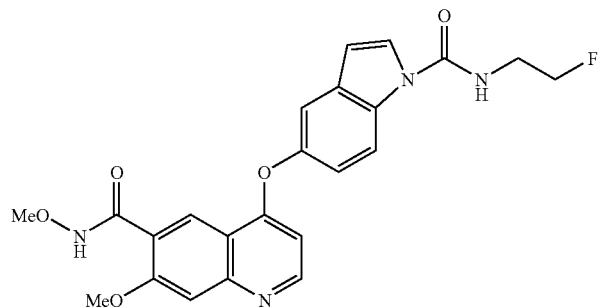
ex. 527
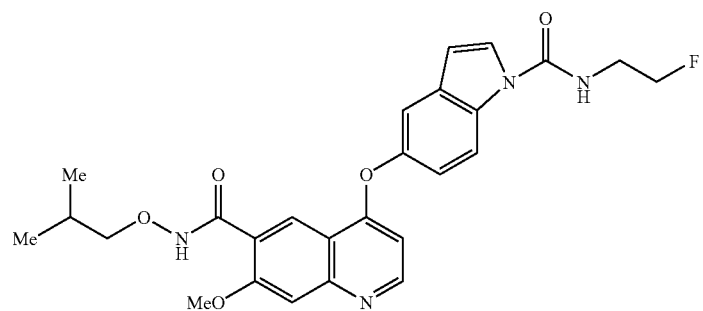
ex. 528
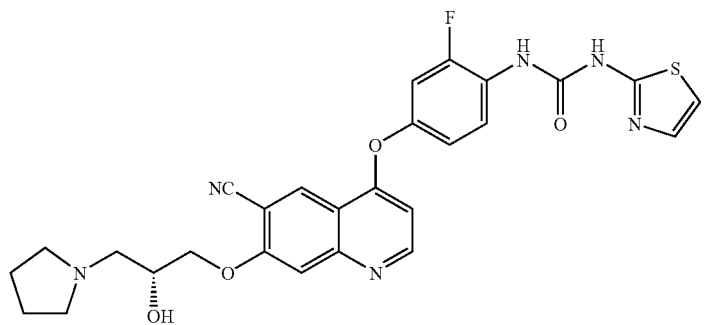
ex. 529
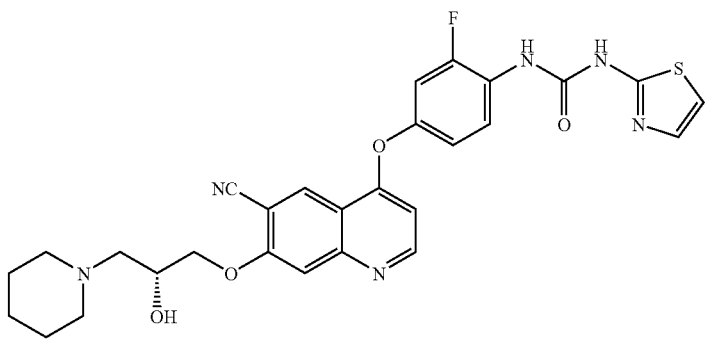

TABLE 42-continued
ex. 530
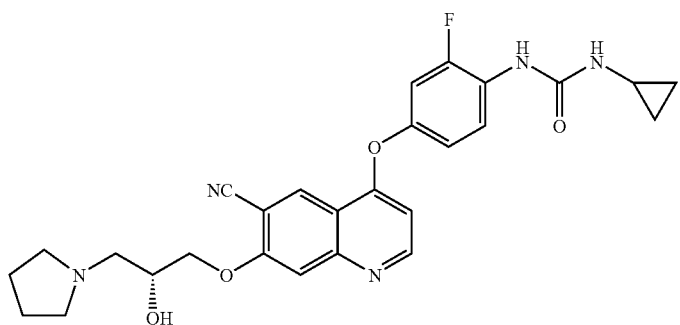
ex. 531
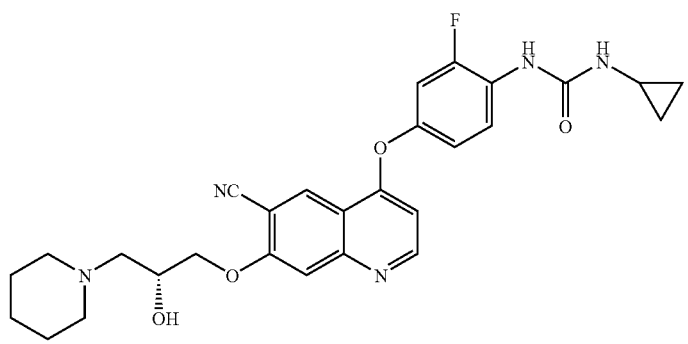
ex. 532
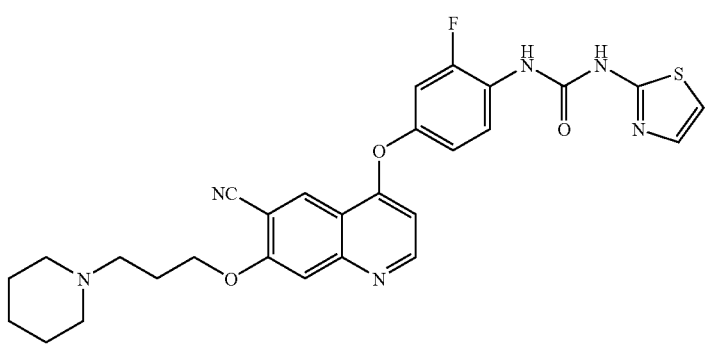
ex. 533
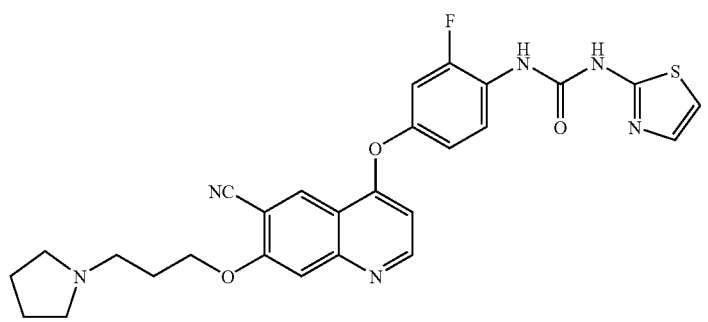

TABLE 42-continued
ex. 534
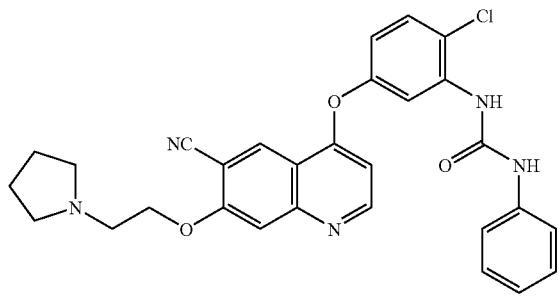
ex. 535
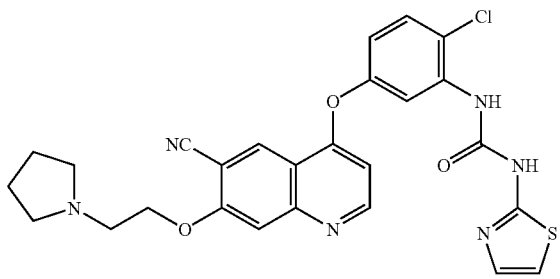
ex. 536
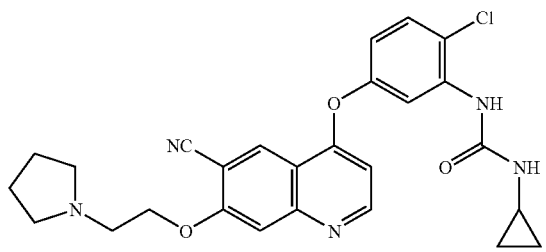
ex. 537
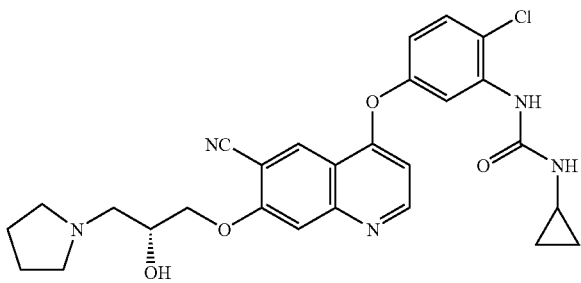
ex. 538
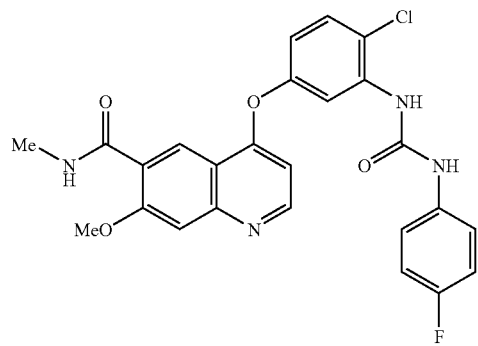

TABLE 42-continued
ex. 539
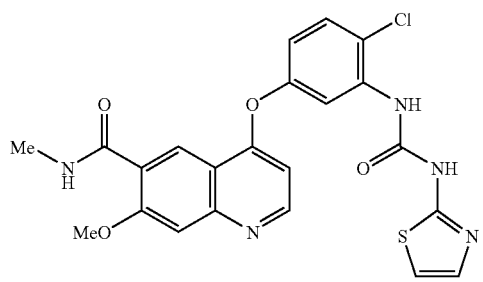
ex. 540
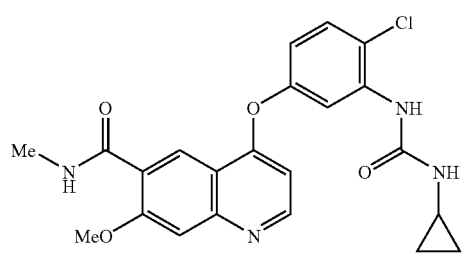
ex. 541
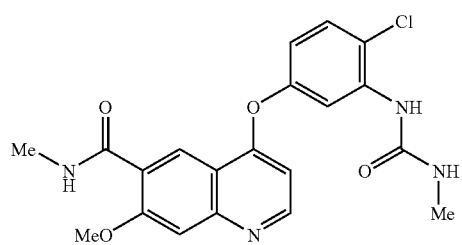
ex. 542
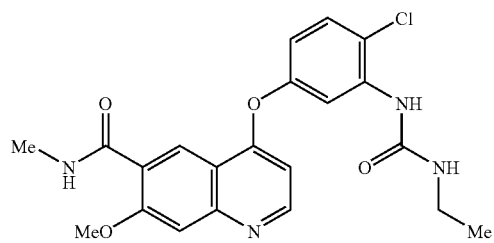
ex. 543
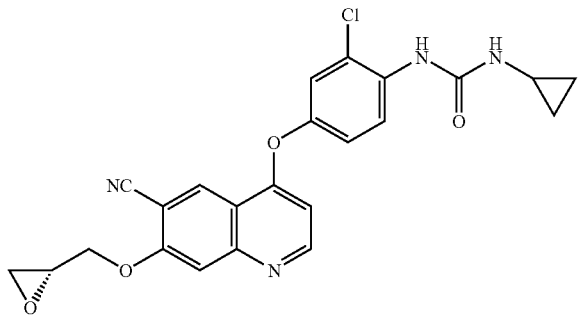

TABLE 42-continued
ex. 544
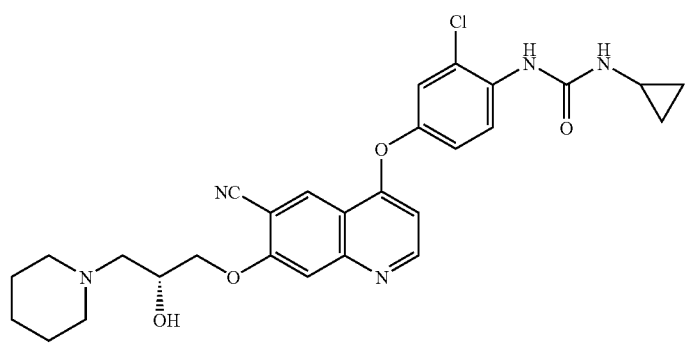
ex. 545
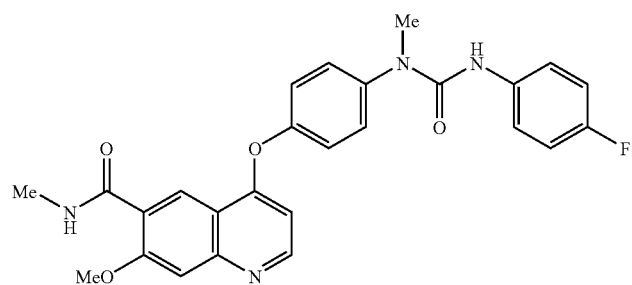
ex. 546
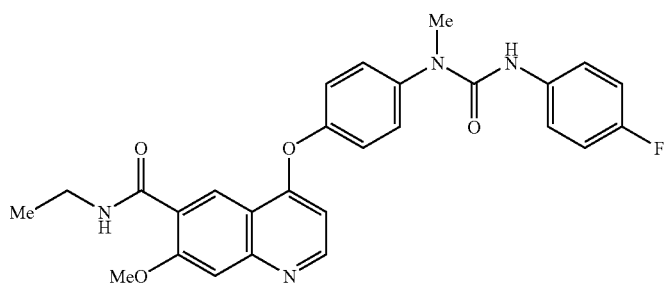
TABLE 43
ex. 547
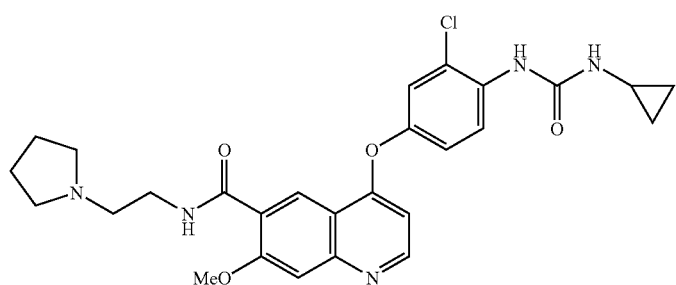

TABLE 43-continued
ex. 548
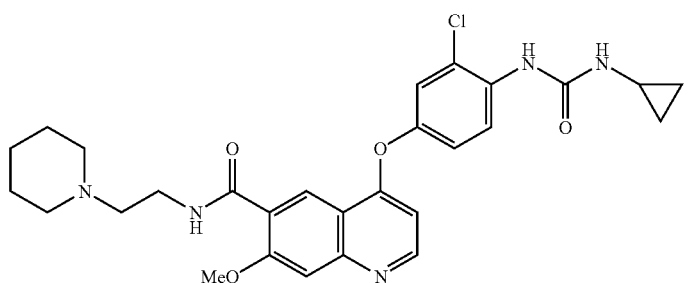
ex. 549
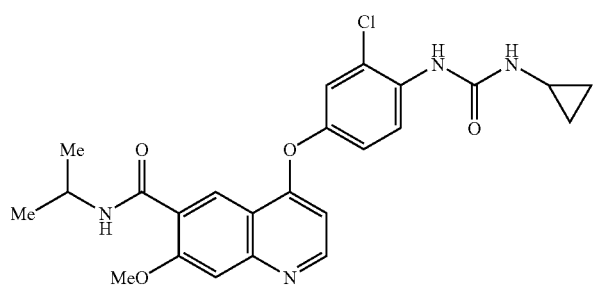
ex. 550
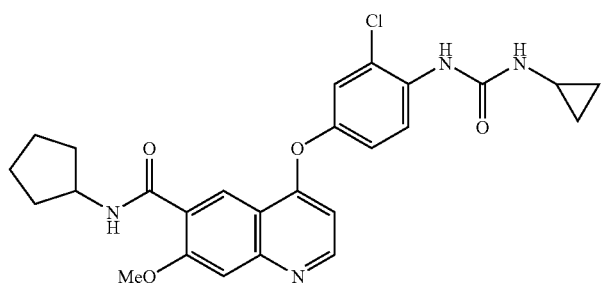
ex. 551
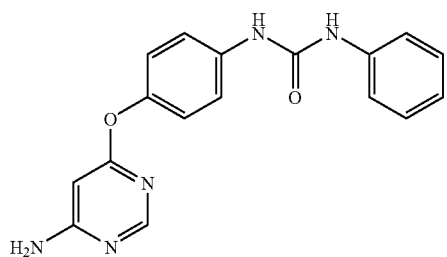
ex. 552
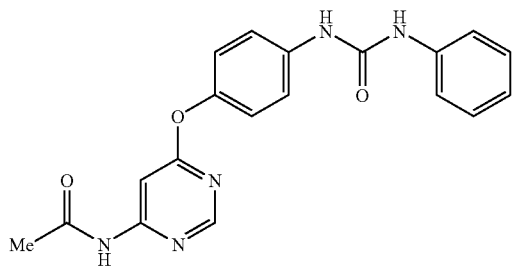

TABLE 43-continued
ex. 553
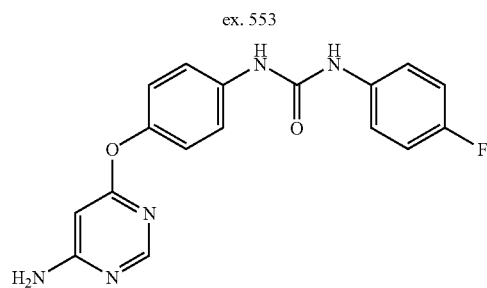
ex. 554
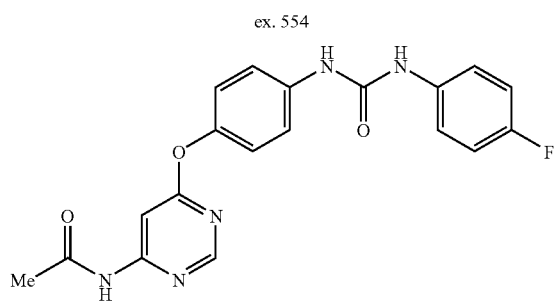
ex. 555
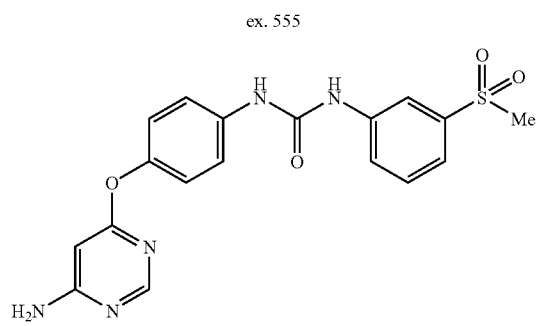
ex. 556
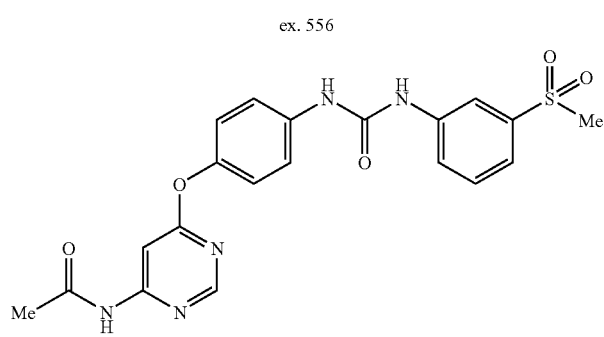
ex. 557
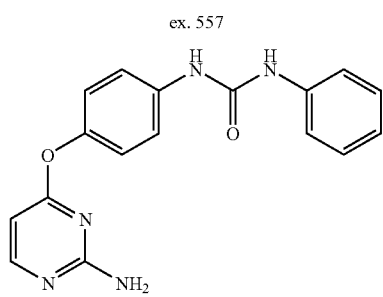

TABLE 43-continued
ex. 558
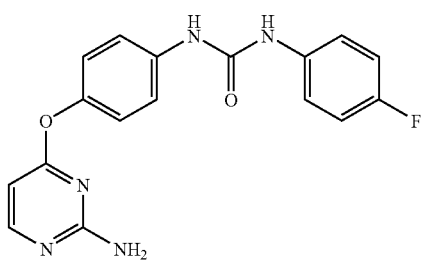
ex. 559
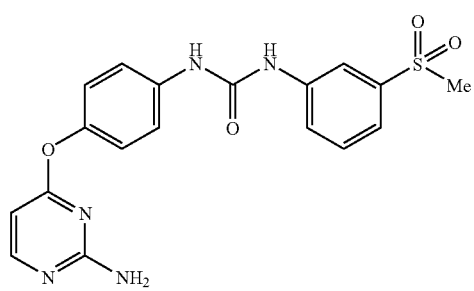
ex. 560
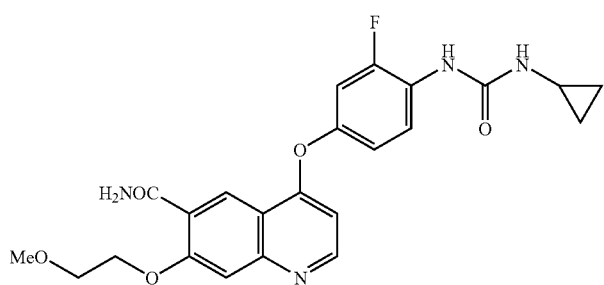
ex. 561
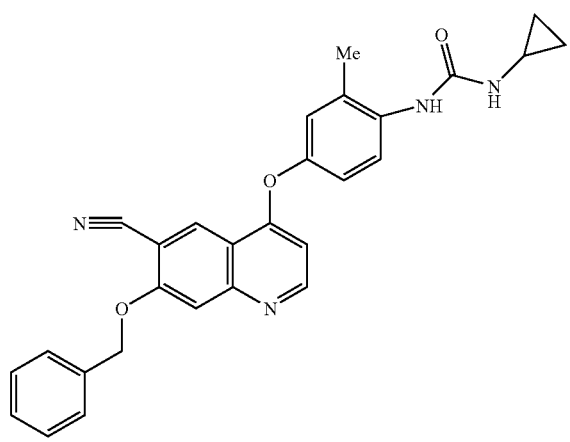

TABLE 43-continued
ex. 562
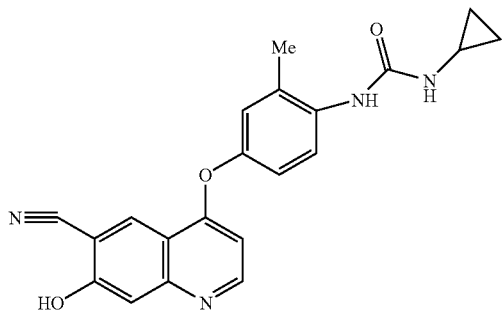
ex. 563
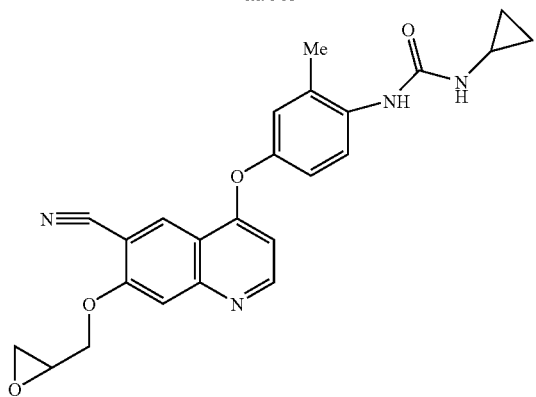
ex. 564
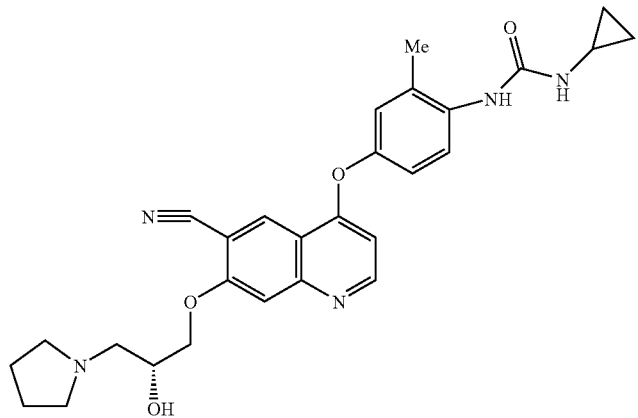
ex. 565
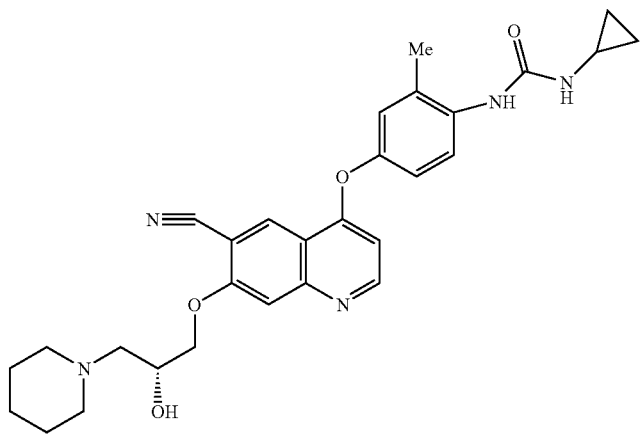

TABLE 43-continued
ex. 566
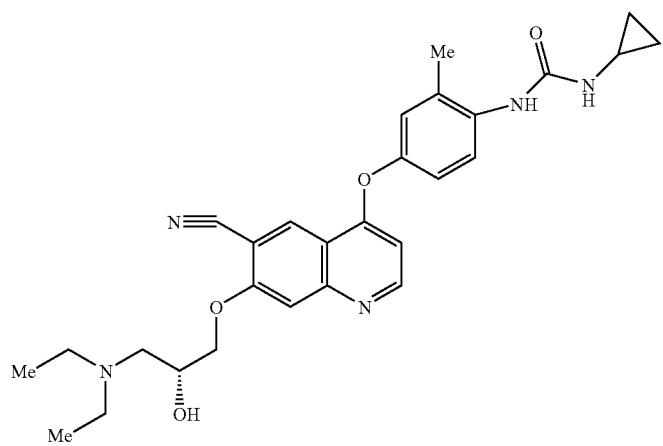
ex. 567
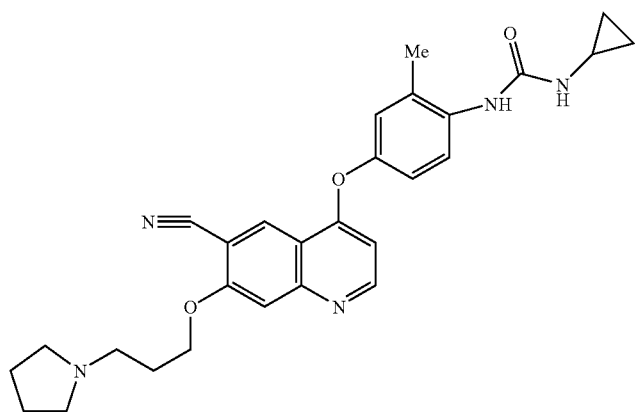
ex. 568
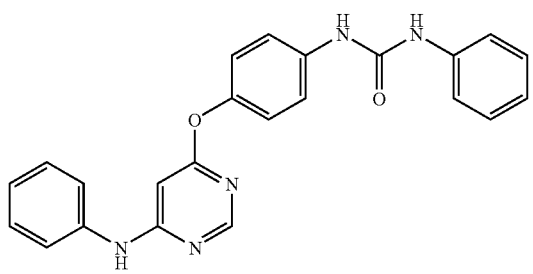
ex. 569
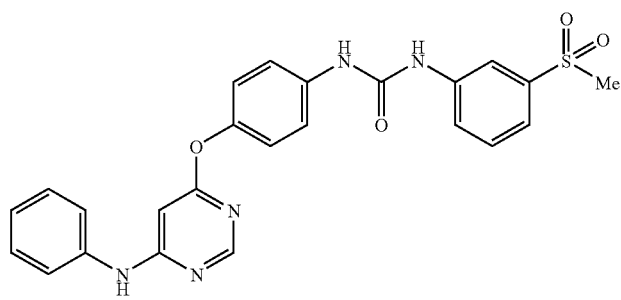

TABLE 43-continued
ex. 570
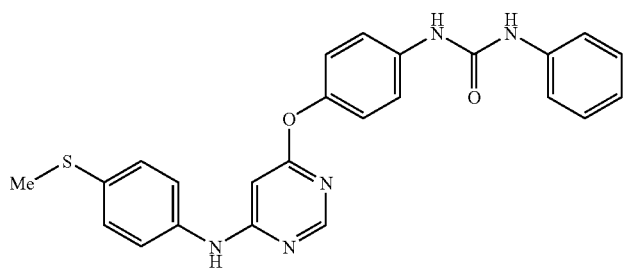
TABLE 44
ex. 571
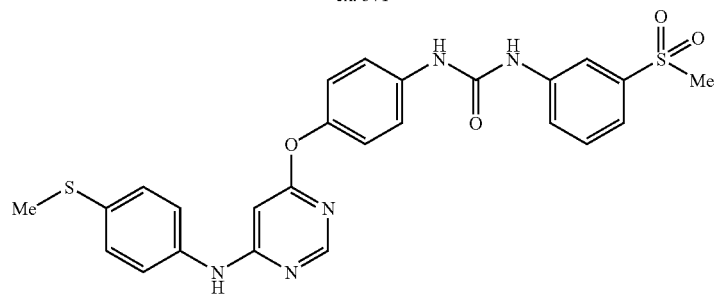
ex. 572
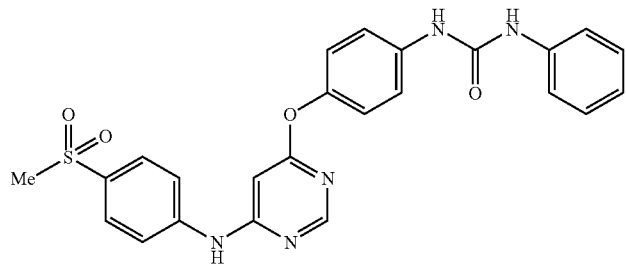
ex. 573
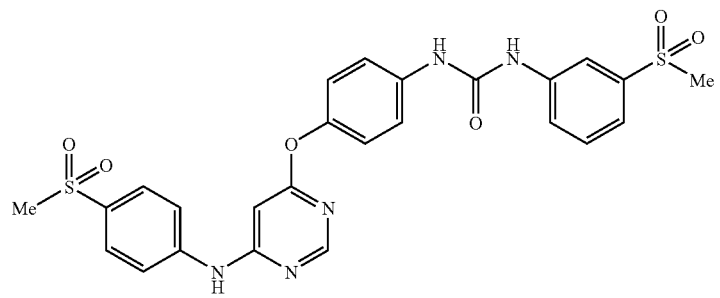
ex. 574
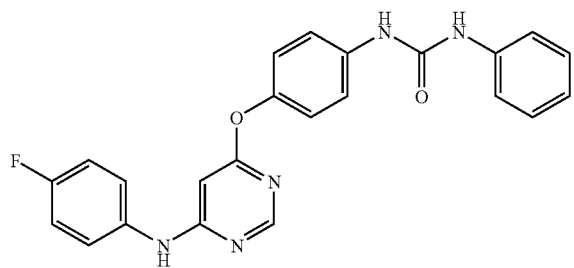

TABLE 44-continued
ex. 575
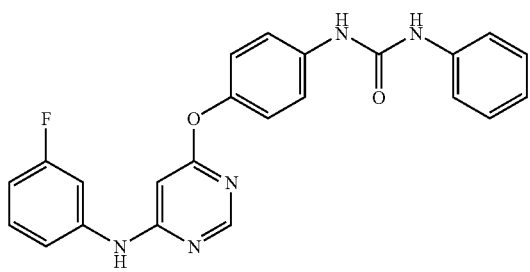
ex. 576
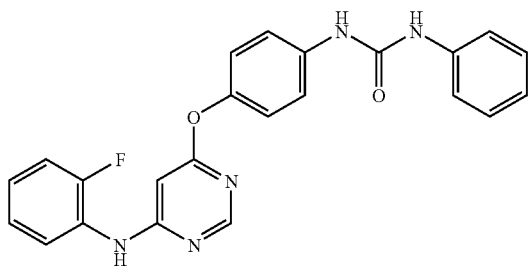
ex. 577
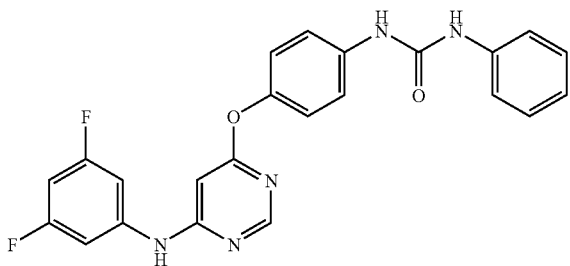
ex. 578
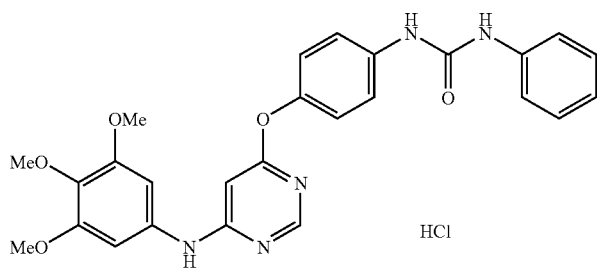
HCl
ex. 579
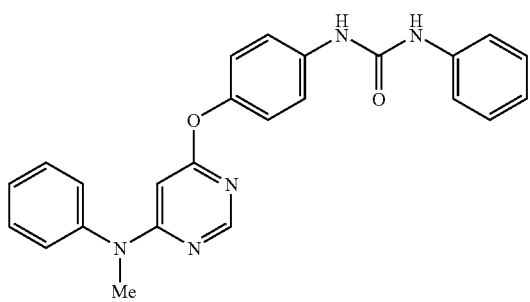

TABLE 44-continued
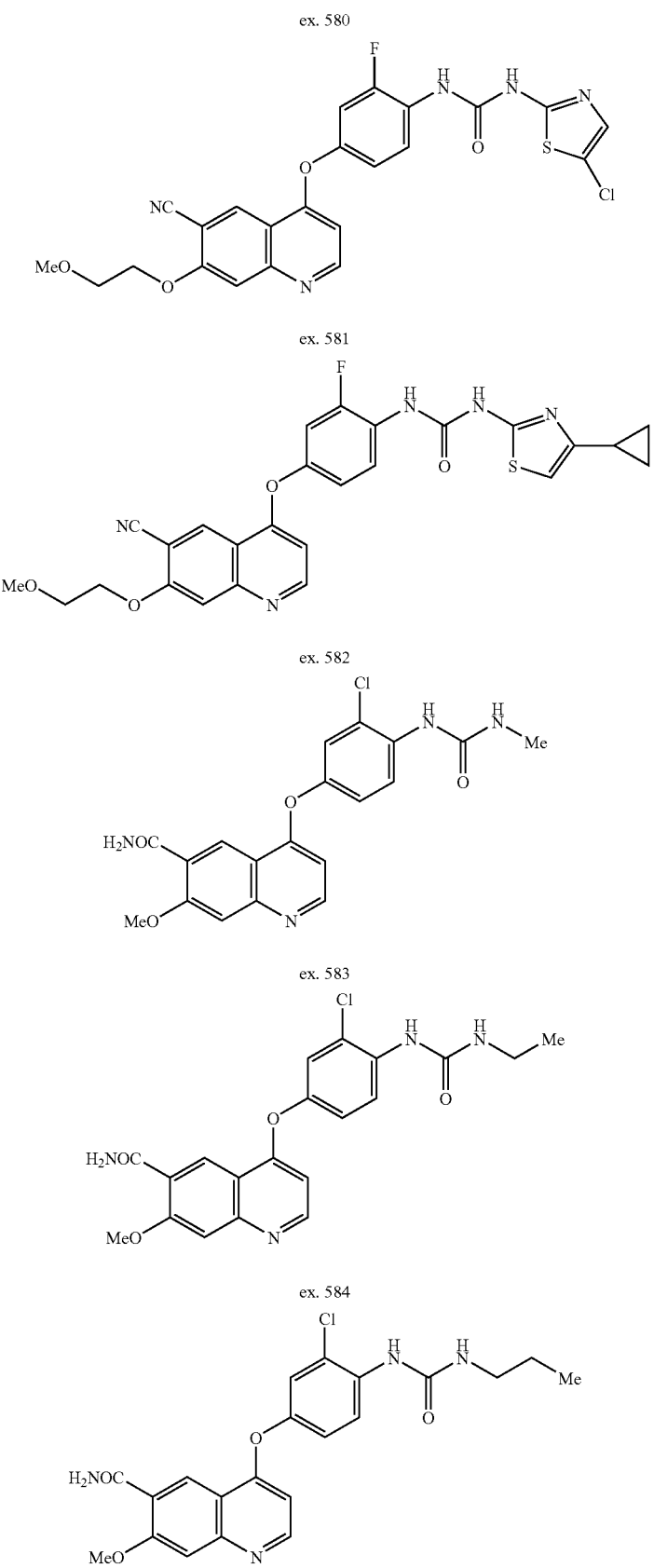

TABLE 44-continued
ex. 585
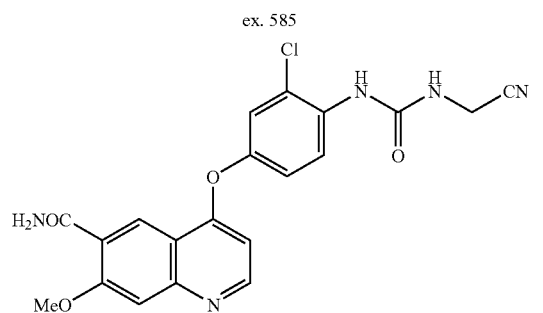
ex. 586
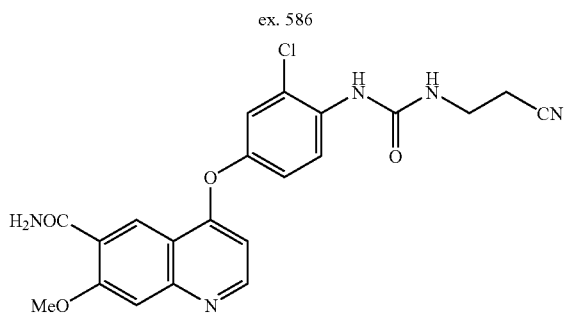
ex. 589
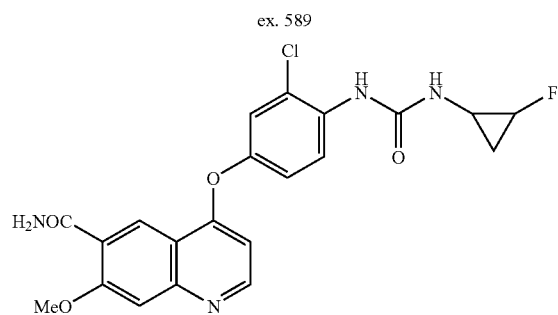
ex. 590
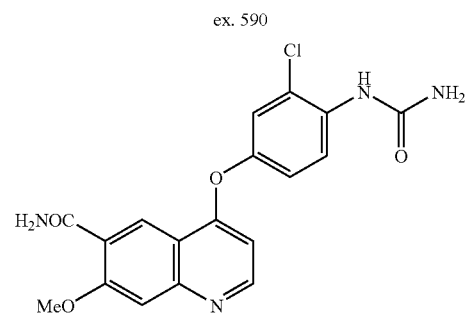
ex. 591
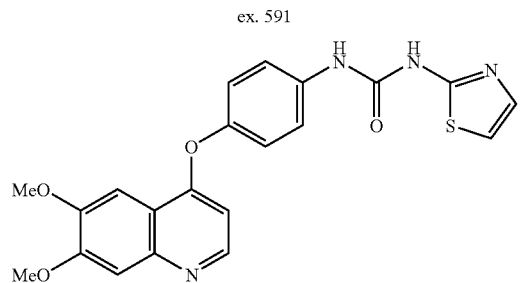

TABLE 44-continued
ex. 592
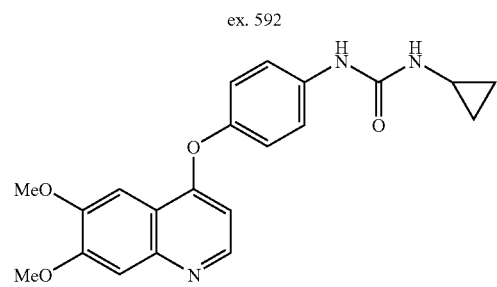
ex. 593
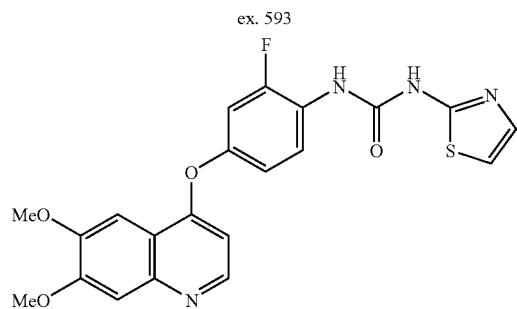
ex. 594
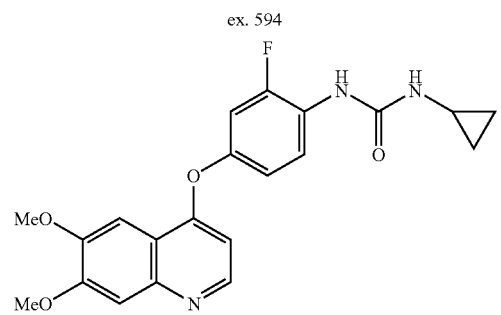
ex. 595
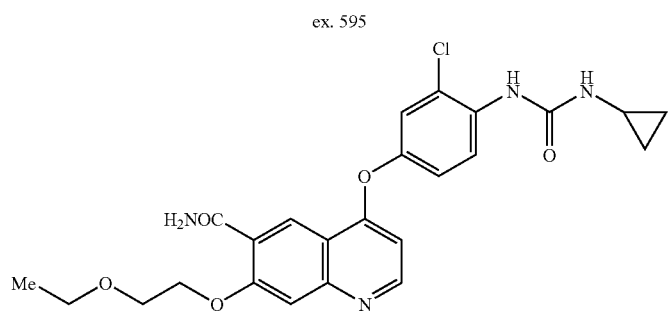
ex. 596
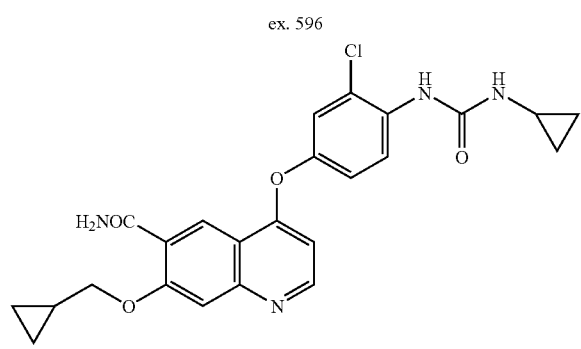

TABLE 45
ex. 597
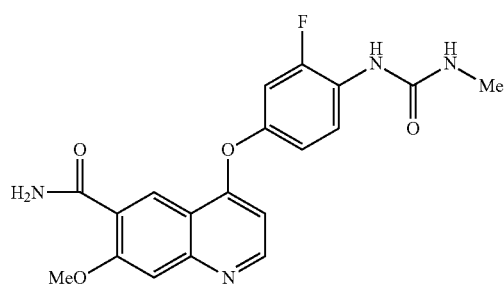
ex. 598
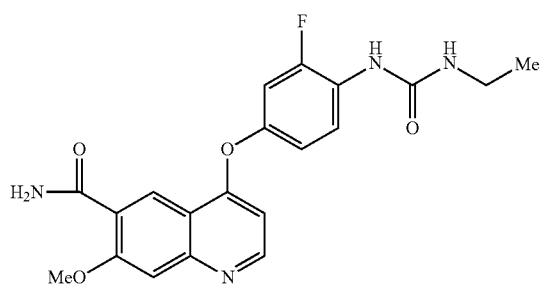
ex. 599
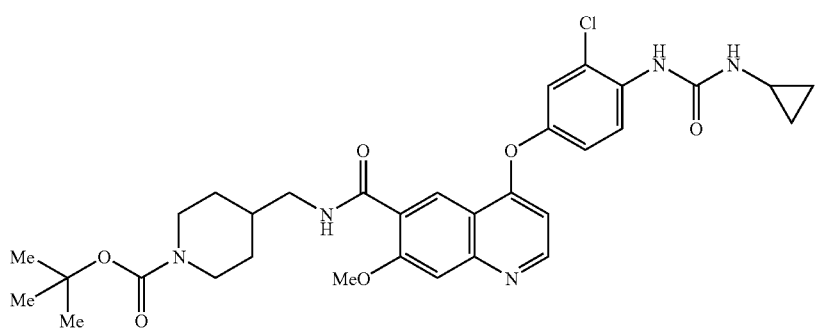
ex. 600
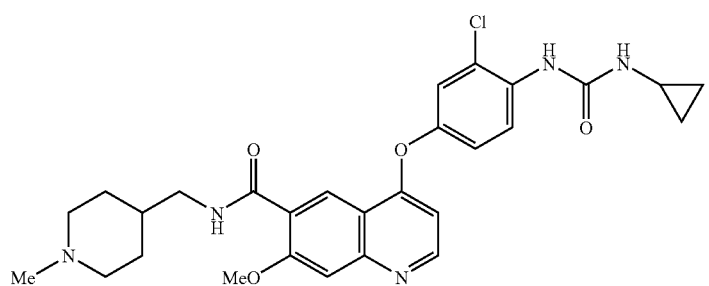

TABLE 45-continued
ex. 601
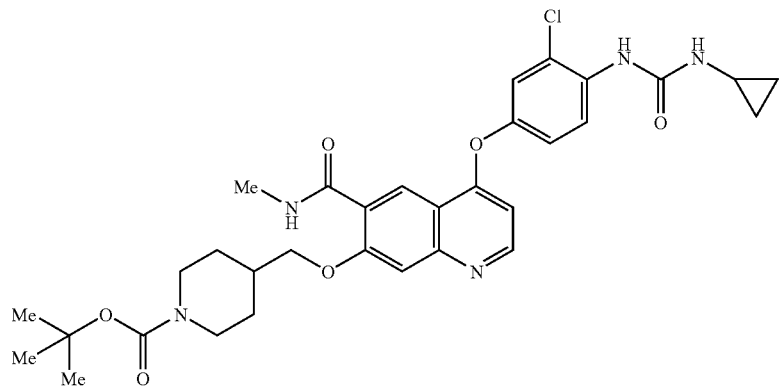
ex. 602
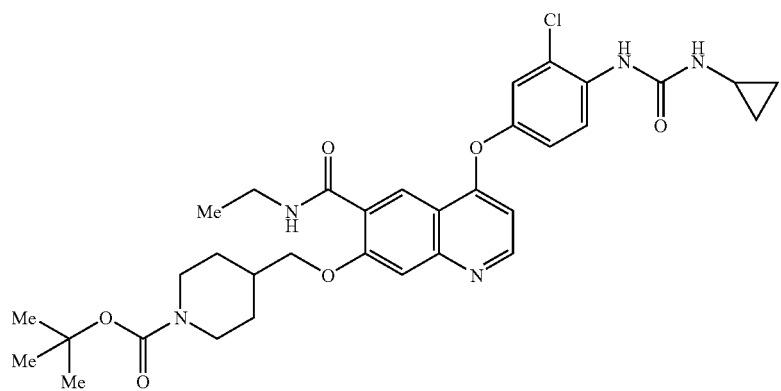
ex. 603
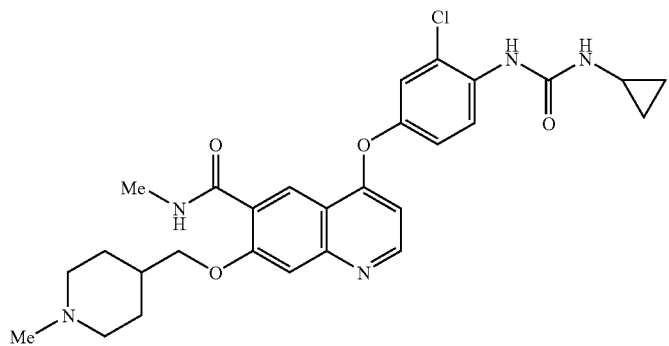
ex. 604
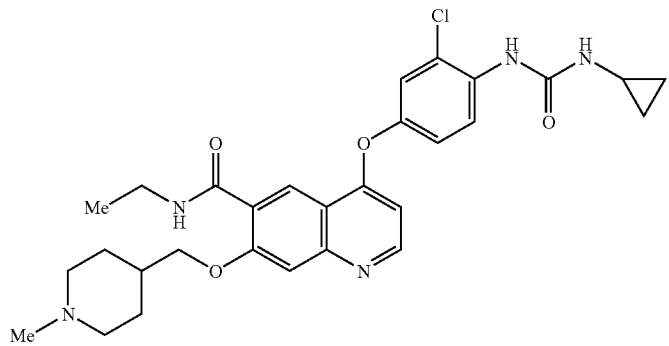

TABLE 45-continued
ex. 605
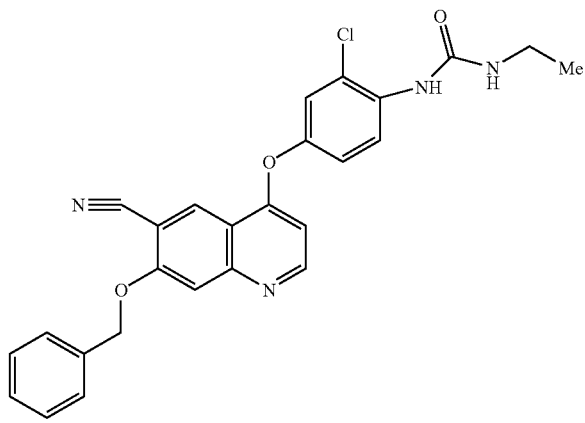
ex. 606
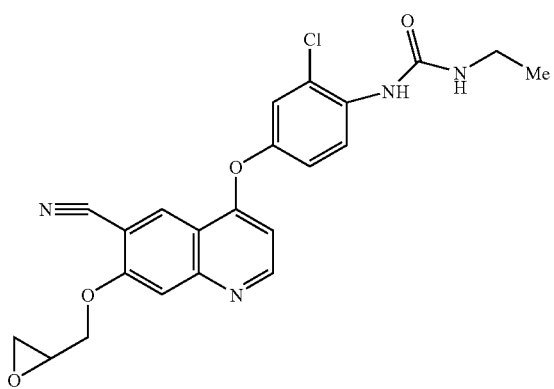
ex. 607
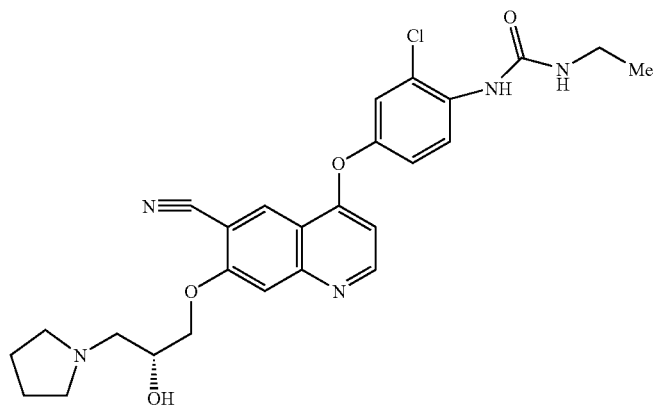

TABLE 45-continued
ex. 608
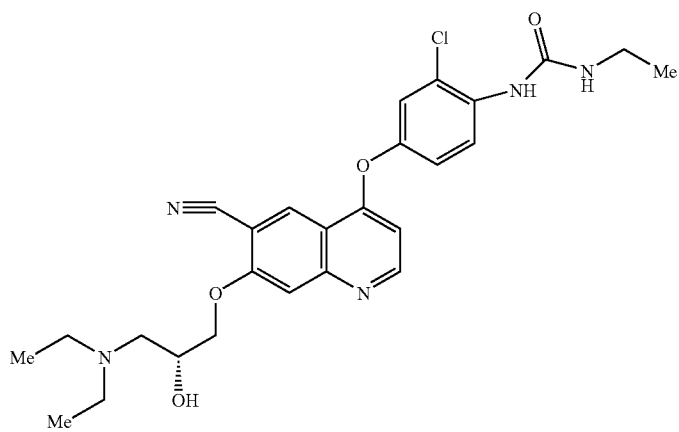
ex. 609
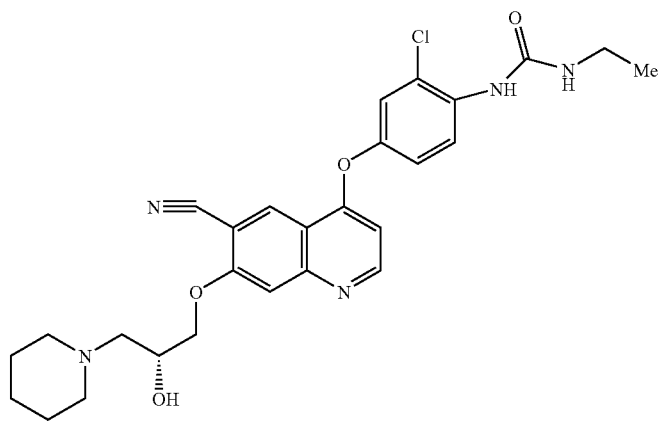
ex. 610
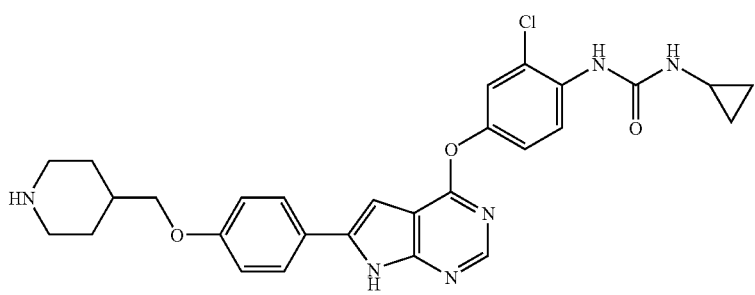
ex. 611
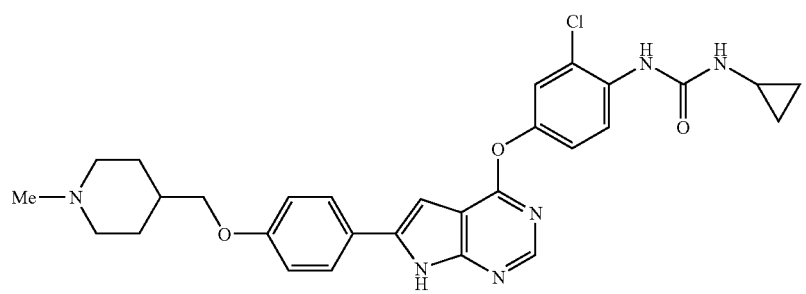

TABLE 45-continued
ex. 612
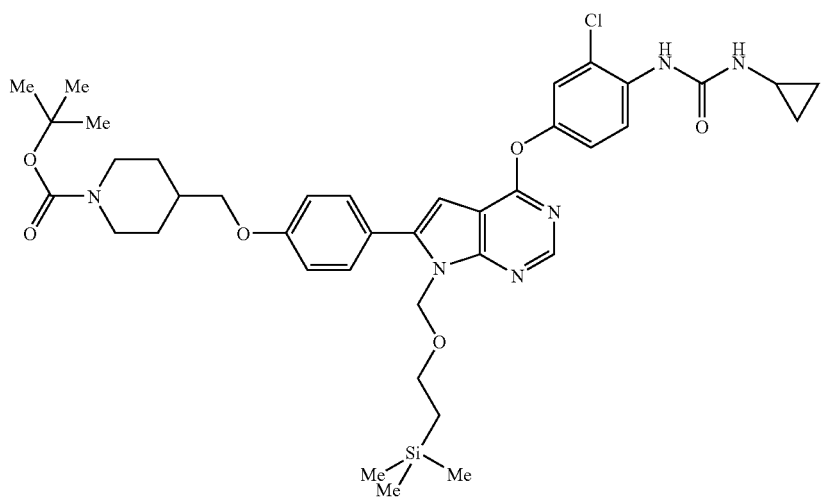
ex. 613
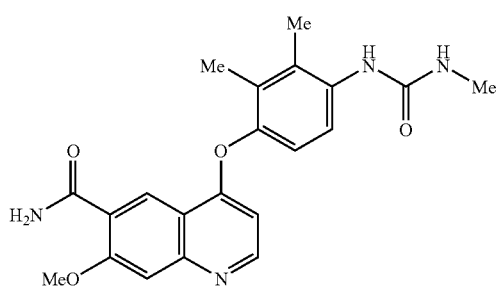
ex. 614
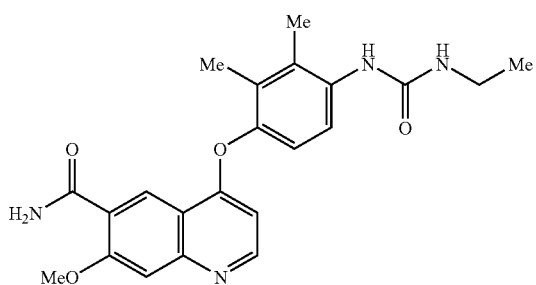
ex. 615
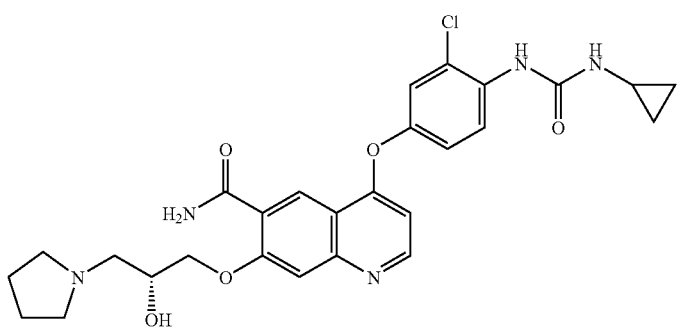

TABLE 45-continued
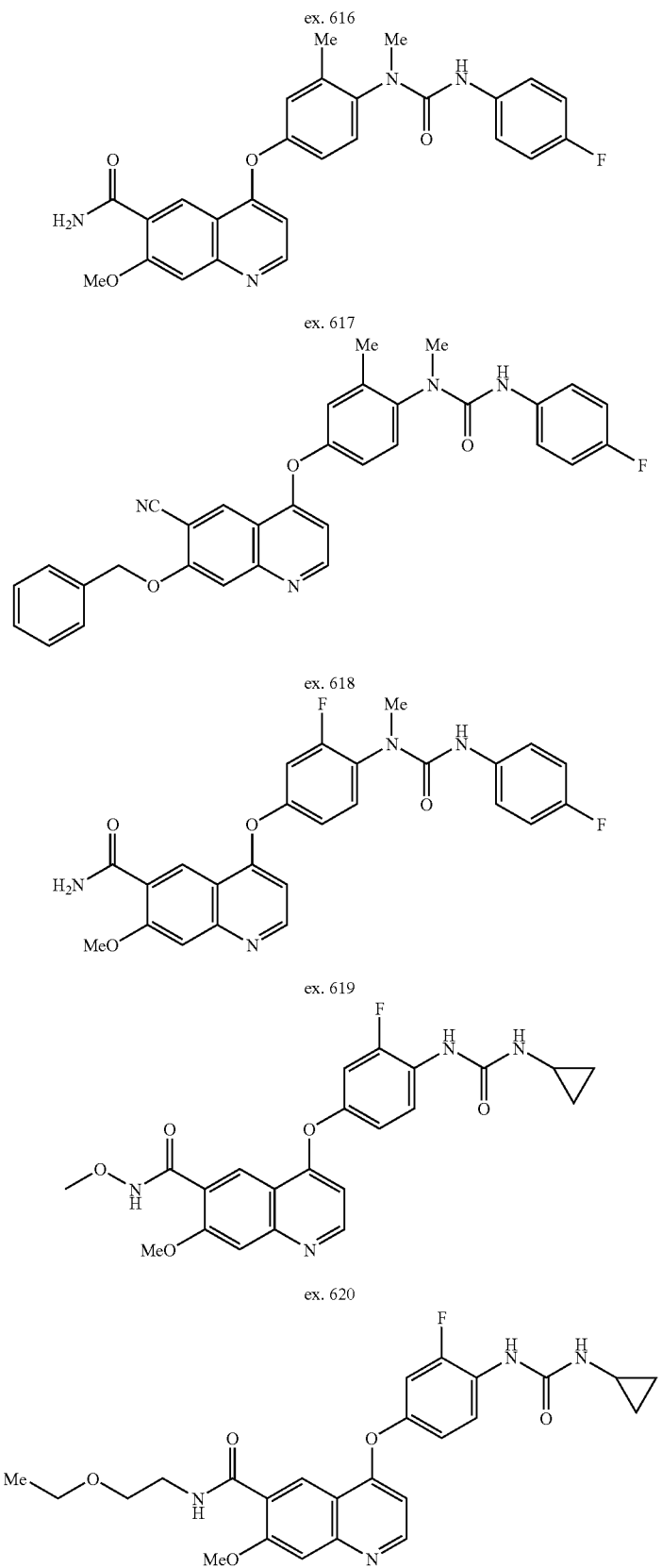

TABLE 46
ex. 621
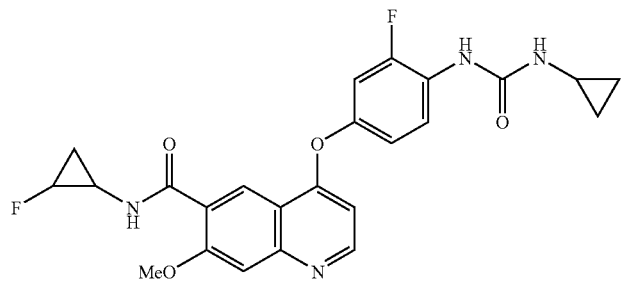
ex. 622
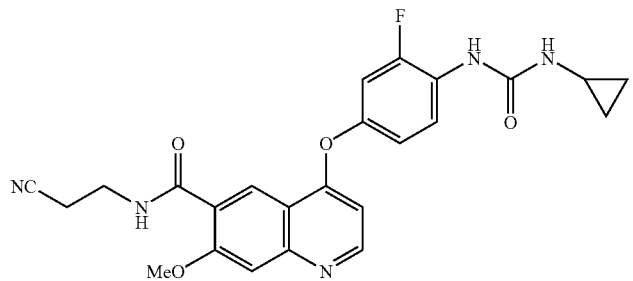
ex. 623
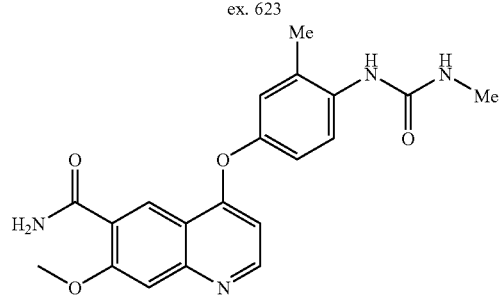
ex. 624
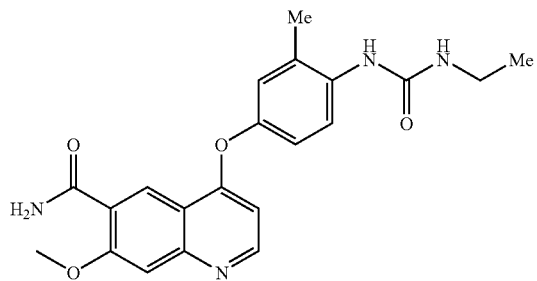
ex. 625
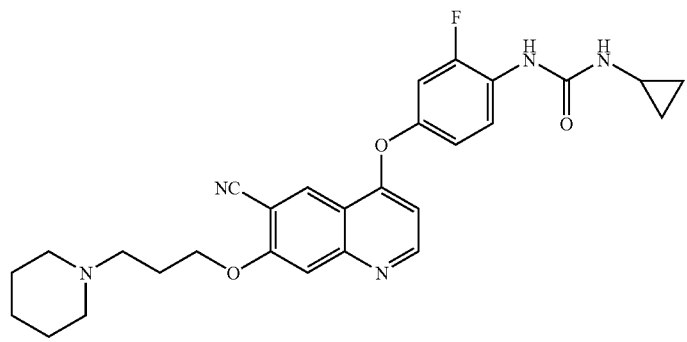

TABLE 46-continued
ex. 626
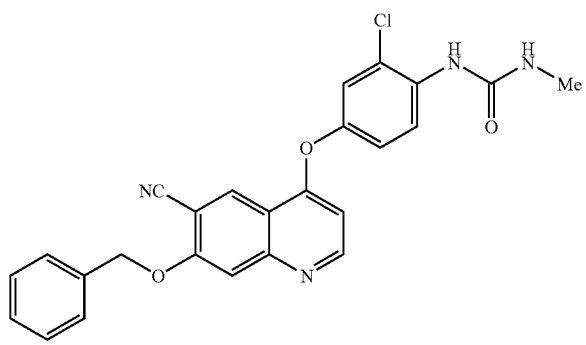
ex. 627
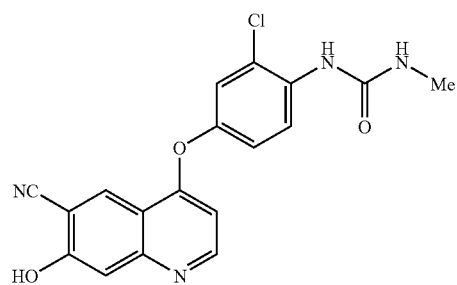
ex. 628
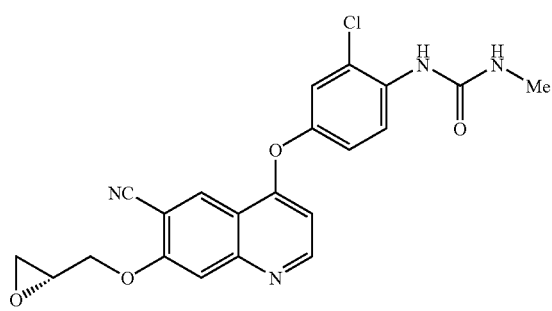
ex. 629
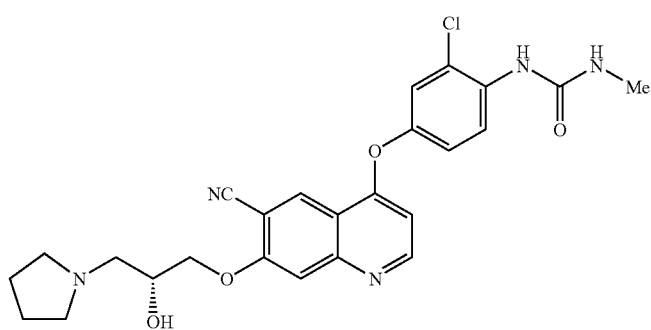

TABLE 46-continued
ex. 630
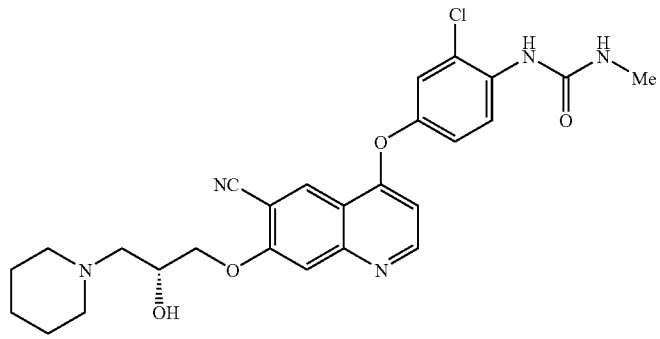
ex. 631
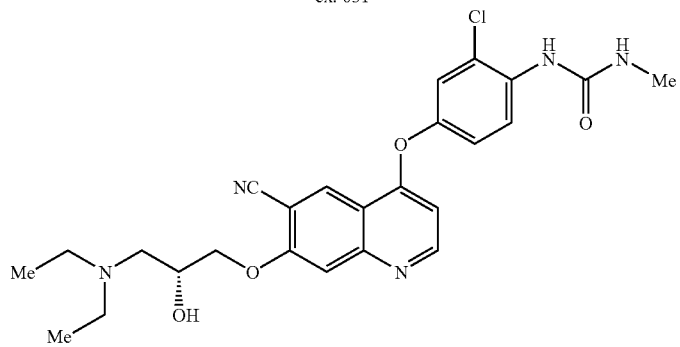
ex. 632
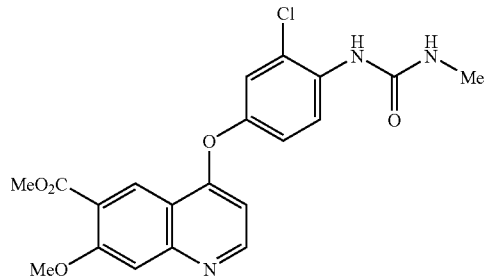
ex. 633
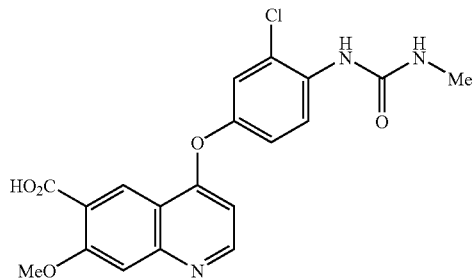
ex. 634
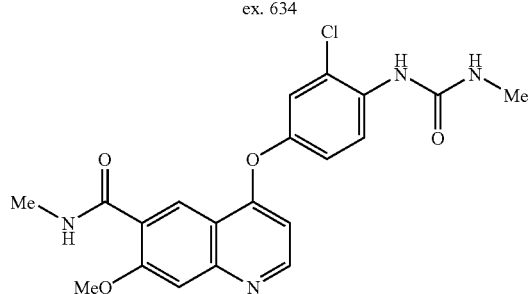

TABLE 46-continued
ex. 635
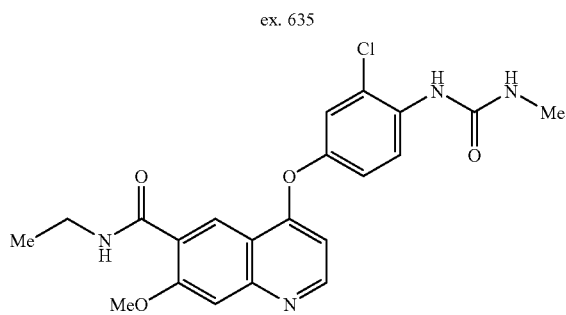
ex. 636
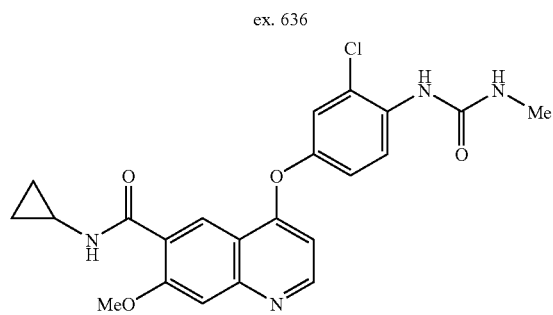
ex. 637
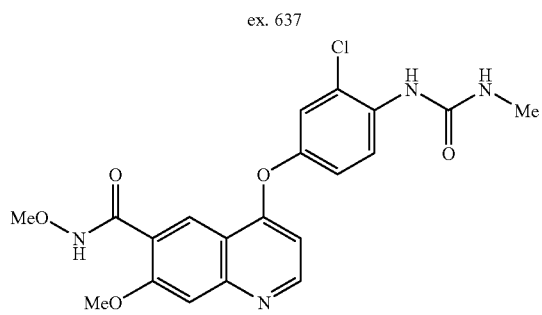
ex. 638
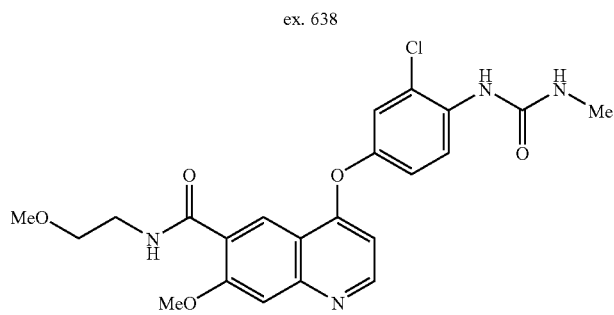
ex. 639
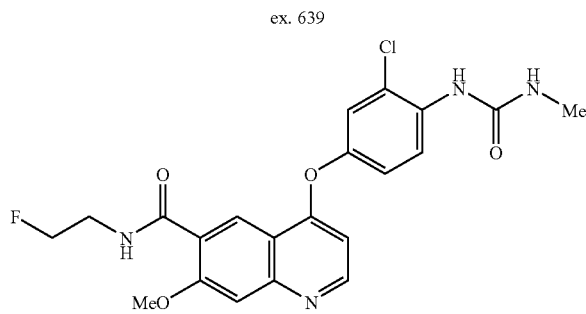

TABLE 46-continued
ex. 640
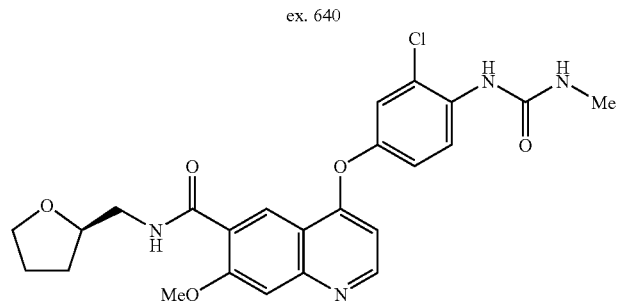
ex. 641
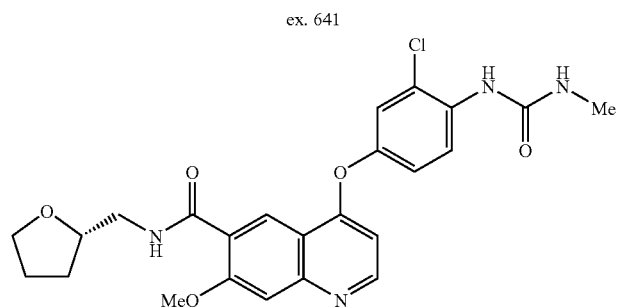
ex. 642
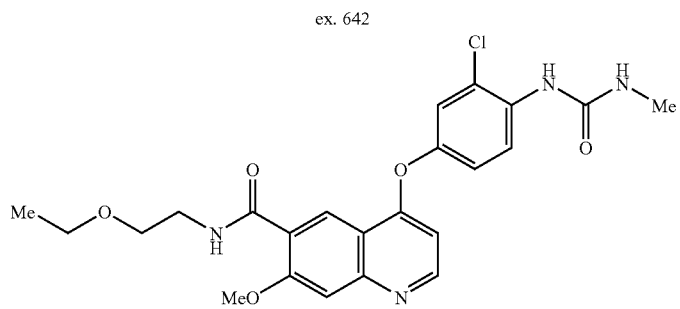
ex. 643
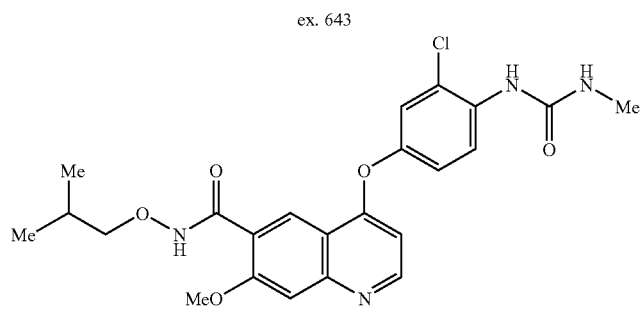
ex. 644
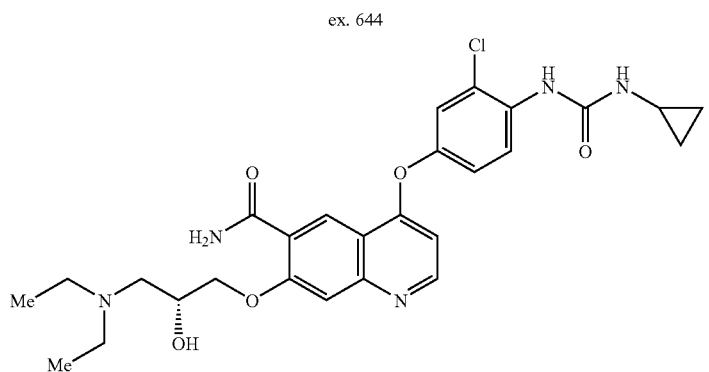

TABLE 47
ex. 645
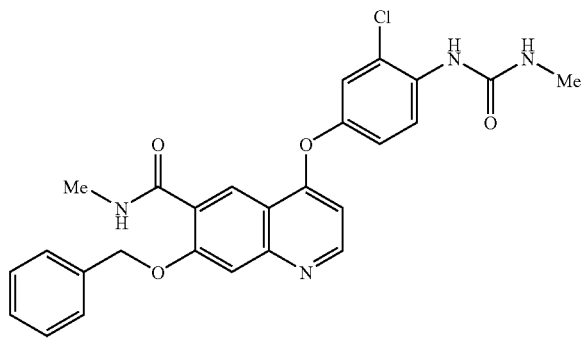
ex. 646
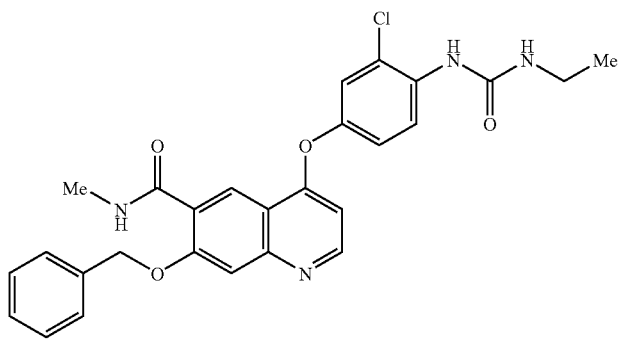
ex. 647
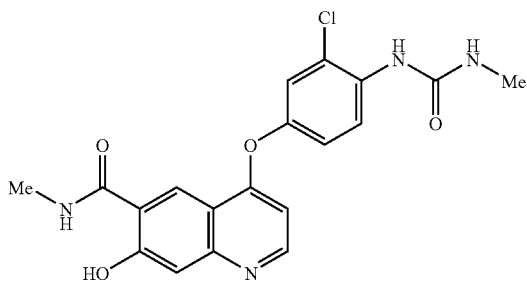
ex. 648
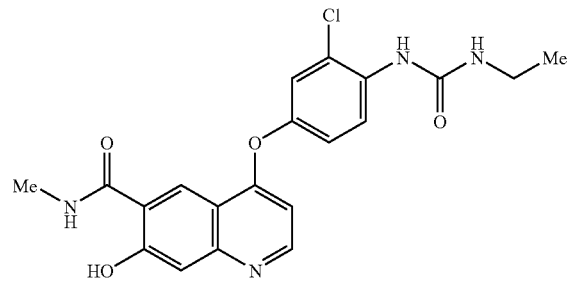

TABLE 47-continued
ex. 649
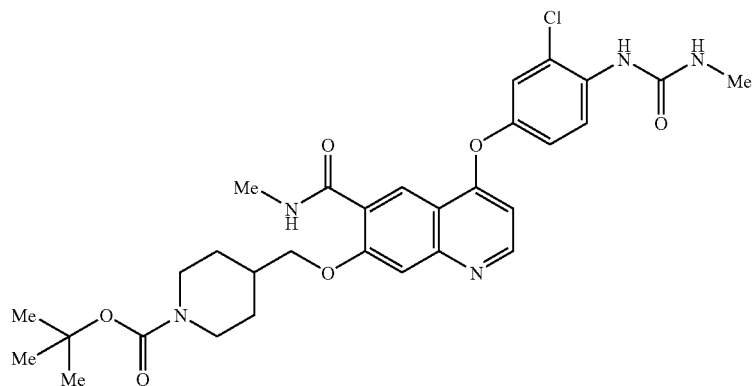
ex. 650
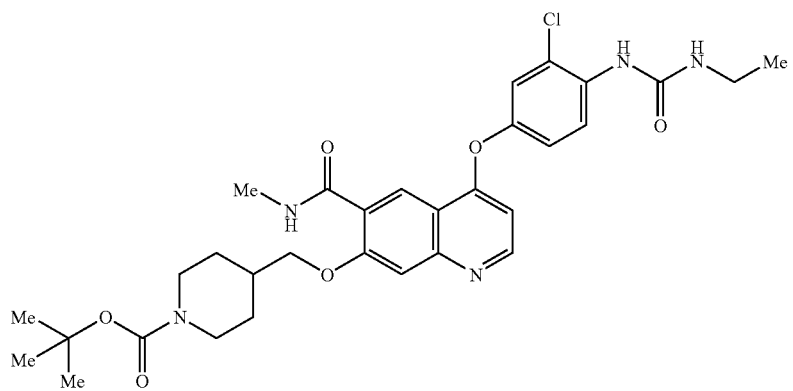
ex. 651
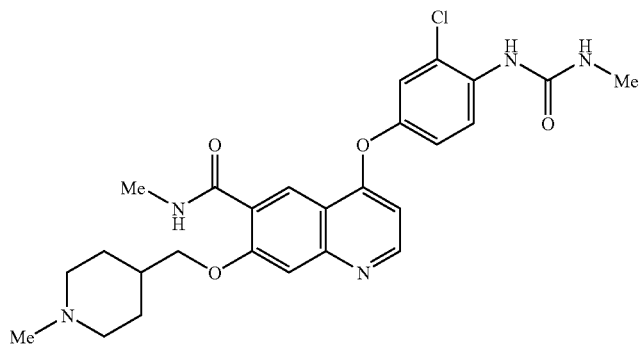
ex. 652
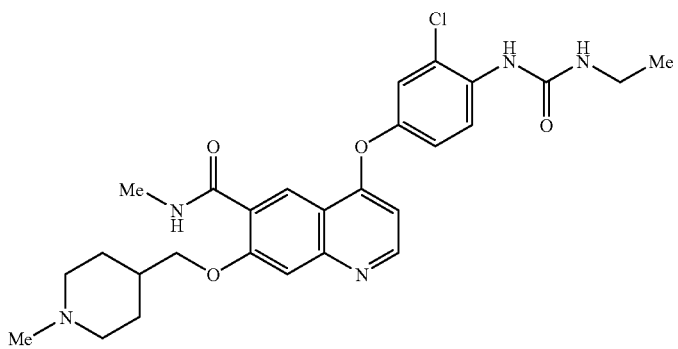

TABLE 47-continued
ex. 653
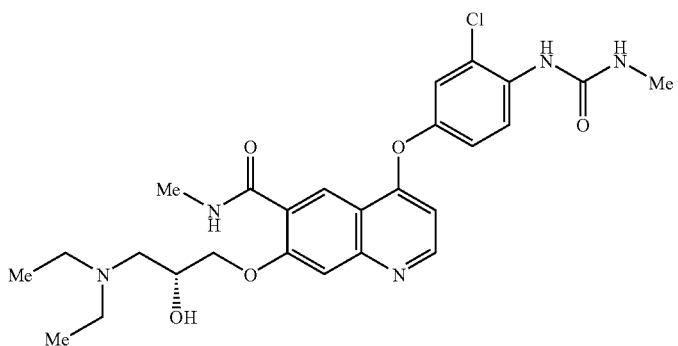
ex. 654
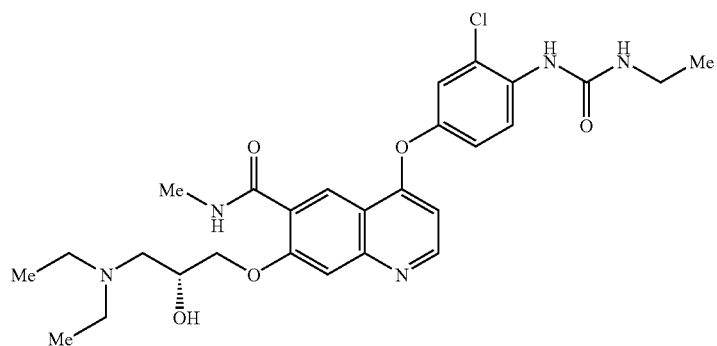
ex. 655
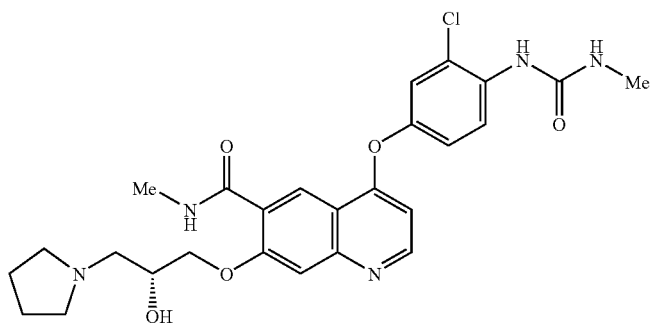
ex. 656
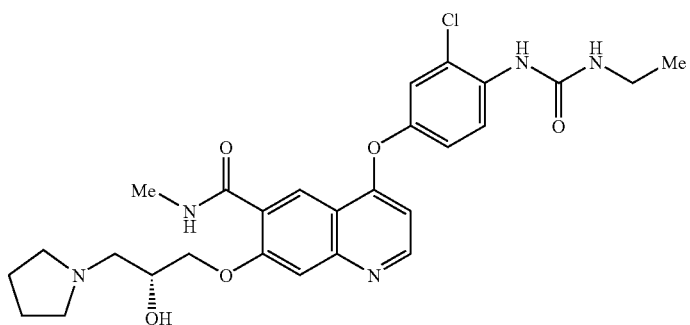

TABLE 47-continued
ex. 657
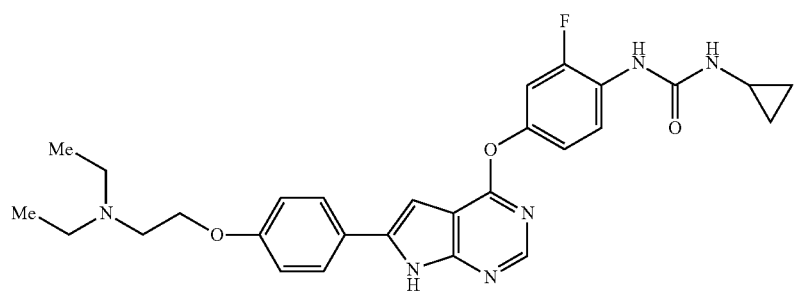
ex. 658
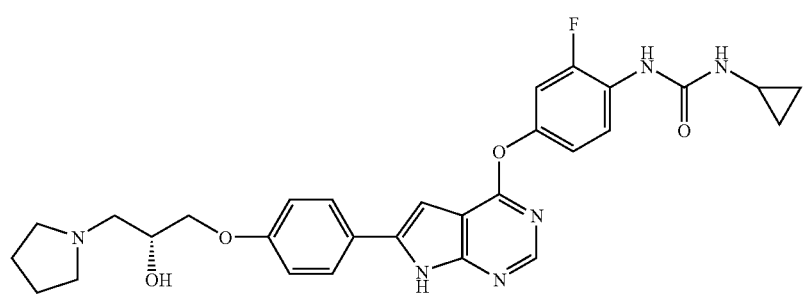
ex. 659
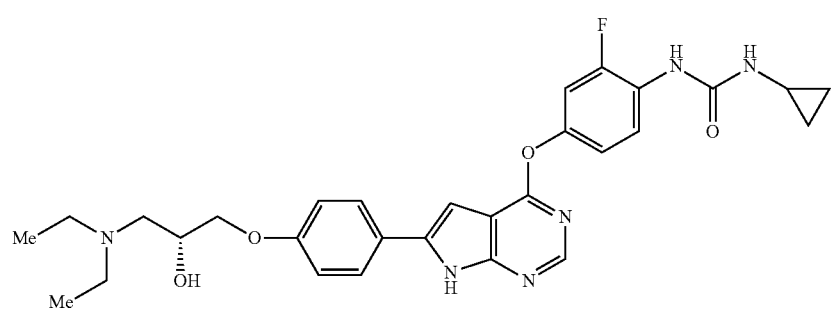
ex. 660
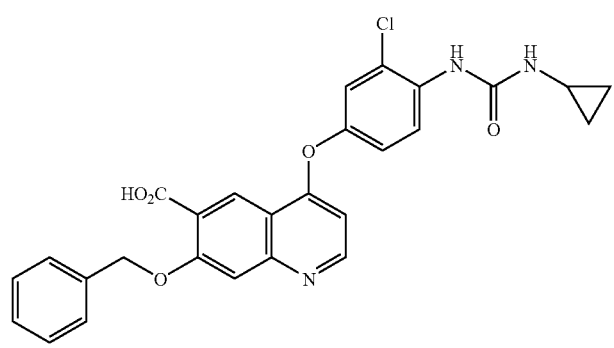

TABLE 47-continued
ex. 661
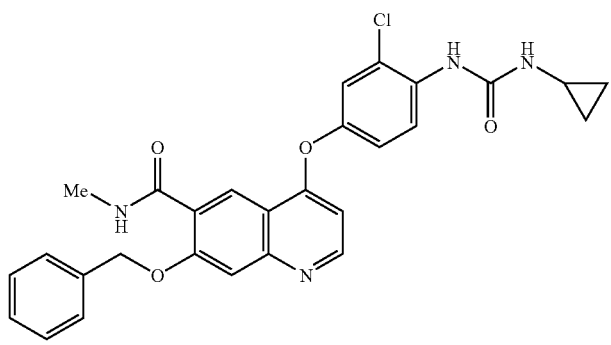
ex. 662
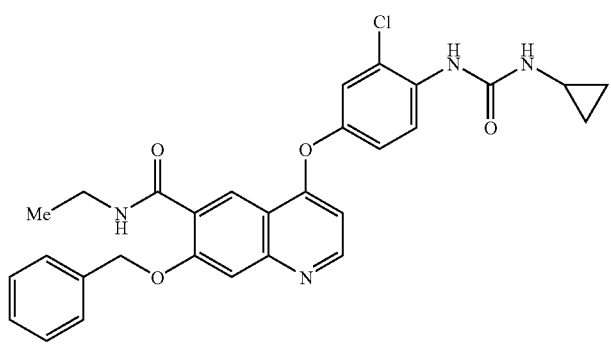
ex. 663
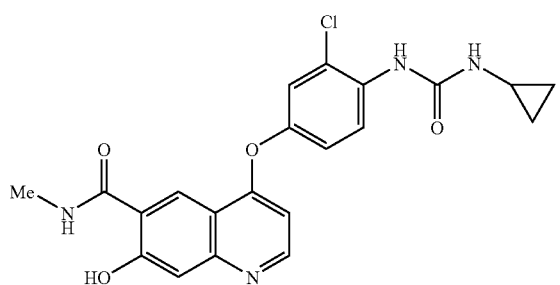
ex. 664
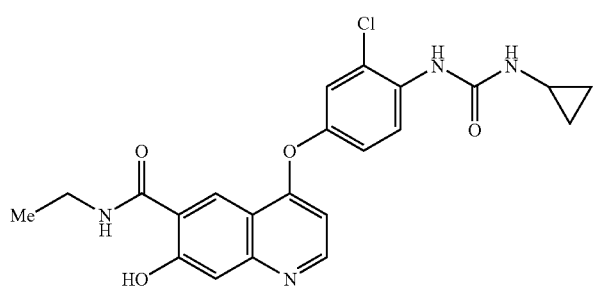

TABLE 47-continued
ex. 665
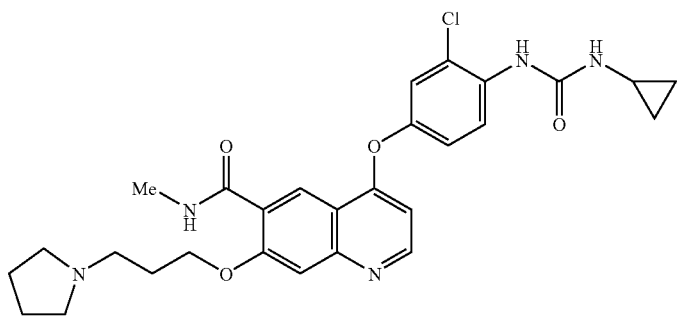
ex. 666
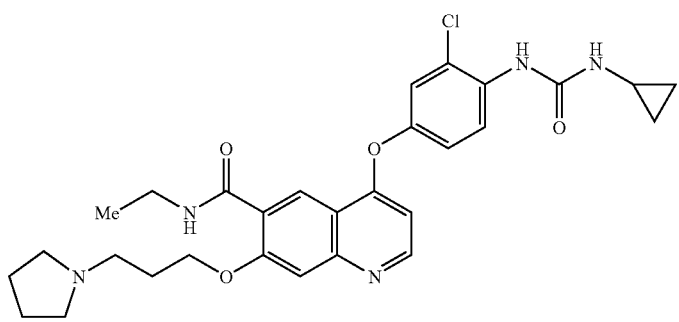
ex. 667
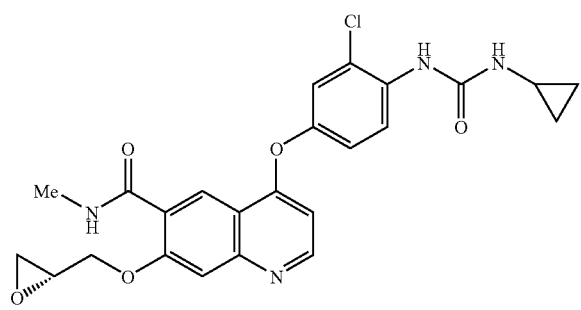
ex. 668
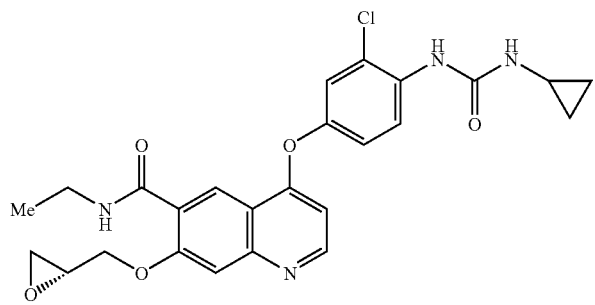

TABLE 48
ex. 669
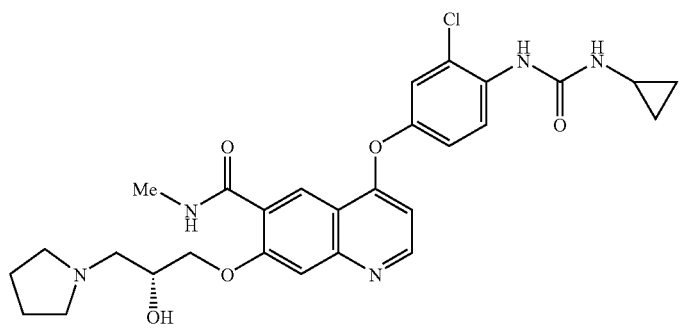
ex. 670
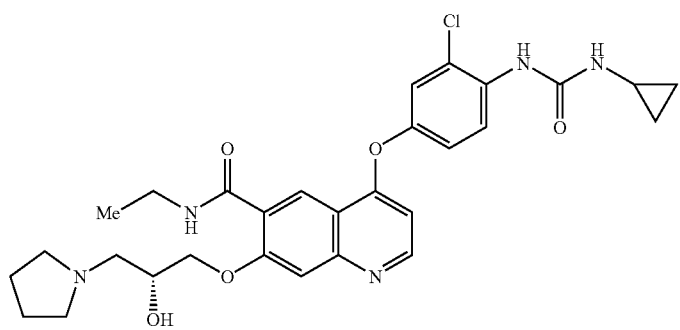
ex. 670-1
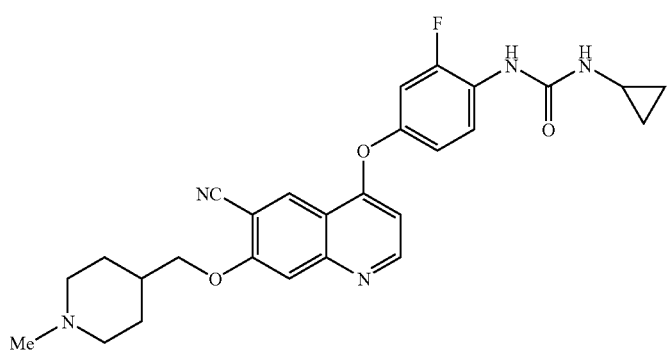
ex. 671
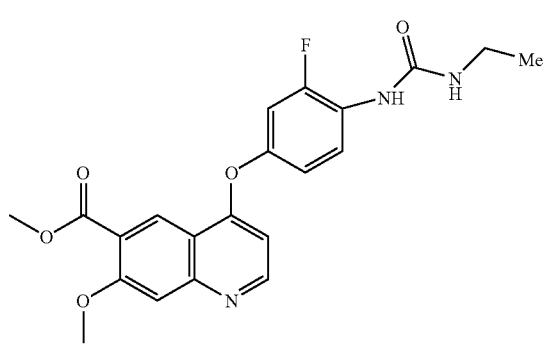

TABLE 48-continued
ex. 672
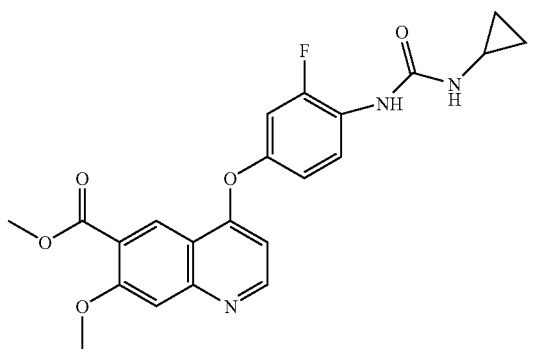
ex. 673
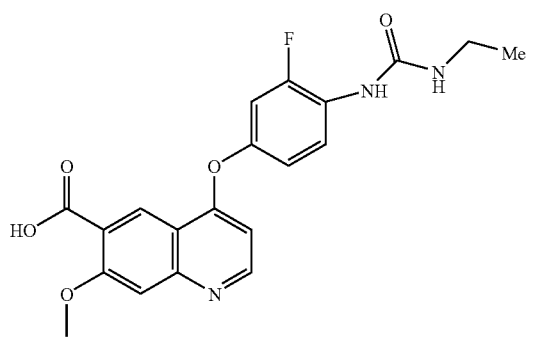
ex. 674
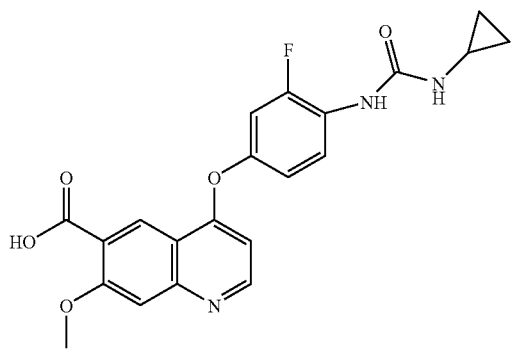
ex. 675
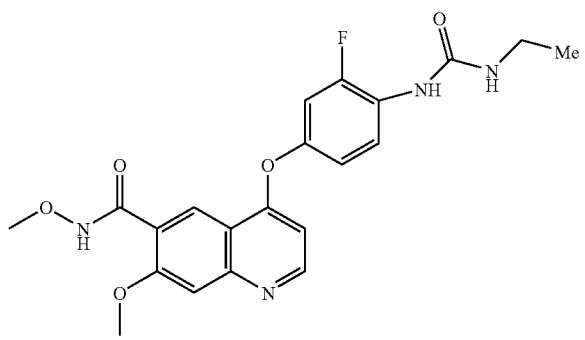

TABLE 48-continued
ex. 676
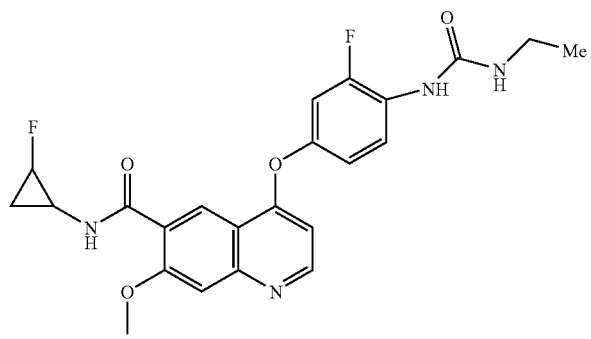
ex. 677
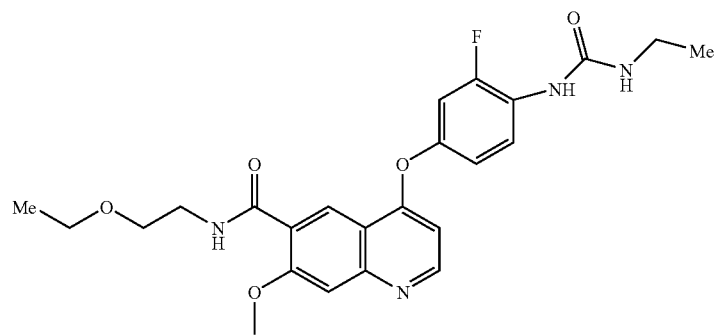
ex. 678
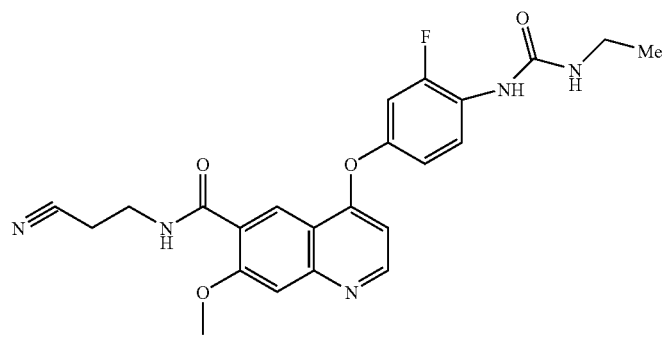
ex. 679
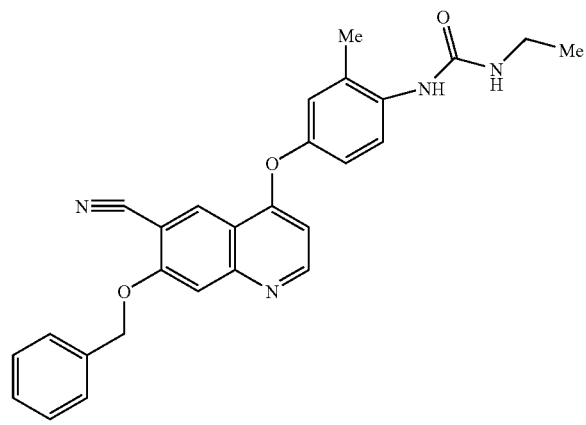

TABLE 48-continued
ex. 680
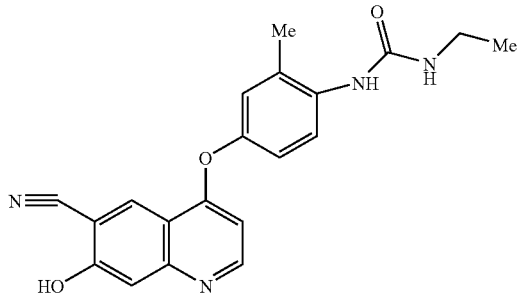
ex. 681
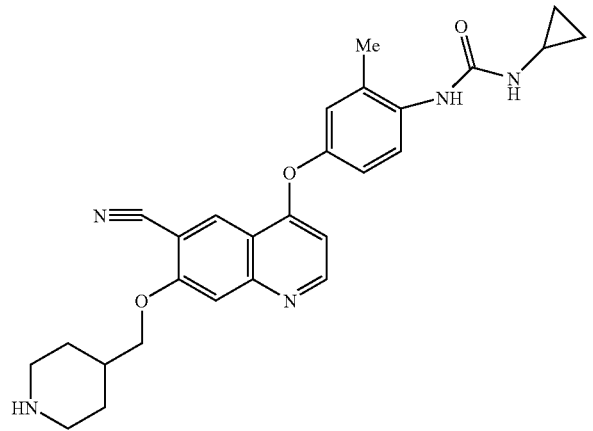
ex. 682
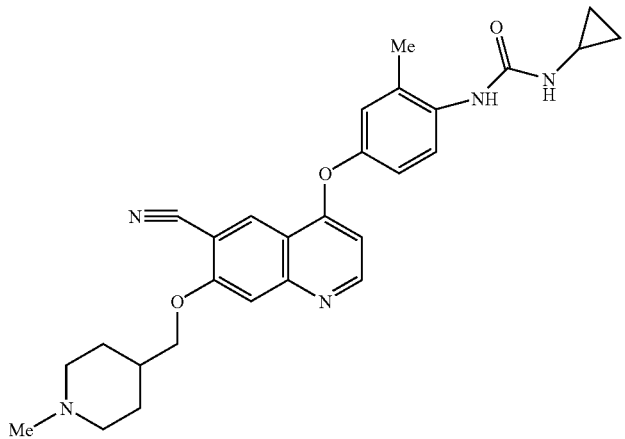
ex. 683
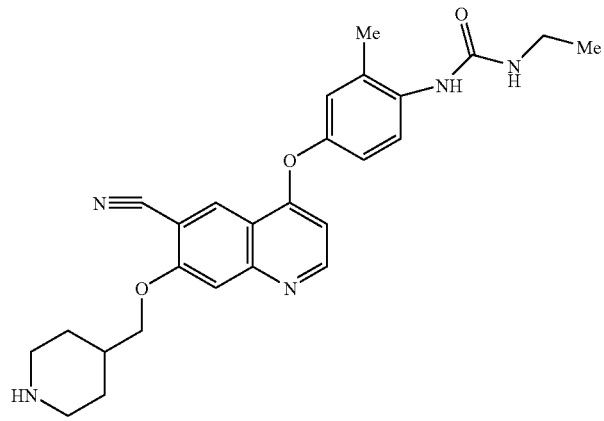

TABLE 48-continued
ex. 684
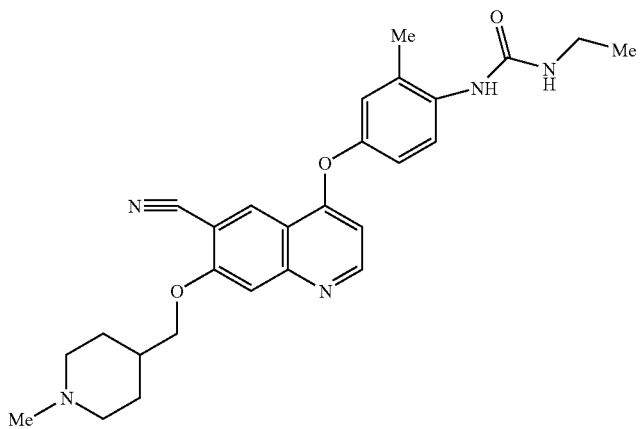
TABLE 49
ex. 697
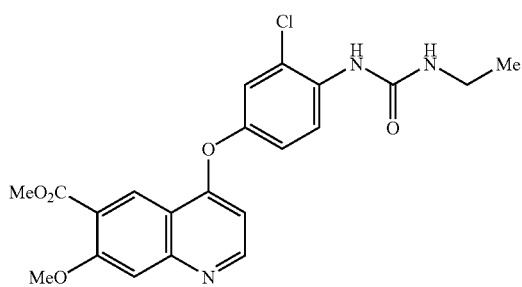
ex. 698
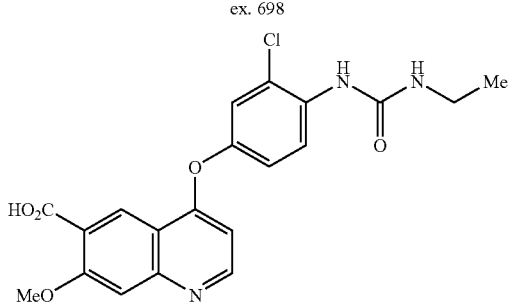
ex. 699
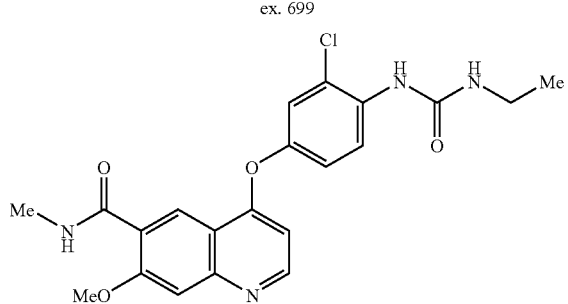

TABLE 49-continued
ex. 700
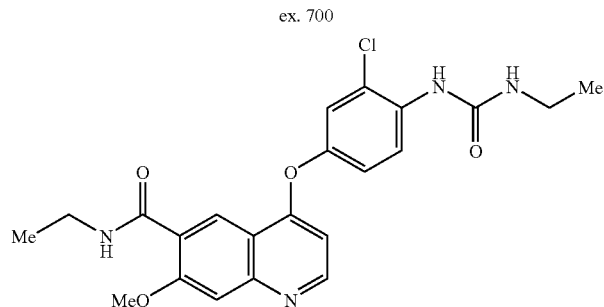
ex. 701
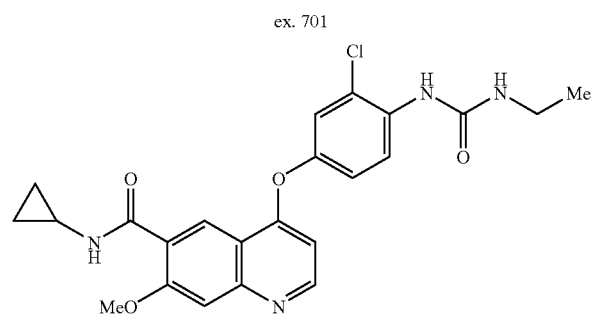
ex. 702
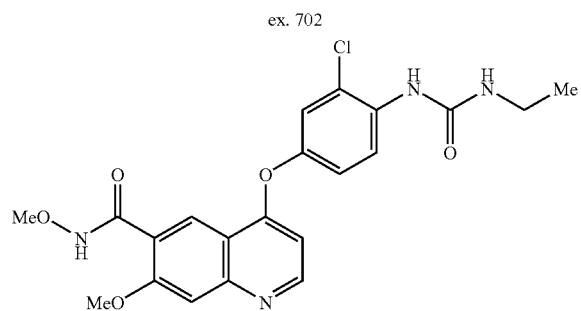
ex. 703
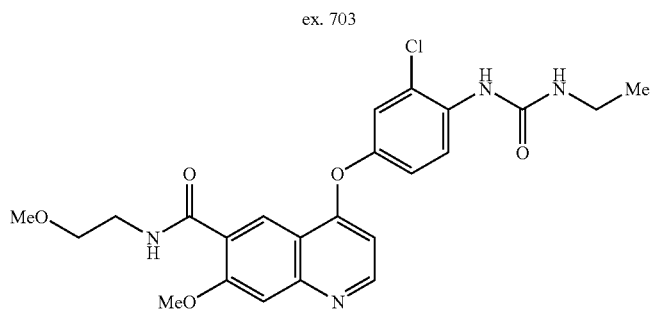
ex. 704
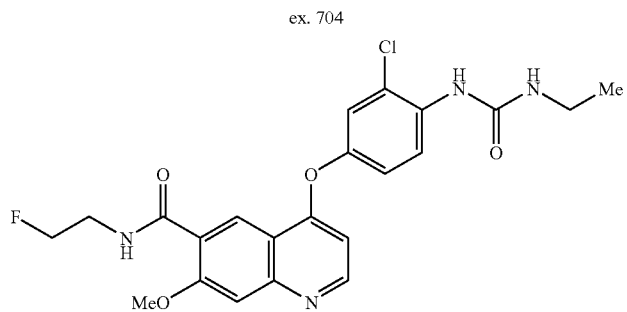

TABLE 49-continued
ex. 705
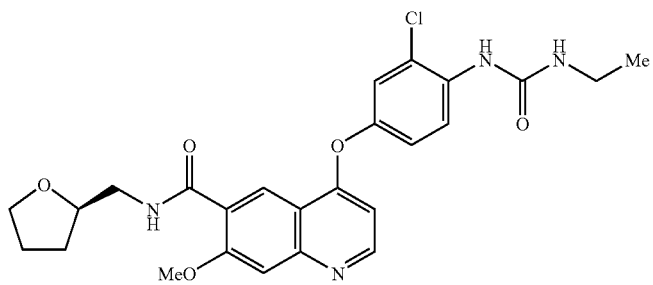
ex. 706
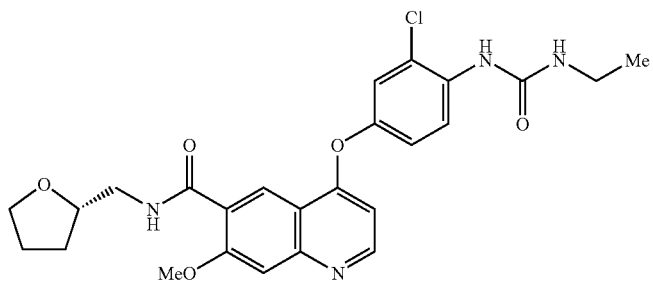
ex. 707
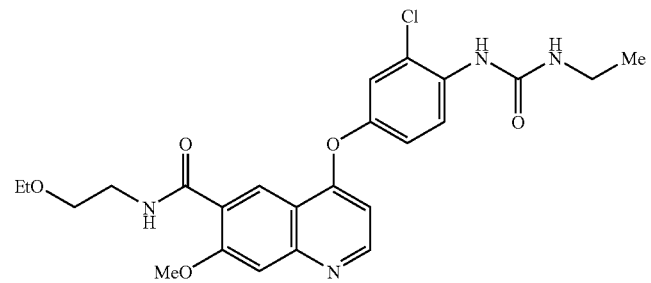
ex. 708
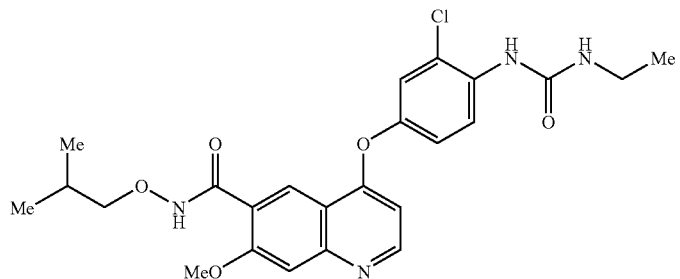
ex. 709
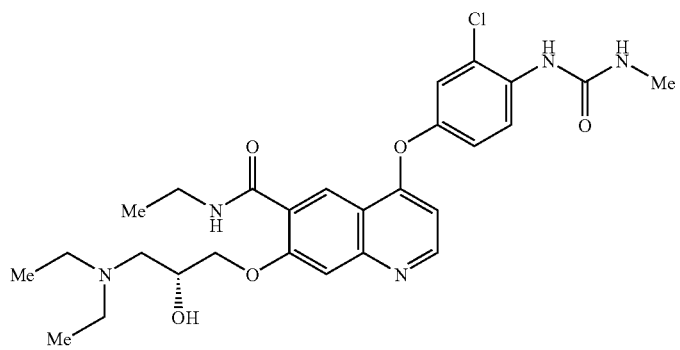

TABLE 49-continued
ex. 710
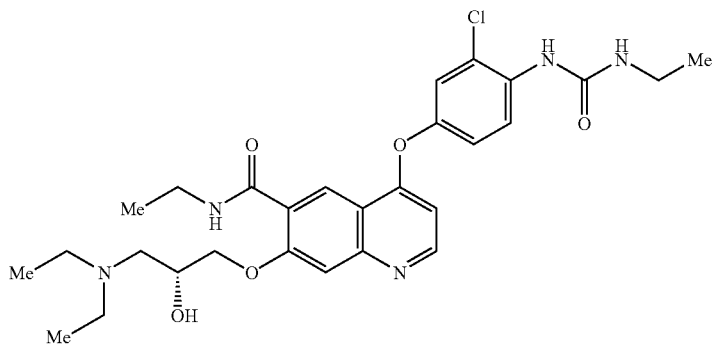
ex. 711
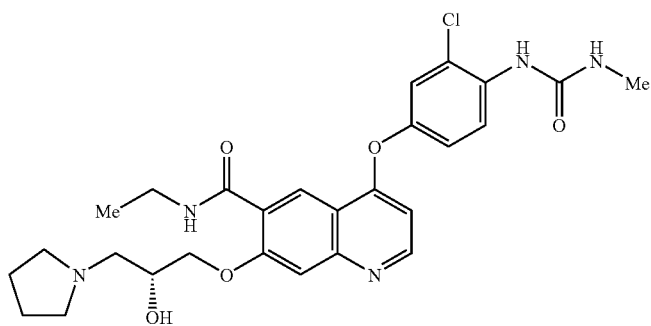
ex. 712
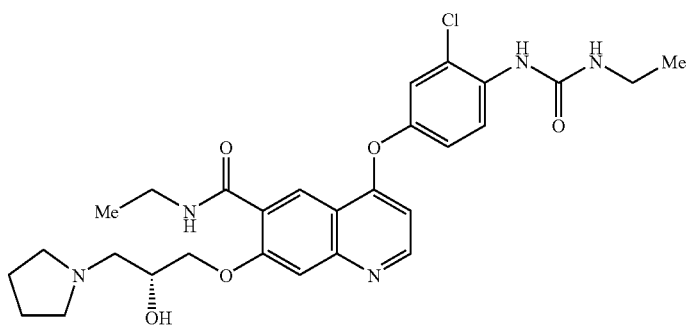
ex. 713
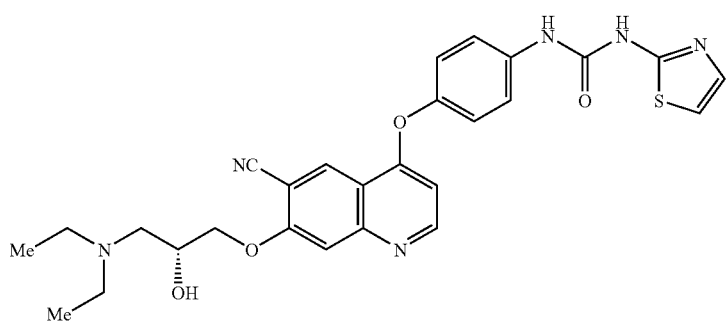

TABLE 49-continued
ex. 714
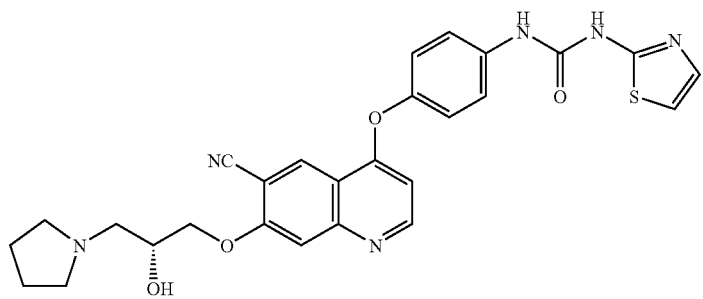
ex. 715
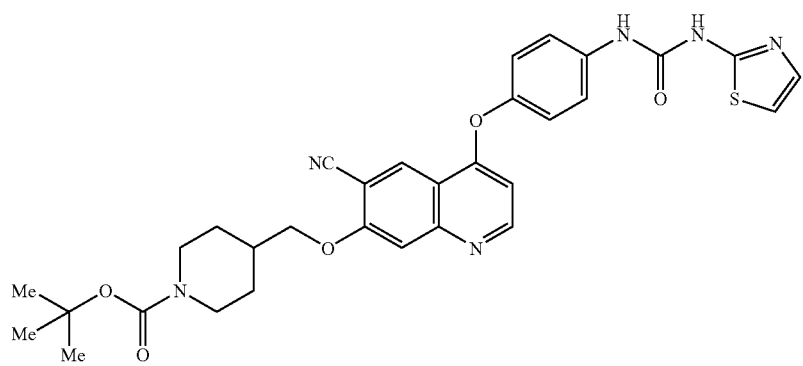
ex. 716
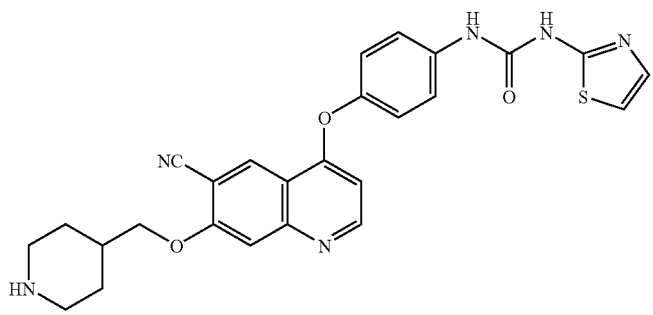
TABLE 50
ex. 717
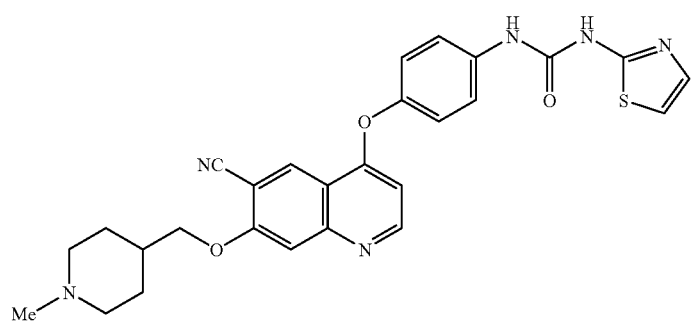

TABLE 50-continued
ex. 718
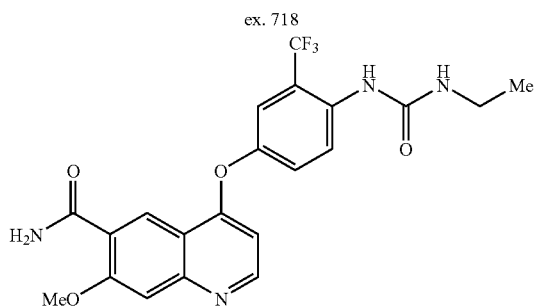
ex. 719
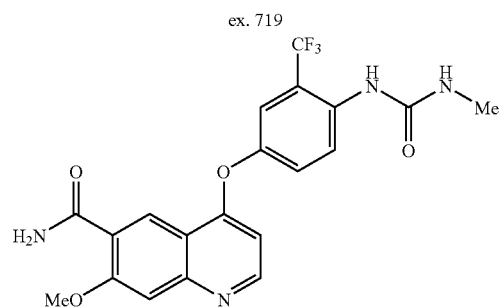
ex. 720
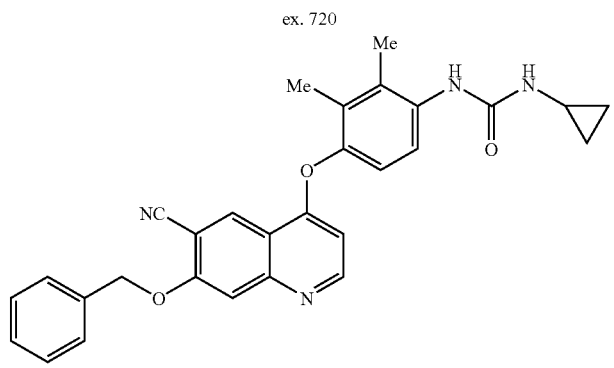
ex. 721
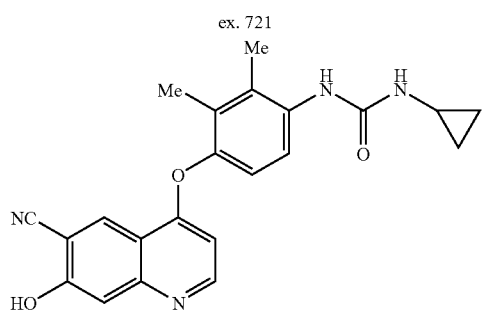
ex. 722
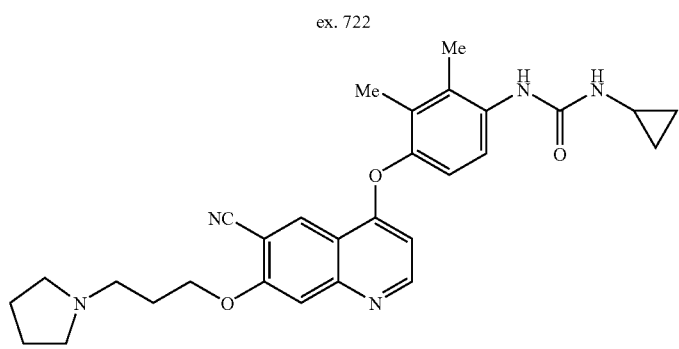

TABLE 50-continued
ex. 723
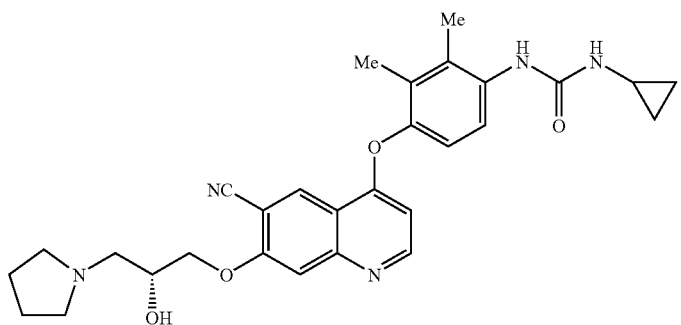
ex. 724
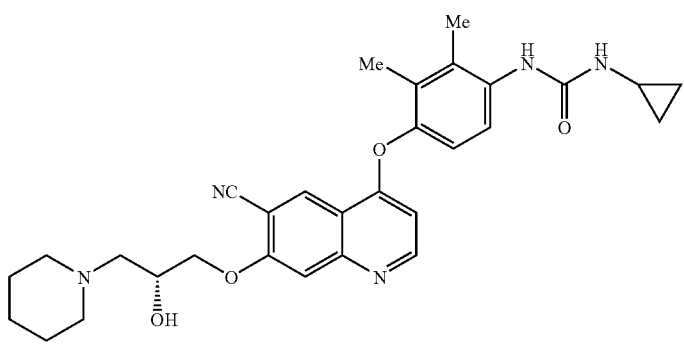
ex. 725
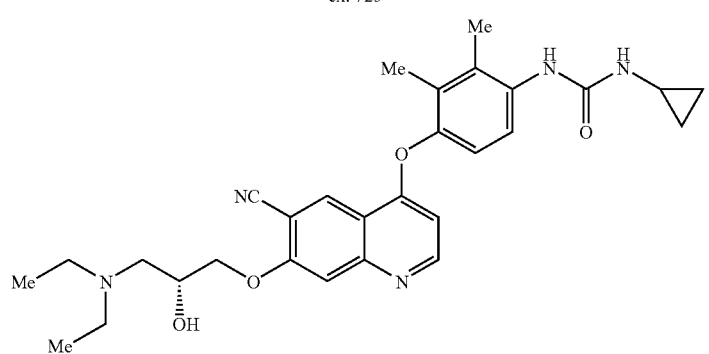
ex. 726
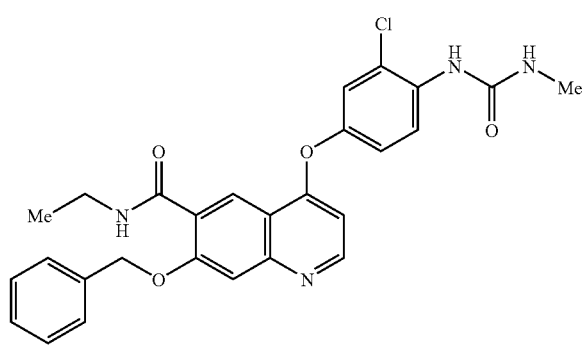

TABLE 50-continued
ex. 727
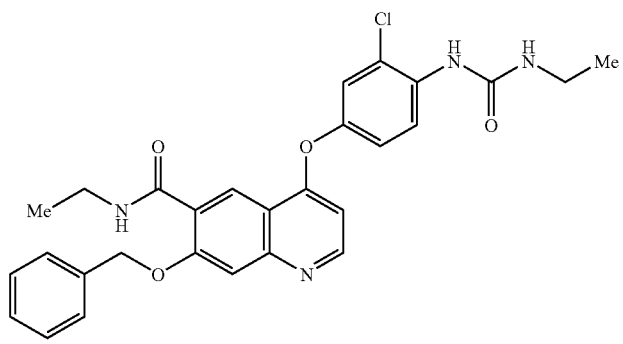
ex. 728
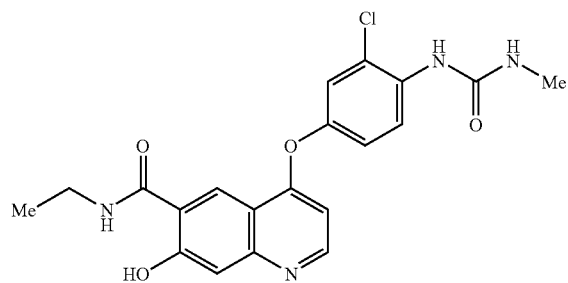
ex. 729
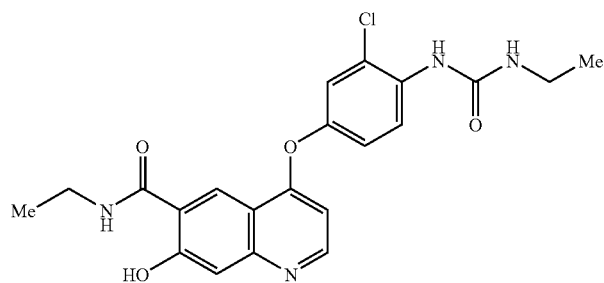
ex. 730
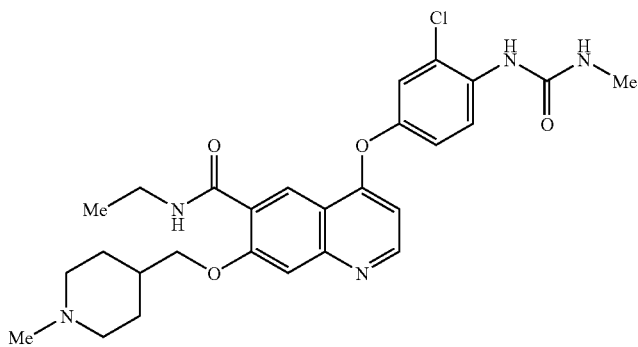

TABLE 50-continued
ex. 731
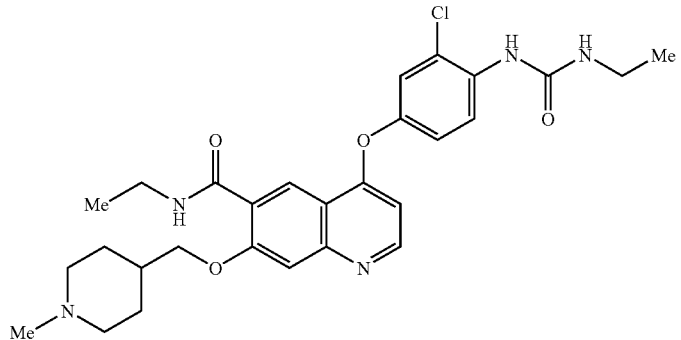
ex. 732
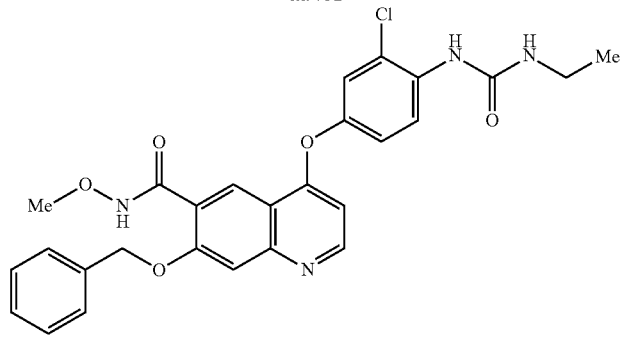
ex. 733
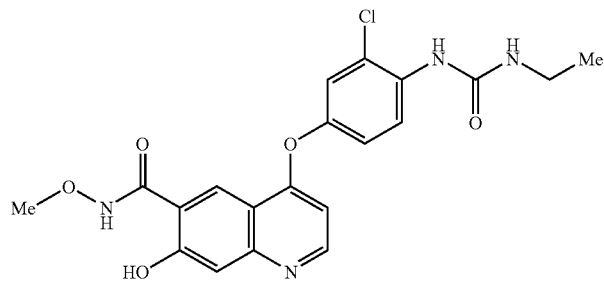
ex. 734
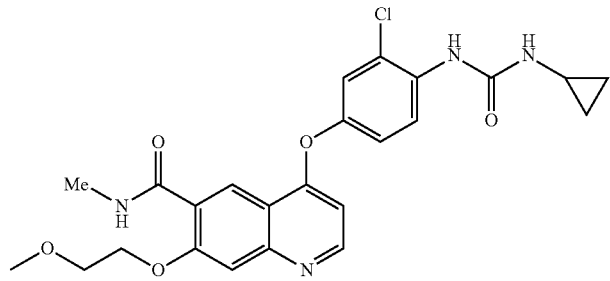
ex. 735
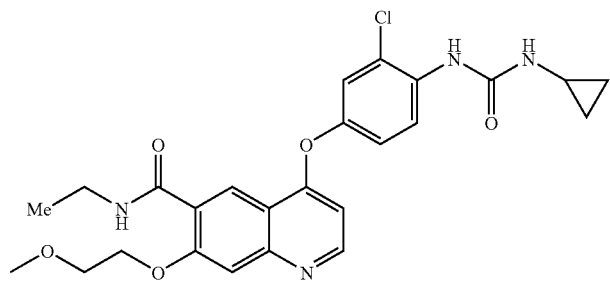

TABLE 50-continued
ex. 736
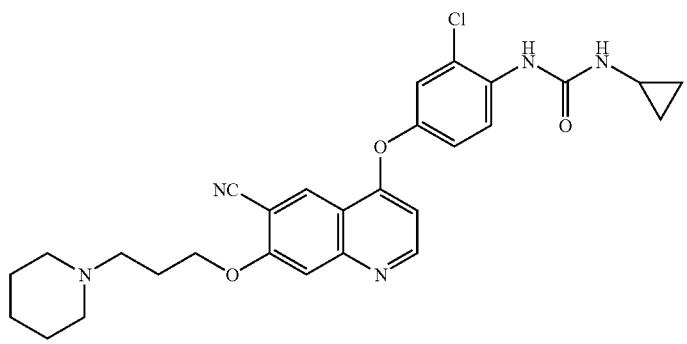
ex. 737
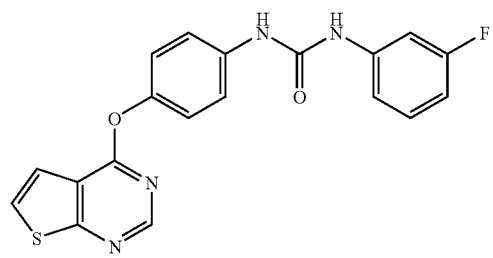
ex. 738
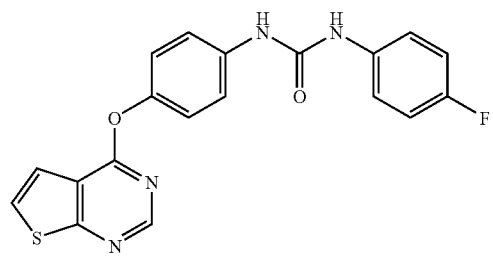
ex. 739
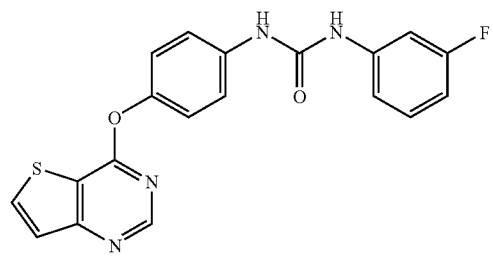
ex. 740
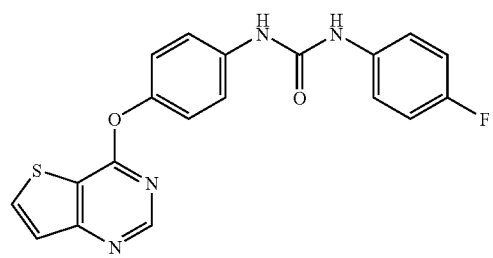

TABLE 50-continued ex. 741

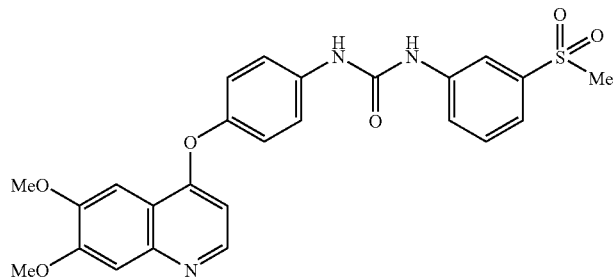

TABLE 51 ex. 742

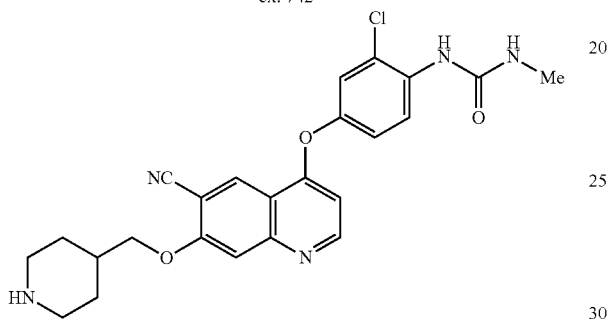

ex. 743

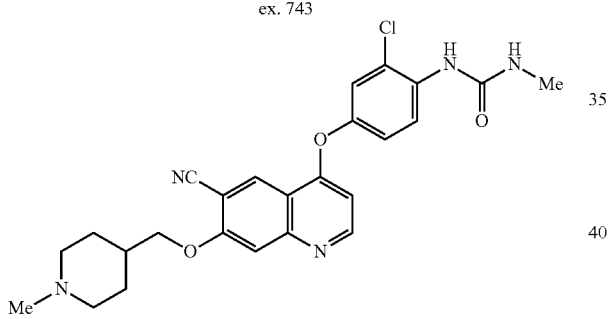

TABLE 51-continued pro. ex. 570-1

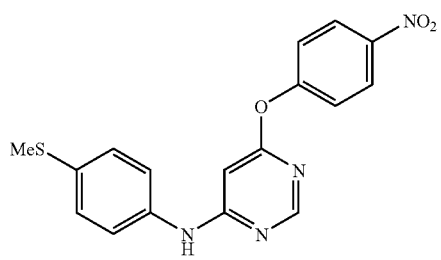

pro. ex. 570-2

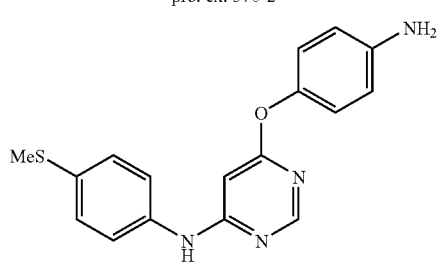

What is claimed is:

1. A compound represented by the following general formula:

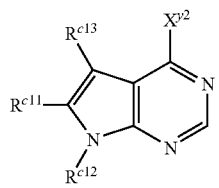
(IIIf)

wherein $R^{c13}$ is a hydrogen atom, cyano, a halogen atom, formyl, an optionally substituted $C_{1-6}$ alkyl group, a group represented by the formula:

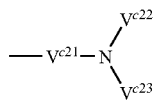

wherein $V^{c21}$ is —CO— or methylene; $V^{c22}$ and $V^{c23}$ are each independently a hydrogen atom, optionally substituted $C_{1-6}$ alkyl group, optionally substituted $C_{2-6}$ alkenyl group, optionally substituted $C_{2-6}$ alkynyl group, optionally substituted $C_{3-8}$ alicyclic hydrocarbon group, optionally substituted 5- to 14-membered heterocyclic group, optionally substituted 5- to 14-membered aromatic heterocyclic group or optionally substituted $C_{6-14}$ aryl group, or a group represented by the formula: —$V^{c21}$—O—$V^{c22}$ wherein $V^{c21}$ and $V^{c22}$ have the same definitions as above;

$X^{y2}$ is an optionally substituted group selected from the group consisting of the following formulas:

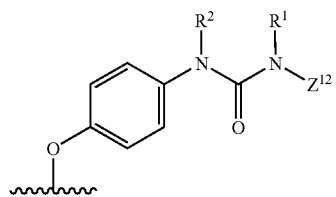

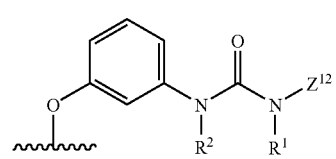

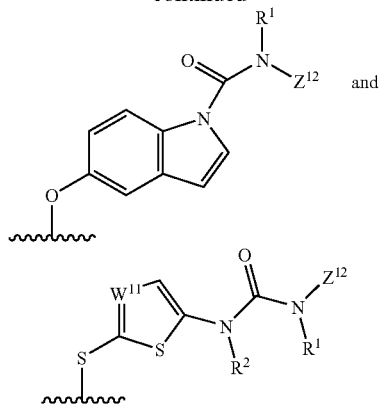

wherein $Z^{12}$ is a hydrogen atom, optionally substituted $C_{1-6}$ alkyl group, optionally substituted $C_{2-6}$ alkenyl group, optionally substituted $C_{2-6}$ alkynyl group, optionally substituted $C_{3-8}$ alicyclic hydrocarbon group, optionally substituted $C_{6-14}$ aryl group, optionally substituted 5- to 14-membered heterocyclic group, optionally substituted 5- to 14-membered aromatic heterocyclic group or a group represented by the formula:

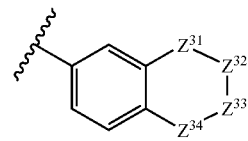

wherein $Z^{31}$, $Z^{33}$ and $Z^{34}$ are each independently methylene, —CO—, —NH— or —O—, and $Z^{32}$ is a single bond, methylene, —CO—, —NH— or —O—, and $R^1$ and $R^2$ are each independently a hydrogen atom, optionally substituted $C_{1-6}$ alkyl group, optionally substituted $C_{2-6}$ alkenyl group, optionally substituted $C_{2-6}$ alkynyl group, optionally substituted $C_{3-8}$ alicyclic hydrocarbon group, optionally substituted $C_{2-7}$ acyl group or optionally substituted $C_{2-7}$ alkoxycarbonyl group; and $W^{11}$ is an optionally substituted carbon atom or a nitrogen atom;

$R^{c11}$ is a group represented by the formula —$V^{c11}$—$V^{c12}$—$V^{c13}$, wherein $V^{c11}$ is a single bond, oxygen atom, optionally substituted benzene ring, optionally substituted 5- to 14-membered aromatic heterocyclic group or —CO—; $V^{c12}$ is a single bond, oxygen atom or optionally substituted $C_{1-6}$ alkylene group; and $V^{c13}$ is an optionally substituted $C_{1-6}$ alkyl group, an optionally substituted $C_{2-6}$ alkenyl group, an optionally substituted $C_{2-6}$ alkynyl group, an optionally substituted $C_{3-8}$ alicyclic hydrocarbon group, hydroxyl, carboxyl, an optionally substituted $C_{2-7}$ alkoxycarbonyl group, an optionally substituted 5- to 14-membered heterocyclic group, an optionally substituted 5- to 14-membered aromatic heterocyclic group, an optionally substituted $C_{6-14}$ aryl group, a group represented by the formula —$NR^{c21}R^{c22}$, wherein $R^{c21}$ and $R^{c22}$ are each independently a hydrogen atom or optionally substituted $C_{1-6}$ alkyl group, or a hydrogen atom; and $R^{c12}$ is a hydrogen atom, optionally substituted $C_{1-6}$ alkyl group or optionally substituted $C_{3-8}$ alicyclic hydrocarbon group;

with the exception of the following compounds (1) and (2):
(1) a compound wherein $R^1$ and $R^2$ are hydrogen atoms and $Z^{12}$ is a $C_{6-14}$ aryl group, a 5- to 14-membered heterocyclic group, a $C_{1-6}$ alkyl group substituted with a 5- to 14-membered aromatic heterocyclic group, a 5- to 10-membered heterocyclic group or a $C_{5-10}$ alicyclic hydrocarbon group, a $C_{2-6}$ alkenyl group substituted with a 5- to 10-membered heterocyclic group or a $C_{5-10}$ alicyclic hydrocarbon group, a $C_{2-6}$ alkynyl group substituted with a 5- to 10-membered heterocyclic group or a $C_{5-10}$ alicyclic hydrocarbon group, or a $C_{3-8}$ alicyclic hydrocarbon group substituted with a 5- to 10-membered heterocyclic group or a $C_{5-10}$ alicyclic hydrocarbon group; and
(2) a compound wherein $X^{y2}$ is a group represented by the formula:

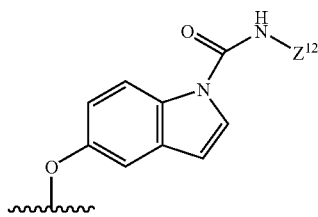

wherein $Z^{12}$ is a $C_{6-14}$ aryl group, a 5- to 14-membered heterocyclic group, a 5- to 14-membered aromatic heterocyclic group, a $C_{1-6}$ alkyl group substituted with a 5- to 10-membered heterocyclic group or a $C_{5-10}$ alicyclic hydrocarbon group, a $C_{2-6}$ alkenyl group substituted with a 5- to 10-membered heterocyclic group or a $C_{5-10}$ alicyclic hydrocarbon group, a $C_{2-6}$ alkynyl group substituted with a 5- to 10-membered heterocyclic group or a $C_{5-10}$ alicyclic hydrocarbon group, or a $C_{3-8}$ alicyclic hydrocarbon group, a salt thereof or a hydrate of the foregoing.

2. A compound according to claim 1, a salt of the compound or a hydrate of the foregoing, wherein $R^{c11}$ is a group represented by the formula:

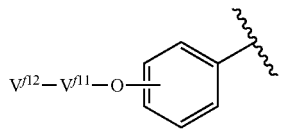

wherein $V^{f11}$ is a single bond, an optionally substituted $C_{1-6}$ alkylene group or a group represented by the formula:

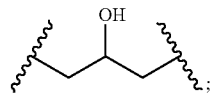

and $V^{f12}$ is a hydrogen atom, a hydroxyl group, an optionally substituted 5- to 14-membered heterocyclic group, an optionally substituted 5- to 14-membered aromatic heterocyclic group, an optionally substituted $C_{6-14}$ aryl group or a group represented by the formula $-NR^{f21}R^{f22}$ wherein $R^{f21}$ and $R^{f22}$ are each independently a hydrogen atom or an optionally substituted $C_{1-6}$ alkyl group.

* * * * *